United States Patent
Hu et al.

(10) Patent No.: US 9,890,167 B2
(45) Date of Patent: Feb. 13, 2018

(54) PYRAZINE COMPOUNDS FOR THE TREATMENT OF INFECTIOUS DISEASES

(71) Applicant: Hoffmann-La Roche Inc., Little Falls, NJ (US)

(72) Inventors: Taishan Hu, Shanghai (CN); Xingchun Han, Shanghai (CN); Buyu Kou, Shanghai (CN); Hong Shen, Shanghai (CN); Shixiang Yan, Shanghai (CN); Zhisen Zhang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/997,346

(22) Filed: Jan. 15, 2016

(65) Prior Publication Data
US 2016/0237090 A1 Aug. 18, 2016

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ............................ C07D 487/04; C07D 519/00
See application file for complete search history.

(56) References Cited

U.S. PATENT DOCUMENTS

| | | | |
|---|---|---|---|
| 2006/0281755 A1* | 12/2006 | Baumann | A61K 31/4709 514/252.18 |
| 2012/0309765 A1 | 12/2012 | Price et al. | |
| 2015/0152073 A1 | 6/2015 | Hartman et al. | |
| 2016/0039825 A1 | 2/2016 | Peng et al. | |

FOREIGN PATENT DOCUMENTS

| | | | |
|---|---|---|---|
| TW | 200932745 | 12/1997 | |
| TW | 201336814 A | 9/2013 | |
| TW | 201446768 A | 12/2014 | |
| WO | 2009/085983 A1 | 7/2009 | |
| WO | 2013/096744 A1 | 6/2013 | |
| WO | 2014/033167 | 3/2014 | |
| WO | 2014/033170 A1 | 3/2014 | |
| WO | 2014/111871 A1 | 7/2014 | |
| WO | 2014/152725 A1 | 9/2014 | |
| WO | WO 2014195311 A1 * | 12/2014 | ........... C07D 487/04 |

OTHER PUBLICATIONS

NCBI Database, http://pubchem.ncbi.nlm.nih.gov/compound/96445842, CID: 96445842—ZINC77973101 Jun. 4, 2016.
NCBI Database, http://pubchem.ncbi.nlm.nih.gov/compound/96445844, CID: 96445844—ZINC77973103 Jun. 4, 2016.
NCBI Database, http://pubchem/ncbi.nlm.nih.gov/compound/96445840, ZINC77973099—CID: 96445840 Jun. 4, 2016.
NCBI Database, http://pubchem/ncbi.nlm.nih.gov/compound/96445841, CID: 96445841—ZINC77973100 Jun. 4, 2016.
NCBI Database, http://pubchem.ncbi.nlm.nih.gov/compound/96445843, CID:96445843—ZINC77973102 Jun. 4, 2016.

* cited by examiner

*Primary Examiner* — Sarah Pihonak
*Assistant Examiner* — Jason A Deck
(74) *Attorney, Agent, or Firm* — Jonathan Duffield

(57) ABSTRACT

The present invention relates to compounds of the formula (I),

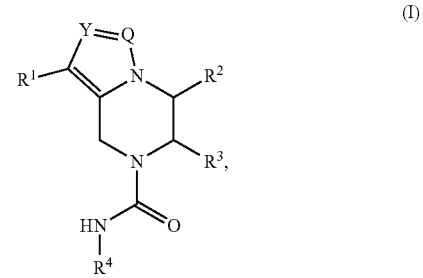

or pharmaceutically acceptable salts, enantiomer or diastereomer thereof, wherein $R^1$ to $R^4$ are as described above. The compounds may be useful for the treatment or prophylaxis of hepatitis B virus infection.

50 Claims, No Drawings

PYRAZINE COMPOUNDS FOR THE TREATMENT OF INFECTIOUS DISEASES

This patent application claims the benefit under 35 U.S.C. § 119(a) of International Application No. PCT/CN2015/070896 filed Jan. 16, 2015, and claims the benefit of International PCT Application No. PCT/CN2015/077356 filed on Apr. 24, 2015, and claims the benefit of International PCT Application No. PCT/CN2015/097403 filed on Dec. 15, 2015. The entire content of these applications is hereby incorporated herein by reference.

The present invention relates to organic compounds useful for therapy and/or prophylaxis in a mammal, and in particular for treating hepatitis B virus infection, and their pharmaceutical activity, manufacture, pharmaceutical compositions containing them and their potential use as medicaments.

FIELD OF THE INVENTION

The present invention relates to compounds of the formula (I),

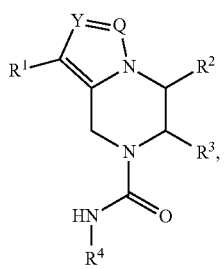

or pharmaceutically acceptable salts, enantiomer or diastereomer thereof, wherein $R^1$ to $R^4$, Y and Q are as described below. The compounds of this invention are useful for the treatment or prophylaxis of hepatitis B virus infection.

Hepatitis B virus (HBV) infection is a major public health problem worldwide, roughly 30% of the world's population show serological evidence of current or past infection. Despite the introduction of a safe and effective prophylactic vaccine against the virus in the early 1980s, it is estimated that there are still more than 240 million chronic HBV carriers worldwide, a high percentage of whom will eventually develop liver cirrhosis or hepatocellular carcinoma (HCC) (WHO Hepatitis B. Fact Sheet N° 204). In the 2010 Global Burden of Disease study (R Lozano, et al. Lancet, 380 (2012), 2095-2128), HBV infection ranked in the top health priorities in the world, and was the tenth leading cause of death (780,000 deaths per year). Recent studies have shown that progression to liver cirrhosis and HCC in patients with chronic HBV infection is significantly associated with circulating HBV DNA levels. Thus, antiviral therapy against HBV is critical to prevent the progression to cirrhosis or development of HCC.

HBV is a small, enveloped virus that belongs to the Hepadnaviridae family. It contains a partly double-stranded DNA genome with approximately 3200 base pairs. HBV have a strong preference for infecting human hepatocytes. The life cycle begins when HBV attaches to the host cell membrane via its envelope proteins. The precise mechanism of viral entry has not been fully elucidated. The viral relaxed circular DNA (rcDNA) containing nucleocapsids are released into the cytoplasm and transported to the nucleus. In the nucleus, the rcDNA is repaired by both viral and cellular enzymes to form covalently closed circular DNA (cccDNA). There is evidence that each infected cell contains 1-50 cccDNA molecules as unique episomal minichromosomes. Both subgenomic RNA (sgRNA) and pregenomic RNA (pgRNA) are transcribed from the cccDNA using the cellular transcriptional machinery. After nuclear export, the pgRNA is translated into the core protein and the viral polymerase. The sgRNA is translated into the regulatory X protein and the three envelope proteins. Self-assembly of the RNA-containing viral nucleocapsid takes place via complex formation of the pgRNA with the core protein and the polymerase. Inside the nucleocapsid, the pgRNA is reverse transcribed into negative-strand DNA. rcDNA is then generated by plus-strand synthesis from the negative-strand DNA. The nucleocapsids are either re-imported to the nucleus for cccDNA amplification or enveloped and released via the endoplasmic reticulum (ER). The reverse transcriptase lacks proofreading activity; thus, mutations of the viral genome are frequent and result in the coexistence of genetically distinct viral species in infected individuals (quasispecies).

Currently, seven treatments are approved for chronic hepatitis B (CHB), including two formulations of interferon (IFN) (conventional IFN and PEG-IFN) and five nucleos(t)ide analogues (NUCs: lamivudine, adefovir dipivoxil, entecavir, telbivudine, and tenofovir disoproxil). The main difference between immunomodulatory agents and NUCs is that PEG-IFN has the advantage of a finite duration of use, whereas the use of NUCs is indefinite. The major drawback of PEG-IFN is its high frequency of adverse events. Some viral genotypes do not show good responses to interferon therapy. Long-term use of NUCs, on the other hand, poses the risk of drug resistance. The ultimate goal of antiviral therapy for CHB is to prevent progression to cirrhosis or HCC via eradication of HBV or persistent viral suppression. The majority of currently treated patients fail to achieve this goal. As indicated above, nucleocapsid assembly is a critical step for HBV genome replication. As the synthesis of viral DNA takes place exclusively within the nucleocapsid, the assembly and disassembly of nucleocapsid must be precisely regulated to ensure correct packaging and release of the viral genome. Nucleocapsid assembly is an evolutionary constraint process that limits the diversity of HBV, and it is highly sensitive to even subtle molecular disturbances. Both assembly and disassembly of nucleocapsid make the process an attractive therapeutic target for the development of new antiviral therapies against various HBV genotypes and drug resistance isolates. A few capsid related anti-HBV compounds have been reported. For example, heteroaryldihydropyrimidines (HAP), including compounds named Bay 41-4109, Bay 38-7690 and Bay 39-5493 (Deres K. et al. Science 2003, 893), and phenylpropenamide derivatives such as AT-61 and AT-130 (Feld J. et al. Antiviral Research 2007, 168-177). Capsid has become a promising drug target with several molecules under clinical stage. There is still a need to develop new treatments for the prophylaxis and treatment of hepatitis B virus infection.

SUMMARY OF THE INVENTION

The present invention relates to novel compounds of formula (I),

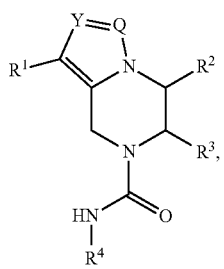

(I)

wherein
R¹ is heterocyclyl, said heterocyclyl being unsubstituted or substituted with one, two or three substituents independently selected from $(C_{1-6}alkyl)_2$aminocarbonyl, $(C_{1-6}alkyl)_2$morpholinylcarbonyl, $C_{1-6}$alkoxy, $C_{1-6}$alkoxy$C_{1-6}$alkyl, $C_{1-6}$alkoxycarbonyl, $C_{1-6}$alkyl, $C_{1-6}$alkyl($C_{1-6}$alkylsulfonyl)amino, $C_{1-6}$alkylaminocarbonyl, $C_{1-6}$alkylcarbonyl, $C_{1-6}$alkylcarbonylamino, $C_{1-6}$alkylimidazolyl, $C_{1-6}$alkylmorpholinylcarbonyl, $C_{1-6}$alkyloxadiazolyl, $C_{1-6}$alkyloxazolyl, $C_{1-6}$alkylpyrazolyl, $C_{1-6}$alkylsulfonyl, $C_{1-6}$alkylsulfonylamino, $C_{1-6}$alkylsulfonyl$C_{1-6}$alkyl, carbamoyl, cyano, dioxopyrrolidinyl, halo$C_{1-6}$alkyl, halo$C_{1-6}$alkyloxadiazolyl, halogen, halopiperidinylcarbonyl, halopyridinyl, halopyrimidinylamino, halopyrimidinyloxy, halopyrrolidinylcarbonyl, hydroxy, hydroxyazetidinylcarbonyl, hydroxy$C_{1-6}$alkyl, hydroxy$C_{1-6}$alkyl($C_{1-6}$alkyl)aminocarbonyl, hydroxy$C_{1-6}$alkylaminocarbonyl, hydroxypyrrolidinylcarbonyl, morpholinylcarbonyl, oxadiazolyl, oxazolyl, oxazolylaminocarbonyl, oxazolyl($C_{1-6}$alkyl)aminocarbonyl, oxazolylcarbonyl, oxazolylcarbonyl($C_{1-6}$alkyl)amino, oxomorpholinyl, oxooxazolidinyl, oxopyrrolidinyl, phenyl, phenyl carbonyl, pyrazolyl$C_{1-6}$alkyl, pyridinyl, pyrimidinyl, pyrimidinylamino, pyrimidinyl($C_{1-6}$alkyl)amino, pyrimidinyloxy, pyrimidinyloxy$C_{1-6}$alkyl, pyrrolidinylcarbonyl and thiazolyl;
heteroaryl, said heteroaryl being unsubstituted or substituted with one, two or three substituents independently selected from halogen, cyano, $C_{1-6}$alkyl, halo$C_{1-6}$alkyl, hydroxy $C_{1-6}$alkyl and $C_{1-6}$alkoxy$C_{1-6}$ alkyl;
phenyl, said phenyl being unsubstituted or substituted with one, two or three substituents independently selected from halogen, cyano, hydroxy, $C_{1-6}$alkyl, $C_{1-6}$alkoxy, $C_{3-7}$cycloalkyl, halo$C_{1-6}$alkoxy and halo$C_{1-6}$alkyl; or
$C_{3-7}$cycloalkyl;
R² and R³ are independently selected from hydrogen and $C_{1-6}$alkyl;
R⁴ is heteroaryl, said heteroaryl being unsubstituted or substituted with one, two or three substituents independently selected from halogen, cyano, $C_{1-6}$alkyl, halo$C_{1-6}$alkyl, $C_{1-6}$alkoxy, $C_{3-7}$cycloalkyl and $(C_{1-6}alkyl)_2$amino;
aryl, said aryl being unsubstituted or substituted with one, two or three substituents independently selected from halogen, cyano, $C_{3-7}$cycloalkyl, $C_{1-6}$alkyl, $C_{2-6}$alkynyl, $C_{1-6}$alkoxy, halo$C_{1-6}$alkyl and halo$C_{1-6}$alkoxy;
phenyl$C_{1-6}$alkyl, said phenyl$C_{1-6}$alkyl being unsubstituted or substituted with one, two or three halogen; or
$C_{3-7}$cycloalkyl;

Y and Q are independently selected from CH and N;
or pharmaceutically acceptable salt, enantiomer or diastereomer thereof.

Objects of the present invention are novel compounds of formula (I), their manufacture, medicaments based on a compound in accordance with the invention and their production as well as the use of compounds of formula (I) as HBV inhibitors and for the treatment or prophylaxis of HBV infection.

DETAILED DESCRIPTION OF THE INVENTION

Definitions

The term "$C_{1-6}$alkyl" denotes a monovalent linear or branched saturated hydrocarbon group of 1 to 6 carbon atoms. In particular embodiments, $C_{1-6}$alkyl has 1 to 6 carbon atoms, and in more particular embodiments 1 to 4 carbon atoms. Examples of $C_{1-6}$alkyl include methyl, ethyl, propyl, isopropyl, n-butyl, iso-butyl, sec-butyl or tert-butyl.

The term "halo" or "halogen" are used interchangeably herein and denote fluoro, chloro, bromo or iodo.

The term "halo$C_{1-6}$alkyl" denotes a $C_{1-6}$alkyl group wherein at least one of the hydrogen atoms of the $C_{1-6}$alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 2-fluoroethyl, trifluoroethyl, fluoromethyl, difluoromethyl, difluoroethyl or trifluoromethyl.

The term "halo$C_{1-6}$alkoxy" denotes a $C_{1-6}$alkoxy group wherein at least one of the hydrogen atoms of the $C_{1-6}$alkoxy group has been replaced by same or different halogen atoms, particularly fluoro atoms. Examples of halo$C_{1-6}$alkoxy include monofluoro-, difluoro- or trifluoro-methoxy, -ethoxy or -propoxy, for example 3,3,3-trifluoropropoxy, 2-fluoroethoxy, trifluoroethoxy, fluoromethoxy, difluoromethoxy, difluoroethoxy or trifluoromethoxy.

The term "halopyridinyl" denotes a pyridinyl substituted once, twice or three times by halogen. Examples of halopyridinyl include, but not limited to, bromopyridinyl, chloropyridinyl, difluoropyridinyl, fluoropyridinyl and fluorochloropyridinyl.

The term "halopyrimidinyl" denotes a pyrimidinyl substituted once, twice or three times by halogen. Examples of halopyrimidinyl include, but not limited to, fluoropyrimidinyl.

The term "halopyrrolidinyl" denotes a pyrrolidinyl substituted once, twice or three times by halogen. Examples of halopyrrolidinyl include, but not limited to, difluoropyrrolidinyl.

The term "halopiperidinyl" denotes a piperidinyl substituted once, twice or three times by halogen. Examples of halopiperidinyl include, but not limited to, difluoropiperidinyl.

The term "pyrimidinyloxy" denotes pyrimidinyl-O—.

The term "halopyrimidinyloxy" denotes halopyrimidinyl-O—, wherein halopyrimidinyl is defined above. Examples of halopyrimidinyloxy include, but not limited to, fluoropyrimidinyloxy.

The term "oxo" denotes a divalent oxygen atom =O.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include, but not limited to, pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl or quinoxalinyl. Heteroaryl can be further substituted by halogen, $C_{1-6}$alkyl, halo$C_{1-6}$alkyl, cyano, $C_{3-7}$cycloalkyl, $(C_{1-6}$alkyl$)_2$amino, $C_{1-6}$alkoxy. Example of heteroaryl include, but not limited to, chloropyridinyl, chlorothiazolyl, cyanopyrazolyl, cyanopyridinyl, fluorochloropyridinyl, fluoropyrazolyl, fluoropyridinyl, fluoropyrimidinyl, hydroxymethylpyrazolyl, methoxymethylpyrazolyl, methylfluoropyridinyl, methylfluoropyrimidinyl, methylpyrazolyl, trifluoromethylpyridinyl and trifluoromethylthiazolyl.

The term "aryl" denotes a monovalent aromatic carbocyclic mono- or bicyclic ring system comprising 6 to 10 carbon ring atoms. Example of monocyclic aryl include, but not limited to, phenyl; and examples of the bicyclic aryl include, but not limited to, indanyl and bicyclo[4.2.0]octa-1(6),2,4-trienyl.

The term "heterocyclyl" denotes a monovalent saturated or partly unsaturated mono or bicyclic ring system of 3 to 10 ring atoms, comprising 1 to 5 ring heteroatoms selected from N, O and S, the remaining ring atoms being carbon. In particular embodiments, heterocyclyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, and lactam include, but not limited to, oxopyrrolidinyl, oxomorpholinyl, oxooxazolidinyl and oxooxazinanyl; monocyclic saturated heterocyclyl can be further substituted by $(C_{1-6}$alkyl$)_2$aminocarbonyl, $(C_{1-6}$alkyl$)_2$morpholinylcarbonyl, $C_{1-6}$alkoxy, $C_{1-6}$alkoxy$C_{1-6}$alkyl, $C_{1-6}$alkyl, $C_{1-6}$alkyl, $C_{1-6}$alkyl$(C_{1-6}$alkylsulfonyl)amino, $C_{1-6}$alkylaminocarbonyl, $C_{1-6}$alkylcarbonylamino, $C_{1-6}$alkylmorpholinylcarbonyl, $C_{1-6}$alkyloxadiazolyl, $C_{1-6}$alkyloxazolyl, $C_{1-6}$alkylpyrazolyl, $C_{1-6}$alkylsulfonyl, $C_{1-6}$alkylsulfonylamino, $C_{1-6}$alkylsulfonyl$C_{1-6}$alkyl, cyano, di oxopyrrolidinyl, halo$C_{1-6}$alkyl, halo$C_{1-6}$alkyloxadiazolyl, halopiperidinylcarbonyl, halopyrimidinylamino, halopyrimidinyloxy, halopyrrolidinylcarbonyl, hydroxy, hydroxyazetidinylcarbonyl, hydroxy$C_{1-6}$alkyl, hydroxy$C_{1-6}$alkyl, hydroxy$C_{1-6}$alkyl$(C_{1-6}$alkyl)aminocarbonyl, hydroxy$C_{1-6}$alkylaminocarbonyl, hydroxypyrrolidinylcarbonyl, morpholinylcarbonyl, oxadiazolyl, oxazolyl, oxazolylaminocarbonyl, oxazolyl$(C_{1-6}$alkyl)aminocarbonyl, oxazolylcarbonyl$(C_{1-6}$alkyl)amino, oxomorpholinyl, oxooxazolidinyl, oxopyrrolidinyl, phenyl, pyrazolyl$C_{1-6}$alkyl, pyridinyl, pyrimidinyl, pyrimidinylamino, pyrimidinyl$C_{1-6}$alkylamino, pyrimidinyloxy, pyrimidinyloxy$C_{1-6}$alkyl, pyrrolidinylcarbonyl and thiazolyl. Examples for substituted monocyclic saturated heterocyclyl include, but not limited to difluoropiperidinyl, methyloxooxazinanyl, dimethyloxooxazinanyl, methoxyoxooxazinanyl, morpholinylcarbonyl(methyl)oxooxazinanyl, dimethyloxopyrrolidinyl, oxazolyloxopyrrolidinyl, dimethylmorpholinyl, methyloxomorpholinyl, hydroxypiperidinyl, cyanooxopyrrolidinyl, trifluoromethyloxopyrrolidinyl, hydroxyoxopyrrolidinyl, acetylpiperidinyl, methylaminocarbonyloxopyrrolidinyl, methoxyoxopyrrolidinyl, dimethyloxooxazolidinyl, phenyl(hydroxy)oxopyrrolidinyl, pyrimidinyloxyoxopyrrolidinyl, pyrimidinyloxy(hydroxy)oxopyrrolidinyl, pyrimidinyloxy(hydroxy)(methyl)oxopyrrolidinyl and pyrimidinylaminohydroxyoxopyrrolidinyl. Examples for bicyclic saturated heterocyclic ring are azabicyclo[3.2.1]octyl, quinuclidinyl, oxaazabicyclo[3.2.1]octanyl, azabicyclo[3.3.1]nonanyl, oxaaza-bicyclo[3.3.1]nonanyl, azabicyclo[3.1.0]hexanyl, oxodiazaspiro[3.4]octanyl, acetyloxodiazaspiro[3.4]octanyl, thiaazabicyclo[3.3.1]nonanyl, oxoazaspiro[2.4]heptanyl, oxoazaspiro[3.4]octanyl, oxoazabicyclo[3.1.0]hexanyl and dioxotetrahydropyrrolo[1,2-a]pyrazinyl. Examples for partly unsaturated heterocyclyl include dihydrofuryl, imidazolinyl, dihydrooxazolyl, tetrahydropyridinyl, dioxopiperazinyl, oxoimidazolidinyl, trioxothiazinanyl and dihydropyranyl; partly unsaturated heterocyclyl can be further substituted by halogen, $C_{1-6}$alkyl, $C_{1-6}$alkylsulfonyl, examples for substituted partly unsaturated heterocyclyl include, but not limited to, methylimidazolidinyl, methyl sulfonyloxoimidazolidinyl and dimethyloxooxazolidinyl.

The term "lactam" denotes a cyclic amide containing from 3 to 10 ring atoms which can comprise one, two or three atoms selected from nitrogen, oxygen and/or sulfur. Lactam can be mono-cyclic ring or bi-cyclic ring which can be further substituted by $(C_{1-6}$alkyl$)_2$aminocarbonyl, $(C_{1-6}$alkyl$)_2$morpholinylcarbonyl, $C_{1-6}$alkoxy, $C_{1-6}$alkoxy$C_{1-6}$alkyl, $C_{1-6}$alkyl$(C_{1-6}$alkylsulfonyl)amino, $C_{1-6}$alkylaminocarbonyl, $C_{1-6}$alkylcarbonylamino, $C_{1-6}$alkylmorpholinylcarbonyl, $C_{1-6}$alkyloxadiazolyl, $C_{1-6}$alkyloxazolyl, $C_{1-6}$alkylpyrazolyl, $C_{1-6}$alkylsulfonyl, $C_{1-6}$alkylsulfonylamino, $C_{1-6}$alkylsulfonyl$C_{1-6}$alkyl, cyano, di oxopyrrolidinyl, halo$C_{1-6}$alkyl, halo$C_{1-6}$alkyloxadiazolyl, halopiperidinylcarbonyl, halopyrimidinylamino, halopyrimidinyloxy, halopyrrolidinylcarbonyl, hydroxy, hydroxyazetidinylcarbonyl, hydroxy$C_{1-6}$alkyl, hydroxy$C_{1-6}$alkyl, hydroxy$C_{1-6}$alkyl$(C_{1-6}$alkyl)aminocarbonyl, hydroxy$C_{1-6}$alkylaminocarbonyl, hydroxypyrrolidinylcarbonyl, morpholinylcarbonyl, oxadiazolyl, oxazolyl, oxazolylaminocarbonyl, oxazolyl$(C_{1-6}$alkyl)aminocarbonyl, oxazolylcarbonyl$(C_{1-6}$alkyl)amino, oxomorpholinyl, oxooxazolidinyl, oxopyrrolidinyl, phenyl, pyrazolyl$C_{1-6}$alkyl, pyridinyl, pyrimidinyl, pyrimidinylamino, pyrimidinyl$C_{1-6}$alkylamino, pyrimidinyloxy, pyrimidinyloxy$C_{1-6}$alkyl, pyrrolidinylcarbonyl and thiazolyl. Examples of lactam include, but not limited to, oxooxazinanyl, methyloxooxazinanyl, dimethyloxooxazinanyl, oxopyrrolidinyl, dimethyloxopyrrolidinyl, cyanooxopyrrolidinyl, hydroxyoxopyrrolidinyl, methoxyoxopyrrolidinyl, trifluoromethyloxopyrrolidinyl, oxazolyloxopyrrolidinyl, oxoazabicyclo[3.1.0]hexanyl, oxomorpholinyl, methyloxomorpholinyl, difluoropyrrolidinyloxopyrrolidinyl, dimethyloxooxazolidinyl, phenyl(hydroxy)oxopyrrolidinyl, pyrimidinyloxyoxopyrrolidinyl, pyrimidinyloxy(hydroxy)oxopyrrolidinyl, pyrimidinyloxy(hydroxy)(methyl)oxopyrrolidinyl and pyrimidinylaminohydroxyoxopyrrolidinyl.

The term "diastereomer" denotes a stereoisomer with two or more centers of chirality and whose molecules are not mirror images of one another. Diastereomers have different physical properties, e.g. melting points, boiling points, spectral properties, activities and reactivities.

The term "enantiomers" denotes two stereoisomers of a compound which are non-superimposable mirror images of one another.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBV

The present invention provides (i) novel compounds having the general formula (I),

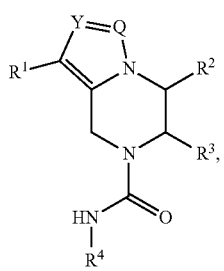

(I)

wherein
R$^1$ is heterocyclyl, said heterocyclyl being unsubstituted or substituted with one, two or three substituents independently selected from (C$_{1-6}$alkyl)$_2$aminocarbonyl, (C$_{1-6}$alkyl)$_2$morpholinylcarbonyl, C$_{1-6}$ alkoxy, C$_{1-6}$ alkoxyC$_{1-6}$ alkyl, C$_{1-6}$ alkoxycarbonyl, C$_{1-6}$alkyl, C$_{1-6}$alkyl(C$_{1-6}$alkylsulfonyl)amino, C$_{1-6}$alkylaminocarbonyl, C$_{1-6}$alkylcarbonyl, C$_{1-6}$alkylcarbonylamino, C$_{1-6}$alkylimidazolyl, C$_{1-6}$alkylmorpholinylcarbonyl, C$_{1-6}$alkyloxadiazolyl, C$_{1-6}$alkyloxazolyl, C$_{1-6}$alkylpyrazolyl, C$_{1-6}$ alkyl sulfonyl, C$_{1-6}$ alkylsulfonylamino, C$_{1-6}$alkylsulfonylC$_{1-6}$alkyl, carbamoyl, cyano, dioxopyrrolidinyl, haloC$_{1-6}$alkyl, haloC$_{1-6}$alkyloxadiazolyl, halogen, halopiperidinylcarbonyl, halopyridinyl, halopyrimidinylamino, halopyrimidinyloxy, halopyrrolidinylcarbonyl, hydroxy, hydroxyazetidinylcarbonyl, hydroxyC$_{1-6}$ alkyl, hydroxyC$_{1-6}$ alkyl (C$_{1-6}$alkyl)aminocarbonyl, hydroxyC$_{1-6}$ alkylaminocarbonyl, hydroxypyrrolidinylcarbonyl, morpholinylcarbonyl, oxadiazolyl, oxazolyl, oxazolylaminocarbonyl, oxazolyl(C$_{1-6}$alkyl)aminocarbonyl, oxazolylcarbonyl, oxazolylcarbonyl(C$_{1-6}$alkyl)amino, oxomorpholinyl, oxooxazolidinyl, oxopyrrolidinyl, phenyl, phenyl carbonyl, pyrazolylC$_{1-6}$alkyk pyridinyl, pyrimidinyl, pyrimidinylamino, pyrimidinyl(C$_{1-6}$alkyl) amino, pyrimidinyloxy, pyrimidinyloxyC$_{1-6}$alkyk pyrrolidinylcarbonyl and thiazolyl;

heteroaryl, said heteroaryl being unsubstituted or substituted with one, two or three substituents independently selected from halogen, cyano, C$_{1-6}$alkyl, haloC$_{1-6}$alkyl, hydroxy C$_{1-6}$alkyl and C$_{1-6}$alkoxy C$_{1-6}$alkyl;

phenyl, said phenyl being unsubstituted or substituted with one, two or three substituents independently selected from halogen, cyano, hydroxy, C$_{1-6}$alkyl, C$_{1-6}$alkoxy, C$_{3-7}$cycloalkyl, haloC$_{1-6}$alkoxy and haloC$_{1-6}$alkyl; or C$_{3-7}$cycloalkyl;

R$^2$ and R$^3$ are independently selected from hydrogen and C$_{1-6}$alkyl;

R$^4$ is heteroaryl, said heteroaryl being unsubstituted or substituted with one, two or three substituents independently selected from halogen, cyano, C$_{1-6}$alkyl, haloC$_{1-6}$alkyl, C$_{1-6}$alkoxy, C$_{3-7}$cycloalkyl and (C$_{1-6}$alkyl)$_2$amino;

aryl, said aryl being unsubstituted or substituted with one, two or three substituents independently selected from halogen, cyano, C$_{3-7}$cycloalkyl, C$_{1-6}$alkyl, C$_{2-6}$alkynyl, C$_{1-6}$alkoxy, haloC$_{1-6}$alkyl and haloC$_{1-6}$alkoxy;

phenylC$_{1-6}$alkyl, said phenylC$_{1-6}$alkyl being unsubstituted or substituted with one, two or three halogen; or C$_{3-7}$cycloalkyl;

Y and Q are independently selected from CH and N;
or pharmaceutically acceptable salt, enantiomer or diastereomer thereof.

A further embodiment of the present invention is (ii) a compound of formula (I), wherein
R$^1$ is azabicyclo[3.1.0]hexanyl;
dioxopiperazinyl;
dioxopyrimidinyl;
dioxotetrahydropyrrolo[1,2-a]pyrazinyl;
morpholinyl, said morpholinyl being unsubstituted or substituted with one, two or three C$_{1-6}$alkyl;
oxaazabicyclo[3.2.1]octanyl;
oxoazabicyclo[3.1.0]hexanyl;
oxoazaspiro[2.4]heptanyl, said oxoazaspiro[2.4]heptanyl being unsubstituted or substituted with hydroxy;
oxoazaspiro[4.4]nonanyl;
oxoazaspiro[3.4]octanyl, said oxoazaspiro[3.4]octanyl being unsubstituted or substituted with hydroxy;
oxodiazaspiro[3.4]octanyl, said oxodiazaspiro[3.4]octanyl being unsubstituted or substituted with one, two or three substituents independently selected from $C_{1-6}$alkylcarbonyl, $C_{1-6}$alkoxycarbonyl, oxazolylcarbonyl and pyrimidinyl;
oxodihydropyrazolo[1,5-a]pyrazinyl;
oxohexahydropyrimidinyl;
oxoimidazolidinyl, said oxoimidazolidinyl being unsubstituted or substituted with one, two or three substituents independently selected from $C_{1-6}$alkyl, $C_{1-6}$alkylcarbonyl, $C_{1-6}$alkylsulfonyl, phenyl, phenylcarbonyl and pyrimidinyl;
oxoindolinyl;
oxoisoindolinyl;
oxomorpholinyl, said oxomorpholinyl being unsubstituted or substituted with one, two or three substituents independently selected from $C_{1-6}$alkyl and oxazolyl;
oxooxaazaspiro[2.4]heptanyl;
oxooxaazaspiro[3.4]octanyl;
oxooxaazaspiro[4.4]nonanyl;
oxooxaazaspiro[4.5]decanyl;
oxooxazinanyl, said oxooxazinanyl being unsubstituted or substituted with one, two or three substituents independently selected from $C_{1-6}$alkyl, $C_{1-6}$alkoxy and morpholinylcarbonyl;
oxooxazolidinyl, said oxooxazolidinyl being unsubstituted or substituted with one, two or three substituents independently selected from $C_{1-6}$alkyl, phenyl, pyridinyl, halopyridinyl, oxazolyl, $C_{1-6}$alkylimidazolyl and $C_{1-6}$alkyloxadiazolyl;
oxopiperidyl, said oxopiperidyl being unsubstituted or substituted with one, two or three substituents independently selected from $C_{1-6}$alkyl and hydroxy;
oxopyrrolidinyl, said oxopyrrolidinyl being unsubstituted or substituted with one, two or three substituents independently selected from ($C_{1-6}$alkyl)$_2$aminocarbonyl, ($C_{1-6}$alkyl)$_2$morpholinylcarbonyl, $C_{1-6}$alkoxy, $C_{1-6}$alkoxyC$_{1-6}$alkyl, $C_{1-6}$alkyl, $C_{1-6}$alkyl($C_{1-6}$alkylsulfonyl)amino, $C_{1-6}$alkylaminocarbonyl, $C_{1-6}$alkylcarbonylamino, $C_{1-6}$alkylmorpholinylcarbonyl, $C_{1-6}$alkyloxadiazolyl, $C_{1-6}$alkyloxazolyl, $C_{1-6}$alkylpyrazolyl, $C_{1-6}$alkylsulfonyl, $C_{1-6}$alkylsulfonylamino, $C_{1-6}$alkylsulfonylC$_{1-6}$alkyl, cyano, dioxopyrrolidinyl, haloC$_{1-6}$alkyl, haloC$_{1-6}$alkyloxadiazolyl, halopiperidinylcarbonyl, halopyrimidinylamino, halopyrimidinyloxy, halopyrrolidinylcarbonyl, hydroxy, hydroxyazetidinylcarbonyl, hydroxyC$_{1-6}$alkyl, hydroxyC$_{1-6}$alkyl($C_{1-6}$alkyl)aminocarbonyl, hydroxyC$_{1-6}$alkylaminocarbonyl, hydroxypyrrolidinylcarbonyl, morpholinylcarbonyl, oxadiazolyl, oxazolyl, oxazolylaminocarbonyl, oxazolyl($C_{1-6}$alkyl)aminocarbonyl, oxazolylcarbonyl($C_{1-6}$alkyl)amino, oxomorpholinyl, oxooxazolidinyl, oxopyrrolidinyl, phenyl, pyrazolylC$_{1-6}$alkyl, pyridinyl, pyrimidinyl, pyrimidinylamino, pyrimidinylC$_{1-6}$alkyl amino, pyrimidinyloxy, pyrimidinyloxyC$_{1-6}$alkyl, pyrrolidinylcarbonyl and thiazolyl;
oxopyrrolo[3,2-c]pyridinyl;
oxopyrrolo[3,4-b]pyridinyl;
oxotetrahydrofuro[3,4-c]pyrrolyl;
oxotetrahydroimidazo[5,1-c][1,4]oxazinyl;
piperidinyl, said piperidinyl being unsubstituted or substituted with one, two or three substituents independently selected from halogen, hydroxy and $C_{1-6}$alkylcarbonyl;
pyrazolyl, said pyrazolyl being unsubstituted or substituted with one, two or three substituents independently selected from halogen, cyano, $C_{1-6}$alkyl, hydroxyC$_{1-6}$alkyl and $C_{1-6}$alkoxyC$_{1-6}$alkyl;
pyridinyl, said pyridinyl being unsubstituted or substituted with one, two or three substituents independently selected from halogen, cyano, $C_{1-6}$alkyl and haloC$_{1-6}$alkyl;
pyrimidinyl, said pyrimidinyl being unsubstituted or substituted with one, two or three substituents independently selected from halogen and $C_{1-6}$alkyl;
pyrrolidinyl, said pyrrolidinyl being unsubstituted or substituted with one, two or three substituents independently selected from halogen, cyano, hydroxy, $C_{1-6}$alkyl, haloC$_{1-6}$alkyl, $C_{1-6}$alkoxy and $C_{1-6}$alkoxyC$_{1-6}$alkyl;
tetrahydrofuranyl;
thiazolyl, said thiazolyl being unsubstituted or substituted with one, two or three substituents independently selected from halogen and haloC$_{1-6}$alkyl;
phenyl, said phenyl being unsubstituted or substituted with one, two or three substituents independently selected from halogen, cyano, hydroxy, $C_{3-7}$cycloalkyl, $C_{1-6}$alkyl, $C_{1-6}$alkoxy, haloC$_{1-6}$alkyl and haloC$_{1-6}$alkoxy; or
$C_{3-7}$cycloalkyl;
$R^2$ and $R^3$ are independently selected from hydrogen and $C_{1-6}$alkyl;
$R^4$ is benzofuranyl;
benzothiophenyl;
benzoxazolyl;
indolyl;
$C_{1-6}$alkylbenzothiazolyl;
pyridinyl, said pyridinyl being unsubstituted or substituted with one, two or three substituents independently selected from halogen, cyano, $C_{1-6}$alkyl, $C_{3-7}$cycloalkyl, $C_{1-6}$alkoxy, haloC$_{1-6}$alkyl and ($C_{1-6}$alkyl)$_2$amino;
bicyclo[4.2.0]octa-1(6),2,4-trienyl;
indanyl;
phenyl, said phenyl being unsubstituted or substituted with one, two or three substituents independently selected from halogen, cyano, $C_{3-7}$cycloalkyl, $C_{1-6}$alkyl, $C_{2-6}$alkynyl, $C_{1-6}$alkoxy, haloC$_{1-6}$alkyl and haloC$_{1-6}$alkoxy;
phenylC$_{1-6}$alkyl, said phenylC$_{1-6}$alkyl being unsubstituted or substituted with one, two or three halogen; or $C_{3-7}$cycloalkyl;
Y and Q are independently selected from CH and N;
or pharmaceutically acceptable salt, enantiomer or diastereomer thereof.

A further embodiment of the present invention is (iii) a compound of formula (I), wherein
$R^1$ is pyrazolyl substituted by halogen, cyano, $C_{1-6}$alkyl, hydroxyC$_{1-6}$alkyl or $C_{1-6}$alkoxyC$_{1-6}$alkyl;
pyridinyl, said pyridinyl being unsubstituted or substituted with one or two substituents independently selected from halogen, cyano, $C_{1-6}$alkyl and haloC$_{1-6}$alkyl;
pyrimidinyl substituted with one or two substituents independently selected from halogen and $C_{1-6}$alkyl;
thiazolyl, said thiazolyl being unsubstituted or substituted by halogen or haloC$_{1-6}$alkyl;
phenyl, said phenyl being unsubstituted or substituted with one or two substituents independently selected from halogen, cyano, hydroxy, $C_{3-7}$cycloalkyl, $C_{1-6}$alkyl, $C_{1-6}$alkoxy, haloC$_{1-6}$alkyl and haloC$_{1-6}$alkoxy;

R² and R³ are independently selected from hydrogen and C$_{1-6}$alkyl with the proviso that R² and R³ are not C$_{1-6}$alkyl simultaneously;

R⁴ is benzothiophenyl;
  benzoxazolyl;
  indolyl;
  benzothiazolyl substituted by C$_{1-6}$alkyl;
  pyridinyl, said pyridinyl being unsubstituted or substituted with one or two substituents independently selected from halogen, cyano, C$_{1-6}$alkyl, C$_{3-7}$cycloalkyl, C$_{1-6}$alkoxy, haloC$_{1-6}$alkyl and (C$_{1-6}$alkyl)$_2$amino;
  bicyclo[4.2.0]octa-1(6),2,4-trienyl;
  phenyl, said phenyl being unsubstituted or substituted with one, two or three substituents independently selected from halogen, cyano, C$_{3-7}$cycloalkyl, C$_{1-6}$alkyl, C$_{2-6}$alkynyl, C$_{1-6}$alkoxy, haloC$_{1-6}$alkyl and haloC$_{1-6}$alkoxy;
  phenylC$_{1-6}$alkyl, said phenylC$_{1-6}$alkyl being unsubstituted or substituted with one or two halogen;
  or C$_{3-7}$cycloalkyl;

Y and Q are independently selected from CH and N;
or pharmaceutically acceptable salt, enantiomer or diastereomer thereof.

A further embodiment of the present invention is (iv) a compound of formula (I), wherein
  R¹ is fluorophenyl, phenyl, chlorophenyl, trifluoromethylphenyl, cyanophenyl, methoxyphenyl, methylphenyl, difluorophenyl, fluorochlorophenyl, difluoromethylphenyl, methylfluorophenyl, cyclopropylphenyl, hydroxyphenyl, trifluoromethoxyphenyl, bromophenyl, methylpyrazolyl, cyanopyrazolyl, fluoropyrazolyl, hydroxymethylpyrazolyl, methoxymethylpyrazolyl, trifluoromethylpyridinyl, cyanopyridinyl, methylfluoropyridinyl, pyridinyl, chloropyridinyl, fluoropyridinyl, fluorochloropyridinyl, fluoropyrimidinyl, methylfluoropyrimidinyl, thiazolyl, trifluoromethylthiazolyl or chlorothiazolyl;
  R² and R³ are independently selected from hydrogen and methyl with the proviso that R² and R³ are not methyl simultaneously;
  R⁴ is phenyl, trifluoromethylphenyl, fluorochlorophenyl, fluorophenyl, chlorophenyl, cyanophenyl, pyridinyl, methylfluoropyridinyl, fluorotrifluoromethylphenyl, trifluorophenyl, fluorochlorobenzyl, dichlorobenzyl, methylchloropyridinyl, methylbenzothiazolyl, benzothiophenyl, trifluoromethylpyridinyl, difluorophenyl, fluorocyanophenyl, indolyl, methylfluorophenyl, chloropyridinyl, cyanopyridinyl, chloromethoxypyridinyl, methyltrifluoromethylphenyl, chlorotrifluoromethylphenyl, chlorocyanophenyl, ethylphenyl, ethynylphenyl, isopropylphenyl, methoxyphenyl, ethynylfluorophenyl, dimethylpyridinyl, fluorobromophenyl, difluoromethoxyphenyl, fluorotrifluoromethoxyphenyl, difluoromethylphenyl, methylphenyl, difluorocyanophenyl, fluorochloropyridinyl, cyclopropylphenyl, methyldifluorophenyl, difluorochlorophenyl, cyclopyldifluorophenyl, difluoroethylphenyl, cyclopropylfluorophenyl, methoxydifluorophenyl, benzyl, fluoropyridinyl, benzoxazolyl, methylpyridinyl, difluoropyridinyl, cyclopentyl, cyclohexyl, bicyclo[4.2.0]octa-1(6),2,4-trienyl, bromopyridinyl, cyclopropylpyridinyl, dimethylaminopyridinyl or difluoromethylpyridinyl;

Y and Q are independently selected from CH and N;
or pharmaceutically acceptable salt, enantiomer or diastereomer thereof.

A further embodiment of the present invention is (v) a compound of formula (I), wherein R¹ is phenyl, said phenyl being unsubstituted or substituted with one, two or three substituents independently selected from halogen, cyano, hydroxy, C$_{3-7}$cycloalkyl, C$_{1-6}$alkyl, C$_{1-6}$alkoxy, haloC$_{1-6}$alkyl and haloC$_{1-6}$alkoxy; or pharmaceutically acceptable salt, enantiomer or diastereomer thereof.

A further embodiment of the present invention is (vi) a compound of formula (I), wherein R¹ is phenyl, bromophenyl, chlorophenyl, cyanophenyl, cyclopropylphenyl, difluorophenyl, difluoromethylphenyl, fluorophenyl, fluorochlorophenyl, fluoromethylphenyl, hydroxyphenyl, methoxyphenyl, methylphenyl, trifluoromethoxyphenyl or trifluoromethylphenyl; or pharmaceutically acceptable salt, enantiomer or diastereomer thereof.

A further embodiment of the present invention is (vii) a compound of formula (I), wherein R⁴ is phenyl, said phenyl being unsubstituted or substituted with one, two or three substituents independently selected from halogen, cyano, C$_{3-7}$cycloalkyl, C$_{1-6}$alkyl, C$_{2-6}$alkynyl, C$_{1-6}$alkoxy, haloC$_{1-6}$alkyl and haloC$_{1-6}$alkoxy; or pharmaceutically acceptable salt, enantiomer or diastereomer thereof.

A further embodiment of the present invention is (viii) a compound of formula (I), wherein R⁴ is phenyl, chlorophenyl, chlorocyanophenyl, chlorotrifluoromethylphenyl, cyanophenyl, cyclopropylphenyl, difluorophenyl, difluoroethylphenyl, difluoromethoxyphenyl, difluoromethylphenyl, ethylphenyl, ethynylphenyl, fluorophenyl, fluorobromophenyl, fluorochlorophenyl, fluorocyanophenyl, fluorocyclopropylphenyl, fluoroethynylphenyl, difluorochlorophenyl, difluorocyanophenyl, difluorocyclopropylphenyl, methoxydifluorophenyl, methyldifluorophenyl, methylfluorophenyl, fluorotrifluoromethoxyphenyl, fluorotrifluoromethylphenyl, isopropylphenyl, methoxyphenyl, methylphenyl, methyltrifluoromethylphenyl, trifluorophenyl or trifluoromethylphenyl; or pharmaceutically acceptable salt, enantiomer or diastereomer thereof.

A further embodiment of the present invention is (ix) a compound of formula (I), wherein
  R¹ is pyrazolyl substituted by halogen or hydroxy C$_{1-6}$alkyl;
    pyridinyl substituted by halogen;
    pyrimidinyl substituted by halogen;
    phenyl substituted once or twice by halogen;
  R² is H;
  R³ is H or C$_{1-6}$alkyl;
  R⁴ is pyridinyl substituted by haloC$_{1-6}$alkyl; or
    phenyl substituted with one, two or three substituents independently selected from halogen and cyano;
  Y and Q are independently selected from CH and N, with proviso that Y and Q are not CH simultaneously;
or pharmaceutically acceptable salt, enantiomer or diastereomer thereof.

A further embodiment of the present invention is (x) a compound of formula (I), wherein
  R¹ is fluoropyrazolyl, hydroxymethylpyroazolyl, fluoropyridinyl, fluoropyrimidinyl, fluorophenyl or difluorophenyl;
  R² is H;
  R³ is H or methyl;
  R⁴ is difluoromethylpyridinyl, fluorochlorophenyl, fluorocyanophenyl or trifluorophenyl;
  Y and Q are independently selected from CH and N, with proviso that Y and Q are not CH simultaneously;
or pharmaceutically acceptable salt, enantiomer or diastereomer thereof.

In another embodiment of the present invention, particular compounds of the present invention are (xi) selected from:

N-(3-cyano-4-fluoro-phenyl)-3-(2,4-difluorophenyl)-6-methyl-6,7-dihydro-4H-pyrazolo[1,5-a]pyrazine-5-carboxamide;

N-(3-chloro-4-fluoro-phenyl)-3-(2,4-difluorophenyl)-6-methyl-6,7-dihydro-4H-pyrazolo[1,5-a]pyrazine-5-carboxamide;

N-(3-chloro-4-fluoro-phenyl)-3-(5-fluoro-2-pyridyl)-6-methyl-6,7-dihydro-4H-pyrazolo[1,5-a]pyrazine-5-carboxamide;

3-(5-fluoro-2-pyridyl)-6-methyl-N-(3,4,5-trifluorophenyl)-6,7-dihydro-4H-pyrazolo[1,5-a]pyrazine-5-carboxamide;

(6S)-N-(3-chloro-4-fluoro-phenyl)-3-(4-fluorophenyl)-6-methyl-6,7-dihydro-4H-pyrazolo[1,5-a]pyrazine-5-carboxamide;

N-(3-chloro-4-fluoro-phenyl)-1-(2,4-difluorophenyl)-6,8-dihydro-5H-imidazo[1,5-a]pyrazine-7-carboxamide;

1-(2,4-difluorophenyl)-N-(3,4,5-trifluorophenyl)-6,8-dihydro-5H-imidazo[1,5-a]pyrazine-7-carboxamide;

N-(3-chloro-4-fluoro-phenyl)-3-(2,4-difluorophenyl)-6,7-dihydro-4H-triazolo[1,5-a]pyrazine-5-carboxamide;

N-(3-chloro-4-fluoro-phenyl)-3-(4-fluoropyrazol-1-yl)-6-methyl-6,7-dihydro-4H-pyrazolo[1,5-a]pyrazine-5-carboxamide;

N-[2-(difluoromethyl)-4-pyridyl]-3-(2,4-difluorophenyl)-6-methyl-6,7-dihydro-4H-pyrazolo[1,5-a]pyrazine-5-carboxamide;

(6S)-3-(5-fluoropyrimidin-2-yl)-6-methyl-N-(3,4,5-trifluorophenyl)-6,7-dihydro-4H-pyrazolo[1,5-a]pyrazine-5-carboxamide; and (6S)-3-[4-(hydroxymethyl)pyrazol-1-yl]-6-methyl-N-(3,4,5-trifluorophenyl)-6,7-dihydro-4H-pyrazolo[1,5-a]pyrazine-5-carboxamide;

or pharmaceutically acceptable salt, enantiomer or diastereomer thereof.

Another embodiment of present invention is (xii) a compound of formula (I), wherein
$R^1$ is azabicyclo[3.1.0]hexanyl;
morpholinyl, said morpholinyl being unsubstituted or substituted twice by $C_{1-6}$alkyl;
oxaazabicyclo[3.2.1]octanyl;
piperidinyl, said piperidinyl being unsubstituted or substituted with one or two substituents independently selected from halogen, hydroxy and $C_{1-6}$alkylcarbonyl;
pyrrolidinyl, said pyrrolidinyl being unsubstituted or substituted with one or two substituents independently selected from halogen, cyano, hydroxy, $C_{1-6}$alkyl, halo$C_{1-6}$alkyl, $C_{1-6}$alkoxy and $C_{1-6}$alkoxy$C_{1-6}$alkyl;
tetrahydrofuranyl; or
$C_{3-7}$cycloalkyl;
$R^2$ is H;
$R^3$ is H or $C_{1-6}$alkyl;
$R^4$ is benzofuranyl;
pyridinyl, said pyridinyl being substituted with one or two substituents independently selected from halogen and halo$C_{1-6}$alkyl;
indanyl;
phenyl, said phenyl being unsubstituted or substituted with one, two or three substituents independently selected from halogen, cyano and $C_{1-6}$alkyl; or phenyl$C_{1-6}$alkyl;
Y is CH when Q is N; or Y is N when Q is CH;

or pharmaceutically acceptable salt, enantiomer or diastereomer thereof.

A further embodiment of present invention is (xiii) a compound of formula (I), wherein
$R^1$ is azabicyclo[3.1.0]hexanyl, cyclohexyl, cyclopentyl, morpholinyl, dimethylmorpholinyl, oxaazabicyclo[3.2.1]octanyl, piperidinyl, difluoropiperidinyl, hydroxypiperidinyl, acetylpiperidinyl, pyrrolidinyl, methylpyrrolidinyl, methoxymethylpyrrolidinyl, methoxypyrrolidinyl, trifluoromethylpyrrolidinyl, cyanopyrrolidinyl, methylhydroxypyrrolidinyl, difluoropyrrolidinyl or tetrahydrofuranyl;
$R^2$ is H;
$R^3$ is H or methyl;
$R^4$ is benzofuranyl, indanyl, benzyl, phenyl, fluorochlorophenyl, fluorocyanophenyl, trifluorophenyl, methyldifluorophenyl, chloropyridinyl, fluorochloropyridinyl or trifluoromethylpyridinyl;
Y is CH when Q is N; or Y is N when Q is CH;
or pharmaceutically acceptable salt, enantiomer or diastereomer thereof.

Another embodiment of present invention is (xiv) a compound of formula (I), wherein
$R^1$ is dioxopiperazinyl;
dioxopyrimidinyl
dioxotetrahydropyrrolo[1,2-a]pyrazinyl;
oxoazabicyclo[3.1.0]hexanyl;
oxoazaspiro[2.4]heptanyl, said oxoazaspiro[2.4]heptanyl being unsubstituted or substituted with hydroxy;
oxoazaspiro[4.4]nonanyl;
oxoazaspiro[3.4]octanyl, said oxoazaspiro[3.4]octanyl being unsubstituted or substituted with hydroxy;
oxodiazaspiro[3.4]octanyl, said oxodiazaspiro[3.4]octanyl being substituted by $C_{1-6}$alkylcarbonyl, $C_{1-6}$alkoxycarbonyl, oxazolylcarbonyl or pyrimidinyl;
oxodihydropyrazolo[1,5-a]pyrazinyl;
oxohexahydropyrimidinyl;
oxoimidazolidinyl, said oxoimidazolidinyl being unsubstituted or substituted with one or two substituents independently selected from $C_{1-6}$alkyl, $C_{1-6}$alkylcarbonyl, $C_{1-6}$alkylsulfonyl, phenyl, phenylcarbonyl and pyrimidinyl;
oxoindolinyl;
oxomorpholinyl, said oxomorpholinyl being unsubstituted or substituted with one or two substituents independently selected from $C_{1-6}$alkyl and oxazolyl;
oxooxaazaspiro[2.4]heptanyl;
oxooxaazaspiro[3.4]octanyl;
oxooxaazaspiro[4.4]nonanyl;
oxooxaazaspiro[4.5]decanyl;
oxooxazinanyl, said oxooxazinanyl being unsubstituted or substituted with one or two substituents independently selected from $C_{1-6}$alkyl, $C_{1-6}$alkoxy and morpholinylcarbonyl;
oxooxazolidinyl, said oxooxazolidinyl being unsubstituted or substituted with one or two substituents independently selected from $C_{1-6}$alkyl, phenyl, pyridinyl, halopyridinyl, oxazolyl, $C_{1-6}$alkylimidazolyl and $C_{1-6}$alkyloxadiazolyl;
oxopiperidyl substituted by $C_{1-6}$alkyl or hydroxy;
oxopyrrolidinyl, said oxopyrrolidinyl being unsubstituted or substituted with one, two or three substituents independently selected from $(C_{1-6}alkyl)_2$aminocarbonyl, $(C_{1-6}alkyl)_2$morpholinylcarbonyl, $C_{1-6}$alkoxy, $C_{1-6}$alkoxy$C_{1-6}$alkyl, $C_{1-6}$alkyl, $C_{1-6}$alkyl$(C_{1-6}$alkylsulfonyl)amino, $C_{1-6}$alkylaminocarbonyl, $C_{1-6}$alkylcarbonylamino, $C_{1-6}$alkylmorpholinylcarbonyl, $C_{1-6}$alkyloxadiazolyl, $C_{1-6}$alkyloxazolyl, $C_{1-6}$alkylpyrazolyl, $C_{1-6}$alkylsulfonyl, $C_{1-6}$alkylsulfonylamino, $C_{1-6}$alkylsulfonyl$C_{1-6}$alkyl, cyano, dioxopyrrolidinyl, halo$C_{1-6}$alkyl, halo-$C_{1-6}$alkyloxadiazolyl, halopiperidinylcarbonyl, halopyrimidinylamino, halopyrimidinyloxy, halopyrrolidinylcarbonyl, hydroxy, hydroxyazetidinylcarbonyl, hydroxy$C_{1-6}$alkyl, hydroxy$C_{1-6}$alkyl, hydroxy$C_{1-6}$alkyl ($C_{1-6}$alkyl)aminocarbonyl, hydroxy$C_{1-6}$alkylaminocarbonyl, hydroxypyrrolidinylcarbonyl, morpholinylcarbonyl, oxadiazolyl, oxazolyl, oxazolylaminocarbonyl, oxazolyl ($C_{1-6}$alkyl)aminocarbonyl, oxazolylcarbonyl ($C_{1-6}$alkyl)amino, oxomorpholinyl, oxooxazolidinyl, oxopyrrolidinyl, phenyl, pyrazolyl$C_{1-6}$alkyl, pyridinyl, pyrimidinyl, pyrimidinylamino, pyrimidinyl ($C_{1-6}$alkyl)amino, pyrimidinyloxy, pyrimidinyloxy$C_{1-6}$alkyl, pyrrolidinylcarbonyl and thiazolyl;

oxopyrrolo[3,2-c]pyridinyl;

oxopyrrolo[3,4-b]pyridinyl;

oxotetrahydrofuro[3,4-c]pyrrolyl;

oxotetrahydroimidazo[5,1-c][1,4]oxazinyl;

$R^2$ and $R^3$ are independently selected from hydrogen and $C_{1-6}$alkyl with the proviso that $R^2$ is not $C_{1-6}$alkyl when $R^3$ is H;

$R^4$ is pyridinyl substituted with one or two substituents independently selected from halogen and halo$C_{1-6}$alkyl;

phenyl substituted with one, two or three substituents independently selected from halogen and halo$C_{1-6}$alkyl;

Y is CH;

Q is N;

or pharmaceutically acceptable salt, enantiomer or diastereomer thereof.

A further embodiment of present invention is (xv) a compound of formula (I), wherein $R^1$ is dioxopiperazinyl, dioxopyrimidinyl, dioxotetrahydropyrrolo[1,2-a]pyrazinyl, oxoazabicyclo[3.1.0]hexanyl, oxoazaspiro[2.4]heptanyl, hydroxy oxoazaspiro[2.4]heptanyl, oxoazaspiro[4.4]nonanyl, oxoazaspiro[3.4]octanyl, hydroxyoxoazaspiro[3.4]octanyl, acetyloxodiazaspiro[3.4]octanyl, methoxycarbonyloxodiazaspiro[3.4]octanyl, ethoxycarbonyloxodiazaspiro[3.4]octanyl, oxazolylcarbonyloxodiazaspiro[3.4]octanyl, pyrimidinyloxodiazaspiro[3.4]octanyl, oxodihydropyrazolo[1,5-a]pyrazinyl, oxohexahydropyrimidinyl, oxoimidazolidinyl, acetyloxoimidazolidinyl, benzoyloxoimidazolidinyl, dimethyloxoimidazolidinyl, methyloxoimidazolidinyl, methyl sulfonyloxoimidazolidinyl, phenyloxoimidazolidinyl, pyrimidinyloxoimidazolidinyl, oxoindolinyl, oxoisoindolinyl, oxomorpholinyl, methyloxomorpholinyl, dimethyloxomorpholinyl, oxazolyloxomorpholinyl, oxooxaazaspiro[4.5]decanyl, oxooxaazaspiro[4.4]nonanyl, oxooxaazaspiro[2.4]heptanyl, oxooxaazaspiro[3.4]octanyl, oxooxazinanyl, methyl oxooxazinanyl, dimethyloxooxazinanyl, methoxyoxooxazinanyl, morpholinylcarbonyl(methyl)oxooxazinanyl, oxooxazolidinyl, dimethyloxooxazolidinyl, chloropyridinyloxooxazolidinyl, fluoropyridinyloxooxazolidinyl, methyloxooxazolidinyl, methylimidazolyloxooxazolidinyl, methyloxadiazolyloxooxazolidinyl, oxazolyloxooxazolidinyl, phenyloxooxazolidinyl, pyridinyloxooxazolidinyl, hydroxyoxopiperidyl, methyloxopiperidyl, oxopyrrolidinyl, acetyl aminooxopyrrolidinyl, cyanooxopyrrolidinyl, difluoropiperidinylcarbonyl(methyl)oxopyrrolidinyl, difluoropyrrolidinylcarbonyloxopyrrolidinyl, difluoropyrrolidinylcarbonyl(methyl)oxopyrrolidinyl, dihydroxyoxopyrrolidinyl, dimethyloxopyrrolidinyl, dimethylaminocarbonyloxopyrrolidinyl, dimethylmorpholinylcarbonyloxopyrrolidinyl, dioxopyrrolidinyloxopyrrolidinyl, ethyloxopyrrolidinyl, fluoropyrimidinylaminooxopyrrolidinyl, fluoropyrimidinyloxyoxopyrrolidinyl, hydroxyoxopyrrolidinyl, hydroxyazetidinylcarbonyloxopyrrolidinyl, hydroxyethyl(methyl)aminocarbonyloxopyrrolidinyl, hydroxy(dimethyl)oxopyrrolidinyl, hydroxydimethylethylaminooxopyrrolidinyl, hydroxymethyloxopyrrolidinyl, hydroxy(methyl)cyanooxopyrrolidinyl, hydroxymethyl(cyano)oxopyrrolidinyl, hydroxymethyl ethyloxopyrrolidinyl, hydroxypyrrolidinylcarbonyloxopyrrolidinyl, methoxyoxopyrrolidinyl, methoxymethyloxopyrrolidinyl, methyloxopyrrolidinyl, methyl(methylsulfonyl)aminooxopyrrolidinyl, methylaminocarbonyloxopyrrolidinyl, methylcyanooxopyrrolidinyl, methyl(hydroxymethyl)oxopyrrolidinyl, methylmorpholinylcarbonyloxopyrrolidinyl, methyloxadiazolyloxopyrrolidinyl, methyloxadiazolyl(methyl)oxopyrrolidinyl, methyl oxazolyloxopyrrolidinyl, methylpyrazolyloxopyrrolidinyl, methyl sulfonyloxopyrrolidinyl, methyl sulfonylaminooxopyrrolidinyl, methyl sulfonylmethyloxopyrrolidinyl, morpholinylcarbonyloxopyrrolidinyl, morpholinylcarbonyl(methyl)oxopyrrolidinyl, oxadiazolyloxopyrrolidinyl, oxadiazolyl(methyl)oxopyrrolidinyl, oxazolyloxopyrrolidinyl, oxazolylaminocarbonyloxopyrrolidinyl, oxazolylcarbonyl(methyl)aminooxopyrrolidinyl, oxazolyl(methyl)aminocarbonyloxopyrrolidinyl, oxomorpholinyloxopyrrolidinyl, oxooxazolidinyloxopyrrolidinyl, oxopyrrolidinyloxopyrrolidinyl, phenyloxopyrrolidinyl, phenyl(hydroxy)oxopyrrolidinyl, pyrazolylmethyloxopyrrolidinyl, pyridinyloxopyrrolidinyl, pyrimidinyloxopyrrolidinyl, pyrimidinylaminooxopyrrolidinyl, pyrimidinyl(methyl)aminooxopyrrolidinyl, pyrimidinyl oxyoxopyrrolidinyl, pyrimidinyloxy(hydroxy)oxopyrrolidinyl, pyrimidinyloxy(hydroxy)(methyl)oxopyrrolidinyl, pyrimidinyloxymethyloxopyrrolidinyl, pyrrolidinylcarbonyloxopyrrolidinyl, thiazolyloxopyrrolidinyl, trifluoromethyloxopyrrolidinyl, trifluoromethyloxadiazolyloxopyrrolidinyl, oxotetrahydrofuro[3,4-c]pyrrolyl, oxotetrahydroimidazo[5,1-c][1,4]oxazinyl, oxopyrrolo[3,4-b]pyridinyl or oxopyrrolo[3,2-c]pyridinyl;

$R^2$ and $R^3$ are independently selected from hydrogen and methyl with the proviso that $R^2$ is not methyl when $R^3$ is H;

$R^4$ is chloropyridinyl, difluoromethylpyridinyl, fluorochloropyridinyl, fluorodifluoromethylpyridinyl, trifluoromethylpyridinyl, difluorochlorophenyl, difluorodifluoromethylphenyl, fluorochlorophenyl, fluorotrifluoromethylphenyl, trifluorophenyl;

Y is CH;

Q is N;

or pharmaceutically acceptable salt, enantiomer or diastereomer thereof.

A further embodiment of present invention is (xvi) a compound of formula (I), wherein $R^1$ is oxoazabicyclo[3.1.0]hexanyl;

oxodiazaspiro[3.4]octanyl substituted by $C_{1-6}$alkoxycarbonyl or pyrimidinyl;

oxoimidazolidinyl;

oxoindolinyl;
oxomorpholinyl, said oxomorpholinyl being unsubstituted or substituted once or twice by $C_{1-6}$alkyl;
oxooxaazaspiro[2.4]heptanyl;
oxooxaazaspiro[4.5]decanyl;
oxooxazinanyl, said oxooxazinanyl being unsubstituted or substituted once or twice by $C_{1-6}$alkyl;
oxooxazolidinyl, said oxooxazolidinyl being unsubstituted or substituted twice by $C_{1-6}$alkyl;
oxopyrrolidinyl said oxopyrrolidinyl being unsubstituted or substituted with one or two substituents independently selected from $(C_{1-6}alkyl)_2$aminocarbonyl, $C_{1-6}$alkyl, $C_{1-6}$alkoxy, $C_{1-6}$alkyloxadiazolyl, cyano, halopyrimidinyloxy, hydroxy, hydroxy$C_{1-6}$alkyl, morpholinylcarbonyl, oxadiazolyl, pyrimidinylamino, pyrimidinyloxy and pyrrolidinylcarbonyl;
or pharmaceutically acceptable salt, enantiomer or diastereomer thereof.

A further embodiment of present invention is (xvii) a compound of formula (I), wherein $R^1$ is oxoazabicyclo[3.1.0]hexanyl, methoxycarbonyloxodiazaspiro[3.4]octanyl, ethoxycarbonyloxodiazaspiro[3.4]octanyl, pyrimidinyloxodiazaspiro[3.4]octanyl, oxoimidazolidinyl, oxoindolinyl, oxomorpholinyl, dimethyl oxomorpholinyl, oxooxaazaspiro[4.5]decanyl, oxooxaazaspiro[2.4]heptanyl, oxooxazinanyl, cyamethyloxooxazinanyl, dimethyloxooxazinanyl, oxooxazolidinyl, dimethyloxooxazolidinyl, oxopyrrolidinyl, cyanooxopyrrolidinyl, hydroxyoxopyrrolidinyl, methoxyoxopyrrolidinyl, trifluoromethyloxopyrrolidinyl, pyrimidinylaminooxopyrrolidinyl, oxadiazolyloxopyrrolidinyl, methyloxadiazolyloxopyrrolidinyl, hydroxymethylcyanooxopyrrolidinyl, methylcyanooxopyrrolidinyl, methyl(hydroxymethyl)oxopyrrolidinyl, morpholinylcarbonyloxopyrrolidinyl, pyrimidinyloxyoxopyrrolidinyl, pyrimidinyloxy(hydroxy)oxopyrrolidinyl, fluoropyrimidinyloxyoxopyrrolidinyl, dimethyl aminocarbonyloxopyrrolidinyl or pyrrolidinylcarbonyloxopyrrolidinyl; or pharmaceutically acceptable salt, enantiomer or diastereomer thereof.

A further embodiment of present invention is (xviii) a compound of formula (I), wherein $R^4$ is pyridinyl substituted by halo$C_{1-6}$alkyl; or phenyl substituted with two or three substituents independently selected from halogen and halo$C_{1-6}$alkyl; or pharmaceutically acceptable salt, enantiomer or diastereomer thereof.

A further embodiment of present invention is (xix) a compound of formula (I), wherein $R^4$ is difluoromethylpyridinyl, fluorochlorophenyl, difluorodifluoromethylphenyl or trifluorophenyl; or pharmaceutically acceptable salt, enantiomer or diastereomer thereof.

A further embodiment of present invention is (xx) a compound of formula (I), wherein
$R^1$ is oxoazabicyclo[3.1.0]hexanyl;
oxodiazaspiro[3.4]octanyl substituted with $C_{1-6}$alkoxycarbonyl or pyrimidinyl;
oxoimidazolidinyl;
oxoindolinyl;
oxomorpholinyl, said oxomorpholinyl being unsubstituted or substituted once or twice by $C_{1-6}$alkyl;
oxooxaazaspiro[2.4]heptanyl;
oxooxaazaspiro[4.5]decanyl;
oxooxazinanyl, said oxooxazinanyl being unsubstituted or substituted once ro twice by $C_{1-6}$alkyl;
oxooxazolidinyl, said oxooxazolidinyl being unsubstituted or substituted once or twice by $C_{1-6}$alkyl;
oxopyrrolidinyl said oxopyrrolidinyl being unsubstituted or substituted with one or two substituents independently selected from $(C_{1-6}alkyl)_2$aminocarbonyl, $C_{1-6}$alkoxy, $C_{1-6}$alkyloxadiazolyl, cyano, halopyrimidinyloxy, halo$C_{1-6}$alkyl, hydroxy, hydroxy$C_{1-6}$alkyl, morpholinylcarbonyl, oxadiazolyl, pyrimidinylamino, pyrimidinyloxy and pyrrolidinylcarbonyl;
$R^2$ is H;
$R^3$ is H or $C_{1-6}$alkyl;
$R^4$ is pyridinyl substituted by halo$C_{1-6}$alkyl; or
phenyl substituted with two or three substituents independently selected from halogen and halo$C_{1-6}$alkyl;
Y is CH;
Q is N;
or pharmaceutically acceptable salt, enantiomer or diastereomer thereof.

A further embodiment of present invention is (xxi) a compound of formula (I), wherein
$R^1$ is oxoazabicyclo[3.1.0]hexanyl, methoxycarbonyloxodiazaspiro[3.4]octanyl, ethoxycarbonyloxodiazaspiro[3.4]octanyl, pyrimidinyloxodiazaspiro[3.4]octanyl, oxoimidazolidinyl, oxoindolinyl, oxomorpholinyl, dimethyloxomorpholinyl, oxooxaazaspiro[4.5]decanyl, oxooxaazaspiro[2.4]heptanyl, oxooxazinanyl, methyloxooxazinanyl, dimethyloxooxazinanyl, oxooxazolidinyl, dimethyloxooxazolidinyl, oxopyrrolidinyl, cyanooxopyrrolidinyl, hydroxyoxopyrrolidinyl, methoxyoxopyrrolidinyl, trifluoromethyloxopyrrolidinyl, pyrimidinylaminooxopyrrolidinyl, oxadiazolyloxopyrrolidinyl, methyloxadiazolyloxopyrrolidinyl, hydroxymethylcyanooxopyrrolidinyl, methylcyanooxopyrrolidinyl, methyl(hydroxymethyl)oxopyrrolidinyl, morpholinylcarbonyloxopyrrolidinyl, pyrimidinyloxyoxopyrrolidinyl, pyrimidinyloxy(hydroxy)oxopyrrolidinyl, fluoropyrimidinyloxyoxopyrrolidinyl, dimethylaminocarbonyloxopyrrolidinyl or pyrrolidinylcarbonyloxopyrrolidinyl;
$R^2$ is H;
$R^3$ is H or methyl;
$R^4$ is difluoromethylpyridinyl, fluorochlorophenyl, difluorodifluoromethylphenyl or trifluorophenyl;
Y is CH;
Q is N;
or pharmaceutically acceptable salt, enantiomer or diastereomer thereof.

In another embodiment of the present invention, particular compounds of the present invention are (xxii) selected from:
N-(3-chloro-4-fluoro-phenyl)-3-(2-oxopyrrolidin-1-yl)-6,7-dihydro-4H-pyrazolo[1,5-a]pyrazine-5-carboxamide;
6-methyl-3-(2-oxopyrrolidin-1-yl)-N-(3,4,5-trifluorophenyl)-6,7-dihydro-4H-pyrazolo[1,5-a]pyrazine-5-carboxamide;
N-(3-chloro-4-fluoro-phenyl)-6-methyl-3-(2-oxopyrrolidin-1-yl)-6,7-dihydro-4H-pyrazolo[1,5-a]pyrazine-5-carboxamide;
(6S)-N-[2-(difluoromethyl)-4-pyridyl]-6-methyl-3-(2-oxopyrrolidin-1-yl)-6,7-dihydro-4H-pyrazolo[1,5-a]pyrazine-5-carboxamide;
(6S)-N-(3-chloro-4-fluoro-phenyl)-3-(4-cyano-2-oxo-pyrrolidin-1-yl)-6-methyl-6,7-dihydro-4H-pyrazolo[1,5-a]pyrazine-5-carboxamide;
(6S)-N-(3-chloro-4-fluoro-phenyl)-3-(4-hydroxy-2-oxopyrrolidin-1-yl)-6-methyl-6,7-dihydro-4H-pyrazolo[1,5-a]pyrazine-5-carboxamide;
(6S)-6-methyl-3-(3-oxomorpholin-4-yl)-N-(3,4,5-trifluorophenyl)-6,7-dihydro-4H-pyrazolo[1,5-a]pyrazine-5-carboxamide;

N-(3-chloro-4-fluoro-phenyl)-6-methyl-3-(2-oxooxazolidin-3-yl)-6,7-dihydro-4H-pyrazolo[1,5-a]pyrazine-5-carboxamide;

(6S)-N-(3-chloro-4-fluoro-phenyl)-3-(4-methoxy-2-oxopyrrolidin-1-yl)-6-methyl-6,7-dihydro-4H-pyrazolo[1,5-a]pyrazine-5-carboxamide;

(6S)-N-[3-(difluoromethyl)-4,5-difluoro-phenyl]-6-methyl-3-(2-oxopyrrolidin-1-yl)-6,7-dihydro-4H-pyrazolo[1,5-a]pyrazine-5-carboxamide;

(6S)-3-(4-cyano-2-oxo-pyrrolidin-1-yl)-6-methyl-N-(3,4,5-trifluorophenyl)-6,7-dihydro-4H-pyrazolo[1,5-a]pyrazine-5-carboxamide;

(6S)-3-[(4R)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4S)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-[2-(difluoromethyl)-4-pyridyl]-6-methyl-3-[2-oxo-4-(trifluoromethyl)pyrrolidin-1-yl]-6,7-dihydro-4H-pyrazolo[1,5-a]pyrazine-5-carboxamide;

(6S)-3-(5,5-dimethyl-2-oxo-oxazolidin-3-yl)-6-methyl-N-(3,4,5-trifluorophenyl)-6,7-dihydro-4H-pyrazolo[1,5-a]pyrazine-5-carboxamide;

(6S)-6-methyl-3-(2-oxo-3-azabicyclo[3.1.0]hexan-3-yl)-N-(3,4,5-trifluorophenyl)-6,7-dihydro-4H-pyrazolo[1,5-a]pyrazine-5-carboxamide;

(6S)-6-methyl-3-[2-oxo-4-(pyrimidin-2-ylamino)pyrrolidin-1-yl]-N-(3,4,5-trifluorophenyl)-6,7-dihydro-4H-pyrazolo[1,5-a]pyrazine-5-carboxamide;

(6S)-N-[3-(difluoromethyl)-4,5-difluoro-phenyl]-6-methyl-3-(3-oxomorpholin-4-yl)-6,7-dihydro-4H-pyrazolo[1,5-a]pyrazine-5-carboxamide;

(6S)-N-[2-(difluoromethyl)-4-pyridyl]-3-(5,5-dimethyl-2-oxo-oxazolidin-3-yl)-6-methyl-6,7-dihydro-4H-pyrazolo[1,5-a]pyrazine-5-carboxamide;

(6S)-N-[3-(difluoromethyl)-4,5-difluoro-phenyl]-3-(5,5-dimethyl-2-oxo-oxazolidin-3-yl)-6-methyl-6,7-dihydro-4H-pyrazolo[1,5-a]pyrazine-5-carboxamide;

(6S)-6-methyl-3-(5-methyl-2-oxo-1,3-oxazinan-3-yl)-N-(3,4,5-trifluorophenyl)-6,7-dihydro-4H-pyrazolo[1,5-a]pyrazine-5-carboxamide;

(6S)-6-methyl-3-[4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(5-methyl-1,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-(2-oxo-1,3-oxazinan-3-yl)-N-(3,4,5-trifluorophenyl)-6,7-dihydro-4H-pyrazolo[1,5-a]pyrazine-5-carboxamide;

(6S)-3-(5,5-dimethyl-2-oxo-1,3-oxazinan-3-yl)-6-methyl-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(3-oxo-8-oxa-2-azaspiro[4.5]decan-2-yl)-6,7-dihydro-4H-pyrazolo[1,5-a]pyrazine-5-carboxamide;

(6S)-6-methyl-3-(5-oxo-4-oxa-6-azaspiro[2.4]heptan-6-yl)-N-(3,4,5-trifluorophenyl)-6,7-dihydro-4H-pyrazolo[1,5-a]pyrazine-5-carboxamide;

methyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate;

ethyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate;

(6S)-6-methyl-3-(7-oxo-2-pyrimidin-2-yl-2,6-diazaspiro[3.4]octan-6-yl)-N-(3,4,5-trifluorophenyl)-6,7-dihydro-4H-pyrazolo[1,5-a]pyrazine-5-carboxamide;

(6S)-6-methyl-3-(2-oxoindolin-1-yl)-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(2-oxopyrrolidin-1-yl)-6,7-dihydro-4H-pyrazolo[1,5-a]pyrazine-5-carboxamide;

(6S)-6-methyl-3-(2-oxopyrrolidin-1-yl)-N-(3,4,5-trifluorophenyl)-6,7-dihydro-4H-pyrazolo[1,5-a]pyrazine-5-carboxamide;

(6S)-3-[4-cyano-4-(hydroxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-(4-cyano-4-methyl-2-oxo-pyrrolidin-1-yl)-N-[3-(difluoro-phenyl]-6-methyl-6,7-dihydro-4H-pyrazolo[1,5-a]pyrazine-5-carboxamide;

(6S)-3-[4-(hydroxymethyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(3-oxomorpholin-4-yl)-6,7-dihydro-4H-pyrazolo[1,5-a]pyrazine-5-carboxamide;

(6S)-N-(3-chloro-4-fluoro-phenyl)-3-(2,2-dimethyl-5-oxomorpholin-4-yl)-6-methyl-6,7-dihydro-4H-pyrazolo[1,5-a]pyrazine-5-carboxamide;

(6S)-N-[3-(difluoromethyl)-4,5-difluoro-phenyl]-6-methyl-3-(2-oxoimidazolidin-1-yl)-6,7-dihydro-4H-pyrazolo[1,5-a]pyrazine-5-carboxamide;

(6S)-3-[(4S)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4R)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[(4S)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;

(6S)-3-[(4S)-4-(5-fluoropyrimidin-2-yl)oxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-(dimethylcarbamoyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[2-oxo-4-(pyrrolidine-1-carbonyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[(4R)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;

(6S)-3-(3-cyano-2-methyl-5-oxo-pyrrolidin-1-yl)-6-methyl-N-(3,4,5-trifluorophenyl)-6,7-dihydro-4H-pyrazolo[1,5-a]pyrazine-5-carboxamide;

(6S)-3-(5-hydroxy-2-oxo-1,3-oxazinan-3-yl)-6-methyl-N-(3,4,5-trifluorophenyl)-6,7-dihydro-4H-pyrazolo[1,5-a]pyrazine-5-carboxamide; and (6S)-3-[(3S,4R)-3-hydroxy-2-oxo-4-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide;

or pharmaceutically acceptable salt, enantiomer or diastereomer thereof.

Another embodiment of present invention is (xxiii) a compound of formula (I), wherein
$R^1$ is oxopyrrolidinyl, said oxopyrrolidinyl being unsubstituted or substituted with one or two substituents independently selected from $(C_{1-6}alkyl)_2$aminocarbonyl, $(C_{1-6}alkyl)_2$morpholinylcarbonyl, $C_{1-6}$alkoxy, $C_{1-6}$alkoxy$C_{1-6}$alkyl, $C_{1-6}$alkyl, $C_{1-6}$alkyl($C_{1-6}$alkylsulfonyl)amino, $C_{1-6}$alkylaminocarbonyl, $C_{1-6}$alkylcarbonylamino, $C_{1-6}$alkylmorpholinylcarbonyl, $C_{1-6}$alkyloxadiazolyl, $C_{1-6}$alkyloxazolyl, $C_{1-6}$alkylpyrazolyl, $C_{1-6}$alkylsulfonyl, $C_{1-6}$alkylsulfonylamino, $C_{1-6}$alkylsulfonyl$C_{1-6}$alkyl, cyano, dioxopyrrolidinyl, halo$C_{1-6}$alkyl, halo$C_{1-6}$alkyloxadiazolyl, halopiperidinylcarbonyl, halopyrimidinylamino, halopyrimidinyloxy, halopyrrolidinylcarbonyl, hydroxy, hydroxyazetidinylcarbonyl, hydroxy$C_{1-6}$alkyl, hydroxy$C_{1-6}$alkyl($C_{1-6}$alkyl)aminocarbonyl, hydroxy$C_{1-6}$alkylaminocarbonyl, hydroxypyrrolidinylcarbonyl, morpholinylcarbonyl, oxadiazolyl, oxazolyl, oxazolylaminocarbonyl, oxazolyl($C_{1-6}$alkyl)aminocarbonyl, oxazolylcarbonyl($C_{1-6}$alkyl)amino, oxomorpholinyl, oxooxazolidinyl, oxopyrrolidinyl, phenyl, pyrazolyl$C_{1-6}$alkyl, pyridinyl, pyrimidinylamino, pyrimidinyl($C_{1-6}$alkyl)amino, pyrimidinyloxy, pyrimidinyloxy-$C_{1-6}$alkyl, pyrrolidinylcarbonyl and thiazolyl;
$R^2$ and $R^3$ are independently selected from hydrogen and $C_{1-6}$alkyl with the proviso that $R^2$ is not $C_{1-6}$alkyl when $R^3$ is H;
$R^4$ is pyridinyl substituted with one or two substituents independently selected from halogen and halo$C_{1-6}$alkyl;
phenyl substituted with one, two or three substituents independently selected from halogen and halo$C_{1-6}$alkyl;
Y is CH;
Q is N;
or pharmaceutically acceptable salt, enantiomer or diastereomer thereof.

A further embodiment of present invention is (xxiv) a compound of formula (I), wherein
$R^1$ is oxopyrrolidinyl, acetyl aminooxopyrrolidinyl, cyanooxopyrrolidinyl, difluoropiperidinylcarbonyl (methyl)oxopyrrolidinyl, difluoropyrrolidinylcarbonyloxopyrrolidinyl, difluoropyrrolidinylcarbonyl(methyl) oxopyrrolidinyl, dihydroxyoxopyrrolidinyl, dimethyloxopyrrolidinyl, dimethylaminocarbonyloxopyrrolidinyl, dimethylmorpholinylcarbonyloxopyrrolidinyl, dioxopyrrolidinyloxopyrrolidinyl, ethyloxypyrrolidinyl, fluoropyrimidinylaminooxopyrrolidinyl, fluoropyrimidinyloxyoxopyrrolidinyl, hydroxyoxopyrrolidinyl, hydroxyazetidinylcarbonyloxopyrrolidinyl, hydroxyethyl(methyl)aminocarbonyloxopyrrolidinyl, hydroxy(dimethyl)oxopyrrolidinyl, hydroxydimethylethylaminooxopyrrolidinyl, hydroxymethyloxopyrrolidinyl, hydroxy(methyl)cyanooxopyrrolidinyl, hydroxymethyl(cyano)oxopyrrolidinyl, hydroxymethylethyloxopyrrolidinyl, hydroxypyrrolidinylcarbonyloxopyrrolidinyl, methoxyoxopyrrolidinyl, methoxymethyloxopyrrolidinyl, methyloxopyrrolidinyl, methyl(methylsulfonyl)aminooxopyrrolidinyl, methylaminocarbonyloxopyrrolidinyl, methylcyanooxopyrrolidinyl, methyl(hydroxymethyl)oxopyrrolidinyl, methylmorpholinylcarbonyloxopyrrolidinyl, methyloxadiazolyloxopyrrolidinyl, methyloxadiazolyl(methyl)oxopyrrolidinyl, methyl oxazolyloxopyrrolidinyl, methylpyrazolyloxopyrrolidinyl, methylsulfonyloxopyrrolidinyl, methyl sulfonylaminooxopyrrolidinyl, methylsulfonylmethyloxopyrrolidinyl, morpholinylcarbonyloxopyrrolidinyl, morpholinylcarbonyl(methyl)oxopyrrolidinyl, oxadiazolyloxopyrrolidinyl, oxadiazolyl(methyl)oxopyrrolidinyl, oxazolyloxopyrrolidinyl, oxazolylaminocarbonyloxopyrrolidinyl, oxazolylcarbonyl(methyl)aminooxopyrrolidinyl, oxazolyl(methyl)aminocarbonyloxopyrrolidinyl, oxomorpholinyloxopyrrolidinyl, oxooxazolidinyloxopyrrolidinyl, oxopyrrolidinyloxopyrrolidinyl, phenyloxopyrrolidinyl, phenyl(hydroxy)oxopyrrolidinyl, pyrazolylmethyloxopyrrolidinyl, pyridinyloxopyrrolidinyl, pyrimidinyloxopyrrolidinyl, pyrimidinylaminooxopyrrolidinyl, pyrimidinyl(methyl)aminooxopyrrolidinyl, pyrimidinyl oxyoxopyrrolidinyl, pyrimidinyloxy(hydroxy)oxopyrrolidinyl, pyrimidinyloxy(hydroxy)(methyl)oxopyrrolidinyl, pyrimidinyloxymethyloxopyrrolidinyl, pyrrolidinylcarbonyloxopyrrolidinyl, thiazolyloxopyrrolidinyl, trifluoromethyloxopyrrolidinyl or trifluoromethyloxadiazolyloxopyrrolidinyl;
$R^2$ and $R^3$ are independently selected from hydrogen and methyl with the proviso that $R^2$ is not methyl when $R^3$ is H;
$R^4$ is chloropyridinyl, difluoromethylpyridinyl, fluorochloropyridinyl, trifluoromethylpyridinyl, difluorochlorophenyl, difluorodifluoromethylphenyl, fluorochlorophenyl, fluorotrifluoromethylphenyl or trifluorophenyl;
Y is CH;
Q is N;
or pharmaceutically acceptable salt, enantiomer or diastereomer thereof.

A further embodiment of present invention is (xxv) a compound of formula (I), wherein $R^1$ is oxopyrrolidinyl, said oxopyrrolidinyl being unsubstituted or substituted with one or two substituents independently selected from $(C_{1-6}alkyl)_2$aminocarbonyl, $C_{1-6}$alkoxy, $C_{1-6}$alkyl, $C_{1-6}$alkyloxadiazolyl, cyano, halo$C_{1-6}$alkyl, halopyrimidinyloxy, hydroxy, hydroxy$C_{1-6}$alkyl, morpholinyl carbonyl, oxadiazolyl, pyrimidinylamino, pyrimidinyloxy and pyrrolidinylcarbonyl; or pharmaceutically acceptable salt, enantiomer or diastereomer thereof.

A further embodiment of present invention is (xxvi) a compound of formula (I), wherein $R^1$ is oxopyrrolidinyl, cyanooxopyrrolidinyl, hydroxyoxopyrrolidinyl, methoxyoxopyrrolidinyl, trifluoromethyloxopyrrolidinyl, pyrimidinylaminooxopyrrolidinyl, oxadiazolyloxopyrrolidinyl, methyloxadiazolyloxopyrrolidinyl, hydroxymethylcyanooxopyrrolidinyl, methylcyanooxopyrrolidinyl, methyl(hydroxymethyl)oxopyrrolidinyl, pyrimidinyloxyoxopyrrolidinyl, pyrimidinyloxy(hydroxy)oxopyrrolidinyl, fluoropyrimidinyloxyoxopyrrolidinyl, morpholinylcarbonyloxopyrrolidinyl, dimethylaminocarbonyloxopyrrolidinyl or pyrrolidinylcarbonyloxopyrrolidinyl; or pharmaceutically acceptable salt, enantiomer or diastereomer thereof.

A further embodiment of present invention is (xxvii) a compound of formula (I), wherein $R^2$ is H; $R^3$ is H or $C_{1-6}$alkyl; or pharmaceutically acceptable salt, enantiomer or diastereomer thereof.

A further embodiment of present invention is (xxviii) a compound of formula (I), wherein $R^2$ is H; $R^3$ is H or methyl; or pharmaceutically acceptable salt, enantiomer or diastereomer thereof.

A further embodiment of present invention is (xxix) a compound of formula (I), wherein $R^4$ is pyridinyl substituted by haloC$_{1-6}$alkyl; or phenyl substituted with one, two or three substituents independently selected from halogen and haloC$_{1-6}$alkyl; or pharmaceutically acceptable salt, enantiomer or diastereomer thereof.

A further embodiment of present invention is (xxx) a compound of formula (I), wherein $R^4$ is difluoromethylpyridinyl, fluorochlorophenyl, difluorodifluoromethylphenyl or trifluorophenyl; or pharmaceutically acceptable salt, enantiomer or diastereomer thereof.

A further embodiment of present invention is (xxxi) a compound of formula (I), wherein
  $R^1$ is oxopyrrolidinyl, said oxopyrrolidinyl being unsubstituted or substituted with one or two substituents independently selected from (C$_{1-6}$alkyl)$_2$aminocarbonyl, C$_{1-6}$alkoxy, C$_{1-6}$alkyl, C$_{1-6}$alkyloxadiazolyl, cyano, haloC$_{1-6}$alkyl, halopyrimidinyloxy, hydroxy, hydroxyC$_{1-6}$alkyl, morpholinylcarbonyl, oxadiazolyl, pyrimidinylamino, pyrimidinyloxy and pyrrolidinylcarbonyl;
  $R^2$ is H;
  $R^3$ is H or C$_{1-6}$alkyl;
  $R^4$ is pyridinyl substituted by haloC$_{1-6}$alkyl; or phenyl substituted with one, two or three substituents independently selected from halogen and haloC$_{1-6}$alkyl;
  Y is CH;
  Q is N;
or pharmaceutically acceptable salt, enantiomer or diastereomer thereof.

A further embodiment of present invention is (xxxii) a compound of formula (I), wherein
  $R^1$ is oxopyrrolidinyl, cyanooxopyrrolidinyl, hydroxyoxopyrrolidinyl, methoxyoxopyrrolidinyl, trifluoromethyloxopyrrolidinyl, pyrimidinylaminooxopyrrolidinyl, oxadiazolyloxopyrrolidinyl, methyloxadiazolyloxopyrrolidinyl, hydroxymethylcyanooxopyrrolidinyl, methylcyanooxopyrrolidinyl, methyl(hydroxymethyl)oxopyrrolidinyl, pyrimidinyloxyoxopyrrolidinyl, pyrimidinyloxy(hydroxy)oxopyrrolidinyl, fluoropyrimidinyloxyoxopyrrolidinyl, morpholinylcarbonyloxopyrrolidinyl, dimethylaminocarbonyloxopyrrolidinyl or pyrrolidinylcarbonyloxopyrrolidinyl;
  $R^2$ is H;
  $R^3$ is H or C$_{1-6}$alkyl;
  $R^4$ is difluoromethylpyridinyl, fluorochlorophenyl, difluorodifluoromethylphenyl or trifluorophenyl;
  Y is CH;
  Q is N;
or pharmaceutically acceptable salt, enantiomer or diastereomer thereof.

In another embodiment of the present invention, particular compounds of the present invention are (xxxiii) selected from:
N-(3-chloro-4-fluoro-phenyl)-3-(2-oxopyrrolidin-1-yl)-6,7-dihydro-4H-pyrazolo[1,5-a]pyrazine-5-carboxamide;
6-methyl-3-(2-oxopyrrolidin-1-yl)-N-(3,4,5-trifluorophenyl)-6,7-dihydro-4H-pyrazolo[1,5-a]pyrazine-5-carboxamide;
N-(3-chloro-4-fluoro-phenyl)-6-methyl-3-(2-oxopyrrolidin-1-yl)-6,7-dihydro-4H-pyrazolo[1,5-a]pyrazine-5-carboxamide;
(6S)-N-(3-chloro-4-fluoro-phenyl)-3-(4-cyano-2-oxo-pyrrolidin-1-yl)-6-methyl-6,7-dihydro-4H-pyrazolo[1,5-a]pyrazine-5-carboxamide;
(6S)-N-(3-chloro-4-fluoro-phenyl)-3-(4-hydroxy-2-oxo-pyrrolidin-1-yl)-6-methyl-6,7-dihydro-4H-pyrazolo[1,5-a]pyrazine-5-carboxamide;
(6S)-N-(3-chloro-4-fluoro-phenyl)-3-(4-methoxy-2-oxo-pyrrolidin-1-yl)-6-methyl-6,7-dihydro-4H-pyrazolo[1,5-a]pyrazine-5-carboxamide;
(6S)-N-[3-(difluoromethyl)-4,5-difluoro-phenyl]-6-methyl-3-(2-oxopyrrolidin-1-yl)-6,7-dihydro-4H-pyrazolo[1,5-a]pyrazine-5-carboxamide;
(6S)-3-(4-cyano-2-oxo-pyrrolidin-1-yl)-6-methyl-N-(3,4,5-trifluorophenyl)-6,7-dihydro-4H-pyrazolo[1,5-a]pyrazine-5-carboxamide;
(6S)-3-[(4R)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-3-[(4S)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-N-[2-(difluoromethyl)-4-pyridyl]-6-methyl-3-[2-oxo-4-(trifluoromethyl)pyrrolidin-1-yl]-6,7-dihydro-4H-pyrazolo[1,5-a]pyrazine-5-carboxamide;
(6S)-6-methyl-3-[2-oxo-4-(pyrimidin-2-ylamino)pyrrolidin-1-yl]-N-(3,4,5-trifluorophenyl)-6,7-dihydro-4H-pyrazolo[1,5-a]pyrazine-5-carboxamide;
(6S)-6-methyl-3-[4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;
(6S)-6-methyl-3-[4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;
(6S)-6-methyl-3-[4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide;
(6S)-6-methyl-3-[4-(5-methyl-1,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide;
(6S)-N-(3-chloro-4-fluoro-phenyl)-6-methyl-3-(2-oxopyrrolidin-1-yl)-6,7-dihydro-4H-pyrazolo[1,5-a]pyrazine-5-carboxamide;
(6S)-6-methyl-3-(2-oxopyrrolidin-1-yl)-N-(3,4,5-trifluorophenyl)-6,7-dihydro-4H-pyrazolo[1,5-a]pyrazine-5-carboxamide;
(6S)-3-[4-cyano-4-(hydroxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-3-(4-cyano-4-methyl-2-oxo-pyrrolidin-1-yl)-N-[3-(difluoromethyl)-4,5-difluoro-phenyl]-6-methyl-6,7-dihydro-4H-pyrazolo[1,5-a]pyrazine-5-carboxamide;
(6S)-3-[4-(hydroxymethyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-3-[(4S)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-3-[(4R)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-6-methyl-3-[(4S)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;
(6S)-3-[(4S)-4-(5-fluoropyrimidin-2-yl)oxy-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-6-methyl-3-[4-(morpholine-4-carbonyl)-2-oxo-pyrrolidin-1-yl]-N-(3,4,5-trifluorophenyl)-6,7-dihydro-4H-pyrazolo[1,5-a]pyrazine-5-carboxamide;

(6S)-3-[4-(dimethylcarbamoyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[2-oxo-4-(pyrrolidine-1-carbonyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[(4R)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;

(6S)-3-(3-cyano-2-methyl-5-oxo-pyrrolidin-1-yl)-6-methyl-N-(3,4,5-trifluorophenyl)-6,7-dihydro-4H-pyrazolo[1,5-a]pyrazine-5-carboxamide; and (6S)-3-[(3S,4R)-3-hydroxy-2-oxo-4-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide;

or pharmaceutically acceptable salt, enantiomer or diastereomer thereof.

The present invention provides (xxxiv) novel compounds having the general formula (I),

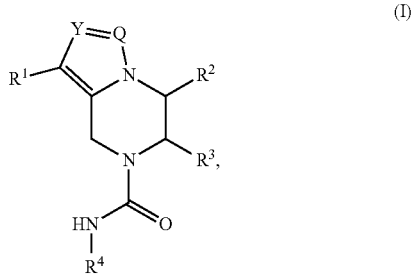

wherein
- $R^1$ is heterocyclyl, said heterocyclyl being unsubstituted or substituted with one to three substituents independently selected from $C_{1-6}$alkyl, $C_{1-6}$alkoxy, $C_{1-6}$alkoxy$C_{1-6}$alkyl, $C_{1-6}$alkylcarbonyl, $C_{1-6}$alkylaminocarbonyl, $C_{1-6}$alkylsulfonyl, halogen, cyano, hydroxy, oxadiazolyl and oxazolyl;
  heteroaryl, said heteroaryl being unsubstituted or substituted with one to three substituents independently selected from halogen, cyano, $C_{1-6}$alkyl and halo$C_{1-6}$alkyl;
  phenyl, said phenyl being unsubstituted or substituted with one to three substituents independently selected from halogen, cyano, hydroxy, $C_{1-6}$alkoxy, $C_{3-7}$cycloalkyl, halo$C_{1-6}$alkoxy and halo$C_{1-6}$alkyl; or
  $C_{3-7}$cycloalkyl;
- $R^2$ and $R^3$ are independently selected from hydrogen and $C_{1-6}$alkyl;
- $R^4$ is heterocyclyl, said heterocyclyl being unsubstituted or substituted with one to three substituents independently selected from halogen and $C_{1-6}$alkyl;
  heteroaryl, said heteroaryl being unsubstituted or substituted with one to three substituents independently selected from halogen, cyano, $C_{1-6}$alkoxy, $C_{3-7}$cycloalkyl and $(C_{1-6}$alkyl$)_2$amino;
  aryl, said aryl being unsubstituted or substituted with one to three substituents independently selected from halogen, cyano, $C_{3-7}$cycloalkyl, $C_{2-6}$alkynyl, $C_{1-6}$alkoxy, halo$C_{1-6}$alkyl and halo$C_{1-6}$alkoxy;
  phenyl$C_{1-6}$alkyl, said phenyl$C_{1-6}$alkyl being unsubstituted or substituted with halogen; or
  $C_{3-7}$cycloalkyl;
- Y and Q are independently selected from CH and N;

or pharmaceutically acceptable salt, enantiomer or diastereomer thereof.

A further embodiment of the present invention is (xxxv) a compound of formula (I), wherein $R^1$ is
- heterocyclyl, said heterocyclyl being unsubstituted or substituted with one to three substituents independently selected from $C_{1-6}$alkyl, $C_{1-6}$alkoxy, halo$C_{1-6}$alkyl, cyano, hydroxy, $C_{1-6}$alkylsulfonyl and oxazolyl;
- heteroaryl, said heteroaryl being unsubstituted or substituted with one to three substituents independently selected from halogen, cyano, halo$C_{1-6}$alkyl and $C_{1-6}$alkyl;
- phenyl, said phenyl being unsubstituted or substituted with one to three halogen; or $C_{3-7}$cycloalkyl;

or pharmaceutically acceptable salt, enantiomer or diastereomer thereof.

A further embodiment of the present invention is (xxxvi) a compound of formula (I), wherein $R^1$ is
- oxopyrrolidinyl, dimethyloxopyrrolidinyl, cyanooxopyrrolidinyl, hydroxyoxopyrrolidinyl, methoxyoxopyrrolidinyl, trifluoromethyloxopyrrolidinyl, oxazolyloxopyrrolidinyl, azabicyclo[3.1.0]hexanyl, oxoazabicyclo[3.1.0]hexanyl, oxomorpholinyl, methyloxomorpholinyl, oxooxazolidinyl, dimethyloxooxazolidinyl, dimethyloxoimidazolidinyl, methylsulfonyloxoimidazolidinyl, trioxothiazinanyl, fluoropyrimidinyl, trifluoromethylpyridinyl, methylfluoropyridinyl, fluoropyridinyl, methylpyrazolyl, cyanopyrazolyl, fluoropyrazolyl, fluorophenyl, difluorophenyl, cyclopentyl or cyclohexyl;

or pharmaceutically acceptable salt, enantiomer or diastereomer thereof.

A further embodiment of the present invention is (xxxvii) a compound of formula (I), wherein $R^4$ is
- phenyl, said phenyl being unsubstituted or substituted with one to three substituents independently selected from halogen, cyano, $C_{3-7}$cycloalkyl, $C_{1-6}$alkyl, halo$C_{1-6}$alkyl and $C_{2-6}$alkynyl; or
- pyridinyl, said pyridinyl being unsubstituted or substituted with one to three substituents independently selected from halogen, $C_{1-6}$alkyl and halo$C_{1-6}$alkyl;

or pharmaceutically acceptable salt, enantiomer or diastereomer thereof.

A further embodiment of the present invention is (xxxviii) a compound of formula (I), wherein $R^4$ is fluorophenyl, chlorophenyl, fluorochlorophenyl, fluorotrifluoromethylphenyl, trifluorophenyl, fluorocyanophenyl, methylfluorophenyl, ethynylfluorophenyl, cyclopropylfluorophenyl, methyldifluorophenyl, difluorochlorophenyl, difluoromethyldifluorophenyl, fluoropyridinyl, chloropyridinyl, methylpyridinyl or difluoromethylpyridinyl; or pharmaceutically acceptable salt, enantiomer or diastereomer thereof.

Another embodiment of the present invention is (xxxix) a compound of formula (I), wherein Y and Q are independently selected from CH and N, provided that Y and Q are not CH simultaneously; or pharmaceutically acceptable salt, enantiomer or diastereomer thereof.

Another embodiment of the present invention is (xl) a compound of formula (I), wherein
- $R^1$ is oxopyrrolidinyl, oxomorpholinyl or oxooxazolidinyl, said oxopyrrolidinyl, oxomorpholinyl and oxooxazolidinyl being unsubstituted or substituted with one to three substituents independently selected from $C_{1-6}$alkyl, halo$C_{1-6}$alkyl, $C_{1-6}$alkoxy, cyano, oxazolyl and hydroxy;
- pyridinyl, pyrimidinyl or pyrazolyl, said pyridinyl, pyrimidinyl or pyrazolyl being unsubstituted or substituted with one to three substituents independently selected from halogen and cyano;
phenyl, said phenyl being unsubstituted or substituted with halogen; or
$C_{3-7}$cycloalkyl;
$R^2$ and $R^3$ are independently selected from hydrogen and $C_{1-6}$alkyl;
$R^4$ is phenyl or pyridinyl, said phenyl or pyridinyl being unsubstituted or substituted with one to three substituents independently selected from halogen, cyano and halo$C_{1-6}$alkyl; or
$C_{3-7}$cycloalkyl;
Y and Q are independently selected from CH and N, provided that Y and Q are not CH simultaneously;
or pharmaceutically acceptable salt, enantiomer or diastereomer thereof.

Another embodiment of the present invention is (xli) a compound of formula (I), wherein
$R^1$ is oxopyrrolidinyl, cyanooxopyrrolidinyl, hydroxyoxopyrrolidinyl, methoxyoxopyrrolidinyl, trifluoromethyloxopyrrolidinyl, oxomorpholinyl, methyloxomorpholinyl, oxazolyloxopyrrolidinyl, oxooxazolidinyl, fluoropyrimidinyl, fluoropyridinyl, cyanopyrazolyl, fluoropyrazolyl, fluorophenyl, difluorophenyl or cyclopentyl;
$R^2$ and $R^3$ are independently selected from hydrogen and methyl;
$R^4$ is fluorochlorophenyl, fluorocyanophenyl, trifluorophenyl, difluoromethyldifluorophenyl, difluoromethylpyridinyl;
Y and Q are independently selected from CH and N, provided that Y and Q are not CH simultaneously;
or pharmaceutically acceptable salt, enantiomer or diastereomer thereof.

In another embodiment, the present invention provides novel compounds having the general formula (I),

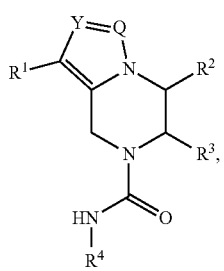

(I)

wherein
$R^1$ is heterocyclyl, said heterocyclyl being unsubstituted or substituted with cyano;
heteroaryl, said heteroaryl being unsubstituted or substituted independently with one, two or three halogen;
phenyl, said phenyl being unsubstituted or substituted independently with one, two or three halogen; or
lactam, said lactam being unsubstituted or substituted with cyano;
$R^2$ and $R^3$ are independently selected from hydrogen and $C_{1-6}$alkyl;
$R^4$ is phenyl, said phenyl being unsubstituted or substituted with one, two or three substituents independently selected from halogen and cyano; or
pyridinyl, said pyridinyl being unsubstituted or substituted with halo$C_{1-6}$alkyl;
Y and Q are independently selected from C and N;

or pharmaceutically acceptable salts, enantiomers or diastereomers thereof.

Another embodiment of present invention is a compound of formula (I),
wherein
$R^1$ is fluorophenyl, difluorophenyl, fluoropyrimidinyl, morpholinyl, oxopyrrolidinyl, cyanooxopyrrolidinyl or oxomorpholinyl;
$R^2$ and $R^3$ are independently selected from hydrogen and methyl;
$R^4$ is fluorochlorophenyl, cyanofluorophenyl, trifluorophenyl or difluoromethylpyridinyl;
Y and Q are independently selected from C and N;
or pharmaceutically acceptable salts, enantiomers or diastereomers thereof.

A further embodiment of present invention is a compound of formula (I), wherein $R^1$ is
phenyl, said phenyl being unsubstituted or substituted independently with one, two or three halogen;
pyrimidinyl, said pyrimidinyl being unsubstituted or substituted independently with one, two or three halogen;
morpholinyl;
or lactam, said lactam being unsubstituted or substituted with cyano;
or pharmaceutically acceptable salts, enantiomers or diastereomers thereof.

In another embodiment of the present invention, compounds of the present invention are selected from:
3-(4-fluorophenyl)-N-phenyl-6,7-dihydro-4H-pyrazolo[1,5-a]pyrazine-5-carboxamide;
N,3-diphenyl-6,7-dihydro-4H-pyrazolo[1,5-a]pyrazine-5-carboxamide;
3-(3-fluorophenyl)-N-phenyl-6,7-dihydro-4H-pyrazolo[1,5-a]pyrazine-5-carboxamide;
3-(3-chlorophenyl)-N-phenyl-6,7-dihydro-4H-pyrazolo[1,5-a]pyrazine-5-carboxamide;
N-phenyl-3-[3-(trifluoromethyl)phenyl]-6,7-dihydro-4H-pyrazolo[1,5-a]pyrazine-5-carboxamide;
3-(2-fluorophenyl)-N-phenyl-6,7-dihydro-4H-pyrazolo[1,5-a]pyrazine-5-carboxamide;
3-(2-chlorophenyl)-N-phenyl-6,7-dihydro-4H-pyrazolo[1,5-a]pyrazine-5-carboxamide;
N-phenyl-3-[2-(trifluoromethyl)phenyl]-6,7-dihydro-4H-pyrazolo[1,5-a]pyrazine-5-carboxamide;
1-(4-fluorophenyl)-N-phenyl-6,8-dihydro-5H-imidazo[1,5-a]pyrazine-7-carboxamide;
3-(4-fluorophenyl)-N-phenyl-6,7-dihydro-4H-triazolo[1,5-a]pyrazine-5-carboxamide;
3-(4-fluorophenyl)-N-[3-(trifluoromethyl)phenyl]-6,7-dihydro-4H-pyrazolo[1,5-a]pyrazine-5-carboxamide;
N-(3-chloro-4-fluoro-phenyl)-8-(4-fluorophenyl)-3,4-dihydro-1H-pyrrolo[1,2-a]pyrazine-2-carboxamide;
N-(2-fluorophenyl)-3-(4-fluorophenyl)-6,7-dihydro-4H-pyrazolo[1,5-a]pyrazine-5-carboxamide;
N,3-bis(4-fluorophenyl)-6,7-dihydro-4H-pyrazolo[1,5-a]pyrazine-5-carboxamide;
N-(3-chlorophenyl)-3-(4-fluorophenyl)-6,7-dihydro-4H-pyrazolo[1,5-a]pyrazine-5-carboxamide;
N-(3-cyanophenyl)-3-(4-fluorophenyl)-6,7-dihydro-4H-pyrazolo[1,5-a]pyrazine-5-carboxamide;
N-(4-chlorophenyl)-3-(4-fluorophenyl)-6,7-dihydro-4H-pyrazolo[1,5-a]pyrazine-5-carboxamide;
3-(2-cyanophenyl)-N-phenyl-6,7-dihydro-4H-pyrazolo[1,5-a]pyrazine-5-carboxamide;
N-(3-fluorophenyl)-3-(4-fluorophenyl)-6,7-dihydro-4H-pyrazolo[1,5-a]pyrazine-5-carboxamide;

N-(4-chloro-3-fluoro-phenyl)-3-(4-fluorophenyl)-6,7-dihydro-4H-pyrazolo[1,5-a]pyrazine-5-carboxamide;
N-(3-chloro-4-fluoro-phenyl)-3-(4-fluorophenyl)-6,7-dihydro-4H-pyrazolo[1,5-a]pyrazine-5-carboxamide;
3-(4-fluorophenyl)-N-(4-pyridyl)-6,7-dihydro-4H-pyrazolo[1,5-a]pyrazine-5-carboxamide;
N-(4-cyanophenyl)-3-(4-fluorophenyl)-6,7-dihydro-4H-pyrazolo[1,5-a]pyrazine-5-carboxamide;
N-(3-chloro-4-fluoro-phenyl)-3-(2-fluorophenyl)-6,7-dihydro-4H-pyrazolo[1,5-a]pyrazine-5-carboxamide;
3-(3-methoxyphenyl)-N-phenyl-6,7-dihydro-4H-pyrazolo[1,5-a]pyrazine-5-carboxamide;
3-cyclopentyl-N-phenyl-6,7-dihydro-4H-pyrazolo[1,5-a]pyrazine-5-carboxamide;
3-(2-methoxyphenyl)-N-phenyl-6,7-dihydro-4H-pyrazolo[1,5-a]pyrazine-5-carboxamide;
N-phenyl-3-[4-(trifluoromethyl)-2-pyridyl]-6,7-dihydro-4H-pyrazolo[1,5-a]pyrazine-5-carboxamide;
3-(4-cyano-2-pyridyl)-N-phenyl-6,7-dihydro-4H-pyrazolo[1,5-a]pyrazine-5-carboxamide;
N-(3-chlorophenyl)-3-(2-fluorophenyl)-6,7-dihydro-4H-pyrazolo[1,5-a]pyrazine-5-carboxamide;
N-(3-chlorophenyl)-3-(o-tolyl)-6,7-dihydro-4H-pyrazolo[1,5-a]pyrazine-5-carboxamide;
N-(5-fluoro-6-methyl-2-pyridyl)-3-(4-fluorophenyl)-6,7-dihydro-4H-pyrazolo[1,5-a]pyrazine-5-carboxamide;
3-(2-fluorophenyl)-N-(4-fluorophenyl)-6,7-dihydro-4H-pyrazolo[1,5-a]pyrazine-5-carboxamide;
3-(2-fluorophenyl)-N-[4-fluoro-3-(trifluoromethyl)phenyl]-6,7-dihydro-4H-pyrazolo[1,5-a]pyrazine-5-carboxamide;
N-(3-chlorophenyl)-3-(2,4-difluorophenyl)-6,7-dihydro-4H-pyrazolo[1,5-a]pyrazine-5-carboxamide;
N-(3-chlorophenyl)-3-(2,3-difluorophenyl)-6,7-dihydro-4H-pyrazolo[1,5-a]pyrazine-5-carboxamide;
3-(3-cyano-2-pyridyl)-N-phenyl-6,7-dihydro-4H-pyrazolo[1,5-a]pyrazine-5-carboxamide;
3-(3-chloro-2-fluoro-phenyl)-N-(3-chlorophenyl)-6,7-dihydro-4H-pyrazolo[1,5-a]pyrazine-5-carboxamide;
3-(5-chloro-2-fluoro-phenyl)-N-(3-chlorophenyl)-6,7-dihydro-4H-pyrazolo[1,5-a]pyrazine-5-carboxamide;
N-(3-chlorophenyl)-3-(2,5-difluorophenyl)-6,7-dihydro-4H-pyrazolo[1,5-a]pyrazine-5-carboxamide;
3-[3-(difluoromethyl)phenyl]-N-phenyl-6,7-dihydro-4H-pyrazolo[1,5-a]pyrazine-5-carboxamide;
3-(5-fluoro-6-methyl-2-pyridyl)-N-phenyl-6,7-dihydro-4H-pyrazolo[1,5-a]pyrazine-5-carboxamide;
3-(5-fluoro-4-methyl-2-pyridyl)-N-phenyl-6,7-dihydro-4H-pyrazolo[1,5-a]pyrazine-5-carboxamide;
N-phenyl-3-(2-pyridyl)-6,7-dihydro-4H-pyrazolo[1,5-a]pyrazine-5-carboxamide+H31;
N-phenyl-3-thiazol-2-yl-6,7-dihydro-4H-pyrazolo[1,5-a]pyrazine-5-carboxamide;
N-phenyl-3-[4-(trifluoromethyl)thiazol-2-yl]-6,7-dihydro-4H-pyrazolo[1,5-a]pyrazine-5-carboxamide;
3-(5-chlorothiazol-2-yl)-N-phenyl-6,7-dihydro-4H-pyrazolo[1,5-a]pyrazine-5-carboxamide;
3-(3,4-difluorophenyl)-N-phenyl-6,7-dihydro-4H-pyrazolo[1,5-a]pyrazine-5-carboxamide;
3-(6-chloro-2-pyridyl)-N-phenyl-6,7-dihydro-4H-pyrazolo[1,5-a]pyrazine-5-carboxamide;
N-(3-chloro-4-fluoro-phenyl)-3-(2,4-difluorophenyl)-6,7-dihydro-4H-pyrazolo[1,5-a]pyrazine-5-carboxamide;
3-(2,4-difluorophenyl)-N-(3,4,5-trifluorophenyl)-6,7-dihydro-4H-pyrazolo[1,5-a]pyrazine-5-carboxamide;
3-(4-fluoro-3-methyl-phenyl)-N-phenyl-6,7-dihydro-4H-pyrazolo[1,5-a]pyrazine-5-carboxamide;
3-(4-fluorophenyl)-6-methyl-N-(3,4,5-trifluorophenyl)-6,7-dihydro-4H-pyrazolo[1,5-a]pyrazine-5-carboxamide;
N-[(3-chloro-4-fluoro-phenyl)methyl]-3-(4-fluorophenyl)-6,7-dihydro-4H-pyrazolo[1,5-a]pyrazine-5-carboxamide;
N-[(3,5-dichlorophenyl)methyl]-3-(4-fluorophenyl)-6,7-dihydro-4H-pyrazolo[1,5-a]pyrazine-5-carboxamide;
N-(4-chloro-5-methyl-2-pyridyl)-3-(4-fluorophenyl)-6,7-dihydro-4H-pyrazolo[1,5-a]pyrazine-5-carboxamide;
3-(4-chloro-2-pyridyl)-N-phenyl-6,7-dihydro-4H-pyrazolo[1,5-a]pyrazine-5-carboxamide;
N-[(2-chloro-3-fluoro-phenyl)methyl]-3-(4-fluorophenyl)-6,7-dihydro-4H-pyrazolo[1,5-a]pyrazine-5-carboxamide;
N-[(2,6-dichlorophenyl)methyl]-3-(4-fluorophenyl)-6,7-dihydro-4H-pyrazolo[1,5-a]pyrazine-5-carboxamide;
3-(2,4-difluorophenyl)-N-(5-fluoro-6-methyl-2-pyridyl)-6,7-dihydro-4H-pyrazolo[1,5-a]pyrazine-5-carboxamide;
N-(3-chloro-4-fluoro-phenyl)-3-(4-fluorophenyl)-6-methyl-6,7-dihydro-4H-pyrazolo[1,5-a]pyrazine-5-carboxamide;
3-(4-fluorophenyl)-N-(2-methyl-1,3-benzothiazol-5-yl)-6,7-dihydro-4H-pyrazolo[1,5-a]pyrazine-5-carboxamide;
N-(benzothiophen-3-yl)-3-(4-fluorophenyl)-6,7-dihydro-4H-pyrazolo[1,5-a]pyrazine-5-carboxamide;
3-(2,4-difluorophenyl)-N-[2-(trifluoromethyl)-4-pyridyl]-6,7-dihydro-4H-pyrazolo[1,5-a]pyrazine-5-carboxamide;
3-(3-cyclopropylphenyl)-N-phenyl-6,7-dihydro-4H-pyrazolo[1,5-a]pyrazine-5-carboxamide;
3-(2-hydroxyphenyl)-N-phenyl-6,7-dihydro-4H-pyrazolo[1,5-a]pyrazine-5-carboxamide;
N-(3-chloro-4-fluoro-phenyl)-3-[4-(trifluoromethyl)-2-pyridyl]-6,7-dihydro-4H-pyrazolo[1,5-a]pyrazine-5-carboxamide;
N-(3-chloro-4-fluoro-phenyl)-3-(5-fluoro-4-methyl-2-pyridyl)-6,7-dihydro-4H-pyrazolo[1,5-a]pyrazine-5-carboxamide;
N-(3-chloro-4-fluoro-phenyl)-3-(5-fluoro-2-pyridyl)-6,7-dihydro-4H-pyrazolo[1,5-a]pyrazine-5-carboxamide;
N-(2-chloro-4-pyridyl)-3-(2,4-difluorophenyl)-6,7-dihydro-4H-pyrazolo[1,5-a]pyrazine-5-carboxamide;
3-[4-(trifluoromethyl)-2-pyridyl]-N-(3,4,5-trifluorophenyl)-6,7-dihydro-4H-pyrazolo[1,5-a]pyrazine-5-carboxamide;
N,3-bis(3-chloro-4-fluoro-phenyl)-6,7-dihydro-4H-pyrazolo[1,5-a]pyrazine-5-carboxamide;
N-(3-chloro-4-fluoro-phenyl)-3-cyclohexyl-6,7-dihydro-4H-pyrazolo[1,5-a]pyrazine-5-carboxamide;
N-(4-cyano-4-fluoro-phenyl)-3-(5-fluoro-4-methyl-2-pyridyl)-6,7-dihydro-4H-pyrazolo[1,5-a]pyrazine-5-carboxamide;
3-(5-fluoro-2-pyridyl)-N-(3,4,5-trifluorophenyl)-6,7-dihydro-4H-pyrazolo[1,5-a]pyrazine-5-carboxamide;
N-(3-cyano-4-fluoro-phenyl)-3-(5-fluoro-2-pyridyl)-6,7-dihydro-4H-pyrazolo[1,5-a]pyrazine-5-carboxamide;
3-(4-fluorophenyl)-N-(1H-indol-6-yl)-6,7-dihydro-4H-pyrazolo[1,5-a]pyrazine-5-carboxamide;
N-(3-chloro-4-fluoro-phenyl)-3-cyclopentyl-6,7-dihydro-4H-pyrazolo[1,5-a]pyrazine-5-carboxamide;
N-(3-cyano-4-fluoro-phenyl)-3-cyclopentyl-6,7-dihydro-4H-pyrazolo[1,5-a]pyrazine-5-carboxamide;
3-(4-fluorophenyl)-N-[4-fluoro-3-(trifluoromethyl)phenyl]-6,7-dihydro-4H-pyrazolo[1,5-a]pyrazine-5-carboxamide;
N-(4-fluoro-3-methyl-phenyl)-3-(4-fluorophenyl)-6,7-dihydro-4H-pyrazolo[1,5-a]pyrazine-5-carboxamide;
3-cyclopentyl-N-indan-5-yl-6,7-dihydro-4H-pyrazolo[1,5-a]pyrazine-5-carboxamide;
3-cyclopentyl-N-indan-1-yl-6,7-dihydro-4H-pyrazolo[1,5-a]pyrazine-5-carboxamide;
N-benzyl-3-cyclopentyl-6,7-dihydro-4H-pyrazolo[1,5-a]pyrazine-5-carboxamide;

N-(3-cyano-4-fluoro-phenyl)-3-(2,4-difluorophenyl)-6-methyl-6,7-dihydro-4H-pyrazolo[1,5-a]pyrazine-5-carboxamide;

N-(3-cyano-4-fluoro-phenyl)-3-(4-fluorophenyl)-6-methyl-6,7-dihydro-4H-pyrazolo[1,5-a]pyrazine-5-carboxamide;

N-(3-chloro-4-fluoro-phenyl)-3-pyrrolidin-1-yl-6,7-dihydro-4H-pyrazolo[1,5-a]pyrazine-5-carboxamide;

3-(2,4-difluorophenyl)-6-methyl-N-[2-(trifluoromethyl)-4-pyridyl]-6,7-dihydro-4H-pyrazolo[1,5-a]pyrazine-5-carboxamide;

N-(3-chloro-4-fluoro-phenyl)-3-(1-piperidyl)-6,7-dihydro-4H-pyrazolo[1,5-a]pyrazine-5-carboxamide;

N-(3-chloro-4-fluoro-phenyl)-3-(4,4-difluoro-1-piperidyl)-6,7-dihydro-4H-pyrazolo[1,5-a]pyrazine-5-carboxamide;

N-(3-chloro-4-fluoro-phenyl)-3-thiazol-2-yl-6,7-dihydro-4H-pyrazolo[1,5-a]pyrazine-5-carboxamide;

N-(3-chloro-4-fluoro-phenyl)-3-(2,4-difluorophenyl)-6-methyl-6,7-dihydro-4H-pyrazolo[1,5-a]pyrazine-5-carboxamide;

N-(2-chloro-4-pyridyl)-3-(2,4-difluorophenyl)-6-methyl-6,7-dihydro-4H-pyrazolo[1,5-a]pyrazine-5-carboxamide;

N-(3-chloro-4-fluoro-phenyl)-3-(5-fluoro-2-pyridyl)-6-methyl-6,7-dihydro-4H-pyrazolo[1,5-a]pyrazine-5-carboxamide;

N-(3-chloro-4-fluoro-phenyl)-3-(3,3-difluoro-1-piperidyl)-6,7-dihydro-4H-pyrazolo[1,5-a]pyrazine-5-carboxamide;

N-(2-chloro-4-pyridyl)-3-cyclopentyl-6-methyl-6,7-dihydro-4H-pyrazolo[1,5-a]pyrazine-5-carboxamide;

N-(2-cyano-4-pyridyl)-3-(4-fluorophenyl)-6,7-dihydro-4H-pyrazolo[1,5-a]pyrazine-5-carboxamide;

N-(2-chloro-6-methoxy-4-pyridyl)-3-(4-fluorophenyl)-6,7-dihydro-4H-pyrazolo[1,5-a]pyrazine-5-carboxamide;

3-(5-fluoro-2-pyridyl)-6-methyl-N-(3,4,5-trifluorophenyl)-6,7-dihydro-4H-pyrazolo[1,5-a]pyrazine-5-carboxamide;

N-(3-cyano-4-fluoro-phenyl)-3-(5-fluoro-2-pyridyl)-6-methyl-6,7-dihydro-4H-pyrazolo[1,5-a]pyrazine-5-carboxamide;

(6R)-N-(3-chloro-4-fluoro-phenyl)-3-(4-fluorophenyl)-6-methyl-6,7-dihydro-4H-pyrazolo[1,5-a]pyrazine-5-carboxamide;

(6S)-N-(3-chloro-4-fluoro-phenyl)-3-(4-fluorophenyl)-6-methyl-6,7-dihydro-4H-pyrazolo[1,5-a]pyrazine-5-carboxamide;

N-(2-chloro-4-pyridyl)-3-cyclopentyl-6,7-dihydro-4H-pyrazolo[1,5-a]pyrazine-5-carboxamide;

N-(benzofuran-6-yl)-3-cyclopentyl-6-methyl-6,7-dihydro-4H-pyrazolo[1,5-a]pyrazine-5-carboxamide;

N-(3-cyano-4-fluoro-phenyl)-3-(4-fluorophenyl)-6,7-dihydro-4H-pyrazolo[1,5-a]pyrazine-5-carboxamide;

N-(3-cyano-5-fluoro-phenyl)-3-(4-fluorophenyl)-6,7-dihydro-4H-pyrazolo[1,5-a]pyrazine-5-carboxamide;

3-(4-fluorophenyl)-N-[4-methyl-3-(trifluoromethyl)phenyl]-6,7-dihydro-4H-pyrazolo[1,5-a]pyrazine-5-carboxamide;

N-[3-chloro-5-(trifluoromethyl)phenyl]-3-(4-fluorophenyl)-6,7-dihydro-4H-pyrazolo[1,5-a]pyrazine-5-carboxamide;

N-(3,4-difluorophenyl)-3-(4-fluorophenyl)-6,7-dihydro-4H-pyrazolo[1,5-a]pyrazine-5-carboxamide;

N-(3-chloro-4-cyano-phenyl)-3-(4-fluorophenyl)-6,7-dihydro-4H-pyrazolo[1,5-a]pyrazine-5-carboxamide;

3-(4-fluorophenyl)-N-(3,4,5-trifluorophenyl)-6,7-dihydro-4H-pyrazolo[1,5-a]pyrazine-5-carboxamide;

N-(3,5-difluorophenyl)-3-(4-fluorophenyl)-6,7-dihydro-4H-pyrazolo[1,5-a]pyrazine-5-carboxamide;

N-[4-chloro-3-(trifluoromethyl)phenyl]-3-(4-fluorophenyl)-6,7-dihydro-4H-pyrazolo[1,5-a]pyrazine-5-carboxamide;

N-(3-ethylphenyl)-3-(4-fluorophenyl)-6,7-dihydro-4H-pyrazolo[1,5-a]pyrazine-5-carboxamide;

N-(3-ethynylphenyl)-3-(4-fluorophenyl)-6,7-dihydro-4H-pyrazolo[1,5-a]pyrazine-5-carboxamide;

3-(4-fluorophenyl)-N-(3-isopropylphenyl)-6,7-dihydro-4H-pyrazolo[1,5-a]pyrazine-5-carboxamide;

3-(4-fluorophenyl)-N-(3-methoxyphenyl)-6,7-dihydro-4H-pyrazolo[1,5-a]pyrazine-5-carboxamide;

N-phenyl-3-[2-(trifluoromethoxy)phenyl]-6,7-dihydro-4H-pyrazolo[1,5-a]pyrazine-5-carboxamide;

3-(3-chloro-4-fluoro-phenyl)-N-phenyl-6,7-dihydro-4H-pyrazolo[1,5-a]pyrazine-5-carboxamide;

3-(m-tolyl)-N-phenyl-6,7-dihydro-4H-pyrazolo[1,5-a]pyrazine-5-carboxamide;

3-(3-bromophenyl)-N-phenyl-6,7-dihydro-4H-pyrazolo[1,5-a]pyrazine-5-carboxamide;

N-(3-ethynyl-4-fluoro-phenyl)-3-(4-fluorophenyl)-6,7-dihydro-4H-pyrazolo[1,5-a]pyrazine-5-carboxamide;

N-(3-chloro-5-fluoro-phenyl)-3-(4-fluorophenyl)-6,7-dihydro-4H-pyrazolo[1,5-a]pyrazine-5-carboxamide;

N-(2-chloro-4-pyridyl)-3-(4-fluorophenyl)-6,7-dihydro-4H-pyrazolo[1,5-a]pyrazine-5-carboxamide;

N-(2,6-dimethyl-4-pyridyl)-3-(4-fluorophenyl)-6,7-dihydro-4H-pyrazolo[1,5-a]pyrazine-5-carboxamide;

3-(4-fluorophenyl)-N-[2-(trifluoromethyl)-4-pyridyl]-6,7-dihydro-4H-pyrazolo[1,5-a]pyrazine-5-carboxamide;

N-(3-chloro-4-fluoro-phenyl)-1-(4-fluorophenyl)-6,8-dihydro-5H-imidazo[1,5-a]pyrazine-7-carboxamide;

N-(3-bromo-4-fluoro-phenyl)-3-(4-fluorophenyl)-6,7-dihydro-4H-pyrazolo[1,5-a]pyrazine-5-carboxamide;

N-[3-(difluoromethoxy)phenyl]-3-(4-fluorophenyl)-6,7-dihydro-4H-pyrazolo[1,5-a]pyrazine-5-carboxamide;

3-(4-fluorophenyl)-N-[4-fluoro-3-(trifluoromethoxy)phenyl]-6,7-dihydro-4H-pyrazolo[1,5-a]pyrazine-5-carboxamide;

N-[3-(difluoromethyl)phenyl]-3-(4-fluorophenyl)-6,7-dihydro-4H-pyrazolo[1,5-a]pyrazine-5-carboxamide;

3-(4-fluorophenyl)-N-(m-tolyl)-6,7-dihydro-4H-pyrazolo[1,5-a]pyrazine-5-carboxamide;

N-phenyl-3-[3-(trifluoromethoxy)phenyl]-6,7-dihydro-4H-pyrazolo[1,5-a]pyrazine-5-carboxamide;

1-(2,4-difluorophenyl)-N-(3-ethynyl-4-fluoro-phenyl)-6,8-dihydro-5H-imidazo[1,5-a]pyrazine-7-carboxamide;

N-(3-chloro-4-fluoro-phenyl)-1-(2,4-difluorophenyl)-6,8-dihydro-5H-imidazo[1,5-a]pyrazine-7-carboxamide;

N-(3-cyano-4-fluoro-phenyl)-1-(2,4-difluorophenyl)-6,8-dihydro-5H-imidazo[1,5-a]pyrazine-7-carboxamide;

N-(3-cyano-4,5-difluoro-phenyl)-1-(2,4-difluorophenyl)-6,8-dihydro-5H-imidazo[1,5-a]pyrazine-7-carboxamide;

1-(2,4-difluorophenyl)-N-(3,4,5-trifluorophenyl)-6,8-dihydro-5H-imidazo[1,5-a]pyrazine-7-carboxamide;

3-(2,4-difluorophenyl)-N-(3-ethynyl-4-fluoro-phenyl)-6,7-dihydro-4H-pyrazolo[1,5-a]pyrazine-5-carboxamide;

N-(6-chloro-5-fluoro-2-pyridyl)-3-(4-fluorophenyl)-6,7-dihydro-4H-pyrazolo[1,5-a]pyrazine-5-carboxamide;

N-(3-cyclopropylphenyl)-3-(4-fluorophenyl)-6,7-dihydro-4H-pyrazolo[1,5-a]pyrazine-5-carboxamide;

N-(3-cyano-4-fluoro-phenyl)-3-(2,4-difluorophenyl)-6,7-dihydro-4H-pyrazolo[1,5-a]pyrazine-5-carboxamide;

N-(6-chloro-5-fluoro-2-pyridyl)-3-(2,4-difluorophenyl)-6,7-dihydro-4H-pyrazolo[1,5-a]pyrazine-5-carboxamide;

N-(3,4-difluoro-5-methyl-phenyl)-3-(4-fluorophenyl)-6,7-dihydro-4H-pyrazolo[1,5-a]pyrazine-5-carboxamide;

N-(3-chloro-4,5-difluoro-phenyl)-3-(4-fluorophenyl)-6,7-dihydro-4H-pyrazolo[1,5-a]pyrazine-5-carboxamide;

N-(3-cyclopropyl-4,5-difluoro-phenyl)-3-(4-fluorophenyl)-6,7-dihydro-4H-pyrazolo[1,5-a]pyrazine-5-carboxamide;

N-[3-(1,1-difluoroethyl)phenyl]-3-(4-fluorophenyl)-6,7-dihydro-4H-pyrazolo[1,5-a]pyrazine-5-carboxamide;
N-(3-chloro-4-fluoro-phenyl)-3-(4-chloro-5-fluoro-2-pyridyl)-6,7-dihydro-4H-pyrazolo[1,5-a]pyrazine-5-carboxamide;
N-(3-chloro-4-fluoro-phenyl)-3-(2-chloro-5-fluoro-4-pyridyl)-6,7-dihydro-4H-pyrazolo[1,5-a]pyrazine-5-carboxamide;
N-(3-cyclopropyl-4-fluoro-phenyl)-3-(2,4-difluorophenyl)-6,7-dihydro-4H-pyrazolo[1,5-a]pyrazine-5-carboxamide;
N-(2-chloro-4-pyridyl)-1-(2,4-difluorophenyl)-6,8-dihydro-5H-imidazo[1,5-a]pyrazine-7-carboxamide;
1-(2,4-difluorophenyl)-N-[2-(trifluoromethyl)-4-pyridyl]-6,8-dihydro-5H-imidazo[1,5-a]pyrazine-7-carboxamide;
N-(3-chloro-4-fluoro-phenyl)-3-(4-fluorophenyl)-6,7-dihydro-4H-triazolo[1,5-a]pyrazine-5-carboxamide;
N-(6-chloro-5-fluoro-2-pyridyl)-1-(2,4-difluorophenyl)-6,8-dihydro-5H-imidazo[1,5-a]pyrazine-7-carboxamide;
N-(3-chloro-4-fluoro-phenyl)-3-(2,4-difluorophenyl)-6,7-dihydro-4H-triazolo[1,5-a]pyrazine-5-carboxamide;
N-(3,4-difluoro-5-methyl-phenyl)-3-(5-fluoro-2-pyridyl)-6-methyl-6,7-dihydro-4H-pyrazolo[1,5-a]pyrazine-5-carboxamide;
N-(3-cyclopropyl-4-fluoro-phenyl)-3-(5-fluoro-2-pyridyl)-6-methyl-6,7-dihydro-4H-pyrazolo[1,5-a]pyrazine-5-carboxamide;
N-(3-chloro-4,5-difluoro-phenyl)-3-(5-fluoro-2-pyridyl)-6-methyl-6,7-dihydro-4H-pyrazolo[1,5-a]pyrazine-5-carboxamide;
N-(3,4-difluoro-5-methoxy-phenyl)-3-(5-fluoro-2-pyridyl)-6-methyl-6,7-dihydro-4H-pyrazolo[1,5-a]pyrazine-5-carboxamide;
N-(3-cyclopropyl-4,5-difluoro-phenyl)-3-(5-fluoro-2-pyridyl)-6-methyl-6,7-dihydro-4H-pyrazolo[1,5-a]pyrazine-5-carboxamide;
N-(6-chloro-5-fluoro-2-pyridyl)-3-(2,4-difluorophenyl)-6-methyl-6,7-dihydro-4H-pyrazolo[1,5-a]pyrazine-5-carboxamide;
N-(3-chloro-4-fluoro-phenyl)-1-cyclopentyl-6,8-dihydro-5H-imidazo[1,5-a]pyrazine-7-carboxamide;
1-cyclopentyl-N-(3,4,5-trifluorophenyl)-6,8-dihydro-5H-imidazo[1,5-a]pyrazine-7-carboxamide;
1-cyclopentyl-N-(3,4-difluoro-5-methyl-phenyl)-6,8-dihydro-5H-imidazo[1,5-a]pyrazine-7-carboxamide;
N-(3-cyclopropyl-4,5-difluoro-phenyl)-1-(2,4-difluorophenyl)-6,8-dihydro-5H-imidazo[1,5-a]pyrazine-7-carboxamide;
N-(3,4-difluoro-5-methoxy-phenyl)-1-(2,4-difluorophenyl)-6,8-dihydro-5H-imidazo[1,5-a]pyrazine-7-carboxamide;
N-(3,4-difluoro-5-methyl-phenyl)-1-(2,4-difluorophenyl)-6,8-dihydro-5H-imidazo[1,5-a]pyrazine-7-carboxamide;
N-(3-chloro-4-fluoro-phenyl)-3-(2-methylpyrrolidin-1-yl)-6,7-dihydro-4H-pyrazolo[1,5-a]pyrazine-5-carboxamide;
N-(3-chloro-4-fluoro-phenyl)-3-morpholino-6,7-dihydro-4H-pyrazolo[1,5-a]pyrazine-5-carboxamide;
N-(3-chloro-4-fluoro-phenyl)-3-(2-oxopyrrolidin-1-yl)-6,7-dihydro-4H-pyrazolo[1,5-a]pyrazine-5-carboxamide;
N-(3-chloro-4-fluoro-phenyl)-3-(4-methylpyrazol-1-yl)-6,7-dihydro-4H-pyrazolo[1,5-a]pyrazine-5-carboxamide;
N-benzyl-3-(4-fluorophenyl)-6-methyl-6,7-dihydro-4H-pyrazolo[1,5-a]pyrazine-5-carboxamide;
3-(4-fluorophenyl)-N-(2-fluoro-4-pyridyl)-6-methyl-6,7-dihydro-4H-pyrazolo[1,5-a]pyrazine-5-carboxamide;
3-(2,4-difluorophenyl)-N-(2-fluoro-4-pyridyl)-6-methyl-6,7-dihydro-4H-pyrazolo[1,5-a]pyrazine-5-carboxamide;
N-(1,3-benzoxazol-6-yl)-3-(4-fluorophenyl)-6,7-dihydro-4H-pyrazolo[1,5-a]pyrazine-5-carboxamide;
3-(4-fluorophenyl)-N-(2-methyl-4-pyridyl)-6,7-dihydro-4H-pyrazolo[1,5-a]pyrazine-5-carboxamide;
N-(2,6-difluoro-4-pyridyl)-3-(4-fluorophenyl)-6,7-dihydro-4H-pyrazolo[1,5-a]pyrazine-5-carboxamide;
3-(2,4-difluorophenyl)-6-methyl-N-(3,4,5-trifluorophenyl)-6,7-dihydro-4H-pyrazolo[1,5-a]pyrazine-5-carboxamide;
3-(2,4-difluorophenyl)-N-(5-fluoro-4-methyl-2-pyridyl)-6-methyl-6,7-dihydro-4H-pyrazolo[1,5-a]pyrazine-5-carboxamide;
N-cyclopentyl-3-(2,4-difluorophenyl)-6-methyl-6,7-dihydro-4H-pyrazolo[1,5-a]pyrazine-5-carboxamide;
N-cyclohexyl-3-(2,4-difluorophenyl)-6-methyl-6,7-dihydro-4H-pyrazolo[1,5-a]pyrazine-5-carboxamide;
N-(3-chloro-4-fluoro-phenyl)-3-tetrahydrofuran-3-yl-6,7-dihydro-4H-pyrazolo[1,5-a]pyrazine-5-carboxamide;
6-methyl-3-(2-oxopyrrolidin-1-yl)-N-(3,4,5-trifluorophenyl)-6,7-dihydro-4H-pyrazolo[1,5-a]pyrazine-5-carboxamide;
N-(4-bicyclo[4.2.0]octa-1(6),2,4-trienyl)-3-(4-fluorophenyl)-6,7-dihydro-4H-pyrazolo[1,5-a]pyrazine-5-carboxamide;
N-(3-chloro-4-fluoro-phenyl)-3-(5-fluoropyrimidin-2-yl)-6,7-dihydro-4H-pyrazolo[1,5-a]pyrazine-5-carboxamide;
N-(3-chloro-4-fluoro-phenyl)-3-(5-fluoro-4-methyl-pyrimidin-2-yl)-6,7-dihydro-4H-pyrazolo[1,5-a]pyrazine-5-carboxamide;
3-(2,4-difluorophenyl)-6-methyl-N-(2-methyl-4-pyridyl)-6,7-dihydro-4H-pyrazolo[1,5-a]pyrazine-5-carboxamide;
N-(2-chloro-4-pyridyl)-3-(5-fluoro-2-pyridyl)-6-methyl-6,7-dihydro-4H-pyrazolo[1,5-a]pyrazine-5-carboxamide;
N-(3-chloro-4-fluoro-phenyl)-3-(4-methylpyrazol-1-yl)-6,7-dihydro-4H-pyrazolo[1,5-a]pyrazine-5-carboxamide;
N-(2-chloro-4-pyridyl)-6-methyl-3-[4-(trifluoromethyl)-2-pyridyl]-6,7-dihydro-4H-pyrazolo[1,5-a]pyrazine-5-carboxamide;
N-(2-chloro-4-pyridyl)-6-methyl-3-(2-oxopyrrolidin-1-yl)-6,7-dihydro-4H-pyrazolo[1,5-a]pyrazine-5-carboxamide;
N-(2-bromo-4-pyridyl)-3-(4-fluorophenyl)-6,7-dihydro-4H-pyrazolo[1,5-a]pyrazine-5-carboxamide;
N-(3-chloro-2-methyl-4-pyridyl)-3-(2,4-di fluorophenyl)-6-methyl-6,7-dihydro-4H-pyrazolo[1,5-a]pyrazine-5-carboxamide;
3-(2,4-difluorophenyl)-N-(5-fluoro-2-methyl-4-pyridyl)-6-methyl-6,7-dihydro-4H-pyrazolo[1,5-a]pyrazine-5-carboxamide;
N-(5-chloro-2-methyl-4-pyridyl)-3-(2,4-di fluorophenyl)-6-methyl-6,7-dihydro-4H-pyrazolo[1,5-a]pyrazine-5-carboxamide;
N-[(2-chloro-3-fluoro-phenyl)methyl]-3-(2,4-difluorophenyl)-6-methyl-6,7-dihydro-4H-pyrazolo[1,5-a]pyrazine-5-carboxamide;
3-(2,4-difluorophenyl)-N-(5-fluoro-6-methyl-2-pyridyl)-6-methyl-6,7-dihydro-4H-pyrazolo[1,5-a]pyrazine-5-carboxamide;
(6S)-3-(5-fluoro-2-pyridyl)-6-methyl-N-(3,4,5-trifluorophenyl)-6,7-dihydro-4H-pyrazolo[1,5-a]pyrazine-5-carboxamide;
N-(3-chloro-4-fluoro-phenyl)-6-methyl-3-(4-methylpyrazol-1-yl)-6,7-dihydro-4H-pyrazolo[1,5-a]pyrazine-5-carboxamide;
N-(3-chloro-4-fluoro-phenyl)-3-(4-cyanopyrazol-1-yl)-6-methyl-6,7-dihydro-4H-pyrazolo[1,5-a]pyrazine-5-carboxamide;
N-(3-chloro-4-fluoro-phenyl)-3-(4-fluoropyrazol-1-yl)-6-methyl-6,7-dihydro-4H-pyrazolo[1,5-a]pyrazine-5-carboxamide;

N-(3-chloro-4-fluoro-phenyl)-6-methyl-3-(2-oxopyrrolidin-1-yl)-6,7-dihydro-4H-pyrazolo[1,5-a]pyrazine-5-carboxamide;
N-[4-fluoro-3-(trifluoromethyl)phenyl]-6-methyl-3-(2-oxopyrrolidin-1-yl)-6,7-dihydro-4H-pyrazolo[1,5-a]pyrazine-5-carboxamide;
3-cyclopentyl-6-methyl-N-(3,4,5-trifluorophenyl)-6,7-dihydro-4H-pyrazolo[1,5-a]pyrazine-5-carboxamide;
3-cyclopentyl-6-methyl-N-[2-(trifluoromethyl)-4-pyridyl]-6,7-dihydro-4H-pyrazolo[1,5-a]pyrazine-5-carboxamide;
N-(6-chloro-5-fluoro-2-pyridyl)-3-cyclopentyl-6-methyl-6,7-dihydro-4H-pyrazolo[1,5-a]pyrazine-5-carboxamide;
N-(2-cyclopropyl-4-pyridyl)-3-(2,4-difluorophenyl)-6,7-dihydro-4H-pyrazolo[1,5-a]pyrazine-5-carboxamide;
3-(2,4-difluorophenyl)-N-[2-(dimethylamino)-4-pyridyl]-6,7-dihydro-4H-pyrazolo[1,5-a]pyrazine-5-carboxamide;
N-(3-chloro-4-fluoro-phenyl)-3-[2-(methoxymethyl)pyrrolidin-1-yl]-6,7-dihydro-4H-pyrazolo[1,5-a]pyrazine-5-carboxamide;
N-(3-chloro-4-fluoro-phenyl)-3-[3-(methoxymethyl)pyrrolidin-1-yl]-6,7-dihydro-4H-pyrazolo[1,5-a]pyrazine-5-carboxamide;
N-(3-chloro-4-fluoro-phenyl)-3-(3-methoxypyrrolidin-1-yl)-6,7-dihydro-4H-pyrazolo[1,5-a]pyrazine-5-carboxamide;
N-(3-chloro-4-fluoro-phenyl)-3-(4,4-dimethyl-2-oxo-pyrrolidin-1-yl)-6-methyl-6,7-dihydro-4H-pyrazolo[1,5-a]pyrazine-5-carboxamide;
N-(3-chloro-4-fluoro-phenyl)-3-[3-(trifluoromethyl)pyrrolidin-1-yl]-6,7-dihydro-4H-pyrazolo[1,5-a]pyrazine-5-carboxamide;
N-(3-chloro-4-fluoro-phenyl)-3-(3-cyanopyrrolidin-1-yl)-6,7-dihydro-4H-pyrazolo[1,5-a]pyrazine-5-carboxamide;
3-(3-azabicyclo[3.1.0]hexan-3-yl)-N-(3-chloro-4-fluoro-phenyl)-6,7-dihydro-4H-pyrazolo[1,5-a]pyrazine-5-carboxamide;
N-(3-chloro-4-fluoro-phenyl)-3-(3-hydroxy-3-methyl-pyrrolidin-1-yl)-6,7-dihydro-4H-pyrazolo[1,5-a]pyrazine-5-carboxamide;
N-(3-chloro-4-fluoro-phenyl)-3-(2,2-dimethylmorpholin-4-yl)-6,7-dihydro-4H-pyrazolo[1,5-a]pyrazine-5-carboxamide;
N-[2-(difluoromethyl)-4-pyridyl]-3-(2,4-difluorophenyl)-6-methyl-6,7-dihydro-4H-pyrazolo[1,5-a]pyrazine-5-carboxamide;
N-(3-chloro-4-fluoro-phenyl)-3-(8-oxa-3-azabicyclo[3.2.1]octan-3-yl)-6,7-dihydro-4H-pyrazolo[1,5-a]pyrazine-5-carboxamide;
N-(3-chloro-4-fluoro-phenyl)-3-(3-oxomorpholin-4-yl)-6,7-dihydro-4H-pyrazolo[1,5-a]pyrazine-5-carboxamide;
N-(3-chloro-4-fluoro-phenyl)-3-(3-methyl-5-oxo-morpholin-4-yl)-6,7-dihydro-4H-pyrazolo[1,5-a]pyrazine-5-carboxamide;
(6S)-N-[2-(difluoromethyl)-4-pyridyl]-6-methyl-3-(2-oxopyrrolidin-1-yl)-6,7-dihydro-4H-pyrazolo[1,5-a]pyrazine-5-carboxamide;
(6S)-N-(3-chloro-4-fluoro-phenyl)-3-(3,3-difluoropyrrolidin-1-yl)-6-methyl-6,7-dihydro-4H-pyrazolo[1,5-a]pyrazine-5-carboxamide;
(6S)-N-(3-chloro-4-fluoro-phenyl)-3-[trans-2,6-dimethylmorpholin-4-yl]-6-methyl-6,7-dihydro-4H-pyrazolo[1,5-a]pyrazine-5-carboxamide;
(6S)-N-(3-chloro-4-fluoro-phenyl)-3-[cis-2,6-dimethylmorpholin-4-yl]-6-methyl-6,7-dihydro-4H-pyrazolo[1,5-a]pyrazine-5-carboxamide;
(6S)-N-(3-chloro-4-fluoro-phenyl)-3-(4-hydroxy-1-piperidyl)-6-methyl-6,7-dihydro-4H-pyrazolo[1,5-a]pyrazine-5-carboxamide;
(6S)-N-(3-chloro-4-fluoro-phenyl)-6-methyl-3-(3-methyl-2-oxo-imidazolidin-1-yl)-6,7-dihydro-4H-pyrazolo[1,5-a]pyrazine-5-carboxamide;
(6S)-N-(3-chloro-4-fluoro-phenyl)-3-(4-cyano-2-oxo-pyrrolidin-1-yl)-6-methyl-6,7-dihydro-4H-pyrazolo[1,5-a]pyrazine-5-carboxamide;
N-(3-chloro-4-fluoro-phenyl)-3-(4-fluorophenyl)-7-methyl-6,7-dihydro-4H-pyrazolo[1,5-a]pyrazine-5-carboxamide;
(6S)-N-(3-chloro-4,5-difluoro-phenyl)-6-methyl-3-(2-oxopyrrolidin-1-yl)-6,7-dihydro-4H-pyrazolo[1,5-a]pyrazine-5-carboxamide;
(6S)-N-(3-chloro-4-fluoro-phenyl)-3-(4-hydroxy-2-oxo-pyrrolidin-1-yl)-6-methyl-6,7-dihydro-4H-pyrazolo[1,5-a]pyrazine-5-carboxamide;
(6S)-6-methyl-3-(3-oxomorpholin-4-yl)-N-(3,4,5-trifluorophenyl)-6,7-dihydro-4H-pyrazolo[1,5-a]pyrazine-5-carboxamide;
3-(1-acetyl-4-piperidyl)-N-(3-chloro-4-fluoro-phenyl)-6-methyl-6,7-dihydro-4H-pyrazolo[1,5-a]pyrazine-5-carboxamide;
(6S)-N-(3-chloro-4, 5-difluoro-phenyl)-6-methyl-3-(3-oxomorpholin-4-yl)-6,7-dihydro-4H-pyrazolo[1,5-a]pyrazine-5-carboxamide;
(6S)-N-(3-chloro-4-fluoro-phenyl)-6-methyl-3-[4-(methylcarbamoyl)-2-oxo-pyrrolidin-1-yl]-6,7-dihydro-4H-pyrazolo[1,5-a]pyrazine-5-carboxamide;
N-(3-chloro-4-fluoro-phenyl)-6-methyl-3-(2-oxooxazolidin-3-yl)-6,7-dihydro-4H-pyrazolo[1,5-a]pyrazine-5-carboxamide;
(6S)-N-(3-chloro-4-fluoro-phenyl)-3-(4-methoxy-2-oxo-pyrrolidin-1-yl)-6-methyl-6,7-dihydro-4H-pyrazolo[1,5-a]pyrazine-5-carboxamide;
(6S)-N-[3-(difluoromethyl)-4,5-difluoro-phenyl]-6-methyl-3-(2-oxopyrrolidin-1-yl)-6,7-dihydro-4H-pyrazolo[1,5-a]pyrazine-5-carboxamide;
(6S)-3-(4-cyano-2-oxo-pyrrolidin-1-yl)-6-methyl-N-(3,4,5-trifluorophenyl)-6,7-dihydro-4H-pyrazolo[1,5-a]pyrazine-5-carboxamide;
(6S)-3-[(4R)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-3-[(4S)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-N-[2-(difluoromethyl)-4-pyridyl]-6-methyl-3-[2-oxo-4-(trifluoromethyl)pyrrolidin-1-yl]-6,7-dihydro-4H-pyrazolo[1,5-a]pyrazine-5-carboxamide;
(6S)-3-(2-acetyl-7-oxo-2,6-di azaspiro[3.1.0.]octan-6-yl)-N-(3-chloro-4-fluoro-phenyl)-6-methyl-6,7-dihydro-4H-pyrazolo[1,5-a]pyrazine-5-carboxamide;
(6S)-6-methyl-3-(2-methyl-5-oxo-morpholin-4-yl)-N-(3,4,5-trifluorophenyl)-6,7-dihydro-4H-pyrazolo[1,5-a]pyrazine-5-carboxamide;
N-(3-chloro-4-fluoro-phenyl)-3-(2,5-dioxopiperazin-1-yl)-6-methyl-6,7-dihydro-4H-pyrazolo[1,5-a]pyrazine-5-carboxamide;
(6S)-N-(3-chloro-4-fluoro-phenyl)-3-(4,4-dimethyl-2-oxo-imidazolidin-1-yl)-6-methyl-6,7-dihydro-4H-pyrazolo[1, 5-a]pyrazine-5-carboxamide;
(6S)-N-(3-chloro-4-fluoro-phenyl)-3-(3, 6-dioxo-4,7,8,8a-tetrahydro-1H-pyrrolo[1,2-a]pyrazin-2-yl)-6-methyl-6,7-dihydro-4H-pyrazolo[1,5-a]pyrazine-5-carboxamide;

(6S)-6-methyl-3-(4-oxazol-5-yl-2-oxo-pyrrolidin-1-yl)-N-(3,4,5-trifluorophenyl)-6,7-dihydro-4H-pyrazolo[1,5-a]pyrazine-5-carboxamide;

(6S)-6-methyl-3-(3-methylsulfonyl-5-oxo-imidazolidin-1-yl)-N-(3,4,5-trifluorophenyl)-6,7-dihydro-4H-pyrazolo[1,5-a]pyrazine-5-carboxamide;

(6S)-3-(5,5-dimethyl-2-oxo-oxazolidin-3-yl)-6-methyl-N-(3,4,5-trifluorophenyl)-6,7-dihydro-4H-pyrazolo[1,5-a]pyrazine-5-carboxamide;

(6S,7S)-6,7-dimethyl-3-(2-oxopyrrolidin-1-yl)-N-(3,4,5-trifluorophenyl)-6,7-dihydro-4H-pyrazolo[1,5-a]pyrazine-5-carboxamide;

(6S)-6-methyl-3-(6-oxo-5-azaspiro[2.4]heptan-5-yl)-N-(3,4,5-trifluorophenyl)-6,7-dihydro-4H-pyrazolo[1,5-a]pyrazine-5-carboxamide;

(6S)-6-methyl-3-(2-oxo-3-azabicyclo[3.1.0]hexan-3-yl)-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(4-methyl-2-oxo-pyrrolidin-1-yl)-6,7-dihydro-4H-pyrazolo[1,5-a]pyrazine-5-carboxamide;

(6S)-N-(3-chloro-4-fluoro-phenyl)-6-methyl-3-[2-oxo-4-(trifluoromethyl)pyrrolidin-1-yl]-6,7-dihydro-4H-pyrazolo[1,5-a]pyrazine-5-carboxamide;

(6S)-N-(3-chloro-4-fluoro-phenyl)-3-(3-hydroxy-2-oxo-pyrrolidin-1-yl)-6-methyl-6,7-dihydro-4H-pyrazolo[1,5-a]pyrazine-5-carboxamide;

(6S)-N-(3-chloro-4-fluoro-phenyl)-3-(4,4-dimethyl-2-oxo-pyrrolidin-1-yl)-6-methyl-6,7-dihydro-4H-pyrazolo[1,5-a]pyrazine-5-carboxamide;

(6S)-N-[2-(difluoromethyl)-4-pyridyl]-3-(4,4-dim ethyl-2-oxo-pyrrolidin-1-yl)-6-methyl-6,7-dihydro-4H-pyrazolo[1,5-a]pyrazine-5-carboxamide;

(6S)-6-methyl-3-[2-oxo-4-(trifluoromethyl)pyrrolidin-1-yl]-N-(3,4,5-trifluorophenyl)-6,7-dihydro-4H-pyrazolo[1,5-a]pyrazine-5-carboxamide;

(6S)-N-(2-chloro-4-pyridyl)-6-methyl-3-[2-oxo-4-(trifluoromethyl)pyrrolidin-1-yl]-6,7-dihydro-4H-pyrazolo[1,5-a]pyrazine-5-carboxamide;

(6S,7R)-6,7-dimethyl-3-(2-oxopyrrolidin-1-yl)-N-(3,4,5-trifluorophenyl)-6,7-dihydro-4H-pyrazolo[1,5-a]pyrazine-5-carboxamide;

(6S)-3-[(3S)-3-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-(6-chloro-5-fluoro-2-pyridyl)-3-(4,4-dimethyl-2-oxo-pyrrolidin-1-yl)-6-methyl-6,7-dihydro-4H-pyrazolo[1,5-a]pyrazine-5-carboxamide;

(6S)-3-[(3R)-3-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-[6-(difluoromethyl)-5-fluoro-2-pyridyl]-6-methyl-3-(3-oxo-2-azaspiro[4.4]nonan-2-yl)-6,7-dihydro-4H-pyrazolo[1,5-a]pyrazine-5-carboxamide;

(6S)-N-[2-(difluoromethyl)-4-pyridyl]-6-methyl-3-(3-oxo-2-azaspiro[4.4]nonan-2-yl)-6,7-dihydro-4H-pyrazolo[1,5-a]pyrazine-5-carboxamide;

(6S)-6-methyl-3-[2-oxo-4-(pyrimidin-2-yloxymethyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[2-oxo-4-(pyrazol-1-ylmethyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[2-oxo-4-(pyrimidin-2-ylamino)pyrrolidin-1-yl]-N-(3,4,5-trifluorophenyl)-6,7-dihydro-4H-pyrazolo[1,5-a]pyrazine-5-carboxamide;

(6S)-3-[4-[(5-fluoropyrimidin-4-yl)amino]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-[3-(difluoromethyl)-4,5-difluoro-phenyl]-6-methyl-3-(3-oxomorpholin-4-yl)-6,7-dihydro-4H-pyrazolo[1,5-a]pyrazine-5-carboxamide;

(6S)-N-[2-(difluoromethyl)-4-pyridyl]-3-(5, 5-dim ethyl-2-oxo-oxazolidin-3-yl)-6-methyl-6,7-dihydro-4H-pyrazolo[1,5-a]pyrazine-5-carboxamide;

(6S,7S)-6,7-dimethyl-3-(2-oxoimidazolidin-1-yl)-N-(3,4,5-trifluorophenyl)-6,7-dihydro-4H-pyrazolo[1,5-a]pyrazine-5-carboxamide;

(6S,7S)-6,7-dimethyl-3-(3-oxomorpholin-4-yl)-N-(3,4,5-trifluorophenyl)-6,7-dihydro-4H-pyrazolo[1,5-a]pyrazine-5-carboxamide;

(6S)-3-(3-benzoyl-5-oxo-imidazolidin-1-yl)-6-methyl-N-(3,4,5-trifluorophenyl)-6,7-dihydro-4H-pyrazolo[1,5-a]pyrazine-5-carboxamide;

(6S)-N-[3-(difluoromethyl)-4,5-difluoro-phenyl]-3-(5,5-dimethyl-2-oxo-oxazolidin-3-yl)-6-methyl-6,7-dihydro-4H-pyrazolo[1,5-a]pyrazine-5-carboxamide;

(6S)-N-[6-(difluoromethyl)-5-fluoro-2-pyridyl]-3-(5,5-dimethyl-2-oxo-oxazolidin-3-yl)-6-methyl-6,7-dihydro-4H-pyrazolo[1,5-a]pyrazine-5-carboxamide;

(6S)-6-methyl-3-(5-methyl-2-oxo-1,3-oxazinan-3-yl)-N-(3,4,5-trifluorophenyl)-6,7-dihydro-4H-pyrazolo[1,5-a]pyrazine-5-carboxamide;

(6S)-3-(2,4-dioxo-1H-pyrimidin-3-yl)-6-methyl-N-(3,4,5-trifluorophenyl)-6,7-dihydro-4H-pyrazolo[1,5-a]pyrazine-5-carboxamide;

(6S)-3-(2,4-dioxopyrimidin-1-yl)-6-methyl-N-(3,4,5-trifluorophenyl)-6,7-dihydro-4H-pyrazolo[1,5-a]pyrazine-5-carboxamide;

(6S)-6-methyl-3-(5-oxo-3-pyrimidin-2-yl-imidazolidin-1-yl)-N-(3,4,5-trifluorophenyl)-6,7-dihydro-4H-pyrazolo[1,5-a]pyrazine-5-carboxamide;

(6S)-6-methyl-3-[4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(5-methyl-1,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[2-oxo-4-[5-(trifluoromethyl)-1,3,4-oxadiazol-2-yl]pyrrolidin-1-yl]-N-(3,4,5-trifluorophenyl)-6,7-dihydro-4H-pyrazolo[1,5-a]pyrazine-5-carboxamide;

(6S)-6-methyl-3-[2-oxo-4-[5-(trifluoromethyl)-1,2,4-oxadiazol-3-yl]pyrrolidin-1-yl]-N-(3,4,5-trifluorophenyl)-6,7-dihydro-4H-pyrazolo[1,5-a]pyrazine-5-carboxamide;

(6S)-N-[2-(difluoromethyl)-4-pyridyl]-3-(5-fluoropyrimidin-2-yl)-6-methyl-6,7-dihydro-4H-pyrazolo[1,5-a]pyrazine-5-carboxamide;

(6S)-6-methyl-3-[5-(1-methylimidazol-2-yl)-2-oxo-oxazolidin-3-yl]-N-(3,4,5-trifluorophenyl)-6,7-dihydro-4H-pyrazolo[1,5-a]pyrazine-5-carboxamide;

(6S)-6-methyl-3-(2-oxo-4-thiazol-5-yl-pyrrolidin-1-yl)-N-(3,4,5-trifluorophenyl)-6,7-dihydro-4H-pyrazolo[1,5-a]pyrazine-5-carboxamide;

(6S)-6-methyl-3-(2-oxo-4-thiazol-2-yl-pyrrolidin-1-yl)-N-(3,4,5-trifluorophenyl)-6,7-dihydro-4H-pyrazolo[1,5-a]pyrazine-5-carboxamide;

(6S)-6-methyl-3-(2-oxo-1,3-oxazinan-3-yl)-N-(3,4,5-trifluorophenyl)-6,7-dihydro-4H-pyrazolo[1,5-a]pyrazine-5-carboxamide;

(6S)-6-methyl-3-(2-oxohexahydropyrimidin-1-yl)-N-(3,4,5-trifluorophenyl)-6,7-dihydro-4H-pyrazolo[1,5-a]pyrazine-5-carboxamide;

(6S)-3-(5, 5-dimethyl-2-oxo-1,3-oxazinan-3-yl)-6-methyl-N-(3,4,5-trifluorophenyl)-6,7-dihydro-4H-pyrazolo[1,5-a]pyrazine-5-carboxamide;

(6S)-N-(3-chloro-4-fluoro-phenyl)-3-[4-(methoxymethyl)-2-oxo-pyrrolidin-1-yl]-6-methyl-6,7-dihydro-4H-pyrazolo[1,5-a]pyrazine-5-carboxamide;

(6S)-N-(3-chloro-4-fluoro-phenyl)-6-methyl-3-(3-oxo-8-oxa-2-azaspiro[4.5]decan-2-yl)-6,7-dihydro-4H-pyrazolo[1,5-a]pyrazine-5-carboxamide;

6S)-N-(3-chloro-4-fluoro-phenyl)-6-methyl-3-(3-methyl-2-oxo-pyrrolidin-1-yl)-6,7-dihydro-(6S)-N-(3-chloro-4-fluoro-phenyl)-3-[4-(hydroxymethyl)-2-oxo-pyrrolidin-1-yl]-6-methyl-6,7-dihydro-4H-pyrazolo[1,5-a]pyrazine-5-carboxamide;

(6S)-3-[4-(methoxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-(methoxymethyl)-2-oxo-pyrrolidin-1-yl]-6-methyl-N-[2-(trifluoromethyl)-4-pyridyl]-6,7-dihydro-4H-pyrazolo[1,5-a]pyrazine-5-carboxamide;

(6S)-N-(3-chloro-4-fluoro-phenyl)-6-methyl-3-(4-oxo-3,3a,6,6a-tetrahydro-1H-furo[3,4-c]pyrrol-5-yl)-6,7-dihydro-4H-pyrazolo[1,5-a]pyrazine-5-carboxamide;

(6S)-N-(3-chloro-4-fluoro-phenyl)-3-(4-ethyl-2-oxo-pyrrolidin-1-yl)-6-methyl-6,7-dihydro-4H-pyrazolo[1,5-a]pyrazine-5-carboxamide;

(6S)-N-(3-chloro-4-fluoro-phenyl)-6-methyl-3-(8-oxo-2-oxa-7-azaspiro[4.4]nonan-7-yl)-6,7-dihydro-4H-pyrazolo[1,5-a]pyrazine-5-carboxamide;

(6S)-N-(3-chloro-4-fluoro-phenyl)-6-methyl-3-(4-methylsulfonyl-2-oxo-pyrrolidin-1-yl)-6,7-dihydro-4H-pyrazolo[1,5-a]pyrazine-5-carboxamide;

(6S)-N-(3-chloro-4-fluoro-phenyl)-3-(4-hydroxy-2-oxo-1-piperidyl)-6-methyl-6,7-dihydro-4H-pyrazolo[1,5-a]pyrazine-5-carboxamide;

(6S)-6-methyl-3-[4-(methyl sulfonylmethyl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-[[methyl(methyl sulfonyl)amino]methyl]-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-(2-oxopyrrolidin-3-yl)-N-(3,4,5-trifluorophenyl)-6,7-dihydro-4H-pyrazolo[1,5-a]pyrazine-5-carboxamide;

(6S)-6-methyl-3-(2-oxo-4-phenyl-pyrrolidin-1-yl)-N-(3,4,5-trifluorophenyl)-6,7-dihydro-4H-pyrazolo[1,5-a]pyrazine-5-carboxamide;

(6S)-3-[4-(1-hydroxy-1-methyl-ethyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-(4-acetamido-2-oxo-pyrrolidin-1-yl)-N-(3-chloro-4-fluoro-phenyl)-6-methyl-6,7-dihydro-4H-pyrazolo[1,5-a]pyrazine-5-carboxamide;

(6S)-N-(3-chloro-4-fluoro-phenyl)-3-[4-(methanesulfonamido)-2-oxo-pyrrolidin-1-yl]-6-methyl-6,7-dihydro-4H-pyrazolo[1,5-a]pyrazine-5-carboxamide;

(6S)-N-(3-chloro-4-fluoro-phenyl)-6-methyl-3-[4-[methyl(methyl sulfonyl)amino]-2-oxo-pyrrolidin-1-yl]-6,7-dihydro-4H-pyrazolo[1,5-a]pyrazine-5-carboxamide;

(6S)-3-[4-(2,5-di oxopyrrolidin-1-yl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[2-oxo-4-(2-oxopyrrolidin-1-yl)pyrrolidin-1-yl]-N-(3,4,5-trifluorophenyl)-6, 7-dihydro-4H-pyrazolo[1,5-a]pyrazine-5-carboxamide;

N-methyl-N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]oxazole-5-carboxamide;

N-methyl-N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]oxazole-4-carboxamide;

N-methyl-N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]oxazole-2-carboxamide;

(6S)-6-methyl-3-[2-oxo-4-(2-oxooxazolidin-3-yl)pyrrolidin-1-yl]-N-(3,4,5-trifluorophenyl)-6,7-dihydro-4H-pyrazolo[1,5-a]pyrazine-5-carboxamide;

(6S)-6-methyl-3-[2-oxo-4-(3-oxomorpholin-4-yl)pyrrolidin-1-yl]-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(5-methyl-2-oxo-oxazolidin-3-yl)-6,7-dihydro-4H-pyrazolo[1,5-a]pyrazine-5-carboxamide;

(6S)-N-(3-chloro-4-fluoro-phenyl)-6-methyl-3-(3-oxo-5,6,8,8a-tetrahydro-1H-imidazo[5,1-c][1,4]oxazin-2-yl)-6,7-dihydro-4H-pyrazolo[1,5-a]pyrazine-5-carboxamide;

(6S)-6-methyl-3-(3-oxo-5,6,8,8a-tetrahydro-1H-imidazo[5,1-c][1,4]oxazin-2-yl)-N-(3,4,5-trifluorophenyl)-6,7-dihydro-4H-pyrazolo[1,5-a]pyrazine-5-carboxamide;

(6S)-N-(2-chloro-4-pyridyl)-3-(5,5-dimethyl-2-oxo-oxazolidin-3-yl)-6-methyl-6,7-dihydro-4H-pyrazolo[1,5-a]pyrazine-5-carboxamide;

(6S)-3-(5,5-dimethyl-2-oxo-oxazolidin-3-yl)-6-methyl-N-[2-(trifluoromethyl)-4-pyridyl]-6,7-dihydro-4H-pyrazolo[1,5-a]pyrazine-5-carboxamide;

(6S)-N-(3-chloro-4-fluoro-phenyl)-6-methyl-3-(4-methyl-2-oxo-imidazolidin-1-yl)-6,7-dihydro-4H-pyrazolo[1,5-a]pyrazine-5-carboxamide;

(6S)-6-methyl-3-[(4R)-2-oxo-4-phenyl-oxazolidin-3-yl]-N-(3,4,5-trifluorophenyl)-6,7-dihydro-4H-pyrazolo[1,5-a]pyrazine-5-carboxamide;

(6S)-6-methyl-3-[(4S)-2-oxo-4-phenyl-oxazolidin-3-yl]-N-(3,4,5-trifluorophenyl)-6,7-dihydro-4H-pyrazolo[1,5-a]pyrazine-5-carboxamide;

(6S)-6-methyl-3-(2-oxo-4-phenyl-imidazolidin-1-yl)-N-(3,4,5-trifluorophenyl)-6,7-dihydro-4H-pyrazolo[1,5-a]pyrazine-5-carboxamide;

(6S)-3-(4,4-dimethyl-2-oxo-imidazolidin-1-yl)-6-methyl-N-(3,4,5-trifluorophenyl)-6,7-dihydro-4H-pyrazolo[1,5-a]pyrazine-5-carboxamide;

(6S)-6-methyl-3-(5-oxo-4-oxa-6-azaspiro[2.4]heptan-6-yl)-N-(3,4,5-trifluorophenyl)-6,7-dihydro-4H-pyrazolo[1,5-a]pyrazine-5-carboxamide;

(6S)-6-methyl-3-(6-oxo-5-oxa-7-azaspiro[3.4]octan-7-yl)-N-(3,4,5-trifluorophenyl)-6,7-dihydro-4H-pyrazolo[1,5-a]pyrazine-5-carboxamide;

methyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate;

ethyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate;

(6S)-6-methyl-3-(5-methyl-2-oxo-pyrrolidin-3-yl)-N-(3,4,5-trifluorophenyl)-6,7-dihydro-4H-pyrazolo[1,5-a]pyrazine-5-carboxamide;

(6S)-6-methyl-3-[2-(oxazole-2-carbonyl)-7-oxo-2,6-diazaspiro[3.4]octan-6-yl]-N-(3,4,5-trifluorophenyl)-6,7-dihydro-4H-pyrazolo[1,5-a]pyrazine-5-carboxamide;

(6S)-6-methyl-3-(7-oxo-2-pyrimidin-2-yl-2,6-diazaspiro[3.4]octan-6-yl)-N-(3,4,5-trifluorophenyl)-6,7-dihydro-4H-pyrazolo[1,5-a]pyrazine-5-carboxamide;

(6S)-6-methyl-3-(2-oxoindolin-1-yl)-N-(3,4,5-trifluorophenyl)-6,7-dihydro-4H-pyrazolo[1,5-a]pyrazine-5-carboxamide;

(6S)-6-methyl-3-(1-oxoisoindolin-2-yl)-N-(3,4,5-trifluorophenyl)-6,7-dihydro-4H-pyrazolo[1,5-a]pyrazine-5-carboxamide;

(6S)-6-methyl-3-(5-oxo-7H-pyrrolo[3,4-b]pyridin-6-yl)-N-(3,4,5-trifluorophenyl)-6,7-dihydro-4H-pyrazolo[1,5-a]pyrazine-5-carboxamide;

(6S)-3-(5-fluoropyrimidin-2-yl)-6-methyl-N-(3,4,5-trifluorophenyl)-6,7-dihydro-4H-pyrazolo[1,5-a]pyrazine-5-carboxamide;

(6S)-3-[4-(hydroxymethyl)pyrazol-1-yl]-6-methyl-N-(3,4,5-trifluorophenyl)-6,7-dihydro-4H-pyrazolo[1,5-a]pyrazine-5-carboxamide;

(6S)-3-[4-(methoxymethyl)pyrazol-1-yl]-6-methyl-N-(3,4,5-trifluorophenyl)-6,7-dihydro-4H-pyrazolo[1,5-a]pyrazine-5-carboxamide;

(6S)-6-methyl-3-(2-oxo-5-phenyl-oxazolidin-3-yl)-N-(3,4,5-trifluorophenyl)-6,7-dihydro-4H-pyrazolo[1,5-a]pyrazine-5-carboxamide;

(6S)-6-methyl-3-[2-oxo-5-(2-pyridyl)oxazolidin-3-yl]-N-(3,4,5-trifluorophenyl)-6,7-dihydro-4H-pyrazolo[1,5-a]pyrazine-5-carboxamide;

(6S)-6-methyl-3-[2-oxo-5-(4-pyridyl)oxazolidin-3-yl]-N-(3,4,5-trifluorophenyl)-6,7-dihydro-4H-pyrazolo[1,5-a]pyrazine-5-carboxamide;

(6S)-6-methyl-3-[2-oxo-5-(3-pyridyl)oxazolidin-3-yl]-N-(3,4,5-trifluorophenyl)-6,7-dihydro-4H-pyrazolo[1,5-a]pyrazine-5-carboxamide;

(6S)-6-methyl-3-(5-oxazol-4-yl-2-oxo-oxazolidin-3-yl)-N-(3,4,5-trifluorophenyl)-6,7-dihydro-4H-pyrazolo[1,5-a]pyrazine-5-carboxamide;

(6S)-6-methyl-3-[4-(2-methyl oxazol-5-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(2-methyl oxazol-4-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[2-oxo-4-(3-pyridyl)pyrrolidin-1-yl]-N-(3,4,5-trifluorophenyl)-6,7-dihydro-4H-pyrazolo[1,5-a]pyrazine-5-carboxamide;

(6S)-6-methyl-3-(4-oxazol-4-yl-2-oxo-pyrrolidin-1-yl)-N-(3,4,5-trifluorophenyl)-6,7-dihydro-4H-pyrazolo[1,5-a]pyrazine-5-carboxamide;

(6S)-6-methyl-3-[2-oxo-4-(2-pyridyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[2-oxo-4-(4-pyridyl)pyrrolidin-1-yl]-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(2-oxopyrrolidin-1-yl)-6,7-dihydro-4H-pyrazolo[1,5-a]pyrazine-5-carboxamide;

(6S)-6-methyl-3-(2-oxopyrrolidin-1-yl)-N-(3,4,5-trifluorophenyl)-6,7-dihydro-4H-pyrazolo[1,5-a]pyrazine-5-carboxamide;

(6S)-6-methyl-3-(5-methyl-2-oxo-1-piperidyl)-N-(3,4,5-trifluorophenyl)-6,7-dihydro-4H-pyrazolo[1,5-a]pyrazine-5-carboxamide;

(6S)-3-(4-cyano-2-oxo-pyrrolidin-1-yl)-N-[2-(difluoromethyl)-4-pyridyl]-6-methyl-6,7-dihydro-4H-pyrazolo[1,5-a]pyrazine-5-carboxamide;

(6S)-3-[4-cyano-4-(hydroxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-(4-cyano-4-methyl-2-oxo-pyrrolidin-1-yl)-N-[3-(difluoromethyl)-4,5-di fluoro-phenyl]-6-methyl-6,7-dihydro-4H-pyrazolo[1,5-a]pyrazine-5-carboxamide;

(6S)-3-[4-(hydroxymethyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[4-[methyl(pyrimidin-2-yl)amino]-2-oxo-pyrrolidin-1-yl]-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(3-oxomorpholin-4-yl)-6,7-dihydro-4H-pyrazolo[1,5-a]pyrazine-5-carboxamide;

(6S)-6-methyl-3-(2-oxooxazolidin-3-yl)-N-(3,4,5-trifluorophenyl)-6,7-dihydro-4H-pyrazolo[1,5-a]pyrazine-5-carboxamide;

(6S)-N-[2-(difluoromethyl)-4-pyridyl]-6-methyl-3-(3-oxomorpholin-4-yl)-6,7-dihydro-4H-pyrazolo[1,5-a]pyrazine-5-carboxamide;

(6S)-N-(2-chloro-4-pyridyl)-6-methyl-3-(3-oxomorpholin-4-yl)-6,7-dihydro-4H-pyrazolo[1,5-a]pyrazine-5-carboxamide;

(6S)-6-methyl-3-(2-oxoimidazolidin-1-yl)-N-(3,4,5-trifluorophenyl)-6,7-dihydro-4H-pyrazolo[1,5-a]pyrazine-5-carboxamide;

(6S)-N-(3-chloro-4-fluoro-phenyl)-3-(2,2-dimethyl-5-oxo-morpholin-4-yl)-6-methyl-6,7-dihydro-4H-pyrazolo[1,5-a]pyrazine-5-carboxamide;

(6S)-6-methyl-3-[(3S)-3-methyl-5-oxo-morpholin-4-yl]-N-(3,4,5-trifluorophenyl)-6,7-dihydro-4H-pyrazolo[1,5-a]pyrazine-5-carboxamide;

(6S)-N-[3-(difluoromethyl)-4,5-difluoro-phenyl]-6-methyl-3-(2-oxoimidazolidin-1-yl)-6,7-dihydro-4H-pyrazolo[1,5-a]pyrazine-5-carboxamide;

(6S)-3-(3-acetyl-5-oxo-imidazolidin-1-yl)-6-methyl-N-(3,4,5-trifluorophenyl)-6,7-dihydro-4H-pyrazolo[1,5-a]pyrazine-5-carboxamide;

(6S)-N-[2-(difluoromethyl)-4-pyridyl]-3-(2,2-dimethyl-5-oxo-morpholin-4-yl)-6-methyl-6,7-dihydro-4H-pyrazolo[1,5-a]pyrazine-5-carboxamide;

(6S)-3-[(4R)-4-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4S)-4-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4S)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4R)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-[2-(difluoromethyl)-4-pyridyl]-3-[(4S)-4-methoxy-2-oxo-pyrrolidin-1-yl]-6-methyl-6,7-dihydro-4H-pyrazolo[1,5-a]pyrazine-5-carboxamide;

(6S)-6-methyl-3-[(4S)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;

(6S)-3-[(4S)-4-(5-fluoropyrimidin-2-yl)oxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-[2-hydroxyethyl(methyl)carbamoyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-[(2-hydroxy-1,1-dimethyl-ethyl)carbamoyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[4-(morpholine-4-carbonyl)-2-oxo-pyrrolidin-1-yl]-N-(3,4,5-trifluorophenyl)-6,7-dihydro-4H-pyrazolo[1,5-a]pyrazine-5-carboxamide;

(6S)-3-[4-[(3S)-3-hydroxypyrrolidine-1-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-[(3R)-3-hydroxypyrrolidine-1-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-(3-hydroxyazetidine-1-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-(dimethylcarbamoyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[2-oxo-4-(pyrrolidine-1-carbonyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(oxazol-2-ylcarbamoyl)-2-oxo-pyrrolidin-1-yl]-N-(3,4,5-trifluorophenyl)-6,7-dihydro-4H-pyrazolo[1,5-a]pyrazine-5-carboxamide;

(6S)-3-[4-(2,2-dimethylmorpholine-4-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[4-[(2R)-2-methylmorpholine-4-carbonyl]-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-[(2S)-2-methylmorpholine-4-carbonyl]-2-oxo-pyrrolidin-1-yl]-N-(3,4,5-trifluorophenyl)-6,7-dihydro-4H-pyrazolo[1,5-a]pyrazine-5-carboxamide;

(6S)-3-[4-[trans-2,6-dimethylmorpholine-4-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-[cis-2,6-dimethylmorpholine-4-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-(3,3-difluoropyrrolidine-1-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[4-[methyl(oxazol-2-yl)carbamoyl]-2-oxo-pyrrolidin-1-yl]-N-(3,4,5-trifluorophenyl)-6,7-dihydro-4H-pyrazolo[1,5-a]pyrazine-5-carboxamide;

(6S)-3-[4-(3,3-difluoropyrrolidine-1-carbonyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-(4,4-difluoropiperidine-1-carbonyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3[4-methyl-4-(morpholine-4-carbonyl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-methyl-4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-methyl-4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-methyl-4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-methyl-4-(5-methyl-11,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[(2S)-2-oxazol-5-yl-5-oxo-morpholin-4-yl]-N-(3,4,5-trifluorophenyl)-6,7-dihydro-4H-pyrazolo[1,5-a]pyrazine-5-carboxamide;

(6S)-6-methyl-3-[5-(3-methyl-1,2,4-oxadiazol-5-yl)-2-oxo-oxazolidin-3-yl]-N-(3,4,5-trifluorophenyl)-6,7-dihydro-4H-pyrazolo[1,5-a]pyrazine-5-carboxamide;

(6S)-3-[5-(6-chloro-3-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide;

(6S)-3-[5-(5-fluoro-2-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide;

(6S)-3-[5-(6-fluoro-2-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide;

(6S)-6-methyl-3-[4-(1-methylpyrazol-4-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-(2-oxo-4-pyrimidin-5-yl-pyrrolidin-1-yl)-N-(3,4,5-trifluorophenyl)-6,7-dihydro-4H-pyrazolo[1,5-a]pyrazine-5-carboxamide;

(6S)-3-[4-[(5-fluoropyrimidin-2-yl)amino]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[(4R)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;

(6S)-3-[(3R,4R)-3,4-dihydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-(3-hydroxy-4,4-dimethyl-2-oxo-pyrrolidin-1-yl)-6-methyl-N-(3,4,5-trifluorophenyl)-6,7-dihydro-4H-pyrazolo[1,5-a]pyrazine-5-carboxamide;

(6S)-6-methyl-3-(2-oxo-3H-pyrrolo[3,2-c]pyridin-1-yl)-N-(3,4,5-trifluorophenyl)-6,7-dihydro-4H-pyrazolo[1,5-a]pyrazine-5-carboxamide;

(6S)-6-methyl-3-(6-oxo-4,7-dihydropyrazolo[1,5-a]pyrazin-5-yl)-N-(3,4,5-trifluorophenyl)-6,7-dihydro-4H-pyrazolo[1,5-a]pyrazine-5-carboxamide;

(6S)-3-(3-cyano-2-methyl-5-oxo-pyrrolidin-1-yl)-6-methyl-N-(3,4,5-trifluorophenyl)-6,7-dihydro-4H-pyrazolo[1,5-a]pyrazine-5-carboxamide;

(6S)-3-(5-hydroxy-2-oxo-1,3-oxazinan-3-yl)-6-methyl-N-(3,4,5-trifluorophenyl)-6,7-dihydro-4H-pyrazolo[1,5-a]pyrazine-5-carboxamide;

(6S)-6-methyl-3-(7-oxo-6-azaspiro[3.4]octan-6-yl)-N-(3,4,5-trifluorophenyl)-6,7-dihydro-4H-pyrazolo[1,5-a]pyrazine-5-carboxamide;

(6S)-3-(8-hydroxy-7-oxo-6-azaspiro[3.4]octan-6-yl)-6-methyl-N-(3,4,5-trifluorophenyl)-6,7-dihydro-4H-pyrazolo[1,5-a]pyrazine-5-carboxamide;

(6S)-3-(7-hydroxy-6-oxo-5-azaspiro[2.4]heptan-5-yl)-6-methyl-N-(3,4,5-trifluorophenyl)-6,7-dihydro-4H-pyrazolo[1,5-a]pyrazine-5-carboxamide;

(6S)-6-methyl-3-(6-methyl-2-oxo-1,3-oxazinan-3-yl)-N-(3,4,5-trifluorophenyl)-6,7-dihydro-4H-pyrazolo[1,5-a]pyrazine-5-carboxamide;

(6S)-6-methyl-3-(4-methyl-2-oxo-1,3-oxazinan-3-yl)-N-(3,4,5-trifluorophenyl)-6,7-dihydro-4H-pyrazolo[1,5-a]pyrazine-5-carboxamide;

(6S)-3-[(3S,4R)-3,4-dihydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(3S,4R)-3-hydroxy-2-oxo-4-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[5-methyl-5-(morpholine-4-carbonyl)-2-oxo-1,3-oxazinan-3-yl]-N-(3,4,5-trifluorophenyl)-6,7-dihydro-4H-pyrazolo[1,5-a]pyrazine-5-carboxamide;

(6S)-3-[(2R,3R,4S)-4-hydroxy-2-methyl-5-oxo-3-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-(2-oxo-4-pyrimidin-2-yl-pyrrolidin-1-yl)-N-(3,4,5-trifluorophenyl)-6,7-dihydro-4H-pyrazolo[1,5-a]pyrazine-5-carboxamide;

(6S)-3-(3-hydroxy-2-oxo-4-phenyl-pyrrolidin-1-yl)-6-methyl-N-(3,4,5-trifluorophenyl)-6,7-dihydro-4H-pyrazolo[1,5-a]pyrazine-5-carboxamide;

(6S)-3-[(5S)-5-methoxy-2-oxo-1,3-oxazinan-3-yl]-6-methyl-N-(3,4,5trifluorophenyl)-6,7-dihydro-4H-pyrazolo[1,5-a]pyrazine-5-carboxamide; and (6S)-3-[(5R)-5-methoxy-2-oxo-1,3-oxazinan-3-yl]-6-methyl-N-(3,4,5trifluorophenyl)-6,7-dihydro-4H-pyrazolo[1,5-a]pyrazine-5-carboxamide;

or pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^4$ are as defined above unless otherwise indicated. Furthermore, and unless explicitly otherwise stated, all reactions, reaction conditions, abbreviations and symbols have the meanings well known to a person of ordinary skill in organic chemistry.

Scheme 1:

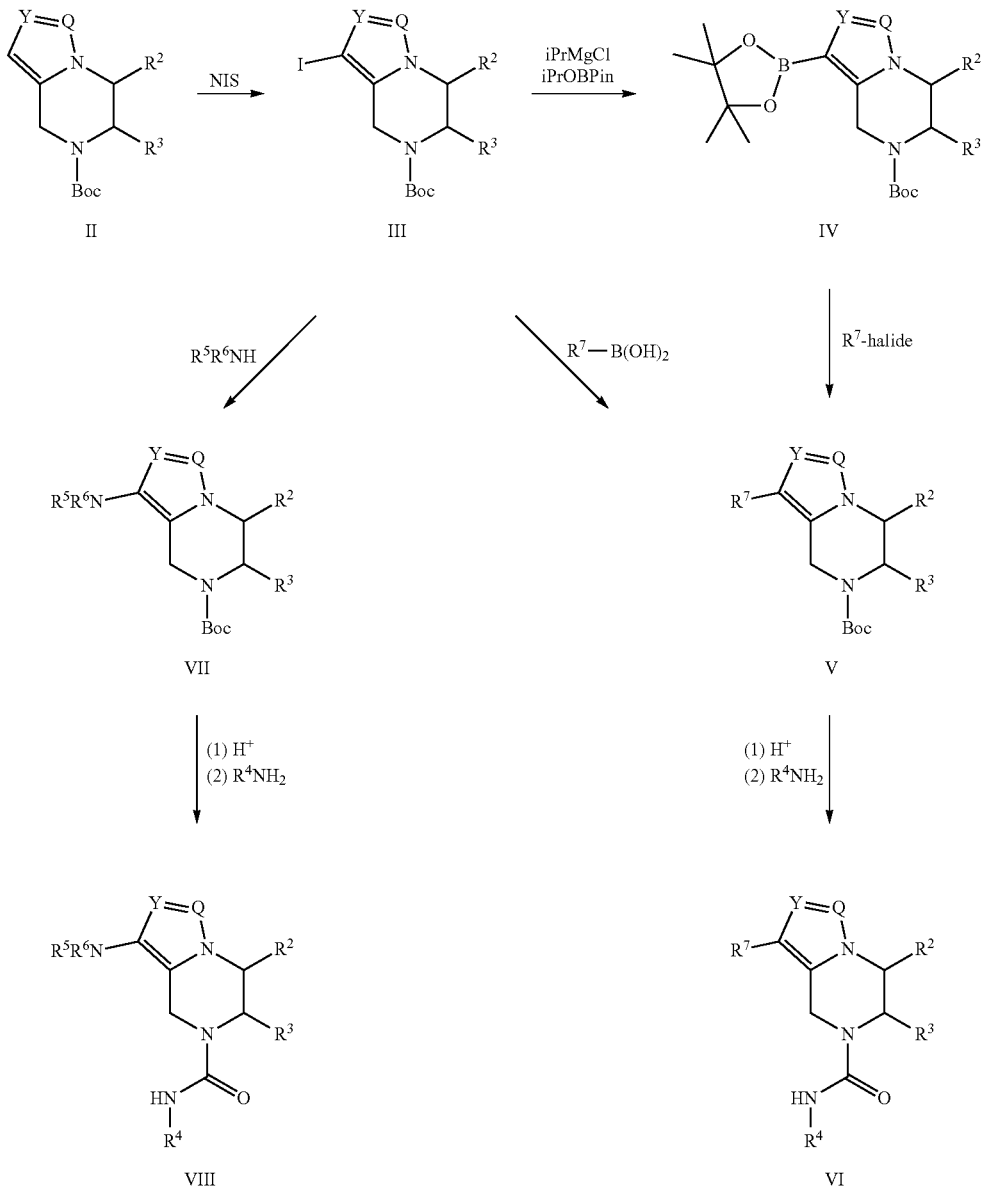

$R^5$ and $R^6$ are independently selected from H, $C_{1-6}$alkyl, heterocyclyl, $C_{3-7}$cycloalkyl, $C_{1-6}$alkylcarbonyl, heterocyclylcarbonyl and $C_{3-7}$cycloalkylcarbonyl; or $R^5$ and $R^6$ together with the nitrogen atom they are attached to form a 3-7 membered heterocyclyl, such as, but not limited to, pyrrolidinyl, piperidinyl, oxopyrrolidinyl, morpholinyl and oxomorpholinyl. $R^7$ is aryl or heteroaryl.

As depicted in Scheme 1, the synthesis of compounds of the present invention started from bicycle II, which was treated with iodinating reagents, such as N-iodosuccinimide, to give iodide III. Bicycle II was brominated with suitable brominating reagents, such as NBS, to give corresponding bromide, which was used in following reactions exemplified with iodide III. Palladium catalyzed Suzuki-Miyaura reaction between iodide III and boronic acid $R^7$—$B(OH)_2$ affords intermediate V (Buchwald, S. L. et al. *Acc Chem Res.* 2008, 41, 1461). Intermediated V was prepared from boronic acid pinacol ester IV and desired halide, $R^1$-halide, while boronic acid pinacol ester IV was prepared according to a known procedure (Bethel, P. A. et al. *Tetrahedron* 2012, 68, 5434) by reacting iodide III with Grignard reagent, such as iPrMgCl, and boronic ester, such as iPrOBPin. Deprotection of intermediate V in acidic conditions, such as HCl in EtOAc and TFA in DCM, followed by urea formation with amine $R^4NH_2$ in the presence of a phosgene equivalent, such as triphosgene and carbonyldiimidazole, affords final compound VI. In the aforementioned urea formation reaction, a suitable isocyanate or phenyl carbamate was used (Padiya, K. J. et al. *Org Lett.* 2012, 14, 2814 and references cited therein). On the other hand, copper catalyzed coupling reaction of iodide III with amine or amide $R^5R^6NH$ afforded intermediate VII, which is then converted into final compound VIII by employing suitable urea formation methods mentioned above.

Scheme 2:

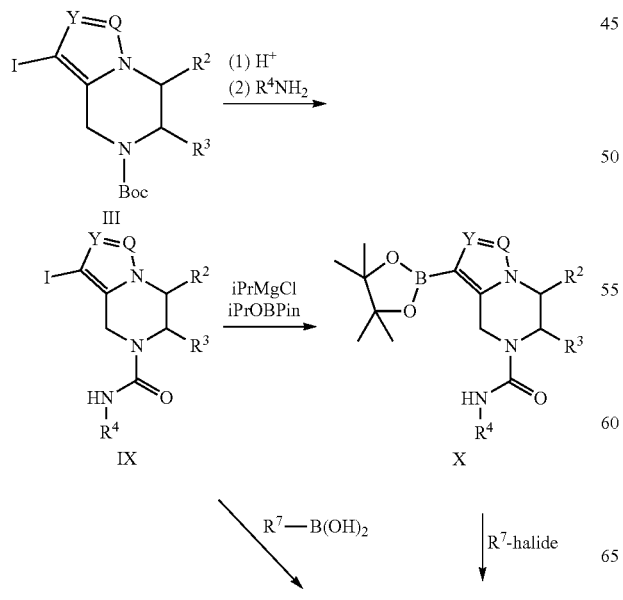

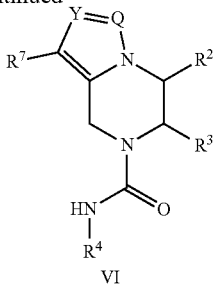

VI $R^7$ is aryl or heteroaryl.

Alternatively, compound VI was prepared according to synthetic route depicted in Scheme 2. That is, iodide III is first converted into urea IX by employing suitable urea formation methods mentioned above. Urea IX then reacted with boronic acid $R^7$—$B(OH)_2$ to give compound VI in the presence of palladium catalyst, or was converted to boronic ester X by known procedure mentioned above. Suzuki-Miyaura reaction of X with desired halide afforded compound VI.

This invention also relates to a process for the preparation of a compound of formula (I) comprising the reaction of:
(a) the reaction of a compound of formula (V),

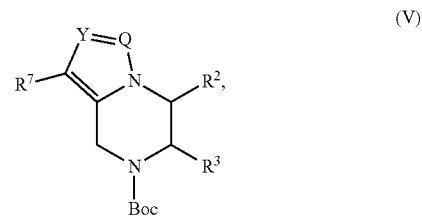

(V)

with an acid followed by urea formation with amine $R^4NH_2$ in the presence of a phosgene equivalent;
(b) the reaction of a compound of formula (VII),

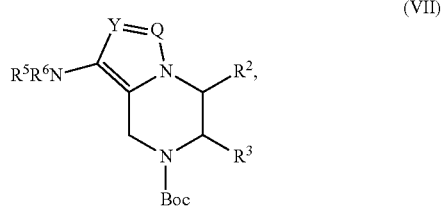

(VII)

with an acid followed by urea formation with amine $R^4NH_2$ in the presence of a phosgene equivalent;
(c) the reaction of a compound of formula (IX),

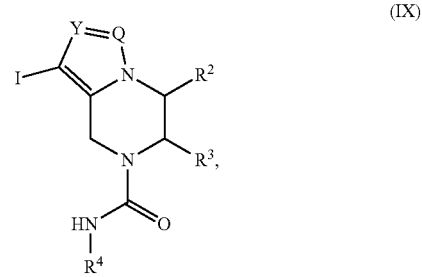

(IX)

with $R^7$—$B(OH)_2$, (d) the reaction of a compound of formula (X),

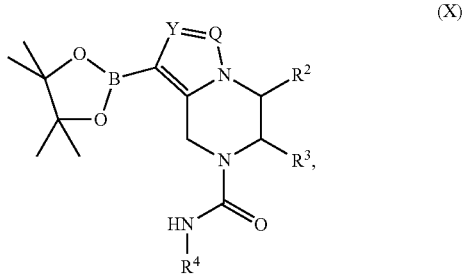

(X)

with halide via Suzuki-Miyaura reaction;
or wherein $R^2$, $R^3$, $R^4$ are defined above; $R^5$ and $R^6$ are independently selected from H, $C_{1-6}$alkyl, $C_{1-6}$heteroalkyl, $C_{3-6}$cycloalkyl, $C_{1-6}$alkylcarbonyl, $C_{1-6}$heteroalkylcarbonyl, $C_{3-6}$cycloalkylcarbonyl and $C_{3-6}$heterocycloalkylcarbonyl; or $R^5$ and $R^6$ together with the nitrogen atom they are attached to form a 3-7 membered heterocyclyl, such as, but not limited to, pyrrolidinyl, piperidinyl, oxopyrrolidinyl, morpholinyl and oxomorpholinyl; $R^7$ is aryl or heteroaryl.

In step (a) and (b), the acid can be for example HCl in EtOAc and TFA in DCM; phosgene equivalent can be for example triphosgene and carbonyldiimidazole.

In step (d), the halide can be $R^7$-halide.

A compound of formula (I) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to the suppression of serum HBV DNA levels, or HBeAg seroconversion to HBeAb, or HBsAg loss, or normalization of alanine aminotransferase levels and improvement in liver histology. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 mg to 1000 mg of the compound of the invention compounded with about 30 mg to 90 mg anhydrous lactose, about 5 mg to 40 mg sodium croscarmellose, about 5 mg to 30 mg polyvinylpyrrolidone (PVP) K30, and about 1 mg to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I), or a stereoisomer or pharmaceutically acceptable salt thereof. In a further embodiment includes a pharmaceutical composition comprising a compound of formula (I), or a stereoisomer or pharmaceutically acceptable salt thereof, together with a pharmaceutically acceptable carrier or excipient.

Indications and Methods of Treatment

The compounds of the invention can inhibit HBV's DNA synthesis and reduce HBV DNA levels. Accordingly, the compounds of the invention are useful for the treatment or prophylaxis of HBV infection.

The invention relates to the use of a compound of formula (I) for the treatment or prophylaxis of HBV infection.

The use of a compound of formula (I) for the preparation of medicaments useful in the treatment or prophylaxis diseases that are related to HBV infection is an object of the invention.

The invention relates in particular to the use of a compound of formula (I) for the preparation of a medicament for the treatment or prophylaxis of HBV infection.

Another embodiment includes a method for the treatment or prophylaxis of HBV infection which method comprises administering an effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations used herein are as follows:
DIPEA: N,N-diisopropylethylamine
DCM: dichloromethane
EA or EtOAc: ethyl acetate
$EC_{50}$: half maximal effective concentration
EDCI: 1-ethyl-3-(3-dimethylaminopropyl)carbodiimide
HATU: 1-[bis(dimethylamino)methylene]-1H-1,2,3-triazolo[4,5-b]pyridinium 3-oxid hexafluorophosphate
HOBT: hydroxybenzotriazole
HPLC: high performance liquid chromatography
iPrOBPin: 2-isopropyl-4,4,5,5-tetramethyl-[1,3,2]dioxaborolane
LCMS liquid chromatography—mass spectrometry
min(s): minute(s)
MS: mass spectrometry
MsCl: methanesulfonyl chloride
NBS: N-bromosuccinimide
NIS: N-iodosuccinimide
PE: petroleum ether
prep-HPLC: preparative high performance liquid chromatography
prep-TLC: preparative thin layer chromatography
SFC: supercritical fluid chromatography
TEA: triethylamine
pgRNA: pre-genomic RNA
qPCR: quantitative polymerase chain reaction
v/v volume ratio General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 μm, OBD™ 30×100 mm) column or SunFire™ Prep-C18 (5 μm, OBD' 30×100 mm) column. Waters AutoP purification System (Column: XBridge™ Prep-C18, 30×100 mm, Sample Manager 2767, Pump 2525, Detector: Micromass ZQ and UV 2487, solvent system: acetonitrile and 0.1% ammonium hydroxide in water). For SFC chiral separation, intermediates were separated by chiral column (Daicel chiralpak IC, 5 μm, 30×250 mm) using Mettler Toledo SFC-Multigram III system, solvent system: 95% $CO_2$ and 5% IPA (0.5% TEA in IPA), back pressure 100bar, detection UV@ 254 nm.

LC/MS spectra of compounds were obtained using a LC/MS (Waters™ Alliance 2795-Micromass ZQ), LC/MS conditions were as follows (running time 6 mins):

Acidic condition: A: 0.1% formic acid in $H_2O$; B: 0.1% formic acid in acetonitrile;

Basic condition: A: 0.1% $NH_3.H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz.

The microwave assisted reactions were carried out in a Biotage Initiator Sixty microwave synthesizer.

All reactions involving air-sensitive reagents were performed under an argon atmosphere. Reagents were used as received from commercial suppliers without further purification unless otherwise noted.

The following examples are intended to illustrate the meaning of the present invention but should by no means represent a limitation within the meaning of the present invention:

PREPARATIVE EXAMPLES

The invention will be more fully understood by reference to the following examples. They should not, however, be construed as limiting the scope of the invention.

Example 1

3-(4-fluorophenyl)-N-phenyl-6,7-dihydro-4H-pyrazolo[1,5-a]pyrazine-5-carboxamide

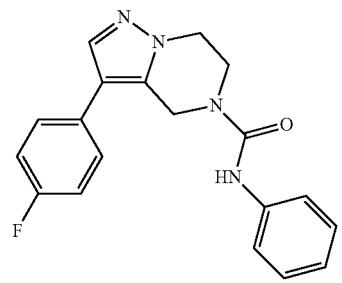 [SMILES: O=C(Nc1ccccc1)N1CCn2ncc(-c3ccc(F)cc3)c2C1]

The title compound was prepared according to following scheme:

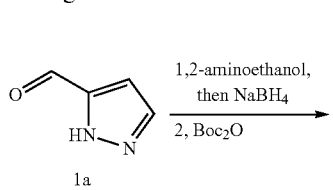

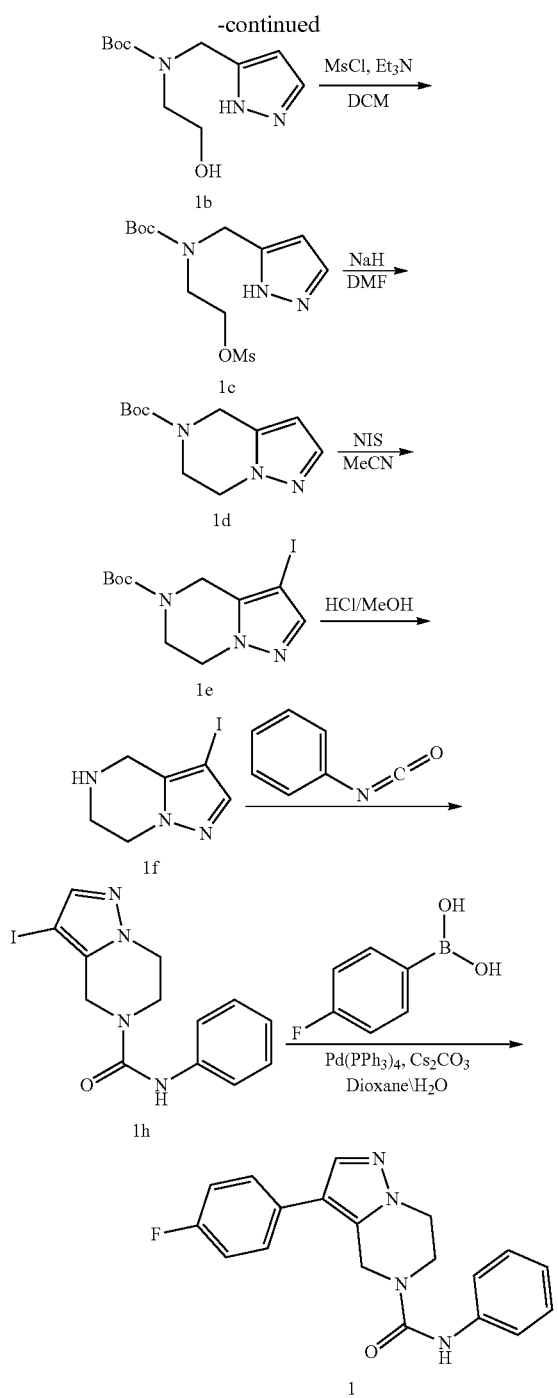

Step 1: Preparation of tert-butyl N-(2-hydroxyethyl)-N-(1H-pyrazol-5-ylmethyl)carbamate (compound 1b)

To a solution of 1H-pyrazole-5-carbaldehyde (compound 1a, 54.0 g, 562.5 mmol) in MeOH (300 mL) was added 2-aminoethanol (41.2 g, 675 mmol), and the reaction mixture was stirred at 25° C. for 1 hour. NaBH$_4$ (25.9 g, 675.0 mmol) was then added at 0° C. and the reaction mixture was stirred for another 1 hour. H$_2$O (300 mL) and Boc$_2$O (147.1 g, 675.0 mmol) were added to the reaction mixture, then the resulting mixture was stirred at room temperature for 12 hours, and extracted with EtOAc (600 mL). The organic layer was dried over Na$_2$SO$_4$, filtered and concentrated. The residue was purified by column chromatography (eluting with 20%~50% EtOAc in petroleum ether) to afford compound 1b (80 g) as a colorless oil. LCMS (M+H$^+$): 320.

Step 2: Preparation of 2-[tert-butoxycarbonyl(1H-pyrazol-5-ylmethyl)amino]ethyl methanesulfonate (compound 1c)

To a solution of tert-butyl N-(2-hydroxyethyl)-N-(1H-pyrazol-5-ylmethyl)carbamate (compound 1b, 80.0 g, 117.2 mmol) and Et$_3$N (100.5 g, 995.6 mmol) in DCM (800 mL) was added MsCl (57.3 g, 497.8 mmol) slowly at 0° C. The resulting mixture was stirred at room temperature for 2 hours, washed with water (500 mL), brine (500 mL) and dried over Na$_2$SO$_4$. The organic layer was concentrated to afford compound 1c (100 g, crude), which was used directly in next step.

Step 3: Preparation of tert-butyl 6,7-dihydro-4H-pyrazolo[1,5-a]pyrazine-5-carboxylate (compound 1d)

To a solution of 2-[tert-butoxycarbonyl(1H-pyrazol-5-ylmethyl)amino]ethyl methanesulfonate (compound 1c, 100.0 g, 313.4 mmol) in DMF (1000 mL) was added NaH (15.0 g, 376.2 mmol) in portions at 0° C. The resulting mixture was stirred at room temperature for 12 hours, poured into water (2000 mL) and extracted with EtOAc (1000 mL) twice. The combined organic layer was dried over Na$_2$SO$_4$, and then concentrated to afford compound 1d (18.0 g). LCMS (M+H$^+$): 224.

Step 4: Preparation of tert-butyl 3-iodo-6,7-dihydro-4H-pyrazolo[1,5-a]pyrazine-5-carboxylate (compound 1e)

To a solution of tert-butyl 6,7-dihydro-4H-pyrazolo[1,5-a]pyrazine-5-carboxylate (compound 1d, 3.3 g, 14.8 mmol) in CH$_3$CN (40 mL) was added NIS (5.0 g, 22.1 mmol) slowly. The reaction mixture was stirred at room temperature for 16 hours and then diluted with EtOAc (50 mL), and washed with brine (50 mL). The organic layer was dried over Na$_2$SO$_4$ and concentrated. The residue was purified by column chromatography (eluting with 10%~80% EtOAc in petroleum ether) to afford compound 1e (4.8 g) as a white solid. LCMS (M+H$^+$): 350. $^1$H NMR (400 MHz, chloroform-d) δ ppm 7.53 (s, 1 H), 4.53 (br, 2 H), 4.20 (t, J=5.27 Hz, 2 H), 3.89 (t, J=5.14 Hz, 2 H), 1.53 (s, 9 H).

Step 5: Preparation of 3-iodo-4,5,6,7-tetrahydropyrazolo[1,5-a]pyrazine (compound 1f)

A solution of tert-butyl 3-iodo-6,7-dihydro-4H-pyrazolo[1,5-a]pyrazine-5-carboxylate (compound 1e, 4.2 g, 12 mmol) in HCl/MeOH (30 mL) was stirred at room temperature for 3 hours.

The reaction mixture was concentrated to afford compound 1f (4 g) in HCl salt as a slight yellow solid. LCMS (M+H$^+$): 250.

Step 6: Preparation of 3-iodo-N-phenyl-6,7-dihydro-4H-pyrazolo[1,5-a]pyrazine-5-carboxamide (compound 1h)

To a solution of 3-iodo-4,5,6,7-tetrahydropyrazolo[1,5-a]pyrazine (compound 1f, 4 g, 14 mmol) in DCM (40 mL) was added isocyanatobenzene (2.5 g, 21 mmol) and Et$_3$N (4.25 g, 42 mmol). The reaction mixture was stirred at room temperature for 1 hour, and then concentrated in vacuo. The residue was purified by column chromatography (eluting with 20%~50% EtOAc in petroleum ether) to afford compound 1h as a white solid (4.8 g). LCMS (M+H$^+$): 369.

Step 7: Preparation of 3-(4-fluorophenyl)-N-phenyl-6,7-dihydro-4H-pyrazolo[1,5-a]pyrazine-5-carboxamide (Example 1)

To a solution of 3-iodo-N-phenyl-6,7-dihydro-4H-pyrazolo[1,5-a]pyrazine-5-carboxamide (compound 1h, 0.1 g, 0.3 mmol) in dioxane/water (10 mL, 10:1, v/v) were added (4-fluorophenyl)boronic acid (40 mg, 0.3 mmol), Pd(PPh$_3$)$_4$ (10 mg, 0.1 mmol) and Cs$_2$CO$_3$ (195 mg, 0.6 mmol). The reaction mixture was stirred at 70° C. for 16 hours under nitrogen and then concentrated in vacuo to afford the crude product, which was purified by prep-HPLC to afford Example 1 as a white solid. LCMS (M+H$^+$): 337. $^1$H NMR (400 MHz, chloroform-d) δ ppm 7.70 (s, 1H), 7.40-7.30 (m, 6H), 7.17-7.08 (m, 3H), 6.45 (br. s, 1H), 4.88 (s, 2H), 4.37 (t, J=5.3 Hz, 2H), 4.05 (t, J=5.4 Hz, 2H).

Example 2

N,3-diphenyl-6,7-dihydro-4H-pyrazolo[1,5-a]pyrazine-5-carboxamide

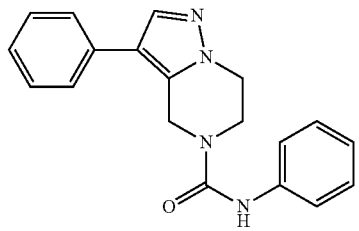 [SMILES: O=C(Nc1ccccc1)N1CCn2ncc(-c3ccccc3)c2C1]

Preparation of Example 2

The title compound was prepared in analogy to the preparation of Example 1 by using phenylboronic acid instead of (4-fluorophenyl)boronic acid. Example 2 was obtained as a white solid (30 mg). LCMS (M+H$^+$): 319. $^1$H NMR (400 MHz, DMSO-d$_6$) δ ppm 8.90 (s, 1H), 7.85 (s, 1H), 7.51-7.38 (m, 6H), 7.30-7.20 (m, 3H), 6.97 (m, 1H), 4.95 (s, 2H), 4.24 (m, 2H), 4.01 (m, 2H).

Example 3

3-(3-fluorophenyl)-N-phenyl-6,7-dihydro-4H-pyrazolo[1,5-a]pyrazine-5-carboxamide

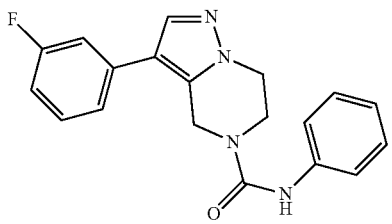 [SMILES: O=C(Nc1ccccc1)N1CCn2ncc(-c3cccc(F)c3)c2C1]

Preparation of Example 3

The title compound was prepared in analogy to the preparation of Example 1 by using (3-fluorophenyl)boronic acid instead of (4-fluorophenyl)boronic acid. Example 3 was obtained as a white solid. LCMS (M+H$^+$): 337. 1H NMR (400 MHz, chloroform-d) δ ppm 7.75 (s, 1H), 7.46-7.31 (m, 5H), 7.18-6.97 (m, 4H), 6.47 (s, 1H), 4.91 (s, 2H), 4.37 (t, J=5.3 Hz, 2H), 4.06 (t, J=5.4 Hz, 2H).

Example 4

3-(3-chlorophenyl)-N-phenyl-6,7-dihydro-4H-pyrazolo pyrazine-5-carboxamide

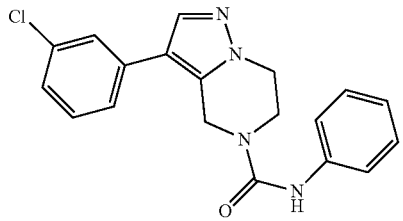 [SMILES: O=C(Nc1ccccc1)N1CCn2ncc(-c3cccc(Cl)c3)c2C1]

Preparation of Example 4

The title compound was prepared in analogy to the preparation of Example 1 by using (3-chlorophenyl)boronic acid instead of (4-fluorophenyl)boronic acid. Example 4 was obtained as a white solid. LCMS (M+H$^+$): 353. $^1$H NMR (400 MHz, chloroform-d) δ ppm 7.75 (s, 1H), 7.41-7.29 (m, 7H), 7.25 (d, J=7.5 Hz, 1H), 7.13 (d, J=6.8 Hz, 1H), 6.48 (s, 1H), 4.91 (s, 2H), 4.38 (t, J=5.3 Hz, 2H), 4.06 (t, J=5.4 Hz, 2H).

Example 5

N-phenyl-3-[3-(trifluoromethyl)phenyl]-6,7-dihydro-4H-pyrazolo[1,5-a]pyrazine-5-carboxamide

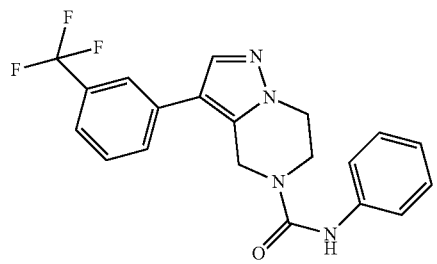 [SMILES: O=C(Nc1ccccc1)N1CCn2ncc(-c3cccc(C(F)(F)F)c3)c2C1]

Preparation of Example 5

The title compound was prepared in analogy to the preparation of Example 1 by using (3-trifluorophenyl)boronic acid instead of (4-fluorophenyl)boronic acid. Example 5 was obtained as a white solid. LCMS (M+H$^+$): 387. $^1$H NMR (400 MHz, CD$_3$OD) δ ppm 7.89 (s, 1H), 7.79-7.71 (m, 2H), 7.69-7.56 (m, 2H), 7.38 (d, J=8.0 Hz, 2H), 7.29 (t, J=7.9 Hz, 2H), 7.11-7.03 (m, 1H), 6.47 (s, 1H), 5.03 (s, 2H), 4.33 (t, J=5.4 Hz, 2H), 4.12 (t, J=5.3 Hz, 2H).

Example 6

3-(2-fluorophenyl)-N-phenyl-6,7-dihydro-4H-pyrazolo[1,5-a]pyrazine-5-carboxamide

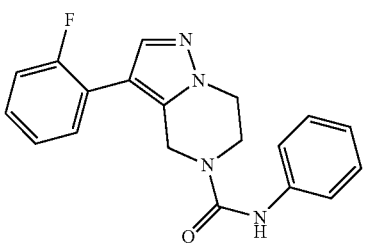 [SMILES: O=C(Nc1ccccc1)N1CCn2ncc(-c3ccccc3F)c2C1]

Preparation of Example 6

The title compound was prepared in analogy to the preparation of Example 1 by using (2-fluorophenyl)boronic acid instead of (4-fluorophenyl)boronic acid. Example 6 was obtained as a white solid. LCMS (M+H⁺): 337. ¹H NMR (400 MHz, chloroform-d) □□ ppm 7.76 (s, 1H), 7.35 (m, 6H), 7.26-7.16 (m, 2H), 7.11 (t, J=6.9 Hz, 1H), 6.47 (s, 1H), 4.81 (s, 2H), 4.40 (t, J=5.4 Hz, 2H), 4.09 (t, J=5.4 Hz, 2H).

Example 7

3-(2-chlorophenyl)-N-phenyl-6,7-dihydro-4H-pyrazolo[1,5-a]pyrazine-5-carboxamide

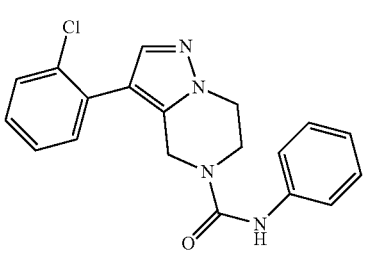 [SMILES: O=C(Nc1ccccc1)N1CCn2ncc(-c3ccccc3Cl)c2C1]

Preparation of Example 7

The title compound was prepared in analogy to the preparation of Example 1 by using (2-chlorophenyl)boronic acid instead of (4-fluorophenyl)boronic acid. Example 7 was obtained as a white solid. LCMS (M+H⁺): 353. ¹H NMR (400 MHz, chloroform-d) δ ppm 7.70 (s, 1H), 7.55-7.49 (m, 1H), 7.38-7.29 (m, 7H), 7.11 (d, J=5.8 Hz, 1H), 6.45 (br. s, 1H), 4.74 (s, 2H), 4.42 (t, J=5.3 Hz, 2H), 4.09 (t, J=5.3 Hz, 2H).

Example 8

N-phenyl-3-[2-(trifluoromethyl)phenyl]-6,7-dihydro-4H-pyrazolo[1,5-a]pyrazine-5-carboxamide

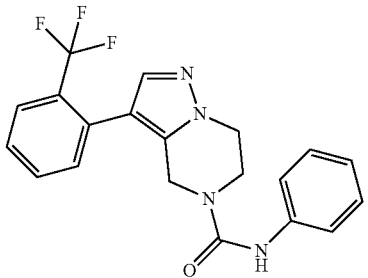 [SMILES: O=C(Nc1ccccc1)N1CCn2ncc(-c3ccccc3C(F)(F)F)c2C1]

Preparation of Example 8

The title compound was prepared in analogy to the preparation of Example 1 by using (2-trifluorophenyl)boronic acid instead of (4-fluorophenyl)boronic acid. Example 8 was obtained as a white solid. LCMS (M+H⁺): 387. ¹H NMR (400 MHz, chloroform-d) δ ppm 7.81 (d, J=7.5 Hz, 1H), 7.64-7.50 (m, 3H), 7.36-7.29 (m, 5H), 7.10 (s, 1H), 6.33 (s, 1H), 4.59 (s, 2H), 4.39 (t, J=5.4 Hz, 2H), 4.06 (t, J=5.5 Hz, 2H).

Example 9

1-(4-fluorophenyl)-N-phenyl-6,8-dihydro-5H-imidazo pyrazine-7-carboxamide

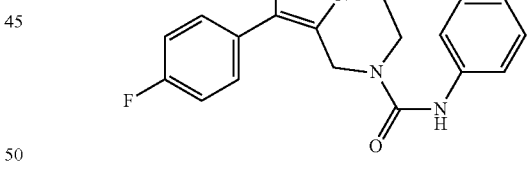

The title compound was prepared according to the following scheme:

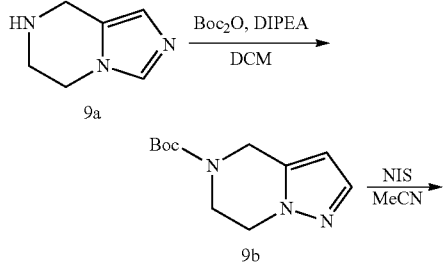

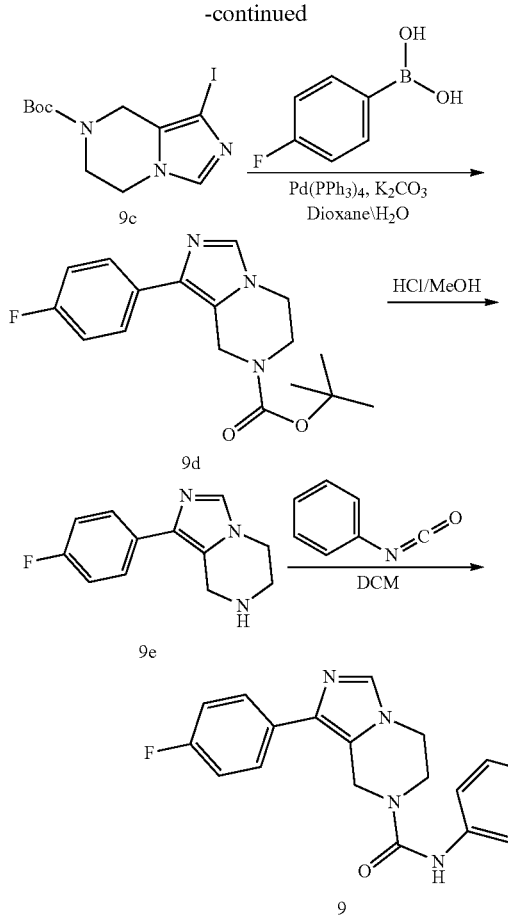

Step 1: Preparation of tert-butyl 6,8-dihydro-5H-imidazo[1,5-a]pyrazine-7-carboxylate (compound 9b)

To a solution of 5,6,7,8-tetrahydroimidazo[1,5-a]pyrazine (compound 9a, 3.7 g, 30 mmol) and DIPEA (11.6 g, 90 mmol) in DCM (50 mL) was added Boc$_2$O (7.2 g, 33 mmol) at 0° C. The resulting mixture was stirred at room temperature for 12 hours, and then concentrated and purified by column chromatography (eluting with 30%~100% EtOAc in petroleum ether) to afford compound 9b (4.7 g) as a white solid. LCMS (M+H$^+$): 224.

Step 2: Preparation of tert-butyl 1-iodo-6,8-dihydro-5H-imidazo[1,5-a]pyrazine-7-carboxylate (compound 9c)

To a solution of tert-butyl 6,8-dihydro-5H-imidazo[1,5-a]pyrazine-7-carboxylate a]pyrazine (compound 9b, 4.6 g, 21 mmol) in CH$_3$CN (50 mL) was added NIS (5.6 g, 2.5 mmol) and then the reaction mixture was stirred at room temperature for 48 hours and then concentrated and the residue was purified by column chromatography (eluting with 10%~80% EtOAc in petroleum ether) to afford compound 9c (5 g) as a yellow solid. LCMS (M+H$^+$): 350.

Step 3: Preparation of tert-butyl 1-(4-fluorophenyl)-6,8-dihydro-5H-imidazo[1,5-a]pyrazine-7-carboxylate (compound 9d)

To a mixture of tert-butyl 1-iodo-6,8-dihydro-5H-imidazo[1,5-a]pyrazine-7-carboxylate (compound 9c, 1.1 g, 3 mmol), (4-fluorophenyl)boronic acid (630 mg, 4.5 mmol) and K$_2$CO$_3$ (1.2 g, 9 mmol) in dioxane/water (10 mL, 5:1, v/v) was added Pd(PPh$_3$)$_4$ (150 mg, 0.015 mmol) under N$_2$. The reaction mixture was stirred at 80° C. for 12 hours, and then concentrated. The residue was purified by column chromatography (eluting with 10%~50% EtOAc in petroleum ether) to afford compound 9d (550 mg). LCMS (M+H$^+$): 318.

Step 4: Preparation of 1-(4-fluorophenyl)-5,6,7,8-tetrahydroimidazo[1,5-a]pyrazine (compound 9e)

A solution of tert-butyl 1-(4-fluorophenyl)-6,8-dihydro-5H-imidazo[1,5-a]pyrazine-7-carboxylate (compound 9d, 550 mg, 1.7 mmol) in HCl/MeOH (20 mL) was stirred at room temperature for 2 hours. Then the reaction mixture was concentrated in vacuo to afford compound 9e (400 mg) as a slight yellow solid, which was used directly without further purification in next step. LCMS (M+H$^+$): 236.

Step 5: Preparation of 1-(4-fluorophenyl)-N-phenyl-6,8-dihydro-5H-imidazo[1,5-a]pyrazine-7-carboxamide (Example 9)

To a solution of 1-(4-fluorophenyl)-5,6,7,8-tetrahydroimidazo[1,5-a]pyrazine (compound 9e, 88 mg, 0.4 mmol) and Et$_3$N (204 mg, 2.0 mmol) in DCM (5 mL) was added isocyanatobenzene (96 mg, 0.8 mmol) and then the reaction mixture was stirred at room temperature for 30 min. The solvent was removed in vacuo and the residue was purified by prep-HPLC to afford 1-(4-fluorophenyl)-N-phenyl-6,8-dihydro-5H-imidazo[1,5-a]pyrazine-7-carboxamide (Example 9, 20 mg) as a white solid. LCMS (M+H$^+$): 337. $^1$H NMR (400 MHz, DMSO-d$_6$) δ ppm 8.85 (s, 1H), 7.75 (s, 1H), 7.71-7.62 (m, 2H), 7.48-7.44 (m, 2H), 7.29-7.22 (m, 4H), 7.04-6.92 (m, 1H), 4.95 (s, 2H), 4.18-4.14 (m, 2H), 3.92-3.88 (m, 2H).

Example 10

3-(4-fluorophenyl)-N-phenyl-6,7-dihydro-4H-triazolo[1,5-a]pyrazine-5-carboxamide

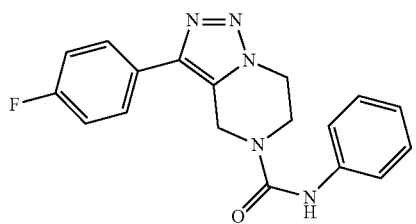 [SMILES: O=C(Nc1ccccc1)N1CCn2nnc(-c3ccc(F)cc3)c2C1]

The title compound was prepared according to the following scheme:

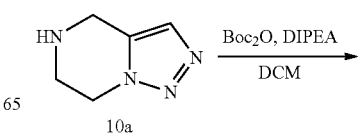

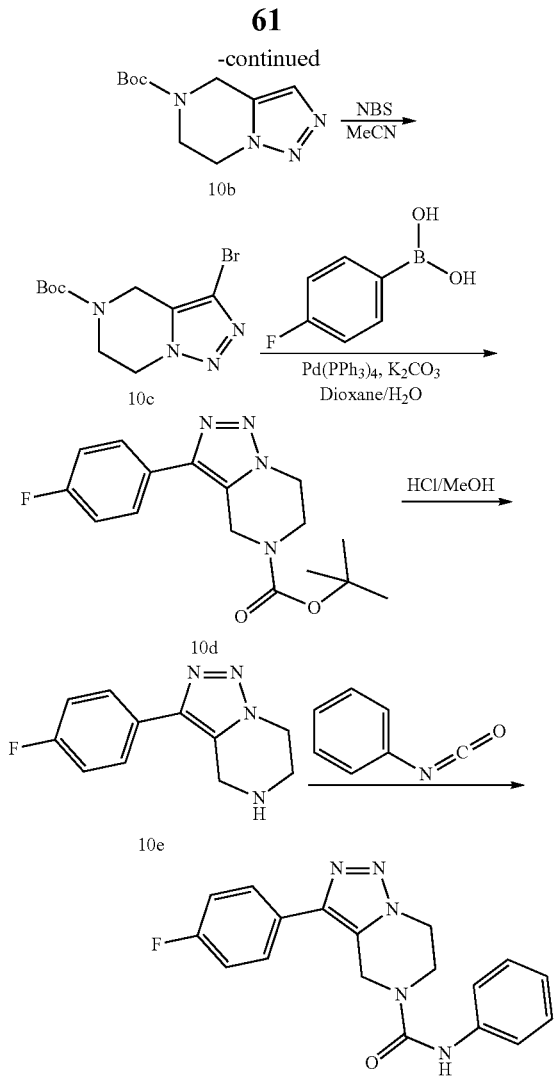

Step 1: Preparation of tert-butyl 6,7-dihydro-4H-triazolo[1,5-a]pyrazine-5-carboxylate (compound 10b)

To a solution of 4,5,6,7-tetrahydrotriazolo[1,5-a]pyrazine (compound 10a, 3.7 g, 30 mmol) and DIPEA (11.6 g, 90 mmol) in DCM (50 mL) was added Boc$_2$O (7.2 g, 33 mmol) at 0° C., and the reaction mixture was stirred at room temperature for 12 hours. The reaction mixture was concentrated and the residue purified by column chromatography (eluting with 30%~100% EtOAc in petroleum ether) to afford compound 10b (4.7 g) as a white solid. LCMS (M+H$^+$): 225.

Step 2: Preparation of tert-butyl 3-bromo-6,7-dihydro-4H-triazolo[1,5-a]pyrazine-5-carboxylate (compound 10c)

To a solution of tert-butyl 6,7-dihydro-4H-triazolo[1,5-a]pyrazine-5-carboxylate (compound 10b, 4.6 g, 21 mmol) in CH$_3$CN (50 mL) was added N-bromosuccinimide (NBS, 5.6 g, 2.5 mmol) and then the reaction mixture was stirred at room temperature for 48 hours. The reaction mixture was concentrated and the residue was purified by column chromatography (eluting with 10%~80% EtOAc in petroleum ether) to afford compound 10c (5 g) as a yellow solid. LCMS (M+H$^+$): 351.

Step 3: Preparation of tert-butyl 3-(4-fluorophenyl)-6,7-dihydro-4H-triazolo[1,5-a]pyrazine-5-carboxylate (compound 10d)

To a mixture of tert-butyl 3-bromo-6,7-dihydro-4H-triazolo[1,5-a]pyrazine-5-carboxylate (compound 10c, 1.1 g, 3 mmol), (4-fluorophenyl)boronic acid (630 mg, 4.5 mmol) and K$_2$CO$_3$ (1.2 g, 9 mmol) in dioxane/water (10 mL, 5:1, v/v) was added Pd(PPh$_3$)$_4$ (150 mg) under N$_2$. The reaction mixture was stirred at 80° C. for 16 hours. Then the reaction was concentrated and the residue was purified by column chromatography (eluting with 10%~50% EtOAc in petroleum ether) to afford compound 10d (550 mg). LCMS (M+H$^+$): 319.

Step 4: Preparation of 3-(4-fluorophenyl)-4,5,6,7-tetrahydrotriazolo[1,5-a]pyrazine (compound 10e)

A solution of tert-butyl 3-(4-fluorophenyl)-6,7-dihydro-4H-triazolo[1,5-a]pyrazine-5-carboxylate (compound 10d, 550 mg, 1.7 mmol) in HCl/MeOH (20 mL) was stirred at room temperature for 2 hours. Then the reaction mixture was concentrated in vacuo to afford compound 10e (400 mg) as a slight yellow solid. LCMS (M+H$^+$): 219.

Step 5: Preparation of 3-(4-fluorophenyl)-N-phenyl-6,7-dihydro-4H-triazolo[1,5-a]pyrazine-5-carboxamide (Example 10)

The title compound was prepared in analogy to the preparation of Example 9 by using 3-(4-fluorophenyl)-4,5,6,7-tetrahydrotriazolo[1,5-a]pyrazine (compound 10e) instead of 1-(4-fluorophenyl)-5,6,7,8-tetrahydroimidazo[1,5-a]pyrazine (compound 9e). Example 10 was obtained as a white solid (45 mg). LCMS (M+H$^+$): 338. $^1$H NMR (400 MHz, DMSO-d$_6$) δ ppm 8.92 (s, 1H), 7.83-7.76 (m, 2H), 7.46 (d, J=7.5 Hz, 2H), 7.36 (t, J=8.8 Hz, 2H), 7.27 (t, J=7.9 Hz, 2H), 7.03-6.96 (m, 1H), 5.05 (s, 2H), 4.51 (t, J=5.3 Hz, 2H), 4.03 (t, J=5.3 Hz, 2H).

Example 11

3-(4-fluorophenyl)-N-[3-(trifluoromethyl)phenyl]-6,7-dihydro-4H-pyrazolo[1,5-a]pyrazine-5-carboxamide

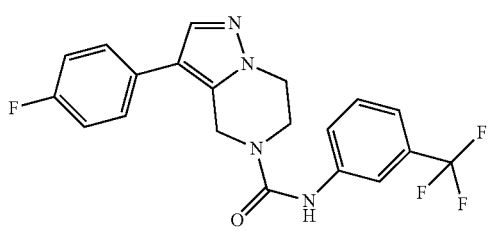 [SMILES: O=C(Nc1cccc(C(F)(F)F)c1)N1CCn2ncc(-c3ccc(F)cc3)c2C1]

The title compound was prepared according to the following scheme:

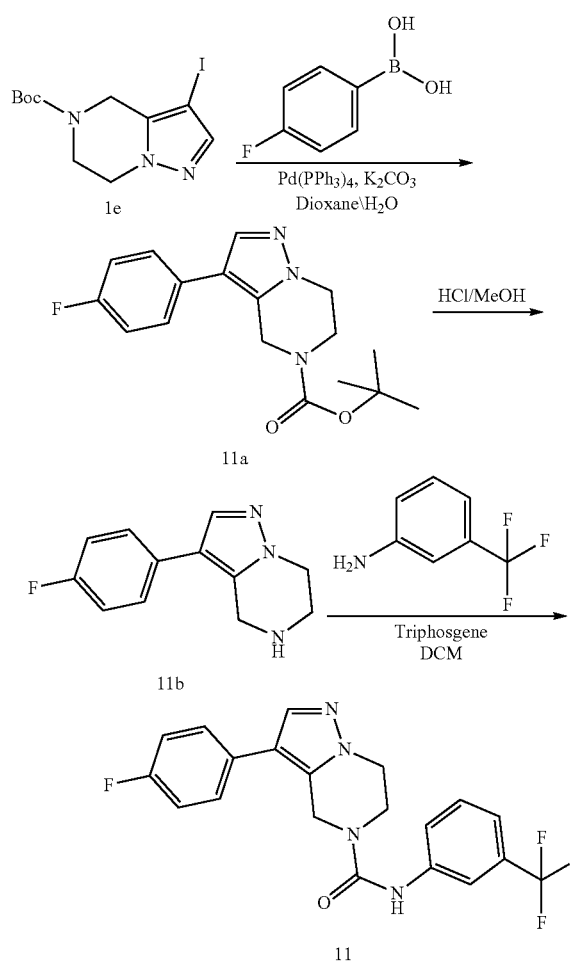

mg). After stirring for 10 min at room temperature, 3-(4-fluorophenyl)-4,5,6,7-tetrahydropyrazolo[1,5-a]pyrazine (compound 11b, 50 mg) was added to the reaction mixture. The resulting mixture was stirred at room temperature for 12 hours, then diluted with EtOAc (10 mL), washed with water (5 mL) and brine (5 mL). The organic layer was concentrated and the residue was purified by prep-HPLC to afford Example 11 (50 mg) as a white solid. LCMS (M+H$^+$): 405. $^1$H NMR (400 MHz, DMSO-d$_6$) δ ppm 9.21 (s, 1H), 7.90 (s, 1H), 7.84 (s, 1H), 7.74 (d, J=8.0 Hz, 1H), 7.54-7.46 (m, 3H), 7.35-7.22 (m, 3H), 4.95 (s, 2H), 4.24 (t, J=5.0 Hz, 2H), 4.02 (t, J=5.1 Hz, 2H).

Example 12

N-(3-chloro-4-fluoro-phenyl)-8-(4-fluorophenyl)-3,4-dihydro-1H-pyrrolo[1,2-a]pyrazine-2-carboxamide

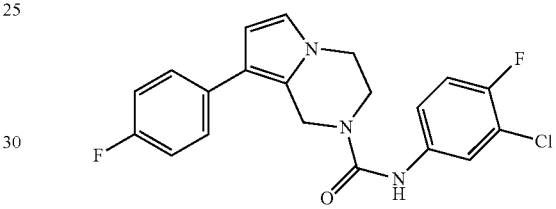

The title compound was prepared according to the following scheme:

Step 1: Preparation of tert-butyl 3-(4-fluorophenyl)-6,7-dihydro-4H-pyrazolo[1,5-a]pyrazine-5-carboxylate (compound 11a)

To a mixture of tert-butyl 3-iodo-6,7-dihydro-4H-pyrazolo[1,5-a]pyrazine-5-carboxylate (compound 1e, 1.1 g, 3 mmol), (4-fluorophenyl)boronic acid (630 mg, 4.5 mmol) and K$_2$CO$_3$ (1.2 g, 9 mmol) in and dioxane/water (10 mL, 5:1, v/v) was added Pd(PPh$_3$)$_4$ (150 mg) under N$_2$. The reaction mixture was stirred at 80° C. for 2 hours. Then the reaction was concentrated and the residue was purified by column chromatography to afford compound 11a (550 mg) as a slight yellow solid. LCMS (M+H$^+$): 318.

Step 2: Preparation of 3-(4-fluorophenyl)-4,5,6,7-tetrahydropyrazolo[1,5-a]pyrazine (compound 11b)

A solution of tert-butyl 3-(4-fluorophenyl)-6,7-dihydro-4H-pyrazolo[1,5-a]pyrazine-5-carboxylate (compound 11a, 550 mg, 1.7 mmol) in HCl/MeOH (20 mL) was stirred at room temperature for 2 hours. Then the reaction mixture was concentrated in vacuo to afford compound 11b (400 mg) as a slight yellow solid. LCMS (M+H$^+$): 218.

Step 3: Preparation of N-(2-fluorophenyl)-3-(4-fluorophenyl)-6,7-dihydro-4H-pyrazolo[1,5-a]pyrazine-5-carboxamide (Example 11)

To a mixture of 3-(trifluoromethyl)aniline (64 mg) and DIPEA (0.1 mL) in DCM (5 mL) was added triphosgene (36

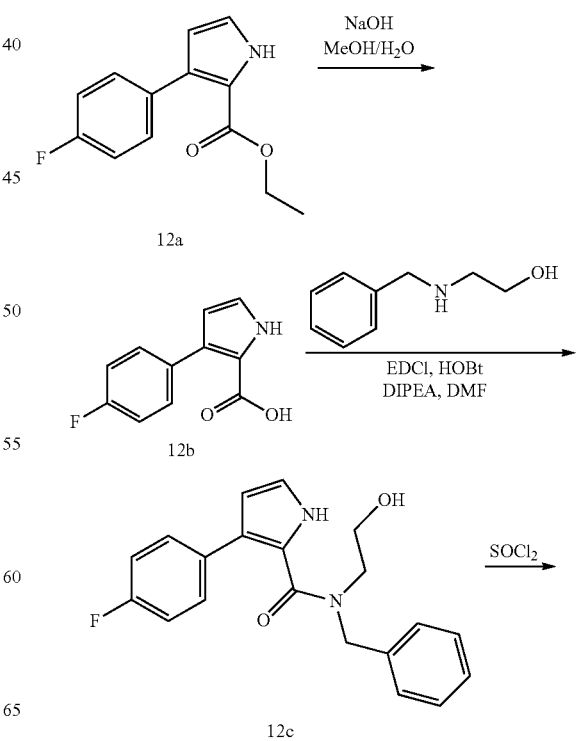

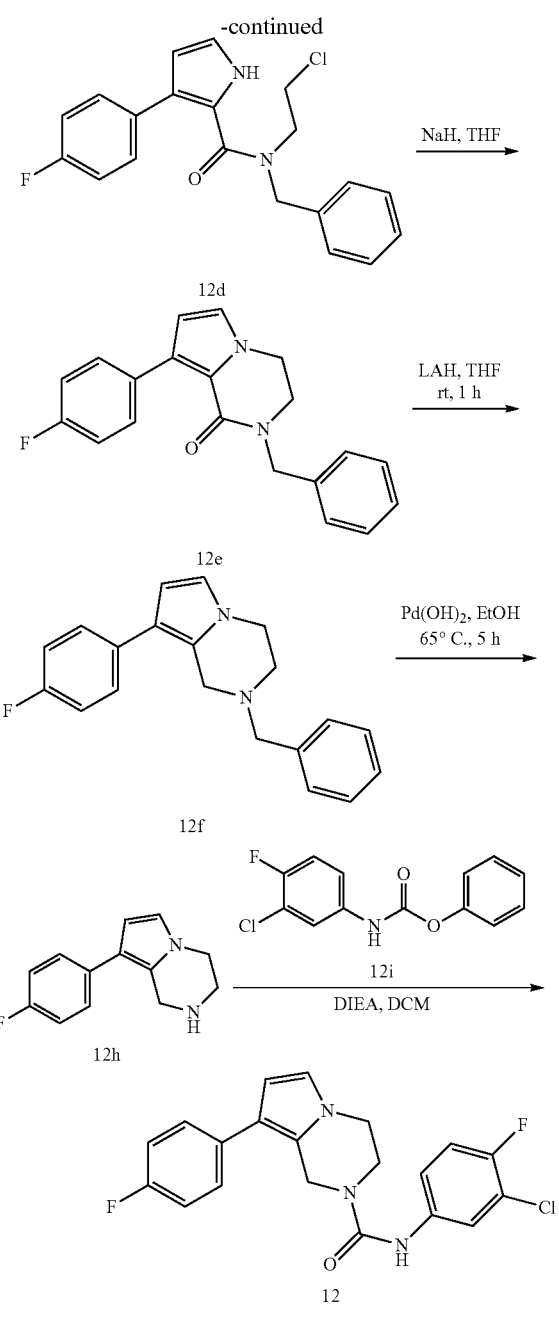

Step 1: Preparation of 3-(4-fluorophenyl)-1H-pyrrole-2-carboxylic acid (compound 12b)

To a solution of 8-(4-fluorophenyl)-1,2,3,4-tetrahydropyrrolo[1,2-a]pyrazine (compound 12a, 2.9 g, 12.4 mmol) (for its synthesis, refer to: Liu, J. et al, *Angew Chem Int. Ed.*, 2013, 52, 6953) in MeOH (13.5 mL) were added sequentially H$_2$O (4.5 mL) and NaOH (750 mg, 18.6 mmol). The reaction mixture was stirred at 75° C. for 5 hours, then cooled down, quenched by adding ice-water, neutralized to pH 6.0 with 1.0 N HCl solution in methanol, extracted with EtOAc/THF (60 mL, 5/2, v/v). The organic layer was dried over Na$_2$SO$_4$, filtered and concentrated to give compound 12b (2.5 g) as a crude product, which was used directly in next step. LCMS (M+H$^+$): 206.

Step 2: Preparation of N-benzyl-3-(4-fluorophenyl)-N-(2-hydroxyethyl)-1H-pyrrole-2-carboxamide (compound 12c)

To a solution of 3-(4-fluorophenyl)-1H-pyrrole-2-carboxylic acid (compound 12b, 2.5 g, 12.4 mmol) in DMF (10 mL) were added 2-(benzylamino)ethanol (2.3 g, 15.0 mmol), EDCI (3.1 g, 16.1 mmol), HOBt (0.5 g, 3.7 mmol) and DIPEA (3.0 mL). The reaction mixture was stirred at room temperature overnight, quenched by adding ice-water, then extracted with EtOAc (60 mL). The organic layer was dried over Na$_2$SO$_4$, filtered and concentrated. The residue was purified by column chromatography (eluting with 40%~60% EtOAc in petroleum ether) to afford compound 12c (3.0 g) as a white solid. LCMS (M+H$^+$): 339.

Step 3: Preparation of N-benzyl-N-(2-chloroethyl)-3-(4-fluorophenyl)-1H-pyrrole-2-carboxamide (compound 12d)

To a solution of N-benzyl-3-(4-fluorophenyl)-N-(2-hydroxyethyl)-1H-pyrrole-2-carboxamide (compound 12c, 676 mg, 2.0 mmol) in dioxane (8.0 mL) was added dropwise thionyl chloride (435 µL, mmol). The resulting mixture was stirred at room temperature for 2 hours, and then quenched by adding ice-water, extracted with EtOAc/petroleum ether (50 mL, 1/1, v/v) twice. The organic layer was dried over Na$_2$SO$_4$, filtered and concentrated to give crude compound 12d (712 mg) which was used directly in next step. LCMS (M+H$^+$): 357.

Step 4: Preparation of 2-benzyl-8-(4-fluorophenyl)-3,4-dihydropyrrolo[1,2-a]pyrazin-1-one (compound 12e)

To a solution of N-benzyl-N-(2-chloroethyl)-3-(4-fluorophenyl)-1H-pyrrole-2-carboxamide (compound 12d, 712 mg, 2.0 mmol) in dry THF (10 mL) was added sodium hydride (60% dispersion in mineral oil, 120 mg, 3.0 mmol). The reaction mixture was stirred at room temperature for 1 hour, diluted with THF (50 mL), and quenched with sodium sulfate decahydrate. The resulting mixture was stirred at room temperature for 1 hour, then filtered and concentrated. The residue was purified by column chromatography (eluting with 25%~35% EtOAc in petroleum ether) to afford compound 12e (512 mg) as a white solid. LCMS (M+H$^+$): 321.

Step 5: Preparation of 2-benzyl-8-(4-fluorophenyl)-3,4-dihydro-1H-pyrrolo[1,2-a]pyrazine (compound 12f)

A solution of 2-benzyl-8-(4-fluorophenyl)-3,4-dihydropyrrolo[1,2-a]pyrazin-1-one (compound 12e, 96 mg, 0.3 mmol) in THF (2.0 mL) was added lithium aluminum hydride (12 mg, 0.3 mmol) and stirred at room temperature for 1 hour. The reaction mixture was diluted with THF (30 mL), quenched by adding sodium sulfate decahydrate. The resulting mixture was stirred at room temperature for 1 hour, then filtered and concentrated to give crude compound 12f (92 mg) which was used directly in next step. LCMS (M+H$^+$): 307.

Step 6: Preparation of 8-(4-fluorophenyl)-1,2,3,4-tetrahydropyrrolo[1,2-a]pyrazine (compound 12h)

To a solution of 2-benzyl-8-(4-fluorophenyl)-3,4-dihydro-1H-pyrrolo[1,2-a]pyrazine (compound 12f, 640 mg, 2.0 mmol) in EtOH (20 mL) was added palladium hydroxide (20% on carbon, wetted with ca. 50% water, 0.5 g). The reaction mixture was heated to reflux under 1 atm. H$_2$ overnight. After cooled to room temperature, the reaction mixture was filtered and concentrated to give crude compound 12h (432 mg) which was used directly in next step. LCMS (M+H$^+$): 217.

Step 7: Preparation of N-(3-chloro-4-fluoro-phenyl)-8-(4-fluorophenyl)-3,4-dihydro-1H-pyrrolo[1,2-a]pyrazine-2-carboxamide (Example 12)

To a solution of 8-(4-fluorophenyl)-1,2,3,4-tetrahydropyrrolo[1,2-a]pyrazine (compound 12h, 54 mg, 0.25 mmol) in DCM (2.0 mL) was added DIPEA (0.1 mL), phenyl N-(3-chloro-4-fluoro-phenyl)carbamate (compound 12i, 80 mg, 0.3 mmol) (for its synthesis, refer to: Sheng, C. et al, *Eur. J. Med. Chem.* 2011, 46, 5276). The reaction mixture was stirred at 40° C. for 3 hours. The reaction mixture was concentrated in vacuo to give the crude product, which was purified by prep-HPLC to afford Example 12 (10 mg). LCMS (M+H$^+$): 388. $^1$H NMR (400 MHz, CD$_3$OD) □Δ ppm 7.59 (dd, J=2.5, 6.8 Hz, 1H), 7.43-7.35 (m, 2H), 7.33-7.27 (m, 1H), 7.18-7.07 (m, 3H), 6.75 (d, J=2.8 Hz, 1H), 6.33 (d, J=2.8 Hz, 1H), 4.88 (s, 2H), 4.12 (d, J=4.5 Hz, 2H), 3.94 (d, J=5.8 Hz, 2H).

Example 13

N-(2-fluorophenyl)-3-(4-fluorophenyl)-6,7-dihydro-4H-pyrazolo[1,5-a]pyrazine-5-carboxamide

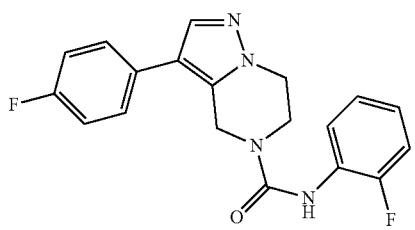 [SMILES: O=C(Nc1ccccc1F)N1CCn2ncc(-c3ccc(F)cc3)c2C1]

Preparation of Example 13

The title compound was prepared in analogy to the preparation of Example 9 by using 3-(4-fluorophenyl)-4,5,6,7-tetrahydropyrazolo[1,5-a]pyrazine (compound 11b, 50 mg) instead of 1-(4-fluorophenyl)-5,6,7,8-tetrahydroimidazo[1,5-a]pyrazine (compound 9e), and 1-fluoro-2-isocyanato-benzene (44 mg) instead of isocyanatobenzene. Example 13 was obtained as a white solid (40 mg). LCMS (M+H$^+$): 355. $^1$H NMR (400 MHz, DMSO-d$_6$) δ ppm 8.92 (s, 1H), 7.83 (s, 1H), 7.53-7.42 (m, 4H), 7.27 (t, J=8.9 Hz, 2H), 7.14-7.06 (m, 2H), 4.92 (s, 2H), 4.22 (t, J=5.3 Hz, 2H), 4.04-3.96 (m, 2H).

Example 14

N,3-bis(4-fluorophenyl)-6,7-dihydro-4H-pyrazolo[1,5-a]pyrazine-5-carboxamide

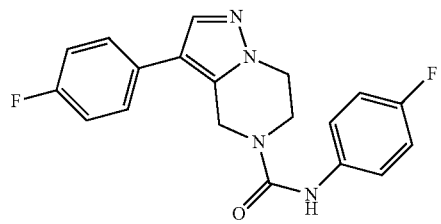 [SMILES: O=C(Nc1ccc(F)cc1)N1CCn2ncc(-c3ccc(F)cc3)c2C1]

Preparation of Example 14

The title compound was prepared in analogy to the preparation of Example 11 by using 4-fluoroaniline instead of 3-(trifluoromethyl)aniline. Example 14 was obtained as a white solid (20 mg). LCMS (M+H$^+$): 355. $^1$H NMR (400 MHz, DMSO-d$_6$) δ ppm 8.92 (s, 1H), 7.83 (s, 1H), 7.54-7.40 (m, 4H), 7.27 (t, J=8.9 Hz, 2H), 7.16-7.04 (m, 2H), 4.92 (s, 2H), 4.22 (t, J=5.3 Hz, 2H), 4.04-3.95 (m, 2H).

Example 15

N-(3-chlorophenyl)-3-(4-fluorophenyl)-6,7-dihydro-4H-pyrazolo[1,5-a]pyrazine-5-carboxamide

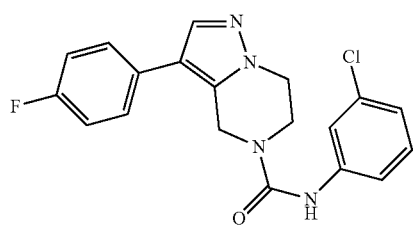 [SMILES: O=C(Nc1cccc(Cl)c1)N1CCn2ncc(-c3ccc(F)cc3)c2C1]

Preparation of Example 15

The title compound was prepared in analogy to the preparation of Example 11 by using 3-chloroaniline instead of 3-(trifluoromethyl)aniline. Example 15 was obtained as a white solid. LCMS (M+H$^+$): 371. $^1$H NMR (400 MHz, DMSO-d$_6$) δ ppm 9.06 (s, 1H), 7.84 (s, 1H), 7.63 (s, 1H), 7.53-7.45 (m, 2H), 7.41 (d, J=8.3 Hz, 1H), 7.33-7.23 (m, 3H), 7.02 (d, J=7.8 Hz, 1H), 4.94 (s, 2H), 4.23 (m, 2H), 4.00 (m, 2H).

Example 16

N-(3-cyanophenyl)-3-(4-fluorophenyl)-6,7-dihydro-4H-pyrazolo[1,5-a]pyrazine-5-carboxamide

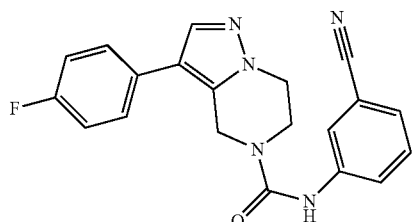

Preparation of Example 16

The title compound was prepared in analogy to the preparation of Example 11 by using 3-aminobenzonitrile instead of 2-fluoroaniline. Example 16 was obtained as a white solid (30 mg). LCMS (M+H$^+$): 362. $^1$H NMR (400 MHz, DMSO-d$_6$) δ ppm 9.21 (s, 1H), 7.92 (s, 1H), 7.84 (s, 1H), 7.76 (d, J=8.0 Hz, 1H), 7.54-7.39 (m, 4H), 7.32-7.22 (m, 2H), 4.95 (s, 2H), 4.24 (m, 2H), 4.02 (m, 2H).

Example 17

N-(4-chlorophenyl)-3-(4-fluorophenyl)-6,7-dihydro-4H-pyrazolo[1,5-a]pyrazine-5-carboxamide

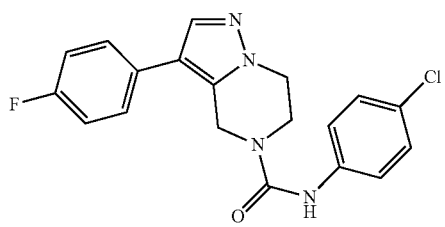 [SMILES: O=C(Nc1ccc(Cl)cc1)N1CCn2ncc(-c3ccc(F)cc3)c2C1]

Preparation of Example 17

The title compound was prepared in analogy to the preparation of Example 11 by using 4-chloroaniline instead of 3-(trifluoromethyl)aniline. Example 17 was obtained as a white solid (30 mg). LCMS (M+H$^+$): 371. $^1$H NMR (400 MHz, DMSO-d$_6$) δ ppm 9.00 (s, 1H), 7.83 (s, 1H), 7.49 (d, J=8.3 Hz, 4H), 7.37-7.22 (m, 4H), 4.93 (s, 2H), 4.27-4.17 (m, 2H), 4.01 (d, J=4.8 Hz, 2H).

Example 18

3-(2-cyanophenyl)-N-phenyl-6,7-dihydro-4H-pyrazolo[1,5-a]pyrazine-5-carboxamide

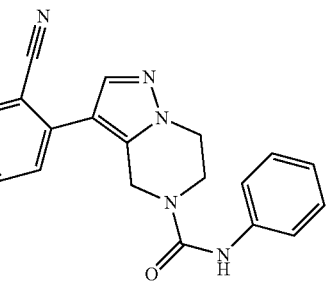

Preparation of Example 18

The title compound was prepared in analogy to the preparation of Example 1 by using (2-cyanophenyl)boronic acid instead of (4-fluorophenyl)boronic acid. Example 18 was obtained as a white solid (20 mg). LCMS (M+H$^+$): 344. $^1$H NMR (400 MHz, DMSO-d$_6$) δ ppm 8.86 (s, 1H), 7.94 (d, J=7.5 Hz, 1H), 7.84 (s, 1H), 7.78 (t, J=7.5 Hz, 1H), 7.59-7.40 (m, 4H), 7.29-7.20 (m, 2H), 7.01-6.92 (m, 1H), 4.84 (s, 2H), 4.28 (t, J=5.0 Hz, 2H), 4.03 (t, J=5.1 Hz, 2H).

Example 19

N-(3-fluorophenyl)-3-(4-fluorophenyl)-6,7-dihydro-4H-pyrazolo[1,5-a]pyrazine-5-carboxamide

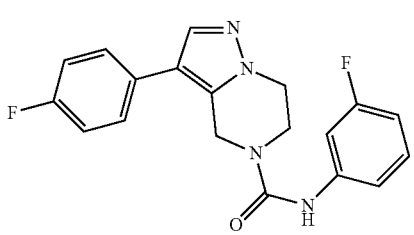 [SMILES: O=C(Nc1cccc(F)c1)N1CCn2ncc(-c3ccc(F)cc3)c2C1]

Preparation of Example 19

The title compound was prepared in analogy to the preparation of Example 11 by using 3-fluoroaniline instead of 2-fluoroaniline. Example 19 was obtained as a white solid (30 mg). LCMS (M+H$^+$): 355. $^1$H NMR (400 MHz, DMSO-d$_6$) δ ppm 9.14-9.01 (m, 1H), 7.83 (s, 1H), 7.50 (dd, J=5.6, 8.2 Hz, 2H), 7.42 (d, J=12.0 Hz, 1H), 7.35-7.18 (m, 4H), 6.78 (t, J=7.8 Hz, 1H), 4.93 (s, 2H), 4.28-4.17 (m, 2H), 4.01 (d, J=5.3 Hz, 2H).

Example 20

N-(4-chloro-3-fluoro-phenyl)-3-(4-fluorophenyl)-6,7-dihydro-4H-pyrazolo[1,5-a]pyrazine-5-carboxamide

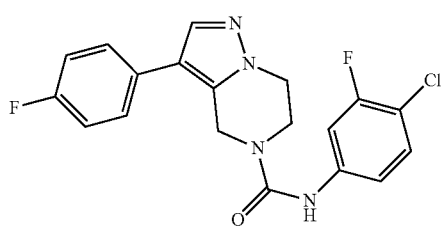 [SMILES: O=C(Nc1ccc(Cl)c(F)c1)N1CCn2ncc(-c3ccc(F)cc3)c2C1]

Preparation of Example 20

The title compound was prepared in analogy to the preparation of Example 11 by using 4-chloro-3-fluoro-aniline instead of 3-(trifluoromethyl)aniline. Example 20 was obtained as a white solid. LCMS (M+H$^+$): 389. $^1$H NMR (400 MHz, DMSO-d$_6$) δ ppm 9.20 (s, 1H), 7.83 (s, 1H), 7.70-7.57 (m, 1H), 7.53-7.40 (m, 3H), 7.35-7.21 (m, 3H), 4.93 (s, 2H), 4.30-4.15 (m, 2H), 4.01 (d, J=4.8 Hz, 2H).

Example 21

N-(3-chloro-4-fluoro-phenyl)-3-(4-fluorophenyl)-6,7-dihydro-4H-pyrazolo[1,5-a]pyrazine-5-carboxamide

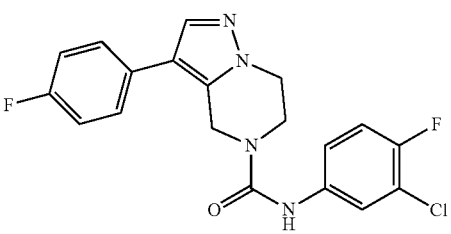 [SMILES: O=C(Nc1ccc(F)c(Cl)c1)N1CCn2ncc(-c3ccc(F)cc3)c2C1]

Preparation of Example 21

The title compound was prepared in analogy to the preparation of Example 11 by using 3-chloro-4-fluoro-aniline instead of 3-(trifluoromethyl)aniline. Example 21 was obtained as a white solid (32 mg). LCMS (M+H$^+$): 389. $^1$H NMR (400 MHz, DMSO-d$_6$) δ ppm 9.05 (s, 1H), 7.83 (s, 1H), 7.72 (dd, J=2.3, 6.8 Hz, 1H), 7.49 (dd, J=5.5, 8.5 Hz, 2H), 7.44-7.38 (m, 1H), 7.30 (td, J=9.0, 18.2 Hz, 3H), 4.93 (s, 2H), 4.22 (t, J=5.0 Hz, 2H), 4.06-3.95 (m, 2H).

Example 22

3-(4-fluorophenyl)-N-(4-pyridyl)-6,7-dihydro-4H-pyrazolo[1,5-a]pyrazine-5-carboxamide

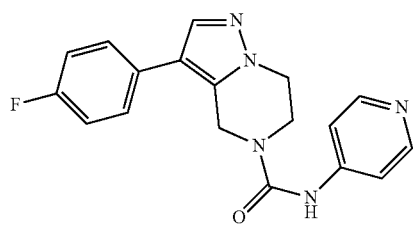 [SMILES: O=C(Nc1ccncc1)N1CCn2ncc(-c3ccc(F)cc3)c2C1]

Preparation of Example 22

The title compound was prepared in analogy to the preparation of Example 11 by using 4-amino-pyridine instead of 3-(trifluoromethyl)aniline. Example 22 was obtained as a white solid (30 mg). LCMS (M+H$^+$): 338. $^1$H NMR (400 MHz, DMSO-d$_6$) δ ppm 9.31 (s, 1H), 8.34 (d, J=6.3 Hz, 2H), 7.83 (s, 1H), 7.56-7.42 (m, 4H), 7.33-7.21 (m, 2H), 4.95 (s, 2H), 4.23 (t, J=5.1 Hz, 2H), 4.11-3.98 (m, 2H).

Example 23

N-(4-cyanophenyl)-3-(4-fluorophenyl)-6,7-dihydro-4H-pyrazolo[1,5-a]pyrazine-5-carboxamide

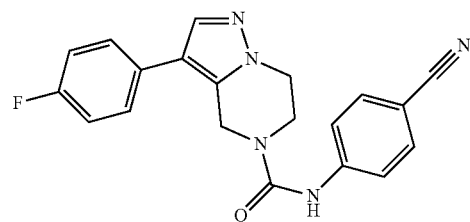 [SMILES: N#Cc1ccc(NC(=O)N2CCn3ncc(-c4ccc(F)cc4)c3C2)cc1]

Preparation of Example 23

The title compound was prepared in analogy to the preparation of Example 11 by using 4-aminobenzonitrile instead of 3-(trifluoromethyl)aniline. Example 23 was obtained as a white solid (35 mg). LCMS (M+H$^+$): 362. $^1$H NMR (400 MHz, DMSO-d$_6$) δ ppm 9.35 (s, 1H), 7.83 (s, 1H), 7.75-7.63 (m, 4H), 7.49 (dd, J=5.5, 8.5 Hz, 2H), 7.27 (t, J=8.8 Hz, 2H), 4.95 (s, 2H), 4.24 (t, J=5.3 Hz, 2H), 4.02 (t, J=5.3 Hz, 2H).

Example 24

N-(3-chloro-4-fluoro-phenyl)-3-(2-fluorophenyl)-6,7-dihydro-4H-pyrazolo[1,5-a]pyrazine-5-carboxamide

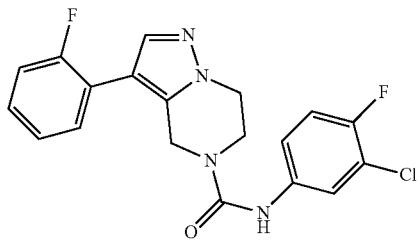 [SMILES: O=C(Nc1ccc(F)c(Cl)c1)N1CCn2ncc(-c3ccccc3F)c2C1]

The title compound was prepared according to the following scheme:

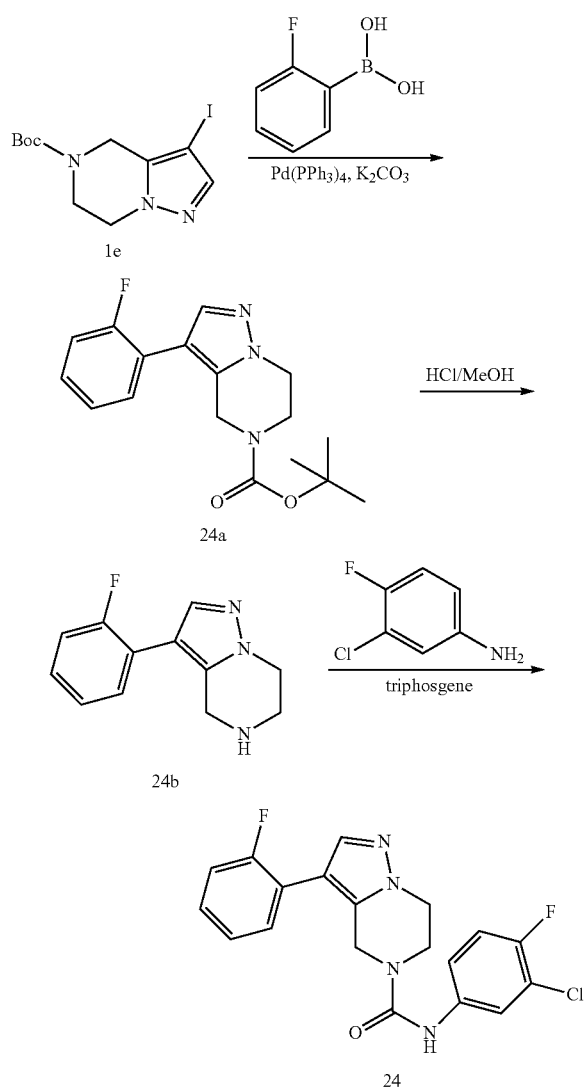

Preparation of 3-(2-fluorophenyl)-4,5,6,7-tetrahydropyrazolo[1,5-a]pyrazine (compound 24b)

The compound 24b was prepared in analogy to compound 11b by using (2-fluorophenyl) boronic acid instead of (4-fluorophenyl)boronic acid. Compound 24b was obtained as a white solid (250 mg). LCMS (M+H$^+$): 218.

Preparation of N-(3-chloro-4-fluoro-phenyl)-3-(2-fluorophenyl)-6,7-dihydro-4H-pyrazolo[1,5-a]pyrazine-5-carboxamide (Example 24)

Example 24 was prepared in analogy to the preparation of Example 11 by using 3-choloro-4-fluoroaniline and 3-(2-fluorophenyl)-4,5,6,7-tetrahydropyrazolo[1,5-a]pyrazine (compound 24b). Example 24 was obtained as a white solid (10 mg). LCMS (M+H$^+$): 389. $^1$H NMR (400 MHz, chloroform-d) □□ ppm 7.77 (s, 1H), 7.50 (dd, J=2.6, 6.5 Hz, 1H), 7.39-7.31 (m, 2H), 7.27-7.16 (m, 3H), 7.12-7.04 (m, 1H), 6.57 (s, 1H), 4.79 (s, 2H), 4.40 (t, J=5.5 Hz, 2H), 4.07 (t, J=5.4 Hz, 2H).

Example 25

3-(3-methoxyphenyl)-N-phenyl-6,7-dihydro-4H-pyrazolo[1,5-a]pyrazine-5-carboxamide

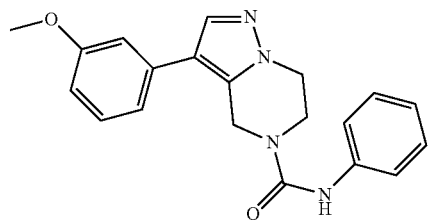 [SMILES: COc1cccc(-c2cnn3c2CN(C(=O)Nc2ccccc2)CC3)c1]

Preparation of Example 25

The title compound was prepared in analogy to the preparation of Example 1 by using (3-methoxylphenyl) boronic acid instead of (4-fluorophenyl)boronic acid. Example 25 was obtained as a white solid. LCMS (M+H$^+$): 349. $^1$H NMR (400 MHz, DMSO-d$_6$) □□ ppm 8.91 (s, 1H), 7.86 (s, 1H), 7.44 (d, J=7.8 Hz, 2H), 7.35 (t, J=7.9 Hz, 1H), 7.25 (t, J=7.8 Hz, 2H), 7.07-6.94 (m, 3H), 6.85 (d, J=8.3 Hz, 1H), 4.95 (s, 2H), 4.22 (t, J=5.0 Hz, 2H), 4.01 (d, J=5.3 Hz, 2H), 3.81 (s, 3H).

Example 26

3-cyclopentyl-N-phenyl-6,7-dihydro-4H-pyrazolo[1,5-a]pyrazine-5-carboxamide

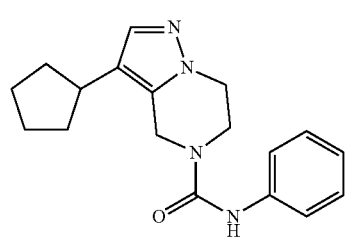 [SMILES: O=C(Nc1ccccc1)N1CCn2ncc(C3CCCC3)c2C1]

The title compound was prepared according to the following scheme:

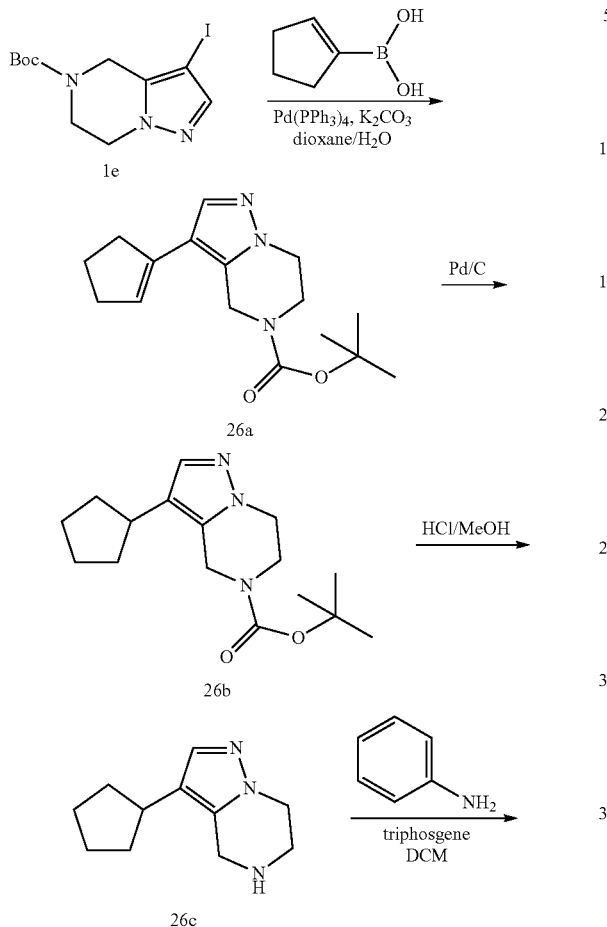

Step 1: Preparation of tert-butyl 3-(cyclopenten-1-yl)-6,7-dihydro-4H-pyrazolo[1,5-a]pyrazine-5-carboxylate (compound 26a)

A mixture of cyclopenten-1-ylboronic acid (144 mg 1.2 mmol), Pd (PPh$_3$)$_4$ (240 mg, 0.03 mmol), Cs$_2$CO$_3$ (800 mg, 2.2 mmol) and tert-butyl 3-iodo-6,7-dihydro-4H-pyrazolo[1,5-a]pyrazine-5-carboxylate (compound 1e, 400 mg, 1.1 mmol) in dioxane/H$_2$O (30 mL, 4:1, v/v) was refluxed for 12 hours under N$_2$. The reaction mixture was diluted with EtOAc (30 mL), washed with water (10 mL) and brine (10 mL). The organic layer was concentrated. The residue was purified by column chromatography to afford compound 26a (275 mg) as a white solid. LCMS (M+H$^+$): 290.

Step 2: Preparation of tert-butyl 3-cyclopentyl-6,7-dihydro-4H-pyrazolo[1,5-a]pyrazine-5-carboxylate (compound 26b)

To a solution of tert-butyl 3-(cyclopenten-1-yl)-6,7-dihydro-4H-pyrazolo[1,5-a]pyrazine-5-carboxylate (compound 26a, 275 mg, 0.9 mmol) in MeOH (20 mL) was added Pd/C (80 mg) under N$_2$, and the reaction mixture was stirred at room temperature for 12 hours under H$_2$. Then the solid was filtered off, the filtrate was concentrated to afford compound 26b (270 mg) as a colorless oil. LCMS (M+H$^+$): 292.

Step 3: Preparation of 3-cyclopentyl-4,5,6,7-tetrahydropyrazolo[1,5-a]pyrazine (compound 26c)

A solution of tert-butyl 3-cyclopentyl-6,7-dihydro-4H-pyrazolo[1,5-a]pyrazine-5-carboxylate (compound 26b, 270 mg, 0.9 mmol) in HCl/MeOH (20 mL) was stirred at room temperature for 2 hours. Then the reaction mixture was concentrated in vacuo to afford compound 26c (230 mg) as a slight yellow solid. LCMS (M+H$^+$): 192.

Step 4: Preparation of 3-cyclopentyl-N-phenyl-6,7-dihydro-4H-pyrazolo[1,5-a]pyrazine-5-carboxamide (Example 26)

The title compound was prepared in analogy to the preparation of Example 11 by using aniline and 3-cyclopentyl-4,5,6,7-tetrahydropyrazolo[1,5-a]pyrazine (compound 26c) instead of 3-(trifluoromethyl)aniline and 3-(4-fluorophenyl)-4,5,6,7-tetrahydropyrazolo[1,5-a]pyrazine, respectively. Example 26 was obtained as a white solid. LCMS (M+H$^+$): 311. $^1$H NMR (400 MHz, DMSO-d$_6$) δ ppm 8.81 (br. s, 1H), 7.46 (d, J=7.8 Hz, 2H), 7.35-7.19 (m, 3H), 6.98 (t, J=7.3 Hz, 1H), 4.69 (s, 2H), 4.15-4.04 (m, 2H), 3.93 (t, J=5.4 Hz, 2H), 2.88-2.76 (m, 1H), 2.26-1.21 (m, 8H).

Example 27

3-(2-methoxyphenyl)-N-phenyl-6,7-dihydro-4H-pyrazolo[1,5-a]pyrazine-5-carboxamide

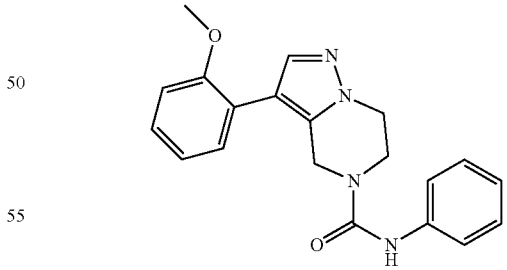

Preparation of Example 27

The title compound was prepared in analogy to the preparation of Example 1 by using (2-methoxylphenyl) boronic acid instead of (4-fluorophenyl)boronic acid. Example 27 was obtained as a white solid. LCMS (M+H$^+$): 349. $^1$H NMR (400 MHz, DMSO-d$_6$) δ ppm 8.84 (s, 1H), 7.63-7.61 (m, 1H), 7.43 (d, J=7.8 Hz, 2H), 7.34-7.21 (m, 4H), 7.09 (d, J=8.3 Hz, 1H), 6.98 (td, J=7.3, 19.0 Hz, 2H), 4.72 (s, 2H), 4.21 (t, J=5.3 Hz, 2H), 4.01 (t, J=5.4 Hz, 2H), 3.81 (s, 3H).

Example 28

N-phenyl-3-[4-(trifluoromethyl)-2-pyridyl]-6,7-dihydro-4H-pyrazolo[1,5-a]pyrazine-5-carboxamide

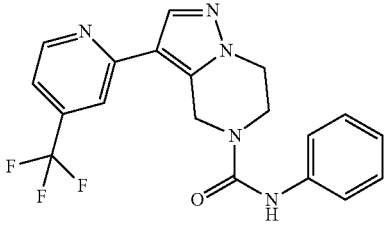 [SMILES: O=C(Nc1ccccc1)N1CCn2ncc(-c3cc(C(F)(F)F)ccn3)c2C1]

Preparation of Example 28

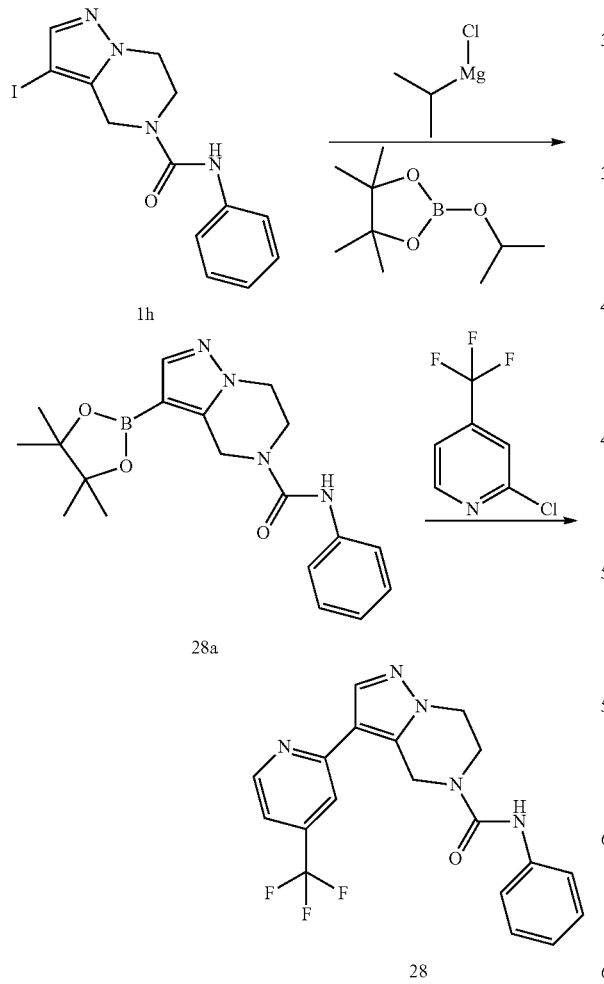

Step 1: Preparation of N-phenyl-3-(4,4,5,5-tetramethyl-1,3,2-dioxaborolan-2-yl)-6,7-dihydro-4H-pyrazolo[1,5-a]pyrazine-5-carboxamide (compound 28a)

To a solution of 3-iodo-N-phenyl-6,7-dihydro-4H-pyrazolo[1,5-a]pyrazine-5-carboxamide (compound 1h, 500 mg, 1.4 mmol) in THF (15 mL) was added isopropyl magnesium chloride (1.7 mL, 3.4 mmol) at 0° C. The reaction mixture was stirred at 0° C. for 0.5 hours, then 2-isopropoxy-4,4,5,5-tetramethyl-1,3,2-dioxaborolane (380 mg, 2 mmol) in THF (5 mL) was added dropwise at 0° C. The reaction mixture was stirred at room temperature for 1 hour. The reaction was quenched with saturated aqueous ammonium chloride solution (20 mL) slowly and extracted with EtOAc (30 mL). The organic layer was washed with brine, and concentrated to afford compound 28a (450 mg) as a white solid. LCMS (M+H$^+$): 369.

Step 2: Preparation of N-phenyl-3-[4-(trifluoromethyl)-2-pyridyl]-6,7-dihydro-4H-pyrazolo[1,5-a]pyrazine-5-carboxamide (Example 28)

To a mixture of N-phenyl-3-(4,4,5,5-tetramethyl-1,3,2-dioxaborolan-2-yl)-6,7-dihydro-4H-pyrazolo[1,5-a]pyrazine-5-carboxamide (compound 28a, 100 mg, 0.3 mmol), 2-chloro-4-(trifluoromethyl)pyridine (108 mg, 0.6 mmol) and K$_2$CO$_3$ (83 mg, 0.6 mmol) in DMSO/H$_2$O (10:1, 2 mL, v/v) was added Pd(dppf)Cl$_2$ (15 mg) under N$_2$. The resulting mixture was stirred at 80° C. for 12 hours. After cooled down, then the reaction mixture was filtered, and concentrated. The residue was purified by prep-HPLC to afford Example 28 (19 mg) as a white solid. LCMS (M+H$^+$): 388. $^1$H NMR (400 MHz, chloroform-d) δ ppm 8.77 (d, J=5.1 Hz, 1H), 8.06 (s, 1H), 7.73 (s, 1H), 7.42-7.33 (m, 5H), 7.16-7.11 (m, 1H), 6.79 (s, 1H), 5.18 (s, 2H), 4.39 (t, J=5.3 Hz, 2H), 4.10 (t, J=5.3 Hz, 2H).

Example 29

3-(4-cyano-2-pyridyl)-N-phenyl-6,7-dihydro-4H-pyrazolo[1,5-a]pyrazine-5-carboxamide

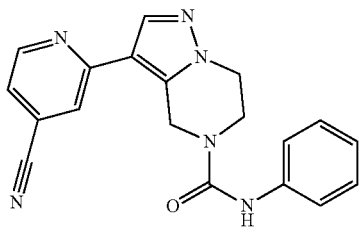 [SMILES: N#Cc1ccnc(-c2cnn3c2CN(C(=O)Nc2ccccc2)CC3)c1]

Preparation of Example 29

The title compound was prepared in analogy to the preparation of Example 28 by using 2-chloropyridine-4-carbonitrile instead of 2-chloro-4-(trifluoromethyl)pyridine. Example 29 was obtained as a white solid (11 mg). LCMS (M+H$^+$): 345. $^1$H NMR (400 MHz, DMSO-d6) δ ppm 8.75 (d, J=4.8 Hz, 1H), 7.98 (s, 1H), 7.74 (s, 1H), 7.42-7.32 (m, 5H), 7.31-7.12 (m, 1H), 6.65 (br. s, 1H), 5.14 (s, 2H), 4.37 (t, J=5.3 Hz, 2H), 4.09 (t, J=5.4 Hz, 2H).

Example 30

N-(3-chlorophenyl)-3-(2-fluorophenyl)-6,7-dihydro-4H-pyrazolo[1,5-a]pyrazine-5-carboxamide

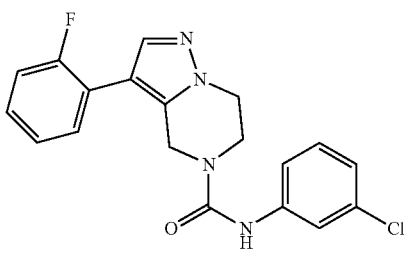 [SMILES: O=C(Nc1cccc(Cl)c1)N1CCn2ncc(-c3ccccc3F)c2C1]

Preparation of Example 30

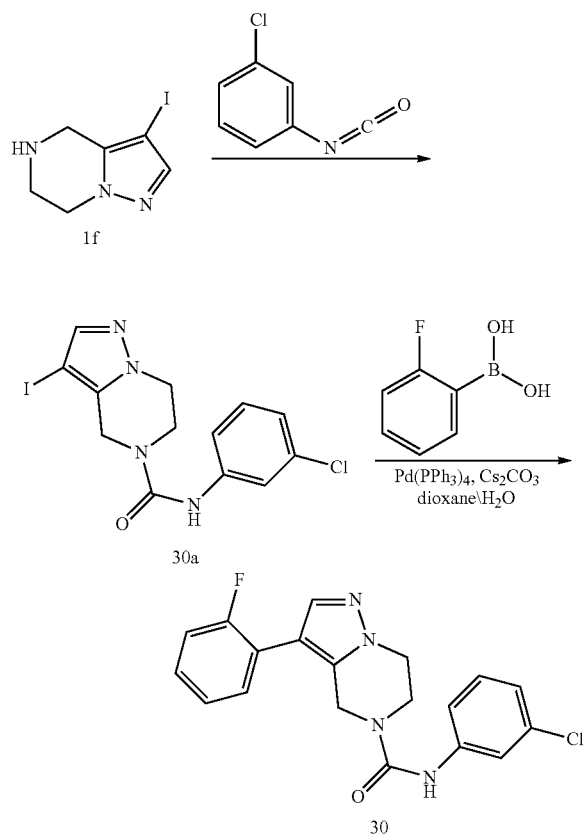

Step 1: Preparation of N-(3-chlorophenyl)-3-iodo-6,7-dihydro-4H-pyrazolo[1,5-a]pyrazine-5-carboxamide (compound 30a)

Compound 30a was prepared in analogy to compound 1h by using 1-chloro-3-isocyanato-benzene (500 mg) instead of isocyanatobenzene. Compound 30a was obtained as a white solid (500 mg). LCMS (M+H$^+$): 403.

Step 2: Preparation of N-(3-chlorophenyl)-3-(2-fluorophenyl)-6,7-dihydro-4H-pyrazolo[1,5-a]pyrazine-5-carboxamide (Example 30)

To a solution of N-(3-chlorophenyl)-3-(2-fluorophenyl)-6,7-dihydro-4H-pyrazolo[1,5-a]pyrazine-5-carboxamide (compound 30a, 0.1 g, 0.3 mmol) in dioxane/water (10 mL, 10:1, v/v) was added (2-fluorophenyl)boronic acid (40 mg, 0.33 mmol), Pd(PPh$_3$)$_4$ (10 mg, 0.09 mmol) and Cs$_2$CO$_3$ (195 mg, 0.6 mmol). The reaction mixture was stirred at 70° C. for 16 hours under nitrogen. The reaction mixture was concentrated and the residue was purified by prep-HPLC to afford Example 30 (5 mg) as a white solid. LCMS (M+H$^+$): 371. $^1$H NMR (400 MHz, DMSO-d$_6$) δ ppm 9.15 (br. s, 1H), 7.78-7.57 (m, 2H), 7.52-7.15 (m, 6H), 7.00 (d, J=7.3 Hz, 1H), 4.91-4.74 (m, 2H), 4.24 (br. s, 2H), 4.04 (br. s, 2H).

Example 31

N-(3-chlorophenyl)-3-(o-tolyl)-6,7-dihydro-4H-pyrazolo[1,5-a]pyrazine-5-carboxamide

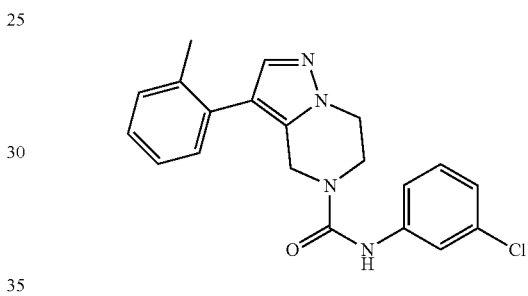

Preparation of Example 31

The title compound was prepared in analogy to the preparation of Example 30 by using (2-methylphenyl)boronic acid instead of (2-fluorophenyl)boronic acid. Example 31 was obtained as a white solid (10 mg). LCMS (M+H$^+$): 367. $^1$H NMR (400 MHz, DMSO-d$_6$) δ ppm 9.04 (s, 1H), 7.59 (d, J=12.8 Hz, 2H), 7.38 (d, J=8.0 Hz, 1H), 7.34-7.15 (m, 5H), 7.00 (d, J=7.9 Hz, 1H), 4.68 (s, 2H), 4.24 (br. s, 2H), 4.02 (br. s, 2H), 2.27 (s, 3H).

Example 32

N-(5-fluoro-6-methyl-2-pyridyl)-3-(4-fluorophenyl)-6,7-dihydro-4H-pyrazolo[1,5-a]pyrazine-5-carboxamide

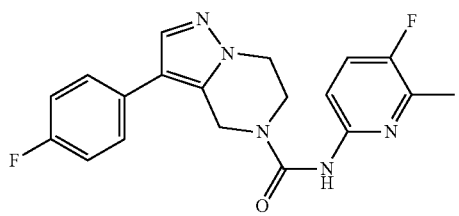 [SMILES: Cc1nc(NC(=O)N2CCn3ncc(-c4ccc(F)cc4)c3C2)ccc1F]

Preparation of Example 32

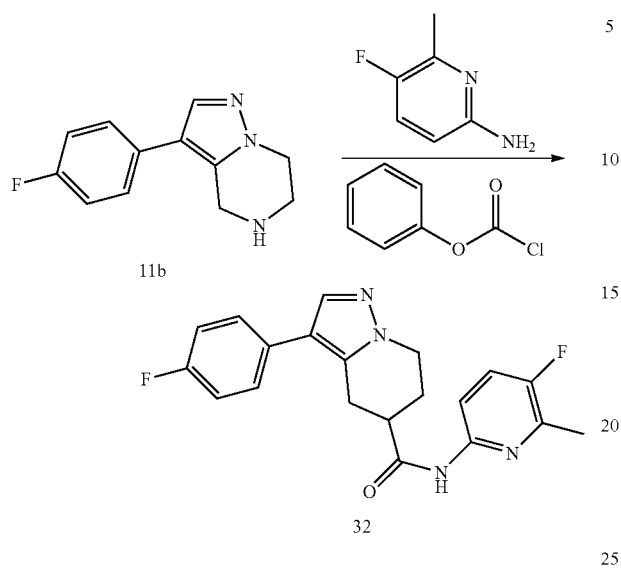

To a mixture of 5-fluoro-6-methyl-pyridin-2-amine (40 mg, 0.32 mmol) and Et$_3$N (65 mg, 0.64 mmol) in THF (5 mL) was added phenyl chloroformate (50 mg, 0.12 mmol) slowly at 0° C. The reaction mixture was stirred at room temperature for 12 hours. The reaction mixture was diluted with EtOAc (20 mL), washed with saturated aqueous NaHCO$_3$ (20 mL) and brine (30 mL), and dried over anhydrous sodium sulfate. The solvents were removed in vacuo. The residue was dissolved in DMF (2 mL), to which 3-(4-fluorophenyl)-4,5,6,7-tetrahydropyrazolo[1,5-a]pyrazine (compound 11b) (41 mg, 0.32 mmol) and DIPEA (0.2 mL) was added. Then the reaction mixture was stirred at 80° C. for 1 hour. The reaction mixture was subjected to prep-HPLC to afford Example 32 as a white solid. LCMS (M+H$^+$): 370. $^1$H NMR (400 MHz, DMSO-d$_6$) δ ppm 9.70 (s, 1H), 7.83 (s, 1H), 7.69-7.62 (m, 1H), 7.59-7.53 (m, 1H), 7.50 (dd, J=5.5, 8.7 Hz, 2H), 7.27 (t, J=8.8 Hz, 2H), 4.95 (s, 2H), 4.20 (t, J=5.3 Hz, 2H), 4.04-3.96 (m, 2H), 2.37 (d, J=2.8 Hz, 3H).

Example 33

3-(2-fluorophenyl)-N-(4-fluorophenyl)-6,7-dihydro-4H-pyrazolo[1,5-a]pyrazine-5-carboxamide

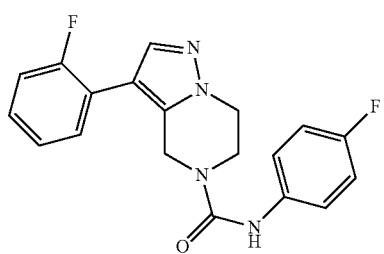 [SMILES: O=C(Nc1ccc(F)cc1)N1CCn2ncc(-c3ccccc3F)c2C1]

Preparation of Example 33

The title compound was prepared in analogy to the preparation of Example 24 by using 4-fluoroaniline instead of 3-choloro-4-fluoroaniline. Example 33 was obtained as a white solid (45 mg). LCMS (M+H$^+$): 355. $^1$H NMR (400 MHz, DMSO-d$_6$) δ ppm 9.01-8.77 (m, 1H), 7.73 (d, J=1.9 Hz, 1H), 7.49-7.41 (m, 3H), 7.39-7.25 (m, 3H), 7.09 (t, J=8.9 Hz, 2H), 4.82 (s, 2H), 4.24 (t, J=5.4 Hz, 2H), 4.08-3.97 (m, 2H).

Example 34

3-(2-fluorophenyl)-N-[4-fluoro-3-(trifluoromethyl)phenyl]-6,7-dihydro-4H-pyrazolo[1,5-a]pyrazine-5-carboxamide

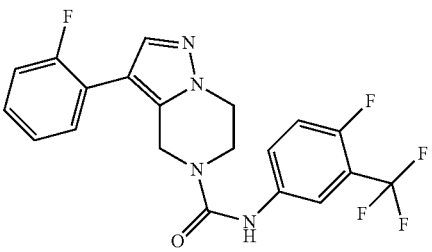 [SMILES: O=C(Nc1ccc(F)c(C(F)(F)F)c1)N1CCn2ncc(-c3ccccc3F)c2C1]

Preparation of Example 34

The title compound was prepared in analogy to the preparation of Example 24 by using 3-trifluoro-4-fluoroaniline instead of 3-choloro-4-fluoroaniline. Example 34 was obtained as a white solid (21 mg). LCMS (M+H$^+$): 423. $^1$H NMR (400 MHz, DMSO-d$_6$) δ ppm 9.18 (s, 1H), 7.89 (dd, J=2.6, 6.3 Hz, 1H), 7.82-7.64 (m, 2H), 7.52-7.21 (m, 5H), 4.84 (s, 2H), 4.26 (t, J=5.4 Hz, 2H), 4.09-3.96 (m, 2H).

Example 35

N-(3-chlorophenyl)-3-(2,4-difluorophenyl)-6,7-dihydro-4H-pyrazolo[1,5-a]pyrazine-5-carboxamide

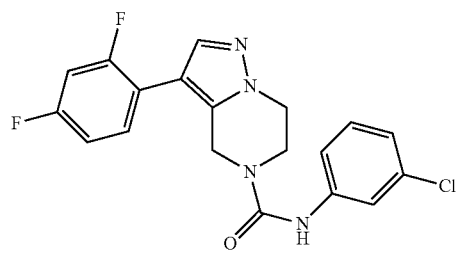 [SMILES: O=C(Nc1cccc(Cl)c1)N1CCn2ncc(-c3ccc(F)cc3F)c2C1]

Preparation of Example 35

The title compound was prepared in analogy to the preparation of Example 30 by using (3,4-difluorophenyl)boronic acid instead of (2-fluorophenyl)boronic acid. Example 35 was obtained as a white solid (15 mg). LCMS (M+H$^+$): 389. $^1$H NMR (400 MHz, chloroform-d) δ ppm 7.67 (s, 1H), 7.46 (s, 1H), 7.37-7.27 (m, 1H), 7.25-7.20 (m, 2H), 7.10-7.04 (m, 1H), 7.01-6.92 (m, 2H), 6.56 (s, 1H), 4.75 (s, 2H), 4.36 (t, J=5.5 Hz, 2H), 4.12-3.98 (m, 2H).

Example 36

N-(3-chlorophenyl)-3-(2,3-difluorophenyl)-6,7-dihydro-4H-pyrazolo[1,5-a]pyrazine-5-carboxamide

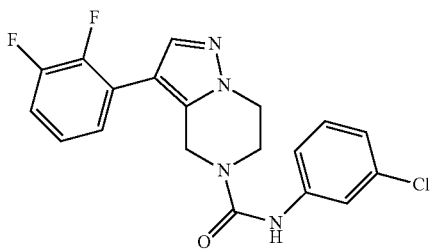 [SMILES: O=C(Nc1cccc(Cl)c1)N1CCn2ncc(-c3cccc(F)c3F)c2C1]

Preparation of Example 36

The title compound was prepared in analogy to the preparation of Example 30 by using (3,4-difluorophenyl)boronic acid instead of (2-fluorophenyl)boronic acid. Example 36 was obtained as a white solid (23 mg). LCMS (M+H+): 389. $^1$H NMR (400 MHz, chloroform-d) δ ppm 7.73 (s, 1H), 7.46 (d, J=1.3 Hz, 1H), 7.26-7.20 (m, 2H), 7.19-7.00 (m, 4H), 6.60 (s, 1H), 4.79 (s, 2H), 4.36 (t, J=5.5 Hz, 2H), 4.07 (t, J=5.5 Hz, 2H).

Example 37

3-(3-cyano-2-pyridyl)-N-phenyl-6,7-dihydro-4H-pyrazolo[1,5-a]pyrazine-5-carboxamide

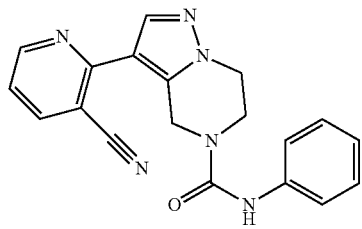 [SMILES: N#Cc1cccnc1-c1cnn2c1CN(C(=O)Nc1ccccc1)CC2]

Preparation of Example 37

The title compound was prepared in analogy to the preparation of Example 28 by using 2-chloropyridine-3-carbonitrile instead of 2-chloro-4-(trifluoromethyl)pyridine. Example 37 was obtained as a white solid (15 mg). LCMS (M+H+): 345. $^1$H NMR (400 MHz, DMSO-d6) δ ppm 8.89 (s, 2H), 8.37-8.32 (m, 1H), 8.28 (s, 1H), 7.43 (s, 3H), 7.31-7.22 (m, 2H), 7.03-6.92 (m, 1H), 5.04 (s, 2H), 4.31-4.27 (m, 2H), 4.06-4.01 (m, 2H).

Example 38

3-(3-chloro-2-fluoro-phenyl)-N-(3-chlorophenyl)-6,7-dihydro-4H-pyrazolo[1,5-a]pyrazine-5-carboxamide

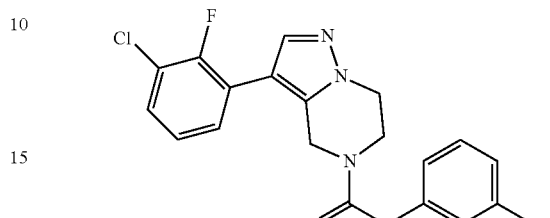

Preparation of Example 38

The title compound was prepared in analogy to the preparation of Example 30 by using (2-fluoro-3-chlorophenyl)boronic acid instead of (2-fluorophenyl)boronic acid. Example 38 was obtained as a white solid (41 mg). LCMS (M+H+): 405. $^1$H NMR (400 MHz, chloroform-d) δ ppm 7.76 (s, 1H), 7.47-7.37 (m, 2H), 7.28-7.21 (m, 3H), 7.20-7.15 (m, 1H), 7.10-7.05 (m, 1H), 6.64 (s, 1H), 4.79 (s, 2H), 4.41 (t, J=5.5 Hz, 2H), 4.07 (t, J=5.5 Hz, 2H).

Example 39

3-(5-chloro-2-fluoro-phenyl)-N-(3-chlorophenyl)-6,7-dihydro-4H-pyrazolo[1,5-a]pyrazine-5-carboxamide

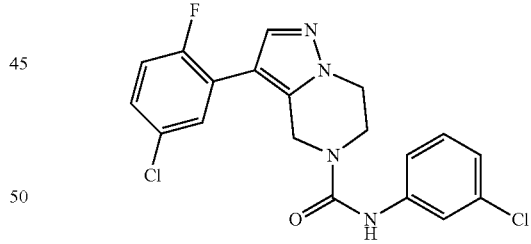

Preparation of Example 39

The title compound was prepared in analogy to the preparation of Example 30 by using (2-fluoro-5-chlorophenyl)boronic acid instead of (2-fluorophenyl)boronic acid. Example 39 was obtained as a white solid (40 mg). LCMS (M+H+): 405. $^1$H NMR (400 MHz, chloroform-d) δ ppm 7.71 (d, J=0.6 Hz, 1H), 7.46 (s, 1H), 7.33 (dd, 6.5 Hz, 1H), 7.30-7.25 (m, 1H), 7.25-7.22 (m, 2H), 7.13 (dd, J=8.8, 9.9 Hz, 1H), 7.09-7.04 (m, 1H), 6.59 (s, 1H), 4.78 (s, 2H), 4.36 (t, J=5.5 Hz, 2H), 4.06 (t, J=5.5 Hz, 2H).

Example 40

N-(3-chlorophenyl)-3-(2,5-difluorophenyl)-6,7-di-hydro-4H-pyrazolo[1,5-a]pyrazine-5-carboxamide

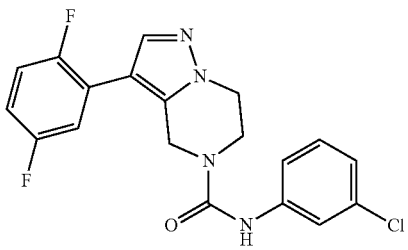 [SMILES: O=C(Nc1cccc(Cl)c1)N1CCn2ncc(-c3cc(F)ccc3F)c2C1]

Preparation of Example 40

The title compound was prepared in analogy to the preparation of Example 30 by using (2,5-difluorophenyl)boronic acid instead of (2-fluorophenyl)boronic acid. Example 40 was obtained as a white solid (23 mg). LCMS (M+H$^+$): 389. $^1$H NMR (400 MHz, chloroform-d) δ ppm 7.76 (s, 1H), 7.42 (s, 1H), 7.25-7.19 (m, 2H), 7.14 (dt, J=4.6, 9.3 Hz, 1H), 7.10-6.95 (m, 3H), 6.74 (s, 1H), 4.79 (s, 2H), 4.38 (t, J=5.4 Hz, 2H), 4.05 (t, J=5.5 Hz, 2H).

Example 41

3-[3-(difluoromethyl)phenyl]-N-phenyl-6,7-dihydro-4H-pyrazolo[1,5-a]pyrazine-5-carboxamide

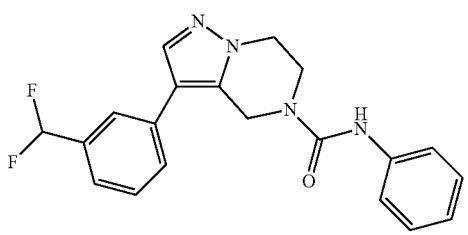 [SMILES: O=C(Nc1ccccc1)N1CCn2ncc(-c3cccc(C(F)F)c3)c2C1]

Preparation of Example 41

The title compound was prepared in analogy to the preparation of Example 28 by using 1-bromo-3-(difluoromethyl)benzene instead of 2-chloro-4-(trifluoromethyl)pyridine. Example 41 was obtained as a white solid. LCMS (M+H$^+$): 369. $^1$H NMR (400 MHz, DMSO-d$_6$) δ ppm 8.91 (s, 1H), 7.90 (s, 1H), 7.67-7.54 (m, 3H), 7.49-7.39 (m, 3H), 7.25 (t, J=7.8 Hz, 2H), 7.05-6.97 (m, 2H), 4.96 (s, 2H), 4.22 (d, J=5.0 Hz, 2H), 4.01 (t, J=5.0 Hz, 2H).

Example 42

3-(5-fluoro-6-methyl-2-pyridyl)-N-phenyl-6,7-di-hydro-4H-pyrazolo[1,5-a]pyrazine-5-carboxamide

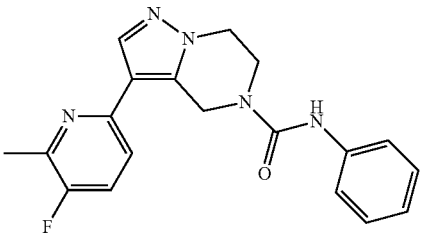 [SMILES: Cc1nc(-c2cnn3c2CN(C(=O)Nc2ccccc2)CC3)ccc1F]

Preparation of Example 42

The title compound was prepared in analogy to the preparation of Example 28 by using 6-chloro-3-fluoro-2-methyl-pyridine instead of 2-chloro-4-(trifluoromethyl)pyridine. Example 42 was obtained as a white solid. LCMS (M+H$^+$): 352. $^1$H NMR (400 MHz, DMSO-d$_6$) δ ppm 8.92 (s, 1H), 8.04 (s, 1H), 7.66-7.53 (m, 2H), 7.44 (d, J=8.0 Hz, 2H), 7.26 (t, J=7.8 Hz, 2H), 6.97 (t, J=7.3 Hz, 1H), 5.04 (s, 2H), 4.22 (t, J=4.9 Hz, 2H), 4.00 (t, J=5.1 Hz, 2H), 2.3 (s, 3H).

Example 43

3-(5-fluoro-4-methyl-2-pyridyl)-N-phenyl-6,7-di-hydro-4H-pyrazolo[1,5-a]pyrazine-5-carboxamide

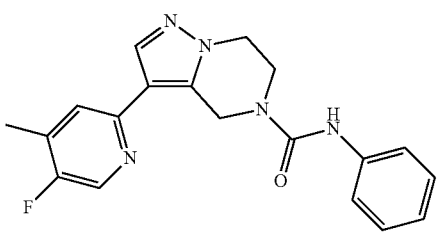 [SMILES: Cc1cc(-c2cnn3c2CN(C(=O)Nc2ccccc2)CC3)ncc1F]

Preparation of Example 43

The title compound was prepared in analogy to the preparation of Example 28 by using 2-chloro-5-fluoro-4-methyl-pyridine instead of 2-chloro-4-(trifluoromethyl)pyridine. Example 43 was obtained as a white solid. LCMS (M+H$^+$): 352. $^1$H NMR (400 MHz, DMSO-d$_6$) δ ppm 8.91 (s, 1H), 8.43 (s, 1H), 8.04 (s, 1H), 7.68 (d, J=6.0 Hz, 1H), 7.43 (d, J=7.8 Hz, 2H), 7.25 (t, J=7.8 Hz, 2H), 7.01-6.89 (m, 1H), 5.02 (s, 2H), 4.26-4.15 (m, 2H), 3.99 (t, J=5.0 Hz, 2H), 2.31 (s, 3H).

Example 44

N-phenyl-3-(2-pyridyl)-6,7-dihydro-4H-pyrazolo[1,5-a]pyrazine-5-carboxamide

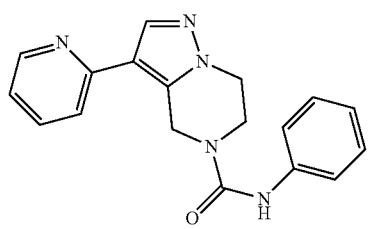 [SMILES: O=C(Nc1ccccc1)N1CCn2ncc(-c3ccccn3)c2C1]

Preparation of Example 44

The title compound was prepared in analogy to the preparation of Example 28 by using 2-chloropyridine instead of 2-chloro-4-(trifluoromethyl)pyridine. Example 44 was obtained as a white solid (30 mg). LCMS (M+H$^+$): 320. $^1$H NMR (400 MHz, methanol-d$_4$) δ ppm 8.68 (d, J=5.1 Hz, 1H), 8.30 (br. s, 1H), 8.15 (s, 1H), 7.91 (d, J=8.2 Hz, 1H), 7.63 (s, 1H), 7.43-7.39 (m, 2H), 7.33-7.28 (m, 2H), 7.09-7.05 (m, 1H), 5.15 (s, 2H), 4.37 (t, J=5.4 Hz, 2H), 4.13 (d, J=5.6 Hz, 2H).

Example 45

N-phenyl-3-thiazol-2-yl-6,7-dihydro-4H-pyrazolo[1,5-a]pyrazine-5-carboxamide

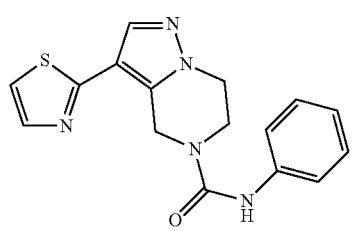 [SMILES: O=C(Nc1ccccc1)N1CCn2ncc(-c3nccs3)c2C1]

Preparation of Example 45

The title compound was prepared in analogy to the preparation of Example 28 by using 2-bromothiazole instead of 2-chloro-4-(trifluoromethyl)pyridine. Example 45 was obtained as a white solid (12 mg). LCMS (M+H$^+$): 326. $^1$H NMR (400 MHz, methanol-d$_4$) δ ppm 8.01 (s, 1H), 7.84 (d, J=3.3 Hz, 1H), 7.53 (d, J=3.4 Hz, 1H), 7.44-7.40 (m, 2H), 7.30 (t, J=7.9 Hz, 2H), 7.10-7.03 (m, 1H), 5.11 (s, 2H), 4.35-4.31 (m, 2H), 4.10 (t, J=5.3 Hz, 2H).

Example 46

N-phenyl-3-[4-(trifluoromethyl)thiazol-2-yl]-6,7-dihydro-4H-pyrazolo[1,5-a]pyrazine-5-carboxamide

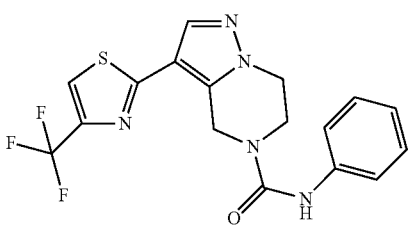 [SMILES: O=C(Nc1ccccc1)N1CCn2ncc(-c3nc(C(F)(F)F)cs3)c2C1]

Preparation of Example 46

The title compound was prepared in analogy to the preparation of Example 28 by using 4-trifluoromethy-2-bromothiazole instead of 2-chloro-4-(trifluoromethyl)pyridine. Example 46 was obtained as a white solid (12 mg). LCMS (M+H$^+$): 394. $^1$H NMR (400 MHz, methanol-d$_4$) δ ppm 8.06 (s, 2H), 7.42-7.38 (m, 2H), 7.34-7.24 (m, 2H), 7.11-7.02 (m, 1H), 5.12 (s, 2H), 4.37-4.32 (m, 2H), 4.10 (s, 2H).

Example 47

3-(5-chlorothiazol-2-yl)-N-phenyl-6,7-dihydro-4H-pyrazolo[1,5-a]pyrazine-5-carboxamide

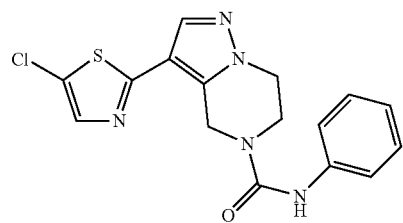 [SMILES: O=C(Nc1ccccc1)N1CCn2ncc(-c3ncc(Cl)s3)c2C1]

Preparation of Example 47

The title compound was prepared in analogy to the preparation of Example 28 by using 5-chloro-2-bromothiazole instead of 2-chloro-4-(trifluoromethyl)pyridine. Example 47 was obtained as a white solid (17 mg). LCMS (M+H$^+$): 360. $^1$H NMR (400 MHz, methanol-d$_4$) δ ppm 7.95 (s, 1H), 7.67 (s, 1H), 7.44-7.39 (m, 2H), 7.34-7.25 (m, 2H), 7.10-7.02 (m, 1H), 5.07 (s, 2H), 4.37-4.27 (m, 2H), 4.10-4.06 (m, 2H).

Example 48

3-(3,4-difluorophenyl)-N-phenyl-6,7-dihydro-4H-pyrazolo[1,5-a]pyrazine-5-carboxamide

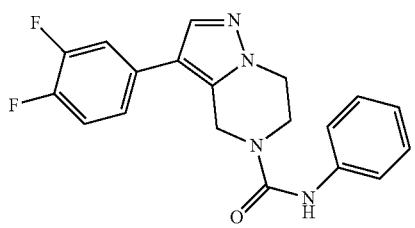 [SMILES: O=C(Nc1ccccc1)N1CCn2ncc(-c3ccc(F)c(F)c3)c2C1]

Preparation of Example 48

The title compound was prepared in analogy to the preparation of Example 1 by using (3,4-difulorophenyl)boronic acid instead of (4-fluorophenyl)boronic acid. Example 48 was obtained as a white solid (10 mg). LCMS (M+H$^+$): 355. $^1$H NMR (400 MHz, DMSO-d$_6$) δ ppm 8.90 (s, 1H), 7.89 (s, 1H), 7.64-7.41 (m, 4H), 7.32-7.17 (m, 3H), 7.05-6.94 (m, 1H), 4.94 (s, 2H), 4.22 (t, J=5.3 Hz, 2H), 4.08-3.88 (m, 2H).

Example 49

3-(6-chloro-2-pyridyl)-N-phenyl-6,7-dihydro-4H-pyrazolo[1,5-a]pyrazine-5-carboxamide

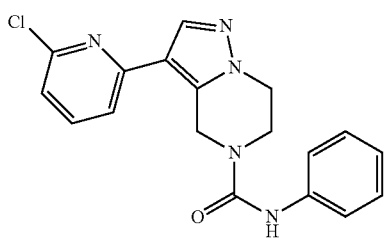 [SMILES: O=C(Nc1ccccc1)N1CCn2ncc(-c3cccc(Cl)n3)c2C1]

Preparation of Example 49

The title compound was prepared in analogy to the preparation of Example 28 by using 2,6-dichloropyridine instead of 2-chloro-4-(trifluoromethyl)pyridine. Example 49 was obtained as a white solid. LCMS (M+H$^+$): 354. $^1$H NMR (400 MHz, DMSO-d$_6$) δ ppm 8.92 (s, 1H), 8.14 (s, 1H), 7.88-7.83 (m, 1H), 7.69 (d, J=7.8 Hz, 1H), 7.46 (d, J=7.8 Hz, 2H), 7.31-7.22 (m, 3H), 7.00-6.95 (m, 1H), 5.04 (s, 2H), 4.25 (t, J=5.1 Hz, 2H), 4.02 (t, J=5.1 Hz, 2H).

Example 50

N-(3-chloro-4-fluoro-phenyl)-3-(2,4-difluorophenyl)-6,7-dihydro-4H-pyrazolo[1,5-a]pyrazine-5-carboxamide

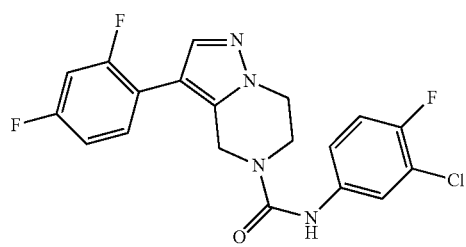 [SMILES: O=C(Nc1ccc(F)c(Cl)c1)N1CCn2ncc(-c3ccc(F)cc3F)c2C1]

The title compound was prepared according to the following scheme:

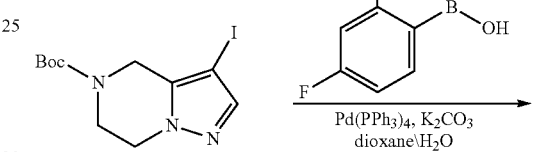
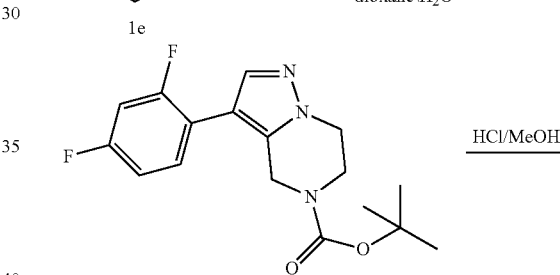
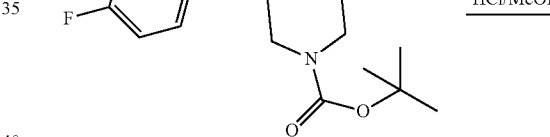
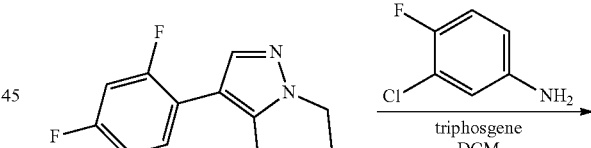
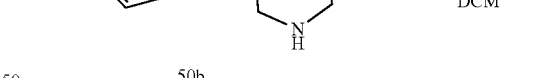
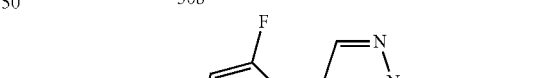
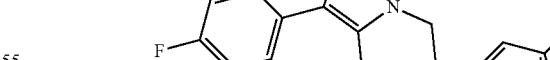
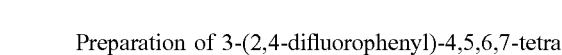

Preparation of 3-(2,4-difluorophenyl)-4,5,6,7-tetrahydropyrazolo[1,5-a]pyrazine (50b)

The compound 50b was prepared in analogy to compound 11b by using (2,4-difluorophenyl)boronic acid instead of (4-fluorophenyl)boronic acid. Compound 50b was obtained as a white solid (250 mg). LCMS (M+H$^+$): 236.

Preparation of N-(3-chloro-4-fluoro-phenyl)-3-(2,4-difluorophenyl)-6,7-dihydro-4H-pyrazolo[1,5-a]pyrazine-5-carboxamide (Example 50)

The title compound was prepared in analogy to the preparation of Example 11 by using 3-choloro-4-fluoroaniline instead of 3-trifluoromethyaniline and 3-(2,4-difluorophenyl)-4,5,6,7-tetrahydropyrazolo[1,5-a]pyrazine (compound 50b) instead of 3-(4-fluorophenyl)-4,5,6,7-tetrahydropyrazolo[1,5-a]pyrazine (compound 11b). Example 50 was obtained as a white solid (10 mg). LCMS (M+H$^+$): 407. $^1$H NMR (400 MHz, DMSO-d$_6$) δ ppm 9.15 (s, 1H), 7.80-7.61 (m, 2H), 7.59-7.24 (m, 4H), 7.24-7.12 (m, 1H), 4.79 (s, 2H), 4.24 (t, J=5.1 Hz, 2H), 4.07-3.93 (m, 2H).

Example 51

3-(2,4-difluorophenyl)-N-(3,4,5-trifluorophenyl)-6,7-dihydro-4H-pyrazolo[1,5-a]pyrazine-5-carboxamide

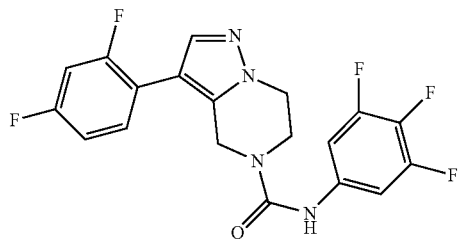 [SMILES: O=C(Nc1cc(F)c(F)c(F)c1)N1CCn2ncc(-c3ccc(F)cc3F)c2C1]

Preparation of Example 51

The title compound was prepared in analogy to the preparation of Example 11 by using 3,4,5-trifluoroaniline instead of 3-trifluoromethylaniline and 3-(2,4-difluorophenyl)-4,5,6,7-tetrahydropyrazolo[1,5-a]pyrazine (compound 50b) instead of 3-(4-fluorophenyl)-4,5,6,7-tetrahydropyrazolo[1,5-a]pyrazine (compound 11b). Example 51 was obtained as a white solid (22 mg). LCMS (M+H$^+$): 409. $^1$H NMR (400 MHz, DMSO-d$_6$) δ ppm 9.31 (d, J=10.0 Hz, 1H), 7.70 (d, J=1.9 Hz, 1H), 7.55-7.29 (m, 4H), 7.19 (dt, J=2.4, 8.5 Hz, 1H), 4.80 (s, 2H), 4.24 (t, J=5.3 Hz, 2H), 4.12-3.93 (m, 2H).

Example 52

3-(4-fluoro-3-methyl-phenyl)-N-phenyl-6,7-dihydro-4H-pyrazolo[1,5-a]pyrazine-5-carboxamide

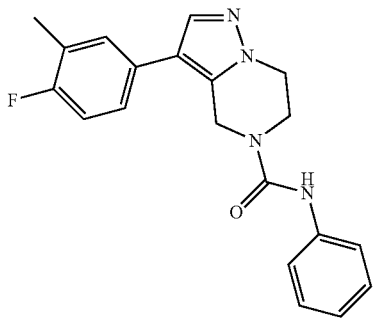 [SMILES: Cc1cc(-c2cnn3c2CN(C(=O)Nc2ccccc2)CC3)ccc1F]

Preparation of Example 52

The title compound was prepared in analogy to the preparation of Example 1 by using (3-methyl-4-fluorophenyl)boronic acid instead of (4-fluorophenyl)boronic acid. Example 52 was obtained as a white solid (26 mg). LCMS (M+H$^+$): 351. $^1$H NMR (400 MHz, DMSO-d$_6$) δ ppm 8.89 (s, 1H), 7.80 (s, 1H), 7.45 (d, J=7.7 Hz, 2H), 7.40-7.35 (m, 1H), 7.31-7.12 (m, 4H), 7.03-6.91 (m, 1H), 4.92 (s, 2H), 4.22 (t, J=5.3 Hz, 2H), 4.07-3.92 (m, 2H), 2.29 (d, J=1.5 Hz, 3H).

Example 53

3-(4-fluorophenyl)-6-methyl-N-(3,4,5-trifluorophenyl)-6,7-dihydro-4H-pyrazolo[1,5-a]pyrazine-5-carboxamide

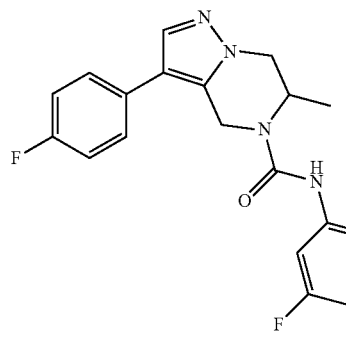

The title compound was prepared according to the following scheme:

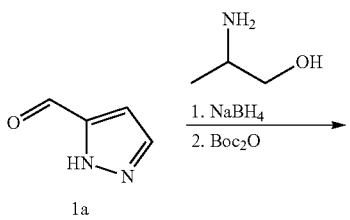

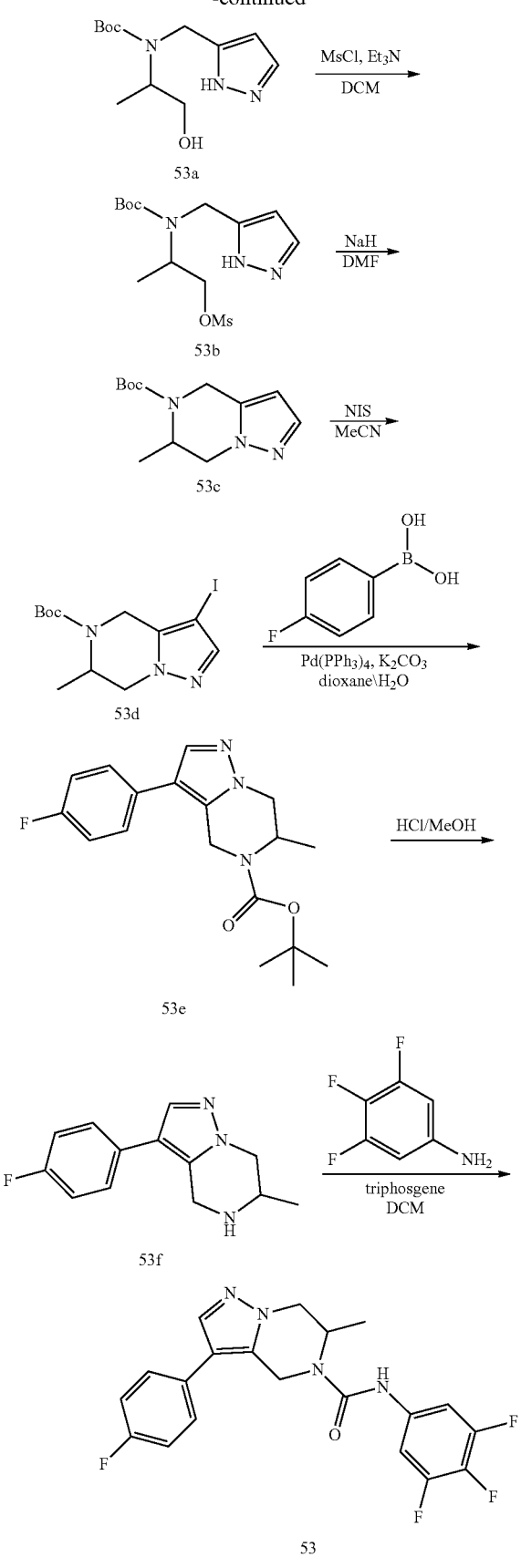

Step 1: Preparation of tert-butyl N-(2-hydroxy-1-methyl-ethyl)-N-(1H-pyrazol-5-ylmethyl)carbamate (compound 53a)

To a solution of 1H-pyrazole-5-carbaldehyde (compound 1a, 54.0 g, 562.5 mmol) in MeOH (300 mL) was added 2-aminopropan-1-ol (41.2 g, 675 mmol) and the reaction mixture was stirred at 25° C. for 1 hour. NaBH$_4$ (25.9 g, 675.0 mmol) was added at 0° C. and the reaction mixture was stirred for another 1 hour followed by the addition of H$_2$O (300 mL) and Boc$_2$O (147.1 g, 675.0 mmol). The resulting mixture was stirred at room temperature for 12 hours, and extracted with EtOAc (600 mL). The organic layer was dried over Na$_2$SO$_4$, filtered and concentrated. The residue was purified by column chromatography (eluting with 0%~5% MeOH in DCM) to afford compound 53a (80 g) as a colorless oil. LCMS (M+H$^+$): 334. $^1$H NMR (400 MHz, chloroform-d) δ ppm 7.55-7.46 (m, 1H), 6.30-6.07 (m, 1H), 4.62-4.37 (m, 2H), 4.33-3.99 (m, 1H), 3.74-3.47 (m, 2H), 1.54-1.27 (m, 9H), 1.12 (d, J=7.0 Hz, 3H).

Step 2: Preparation of 2-[tert-butoxycarbonyl(1H-pyrazol-5-ylmethyl)amino]propyl methanesulfonate (compound 53b)

To a mixture of tert-butyl N-(2-hydroxy-1-methyl-ethyl)-N-(1H-pyrazol-5-ylmethyl)carbamate (compound 53a, 80.0 g, 117.2 mmol) and Et$_3$N (100.5 g, 995.6 mmol) in DCM (800 mL) was added MsCl (57.3 g, 497.8 mmol) slowly at 0° C. The resulting mixture was stirred at room temperature for 2 hours, then washed with water (500 mL), brine (500 mL), and dried over Na$_2$SO$_4$. The organic layer was concentrated to afford compound 53b (100 g, crude), which was used directly in next step.

Step 3: Preparation of tert-butyl 6-methyl-6,7-dihydro-4H-pyrazolo[1,5-a]pyrazine-5-carboxylate (compound 53c)

To a solution of 2-[tert-butoxycarbonyl(1H-pyrazol-5-ylmethyl)amino]propyl methanesulfonate (compound 53b, 100.0 g, 313.4 mmol) in DMF (1000 mL) was added NaH (15.0 g, 376.2 mmol) in portions at 0° C. The reaction mixture was then stirred at room temperature for 12 hours, poured into water (2000 mL) and extracted with EtOAc (1000 mL) twice. The organic layers were combined and concentrated. The residue was purified by column chromatography (eluting with 10%~80% EtOAc in petroleum ether) to afford compound 53c (18.0 g) as a colorless oil. LCMS (M+H$^+$): 238. $^1$H NMR (400 MHz, chloroform-d) δ ppm 7.55-7.46 (m, 1H), 6.20 (s, 1H), 4.98-4.91 (m, 1H), 4.85-4.76 (m, 1H), 4.45-4.33 (m, 1H), 4.26-4.18 (m, 1H), 4.16-4.08 (m, 1H), 1.53 (s, 9H), 1.23-1.10 (m, 3H).

Step 4: Preparation of tert-butyl 3-iodo-6-methyl-6,7-dihydro-4H-pyrazolo[1,5-a]pyrazine-5-carboxylate (compound 53d)

To a solution of tert-butyl 6-methyl-6,7-dihydro-4H-pyrazolo[1,5-a]pyrazine-5-carboxylate (compound 53c, 3.3 g, 14.8 mmol) in CH$_3$CN (40 mL) was added NIS (5.0 g, 22.1 mmol) slowly. The reaction mixture was stirred at room temperature for 16 hours and then extracted with EtOAc (50 mL), washed with brine (50 mL). The organic layer was dried over Na$_2$SO$_4$ and concentrated, and the residue was purified by column chromatography (eluting with 10%~80% EtOAc in petroleum ether) to afford compound 53d (4.8 g) as a white solid.

Step 5: Preparation of tert-butyl 3-(4-fluorophenyl)-6-methyl-6,7-dihydro-4H-pyrazolo[1,5-a]pyrazine-5-carboxylate (compound 53e)

To a mixture of tert-butyl 3-iodo-6-methyl-6,7-dihydro-4H-pyrazolo[1,5-a]pyrazine-5-carboxylate (compound 53d, 1.1 g, 3 mmol), (4-fluorophenyl)boronic acid (630 mg, 4.5 mmol) and $K_2CO_3$ (1.2 g, 9 mmol) in and dioxane/water (10 mL, 5:1, v/v) was added $Pd(PPh_3)_4$ (150 mg) under $N_2$. The reaction mixture was stirred at 80° C. for 2 hours. The reaction was concentrated and the residue was purified by column chromatography to afford compound 53e (550 mg) a slight yellow solid. LCMS (M+H$^+$): 332.

Step 6: Preparation of 3-(4-fluorophenyl)-6-methyl-4,5,6,7-tetrahydropyrazolo[1,5-a]pyrazine (compound 53f)

A solution of tert-butyl 3-(4-fluorophenyl)-6-methyl-6,7-dihydro-4H-pyrazolo[1,5-a]pyrazine-5-carboxylate (compound 53e, 550 mg, 1.7 mmol) in HCl/MeOH (20 mL) was stirred at room temperature for 2 hours. Then the reaction mixture was concentrated in vacuo to afford compound 53f (400 mg) as a slight yellow solid. LCMS (M+H$^+$): 232.

Step 7: Preparation of 3-(4-fluorophenyl)-6-methyl-N-(3,4,5-trifluorophenyl)-6,7-dihydro-4H-pyrazolo[1,5-a]pyrazine-5-carboxamide (Example 53)

The title compound was prepared in analogy to the preparation of Example 11 by using 3,4,5-trifluoroaniline instead of 3-trifluoromethylaniline and 3-(4-fluorophenyl)-6-methyl-4,5,6,7-tetrahydropyrazolo[1,5-a]pyrazine (compound 53f) instead of 3-(4-fluorophenyl)-4,5,6,7-tetrahydropyrazolo[1,5-a]pyrazine (compound 11b). Example 53 was obtained as a white solid (16 mg). LCMS (M+H$^+$): 405. $^1$H NMR (400 MHz, DMSO-d$_6$) δ ppm 9.12 (s, 1H), 7.86 (s, 1H), 7.55 (dd, J=5.4, 8.8 Hz, 2H), 7.43 (dd, J=6.5, 10.7 Hz, 2H), 7.27 (t, J=8.8 Hz, 2H), 5.19 (d, J=16.7 Hz, 1H), 4.95-4.87 (m, 1H), 4.66 (d, J=16.6 Hz, 1H), 4.28-4.17 (m, 1H), 3.54 (s, 1H), 1.18 (d, J=6.9 Hz, 3H).

Example 54

N-[(3-chloro-4-fluoro-phenyl)methyl]-3-(4-fluorophenyl)-6,7-dihydro-4H-pyrazolo[1,5-a]pyrazine-5-carboxamide

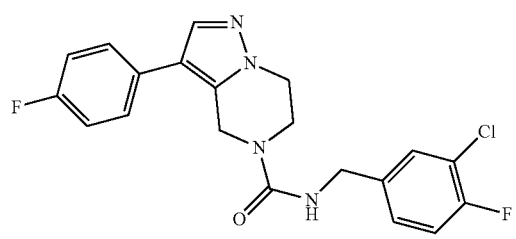 [SMILES: O=C(NCc1ccc(F)c(Cl)c1)N1CCn2ncc(-c3ccc(F)cc3)c2C1]

Preparation of Example 54

The title compound was prepared in analogy to the preparation of Example 11 by using (3-chloro-4-fluoro-phenyl)methanamine instead of 3-(trifluoromethyl)aniline. Example 54 was obtained as a white solid (27 mg). LCMS (M+H$^+$): 403. $^1$H NMR (400 MHz, DMSO-d$_6$) δ ppm 7.81 (s, 1H), 7.55 (t, J=5.6 Hz, 1H), 7.50-7.46 (m, 3H), 7.35-7.25 (m, 4H), 4.81 (s, 2H), 4.25 (d, J=5.5 Hz, 2H), 4.14 (t, J=5.6 Hz, 2H), 3.89 (t, J=5.6 Hz, 2H).

Example 55

N-[(3,5-dichlorophenyl)methyl]-3-(4-fluorophenyl)-6,7-dihydro-4H-pyrazolo[1,5-a]pyrazine-5-carboxamide

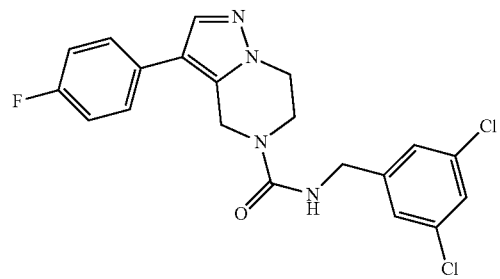 [SMILES: O=C(NCc1cc(Cl)cc(Cl)c1)N1CCn2ncc(-c3ccc(F)cc3)c2C1]

Preparation of Example 55

The title compound was prepared in analogy to the preparation of Example 11 by using (3,5-dichloro-phenyl)methanamine instead of 3-(trifluoromethyl)aniline. Example 55 was obtained as a white solid. LCMS (M+H$^+$): 419. $^1$H NMR (400 MHz, DMSO-d$_6$) δ ppm 7.86-7.74 (m, 1H), 7.59 (t, J=5.7 Hz, 1H), 7.52-7.40 (m, 3H), 7.31 (d, J=1.9 Hz, 2H), 7.29-7.14 (m, 2H), 4.82 (s, 2H), 4.26 (d, J=5.8 Hz, 2H), 4.15 (t, J=5.3 Hz, 2H), 3.89 (t, J=5.3 Hz, 2H).

Example 56

N-(4-chloro-5-methyl-2-pyridyl)-3-(4-fluorophenyl)-6,7-dihydro-4H-pyrazolo[1,5-a]pyrazine-5-carboxamide

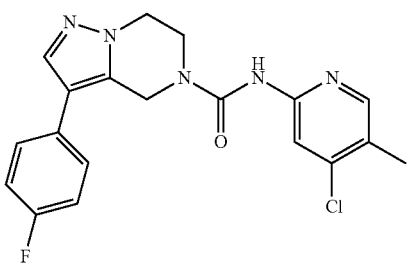 [SMILES: Cc1cnc(NC(=O)N2CCn3ncc(-c4ccc(F)cc4)c3C2)cc1Cl]

Preparation of Example 56

The title compound was prepared in analogy to the preparation of Example 32 by using 4-chloro-5-methyl-pyridin-2-amine instead of 5-fluoro-6-methyl-pyridin-2-amine. Example 56 was obtained as a white solid (21 mg). LCMS (M+H$^+$): 386. $^1$H NMR (400 MHz, DMSO-d$_6$) δ ppm 9.85 (s, 1H), 8.21 (s, 1H), 7.91 (s, 1H), 7.83 (s, 1H), 7.50 (dd, J=5.5, 8.8 Hz, 2H), 7.34-7.19 (m, 2H), 4.96 (s, 2H), 4.25-4.16 (m, 2H), 4.05-3.97 (m, 2H), 2.25 (s, 3H).

Example 57

3-(4-chloro-2-pyridyl)-N-phenyl-6,7-dihydro-4H-pyrazolo[1,5-a]pyrazine-5-carboxamide

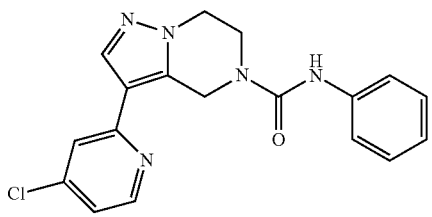 [SMILES: O=C(Nc1ccccc1)N1CCn2ncc(-c3cc(Cl)ccn3)c2C1]

Preparation of Example 57

The title compound was prepared in analogy to the preparation of Example 28 by using 2,4-dichloropyridine instead of 2-chloro-4-(trifluoromethyl)pyridine. Example 57 was obtained as a white solid. LCMS (M+H⁺): 354. ¹H NMR (400 MHz, DMSO-d₆) δ ppm 9.07 (s, 1H), 8.55 (d, J=5.5 Hz, 1H), 8.22 (s, 1H), 7.89 (d, J=1.8 Hz, 1H), 7.49 (d, J=7.8 Hz, 2H), 7.31 (dd, 5.4 Hz, 1H), 7.25 (t, J=7.9 Hz, 2H), 6.96 (t, J=7.4 Hz, 1H), 5.05 (s, 2H), 4.24 (t, J=5.1 Hz, 2H), 4.03 (t, J=5.1 Hz, 2H).

Example 58

N-[(2-chloro-3-fluoro-phenyl)methyl]-3-(4-fluoro-phenyl)-6,7-dihydro-4H-pyrazolo[1,5-a]pyrazine-5-carboxamide

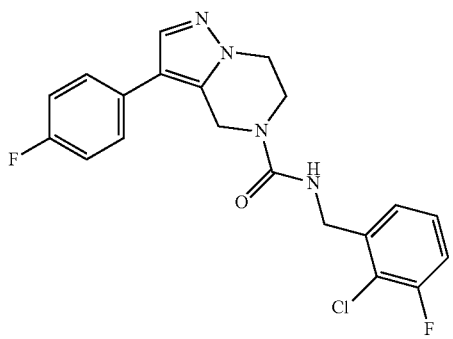 [SMILES: O=C(NCc1cccc(F)c1Cl)N1CCn2ncc(-c3ccc(F)cc3)c2C1]

Preparation of Example 58

The title compound was prepared in analogy to the preparation of Example 11 by using (2-chloro-3fluoro-phenyl)methanamine instead of 3-(trifluoromethyl)aniline. Example 58 was obtained as a white solid (26 mg). LCMS (M+H⁺): 403. ¹H NMR (400 MHz, DMSO-d₆) δ ppm 7.82 (s, 1H), 7.57 (t, J=5.5 Hz, 1H), 7.48 (dd, J=5.4, 8.7 Hz, 2H), 7.38-7.15 (m, 5H), 4.84 (s, 2H), 4.37 (d, J=5.5 Hz, 2H), 4.17 (t, J=5.1 Hz, 2H), 3.92 (d, J=5.3 Hz, 2H).

Example 59

N-[(2,6-dichlorophenyl)methyl]-3-(4-fluorophenyl)-6,7-dihydro-4H-pyrazolo[1,5-a]pyrazine-5-carboxamide

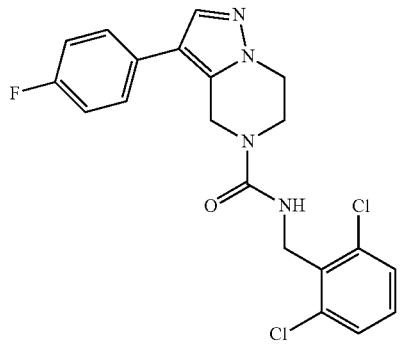 [SMILES: O=C(NCc1c(Cl)cccc1Cl)N1CCn2ncc(-c3ccc(F)cc3)c2C1]

Preparation of Example 59

The title compound was prepared in analogy to the preparation of Example 11 by using (2,5-dichloro-phenyl)methanamine instead of 3-(trifluoromethyl)aniline. Example 59 was obtained as a white solid (21 mg). LCMS (M+H⁺): 419. ¹H NMR (400 MHz, DMSO-d₆) δ ppm 7.78 (s, 1H), 7.53-7.41 (m, 4H), 7.39-7.31 (m, 1H), 7.28-7.17 (m, 2H), 7.09 (br. s, 1H), 4.76 (s, 2H), 4.49 (d, J=4.3 Hz, 2H), 4.10 (d, J=5.3 Hz, 2H), 3.87 (d, J=5.0 Hz, 2H).

Example 60

3-(2,4-difluorophenyl)-N-(5-fluoro-6-methyl-2-pyridyl)-6,7-dihydro-4H-pyrazolo[1,5-a]pyrazine-5-carboxamide

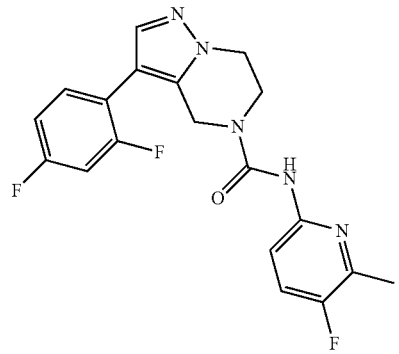 [SMILES: Cc1nc(NC(=O)N2CCn3ncc(-c4ccc(F)cc4F)c3C2)ccc1F]

Preparation of Example 60

To a mixture of 5-fluoro-6-methyl-pyridin-2-amine (40 mg, 0.32 mmol) and Et₃N (65 mg, 0.64 mmol) in THF (5 mL) was added phenyl chloroformate (50 mg, 0.12 mmol) at 0° C. After stirred at room temperature for 12 hours, the reaction mixture was diluted with EtOAc (20 mL), washed with saturated aqueous NaHCO₃ (20 mL). The separated organic layer was washed with brine (30 mL), dried over anhydrous sodium sulfate. The solvent was removed in vacuo. The residue was dissolved in DMF (2 mL), to which were added 3-(2,4-difluorophenyl)-4,5,6,7-tetrahydropyrazolo[1,5-a]pyrazine (compound 50b, 44 mg, 0.32 mmol) and DIPEA (0.2 mL). The resulting mixture was stirred at 80° C. for 1 hour, then subjected to purification by prep-HPLC to afford Example 60 (16 mg) as a white solid. LCMS (M+H$^+$): 388. $^1$H NMR (400 MHz, DMSO-d$_6$) δ ppm 9.63 (br. s, 1H), 8.43 (br. s, 1H), 7.66-7.61 (m, 1H), 7.59-7.45 (m, 2H), 7.41-7.30 (m, 1H), 7.23-7.11 (m, 1H), 4.81 (s, 2H), 4.21 (d, J=5.0 Hz, 2H), 4.02 (s, 2H), 2.36 (d, J=2.5 Hz, 3H).

Example 61

N-(3-chloro-4-fluoro-phenyl)-3-(4-fluorophenyl)-6-methyl-6,7-dihydro-4H-pyrazolo[1,5-a]pyrazine-5-carboxamide

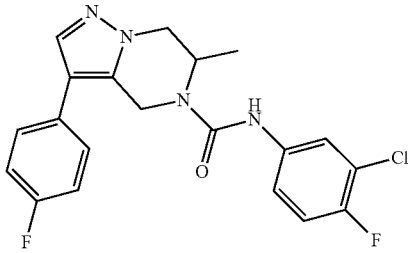 [SMILES: CC1Cn2ncc(-c3ccc(F)cc3)c2CN1C(=O)Nc1ccc(F)c(Cl)c1]

Preparation of Example 61

The title compound was prepared in analogy to the preparation of Example 11 by using 3-chloro-4-fluoroaniline instead of 3-trifluoromethylaniline and 3-(4-fluorophenyl)-6-methyl-4,5,6,7-tetrahydropyrazolo[1,5-a]pyrazine (compound 53f) instead of 3-(4-fluorophenyl)-4,5,6,7-tetrahydropyrazolo[1,5-a]pyrazine (compound 11b). Example 61 was obtained as a white solid (27 mg). LCMS (M+H$^+$): 403. $^1$H NMR (400 MHz, DMSO-d$_6$) δ ppm 8.96 (s, 1H), 7.86 (s, 1H), 7.74 (dd, J=2.5, 6.9 Hz, 1H), 7.55 (dd, J=5.5, 8.8 Hz, 2H), 7.45-7.40 (m, 1H), 7.36-7.30 (m, 1H), 7.27 (t, J=8.8 Hz, 2H), 5.20 (d, J=16.7 Hz, 1H), 4.96-4.87 (m, 1H), 4.65 (d, J=16.7 Hz, 1H), 4.29-4.22 (m, 1H), 4.21-4.14 (m, 1H), 1.18 (d, J=6.8 Hz, 3H).

Example 62

3-(4-fluorophenyl)-N-(2-methyl-1,3-benzothiazol-5-yl)-6,7-dihydro-4H-pyrazolo[1,5-a]pyrazine-5-carboxamide

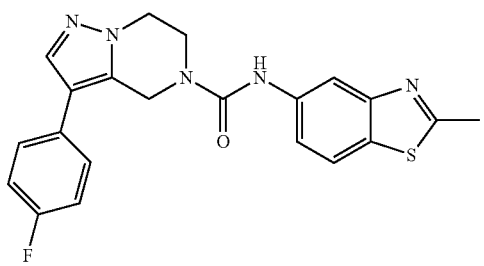 [SMILES: Cc1nc2cc(NC(=O)N3CCn4ncc(-c5ccc(F)cc5)c4C3)ccc2s1]

Preparation of Example 62

The title compound was prepared in analogy to the preparation of Example 11 by using 2-methyl-1,3-benzothiazol-5-amine instead of 3-(trifluoromethyl)aniline. Example 62 was obtained as a white solid (33 mg). LCMS (M+H$^+$): 408. $^1$H NMR (400 MHz, DMSO-d$_6$) δ ppm 9.06 (s, 1H), 8.07 (d, J=1.8 Hz, 1H), 7.92-7.82 (m, 2H), 7.56-7.44 (m, 3H), 7.33-7.21 (m, 2H), 4.97 (s, 2H), 4.25 (t, J=5.3 Hz, 2H), 4.04 (t, J=5.1 Hz, 2H), 2.81-2.73 (m, 3H).

Example 63

N-(benzothiophen-3-yl)-3-(4-fluorophenyl)-6,7-dihydro-4H-pyrazolo[1,5-a]pyrazine-5-carboxamide

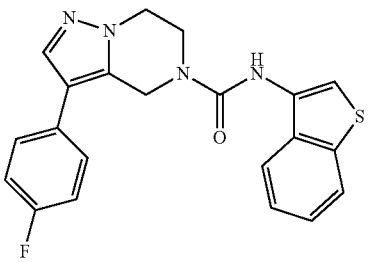 [SMILES: O=C(Nc1csc2ccccc12)N1CCn2ncc(-c3ccc(F)cc3)c2C1]

Preparation of Example 63

The title compound was prepared in analogy to the preparation of Example 11 by using 2-methyl-1,3-benzothiazol-5-amine instead of 3-(trifluoromethyl)aniline. Example 63 was obtained as a white solid (24 mg). LCMS (M+H$^+$): 393. $^1$H NMR (400 MHz, DMSO-d$_6$) δ ppm 9.04 (s, 1H), 7.96-7.91 (m, 1H), 7.88-7.84 (m, 2H), 7.58 (s, 1H), 7.55-7.49 (m, 2H), 7.44-7.37 (m, 2H), 7.28 (t, J=8.8 Hz, 2H), 5.00 (s, 2H), 4.26 (t, J=5.2 Hz, 2H), 4.07 (t, J=5.4 Hz, 2H).

Example 64

3-(2,4-difluorophenyl)-N-[2-(trifluoromethyl)-4-pyridyl]-6,7-dihydro-4H-pyrazolo[1,5-a]pyrazine-5-carboxamide

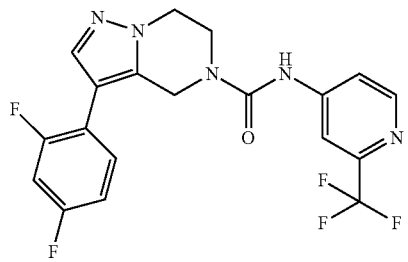 [SMILES: O=C(Nc1ccnc(C(F)(F)F)c1)N1CCn2ncc(-c3ccc(F)cc3F)c2C1]

Preparation of Example 64

The title compound was prepared in analogy to the preparation of Example 11 by using 2-(trifluoromethyl)pyridin-4-amine instead of 3-trifluoromethylaniline and 3-(2, 4-difluorophenyl)-4,5,6,7-tetrahydropyrazolo[1,5-a]

pyrazine instead of 3-(4-fluorophenyl)-4,5,6,7-tetrahydro-pyrazolo[1,5-a]pyrazine (compound 11b). Example 64 was afforded as a white solid (10 mg). LCMS (M+H+): 424. ¹H NMR (400 MHz, DMSO-d₆) δδ ppm 9.64 (s, 1H), 8.52 (d, J=5.5 Hz, 1H), 8.00 (d, J=1.8 Hz, 1H), 7.72 (s, 2H), 7.55-7.46 (m, 1H), 7.44-7.35 (m, 1H), 7.20 (dt, 8.3 Hz, 1H), 4.84 (s, 2H), 4.27 (t, J=5.3 Hz, 2H), 4.06 (t, J=5.3 Hz, 2H).

Example 65

3-(3-cyclopropylphenyl)-N-phenyl-6,7-dihydro-4H-pyrazolo[1,5-a]pyrazine-5-carboxamide

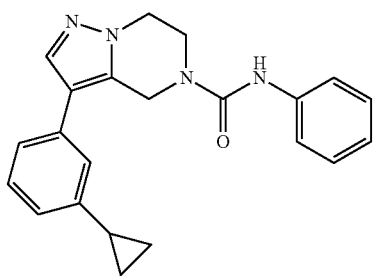 [SMILES: O=C(Nc1ccccc1)N1CCn2ncc(-c3cccc(C4CC4)c3)c2C1]

Preparation of Example 65

The title compound was prepared in analogy to the preparation of Example 28 by using 1-bromo-3-cyclopropyl-benzene instead of 2-chloro-4-(trifluoromethyl)pyridine. Example 65 was obtained as a white solid (15 mg). LCMS (M+H+): 359. ¹H NMR (400 MHz, chloroform-d) δ ppm 7.76 (s, 1H), 7.39-7.31 (m, 5H), 7.10 (br. s, 3H), 7.03-6.96 (m, 1H), 6.70-6.53 (m, 1H), 4.90 (s, 2H), 4.38 (m, 2H), 4.04 (m, 2H), 2.00-1.90 (m, 1H), 1.11-0.98 (m, 2H), 0.81-0.68 (m, 2H).

Example 66

3-(2-hydroxyphenyl)-N-phenyl-6,7-dihydro-4H-pyrazolo[1,5-a]pyrazine-5-carboxamide

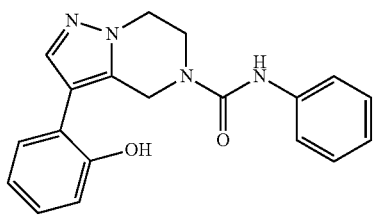 [SMILES: O=C(Nc1ccccc1)N1CCn2ncc(-c3ccccc3O)c2C1]

Preparation of Example 66

The title compound was prepared in analogy to the preparation of Example 28 by using 2-bromophenol instead of 2-chloro-4-(trifluoromethyl)pyridine. Example 66 was obtained as a white solid. LCMS (M+H+): 335. ¹H NMR (400 MHz, DMSO-d₆) δ ppm 9.65 (br. s, 1H), 8.84 (s, 1H), 7.64 (s, 1H), 7.43 (d, J=8.0 Hz, 2H), 7.27-7.17 (m, 3H), 7.12 (t, J=7.7 Hz, 1H), 6.99-6.90 (m, 2H), 6.85 (t, J=7.0 Hz, 1H), 4.76 (s, 2H), 4.21 (m, 2H), 4.00 (m, 2H).

Example 67

N-(3-chloro-4-fluoro-phenyl)-3-[4-(trifluoromethyl)-2-pyridyl]-6,7-dihydro-4H-pyrazolo[1,5-a]pyrazine-5-carboxamide

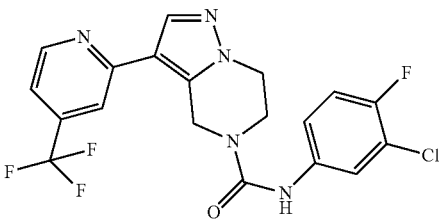 [SMILES: O=C(Nc1ccc(F)c(Cl)c1)N1CCn2ncc(-c3cc(C(F)(F)F)ccn3)c2C1]

The title compound was prepared according to the following scheme:

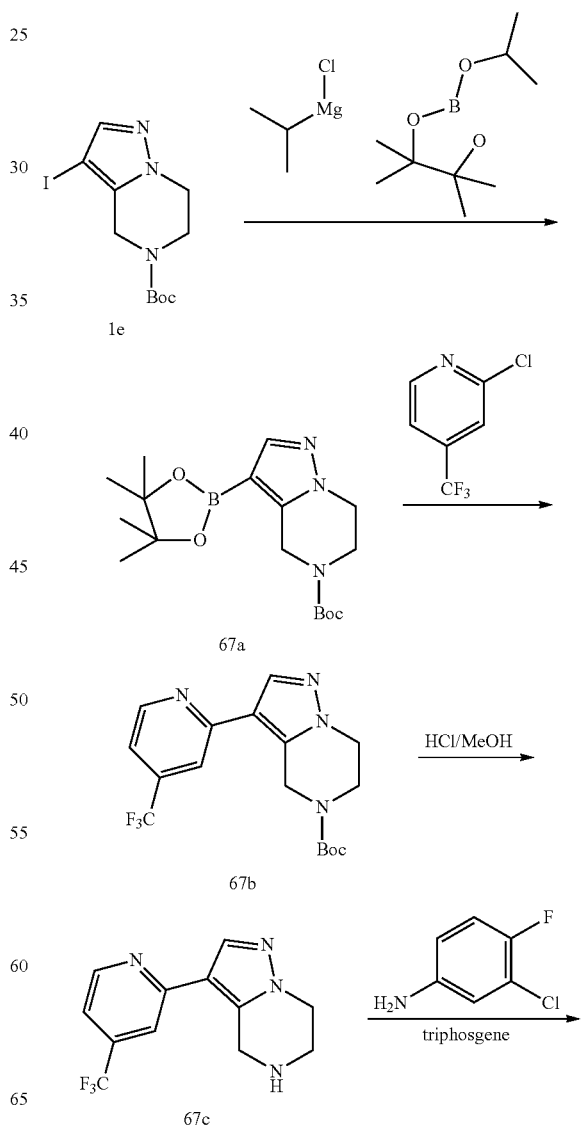

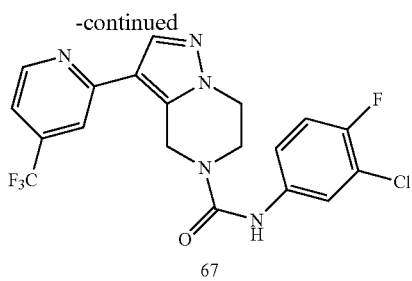

Step 1: Preparation of tert-butyl 3-(4,4,5,5-tetramethyl-1,3,2-dioxaborolan-2-yl)-6,7-dihydro-4H-pyrazolo[1,5-a]pyrazine-5-carboxylate (compound 67a)

To a solution of tert-butyl 3-iodo-6,7-dihydro-4H-pyrazolo[1,5-a]pyrazine-5-carboxylate (compound 1e, 500 mg, 1.4 mmol) in THF (15 mL) was added isopropyl magnesium chloride (1.7 mL, 3.4 mmol) at 0° C. The reaction mixture was stirred at 0° C. for 0.5 hours, then 2-isopropoxy-4,4,5,5-tetramethyl-1,3,2-dioxaborolane (380 mg, 2 mmol) in THF (5 mL) was added dropwise at 0° C. The reaction mixture was stirred at room temperature for 1 hour, then quenched with saturated aqueous ammonium chloride solution (20 mL), and extracted with EtOAc (30 mL). The organic layer was washed with brine, and concentrated to afford compound 67a (450 mg) as a white solid. LCMS (M+H⁺): 350.

Step 2: Preparation of tert-butyl 3-[4-(trifluoromethyl)-2-pyridyl]-6,7-dihydro-4H-pyrazolo[1,5-a]pyrazine-5-carboxylate (compound 67b)

To a mixture of tert-butyl 3-(4,4,5,5-tetramethyl-1,3,2-dioxaborolan-2-yl)-6,7-dihydro-4H-pyrazolo[1,5-a]pyrazine-5-carboxylate (compound 67a, 450 mg, 1.3 mmol), 2-chloro-4-(trifluoromethyl)pyridine (324 mg, 1.8 mmol) and $K_2CO_3$ (252 mg, 1.8 mmol) in $DMSO/H_2O$ (10 mL, 10:1, v/v) was added Pd(dppf)Cl$_2$ (50 mg) under $N_2$. The reaction mixture was stirred at 80° C. for 12 hours. Then the reaction mixture was filtered, the filtrate was purified by column chromatography to afford compound 67b (300 mg) as a white solid. LCMS (M+H⁺): 369.

Step 3: Preparation of 3-[4-(trifluoromethyl)-2-pyridyl]-4,5,6,7-tetrahydropyrazolo[1,5-a]pyrazine (compound 67c)

A solution of tert-butyl 3-[4-(trifluoromethyl)-2-pyridyl]-6,7-dihydro-4H-pyrazolo[1,5-a]pyrazine-5-carboxylate (compound 67b, 300 mg, 1.7 mmol) in HCl/MeOH (20 mL) was stirred at room temperature for 2 hours. Then the reaction mixture was concentrated in vacuo to afford compound 67c (200 mg) as a slight yellow solid. LCMS (M+H⁺): 269.

Step 4: Preparation of N-(3-chloro-4-fluoro-phenyl)-3-[4-(trifluoromethyl)-2-pyridyl]-6,7-dihydro-4H-pyrazolo[1,5-a]pyrazine-5-carboxamide (Example 67)

The title compound was prepared in analogy to the preparation of Example 11 by using 3-chloro-4-fluoroaniline and 3-[4-(trifluoromethyl)-2-pyridyl]-4,5,6,7-tetrahydropyrazolo[1,5-a]pyrazine (compound 67c) instead of 3-(trifluoromethyl)aniline and 3-(4-fluorophenyl)-4,5,6,7-tetrahydropyrazolo[1,5-a]pyrazine (compound 11b), respectively. Example 67 was obtained as a white solid (8 mg). LCMS (M+H⁺): 440. ¹H NMR (400 MHz, DMSO-d₆) δ ppm 9.13 (br. s, 1H), 8.85 (d, J=5.0 Hz, 1H), 8.35 (s, 1H), 8.08 (br. s, 1H), 7.74 (d, J=4.4 Hz, 1H), 7.52 (d, J=4.3 Hz, 1H), 7.40 (br. s, 1H), 7.36-7.24 (m, 1H), 5.09 (s, 2H), 4.26 (m, 2H), 4.01 (m, 2H).

Example 68

N-(3-chloro-4-fluoro-phenyl)-3-(5-fluoro-4-methyl-2-pyridyl)-6,7-dihydro-4H-pyrazolo[1,5-a]pyrazine-5-carboxamide

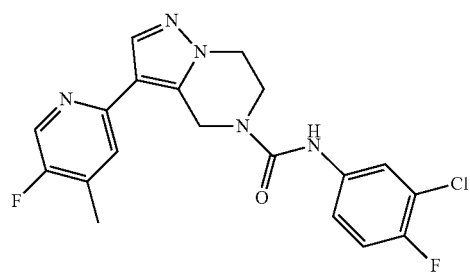 [SMILES: Cc1cc(-c2cnn3c2CN(C(=O)Nc2ccc(F)c(Cl)c2)CC3)ncc1F]

The title compound was prepared according to the following scheme:

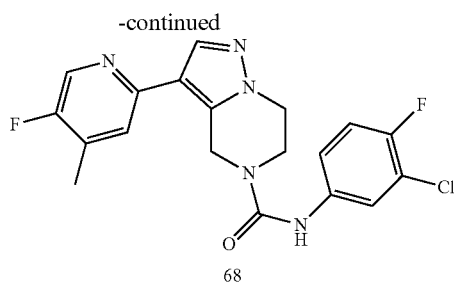

68

Preparation of 3-(5-fluoro-4-methyl-2-pyridyl)-4,5,6,7-tetrahydropyrazolo[1,5-a]pyrazine (compound 68b)

The compound 68b was prepared in analogy to compound 67c by using 2-chloro-5-fluoro-4-methyl-pyridine instead of 2-chloro-4-(trifluoromethyl)pyridine. Compound 68b was obtained as a white solid (250 mg). LCMS (M+H$^+$): 233.

Preparation of N-(3-chloro-4-fluoro-phenyl)-3-(5-fluoro-4-methyl-2-pyridyl)-6,7-dihydro-4H-pyrazolo[1,5-a]pyrazine-5-carboxamide (Example 68)

The title compound was prepared in analogy to the preparation of Example 11 by using 3-chloro-4-fluoroaniline and 3-(5-fluoro-4-methyl-2-pyridyl)-4,5,6,7-tetrahydropyrazolo[1,5-a]pyrazine (compound 68b) instead of 3-(trifluoromethyl)aniline and 3-(4-fluorophenyl)-4,5,6,7-tetrahydropyrazolo[1,5-a]pyrazine (compound 11b), respectively. Example 68 was obtained as a white solid (30 mg). LCMS (M+H$^+$): 404. $^1$H NMR (400 MHz, DMSO-d$_6$) δ ppm 9.09 (s, 1H), 8.45 (d, J=1.0 Hz, 1H), 8.06 (s, 1H), 7.78-7.67 (m, 2H), 7.45-7.39 (m, 1H), 7.35-7.29 (m, 1H), 5.03 (s, 2H), 4.23 (t, J=5.3 Hz, 2H), 3.99 (t, J=5.3 Hz, 2H), 2.32 (s, 3H).

Example 69

N-(3-chloro-4-fluoro-phenyl)-3-(5-fluoro-2-pyridyl)-6,7-dihydro-4H-pyrazolo[1,5-a]pyrazine-5-carboxamide

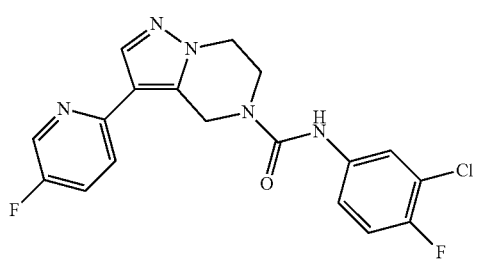

The title compound was prepared according to the following scheme:

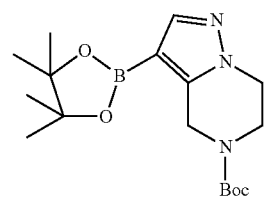 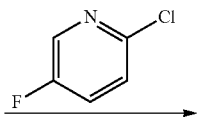

67a

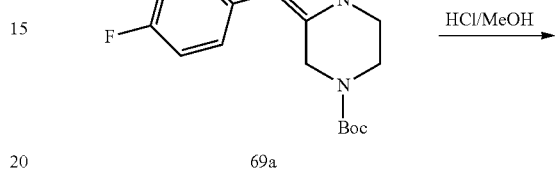

69a

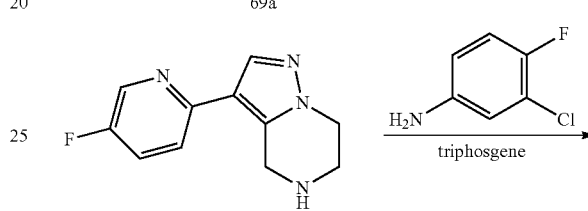

69b

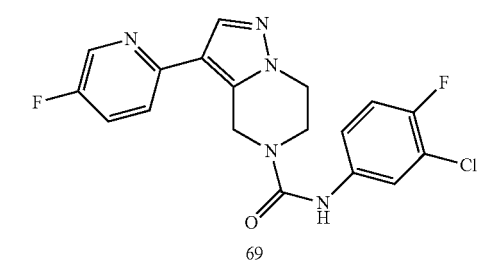

69

Preparation of 3-(5-fluoro-2-pyridyl)-4,5,6,7-tetrahydropyrazolo[1,5-a]pyrazine (compound 69b)

The compound 69b was prepared in analogy to compound 67c by using 2-chloro-5-fluoro-pyridine instead of 2-chloro-4-(trifluoromethyl)pyridine. Compound 69b was obtained as a white solid (250 mg). LCMS (M+H$^+$): 219.

Preparation of N-(3-chloro-4-fluoro-phenyl)-3-(5-fluoro-2-pyridyl)-6,7-dihydro-4H-pyrazolo[1,5-a]pyrazine-5-carboxamide (Example 69)

The title compound was prepared in analogy to the preparation of Example 11 by using 3-chloro-4-fluoroaniline instead of 3-(trifluoromethyl)aniline and 3-(5-fluoro-2-pyridyl)-4,5,6,7-tetrahydropyrazolo[1,5-a]pyrazine (compound 69b) instead of 3-(4-fluorophenyl)-4,5,6,7-tetrahydropyrazolo[1,5-a]pyrazine (compound 11b). Example 69 was obtained as a white solid (50 mg). LCMS (M+H$^+$): 390. $^1$H NMR (400 MHz, DMSO-d$_6$) δ ppm 9.09 (s, 1H), 8.58 (d, J=2.5 Hz, 1H), 8.10 (s, 1H), 7.78 (s, 3H), 7.45-7.39 (m, 1H), 7.36-7.29 (m, 1H), 5.04 (s, 2H), 4.24 (t, J=5.3 Hz, 2H), 4.00 (t, J=5.3 Hz, 2H).

Example 70

N-(2-chloro-4-pyridyl)-3-(2,4-difluorophenyl)-6,7-dihydro-4H-pyrazolo[1,5-a]pyrazine-5-carboxamide

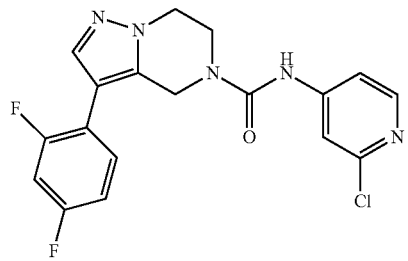 [SMILES: O=C(Nc1ccnc(Cl)c1)N1CCn2ncc(-c3ccc(F)cc3F)c2C1]

Preparation of Example 70

The title compound was prepared in analogy to the preparation of Example 11 by using 2-chloropyridin-4-amine instead of 3-trifuloromethylaniline and 3-(2,4-difluorophenyl)-4,5,6,7-tetrahydropyrazolo[1,5-a]pyrazine instead of 3-(4-fluorophenyl)-4,5,6,7-tetrahydropyrazolo[1,5-a]pyrazine (compound 11b). Example 70 was obtained as a white solid (27 mg). LCMS (M+H$^+$): 390. $^1$H NMR (400 MHz, DMSO-d$_6$) δ ppm 9.49 (s, 1H), 8.16 (d, J=5.8 Hz, 1H), 7.71 (d, J=1.3 Hz, 1H), 7.61 (d, J=1.3 Hz, 1H), 7.55-7.30 (m, 3H), 7.25-7.13 (m, 1H), 4.82 (s, 2H), 4.26 (t, J=5.3 Hz, 2H), 4.10-3.98 (m, 2H).

Example 71

3-[4-(trifluoromethyl)-2-pyridyl]-N-(3,4,5-trifluorophenyl)-6,7-dihydro-4H-pyrazolo[1,5-a]pyrazine-5-carboxamide

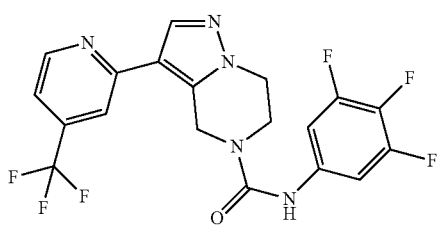 [SMILES: O=C(Nc1cc(F)c(F)c(F)c1)N1CCn2ncc(-c3cc(C(F)(F)F)ccn3)c2C1]

Preparation of Example 71

The title compound was prepared in analogy to Example 11 by using 3,4,5-trifluoroaniline instead of 3-(trifluoromethyl)aniline and 3-[4-(trifluoromethyl)-2-pyridyl]-4,5,6,7-tetrahydropyrazolo[1,5-a]pyrazine (compound 67c) instead of 3-(4-fluorophenyl)-4,5,6,7-tetrahydropyrazolo[1,5-a]pyrazine (compound 11b). Example 71 was obtained as a white solid. LCMS (M+H$^+$): 442. $^1$H NMR (400 MHz, DMSO-d$_6$) δ ppm 9.35 (s, 1H), 8.85 (d, J=5.1 Hz, 1H), 8.35 (s, 1H), 8.09 (s, 1H), 7.52 (d, J=5.0 Hz, 1H), 7.43 (dd, J=6.4, 10.7 Hz, 2H), 5.09 (s, 2H), 4.26 (d, J=5.3 Hz, 2H), 4.03 (d, J=5.4 Hz, 2H).

Example 72

N,3-bis(3-chloro-4-fluoro-phenyl)-6,7-dihydro-4H-pyrazolo[1,5-a]pyrazine-5-carboxamide

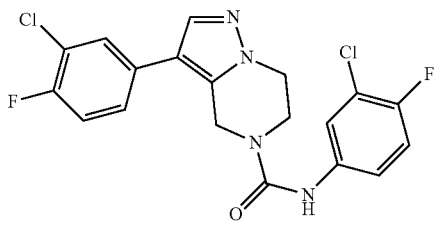 [SMILES: O=C(Nc1ccc(F)c(Cl)c1)N1CCn2ncc(-c3ccc(F)c(Cl)c3)c2C1]

The title compound was prepared according to the following scheme:

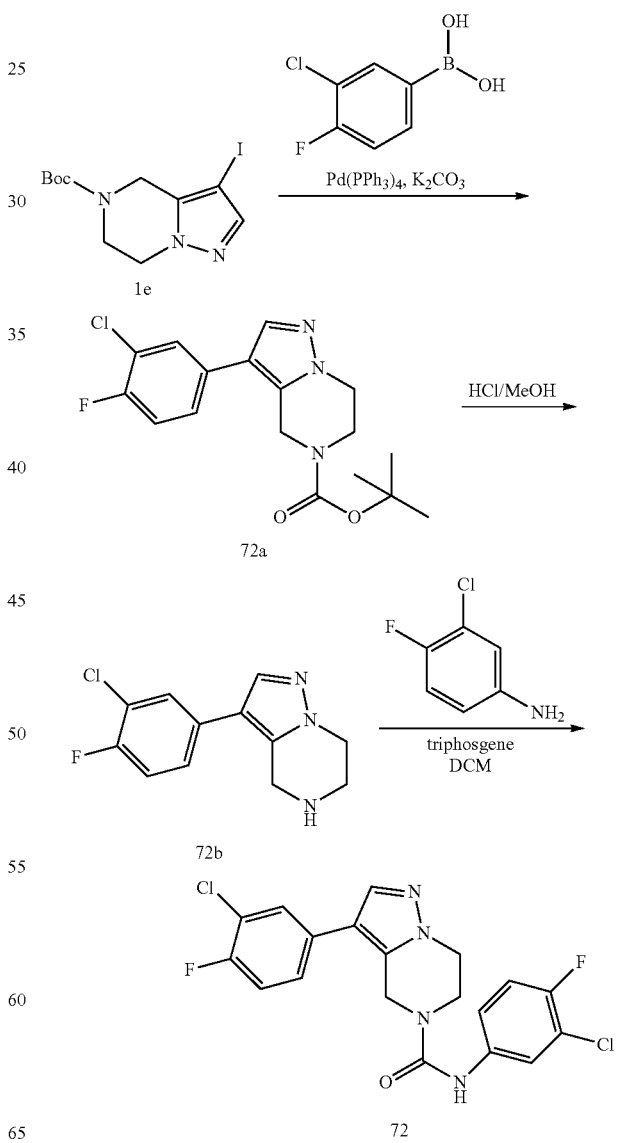

Preparation of 3-(3-chloro-4-fluoro-phenyl)-4,5,6,7-tetrahydropyrazolo[1,5-a]pyrazine (compound 72b)

The compound 72b was prepared in analogy to compound 11b by using (3-chloro-4-fluoro-phenyl)boronic acid (300 mg) instead of (4-fluoro-phenyl)boronic acid. Compound 72b was obtained as a white solid (250 mg). LCMS (M+H$^+$): 252.

Preparation of N,3-bis(3-chloro-4-fluoro-phenyl)-6,7-dihydro-4H-pyrazolo[1,5-a]pyrazine-5-carboxamide (Example 72)

The title compound was prepared in analogy to the preparation of Example 11 by using 3-chloro-4-fluoroaniline instead of 3-(trifluoromethyl)aniline and 3-(3-chloro-4-fluoro-phenyl)-4,5,6,7-tetrahydropyrazolo[1,5-a]pyrazine (compound 72b) instead of 3-(4-fluorophenyl)-4,5,6,7-tetrahydropyrazolo[1,5-a]pyrazine (compound 11b). Example 72 was obtained as a white solid (10 mg). LCMS (M+H$^+$): 443. $^1$H NMR (400 MHz, DMSO-d$_6$) δ ppm 9.09 (s, 1H), 7.90 (s, 1H), 7.76-7.61 (m, 2H), 7.55-7.37 (m, 3H), 7.37-7.27 (m, 1H), 4.95 (s, 2H), 4.22 (d, J=4.8 Hz, 2H), 3.99 (m, 2H).

Example 73

N-(3-chloro-4-fluoro-phenyl)-3-cyclohexyl-6,7-dihydro-4H-pyrazolo[1,5-a]pyrazine-5-carboxamide

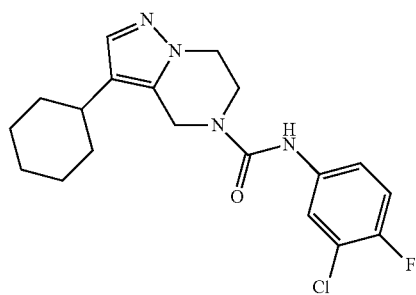 [SMILES: O=C(Nc1ccc(F)c(Cl)c1)N1CCn2ncc(C3CCCCC3)c2C1]

The title compound was prepared according to the following scheme:

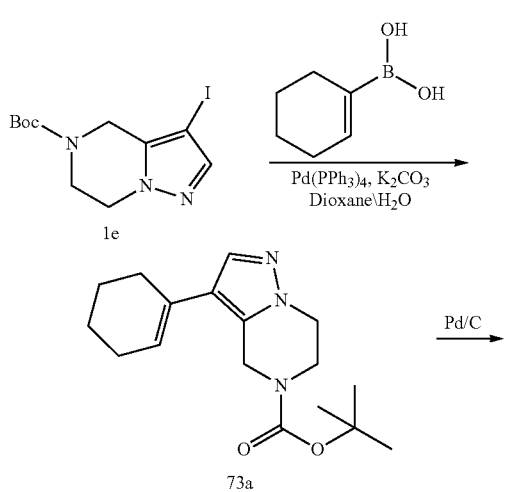

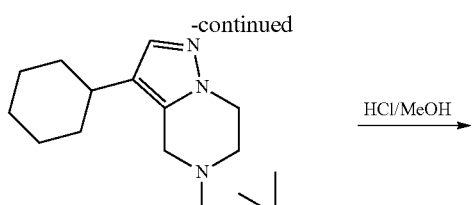

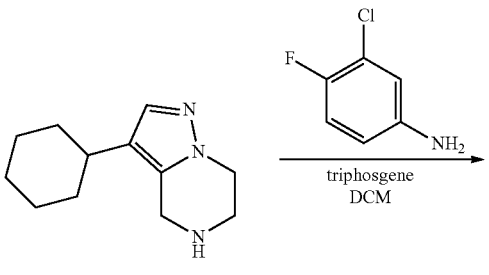

Preparation of 3-cyclohexyl-4,5,6,7-tetrahydropyrazolo[1,5-a]pyrazine (compound 73c)

The compound 73c was prepared in analogy to compound 26c by using cyclohexen-1-ylboronic acid instead of cyclopenten-1-ylboronic acid. Compound 73c was obtained as a white solid (250 mg). LCMS (M+H$^+$): 306.

Preparation of N-(3-chloro-4-fluoro-phenyl)-3-cyclohexyl-6,7-dihydro-4H-pyrazolo[1,5-a]pyrazine-5-carboxamide (Example 73)

The title compound was prepared in analogy to the preparation of Example 11 by using 3-chloro-4-fluoroaniline instead of 3-(trifluoromethyl)aniline and 3-cyclohexyl-4,5,6,7-tetrahydropyrazolo[1,5-a]pyrazine (compound 73c) instead of 3-(4-fluorophenyl)-4,5,6,7-tetrahydropyrazolo[1,5-a]pyrazine (compound 11b). Example 73 was obtained as a white solid (10 mg). LCMS (M+H$^+$): 377. $^1$H NMR (400 MHz, DMSO-d$_6$) δ ppm 8.98 (s, 1H), 7.75 (dd, J=2.5, 6.8 Hz, 1H), 7.44 (td, J=4.3, 7.2 Hz, 1H), 7.36-7.32 (m, 1H), 7.31-7.29 (m, 1H), 4.69 (s, 2H), 4.13-4.08 (m, 2H), 3.95-3.90 (m, 2H), 2.42 (m, 1H), 1.86-1.63 (m, 5H), 1.38-1.20 (m, 5H).

Example 74

N-(3-cyano-4-fluoro-phenyl)-3-(5-fluoro-4-methyl-2-pyridyl)-6,7-dihydro-4H-pyrazolo[1,5-a]pyrazine-5-carboxamide

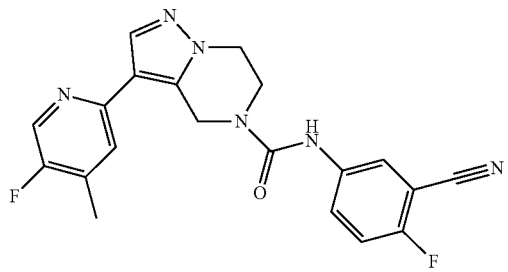 [SMILES: Cc1cc(-c2cnn3c2CN(C(=O)Nc2ccc(F)c(C#N)c2)CC3)ncc1F]

Preparation of Example 74

The title compound was prepared in analogy to the preparation of Example 11 by using 5-amino-2-fluoro-benzonitrile instead of 3-(trifluoromethyl)aniline and 3-(5-fluoro-4-methyl-2-pyridyl)-4,5,6,7-tetrahydropyrazolo[1,5-a]pyrazine (compound 68b) instead of 3-(4-fluorophenyl)-4,5,6,7-tetrahydropyrazolo[1,5-a]pyrazine (compound 11b). Example 74 was obtained as a white solid (16 mg). LCMS (M+H$^+$): 396. $^1$H NMR (400 MHz, DMSO-d$_6$) δ ppm 9.25 (s, 1H), 8.45 (s, 1H), 8.06 (s, 1H), 7.95 (d, J=2.8 Hz, 1H), 7.82-7.76 (m, 1H), 7.71 (d, J=6.0 Hz, 1H), 7.51-7.43 (m, 1H), 5.05 (s, 2H), 4.24 (t, J=5.2 Hz, 2H), 4.03-3.99 (m, 2H), 2.32 (s, 3H).

Example 75

3-(5-fluoro-2-pyridyl)-N-(3,4,5-trifluorophenyl)-6,7-dihydro-4H-pyrazolo[1,5-a]pyrazine-5-carboxamide

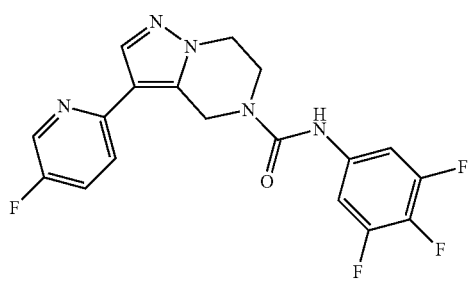 [SMILES: O=C(Nc1cc(F)c(F)c(F)c1)N1CCn2ncc(-c3ccc(F)cn3)c2C1]

Preparation of Example 75

The title compound was prepared in analogy to the preparation of Example 11 by using 3,4,5-trifluoroaniline instead of 3-(trifluoromethyl)aniline and 3-(5-fluoro-2-pyridyl)-4,5,6,7-tetrahydropyrazolo[1,5-a]pyrazine (compound 69b) instead of 3-(4-fluorophenyl)-4,5,6,7-tetrahydropyrazolo[1,5-a]pyrazine (compound 11b). Example 75 was obtained as a white solid (50 mg). LCMS (M+H$^+$): 392. $^1$H NMR (400 MHz, DMSO-d$_6$) δ ppm 9.35-9.22 (m, 1H), 8.58 (d, J=2.6 Hz, 1H), 8.11 (s, 1H), 7.82-7.68 (m, 2H), 7.51-7.36 (m, 2H), 5.05 (s, 2H), 4.24 (t, J=5.3 Hz, 2H), 4.01 (t, J=5.0 Hz, 2H).

Example 76

N-(3-cyano-4-fluoro-phenyl)-3-(5-fluoro-2-pyridyl)-6,7-dihydro-4H-pyrazolo[1,5-a]pyrazine-5-carboxamide

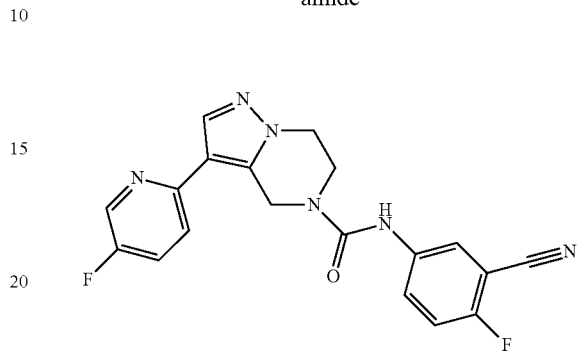

Preparation of Example 76

The title compound was prepared in analogy to the preparation of Example 11 by using 5-amino-2-fluoro-benzonitrile instead of 3-(trifluoromethyl)aniline and 3-(5-fluoro-2-pyridyl)-4,5,6,7-tetrahydropyrazolo[1,5-a]pyrazine (compound 69b) instead of 3-(4-fluorophenyl)-4,5,6,7-tetrahydropyrazolo[1,5-a]pyrazine (compound 11b). Example 76 was obtained as a white solid (42 mg). LCMS (M+H$^+$): 381. $^1$H NMR (400 MHz, DMSO-d$_6$) δ ppm 9.26 (s, 1H), 8.58 (d, J=2.5 Hz, 1H), 8.11 (s, 1H), 7.94 (dd, J=2.6, 5.8 Hz, 1H), 7.83-7.71 (m, 3H), 7.46 (t, J=9.2 Hz, 1H), 5.06 (s, 2H), 4.25 (t, J=5.3 Hz, 2H), 4.01 (t, J=5.3 Hz, 2H).

Example 77

3-(4-fluorophenyl)-N-(1H-indol-6-yl)-6,7-dihydro-4H-pyrazolo[1,5-a]pyrazine-5-carboxamide

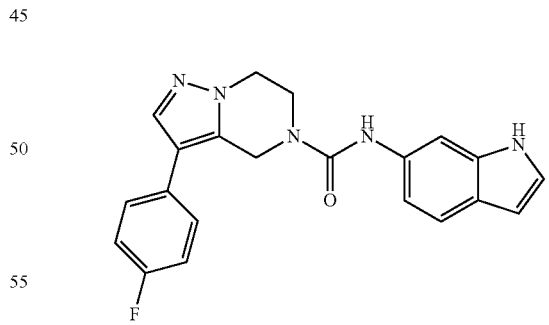

Preparation of Example 77

The title compound was prepared in analogy to the preparation of Example 11 by using 1H-indol-6-amine instead of 3-(trifluoromethyl)aniline. Example 77 was obtained as a white solid (17 mg). LCMS (M+H$^+$):376. $^1$H NMR (400 MHz, DMSO-d$_6$) δ ppm 10.92 (s, 1H), 8.78 (s, 1H), 7.83 (s, 1H), 7.60 (s, 1H), 7.55-7.47 (m, 2H), 7.39 (d, J=8.5 Hz, 1H), 7.31-7.18 (m, 3H), 7.00 (d, J=8.3 Hz, 1H), 6.33 (s, 1H), 4.96-4.93 (m, 2H), 4.25-4.21 (m, 2H), 4.03-4.00 (m, 2H).

Example 78

N-(3-chloro-4-fluoro-phenyl)-3-cyclopentyl-6,7-dihydro-4H-pyrazolo[1,5-a]pyrazine-5-carboxamide

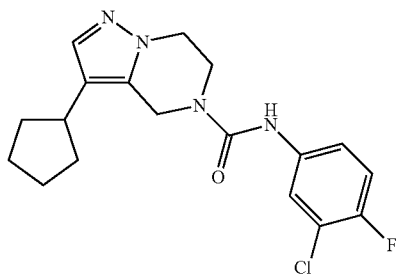 [SMILES: O=C(Nc1ccc(F)c(Cl)c1)N1CCn2ncc(C3CCCC3)c2C1]

Preparation of Example 78

The title compound was prepared in analogy to the preparation of Example 11 by using 3-chloro-4-fluoroaniline instead of 3-(trifluoromethyl)aniline and 3-cyclopentyl-4,5,6,7-tetrahydropyrazolo[1,5-a]pyrazine (compound 26c) instead of 3-(4-fluorophenyl)-4,5,6,7-tetrahydropyrazolo[1,5-a]pyrazine (compound 11b). Example 78 was obtained as a white solid. LCMS (M+H$^+$): 363. $^1$H NMR (400 MHz, DMSO-d$_6$) δ ppm 9.00 (s, 1H), 7.76 (dd, J=2.5, 6.8 Hz, 1H), 7.47-7.43 (m, 1H), 7.38-7.27 (m, 2H), 4.69 (s, 2H), 4.15-4.05 (m, 2H), 3.93 (t, J=5.3 Hz, 2H), 2.88-2.76 (m, 1H), 2.02-1.89 (m, 2H), 1.78-1.55 (m, 4H), 1.49-1.39 (m, 2H).

Example 79

N-(3-cyano-4-fluoro-phenyl)-3-cyclopentyl-6,7-dihydro-4H-pyrazolo[1,5-a]pyrazine-5-carboxamide

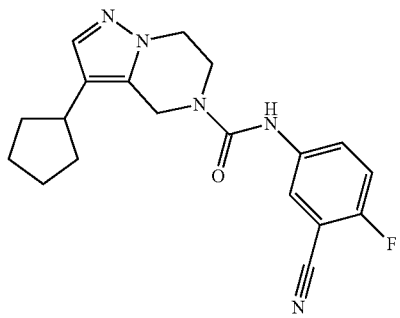 [SMILES: N#Cc1cc(NC(=O)N2CCn3ncc(C4CCCC4)c3C2)ccc1F]

Preparation of Example 79

The title compound was prepared in analogy to the preparation of Example 11 by using 5-amino-2-fluorobenzonitrile instead of 3-(trifluoromethyl)aniline and 3-cyclopentyl-4,5,6,7-tetrahydropyrazolo[1,5-a]pyrazine (compound 26c) instead of 3-(4-fluorophenyl)-4,5,6,7-tetrahydropyrazolo[1,5-a]pyrazine (compound 11b).

Example 79 was obtained as a white solid. LCMS (M+H$^+$): 354. $^1$H NMR (400 MHz, DMSO-d$_6$) δ ppm 7.76-7.72 (m, 1H), 7.63 (dd, 5.3 Hz, 1H), 7.49 (s, 1H), 7.37 (s, 1H), 7.16 (t, J=8.8 Hz, 1H), 4.74 (s, 2H), 4.23 (t, J=5.3 Hz, 2H), 3.98 (t, J=5.3 Hz, 2H), 2.88-2.73 (m, 1H), 2.06-1.98 (m, 2H), 1.82-1.60 (m, 4H), 1.56-1.44 (m, 2H).

Example 80

3-(4-fluorophenyl)-N-[4-fluoro-3-(trifluoromethyl)phenyl]-6,7-dihydro-4H-pyrazolo[1,5-a]pyrazine-5-carboxamide

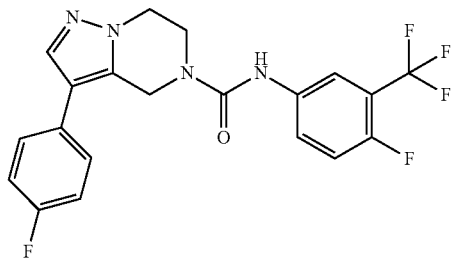 [SMILES: O=C(Nc1ccc(F)c(C(F)(F)F)c1)N1CCn2ncc(-c3ccc(F)cc3)c2C1]

Preparation of Example 80

The title compound was prepared in analogy to the preparation of Example 11 by using 4-fluoro-3-trifluoromethylaniline instead of 3-(trifluoromethyl)aniline. Example 80 was obtained as a white solid (17 mg). LCMS (M+H$^+$): 423. $^1$H NMR (400 MHz, DMSO-d$_6$) δ ppm 9.21 (s, 1H), 7.98-7.71 (m, 3H), 7.57-7.37 (m, 3H), 7.27 (t, J=8.8 Hz, 2H), 4.94 (s, 2H), 4.23 (d, J=4.8 Hz, 2H), 4.02 (d, J=5.0 Hz, 2H).

Example 81

N-(4-fluoro-3-methyl-phenyl)-3-(4-fluorophenyl)-6,7-dihydro-4H-pyrazolo[1,5-a]pyrazine-5-carboxamide

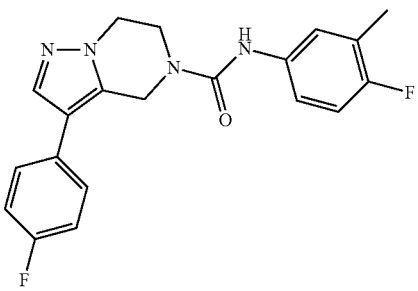 [SMILES: Cc1cc(NC(=O)N2CCn3ncc(-c4ccc(F)cc4)c3C2)ccc1F]

Preparation of Example 81

The title compound was prepared in analogy to the preparation of Example 11 by using 4-fluoro-3-methylaniline instead of 3-(trifluoromethyl)aniline. Example 81 was obtained as a white solid (36 mg). LCMS (M+H$^+$): 369. $^1$H NMR (400 MHz, DMSO-d$_6$) δ ppm 8.86 (s, 1H), 7.82 (s, 1H), 7.49 (dd, J=5.6, 8.4 Hz, 2H), 7.38-7.22 (m, 4H), 7.02

(t, J=9.2 Hz, 1H), 4.91 (s, 2H), 4.21 (t, J=5.1 Hz, 2H), 3.99 (t, J=5.0 Hz, 2H), 2.19 (s, 3H).

Example 82

3-cyclopentyl-N-indan-5-yl-6,7-dihydro-4H-pyrazolo[1,5-a]pyrazine-5-carboxamide

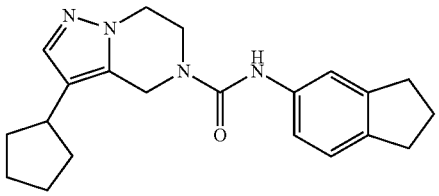 [SMILES: O=C(Nc1ccc2c(c1)CCC2)N1CCn2ncc(C3CCCC3)c2C1]

Preparation of Example 82

The title compound was prepared in analogy to the preparation of Example 11 by using indan-5-amine instead of 3-(trifluoromethyl)aniline and 3-cyclopentyl-4,5,6,7-tetrahydropyrazolo[1,5-a]pyrazine (compound 26c) instead of 3-(4-fluorophenyl)-4,5,6,7-tetrahydropyrazolo[1,5-a]pyrazine (compound 11b). Example 82 was obtained as a white solid. LCMS (M+H$^+$): 351. $^1$H NMR (400 MHz, chloroform-d) δ ppm 7.50 (s, 1H), 7.30-7.24 (m, 1H), 7.16 (d, J=8.0 Hz, 1H), 7.04 (d, J=7.5 Hz, 1H), 6.81 (br. s, 1H), 4.72 (s, 2H), 4.43-4.17 (m, 2H), 3.96 (s, 2H), 2.94-2.76 (m, 5H), 2.15-1.98 (m, 4H), 1.87-1.62 (m, 4H), 1.57-1.44 (m, 2H).

Example 83

3-cyclopentyl-N-indan-1-yl-6,7-dihydro-4H-pyrazolo[1,5-a]pyrazine-5-carboxamide

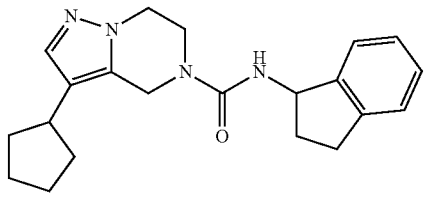 [SMILES: O=C(NC1CCc2ccccc21)N1CCn2ncc(C3CCCC3)c2C1]

Preparation of Example 83

The title compound was prepared in analogy to the preparation of Example 11 by using indan-1-amine instead of 3-(trifluoromethyl)aniline and 3-cyclopentyl-4,5,6,7-tetrahydropyrazolo[1,5-a]pyrazine (compound 26c) instead of 3-(4-fluorophenyl)-4,5,6,7-tetrahydropyrazolo[1,5-a]pyrazine (compound 11b). Example 83 was obtained as a white solid. LCMS (M+H$^+$): 351. $^1$H NMR (400 MHz, chloroform-d) δ ppm 7.49 (s, 1H), 7.36 (d, J=6.8 Hz, 1H), 7.32-7.29 (m, 2H), 7.28-7.24 (m, 1H), 5.45 (d, J=6.8 Hz, 1H), 5.17-4.79 (m, 1H), 4.63 (s, 2H), 4.34 (t, J=5.1 Hz, 2H), 3.92 (t, J=5.3 Hz, 2H), 3.09-2.99 (m, 1H), 2.96-2.76 (m, 2H), 2.72-2.64 (m, 1H), 2.09-1.96 (m, 2H), 1.92-1.60 (m, 5H), 1.57-1.45 (m, 2H).

Example 84

N-benzyl-3-cyclopentyl-6,7-dihydro-4H-pyrazolo[1,5-a]pyrazine-5-carboxamide

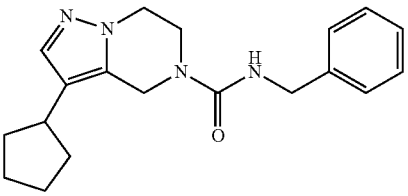 [SMILES: O=C(NCc1ccccc1)N1CCn2ncc(C3CCCC3)c2C1]

Preparation of Example 84

The title compound was prepared in analogy to the preparation of Example 11 by using benzylamine instead of 3-(trifluoromethyl)aniline and 3-cyclopentyl-4,5,6,7-tetrahydropyrazolo[1,5-a]pyrazine (compound 26c) instead of 3-(4-fluorophenyl)-4,5,6,7-tetrahydropyrazolo[1,5-a]pyrazine (compound 11b). Example 84 was obtained as a white solid. LCMS (M+H$^+$): 325. $^1$H NMR (400 MHz, chloroform-d) δ ppm 7.45 (s, 1H), 7.39-7.24 (m, 5H), 5.29 (br. s, 1H), 4.66-4.56 (m, 2H), 4.50-4.37 (m, 2H), 4.27 (t, J=5.1 Hz, 2H), 3.88 (t, J=5.1 Hz, 2H), 2.86-2.72 (m, 1H), 2.07-1.97 (m, 2H), 1.84-1.62 (m, 4H), 1.56-1.42 (m, 2H).

Example 85

N-(3-cyano-4-fluoro-phenyl)-3-(2,4-difluorophenyl)-6-methyl-6,7-dihydro-4H-pyrazolo[1,5-a]pyrazine-5-carboxamide

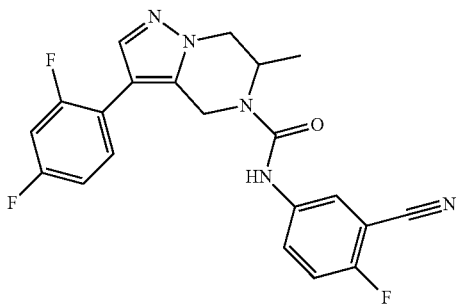 [SMILES: CC1Cn2ncc(-c3ccc(F)cc3F)c2CN1C(=O)Nc1ccc(F)c(C#N)c1]

The title compound was prepared according to the following scheme:

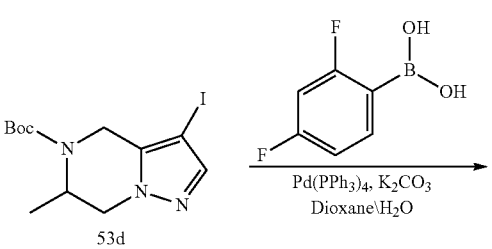

117

-continued

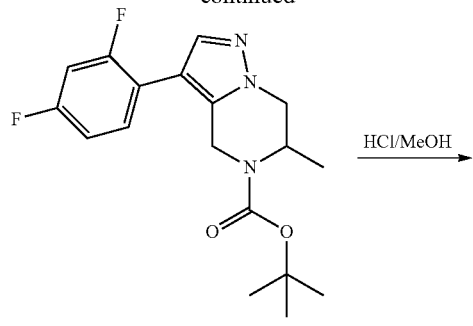

85a

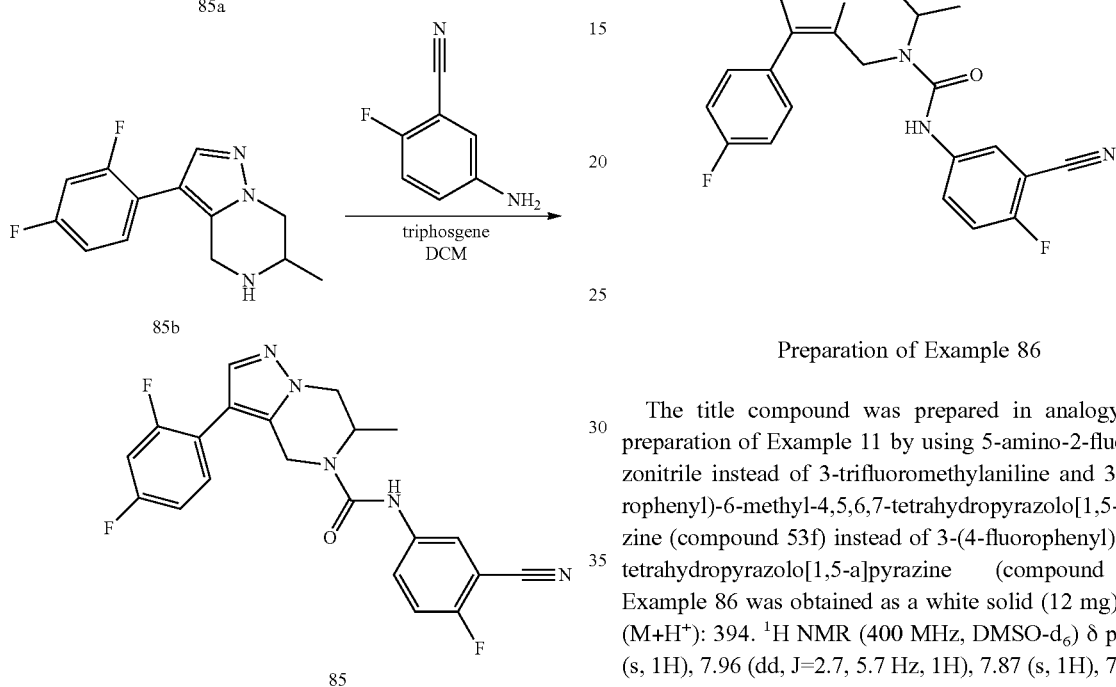

85

Preparation of 3-(2,4-difluorophenyl)-6-methyl-4,5,6,7-tetrahydropyrazolo[1,5-a]pyrazine (compound 85b)

The compound 85b was prepared in analogy to compound 53f by using (2,4-difluorophenyl)boronic acid instead of (4-fluorophenyl)boronic acid. Compound 85b was obtained as a white solid (250 mg). LCMS (M+H⁺): 250.

Preparation of N-(3-cyano-4-fluoro-phenyl)-3-(2,4-difluorophenyl)-6-methyl-6,7-dihydro-4H-pyrazolo[1,5-a]pyrazine-5-carboxamide (Example 85)

The title compound was prepared in analogy to the preparation of Example 11 by using 5-amino-2-fluorobenzonitrile instead of 3-(trifluoromethyl)aniline and 3-(2,4-difluorophenyl)-6-methyl-4,5,6,7-tetrahydropyrazolo[1,5-a]pyrazine (compound 85b) instead of 3-(4-fluorophenyl)-4,5,6,7-tetrahydropyrazolo[1,5-a]pyrazine (compound 11b). Example 85 was obtained as a white solid (33 mg). LCMS (M+H⁺): 412. ¹H NMR (400 MHz, DMSO-d₆) δ ppm 9.09 (s, 1H), 7.94 (dd, J=2.7, 5.7 Hz, 1H), 7.82-7.75 (m, 1H), 7.73 (d, J=1.9 Hz, 1H), 7.56 (dt, J=6.7, 8.8 Hz, 1H), 7.45 (t, J=9.1 Hz, 1H), 7.40-7.36 (m, 1H), 7.19 (dt, J=2.3, 8.3 Hz, 1H),

118

5.08 (d, J=16.8 Hz, 1H), 4.99-4.89 (m, 1H), 4.53 (d, J=16.9 Hz, 1H), 4.32-4.14 (m, 2H), 1.20 (d, J=6.8 Hz, 3H).

Example 86

N-(3-cyano-4-fluoro-phenyl)-3-(4-fluorophenyl)-6-methyl-6,7-dihydro-4H-pyrazolo[1,5-a]pyrazine-5-carboxamide

Preparation of Example 86

The title compound was prepared in analogy to the preparation of Example 11 by using 5-amino-2-fluoro-benzonitrile instead of 3-trifluoromethylaniline and 3-(4-fluorophenyl)-6-methyl-4,5,6,7-tetrahydropyrazolo[1,5-a]pyrazine (compound 53f) instead of 3-(4-fluorophenyl)-4,5,6,7-tetrahydropyrazolo[1,5-a]pyrazine (compound 11b). Example 86 was obtained as a white solid (12 mg). LCMS (M+H⁺): 394. ¹H NMR (400 MHz, DMSO-d₆) δ ppm 9.16 (s, 1H), 7.96 (dd, J=2.7, 5.7 Hz, 1H), 7.87 (s, 1H), 7.84-7.76 (m, 1H), 7.56 (dd, J=5.4, 8.8 Hz, 2H), 7.50-7.41 (m, 1H), 7.27 (t, J=8.8 Hz, 2H), 5.22 (d, J=16.7 Hz, 1H), 5.03-4.85 (m, 1H), 4.67 (d, J=16.7 Hz, 1H), 4.31-4.24 (m, 1H), 4.23-4.12 (m, 1H), 1.19 (d, J=6.8 Hz, 3H).

Example 87

N-(3-chloro-4-fluoro-phenyl)-3-pyrrolidin-1-yl-6,7-dihydro-4H-pyrazolo[1,5-a]pyrazine-5-carboxamide

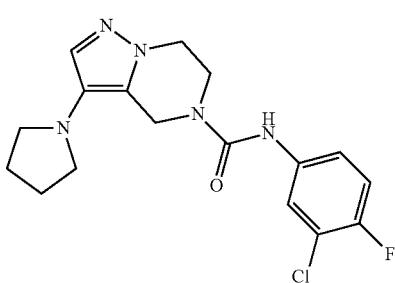 [SMILES: O=C(Nc1ccc(F)c(Cl)c1)N1CCn2ncc(N3CCCC3)c2C1]

The title compound was prepared according to the following scheme:

119

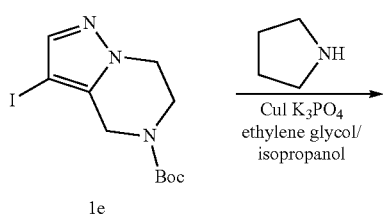

1e

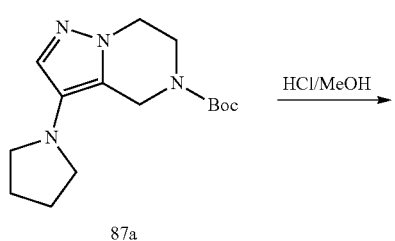

87a

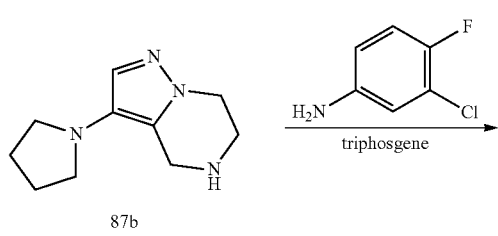

87b

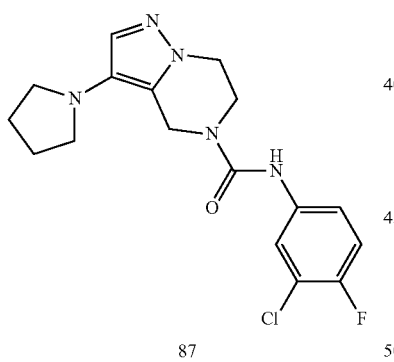

87

Step 1: Preparation of tert-butyl 3-pyrrolidin-1-yl-6,7-dihydro-4H-pyrazolo[1,5-a]pyrazine-5-carboxylate (compound 87a)

To a solution of tert-butyl 3-iodo-6,7-dihydro-4H-pyrazolo[1,5-a]pyrazine-5-carboxylate (compound 1e, 350 mg 1.0 mmol), pyrrolidine (140 mg, 2.0 mmol) and $K_3PO_4$ (636 mg, 3.0 mmol) in ethane-1,2-diol/propan-2-ol (10 mL, 2:1, v/v) were added CuI (40 mg 0.2 mmol) under $N_2$. The reaction mixture was stirred at microwave for 2 hours at 120° C., and then filtered. The filtrate was concentrated, and the residue was purified by column chromatography to afford compound 87a (100 mg) as a slight yellow oil. LCMS (M+H$^+$): 293.

120

Step 2: Preparation of 3-pyrrolidin-1-yl-4,5,6,7-tetrahydropyrazolo[1,5-a]pyrazine (compound 87b)

A solution of tert-butyl 3-pyrrolidin-1-yl-6,7-dihydro-4H-pyrazolo[1,5-a]pyrazine-5-carboxylate (compound 87a, 88 mg, 0.3 mmol) in HCl/MeOH (20 mL) was stirred at room temperature for 2 hours. Then the reaction mixture was concentrated in vacuo to afford compound 87b (80 mg) as a slight yellow solid. LCMS (M+H$^+$): 293.

Step 3: Preparation of N-(3-chloro-4-fluoro-phenyl)-3-pyrrolidin-1-yl-6,7-dihydro-4H-pyrazolo[1,5-a]pyrazine-5-carboxamide (Example 87)

The title compound was prepared in analogy to the preparation of Example 11 by using 3-chloro-4-fluoroaniline instead of 3-(trifluoromethyl)aniline and 3-pyrrolidin-1-yl-4,5,6,7-tetrahydropyrazolo[1,5-a]pyrazine (compound 87b) instead of 3-(4-fluorophenyl)-4,5,6,7-tetrahydropyrazolo[1,5-a]pyrazine (compound 11b). Example 87 was obtained as a white solid. LCMS (M+H$^+$): 364. $^1$H NMR (400 MHz, chloroform-d) δ ppm 7.58 (dd, J=2.5, 6.5 Hz, 1H), 7.28-7.21 (m, 2H), 7.13-7.07 (m, 1H), 6.68 (br. s, 1H), 4.82 (s, 2H), 4.25 (t, J=5.4 Hz, 2H), 4.00 (t, J=5.5 Hz, 2H), 3.15 (m, 4H), 2.00 (m, 4H).

Example 88

3-(2,4-difluorophenyl)-6-methyl-N-[2-(trifluoromethyl)-4-pyridyl]-6,7-dihydro-4H-pyrazolo[1,5-a]pyrazine-5-carboxamide

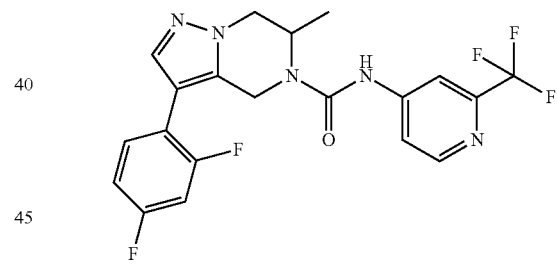

Preparation of Example 88

The title compound was prepared in analogy to the preparation of Example 11 by using 2-(trifluoromethyl)pyridin-4-amine instead of 3-(trifluoromethyl)aniline and 3-(2,4-difluorophenyl)-6-methyl-4,5,6,7-tetrahydropyrazolo[1,5-a]pyrazine (compound 85b) instead of 3-(4-fluorophenyl)-4,5,6,7-tetrahydropyrazolo[1,5-a]pyrazine (compound 11b). Example 88 was obtained as a white solid (28 mg). LCMS (M+H$^+$): 438. $^1$H NMR (400 MHz, DMSO-d$_6$) δ ppm 9.55 (s, 1H), 8.52 (d, J=5.8 Hz, 1H), 8.02 (d, J=1.5 Hz, 1H), 7.78-7.70 (m, 2H), 7.62-7.52 (m, 1H), 7.43-7.33 (m, 1H), 7.20 (dt, J=2.3, 8.4 Hz, 1H), 5.12 (d, J=16.8 Hz, 1H), 5.01-4.89 (m, 1H), 4.57 (d, J=17.1 Hz, 1H), 4.35-4.28 (m, 1H), 4.27-4.19 (m, 1H), 1.22 (d, J=6.8 Hz, 3H).

Example 89

N-(3-chloro-4-fluoro-phenyl)-3-(1-piperidyl)-6,7-dihydro-4H-pyrazolo[1,5-a]pyrazine-5-carboxamide

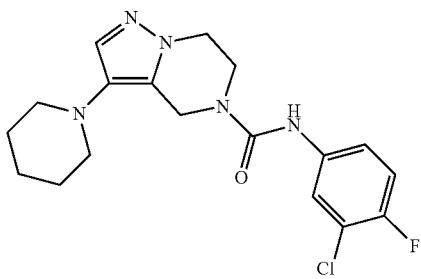 [SMILES: O=C(Nc1ccc(F)c(Cl)c1)N1CCn2ncc(N3CCCCC3)c2C1]

The title compound was prepared according to the following scheme:

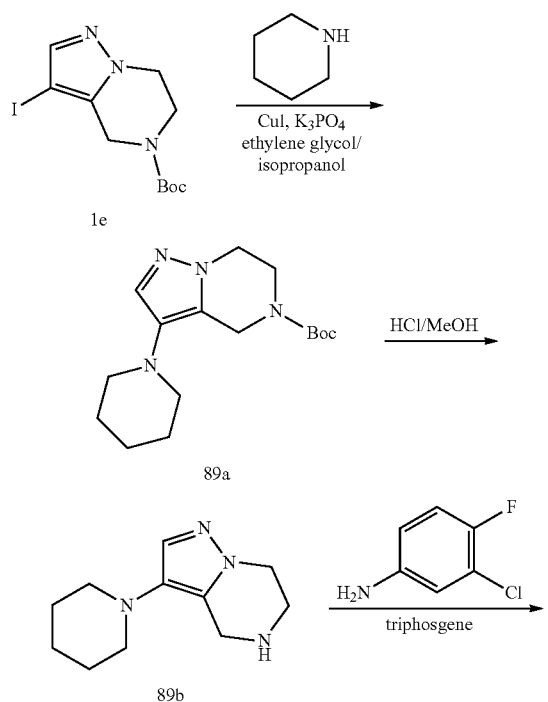

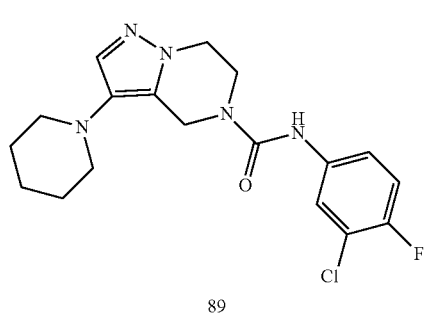

Preparation of 3-(1-piperidyl)-4,5,6,7-tetrahydropyrazolo[1,5-a]pyrazine (compound 89b)

The compound 89b was prepared in analogy to compound 87b by using piperidine instead of pyrrolidine. Compound 89b was obtained as a slight yellow solid (90 mg). LCMS (M+H$^+$): 207.

Preparation of N-(3-chloro-4-fluoro-phenyl)-3-(1-piperidyl)-6,7-dihydro-4H-pyrazolo[1,5-a]pyrazine-5-carboxamide (Example 89)

The title compound was prepared in analogy to the preparation of Example 11 by using 3-chloro-4-fluoroaniline instead of 3-(trifluoromethyl)aniline and 3-(1-piperidyl)-4,5,6,7-tetrahydropyrazolo[1,5-a]pyrazine (compound 89b) instead of 3-(4-fluorophenyl)-4,5,6,7-tetrahydropyrazolo[1,5-a]pyrazine (compound 11b). Example 89 was obtained as a white solid. LCMS (M+H$^+$): 378. $^1$H NMR (400 MHz, DMSO-d$_6$) δ ppm 9.03 (br. s, 1H), 7.75 (dd, J=2.5, 6.8 Hz, 1H), 7.47-7.40 (m, 1H), 7.36-7.29 (m, 1H), 7.25 (s, 1H), 4.64 (s, 2H), 4.09 (t, J=5.4 Hz, 2H), 3.91 (t, J=5.3 Hz, 2H), 2.85-2.72 (m, 4H), 1.61 (d, J=5.0 Hz, 4H), 1.48 (d, J=5.3 Hz, 2H).

Example 90

N-(3-chloro-4-fluoro-phenyl)-3-(4,4-difluoro-1-piperidyl)-6,7-dihydro-4H-pyrazolo[1,5-a]pyrazine-5-carboxamide

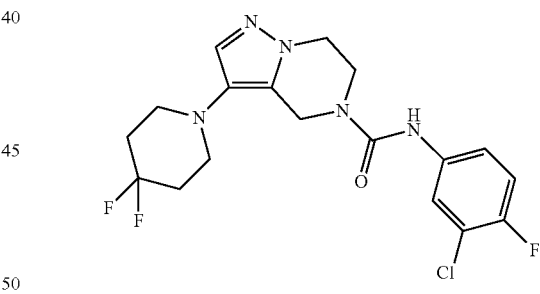

The title compound was prepared according to the following scheme:

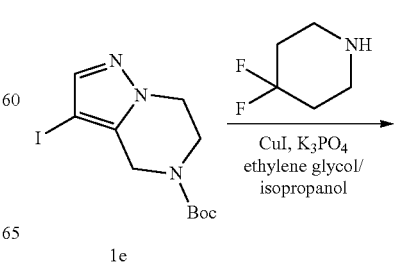

Example 91

N-(3-chloro-4-fluoro-phenyl)-3-thiazol-2-yl-6,7-dihydro-4H-pyrazolo[1,5-a]pyrazine-5-carboxamide

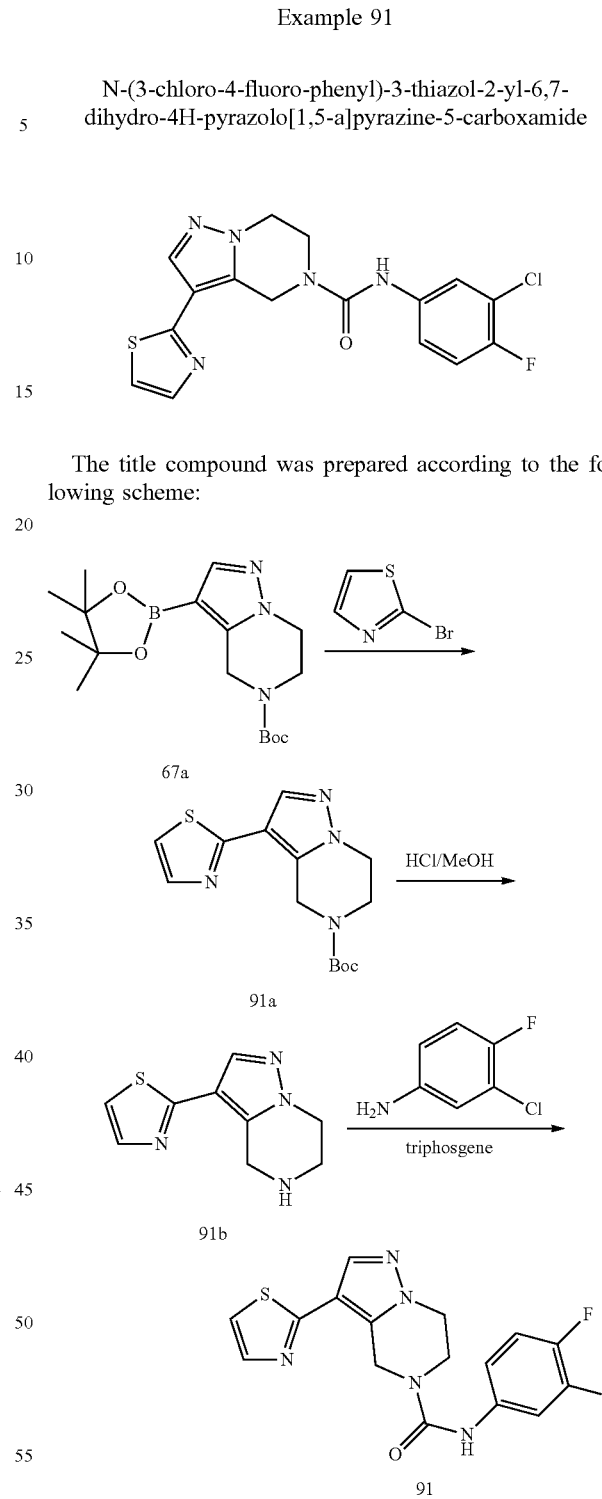

The title compound was prepared according to the following scheme:

Preparation of 3-(4,4-difluoro-1-piperidyl)-4,5,6,7-tetrahydropyrazolo[1,5-a]pyrazine (compound 90b)

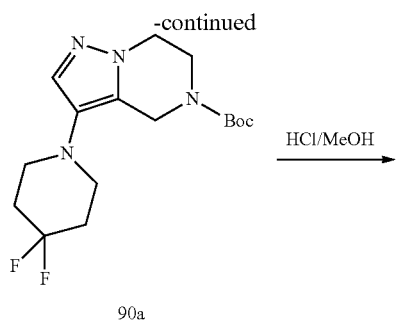

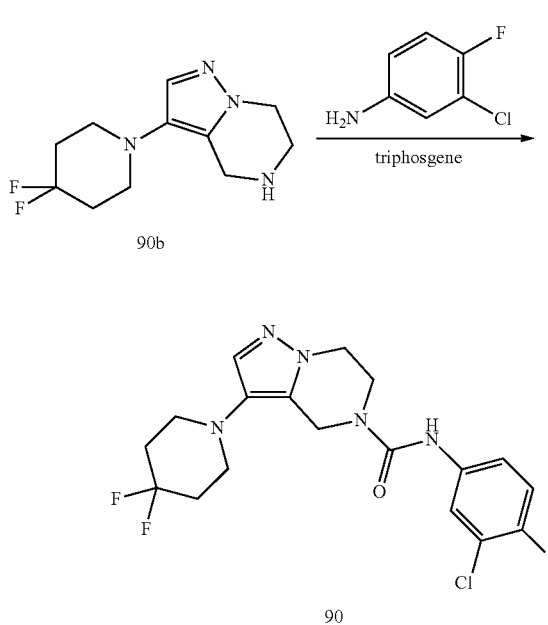

The compound 90b was prepared in analogy to compound 87b by using 4,4-difluoropiperidine instead of pyrrolidine. Compound 90b was obtained as a slight yellow solid (90 mg). LCMS (M+H⁺): 243.

Preparation of N-(3-chloro-4-fluoro-phenyl)-3-(4,4-difluoro-1-piperidyl)-6,7-dihydro-4H-pyrazolo[1,5-a]pyrazine-5-carboxamide (Example 90)

The title compound was prepared in analogy to the preparation of Example 11 by using 3-chloro-4-fluoroaniline instead of 3-(trifluoromethyl)aniline and 3-(4,4-difluoro-1-piperidyl)-4,5,6,7-tetrahydropyrazolo[1,5-a]pyrazine (compound 90b) instead of 3-(4-fluorophenyl)-4,5,6,7-tetrahydropyrazolo[1,5-a]pyrazine (compound 11b). Example 90 was obtained as a white solid. LCMS (M+H⁺): 414. $^1$H NMR (400 MHz, DMSO-d$_6$) δ ppm 9.03 (s, 1H), 7.75 (dd, J=2.5, 6.8 Hz, 1H), 7.50-7.39 (m, 1H), 7.37-7.23 (m, 2H), 4.66 (s, 2H), 4.15-4.04 (m, 2H), 3.92 (t, J=5.3 Hz, 2H), 2.96 (t, J=5.4 Hz, 4H), 2.16-1.96 (m, 4H).

Preparation of 2-(4,5,6,7-tetrahydropyrazolo[1,5-a]pyrazin-3-yl)thiazole (compound 91b)

The compound 91b was prepared in analogy to compound 67c by using 2-bromothiazole instead of 2-chloro-4-(trifluoromethyl)pyridine. Compound 91b was obtained as a white solid (250 mg). LCMS (M+H⁺): 207.

Preparation of N-(3-chloro-4-fluoro-phenyl)-3-thiazol-2-yl-6,7-dihydro-4H-pyrazolo[1,5-a]pyrazine-5-carboxamide (Example 91)

The title compound was prepared in analogy to the preparation of Example 11 by using 3-chloro-4-fluoroaniline instead of 3-(trifluoromethyl)aniline and 2-(4,5,6,7-tetrahydropyrazolo[1,5-a]pyrazin-3-yl)thiazole (compound 91b) instead of 3-(4-fluorophenyl)-4,5,6,7-tetrahydropyrazolo[1,5-a]pyrazine (compound 11b). Example 91 was obtained as a white solid (12 mg). LCMS (M+H$^+$): 378. $^1$H NMR (400 MHz, DMSO-d$_6$) δ ppm 9.20 (s, 1H), 8.00 (s, 1H), 7.85 (d, J=3.3 Hz, 1H), 7.74 (dd, J=2.6, 6.9 Hz, 1H), 7.64 (d, J=3.3 Hz, 1H), 7.43 (dt, J=2.6, 4.5 Hz, 1H), 7.36-7.28 (m, 1H), 5.00 (s, 2H), 4.26 (t, J=5.3 Hz, 2H), 4.02 (t, J=5.3 Hz, 2H).

Example 92

N-(3-chloro-4-fluoro-phenyl)-3-(2,4-difluorophenyl)-6-methyl-6,7-dihydro-4H-pyrazolo[1,5-a]pyrazine-5-carboxamide

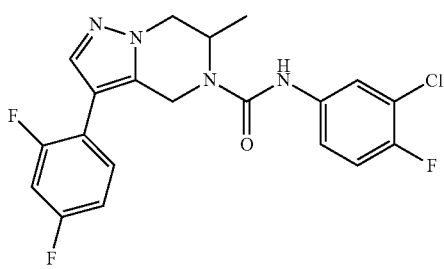 [SMILES: CC1Cn2ncc(-c3ccc(F)cc3F)c2CN1C(=O)Nc1ccc(F)c(Cl)c1]

Preparation of Example 92

The title compound was prepared in analogy to the preparation of Example 11 by using 3-chloro-4-fluoroaniline instead of 3-(trifluoromethyl)aniline and 3-(2,4-difluorophenyl)-6-methyl-4,5,6,7-tetrahydropyrazolo[1,5-a]pyrazine (compound 85b) instead of 3-(4-fluorophenyl)-4,5,6,7-tetrahydropyrazolo[1,5-a]pyrazine (compound 11b). Example 92 was obtained as a white solid (24 mg). LCMS (M+H$^+$): 421. $^1$H NMR (400 MHz, DMSO-d$_6$) δ ppm 8.97 (s, 1H), 7.77-7.68 (m, 2H), 7.65-7.51 (m, 1H), 7.45-7.25 (m, 3H), 7.24-7.12 (m, 1H), 5.08 (d, J=16.8 Hz, 1H), 4.99-4.87 (m, 1H), 4.51 (d, J=16.8 Hz, 1H), 4.32-4.24 (m, 1H), 4.24-4.16 (m, 1H), 1.19 (d, J=6.8 Hz, 3H).

Example 93

N-(2-chloro-4-pyridyl)-3-(2,4-difluorophenyl)-6-methyl-6,7-dihydro-4H-pyrazolo[1,5-a]pyrazine-5-carboxamide

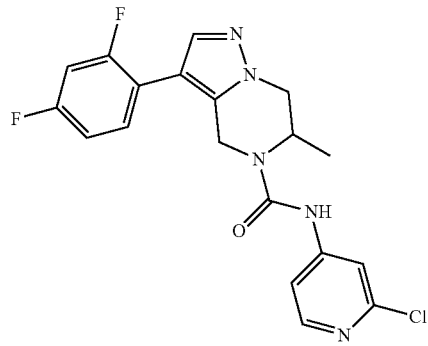 [SMILES: CC1Cn2ncc(-c3ccc(F)cc3F)c2CN1C(=O)Nc1ccnc(Cl)c1]

Preparation of Example 93

The title compound was prepared in analogy to the preparation of Example 11 by using 2-chloro-pyridin-4-amine instead of 3-(trifluoromethyl)aniline and 3-(2,4-difluorophenyl)-6-methyl-4,5,6,7-tetrahydropyrazolo[1,5-a]pyrazine (compound 85b) instead of 3-(4-fluorophenyl)-4,5,6,7-tetrahydropyrazolo[1,5-a]pyrazine (compound 11b). Example 93 was obtained as a white solid (10 mg). LCMS (M+H$^+$): 404. $^1$H NMR (400 MHz, DMSO-d$_6$) δ ppm 9.51 (s, 1H), 8.17 (d, J=5.5 Hz, 1H), 7.73 (s, 1H), 7.64 (s, 1H), 7.57 (d, J=7.8 Hz, 1H), 7.47 (s, 1H), 7.42-7.32 (m, 1H), 7.19 (s, 1H), 5.10 (d, J=17.3 Hz, 1H), 4.94 (m, 1H), 4.55 (d, J=16.6 Hz, 1H), 4.35-4.17 (m, 2H), 1.26-1.16 (m, 3H).

Example 94

N-(3-chloro-4-fluoro-phenyl)-3-(5-fluoro-2-pyridyl)-6-methyl-6,7-dihydro-4H-pyrazolo[1,5-a]pyrazine-5-carboxamide

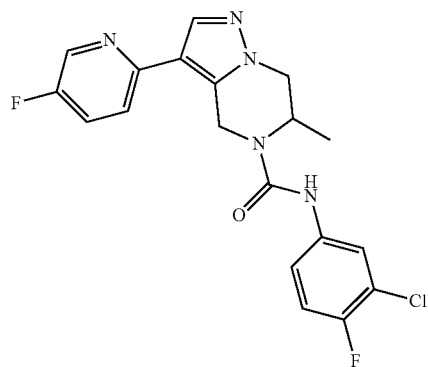 [SMILES: CC1Cn2ncc(-c3ccc(F)cn3)c2CN1C(=O)Nc1ccc(F)c(Cl)c1]

The title compound was prepared according to the following scheme

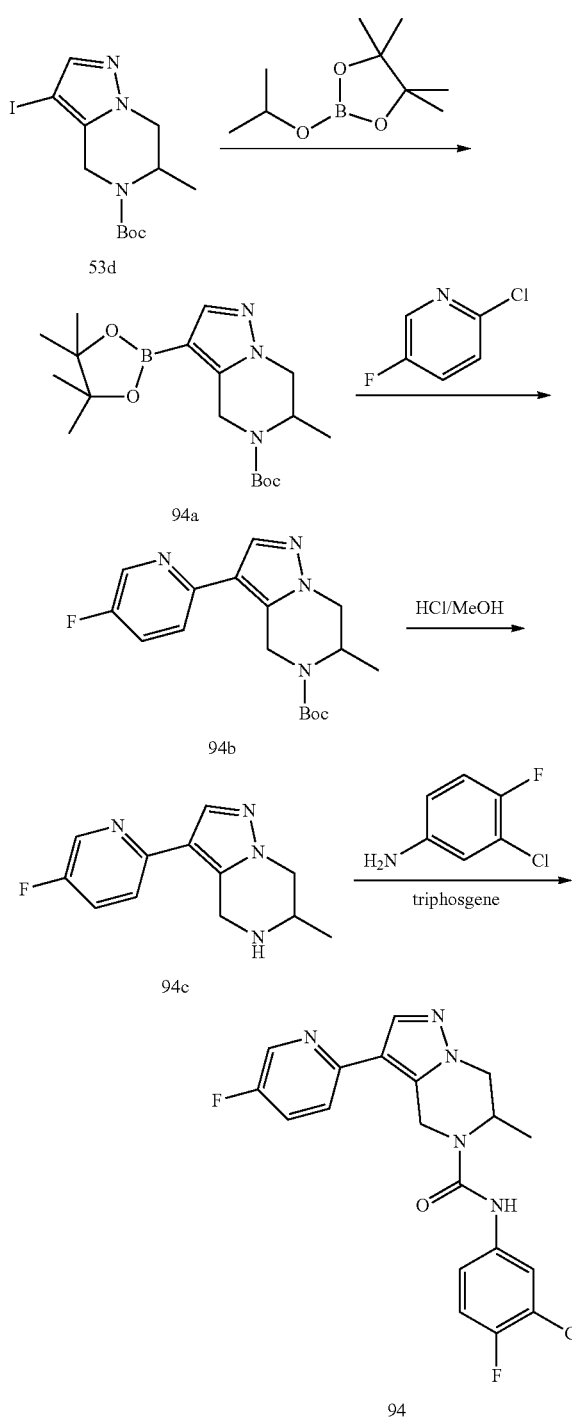

4H-pyrazolo[1,5-a]pyrazine-5-carboxylate (compound 1e). Compound 94c was obtained as a white solid (250 mg). LCMS (M+H$^+$): 233.

Preparation of N-(3-chloro-4-fluoro-phenyl)-3-(5-fluoro-2-pyridyl)-6-methyl-6,7-dihydro-4H-pyrazolo[1,5-a]pyrazine-5-carboxamide (Example 94)

The title compound was prepared in analogy to the preparation of Example 11 by using 3-chloro-4-fluoroaniline instead of 3-(trifluoromethyl)aniline and 3-(5-fluoro-2-pyridyl)-6-methyl-4,5,6,7-tetrahydropyrazolo[1,5-a]pyrazine (compound 94b) instead of 3-(4-fluorophenyl)-4,5,6,7-tetrahydropyrazolo[1,5-a]pyrazine (compound 11b). Example 94 was obtained as a white solid (48 mg). LCMS (M+H$^+$): 404. $^1$H NMR (400 MHz, DMSO-d$_6$) δ ppm 9.03 (s, 1H), 8.58 (d, J=2.9 Hz, 1H), 8.14 (s, 1H), 7.84-7.72 (m, 3H), 7.47-7.40 (m, 1H), 7.37-7.30 (m, 1H), 5.44 (d, J=18.1 Hz, 1H), 4.93-4.84 (m, 1H), 4.62 (d, J=18.2 Hz, 1H), 4.28 (d, J=4.4 Hz, 1H), 4.23-4.17 (m, 1H), 1.18 (d, J=6.8 Hz, 3H).

Example 95

N-(3-chloro-4-fluoro-phenyl)-3-(3,3-difluoro-1-piperidyl)-6,7-dihydro-4H-pyrazolo[1,5-a]pyrazine-5-carboxamide

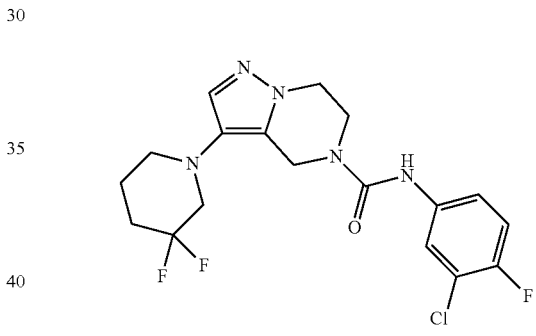

The title compound was prepared according to the following scheme:

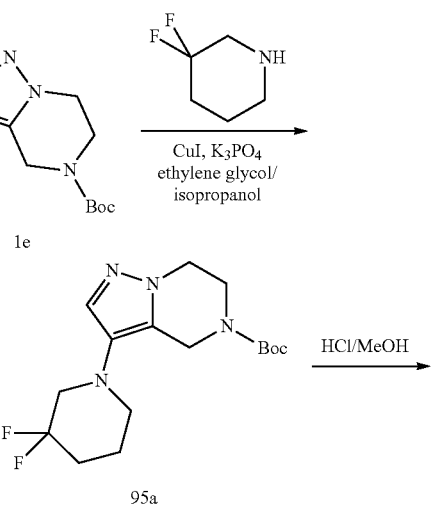

Preparation of 3-(5-fluoro-2-pyridyl)-6-methyl-4,5,6,7-tetrahydropyrazolo[1,5-a]pyrazine (compound 94c)

The compound 94c was prepared in analogy to compound 67c by using 2-chloro-5-fluoro-pyridine instead of 2-chloro-4-(trifluoromethyl)pyridine and tert-butyl 3-iodo-6-methyl-6,7-dihydro-4H-pyrazolo[1,5-a]pyrazine-5-carboxylate (compound 53d) instead of tert-butyl 3-iodo-6,7-dihydro- -continued

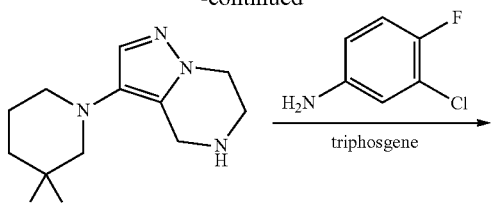

95b

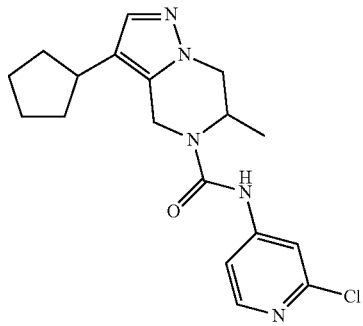 [SMILES: CC1Cn2ncc(C3CCCC3)c2CN1C(=O)Nc1ccnc(Cl)c1]

95

Preparation of 3-(3,3-difluoro-1-piperidyl)-4,5,6,7-tetrahydropyrazolo[1,5-a]pyrazine (compound 95b)

The compound 95b was prepared in analogy to compound 87b by using 4,4-difluoropiperidine instead of pyrrolidine. Compound 95b was afforded as a slight yellow solid (90 mg). LCMS (M+H$^+$): 243.

Preparation of N-(3-chloro-4-fluoro-phenyl)-3-(3,3-difluoro-1-piperidyl)-6,7-dihydro-4H-pyrazolo[1,5-a]pyrazine-5-carboxamide (Example 95)

The title compound was prepared in analogy to the preparation of Example 11 by using 3-chloro-4-fluoroaniline instead of 3-(trifluoromethyl)aniline and 3-(3,3-difluoro-1-piperidyl)-4,5,6,7-tetrahydropyrazolo[1,5-a]pyrazine (compound 95b) instead of 3-(4-fluorophenyl)-4,5,6,7-tetrahydropyrazolo[1,5-a]pyrazine (compound 11b). Example 95 was obtained as a white solid (10 mg). LCMS (M+H$^+$): 414. $^1$H NMR (400 MHz, DMSO-d$_6$) δ ppm 9.09 (s, 1H), 7.75 (dd, J=2.5, 7.0 Hz, 1H), 7.44 (d, J=7.5 Hz, 1H), 7.35-7.28 (m, 2H), 4.65 (s, 2H), 4.10 (d, J=5.0 Hz, 2H), 3.93 (d, J=5.3 Hz, 2H), 3.09 (t, J=11.5 Hz, 2H), 2.84 (m, 2H), 1.97 (dd, J=6.5, 13.6 Hz, 2H), 1.78 (m, 2H).

Example 96

N-(2-chloro-4-pyridyl)-3-cyclopentyl-6-methyl-6,7-dihydro-4H-pyrazolo[1,5-a]pyrazine-5-carboxamide

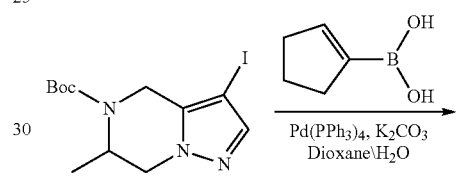

The title compound was prepared according to the following scheme:

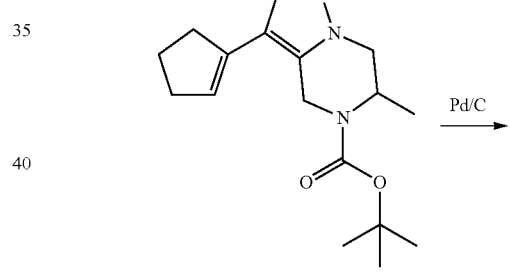

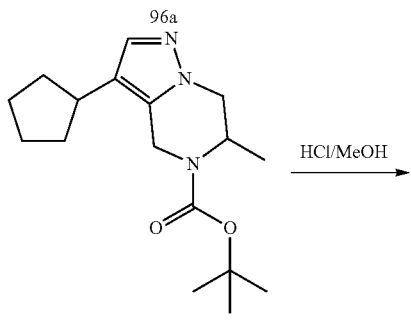

96b

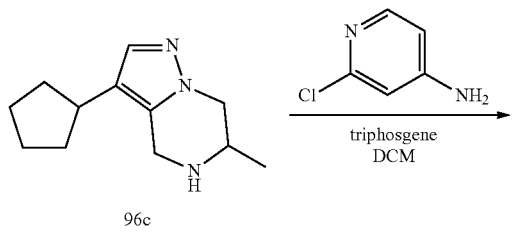

96c

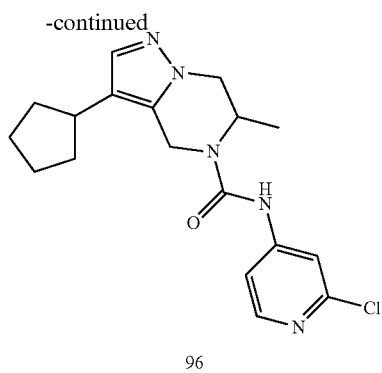

96

Preparation of 3-cyclopentyl-6-methyl-4,5,6,7-tetra-hydropyrazolo[1,5-a]pyrazine (compound 96c)

The compound 96c was prepared in analogy to compound 26c by using tert-butyl 3-iodo-6-methyl-6,7-dihydro-4H-pyrazolo[1,5-a]pyrazine-5-carboxylate (compound 53d) instead of tert-butyl 3-iodo-6,7-dihydro-4H-pyrazolo[1,5-a]pyrazine-5-carboxylate (compound 1e). Compound 96c was obtained as a slight yellow solid (90 mg). LCMS (M+H$^+$): 257.

Preparation of N-(2-chloro-4-pyridyl)-3-cyclopentyl-6-methyl-6,7-dihydro-4H-pyrazolo[1,5-a]pyrazine-5-carboxamide (Example 96)

The title compound was prepared in analogy to the preparation of Example 11 by using 2-chloro-pyridin-4-amine instead of 3-(trifluoromethyl)aniline and 3-cyclopentyl-6-methyl-4,5,6,7-tetrahydropyrazolo[1,5-a]pyrazine (compound 96c) instead of 3-(4-fluorophenyl)-4,5,6,7-tetrahydropyrazolo[1,5-a]pyrazine (compound 11b). Example 96 was obtained as a white solid (8 mg). LCMS (M+H$^+$): 360. $^1$H NMR (400 MHz, DMSO-d$_6$) δ ppm 9.33 (s, 1H), 8.19 (d, J=5.8 Hz, 1H), 7.68 (d, J=1.8 Hz, 1H), 7.50 (dd, J=1.8, 5.7 Hz, 1H), 7.34 (s, 1H), 5.00 (d, J=16.3 Hz, 1H), 4.94-4.82 (m, 1H), 4.40 (d, J=16.2 Hz, 1H), 4.22-4.13 (m, 1H), 4.12-4.05 (m, 1H), 2.92-2.78 (m, 1H), 1.99 (m, 2H), 1.79-1.69 (m, 2H), 1.67-1.55 (m, 2H), 1.47 (m, 2H), 1.11 (d, J=6.8 Hz, 3H).

Example 97

N-(2-cyano-4-pyridyl)-3-(4-fluorophenyl)-6,7-dihydro-4H-pyrazolo[1,5-a]pyrazine-5-carboxamide

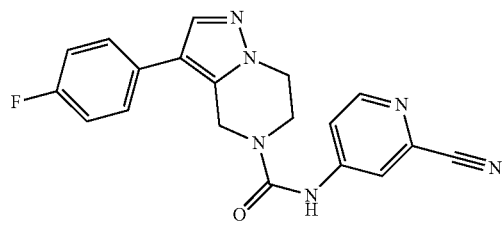 [SMILES: N#Cc1cc(NC(=O)N2CCn3ncc(-c4ccc(F)cc4)c3C2)ccn1]

Preparation of Example 97

The title compound was prepared in analogy to the preparation of Example 11 by using 4-aminopyridine-2-carbonitrile instead of 3-(trifluoromethyl)aniline. Example 97 was obtained as a white solid (24 mg). LCMS (M+H$^+$): 363. $^1$H NMR (400 MHz, DMSO-d$_6$) δ ppm 9.75 (br.s, 1 H), 8.50 (d, J=5.6 Hz, 1H), 8.05 (s, 1H), 7.84 (s, 1H), 7.79-7.70 (m, 1H), 7.50 (dd, J=5.5, 8.6 Hz, 2H), 7.28 (t, J=8.8 Hz, 2H), 4.98 (s, 2H), 4.25 (t, J=5.1 Hz, 2H), 4.04 (t, J=5.1 Hz, 2H).

Example 98

N-(2-chloro-6-methoxy-4-pyridyl)-3-(4-fluorophenyl)-6,7-dihydro-4H-pyrazolo[1,5-a]pyrazine-5-carboxamide

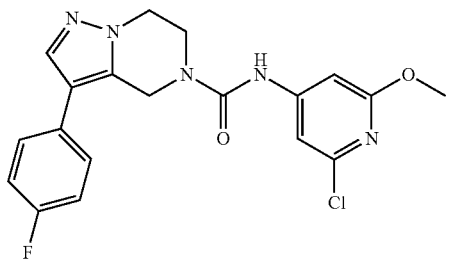 [SMILES: COc1cc(NC(=O)N2CCn3ncc(-c4ccc(F)cc4)c3C2)cc(Cl)n1]

Preparation of Example 98

The title compound was prepared in analogy to the preparation of Example 11 by using 2-chloro-6-methoxy-pyridin-4-amine instead of 3-(trifluoromethyl)aniline. Example 98 was obtained as a white solid. LCMS (M+H$^+$): 402. $^1$H NMR (400 MHz, DMSO-d$_6$) δ ppm 9.45 (br. s, 1H), 7.83 (s, 1H), 7.49 (dd, J=5.5, 8.7 Hz, 2H), 7.34-7.20 (m, 3H), 6.96 (s, 1H), 4.94 (s, 2H), 4.23 (t, J=5.1 Hz, 2H), 4.01 (t, J=5.3 Hz, 2H), 3.80 (s, 3H).

Example 99

3-(5-fluoro-2-pyridyl)-6-methyl-N-(3,4,5-trifluorophenyl)-6,7-dihydro-4H-pyrazolo[1,5-a]pyrazine-5-carboxamide

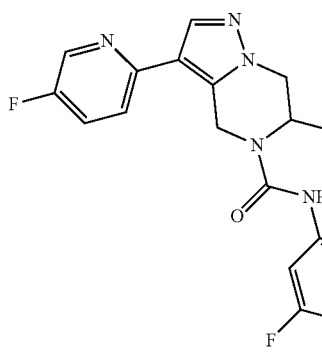

Preparation of Example 99

The title compound was prepared in analogy to the preparation of Example 11 by using 3,4,5-trifluoroaniline instead of 3-(trifluoromethyl)aniline and 3-(5-fluoro-2- pyridyl)-6-methyl-4,5,6,7-tetrahydropyrazolo[1,5-a]pyrazine (compound 94b) instead of 3-(4-fluorophenyl)-4,5,6,7-tetrahydropyrazolo[1,5-a]pyrazine (compound 11b). Example 99 was obtained as a white solid (17 mg). LCMS (M+H+): 406. $^1$H NMR (400 MHz, DMSO-$d_6$) δ ppm 9.18 (s, 1H), 8.59 (d, J=2.8 Hz, 1H), 8.14 (s, 1H), 7.85-7.73 (m, 2H), 7.43 (dd, J=6.6, 10.7 Hz, 2H), 5.47-5.38 (m, 1H), 4.92-4.85 (m, 1H), 4.69-4.59 (m, 1H), 4.36-4.27 (m, 1H), 4.23-4.17 (m, 1H), 1.18 (d, J=6.8 Hz, 3H).

Example 100

N-(3-cyano-4-fluoro-phenyl)-3-(5-fluoro-2-pyridyl)-6-methyl-6,7-dihydro-4H-pyrazolo[1,5-a]pyrazine-5-carboxamide

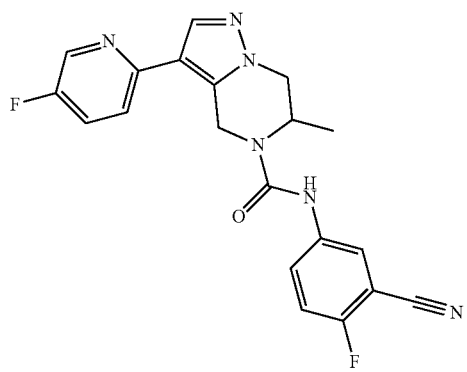 [SMILES: CC1Cn2ncc(-c3ccc(F)cn3)c2CN1C(=O)Nc1ccc(F)c(C#N)c1]

Preparation of Example 100

The title compound was prepared in analogy to the preparation of Example 11 by using 5-amino-2-fluoro-benzonitrile instead of 3-(trifluoromethyl)aniline and 3-(5-fluoro-2-pyridyl)-6-methyl-4,5,6,7-tetrahydropyrazolo[1,5-a]pyrazine (compound 94b) instead of 3-(4-fluorophenyl)-4,5,6,7-tetrahydropyrazolo[1,5-a]pyrazine (compound 11b). Example 100 was obtained as a white solid. LCMS (M+H+): 395. $^1$H NMR (400 MHz, DMSO-$d_6$) δ ppm 9.22 (s, 1H), 8.58 (d, J=2.8 Hz, 1H), 8.14 (s, 1H), 7.98-7.94 (m, 1H), 7.84-7.74 (m, 3H), 7.46 (s, 1H), 5.45 (d, J=18.1 Hz, 1H), 4.95-4.87 (m, 1H), 4.69-4.605 (m, 1H), 4.34-4.28 (m, 1H), 4.23-4.18 (m, 1H), 1.19 (d, J=6.8 Hz, 3H).

Example 101

(6R)—N-(3-chloro-4-fluoro-phenyl)-3-(4-fluorophenyl)-6-methyl-6,7-dihydro-4H-pyrazolo[1,5-a]pyrazine-5-carboxamide

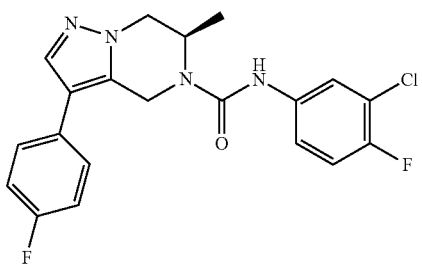 [SMILES: C[C@@H]1Cn2ncc(-c3ccc(F)cc3)c2CN1C(=O)Nc1ccc(F)c(Cl)c1]

The title compound was prepared according to the following scheme:

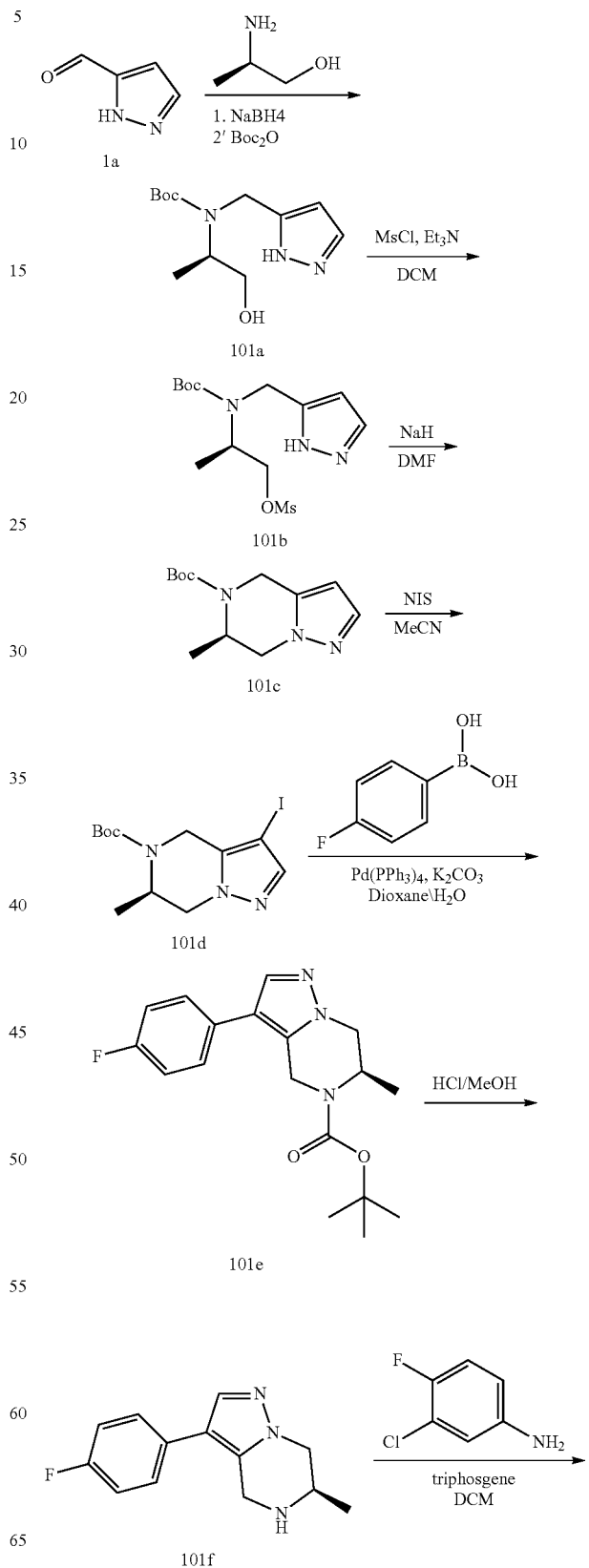

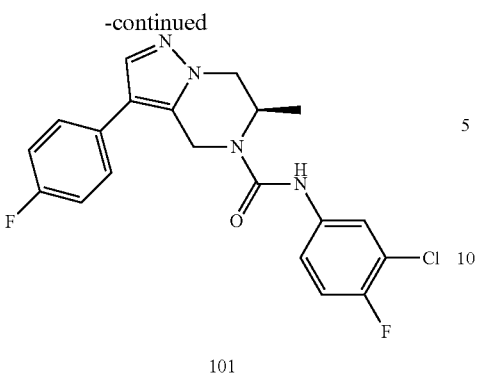

101

Preparation of (6R)-3-(4-fluorophenyl)-6-methyl-4,5,6,7-tetrahydropyrazolo[1,5-a]pyrazine (compound 101f)

The compound 101f was prepared in analogy to compound 53f by using (2R)-2-aminopropan-1-ol instead of 2-aminopropan-1-ol. Compound 101f was obtained as a white solid. LCMS (M+H$^+$): 232.

Preparation of (6R)—N-(3-chloro-4-fluoro-phenyl)-3-(4-fluorophenyl)-6-methyl-6,7-dihydro-4H-pyrazolo[1,5-a]pyrazine-5-carboxamide (Example 101)

The title compound was prepared in analogy to the preparation of Example 11 by using 3-chloro-4-fluoroaniline instead of 3-trifluoromethylaniline and (6R)-3-(4-fluorophenyl)-6-methyl-4,5,6,7-tetrahydropyrazolo[1,5-a]pyrazine (compound 101f) instead of 3-(4-fluorophenyl)-4,5,6,7-tetrahydropyrazolo[1,5-a]pyrazine (compound 11b). Example 101 was obtained as a white solid (8 mg). LCMS (M+H$^+$): 403. $^1$H NMR (400 MHz, CD$_3$OD) δ ppm 7.81 (s, 1H), 7.63 (dd, J=2.6, 6.7 Hz, 1H), 7.54 (dd, J=5.3, 8.8 Hz, 2H), 7.37-7.33 (m, 1H), 7.18 (dt, J=1.9, 8.8 Hz, 3H), 5.23 (d, J=16.6 Hz, 1H), 5.07-4.97 (m, 1H), 4.72 (d, J=16.3 Hz, 1H), 4.37 (dd, J=4.3, 12.5 Hz, 1H), 4.23 (d, J=13.8 Hz, 1H), 1.29 (d, J=6.8 Hz, 3H).

Example 102

(6S)—N-(3-chloro-4-fluoro-phenyl)-3-(4-fluorophenyl)-6-methyl-6,7-dihydro-4H-pyrazolo[1,5-a]pyrazine-5-carboxamide

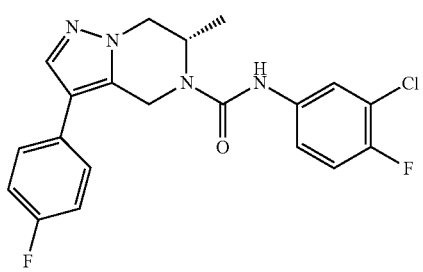 [SMILES: C[C@H]1Cn2ncc(-c3ccc(F)cc3)c2CN1C(=O)Nc1ccc(F)c(Cl)c1]

The title compound was prepared according to the following scheme:

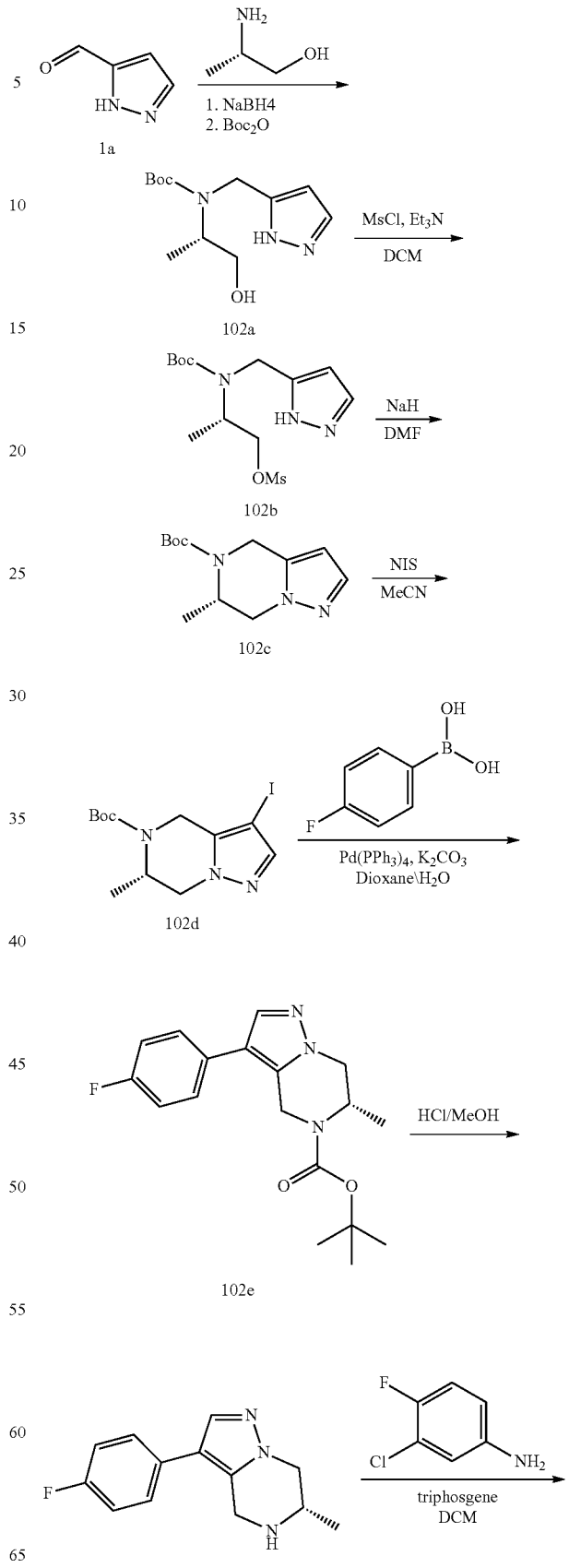

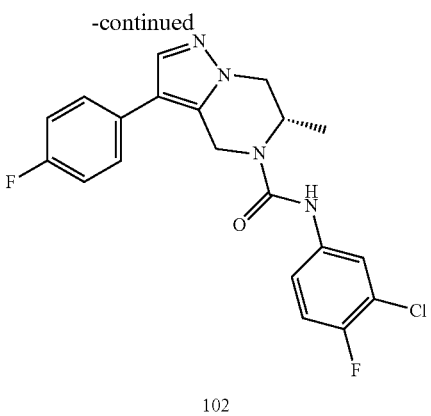

102

Preparation of (6S)-3-(4-fluorophenyl)-6-methyl-4,5,6,7-tetrahydropyrazolo[1,5-a]pyrazine (compound 102f)

The compound 102f was prepared in analogy to compound 53f by using (2S)-2-aminopropan-1-ol instead of 2-aminopropan-1-ol. Compound 102f was obtained as a white solid (2 g). LCMS (M+H$^+$): 232.

Preparation of (6S)—N-(3-chloro-4-fluoro-phenyl)-3-(4-fluorophenyl)-6-methyl-6,7-dihydro-4H-pyrazolo[1,5-a]pyrazine-5-carboxamide (Example 102)

The title compound was prepared in analogy to the preparation of Example 11 by using 3-chloro-4-fluoroaniline instead of 3-trifluoromethylaniline and (6S)-3-(4-fluorophenyl)-6-methyl-4,5,6,7-tetrahydropyrazolo[1,5-a]pyrazine (compound 102f) instead of 3-(4-fluorophenyl)-4,5,6,7-tetrahydropyrazolo[1,5-a]pyrazine (compound 11b). Example 102 was obtained as a white solid (8 mg). LCMS (M+H$^+$): 403. $^1$H NMR (400 MHz, CD$_3$OD) δ ppm 7.81 (s, 1H), 7.63 (dd, J=2.6, 6.7 Hz, 1H), 7.54 (dd, J=5.3, 8.8 Hz, 2H), 7.37-7.33 (m, 1H), 7.18 (dt, J=1.9, 8.8 Hz, 3H), 5.23 (d, J=16.6 Hz, 1H), 5.07-4.97 (m, 1H), 4.72 (d, J=16.3 Hz, 1H), 4.37 (dd, J=4.3, 12.5 Hz, 1H), 4.23 (d, J=13.8 Hz, 1H), 1.29 (d, J=6.8 Hz, 3H).

Example 103

N-(2-chloro-4-pyridyl)-3-cyclopentyl-6,7-dihydro-4H-pyrazolo[1,5-a]pyrazine-5-carboxamide

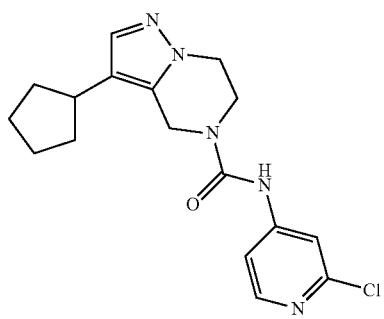 [SMILES: O=C(Nc1ccnc(Cl)c1)N1CCn2ncc(C3CCCC3)c2C1]

Preparation of Example 103

The title compound was prepared in analogy to the preparation of Example 11 by using 2-chloro-pyridin-4-amine instead of 3-(trifluoromethyl)aniline and 3-cyclopentyl-4,5,6,7-tetrahydropyrazolo[1,5-a]pyrazine (compound 26c) instead of 3-(4-fluorophenyl)-4,5,6,7-tetrahydropyrazolo[1,5-a]pyrazine (compound 11b). Example 103 was obtained as a white solid (15 mg). LCMS (M+H$^+$): 346. $^1$H NMR (400 MHz, DMSO-d$_6$) δ ppm 9.44 (s, 1H), 8.18 (d, J=5.6 Hz, 1H), 7.66 (d, J=1.5 Hz, 1H), 7.48 (dd, J=1.6, 5.6 Hz, 1H), 7.32 (s, 1H), 4.71 (s, 2H), 4.13 (t, J=5.2 Hz, 2H), 3.95 (t, J=5.1 Hz, 2H), 2.89-2.76 (m, 1H), 1.96 (d, J=6.8 Hz, 2H), 1.78-1.55 (m, 4H), 1.52-1.40 (m, 2H).

Example 104

N-(benzofuran-6-yl)-3-cyclopentyl-6-methyl-6,7-dihydro-4H-pyrazolo[1,5-a]pyrazine-5-carboxamide

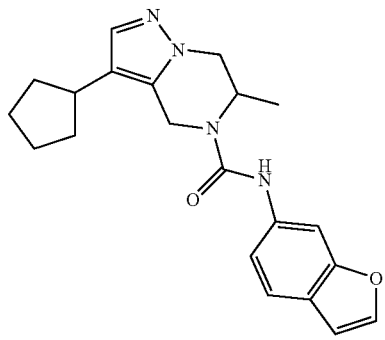 [SMILES: CC1Cn2ncc(C3CCCC3)c2CN1C(=O)Nc1ccc2ccoc2c1]

Preparation of Example 104

The title compound was prepared in analogy to the preparation of Example 11 by using benzofuran-6-amine instead of 3-(trifluoromethyl)aniline and 3-cyclopentyl-6-methyl-4,5,6,7-tetrahydropyrazolo[1,5-a]pyrazine (compound 96c) instead of 3-(4-fluorophenyl)-4,5,6,7-tetrahydropyrazolo[1,5-a]pyrazine (compound 11b). Example 104 was obtained as a white solid. LCMS (M+H$^+$): 365. $^1$H NMR (400 MHz, chloroform-d) δ ppm 7.80 (s, 1H), 7.61 (d, J=2.3 Hz, 1H), 7.52 (d, J=8.3 Hz, 1H), 7.41 (s, 1H), 7.14 (dd, J=1.9, 8.4 Hz, 1H), 6.74 (d, J=1.3 Hz, 1H), 6.61 (s, 1H), 4.99-4.83 (m, 2H), 4.52 (d, J=15.3 Hz, 1H), 4.31 (dd, J=4.1, 12.7 Hz, 1H), 4.16 (d, J=12.5 Hz, 1H), 2.90-2.81 (m, 1H), 2.10-1.99 (m, 2H), 1.83-1.55 (m, 6H), 1.25 (d, J=6.8 Hz, 3H).

Example 105

N-(3-cyano-4-fluoro-phenyl)-3-(4-fluorophenyl)-6,7-dihydro-4H-pyrazolo[1,5-a]pyrazine-5-carboxamide

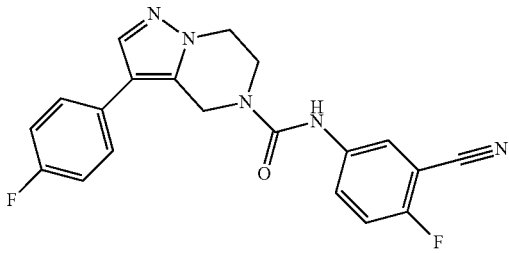 [SMILES: N#Cc1cc(NC(=O)N2CCn3ncc(-c4ccc(F)cc4)c3C2)ccc1F]

Preparation of Example 105

The title compound was prepared in analogy to the preparation of Example 11 by using 5-amino-2-fluoro-benzonitrile instead of 3-(trifluoromethyl)aniline. Example 105 was obtained as a white solid (22 mg). LCMS (M+H$^+$): 380. $^1$H NMR (400 MHz, DMSO-d$_6$) δ ppm 9.28 (s, 1H), 7.95 (dd, J=2.6, 5.6 Hz, 1H), 7.86-7.76 (m, 2H), 7.54-7.40 (m, 3H), 7.27 (t, J=8.8 Hz, 2H), 4.95 (s, 2H), 4.23 (t, J=5.1 Hz, 2H), 4.02 (t, J=5.3 Hz, 2H).

Example 106

N-(3-cyano-5-fluoro-phenyl)-3-(4-fluorophenyl)-6,7-dihydro-4H-pyrazolo[1,5-a]pyrazine-5-carboxamide

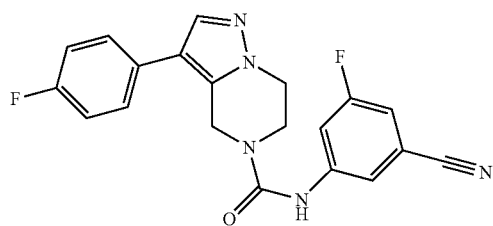 [SMILES: N#Cc1cc(F)cc(NC(=O)N2CCn3ncc(-c4ccc(F)cc4)c3C2)c1]

The title compound was prepared according to the following scheme:

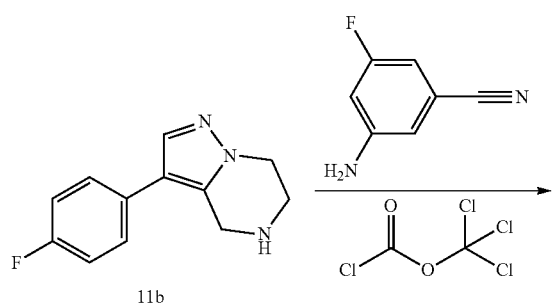

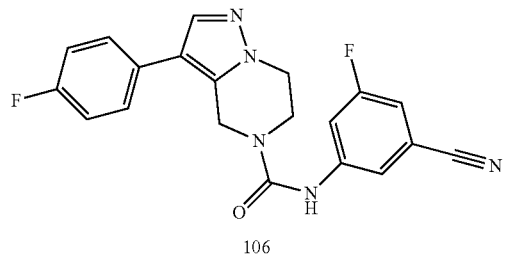

Preparation of Example 106

To a solution of 3-amino-5-fluoro-benzonitrile (30 mg, 0.2 mmol) in DCM (1 mL), was added trichloromethyl carbonochloridate (19 mg, 0.1 mmol). Then the reaction mixture was stirred at room temperature for 10 mins, to previous reaction mixture was added another mixture of 3-(4-fluorophenyl)-4,5,6,7-tetrahydropyrazolo[1,5-a]pyrazine (compound 11b, 22 mg, 0.1 mmol) and DIPEA (65 mg, 0.5 mmol) in DCM (1 mL) slowly. The resulting mixture was stirred at room temperature for 5 min and then diluted with EtOAc (10 mL), washed with water (5 mL), brine (5 mL). The organic layer was dried over Na$_2$SO$_4$ and concentrated. The residue was purified by prep-HPLC to afford Example 106 (4 mg) as a white solid. LCMS (M+H$^+$): 380. $^1$H NMR (400 MHz, CD$_3$OD) δ ppm 7.77 (s, 1H), 7.71-7.60 (m, 2H), 7.49 (dd, J=5.3, 8.8 Hz, 2H), 7.25-7.12 (m, 3H), 5.00 (s, 2H), 4.32 (t, J=5.5 Hz, 2H), 4.11 (t, J=5.5 Hz, 2H).

Example 107

3-(4-fluorophenyl)-N-[4-methyl-3-(trifluoromethyl)phenyl]-6,7-dihydro-4H-pyrazolo[1,5-a]pyrazine-5-carboxamide

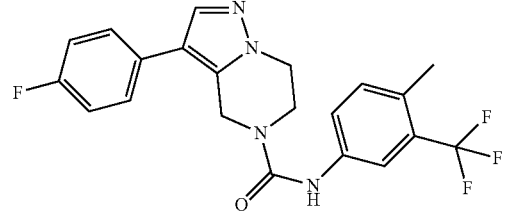 [SMILES: Cc1ccc(NC(=O)N2CCn3ncc(-c4ccc(F)cc4)c3C2)cc1C(F)(F)F]

Preparation of Example 107

The title compound was prepared in analogy to the preparation of Example 106 by using 4-methyl-3-trifluoromethyl-aniline instead of 3-amino-5-fluoro-benzonitrile. Example 107 was obtained as a white solid (30 mg). LCMS (M+H$^+$): 419. $^1$H NMR (400 MHz, CD$_3$OD) δ ppm 7.79-7.71 (m, 2H), 7.54 (dd, J=2.1, 8.4 Hz, 1H), 7.49 (dd, J=5.3, 8.8 Hz, 2H), 7.28 (d, J=8.3 Hz, 1H), 7.22-7.11 (m, 2H), 4.98 (s, 2H), 4.31 (t, J=5.4 Hz, 2H), 4.09 (t, J=5.4 Hz, 2H), 2.42 (d, J=1.5 Hz, 3H).

Example 108

N-[3-chloro-5-(trifluoromethyl)phenyl]-3-(4-fluorophenyl)-6,7-dihydro-4H-pyrazolo[1,5-a]pyrazine-5-carboxamide

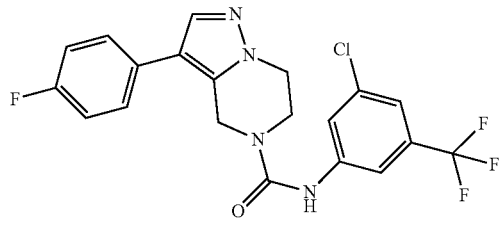 [SMILES: O=C(Nc1cc(Cl)cc(C(F)(F)F)c1)N1CCn2ncc(-c3ccc(F)cc3)c2C1]

Preparation of Example 108

The title compound was prepared in analogy to the preparation of Example 106 by using 3-chloro-5-(trifluoromethyl)aniline instead of 3-amino-5-fluoro-benzonitrile. Example 108 was obtained as a white solid (10 mg). LCMS (M+H$^+$): 439. $^1$H NMR (400 MHz, CD$_3$OD) δ ppm 7.87-7.81 (m, 1H), 7.80-7.72 (m, 2H), 7.49 (dd, J=5.3, 8.8 Hz, 2H), 7.33 (s, 1H), 7.18 (t, J=8.9 Hz, 2H), 5.00 (s, 2H), 4.32 (t, J=5.4 Hz, 2H), 4.11 (t, J=5.4 Hz, 2H).

Example 109

N-(3,4-difluorophenyl)-3-(4-fluorophenyl)-6,7-dihydro-4H-pyrazolo[1,5-a]pyrazine-5-carboxamide

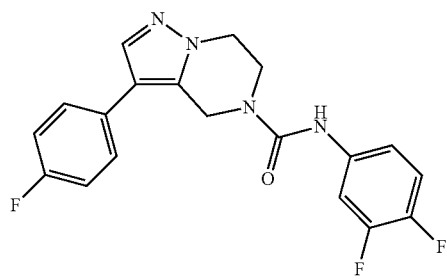 [SMILES: O=C(Nc1ccc(F)c(F)c1)N1CCn2ncc(-c3ccc(F)cc3)c2C1]

Preparation of Example 109

The title compound was prepared in analogy to the preparation of Example 106 by using 3,4-difluoroaniline instead of 3-amino-5-fluoro-benzonitrile. Example 109 was obtained as a white solid (9 mg). LCMS (M+H$^+$): 373. $^1$H NMR (400 MHz, CD$_3$OD) δ ppm 7.77 (s, 1H), 7.53-7.41 (m, 3H), 7.23-7.10 (m, 4H), 4.97 (s, 2H), 4.30 (t, J=5.4 Hz, 2H), 4.10 (t, J=5.4 Hz, 2H).

Example 110

N-(3-chloro-4-cyano-phenyl)-3-(4-fluorophenyl)-6,7-dihydro-4H-pyrazolo[1,5-a]pyrazine-5-carboxamide

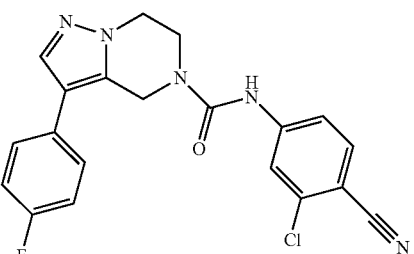

Preparation of Example 110

The title compound was prepared in analogy to the preparation of Example 106 by using 4-amino-2-chloro-benzonitrile instead of 3-amino-5-fluoro-benzonitrile. Example 110 was obtained as a white solid (5 mg). LCMS (M+H$^+$): 396. $^1$H NMR (400 MHz, CD$_3$OD) δ ppm 7.89-7.84 (m, 1H), 7.77 (s, 1H), 7.68 (d, J=8.5 Hz, 1H), 7.58-7.44 (m, 3H), 7.18 (t, J=8.8 Hz, 2H), 5.00 (s, 2H), 4.30 (t, J=5.4 Hz, 2H), 4.10 (t, J=5.4 Hz, 2H).

Example 111

3-(4-fluorophenyl)-N-(3,4,5-trifluorophenyl)-6,7-dihydro-4H-pyrazolo[1,5-a]pyrazine-5-carboxamide

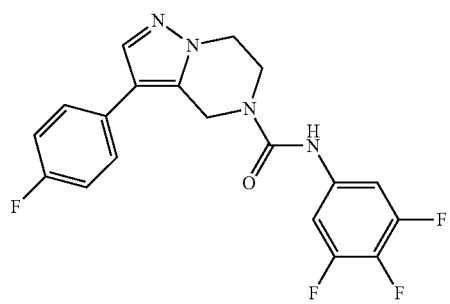 [SMILES: O=C(Nc1cc(F)c(F)c(F)c1)N1CCn2ncc(-c3ccc(F)cc3)c2C1]

Preparation of Example 111

The title compound was prepared in analogy to the preparation of Example 106 by using 3,4,5-trifluoroaniline instead of 3-amino-5-fluoro-benzonitrile. Example 111 was obtained as a white solid (5 mg). LCMS (M+H$^+$): 391. $^1$H NMR (400 MHz, CD$_3$OD) δ ppm 7.77 (s, 1H), 7.49 (dd, J=5.3, 8.8 Hz, 2H), 7.27 (dd, J=6.5, 10.3 Hz, 2H), 7.18 (t, J=8.9 Hz, 2H), 4.97 (s, 2H), 4.30 (t, J=5.4 Hz, 2H), 4.08 (t, J=5.4 Hz, 2H).

Example 112

N-(3,5-difluorophenyl)-3-(4-fluorophenyl)-6,7-dihydro-4H-pyrazolo[1,5-a]pyrazine-5-carboxamide

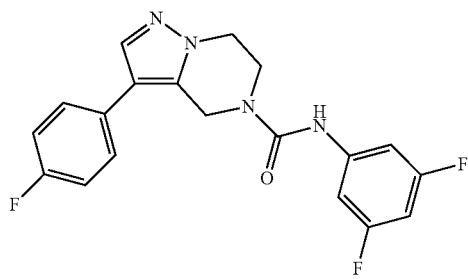 [SMILES: O=C(Nc1cc(F)cc(F)c1)N1CCn2ncc(-c3ccc(F)cc3)c2C1]

Preparation of Example 112

The title compound was prepared in analogy to the preparation of Example 106 by using 3,5-difluoroaniline instead of 3-amino-5-fluoro-benzonitrile. Example 112 was obtained as a white solid (10 mg). LCMS (M+H$^+$): 373. $^1$H NMR (400 MHz, CD$_3$OD) δ ppm 7.77 (s, 1H), 7.49 (dd, J=5.4, 8.9 Hz, 2H), 7.23-7.08 (m, 4H), 6.64-6.49 (m, 1H), 4.98 (s, 2H), 4.31 (t, J=5.4 Hz, 2H), 4.10 (t, J=5.4 Hz, 2H).

Example 113

N-[4-chloro-3-(trifluoromethyl)phenyl]-3-(4-fluorophenyl)-6,7-dihydro-4H-pyrazolo[1,5-a]pyrazine-5-carboxamide

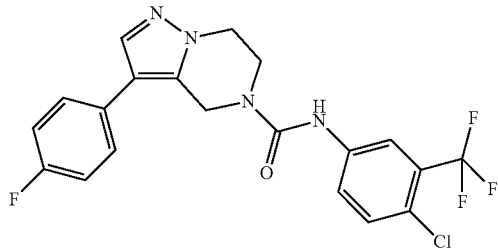 [SMILES: O=C(Nc1ccc(Cl)c(C(F)(F)F)c1)N1CCn2ncc(-c3ccc(F)cc3)c2C1]

Preparation of Example 113

The title compound was prepared in analogy to the preparation of Example 106 by using 4-chloro-3-(trifluoromethyl)aniline instead of 3-amino-5-fluoro-benzonitrile. Example 113 was obtained as a white solid (12 mg). LCMS (M+H$^+$): 439. $^1$H NMR (400 MHz, CD$_3$OD) δ ppm 7.93 (d, J=2.5 Hz, 1H), 7.77 (s, 1H), 7.69 (dd, J=2.5, 8.8 Hz, 1H), 7.55-7.43 (m, 3H), 7.18 (t, J=8.8 Hz, 2H), 5.00 (s, 2H), 4.32 (t, J=5.4 Hz, 2H), 4.12 (t, J=5.4 Hz, 2H).

Example 114

N-(3-ethylphenyl)-3-(4-fluorophenyl)-6,7-dihydro-4H-pyrazolo[1,5-a]pyrazine-5-carboxamide

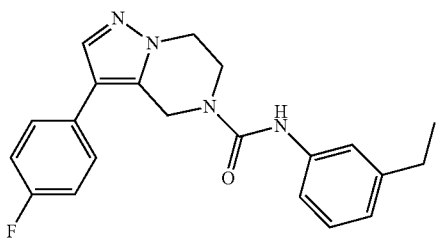

Preparation of Example 114

The title compound was prepared in analogy to the preparation of Example 106 by using 3-ethylaniline instead of 3-amino-5-fluoro-benzonitrile. Example 114 was obtained as a white solid (11 mg). LCMS (M+H$^+$): 365. $^1$H NMR (400 MHz, CD$_3$OD) δ ppm 7.77 (s, 1H), 7.58-7.42 (m, 2H), 7.32-7.07 (m, 5H), 6.99-6.81 (m, 1H), 4.98 (s, 2H), 4.31 (t, J=5.4 Hz, 2H), 4.09 (t, J=5.4 Hz, 2H), 2.63 (q, J=7.5 Hz, 2H), 1.24 (t, J=7.7 Hz, 3H).

Example 115

N-(3-ethynylphenyl)-3-(4-fluorophenyl)-6,7-dihydro-4H-pyrazolo[1,5-a]pyrazine-5-carboxamide

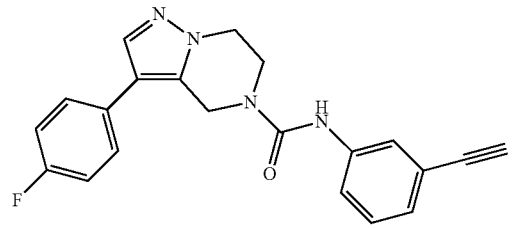 [SMILES: C#Cc1cccc(NC(=O)N2CCn3ncc(-c4ccc(F)cc4)c3C2)c1]

Preparation of Example 115

The title compound was prepared in analogy to the preparation of Example 106 by using 3-ethynylaniline instead of 3-amino-5-fluoro-benzonitrile. Example 115 was obtained as a white solid (12 mg). LCMS (M+H$^+$): 361. $^1$H NMR (400 MHz, CD$_3$OD) δ ppm 7.77 (s, 1H), 7.56 (t, J=1.8 Hz, 1H), 7.53-7.46 (m, 2H), 7.45-7.40 (m, 1H), 7.27 (t, J=8.0 Hz, 1H), 7.22-7.12 (m, 3H), 4.98 (s, 2H), 4.31 (t, J=5.4 Hz, 2H), 4.10 (t, J=5.5 Hz, 2H), 3.47 (s, 1H).

Example 116

3-(4-fluorophenyl)-N-(3-isopropylphenyl)-6,7-di-hydro-4H-pyrazolo[1,5-a]pyrazine-5-carboxamide

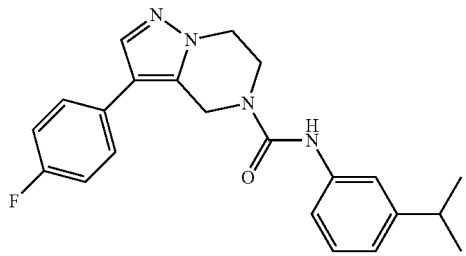 [SMILES: CC(C)c1cccc(NC(=O)N2CCn3ncc(-c4ccc(F)cc4)c3C2)c1]

Preparation of Example 116

The title compound was prepared in analogy to the preparation of Example 106 by using 3-isopropylaniline instead of 3-amino-5-fluoro-benzonitrile. Example 116 was obtained as a white solid (17 mg). LCMS (M+H$^+$): 379. $^1$H NMR (400 MHz, CD$_3$OD) δ ppm 7.77 (s, 1H), 7.50 (dd, J=5.4, 8.9 Hz, 2H), 7.28 (s, 1H), 7.25-7.12 (m, 4H), 7.01-6.90 (m, 1H), 4.98 (s, 2H), 4.31 (t, J=5.5 Hz, 2H), 4.10 (t, J=5.5 Hz, 2H), 2.91-2.83 (m, 1H), 1.25 (d, J=7.0 Hz, 6H).

Example 117

3-(4-fluorophenyl)-N-(3-methoxyphenyl)-6,7-di-hydro-4H-pyrazolo[1,5-a]pyrazine-5-carboxamide

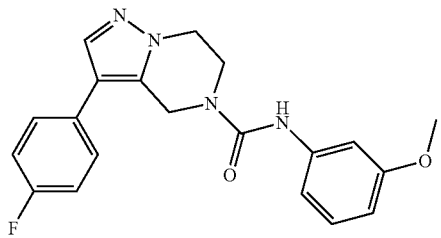 [SMILES: COc1cccc(NC(=O)N2CCn3ncc(-c4ccc(F)cc4)c3C2)c1]

Preparation of Example 117

The title compound was prepared in analogy to the preparation of Example 106 by using 3-methoxyl aniline instead of 3-amino-5-fluoro-benzonitrile. Example 117 was obtained as a white solid (10 mg). LCMS (M+H$^+$): 367. $^1$H NMR (400 MHz, CD$_3$OD) δ ppm 7.77 (s, 1H), 7.49 (dd, J=5.3, 8.8 Hz, 2H), 7.18 (dt, J=8.5 Hz, 3H), 7.07 (t, J=2.2 Hz, 1H), 6.96 (dd, J=1.2, 8.1 Hz, 1H), 6.63 (dd, J=1.8, 8.2 Hz, 1H), 4.97 (s, 2H), 4.31 (t, J=5.5 Hz, 2H), 4.09 (t, J=5.5 Hz, 2H), 3.78 (s, 3H).

Example 118

N-phenyl-3-[2-(trifluoromethoxy)phenyl]-6,7-di-hydro-4H-pyrazolo[1,5-a]pyrazine-5-carboxamide

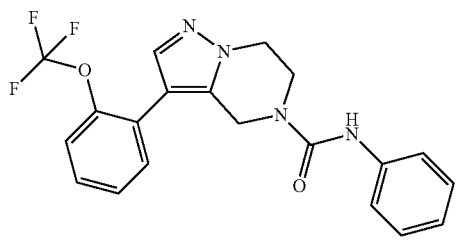 [SMILES: O=C(Nc1ccccc1)N1CCn2ncc(-c3ccccc3OC(F)(F)F)c2C1]

Preparation of Example 118

The title compound was prepared in analogy to the preparation of Example 1 by using 2-(trifluoromethoxy) phenyl-boronic acid instead of (4-fluorophenyl)boronic acid. Example 118 was obtained as a white solid (21 mg). LCMS (M+H$^+$): 403. $^1$H NMR (400 MHz, CD$_3$OD) δ ppm 7.69 (s, 1H), 7.56-7.48 (m, 1H), 7.47-7.42 (m, 3H), 7.41-7.34 (m, 2H), 7.33-7.24 (m, 2H), 7.10-7.01 (m, 1H), 4.84 (s, 2H), 4.34 (t, J=5.5 Hz, 2H), 4.10 (t, J=5.5 Hz, 2H).

Example 119

3-(3-chloro-4-fluoro-phenyl)-N-phenyl-6,7-dihydro-4H-pyrazolo[1,5-a]pyrazine-5-carboxamide

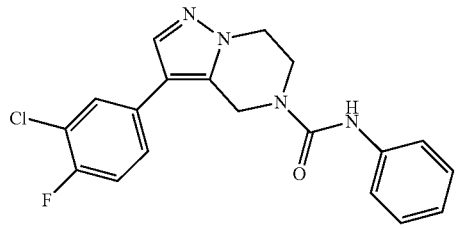 [SMILES: O=C(Nc1ccccc1)N1CCn2ncc(-c3ccc(F)c(Cl)c3)c2C1]

Preparation of Example 119

The title compound was prepared in analogy to the preparation of Example 1 by using (3-chloro-4-fluorophenyl)boronic acid instead of (4-fluorophenyl)boronic acid. Example 119 was obtained as a white solid (32 mg). LCMS (M+H$^+$): 371. $^1$H NMR (400 MHz, CD$_3$OD) δ ppm 7.80 (s, 1H), 7.59 (dd, J=1.9, 7.0 Hz, 1H), 7.49-7.35 (m, 3H), 7.35-7.23 (m, 3H), 7.12-7.01 (m, 1H), 4.98 (s, 2H), 4.31 (t, J=5.4 Hz, 2H), 4.09 (t, J=5.4 Hz, 2H).

Example 120

3-(m-tolyl)-N-phenyl-6,7-dihydro-4H-pyrazolo[1,5-a]pyrazine-5-carboxamide

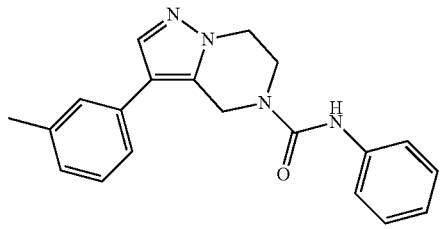 [SMILES: Cc1cccc(-c2cnn3c2CN(C(=O)Nc2ccccc2)CC3)c1]

Preparation of Example 120

The title compound was prepared in analogy to the preparation of Example 1 by using (3-methyl-phenyl)boronic acid instead of (4-fluorophenyl)boronic acid. Example 120 was obtained as a white solid. LCMS (M+H$^+$): 333. $^1$H NMR (400 MHz, CD$_3$OD) δ ppm 7.77 (s, 1H), 7.43-7.36 (m, 2H), 7.34-7.21 (m, 5H), 7.15-7.01 (m, 2H), 4.99 (s, 2H), 4.31 (t, J=5.5 Hz, 2H), 4.09 (t, J=5.5 Hz, 2H), 2.40 (s, 3H).

Example 121

3-(3-bromophenyl)-N-phenyl-6,7-dihydro-4H-pyrazolo[1,5-a]pyrazine-5-carboxamide

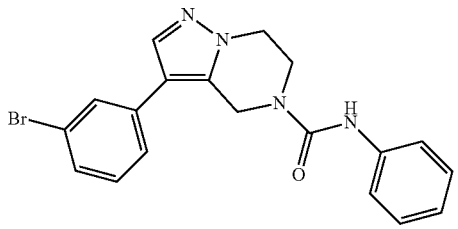 [SMILES: O=C(Nc1ccccc1)N1CCn2ncc(-c3cccc(Br)c3)c2C1]

Preparation of Example 121

The title compound was prepared in analogy to the preparation of Example 1 by using (3-bromophenyl)boronic acid instead of (4-fluorophenyl)boronic acid. Example 121 was obtained as a white solid (14 mg). LCMS (M+H$^+$): 397. $^1$H NMR (400 MHz, CD$_3$OD) δ ppm 7.82 (s, 1H), 7.65 (s, 1H), 7.50-7.42 (m, 2H), 7.41-7.34 (m, 3H), 7.33-7.24 (m, 2H), 7.10-7.01 (m, 1H), 5.00 (s, 2H), 4.32 (t, J=5.5 Hz, 2H), 4.10 (t, J=5.4 Hz, 2H).

Example 122

N-(3-ethynyl-4-fluoro-phenyl)-3-(4-fluorophenyl)-6,7-dihydro-4H-pyrazolo[1,5-a]pyrazine-5-carboxamide

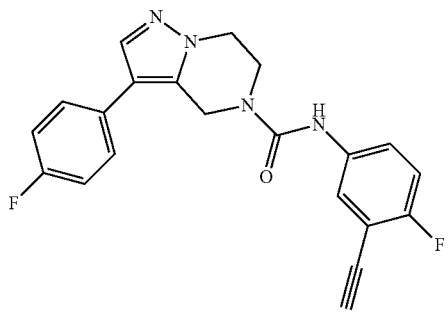 [SMILES: C#Cc1cc(NC(=O)N2CCn3ncc(-c4ccc(F)cc4)c3C2)ccc1F]

Preparation of Example 122

The title compound was prepared in analogy to the preparation of Example 106 by using 3-ethynyl-4-fluoroaniline instead of 3-amino-5-fluoro-benzonitrile. Example 122 was obtained as a white solid (10 mg). LCMS (M+H$^+$): 379. $^1$H NMR (400 MHz, CD$_3$OD) δ ppm 8.57 (s, 1H), 7.77 (s, 1H), 7.55 (dd, J=2.8, 6.3 Hz, 1H), 7.52-7.47 (m, 1H), 7.44-7.39 (m, 1H), 7.18 (t, J=8.8 Hz, 2H), 7.08 (t, J=9.0 Hz, 1H), 4.97 (s, 2H), 4.31 (t, J=5.5 Hz, 2H), 4.09 (t, J=5.4 Hz, 2H), 3.76 (s, 1H).

Example 123

N-(3-chloro-5-fluoro-phenyl)-3-(4-fluorophenyl)-6,7-dihydro-4H-pyrazolo[1,5-a]pyrazine-5-carboxamide

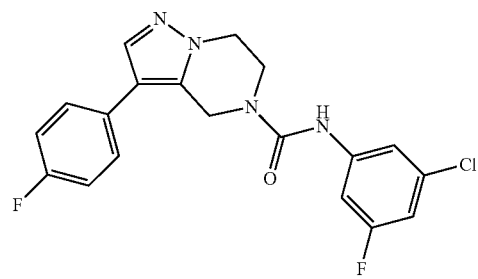 [SMILES: O=C(Nc1cc(F)cc(Cl)c1)N1CCn2ncc(-c3ccc(F)cc3)c2C1]

Preparation of Example 123

The title compound was prepared in analogy to the preparation of Example 106 by using 3-chloro-5-fluoroaniline instead of 3-amino-5-fluoro-benzonitrile. Example 123 was obtained as a white solid (9 mg). LCMS (M+H$^+$): 389. $^1$H NMR (400 MHz, CD$_3$OD) δ ppm 7.77 (s, 1H), 7.53-7.45 (m, 2H), 7.35 (d, J=0.9 Hz, 1H), 7.28 (td, J=2.1, 11.2 Hz, 1H), 7.22-7.14 (m, 2H), 6.84 (td, J=2.0, 8.5 Hz, 1H), 4.98 (s, 2H), 4.31 (t, J=5.4 Hz, 2H), 4.09 (t, J=5.5 Hz, 2H).

Example 124

N-(2-chloro-4-pyridyl)-3-(4-fluorophenyl)-6,7-dihydro-4H-pyrazolo[1,5-a]pyrazine-5-carboxamide

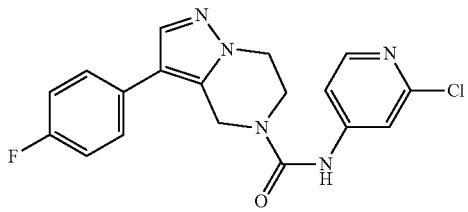 [SMILES: O=C(Nc1ccnc(Cl)c1)N1CCn2ncc(-c3ccc(F)cc3)c2C1]

Preparation of Example 124

The title compound was prepared in analogy to the preparation of Example 106 by using 2-chloropyridin-4-amine instead of 3-amino-5-fluoro-benzonitrile. Example 124 was obtained as a white solid (10 mg). LCMS (M+H$^+$): 372. $^1$H NMR (400 MHz, CD$_3$OD) δ ppm 8.15 (d, J=5.9 Hz, 1H), 7.77 (s, 1H), 7.69 (d, J=1.9 Hz, 1H), 7.53-7.43 (m, 3H), 7.19 (t, J=8.8 Hz, 2H), 5.00 (s, 2H), 4.32 (t, J=5.4 Hz, 2H), 4.11 (t, J=5.4 Hz, 2H).

Example 125

N-(2,6-dimethyl-4-pyridyl)-3-(4-fluorophenyl)-6,7-dihydro-4H-pyrazolo[1,5-a]pyrazine-5-carboxamide

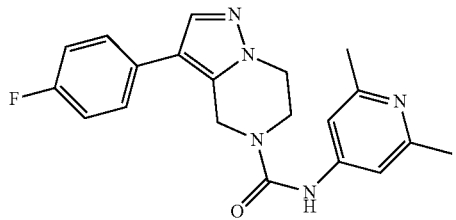 [SMILES: Cc1cc(NC(=O)N2CCn3ncc(-c4ccc(F)cc4)c3C2)cc(C)n1]

Preparation of Example 125

The title compound was prepared in analogy to the preparation of Example 106 by using 2,6-dimethylpyridin-4-amine instead of 3-amino-5-fluoro-benzonitrile. Example 125 was obtained as a white solid (10 mg). LCMS (M+H$^+$): 366. $^1$H NMR (400 MHz, CD$_3$OD) δ ppm 7.77 (s, 1H), 7.48 (dd, J=5.3, 8.8 Hz, 2H), 7.41 (s, 2H), 7.18 (t, J=8.8 Hz, 2H), 5.00 (s, 2H), 4.32 (t, J=5.5 Hz, 2H), 4.11 (t, J=5.5 Hz, 2H), 2.52 (s, 6H).

Example 126

3-(4-fluorophenyl)-N-[2-(trifluoromethyl)-4-pyridyl]-6,7-dihydro-4H-pyrazolo[1,5-a]pyrazine-5-carboxamide

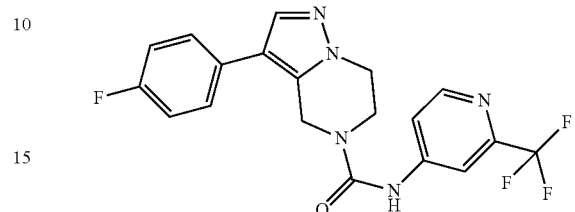

Preparation of Example 126

The title compound was prepared in analogy to the preparation of Example 106 by using 2-(trifluoromethyl)pyridin-4-amine instead of 3-amino-5-fluoro-benzonitrile. Example 126 was obtained as a white solid (9 mg). LCMS (M+H$^+$): 406. $^1$H NMR (400 MHz, CD$_3$OD) δ ppm 8.48 (d, J=5.8 Hz, 1H), 8.02 (d, J=2.0 Hz, 1H), 7.77 (s, 1H), 7.74 (dd, J=2.0, 5.6 Hz, 1H), 7.49 (dd, J=5.3, 8.8 Hz, 2H), 7.26-7.13 (m, 2H), 5.02 (s, 2H), 4.36-4.32 (t, J=5.5 Hz, 2H), 4.13 (t, J=5.5 Hz, 2H).

Example 127

N-(3-chloro-4-fluoro-phenyl)-1-(4-fluorophenyl)-6,8-dihydro-5H-imidazo[1,5-a]pyrazine-7-carboxamide

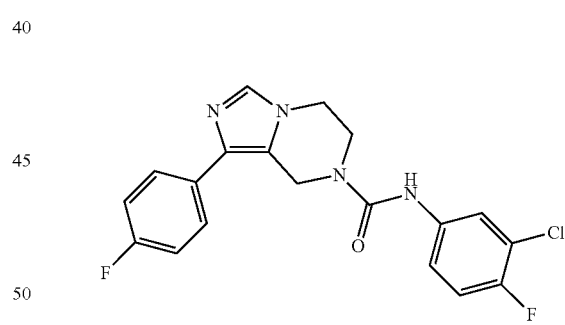

Preparation of Example 127

The title compound was prepared in analogy to the preparation of Example 106 by using 3-chloro-4-fluoroaniline instead of 3-amino-5-fluoro-benzonitrile and 1-(4-fluorophenyl)-5,6,7,8-tetrahydroimidazo[1,5-a]pyrazine (compound 9e) instead of 3-(4-fluorophenyl)-4,5,6,7-tetrahydropyrazolo[1,5-a]pyrazine (compound 11b). Example 127 was obtained as a white solid (21 mg). LCMS (M+H$^+$): 389. $^1$H NMR (400 MHz, CD$_3$OD) δ ppm 7.76 (s, 1H), 7.69-7.59 (m, 3H), 7.35-7.31 (m, 1H), 7.23-7.11 (m, 3H), 4.99 (s, 2H), 4.27 (t, J=5.4 Hz, 2H), 3.99 (t, J=5.4 Hz, 2H).

Example 128

N-(3-bromo-4-fluoro-phenyl)-3-(4-fluorophenyl)-6,7-dihydro-4H-pyrazolo[1,5-a]pyrazine-5-carboxamide

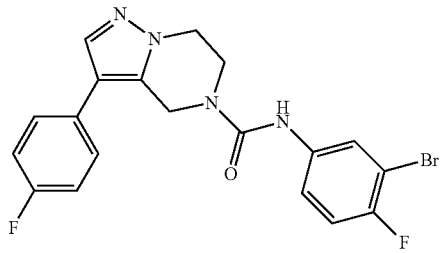 [SMILES: O=C(Nc1ccc(F)c(Br)c1)N1CCn2ncc(-c3ccc(F)cc3)c2C1]

Preparation of Example 128

The title compound was prepared in analogy to the preparation of Example 106 by using 3-bromo-4-fluoro-aniline instead of 3-amino-5-fluoro-benzonitrile. Example 128 was obtained as a white solid (3 mg). LCMS (M+H$^+$): 433. $^1$H NMR (400 MHz, CD$_3$OD) δ ppm 7.80-7.70 (m, 2H), 7.49 (dd, J=5.3, 9.0 Hz, 2H), 7.39-7.35 (m, 1H), 7.23-7.08 (m, 3H), 4.97 (s, 2H), 4.31 (t, J=5.5 Hz, 2H), 4.08 (t, J=5.4 Hz, 2H).

Example 129

N-[3-(difluoromethoxy)phenyl]-3-(4-fluorophenyl)-6,7-dihydro-4H-pyrazolo[1,5-a]pyrazine-5-carboxamide

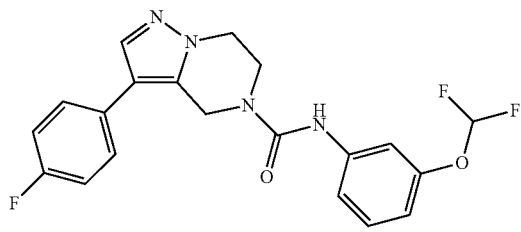 [SMILES: O=C(Nc1cccc(OC(F)F)c1)N1CCn2ncc(-c3ccc(F)cc3)c2C1]

Preparation of Example 129

The title compound was prepared in analogy to the preparation of Example 106 by using 3-(difluoromethoxy)aniline instead of 3-amino-5-fluoro-benzonitrile. Example 129 was obtained as a white solid (6 mg). LCMS (M+H$^+$): 403. $^1$H NMR (400 MHz, CD$_3$OD) δ ppm 7.77 (s, 1H), 7.49 (dd, J=5.3, 8.8 Hz, 2H), 7.36-7.22 (m, 3H), 7.18 (t, J=8.8 Hz, 2H), 6.80 (t, J=76 Hz, 1H), 6.83 (d, J=7.8 Hz, 1H), 4.98 (s, 2H), 4.31 (t, J=5.4 Hz, 2H), 4.10 (t, J=5.5 Hz, 2H).

Example 130

3-(4-fluorophenyl)-N-[4-fluoro-3-(trifluoromethoxy)phenyl]-6,7-dihydro-4H-pyrazolo[1,5-a]pyrazine-5-carboxamide

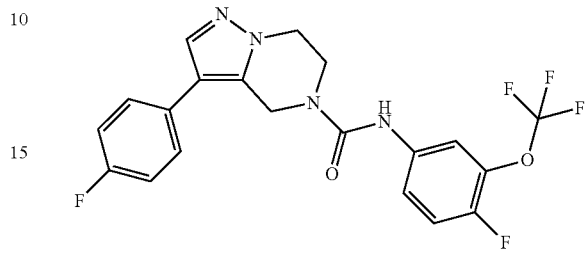

Preparation of Example 130

The title compound was prepared in analogy to the preparation of Example 106 by using 4-fluoro-3-(trifluoromethoxy)aniline instead of 3-amino-5-fluoro-benzonitrile. Example 130 was obtained as a white solid (6 mg). LCMS (M+H$^+$): 439. $^1$H NMR (400 MHz, CD$_3$OD) δ ppm 7.77 (s, 1H), 7.62 (dd, J=1.1, 6.9 Hz, 1H), 7.53-7.46 (m, 2H), 7.42-7.38 (m, 1H), 7.29-7.11 (m, 3H), 4.98 (s, 2H), 4.31 (t, J=5.4 Hz, 2H), 4.09 (t, J=5.5 Hz, 2H).

Example 131

N-[3-(difluoromethyl)phenyl]-3-(4-fluorophenyl)-6,7-dihydro-4H-pyrazolo[1,5-a]pyrazine-5-carboxamide

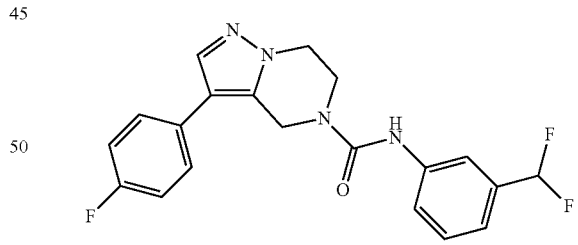

Preparation of Example 131

The title compound was prepared in analogy to the preparation of Example 106 by using 3-(difluoromethyl)aniline instead of 3-amino-5-fluoro-benzonitrile. Example 131 was obtained as a white solid (12 mg). LCMS (M+H$^+$): 387. $^1$H NMR (400 MHz, CD$_3$OD) δ ppm 7.77 (s, 1H), 7.65 (s, 1H), 7.59-7.45 (m, 3H), 7.41 (t, J=7.9 Hz, 1H), 7.24-7.13 (m, 3H), 6.73 (t, J=56 Hz, 1H), 4.99 (s, 2H), 4.32 (t, J=5.4 Hz, 2H), 4.11 (t, J=5.4 Hz, 2H).

Example 132

3-(4-fluorophenyl)-N-(m-tolyl)-6,7-dihydro-4H-pyrazolo[1,5-a]pyrazine-5-carboxamide

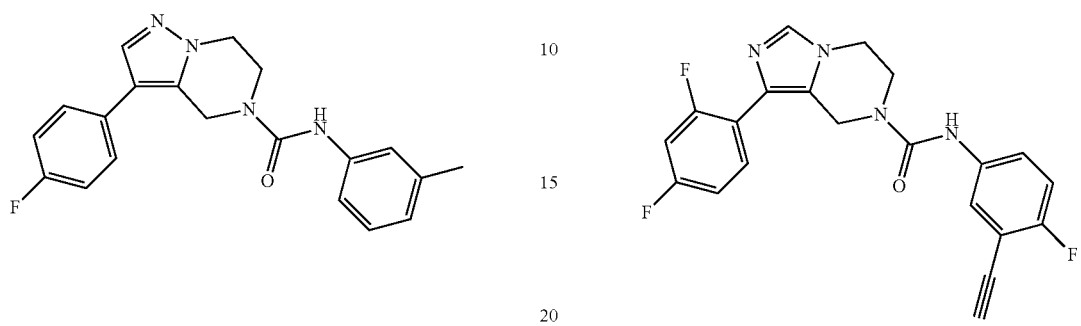

Preparation of Example 132

The title compound was prepared in analogy to the preparation of Example 106 by using 3-methylaniline instead of 3-amino-5-fluoro-benzonitrile. Example 132 was obtained as a white solid (5 mg). LCMS (M+H$^+$): 351. $^1$H NMR (400 MHz, CD$_3$OD) δ ppm 7.77 (s, 1H), 7.49 (dd, J=5.3, 8.5 Hz, 2H), 7.27-7.08 (m, 5H), 6.90 (d, J=3.8 Hz, 1H), 4.97 (s, 2H), 4.31 (t, J=5.4 Hz, 2H), 4.09 (t, J=5.4 Hz, 2H), 2.32 (s, 3H).

Example 133

N-phenyl-3-[3-(trifluoromethoxy)phenyl]-6,7-dihydro-4H-pyrazolo[1,5-a]pyrazine-5-carboxamide

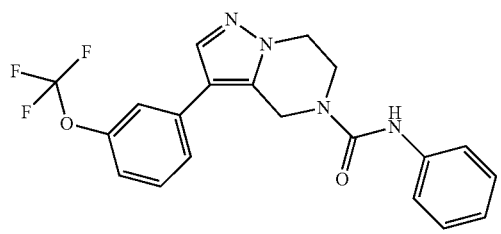 [SMILES: O=C(Nc1ccccc1)N1CCn2ncc(-c3cccc(OC(F)(F)F)c3)c2C1]

Preparation of Example 133

The title compound was prepared in analogy to the preparation of Example 1 by using 3-(trifluoromethoxy) phenyl-boronic acid instead of (4-fluorophenyl)boronic acid. Example 133 was obtained as a white solid (21 mg). LCMS (M+H$^+$): 403. $^1$H NMR (400 MHz, CD$_3$OD) δ ppm 7.86 (s, 1H), 7.58-7.44 (m, 2H), 7.42-7.36 (m, 3H), 7.29 (t, J=7.9 Hz, 2H), 7.21 (d, J=8.0 Hz, 1H), 7.11-7.02 (m, 1H), 5.02 (s, 2H), 4.33 (t, J=5.4 Hz, 2H), 4.11 (t, J=5.4 Hz, 2H).

Example 134

1-(2,4-difluorophenyl)-N-(3-ethynyl-4-fluoro-phenyl)-6,8-dihydro-5H-imidazo[1,5-a]pyrazine-7-carboxamide The title compound was prepared according to the following scheme:

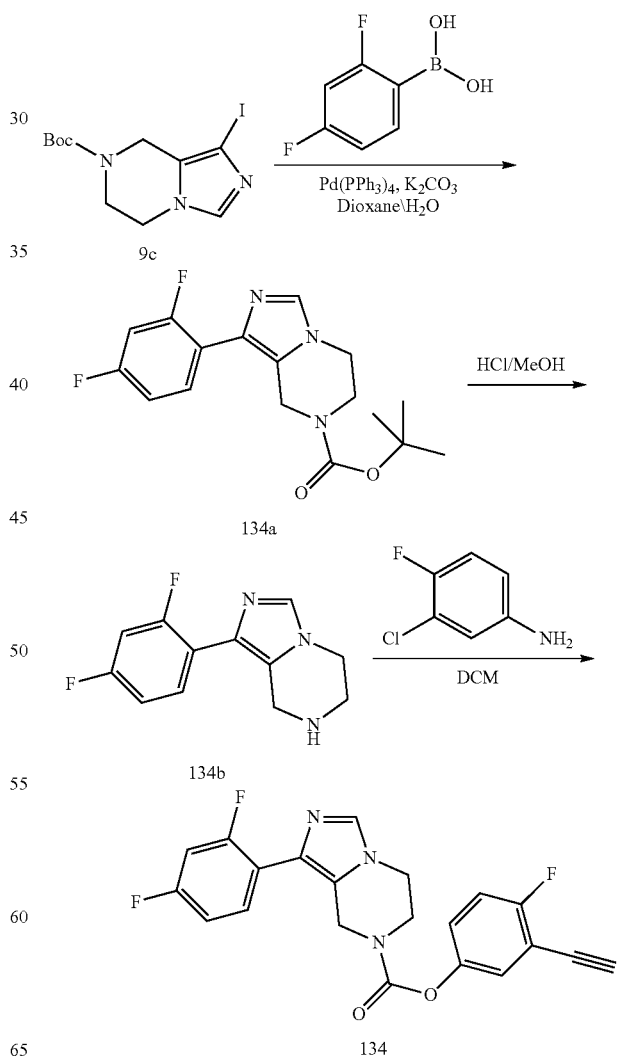

Preparation of 1-(2,4-difluorophenyl)-5,6,7,8-tetra-hydroimidazo[1,5-a]pyrazine (compound 134b)

The compound 134b was prepared in analogy to compound 9e by using (2,4-difluorophenyl)boronic acid instead of (4-fluorophenyl)boronic acid. Compound 134b was obtained as a white solid (250 mg). LCMS (M+H$^+$): 236.

Preparation of 1-(2,4-difluorophenyl)-N-(3-ethynyl-4-fluoro-phenyl)-6,8-dihydro-5H-imidazo[1,5-a]pyrazine-7-carboxamide (Example 134)

The title compound was prepared in analogy to the preparation of Example 106 by using 3-ethynyl-4-fluoro-aniline instead of 3-amino-5-fluoro-benzonitrile and 1-(2,4-difluorophenyl)-5,6,7,8-tetrahydroimidazo[1,5-a]pyrazine (compound 134b) instead of 3-(4-fluorophenyl)-4,5,6,7-tetrahydropyrazolo[1,5-a]pyrazine (compound 11b). Example 134 was obtained as a white solid (11 mg). LCMS (M+H$^+$): 397. $^1$H NMR (400 MHz, CD$_3$OD) δ ppm 7.81 (s, 1H), 7.70-7.59 (m, 1H), 7.53 (dd, J=2.8, 6.3 Hz, 1H), 7.41-7.37 (m, 1H), 7.15-7.01 (m, 3H), 4.81 (s, 2H), 4.28 (t, J=5.5 Hz, 2H), 3.99 (J=5.5 Hz, 2H), 3.75 (s, 1H).

Example 135

N-(3-chloro-4-fluoro-phenyl)-1-(2,4-difluorophenyl)-6,8-dihydro-5H-imidazo[1,5-a]pyrazine-7-carboxamide

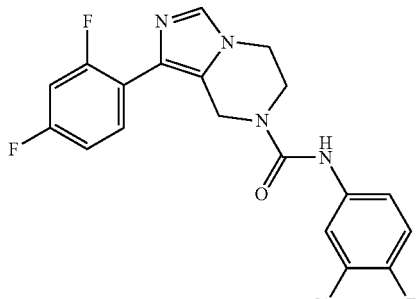

Preparation of Example 135

The title compound was prepared in analogy to the preparation of Example 106 by using 3-chloro-4-fluoro-aniline instead of 3-amino-5-fluoro-benzonitrile and 1-(2,4-difluorophenyl)-5,6,7,8-tetrahydroimidazo[1,5-a]pyrazine (compound 134b) instead of 3-(4-fluorophenyl)-4,5,6,7-tetrahydropyrazolo[1,5-a]pyrazine (compound 11b). Example 135 was obtained as a white solid (18 mg). LCMS (M+H$^+$): 407. $^1$H NMR (400 MHz, CD$_3$OD) δ ppm 7.82 (s, 1H), 7.69-7.56 (m, 2H), 7.32-7.28 (m, 1H), 7.20-7.00 (m, 3H), 4.81 (d, J=1.0 Hz, 2H), 4.28 (t, J=5.4 Hz, 2H), 3.99 (J=5.5 Hz, 2H).

Example 136

N-(3-cyano-4-fluoro-phenyl)-1-(2,4-difluorophenyl)-6,8-dihydro-5H-imidazo[1,5-a]pyrazine-7-carboxamide

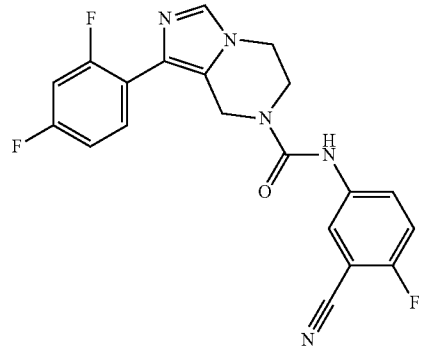 [SMILES: N#Cc1cc(NC(=O)N2CCn3cnc(-c4ccc(F)cc4F)c3C2)ccc1F]

Preparation of Example 136

The title compound was prepared in analogy to the preparation of Example 106 by using 5-amino-2-fluoro-benzonitrile instead of 3-amino-5-fluoro-benzonitrile and 1-(2,4-difluorophenyl)-5,6,7,8-tetrahydroimidazo[1,5-a]pyrazine (compound 134b) instead of 3-(4-fluorophenyl)-4,5,6,7-tetrahydropyrazolo[1,5-a]pyrazine (compound 11b). Example 136 was obtained as a white solid (23 mg). LCMS (M+H$^+$): 398. $^1$H NMR (400 MHz, CD$_3$OD) δ ppm 7.87-7.76 (m, 2H), 7.74-7.58 (m, 2H), 7.28 (t, J=9.0 Hz, 1H), 7.15-7.04 (m, 2H), 4.82 (d, J=1.0 Hz, 2H), 4.29 (t, J=5.5 Hz, 2H), 4.00 (t, J=5.5 Hz, 2H).

Example 137

N-(3-cyano-4,5-difluoro-phenyl)-1-(2,4-difluorophenyl)-6,8-dihydro-5H-imidazo[1,5-a]pyrazine-7-carboxamide

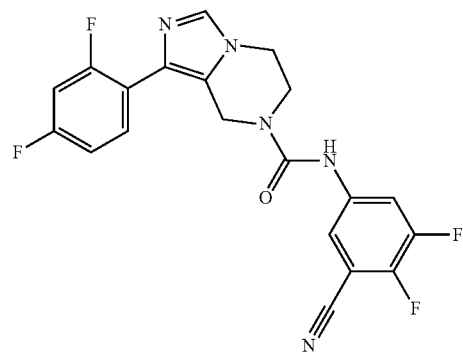 [SMILES: N#Cc1cc(NC(=O)N2CCn3cnc(-c4ccc(F)cc4F)c3C2)cc(F)c1F]

Preparation of Example 137

The title compound was prepared in analogy to the preparation of Example 106 by using 5-amino-2,3-difluoro-benzonitrile instead of 3-amino-5-fluoro-benzonitrile and 1-(2,4-difluorophenyl)-5,6,7,8-tetrahydroimidazo[1,5-a]

pyrazine (compound 134b) instead of 3-(4-fluorophenyl)-4,5,6,7-tetrahydropyrazolo[1,5-a]pyrazine (compound 11b). Example 137 was obtained as a white solid (8 mg). LCMS (M+H⁺): 416. ¹H NMR (400 MHz, CD₃OD) δ ppm 7.83 (s, 1H), 7.70-7.53 (m, 2H), 7.29-7.25 (m, 1H), 7.13-7.02 (m, 2H), 4.85 (d, J=1.0 Hz, 2H), 4.32 (t, J=5.4 Hz, 2H), 4.03 (t, J=5.4 Hz, 2H).

Example 138

1-(2,4-difluorophenyl)-N-(3,4,5-trifluorophenyl)-6,8-dihydro-5H-imidazo[1,5-a]pyrazine-7-carboxamide

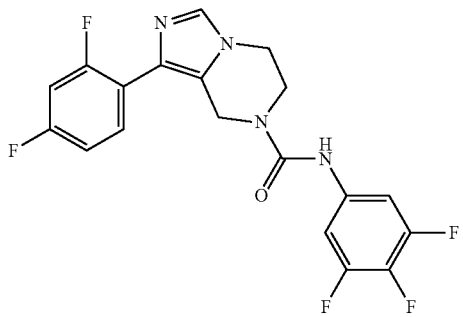 [SMILES: O=C(Nc1cc(F)c(F)c(F)c1)N1CCn2cnc(-c3ccc(F)cc3F)c2C1]

Preparation of Example 138

The title compound was prepared in analogy to the preparation of Example 106 by using 3,4,5-trifluoroaniline instead of 3-amino-5-fluoro-benzonitrile and 1-(2,4-difluorophenyl)-5,6,7,8-tetrahydroimidazo[1,5-a]pyrazine (compound 134b) instead of 3-(4-fluorophenyl)-4,5,6,7-tetrahydropyrazolo[1,5-a]pyrazine (compound 11b). Example 138 was obtained as a white solid (10 mg). LCMS (M+H⁺): 409. ¹H NMR (400 MHz, CD₃OD) δ ppm 7.82 (s, 1H), 7.64 (dt, J=6.5, 8.7 Hz, 1H), 7.30-7.17 (m, 2H), 7.14-7.02 (m, 2H), 4.80 (d, J=1.0 Hz, 2H), 4.28 (t, J=5.4 Hz, 2H), 3.98 (t, J=5.4 Hz, 2H).

Example 139

3-(2,4-difluorophenyl)-N-(3-ethynyl-4-fluoro-phenyl)-6,7-dihydro-4H-pyrazolo[1,5-a]pyrazine-5-carboxamide

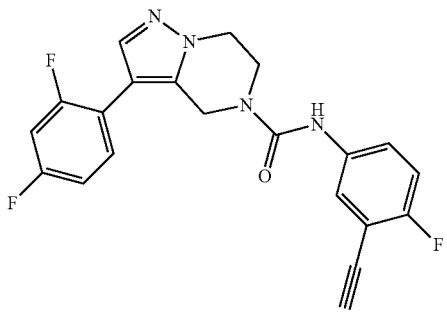 [SMILES: C#Cc1cc(NC(=O)N2CCn3ncc(-c4ccc(F)cc4F)c3C2)ccc1F]

Preparation of Example 139

The title compound was prepared in analogy to the preparation of Example 106 by using 3-ethynyl-4-fluoro-aniline instead of 3-amino-5-fluoro-benzonitrile and 3-(2,4-difluorophenyl)-4,5,6,7-tetrahydropyrazolo[1,5-a]pyrazine (compound 60b) instead of 3-(4-fluorophenyl)-4,5,6,7-tetrahydropyrazolo[1,5-a]pyrazine (compound 11b). Example 70 was obtained as a white solid (9 mg). LCMS (M+H⁺): 397. ¹H NMR (400 MHz, CD₃OD) δ ppm 7.72 (d, J=1.5 Hz, 1H), 7.57-7.44 (m, 2H), 7.42-7.38 (m, 1H), 7.17-6.99 (m, 3H), 4.86 (s, 2H), 4.32 (t, J=5.5 Hz, 2H), 4.09 (t, J=5.5 Hz, 2H), 3.76 (s, 1H).

Example 140

N-(6-chloro-5-fluoro-2-pyridyl)-3-(4-fluorophenyl)-6,7-dihydro-4H-pyrazolo[1,5-a]pyrazine-5-carboxamide

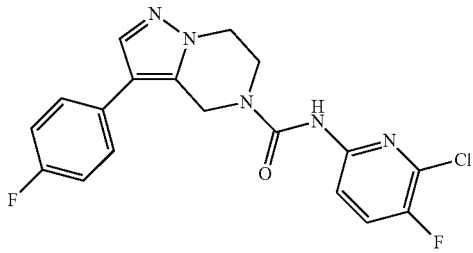 [SMILES: O=C(Nc1ccc(F)c(Cl)n1)N1CCn2ncc(-c3ccc(F)cc3)c2C1]

The title compound was prepared according to the following scheme:

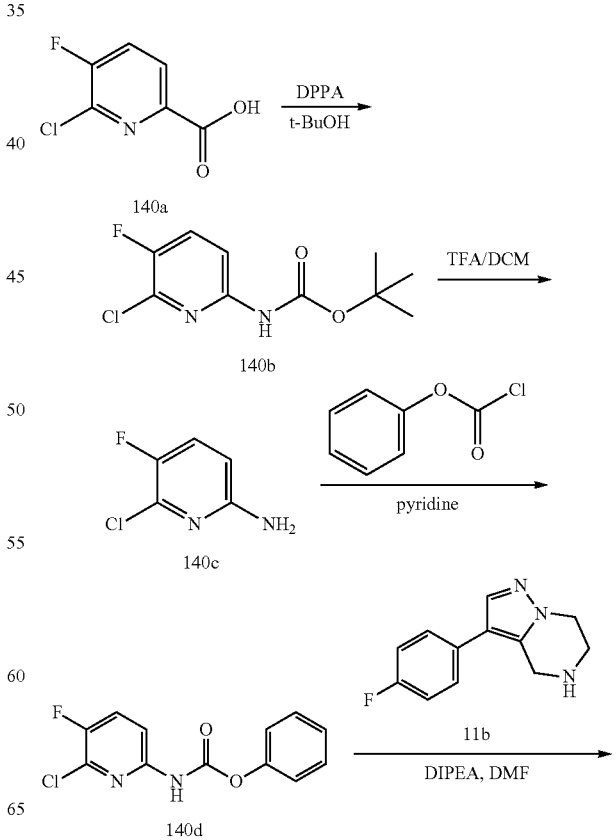

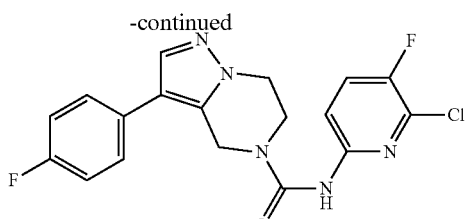

140

Step 1: Preparation of tert-butyl N-(6-chloro-5-fluoro-2-pyridyl)carbamate (compound 140b)

To a solution of 6-chloro-5-fluoro-pyridine-2-carboxylic acid (compound 140a, 1.8 g, 10 mmol) and Et₃N (1.4 mL, 10 mmol) in tert-butanol (40 mL) was added diphenylphosphoryl azide (2.1 mL, 10 mmol) and the reaction mixture was stirred at 85° C. for 2 hours. Then the reaction mixture was concentrated and the residue was purified by column chromatography (eluting with 5%~30% EtOAc in petroleum ether) to afford compound 140b (1.5 g) as a slight yellow oil. LCMS (M+H⁺): 247.

Step 2: Preparation of 6-chloro-5-fluoro-pyridin-2-amine (compound 140c)

A solution of tert-butyl N-(6-chloro-5-fluoro-2-pyridyl) carbamate (compound 140b, 1.5 g, 6 mmol) in TFA/DCM (10 mL, 1:1, v/v) was stirred at room temperature for 2 hours. The reaction mixture was concentrated, the residue was diluted with EtOAc (30 mL), washed with saturated aqueous NaHCO₃ (50 mL) and brine (500 mL). The organic layer was dried over Na₂SO₄ and concentrated to afford compound 140c (880 mg) which was used directly in next step.

Step 3: Preparation of phenyl N-(6-chloro-5-fluoro-2-pyridyl)carbamate (compound 140d)

To a solution of 6-chloro-5-fluoro-pyridin-2-amine (compound 140c, 880 mg, 6 mmol) and Pyridine (2 mL) in THF/DCM (10 mL, 1:1, v/v) was added phenyl carbonochloridate (1.4 g, 9 mmol) slowly at 0° C. The resulting mixture was stirred at room temperature for 2 hours, then poured into water (20 mL) and extracted with EtOAc (20 mL) twice. The organic layers were combined and concentrated, the residue was purified by column chromatography (eluting with 5%~30% EtOAc in petroleum ether) to afford compound 140d (800 mg) as a white solid. LCMS (M+H⁺): 267.

Step 4: Preparation of N-(6-chloro-5-fluoro-2-pyridyl)-3-(4-fluorophenyl)-6,7-dihydro-4H-pyrazolo[1,5-a]pyrazine-5-carboxamide (Example 140)

A mixture of phenyl N-(6-chloro-5-fluoro-2-pyridyl)carbamate (compound 140d, 27 mg, 0.1 mmol), 3-(4-fluorophenyl)-4,5,6,7-tetrahydropyrazolo[1,5-a]pyrazine (compound 11b, 22 mg, 0.1 mmol) and DIPEA (65 mg, 0.5 mmol) in DMF (2 mL) was stirred at 70° C. for 1 hour. Then the reaction mixture was purified by prep-HPLC to afford Example 140 as a white solid. LCMS (M+H⁺): 390. ¹H NMR (400 MHz, CD₃OD) δ ppm 7.83 (dd, J=3.1, 8.9 Hz, 1H), 7.77 (s, 1H), 7.65 (dd, J=8.0, 8.8 Hz, 1H), 7.49 (dd, J=5.3, 8.8 Hz, 2H), 7.17 (t, J=8.9 Hz, 2H), 4.98 (s, 2H), 4.30 (t, J=5.4 Hz, 2H), 4.09 (t, J=5.4 Hz, 2H).

Example 141

N-(3-cyclopropylphenyl)-3-(4-fluorophenyl)-6,7-dihydro-4H-pyrazolo[1,5-a]pyrazine-5-carboxamide

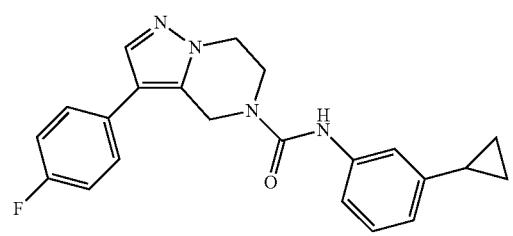 [SMILES: O=C(Nc1cccc(C2CC2)c1)N1CCn2ncc(-c3ccc(F)cc3)c2C1]

Preparation of Example 141

The title compound was prepared in analogy to the preparation of Example 106 by using 3-cyclopropylaniline (CAS: 485402-64-0, catalog number: AQ14074, Shanghai AQBioPharma Co. Ltd) instead of 3-amino-5-fluoro-benzonitrile. Example 141 was obtained as a white solid (6 mg). LCMS (M+H⁺): 377. ¹H NMR (400 MHz, CD₃OD) δ ppm 7.77 (s, 1H), 7.49 (dd, J=5.3, 8.8 Hz, 2H), 7.25-7.04 (m, 5H), 6.87-6.73 (m, 1H), 4.97 (s, 2H), 4.31 (t, J=5.4 Hz, 2H), 4.09 (t, J=5.4 Hz, 2H), 1.96-1.79 (m, 1H), 1.00-0.90 (m, 2H), 0.74-0.60 (m, 2H).

Example 142

N-(3-cyano-4-fluoro-phenyl)-3-(2,4-difluorophenyl)-6,7-dihydro-4H-pyrazolo[1,5-a]pyrazine-5-carboxamide

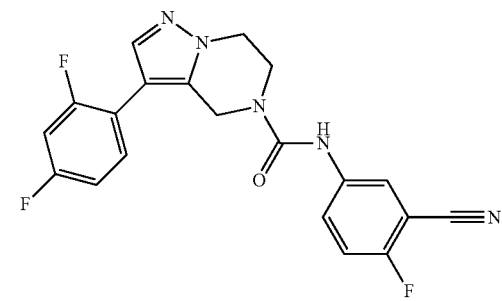 [SMILES: N#Cc1cc(NC(=O)N2CCn3ncc(-c4ccc(F)cc4F)c3C2)ccc1F]

Preparation of Example 142

The title compound was prepared in analogy to the preparation of Example 106 by using 5-amino-2-fluoro-benzonitrile instead of 3-amino-5-fluoro-benzonitrile and 3-(2,4-difluorophenyl)-4,5,6,7-tetrahydropyrazolo[1,5-a]pyrazine (compound 50b) instead of 3-(4-fluorophenyl)-4,5,6,7-tetrahydropyrazolo[1,5-a]pyrazine (compound 11b). Example 142 was obtained as a white solid (4 mg). LCMS (M+H⁺): 398. ¹H NMR (400 MHz, CD₃OD) δ ppm 7.87-7.77 (m, 1H), 7.75-7.65 (m, 2H), 7.54-7.40 (m, 1H), 7.29 (t, J=8.9 Hz, 1H), 7.15-7.01 (m, 2H), 4.87 (s, 2H), 4.33 (t, J=5.4 Hz, 2H), 4.11 (t, J=5.5 Hz, 2H).

Example 143

N-(6-chloro-5-fluoro-2-pyridyl)-3-(2,4-difluorophenyl)-6,7-dihydro-4H-pyrazolo[1,5-a]pyrazine-5-carboxamide

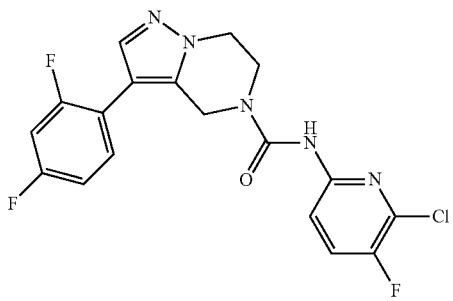 [SMILES: O=C(Nc1ccc(F)c(Cl)n1)N1CCn2ncc(-c3ccc(F)cc3F)c2C1]

Preparation of Example 143

The title compound was prepared in analogy to the preparation of Example 140 by using 3-(2,4-difluorophenyl)-4,5,6,7-tetrahydropyrazolo[1,5-a]pyrazine (compound 60b) instead of 3-(4-fluorophenyl)-4,5,6,7-tetrahydropyrazolo[1,5-a]pyrazine (compound 11b). Example 143 was obtained as a white solid. LCMS (M+H$^+$): 408. $^1$H NMR (400 MHz, CD$_3$OD) δ ppm 7.81 (dd, 8.8 Hz, 1H), 7.71 (d, J=1.3 Hz, 1H), 7.64 (t, J=8.4 Hz, 1H), 7.54-7.42 (m, 1H), 7.14-7.02 (m, 2H), 4.87 (s, 2H), 4.32 (t, J=5.5 Hz, 2H), 4.12 (t, J=5.5 Hz, 2H).

Example 144

N-(3,4-difluoro-5-methyl-phenyl)-3-(4-fluorophenyl)-6,7-dihydro-4H-pyrazolo[1,5-a]pyrazine-5-carboxamide

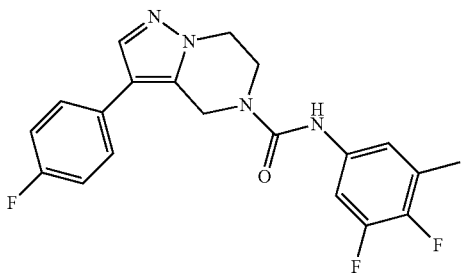 [SMILES: Cc1cc(NC(=O)N2CCn3ncc(-c4ccc(F)cc4)c3C2)cc(F)c1F]

Preparation of Example 144

The title compound was prepared in analogy to the preparation of Example 106 by using 3,4-difluoro-5-methyl-aniline (CAS: 1505944-46-6, catalog number: AQ14079, Shanghai AQBioPharma Co. Ltd) instead of 3-amino-5-fluoro-benzonitrile. Example 144 was obtained as a white solid (10 mg). LCMS (M+H$^+$): 387. $^1$H NMR (400 MHz, DMSO-d$_6$) δ ppm 8.99 (s, 1H), 7.83 (s, 1H), 7.49 (dd, J=5.4, 8.9 Hz, 2H), 7.44-7.38 (m, 1H), 7.32-7.22 (m, 2H), 7.11 (d, J=6.0 Hz, 1H), 4.92 (s, 2H), 4.21 (t, J=5.4 Hz, 2H), 3.99 (t, J=5.4 Hz, 2H), 2.24 (d, J=2.0 Hz, 3H).

Example 145

N-(3-chloro-4,5-difluoro-phenyl)-3-(4-fluorophenyl)-6,7-dihydro-4H-pyrazolo[1,5-a]pyrazine-5-carboxamide

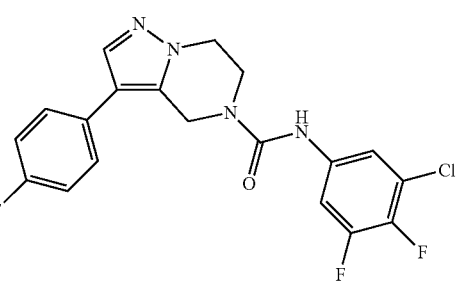

Preparation of Example 145

The title compound was prepared in analogy to the preparation of Example 106 by using 3-chloro-4,5-difluoro-aniline (CAS: 149144-05-8, catalog number: AQ14076, Shanghai AQBioPharma Co. Ltd) instead of 3-amino-5-fluoro-benzonitrile. Example 145 was obtained as a white solid (10 mg). LCMS (M+H$^+$): 407. $^1$H NMR (400 MHz, CD$_3$OD) δ ppm 7.77 (s, 1H), 7.50-7.35 (m, 4H), 7.18 (t, J=8.8 Hz, 2H), 4.97 (s, 2H), 4.31 (t, J=5.4 Hz, 2H), 4.08 (t, J=5.4 Hz, 2H).

Example 146

N-(3-cyclopropyl-4,5-difluoro-phenyl)-3-(4-fluorophenyl)-6,7-dihydro-4H-pyrazolo[1,5-a]pyrazine-5-carboxamide

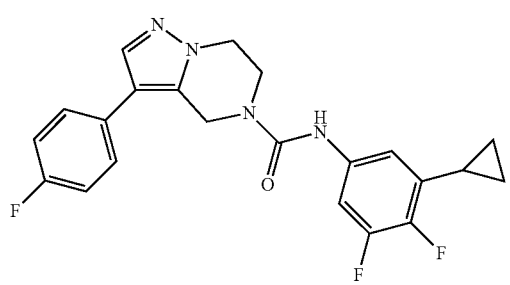 [SMILES: O=C(Nc1cc(F)c(F)c(C2CC2)c1)N1CCn2ncc(-c3ccc(F)cc3)c2C1]

Preparation of Example 146

The title compound was prepared in analogy to the preparation of Example 106 by using 3-cyclopropyl-4,5-difluoro-aniline (catalog number: AQ14078, Shanghai AQBioPharma Co. Ltd) instead of 3-amino-5-fluoro-benzonitrile. Example 146 was obtained as a white solid (10 mg). LCMS (M+H$^+$): 413. $^1$H NMR (400 MHz, CD$_3$OD) δ ppm 7.77 (s, 1H), 7.48 (dd, J=5.3, 8.8 Hz, 2H), 7.29-7.12 (m, 3H), 6.79-6.69 (m, 1H), 4.95 (s, 2H), 4.30 (t, J=5.5 Hz, 2H), 4.07 (t, J=5.5 Hz, 2H), 2.16-2.03 (m, 1H), 1.09-0.98 (m, 2H), 0.80-0.68 (m, 2H).

Example 147

N-[3-(1,1-difluoroethyl)phenyl]-3-(4-fluorophenyl)-6,7-dihydro-4H-pyrazolo[1,5-a]pyrazine-5-carboxamide

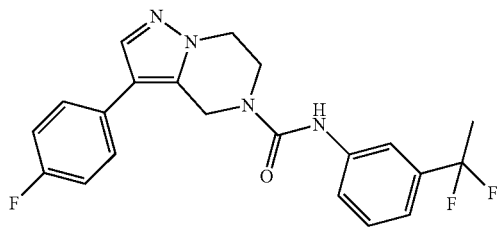 [SMILES: CC(F)(F)c1cccc(NC(=O)N2CCn3ncc(-c4ccc(F)cc4)c3C2)c1]

The title compound was prepared according to the following scheme:

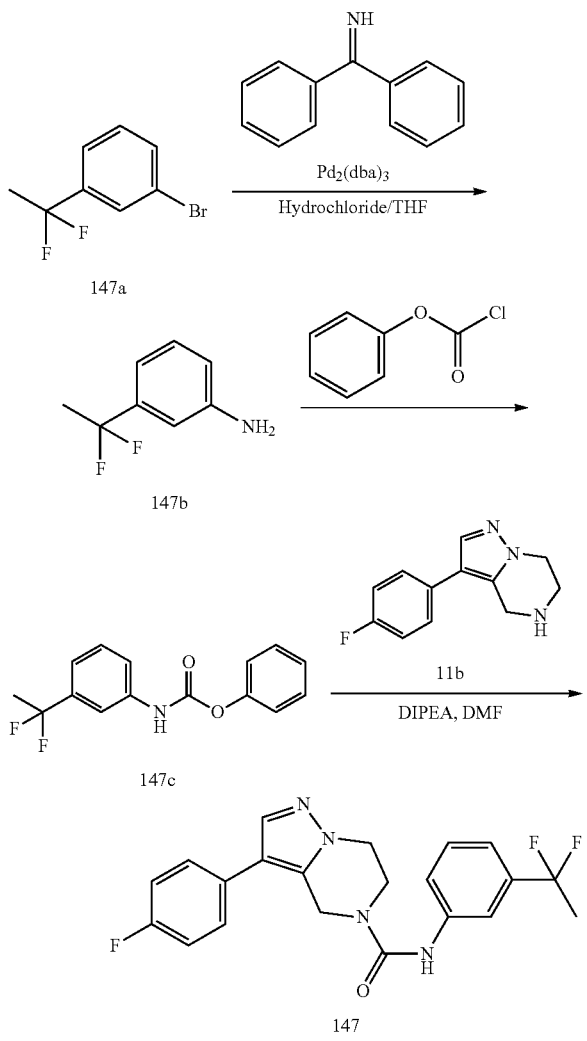

Step 1: Preparation of 3-(1,1-difluoroethyl)aniline (compound 147b)

To a mixture of 1-bromo-3-(1,1-difluoroethyl)benzene (compound 147a, 440 mg, 2 mmol)), diphenylmethanimine (545 mg, 3 mmol), 2-Dicyclohexylphosphino-2',6'-dimethoxy-1,1'-biphenyl (164 mg, 0.4 mmol) and $Cs_2CO_3$ (1.4 g, 4 mmol) in toluene (20 mL) was added $Pd_2(dba)_3$ (163 mg, 0.2 mmol) under nitrogen. The reaction mixture was stirred at 110° C. for 16 hours under nitrogen. After cooled down to room temperature, the reaction mixture was washed with brine (20 mL) and the organic layer was concentrated. The residue was dissolved in THF (10 mL) and hydrochloride acid (2 mL, 12 M). The reaction mixture was stirred at room temperature for 2 hours and then diluted with EtOAc and petroleum ether (20 mL, 1:1, v/v), washed with Hydrochloride acid (20 mL, 2 M). The aqueous layer was neutralized to pH~7 and extracted with EtOAc (20 mL) twice. The organic layer was dried and concentrated to afford compound 147b (158 mg) as a slight yellow oil. LCMS (M+H$^+$): 158.

Step 2: Preparation of phenyl N-[3-(1,1-difluoroethyl)phenyl]carbamate (compound 147c)

To a solution of 3-(1,1-difluoroethyl)aniline (compound 147b, 158 mg, 1 mmol) and Pyridine (0.5 mL) in THF/DCM (5 mL, 1:1, v/v) was added phenyl carbonochloridate (234 mg, 1.5 mmol) slowly at 0° C. The resulting mixture was stirred at room temperature for 2 hours, poured into water (20 mL) and extracted with EtOAc (20 mL) twice. The organic layer was combined and concentrated, the residue was purified by column chromatography (eluting with 0%~20% EtOAc in petroleum ether) to afford compound 147c (80 mg) as a white solid. LCMS (M+H$^+$): 278.

Step 3: Preparation of N-[3-(1,1-difluoroethyl)phenyl]-3-(4-fluorophenyl)-6,7-dihydro-4H-pyrazolo[1,5-a]pyrazine-5-carboxamide (Example 147)

The title compound was prepared in analogy to the preparation of Example 140 by using N-[3-(1,1-difluoroethyl)phenyl]carbamate (compound 147c) instead of N-(6-chloro-5-fluoro-2-pyridyl)-3-(4-fluorophenyl)-6,7-dihydro-4H-pyrazolo[1,5-a]pyrazine-5-carboxamide (compound 140d). Example 147 was obtained as a white solid (4 mg). LCMS (M+H$^+$): 401. $^1$H NMR (400 MHz, CD$_3$OD) δ ppm 7.77 (s, 1H), 7.63 (s, 1H), 7.50 (dd, J=5.3, 8.8 Hz, 2H), 7.38 (t, J=7.9 Hz, 1H), 7.26-7.13 (m, 4H), 4.99 (s, 2H), 4.32 (t, J=5.5 Hz, 2H), 4.11 (t, J=5.5 Hz, 2H), 1.91 (t, J=18.2 Hz, 3H).

Example 148 and Example 149
N-(3-chloro-4-fluoro-phenyl)-3-(4-chloro-5-fluoro-2-pyridyl)-6,7-dihydro-4H-pyrazolo[1,5-a]pyrazine-5-carboxamide and N-(3-chloro-4-fluoro-phenyl)-3-(2-chloro-5-fluoro-4-pyridyl)-6,7-dihydro-4H-pyrazolo[1,5-a]pyrazine-5-carboxamide
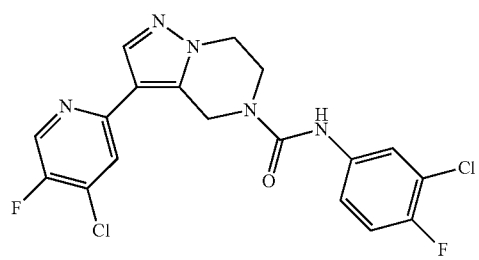
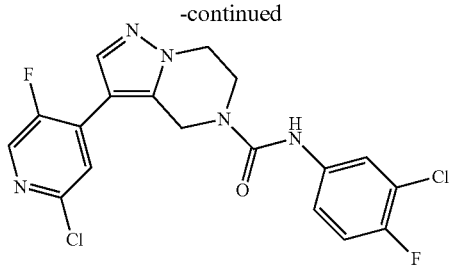
The title compound was prepared according to the following scheme:
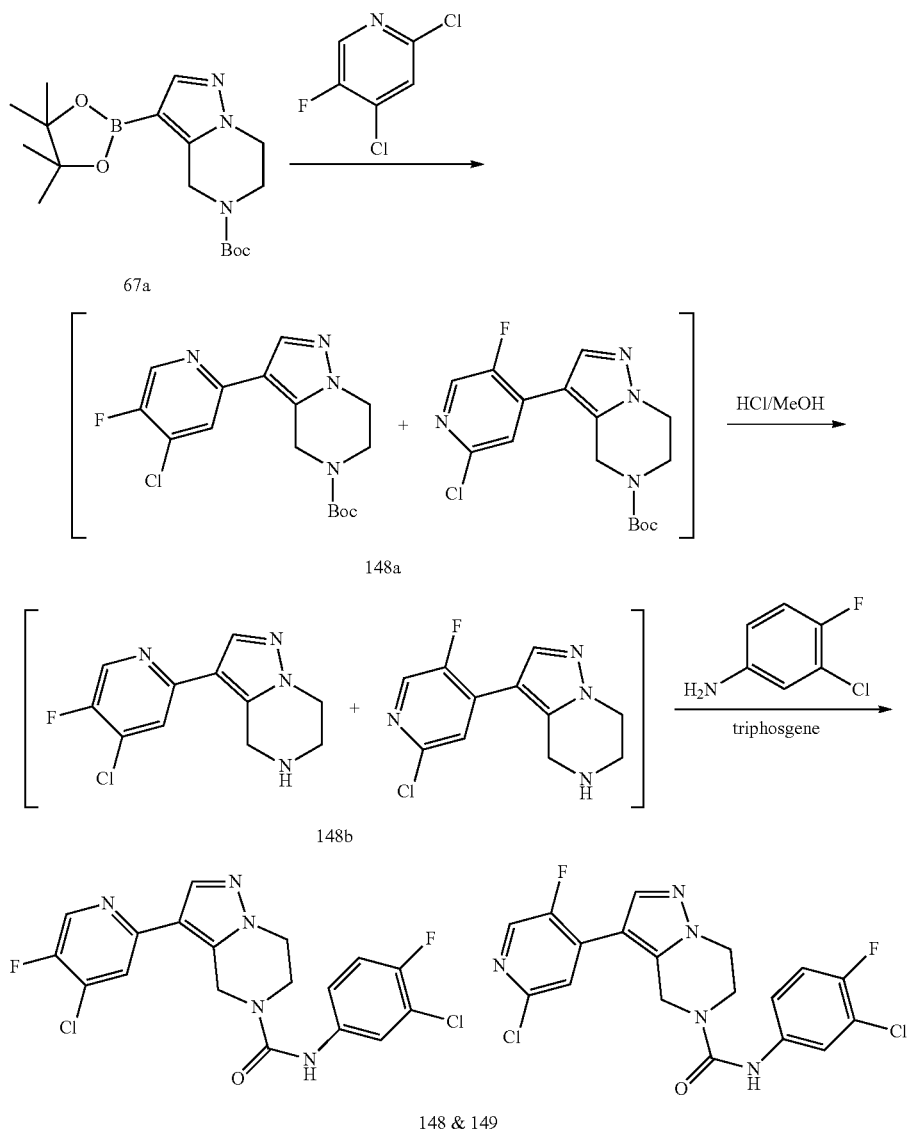

Preparation of [3-(4-chloro-5-fluoro-2-pyridyl)-4,5,6,7-tetrahydropyrazolo[1,5-a]pyrazine and 3-(2-chloro-5-fluoro-4-pyridyl)-4,5,6,7-tetrahydropyrazolo[1,5-a]pyrazine] (compound 148b)

The compound 148b was prepared in analogy to compound 67c by using 2,4-dichloro-5-fluoro-pyridine instead of 2-chloro-4-(trifluoromethyl)pyridine. Compound 148b was obtained as a white solid (50 mg). LCMS (M+H$^+$): 253.

Preparation of N-(3-chloro-4-fluoro-phenyl)-3-(4-chloro-5-fluoro-2-pyridyl)-6,7-dihydro-4H-pyrazolo[1,5-a]pyrazine-5-carboxamide and N-(3-chloro-4-fluoro-phenyl)-3-(2-chloro-5-fluoro-4-pyridyl)-6,7-dihydro-4H-pyrazolo[1,5-a]pyrazine-5-carboxamide (Example 148 and 149)

The title compound was prepared in analogy to the preparation of Example 140 by using phenyl N-(3-chloro-4-fluoro-phenyl)carbamate (compound 12i) instead of phenyl N-(6-chloro-5-fluoro-2-pyridyl)carbamate (compound 140d) and compound 148b instead of 3-(4-fluorophenyl)-4,5,6,7-tetrahydropyrazolo[1,5-a]pyrazine (compound 11b).

Example 148 (2 mg) was obtained as a white solid. LCMS (M+H$^+$): 424. $^1$H NMR (400 MHz, CD$_3$OD) δ ppm 8.36 (d, J=2.3 Hz, 1H), 7.96 (d, J=2.5 Hz, 1H), 7.61 (dd, J=2.5, 6.8 Hz, 1H), 7.58 (d, J=5.5 Hz, 1H), 7.34-7.30 (m, 1H), 7.17 (t, J=9.0 Hz, 1H), 5.00 (s, 2H), 4.34 (t, J=5.4 Hz, 2H), 4.11 (t, J=5.5 Hz, 2H).

Example 149 (18 mg) was obtained as a white solid. LCMS (M+H$^+$): 424. $^1$H NMR (400 MHz, CD$_3$OD) δ ppm 8.55 (d, J=1.3 Hz, 1H), 8.07 (s, 1H), 7.90 (d, J=5.8 Hz, 1H), 7.62 (dd, J=2.6, 6.7 Hz, 1H), 7.36-7.31 (m, 1H), 7.17 (t, J=9.0 Hz, 1H), 5.16 (s, 2H), 4.31 (t, J=5.4 Hz, 2H), 4.06 (t, J=5.5 Hz, 2H).

Example 150

N-(3-cyclopropyl-4-fluoro-phenyl)-3-(2,4-difluorophenyl)-6,7-dihydro-4H-pyrazolo[1,5-a]pyrazine-5-carboxamide

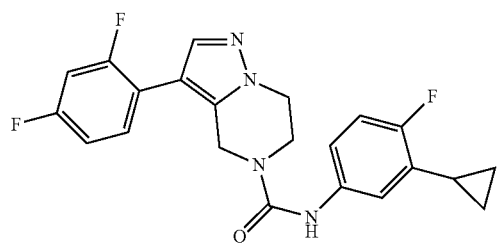 [SMILES: O=C(Nc1ccc(F)c(C2CC2)c1)N1CCn2ncc(-c3ccc(F)cc3F)c2C1]

Preparation of Example 150

The title compound was prepared in analogy to the preparation of Example 106 by using 3-cyclopropyl-4-fluoro-aniline (CAS: 890129-90-5, catalog number: AQ14079, Shanghai AQBioPharma Co. Ltd) instead of 3-amino-5-fluoro-benzonitrile and 3-(2,4-difluorophenyl)-4,5,6,7-tetrahydropyrazolo[1,5-a]pyrazine (compound 60b, 40 mg) instead of 3-(4-fluorophenyl)-4,5,6,7-tetrahydropyrazolo[1,5-a]pyrazine (compound 11b). Example 150 was obtained as a white solid (13 mg). LCMS (M+H$^+$): 413. $^1$H NMR (400 MHz, chloroform-d) δ ppm 7.68 (s, 1H), 7.38- 7.27 (m, 1H), 7.10-6.86 (m, 5H), 6.57 (br. s, 1H), 4.74 (s, 2H), 4.36 (br. s, 2H), 4.04 (br. s, 2H), 2.09-2.03 (m, 1H), 1.04-0.91 (m, 2H), 0.77-0.63 (m, 2H).

Example 151

N-(2-chloro-4-pyridyl)-1-(2,4-difluorophenyl)-6,8-dihydro-5H-imidazo[1,5-a]pyrazine-7-carboxamide

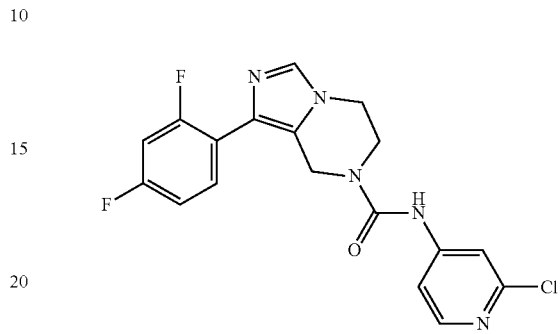

Preparation of Example 151

The title compound was prepared in analogy to the preparation of Example 106 by using 2-chloro-pyridin-4-amine instead of 3-amino-5-fluoro-benzonitrile and 1-(2,4-difluorophenyl)-5,6,7,8-tetrahydroimidazo[1,5-a]pyrazine (compound 134b) instead of 3-(4-fluorophenyl)-4,5,6,7-tetrahydropyrazolo[1,5-a]pyrazine (compound 11b). Example 151 was obtained as a white solid (2 mg). LCMS (M+H$^+$): 390. $^1$H NMR (400 MHz, CD$_3$OD) δ ppm 8.13 (d, J=5.8 Hz, 1H), 7.82 (s, 1H), 7.70-7.59 (m, 2H), 7.44 (dd, J=2.0, 5.8 Hz, 1H), 7.16-7.02 (m, 2H), 4.83 (s, 2H), 4.30 (t, J=5.5 Hz, 2H), 4.01 (t, J=5.5 Hz, 2H).

Example 152

1-(2,4-difluorophenyl)-N-[2-(trifluoromethyl)-4-pyridyl]-6,8-dihydro-5H-imidazo[1,5-a]pyrazine-7-carboxamide

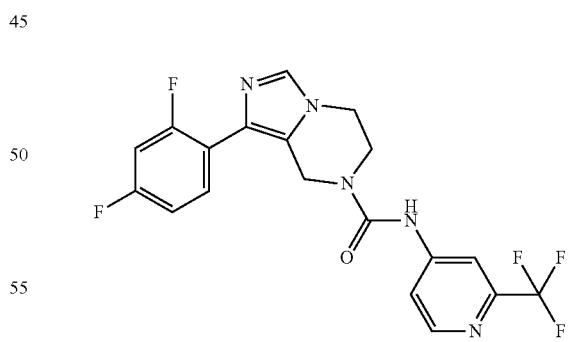

Preparation of Example 152

The title compound was prepared in analogy to the preparation of Example 106 by using 2-(trifluoromethyl)pyridine-4-amine instead of 3-amino-5-fluoro-benzonitrile and 1-(2,4-difluorophenyl)-5,6,7,8-tetrahydroimidazo[1,5-a]pyrazine (compound 134b) instead of 3-(4-fluorophenyl)-4,5,6,7-tetrahydropyrazolo[1,5-a]pyrazine (compound 11b).

Example 152 was obtained as a white solid (2 mg). LCMS (M+H⁺): 424. ¹H NMR (400 MHz, CD₃OD) δ ppm 7.99 (s, 1H), 7.78 (s, 1H), 7.75 (d, J=1.3 Hz, 1H), 7.54-7.45 (m, 2H), 7.41 (dd, J=1.9, 8.9 Hz, 1H), 7.18 (t, J=8.8 Hz, 1H), 5.01 (s, 2H), 4.33 (t, J=5.5 Hz, 2H), 4.12 (t, J=5.4 Hz, 2H).

Example 153

N-(3-chloro-4-fluoro-phenyl)-3-(4-fluorophenyl)-6,7-dihydro-4H-triazolo[1,5-a]pyrazine-5-carboxamide

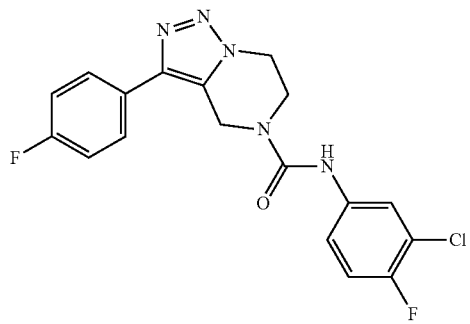 [SMILES: O=C(Nc1ccc(F)c(Cl)c1)N1CCn2nnc(-c3ccc(F)cc3)c2C1]

Preparation of Example 153

The title compound was prepared in analogy to the preparation of Example 140 by using phenyl N-(3-chloro-4-fluoro-phenyl)carbamate (compound 12i) instead of phenyl N-(6-chloro-5-fluoro-2-pyridyl)carbamate (compound 140d) and 3-(4-fluorophenyl)-4,5,6,7-tetrahydrotriazolo[1,5-a]pyrazine (compound 10e) instead of 3-(4-fluorophenyl)-4,5,6,7-tetrahydropyrazolo[1,5-a]pyrazine (compound 11b). Example 153 was obtained as a white solid (5 mg). LCMS (M+H⁺): 390. ¹H NMR (400 MHz, CD₃OD) δ ppm 7.85-7.75 (m, 2H), 7.64 (dd, J=2.6, 6.7 Hz, 1H), 7.37-7.33 (m, 1H), 7.27 (t, J=8.8 Hz, 2H), 7.18 (t, J=9.0 Hz, 1H), 5.09 (s, 2H), 4.58 (t, J=5.4 Hz, 2H), 4.11 ((t, J=5.4 Hz, 2H).

Example 154

N-(6-chloro-5-fluoro-2-pyridyl)-1-(2,4-difluorophenyl)-6,8-dihydro-5H-imidazo[1,5-a]pyrazine-7-carboxamide

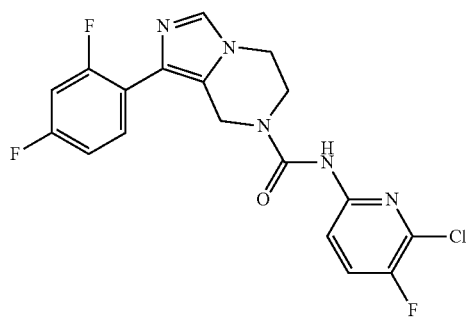 [SMILES: O=C(Nc1ccc(F)c(Cl)n1)N1CCn2cnc(-c3ccc(F)cc3F)c2C1]

Preparation of Example 154

The title compound was prepared in analogy to the preparation of Example 140 by using 1-(2,4-difluorophenyl)-5,6,7,8-tetrahydroimidazo[1,5-a]pyrazine (compound 134b) instead of 3-(4-fluorophenyl)-4,5,6,7-tetrahydropyrazolo[1,5-a]pyrazine (compound 11b). Example 154 was obtained as a white solid (5 mg). LCMS (M+H⁺): 408. ¹H NMR (400 MHz, CD₃OD) δ ppm 7.84-7.77 (m, 2H), 7.69-7.59 (m, 2H), 7.15-7.01 (m, 2H), 4.82 (d, J=0.8 Hz, 2H), 4.29 (t, J=5.5 Hz, 2H), 4.00 (t, J=5.5 Hz, 2H).

Example 155

N-(3-chloro-4-fluoro-phenyl)-3-(2,4-difluorophenyl)-6,7-dihydro-4H-triazolo[1,5-a]pyrazine-5-carboxamide

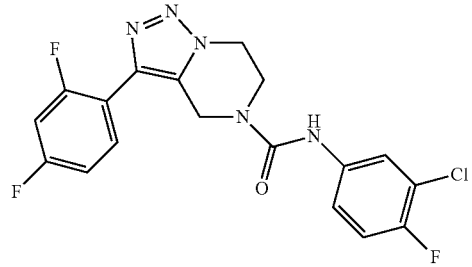 [SMILES: O=C(Nc1ccc(F)c(Cl)c1)N1CCn2nnc(-c3ccc(F)cc3F)c2C1]

The title compound was prepared according to the following scheme:

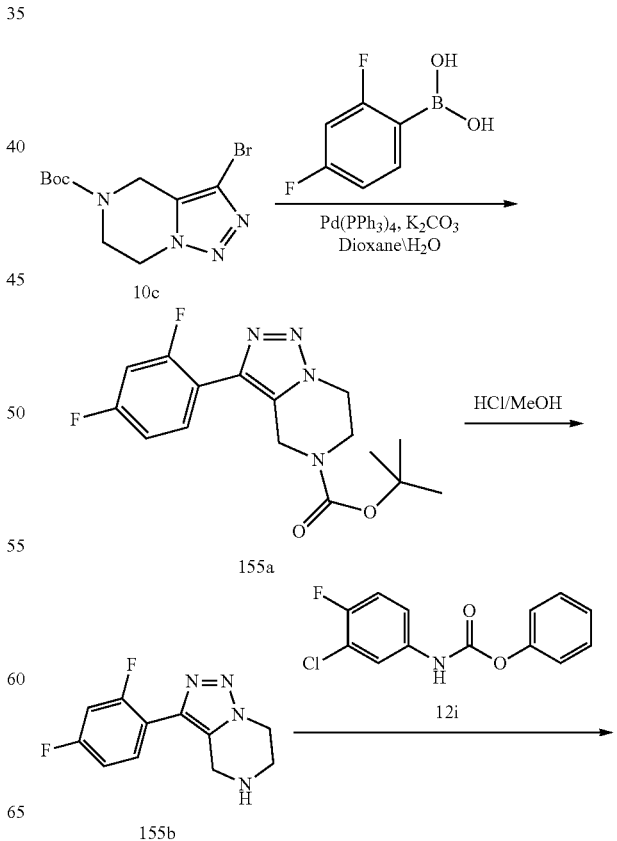

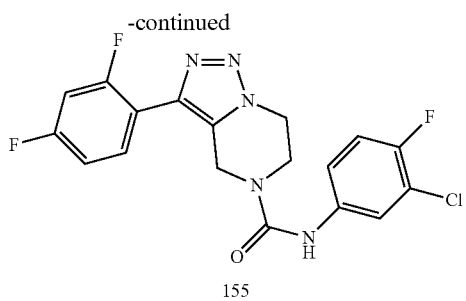

155

Preparation of 3-(2,4-difluorophenyl)-4,5,6,7-tetrahydrotriazolo[1,5-a]pyrazine (compound 155b)

The compound 155b was prepared in analogy to compound 10e by using (2,4-difluorophenyl)boronic acid instead of (4-fluorophenyl)boronic acid. Compound 155b was obtained as a white solid (50 mg). LCMS (M+H$^+$): 237.

Preparation of N-(3-chloro-4-fluoro-phenyl)-3-(2,4-difluorophenyl)-6,7-dihydro-4H-triazolo[1,5-a]pyrazine-5-carboxamide (Example 155)

The title compound was prepared in analogy to the preparation of Example 140 by using phenyl N-(3-chloro-4-fluoro-phenyl)carbamate (compound 12i) instead of phenyl N-(6-chloro-5-fluoro-2-pyridyl)carbamate (compound 140d) and 3-(2,4-difluorophenyl)-4,5,6,7-tetrahydrotriazolo[1,5-a]pyrazine (compound 155b) instead of 3-(4-fluorophenyl)-4,5,6,7-tetrahydropyrazolo[1,5-a]pyrazine (compound 11b). Example 155 was obtained as a white solid (7 mg). LCMS (M+H$^+$): 408. $^1$H NMR (400 MHz, CD$_3$OD) δ ppm 7.80 (dt, J=6.5, 8.8 Hz, 1H), 7.61 (dd, J=2.6, 6.7 Hz, 1H), 7.35-7.27 (m, 1H), 7.23-7.11 (m, 3H), 4.94 (s, 2H), 4.60 (t, J=5.5 Hz, 2H), 4.13 (t, J=5.5 Hz, 2H).

Example 156

N-(3,4-difluoro-5-methyl-phenyl)-3-(5-fluoro-2-pyridyl)-6-methyl-6,7-dihydro-4H-pyrazolo[1,5-a]pyrazine-5-carboxamide

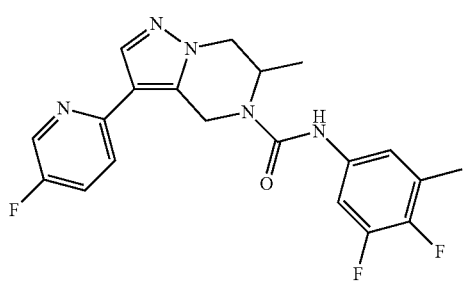 [SMILES: Cc1cc(NC(=O)N2Cc3c(-c4ccc(F)cn4)cnn3CC2C)cc(F)c1F]

Preparation of Example 156

The title compound was prepared in analogy to the preparation of Example 106 by using 3,4-difluoro-5-methyl-aniline (CAS: 1505944-46-6, catalog number: AQ14079, Shanghai AQBioPharma Co. Ltd) instead of 3-amino-5-fluoro-benzonitrile and 3-(5-fluoro-2-pyridyl)-6-methyl-4,5,6,7-tetrahydropyrazolo[1,5-a]pyrazine (compound 94b) instead of 3-(4-fluorophenyl)-4,5,6,7-tetrahydropyrazolo[1,5-a]pyrazine (compound 11b). Example 156 was obtained as a white solid (8 mg). LCMS (M+H$^+$): 402. $^1$H NMR (400 MHz, CD$_3$OD) δ ppm 8.50 (d, J=3.0 Hz, 1H), 8.06 (s, 1H), 7.75 (dd, J=4.1, 8.9 Hz, 1H), 7.61 (dt, J=3.0, 8.7 Hz, 1H), 7.30-7.26 (m, 1H), 7.10-6.96 (m, 1H), 5.46 (d, J=18.1 Hz, 1H), 5.04-4.94 (m, 1H), 4.83 (d, J=17.8 Hz, 1H), 4.37 (dd, J=4.5, 12.8 Hz, 1H), 4.29-4.17 (m, 1H), 2.30 (d, J=2.3 Hz, 3H), 1.29 (d, J=6.8 Hz, 3H).

Example 157

N-(3-cyclopropyl-4-fluoro-phenyl)-3-(5-fluoro-2-pyridyl)-6-methyl-6,7-dihydro-4H-pyrazolo[1,5-a]pyrazine-5-carboxamide

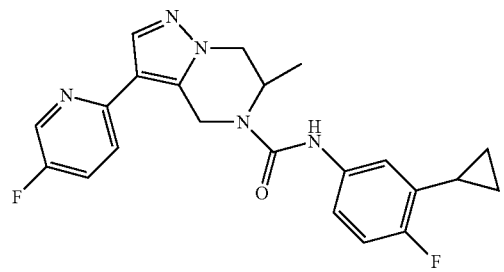 [SMILES: CC1Cn2ncc(-c3ccc(F)cn3)c2CN1C(=O)Nc1ccc(F)c(C2CC2)c1]

Preparation of Example 157

The title compound was prepared in analogy to the preparation of Example 106 by using 3-cyclopropyl-4-fluoro-aniline instead of 3-amino-5-fluoro-benzonitrile and 3-(5-fluoro-2-pyridyl)-6-methyl-4,5,6,7-tetrahydropyrazolo[1,5-a]pyrazine (compound 94b) instead of 3-(4-fluorophenyl)-4,5,6,7-tetrahydropyrazolo[1,5-a]pyrazine (compound 11b). Example 157 was obtained as a white solid (9 mg). LCMS (M+H$^+$): 410. $^1$H NMR (400 MHz, CD$_3$OD) δ ppm 8.50 (d, J=3.0 Hz, 1H), 8.06 (s, 1H), 7.74 (dd, J=4.3, 8.8 Hz, 1H), 7.61 (dt, J=3.0, 8.7 Hz, 1H), 7.19-7.15 (m, 1H), 7.06-6.92 (m, 2H), 5.46 (d, J=17.8 Hz, 1H), 5.06-4.96 (m, 1H), 4.82 (d, J=18.1 Hz, 1H), 4.37 (dd, J=4.3, 12.5 Hz, 1H), 4.22 (d, J=12.3 Hz, 1H), 2.18-2.01 (m, 1H), 1.28 (d, J=7.0 Hz, 3H), 1.04-0.92 (m, 2H), 0.81-0.67 (m, 2H).

Example 158

N-(3-chloro-4,5-difluoro-phenyl)-3-(5-fluoro-2-pyridyl)-6-methyl-6,7-dihydro-4H-pyrazolo[1,5-a]pyrazine-5-carboxamide

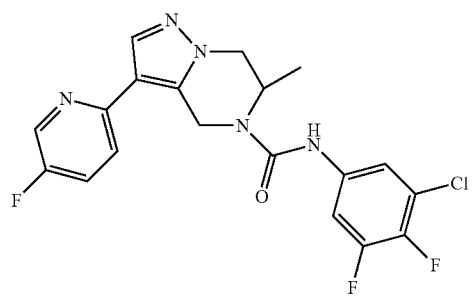

Preparation of Example 158

The title compound was prepared in analogy to the preparation of Example 106 by using 3-chloro-4,5-difluoro-aniline (CAS: 149144-05-8, catalog number: AQ14076, Shanghai AQBioPharma Co. Ltd) instead of 3-amino-5-fluoro-benzonitrile and 3-(5-fluoro-2-pyridyl)-6-methyl-4,5,6,7-tetrahydropyrazolo[1,5-a]pyrazine (compound 94b) instead of 3-(4-fluorophenyl)-4,5,6,7-tetrahydropyrazolo[1,5-a]pyrazine (compound 11b). Example 158 was obtained as a white solid (11 mg). LCMS (M+H$^+$): 422. $^1$H NMR (400 MHz, CD$_3$OD) δ ppm 8.51 (d, J=3.0 Hz, 1H), 8.06 (s, 1H), 7.75 (dd, J=4.4, 8.9 Hz, 1H), 7.61 (dt, J=3.0, 8.7 Hz, 1H), 7.51-7.40 (m, 2H), 5.47 (d, J=17.8 Hz, 1H), 5.05-4.97 (m, 1H), 4.84 (d, J=18.1 Hz, 1H), 4.38 (dd, J=4.6, 12.9 Hz, 1H), 4.23 (d, J=12.5 Hz, 1H), 1.29 (d, J=6.8 Hz, 3H).

Example 159

N-(3,4-difluoro-5-methoxy-phenyl)-3-(5-fluoro-2-pyridyl)-6-methyl-6,7-dihydro-4H-pyrazolo[1,5-a]pyrazine-5-carboxamide

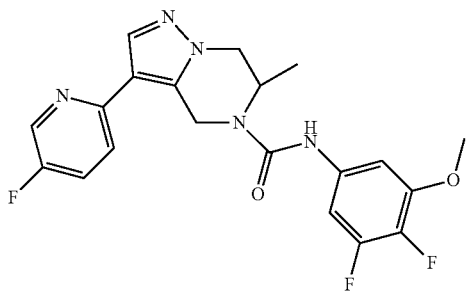 [SMILES: COc1cc(NC(=O)N2Cc3c(-c4ccc(F)cn4)cnn3CC2C)cc(F)c1F]

Preparation of Example 159

The title compound was prepared in analogy to the preparation of Example 106 by using 3,4-difluoro-5-methoxyl-aniline (CAS: 1195190-12-5, catalog number: AQ12805, Shanghai AQBioPharma Co. Ltd) instead of 3-amino-5-fluoro-benzonitrile and 3-(5-fluoro-2-pyridyl)-6-methyl-4,5,6,7-tetrahydropyrazolo[1,5-a]pyrazine (compound 94b) instead of 3-(4-fluorophenyl)-4,5,6,7-tetrahydropyrazolo[1,5-a]pyrazine (compound 11b). Example 159 was obtained as a white solid (5 mg). LCMS (M+H$^+$): 418. $^1$H NMR (400 MHz, CD$_3$OD) δ ppm 8.51 (d, J=3.0 Hz, 1H), 8.07 (s, 1H), 7.75 (dd, J=4.3, 8.8 Hz, 1H), 7.61 (dt, J=2.9, 8.6 Hz, 1H), 7.10-6.97 (m, 2H), 5.48 (d, J=17.8 Hz, 1H), 5.05-4.99 (m, 1H), 4.84 (d, J=18.1 Hz, 1H), 4.38 (dd, J=4.4, 12.9 Hz, 1H), 4.23 (d, J=13.3 Hz, 1H), 3.90 (s, 3H), 1.30 (d, J=7.0 Hz, 3H).

Example 160

N-(3-cyclopropyl-4,5-difluoro-phenyl)-3-(5-fluoro-2-pyridyl)-6-methyl-6,7-dihydro-4H-pyrazolo[1,5-a]pyrazine-5-carboxamide

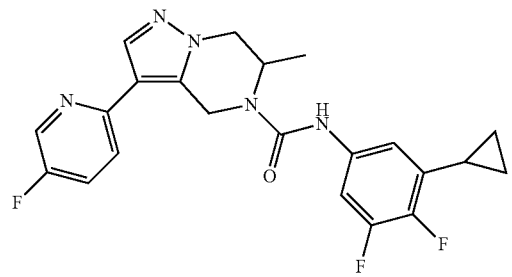 [SMILES: CC1Cn2ncc(-c3ccc(F)cn3)c2CN1C(=O)Nc1cc(F)c(F)c(C2CC2)c1]

Preparation of Example 160

The title compound was prepared in analogy to the preparation of Example 106 by using 3-cyclopropyl-4,5-difluoro-aniline (catalog number: AQ14078, Shanghai AQBioPharma Co. Ltd) instead of 3-amino-5-fluoro-benzonitrile and 3-(5-fluoro-2-pyridyl)-6-methyl-4,5,6,7-tetrahydropyrazolo[1,5-a]pyrazine (compound 94b) instead of 3-(4-fluorophenyl)-4,5,6,7-tetrahydropyrazolo[1,5-a]pyrazine (compound 11b). Example 160 was obtained as a white solid (8 mg). LCMS (M+H$^+$): 428. $^1$H NMR (400 MHz, CD$_3$OD) δ ppm 8.50 (d, J=3.0 Hz, 1H), 8.06 (s, 1H), 7.75 (dd, J=4.1, 8.9 Hz, 1H), 7.61 (dt, J=3.0, 8.7 Hz, 1H), 7.27-7.23 (m, 1H), 6.83-6.72 (m, 1H), 5.46 (d, J=18.1 Hz, 1H), 5.04-4.96 (m, 1H), 4.82 (d, J=17.8 Hz, 2H), 4.37 (dd, J=4.5, 12.8 Hz, 1H), 4.22 (d, J=13.1 Hz, 1H), 2.18-2.07 (m, 1H), 1.28 (d, J=6.8 Hz, 3H), 1.12-0.97 (m, 2H), 0.84-0.69 (m, 2H).

Example 161

N-(6-chloro-5-fluoro-2-pyridyl)-3-(2,4-difluorophenyl)-6-methyl-6,7-dihydro-4H-pyrazolo[1,5-a]pyrazine-5-carboxamide

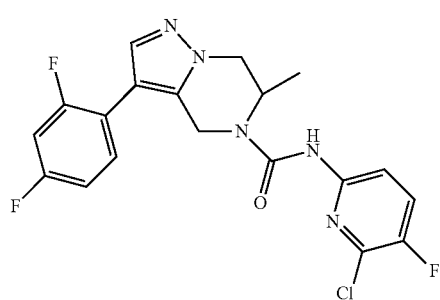 [SMILES: CC1Cn2ncc(-c3ccc(F)cc3F)c2CN1C(=O)Nc1ccc(F)c(Cl)n1]

Preparation of Example 161

The title compound was prepared in analogy to the preparation of Example 140 by using 3-(2,4-difluorophenyl)-6-methyl-4,5,6,7-tetrahydropyrazolo[1,5-a]pyrazine (compound 85b) instead of 3-(4-fluorophenyl)-4,5,6,7-tetrahydropyrazolo[1,5-a]pyrazine (compound 11b). Example 161 was afforded as a white solid (5 mg). LCMS (M+H+): 422. ¹H NMR (400 MHz, CD₃OD) δ ppm 7.83 (dd, J=3.0, 8.8 Hz, 1H), 7.75 (d, J=1.8 Hz, 1H), 7.66 (dd, J=7.8, 8.8 Hz, 1H), 7.57-7.47 (m, 1H), 7.17-7.03 (m, 2H), 5.15 (d, J=16.8 Hz, 1H), 5.05-4.99 (m, 1H), 4.61 (d, J=16.8 Hz, 1H), 4.39 (dd, J=4.3, 12.8 Hz, 1H), 4.24 (d, J=12.8 Hz, 1H), 1.30 (d, J=7.0 Hz, 3H).

Example 162

N-(3-chloro-4-fluoro-phenyl)-1-cyclopentyl-6,8-dihydro-5H-imidazo[1,5-a]pyrazine-7-carboxamide The title compound was prepared according to the following scheme:

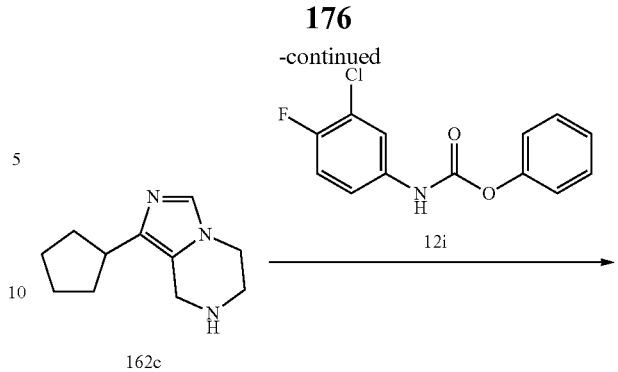

Preparation of 1-cyclopentyl-5,6,7,8-tetrahydroimidazo[1,5-a]pyrazine (compound 162c)

The compound 162c was prepared in analogy to compound 26c by using tert-butyl 1-iodo-6,8-dihydro-5H-imidazo[1,5-a]pyrazine-7-carboxylate (compound 9c) instead of tert-butyl 3-iodo-6,7-dihydro-4H-pyrazolo[1,5-a]pyrazine-5-carboxylate (compound 1e). Compound 162c was obtained as a slight yellow solid (40 mg). LCMS (M+H+): 192.

Preparation of N-(3-chloro-4-fluoro-phenyl)-1-cyclopentyl-6,8-dihydro-5H-imidazo[1,5-a]pyrazine-7-carboxamide (Example 162)

The title compound was prepared in analogy to the preparation of Example 140 by using phenyl N-(3-chloro-4-fluoro-phenyl)carbamate (compound 12i) instead of phenyl N-(6-chloro-5-fluoro-2-pyridyl)carbamate (compound 140d) and 1-cyclopentyl-5,6,7,8-tetrahydroimidazo[1,5-a]pyrazine (compound 162c) instead of 3-(4-fluorophenyl)-4,5,6,7-tetrahydropyrazolo[1,5-a]pyrazine (compound 11b). Example 162 was obtained as a white solid (37 mg). LCMS (M+H+): 363. ¹H NMR (400 MHz, CD₃OD) δ ppm 7.70 (s, 1H), 7.63 (dd, J=2.5, 6.5 Hz, 1H), 7.39-7.29 (m, 1H), 7.17 (t, J=8.9 Hz, 1H), 4.77 (s, 2H), 4.18 (t, J=5.3 Hz, 2H), 3.92 (t, J=5.4 Hz, 2H), 3.07-2.92 (m, 1H), 2.06-1.92 (m, 2H), 1.90-1.78 (m, 2H), 1.77-1.64 (m, 4H).

Example 163

1-cyclopentyl-N-(3,4,5-trifluorophenyl)-6,8-dihydro-5H-imidazo[1,5-a]pyrazine-7-carboxamide

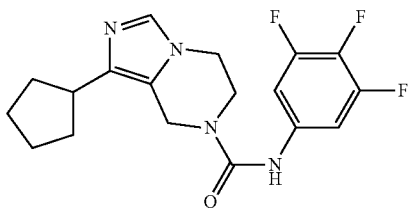 [SMILES: O=C(Nc1cc(F)c(F)c(F)c1)N1CCn2cnc(C3CCCC3)c2C1]

Preparation of Example 163

The title compound was prepared in analogy to the preparation of Example 106 by using 3,4,5-trifluoroaniline instead of 3-amino-5-fluoro-benzonitrile and 1-cyclopentyl-5,6,7,8-tetrahydroimidazo[1,5-a]pyrazine (compound 162c) instead of 3-(4-fluorophenyl)-4,5,6,7-tetrahydropyrazolo[1,5-a]pyrazine (compound 11b). Example 163 was obtained as a white solid (6 mg). LCMS (M+H$^+$): 365. $^1$H NMR (400 MHz, chloroform-d) δ ppm 8.31 (br. s, 1H), 7.90 (br. s, 1H), 7.35-7.28 (m, 2H), 4.74 (s, 2H), 4.33 (t, J=5.0 Hz, 2H), 4.03 (t, J=5.0 Hz, 2H), 3.03-2.95 (m, 1H), 2.09-1.96 (m, 2H), 1.90-1.58 (m, 6H).

Example 164

1-cyclopentyl-N-(3,4-difluoro-5-methyl-phenyl)-6,8-dihydro-5H-imidazo[1,5-a]pyrazine-7-carboxamide

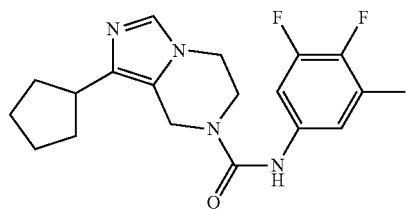 [SMILES: Cc1cc(NC(=O)N2CCn3cnc(C4CCCC4)c3C2)cc(F)c1F]

Preparation of Example 164

The title compound was prepared in analogy to the preparation of Example 106 by using 3,4-difluoro-5-methyl-aniline (CAS: 1505944-46-6, catalog number: AQ14079, Shanghai AQBioPharma Co. Ltd) instead of 3-amino-5-fluoro-benzonitrile and 1-cyclopentyl-5,6,7,8-tetrahydroimidazo[1,5-a]pyrazine (compound 162c) instead of 3-(4-fluorophenyl)-4,5,6,7-tetrahydropyrazolo[1,5-a]pyrazine (compound 11b). Example 164 was obtained as a white solid (9 mg). LCMS (M+H$^+$): 361. $^1$H NMR (400 MHz, chloroform-d) δ ppm 8.69 (br. s, 1H), 7.92 (br. s, 1H), 7.37-7.30 (m, 1H), 7.11 (d, J=5.5 Hz, 1H), 4.72 (s, 2H), 4.42 (br. s, 2H), 4.04 (br. s, 2H), 3.06-2.93 (m, 1H), 2.05 (d, J=8.9 Hz, 2H), 1.84 (d, J=6.1 Hz, 2H), 1.77-1.60 (m, 5H).

Example 165

N-(3-cyclopropyl-4,5-difluoro-phenyl)-1-(2,4-difluorophenyl)-6,8-dihydro-5H-imidazo[1,5-a]pyrazine-7-carboxamide

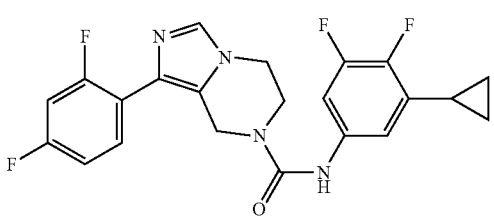 [SMILES: O=C(Nc1cc(F)c(F)c(C2CC2)c1)N1CCn2cnc(-c3ccc(F)cc3F)c2C1]

Preparation of Example 165

The title compound was prepared in analogy to the preparation of Example 106 by using 3-cyclopropyl-4,5-difluoro-aniline (catalog number: AQ14078, Shanghai AQBioPharma Co. Ltd) instead of 3-amino-5-fluoro-benzonitrile and 1-(2,4-difluorophenyl)-5,6,7,8-tetrahydroimidazo[1,5-a]pyrazine (compound 134b) instead of 3-(4-fluorophenyl)-4,5,6,7-tetrahydropyrazolo[1,5-a]pyrazine (compound 11b). Example 165 was obtained as a white solid (15 mg). LCMS (M+H$^+$): 431. $^1$H NMR (400 MHz, chloroform-d) δ ppm 8.22 (br. s, 1H), 7.68 (br. s, 1H), 7.22-7.05 (m, 2H), 7.04-6.84 (m, 2H), 6.67 (br. s, 1H), 4.74 (br. s, 2H), 4.35 (br. s, 2H), 4.03 (br. s, 2H), 2.11-2.03 (m, 1H), 0.99 (d, J=8.3 Hz, 2H), 0.70 (d, J=5.3 Hz, 2H).

Example 166

N-(3,4-difluoro-5-methoxy-phenyl)-1-(2,4-difluorophenyl)-6,8-dihydro-5H-imidazo[1,5-a]pyrazine-7-carboxamide

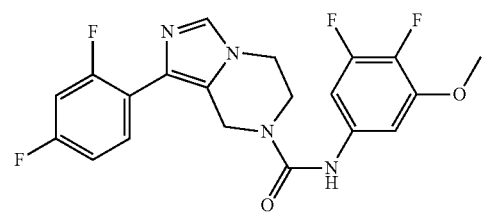 [SMILES: COc1cc(NC(=O)N2CCn3cnc(-c4ccc(F)cc4F)c3C2)cc(F)c1F]

Preparation of Example 166

The title compound was prepared in analogy to the preparation of Example 106 by using 3,4-difluoro-5-methoxyl-aniline (CAS: 1195190-12-5, catalog number: AQ12805, Shanghai AQBioPharma Co. Ltd) instead of 3-amino-5-fluoro-benzonitrile and 1-(2,4-difluorophenyl)-5,6,7,8-tetrahydroimidazo[1,5-a]pyrazine (compound 134b) instead of 3-(4-fluorophenyl)-4,5,6,7-tetrahydropyrazolo[1,5-a]pyrazine (compound 11b). Example 166 was obtained as a white solid (12 mg). LCMS (M+H$^+$): 421. $^1$H NMR (400 MHz, chloroform-d & CD$_3$OD) δ ppm 7.89 (s, 1H), 7.37 (dt, J=6.5, 8.5 Hz, 1H), 6.87-6.64 (m, 4H), 4.59 (s, 2H), 4.10 (t, J=5.3 Hz, 2H), 3.78 (t, J=5.3 Hz, 2H), 3.65 (s, 3H).

Example 167

N-(3,4-difluoro-5-methyl-phenyl)-1-(2,4-difluoro-phenyl)-6,8-dihydro-5H-imidazo[1,5-a]pyrazine-7-carboxamide

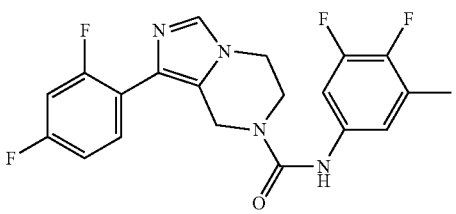 [SMILES: Cc1cc(NC(=O)N2CCn3cnc(-c4ccc(F)cc4F)c3C2)cc(F)c1F]

Preparation of Example 167

The title compound was prepared in analogy to the preparation of Example 106 by using 3,4-difluoro-5-methyl-aniline (CAS: 1505944-46-6, catalog number: AQ14079, Shanghai AQBioPharma Co. Ltd) instead of 3-amino-5-fluoro-benzonitrile and 1-(2,4-difluorophenyl)-5,6,7,8-tetrahydroimidazo[1,5-a]pyrazine (compound 134b) instead of 3-(4-fluorophenyl)-4,5,6,7-tetrahydropyrazolo[1,5-a]pyrazine (compound 11b). Example 167 was obtained ed as a white solid (11 mg). LCMS (M+H$^+$): 405. $^1$H NMR (400 MHz, chloroform-d) δ ppm 8.07 (br. s, 1H), 7.69 (br. s, 1H), 7.20 (t, J=7.0 Hz, 1H), 7.07-6.83 (m, 4H), 4.74 (br. s, 2H), 4.30 (br. s, 2H), 4.02 (br. s, 2H), 2.25 (s, 3H).

Example 168

N-(3-chloro-4-fluoro-phenyl)-3-(2-methylpyrrolidin-1-yl)-6,7-dihydro-4H-pyrazolo[1,5-a]pyrazine-5-carboxamide

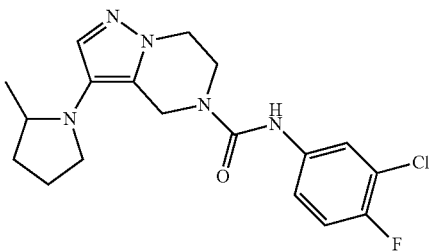 [SMILES: CC1CCCN1c1cnn2c1CN(C(=O)Nc1ccc(F)c(Cl)c1)CC2]

The title compound was prepared according to the following scheme:

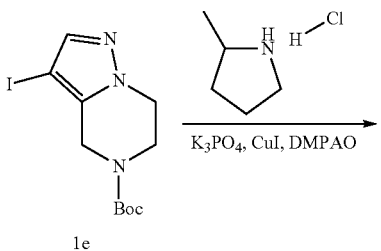

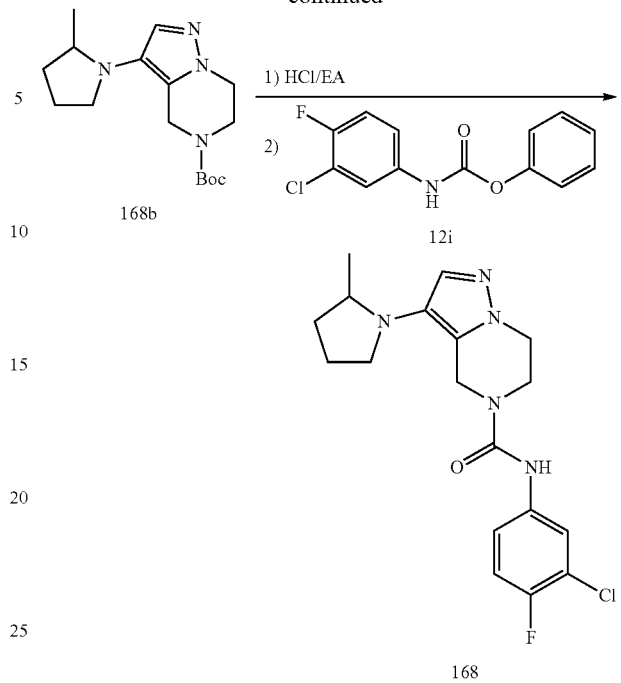

Step 1: Preparation of tert-butyl 3-(2-methylpyrrolidin-1-yl)-6,7-dihydro-4H-pyrazolo[1,5-a]pyrazine-5-carboxylate (compound 168b)

To a mixture of 3-iodo-6,7-dihydro-4H-pyrazolo[1,5-a]pyrazine-5-carboxylate (compound 1e, 45 mg 0.13 mmol), K$_3$PO$_4$ (54 mg, 0.25 mmol), CuI (4.8 mg 25 μmol) and 2-(2,6-dimethylanilino)-2-oxo-acetic acid (DMPAO, 4.9 mg, 25 μmol) in DMSO (5.0 mL) was added 2-methylpyrrolidine hydrochloride (22 mg, 25 μmol). The reaction mixture was flushed with nitrogen and sealed. Then the reaction mixture was stirred at 100° C. in microwave for 2 hours. To the reaction mixture was added K$_2$CO$_3$ (35 mg, 0.25 mmol), and CuI (4.8 mg, 25 μmol). The reaction mixture was subjected to microwave at 120° C. for another 2 hours. The reaction mixture was diluted with ethyl acetate, washed with water. The organic layer was separated and concentrated. The residue was purified by column chromatography (eluting with 60%~70% EtOAc in petroleum ether) to give compound 168b (12 mg). LCMS (M+H$^+$): 307.

Step 2: Preparation of N-(3-chloro-4-fluoro-phenyl)-3-(2-methylpyrrolidin-1-yl)-6,7-dihydro-4H-pyrazolo[1,5-a]pyrazine-5-carboxamide (Example 168)

A solution of tert-butyl 3-(2-methylpyrrolidin-1-yl)-6,7-dihydro-4H-pyrazolo[1,5-a]pyrazine-5-carboxylate (compound 168b, 31 mg, 0.1 mmol) in HCl/EA (1N, 5.0 mL) was stirred at room temperature overnight. Petroleum ether (45 mL) was added. The reaction mixture was centrifuged, and a yellowish solid was collected. The solid was dissolved in DCM (3.0 mL), to which was added DIPEA (0.1 mL) and phenyl N-(3-chloro-4-fluoro-phenyl)carbamate (32 mg, 0.3 mmol). The reaction mixture was stirred at 40° C. for 3 hours, and then concentrated in vacuo to give crude product, which was purified by preparative HPLC to afford Example 168 (10 mg). LCMS (M+H$^+$): 378. $^1$H NMR (400 MHz, chloroform-d) δ ppm 7.65 (dd, J=2.5, 6.5 Hz, 1H), 7.38 (s, 1H), 7.30 (br. s, 1H), 7.18-7.02 (m, 2H), 5.00-4.83 (m, 2H), 4.29-4.19 (m, 2H), 4.19-4.07 (m, 1H), 4.00-3.91 (m, 1H), 3.64-3.52 (m, 1H), 3.45-3.36 (m, 1H), 3.10-2.98 (m, 1H), 2.24-2.20 (m, 1H), 2.14-2.06 (m, 1H), 2.03-1.94 (m, 1H), 1.82-1.70 (m, 1H), 1.23 (d, J=6.0 Hz, 3H).

Example 169

N-(3-chloro-4-fluoro-phenyl)-3-morpholino-6,7-dihydro-4H-pyrazolo[1,5-a]pyrazine-5-carboxamide The title compound was prepared according to the following scheme:

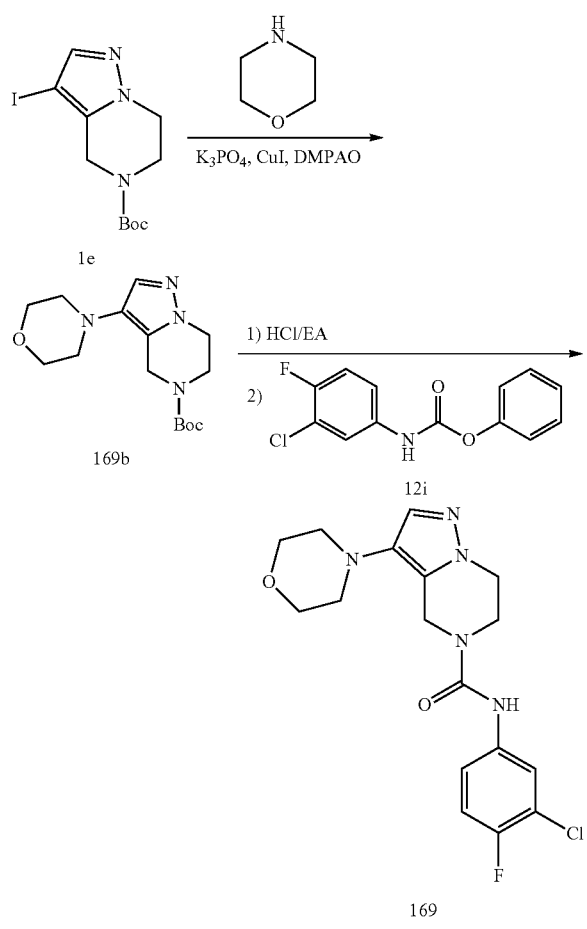

Preparation of N-(3-chloro-4-fluoro-phenyl)-3-(2-methylpyrrolidin-1-yl)-6,7-dihydro-4H-pyrazolo[1,5-a]pyrazine-5-carboxamide (Example 169)

The title compound was prepared in analogy to Example 168 by using morpholine instead of 2-methylpyrrolidine hydrochloride. Example 169 was obtained as a slight yellow solid (15 mg). LCMS (M+H$^+$): 380. $^1$H NMR (400 MHz, chloroform-d) δ ppm 7.59 (dd, J=2.4, 6.4 Hz, 1H), 7.41 (s, 1H), 7.28-7.24 (m, 1H), 7.13-7.05 (m, 1H), 6.93 (br. s, 1H), 4.80 (s, 2H), 4.31-4.21 (m, 2H), 4.02 (d, J=5.0 Hz, 2H), 3.96-3.89 (m, 4H), 3.08-2.97 (m, 4H).

Example 170

N-(3-chloro-4-fluoro-phenyl)-3-(2-oxopyrrolidin-1-yl)-6,7-dihydro-4H-pyrazolo[1,5-a]pyrazine-5-carboxamide The title compound was prepared according to the following scheme:

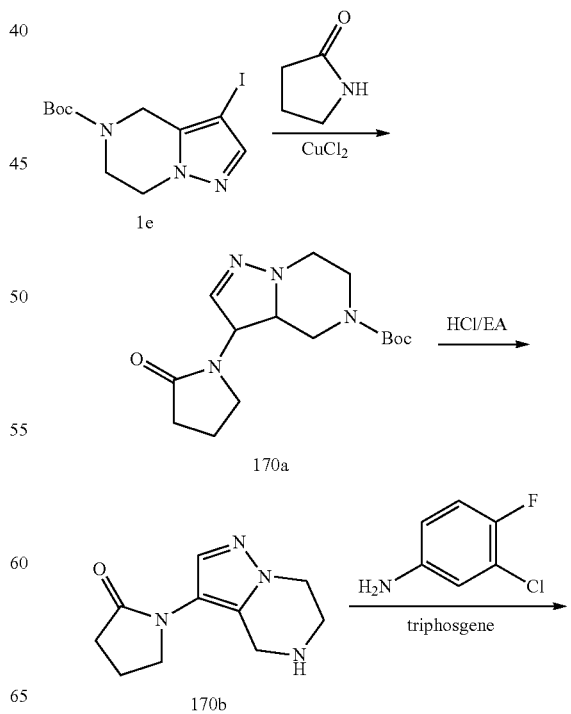

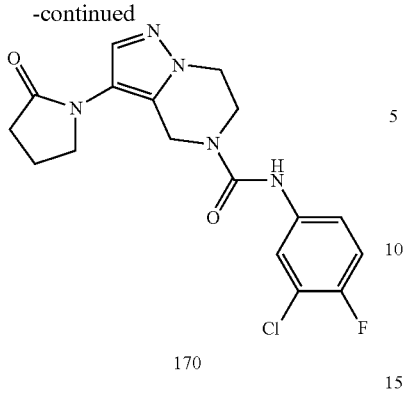

170

Step 1: Preparation of tert-butyl 3-(2-oxopyrrolidin-1-yl)-6,7-dihydro-4H-pyrazolo[1,5-a]pyrazine-5-carboxylate (compound 170a)

An oven-dried resealable Schlenk tube was charged with CuCl$_2$ (13.5 mg, 0.1 mmol), K$_3$PO$_4$ (424.5 mg, 2.0 mmol), tert-butyl 3-iodo-6,7-dihydro-4H-pyrazolo[1,5-a]pyrazine-5-carboxylate (compound 1e, 350 mg, 1 mmol), pyrrolidin-2-one (102 mg, 1.2 mmol), (1R,2R)-N1,N2-dimethylcyclohexane-1,2-diamine (14.2 mg, 0.1 mmol) and dioxane (2 mL). The tube was flushed with N$_2$ and sealed. The reaction mixture was stirred at 110° C. for 23 hours. The reaction mixture was concentrated and the residue was purified by prep-TLC to afford compound 170a (80.0 mg) as white solid.

Step 2: Preparation of 1-(4,5,6,7-tetrahydropyrazolo[1,5-a]pyrazin-3-yl)pyrrolidin-2-one (compound 170b)

A solution of tert-butyl 3-(2-oxopyrrolidin-1-yl)-6,7-dihydro-4H-pyrazolo[1,5-a]pyrazine-5-carboxylate (compound 170a, 40.0 mg) in HCl/EtOAc (5 mL) was stirred at room temperature for 2 hours. Then the reaction mixture was concentrated in vacuo to afford compound 170b (30 mg) in HCl salt as a white solid.

Step 3: Preparation of N-(3-chloro-4-fluoro-phenyl)-3-(2-oxopyrrolidin-1-yl)-6,7-dihydro-4H-pyrazolo[1,5-a]pyrazine-5-carboxamide (Example 170)

To a mixture of 3-chloro-4-fluoro-aniline (27 mg) and DIPEA (0.1 mL) in DCM (3 mL) was added triphosgene (25 mg). After stirring for 30 min at room temperature, 1-(4,5,6,7-tetrahydropyrazolo[1,5-a]pyrazin-3-yl)pyrrolidin-2-one (compound 170b, 30 mg) was added. The resulting mixture was stirred at room temperature for 1 hour, then concentrated. The residue was purified by prep-HPLC to afford Example 170 (13 mg) as a white solid. LCMS (M+H$^+$): 378. $^1$H NMR (400 MHz, DMSO-d$_6$) δ ppm 9.02 (s, 1H), 7.73 (dd, J=2.6, 6.8 Hz, 1H), 7.57 (s, 1H), 7.45-7.39 (m, 1H), 7.35-7.29 (m, 1H), 4.68 (s, 2H), 4.17-4.14 (m, 2H), 3.97-3.93 (m, 2H), 3.73 (t, J=7.1 Hz, 2H), 2.44-2.38 (m, 2H), 2.10 (t, J=7.6 Hz, 2H).

Example 171

N-(3-chloro-4-fluoro-phenyl)-3-(4-methylpyrazol-1-yl)-6,7-dihydro-4H-pyrazolo[1,5-a]pyrazine-5-carboxamide

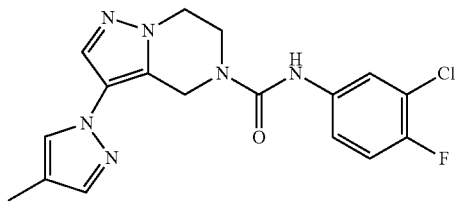 [SMILES: Cc1cnn(-c2cnn3c2CN(C(=O)Nc2ccc(F)c(Cl)c2)CC3)c1]

The title compound was prepared according to the following scheme:

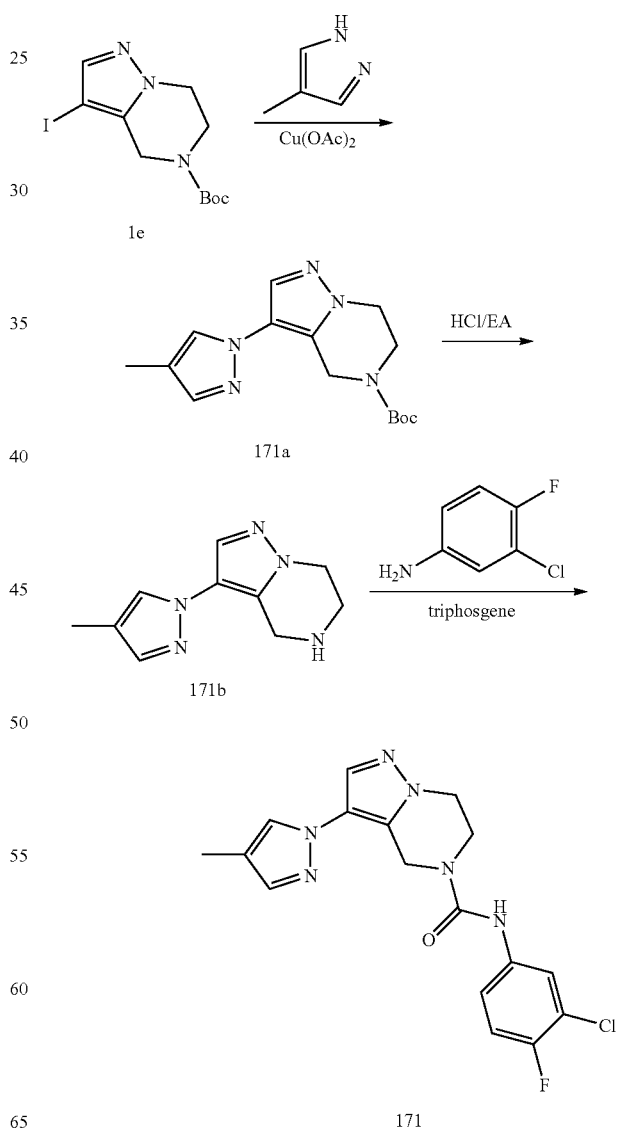

Step 1: Preparation of tert-butyl 3-(4-methylpyrazol-1-yl)-6,7-dihydro-4H-pyrazolo[1,5-a]pyrazine-5-carboxylate (compound 171a)

To a mixture of tert-butyl 3-iodo-6,7-dihydro-4H-pyrazolo[1,5-a]pyrazine-5-carboxylate (compound 1e, 349 mg, 1.0 mmol), Cu(AcO)$_2$ (18 mg, 0.1 mmol) and Cs$_2$CO$_3$ (651 mg, 2.0 mmol) in DMF (2.0 mL) was added 4-methyl-1H-pyrazole (102 mg, 1.5 mmol), and the reaction mixture was stirred at 110° C. for 18 hours. The reaction mixture was filtered and the filtrate was purified by prep-HPLC to afford compound 171a (50 mg).

Step 2: Preparation of 3-(4-methylpyrazol-1-yl)-6,7-dihydro-4H-pyrazolo[1,5-a]pyrazine (compound 171b)

A mixture of tert-butyl 3-(4-methylpyrazol-1-yl)-6,7-dihydro-4H-pyrazolo[1,5-a]pyrazine-5-carboxylate (compound 171a, 40 mg, 0.1 mmol) in HCl/EA (1N, 5.0 mL) was stirred at room temperature for 2 hours. The reaction mixture was concentrated to afford compound 171b (40 mg).

Step 3: Preparation of N-(3-chloro-4-fluoro-phenyl)-3-(4-methylpyrazol-1-yl)-6,7-dihydro-4H-pyrazolo[1,5-a]pyrazine-5-carboxamide (Example 171)

To a mixture of 3-chloro-4-fluoro-aniline (29 mg, 0.2 mmol) and DIPEA (65 mg, 0.5 mmol) in DCM (3.0 mL) was added triphosgene (30 mg, 0.1 mmol) at 0° C. The reaction mixture was stirred at 0° C. for 30 mins, then 3-(4-methylpyrazol-1-yl)-6,7-dihydro-4H-pyrazolo[1,5-a]pyrazine (compound 171b, 40 mg) was added. The reaction mixture was stirred at room temperature for 1 hour. The reaction mixture was concentrated and the residue was purified by prep-HPLC to afford Example 171 (20.0 mg) as white solid. LCMS (M+1): 375. $^1$H NMR (400 MHz, DMSO-d6) δ ppm 9.08 (s, 1H), 7.93 (s, 1H), 7.83 (s, 1H), 7.74-7.71 (m, 1H), 7.51 (s, 1H), 7.40 (dd, J=2.6, 4.3 Hz, 1H), 7.35-7.29 (m, 1H), 4.91 (s, 2H), 4.21 (t, J=5.2 Hz, 2H), 3.98 (t, J=5.3 Hz, 2H), 2.09 (s, 3H).

Example 172

N-benzyl-3-(4-fluorophenyl)-6-methyl-6,7-dihydro-4H-pyrazolo[1,5-a]pyrazine-5-carboxamide

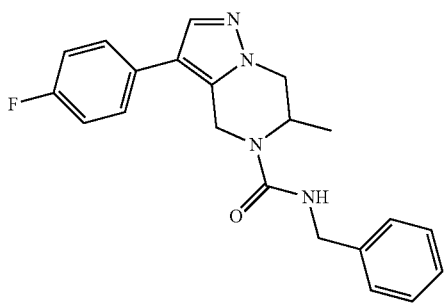 [SMILES: CC1Cn2ncc(-c3ccc(F)cc3)c2CN1C(=O)NCc1ccccc1]

Preparation of Example 172

The title compound was prepared in analogy to the preparation of Example 11 by using benzyl amine instead of 3-trifluoromethylaniline, and 3-(4-fluorophenyl)-6-methyl-4,5,6,7-tetrahydropyrazolo[1,5-a]pyrazine (compound 53f) instead of 3-(4-fluorophenyl)-4,5,6,7-tetrahydropyrazolo[1,5-a]pyrazine (compound 11b). Example 172 was obtained as a white solid (18 mg). LCMS (M+H$^+$): 365. $^1$H NMR (400 MHz, DMSO-d$_6$) δ ppm 7.85 (s, 1H), 7.54 (dd, J=5.3, 8.8 Hz, 2H), 7.44 (s, 1H), 7.34-7.21 (m, 7H), 5.08 (d, J=16.7 Hz, 1H), 4.84 (d, J=5.1 Hz, 1H), 4.51 (d, J=16.7 Hz, 1H), 4.32 (t, J=6.6 Hz, 2H), 4.23-4.17 (m, 1H), 4.15-4.09 (m, 1H), 1.11 (d, J=6.9 Hz, 3H).

Example 173

3-(4-fluorophenyl)-N-(2-fluoro-4-pyridyl)-6-methyl-6,7-dihydro-4H-pyrazolo[1,5-a]pyrazine-5-carboxamide

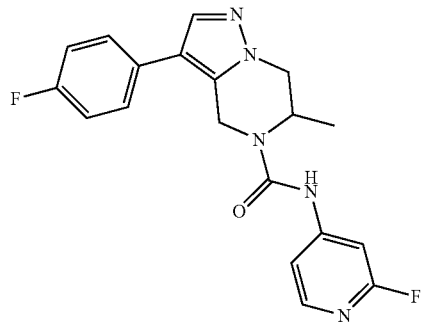 [SMILES: CC1Cn2ncc(-c3ccc(F)cc3)c2CN1C(=O)Nc1ccnc(F)c1]

Preparation of Example 173

The title compound was prepared in analogy to the preparation of Example 60 by using 2-fluoropyridin-4-amine instead of 5-fluoro-6-methyl-pyridin-2-amine and 3-(4-fluorophenyl)-6-methyl-4,5,6,7-tetrahydropyrazolo[1,5-a]pyrazine (compound 53f) instead of 3-(2,4-difluorophenyl)-4,5,6,7-tetrahydropyrazolo[1,5-a]pyrazine (compound 60b). Example 173 was obtained as a white solid (24 mg). LCMS (M+H$^+$): 370. $^1$H NMR (400 MHz, DMSO-d$_6$) δ ppm 9.50 (s, 1H), 8.03 (d, J=5.8 Hz, 1H), 7.87 (s, 1H), 7.55 (dd, J=5.5, 8.8 Hz, 2H), 7.37 (d, J=5.6 Hz, 1H), 7.32-7.24 (m, 3H), 5.23 (d, J=16.4 Hz, 1H), 4.94 (br. s, 1H), 4.70 (d, J=16.7 Hz, 1H), 4.32-4.25 (m, 1H), 4.23-4.16 (m, 1H), 1.20 (d, J=6.8 Hz, 3H).

Example 174

3-(2,4-difluorophenyl)-N-(2-fluoro-4-pyridyl)-6-methyl-6,7-dihydro-4H-pyrazolo[1,5-a]pyrazine-5-carboxamide

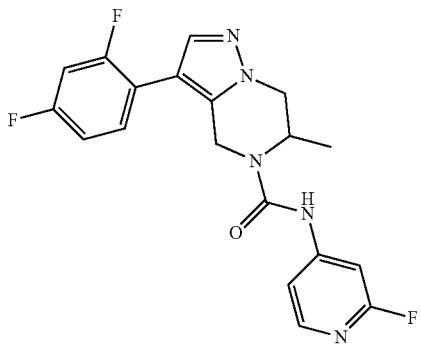 [SMILES: CC1Cn2ncc(-c3ccc(F)cc3F)c2CN1C(=O)Nc1ccnc(F)c1]

Preparation of Example 174

The title compound was prepared in analogy to the preparation of Example 60 by using 2-fluoropyridin-4-amine instead of 5-fluoro-6-methyl-pyridin-2-amine and 3-(2,4-difluorophenyl)-6-methyl-4,5,6,7-tetrahydropyrazolo[1,5-a]pyrazine (compound 85b) instead of 3-(2,4-difluorophenyl)-4,5,6,7-tetrahydropyrazolo[1,5-a]pyrazine (compound 60b). Example 174 was obtained as a white solid (3 mg). LCMS (M+H$^+$): 388. $^1$H NMR (400 MHz, DMSO-d$_6$) δ ppm 9.42 (s, 1H), 8.01 (d, J=6.0 Hz, 1H), 7.74 (s, 1H), 7.56 (s, 1H), 7.37 (d, J=10.2 Hz, 2H), 7.28 (s, 1H), 7.21 (d, J=7.8 Hz, 1H), 5.10 (d, J=17.2 Hz, 1H), 4.94 (s, 1H), 4.56 (d, J=16.4 Hz, 1H), 4.31-4.23 (m, 1H), 4.04 (s, 1H), 1.21 (d, J=7.0 Hz, 3H).

Example 175

N-(1,3-benzoxazol-6-yl)-3-(4-fluorophenyl)-6,7-dihydro-4H-pyrazolo[1,5-a]pyrazine-5-carboxamide

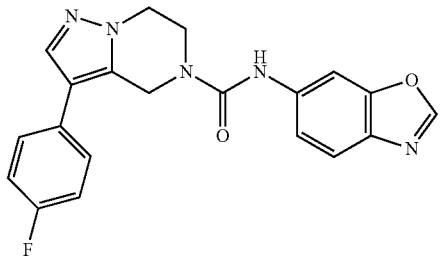 [SMILES: O=C(Nc1ccc2ncoc2c1)N1CCn2ncc(-c3ccc(F)cc3)c2C1]

Preparation of Example 175

The title compound was prepared in analogy to the preparation of Example 60 by using 1,3-benzoxazol-6-amine instead of 5-fluoro-6-methyl-pyridin-2-amine and 3-(4-fluorophenyl)-4,5,6,7-tetrahydropyrazolo[1,5-a]pyrazine (compound 11b) instead of 3-(2,4-difluorophenyl)-4,5,6,7-tetrahydropyrazolo[1,5-a]pyrazine (compound 60b). Example 175 was obtained as a white solid (11 mg). LCMS (M+H$^+$): 378. $^1$H NMR (400 MHz, DMSO-d$_6$) δ ppm 9.14 (s, 1H), 8.61 (s, 1H), 7.98 (d, J=1.6 Hz, 1H), 7.84 (s, 1H), 7.67 (d, J=8.5 Hz, 1H), 7.51 (dd, 5.4 Hz, 2H), 7.40 (dd, J=8.7, 1.9 Hz, 1H), 7.28 (t, J=8.8 Hz, 2H), 4.96 (s, 2H), 4.24 (t, J=5.2 Hz, 2H), 4.03 (t, J=5.1 Hz, 2H).

Example 176

3-(4-fluorophenyl)-N-(2-methyl-4-pyridyl)-6,7-dihydro-4H-pyrazolo[1,5-a]pyrazine-5-carboxamide

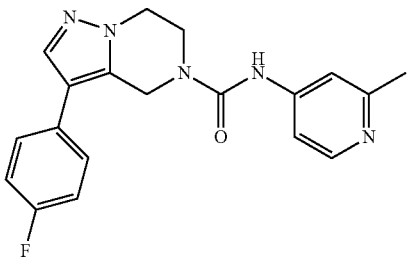 [SMILES: Cc1cc(NC(=O)N2CCn3ncc(-c4ccc(F)cc4)c3C2)ccn1]

Preparation of Example 176

The title compound was prepared in analogy to the preparation of Example 60 by using 2-methylpyridin-4-amine instead of 5-fluoro-6-methyl-pyridin-2-amine and 3-(4-fluorophenyl)-4,5,6,7-tetrahydropyrazolo[1,5-a]pyrazine (compound 11b) instead of 3-(2,4-difluorophenyl)-4,5,6,7-tetrahydropyrazolo[1,5-a]pyrazine (compound 60b). Example 176 was obtained as a white solid (5 mg). LCMS (M+H$^+$): 352. $^1$H NMR (400 MHz, DMSO-d$_6$) δ ppm 8.22-8.18 (m, 2H), 7.83 (s, 1H), 7.54-7.45 (m, 2H), 7.37-7.23 (m, 4H), 4.94 (s, 2H), 4.27-4.18 (m, 2H), 4.01 (t, J=5.4 Hz, 2H), 2.37 (s, 3H).

Example 177

N-(2,6-difluoro-4-pyridyl)-3-(4-fluorophenyl)-6,7-dihydro-4H-pyrazolo[1,5-a]pyrazine-5-carboxamide

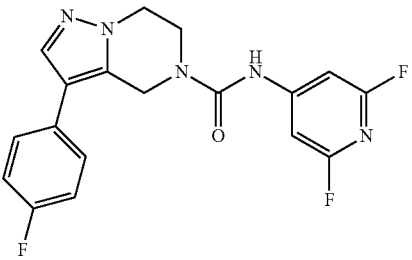 [SMILES: O=C(Nc1cc(F)nc(F)c1)N1CCn2ncc(-c3ccc(F)cc3)c2C1]

Preparation of Example 177

The title compound was prepared in analogy to the preparation of Example 60 by using 2,6-difluoropyridin-4-amine instead of 5-fluoro-6-methyl-pyridin-2-amine and 3-(4-fluorophenyl)-4,5,6,7-tetrahydropyrazolo[1,5-a]pyrazine (compound 11b) instead of 3-(2,4-difluorophenyl)-4,5,6,7-tetrahydropyrazolo[1,5-a]pyrazine (compound 60b). Example 177 was obtained as a white solid (14 mg). LCMS (M+H⁺): 374. ¹H NMR (400 MHz, DMSO-d₆) δ ppm 9.92 (br. s, 1H), 7.84 (s, 1H), 7.49 (dd, J=5.5, 8.7 Hz, 2H), 7.28 (t, J=8.8 Hz, 2H), 7.16 (s, 2H), 4.97 (s, 2H), 4.25 (t, J=5.3 Hz, 2H), 4.03 (t, J=5.3 Hz, 2H).

Example 178

3-(2,4-difluorophenyl)-6-methyl-N-(3,4,5-trifluorophenyl)-6,7-dihydro-4H-pyrazolo[1,5-a]pyrazine-5-carboxamide

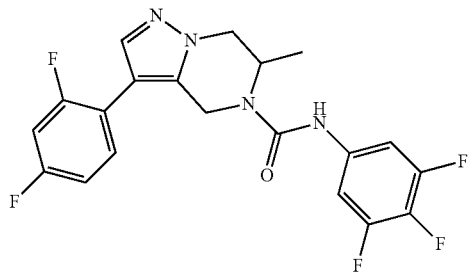 [SMILES: CC1Cn2ncc(-c3ccc(F)cc3F)c2CN1C(=O)Nc1cc(F)c(F)c(F)c1]

Preparation of Example 178

The title compound was prepared in analogy to the preparation of Example 11 by using 3,4,5-trifluoroaniline instead of 3-(trifluoromethyl)aniline and 3-(2,4-difluorophenyl)-6-methyl-4,5,6,7-tetrahydropyrazolo[1,5-a]pyrazine (compound 85b) instead of 3-(4-fluorophenyl)-4,5,6,7-tetrahydropyrazolo[1,5-a]pyrazine (compound 11b). Example 178 was obtained as a white solid (5 mg). LCMS (M+H⁺): 423. ¹H NMR (400 MHz, DMSO-d₆) δ ppm 9.06 (s, 1H), 7.72 (d, J=1.9 Hz, 1H), 7.60-7.52 (m, 1H), 7.45-7.33 (m, 3H), 7.19 (dt, J=2.1, 8.5 Hz, 1H), 5.06 (d, J=16.8 Hz, 1H), 4.95-4.87 (m, 1H), 4.52 (d, J=16.9 Hz, 1H), 4.32-4.25 (m, 1H), 4.24-4.18 (m, 1H), 1.19 (d, J=6.8 Hz, 3H).

Example 179

3-(2,4-difluorophenyl)-N-(5-fluoro-4-methyl-2-pyridyl)-6-methyl-6,7-dihydro-4H-pyrazolo[1,5-a]pyrazine-5-carboxamide

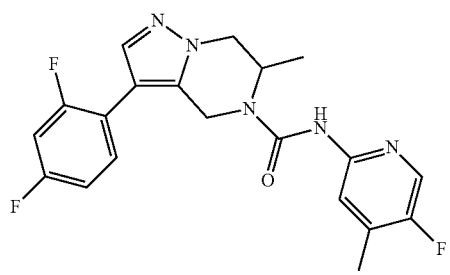 [SMILES: Cc1cc(NC(=O)N2Cc3c(-c4ccc(F)cc4F)cnn3CC2C)ncc1F]

Preparation of Example 179

The title compound was prepared in analogy to the preparation of Example 60 by using 5-fluoro-4-methylpyridin-2-amine instead of 3-(2,4-difluorophenyl)-6-methyl-4,5,6,7-tetrahydropyrazolo[1,5-a]pyrazine (compound 85b) instead of 3-(2,4-difluorophenyl)-4,5,6,7-tetrahydropyrazolo[1,5-a]pyrazine (compound 60b). Example 179 was obtained as a white solid (15 mg). LCMS (M+H⁺): 402. ¹H NMR (400 MHz, DMSO-d₆) δ ppm 9.53 (s, 1H), 8.14 (s, 1H), 7.74-7.70 (m, 2H), 7.62-7.56 (m, 1H), 7.39-7.35 (m, 1H), 7.19 (dt, J=2.2, 8.4 Hz, 1H), 5.17 (d, J=16.9 Hz, 1H), 4.98-4.94 (m, 1H), 4.51 (d, J=16.9 Hz, 1H), 4.31-4.24 (m, 1H), 4.20-4.15 (m, 1H), 2.26 (s, 3H), 1.18 (d, J=6.9 Hz, 3H).

Example 180

N-cyclopentyl-3-(2,4-difluorophenyl)-6-methyl-6,7-dihydro-4H-pyrazolo[1,5-a]pyrazine-5-carboxamide

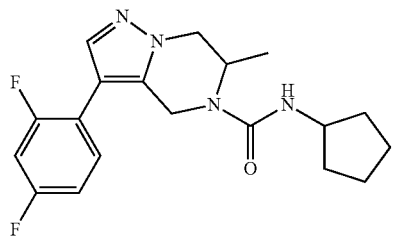 [SMILES: CC1Cn2ncc(-c3ccc(F)cc3F)c2CN1C(=O)NC1CCCC1]

Preparation of Example 180

The title compound was prepared in analogy to the preparation of Example 11 by using cyclopentanamine instead of 3-(trifluoromethyl)aniline and 3-(2,4-difluorophenyl)-6-methyl-4,5,6,7-tetrahydropyrazolo[1,5-a]pyrazine (compound 85b) instead of 3-(4-fluorophenyl)-4,5,6,7-tetrahydropyrazolo[1,5-a]pyrazine (compound 11b). Example 180 was obtained as a white solid (9 mg). LCMS (M+H⁺): 361. ¹H NMR (400 MHz, DMSO-d₆) δ ppm 7.69 (d, J=2.1 Hz, 1H), 7.53 (dt, J=6.7, 8.8 Hz, 1H), 7.39-7.35 (m, 1H), 7.18 (dt, J=2.2, 8.4 Hz, 1H), 6.55 (d, J=6.9 Hz, 1H), 4.91 (d, J=16.9 Hz, 1H), 4.84-4.76 (m, 1H), 4.29 (d, J=16.8 Hz, 1H), 4.17 (dd, J=4.3, 12.7 Hz, 1H), 4.13-4.09 (m, 1H), 3.96-3.89 (m, 1H), 1.85-1.75 (m, 2H), 1.67-1.58 (m, 2H), 1.51-1.32 (m, 4H), 1.10 (d, J=6.8 Hz, 3H).

Example 181

N-cyclohexyl-3-(2,4-difluorophenyl)-6-methyl-6,7-dihydro-4H-pyrazolo[1,5-a]pyrazine-5-carboxamide

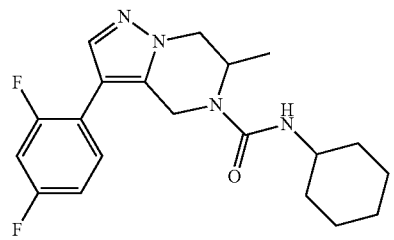 [SMILES: CC1Cn2ncc(-c3ccc(F)cc3F)c2CN1C(=O)NC1CCCCC1]

Preparation of Example 181

The title compound was prepared in analogy to the preparation of Example 11 by using cyclohexanamine instead of 3-(trifluoromethyl)aniline and 3-(2,4-difluorophenyl)-6-methyl-4,5,6,7-tetrahydropyrazolo[1,5-a]pyrazine (compound 85b) instead of 3-(4-fluorophenyl)-4,5,6,7-tetrahydropyrazolo[1,5-a]pyrazine (compound 11b). Example 181 was obtained as a white solid (2 mg). LCMS (M+H$^+$): 375. $^1$H NMR (400 MHz, DMSO-d$_6$) δ ppm 7.69 (d, J=2.3 Hz, 1H), 7.57-7.49 (m, 1H), 7.41-7.34 (m, 1H), 7.19 (t, J=8.2 Hz, 1H), 6.47 (d, J=8.2 Hz, 1H), 4.90 (d, J=17.1 Hz, 1H), 4.80 (s, 1H), 4.28 (d, J=17.2 Hz, 1H), 4.15 (d, J=4.8 Hz, 1H), 4.13-4.08 (m, 1H), 1.78-1.67 (m, 5H), 1.55 (br. s, 1H), 1.25-1.14 (m, 5H), 1.09 (d, J=6.8 Hz, 3H).

Example 182

N-(3-chloro-4-fluoro-phenyl)-3-tetrahydrofuran-3-yl-6,7-dihydro-4H-pyrazolo[1,5-a]pyrazine-5-carboxamide

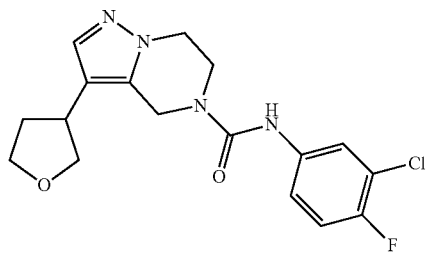 [SMILES: O=C(Nc1ccc(F)c(Cl)c1)N1CCn2ncc(C3CCOC3)c2C1]

The title compound was prepared according to the following scheme:

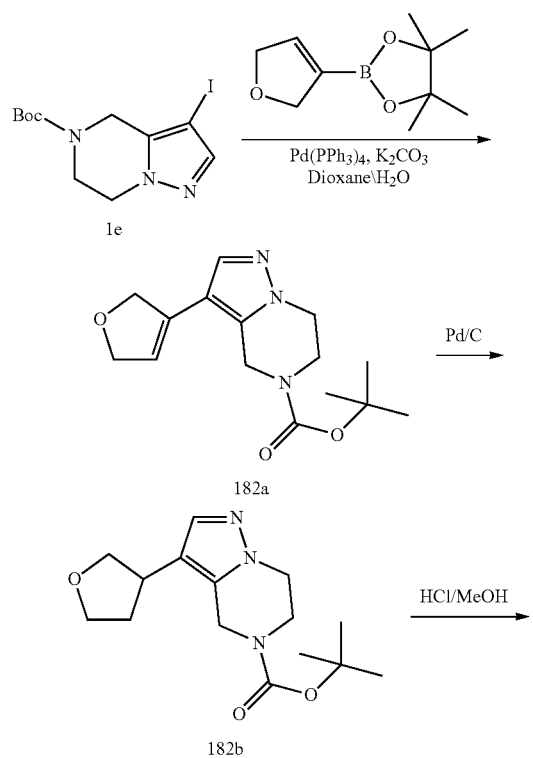

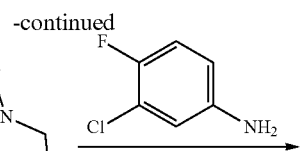

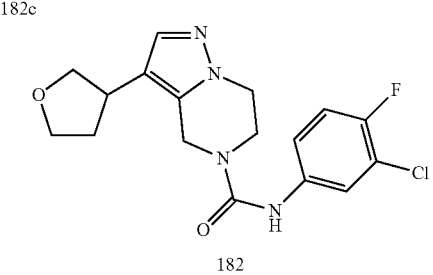

Preparation of 3-tetrahydrofuran-3-yl-4,5,6,7-tetrahydropyrazolo[1,5-a]pyrazine (compound 182c)

The compound 182c was prepared in analogy to compound 26c by using 2-(2,5-dihydrofuran-3-yl)-4,4,5,5-tetramethyl-1,3,2-dioxaborolane instead of cyclopenten-1-yl-boronic acid. Compound 182c was obtained as a white solid (60 mg). LCMS (M+H$^+$): 306.

Preparation of N-(3-chloro-4-fluoro-phenyl)-3-tetrahydrofuran-3-yl-6,7-dihydro-4H-pyrazolo[1,5-a]pyrazine-5-carboxamide (Example 182)

The title compound was prepared in analogy to the preparation of Example 11 by using 3-chloro-4-fluoroaniline instead of 3-(trifluoromethyl)aniline and 3-tetrahydrofuran-3-yl-4,5,6,7-tetrahydropyrazolo[1,5-a]pyrazine (compound 182c) instead of 3-(4-fluorophenyl)-4,5,6,7-tetrahydropyrazolo[1,5-a]pyrazine (compound 11b). Example 182 was obtained as a white solid (13 mg). LCMS (M+H$^+$): 365. $^1$H NMR (400 MHz, CD$_3$OD) δ ppm 7.64 (dd, J=2.6, 6.7 Hz, 1H), 7.44 (s, 1H), 7.37-7.33 (m, 1H), 7.18 (t, J=9.0 Hz, 1H), 4.80 (d, J=2.0 Hz, 2H), 4.25-4.18 (m, 2H), 4.14-3.98 (m, 4H), 3.91 (q, J=7.6 Hz, 1H), 3.64 (t, J=7.8 Hz, 1H), 3.41-3.34 (m, 1H), 2.39-2.33 (m, 1H), 2.09-1.90 (m, 1H).

Example 183

6-methyl-3-(2-oxopyrrolidin-1-yl)-N-(3,4,5-trifluorophenyl)-6,7-dihydro-4H-pyrazolo[1,5-a]pyrazine-5-carboxamide

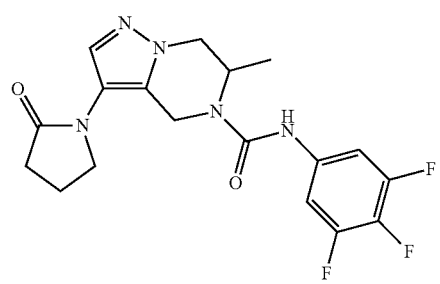 [SMILES: CC1Cn2ncc(N3CCCC3=O)c2CN1C(=O)Nc1cc(F)c(F)c(F)c1]

The title compound was prepared according to the following scheme:

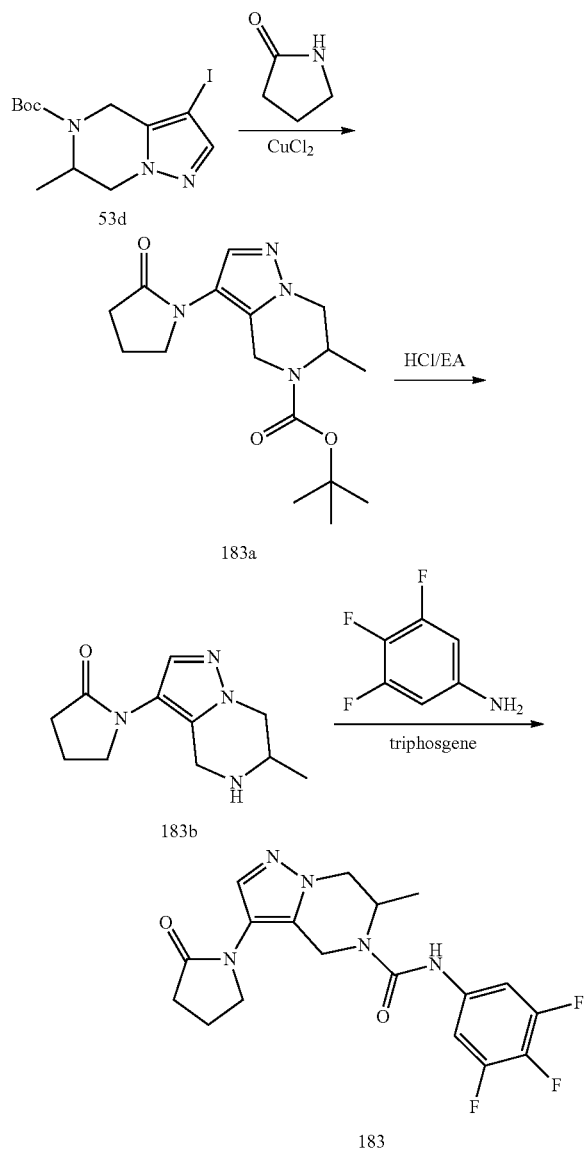

Preparation of 1-(6-methyl-4,5,6,7-tetrahydropyrazolo[1,5-a]pyrazin-3-yl)pyrrolidin-2-one (compound 183b)

The compound 183b was prepared in analogy to the preparation of compound 170b by using pyrollidin-2-one and tert-butyl 3-iodo-6-methyl-6,7-dihydro-4H-pyrazolo[1,5-a]pyrazine-5-carboxylate (compound 53d) instead of tert-butyl 3-iodo-6,7-dihydro-4H-pyrazolo[1,5-a]pyrazine-5-carboxylate (compound 1e). Compound 183 (240 mg) was obtained as a slight yellow solid. LCMS (M+H$^+$): 251.

Preparation of 6-methyl-3-(2-oxopyrrolidin-1-yl)-N-(3,4,5-trifluorophenyl)-6,7-dihydro-4H-pyrazolo[1,5-a]pyrazine-5-carboxamide (Example 183)

The title compound was prepared in analogy to the preparation of Example 170 by using 3,4,5-trifluoroaniline instead of 3-chloro-4-fluoro-aniline and 1-(6-methyl-4,5,6,7-tetrahydropyrazolo[1,5-a]pyrazin-3-yl)pyrrolidin-2-one (compound 183b) instead of 1-(4,5,6,7-tetrahydropyrazolo[1,5-a]pyrazin-3-yl)pyrrolidin-2-one (compound 170b). Example 183 was obtained as a white solid (23 mg). LCMS (M+H$^+$): 394. $^1$H NMR (400 MHz, DMSO-d$_6$) δ ppm 9.10 (s, 1H), 7.60 (s, 1H), 7.47-7.39 (m, 2H), 5.03-4.95 (m, 1H), 4.91-4.82 (m, 1H), 4.49-4.33 (m, 1H), 4.24-4.17 (m, 1H), 4.15-4.09 (m, 1H), 3.86-3.64 (m, 2H), 2.44-2.38 (m, 2H), 2.16-2.05 (m, 2H), 1.14 (d, J=6.8 Hz, 3H).

Example 184

N-(4-bicyclo[4.2.0]octa-1(6),2,4-trienyl)-3-(4-fluorophenyl)-6,7-dihydro-4H-pyrazolo[1,5-a]pyrazine-5-carboxamide

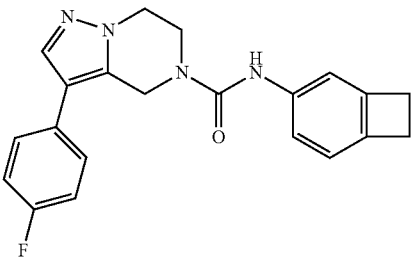 [SMILES: O=C(Nc1ccc2c(c1)CC2)N1CCn2ncc(-c3ccc(F)cc3)c2C1]

Preparation of Example 184

The title compound was prepared in analogy to the preparation of Example 11 by using bicyclo[4.2.0]octa-1,3,5-trien-4-amine (for its synthesis, refer to: U.S. Pat. No. 5,274,135) instead of 3-(trifluoromethyl)aniline Example 184 was obtained as a white solid (14 mg). LCMS (M+H$^+$): 363. $^1$H NMR (400 MHz, DMSO-d$_6$) δ ppm 8.78 (s, 1H), 7.83 (s, 1H), 7.49 (d, J=5.4 Hz, 2H), 7.27 (t, J=8.9 Hz, 2H), 7.22-7.19 (m, 1H), 7.17-7.12 (m, 1H), 6.96 (s, 1H), 4.91 (s, 2H), 4.22-4.18 (m, 2H), 3.99 (d, J=5.5 Hz, 2H), 3.06 (s, 4H).

Example 185

N-(3-chloro-4-fluoro-phenyl)-3-(5-fluoropyrimidin-2-yl)-6,7-dihydro-4H-pyrazolo[1,5-a]pyrazine-5-carboxamide

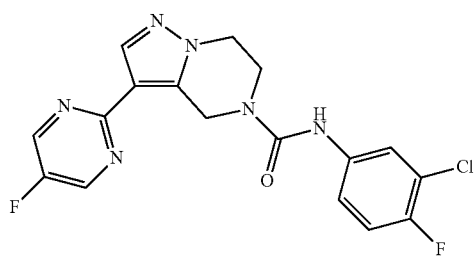 [SMILES: O=C(Nc1ccc(F)c(Cl)c1)N1CCn2ncc(-c3ncc(F)cn3)c2C1]

The title compound was prepared according to the following scheme:

195

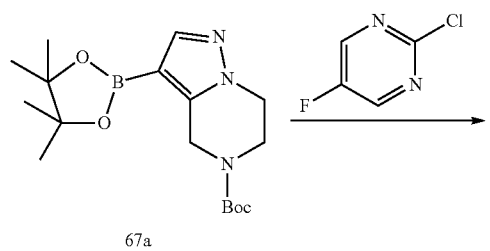
67a

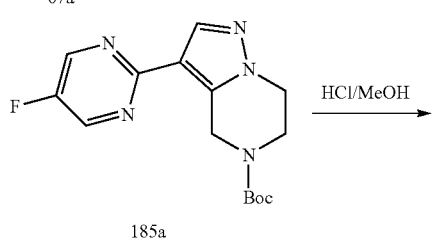
185a

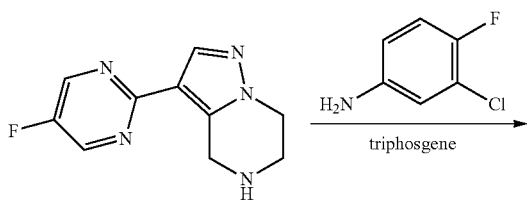
185b

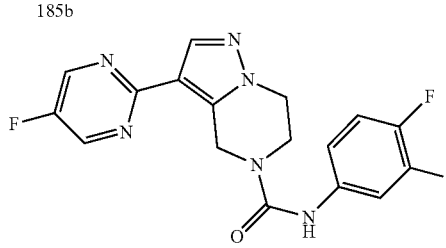
185

Preparation of 3-(5-fluoropyrimidin-2-yl)-4,5,6,7-tetrahydropyrazolo[1,5-a]pyrazine (compound 185b)

The compound 185b was prepared in analogy to compound 67c by using 2-chloro-5-fluoropyrimidine instead of 2-chloro-4-(trifluoromethyl)pyridine.

Preparation of N-(3-chloro-4-fluoro-phenyl)-3-(5-fluoropyrimidin-2-yl)-6,7-dihydro-4H-pyrazolo[1,5-a]pyrazine-5-carboxamide (Example 185)

The title compound was prepared in analogy to the preparation of Example 170 by using 3-(5-fluoropyrimidin-2-yl)-4,5,6,7-tetrahydropyrazolo[1,5-a]pyrazine (compound 185b) instead of 1-(4,5,6,7-tetrahydropyrazolo[1,5-a]pyrazin-3-yl)pyrrolidin-2-one (compound 170b). Example 185 was obtained as a white solid (28 mg). LCMS (M+H$^+$): 391. $^1$H NMR (400 MHz, DMSO-d$_6$) δ ppm 9.12 (s, 1H), 8.89 (s, 2H), 8.08 (s, 1H), 7.73 (dd, J=2.5, 6.9 Hz, 1H), 7.49-7.16 (m, 2H), 5.06 (s, 2H), 4.26 (br. s, 2H), 4.01 (d, J=5.5 Hz, 2H).

196

Example 186

N-(3-chloro-4-fluoro-phenyl)-3-(5-fluoro-4-methyl-pyrimidin-2-yl)-6,7-dihydro-4H-pyrazolo[1,5-a]pyrazine-5-carboxamide

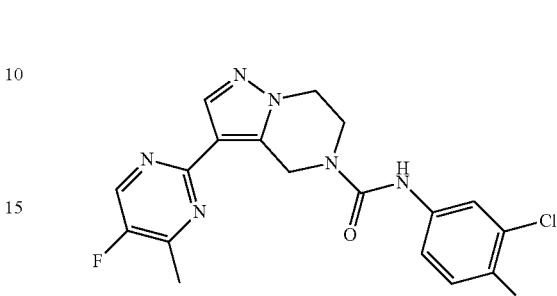

The title compound was prepared according to the following scheme:

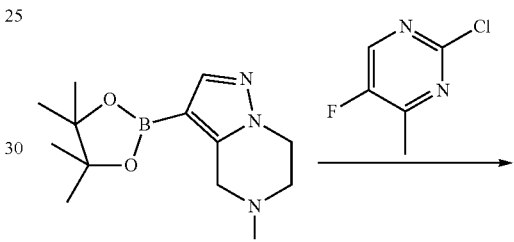
67a

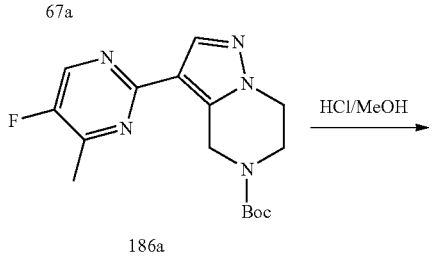
186a

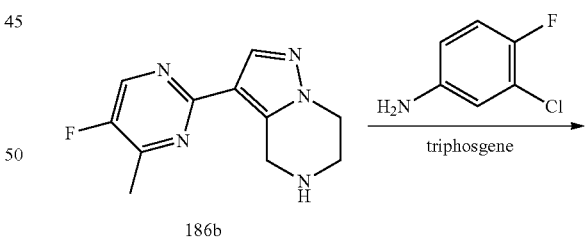
186b

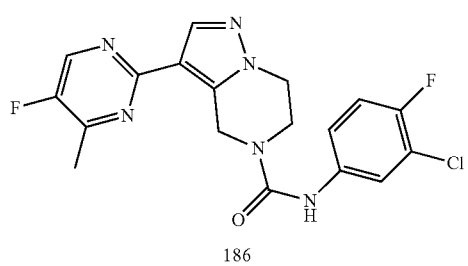
186

Preparation of 3-(5-fluoro-4-methyl-pyrimidin-2-yl)-4,5,6,7-tetrahydropyrazolo[1,5-a]pyrazine (compound 186b)

The compound 186b was prepared in analogy to compound 67c by using 2-chloro-5-fluoro-4-methyl-pyrimidine instead of 2-chloro-4-(trifluoromethyl)pyridine.

Preparation of N-(3-chloro-4-fluoro-phenyl)-3-(5-fluoro-4-methyl-pyrimidin-2-yl)-6,7-dihydro-4H-pyrazolo[1,5-a]pyrazine-5-carboxamide (Example 186)

The title compound was prepared in analogy to the preparation of Example 170 by using 3-(5-fluoro-4-methyl-pyrimidin-2-yl)-4,5,6,7-tetrahydropyrazolo[1,5-a]pyrazine (compound 186b) instead of 1-(4,5,6,7-tetrahydropyrazolo[1,5-a]pyrazin-3-yl)pyrrolidin-2-one (compound 170b). Example 186 was obtained as a white solid (21 mg). LCMS (M+H$^+$): 405. $^1$H NMR (400 MHz, CD$_3$OD) δ ppm 8.51 (d, J=3.0 Hz, 1H), 8.13 (d, J=3.8 Hz, 1H), 7.61 (dd, J=2.6, 6.6 Hz, 1H), 7.40-7.27 (m, 1H), 7.16 (t, J=9.2 Hz, 1H), 5.17 (s, 2H), 4.30 (br, 2H), 4.13-4.01 (br, 2H), 2.55 (s, 3H).

Example 187

3-(2,4-difluorophenyl)-6-methyl-N-(2-methyl-4-pyridyl)-6,7-dihydro-4H-pyrazolo[1,5-a]pyrazine-5-carboxamide

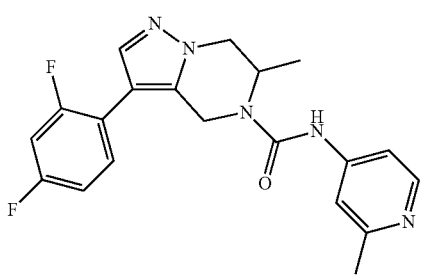 [SMILES: Cc1cc(NC(=O)N2Cc3c(-c4ccc(F)cc4F)cnn3CC2C)ccn1]

Preparation of Example 187

The title compound was prepared in analogy to the preparation of Example 60 by using 2-methylpyridin-4-amine instead of 5-fluoro-6-methyl-pyridin-2-amine and 3-(2,4-difluorophenyl)-6-methyl-4,5,6,7-tetrahydropyrazolo[1,5-a]pyrazine (compound 85b) instead of 3-(2,4-difluorophenyl)-4,5,6,7-tetrahydropyrazolo[1,5-a]pyrazine (compound 60b). Example 187 was obtained as a white solid (32 mg). LCMS (M+H$^+$): 384. $^1$H NMR (400 MHz, CD$_3$OD) δ ppm 8.48 (d, J=6.3 Hz, 1H), 7.75 (br. s, 3H), 7.62-7.51 (m, 1H), 7.45-7.34 (m, 1H), 7.26-7.15 (m, 1H), 5.12 (d, J=17.1 Hz, 1H), 4.97 (br. s, 1H), 4.63 (d, J=16.8 Hz, 1H), 4.39-4.20 (m, 2H), 2.59 (s, 3H), 1.24 (d, J=6.4 Hz, 3H).

Example 188

N-(2-chloro-4-pyridyl)-3-(5-fluoro-2-pyridyl)-6-methyl-6,7-dihydro-4H-pyrazolo[1,5-a]pyrazine-5-carboxamide

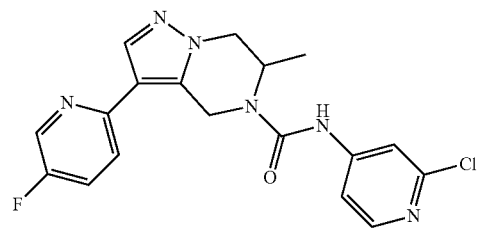 [SMILES: CC1Cn2ncc(-c3ccc(F)cn3)c2CN1C(=O)Nc1ccnc(Cl)c1]

Preparation of Example 188

The title compound was prepared in analogy to the preparation of Example 60 by using 2-chloropyridin-4-amine instead of 5-fluoro-6-methyl-pyridin-2-amine and 3-(5-fluoro-2-pyridyl)-6-methyl-4,5,6,7-tetrahydropyrazolo[1,5-a]pyrazine (compound 94b) instead of 3-(2,4-difluorophenyl)-4,5,6,7-tetrahydropyrazolo[1,5-a]pyrazine (compound 60b). Example 188 was obtained as a white solid (26 mg). LCMS (M+H$^+$): 387. $^1$H NMR (400 MHz, DMSO-d$_6$) δ ppm 9.79 (s, 1H), 8.60-8.58 (m, 1H), 8.21-8.18 (m, 1H), 8.15 (s, 1H), 7.88-7.75 (m, 2H), 7.72-7.70 (m, 1H), 7.59-7.48 (m, 1H), 5.51-5.44 (m, 1H), 5.03-4.94 (m, 1H), 4.71-4.61 (m, 1H), 4.36-4.30 (m, 1H), 4.22-4.17 (m, 1H), 1.19 (d, J=6.8 Hz, 3H).

Example 189

N-(2-chloro-4-pyridyl)-6-methyl-3-[4-(trifluoromethyl)-2-pyridy]-6,7-dihydro-4H-pyrazolo[1,5-a]pyrazine-5-carboxamide

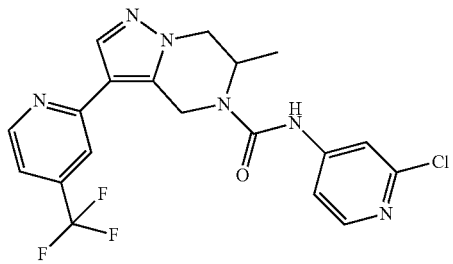 [SMILES: CC1Cn2ncc(-c3cc(C(F)(F)F)ccn3)c2CN1C(=O)Nc1ccnc(Cl)c1]

Preparation of Example 189

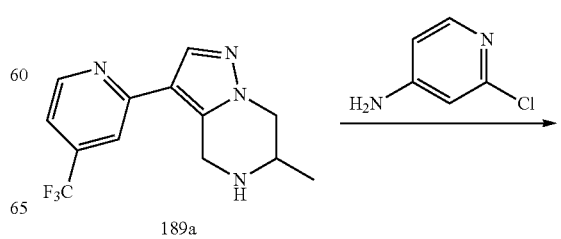

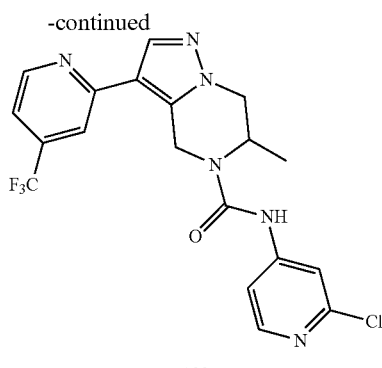

189

The compound 189a was prepared in analogy to compound 67c by using tert-butyl 3-iodo-6-methyl-6,7-dihydro-4H-pyrazolo[1,5-a]pyrazine-5-carboxylate (compound 53d) instead of tert-butyl 3-iodo-6,7-dihydro-4H-pyrazolo[1,5-a]pyrazine-5-carboxylate (compound 1e).

The Example 189 was prepared in analogy to the preparation of Example 60 by using 2-chloropyridin-4-amine instead of 5-fluoro-6-methyl-pyridin-2-amine and 6-methyl-3-[4-(trifluoromethyl)-2-pyridyl]-4,5,6,7-tetrahydropyrazolo[1,5-a]pyrazine (compound 189a) instead of 3-(2,4-difluorophenyl)-4,5,6,7-tetrahydropyrazolo[1,5-a]pyrazine (compound 60b). Example 189 was obtained as a white solid (10 mg). LCMS (M+H$^+$): 437. $^1$H NMR (400 MHz, DMSO-d$_6$) δ ppm 9.73 (s, 1H), 8.87-8.84 (m, 1H), 8.39 (s, 1H), 8.20-8.17 (m, 1H), 8.12-8.10 (m, 1H), 7.69 (s, 1H), 7.54-7.50 (m, 2H), 5.52 (d, J=18.4 Hz, 1H), 5.01-4.91 (m, 1H), 4.71-4.65 (m, 1H), 4.38-4.31 (m, 1H), 4.23 (br, 1H), 1.20 (d, J=6.8 Hz, 3H).

Example 190

6-methyl-N-[2-(trifluoromethyl)-4-pyridyl]-3-[4-(trifluoromethyl)-2-pyridyl]-6,7-dihydro-4H-pyrazolo[1,5-a]pyrazine-5-carboxamide

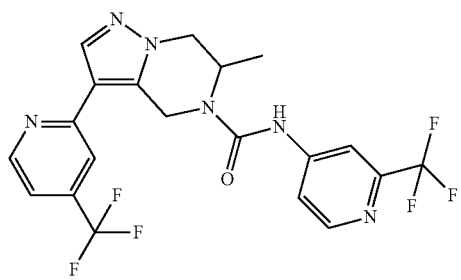 [SMILES: CC1Cn2ncc(-c3cc(C(F)(F)F)ccn3)c2CN1C(=O)Nc1ccnc(C(F)(F)F)c1]

Preparation of Example 190

The title compound was prepared in analogy to the preparation of Example 60 by using 2-trifluoromethylpyridin-4-amine instead of 5-fluoro-6-methyl-pyridin-2-amine and 36-methyl-3-[4-(trifluoromethyl)-2-pyridyl]-4,5,6,7-tetrahydropyrazolo[1,5-a]pyrazine (compound 189a) instead of 3-(2,4-difluorophenyl)-4,5,6,7-tetrahydropyrazolo[1,5-a]pyrazine (compound 60b). Example 190 was obtained as a white solid (13 mg). LCMS (M+H$^+$): 471. $^1$H NMR (400 MHz, DMSO-d$_6$) δ ppm 9.76(s, 1H), 8.88-8.85 (m, 1H), 8.54-8.52 (m, 1H), 8.40 (s, 1H), 8.13-8.11 (m, 1H), 8.07-8.05 (m, 1H), 7.78-7.74 (m, 1H), 7.55-7.51 (m, 1H), 5.57-5.48 (m, 1H), 4.99-4.93 (m, 1H), 4.74-4.66 (m, 1H), 4.39-4.32 (m, 1H), 4.27-4.19 (m, 1H), 1.21 (d, J=6.8 Hz, 3H).

Example 191

N-(2-chloro-4-pyridyl)-6-methyl-3-(2-oxopyrrolidin-1-yl)-6,7-dihydro-4H-pyrazolo[1,5-a]pyrazine-5-carboxamide

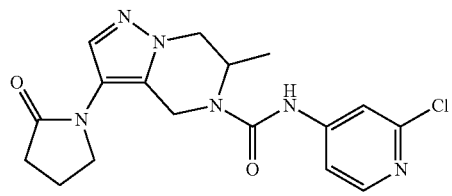 [SMILES: CC1Cn2ncc(N3CCCC3=O)c2CN1C(=O)Nc1ccnc(Cl)c1]

Preparation of Example 191

The title compound was prepared in analogy to the preparation of Example 60 by using 2-chloropyridin-4-amine instead of 5-fluoro-6-methyl-pyridin-2-amine and 1-(6-methyl-4,5,6,7-tetrahydropyrazolo[1,5-a]pyrazin-3-yl)pyrrolidin-2-one (compound 183b) instead of 3-(2,4-difluorophenyl)-4,5,6,7-tetrahydropyrazolo[1,5-a]pyrazine (compound 60b). Example 191 was obtained as a white solid (27 mg). LCMS (M+H$^+$): 375. $^1$H NMR (400 MHz, DMSO-d$_6$) δ ppm 9.56 (s, 1H), 8.16 (d, J=5.7 Hz, 1H), 7.67 (d, J=1.5 Hz, 1H), 7.60 (s, 1H), 7.53-7.43 (m, 1H), 5.11-5.00 (m, 1H), 4.95-4.83 (m, 1H), 4.47-4.36 (m, 1H), 4.27-4.18 (m, 1H), 4.15-4.07 (m, 1H), 3.85-3.63 (m, 2H), 2.40 (s, 2H), 2.10 (d, J=7.7 Hz, 2H), 1.14 (d, J=6.6 Hz, 3H).

Example 192

N-(2-bromo-4-pyridyl)-3-(4-fluorophenyl)-6,7-dihydro-4H-pyrazolo[1,5-a]pyrazine-5-carboxamide

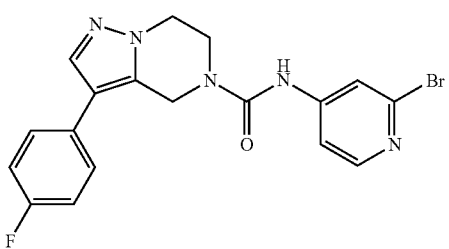 [SMILES: O=C(Nc1ccnc(Br)c1)N1CCn2ncc(-c3ccc(F)cc3)c2C1]

Preparation of Example 192

The title compound was prepared in analogy to the preparation of Example 60 by using 2-bromopyridin-4-amine instead of 5-fluoro-6-methyl-pyridin-2-amine and 3-(4-fluorophenyl)-4,5,6,7-tetrahydropyrazolo[1,5-a]pyrazine (compound 11b) instead of 3-(2,4-difluorophenyl)-4,5,6,7-tetrahydropyrazolo[1,5-a]pyrazine (compound 60b). Example 192 was obtained as a white solid (7 mg). LCMS (M+H$^+$): 416. $^1$H NMR (400 MHz, DMSO-d$_6$) δ ppm 9.49

(s, 1H), 8.15 (d, J=5.6 Hz, 1H), 7.84 (s, 1H), 7.77 (d, J=1.9 Hz, 1H), 7.53-7.46 (m, 3H), 7.28 (t, J=8.9 Hz, 2H), 4.95 (s, 2H), 4.23 (d, J=5.3 Hz, 2H), 4.07-3.98 (m, 2H).

Example 193

N-(3-chloro-2-methyl-4-pyridyl)-3-(2,4-difluorophenyl)-6-methyl-6,7-dihydro-4H-pyrazolo[1,5-a]pyrazine-5-carboxamide

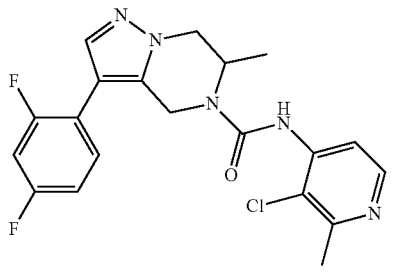 [SMILES: Cc1nccc(NC(=O)N2Cc3c(-c4ccc(F)cc4F)cnn3CC2C)c1Cl]

Preparation of Example 193

The title compound was prepared in analogy to the preparation of Example 60 by using 3-chloro-2-methyl-pyridin-4-amine instead of 5-fluoro-6-methyl-pyridin-2-amine and 3-(2,4-difluorophenyl)-6-methyl-4,5,6,7-tetrahydropyrazolo[1,5-a]pyrazine (compound 85b) instead of 3-(2,4-difluorophenyl)-4,5,6,7-tetrahydropyrazolo[1,5-a]pyrazine (compound 60b). Example 193 was obtained as a white solid (12 mg). LCMS (M+H$^+$): 418. $^1$H NMR (400 MHz, DMSO-d$_6$) δ ppm 8.62 (s, 1H), 8.23 (d, J=5.5 Hz, 1H), 7.74 (d, J=1.9 Hz, 1H), 7.59-7.52 (m, 2H), 7.43-7.34 (m, 1H), 7.23-7.15 (m, 1H), 5.08 (d, J=16.4 Hz, 1H), 4.90 (d, J=5.4 Hz, 1H), 4.60 (d, J=16.8 Hz, 1H), 4.33 (dd, J=4.4, 12.5 Hz, 1H), 4.25-4.19 (m, 1H), 1.20 (d, J=6.9 Hz, 3H).

Example 194

3-(2,4-difluorophenyl)-N-(5-fluoro-2-methyl-4-pyridyl)-6-methyl-6,7-dihydro-4H-pyrazolo[1,5-a]pyrazine-5-carboxamide

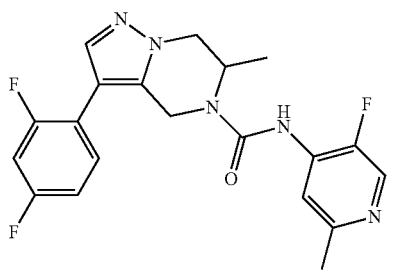 [SMILES: Cc1cc(NC(=O)N2Cc3c(-c4ccc(F)cc4F)cnn3CC2C)c(F)cn1]

Preparation of Example 194

The title compound was prepared in analogy to the preparation of Example 60 by using 5-fluoro-2-methyl-pyridin-4-amine instead of 5-fluoro-6-methyl-pyridin-2-amine and 3-(2,4-difluorophenyl)-6-methyl-4,5,6,7-tetrahydropyrazolo[1,5-a]pyrazine (compound 85b) instead of 3-(2,4-difluorophenyl)-4,5,6,7-tetrahydropyrazolo[1,5-a]pyrazine (compound 60b). Example 194 was obtained as a white solid (40 mg). LCMS (M+H$^+$): 402. $^1$H NMR (400 MHz, DMSO-d$_6$) δ ppm 9.00 (br. s, 1H), 8.30 (d, J=2.9 Hz, 1H), 7.74 (d, J=2.0 Hz, 1H), 7.56 (dt, J=6.6, 8.8 Hz, 1H), 7.50 (d, J=6.5 Hz, 1H), 7.42-7.33 (m, 1H), 7.23-7.15 (m, 1H), 5.08 (d, J=17.1 Hz, 1H), 4.96-4.85 (m, 1H), 4.56 (d, J=16.9 Hz, 1H), 4.35-4.26 (m, 1H), 4.24-4.15 (m, 1H), 2.38 (s, 3H), 1.20 (d, J=6.8 Hz, 3H).

Example 195

N-(5-chloro-2-methyl-4-pyridyl)-3-(2,4-difluorophenyl)-6-methyl-6,7-dihydro-4H-pyrazolo[1,5-a]pyrazine-5-carboxamide

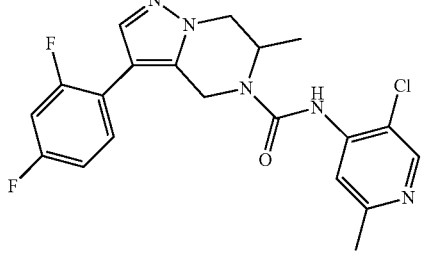

Preparation of Example 195

The title compound was prepared in analogy to the preparation of Example 60 by using 5-chloro-2-methyl-pyridin-4-amine instead of 5-fluoro-6-methyl-pyridin-2-amine and 3-(2,4-difluorophenyl)-6-methyl-4,5,6,7-tetrahydropyrazolo[1,5-a]pyrazine (compound 85b) instead of 3-(2,4-difluorophenyl)-4, 5, 6,7-tetrahydropyrazolo[1,5-a]pyrazine (compound 60b). Example 195 was obtained as a white solid (10 mg). LCMS (M+H$^+$): 418. $^1$H NMR (400 MHz, DMSO-d$_6$) δ ppm 8.68 (br. s, 1H), 8.38 (s, 1H), 7.74 (d, J=1.9 Hz, 1H), 7.59-7.54 (m, 1H), 7.53 (s, 1H), 7.44-7.34 (m, 1H), 7.19 (dt, J=2.3, 8.4 Hz, 1H), 5.08 (d, J=16.7 Hz, 1H), 4.95-4.85 (m, 1H), 4.59 (d, J=16.8 Hz, 1H), 4.37-4.28 (m, 1H), 4.25-4.18 (m, 1H), 2.41 (s, 3H), 1.20 (d, J=6.8 Hz, 3H).

Example 196

N-[(2-chloro-3-fluoro-phenyl)methyl]-3-(2,4-difluorophenyl)-6-methyl-6,7-dihydro-4H-pyrazolo[1,5-a]pyrazine-5-carboxamide

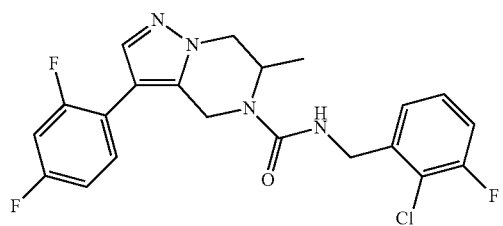 [SMILES: CC1Cn2ncc(-c3ccc(F)cc3F)c2CN1C(=O)NCc1cccc(F)c1Cl]

Preparation of Example 196

The title compound was prepared in analogy to the preparation of Example 11 by using (2-chloro-3-fluorophenyl)methanamine instead of 3-(trifluoromethyl)aniline and 3-(2,4-difluorophenyl)-6-methyl-4,5,6,7-tetrahydropyrazolo[1,5-a]pyrazine (compound 85b) instead of 3-(4-fluorophenyl)-4,5,6,7-tetrahydropyrazolo[1,5-a]pyrazine (compound 11b). Example 196 was obtained as a white solid (11 mg). LCMS (M+H⁺): 435. ¹H NMR (400 MHz, DMSO-$d_6$) δ ppm 7.72 (d, J=2.1 Hz, 1H), 7.55 (dt, J=6.6, 8.8 Hz, 1H), 7.47 (t, J=5.3 Hz, 1H), 7.41-7.26 (m, 3H), 7.21-7.14 (m, 2H), 4.97 (d, J=16.8 Hz, 1H), 4.87-4.79 (m, 1H), 4.45-4.35 (m, 3H), 4.27-4.21 (m, 1H), 4.19-4.14 (m, 1H), 1.13 (d, J=6.8 Hz, 3H).

Example 197

3-(2,4-difluorophenyl)-N-(5-fluoro-6-methyl-2-pyridyl)-6-methyl-6,7-dihydro-4H-pyrazolo[1,5-a]pyrazine-5-carboxamide

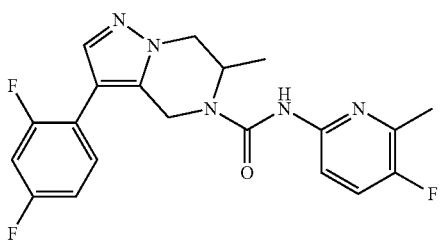 [SMILES: Cc1nc(NC(=O)N2Cc3c(-c4ccc(F)cc4F)cnn3CC2C)ccc1F]

Preparation of Example 197

The title compound was prepared in analogy to the preparation of Example 60 by using 3-fluoro-2-methyl-pyridin-4-amine instead of 5-fluoro-6-methyl-pyridin-2-amine and 3-(2,4-difluorophenyl)-6-methyl-4,5,6,7-tetrahydropyrazolo[1,5-a]pyrazine (compound 85b) instead of 3-(2,4-difluorophenyl)-4,5,6,7-tetrahydropyrazolo[1,5-a]pyrazine (compound 60b). Example 197 was obtained as a white solid (6 mg). LCMS (M+H⁺): 402. ¹H NMR (400 MHz, DMSO-$d_6$) δ ppm 9.53 (s, 1H), 7.72 (d, J=2.1 Hz, 1H), 7.67-7.62 (m, 1H), 7.60-7.54 (m, 2H), 7.42-7.33 (m, 1H), 7.20 (dt, J=2.1, 8.5 Hz, 1H), 5.16 (d, J=16.8 Hz, 1H), 5.00-4.92 (m, 1H), 4.51 (d, J=17.1 Hz, 1H), 4.32-4.24 (m, 1H), 4.20-4.13 (m, 1H), 2.37 (d, J=2.9 Hz, 3H), 1.17 (d, J=6.9 Hz, 3H).

Example 198

(6S)-3-(5-fluoro-2-pyridyl)-6-methyl-N-(3,4,5-trifluorophenyl)-6,7-dihydro-4H-pyrazolo[1,5-a]pyrazine-5-carboxamide

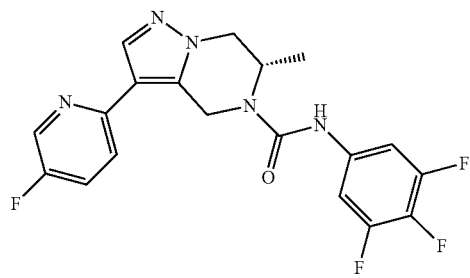 [SMILES: C[C@H]1Cn2ncc(-c3ccc(F)cn3)c2CN1C(=O)Nc1cc(F)c(F)c(F)c1]

Preparation of Example 198

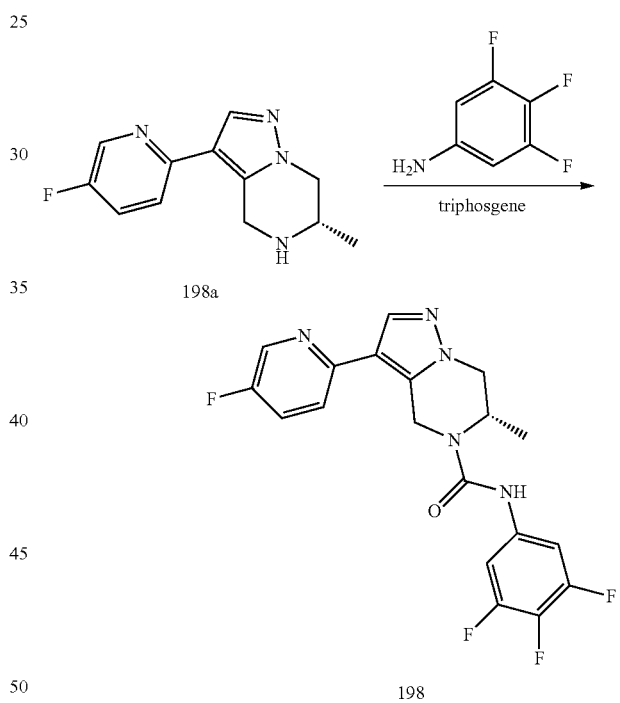

The compound 198a was prepared in analogy to compound 67c by using 2-chloro-5-fluoro-pyridine instead of 2-chloro-4-(trifluoromethyl)pyridine and (6S)-tert-butyl 3-iodo-6-methyl-6,7-dihydro-4H-pyrazolo[1,5-a]pyrazine-5-carboxylate (compound 102d) instead of tert-butyl 3-iodo-6,7-dihydro-4H-pyrazolo[1,5-a]pyrazine-5-carboxylate (compound 1e).

The Example 198 was prepared in analogy to the preparation of Example 11 by using 3,4,5-trifluoroaniline instead of 3-(trifluoromethyl)aniline and (6S)-3-(5-fluoro-2-pyridyl)-6-methyl-4,5,6,7-tetrahydropyrazolo[1,5-a]pyrazine (compound 198a) instead of 3-(4-fluorophenyl)-4,5,6,7-tetrahydropyrazolo[1,5-a]pyrazine (compound 11b). Example 198 was obtained as a white solid (6 mg). LCMS (M+H⁺): 406. ¹H NMR (400 MHz, DMSO-$d_6$) δ ppm 9.21

(s, 1H), 8.59-8.57 (m, 1H), 8.14 (s, 1H), 7.85-7.71 (m, 2H), 7.51-7.37 (m, 2H), 5.46-5.38 (m, 1H), 4.93-4.82 (m, 1H), 4.68-4.57 (m, 1H), 4.33-4.26 (m, 1H), 4.24-4.16 (m, 1H), 1.20-1.14 (m, 3H).

Example 199

N-(3-chloro-4-fluoro-phenyl)-6-methyl-3-(4-methyl-pyrazol-1-yl)-6,7-dihydro-4H-pyrazolo[1,5-a]pyrazine-5-carboxamide

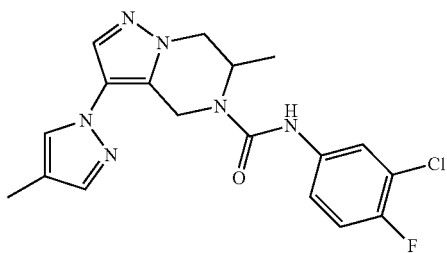 [SMILES: Cc1cnn(-c2cnn3c2CN(C(=O)Nc2ccc(F)c(Cl)c2)C(C)C3)c1]

The title compound was prepared according to the following scheme:

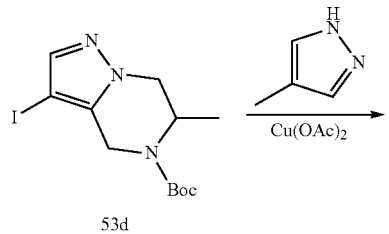

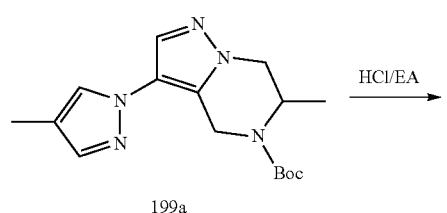

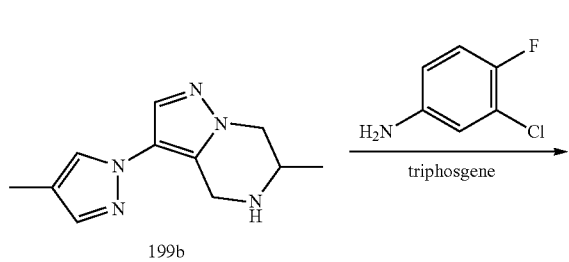

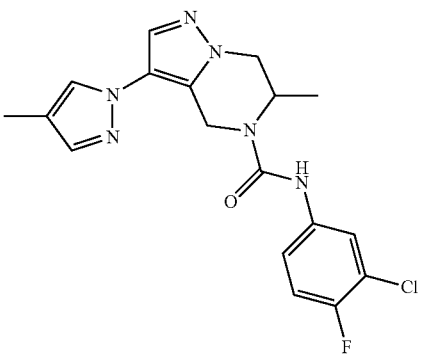

199

Preparation of N-(3-chloro-4-fluoro-phenyl)-6-methyl-3-(4-methylpyrazol-1-yl)-6,7-dihydro-4H-pyrazolo[1,5-a]pyrazine-5-carboxamide (Example 199)

The title compound was prepared in analogy to the preparation of Example 171 by using tert-butyl 3-iodo-6-methyl-6,7-dihydro-4H-pyrazolo[1,5-a]pyrazine-5-carboxylate (compound 53d) instead of tert-butyl 3-iodo-6,7-dihydro-4H-pyrazolo[1,5-a]pyrazine-5-carboxylate (compound 1e). Example 199 was obtained as a white solid (10 mg). LCMS (M+H$^+$): 389. $^1$H NMR (400 MHz, CD$_3$OD) δ ppm 7.78 (d, J=13.3 Hz, 2H), 7.62 (dd, J=2.6, 6.7 Hz, 1H), 7.53 (s, 1H), 7.36-7.29 (m, 1H), 7.16 (t, J=9.0 Hz, 1H), 5.22 (d, J=17.1 Hz, 1H), 5.08-4.96 (m, 1H), 4.67 (d, J=17.1 Hz, 1H), 4.40-4.30 (m, 1H), 4.26-4.12 (m, 1H), 2.17 (s, 3H), 1.29 (d, J=6.9 Hz, 3H).

Example 200

N-(3-chloro-4-fluoro-phenyl)-3-(4-cyanopyrazol-1-yl)-6-methyl-6,7-dihydro-4H-pyrazolo[1,5-a]pyrazine-5-carboxamide

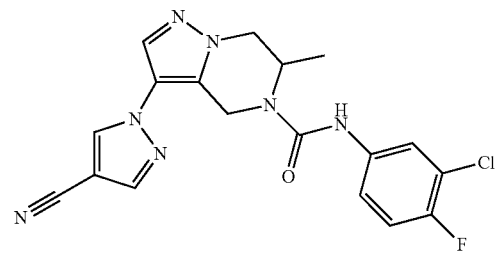 [SMILES: CC1Cn2ncc(-n3cc(C#N)cn3)c2CN1C(=O)Nc1ccc(F)c(Cl)c1]

The title compound was prepared according to the following scheme:

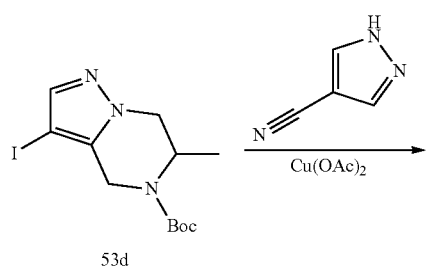

Preparation of N-(3-chloro-4-fluoro-phenyl)-3-(4-cyanopyrazol-1-yl)-6-methyl-6,7-dihydro-4H-pyrazolo[1,5-a]pyrazine-5-carboxamide (Example 200)

The title compound was prepared in analogy to the preparation of Example 171 by using tert-butyl 3-iodo-6-methyl-6,7-dihydro-4H-pyrazolo[1,5-a]pyrazine-5-carboxylate (compound 53d) instead of tert-butyl 3-iodo-6,7-dihydro-4H-pyrazolo[1,5-a]pyrazine-5-carboxylate (compound 1e) and 1H-pyrazole-4-carbonitrile instead of 4-methyl-1H-pyrazole. Example 200 was obtained as a white solid (5 mg). LCMS (M+H$^+$): 400. $^1$H NMR (400 MHz, DMSO-d$_6$) δ ppm 9.06-8.98 (m, 2H), 8.36 (s, 1H), 7.99 (s, 1H), 7.73 (dd, J=2.5, 6.9 Hz, 1H), 7.45-7.38 (m, 1H), 7.36-7.29 (m, 1H), 5.26 (d, J=17.4 Hz, 1H), 4.95-4.87 (m, 1H), 4.55 (d, J=17.4 Hz, 1H), 4.33-4.25 (m, 1H), 4.23-4.16 (m, 1H), 1.18 (d, J=6.9 Hz, 3H).

Example 201

N-(3-chloro-4-fluoro-phenyl)-3-(4-fluoropyrazol-1-yl)-6-methyl-6,7-dihydro-4H-pyrazolo[1,5-a]pyrazine-5-carboxamide

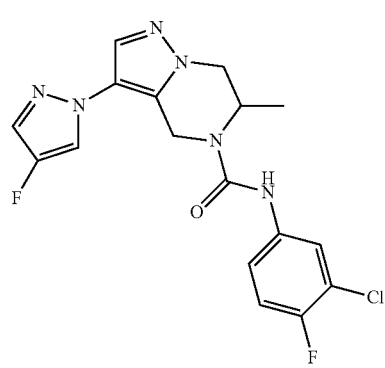

The title compound was prepared according to the following scheme:

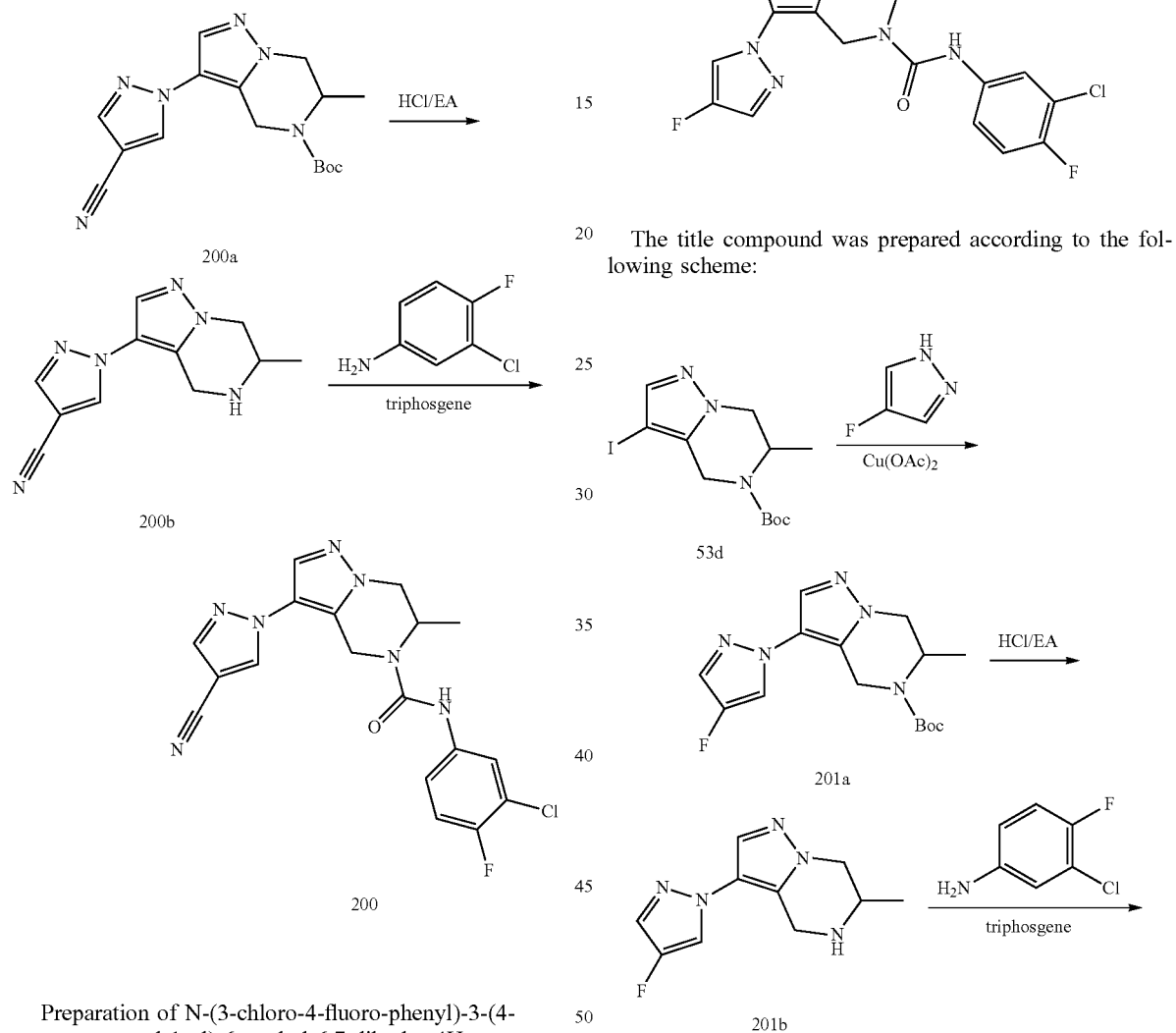

Preparation of N-(3-chloro-4-fluoro-phenyl)-3-(4-fluoropyrazol-1-yl)-6-methyl-6,7-dihydro-4H-pyrazolo[1,5-a]pyrazine-5-carboxamide (Example 201)

The title compound was prepared in analogy to the preparation of Example 171 by using tert-butyl 3-iodo-6-methyl-6,7-dihydro-4H-pyrazolo[1,5-a]pyrazine-5-carboxylate (compound 53d) instead of tert-butyl 3-iodo-6,7-dihydro-4H-pyrazolo[1,5-a]pyrazine-5-carboxylate (compound 1e) and 4-fluoro-1H-pyrazole instead of 4-methyl-1H-pyrazole. Example 201 was obtained as a white solid (15 mg). LCMS (M+H$^+$): 393. $^1$H NMR (400 MHz, DMSO-d$_6$) δ ppm 9.00 (s, 1H), 8.40 (d, J=4.3 Hz, 1H), 7.88 (s, 1H), 7.82-7.71 (m, 2H), 7.45-7.39 (m, 1H), 7.33 (t, J=9.1 Hz, 1H), 5.24 (d, J=17.6 Hz, 1H), 4.90 (d, J=3.8 Hz, 1H), 4.53 (d, J=17.6 Hz, 1H), 4.31-4.23 (m, 1H), 4.21-4.14 (m, 1H), 1.17 (d, J=6.8 Hz, 3H).

Example 202

N-(3-chloro-4-fluoro-phenyl)-6-methyl-3-(2-oxopyrrolidin-1-yl)-6,7-dihydro-4H-pyrazolo[1,5-a]pyrazine-5-carboxamide

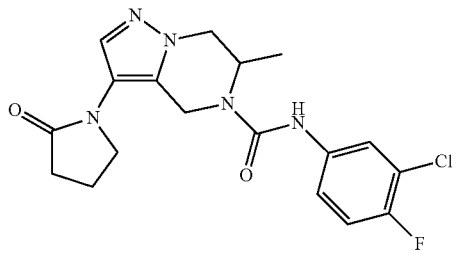 [SMILES: CC1Cn2ncc(N3CCCC3=O)c2CN1C(=O)Nc1ccc(F)c(Cl)c1]

Preparation of Example 202

The title compound was prepared in analogy to the preparation of Example 170 by using 1-(6-methyl-4,5,6,7-tetrahydropyrazolo[1,5-a]pyrazin-3-yl)pyrrolidin-2-one (compound 183b) instead of 1-(4,5,6,7-tetrahydropyrazolo[1,5-a]pyrazin-3-yl)pyrrolidin-2-one (compound 170b). Example 202 was obtained as a white solid (15 mg). LCMS (M+H$^+$): 392. $^1$H NMR (400 MHz, DMSO-d$_6$) δ ppm 9.05 (s, 1H), 7.75 (s, 1H), 7.61 (s, 1H), 7.49-7.43 (m, 1H), 7.32 (s, 1H), 5.07-4.97 (m, 1H), 4.94-4.84 (m, 1H), 4.42-4.34 (m, 1H), 4.22-4.18 (m, 2H), 3.85-3.68 (m, 2H), 2.44-2.37 (m, 2H), 2.15-2.05 (m, 2H), 1.13 (d, J=6.8 Hz, 3H).

Example 203

N-[4-fluoro-3-(trifluoromethyl)phenyl]-6-methyl-3-(2-oxopyrrolidin-1-yl)-6,7-dihydro-4H-pyrazolo[1,5-a]pyrazine-5-carboxamide

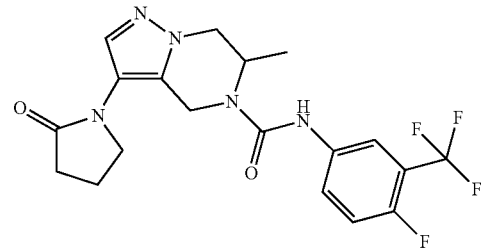 [SMILES: CC1Cn2ncc(N3CCCC3=O)c2CN1C(=O)Nc1ccc(F)c(C(F)(F)F)c1]

Preparation of Example 203

The title compound was prepared in analogy to the preparation of Example 170 by using 4-fluoro-3-(trifluoromethyl)aniline instead of 3-chloro-4-fluoro-aniline and 1-(6-methyl-4,5,6,7-tetrahydropyrazolo[1,5-a]pyrazin-3-yl)pyrrolidin-2-one one (compound 183b) instead of 1-(4,5,6,7-tetrahydropyrazolo[1,5-a]pyrazin-3-yl)pyrrolidin-2-one (compound 170b). Example 203 was obtained as a white solid (13 mg). LCMS (M+H$^+$): 426. $^1$H NMR (400 MHz, DMSO-d$_6$) δ ppm 9.15 (s, 1H), 7.96-7.92 (m, 1H), 7.84-7.78 (m, 1H), 7.61 (s, 1H), 7.48-7.38 (m, 1H), 5.11-4.97 (m, 1H), 4.94-4.84 (m, 1H), 4.47-4.34 (m, 1H), 4.25-4.17 (m, 1H), 4.15-4.08 (m, 1H), 3.84-3.77 (m, 2H), 2.44-2.37 (m, 2H), 2.15-2.02 (m, 2H), 1.14 (d, J=6.8 Hz, 3H).

Example 204

3-cyclopentyl-6-methyl-N-(3,4,5-trifluorophenyl)-6,7-dihydro-4H-pyrazolo[1,5-a]pyrazine-5-carboxamide

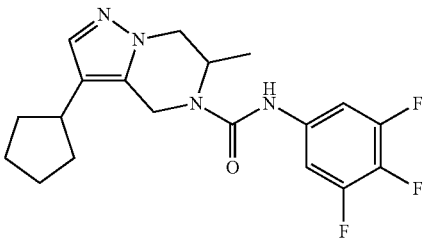 [SMILES: CC1Cn2ncc(C3CCCC3)c2CN1C(=O)Nc1cc(F)c(F)c(F)c1]

Preparation of Example 204

The title compound was prepared in analogy to the preparation of Example 106 by using 3,4,5-trifluoroaniline instead of 3-amino-5-fluoro-benzonitrile and 3-cyclopentyl-6-methyl-4,5,6,7-tetrahydropyrazolo[1,5-a]pyrazine (compound 96c) instead of 3-(4-fluorophenyl)-4,5,6,7-tetrahydropyrazolo[1,5-a]pyrazine (compound 11b). Example 204 was obtained as a white solid (12 mg). LCMS (M+H$^+$): 379. $^1$H NMR (400 MHz, CD$_3$OD) δ ppm 7.43-7.37 (m, 1H), 7.35-7.27 (m, 2H), 5.03 (d, J=16.3 Hz, 1H), 4.97-4.91 (m, 1H), 4.49 (d, J=16.3 Hz, 1H), 4.26 (dd, J=4.3, 12.5 Hz, 1H), 4.16-4.10 (m, 1H), 2.99-2.93 (m, 1H), 2.18-1.98 (m, 2H), 1.89-1.78 (m, 2H), 1.77-1.65 (m, 2H), 1.63-1.50 (m, 2H), 1.21 (d, J=6.8 Hz, 3H).

Example 205

3-cyclopentyl-6-methyl-N-[2-(trifluoromethyl)-4-pyridyl]-6,7-dihydro-4H-pyrazolo[1,5-a]pyrazine-5-carboxamide

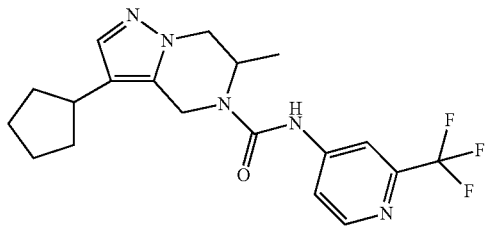 [SMILES: CC1Cn2ncc(C3CCCC3)c2CN1C(=O)Nc1ccnc(C(F)(F)F)c1]

Preparation of Example 205

The title compound was prepared in analogy to the preparation of Example 106 by using 2-(trifluoromethyl)pyridin-4-amine instead of 3-amino-5-fluoro-benzonitrile and 3-cyclopentyl-6-methyl-4,5,6,7-tetrahydropyrazolo[1,5-a]pyrazine (compound 96c) instead of 3-(4-fluorophenyl)-4,5,6,7-tetrahydropyrazolo[1,5-a]pyrazine (compound 11b). Example 205 was obtained as a white solid (2 mg). LCMS (M+H$^+$): 394. $^1$H NMR (400 MHz, CD$_3$OD) δ ppm 8.50 (d, J=5.5 Hz, 1H), 8.06 (d, J=2.0 Hz, 1H), 7.78 (dd, 5.6 Hz, 1H), 7.41 (s, 1H), 5.10 (d, J=16.3 Hz, 1H), 5.03-4.94 (m, 1H), 4.55 (d, J=16.3 Hz, 1H), 4.29 (dd, J=4.1, 12.7 Hz, 1H), 4.15 (dd, J=1.1, 12.7 Hz, 1H), 3.05-2.86 (m, 1H), 2.15-2.03 (m, 2H), 1.90-1.79 (m, 2H), 1.78-1.68 (m, 2H), 1.64-1.52 (m, 2H), 1.24 (d, J=6.8 Hz, 3H).

Example 206

N-(6-chloro-5-fluoro-2-pyridyl)-3-cyclopentyl-6-methyl-6,7-dihydro-4H-pyrazolo[1,5-a]pyrazine-5-carboxamide

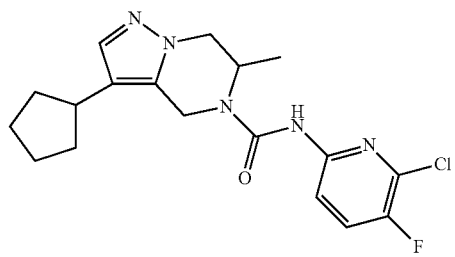 [SMILES: CC1Cn2ncc(C3CCCC3)c2CN1C(=O)Nc1ccc(F)c(Cl)n1]

Preparation of Example 206

The title compound was prepared in analogy to the preparation of Example 140 by using 3-cyclopentyl-6-methyl-4,5,6,7-tetrahydropyrazolo[1,5-a]pyrazine (compound 96c) instead of 3-(4-fluorophenyl)-4,5,6,7-tetrahydropyrazolo[1,5-a]pyrazine (compound 11b). Example 206 was obtained as a white solid (6 mg). LCMS (M+H$^+$): 378. $^1$H NMR (400 MHz, CD$_3$OD) δ ppm 7.85 (dd, J=3.1, 8.9 Hz, 1H), 7.67 (dd, J=7.9, 8.9 Hz, 1H), 7.39 (s, 1H), 5.06 (d, J=16.6 Hz, 1H), 4.99-4.93 (m, 1H), 4.51 (d, J=16.3 Hz, 1H), 4.27 (dd, J=4.4, 12.7 Hz, 1H), 4.12 (dd, J=1.3, 12.8 Hz, 1H), 3.02-2.84 (m, 1H), 2.14-2.02 (m, 2H), 1.89-1.64 (m, 4H), 1.63-1.50 (m, 2H), 1.23 (d, J=6.8 Hz, 3H).

Example 207

N-(2-cyclopropyl-4-pyridyl)-3-(2,4-difluorophenyl)-6,7-dihydro-4H-pyrazolo[1,5-a]pyrazine-5-carboxamide

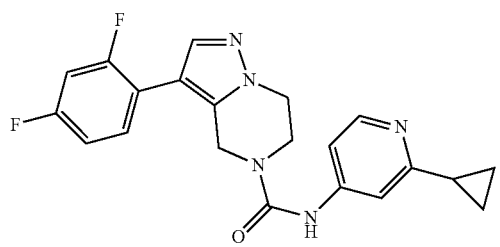 [SMILES: O=C(Nc1ccnc(C2CC2)c1)N1CCn2ncc(-c3ccc(F)cc3F)c2C1]

Preparation of Example 207

The title compound was prepared in analogy to the preparation of Example 106 by using 2-cyclopropylpyridin-4-amine (AB140912, Shanghai AQBioPharma Co. Ltd) instead of 3-amino-5-fluoro-benzonitrile and 3-(2,4-difluorophenyl)-4,5,6,7-tetrahydropyrazolo[1,5-a]pyrazine (compound 50b) instead of 3-(4-fluorophenyl)-4,5,6,7-tetrahydropyrazolo[1,5-a]pyrazine (compound 11b). Example 207 was obtained as a white solid (7 mg). LCMS (M+H$^+$): 396. $^1$H NMR (400 MHz, CD$_3$OD) δ ppm 8.28 (d, J=7.0 Hz, 1H), 7.78 (dd, J=2.3, 7.0 Hz, 1H), 7.72 (d, J=1.3 Hz, 1H), 7.58 (d, J=2.0 Hz, 1H), 7.53-7.43 (m, 1H), 7.17-7.04 (m, 2H), 4.92 (s, 2H), 4.35 (t, J=5.5 Hz, 2H), 4.16 (t, J=5.5 Hz, 2H), 2.26-2.19 (m, 1H), 1.46-1.33 (m, 2H), 1.16-1.05 (m, 2H).

Example 208

3-(2,4-difluorophenyl)-N-[2-(dimethylamino)-4-pyridyl]-6,7-dihydro-4H-pyrazolo[1,5-a]pyrazine-5-carboxamide

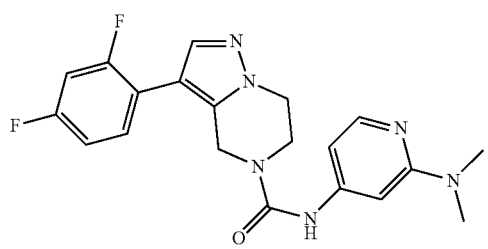 [SMILES: CN(C)c1cc(NC(=O)N2CCn3ncc(-c4ccc(F)cc4F)c3C2)ccn1]

Preparation of Example 208

The title compound was prepared in analogy to the preparation of Example 106 by using N2,N2-dimethylpyridine-2,4-diamine (catalog number: AQ14094, Shanghai AQBioPharma Co. Ltd) instead of 3-amino-5-fluoro-benzonitrile and 3-(2,4-difluorophenyl)-4,5,6,7-tetrahydropyrazolo[1,5-a]pyrazine (compound 50b) instead of 3-(4-fluorophenyl)-4,5,6,7-tetrahydropyrazolo[1,5-a]pyrazine (compound 11b). Example 208 was obtained as a white solid (26 mg). LCMS (M+H+): 399. ¹H NMR (400 MHz, CD₃OD) δ ppm 7.79 (d, J=6.8 Hz, 1H), 7.72 (d, J=1.5 Hz, 1H), 7.54-7.42 (m, 1H), 7.17-7.02 (m, 3H), 6.89 (dd, J=1.9, 6.7 Hz, 1H), 4.89 (s, 2H), 4.33 (t, J=5.5 Hz, 2H), 4.13 (t, J=5.5 Hz, 2H), 3.14 (s, 6H).

Example 209

N-(3-chloro-4-fluoro-phenyl)-3-[2-(methoxymethyl)pyrrolidin-1-yl]-6,7-dihydro-4H-pyrazolo[1,5-a]pyrazine-5-carboxamide

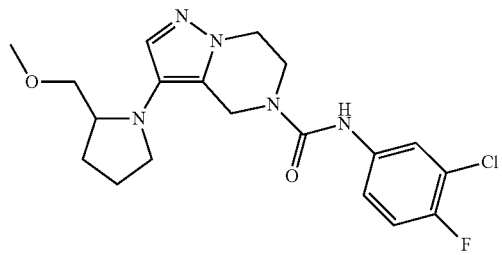 [SMILES: COCC1CCCN1c1cnn2c1CN(C(=O)Nc1ccc(F)c(Cl)c1)CC2]

The title compound was prepared according to the following scheme:

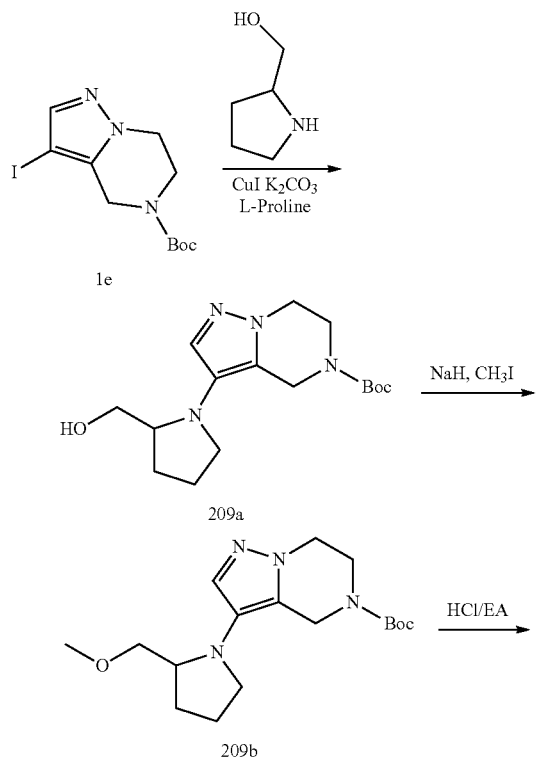

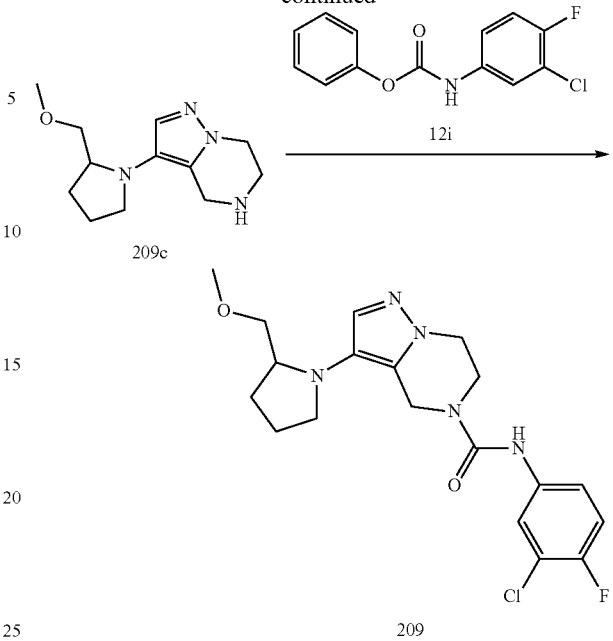

Step 1: Preparation of [1-(5-methyl-6,7-dihydro-4H-pyrazolo[1,5-a]pyrazin-3-yl)pyrrolidin-2-yl]methanol (compound 209a)

A mixture of tert-butyl 3-iodo-6,7-dihydro-4H-pyrazolo[1,5-a]pyrazine-5-carboxylate (compound 1e, 175 mg 0.5 mmol), pyrrolidin-2-ylmethanol (100 mg, 1.0 mmol), L-proline (23 mg, 0.2 mmol), CuI (19 mg 0.1 mmol) and K₂CO₃ (207 mg, 1.5 mmol) in DMSO (5 mL) was stirred in microwave for 2 hours at 120° C. The reaction mixture was diluted with water, extracted with EtOAc. The organic layer was concentrated. The residue was purified by column chromatography to afford compound 209a (150 mg) as a slight yellow oil. LCMS (M+H+): 323.

Step 2: Preparation of tert-butyl 3-[2-(methoxymethyl)pyrrolidin-1-yl]-6,7-dihydro-4H-pyrazolo[1,5-a]pyrazine-5-carboxylate (compound 209b)

To a solution of [1-(5-methyl-6,7-dihydro-4H-pyrazolo[1,5-a]pyrazin-3-yl)pyrrolidin-2-yl]methanol (compound 209a, 67 mg, 0.3 mmol) in THF (10 mL) was added NaH (36 mg, 0.6 mmol, 60% oil dispersion) slowly at room temperature and then Methyl iodide (85 mg, 0.6 mmol). The reaction mixture was stirred at room temperature for 2 hours and then was quenched with water, extracted with EtOAc. The organic layer was dried and concentrated in vacuo to afford compound 209b (70 mg) as a slight yellow oil. LCMS (M+H+): 337.

Step 3: Preparation of 3-[2-(methoxymethyl)pyrrolidin-1-yl]-4,5,6,7-tetrahydropyrazolo[1,5-a]pyrazine (compound 209c)

A solution of tert-butyl 3-[2-(methoxymethyl)pyrrolidin-1-yl]-6,7-dihydro-4H-pyrazolo[1,5-a]pyrazine-5-carboxylate (compound 209b, 70 mg, 0.3 mmol) in HCl/EA (10 mL) was stirred at room temperature for 2 hours. Then the reaction mixture was concentrated in vacuo to afford compound 209c (60 mg) as a slight yellow solid. LCMS (M+H+): 237.

Step 4: Preparation of N-(3-chloro-4-fluoro-phenyl)-3-[2-(methoxymethyl)pyrrolidin-1-yl]-6,7-dihydro-4H-pyrazolo[1,5-a]pyrazine-5-carboxamide (Example 209)

The title compound was prepared in analogy to the preparation of Example 140 by using phenyl N-(3-chloro-4-fluoro-phenyl)carbamate (compound 12i) instead of phenyl N-(6-chloro-5-fluoro-2-pyridyl)carbamate (compound 140d) and 3-[2-(methoxymethyl)pyrrolidin-1-yl]-4,5,6,7-tetrahydropyrazolo[1,5-a]pyrazine (compound 209c) instead of 3-(4-fluorophenyl)-4,5,6,7-tetrahydropyrazolo[1,5-a]pyrazine (compound 11b). Example 209 was obtained as a white solid (5 mg). LCMS (M+H+): 408. $^1$H NMR (400 MHz, CD$_3$OD) δ ppm 7.63 (dd, J=2.6, 6.7 Hz, 1H), 7.38-7.29 (m, 2H), 7.17 (t, J=8.9 Hz, 1H), 4.84 (d, J=16.3 Hz, 1H), 4.76 (d, J=16.3 Hz, 1H), 4.62 (br. s, 2H), 4.23-4.14 (m, 2H), 4.13-4.03 (m, 1H), 3.96-3.91 (m, 1H), 3.51-3.36 (m, 3H), 3.32-3.28 (m, 2H), 3.00-2.88 (m, 1H), 2.16-2.02 (m, 1H), 1.98-1.76 (m, 3H).

Example 210

N-(3-chloro-4-fluoro-phenyl)-3-[3-(methoxymethyl)pyrrolidin-1-yl]-6,7-dihydro-4H-pyrazolo[1,5-a]pyrazine-5-carboxamide

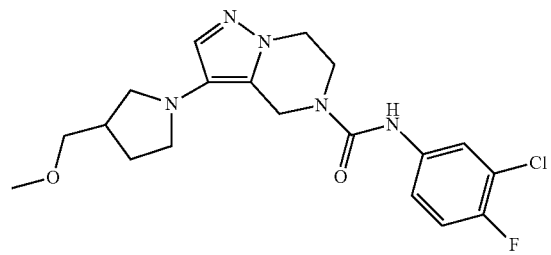 [SMILES: COCC1CCN(c2cnn3c2CN(C(=O)Nc2ccc(F)c(Cl)c2)CC3)C1]

The title compound was prepared according to the following scheme:

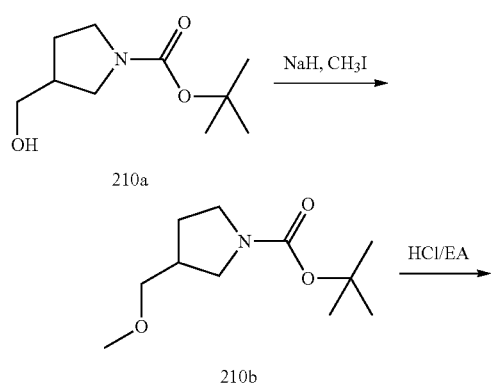

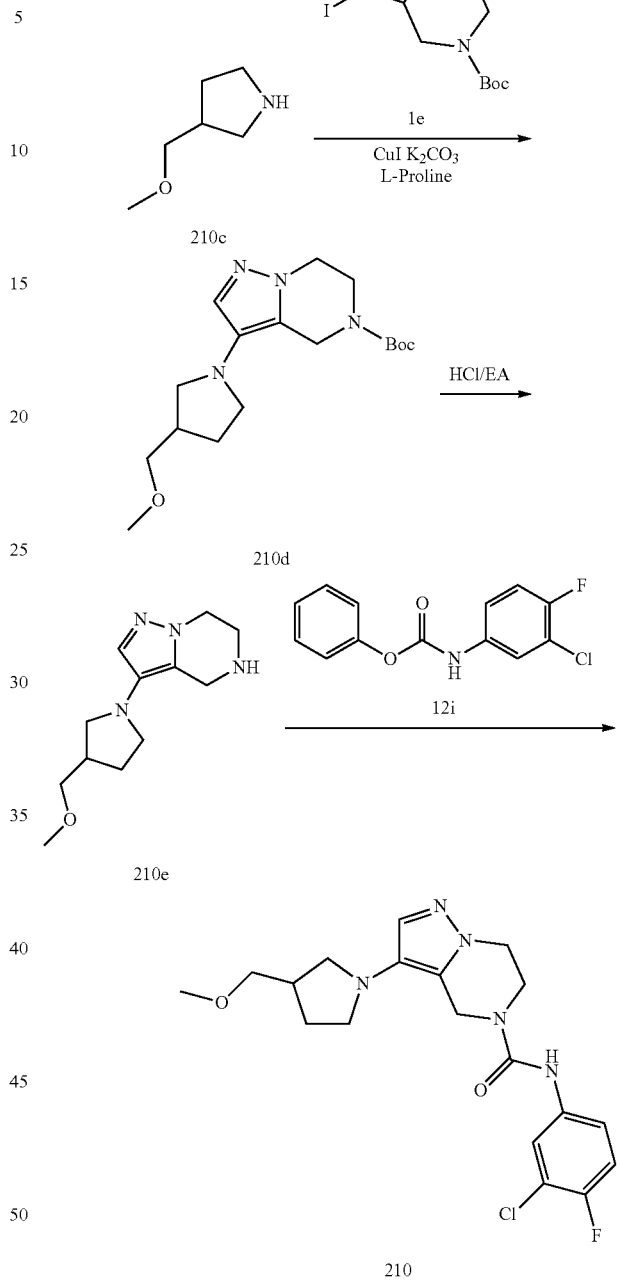

Step 1: Preparation of tert-butyl 3-(methoxymethyl)pyrrolidine-1-carboxylate (compound 210b)

To a solution of tert-butyl 3-(hydroxymethyl)pyrrolidine-1-carboxylate (compound 210a, 1.1 g, 5 mmol) in THF (30 mL) was added NaH (600 mg, 10 mmol, 60% oil dispersion) slowly at room temperature and followed by addition of methyl iodide (852 mg, 0.6 mmol). The reaction mixture was stirred at room temperature for 2 hours and then was quenched with water, extracted with EtOAc. The organic layer was dried and concentrated in vacuo to afford compound 210b (1.2 g) as a slight yellow oil. LCMS (M+H+): 216.

Step 2: Preparation of 3-(methoxymethyl)pyrrolidine (compound 210c)

A solution of tert-butyl 3-(methoxymethyl)pyrrolidine-1-carboxylate (compound 210b, 1.2 g, 5 mmol) in HCl/EA (30 mL) was stirred at room temperature for 2 hours. Then the reaction mixture was concentrated in vacuo to afford compound 210c (1 g) as a slight yellow solid. LCMS (M+H+): 116.

Step 3: Preparation of tert-butyl 3-[3-(methoxymethyl)pyrrolidin-1-yl]-6,7-dihydro-4H-pyrazolo[1,5-a]pyrazine-5-carboxylate (compound 210d)

To a mixture of 3-iodo-6,7-dihydro-4H-pyrazolo[1,5-a]pyrazine-5-carboxylate (compound 1e, 175 mg 0.5 mmol), 3-(methoxymethyl)pyrrolidine (compound 210c, 116 mg, 1.0 mmol), L-proline (23 mg, 0.2 mmol) and K$_2$CO$_3$ (207 mg, 1.5 mmol) in DMSO (5 mL) was added CuI (19 mg 0.1 mmol) under N$_2$. The resulting mixture was stirred in microwave for 2 hours at 120° C., diluted with water, and extracted with EtOAc. The organic layer was concentrated. The residue was purified by column chromatography to afford compound 210d (150 mg) as a slight yellow oil. LCMS (M+H+): 337.

Step 4: Preparation of 3-[3-(methoxymethyl)pyrrolidin-1-yl]-4,5,6,7-tetrahydropyrazolo[1,5-a]pyrazine (compound 210e)

A solution of tert-butyl 3-[3-(methoxymethyl)pyrrolidin-1-yl]-6,7-dihydro-4H-pyrazolo[1,5-a]pyrazine-5-carboxylate (compound 210d, 70 mg, 0.3 mmol) in HCl/EA (10 mL) was stirred at room temperature for 2 hours. Then the reaction mixture was concentrated in vacuo to afford compound 210e (60 mg) as a slight yellow solid. LCMS (M+H+): 237.

Step 5: Preparation of N-(3-chloro-4-fluoro-phenyl)-3-[3-(methoxymethyl)pyrrolidin-1-yl]-6,7-dihydro-4H-pyrazolo[1,5-a]pyrazine-5-carboxamide (Example 210)

The title compound was prepared in analogy to the preparation of Example 140 by using phenyl N-(3-chloro-4-fluoro-phenyl)carbamate (compound 12i) instead of phenyl N-(6-chloro-5-fluoro-2-pyridyl)carbamate (compound 140d) and 3-[2-(methoxymethyl)pyrrolidin-1-yl]-4,5,6,7-tetrahydropyrazolo[1,5-a]pyrazine (compound 210e) instead of 3-(4-fluorophenyl)-4,5,6,7-tetrahydropyrazolo[1,5-a]pyrazine (compound 11b). Example 210 was obtained as a white solid (8 mg). LCMS (M+H+): 408. $^1$H NMR (400 MHz, CD$_3$OD) δ ppm 7.62 (dd, J=2.6, 6.7 Hz, 1H), 7.36-7.32 (m, 1H), 7.21 (s, 1H), 7.17 (t, J=8.9 Hz, 1H), 4.83 (s, 2H), 4.18 (t, J=5.5 Hz, 2H), 4.00 (t, J=5.5 Hz, 2H), 3.43 (d, J=1.8 Hz, 2H), 3.41 (d, J=2.8 Hz, 2H), 3.38 (s, 3H), 3.35 (d, J=2.0 Hz, 1H), 3.24 (t, J=8.4 Hz, 1H), 3.18-3.09 (m, 1H), 2.92 (dd, J=6.0, 9.0 Hz, 1H), 2.62-2.57 (m, 1H), 2.17-2.05 (m, 1H), 1.72-1.67 (m, 1H).

Example 211

N-(3-chloro-4-fluoro-phenyl)-3-(3-methoxypyrrolidin-1-yl)-6,7-dihydro-4H-pyrazolo[1,5-a]pyrazine-5-carboxamide

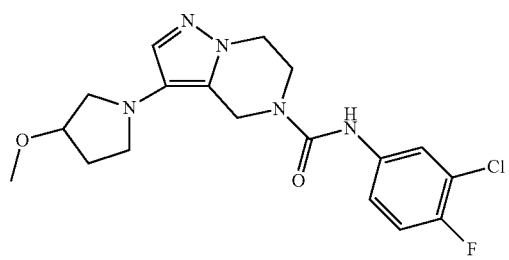 [SMILES: COC1CCN(c2cnn3c2CN(C(=O)Nc2ccc(F)c(Cl)c2)CC3)C1]

The title compound was prepared according to the following scheme:

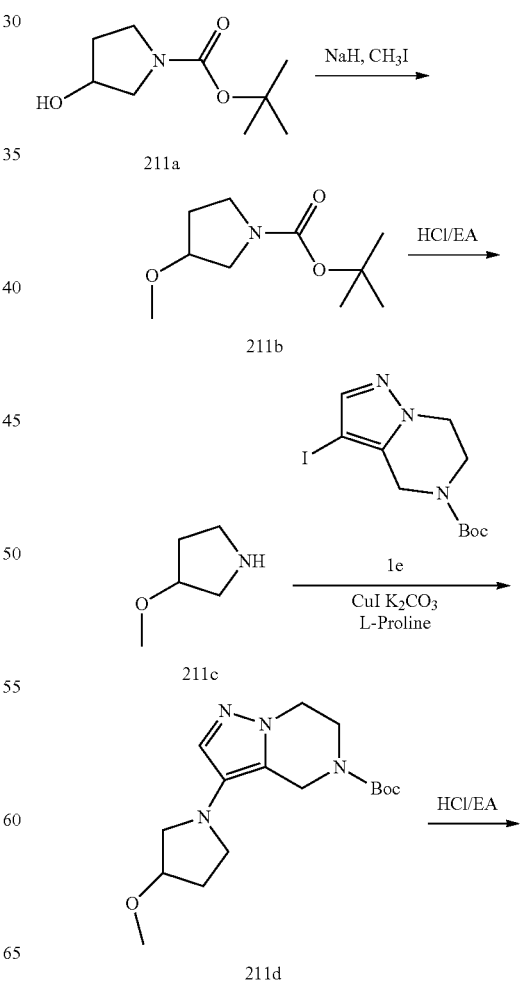

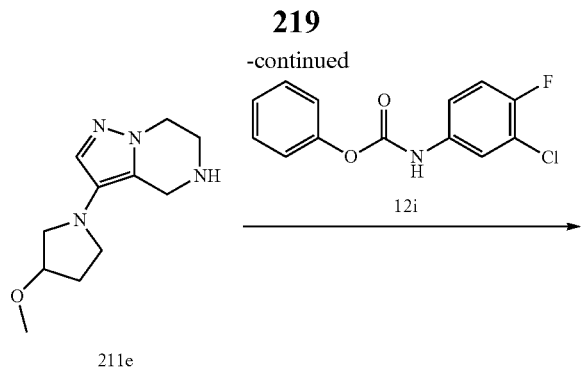

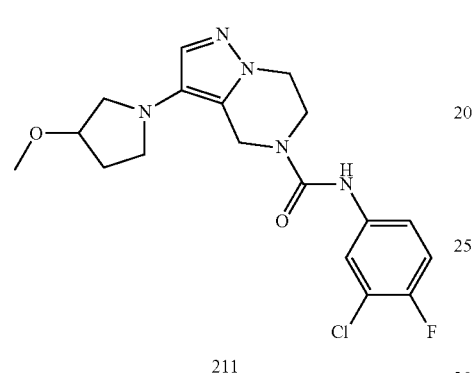

Preparation of 3-(3-methoxypyrrolidin-1-yl)-4,5,6,7-tetrahydropyrazolo[1,5-a]pyrazine (compound 211e)

The compound 211e was prepared in analogy to compound 210e by using tert-butyl 3-hydroxypyrrolidine-1-carboxylate (compound 211a, 1 g) instead of 3-(hydroxymethyl)pyrrolidine-1-carboxylate (compound 210a). Compound 211e was obtained as a slight yellow solid (60 mg). LCMS (M+H$^+$): 223.

Preparation of N-(3-chloro-4-fluoro-phenyl)-3-(3-methoxypyrrolidin-1-yl)-6,7-dihydro-4H-pyrazolo[1,5-a]pyrazine-5-carboxamide (Example 211)

The title compound was prepared in analogy to the preparation of Example 140 by using phenyl N-(3-chloro-4-fluoro-phenyl)carbamate (compound 12i) instead of phenyl N-(6-chloro-5-fluoro-2-pyridyl)carbamate (compound 140d) and 3-(3-methoxypyrrolidin-1-yl)-4,5,6,7-tetrahydropyrazolo[1,5-a]pyrazine (compound 211e) instead of 3-(4-fluorophenyl)-4,5,6,7-tetrahydropyrazolo[1,5-a]pyrazine (compound 11b). Example 211 was obtained as a white solid (2 mg). LCMS (M+H$^+$): 394. $^1$H NMR (400 MHz, CD$_3$OD) δ ppm 7.63 (dd, J=2.6, 6.7 Hz, 1H), 7.36-7.33 (m, 1H), 7.23 (s, 1H), 7.18 (t, J=9.0 Hz, 1H), 4.83 (s, 2H), 4.21-4.16 (m, 2H), 4.12-4.07 (m, 1H), 4.04-3.97 (m, 2H), 3.36 (s, 3H), 3.31-3.25 (m, 2H), 3.17 (dd, J=2.5, 10.3 Hz, 1H), 3.07-3.04 (m, 1H), 2.25-2.16 (m, 1H), 2.07-1.93 (m, 1H).

Example 212

N-(3-chloro-4-fluoro-phenyl)-3-(4,4-dimethyl-2-oxo-pyrrolidin-1-yl)-6-methyl-6,7-dihydro-4H-pyrazolo[1,5-a]pyrazine-5-carboxamide The title compound was prepared according to the following scheme:

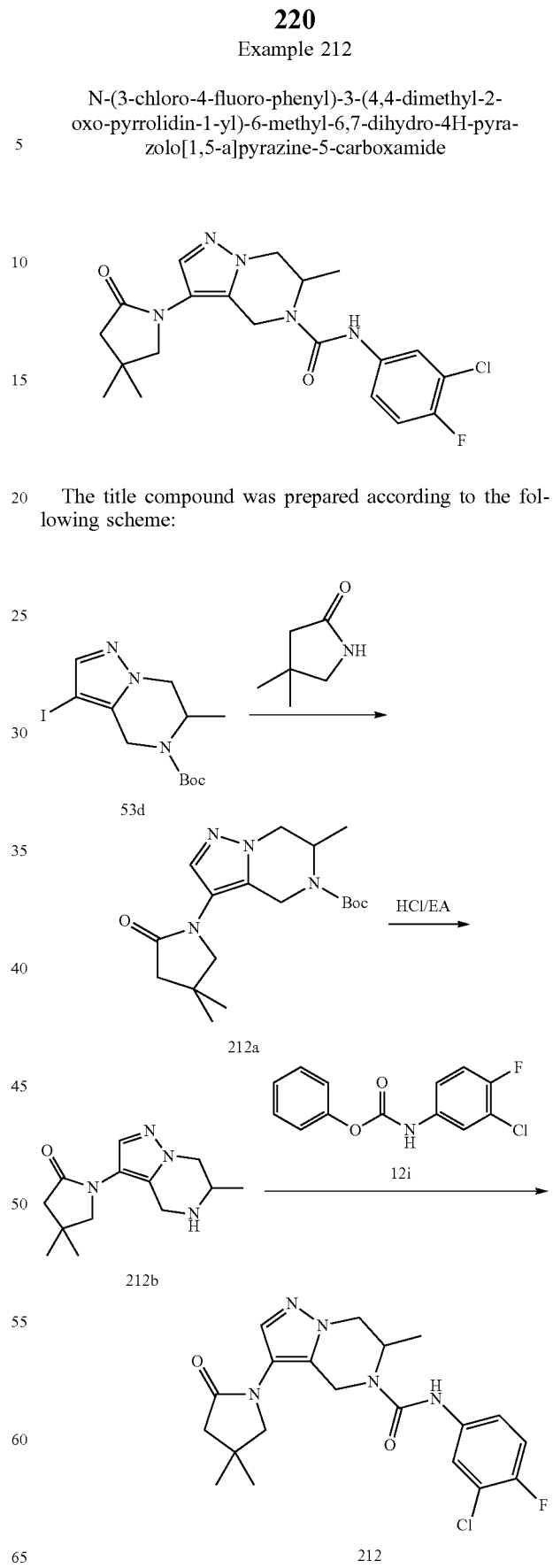

221

Step 1: Preparation of tert-butyl 3-(4,4-dimethyl-2-oxo-pyrrolidin-1-yl)-6-methyl-6,7-dihydro-4H-pyrazolo[1,5-a]pyrazine-5-carboxylate (compound 212a)

To mixture of tert-butyl 3-iodo-6-methyl-6,7-dihydro-4H-pyrazolo[1,5-a]pyrazine-5-carboxylate (compound 53d, 182 mg 0.5 mmol), 4,4-dimethylpyrrolidin-2-one (120 mg, 1.0 mmol), (1S,2S)-cyclohexane-1,2-diamine (23 mg, 0.2 mmol), CuI (19 mg 0.1 mmol) and $K_3PO_4$ (318 mg, 1.5 mmol) in DMSO (5 mL) under $N_2$ was stirred in microwave for 2 hours at 120° C. The reaction mixture was diluted with water, extracted with EtOAc. The organic layer was concentrated to afford compound 212a (150 mg) as a slight yellow oil. LCMS (M+H$^+$): 349.

Step 2: Preparation of 4,4-dimethyl-1-(6-methyl-4,5,6,7-tetrahydropyrazolo[1,5-a]pyrazin-3-yl)pyrrolidin-2-one (compound 212b)

A solution of tert-butyl 3-(4,4-dimethyl-2-oxo-pyrrolidin-1-yl)-6-methyl-6,7-dihydro-4H-pyrazolo[1,5-a]pyrazine-5-carboxylate (compound 212a, 150 mg, 0.4 mmol) in HCl/EA (15 mL) was stirred at room temperature for 2 hours. Then the reaction mixture was concentrated in vacuo to afford compound 212b (120 mg) as a slight yellow solid. LCMS (M+H$^+$): 249.

Step 3: Preparation of N-(3-chloro-4-fluoro-phenyl)-3-(4,4-dimethyl-2-oxo-pyrrolidin-1-yl)-6-methyl-6,7-dihydro-4H-pyrazolo[1,5-a]pyrazine-5-carboxamide (Example 212)

The title compound was prepared in analogy to the preparation of Example 140 by using phenyl N-(3-chloro-4-fluoro-phenyl)carbamate (compound 12i) instead of phenyl N-(6-chloro-5-fluoro-2-pyridyl)carbamate (compound 140d) and 4,4-dimethyl-1-(6-methyl-4,5,6,7-tetrahydropyrazolo[1,5-a]pyrazin-3-yl)pyrrolidin-2-one (compound 212b) instead of 3-(4-fluorophenyl)-4,5,6,7-tetrahydropyrazolo[1,5-a]pyrazine (compound 11b). Example 212 was obtained as a white solid (10 mg). LCMS (M+H$^+$): 420. $^1$H NMR (400 MHz, CD$_3$OD) δ ppm 7.66-7.57 (m, 2H), 7.35-7.33 (m, 1H), 7.17 (t, J=8.9 Hz, 1H), 5.04 (d, J=16.8 Hz, 1H), 4.99-4.93 (m, 1H), 4.51 (d, J=16.8 Hz, 1H), 4.30 (dd, J=4.4, 12.7 Hz, 1H), 4.19-4.16 (m, 1H), 3.67-3.51 (m, 2H), 2.41 (s, 2H), 1.36-1.17 (m, 9H).

Example 213

N-(3-chloro-4-fluoro-phenyl)-3-[3-(trifluoromethyl)pyrrolidin-1-yl]-6,7-dihydro-4H-pyrazolo[1,5-a]pyrazine-5-carboxamide

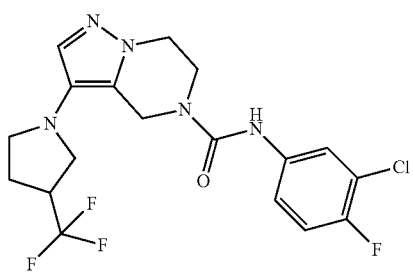 [SMILES: O=C(Nc1ccc(F)c(Cl)c1)N1CCn2ncc(N3CCC(C(F)(F)F)C3)c2C1]

222

The title compound was prepared according to the following scheme:

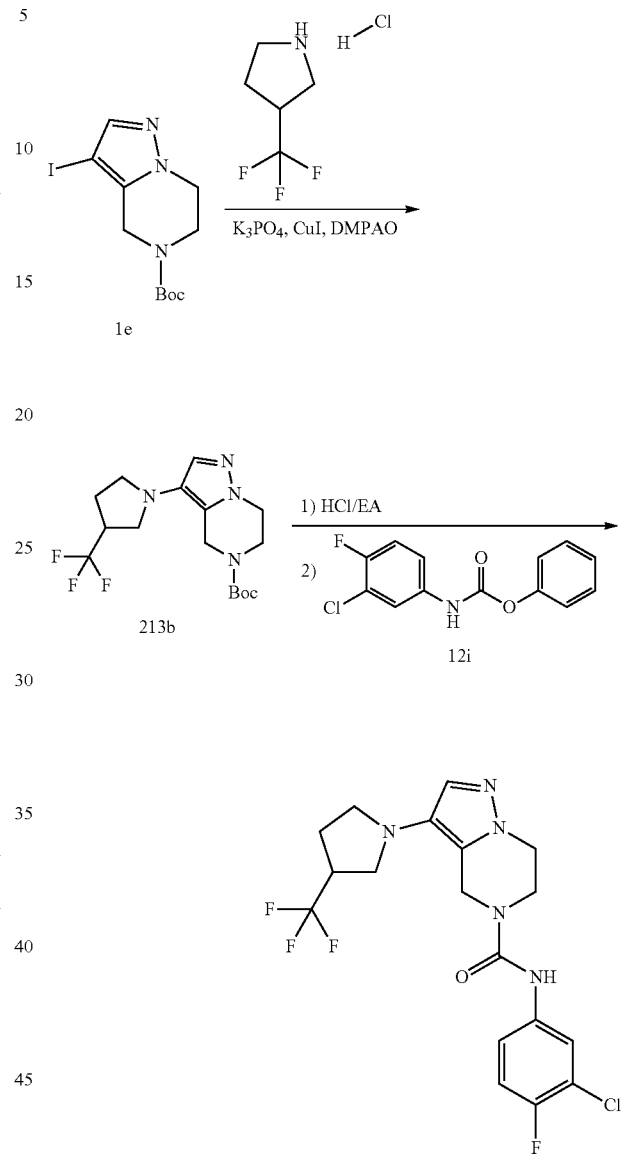

Preparation of N-(3-chloro-4-fluoro-phenyl)-3-[3-(trifluoromethyl)pyrrolidin-1-yl]-6,7-dihydro-4H-pyrazolo[1,5-a]pyrazine-5-carboxamide (Example 213)

The title compound was prepared in analogy to Example 168 by using 3-(trifluoromethyl)pyrrolidine hydrochloride instead of 2-methylpyrrolidine hydrochloride. Example 213 was obtained as a solid (5.0 mg). LCMS (M+H$^+$): 432. $^1$H NMR (400 MHz, chloroform-d) δ ppm 7.55 (dd, J=2.6, 6.4 Hz, 1H), 7.25-7.19 (m, 2H), 7.12 (d, J=8.5 Hz, 1H), 4.74 (s, 2H), 4.26 (t, J=5.4 Hz, 2H), 4.01-3.94 (m, 2H), 3.34 (s, 1H), 3.18 (s, 3H), 3.04 (d, J=9.5 Hz, 1H), 2.30-2.20 (m, 1H), 2.17-2.08 (m, 1H).

Example 214

N-(3-chloro-4-fluoro-phenyl)-3-(3-cyanopyrrolidin-1-yl)-6,7-dihydro-4H-pyrazolo[1,5-a]pyrazine-5-carboxamide

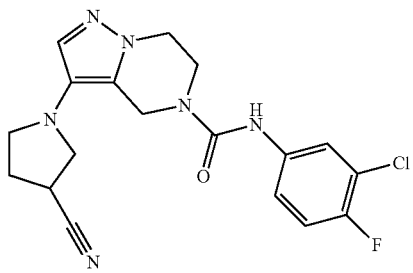 [SMILES: N#CC1CCN(c2cnn3c2CN(C(=O)Nc2ccc(F)c(Cl)c2)CC3)C1]

The title compound was prepared according to the following scheme:

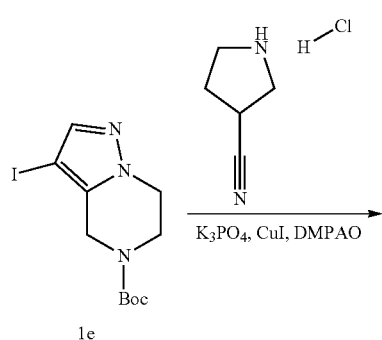

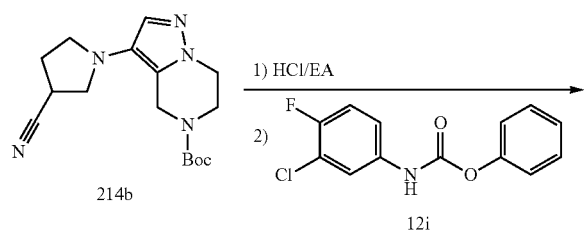

Preparation of N-(3-chloro-4-fluoro-phenyl)-3-(3-cyanopyrrolidin-1-yl)-6,7-dihydro-4H-pyrazolo[1,5-a]pyrazine-5-carboxamide (Example 214)

The title compound was prepared in analogy to Example 168 by using pyrrolidine-3-carbonitrile hydrochloride instead of 2-methylpyrrolidine hydrochloride. Example 214 was obtained as a solid (7.2 mg). LCMS (M+H$^+$): 389. $^1$H NMR (400 MHz, chloroform-d) δ ppm 7.54 (dd, J=2.6, 6.4 Hz, 1H), 7.27-7.20 (m, 2H), 7.13-7.04 (m, 1H), 6.72 (s, 1H), 4.79-4.68 (m, 2H), 4.25 (t, J=5.4 Hz, 2H), 4.03-3.94 (m, 2H), 3.40-3.34 (m, 2H), 3.33-3.26 (m, 1H), 3.25-3.11 (m, 2H), 2.47-2.25 (m, 2H).

Example 215

3-[3-azabicyclo[3.1.0]hexan-3-yl]-N-(3-chloro-4-fluoro-phenyl)-6,7-dihydro-4H-pyrazolo[1,5-a]pyrazine-5-carboxamide

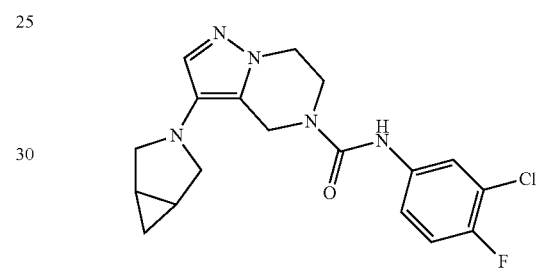

The title compound was prepared according to the following scheme:

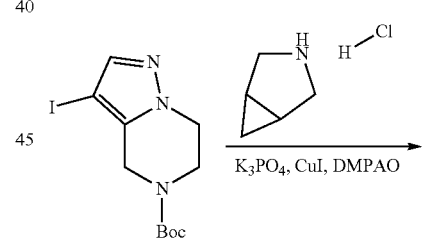

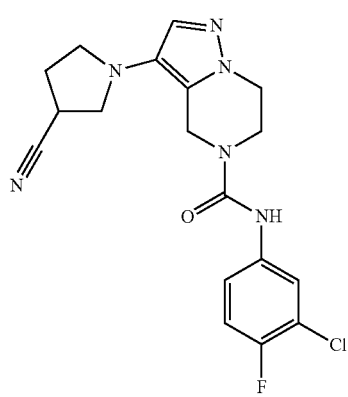

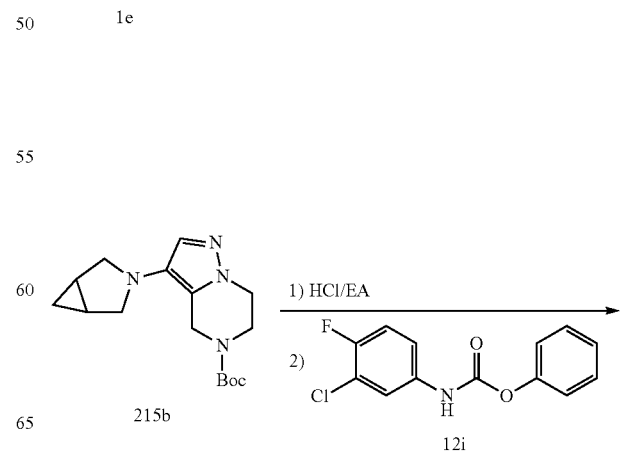

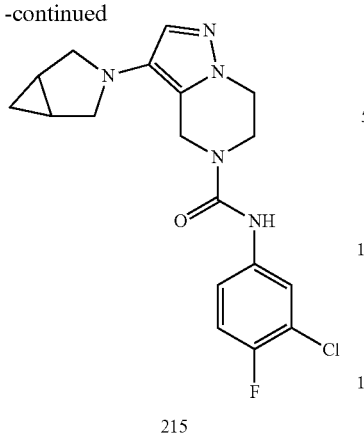

215

Preparation of 3-[3-azabicyclo[3.1.0]hexan-3-yl]-N-(3-chloro-4-fluoro-phenyl)-6,7-dihydro-4H-pyrazolo[1,5-a]pyrazine-5-carboxamide (Example 215)

The title compound was prepared in analogy to Example 168 by using 3-azabicyclo[3.1.0]hexane hydrochloride instead of 2-methylpyrrolidine hydrochloride. Example 215 was obtained as a solid (2.4 mg). LCMS (M+H$^+$): 376. $^1$H NMR (400 MHz, CD$_3$OD) δ ppm 7.62 (dd, J=2.6, 6.7 Hz, 1H), 7.34 (ddd, J=2.6, 4.2, 9.0 Hz, 1H), 7.24-7.08 (m, 2H), 4.80 (s, 2H), 4.21-4.12 (m, 2H), 4.04-3.94 (m, 2H), 3.42 (d, J=8.0 Hz, 2H), 3.02 (d, J=7.8 Hz, 2H), 1.63-1.53 (m, 2H), 0.68 (q, J=4.0 Hz, 1H), 0.57 (dt, J=4.4, 7.7 Hz, 1H).

Example 216

N-(3-chloro-4-fluoro-phenyl)-3-(3-hydroxy-3-methyl-pyrrolidin-1-yl)-6,7-dihydro-4H-pyrazolo[1,5-a]pyrazine-5-carboxamide

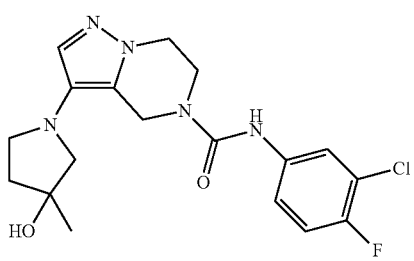 [SMILES: CC1(O)CCN(c2cnn3c2CN(C(=O)Nc2ccc(F)c(Cl)c2)CC3)C1]

The title compound was prepared according to the following scheme:

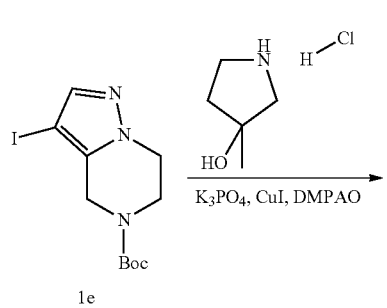

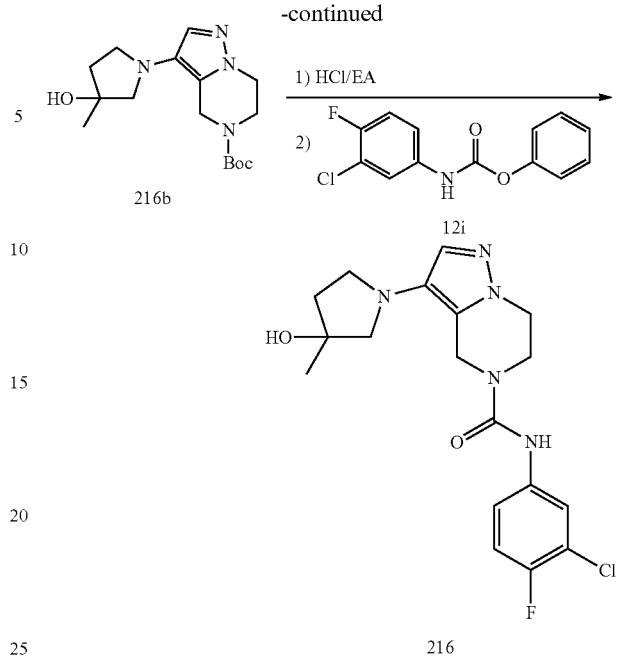

Preparation of N-(3-chloro-4-fluoro-phenyl)-3-(3-hydroxy-3-methyl-pyrrolidin-1-yl)-6,7-dihydro-4H-pyrazolo[1,5-a]pyrazine-5-carboxamide (Example 216)

The title compound was prepared in analogy to Example 168 by using 3-methylpyrrolidin-3-ol hydrochloride instead of 2-methylpyrrolidine hydrochloride. Example 216 was obtained as a solid (0.5 mg). LCMS (M+H$^+$): 394. $^1$H NMR (400 MHz, CD$_3$OD) δ ppm 7.62 (dd, 6.5 Hz, 1H), 7.38-7.31 (m, 1H), 7.22-7.17 (m, 2H), 4.84 (s, 2H), 4.22-4.14 (m, 2H), 4.04-3.97 (m, 2H), 3.46-3.35 (m, 2H), 3.21-3.14 (m, 2H), 2.05-1.97 (m, 2H), 1.45 (s, 3H).

Example 217

N-(3-chloro-4-fluoro-phenyl)-3-(2,2-dimethylmorpholin-4-yl)-6,7-dihydro-4H-pyrazolo[1,5-a]pyrazine-5-carboxamide

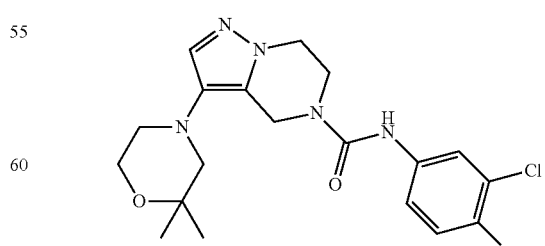

The title compound was prepared according to the following scheme:

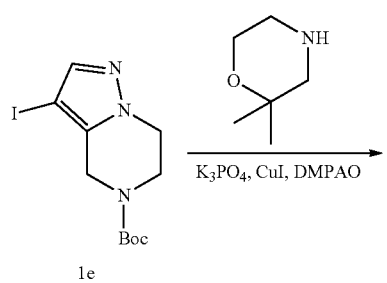
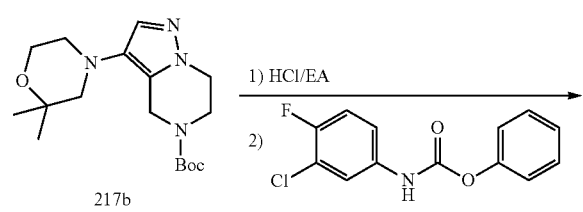
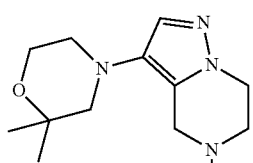

Preparation of N-(3-chloro-4-fluoro-phenyl)-3-(2,2-dimethylmorpholin-4-yl)-6,7-dihydro-4H-pyrazolo[1,5-a]pyrazine-5-carboxamide (Example 217)

The title compound was prepared in analogy to Example 168 by using 2,2-dimethylmorpholine instead of 2-methyl-pyrrolidine hydrochloride. Example 217 was obtained as a solid (12.2 mg). LCMS (M+H⁺): 408. ¹H NMR (400 MHz, CD₃OD) δ ppm 7.62 (dd, J=2.6, 6.7 Hz, 1H), 7.38-7.31 (m, 2H), 7.18 (t, J=8.9 Hz, 1H), 4.74 (s, 2H), 4.22-4.16 (m, 2H), 4.06-3.96 (m, 2H), 3.88-3.83 (m, 2H), 2.88-2.83 (m, 2H), 2.71 (s, 2H), 1.34 (s, 6H).

Example 218

N-[2-(difluoromethyl)-4-pyridyl]-3-(2,4-difluoro-phenyl)-6-methyl-6,7-dihydro-4H-pyrazolo[1,5-a]pyrazine-5-carboxamide

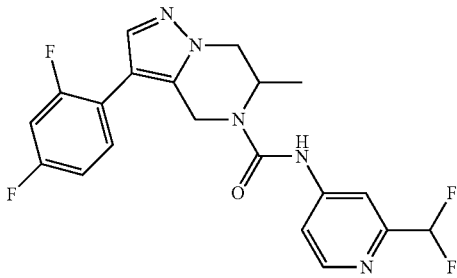 [SMILES: CC1Cn2ncc(-c3ccc(F)cc3F)c2CN1C(=O)Nc1ccnc(C(F)F)c1]

The title compound was prepared according to the following scheme:

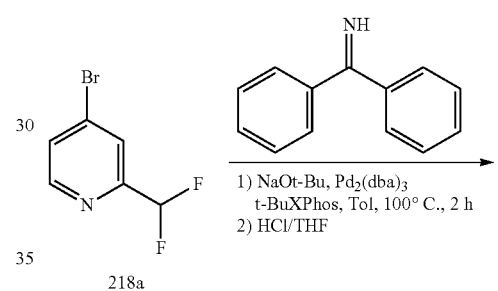
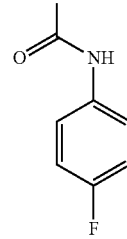
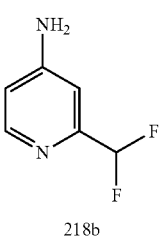
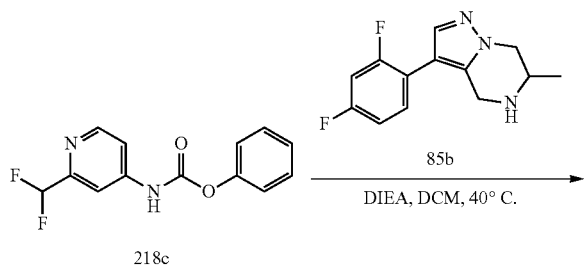

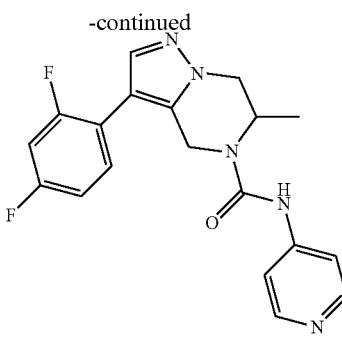

218

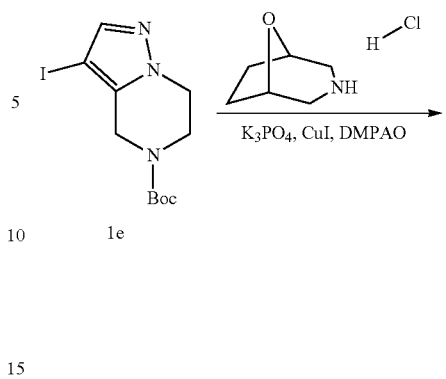

1e

Preparation of phenyl N-[2-(difluoromethyl)-4-pyridyl]carbamate (218c)

The compound 218c was prepared in analogy to compound 147c by using 4-bromo-2-(difluoromethyl)pyridine instead of 1-bromo-3-(1,1-difluoroethyl)benzene (compound 147a). Compound 218c was obtained as a yellow solid (264 mg). LCMS (M–H⁺): 263.

Preparation of N-[2-(difluoromethyl)-4-pyridyl]-3-(2,4-difluorophenyl)-6-methyl-6,7-dihydro-4H-pyrazolo[1,5-a]pyrazine-5-carboxamide (Example 218)

The title compound was prepared in analogy to Example 12 by using 3-(2,4-difluorophenyl)-6-methyl-4,5,6,7-tetrahydropyrazolo[1,5-a]pyrazine (compound 85b) instead of 8-(4-fluorophenyl)-1,2,3,4-tetrahydropyrrolo[1,2-a]pyrazine (compound 12h) and phenyl N-[2-(difluoromethyl)-4-pyridyl]carbamate (compound 218c) instead of phenyl N-(3-chloro-4-fluoro-phenyl)carbamate (compound 12i). Example 218 was obtained as a solid (30.3 mg). LCMS (M+H⁺): 420. $^1$H NMR (400 MHz, CD$_3$OD) δ ppm 8.41 (d, J=5.8 Hz, 1H), 7.87 (d, J=2.3 Hz, 1H), 7.74 (d, J=1.5 Hz, 1H), 7.66 (dd, 5.8 Hz, 1H), 7.55-7.48 (m, 1H), 7.14-7.05 (m, 2H), 6.82-6.50 (m, 1H), 5.16 (d, J=16.8 Hz, 1H), 5.08-5.01 (m, 1H), 4.65 (d, J=16.8 Hz, 1H), 4.40 (dd, J=4.4, 12.9 Hz, 1H), 4.29-4.24 (m, 1H), 1.32 (d, J=6.8 Hz, 3H).

Example 219

N-(3-chloro-4-fluoro-phenyl)-3-(8-oxa-3-azabicyclo[3.2.1]octan-3-yl)-6,7-dihydro-4H-pyrazolo[1,5-a]pyrazine-5-carboxamide

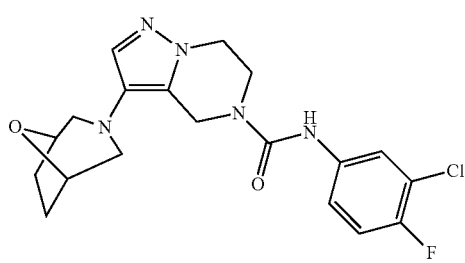 [SMILES: O=C(Nc1ccc(F)c(Cl)c1)N1CCn2ncc(N3CC4CCC(C3)O4)c2C1]

The title compound was prepared according to the following scheme:

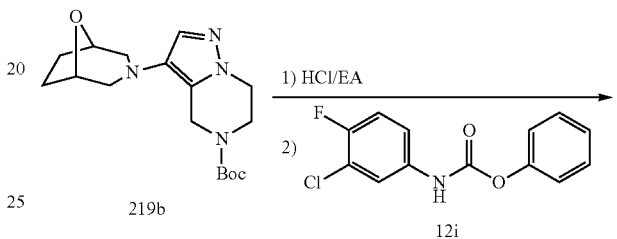

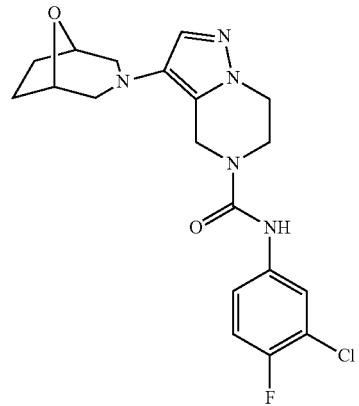

219

Preparation of N-(3-chloro-4-fluoro-phenyl)-3-[8-oxa-3-azabicyclo[3.2.1]octan-3-yl]-6,7-dihydro-4H-pyrazolo[1,5-a]pyrazine-5-carboxamide (Example 219)

The title compound was prepared in analogy to Example 168 by using 8-oxa-3-azabicyclo[3.2.1]octane hydrochloride instead of 2-methylpyrrolidine hydrochloride. Example 219 was obtained as a solid (6.4 mg). LCMS (M+H⁺): 406. $^1$H NMR (400 MHz, chloroform-d) δ ppm 7.52 (dd, J=2.6, 6.4 Hz, 1H), 7.29 (s, 1H), 7.21 (dd, J=2.9, 3.9 Hz, 1H), 7.13-7.07 (m, 1H), 6.57 (s, 1H), 4.67 (s, 2H), 4.44-4.36 (m, 2H), 4.28-4.20 (m, 2H), 3.95 (t, J=5.4 Hz, 2H), 3.06-2.98 (m, 2H), 2.81 (d, J=11.0 Hz, 2H), 2.08-1.97 (m, 4H).

Example 220

N-(3-chloro-4-fluoro-phenyl)-3-(3-oxomorpholin-4-yl)-6,7-dihydro-4H-pyrazolo[1,5-a]pyrazine-5-carboxamide

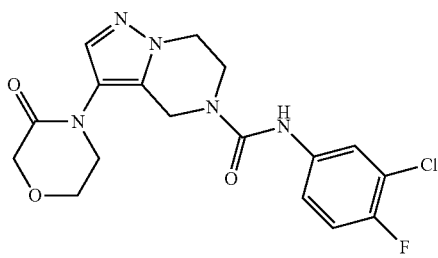 [SMILES: O=C(Nc1ccc(F)c(Cl)c1)N1CCn2ncc(N3CCOCC3=O)c2C1]

The title compound was prepared according to the following scheme:

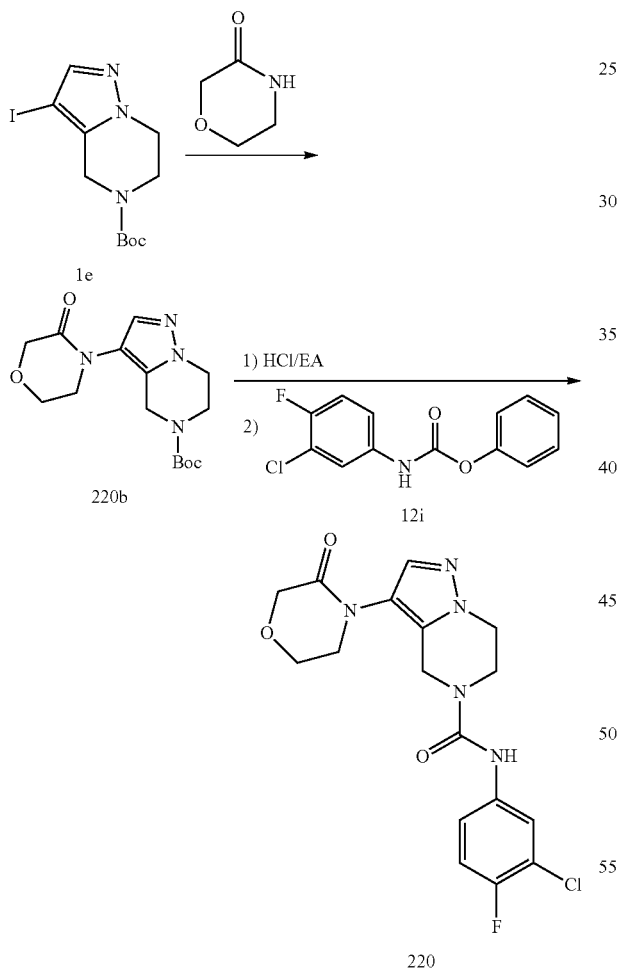

Step 1: Preparation of tert-butyl 3-(3-oxomorpholin-4-yl)-6,7-dihydro-4H-pyrazolo[1,5-a]pyrazine-5-carboxylate (compound 220b)

To a mixture of morpholin-3-one (24 mg, 0.24 mmol), tert-butyl 3-iodo-6,7-dihydro-4H-pyrazolo[1,5-a]pyrazine-5-carboxylate (compound 1e, 70 mg, 0.20 mmol), $K_3PO_4$ (85 mg, 0.40 mmol), CuI (7.6 mg, 40 μmol) and (1R,2R)-N1,N2-dimethylcyclohexane-1,2-diamine (5.7 mg, 40 μmol) was suspended in DMSO (5.0 mL). The reaction mixture was flushed with nitrogen and sealed. Then the reaction mixture was stirred at 105° C. in microwave for 2 hours. The reaction mixture was diluted with ethyl acetate, washed with water. The organic layer was concentrated to give crude compound 220b (65 mg). LCMS (M+H$^+$): 323.

Step 2: Preparation of N-(3-chloro-4-fluoro-phenyl)-3-(3-oxomorpholin-4-yl)-6,7-dihydro-4H-pyrazolo[1,5-a]pyrazine-5-carboxamide (Example 220)

A solution of tert-butyl 3-(3-oxomorpholin-4-yl)-6,7-dihydro-4H-pyrazolo[1,5-a]pyrazine-5-carboxylate (compound 220b, 129 mg, 0.40 mmol) in HCl/EA (1N, 5.0 mL) was stirred at room temperature overnight. Petroleum ether (45 mL) was added. The reaction mixture was centrifuged, and a yellowish solid was collected. The obtained solid was dissolved in DCM (3.0 mL), to which DIPEA (0.4 mL) and phenyl N-(3-chloro-4-fluoro-phenyl)carbamate (128 mg, 0.48 mmol) were added. The reaction mixture was stirred at 40° C. for 3 hours. The reaction mixture was concentrated in vacuo to give crude product, which was purified by preparative HPLC to afford Example 220 (61 mg). LCMS (M+H$^+$): 394. $^1$H NMR (400 MHz, chloroform-d) δ ppm 7.85 (s, 1H), 7.65 (dd, J=2.5, 6.5 Hz, 1H), 7.50 (s, 1H), 7.35-7.30 (m, 1H), 7.05 (t, J=8.8 Hz, 1H), 4.61 (s, 2H), 4.39 (s, 2H), 4.27-4.20 (m, 2H), 4.13-4.05 (m, 4H), 3.86-3.81 (m, 2H).

Example 221

N-(3-chloro-4-fluoro-phenyl)-3-(3-methyl-5-oxo-morpholin-4-yl)-6,7-dihydro-4H-pyrazolo[1,5-a]pyrazine-5-carboxamide

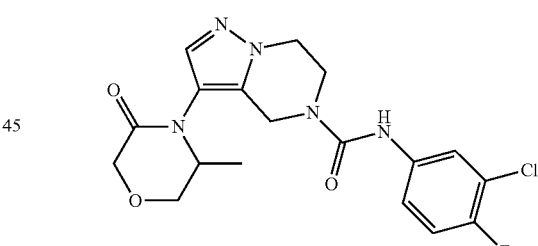

The title compound was prepared according to the following scheme:

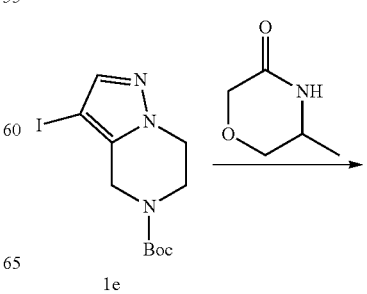

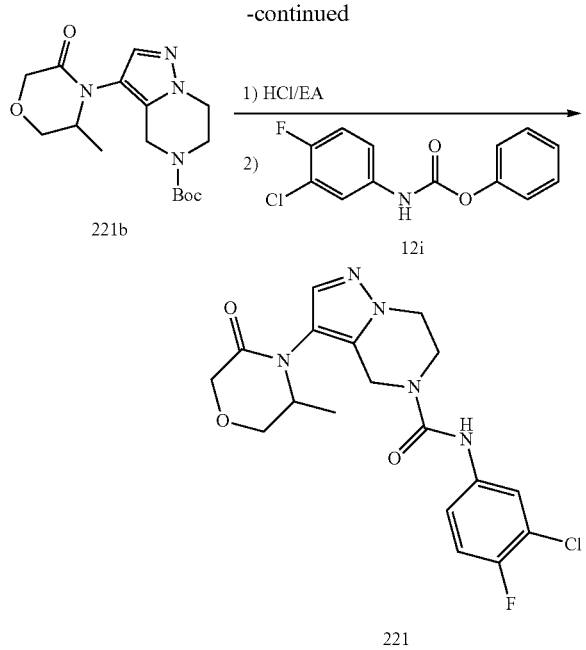

Preparation of N-(3-chloro-4-fluoro-phenyl)-3-(3-methyl-5-oxo-morpholin-4-yl)-6,7-dihydro-4H-pyrazolo[1,5-a]pyrazine-5-carboxamide (Example 221)

The title compound was prepared in analogy to Example 220 by using 5-methylmorpholin-3-one instead of morpholin-3-one. Example 221 was obtained as a solid (24.5 mg). LCMS (M+H$^+$): 408. $^1$H NMR (400 MHz, chloroform-d) δ ppm 7.83 (s, 1H), 7.64 (dd, J=2.6, 6.7 Hz, 1H), 7.47 (s, 1H), 7.35-7.29 (m, 1H), 7.04 (t, J=8.9 Hz, 1H), 4.83-4.76 (m, 1H), 4.52-4.45 (m, 1H), 4.42-4.33 (m, 2H), 4.32 (s, 1H), 4.32-4.26 (m, 1H), 4.26-4.20 (m, 2H), 4.11 (dd, J=3.5, 11.8 Hz, 1H), 4.03-3.97 (m, 1H), 3.80 (dd, J=4.1, 11.9 Hz, 1H), 3.77-3.69 (m, 1H), 1.28 (d, J=6.3 Hz, 3H).

Example 223

(6S)-N-[2-(difluoromethyl)-4-pyridyl]-6-methyl-3-(2-oxopyrrolidin-1-yl)-6,7-dihydro-4H-pyrazolo[1,5-a]pyrazine-5-carboxamide

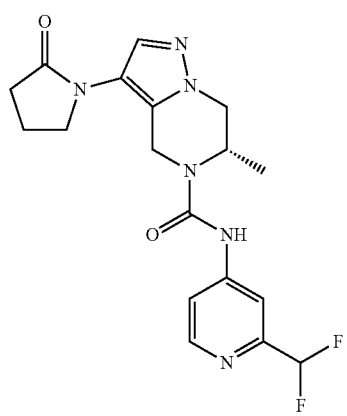 [SMILES: C[C@H]1Cn2ncc(N3CCCC3=O)c2CN1C(=O)Nc1ccnc(C(F)F)c1]

The title compound was prepared according to the following scheme:

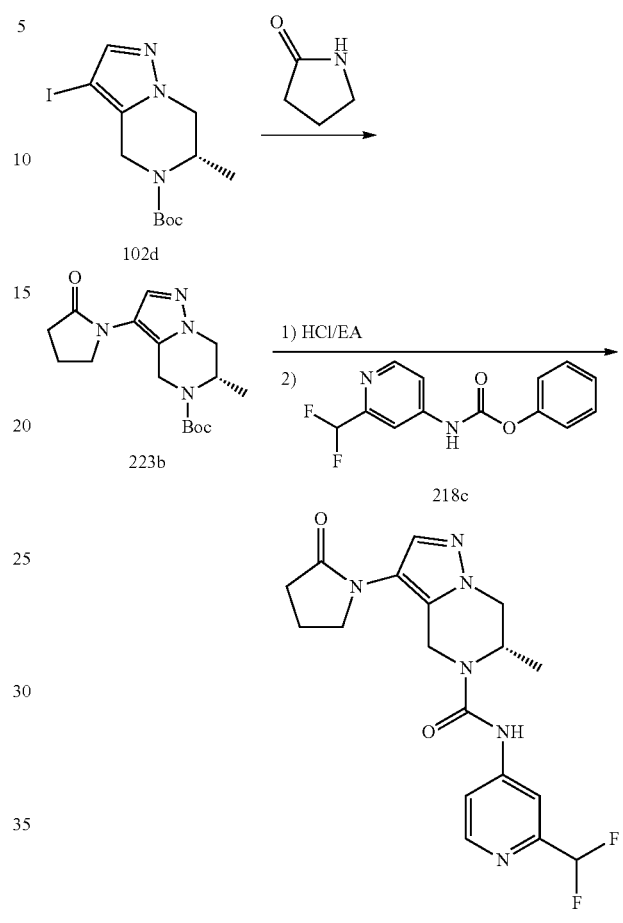

Step 1: Preparation of tert-butyl(6S)-6-methyl-3-(2-oxopyrrolidin-1-yl)-6,7-dihydro-4H-pyrazolo[1,5-a]pyrazine-5-carboxylate (compound 223b)

To a mixture of pyrrolidin-2-one (102 mg, 1.2 mmol), tert-butyl (6S)-3-iodo-6-methyl-6,7-dihydro-4H-pyrazolo[1,5-a]pyrazine-5-carboxylate (compound 102d, 363 mg, 1.0 mmol), K$_3$PO$_4$ (424 mg, 2.0 mmol), CuI (38.1 mg, 200 µmol) and (1R,2R)-N1,N2-dimethylcyclohexane-1,2-diamine (28.4 mg, 200 µmol) was suspended in DMSO (5.0 mL). The reaction mixture was flushed with nitrogen and sealed. Then the reaction mixture was stirred at 105° C. in microwave for 2 hours. The reaction mixture was diluted with ethyl acetate, and washed with water. The organic layer was concentrated to give crude compound 223b (320 mg). LCMS (M+H$^+$): 321.

Step 2: Preparation of (6S)-N-[2-(difluoromethyl)-4-pyridyl]-6-methyl-3-(2-oxopyrrolidin-1-yl)-6,7-dihydro-4H-pyrazolo[1,5-a]pyrazine-5-carboxamide (Example 223)

A solution of tert-butyl (6S)-6-methyl-3-(2-oxopyrrolidin-1-yl)-6,7-dihydro-4H-pyrazolo[1,5-a]pyrazine-5-carboxylate (compound 223b, 64 mg, 0.20 mmol) in HCl/EA (1N, 5.0 mL) was stirred at room temperature overnight. Petroleum ether (45 mL) was added. The reaction mixture was centrifuged, and a yellowish solid was collected. The obtained solid was dissolved in DCM (3.0 mL), to which DIPEA (0.4 mL) and phenyl N-[2-(difluoromethyl)-4-pyridyl]carbamate (compound 218c, 63.4 mg, 0.24 mmol) were added. The reaction mixture was stirred at 40° C. for 3 hours. The reaction mixture was concentrated in vacuo to give crude product, which was purified by preparative HPLC to afford Example 223 (11.3 mg). LCMS (M+H$^+$): 391. $^1$H NMR (400 MHz, chloroform-d) δ ppm 8.51 (s, 1H), 8.46 (d, J=5.8 Hz, 1H), 7.82 (d, J=2.0 Hz, 1H), 7.65 (d, J=5.5 Hz, 1H), 7.42 (s, 1H), 6.75-6.42 (m, 1H), 5.21 (d, J=16.8 Hz, 1H), 5.11-5.03 (m, 1H), 4.37 (d, J=16.8 Hz, 1H), 4.34-4.29 (m, 1H), 4.05-3.93 (m, 2H), 3.85-3.75 (m, 1H), 2.69-2.60 (m, 2H), 2.34-2.23 (m, 2H), 1.43 (d, J=6.8 Hz, 3H).

Example 224

(6S)-N-(3-chloro-4-fluoro-phenyl)-3-(3,3-difluoro-pyrrolidin-1-yl)-6-methyl-6,7-dihydro-4H-pyrazolo[1,5-a]pyrazine-5-carboxamide

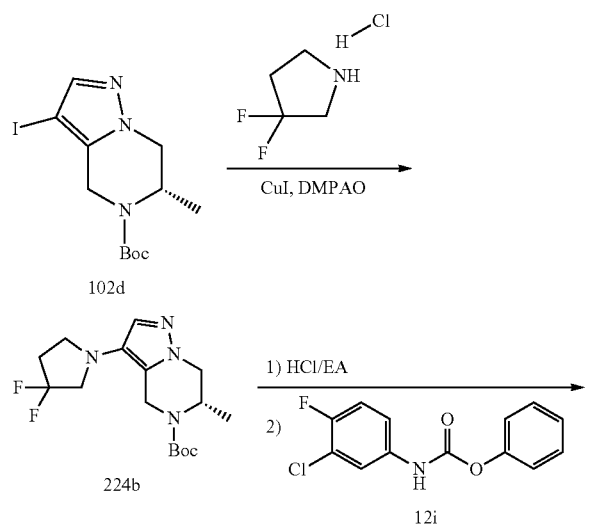

The title compound was prepared according to the following scheme:

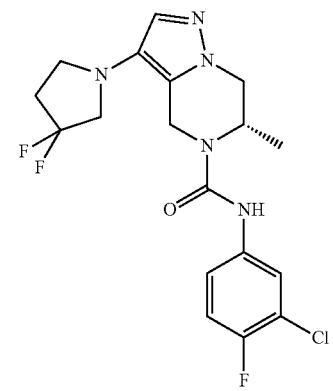

224

Preparation of (6S)-N-(3-chloro-4-fluoro-phenyl)-3-(3,3-difluoropyrrolidin-1-yl)-6-methyl-6,7-dihydro-4H-pyrazolo[1,5-a]pyrazine-5-carboxamide (Example 224)

The title compound was prepared in analogy to Example 168 by using 3,3-difluoropyrrolidine hydrochloride instead of 2-methylpyrrolidine hydrochloride. Example 224 was obtained as a solid (14.4 mg). LCMS (M+H$^+$): 414. $^1$H NMR (400 MHz, chloroform-d) δ ppm 7.57 (dd, 6.5 Hz, 1H), 7.28-7.21 (m, 2H), 7.14-7.08 (m, 1H), 6.48 (s, 1H), 4.88 (d, J=15.3 Hz, 2H), 4.51 (d, J=15.1 Hz, 1H), 4.30 (dd, J=4.1, 12.7 Hz, 1H), 4.18-4.11 (m, 1H), 3.46 (t, J=13.2 Hz, 2H), 3.31 (t, J=7.0 Hz, 2H), 2.52-2.39 (m, 2H), 1.26 (d, J=6.8 Hz, 3H).

Example 225

(6S)-N-(3-chloro-4-fluoro-phenyl)-3-[trans-2,6-dimethylmorpholin-4-yl]-6-methyl-6,7-dihydro-4H-pyrazolo[1,5-a]pyrazine-5-carboxamide

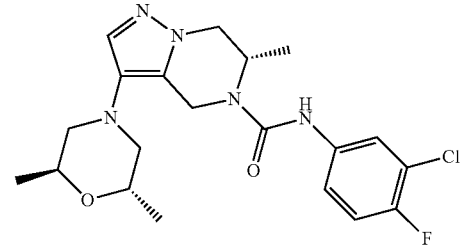 [SMILES: C[C@H]1CN(c2cnn3c2CN(C(=O)Nc2ccc(F)c(Cl)c2)[C@@H](C)C3)C[C@H](C)O1]

The title compound was prepared according to the following scheme:

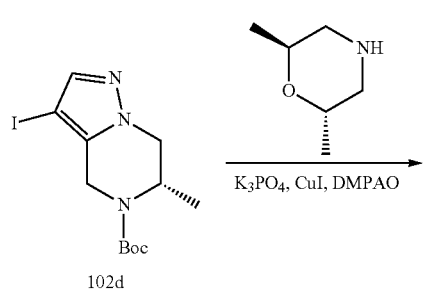

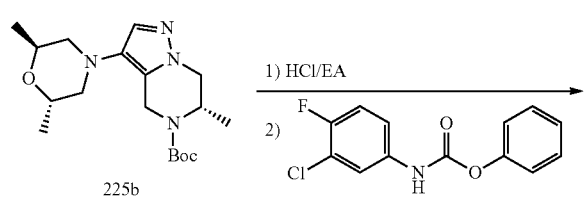

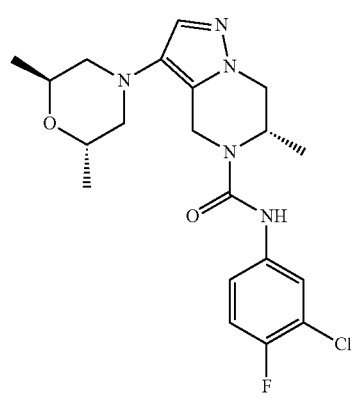

225

Preparation of (6S)-N-(3-chloro-4-fluoro-phenyl)-3-[trans-2,6-dimethylmorpholin-4-yl]-6-methyl-6,7-dihydro-4H-pyrazolo[1,5-a]pyrazine-5-carboxamide (Example 225)

The title compound was prepared in analogy to Example 168 by using trans-2,6-dimethylmorpholine instead of 2-methylpyrrolidine hydrochloride. Example 225 was obtained as a solid (25.8 mg). LCMS (M+H$^+$): 422. $^1$H NMR (400 MHz, chloroform-d) δ ppm 7.56 (dd, J=2.5, 6.5 Hz, 1H), 7.36 (d, J=6.3 Hz, 1H), 7.26-7.18 (m, 1H), 7.16-7.07 (m, 1H), 6.38 (s, 1H), 4.89-4.78 (m, 2H), 4.46 (dd, J=6.7, 15.4 Hz, 1H), 4.30 (dd, J=4.3, 12.8 Hz, 1H), 4.19-4.11 (m, 3H), 2.96 (dd, J=3.3, 11.0 Hz, 2H), 2.65-2.58 (m, 2H), 1.34 (d, J=6.5 Hz, 6H), 1.27 (dd, J=1.5, 6.8 Hz, 3H).

Example 226

(6S)-N-(3-chloro-4-fluoro-phenyl)-3-[cis-2,6-dimethylmorpholin-4-yl]-6-methyl-6,7-dihydro-4H-pyrazolo[1,5-a]pyrazine-5-carboxamide

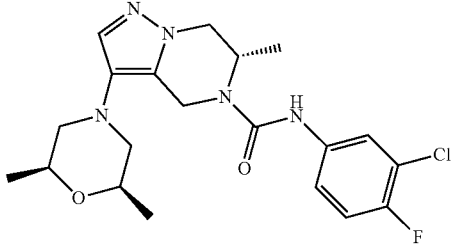 [SMILES: C[C@@H]1CN(c2cnn3c2CN(C(=O)Nc2ccc(F)c(Cl)c2)[C@@H](C)C3)C[C@H](C)O1]

The title compound was prepared according to the following scheme:

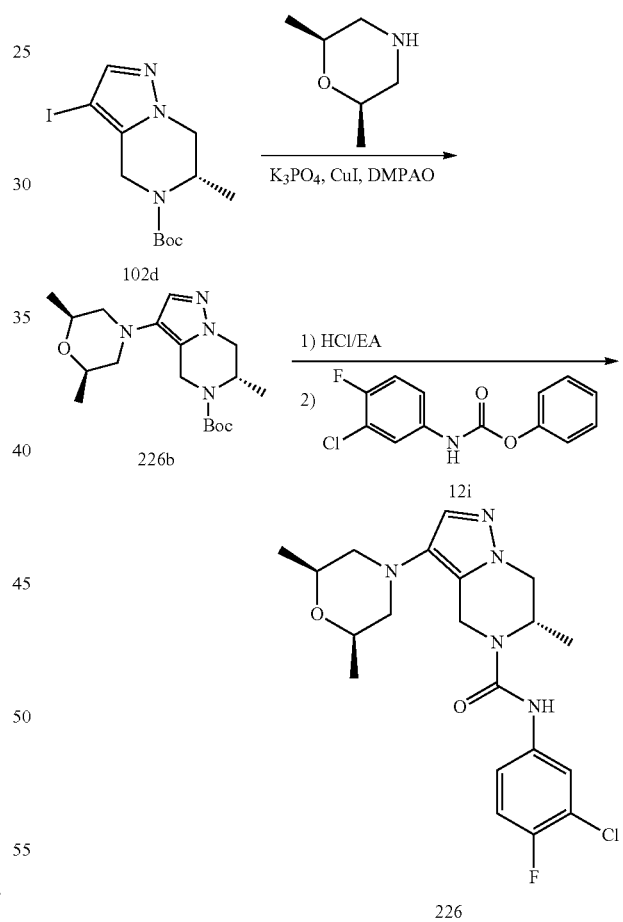

Preparation of (6S)-N-(3-chloro-4-fluoro-phenyl)-3-[cis-2,6-dimethylmorpholin-4-yl]-6-methyl-6,7-dihydro-4H-pyrazolo[1,5-a]pyrazine-5-carboxamide (Example 226)

The title compound was prepared in analogy to Example 168 by using cis-2,6-dimethylmorpholine instead of 2-methylpyrrolidine hydrochloride. Example 226 was obtained as a solid (34.0 mg). LCMS (M+H+): 422. ¹H NMR (400 MHz, chloroform-d) δ ppm 7.55 (dd, J=2.6, 6.4 Hz, 1H), 7.36 (s, 1H), 7.27-7.21 (m, 1H), 7.10 (t, J=8.5 Hz, 1H), 6.51 (s, 1H), 4.93-4.85 (m, 1H), 4.82 (d, J=15.3 Hz, 1H), 4.48 (d, J=15.3 Hz, 1H), 4.29 (dd, J=4.3, 12.8 Hz, 1H), 4.18-4.11 (m, 1H), 3.87-3.78 (m, 2H), 2.97-2.90 (m, 2H), 2.48-2.40 (m, 2H), 1.27-1.20 (m, 9H).

Example 227

(6S)-N-(3-chloro-4-fluoro-phenyl)-3-(4-hydroxy-1-piperidyl)-6-methyl-6,7-dihydro-4H-pyrazolo[1,5-a]pyrazine-5-carboxamide Preparation of (6S)-N-(3-chloro-4-fluoro-phenyl)-3-(4-hydroxy-1-piperidyl)-6-methyl-6,7-dihydro-4H-pyrazolo[1,5-a]pyrazine-5-carboxamide (Example 227)

The title compound was prepared in analogy to Example 168 by using piperidin-4-ol instead of 2-methylpyrrolidine hydrochloride. Example 227 was obtained as a solid (31.3 mg). LCMS (M+H+): 408. ¹H NMR (400 MHz, chloroform-d) δ ppm 7.58 (dd, J=2.6, 6.4 Hz, 1H), 7.38 (s, 1H), 7.27-7.21 (m, 1H), 7.11 (t, J=8.7 Hz, 1H), 6.55 (br. s., 1H), 4.98-4.89 (m, 1H), 4.82 (d, J=15.3 Hz, 1H), 4.49 (d, J=15.3 Hz, 1H), 4.29 (dd, J=4.3, 12.8 Hz, 1H), 4.14 (dd, J=1.1, 12.7 Hz, 1H), 3.90-3.82 (m, 1H), 3.14 (dd, J=4.6, 11.2 Hz, 2H), 2.78 (t, J=9.9 Hz, 2H), 2.02 (d, J=9.3 Hz, 2H), 1.79-1.67 (m, 4H), 1.24 (d, J=7.0 Hz, 3H).

Example 228

(6S)-N-(3-chloro-4-fluoro-phenyl)-6-methyl-3-(3-methyl-2-oxo-imidazolidin-1-yl)-6,7-dihydro-4H-pyrazolo[1,5-a]pyrazine-5-carboxamide

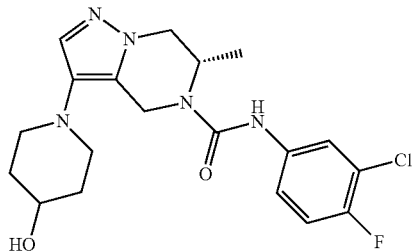 [SMILES: C[C@H]1Cn2ncc(N3CCC(O)CC3)c2CN1C(=O)Nc1ccc(F)c(Cl)c1]

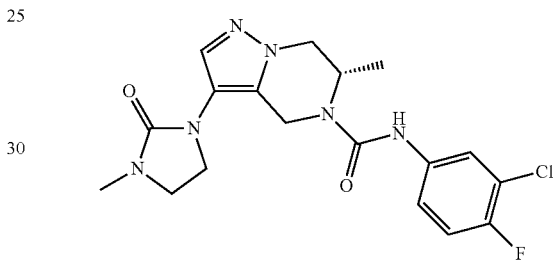

The title compound was prepared according to the following scheme:

The title compound was prepared according to the following scheme:

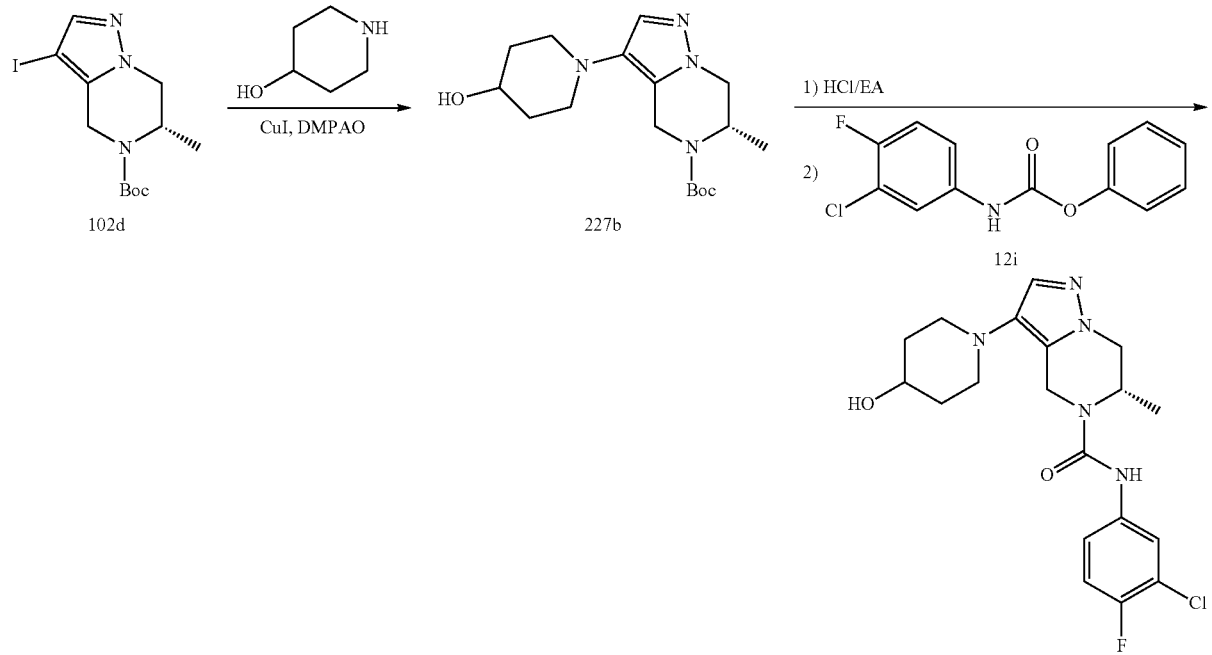

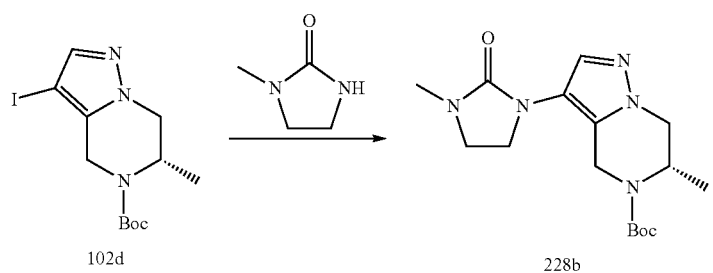 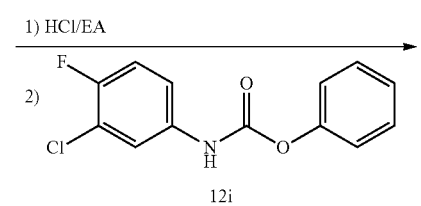

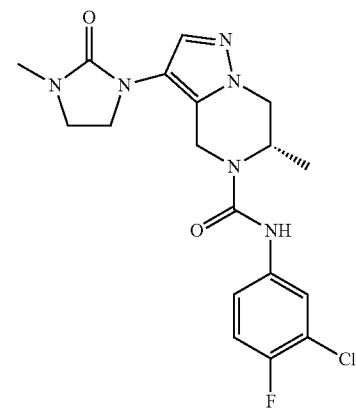

Preparation of (6S)-N-(3-chloro-4-fluoro-phenyl)-6-methyl-3-(3-methyl-2-oxo-imidazolidin-1-yl)-6,7-dihydro-4H-pyrazolo[1,5-a]pyrazine-5-carboxamide (Example 228)

The title compound was prepared in analogy to Example 220 by using 1-methylimidazolidin-2-one instead of morpholin-3-one and tert-butyl (6S)-3-iodo-6-methyl-6,7-dihydro-4H-pyrazolo[1,5-a]pyrazine-5-carboxylate (compound 102d) instead of tert-butyl 3-iodo-6,7-dihydro-4H-pyrazolo[1,5-a]pyrazine-5-carboxylate (compound 1e). Example 228 was obtained as a solid (15.1 mg). LCMS (M+H$^+$): 407. $^1$H NMR (400 MHz, chloroform-d) δ ppm 7.89 (s, 1H), 7.68 (dd, J=2.6, 6.7 Hz, 1H), 7.42-7.35 (m, 2H), 7.05 (t, J=8.9 Hz, 1H), 5.17 (d, J=16.6 Hz, 1H), 5.08 (t, J=7.2 Hz, 1H), 4.41 (d, J=16.6 Hz, 1H), 4.29 (dd, J=5.5, 12.8 Hz, 1H), 4.04-3.98 (m, 1H), 3.87 (d, J=8.8 Hz, 1H), 3.72 (d, J=6.3 Hz, 1H), 3.60-3.52 (m, 2H), 2.93 (s, 3H), 1.39 (d, J=7.0 Hz, 3H).

Example 229

(6S)-N-(3-chloro-4-fluoro-phenyl)-3-(4-cyano-2-oxo-pyrrolidin-1-yl)-6-methyl-6,7-dihydro-4H-pyrazolo[1,5-a]pyrazine-5-carboxamide

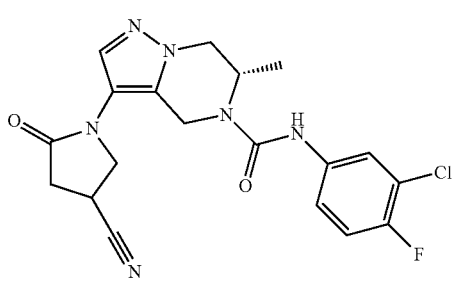 [SMILES: C[C@H]1Cn2ncc(N3CC(C#N)CC3=O)c2CN1C(=O)Nc1ccc(F)c(Cl)c1]

The title compound was prepared according to the following scheme:

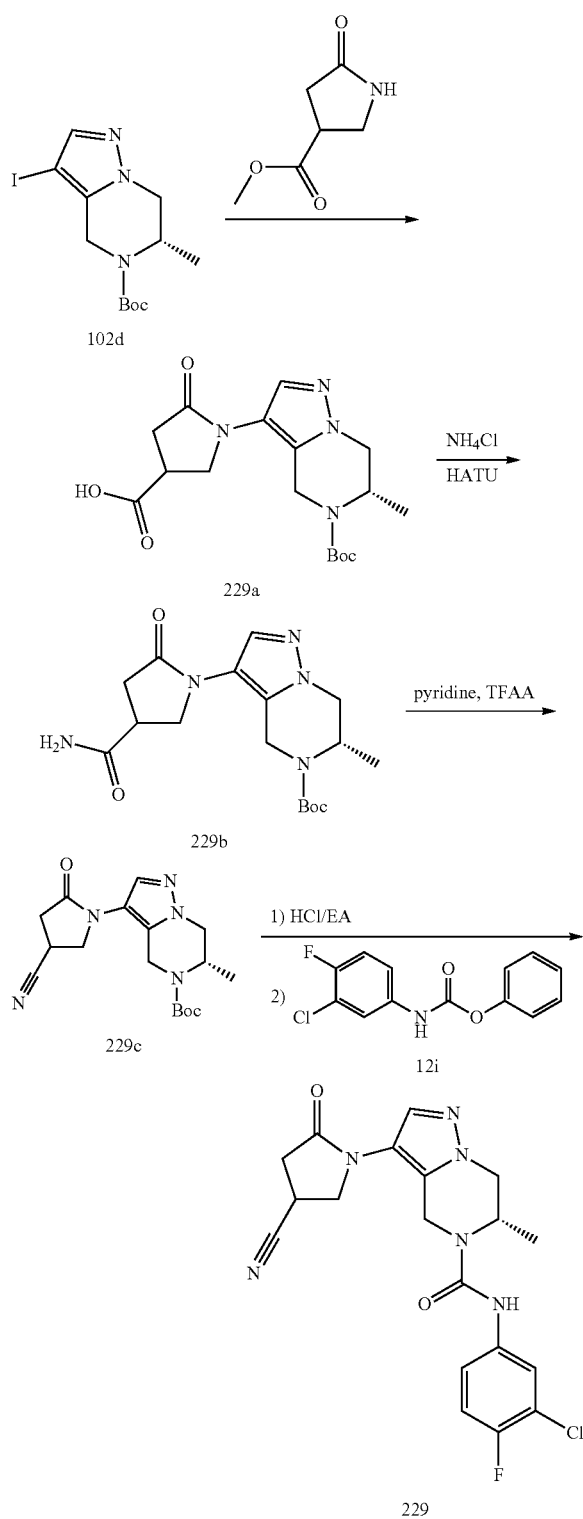

Step 1: Preparation of 1-[(6S)-5-tert-butoxycarbonyl-6-methyl-6,7-dihydro-4H-pyrazolo[1,5-a]pyrazin-3-yl]-5-oxo-pyrrolidine-3-carboxylic acid (compound 229a)

A mixture of tert-butyl (6S)-3-iodo-6-methyl-6,7-dihydro-4H-pyrazolo[1,5-a]pyrazine-5-carboxylate (compound 102d, 364 mg, 1.0 mmol), methyl 5-oxopyrrolidine-3-carboxylate (286 mg, 2.0 mmol), (1S,2S)-cyclohexane-1,2-diamine (46 mg, 0.4 mmol), CuI (38 mg 0.2 mmol) and $K_3PO_4$ (636 mg, 3 mmol) in DMSO (10 mL) under $N_2$ was stirred at microwave for 2 hours at 120° C. The reaction mixture was diluted with hydrochloride acid (0.5 M, 10 mL), extracted with EtOAc (20 mL) twice. The organic layer was concentrated to afford compound 229a (200 mg) as a slight yellow solid. LCMS (M+H$^+$): 365.

Step 2: Preparation of tert-butyl (6S)-3-(4-carbamoyl-2-oxo-pyrrolidin-1-yl)-6-methyl-6,7-dihydro-4H-pyrazolo[1,5-a]pyrazine-5-carboxylate (compound 229b)

A mixture of 1-[(6S)-5-tert-butoxycarbonyl-6-methyl-6,7-dihydro-4H-pyrazolo[1,5-a]pyrazin-3-yl]-5-oxo-pyrrolidine-3-carboxylic acid (compound 229a, 183 mg, 0.5 mmol), HATU (210 mg, 0.6 mmol), NH$_4$Cl (138 mg, 2.5 mmol) and DIPEA (770 mg, 6 mmol) in THF (10 mL) was stirred at 60° C. for 2 hours. The reaction mixture was diluted with hydrochloride acid (0.5 M, 15 mL), and extracted with EtOAc (20 mL) twice. The organic layer was concentrated to afford compound 229b (150 mg) as a slight yellow solid. LCMS (M+H$^+$): 364.

Step 3: Preparation of tert-butyl (6S)-3-(4-cyano-2-oxo-pyrrolidin-1-yl)-6-methyl-6,7-dihydro-4H-pyrazolo[1,5-a]pyrazine-5-carboxylate (compound 229c)

To a solution of tert-butyl (6S)-3-(4-carbamoyl-2-oxo-pyrrolidin-1-yl)-6-methyl-6,7-dihydro-4H-pyrazolo[1,5-a]pyrazine-5-carboxylate (compound 229b, 150 mg, 0.41 mmol) in dry tetrahydrofuran (5.0 mL) at 0° C. under nitrogen was added pyridine (0.5 mL, 6.2 mmol) followed by dropwise addition of a solution of trifluoroacetic anhydride (0.5 mL, 3.5 mmol) in dry tetrahydrofuran (1.0 mL). The resulting reaction mixture was allowed to warm slowly to room temperature, and stirred overnight, then quenched with ice-water, and extracted with EtOAc (20 mL) twice. The organic layer was concentrated to afford compound 229c (138 mg) as a slight yellow solid. LCMS (M+H$^+$): 346.

Step 4: Preparation of (6S)-N-(3-chloro-4-fluorophenyl)-3-(4-cyano-2-oxo-pyrrolidin-1-yl)-6-methyl-6,7-dihydro-4H-pyrazolo[1,5-a]pyrazine-5-carboxamide (Example 229)

The title compound was prepared in analogy to Example 220 by using tert-butyl (6S)-3-(4-cyano-2-oxo-pyrrolidin-1-yl)-6-methyl-6,7-dihydro-4H-pyrazolo[1,5-a]pyrazine-5-carboxylate (compound 229c) instead of tert-butyl 3-(3-oxomorpholin-4-yl)-6,7-dihydro-4H-pyrazolo[1,5-a]pyrazine-5-carboxylate (compound 220b). Example 229 was obtained as a solid (29.4 mg). LCMS (M+H$^+$): 417. $^1$H NMR (400 MHz, chloroform-d) δ ppm 7.65-7.58 (m, 1H), 7.45 (d, J=9.0 Hz, 1H), 7.33-7.29 (m, 1H), 7.26-7.18 (m, 1H), 7.07 (dt, J=1.0, 8.8 Hz, 1H), 5.15-4.96 (m, 2H), 4.43 (m, 1H), 4.31 (m, 1H), 4.22 (dd, J=8.0, 10.0 Hz, 0.5H), 4.15-4.05 (m, 2H), 4.03 (dd, J=5.1, 10.2 Hz, 0.5H), 3.63-3.53 (m, 1H), 3.07-2.90 (m, 2H), 1.36 (m, 3H).

Example 230

N-(3-chloro-4-fluoro-phenyl)-3-(4-fluorophenyl)-7-methyl-6,7-dihydro-4H-pyrazolo[1,5-a]pyrazine-5-carboxamide

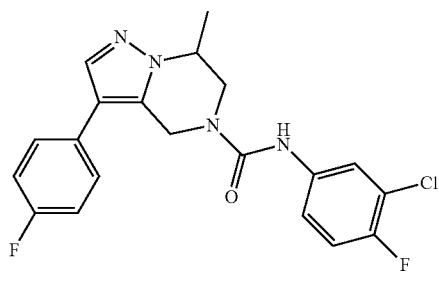 [SMILES: CC1CN(C(=O)Nc2ccc(F)c(Cl)c2)Cc2c(-c3ccc(F)cc3)cnn21]

The title compound was prepared according to the following scheme:

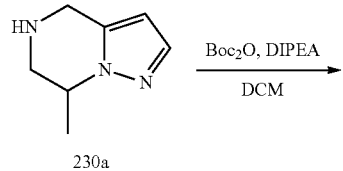

230a

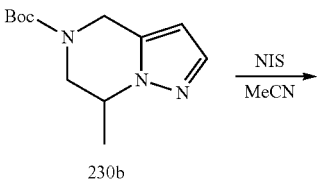

230b

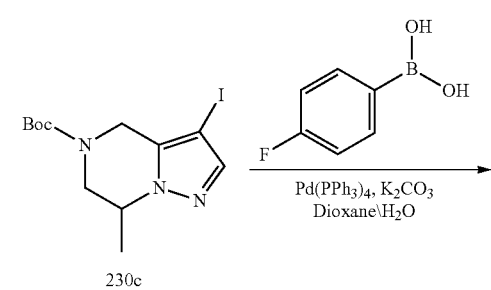

230c

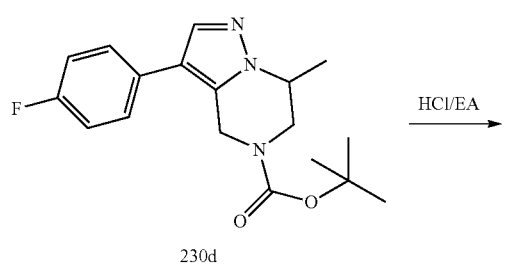

230d

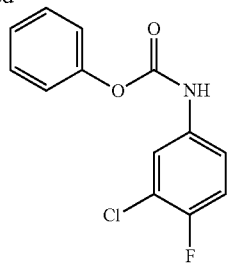

12i

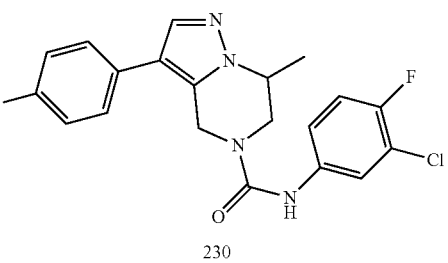

230

Preparation of 3-(4-fluorophenyl)-7-methyl-4,5,6,7-tetrahydropyrazolo[1,5-a]pyrazine (compound 230e)

The compound 230e was prepared in analogy to compound 9e by using 7-methyl-4,5,6,7-tetrahydropyrazolo[1,5-a]pyrazine (compound 230a, catalog number: PBCS1406244, PharmBlock(Nanjing) R&D Co. Ltd.) instead of 5,6,7,8-tetrahydroimidazo[1,5-a]pyrazine (compound 9a). Compound 230e was obtained as a white solid (250 mg). LCMS (M+H$^+$): 232.

Preparation of N-(3-chloro-4-fluoro-phenyl)-3-(4-fluorophenyl)-7-methyl-6,7-dihydro-4H-pyrazolo[1,5-a]pyrazine-5-carboxamide (Example 230)

The title compound was prepared in analogy to the preparation of Example 140 by using phenyl N-(3-chloro-4-fluoro-phenyl)carbamate (compound 12i) instead of phenyl N-(6-chloro-5-fluoro-2-pyridyl)carbamate (compound 140d) and 3-(4-fluorophenyl)-7-methyl-4,5,6,7-tetrahydropyrazolo[1,5-a]pyrazine (compound 230e) instead of 3-(4-fluorophenyl)-4,5,6,7-tetrahydropyrazolo[1,5-a]pyrazine (compound 11b). Example 230 was obtained as a white solid (21 mg). LCMS (M+H$^+$): 403. $^1$H NMR (400 MHz, CD$_3$OD) δ ppm 7.77 (s, 1H), 7.61 (dd, J=2.6, 6.7 Hz, 1H), 7.49 (dd, J=5.3, 9.0 Hz, 2H), 7.33-7.31 (m, 1H), 7.22-7.12 (m, 3H), 4.98 (s, 2H), 4.52-4.48 (m, 1H), 4.09 (dd, J=4.0, 14.1 Hz, 1H), 3.88 (dd, J=6.1, 13.9 Hz, 1H), 1.59 (d, J=6.5 Hz, 3H).

Example 231

(6S)-N-(3-chloro-4,5-difluoro-phenyl)-6-methyl-3-(2-oxopyrrolidin-1-yl)-6,7-dihydro-4H-pyrazolo[1,5-a]pyrazine-5-carboxamide

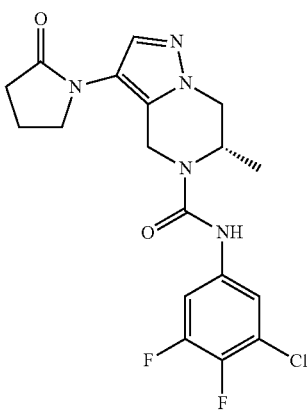 [SMILES: C[C@H]1Cn2ncc(N3CCCC3=O)c2CN1C(=O)Nc1cc(F)c(F)c(Cl)c1]

The title compound was prepared according to the following scheme:

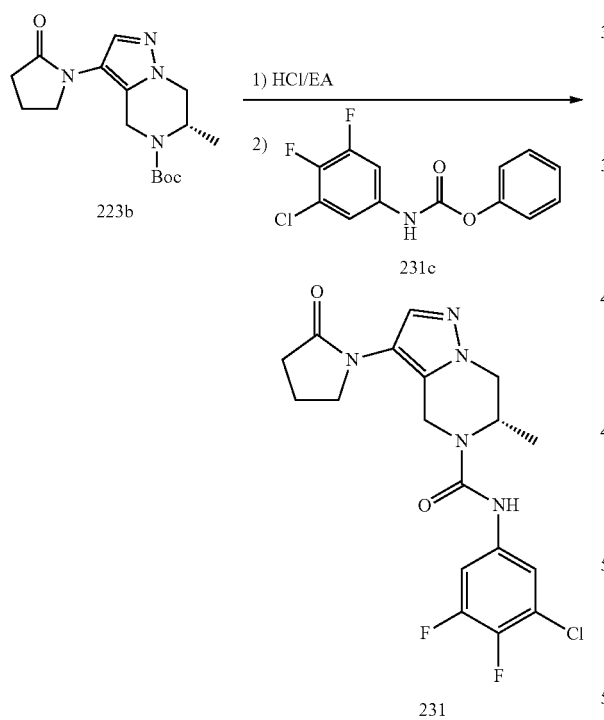

Preparation of (6S)-N-(3-chloro-4,5-difluoro-phenyl)-6-methyl-3-(2-oxopyrrolidin-1-yl)-6,7-dihydro-4H-pyrazolo[1,5-a]pyrazine-5-carboxamide (Example 231)

The title compound was prepared in analogy to Example 223 by using phenyl N-(3-chloro-4,5-difluoro-phenyl)carbamate (compound 231c) instead of phenyl N-[2-(difluoromethyl)-4-pyridyl]carbamate (compound 218c). Example 231 was obtained as a solid (24.0 mg). LCMS (M+H$^+$): 410. $^1$H NMR (400 MHz, chloroform-d) δ ppm 8.04 (s, 1H), 7.46-7.37 (m, 3H), 5.13 (d, J=17.1 Hz, 1H), 5.09-5.02 (m, 1H), 4.36-4.27 (m, 2H), 4.03-3.94 (m, 2H), 3.77 (ddd, J=5.4, 7.9, 9.5 Hz, 1H), 2.70-2.57 (m, 2H), 2.34-2.23 (m, 2H), 1.41 (d, J=6.8 Hz, 3H).

The compound 231c was prepared in analogy to compound 147c by using 3-chloro-4,5-difluoro-aniline instead of 3-(1,1-difluoroethyl)aniline (compound 147b).

Example 232

(6S)-N-(3-chloro-4-fluoro-phenyl)-3-(4-hydroxy-2-oxo-pyrrolidin-1-yl)-6-methyl-6,7-dihydro-4H-pyrazolo[1,5-a]pyrazine-5-carboxamide

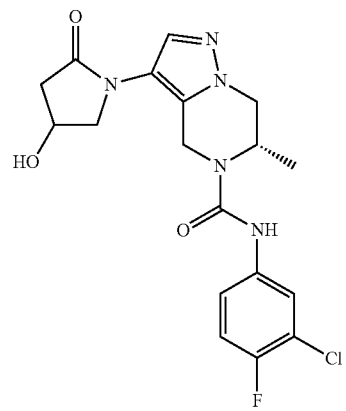 [SMILES: C[C@H]1Cn2ncc(N3CC(O)CC3=O)c2CN1C(=O)Nc1ccc(F)c(Cl)c1]

The title compound was prepared according to the following scheme:

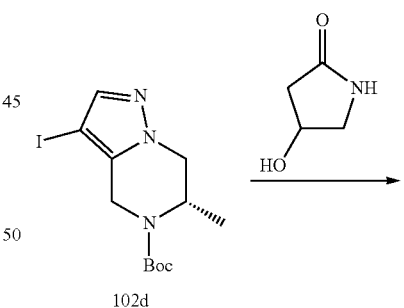

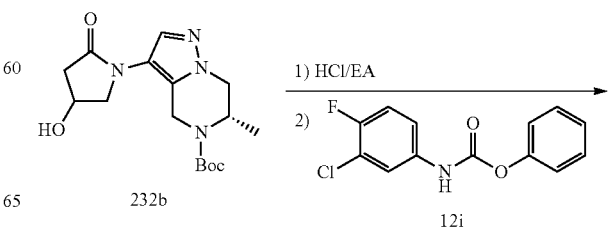

Preparation of (6S)-N-(3-chloro-4-fluoro-phenyl)-3-(4-hydroxy-2-oxo-pyrrolidin-1-yl)-6-methyl-6,7-dihydro-4H-pyrazolo[1,5-a]pyrazine-5-carboxamide (Example 232)

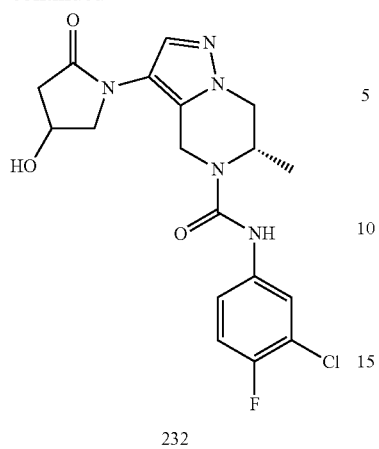

The title compound was prepared in analogy to Example 223 by using 4-hydroxypyrrolidin-2-one instead of pyrrolidin-2-one, and phenyl N-(3-chloro-4-fluoro-phenyl)carbamate (compound 12i) instead of phenyl N-[2-(difluoromethyl)-4-pyridyl]carbamate (compound 218c). Example 232 was obtained as a solid (9.5 mg). LCMS (M+H$^+$): 408. $^1$H NMR (400 MHz, chloroform-d) δ ppm 7.66-7.60 (m, 1H), 7.50 (s, 1H), 7.43 (d, J=12.8 Hz, 1H), 7.34-7.29 (m, 1H), 7.05 (dt, J=5.3, 8.8 Hz, 1H), 5.18 (d, J=16.8 Hz, 0.5H), 5.10 (t, J=6.8 Hz, 1H), 5.01 (d, J=16.6 Hz, 0.5H), 4.77-4.69 (m, 1H), 4.48 (d, J=16.6 Hz, 0.5H), 4.38 (d, J=16.8 Hz, 0.5H), 4.30 (dd, J=5.3, 12.8 Hz, 1H), 4.22-4.15 (m, 0.5H), 4.10-4.03 (m, 1.5H), 3.82-3.76 (m, 0.5H), 3.71-3.64 (m, 0.5H), 2.97-2.88 (m, 1H), 2.63-2.53 (m, 1H), 1.36 (dd, J=1.5, 7.0 Hz, 3H).

Example 233

(6S)-6-methyl-3-(3-oxomorpholin-4-yl)-N-(3,4,5-trifluorophenyl)-6,7-dihydro-4H-pyrazolo[1,5-a]pyrazine-5-carboxamide

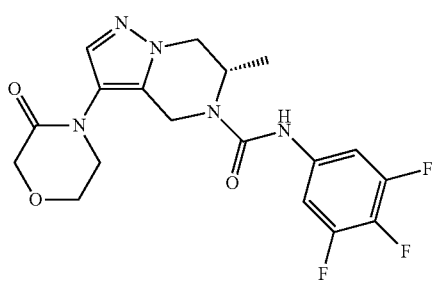 [SMILES: C[C@H]1Cn2ncc(N3CCOCC3=O)c2CN1C(=O)Nc1cc(F)c(F)c(F)c1]

The title compound was prepared according to the following scheme:

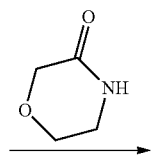

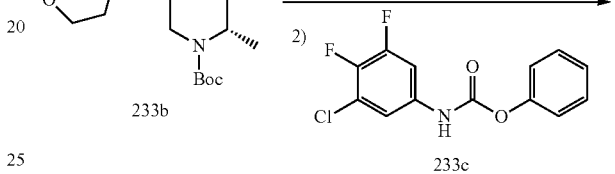

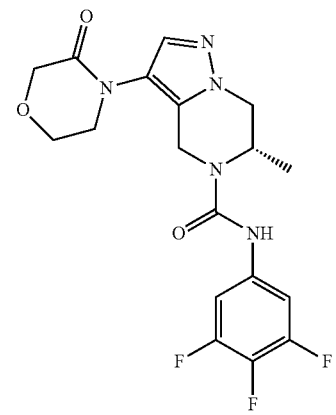

Preparation of (6S)-6-methyl-3-(3-oxomorpholin-4-yl)-N-(3,4,5-trifluorophenyl)-6,7-dihydro-4H-pyrazolo[1,5-a]pyrazine-5-carboxamide (Example 233)

The title compound was prepared in analogy to Example 223 by using morpholin-3-one instead of pyrrolidin-2-one, phenyl N-(3,4,5-trifluorophenyl)carbamate (compound 233c) instead of phenyl N-[2-(difluoromethyl)-4-pyridyl]carbamate (compound 218c). Example 233 was obtained as a solid (613 mg). LCMS (M+H$^+$): 410. $^1$H NMR (400 MHz, DMSO-d$_6$) δ ppm 9.07 (s, 1H), 7.63 (s, 1H), 7.47-7.39 (m, 2H), 4.91-4.82 (m, 2H), 4.31-4.11 (m, 5H), 3.97 (t, J=5.0 Hz, 2H), 3.79-3.65 (m, 2H), 1.13 (d, J=6.8 Hz, 3H).

The compound 233c was prepared in analogy to compound 147c by using 3,4,5-trifluoroaniline instead of 3-(1,1-difluoroethyl)aniline (compound 147b).

Example 234

3-(1-acetyl-4-piperidyl)-N-(3-chloro-4-fluoro-phenyl)-6-methyl-6,7-dihydro-4H-pyrazolo[1,5-a]pyrazine-5-carboxamide

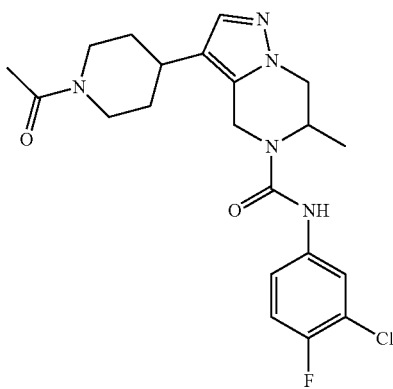 [SMILES: CC(=O)N1CCC(c2cnn3c2CN(C(=O)Nc2ccc(F)c(Cl)c2)C(C)C3)CC1]

The title compound was prepared according to the following scheme:

Preparation of 3-(1-acetyl-4-piperidyl)-N-(3-chloro-4-fluoro-phenyl)-6-methyl-6,7-dihydro-4H-pyrazolo[1,5-a]pyrazine-5-carboxamide (Example 234)

The title compound was prepared in analogy to Example 96 by using 1-[4-(4,4,5,5-tetramethyl-1,3,2-dioxaborolan-2-yl)-3,6-dihydro-2H-pyridin-1-yl]ethanone instead of cyclopenten-1-ylboronic acid. Example 234 was obtained as a solid (22.3 mg). LCMS (M+H$^+$): 434. $^1$H NMR (400 MHz, chloroform-d) δ ppm 7.57-7.53 (m, 1H), 7.39 (s, 1H), 7.28-7.23 (m, 1H), 7.11 (t, J=8.8 Hz, 1H), 6.68 (d, J=15.1 Hz, 1H), 4.93-4.83 (m, 2H), 4.75 (d, J=11.5 Hz, 1H), 4.49 (dd, J=3.6, 15.4 Hz, 1H), 4.36-4.29 (m, 1H), 4.22-4.16 (m, 1H), 3.94 (d, J=13.8 Hz, 1H), 3.22-3.14 (m, 1H), 2.74-2.61 (m, 2H), 2.15 (s, 3H), 1.97-1.85 (m, 2H), 1.70-1.63 (m, 1H), 1.58-1.51 (m, 1H), 1.26 (dd, J=2.8, 6.8 Hz, 3H).

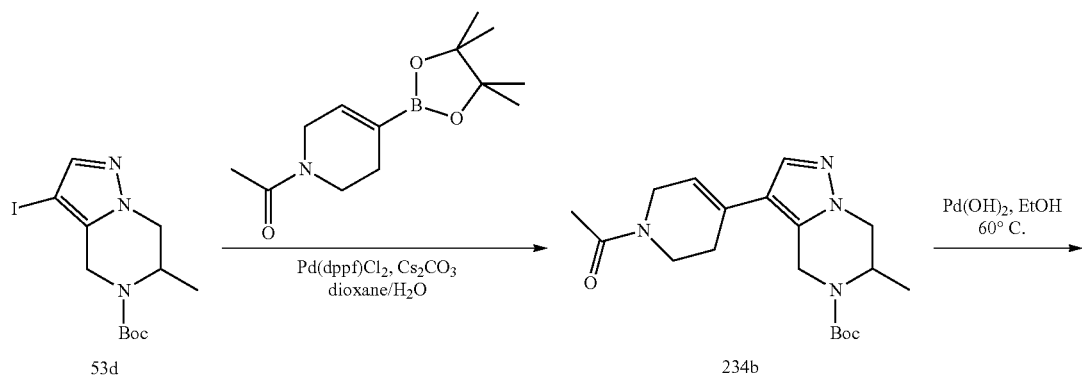

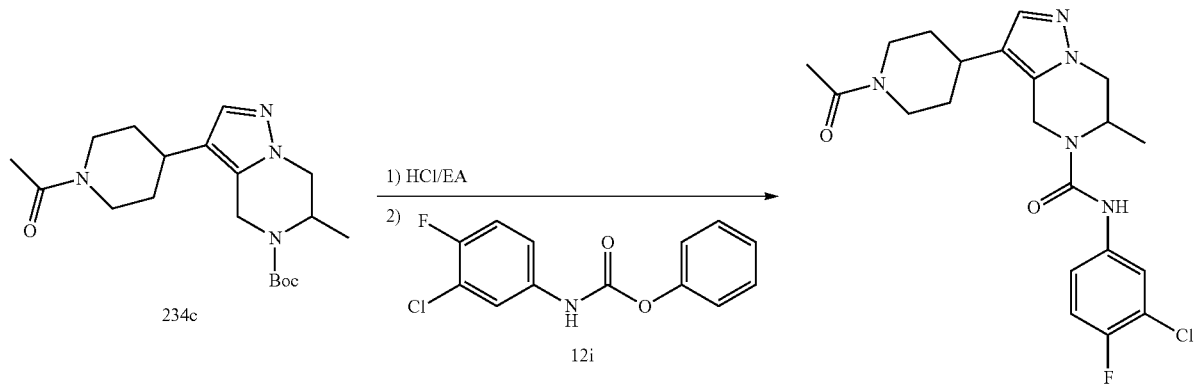

Example 235

(6S)-N-(3-chloro-4,5-difluoro-phenyl)-6-methyl-3-(3-oxomorpholin-4-yl)-6,7-dihydro-4H-pyrazolo[1,5-a]pyrazine-5-carboxamide

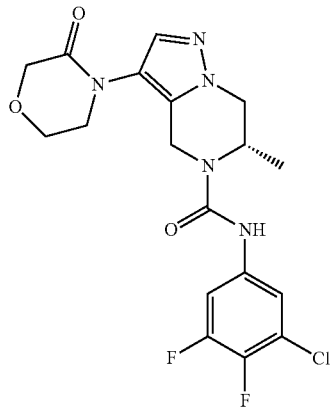 [SMILES: C[C@H]1Cn2ncc(N3CCOCC3=O)c2CN1C(=O)Nc1cc(F)c(F)c(Cl)c1]

The title compound was prepared according to the following scheme:

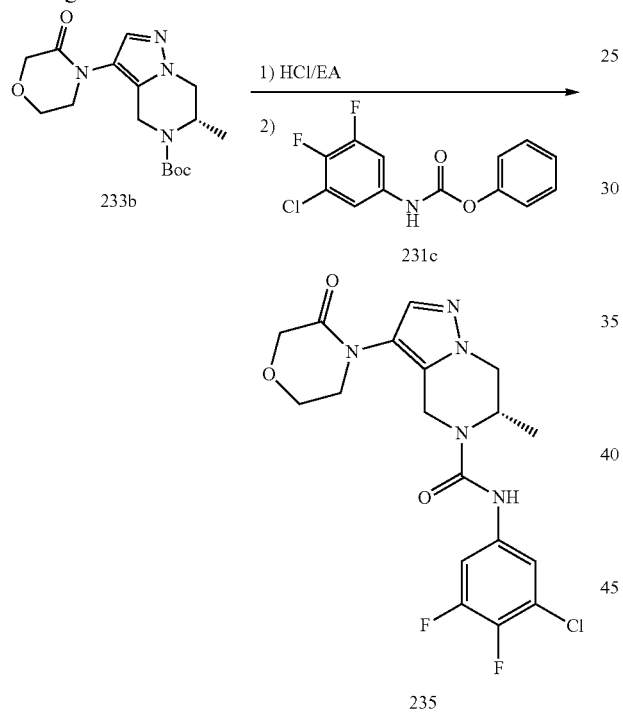

Preparation of (6S)-N-(3-chloro-4,5-difluoro-phenyl)-6-methyl-3-(3-oxomorpholin-4-yl)-6,7-dihydro-4H-pyrazolo[1,5-a]pyrazine-5-carboxamide (Example 235)

The title compound was prepared in analogy to the preparation of Example 223 by using phenyl N-(3-chloro-4,5-difluoro-phenyl)carbamate (compound 231c) instead of phenyl N-[2-(difluoromethyl)-4-pyridyl]carbamate (compound 218c), and tert-butyl (6S)-6-methyl-3-(3-oxomorpholin-4-yl)-6,7-dihydro-4H-pyrazolo[1,5-a]pyrazine-5-carboxylate (compound 233b) instead of tert-butyl (6S)-6-methyl-3-(2-oxopyrrolidin-1-yl)-6,7-dihydro-4H-pyrazolo[1,5-a]pyrazine-5-carboxylate (compound 223b). Example 235 was obtained as a solid (37.8 mg). LCMS (M+H$^+$): 426. $^1$H NMR (400 MHz, chloroform-d) δ ppm 7.76 (s, 1H), 7.52 (s, 1H), 7.45-7.32 (m, 2H), 5.08 (t, J=6.7 Hz, 1H), 4.88 (d, J=16.8 Hz, 1H), 4.40 (s, 2H), 4.34-4.27 (m, 2H), 4.16-4.01 (m, 3H), 4.01-3.92 (m, 1H), 3.78-3.69 (m, 1H), 1.41 (d, J=7.0 Hz, 3H).

Example 236

(6S)-N-(3-chloro-4-fluoro-phenyl)-6-methyl-3-[4-(methylcarbamoyl)-2-oxo-pyrrolidin-1-yl]-6,7-dihydro-4H-pyrazolo[1,5-a]pyrazine-5-carboxamide

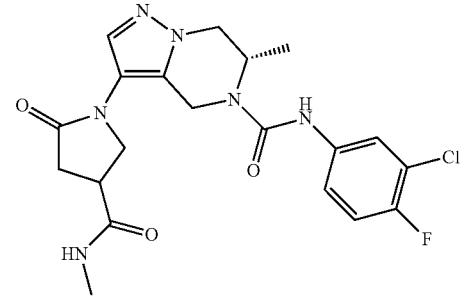 [SMILES: CNC(=O)C1CC(=O)N(c2cnn3c2CN(C(=O)Nc2ccc(F)c(Cl)c2)[C@@H](C)C3)C1]

The title compound was prepared according to the following scheme:

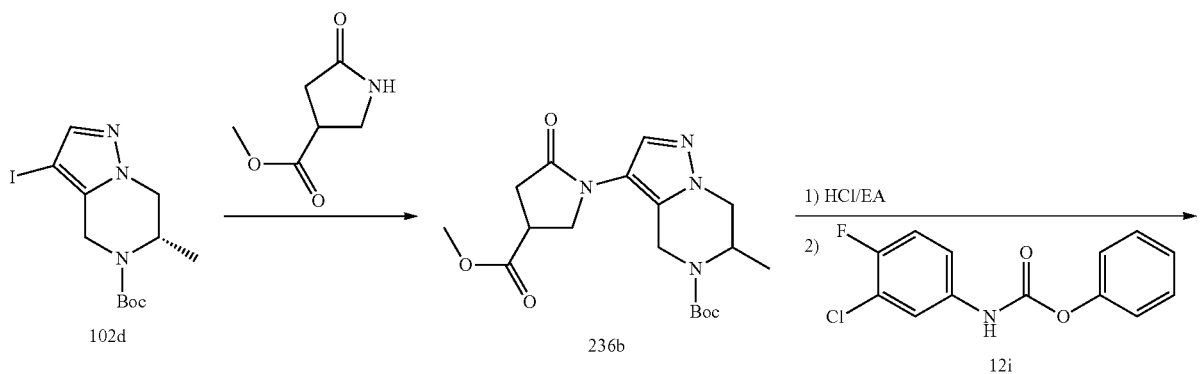

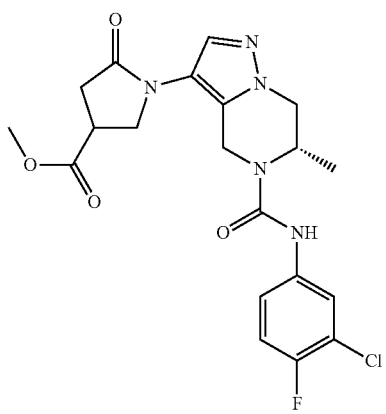

236c

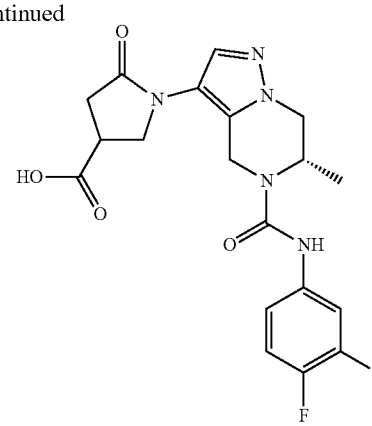

236d

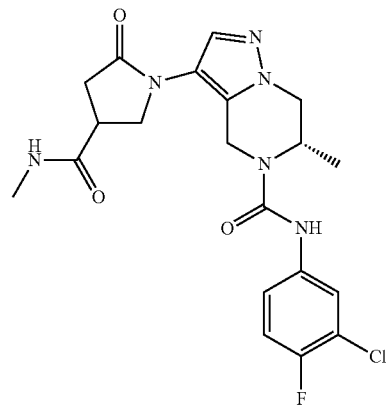

236

Preparation of methyl 1-[(6S)-5-[(3-chloro-4-fluoro-phenyl)carbamoyl]-6-methyl-6,7-dihydro-4H-pyrazolo[1,5-a]pyrazin-3-yl]-5-oxo-pyrrolidine-3-carboxylate (compound 236c)

Compound 236c was prepared in analogy to Example 223 by using methyl 5-oxopyrrolidine-3-carboxylate instead of pyrrolidin-2-one and phenyl N-(3-chloro-4-fluoro-phenyl)carbamate (compound 12i) instead of phenyl N-[2-(difluoromethyl)-4-pyridyl]carbamate (compound 218c). Compound 236c was obtained as a solid (132 mg). LCMS (M+H$^+$): 450.

Preparation of 1-[(6S)-5-[(3-chloro-4-fluoro-phenyl)carbamoyl]-6-methyl-6,7-dihydro-4H-pyrazolo[1,5-a]pyrazin-3-yl]-5-oxo-pyrrolidine-3-carboxylic acid (compound 236d)

To a solution of methyl 1-[(6S)-5-[(3-chloro-4-fluoro-phenyl)carbamoyl]-6-methyl-6,7-dihydro-4H-pyrazolo[1,5-a]pyrazin-3-yl]-5-oxo-pyrrolidine-3-carboxylate (compound 236c, 120 mg, 0.27 mmol) in tetrahydrofuran (0.6 mL) was added lithium hydroxide monohydrate (56 mg, 1.33 mmol) in water (0.6 mL). The reaction mixture was stirred at room temperature for 3 hours. Then the reaction mixture was neutralized with 1N solution of hydrogen chloride in ethyl acetate, diluted with tetrahydrofuran and dried. The organic phase was separated and concentrated. The residue was purified by prep-HPLC to give compound 236d (51 mg). LCMS (M+H$^+$): 436.

Preparation of (6S)-N-(3-chloro-4-fluoro-phenyl)-6-methyl-3-[4-(methylcarbamoyl)-2-oxo-pyrrolidin-1-yl]-6,7-dihydro-4H-pyrazolo[1,5-a]pyrazine-5-carboxamide (Example 236)

To a solution of compound 1-[(6S)-5-[(3-chloro-4-fluoro-phenyl)carbamoyl]-6-methyl-6,7-dihydro-4H-pyrazolo[1,5-a]pyrazin-3-yl]-5-oxo-pyrrolidine-3-carboxylic acid (236d, 20 mg, 45.9 μmol) in dichloromethane (3.0 mL) were added methanamine hydrochloride (9.3 mg, 138 μmol), 1-ethyl-3-3-dimethylaminopropyl carbodiimide hydrochloride (11.4 mg, 59.7 μmol), 1-hydroxybenzotriazole (1.9 mg, 13.8 μmol) and diisopropylethylamine (29.7 mg, 39.3 μL). The reaction mixture was stirred at room temperature for 2 hours. The reaction mixture was washed with water, extracted with dichloromathane twice. The organic phases were combined and dried over Na$_2$SO$_4$, filtrated and concentrated. The residue was purified by silica gel column to afford Example 236 (14.3 mg). LCMS (M+H$^+$): 449. $^1$H NMR (400 MHz, chloroform-d) δ ppm 7.66-7.54 (m, 2H), 7.45 (d, J=5.3 Hz, 1H), 7.36-7.29 (m, 1H), 7.04 (t, J=8.8 Hz, 1H), 5.78 (br. s., 1H), 5.16-5.03 (m, 2H), 4.43 (dd, J=5.1, 16.7 Hz, 1H), 4.32-4.22 (m, 1H), 4.11-3.89 (m, 3H), 3.27-3.18 (m, 1H), 2.94-2.76 (m, 5H), 1.35 (dd, J=4.0, 7.0 Hz, 3H).

Example 237

N-(3-chloro-4-fluoro-phenyl)-6-methyl-3-(2-oxooxazolidin-3-yl)-6,7-dihydro-4H-pyrazolo[1,5-a]pyrazine-5-carboxamide

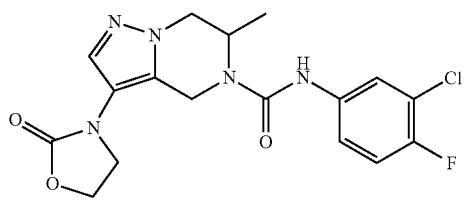 [SMILES: CC1Cn2ncc(N3CCOC3=O)c2CN1C(=O)Nc1ccc(F)c(Cl)c1]

The title compound was prepared according to the following scheme:

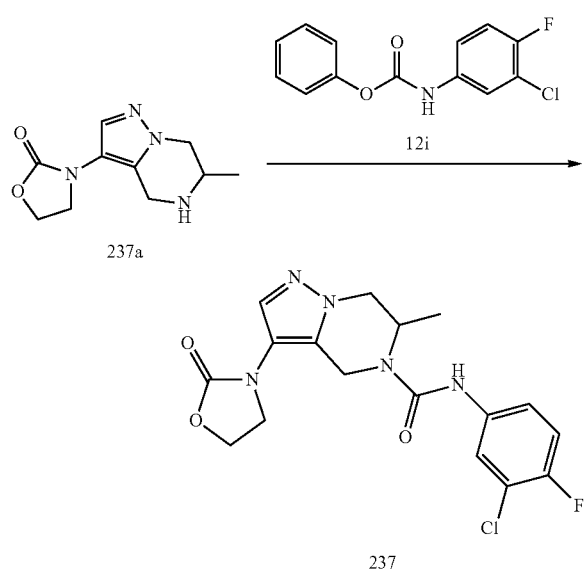

Preparation of 3-(6-methyl-4,5,6,7-tetrahydropyrazolo[1,5-a]pyrazin-3-yl)oxazolidin-2-one (compound 237a)

Compound 237a was prepared in analogy to 4,4-dimethyl-1-(6-methyl-4,5,6,7-tetrahydropyrazolo[1,5-a]pyrazin-3-yl)pyrrolidin-2-one (compound 212b) by using oxazolidin-2-one instead of 4,4-dimethylpyrrolidin-2-one.

Preparation of N-(3-chloro-4-fluoro-phenyl)-6-methyl-3-(2-oxooxazolidin-3-yl)-6,7-dihydro-4H-pyrazolo[1,5-a]pyrazine-5-carboxamide (Example 237)

The title compound was prepared in analogy to the preparation of Example 140 by using phenyl N-(3-chloro-4-fluoro-phenyl)carbamate (compound 12i) instead of phenyl N-(6-chloro-5-fluoro-2-pyridyl)carbamate (compound 140d) and 3-(6-methyl-4,5,6,7-tetrahydropyrazolo[1,5-a]pyrazin-3-yl)oxazolidin-2-one (compound 237a) instead of 3-(4-fluorophenyl)-4,5,6,7-tetrahydropyrazolo[1,5-a]pyrazine (compound 11b). Example 237 was obtained as a white solid. LCMS (M+H$^+$): 394. $^1$H NMR (400 MHz, DMSO-d$_6$) δ ppm 8.95 (s, 1H), 7.74 (dd, J=2.4, 6.9 Hz, 1H), 7.62 (s, 1H), 7.44-7.42 (m, 1H), 7.35-7.27 (m, 1H), 5.05 (d, J=16.8 Hz, 1H), 4.89 (t, J=16.6 Hz, 1H), 4.47-4.36 (m, 3H), 4.13-4.07 (m, 2H), 4.01-3.92 (m, 2H), 1.14 (d, J=6.8 Hz, 3H).

Example 238

(6S)-N-(3-chloro-4-fluoro-phenyl)-3-(4-methoxy-2-oxo-pyrrolidin-1-yl)-6-methyl-6,7-dihydro-4H-pyrazolo[1,5-a]pyrazine-5-carboxamide

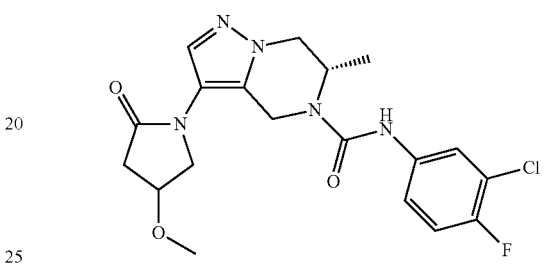

The title compound was prepared according to the following scheme:

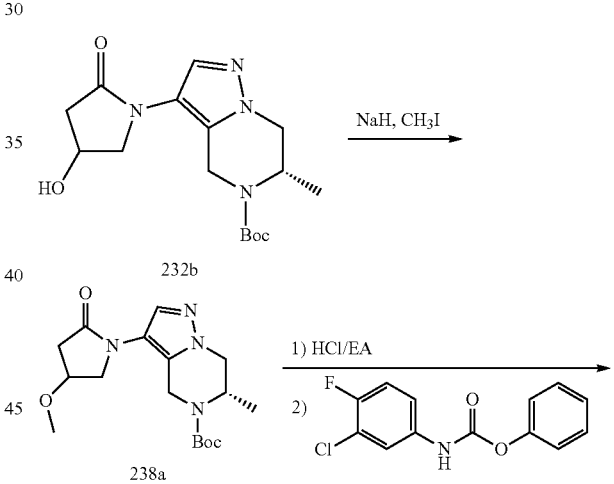

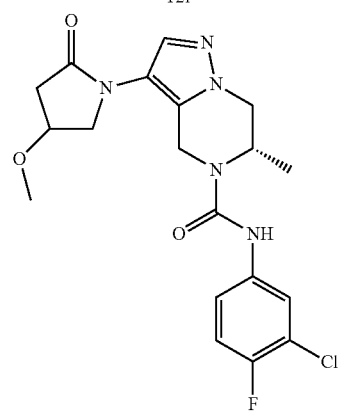

259

Preparation of tert-butyl (6S)-3-(4-methoxy-2-oxo-pyrrolidin-1-yl)-6-methyl-6,7-dihydro-4H-pyrazolo[1,5-a]pyrazine-5-carboxylate (compound 238a)

Compound 238a was prepared in analogy to compound 210b by using compound 232b instead of tert-butyl 3-(hydroxymethyl)pyrrolidine-1-carboxylate (compound 210a).

Preparation of ((6S)-N-(3-chloro-4-fluoro-phenyl)-3-(4-methoxy-2-oxo-pyrrolidin-1-yl)-6-methyl-6,7-dihydro-4H-pyrazolo[1,5-a]pyrazine-5-carboxamide (Example 238)

The title compound was prepared in analogy to the preparation of Example 223 by using compound 238a and compound 12i instead of compounds 223b and 218c, respectively. Example 238 was obtained as a solid. LCMS (M+H$^+$): 422. $^1$H NMR (400 MHz, DMSO-d$_6$) δ ppm 8.95 (d, J=5.0 Hz, 1H), 7.73 (dd, J=2.4, 6.9 Hz, 1H), 7.62 (d, J=6.0 Hz, 1H), 7.45-7.38 (m, 1H), 7.36-7.28 (m, 1H), 4.98 (t, J=16.6 Hz, 1H), 4.90-4.82 (m, 1H), 4.47-4.30 (m, 1H), 4.24-4.17 (m, 1H), 4.17-4.08 (m, 2H), 4.07-3.95 (m, 1H), 3.75-3.64 (m, 1H), 3.29 (d, J=3.0 Hz, 3H), 2.81-2.70 (m, 1H), 2.35 (d, J=10.8 Hz, 1H), 1.26-1.08 (m, 3H)

Example 239

(6S)-N-[3-(difluoromethyl)-4,5-difluoro-phenyl]-6-methyl-3-(2-oxopyrrolidin-1-yl)-6,7-dihydro-4H-pyrazolo[1,5-a]pyrazine-5-carboxamide

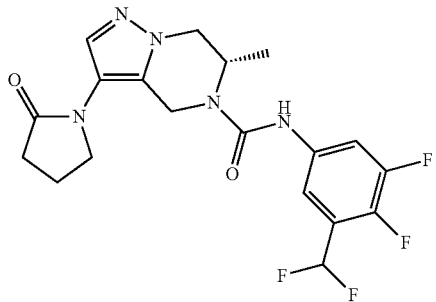 [SMILES: C[C@H]1Cn2ncc(N3CCCC3=O)c2CN1C(=O)Nc1cc(F)c(F)c(C(F)F)c1]

The title compound was prepared according to the following scheme:

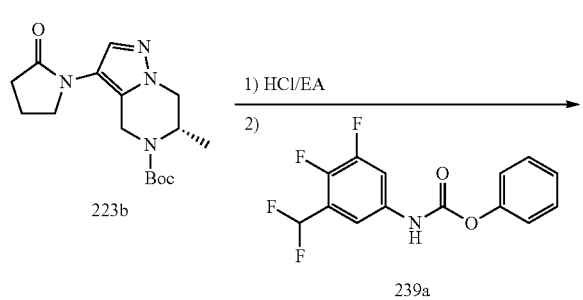

260

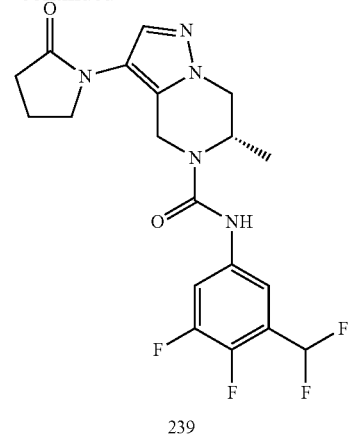

Preparation of phenyl N-[3-(difluoromethyl)-4,5-difluoro-phenyl]carbamate (compound 239a)

Compound 239a was prepared in analogy to compound 147c by using 5-bromo-1-(difluoromethyl)-2,3-difluoro-benzene (catalog number: ABF12819, Shanghai AQBioPharma Co. Ltd) instead of 1-bromo-3-(1,1-difluoroethyl)benzene.

Preparation of (6S)-N-[3-(difluoromethyl)-4,5-difluoro-phenyl]-6-methyl-3-(2-oxopyrrolidin-1-yl)-6,7-dihydro-4H-pyrazolo[1,5-a]pyrazine-5-carboxamide (Example 239)

The title compound was prepared in analogy to Example 223 by using phenyl N-[3-(difluoromethyl)-4,5-difluoro-phenyl]carbamate (compound 239a) instead of phenyl N-[2-(difluoromethyl)-4-pyridyl] (compound 218c). Example 239 was obtained as a solid (50 mg). LCMS (M+H$^+$): 426. $^1$H NMR (400 MHz, MeOD) δ ppm 7.74-7.66 (m, 1H), 7.63 (s, 1H), 7.49-7.43 (m, 1H), 7.01 (t, J=48 Hz, 2H), 5.05 (d, J=16.8 Hz, 1H), 5.01-4.94 (m, 1H), 4.52 (d, J=17.1 Hz, 1H), 4.31 (dd, J=4.5, 12.8 Hz, 1H), 4.17 (d, J=13.8 Hz, 1H), 3.93-3.81 (m, 2H), 2.62-2.52 (m, 2H), 2.33-2.17 (m, 2H), 1.28 (d, J=7.0 Hz, 3H).

Example 240

(6S)-3-(4-cyano-2-oxo-pyrrolidin-1-yl)-6-methyl-N-(3,4,5-trifluorophenyl)-6,7-dihydro-4H-pyrazolo[1,5-a]pyrazine-5-carboxamide

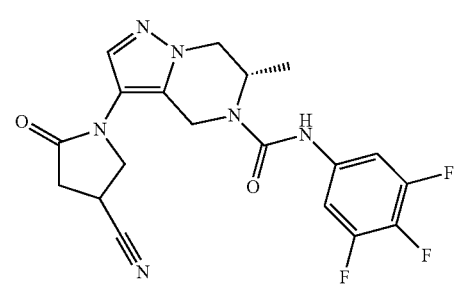 [SMILES: C[C@H]1Cn2ncc(N3CC(C#N)CC3=O)c2CN1C(=O)Nc1cc(F)c(F)c(F)c1]

The title compound was prepared according to the following scheme:

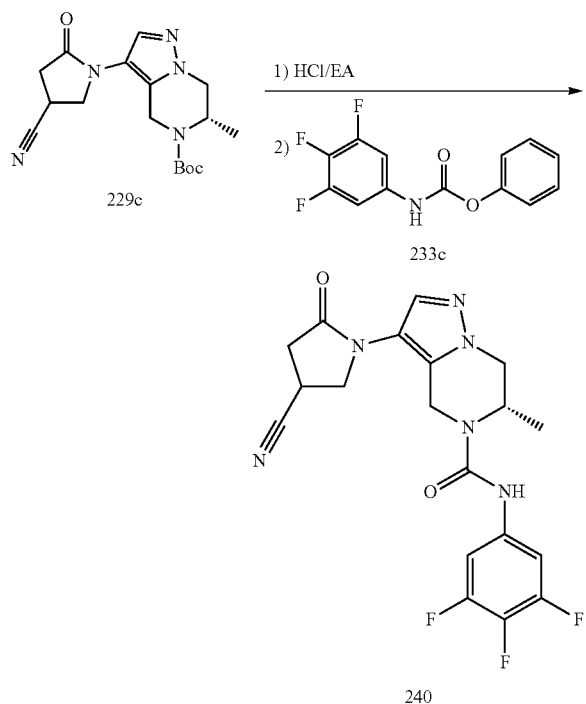

Preparation of (6S)-3-(4-cyano-2-oxo-pyrrolidin-1-yl)-6-methyl-N-(3,4,5-trifluorophenyl)-6,7-dihydro-4H-pyrazolo[1,5-a]pyrazine-5-carboxamide (Example 240)

The title compound was prepared in analogy to Example 220 by using phenyl N-(3,4,5-trifluorophenyl)carbamate (compound 233c) instead of phenyl N-(3-chloro-4-fluorophenyl)carbamate (compound 12i) and tert-butyl (6S)-3-(4-cyano-2-oxo-pyrrolidin-1-yl)-6-methyl-6,7-dihydro-4H-pyrazolo[1,5-a]pyrazine-5-carboxylate (compound 229c) instead of tert-butyl 3-(3-oxomorpholin-4-yl)-6,7-dihydro-4H-pyrazolo[1,5-a]pyrazine-5-carboxylate (compound 220b). Example 240 was obtained as a solid (40 mg). LCMS (M+H$^+$): 419. $^1$H NMR (400 MHz, MeOD) δ ppm 7.65 (d, J=1.8 Hz, 1H), 7.35-7.25 (m, 2H), 5.04 (d, J=17.1 Hz, 1H), 5.00-4.93 (m, 1H), 4.50 (d, J=17.3 Hz, 1H), 4.35-4.26 (m, 1H), 4.21-4.02 (m, 3H), 3.83-3.73 (m, 1H), 3.05-2.94 (m, 1H), 2.92-2.81 (m, 1H), 1.29-1.26 (m, 3H).

Example 240 was subjected to chiral separation to give Example 240-1 and Example 240-2 with the names of these two compounds: (6S)-3-[(4R)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide and (6S)-3-[(4S)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide. (Preparative SFC conditions: Column: AD-H, 250×20 mm ID.; Mobile phase: A for CO$_2$, B for MeOH; Eluent: B 30%; Flow rate: 65 mL/min; Back pressure: 100 bar; column temperature: 35° C.).

Example 240-1 (Retention Time, 1.95 min). LCMS (M+H$^+$): 419. $^1$H NMR (400 MHz, MeOD) δ ppm 7.65 (s, 1H), 7.28 (dd, J=6.5, 10.3 Hz, 2H), 5.04 (d, J=17.1 Hz, 1H), 4.99-4.92 (m, 1H), 4.50 (d, J=17.1 Hz, 1H), 4.31 (dd, 12.5 Hz, 1H), 4.22-4.11 (m, 2H), 4.05 (dd, J=6.3, 9.8 Hz, 1H), 3.86-3.71 (m, 1H), 3.00 (dd, J=9.3, 17.1 Hz, 1H), 2.86 (dd, J=9.3, 17.1 Hz, 1H), 1.27 (d, J=6.8 Hz, 3H).

Example 240-2 (Retention Time, 2.72 min). LCMS (M+H$^+$): 419. $^1$H NMR (400 MHz, MeOD) δ ppm 7.65 (s, 1H), 7.28 (dd, J=6.3, 10.3 Hz, 2H), 5.04 (d, J=16.8 Hz, 1H), 4.98-4.93 (m, 1H), 4.50 (d, J=16.8 Hz, 1H), 4.30 (dd, J=4.5, 12.8 Hz, 1H), 4.21-4.04 (m, 3H), 3.85-3.71 (m, 1H), 3.00 (dd, J=9.3, 17.1 Hz, 1H), 2.88 (dd, J=9.3, 17.1 Hz, 1H), 1.28 (d, J=7.0 Hz, 3H).

Example 241

(6S)-N-[2-(difluoromethyl)-4-pyridyl]-6-methyl-3-[2-oxo-4-(trifluoromethyl)pyrrolidin-1-yl]-6,7-dihydro-4H-pyrazolo[1,5-a]pyrazine-5-carboxamide

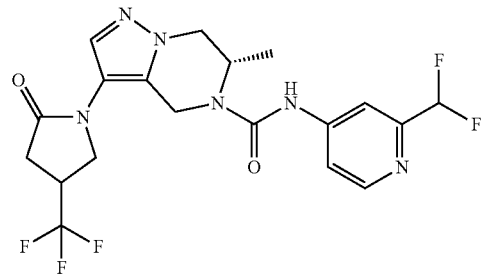 [SMILES: C[C@H]1Cn2ncc(N3CC(C(F)(F)F)CC3=O)c2CN1C(=O)Nc1ccnc(C(F)F)c1]

The title compound was prepared according to the following scheme:

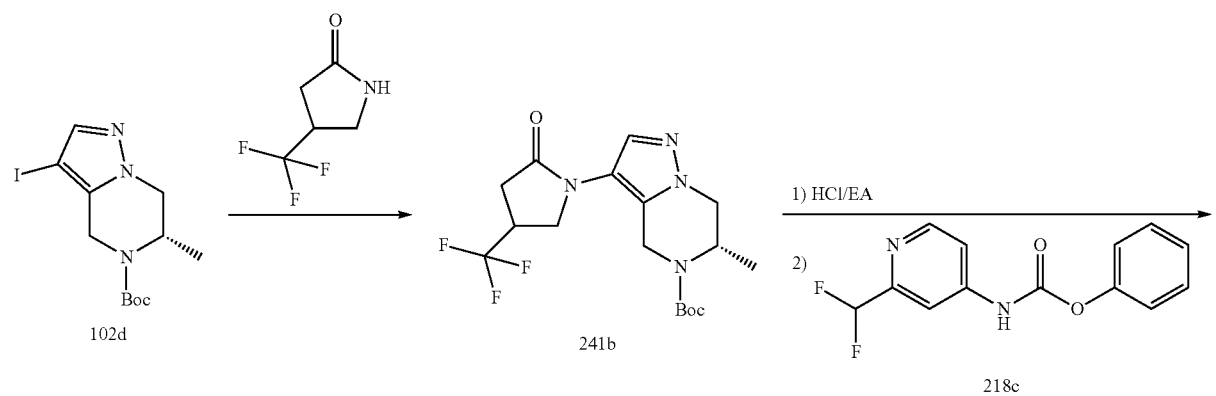

-continued

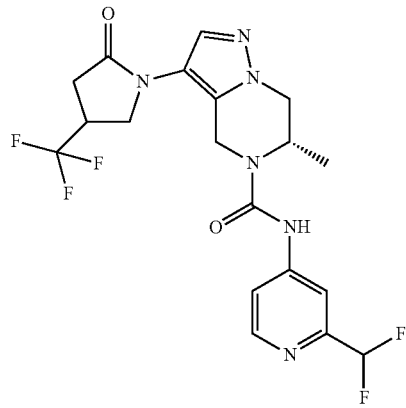

241

Preparation of (6S)-N-[2-(difluoromethyl)-4-pyridyl]-6-methyl-3-[2-oxo-4-(trifluoromethyl)pyrrolidin-1-yl]-6,7-dihydro-4H-pyrazolo[1,5-a]pyrazine-5-carboxamide (Example 241)

The title compound was prepared in analogy to Example 220 by using 4-(trifluoromethyl)pyrrolidin-2-one instead of morpholin-3-one, phenyl N-[2-(difluoromethyl)-4-pyridyl]carbamate (compound 218c) instead of phenyl N-(3-chloro-4-fluoro-phenyl)carbamate (compound 12i) and tert-butyl (6S)-3-iodo-6-methyl-6,7-dihydro-4H-pyrazolo[1,5-a]pyrazine-5-carboxylate (compound 102d) instead of tert-butyl 3-iodo-6,7-dihydro-4H-pyrazolo[1,5-a]pyrazine-5-carboxylate (compound 1e). Example 241 was obtained as a solid (18 mg). LCMS (M+H$^+$): 459. $^1$H NMR (400 MHz, MeOD) δ ppm 8.42 (d, J=5.8 Hz, 1H), 7.86 (s, 1H), 7.71-7.62 (m, 2H), 6.67 (t, J=48.0 Hz, 1H), 5.11 (d, J=12.3 Hz, 0.5H), 5.07 (d, J=12.0 Hz, 0.5H), 5.03-4.95 (m, 1H), 4.55 (d, J=9.8 Hz, 0.5H), 4.51 (d, J=9.8 Hz, 0.5H), 4.33 (td, J=3.6, 12.8 Hz, 1H), 4.22-4.07 (m, 2H), 3.98-3.91 (m, 1H), 3.59-3.45 (m, 1H), 2.98-2.87 (m, 1H), 2.76-2.65 (m, 1H), 1.30 (dd, J=3.5, 6.8 Hz, 3H)

Example 242

(6S)-3-(2-acetyl-7-oxo-2,6-diazaspiro[3.4]octan-6-yl)-N-(3-chloro-4-fluoro-phenyl)-6-methyl-6,7-dihydro-4H-pyrazolo[1,5-a]pyrazine-5-carboxamide

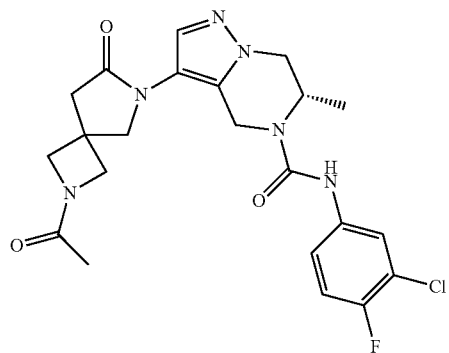 [SMILES: CC(=O)N1CC2(CC(=O)N(c3cnn4c3CN(C(=O)Nc3ccc(F)c(Cl)c3)[C@@H](C)C4)C2)C1]

The title compound was prepared according to the following scheme:

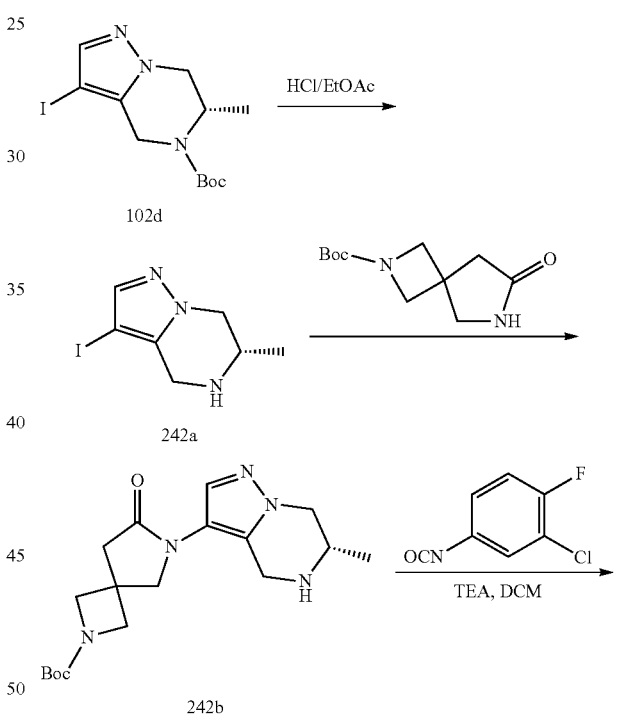

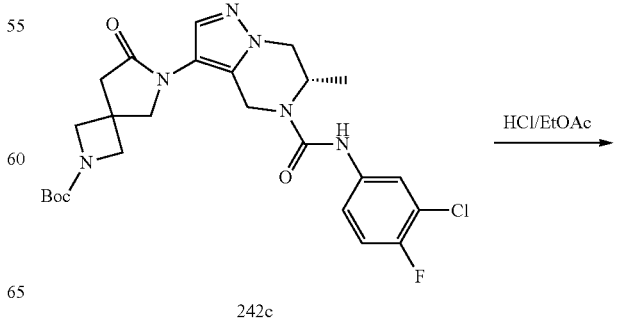

242c

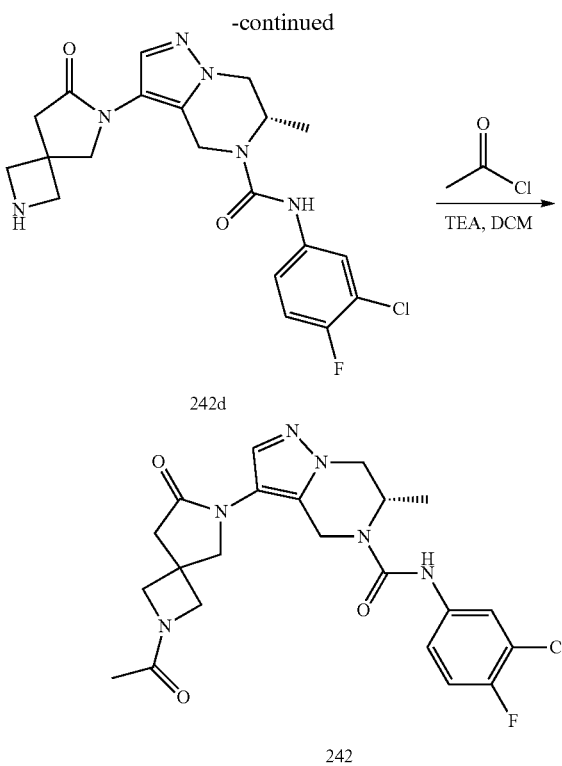

Step 1: Preparation of (6S)-3-iodo-6-methyl-4,5,6,7-tetrahydropyrazolo[1,5-a]pyrazine (compound 242a)

To a mixture of tert-butyl (6S)-3-iodo-6-methyl-6,7-dihydro-4H-pyrazolo[1,5-a]pyrazine-5-carboxylate (compound 102d, 2.0 g, 5.5 mmol) was added HCl/EtOAc (50.0 mL) and the reaction mixture was stirred at room temperature for 1 hour. The solvent was removed in vacuo, the residue was basified by $K_2CO_3$ in DCM (100.0 mL). The solid was filtered off and organic layer was evaporated to give compound 242a (1.3 g). LCMS (M+H$^+$): 263.

Step 2: Preparation of tert-butyl 6-[(6S)-6-methyl-4,5,6,7-tetrahydropyrazolo[1,5-a]pyrazin-3-yl]-7-oxo-2,6-diazaspiro[3.4]octane-2-carboxylate (compound 242b)

To a solution of tert-butyl 6-oxo-2,7-diazaspiro[3.4]octane-2-carboxylate (271.5 mg, 1.2 mmol) in dioxane (15 mL) was added (6S)-3-iodo-6-methyl-4,5,6,7-tetrahydropyrazolo[1,5-a]pyrazine(compound 242a, 263.0 mg, 1.0 mmol), (1R,2R)-N1,N2-dimethylcyclohexane-1,2-diamine (14.2 mg, 0.1 mmol), $K_3PO_4$ (637.0 mg, 3.0 mmol) and CuI (19.0 mg, 0.1 mmol) under $N_2$, and the reaction mixture was stirred at 120° C. for 12 hours, then filtered and concentrated under the reduce pressure, the residue was purified by silica gel column chromatography (DCM/MeOH=50/1 to 20/1) to give compound 242b (200 mg) as white oil. LCMS (M+H$^+$): 362.

Step 3: Preparation of tert-butyl 6-[(6S)-5-[(3-chloro-4-fluoro-phenyl)carbamoyl]-6-methyl-6,7-dihydro-4H-pyrazolo[1,5-a]pyrazin-3-yl]-7-oxo-2,6-diazaspiro[3.4]octane-2-carboxylate (compound 242c)

To a solution of tert-butyl 6-[(6S)-6-methyl-4,5,6,7-tetrahydropyrazolo[1,5-a]pyrazin-3-yl]-7-oxo-2,6-diazaspiro[3.4]octane-2-carboxylate (compound 242b, 94.9 mg, 0.55 mmol) and Et$_3$N (111.7 mg, 1.106 mmol) in DCM (5 mL) was added 2-chloro-1-fluoro-4-isocyanato-benzene (200.0 mg, 0.55 mmol) at 20° C., and then the reaction mixture was stirred at 20° C. for 1 hour. Then the reaction mixture was diluted with water, extracted with EtOAc (50 mL). The organic layer was dried over Na$_2$SO$_4$ and evaporated to dryness to give compound 242c (280.0 mg) as white solid. LCMS (M+H$^+$): 533.

Step 4: Preparation of (6S)-N-(3-chloro-4-fluoro-phenyl)-6-methyl-3-(7-oxo-2,6-diazaspiro[3.4]octan-6-yl)-6,7-dihydro-4H-pyrazolo[1,5-a]pyrazine-5-carboxamide (compound 242d)

To a mixture of tert-butyl 6-[(6S)-5-[(3-chloro-4-fluoro-phenyl)carbamoyl]-6-methyl-6,7-dihydro-4H-pyrazolo[1,5-a]pyrazin-3-yl]-7-oxo-2,6-diazaspiro[3.4]octane-2-carboxylate(compound 242c, 100.0 mg, 0.188 mmol) was added HCl/EtOAc (10 mL) and the reaction mixture was stirred for 1 hour. Then the solvent was removed in vacuo to give compound 242d (88 mg). LCMS (M+H$^+$): 433.

Step 5: Preparation of (6S)-3-(2-acetyl-7-oxo-2,6-diazaspiro[3.4]octan-6-yl)-N-(3-chloro-4-fluoro-phenyl)-6-methyl-6,7-dihydro-4H-pyrazolo[1,5-a]pyrazine-5-carboxamide (Example 242)

To a solution of (6S)-N-(3-chloro-4-fluoro-phenyl)-6-methyl-3-(7-oxo-2,6-diazaspiro[3.4]octan-6-yl)-6,7-dihydro-4H-pyrazolo[1,5-a]pyrazine-5-carboxamide (compound 242d, 88.0 mg, 0.187 mmol) in DCM (10.0 mL) was added Et$_3$N (37.8 mg, 0.374 mmol) and acetyl chloride (30.5 mg, 0.281 mmol). The reaction mixture was stirred at room temperature for 1 hour. A few drops of water was added, the solvent was removed in vacuo, the residue was purified by prep-HPLC to give Example 242 (20 mg) as white solid. LCMS (M+H$^+$): 475. $^1$H NMR (400 MHz, DMSO-d$_6$) δ ppm 8.99 (s, 1H), 7.74 (dd, J=2.3, 6.8 Hz, 1H), 7.61 (s, 1H), 7.47-7.39 (m, 1H), 7.37-7.27 (m, 1H), 5.03-4.94 (m, 1H), 4.90-4.81 (m, 1H), 4.37 (dd, J=2.9, 17.2 Hz, 1H), 4.25-4.07 (m, 4H), 4.04-3.85 (m, 4H), 2.80-2.72 (m, 2H), 1.77 (s, 3H), 1.14 (d, J=6.3 Hz, 3H).

Example 243

(6S)-6-methyl-3-(2-methyl-5-oxo-morpholin-4-yl)-N-(3,4,5-trifluorophenyl)-6,7-dihydro-4H-pyrazolo[1,5-a]pyrazine-5-carboxamide

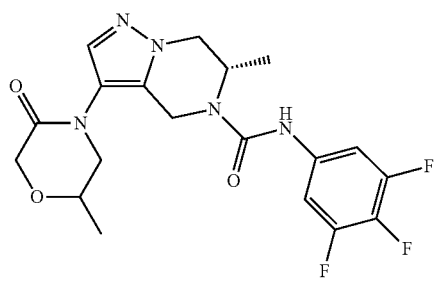 [SMILES: CC1CN(c2cnn3c2CN(C(=O)Nc2cc(F)c(F)c(F)c2)[C@@H](C)C3)C(=O)CO1]

The title compound was prepared according to the following scheme:

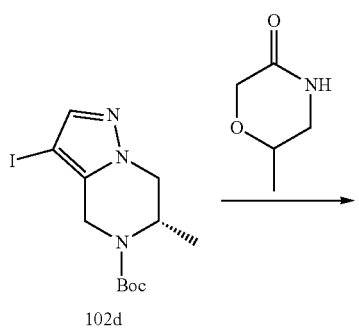

102d

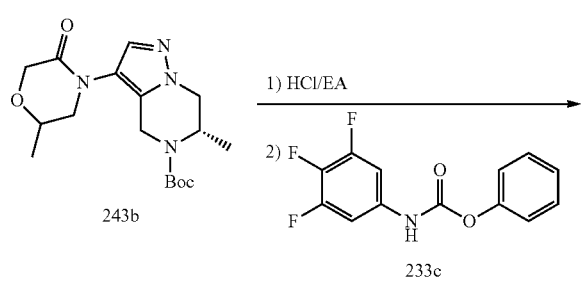

243b

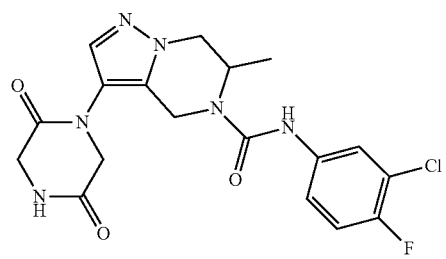 [SMILES: CC1Cn2ncc(N3CC(=O)NCC3=O)c2CN1C(=O)Nc1ccc(F)c(Cl)c1]

233c

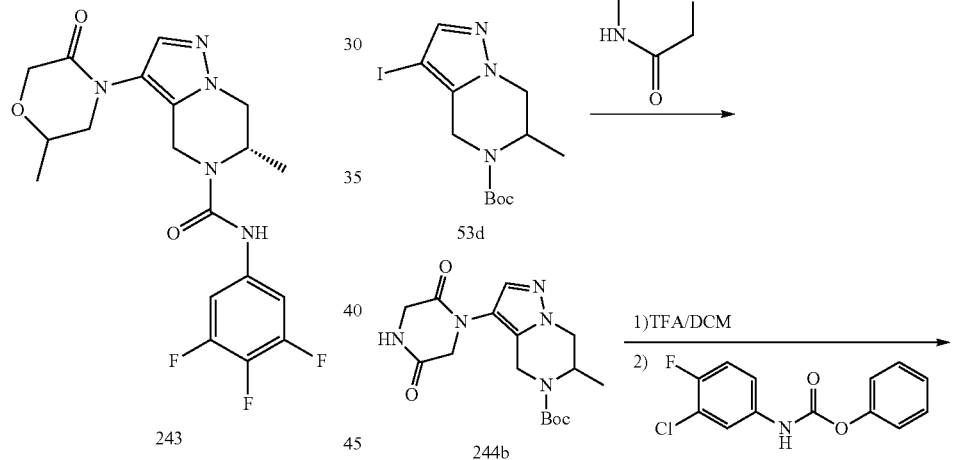

243

Preparation of (6S)-6-methyl-3-(2-methyl-5-oxo-morpholin-4-yl)-N-(3,4,5-trifluorophenyl)-6,7-dihydro-4H-pyrazolo[1,5-a]pyrazine-5-carboxamide (Example 243)

The title compound was prepared in analogy to Example 223 by using 6-methylmorpholin-3-one instead of pyrrolidin-2-one, and phenyl N-(3,4,5-trifluorophenyl)carbamate (compound 233c) instead of phenyl N-[2-(difluoromethyl)-4-pyridyl]carbamate (compound 218c). Example 243 was obtained as a solid (63 mg). LCMS (M+H⁺): 424. ¹H NMR (400 MHz, chloroform-d) δ ppm 7.96-7.75 (m, 1H), 7.51 (s, 1H), 7.28-7.18 (m, 2H), 5.15-5.03 (m, 1H), 4.95-4.78 (m, 1H), 4.51-4.42 (m, 1H), 4.40-4.22 (m, 3H), 4.17-3.97 (m, 2H), 3.85-3.68 (m, 1H), 3.65-3.50 (m, 1H), 1.46-1.36 (m, 6H).

Example 244

N-(3-chloro-4-fluoro-phenyl)-3-(2,5-dioxopiperazin-1-yl)-6-methyl-6,7-dihydro-4H-pyrazolo[1,5-a]pyrazine-5-carboxamide

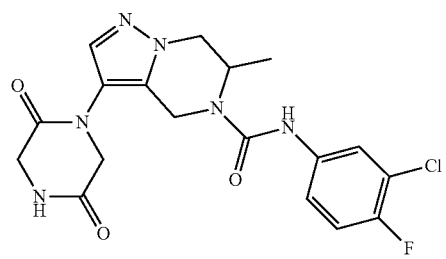 [SMILES: CC1Cn2ncc(N3CC(=O)NCC3=O)c2CN1C(=O)Nc1ccc(F)c(Cl)c1]

The title compound was prepared according to the following scheme:

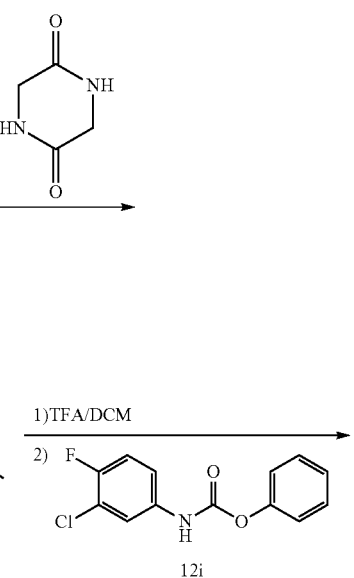

53d

244b

12i

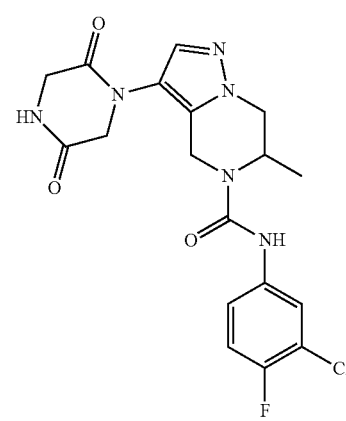

244

Step 1: Preparation of tert-butyl 3-(2,5-dioxopiperazin-1-yl)-6-methyl-6,7-dihydropyrazolo[1,5-a]pyrazine-5(4H)-carboxylate (compound 244b)

The reaction mixture of piperazine-2,5-dione (1.41 g, 12.4 mmol), tert-butyl 3-iodo-6-methyl-6,7-dihydro-4H-pyrazolo[1,5-a]pyrazine-5-carboxylate (compound 53d, 300 mg, 826 µmol), $K_3PO_4$ (351 mg, 1.65 mmol), CuI (31.5 mg, 165 µmol) and (1R,2R)-N1,N2-dimethylcyclohexane-1,2-diamine (23.5 mg, 165 µmol) in DMSO (15 mL) was flushed with nitrogen and sealed. The reaction mixture was heated to 105° C. in microwave for 1 hour. The reaction mixture was cooled down. After diluted with ethyl acetate, the reaction mixture was washed with ice-water, extracted by ethyl acetate three times. Then the combined organic layer was dried over $Na_2SO_4$ and concentrated in vacuo. The residue was purified by column to give compound 244b (144 mg). LCMS (M+H$^+$): 350.

Step 2: Preparation of N-(3-chloro-4-fluoro-phenyl)-3-(2,5-dioxopiperazin-1-yl)-6-methyl-6,7-dihydro-4H-pyrazolo[1,5-a]pyrazine-5-carboxamide (Example 244)

A mixture of tert-butyl 3-(2,5-dioxopiperazin-1-yl)-6-methyl-6,7-dihydropyrazolo[1,5-a]pyrazine-5(4H)-carboxylate (compound 244b, 100 mg, 286 µmol) trifluoroacetic acid (2 mL, 26 mmol,) and DCM (1 mL) was stirred at room temperature for 1 hour. The reaction mixture was concentrated, the residue was dissolved in DMF (3 mL), then DIPEA (754 mg, 1 mL, 5.83 mmol) and phenyl (3-chloro-4-fluorophenyl)carbamate (compound 12i, 114 mg, 429 µmol) were added.

The reaction mixture was stirred at 40° C. for 3 hours. The reaction mixture was purified by prep-HPLC to give Example 244 (16 mg). LCMS (M+H$^+$): 421. $^1$H NMR (400 MHz, chloroform-d) δ ppm 7.63-7.55 (m, 1H), 7.52 (s, 1H), 7.31-7.29 (m, 1H), 7.19 (s, 1H), 7.08 (s, 1H), 6.35-6.26 (m, 1H), 5.12-5.03 (m, 1H), 4.86 (d, J=16.6 Hz, 1H), 4.53-4.45 (m, 1H), 4.35 (dd, J=5.6, 16.9 Hz, 3H), 4.24 (s, 2H), 4.11 (d, J=13.8 Hz, 1H), 1.36 (d, J=7.0 Hz, 3H).

Example 245

(6S)-N-(3-chloro-4-fluoro-phenyl)-3-(4,4-dimethyl-2-oxo-imidazolidin-1-yl)-6-methyl-6,7-dihydro-4H-pyrazolo[1,5-a]pyrazine-5-carboxamide

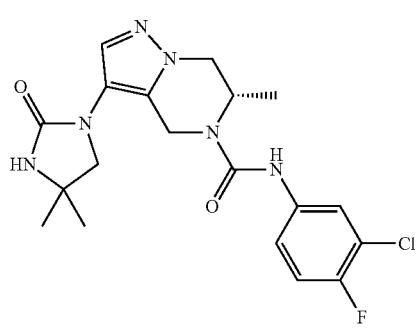 [SMILES: C[C@H]1Cn2ncc(N3CC(C)(C)NC3=O)c2CN1C(=O)Nc1ccc(F)c(Cl)c1]

The title compound was prepared according to the following scheme:

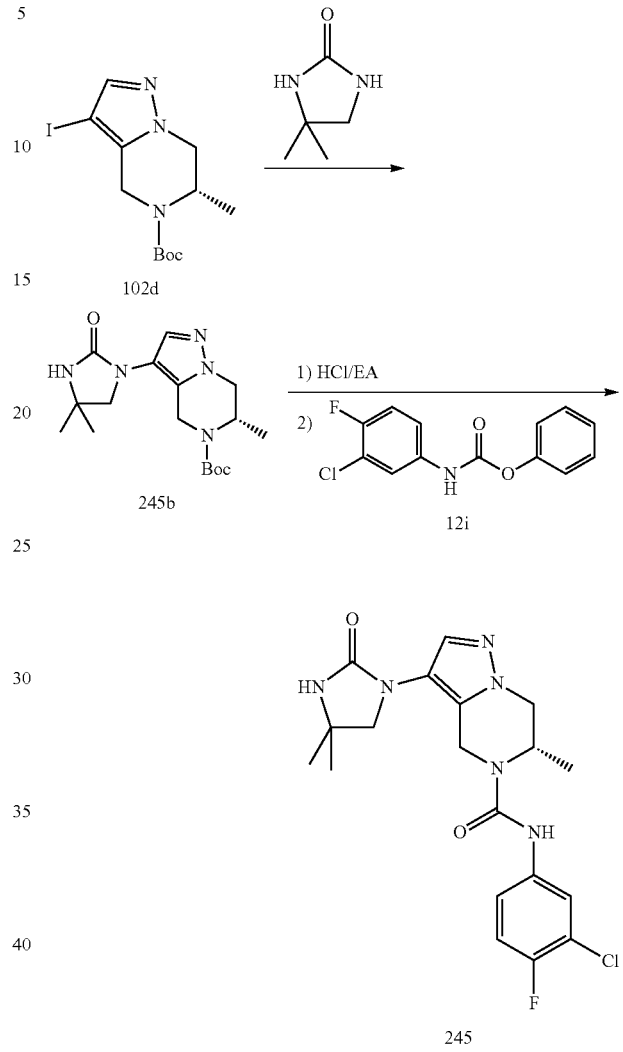

Preparation of (6S)-N-(3-chloro-4-fluoro-phenyl)-3-(4-hydroxy-2-oxo-pyrrolidin-1-yl)-6-methyl-6,7-dihydro-4H-pyrazolo[1,5-a]pyrazine-5-carboxamide (Example 232)

The title compound was prepared in analogy to Example 223 by using 4,4-dimethylimidazolidin-2-one instead of pyrrolidin-2-one, and phenyl N-(3-chloro-4-fluoro-phenyl)carbamate (compound 12i) instead of phenyl N-[2-(difluoromethyl)-4-pyridyl]carbamate (compound 218c). Example 245 was obtained as a solid (8.6 mg). LCMS (M+H$^+$): 421. $^1$H NMR (400 MHz, chloroform-d) δ ppm 7.75 (s, 1H), 7.65 (dd, J=2.8, 6.5 Hz, 1H), 7.39-7.30 (m, 2H), 7.05 (t, J=8.9 Hz, 1H), 5.18 (d, J=16.8 Hz, 1H), 5.09 (s, 1H), 4.54 (s, 1H), 4.41 (d, J=16.8 Hz, 1H), 4.28 (dd, J=5.3, 12.8 Hz, 1H), 4.03 (d, J=2.0 Hz, 1H), 3.73 (d, J=8.5 Hz, 1H), 3.56 (d, J=8.5 Hz, 1H), 1.47 (s, 3H), 1.45 (s, 3H), 1.39 (d, J=7.0 Hz, 3H).

Example 246

(6S)-N-(3-chloro-4-fluoro-phenyl)-3-(3,6-dioxo-4,7,8,8a-tetrahydro-1H-pyrrolo[1,2-a]pyrazin-2-yl)-6-methyl-6,7-dihydro-4H-pyrazolo[1,5-a]pyrazine-5-carboxamide

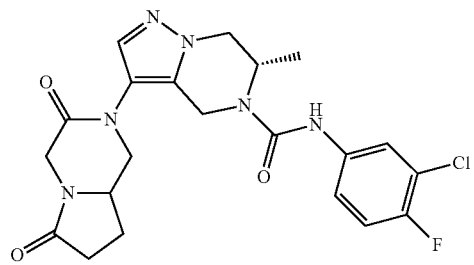 [SMILES: C[C@H]1Cn2ncc(N3CC4CCC(=O)N4CC3=O)c2CN1C(=O)Nc1ccc(F)c(Cl)c1]

The title compound was prepared according to the following scheme:

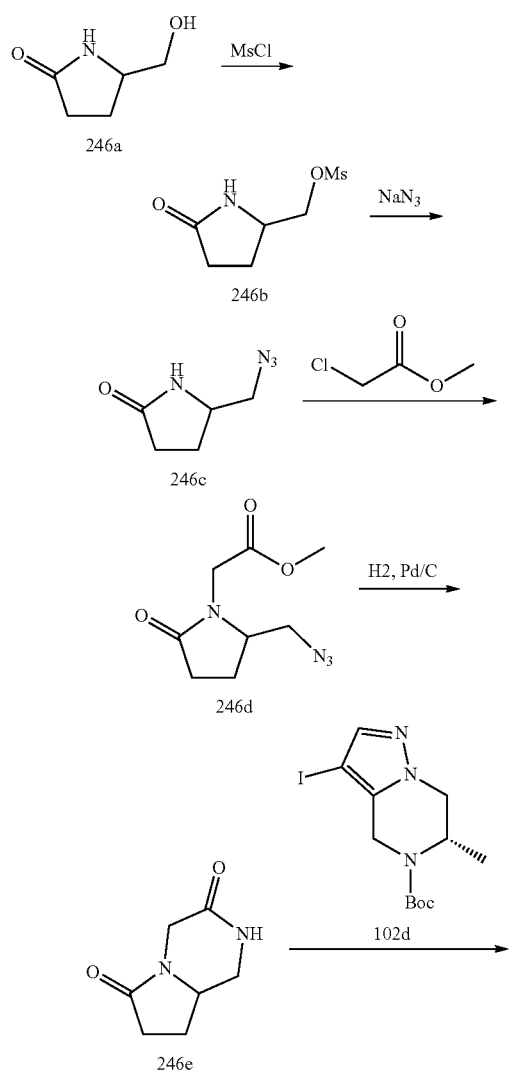

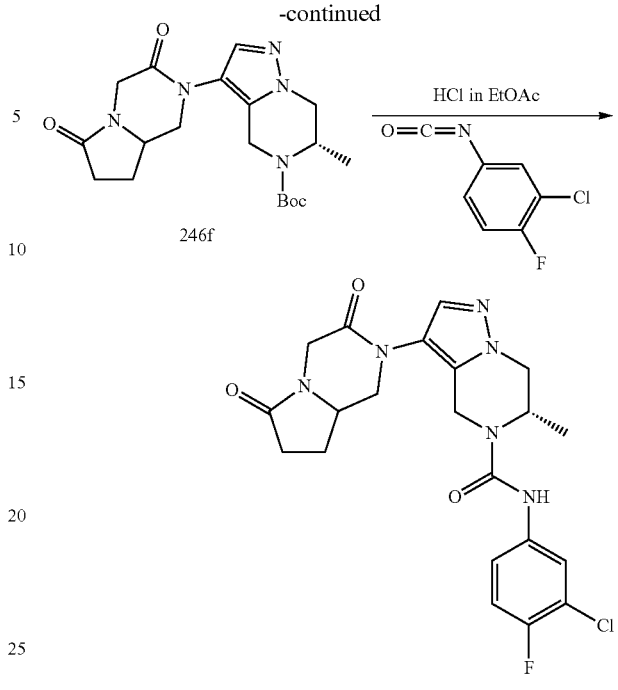

Step 1: Preparation of (5-oxopyrrolidin-2-yl)methyl methanesulfonate (compound 246b)

To a mixture of compound 246a (2.0 g, 17.4 mmol) and TEA (5.3 g, 52 mmol) in DCM (20 mL) was added MsCl (5.97 g, 52 mmol) at 0° C. The resulting mixture was stirred at room temperature for 3 hours, and then concentrated and purified by silica gel chromatography to afford compound 246b as a white solid (3.2 g).

Step 2: Preparation of 5-(azidomethyl)pyrrolidin-2-one (compound 246c)

To a solution of (5-oxopyrrolidin-2-yl)methyl methanesulfonate (compound 246b, 1.0 g, 5.2 mmol) in DMF (20.0 mL) was added NaN$_3$ (2.51 g, 38.5 mmol) and K$_2$CO$_3$ (5.32 g, 38.5 mmol). The reaction mixture was heated to 80° C. for 16 hours. The reaction mixture was filtered, and the filtrate was concentrated and purified by chromatography (PE/EtOAc=1/1 to pure EtOAc) to give compound 246c as yellow oil (0.3 g).

Step 3: Preparation of methyl 2-[2-(azidomethyl)-5-oxo-pyrrolidin-1-yl]acetate (compound 246d)

To a solution of 5-(azidomethyl)pyrrolidin-2-one (compound 246c, 100.0 mg, 0.71 mmol) in THF (5.0 mL) was added NaH (42.8 mg, 1.07 mmol) at 0° C., the reaction mixture was warmed to room temperature and stirred for 1 hour. Then the reaction mixture was cooled to 0° C. and methyl 2-chloroacetate (116.2 mg, 1.07 mmol) was added and the reaction mixture was stirred at room temperature for 16 hours. Then the reaction mixture was concentrated and the residue was purified by prep-TLC (EtOAc) to give compound 246d (80.0 mg) as colorless oil. LCMS (M+H$^+$): 213.

Step 4: Preparation of 1,2,4,7,8,8a-hexahydropyrrolo[1,2-a]pyrazine-3,6-dione (compound 246e)

To a solution of methyl 2-[2-(azidomethyl)-5-oxo-pyrrolidin-1-yl]acetate (compound 246d, 80.0 mg, 0.38 mmol) in MeOH (5.0 mL) was added Pd/C (10.0 mg) under N$_2$. The reaction mixture was stirred at room temperature under H$_2$ (50 psi) for 16 hours. The reaction mixture was filtered and the filtrate was concentrated to give compound 246e as a red oil (50.0 mg). LCMS (M+H$^+$): 155.

Step 5: Preparation of tert-butyl (6S)-3-(3,6-dioxo-4,7,8,8a-tetrahydro-1H-pyrrolo[1,2-a]pyrazin-2-yl)-6-methyl-6,7-dihydro-4H-pyrazolo[1,5-a]pyrazine-5-carboxylate (compound 246f)

The reaction mixture of tert-butyl (6S)-3-iodo-6-methyl-6,7-dihydro-4H-pyrazolo[1,5-a]pyrazine-5-carboxylate (compound 102d, 117.8 mg, 0.32 mmol), 1,2,4,7,8,8a-hexahydropyrrolo[1,2-a]pyrazine-3,6-dione (compound 246e, 50.0 mg, 0.32 mmol), (1R,2R)-N1,N2-dimethylcyclohexane-1,2-diamine (4.6 mg, 0.03 mmol), CuI (6.1 mg, 0.03 mmol) and K$_3$PO$_4$ (135.9 mg, 0.64 mmol) in dioxane (5.0 mL) was degassed and stirred at 120° C. under N$_2$ for 16 hours. The reaction mixture was concentrated and purified by silica gel chromatography (DCM/MeOH=20/1) to give compound 246f as yellow oil (28.0 mg). LCMS (M+H$^+$): 390

Step 6: Preparation of (6S)-N-(3-chloro-4-fluorophenyl)-3-(3,6-dioxo-4,7,8,8a-tetrahydro-1H-pyrrolo[1,2-a]pyrazin-2-yl)-6-methyl-6,7-dihydro-4H-pyrazolo[1,5-a]pyrazine-5-carboxamide (Example 246)

A solution of tert-butyl (6S)-3-(3,6-dioxo-4,7,8,8a-tetrahydro-1H-pyrrolo[1,2-a]pyrazin-2-yl)-6-methyl-6,7-dihydro-4H-pyrazolo[1,5-a]pyrazine-5-carboxylate (compound 246f, 100.0 mg, 0.26 mmol) in HCl/EtOAc (5.0 mL) was stirred at room temperature for 2 hours. The reaction mixture was concentrated and the residue was added to a solution of Et$_3$N (37.3 mg, 0.368 mmol) in DCM (5.0 mL). Then 2-chloro-1-fluoro-4-isocyanato-benzene (21.1 mg, 0.123 mmol) was added and stirred at room temperature for 1 hour. The reaction mixture was concentrated, the residue was purified by prep-HPLC to give Example 246 as white solid (10.0 mg). LCMS (M+H$^+$): 461. $^1$H NMR (400 MHz, MeOD) δ ppm 7.70-7.55 (m, 2H), 7.33 (dt, J=8.9, 3.4 Hz, 1H), 7.24-7.09 (m, 1H), 5.03-4.91 (m, 2H), 4.57-4.10 (m, 5H), 3.93 (d, J=18.4 Hz, 1H), 3.88-3.67 (m, 2H), 2.59-2.50 (m, 2H), 2.46-2.32 (m, 1H), 1.92-1.79 (m, 1H), 1.27 (t, J=7.3 Hz, 3H).

Example 247

(6S)-6-methyl-3-(4-oxazol-5-yl-2-oxo-pyrrolidin-1-yl)-N-(3,4,5-trifluorophenyl)-6,7-dihydro-4H-pyrazolo[1,5-a]pyrazine-5-carboxamide

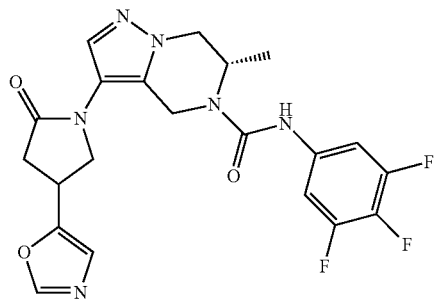 [SMILES: C[C@H]1Cn2ncc(N3CC(c4cnco4)CC3=O)c2CN1C(=O)Nc1cc(F)c(F)c(F)c1]

The title compound was prepared according to the following scheme:

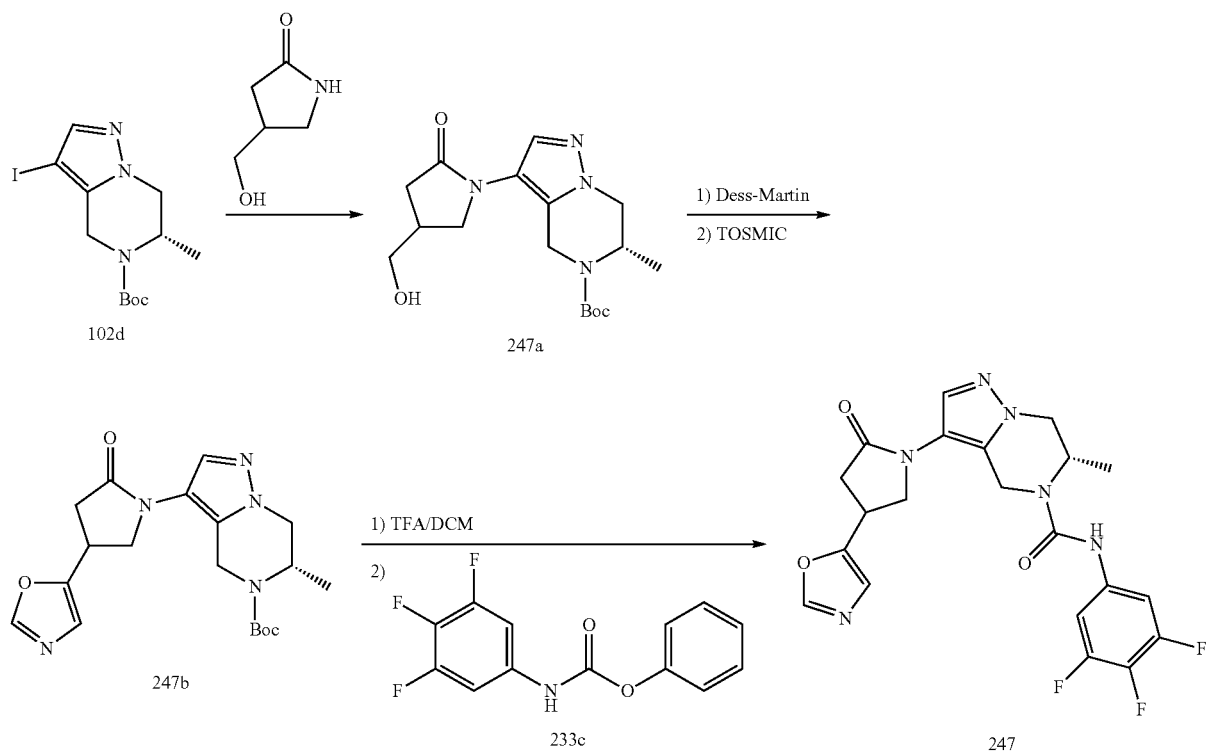

Step 1: Preparation of (6S)-tert-butyl 3-(4-(hydroxymethyl)-2-oxopyrrolidin-1-yl)-6-methyl-6,7-dihydropyrazolo[1,5-a]pyrazine-5(4H)-carboxylate (compound 247a)

To a 20 mL microwave vial was added tert-butyl (6S)-3-iodo-6-methyl-6,7-dihydro-4H-pyrazolo[1,5-a]pyrazine-5-carboxylate (compound 102d, 1 g, 2.75 mmol), 4-(hydroxymethyl)pyrrolidin-2-one (634 mg, 5.51 mmol), copper (I) iodide (105 mg, 0.55 mmol), potassium phosphate (1.17 g, 5.51 mmol), (1R,2R)-N1,N2-dimethylcyclohexane-1,2-diamine (157 mg, 1.1 mmol), and DMSO (15 mL). The vial was sealed and heated in microwave at 105° C. for 1 hour. The reaction mixture was poured into 50 mL of $H_2O$ and extracted with EtOAc (50 mL) twice. The organic layers were combined and then concentrated in vacuo to give a residue, which was purified by flash chromatography (silica gel, 0% to 80% EtOAc(contain 10% MeOH) in hexanes) to give compound 247a (800 mg) as light yellow oil. LCMS (M+H$^+$): 351

Step 2: Preparation of (6S)-tert-butyl 6-methyl-3-(4-(oxazol-5-yl)-2-oxopyrrolidin-1-yl)-6,7-dihydropyrazolo[1,5-a]pyrazine-5(4H)-carboxylate (compound 247b)

A mixture of (6S)-tert-butyl 3-(4-(hydroxymethyl)-2-oxopyrrolidin-1-yl)-6-methyl-6,7-dihydropyrazolo[1,5-a]pyrazine-5(4H)-carboxylate (compound 247a, 500 mg, 1.43 mmol) and Dess-Martin periodinane (1.21 g, 2.85 mmol) in DCM (10 mL) was stirred at room temperature for 2 hours. Then the reaction mixture was filtered, and the filtrate was concentrated to give a crude product. The crude product was dissolved in MeOH (20 mL), to which was added $K_2CO_3$ (1.59 g, 11.5 mmol), and TOSMIC (1.12 g, 5.74 mmol). The reaction mixture was heated to 80° C. and stirred for 16 hours. The reaction mixture was concentrated in vacuo. The crude product was purified by flash chromatography (silica gel, 20% to 100% EtOAc in hexanes) to give compound 247a as light yellow oil (80 mg). LCMS (M+H$^+$): 388.

Step 3: Preparation of (6S)-6-methyl-3-(4-oxazol-5-yl-2-oxo-pyrrolidin-1-yl)-N-(3,4,5-trifluorophenyl)-6,7-dihydro-4H-pyrazolo[1,5-a]pyrazine-5-carboxamide (Example 247)

(6S)-Tert-butyl 6-methyl-3-(4-(oxazol-5-yl)-2-oxopyrrolidin-1-yl)-6,7-dihydropyrazolo[1,5-a]pyrazine-5(4H)-carboxylate (compound 247b, 80 mg, 206 μmol) was added to a solution of hydrogen chloride in EtOAc (1M, 10 mL). The reaction mixture was stirred at room temperature for 16 hours, then concentrated to give a white solid. To the solid was added DMF (3 mL), DIPEA (377 mg, 2.92 mmol) and phenyl (3,4,5-trifluorophenyl)carbamate (compound 233c, 38.5 mg, 144 μmol). The resulting mixture was stirred at 40° C. for 3 hours, and then purified by prep-HPLC to give Example 247 as white solid (12 mg). LCMS (M+H$^+$): 461. $^1$H NMR (400 MHz, chloroform-d) δ ppm 8.05-7.84 (m, 2H), 7.43 (d, J=7.8 Hz, 1H), 7.28-7.21 (m, 2H), 7.01 (d, J=9.8 Hz, 1H), 5.17-5.03 (m, 2H), 4.45-4.18 (m, 2.5H), 4.13-3.94 (m, 3H), 3.87 (d, J=9.8 Hz, 0.5H), 3.12-2.95 (m, 1H), 2.94-2.77 (m, 1H), 1.37 (d, J=7.0 Hz, 3H).

Example 248

(6S)-6-methyl-3-(3-methylsulfonyl-5-oxo-imidazolidin-1-yl)-N-(3,4,5-trifluorophenyl)-6,7-dihydro-4H-pyrazolo[1,5-a]pyrazine-5-carboxamide

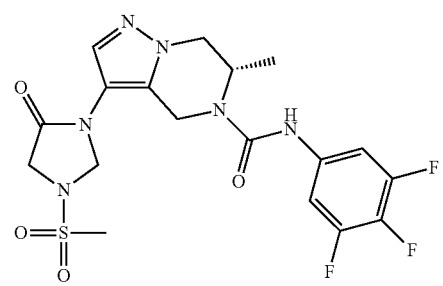 [SMILES: C[C@H]1Cn2ncc(N3CN(S(C)(=O)=O)CC3=O)c2CN1C(=O)Nc1cc(F)c(F)c(F)c1]

The title compound was prepared according to the following scheme:

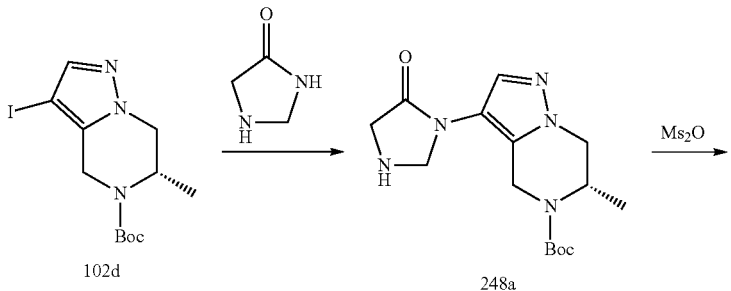

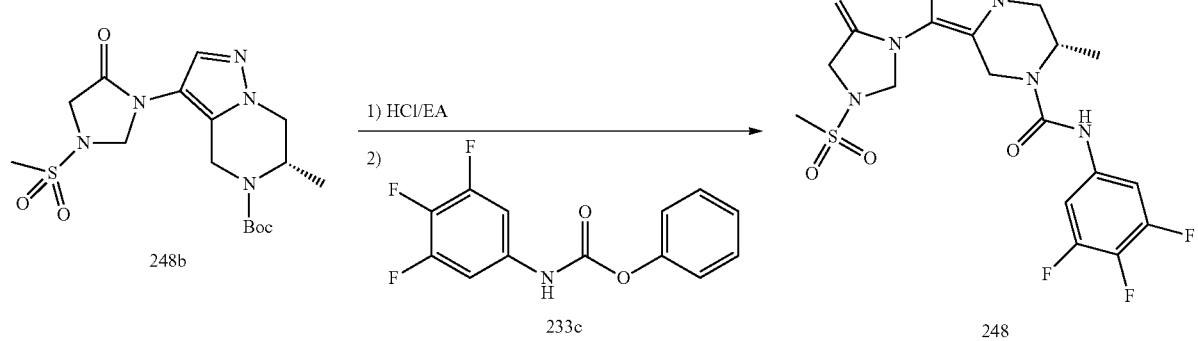

Step 1: Preparation of (S)-tert-butyl 6-methyl-3-(5-oxoimidazolidin-1-yl)-6,7-dihydropyrazolo[1,5-a]pyrazine-5(4H)-carboxylate (compound 248a)

A 20 mL microwave vial was charged with tert-butyl (6S)-3-iodo-6-methyl-6,7-dihydro-4H-pyrazolo[1,5-a]pyrazine-5-carboxylate (compound 102d, 1 g, 2.75 mmol), imidazolidin-4-one (474 mg, 5.51 mmol), copper (I) iodide (105 mg, 551 µmol), potassium phosphate (1.17 g, 5.51 mmol),(1S,2S)-cyclohexane-1,2-diamine (126 mg, 1.1 mmol) and dioxane (15 mL). The vial was sealed and heated in microwave at 120° C. for 2.5 hours. The reaction mixture was filtered and the filtrate was concentrated in vacuo to give a crude product, which was purified by flash chromatography (silica gel, 0% to 80% EtOAc(contain 10% MeOH) in heptane) to give compound 248a as light yellow oil (400 mg). LCMS (M+H$^+$): 322.

Step 2: Preparation of (S)-tert-butyl 6-methyl-3-(3-(methylsulfonyl)-5-oxoimidazolidin-1-yl)-6,7-dihydropyrazolo[1,5-a]pyrazine-5(4H)-carboxylate (compound 248b)

A mixture of (S)-tert-butyl 6-methyl-3-(5-oxoimidazolidin-1-yl)-6,7-dihydropyrazolo[1,5-a]pyrazine-5(4H)-carboxylate (compound 248a, 100 mg, 0.31 mmol), methanesulfonic anhydride (108 mg, 0.62 mmol) and N-ethyl-N-isopropylpropan-2-amine (201 mg, 1.56 mmol) in DCM (5 mL) was stirred at room temperature for 2 hours. The reaction mixture was concentrated in vacuo. The obtained residue was purified by flash chromatography (silica gel, 30% to 100% EtOAc (contain 10% Methanol) in hexanes) to give compound 248b as a colorless oil (80 mg). LCMS (M+H$^+$): 400.

Step 3: Preparation of (6S)-6-methyl-3-(3-methylsulfonyl-5-oxo-imidazolidin-1-yl)-N-(3,4,5-trifluorophenyl)-6,7-dihydro-4H-pyrazolo[1,5-a]pyrazine-5-carboxamide (Example 248)

(S)-Tert-butyl 6-methyl-3-(3-(methylsulfonyl)-5-oxoimidazolidin-1-yl)-6,7-dihydropyrazolo[1,5-a]pyrazine-5(4H)-carboxylate (compound 248b, 80 mg, 200 µmol) was added to a solution of hydrogen chloride in EtOAc (1M, 10 mL), and the reaction mixture was stirred at room temperature for 16 hours. After removal of the solvent, the resulting light yellow solid was dissolved in DMF (5 mL), to which was added DIPEA (377 mg, 2.92 mmol) and phenyl (3,4,5-trifluorophenyl)carbamate (64.1 mg, 240 µmol). The reaction mixture was stirred at 40° C. for 3 hours, and then purified by prep-HPLC to give Example 248 as a white solid (39 mg). LCMS (M+H$^+$): 473. $^1$H NMR (400 MHz, chloroform-d) δ ppm 7.48 (s, 1H), 7.42 (brs, 1H), 7.26-7.17 (m, 2H), 5.22 (d, J=6.0 Hz, 1H), 5.13 (d, J=6.3 Hz, 1H), 5.12-5.05 (m, 1H), 5.01 (d, J=16.6 Hz, 1H)4.42 (d, J=16.8 Hz, 1H), 4.32 (dd, J=5.1, 12.9 Hz, 1H), 4.26-4.15 (m, 2H), 4.09 (dd, J=1.6, 12.9 Hz, 1H), 3.08 (s, 3H), 1.38 (d, J=7.0 Hz, 3H).

Example 250

(6S)-3-(5,5-dimethyl-2-oxo-oxazolidin-3-yl)-6-methyl-N-(3,4,5-trifluorophenyl)-6,7-dihydro-4H-pyrazolo[1,5-a]pyrazine-5-carboxamide

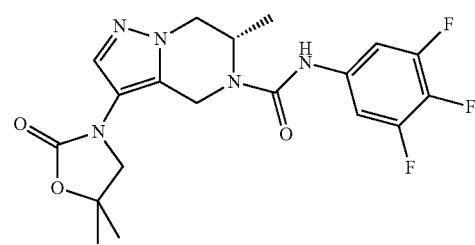 [SMILES: C[C@H]1Cn2ncc(N3CC(C)(C)OC3=O)c2CN1C(=O)Nc1cc(F)c(F)c(F)c1]

The title compound was prepared according to the following scheme:

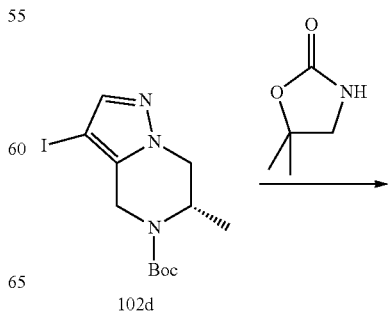

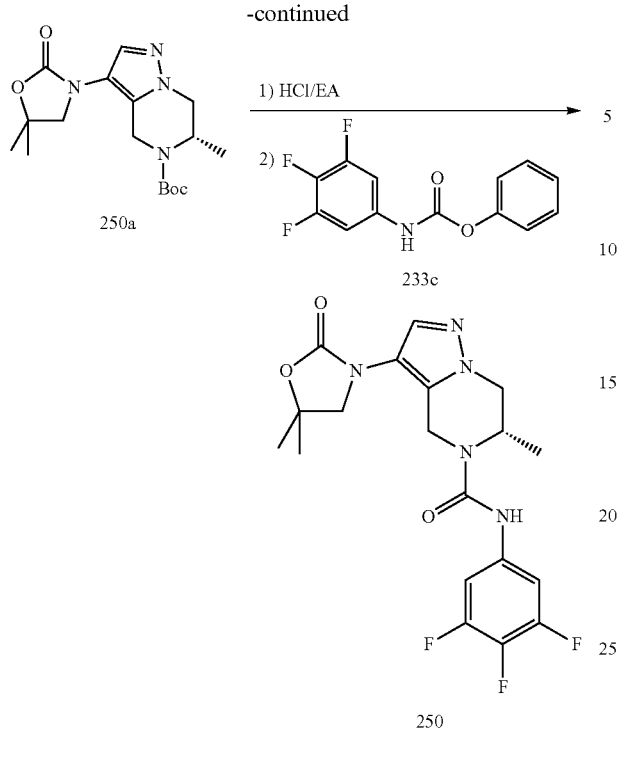

Preparation of (6S)-3-(5,5-dimethyl-2-oxo-oxazolidin-3-yl)-6-methyl-N-(3,4,5-trifluorophenyl)-6,7-dihydro-4H-pyrazolo[1,5-a]pyrazine-5-carboxamide (Example 250)

The title compound was prepared in analogy to Example 223 by using 5,5-dimethyloxazolidin-2-one instead of pyrrolidin-2-one and phenyl N-(3,4,5-trifluoro-phenyl)carbamate (compound 233c) instead of phenyl N-[2-(difluoromethyl)-4-pyridyl]carbamate (compound 218c). Example 250 was obtained as a white solid (110 mg). LCMS (M+H$^+$): 424. $^1$H NMR (400 MHz, MeOD) δ ppm 7.65 (s, 1H), 7.31-7.27 (m, 2H), 5.07 (d, J=16.8 Hz, 1H), 5.01-4.94 (m, 1H), 4.55 (d, J=16.8 Hz, 1H), 4.30 (dd, J=4.4, 12.9 Hz, 1H), 4.20-4.11 (m, 1H), 3.89-3.75 (m, 2H), 1.58 (s, 6H), 1.27 (d, J=6.8 Hz, 3H).

Example 251

(6S,7S)-6,7-dimethyl-3-(2-oxopyrrolidin-1-yl)-N-(3,4,5-trifluorophenyl)-6,7-dihydro-4H-pyrazolo[1,5-a]pyrazine-5-carboxamide

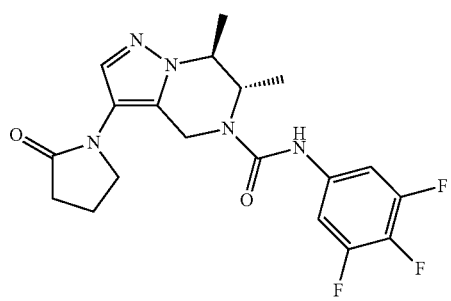 [SMILES: C[C@H]1[C@H](C)n2ncc(N3CCCC3=O)c2CN1C(=O)Nc1cc(F)c(F)c(F)c1]

The title compound was prepared according to the following scheme:

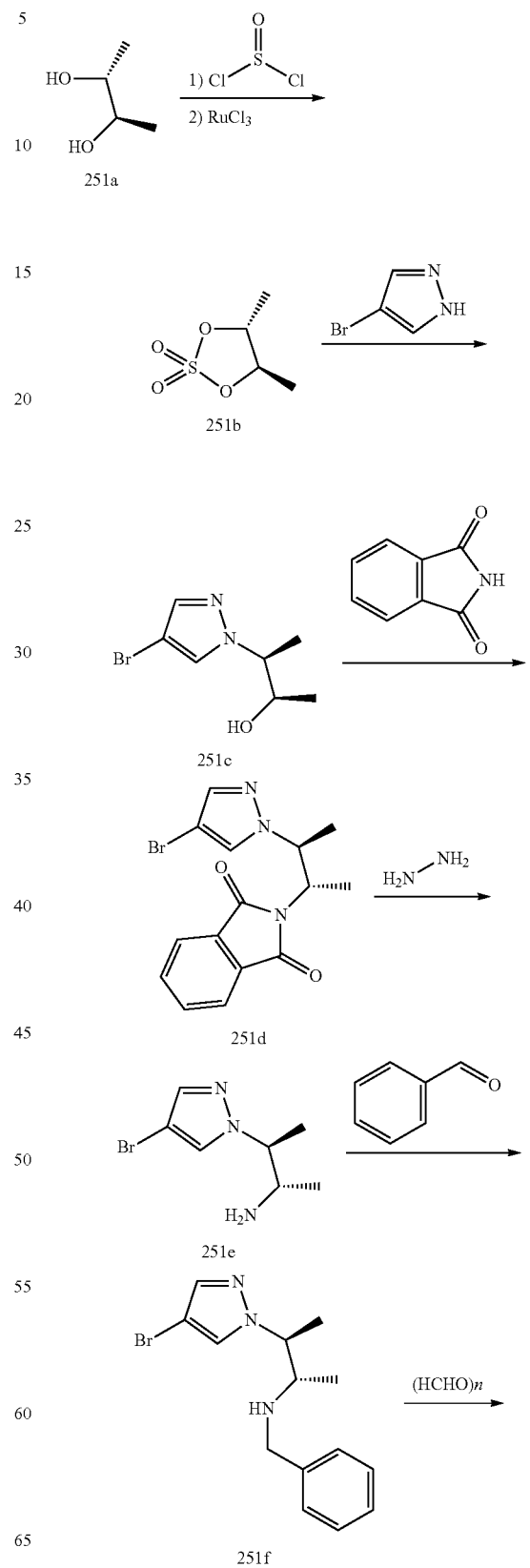

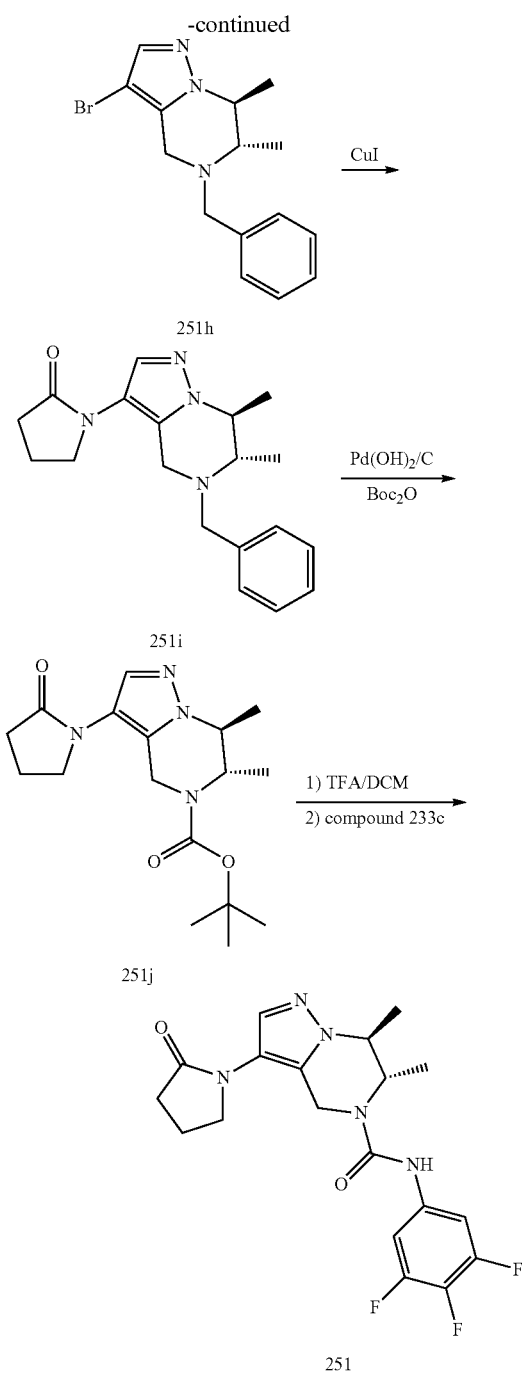

stirred solution of the crude residue in acetonitrile (200 mL) at 0° C. were added sodium periodate (17.8 g, 83.2 mmol), water (150 mL) and rhodium (III) chloride (1.16 g, 5.55 mmol) sequentially and the reaction mixture was stirred at 0° C. for 3 hours. The two layers were separated and the aqueous layer was extracted three times with EtOAc. The combined organic layer was washed with saturated aqueous NaHCO$_3$ and brine, and then dried over MgSO$_4$, filtered and concentrated to give compound 251b as a colorless oil (8 g).

Step 2: Preparation of (2R,3S)-3-(4-bromo-1H-pyrazol-1-yl)butan-2-ol (compound 251c)

A mixture of (4R,5R)-4,5-dimethyl-1,3,2-dioxathiolane 2,2-dioxide (compound 251b, 8 g, 52.6 mmol), 4-bromo-1H-pyrazole (11.6 g, 78.9 mmol) and Cs$_2$CO$_3$ (34.3 g, 105 mmol) in DMF (50 mL) was stirred at room temperature for 16 hours. The reaction mixture was filtered and concentrated. The resulting residue was taken up in 400 mL of 1:2 THF: 50% aq. H$_2$SO$_4$, and stirred vigorously for 48 hours. The reaction mixture was then carefully basified with 10 M NaOH, and the layers were separated. The aqueous layer was extracted twice with DCM, and the combined organic layer was washed with brine, dried over MgSO$_4$, filtered and concentrated to give compound 251c as a colorless oil (8 g). LCMS (M+H$^+$): 219

Step 3: Preparation of 2-O2S,3S)-3-(4-bromo-1H-pyrazol-1-yl)butan-2-yl)isoindoline-1,3-dione (compound 251d)

To a mixture of (2R,3S)-3-(4-bromo-1H-pyrazol-1-yl)butan-2-ol (compound 251c, 8 g, 36.5 mmol), isoindoline-1,3-dione (5.91 g, 40.2 mmol) and triphenylphosphine (12.5 g, 47.5 mmol) in THF (75 mL) was added DIAD (11.1 g, 54.8 mmol) dropwise at room temperature. Then the reaction mixture was stirred at room temperature for 2 hours, and concentrated in vacuo. The crude product was purified by flash chromatography (silica gel, 0% to 50% EtOAc in hexanes) to give compound 251d as a white solid (5 g). LCMS (M+H$^+$): 348

Step 4: Preparation of (2S,3S)-3-(4-bromo-1H-pyrazol-1-yl)butan-2-amine (compound 251e)

A mixture of 2-((2S,3S)-3-(4-bromo-1H-pyrazol-1-yl)butan-2-yl)isoindoline-1,3-dione (compound 251d, 5 g, 14.4 mmol) and Hydrazine hydrate (7.19 g, 144 mmol) in MeOH (50 mL) was stirred at 80° C. for 15 hours. The reaction mixture was concentrated in vacuo. The residue was dissolved in DCM, the solid was filtered off and the filtrate was concentrated to give compound 251e as a slight yellow oil (3 g). LCMS (M+H$^+$): 218

Step 5: Preparation of (2S,3S)-N-benzyl-3-(4-bromo-1H-pyrazol-1-yl)butan-2-amine (compound 251f)

A mixture (2S,3S)-3-(4-bromo-1H-pyrazol-1-yl)butan-2-amine (compound 251e, 3 g, 13.8 mmol) and benzaldehyde (1.61 g, 15.1 mmol) in MeOH (50 mL) was stirred for 2 hours at room temperature. Then sodium borohydride (624 mg, 16.5 mmol) was added slowly at 0° C. in 30 mins and the reaction mixture was stirred at room temperature for another 30 mins. The reaction mixture was poured into 100 mL of H$_2$O and extracted with EtOAc (100 mL) twice. The organic layers were combined, dried over Na$_2$SO$_4$ and then Step 1: Preparation of (4R,5R)-4,5-dimethyl-1,3,2-dioxathiolane 2,2-dioxide (compound 251b)

A solution of SOCl$_2$ (7.26 g, 4.45 mL, 61 mmol) in DCM (50 mL) was added dropwise to a stirred mixture of (2R,3R)-butane-2,3-diol (5 g, 55.5 mmol), imidazole (18.9 g, 277 mmol) and triethylamine (19.6 g, 27.1 mL, 194 mmol) in DCM (200 mL) at 0° C., and the reaction mixture was stirred for 1 hour at 0° C. The reaction mixture was quenched with H$_2$O and extracted twice with DCM. The combined organic layer was washed with H$_2$O, dried over MgSO$_4$, filtered and concentrated to give a residue. To a concentrated in vacuo. The crude product was purified by flash chromatography (silica gel, 0% to 50% EtOAc in hexanes) to give compound 251f as light yellow oil (4 g). LCMS (M+H$^+$): 308

Step 6: Preparation of (6S,7S)-5-benzyl-3-bromo-6,7-dimethyl-4,5,6,7-tetrahydropyrazolo[1,5-a]pyrazine (compound 251h)

To a stirred solution of (2S,3S)-N-benzyl-3-(4-bromo-1H-pyrazol-1-yl)butan-2-amine (compound 251d, 4 g, 13 mmol) in acetonitrile (50 mL) was added paraformaldehyde (1.95 g, 64.9 mmol) and 2,2,2-trifluoroacetic acid (296 mg, 2.6 mmol), and the reaction mixture was stirred at 70° C. for 6 hours. The reaction mixture was concentrated and the residue was then taken up in EtOAc, and washed with NaHCO$_3$ aq. solution and brine. The organic layer was concentrated and the residue was purified on a silica gel column (heptane: EtOAc 1:0 to 9:1) to give compound 251h as a colorless oil (2.3 g). LCMS (M+H$^+$): 320

Step 7: Preparation of 1-((6S,7S)-5-benzyl-6,7-dimethyl-4,5,6,7-tetrahydropyrazolo[1,5-a]pyrazin-3-yl)pyrrolidin-2-one (compound 251i)

A 10 mL microwave vial was charged with (6S,7S)-5-benzyl-3-bromo-6,7-dimethyl-4,5,6,7-tetrahydropyrazolo[1,5-a]pyrazine (compound 251h, 300 mg, 0.94 mmol), copper (I) iodide (35.7 mg, 0.19 mmol), potassium carbonate (388 mg, 2.81 mmol), pyrrolidin-2-one (159 mg, 1.87 mmol), N1,N2-dimethylethane-1,2-diamine (33 mg, 0.38 mmol), and dioxane (5 mL). The vial was sealed and heated in microwave at 125° C. for 2 hours. The reaction mixture was poured into 20 mL of H$_2$O and extracted with EtOAc (20 mL) twice. The organic layers were combined, dried, and then concentrated in vacuo. The crude product was purified by flash chromatography (silica gel, 20% to 50% EtOAc in hexanes, where EtOAc contains 10% MeOH) to give compound 251i (200 mg) as a colorless oil. LCMS (M+H$^+$): 325

Step 8: Preparation of (6S,7S)-tert-butyl 6,7-dimethyl-3-(2-oxopyrrolidin-1-yl)-6,7-dihydropyrazolo[1,5-a]pyrazine-5(4H)-carboxylate (compound 251j)

A mixture of 1-((6S,7S)-5-benzyl-6,7-dimethyl-4,5,6,7-tetrahydropyrazolo[1,5-a]pyrazin-3-yl)pyrrolidin-2-one (compound 251i, 200 mg, 616 μmol), Boc$_2$O(402 mg, 1.8 mmol) and Pd(OH)$_2$/C (43.3 mg, 61.6 μmol) in EtOH (50 mL) was stirred at 50° C. for 16 hours under hydrogen. The reaction mixture was filtered through celite. The filtrate was concentrated to give compound 251j (200 mg) as a colorless oil. LCMS (M+H$^+$): 335

Step 9: Preparation of (6S,7S)-6,7-dimethyl-3-(2-oxopyrrolidin-1-yl)-N-(3,4,5-trifluorophenyl)-6,7-dihydro-4H-pyrazolo[1,5-a]pyrazine-5-carboxamide (Example 251)

A solution of (6S,7S)-tert-butyl 6,7-dimethyl-3-(2-oxopyrrolidin-1-yl)-6,7-dihydropyrazolo[1,5-a]pyrazine-5(4H)-carboxylate (compound 251j, 200 mg, 0.60 mmol) in 2,2,2-trifluoroacetic acid (2 mL) and DCM (2 mL) was stirred at room temperature for 30 mins. The reaction mixture was concentrated, and the residue was dissolved in DMF (5 mL), to which was added N-ethyl-N-isopropylpropan-2-amine (386 mg, 2.99 mmol) and phenyl (3,4,5-trifluorophenyl) carbamate (192 mg, 0.72 mmol). The reaction mixture was stirred at 70° C. for 0.5 hours. The reaction mixture was diluted with EtOAc (30 mL), and washed with water. The organic layer was dried and concentrated, and the residue was purified by flash chromatography to give Example 251 (100 mg) as a white powder. LCMS (M+H$^+$): 408. $^1$H NMR (400 MHz, MeOD) δ ppm 7.64 (s, 1H), 7.36-7.25 (m, 2H), 5.06 (d, J=16.8 Hz, 1H), 4.82-4.73 (m, 1H), 4.50 (d, J=16.8 Hz, 1H), 4.41-4.33 (m, 1H), 3.92-3.80 (m, 2H), 2.61-2.52 (m, 2H), 2.25 (q, J=7.6 Hz, 2H), 1.45 (d, J=6.8 Hz, 3H), 1.25 (d, J=7.0 Hz, 3H).

Example 252

(6S)-6-methyl-3-(6-oxo-5-azaspiro[2.4]heptan-5-yl)-N-(3,4,5-trifluorophenyl)-6,7-dihydro-4H-pyrazolo[1,5-a]pyrazine-5-carboxamide

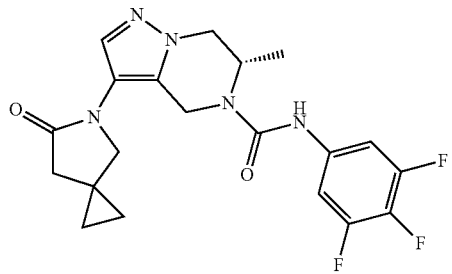 [SMILES: C[C@H]1Cn2ncc(N3CC4(CC4)CC3=O)c2CN1C(=O)Nc1cc(F)c(F)c(F)c1]

The title compound was prepared according to the following scheme:

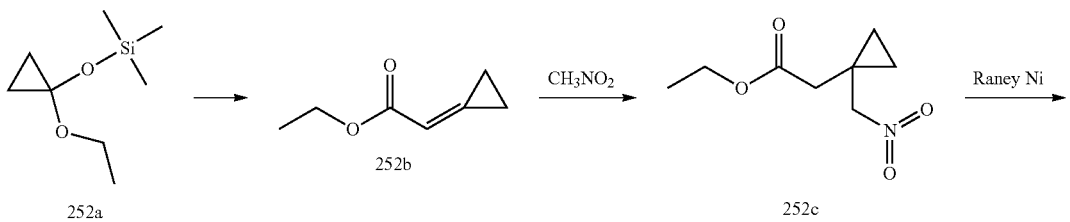

-continued

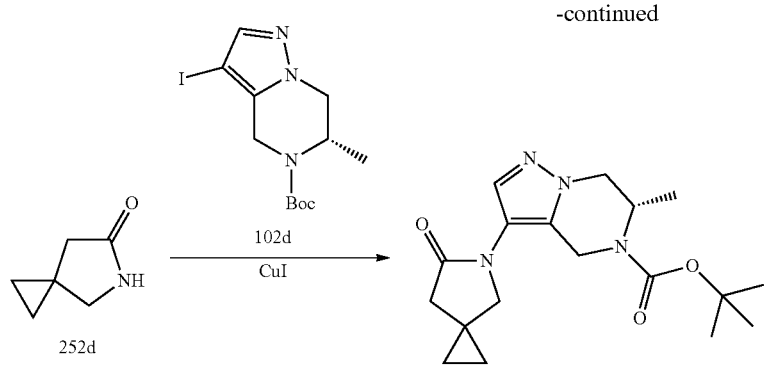

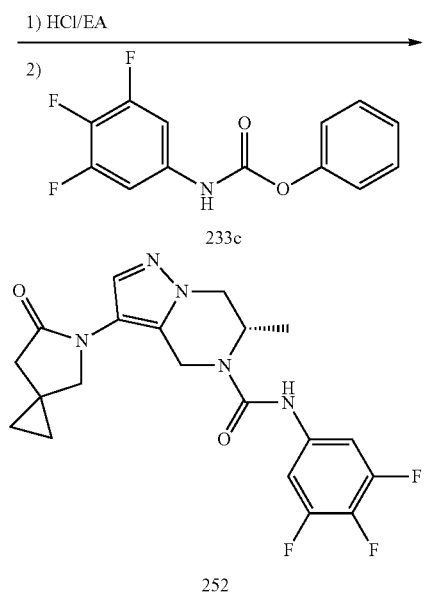

Preparation of 5-azaspiro[2.4]heptan-6-one (compound 252d)

Step 1: A solution of (1-ethoxycyclopropoxy)trimethylsilane (compound 252a, 50 g, 287 mmol) in MeOH (150 mL) was stirred at 20° C. for 1 hour and then concentrated under reduced pressure. The residue was dissolved in toluene (500 mL). To the above solution was added benzoic acid (7.0 g, 57.4 mmol). The mixture was heated to 90° C. with stirring, then a solution of (carbethoxymethylene)triphenylphosphorane (100 g, 287 mmol) in toluene (1200 mL) was added at the same temperature. The resulting mixture was stirred at 90° C. for 16 hours, and then concentrated under reduced pressure. The residue was purified by column chromatography to give ethyl 2-cyclopropylideneacetate (compound 252b, 6 g) as a colorless oil.

Step 2: To a solution of ethyl 2-cyclopropylideneacetate (compound 252b, 5.0 g, 39.7 mmol) in nitromethane (50 mL) and THF (50 mL) was added DBU (4.96 g, 19.8 mmol). The mixture was stirred at room temperature for 16 hours, and then concentrated under reduced pressure. The residue was purified by column chromatography to give compound 252c as a colorless oil (3.5 g).

Step 3: A mixture of ethyl 2-[1-(nitromethyl)cyclopropyl] acetate (compound 252c, 3.5 g, 18.7 mmol) and Raney Ni (500 mg) in MeOH (70 mL) was stirred at 50° C. under 50 psi of hydrogen for 16 hours. The mixture was filtered and the filtrate was concentrated under reduced pressure. The residue was triturated with methyl tert-butyl ether and PE to give compound 252d as a white solid (850 mg). LCMS (M+H$^+$): 112.

Preparation of (6S)-6-methyl-3-(6-oxo-5-azaspiro [2.4]heptan-5-yl)-N-(3,4,5-trifluorophenyl)-6,7-dihydro-4H-pyrazolo[1,5-a]pyrazine-5-carboxamide (Example 252)

The title compound was prepared in analogy to Example 223 by using 5-azaspiro[2.4]heptan-6-one (compound 252d) instead of pyrrolidin-2-one and phenyl N-(3,4,5-trifluorophenyl)carbamate (compound 233c) instead of phenyl N-[2-(difluoromethyl)-4-pyridyl]carbamate (compound 218c). Example 252 was obtained as a white solid (30 mg). LCMS (M+H$^+$): 420. $^1$H NMR (400 MHz, CDCl$_3$) δ ppm 8.07 (s, 1H), 7.40 (s, 1H), 7.30 (s, 2H), 5.21-5.02 (m, 2H), 4.42-4.26 (m, 2H), 4.01 (dd, 1H), 3.92 (d, 1H), 3.57 (d, 1H), 2.79-2.69 (m, 1H), 2.63-2.52 (m, 1H), 1.42 (d, 3H), 0.91-0.74 (m, 4H).

Example 253

(6S)-6-methyl-3-(2-oxo-3-azabicyclo[3.1.0]hexan-3-yl)-N-(3,4,5-trifluorophenyl)-6,7-dihydro-4H-pyrazolo[1,5-a]pyrazine-5-carboxamide

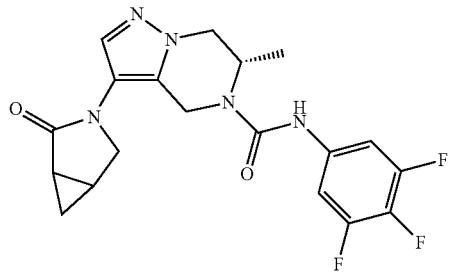 [SMILES: C[C@H]1Cn2ncc(N3CC4CC4C3=O)c2CN1C(=O)Nc1cc(F)c(F)c(F)c1]

The title compound was prepared according to the following scheme:

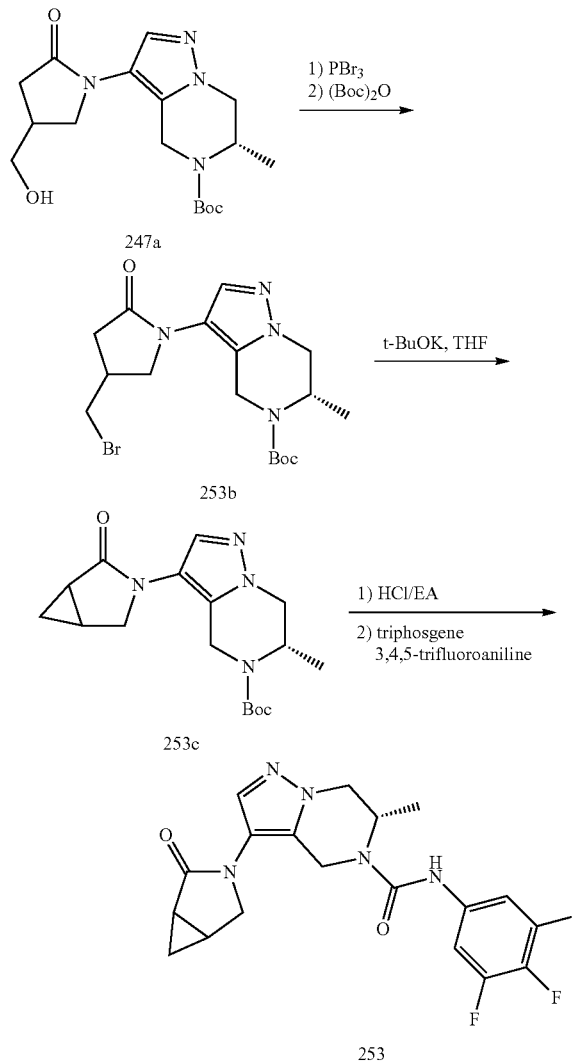

Step 1: Preparation of tert-butyl (6S)-3-[4-(bromomethyl)-2-oxo-pyrrolidin-1-yl]-6-methyl-6,7-dihydro-4H-pyrazolo[1,5-a]pyrazine-5-carboxylate (compound 253b)

To a solution of tert-butyl (6S)-3-[4-(hydroxymethyl)-2-oxo-pyrrolidin-1-yl]-6-methyl-6,7-dihydro-4H-pyrazolo[1,5-a]pyrazine-5-carboxylate (compound 247a, 50.0 mg, 0.14 mmol) in toluene (5.0 mL) was added dropwise PBr₃ (43.0 mg, 0.16 mmol) at 0° C., then the reaction mixture was stirred at 80° C. for 12 hours. The reaction was quenched by H₂O (20 mL) and extracted with EtOAc (50 mL) twice. The organic phases were combined and concentrated in vacuo to give a crude product. To a solution of the crude product (40.0 mg, 0.11 mmol) in dioxane (5.0 mL) was added (Boc)₂O (28.34 mg, 0.13 mmol) and a solution of NaHCO₃ (10 mg) in H₂O (5.0 mL), and then the reaction mixture was stirred at room temperature for 12 hours. The reaction mixture was concentrated and the residue was purified by prep-HPLC to give compound 253b (20 mg). LCMS (M+H⁺): 413.

Step 2: Preparation of tert-butyl (6S)-6-methyl-3-(2-oxo-3-azabicyclo[3.1.0]hexan-3-yl)-6,7-dihydro-4H-pyrazolo[1,5-a]pyrazine-5-carboxylate (compound 253c)

To a solution of tert-butyl (6S)-3-[4-(bromomethyl)-2-oxo-pyrrolidin-1-yl]-6-methyl-6,7-dihydro-4H-pyrazolo[1,5-a]pyrazine-5-carboxylate (compound 253b, 20 mg, 0.05 mmol) in THF (5 mL) was added a solution of t-BuOK in THF (0.1 mL, 1.0 mol/L) at 0° C., and then the reaction mixture was stirred at room temperature for 4 hours. Then H₂O (10 mL) and EtOAc (50 mL) were added, and the organic phase was separated and concentrated to provide compound 253c (20 mg). LCMS (M+H⁺): 333.

Step 3: Preparation of (6S)-6-methyl-3-(2-oxo-3-azabicyclo[3.1.0]hexan-3-yl)-N-(3,4,5-trifluorophenyl)-6,7-dihydro-4H-pyrazolo[1,5-a]pyrazine-5-carboxamide (Example 253)

The title compound was prepared in analogy to the preparation of Example 11 by 3,4,5-trifluoroaniline instead of 3-(trifluoromethyl)aniline and tert-butyl (6S)-6-methyl-3-(2-oxo-3-azabicyclo[3.1.0]hexan-3-yl)-6,7-dihydro-4H-pyrazolo[1,5-a]pyrazine-5-carboxylate (compound 253c) instead of tert-butyl 3-(4-fluorophenyl)-6,7-dihydro-4H-pyrazolo[1,5-a]pyrazine-5-carboxylate (compound 11a). Example 253 was obtained as a white solid. LCMS (M+H⁺): 406. ¹H NMR (400 MHz, DMSO-d₆) δ ppm 9.09 (s, 0.5H), 9.08 (s, 0.5H), 7.55 (s, 0.5H), 7.54 (s, 0.5H) 7.46-7.38 (m, 2H), 4.98-4.79 (m, 2H), 4.32 (d, J=17.1 Hz, 1H), 4.21-4.13 (m, 1H), 4.12-4.07 (m, 1H), 3.98 (dd, J=6.0, 10.0 Hz, 1H), 3.89 (dd, J=5.9, 10.2 Hz, 1H), 2.04 (br. s., 1H), 1.93 (br. s., 1H), 1.22-1.06 (m, 4H), 0.77-0.71 (m, 1H).

Example 254

(6S)-N-(3-chloro-4-fluoro-phenyl)-6-methyl-3-(4-methyl-2-oxo-pyrrolidin-1-yl)-6,7-dihydro-4H-pyrazolo[1,5-a]pyrazine-5-carboxamide

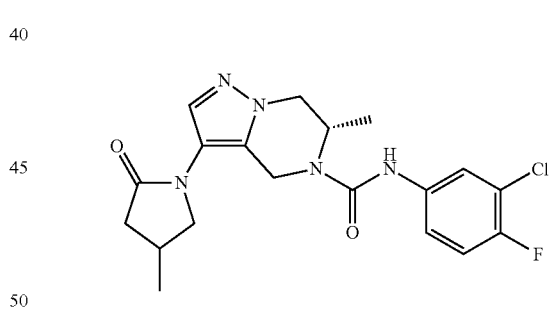

The title compound was prepared according to the following scheme:

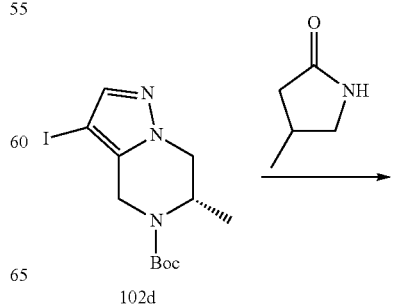

Example 255

(6S)-N-(3-chloro-4-fluoro-phenyl)-6-methyl-3-[2-oxo-4-(trifluoromethyl)pyrrolidin-1-yl]-6,7-dihydro-4H-pyrazolo[1,5-a]pyrazine-5-carboxamide

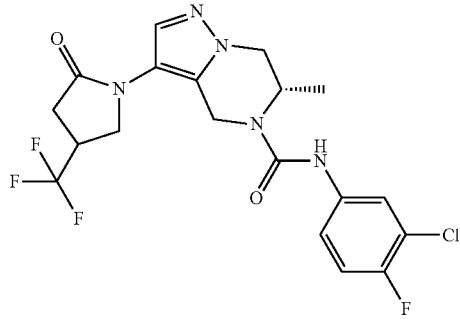 [SMILES: C[C@H]1Cn2ncc(N3CC(C(F)(F)F)CC3=O)c2CN1C(=O)Nc1ccc(F)c(Cl)c1]

The title compound was prepared according to the following scheme:

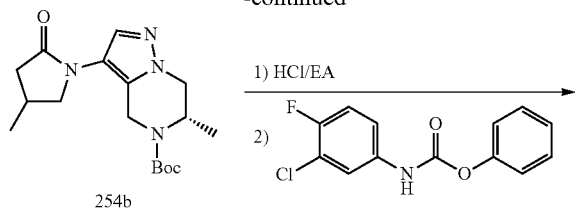

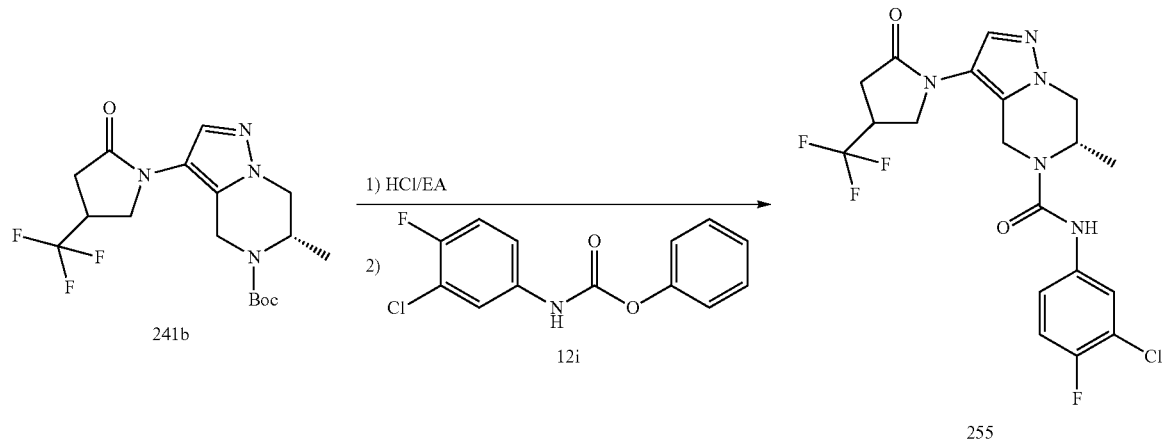 [SMILES: C[C@H]1Cn2ncc(N3CC(C(F)(F)F)CC3=O)c2CN1C(=O)OC(C)(C)C ; O=C(Nc1ccc(F)c(Cl)c1)Oc1ccccc1 ; C[C@H]1Cn2ncc(N3CC(C(F)(F)F)CC3=O)c2CN1C(=O)Nc1ccc(F)c(Cl)c1]

Preparation of (6S)-N-(3-chloro-4-fluoro-phenyl)-6-methyl-3-(4-methyl-2-oxo-pyrrolidin-1-yl)-6,7-dihydro-4H-pyrazolo[1,5-a]pyrazine-5-carboxamide (Example 254)

The title compound was prepared in analogy to Example 223 by using 4-methylpyrrolidin-2-one instead of pyrrolidin-2-one, and phenyl N-(3-chloro-4-fluoro-phenyl)carbamate (compound 12i) instead of phenyl N-[2-(difluoromethyl)-4-pyridyl]carbamate (compound 218c). Example 254 was obtained as a solid (48 mg). LCMS (M+H⁺): 406. ¹H NMR (400 MHz, MeOD) δ ppm 7.67-7.56 (m, 2H), 7.38-7.32 (m, 1H), 7.22-7.12 (m, 1H), 5.08-4.94 (m, 2H), 4.56-4.45 (m, 1H), 4.33-4.26 (m, 1H), 4.20-4.11 (m, 1H), 4.00-3.94 (m, 1H), 3.51-3.44 (m, 1H), 2.76-2.62 (m, 2H), 2.27-2.17 (m, 1H), 1.30-1.20 (m, 6H).

Preparation of (6S)-N-(3-chloro-4-fluoro-phenyl)-6-methyl-3-[2-oxo-4-(trifluoromethyl)pyrrolidin-1-yl]-6,7-dihydro-4H-pyrazolo[1,5-a]pyrazine-5-carboxamide (Example 255)

The title compound was prepared in analogy to Example 223 by using 4-(trifluoromethyl)pyrrolidin-2-one instead of pyrrolidin-2-one, and phenyl N-(3-chloro-4-fluoro-phenyl)carbamate (compound 12i) instead of phenyl N-[2-(difluoromethyl)-4-pyridyl]carbamate (compound 218c). Example 255 was obtained as a white solid (21 mg). LCMS (M+H⁺): 460. ¹H NMR (400 MHz, MeOD) δ ppm 7.66 (s, 1H), 7.64-7.58 (m, 1H), 7.37-7.31 (m, 1H), 7.21-7.13 (m, 1H), 5.09-4.92 (m, 2H), 4.52-4.45 (m, 1H), 4.32-4.28 (m, 1H), 4.21-4.07 (m, 2H), 3.98-3.94 (m, 1H), 3.58-3.45 (m, 1H), 2.98-2.85 (m, 1H), 2.74-2.68 (m, 1H), 1.29-1.26 (m, 3H)

Example 256

(6S)-N-(3-chloro-4-fluoro-phenyl)-3-(3-hydroxy-2-oxo-pyrrolidin-1-yl)-6-methyl-6,7-dihydro-4H-pyrazolo[1,5-a]pyrazine-5-carboxamide

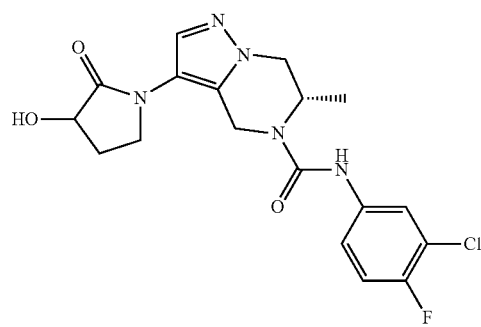 [SMILES: C[C@H]1Cn2ncc(N3CCC(O)C3=O)c2CN1C(=O)Nc1ccc(F)c(Cl)c1]

The title compound was prepared according to the following scheme:

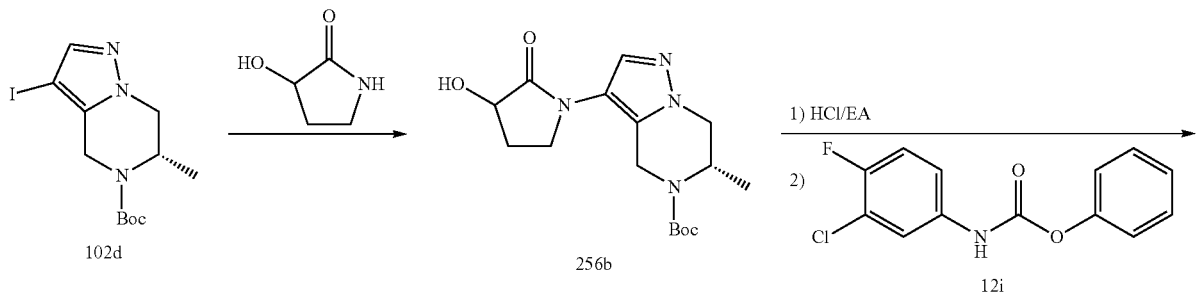

Preparation of (6S)-N-(3-chloro-4-fluoro-phenyl)-3-(3-hydroxy-2-oxo-pyrrolidin-1-yl)-6-methyl-6,7-dihydro-4H-pyrazolo[1,5-a]pyrazine-5-carboxamide (Example 256)

The title compound was prepared in analogy to Example 223 by using 3-hydroxylpyrrolidin-2-one instead of pyrrolidin-2-one and phenyl N-(3-chloro-4-fluoro-phenyl)carbamate (compound 12i) instead of phenyl N-[2-(difluoromethyl)-4-pyridyl]carbamate (compound 218c). Example 256 was obtained as a solid (18 mg). LCMS (M+H$^+$): 408. $^1$H NMR (400 MHz, MeOD) δ ppm 7.65 (s, 1H), 7.63 (dd, J=2.5, 6.8 Hz, 1H), 7.37-7.33 (m, 1H), 7.17 (t, J=8.9 Hz, 1H), 5.03 (d, J=17.1 Hz, 1H), 4.99-4.97 (m, 1H), 4.58 (d, J=17.1 Hz, 1H), 4.47 (t, J=8.4 Hz, 1H), 4.30 (dd, J=4.4, 12.7 Hz, 1H), 4.17 (dd, J=1.0, 12.8 Hz, 1H), 3.85-3.70 (m, 2H), 2.64-2.52 (m, 1H), 2.14-2.02 (m, 1H), 1.29 (d, J=7.0 Hz, 3H)

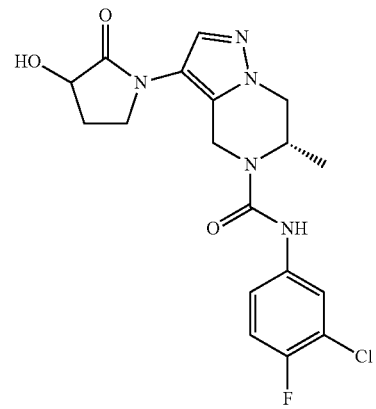

Example 257

(6S)-N-(3-chloro-4-fluoro-phenyl)-3-(4,4-dimethyl-2-oxo-pyrrolidin-1-yl)-6-methyl-6,7-dihydro-4H-pyrazolo[1,5-a]pyrazine-5-carboxamide

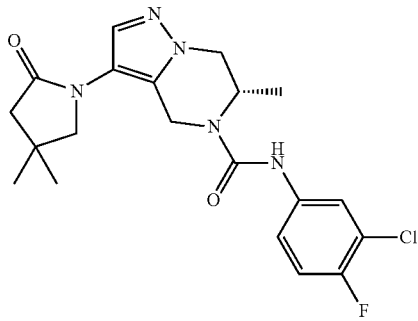 [SMILES: C[C@H]1Cn2ncc(N3CC(C)(C)CC3=O)c2CN1C(=O)Nc1ccc(F)c(Cl)c1]

The title compound was prepared according to the following scheme:

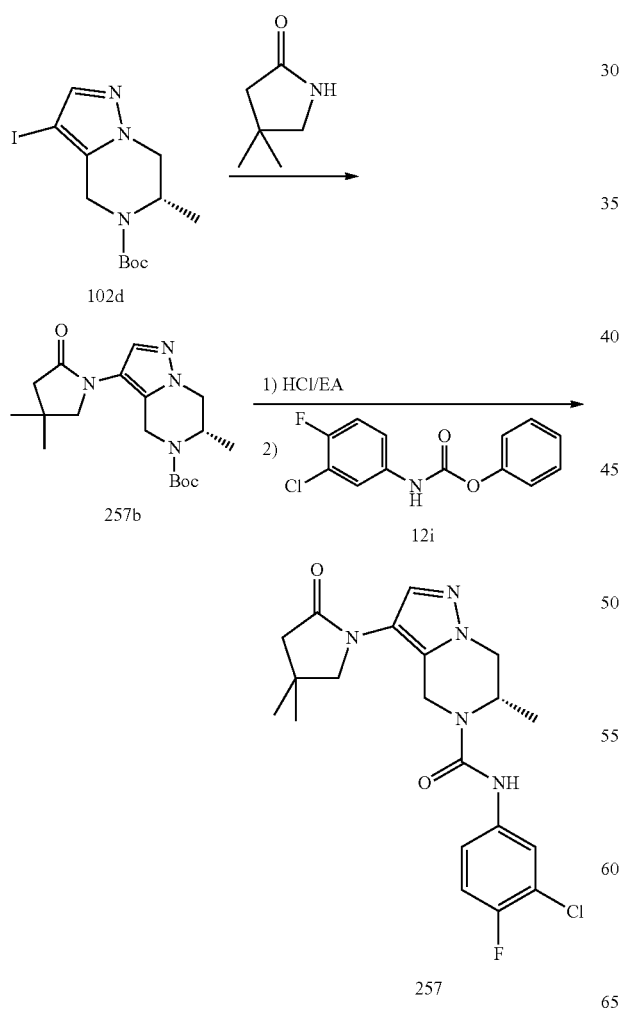

Preparation of (6S)-N-(3-chloro-4-fluoro-phenyl)-3-(4,4-dimethyl-2-oxo-pyrrolidin-1-yl)-6-methyl-6,7-dihydro-4H-pyrazolo[1,5-a]pyrazine-5-carboxamide (Example 257)

The title compound was prepared in analogy to Example 223 by using 4,4-dimethylpyrrolidin-2-one instead of pyrrolidin-2-one and phenyl N-(3-chloro-4-fluoro-phenyl)carbamate (compound 12i) instead of phenyl N-[2-(difluoromethyl)-4-pyridyl]carbamate (compound 218c). Example 257 was obtained as a solid (5 mg). LCMS (M+H$^+$): 420. $^1$H NMR (400 MHz, MeOD) δ ppm 7.65-7.59 (m, 2H), 7.34-7.31(m, 1H), 7.17 (t, J=8.9 Hz, 1H), 5.04 (d, J=16.8 Hz, 1H), 5.00-4.93 (m, 1H), 4.51 (d, J=17.1 Hz, 1H), 4.30 (dd, J=4.5, 12.8 Hz, 1H), 4.16 (dd, J=1.1, 12.7 Hz, 1H), 3.66-3.53 (m, 2H), 2.41 (s, 2H), 1.32-1.23 (m, 9H)

Example 258

(6S)-N-[2-(difluoromethyl)-4-pyridyl]-3-(4,4-dimethyl-2-oxo-pyrrolidin-1-yl)-6-methyl-6,7-dihydro-4H-pyrazolo[1,5-a]pyrazine-5-carboxamide

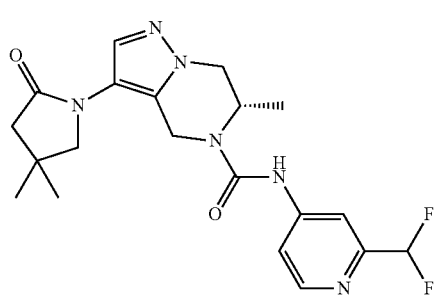 [SMILES: C[C@H]1Cn2ncc(N3CC(C)(C)CC3=O)c2CN1C(=O)Nc1ccnc(C(F)F)c1]

Preparation of (6S)-N-[2-(difluoromethyl)-4-pyridyl]-3-(4,4-dimethyl-2-oxo-pyrrolidin-1-yl)-6-methyl-6,7-dihydro-4H-pyrazolo[1,5-a]pyrazine-5-carboxamide

Example 258

The title compound was prepared in analogy to Example 223 by using 4,4-dimethylpyrrolidin-2-one instead of pyrrolidin-2-one. Example 258 was obtained as a solid (5 mg). LCMS (M+H$^+$): 419. $^1$H NMR (400 MHz, MeOD) δ ppm 8.43 (d, J=5.5 Hz, 1H), 7.87 (d, J=2.0 Hz, 1H), 7.68 (dd, J=2.3, 5.8 Hz, 1H), 7.62 (s, 1H), 6.67 (t, J=54 Hz, 1H), 5.10 (d, J=17.1 Hz, 1H), 5.05-4.97 (m, 1H), 4.55 (d, J=16.8 Hz, 1H), 4.33 (dd, J=4.3, 12.8 Hz, 1H), 4.18 (d, J=14.1 Hz, 1H), 3.66-3.56 (m, 2H), 2.42 (s, 2H), 1.33-1.25 (m, 9H)

Example 259

(6S)-6-methyl-3-[2-oxo-4-(trifluoromethyl)pyrrolidin-1-yl]-N-(3,4,5-trifluorophenyl)-6,7-dihydro-4H-pyrazolo[1,5-a]pyrazine-5-carboxamide

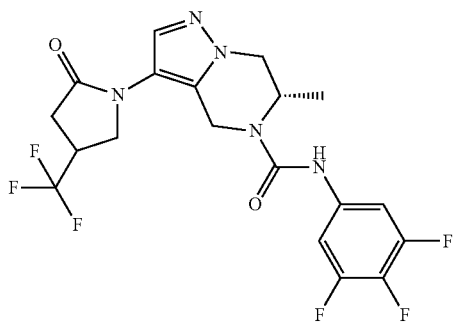 [SMILES: C[C@H]1Cn2ncc(N3CC(C(F)(F)F)CC3=O)c2CN1C(=O)Nc1cc(F)c(F)c(F)c1]

Preparation of 6S)-6-methyl-3-[2-oxo-4-(trifluoromethyl)pyrrolidin-1-yl]-N-(3,4,5-trifluorophenyl)-6,7-dihydro-4H-pyrazolo[1,5-a]pyrazine-5-carboxamide (Example 259)

The title compound was prepared in analogy to Example 223 by using 4-(trifluoromethyl)pyrrolidin-2-one instead of pyrrolidin-2-one and phenyl N-[3,4,5-trifluoro-phenyl]carbamate (compound 233c) instead of phenyl N-[2-(difluoromethyl)-4-pyridyl]carbamate (compound 218c). Example 259 was obtained as a white solid (38 mg). LCMS (M+H$^+$): 462. $^1$H NMR (400 MHz, MeOD) δ ppm 7.66 (s, 1H), 7.33-7.23 (m, 2H), 5.09-4.92 (m, 2H), 4.52-4.46 (m, 1H), 4.32-4.28 (m, 1H), 4.21-4.07 (m, 2H), 4.00-3.89 (m, 1H), 3.57-3.45 (m, 1H), 2.98-2.86 (m, 1H), 2.74-2.69 (m, 1H), 1.29-1.26 (m, 3H)

Example 260

(6S)-N-(2-chloro-4-pyridyl)-6-methyl-3-[2-oxo-4-(trifluoromethyl)pyrrolidin-1-yl]-6,7-dihydro-4H-pyrazolo[1,5-a]pyrazine-5-carboxamide

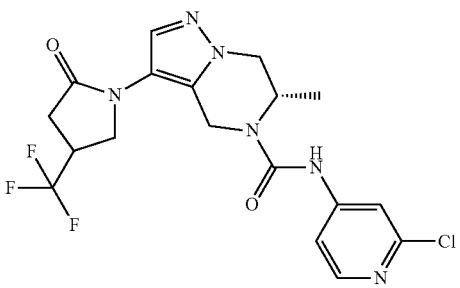 [SMILES: C[C@H]1Cn2ncc(N3CC(C(F)(F)F)CC3=O)c2CN1C(=O)Nc1ccnc(Cl)c1]

Preparation of (6S)-N-(2-chloro-4-pyridyl)-6-methyl-3-[2-oxo-4-(trifluoromethyl)pyrrolidin-1-yl]-6,7-dihydro-4H-pyrazolo[1,5-a]pyrazine-5-carboxamide (Example 260)

The title compound was prepared in analogy to Example 223 by using 4-(trifluoromethyl)pyrrolidin-2-one instead of pyrrolidin-2-one and phenyl N-(2-chloro-4-pyridyl)carbamate instead of phenyl N-[2-(difluoromethyl)-4-pyridyl]carbamate (compound 218c). Example 260 was obtained as a white solid (18 mg). LCMS (M+H$^+$): 443. $^1$H NMR (400 MHz, MeOD) δ ppm 8.15 (d, J=5.8 Hz, 1H), 7.72-7.64 (m, 2H), 7.47-7.45 (m, 1H), 5.11-5.04 (m, 1H), 4.99-4.95 (m, 1H), 4.55-4.52 (m, 1H), 4.38-4.27 (m, 1H), 4.17-4.06 (m, 2H), 3.97-3.93 (m, 1H), 3.56-3.46 (m, 1H), 2.98-2.85 (m, 1H), 2.78-2.66 (m, 1H), 1.31-1.28 (m, 3H)

Example 261

(6S,7R)-6,7-dimethyl-3-(2-oxopyrrolidin-1-yl)-N-(3,4,5-trifluorophenyl)-6,7-dihydro-4H-pyrazolo[1,5-a]pyrazine-5-carboxamide

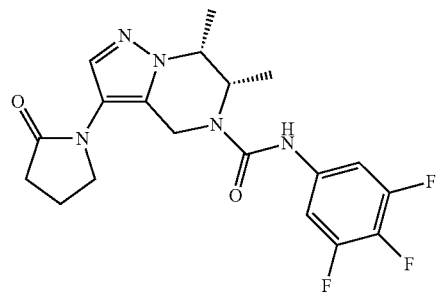 [SMILES: C[C@@H]1[C@H](C)N(C(=O)Nc2cc(F)c(F)c(F)c2)Cc2c(N3CCCC3=O)cnn21]

The title compound was prepared according to the following scheme:

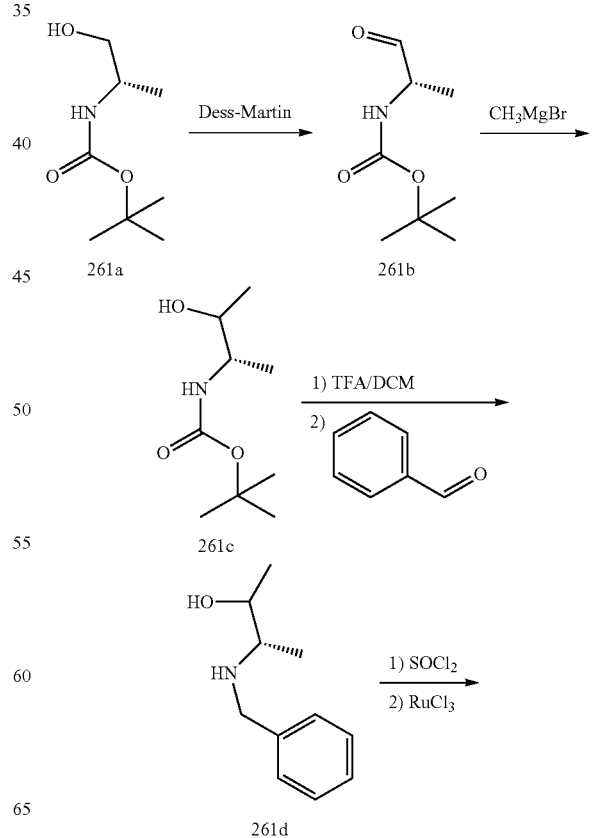

297
-continued

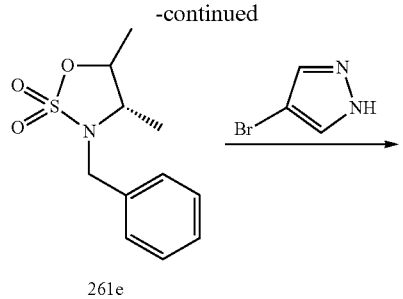

261e

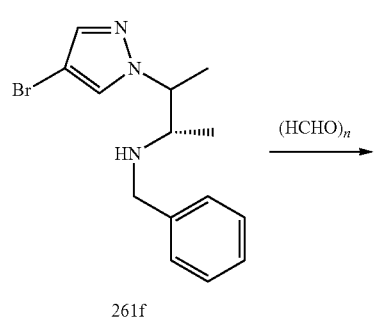

261f

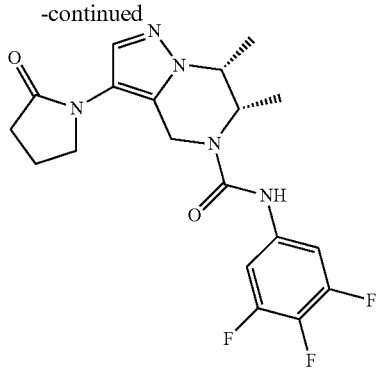

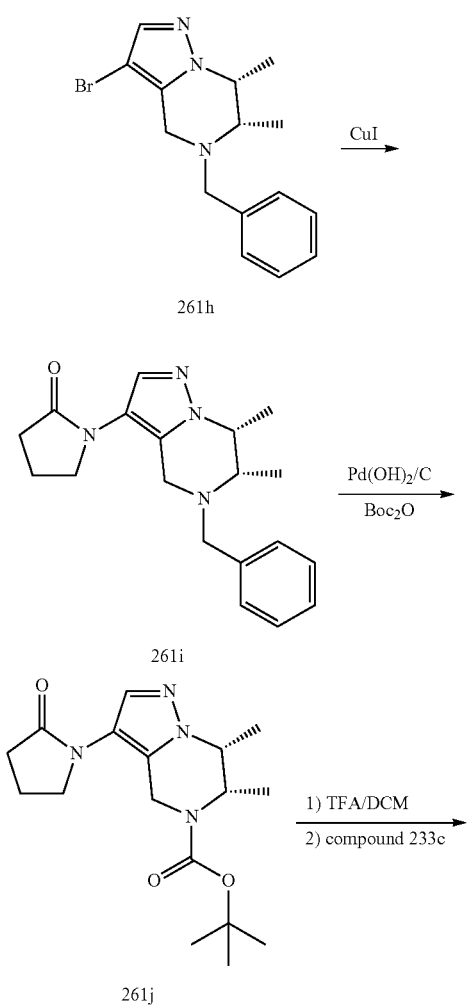

298
-continued

261

Step 1: Preparation of (S)-tert-butyl (1-oxopropan-2-yl)carbamate (compound 261b)

To a solution of (S)-tert-butyl (1-hydroxypropan-2-yl)carbamate (compound 261a, 8.76 g, 50 mmol) in DCM (200 mL) was added Dess-Martin periodinane (31.8 g, 75 mmol) slowly. After stirred at room temperature for 2 hours, the reaction mixture was filtered through silica gel. The filtrate was concentrated in vacuo to give compound 261b as a colorless oil (10 g).

Step 2: Preparation of tert-butyl ((2S)-3-hydroxybutan-2-yl)carbamate (compound 261c)

To a solution of (S)-tert-butyl (1-oxopropan-2-yl)carbamate (compound 261b, 8.66 g, 50 mmol) in THF (100 mL) was added methylmagnesium bromide (150 mL, 150 mmol) slowly at −78° C. The reaction mixture was stirred at −78° C. for 2 hours and then quenched with water. The reaction mixture was poured into 200 mL brine and extracted with EtOAc (100 mL) twice. The organic layers were combined, dried and concentrated in vacuo to give crude compound 261c as a colorless oil (9 g). LCMS (M+H$^+$): 190

Step 3: Preparation of tert-butyl (3S)-3-(benzylamino)butan-2-ol (compound 261d)

A mixture of tert-butyl ((2S)-3-hydroxybutan-2-yl)carbamate (compound 261c, 8 g, 25.4 mmol) and trifluoroacetic acid (28.9 g, 19.5 mL, 254 mmol) in DCM (40 mL) was stirred at room temperature for 1 hour. The reaction mixture was concentrated in vacuo and the residue was dissolved in DCM (100 mL), to which benzaldehyde (2.69 g, 25.4 mmol) and sodium triacetoxyborohydride (10.8 g, 50.7 mmol) were added. The reaction mixture was stirred at room temperature for 16 hours. Then the reaction mixture was poured into 250 mL saturated aqueous NaHCO$_3$ and extracted with EtOAc (200 mL) twice. The combined organic phase was dried over Na$_2$SO$_4$ and concentrated in vacuo. The crude product was purified by flash chromatography (silica gel, 20% to 80% EtOAc in hexanes) to give compound 261d as a light yellow oil (2 g). LCMS (M+H$^+$): 180.

Step 4: Preparation of (5S)-3-benzyl-4,5-dimethyl-1,2,3-oxathiazolidine 2,2-dioxide (compound 261e)

A solution of SOCl$_2$ (1.46 g, 896 µL, 12.3 mmol) in DCM (10 mL) was added dropwise to a stirred mixture of (3S)-3-(benzylamino)butan-2-ol (compound 261d, 2 g, 11.2 mmol), imidazole (3.8 g, 55.8 mmol) and triethylamine (3.95 g, 39 mmol) in DCM (50 mL) at 0° C., and the reaction mixture was allowed to stirred at 0° C. for 1 hour. The reaction mixture was quenched with H₂O and extracted twice with DCM. The combined organic layer was washed with H₂O, dried over MgSO₄, filtered and concentrated. To a stirred solution of the crude residue in acetonitrile (100 mL) at 0° C. were added sodium periodate (3.82 g, 17.9 mmol), water (75 mL) and rhodium (III) chloride (233 mg, 1.12 mmol) sequentially and the reaction mixture was stirred at 0° C. for 3 hours. The two layers were separated and the aqueous layer was extracted three times with EtOAc. The combined organic layer was washed with saturated aqueous NaHCO₃ and brine, the organic layer was dried over MgSO₄, filtered and concentrated to give compound 261e as a colorless oil (3 g), LCMS (M+H$^+$): 242.

Step 5: Preparation of (2S)-N-benzyl-3-(4-bromo-1H-pyrazol-1-yl)butan-2-amine (compound 261f)

A mixture of (5S)-3-benzyl-4,5-dimethyl-1,2,3-oxathiazolidine 2,2-dioxide (compound 261e, 3 g, 10.6 mmol), 4-bromo-1H-pyrazole (3.11 g, 21.1 mmol) and Cs₂CO₃ (6.89 g, 21.1 mmol) in DMF (50 mL) was stirred at room temperature for 16 hours. The reaction mixture was filtered and concentrated. The residue was dissolved in DCM and 20% aq.H₂SO₄ (150 mL, 1:1) and stirred vigorously for 12 hours. The reaction mixture was then carefully basified with 10 M NaOH, the layers were separated. The aqueous layer was extracted twice with DCM, and the combined organic layer was washed with brine, dried over MgSO₄, filtered and concentrated. The crude product was purified by flash chromatography (silica gel, 20% to 60% EtOAc in hexanes) to give compound 261f as a colorless oil (1 g). LCMS (M+H$^+$): 308

Preparation of (6S,7R)-6,7-dimethyl-3-(2-oxopyrrolidin-1-yl)-N-(3,4,5-trifluorophenyl)-6,7-dihydro-4H-pyrazolo[1,5-a]pyrazine-5-carboxamide (Example 261)

The title compound was prepared in analogy to Example 251 by using (2S)-N-benzyl-3-(4-bromo-1H-pyrazol-1-yl)butan-2-amine (compound 261f) instead of (2S,3S)-3-(4-bromo-1H-pyrazol-1-yl)butan-2-amine (compound 251e). Example 261 was obtained as a white solid (12 mg). LCMS (M+H$^+$): 408. $^1$H NMR (400 MHz, MeOD) δ ppm 7.62 (s, 1H), 7.32-7.26 (m, 2H), 5.00 (d, J=16.8 Hz, 2H), 4.79-4.71 (m, 1H), 4.50 (d, J=16.8 Hz, 1H), 4.46-4.39 (m, 1H), 3.93-3.80 (m, 2H), 2.60-2.52 (m, 2H), 2.29-2.21 (m, 2H), 1.62 (d, J=6.8 Hz, 3H), 1.16 (d, J=6.8 Hz, 3H).

Example 262

(6S)-3-[(3S)-3-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide

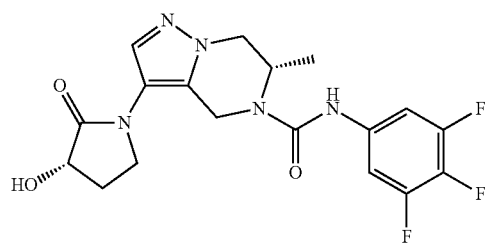 [SMILES: C[C@H]1Cn2ncc(N3CC[C@H](O)C3=O)c2CN1C(=O)Nc1cc(F)c(F)c(F)c1]

The title compound was prepared according to the following scheme:

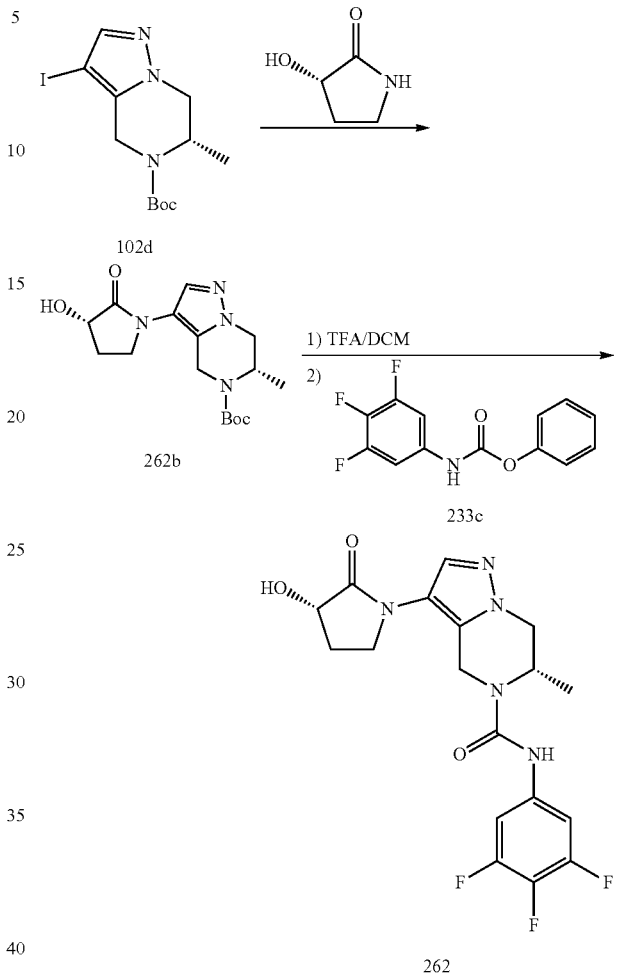

Preparation of (6S)-3-[(3S)-3-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide (Example 262)

Step 1: To a 25 mL microwave vial was added (S)-tert-butyl 3-iodo-6-methyl-6,7-dihydropyrazolo[1,5-a]pyrazine-5(4H)-carboxylate (150 mg, 413 μmol), (S)-3-hydroxypyrrolidin-2-one (83.5 mg, 826 μmol), copper (I) iodide (15.7 mg, 82.6 μmol), potassium phosphate (175 mg, 826 μmol) and (1S,2S)-cyclohexane-1,2-diamine (18.9 mg, 165 μmol) in dioxane (15 mL). The vial was capped and heated in the microwave at 120° C. for 2.5 hours. The reaction mixture was filtered and the filtrate was concentrated in vacuo to give crude product, which was purified by flash chromatography (silica gel) to give compound 262b as a light brown oil (200 mg). LCMS (M+H$^+$): 337.

Step 2: A mixture of (S)-tert-butyl 3-((S)-3-hydroxy-2-oxopyrrolidin-1-yl)-6-methyl-6,7-dihydropyrazolo[1,5-a]pyrazine-5(4H)-carboxylate (200 mg, 595 μmol) in DCM (10 mL) and TFA (5 mL) was stirred at room temperature for 30 minutes. The reaction mixture was concentrated, and the residue was dissolved in DMF (3 mL), to which was added N-ethyl-N-isopropylpropan-2-amine (384 mg, 2.97 mmol) and phenyl (3,4,5-trifluorophenyl)carbamate (191 mg, 713 µmol). The reaction mixture was stirred at 70° C. for 0.5 hours. Then the reaction mixture was diluted with ethyl acetate (30 mL), and washed with water. The organic layer was dried and concentrated. The crude material was purified by preparative HPLC to give Example 262 as a white solid (12 mg). LCMS (M+H$^+$): 410. $^1$H NMR (400 MHz, MeOD) δ ppm 7.65 (s, 1H), 7.33-7.26 (m, 2H), 5.03 (d, J=17.1 Hz, 1H), 4.99-4.95 (m, 1H), 4.58 (d, J=17.1 Hz, 1H), 4.47 (t, J=8.4 Hz, 1H), 4.35-4.26 (m, 1H), 4.16 (dd, J=1.0, 12.8 Hz, 1H), 3.84-3.72 (m, 2H), 2.61-2.57 (m, 1H), 2.16-2.00 (m, 1H), 1.29 (d, J=7.0 Hz, 3H).

Example 263

(6S)-N-(6-chloro-5-fluoro-2-pyridyl)-3-(4,4-dimethyl-2-oxo-pyrrolidin-1-yl)-6-methyl-6,7-dihydro-4H-pyrazolo[1,5-a]pyrazine-5-carboxamide

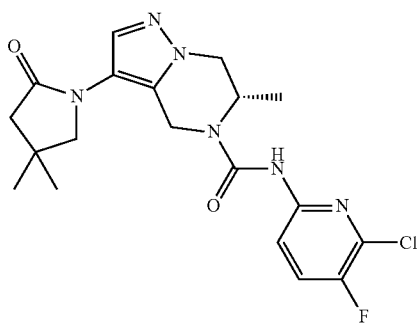 [SMILES: C[C@H]1Cn2ncc(N3CC(C)(C)CC3=O)c2CN1C(=O)Nc1ccc(F)c(Cl)n1]

Preparation of (6S)-N-(6-chloro-5-fluoro-2-pyridyl)-3-(4,4-dimethyl-2-oxo-pyrrolidin-1-yl)-6-methyl-6,7-dihydro-4H-pyrazolo[1,5-a]pyrazine-5-carboxamide (Example 263)

The title compound was prepared in analogy to Example 223 by using 4,4-dimethylpyrrolidin-2-one instead of pyrrolidin-2-one and phenyl N-(6-chloro-5-fluoro-2-pyridyl)carbamate (compound 140d) instead of phenyl N-[2-(difluoromethyl)-4-pyridyl]carbamate (compound 218c). Example 263 was obtained as a solid (22 mg). LCMS (M+H$^+$): 421. $^{11}$H NMR (400 MHz, MeOD) δ ppm 7.83 (dd, J=3.0, 8.8 Hz, 1H), 7.71-7.59 (m, 2H), 5.07 (d, J=16.8 Hz, 1H), 5.03-4.96 (m, 1H), 4.52 (d, J=17.1 Hz, 1H), 4.30 (dd, J=4.4, 12.7 Hz, 1H), 4.16 (dd, J=1.0, 12.8 Hz, 1H), 3.66-3.55 (m, 2H), 2.41 (s, 2H), 1.31-1.24 (m, 9H)

Example 264

(6S)-3-[(3R)-3-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide

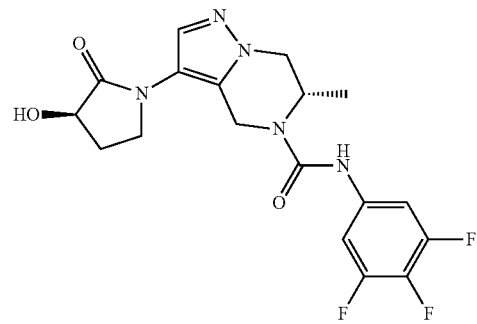 [SMILES: C[C@H]1Cn2ncc(N3CC[C@@H](O)C3=O)c2CN1C(=O)Nc1cc(F)c(F)c(F)c1]

Preparation of (6S)-3-[(3R)-3-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide (Example 264)

The title compound was prepared in analogy to Example 223 by using (3R)-3-hydroxypyrrolidin-2-one instead of pyrrolidin-2-one and phenyl N-(3,4,5-trifluorophenyl)carbamate (compound 233c) instead of phenyl N-[2-(difluoromethyl)-4-pyridyl]carbamate (compound 218c). Example 264 was obtained as a solid (13 mg). LCMS (M+H$^+$): 410. $^1$H NMR (400 MHz, MeOD) δ ppm 7.65 (s, 1H), 7.34-7.27 (m, 2H), 5.10 (d, J=17.1 Hz, 1H), 4.98-4.95 (m, 1H), 4.54-4.42 (m, 2H), 4.30 (dd, J=4.4, 12.9 Hz, 1H), 4.16 (dd, J=1.3, 12.8 Hz, 1H), 3.78 (dd, J=4.8, 8.8 Hz, 2H), 2.64-2.52 (m, 1H), 2.16-2.01 (m, 1H), 1.26 (d, J=7.0 Hz, 3H)

Example 265

(6S)-N-[6-(difluoromethyl)-5-fluoro-2-pyridyl]-6-methyl-3-(3-oxo-2-azaspiro[4.4]nonan-2-yl)-6,7-dihydro-4H-pyrazolo[1,5-a]pyrazine-5-carboxamide

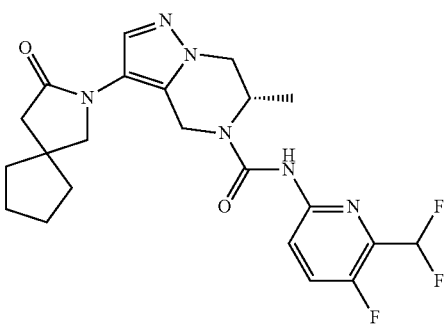 [SMILES: C[C@H]1Cn2ncc(N3CC4(CCCC4)CC3=O)c2CN1C(=O)Nc1ccc(F)c(C(F)F)n1]

The title compound was prepared according to the following scheme:

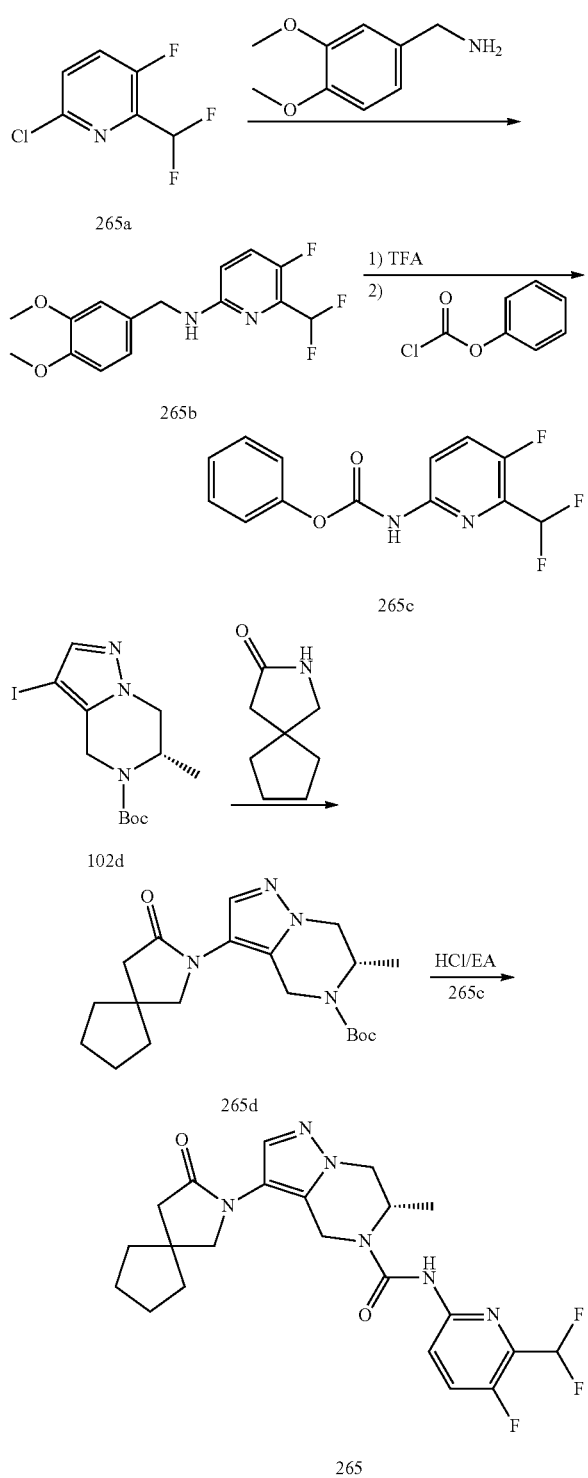

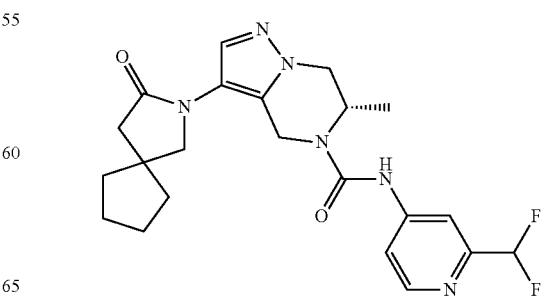

Preparation of 6-(difluoromethyl)-N-(3,4-dimethoxybenzyl)-5-fluoropyridin-2-amine (compound 265b)

To a mixture of 3,4-dimethoxybenzylamine (752 mg, 4.5 mmol) and 6-chloro-2-(difluoromethyl)-3-fluoropyridine (545 mg, 3.0 mmol) in dioxane (15.0 mL) was added cesium carbonate (1.95 g, 6 mmol), tris(dibenzylideneacetone)dipalladium (137 mg, 0.15 mmol) and 4,5-bis(diphenylphosphino)-9,9-dimethylxanthene (174 mg, 0.30 mmol). The reaction mixture was flushed with nitrogen and refluxed for 5 hours. The reaction mixture was cooled down, diluted with EtOAc, and washed with ice-water. The organic phase was separated and concentrated. The residue was purified by silica gel column to give compound 265b (375 mg). LCMS (M+H$^+$): 313.

Preparation of phenyl (6-(difluoromethyl)-5-fluoropyridin-2-yl)carbamate (compound 265c)

The reaction mixture of compound 6-(difluoromethyl)-N-(3,4-dimethoxybenzyl)-5-fluoropyridin-2-amine (compound 265b, 312 mg, 1.0 mmol) and trifluoroacetic acid (3.0 mL) was stirred under reflux overnight in a sealed tube. The reaction mixture was cooled and concentrated. The residue was dissolved in DCM (3.0 mL), to which was added DIPEA (1.0 mL, 5.83 mmol) and phenyl chloroformate (235 mg, 1.5 mmol). The reaction mixture was stirred at 40° C. for 3 hours. The reaction mixture was concentrated and the residue was purified by silica gel column to give compound 265c (141 mg). LCMS (M+H$^+$): 283.

Preparation of (6S)-N-[6-(difluoromethyl)-5-fluoro-2-pyridyl]-6-methyl-3-(3-oxo-2-azaspiro[4.4]nonan-2-yl)-6,7-dihydro-4H-pyrazolo[1,5-a]pyrazine-5-carboxamide (Example 265)

The title compound was prepared in analogy to Example 223 by using 2-azaspiro[4.4]nonan-3-one instead of pyrrolidin-2-one and phenyl (6-(difluoromethyl)-5-fluoropyridin-2-yl)carbamate (compound 265c) instead of phenyl N-[2-(difluoromethyl)-4-pyridyl]carbamate (compound 218c). Example 265 was obtained as a white solid (15 mg). LCMS (M+H$^+$): 463. $^1$H NMR (400 MHz, MeOD) δ ppm 8.04 (dd, J=3.4, 9.2 Hz, 1H), 7.71 (t, J=9.3 Hz, 1H), 7.63 (s, 1H), 6.83 (t, J=56 Hz, 1H), 5.09 (d, J=16.8 Hz, 1H), 5.03-4.96 (m, 1H), 4.54 (d, J=16.8 Hz, 1H), 4.32 (dd, 12.5 Hz, 1H), 4.21-4.12 (m, 1H), 3.80-3.63 (m, 2H), 2.53 (s, 2H), 1.79 (s, 8H), 1.29 (d, J=6.8 Hz, 3H)

Example 266

(6S)-N-[2-(difluoromethyl)-4-pyridyl]-6-methyl-3-(3-oxo-2-azaspiro[4.4]nonan-2-yl)-6,7-dihydro-4H-pyrazolo[1,5-a]pyrazine-5-carboxamide Preparation of (6S)-N-[2-(difluoromethyl)-4-pyridyl]-6-methyl-3-(3-oxo-2-azaspiro[4.4]nonan-2-yl)-6,7-dihydro-4H-pyrazolo[1,5-a]pyrazine-5-carboxamide (Example 266)

The title compound was prepared in analogy to Example 223 by using 2-azaspiro[4.4]nonan-3-one instead of pyrrolidin-2-one. Example 266 was obtained as a white solid (44 mg). LCMS (M+H$^+$): 445. $^1$H NMR (400 MHz, MeOD) δ ppm 8.42 (d, J=5.5 Hz, 1H), 7.87 (d, J=2.0 Hz, 1H), 7.68 (dd, J=2.3, 5.8 Hz, 1H), 7.62 (s, 1H), 6.67 (t, J=56 Hz, 1H), 5.10 (d, J=17.1 Hz, 1H), 5.04-4.95 (m, 1H), 4.55 (d, J=16.8 Hz, 1H), 4.32 (dd, J=4.5, 12.8 Hz, 1H), 4.17 (dd, J=1.1, 12.7 Hz, 1H), 3.77-3.67 (m, 2H), 2.53 (s, 2H), 1.79 (s, 8H), 1.30 (d, J=6.8 Hz, 3H).

Example 267

(6S)-6-methyl-3-[2-oxo-4-(pyrimidin-2-yloxymethyl)pyrrolidin-1-yl]-N-(3,4,5-trifluorophenyl)-6,7-dihydro-4H-pyrazolo[1,5-a]pyrazine-5-carboxamide

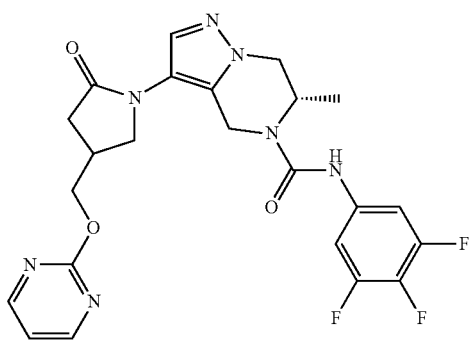 [SMILES: C[C@H]1Cn2ncc(N3CC(COc4ncccn4)CC3=O)c2CN1C(=O)Nc1cc(F)c(F)c(F)c1]

The title compound was prepared according to the following scheme:

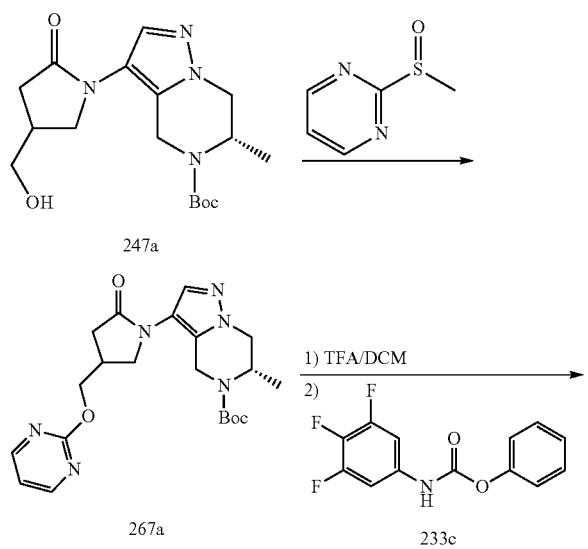

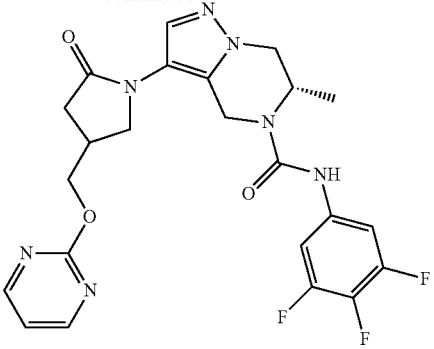

267

Step 1: Preparation of (6S)-tert-butyl 6-methyl-3-(2-oxo-4-((pyrimidin-2-yloxy)methyl)pyrrolidin-1-yl)-6,7-dihydropyrazolo[1,5-a]pyrazine-5(4H)-carboxylate (compound 267a)

A 10 mL vial was charged with (6S)-tert-butyl 3-(4-(hydroxymethyl)-2-oxopyrrolidin-1-yl)-6-methyl-6,7-dihydropyrazolo[1,5-a]pyrazine-5(4H)-carboxylate (compound 247a, 105 mg, 300 μmol), 2-(methylsulfinyl)pyrimidine (63.9 mg, 449 μmol), potassium carbonate (82.8 mg, 599 μmol) and dioxane (5 mL). The vial was sealed and heated at 80° C. for 16 hours. The reaction mixture was poured into 20 mL of H$_2$O and extracted with EtOAc twice. The organic layers were combined, washed with brine (50 mL) and then concentrated to give crude compound 267a as a light yellow oil (100 mg). LCMS (M+H$^+$): 429

Step 2: Preparation pf (6S)-6-methyl-3-[2-oxo-4-(pyrimidin-2-yloxymethyl)pyrrolidin-1-yl]-N-(3,4,5-trifluorophenyl)-6,7-dihydro-4H-pyrazolo[1,5-a] pyrazine-5-carboxamide (Example 267)

A solution of (6S)-tert-butyl 6-methyl-3-(2-oxo-4-((pyrimidin-2-yloxy)methyl)pyrrolidin-1-yl)-6,7-dihydropyrazolo[1,5-a]pyrazine-5(4H)-carboxylate (compound 267a, 100 mg, 233 μmol) in 2,2,2-trifluoroacetic acid (4.96 g, 43.5 mmol) and DCM (5 mL) was stirred at room temperature for 30 mins. The reaction mixture was concentrated, the residue was dissolved in DMF (5 mL), to which then was added N-ethyl-N-isopropylpropan-2-amine (151 mg, 1.17 mmol) and phenyl (3,4,5-trifluorophenyl)carbamate (74.8 mg, 280 μmol). The reaction mixture was stirred at 70° C. for 0.5 hour. The reaction mixture was diluted with ethyl acetate (30 mL), and washed with water. The combined organic layer was dried over Na$_2$SO$_4$, and concentrated under vacuum. The crude product was purified by prep-HPLC to give Example 267 as a white solid (58 mg). LCMS (M+H$^+$): 502. $^1$H NMR (400 MHz, MeOD) δ ppm 8.59 (dd, J=3.4, 4.8 Hz, 2H), 7.65 (d, J=2.1 Hz, 1H), 7.31-7.27 (m, 2H), 7.14 (dt, J=1.5, 4.9 Hz, 1H), 5.12-5.02 (m, 1H), 5.01-4.95 (m, 1H), 4.61-4.49 (m, 3H), 4.30 (dd, J=4.2, 12.7 Hz, 1H), 4.20-4.05 (m, 2H), 3.90-3.80 (m, 1H), 3.15-3.11 (m, 1H), 2.86-2.79 (m, 1H), 2.59-2.53 m, 1H), 1.28-1.25 (m, 3H).

Example 268

(6S)-6-methyl-3-[2-oxo-4-(pyrazol-1-ylmethyl)pyrrolidin-1-yl]-N-(3,4,5-trifluorophenyl)-6,7-dihydro-4H-pyrazolo[1,5-a]pyrazine-5-carboxamide

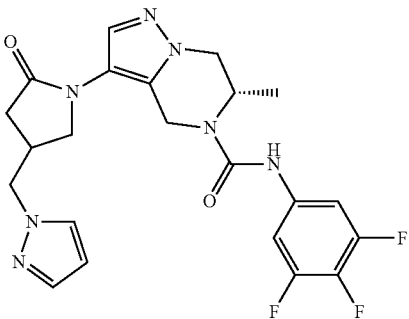 [SMILES: C[C@H]1Cn2ncc(N3CC(Cn4cccn4)CC3=O)c2CN1C(=O)Nc1cc(F)c(F)c(F)c1]

The title compound was prepared according to the following scheme:

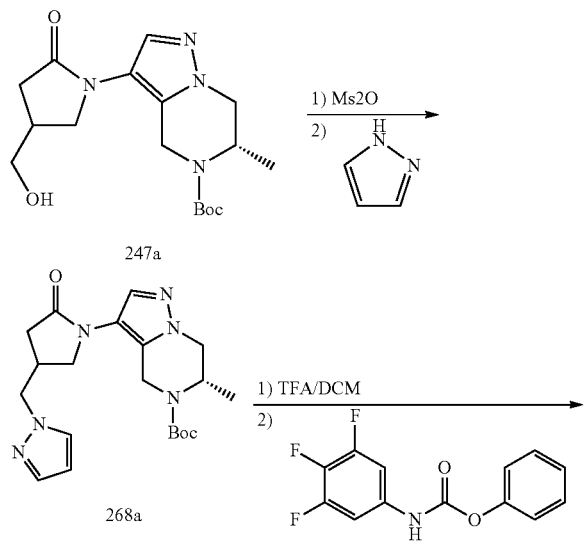

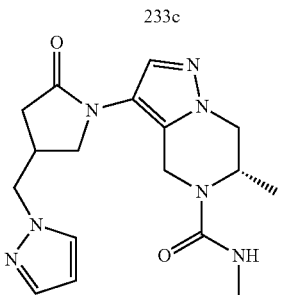

Step 1: Preparation of (6S)-tert-butyl 3-(4-((1H-pyrazol-1-yl)methyl)-2-oxopyrrolidin-1-yl)-6-methyl-6,7-dihydropyrazolo[1,5-a]pyrazine-5(4H)-carboxylate (compound 268a)

To a mixture of (6S)-tert-butyl 3-(4-(hydroxymethyl)-2-oxopyrrolidin-1-yl)-6-methyl-6,7-dihydropyrazolo[1,5-a]pyrazine-5(4H)-carboxylate (compound 247a, 200 mg, 571 µmol) and DIPEA (221 mg, 1.71 mmol) in DCM (10 mL) was added methanesulfonic anhydride (199 mg, 1.14 mmol) slowly. After stirred at room temperature for 1 hour, the reaction mixture was poured into 50 mL of H₂O and extracted with DCM (50 mL). The organic layers were dried over Na₂SO₄ and concentrated in vacuo to give an oil. To a solution of the oil in acetonitrile (10 mL) was added 1H-pyrazole (47.7 mg, 700 µmol) and Cs₂CO₃ (342 mg, 1.05 mmol). The reaction mixture was heated to 80° C. for 2 hours. The reaction mixture was concentrated and the residue was purified by flash chromatography to give compound 268a as a colorless oil. LCMS (M+H⁺): 401.

Step 2: Preparation of (6S)-6-methyl-3-[2-oxo-4-(pyrazol-1-ylmethyl)pyrrolidin-1-yl]-N-(3,4,5-trifluorophenyl)-6,7-dihydro-4H-pyrazolo[1,5-a]pyrazine-5-carboxamide (Example 268)

A solution of (6S)-tert-butyl 3-(4-((1H-pyrazol-1-yl)methyl)-2-oxopyrrolidin-1-yl)-6-methyl-6,7-dihydropyrazolo[1,5-a]pyrazine-5(4H)-carboxylate (compound 268a, 100 mg, 250 µmol) in 2,2,2-trifluoroacetic acid (2 mL) and DCM (5 mL) was stirred at room temperature for 30 mins, and then concentrated. The residue was dissolved in DMF (5 mL), to which was added N-ethyl-N-isopropylpropan-2-amine (161 mg, 1.25 mmol) and phenyl (3,4,5-trifluorophenyl)carbamate (80.1 mg, 300 µmol). The reaction mixture was stirred at 70° C. for 0.5 hours. The reaction mixture was purified by prep-HPLC to give Example 268 as a white solid (60 mg). LCMS (M+H⁺): 474. ¹H NMR (400 MHz, MeOD) δ ppm 7.62 (d, J=2.1 Hz, 1H), 7.47 (s, 1H), 7.42 (d, J=1.5 Hz, 1H), 7.22-7.13 (m, 2H), 6.22 (t, J=2.1 Hz, 1H), 4.88 (d, J=16.9 Hz, 1H), 4.84-4.78 (m, 1H), 4.33 (d, J=16.9 Hz, 1H), 4.24 (d, J=7.0 Hz, 2H), 4.16 (dd, J=4.5, 12.8 Hz, 1H), 4.03 (dd, J=1.1, 12.7 Hz, 1H), 3.78 (dd, J=7.9, 10.0 Hz, 1H), 3.60 (dd, J=5.3, 10.0 Hz, 1H), 3.05-2.93 (m, 1H), 2.58 (dd, J=9.0, 17.4 Hz, 1H), 2.33 (dd, J=6.2, 17.4 Hz, 1H), 1.14 (d, J=6.8 Hz, 3H).

Example 269

(6S)-6-methyl-3-[2-oxo-4-(pyrimidin-2-ylamino)pyrrolidin-1-yl]-N-(3,4,5-trifluorophenyl)-6,7-dihydro-4H-pyrazolo[1,5-a]pyrazine-5-carboxamide

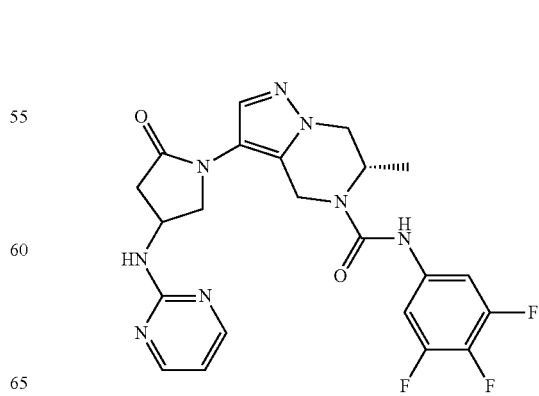

The title compound was prepared according to the following scheme:

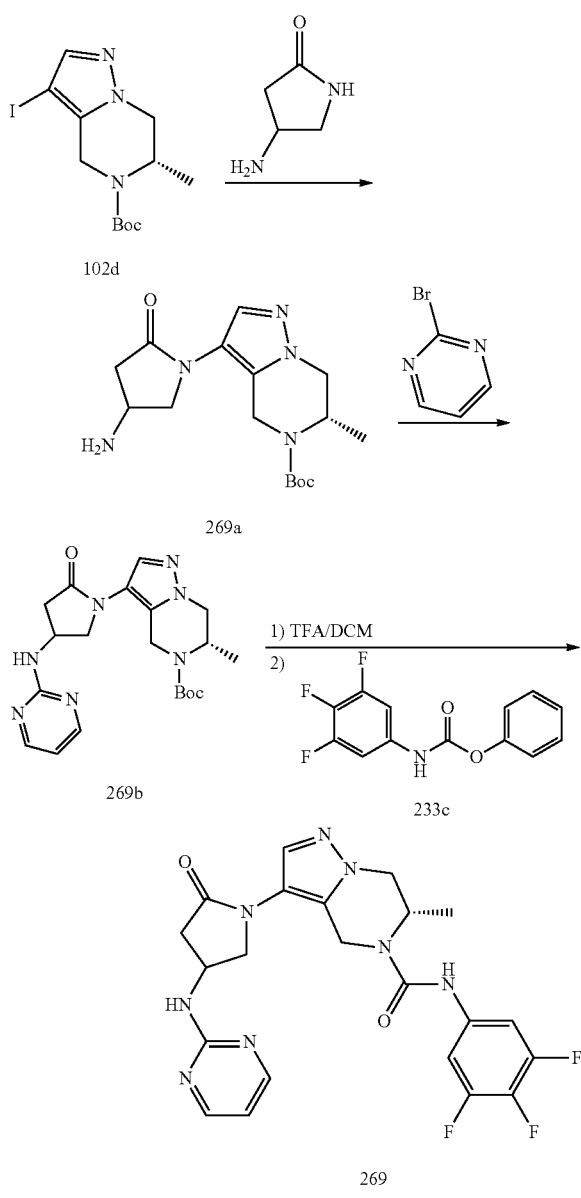

Step 1: Preparation of (6S)-tert-butyl 3-(4-amino-2-oxopyrrolidin-1-yl)-6-methyl-6,7-dihydropyrazolo[1,5-a]pyrazine-5(4H)-carboxylate (compound 269a)

A mixture of 4-aminopyrrolidin-2-one (276 mg, 2.75 mmol), (S)-tert-butyl 3-iodo-6-methyl-6,7-dihydropyrazolo[1,5-a]pyrazine-5(4H)-carboxylate (1 g, 2.75 mmol), potassium phosphate (877 mg, 4.13 mmol), copper(I) iodide (210 mg, 1.1 mmol) and (1R,2R)-N1,N2-dimethylcyclohexane-1,2-diamine (157 mg, 1.1 mmol) in DMSO (5 mL) was heated in microwave at 120° C. for 2 hours. The reaction mixture was diluted with water, and extracted with DCM/iPrOH (v/v=5:1, 30 mL) two times. The combined organic layer was dried over Na$_2$SO$_4$ and concentrated. The crude product was purified by flash chromatography (silica gel, 10% to 30% MeOH in DCM) to give compound 269a as a colorless oil (500 mg). LCMS (M+H$^+$): 336.

Step 2: Preparation of (6S)-tert-butyl 6-methyl-3-(2-oxo-4-(pyrimidin-2-ylamino)pyrrolidin-1-yl)-6,7-dihydropyrazolo[1,5-a]pyrazine-5(4H)-carboxylate (compound 269b)

To a mixture of (6S)-tert-butyl 3-(4-amino-2-oxopyrrolidin-1-yl)-6-methyl-6,7-dihydropyrazolo[1,5-a]pyrazine-5(4H)-carboxylate (compound 269a, 339 mg, 1.01 mmol) in dry dioxane was added 2-bromopyrimidine (209 mg, 1.31 mmol) and DIPEA (392 mg, 3.03 mmol). The reaction mixture was heated under reflux overnight, and then concentrated. The obtained residue was then taken up in DCM, and washed with brine. The organic layer was separated, dried over Na$_2$SO$_4$ and concentrated in vacuo to afford crude compound 269b as a yellow oil, which was directly used in next step without further purification. LCMS (M+H$^+$): 414.

Step 3: Preparation of (6S)-6-methyl-3-[2-oxo-4-(pyrimidin-2-ylamino)pyrrolidin-1-yl]-N-(3,4,5-trifluorophenyl)-6,7-dihydro-4H-pyrazolo[1,5-a]pyrazine-5-carboxamide (Example 269)

A solution of (6S)-tert-butyl 6-methyl-3-(2-oxo-4-(pyrimidin-2-ylamino)pyrrolidin-1-yl)-6,7-dihydropyrazolo[1,5-a]pyrazine-5(4H)-carboxylate (compound 269b, 418 mg, 1.01 mmol) in TFA (4 mL) and DCM (4 mL) was stirred at room temperature for 2 hours. The solvents were then removed and the residue was dissolved in DCM, to which was added phenyl (3,4,5-trifluorophenyl)carbamate (405 mg, 1.52 mmol) and DIPEA (1.31 g, 10.1 mmol). The reaction mixture was stirred at room temperature overnight. After concentration, the reaction mixture was purified by prep-HPLC purification to give Example 269 as a white solid (40 mg). LCMS (M+H$^+$): 487. $^1$H NMR (400 MHz, MeOD) δ ppm 8.22 (d, J=4.8 Hz, 2H), 7.51 (d, J=1.3 Hz, 1H), 7.19-7.14 (m, 2H), 6.57 (t, J=4.6 Hz, 1H), 4.94 (dd, J=2.4, 17.0 Hz, 1H), 4.87-4.79 (m, 1H), 4.68-4.58 (m, 1H), 4.40 (dd, J=5.1, 17.0 Hz, 1H), 4.22-4.08 (m, 2H), 4.03 (dd, J=0.8, 12.8 Hz, 1H), 3.65 (dt, J=4.1, 9.9 Hz, 1H), 2.90 (dd, J=8.4, 17.1 Hz, 1H), 2.51 (dd, J=4.9, 17.4 Hz, 1H), 1.16-1.13 (m, 3H).

Example 270

(6S)-3-[4-[(5-fluoropyrimidin-4-yl)amino]-2-oxo-pyrrolidin-1-yl]-6-methyl-N-(3,4,5-trifluorophenyl)-6,7-dihydro-4H-pyrazolo[1,5-a]pyrazine-5-carboxamide

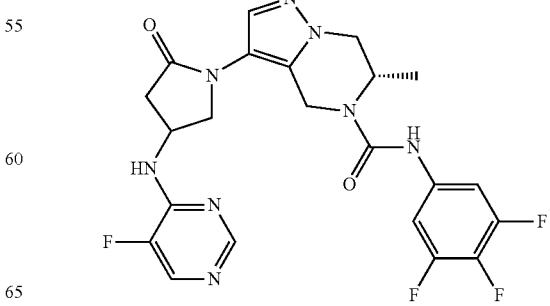

311

The title compound was prepared according to the following scheme:

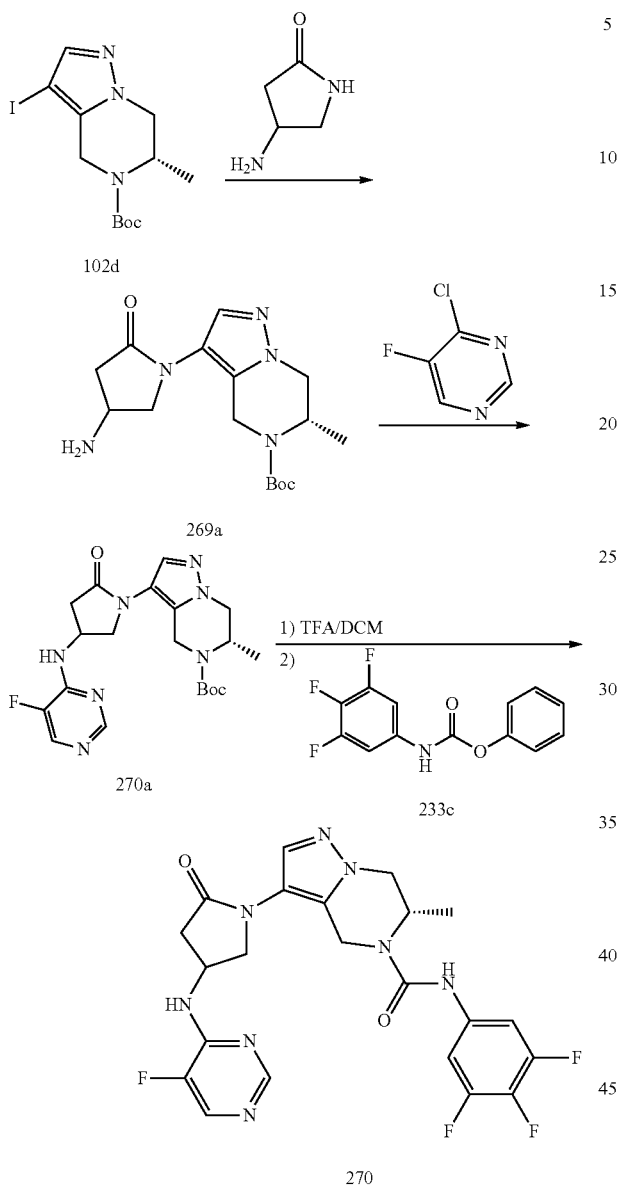

Preparation of Example 270

The title compound was prepared in analogy to Example 269 by using 4-chloro-5-fluoropyrimidine instead of 2-chloro-pyrimidine. Example 270 was obtained as a solid (300 mg). LCMS (M+H$^+$): 505. $^1$H NMR (400 MHz, MeOD) δ ppm 8.42-8.31 (m, 1H), 8.23-8.02 (m, 1H), 7.65 (d, J=2.4 Hz, 1H), 7.33-7.24 (m, 2H), 5.07 (dd, J=1.9, 16.9 Hz, 1H), 4.98-4.93 (m, 2H), 4.52 (d, J=17.0 Hz, 1H), 4.36-4.24 (m, 2H), 4.19-4.12 (m, 1H), 3.89-3.77 (m, 1H), 3.06 (ddd, J=1.6, 8.6, 17.5 Hz, 1H), 2.77-2.66 (m, 1H), 1.32-1.23 (m, 3H).

Example 271

(6S)-N-[3-(difluoromethyl)-4,5-difluoro-phenyl]-6-methyl-3-(3-oxomorpholin-4-yl)-6,7-dihydro-4H-pyrazolo[1,5-a]pyrazine-5-carboxamide

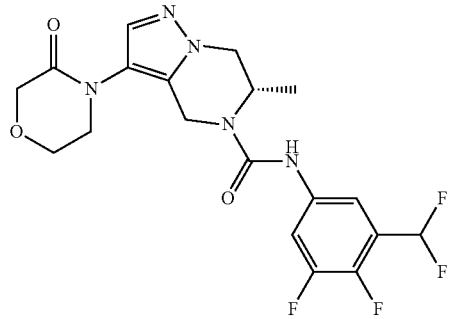 [SMILES: C[C@H]1Cn2ncc(N3CCOCC3=O)c2CN1C(=O)Nc1cc(F)c(F)c(C(F)F)c1]

Preparation of (6S)-N-[3-(difluoromethyl)-4,5-difluoro-phenyl]-6-methyl-3-(3-oxomorpholin-4-yl)-6,7-dihydro-4H-pyrazolo[1,5-a]pyrazine-5-carboxamide (Example 271)

The title compound was prepared in analogy to Example 223 by using morpholin-3-one instead of pyrrolidin-2-one and phenyl N-[3-(difluoromethyl)-4,5-difluoro-phenyl]carbamate (compound 239a) instead of phenyl N-[2-(difluoromethyl)-4-pyridyl]carbamate (compound 218c). Example 271 was obtained as a white solid (45 mg). LCMS (M+H$^+$): 442. $^1$H NMR (400 MHz, CDCl$_3$) δ ppm 7.83 (s, 1H), 7.72-7.68 (m, 1H), 7.52 (s, 1H), 7.38 (br. s., 1H), 6.86 (t, J=56 Hz, 1H), 5.14-5.04 (m, 1H), 4.90 (d, J=16.8 Hz, 1H), 4.39 (s, 2H), 4.36-4.25 (m, 2H), 4.16-4.01 (m, 3H), 4.00-3.91 (m, 1H), 3.76-3.70 (m, 1H), 1.40 (d, J=7.0 Hz, 3H).

Example 272

(6S)-N-[2-(difluoromethyl)-4-pyridyl]-3-(5,5-dimethyl-2-oxo-oxazolidin-3-yl)-6-methyl-6,7-dihydro-4H-pyrazolo[1,5-a]pyrazine-5-carboxamide

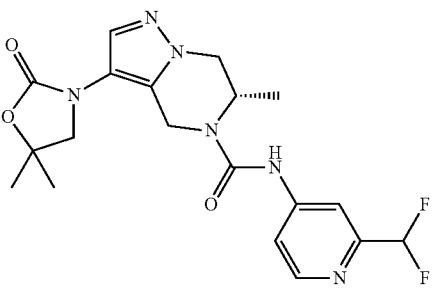 [SMILES: C[C@H]1Cn2ncc(N3CC(C)(C)OC3=O)c2CN1C(=O)Nc1ccnc(C(F)F)c1]

Preparation of (6S)-N-[2-(difluoromethyl)-4-pyridyl]-3-(5,5-dimethyl-2-oxo-oxazolidin-3-yl)-6-methyl-6,7-dihydro-4H-pyrazolo[1,5-a]pyrazine-5-carboxamide (Example 272)

The title compound was prepared in analogy to Example 223 by using 5,5-dimethyloxazolidin-2-one instead of pyrrolidin-2-one. Example 272 was obtained as a white solid (35 mg). LCMS (M+H⁺): 421. ¹H NMR (400 MHz, CDCl₃) δ ppm 8.88 (br. s., 1H), 8.45 (br. s., 1H), 8.01 (br. s., 1H), 7.83 (br. s., 1H), 7.44 (s, 1H), 6.72 (t, J=55 Hz, 1H), 5.27 (d, J=16.8 Hz, 1H), 5.14 (br. s., 1H), 4.55 (d, J=16.6 Hz, 1H), 4.33 (d, J=9.3 Hz, 1H), 4.09 (d, J=12.3 Hz, 1H), 3.82 (d, J=8.3 Hz, 1H), 3.73 (d, J=8.5 Hz, 1H), 1.61 (d, J=4.5 Hz, 6H), 1.36 (d, J=6.5 Hz, 3H)

Example 273

(6S,7S)-6,7-dimethyl-3-(2-oxoimidazolidin-1-yl)-N-(3,4,5-trifluorophenyl)-6,7-dihydro-4H-pyrazolo[1,5-a]pyrazine-5-carboxamide

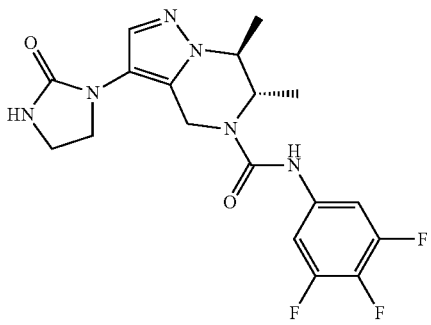 [SMILES: C[C@H]1[C@H](C)n2ncc(N3CCNC3=O)c2CN1C(=O)Nc1cc(F)c(F)c(F)c1]

Preparation of (6S,7S)-6,7-dimethyl-3-(2-oxoimidazolidin-1-yl)-N-(3,4,5-trifluorophenyl)-6,7-dihydro-4H-pyrazolo[1,5-a]pyrazine-5-carboxamide (Example 273)

The title compound was prepared in analogy to Example 251 by using imidazolidin-2-one instead of pyrrolidin-2-one. Example 273 was obtained as a white solid (30 mg). LCMS (M+H⁺): 409. ¹H NMR (400 MHz, CDCl₃) δ ppm 7.84 (br. s., 1H), 7.41 (s, 1H), 7.27-7.20 (m, 2H), 5.11 (d, J=16.6 Hz, 1H), 4.84-4.76 (m, 1H), 4.43 (d, J=16.6 Hz, 1H), 4.31-4.20 (m, 1H), 4.00 (q, J=8.6 Hz, 1H), 3.91-3.79 (m, 1H), 3.66 (t, J=8.0 Hz, 2H), 1.47 (d, J=6.5 Hz, 3H), 1.30 (d, J=6.8 Hz, 3H)

Example 274

(6S,7S)-6,7-dimethyl-3-(3-oxomorpholin-4-yl)-N-(3,4,5-trifluorophenyl)-6,7-dihydro-4H-pyrazolo[1,5-a]pyrazine-5-carboxamide

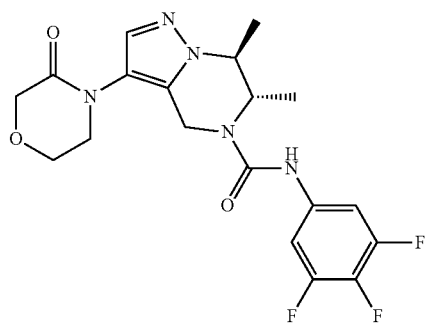 [SMILES: C[C@H]1[C@H](C)n2ncc(N3CCOCC3=O)c2CN1C(=O)Nc1cc(F)c(F)c(F)c1]

Preparation of (6S,7S)-6,7-dimethyl-3-(3-oxomorpholin-4-yl)-N-(3,4,5-trifluorophenyl)-6,7-dihydro-4H-pyrazolo[1,5-a]pyrazine-5-carboxamide (Example 274)

The title compound was prepared in analogy to Example 251 by using morpholin-3-one instead of pyrrolidin-2-one. Example 274 was obtained as a white solid (23 mg). LCMS (M+H⁺): 424. ¹H NMR (400 MHz, CDCl₃) δ ppm 7.53 (s, 1H), 7.45 (s, 1H), 7.29-7.22 (m, 2H), 4.88 (d, J=16.3 Hz, 1H), 4.84-4.77 (m, 1H), 4.38 (s, 2H), 4.36-4.27 (m, 2H), 4.15-4.01 (m, 2H), 3.99-3.88 (m, 1H), 3.77-3.72 (m, 1H), 1.49 (d, J=6.8 Hz, 3H), 1.31 (d, J=7.0 Hz, 3H)

Example 275

(6S)-3-(3-benzoyl-5-oxo-imidazolidin-1-yl)-6-methyl-N-(3,4,5-trifluorophenyl)-6,7-dihydro-4H-pyrazolo[1,5-a]pyrazine-5-carboxamide

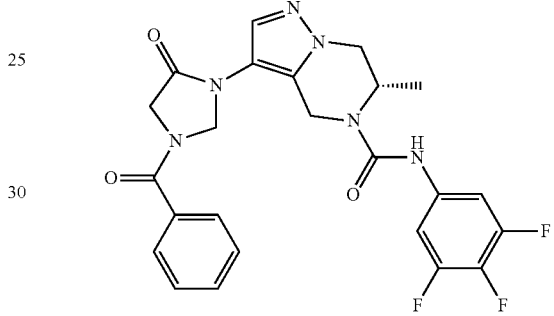

The title compound was prepared according to the following scheme:

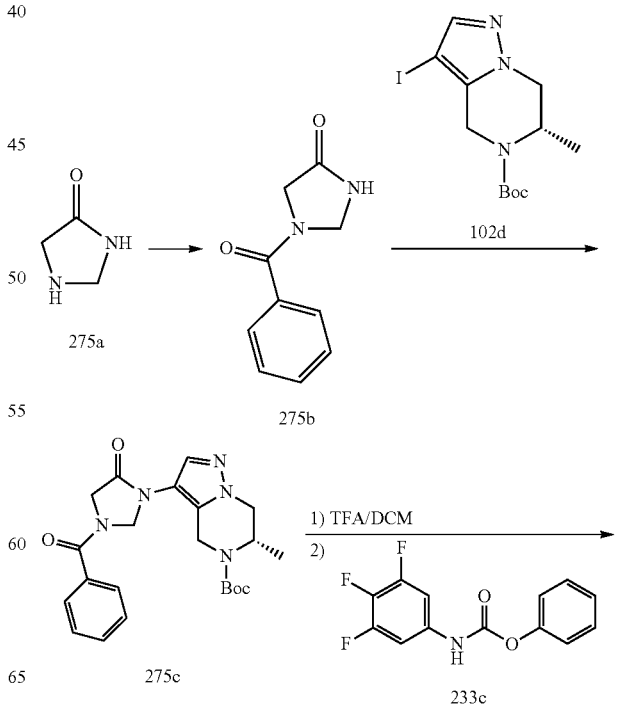

-continued

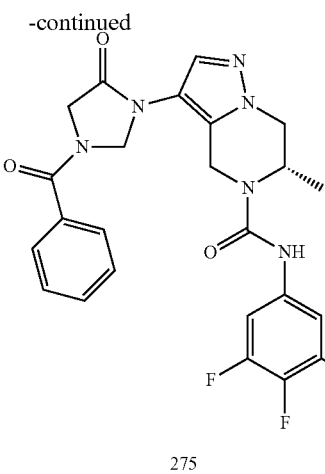

275

Preparation of 1-benzoylimidazolidin-4-one (compound 275b)

To a suspension of imidazolidin-4-one (861 mg, 10 mmol) and K$_2$CO$_3$ (5.53 g, 40 mmol) in THF (30 mL) was added slowly benzoyl chloride (1.41 g, 10 mmol). Then the reaction mixture was stirred at room temperature for 15 hours. Then the solid was filtered and the filtrate was concentrated to give crude compound 275b as a light yellow solid (1.5 g). LCMS (M+H$^+$): 191.

Preparation of (6S)-3-(3-benzoyl-5-oxo-imidazolidin-1-yl)-6-methyl-N-(3,4,5-trifluorophenyl)-6,7-dihydro-4H-pyrazolo[1,5-a]pyrazine-5-carboxamide (Example 275)

The title compound was prepared in analogy to Example 262 by using 1-benzoylimidazolidin-4-one (compound 275b) instead of (S)-3-hydroxypyrrolidin-2-one. Example 275 was obtained as a white solid (36 mg). LCMS (M+H$^+$): 499. $^1$H NMR (400 MHz, MeOD) δ ppm 7.77 (br. s., 1H), 7.65-7.62 (m, 2H), 7.60-7.51 (m, 3H), 7.32-7.26 (m, 2H), 5.43 (d, J=9.3 Hz, 1H), 5.35-5.23 (m, 1H), 5.16-5.01 (m, 1H), 4.96 (br. s., 1H), 4.58-4.45 (m, 1H), 4.43-4.25 (m, 3H), 4.23-4.13 (m, 1H), 1.30-1.26 m, 3H).

Example 276

(6S)-N-[3-(difluoromethyl)-4,5-difluoro-phenyl]-3-(5,5-dimethyl-2-oxo-oxazolidin-3-yl)-6-methyl-6,7-dihydro-4H-pyrazolo[1,5-a]pyrazine-5-carboxamide

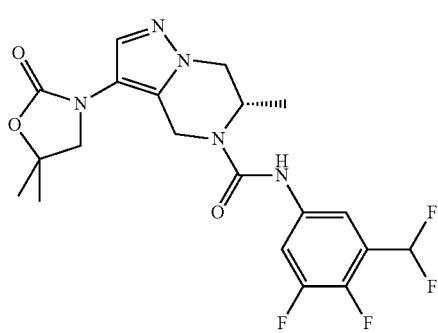 [SMILES: C[C@H]1Cn2ncc(N3CC(C)(C)OC3=O)c2CN1C(=O)Nc1cc(F)c(F)c(C(F)F)c1]

Preparation of (6S)-N-[3-(difluoromethyl)-4,5-difluoro-phenyl]-3-(5,5-dimethyl-2-oxo-oxazolidin-3-yl)-6-methyl-6,7-dihydro-4H-pyrazolo[1,5-a]pyrazine-5-carboxamide (Example 276)

The title compound was prepared in analogy to Example 223 by using 5,5-dimethyloxazolidin-2-one instead of pyrrolidin-2-one and phenyl N-[3-(difluoromethyl)-4,5-difluoro-phenyl]carbamate (compound 239a) instead of phenyl N-[2-(difluoromethyl)-4-pyridyl]carbamate (compound 218c). Example 276 was obtained as a white solid (28 mg). LCMS (M+H$^+$): 456. $^1$H NMR (400 MHz, MeOD) δ ppm 7.78-7.60 (m, 2H), 7.46 (d, J=2.3 Hz, 1H), 7.01 (t, J=56 Hz, 1H), 5.09 (d, J=16.8 Hz, 1H), 5.03-4.95 (m, 1H), 4.56 (d, J=16.8 Hz, 1H), 4.37-4.25 (m, 1H), 4.17 (dd, J=1.0, 12.8 Hz, 1H), 3.91-3.76 (m, 2H), 1.58 (s, 6H), 1.27 (d, J=6.8 Hz, 3H).

Example 277

(6S)-N-[6-(difluoromethyl)-5-fluoro-2-pyridyl]-3-(5,5-dimethyl-2-oxo-oxazolidin-3-yl)-6-methyl-6,7-dihydro-4H-pyrazolo[1,5-a]pyrazine-5-carboxamide

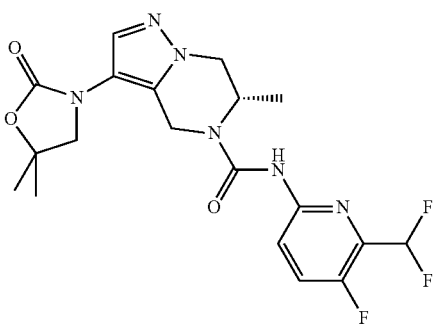 [SMILES: C[C@H]1Cn2ncc(N3CC(C)(C)OC3=O)c2CN1C(=O)Nc1ccc(F)c(C(F)F)n1]

Preparation of (6S)-N-[6-(difluoromethyl)-5-fluoro-2-pyridyl]-3-(5,5-dimethyl-2-oxo-oxazolidin-3-yl)-6-methyl-6,7-dihydro-4H-pyrazolo[1,5-a]pyrazine-5-carboxamide (Example 277)

The title compound was prepared in analogy to Example 223 by using 5,5-dimethyloxazolidin-2-one instead of pyrrolidin-2-one and phenyl phenyl N-[6-(difluoromethyl)-5-fluoro-2-pyridyl]carbamate (compound 265b) instead of phenyl N-[2-(difluoromethyl)-4-pyridyl]carbamate (compound 218c). Example 277 was obtained as a white solid (10 mg). LCMS (M+H$^+$): 439. $^1$H NMR (400 MHz, MeOD) δ ppm 8.06 (dd, J=3.3, 9.3 Hz, 1H), 7.71 (t, J=9.3 Hz, 1H), 7.65 (s, 1H), 6.84 (t, J=56 Hz, 1H), 5.14 (d, J=17.1 Hz, 1H), 5.06-4.98 (m, 1H), 4.58 (d, J=17.1 Hz, 1H), 4.32 (dd, J=4.6, 12.9 Hz, 1H), 4.22-4.13 (m, 1H), 3.83 (q, J=8.7 Hz, 2H), 1.59 (s, 6H), 1.28 (d, J=6.8 Hz, 3H).

Example 278

(6S)-6-methyl-3-(5-methyl-2-oxo-1,3-oxazinan-3-yl)-N-(3,4,5-trifluorophenyl)-6,7-dihydro-4H-pyrazolo[1,5-a]pyrazine-5-carboxamide

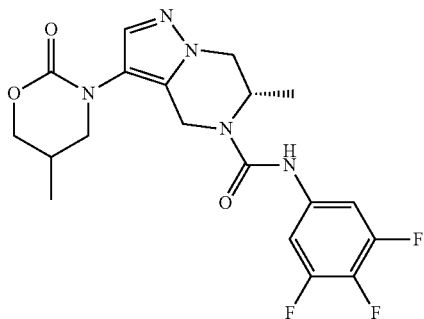 [SMILES: CC1COC(=O)N(c2cnn3c2CN(C(=O)Nc2cc(F)c(F)c(F)c2)[C@@H](C)C3)C1]

Preparation of (6S)-6-methyl-3-(5-methyl-2-oxo-1,3-oxazinan-3-yl)-N-(3,4,5-trifluorophenyl)-6,7-dihydro-4H-pyrazolo[1,5-a]pyrazine-5-carboxamide (Example 278)

The title compound was prepared in analogy to Example 223 by using 5-methyl-1,3-oxazinan-2-one instead of pyrrolidin-2-one and phenyl N-(3,4,5-trifluoro-phenyl)carbamate (compound 233c) instead of phenyl N-[2-(difluoromethyl)-4-pyridyl]carbamate (compound 218c). Example 278 was obtained as a white solid (70 mg). LCMS (M+H$^+$): 424. $^1$H NMR (400 MHz, MeOD) δ ppm 7.52 (s, 1H), 7.23-7.13 (m, 2H), 4.84 (dd, J=6.1, 16.8 Hz, 2H), 4.37-4.25 (m, 2H), 4.23-4.14 (m, 1H), 4.09-3.97 (m, 2H), 3.68-3.54 (m, 1H), 3.34 (ddd, J=9.3, 11.4, 15.1 Hz, 1H), 2.37-2.33 (m, 1H), 1.15 (dd, J=2.1, 6.9 Hz, 3H), 1.01 (d, J=6.7 Hz, 3H)

Example 279 and Example 280

(6S)-3-(2,4-dioxo-1H-pyrimidin-3-yl)-6-methyl-N-(3,4,5-trifluorophenyl)-6,7-dihydro-4H-pyrazolo[1,5-a]pyrazine-5-carboxamide and (6S)-3-(2,4-dioxopyrimidin-1-yl)-6-methyl-N-(3,4,5-trifluorophenyl)-6,7-dihydro-4H-pyrazolo[1,5-a]pyrazine-5-carboxamide

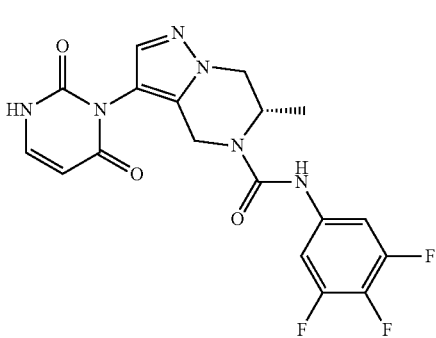

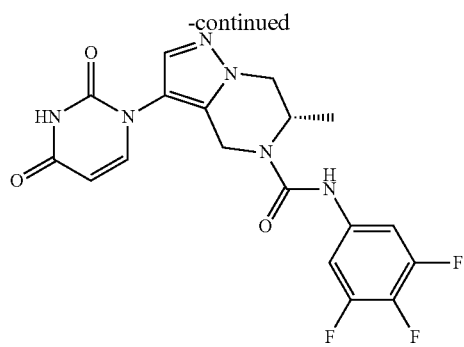

Preparation of (6S)-3-(2,4-dioxo-1H-pyrimidin-3-yl)-6-methyl-N-(3,4,5-trifluorophenyl)-6,7-dihydro-4H-pyrazolo[1,5-a]pyrazine-5-carboxamide and (6S)-3-(2,4-dioxopyrimidin-1-yl)-6-methyl-N-(3,4,5-trifluorophenyl)-6,7-dihydro-4H-pyrazolo[1,5-a]pyrazine-5-carboxamide The title compounds were prepared in analogy to Example 223 by using 1H-pyrimidine-2,4-dione instead of pyrrolidin-2-one and phenyl N-(3,4,5-trifluoro-phenyl)carbamate (compound 233c) instead of phenyl N-[2-(difluoromethyl)-4-pyridyl]carbamate (compound 218c).

Example 279 was obtained as a white solid (5 mg). LCMS (M+H$^+$): 421. $^1$H NMR (400 MHz, MeOD) δ ppm 7.59 (s, 1H), 7.52 (d, J=7.7 Hz, 1H), 7.31-7.23 (dd, J=6.4, 10.3 Hz, 2H), 5.83 (d, J=7.7 Hz, 1H), 5.06-4.98 (m, 1H), 4.91-4.84 (m, 1H), 4.41-4.29 (m, 2H), 4.20 (d, J=12.6 Hz, 1H), 1.29 (d, J=6.8 Hz, 3H)

Example 280 was obtained as a white solid (5 mg). LCMS (M+H$^+$): 421. $^1$H NMR (400 MHz, MeOD) δ ppm 7.71 (s, 1H), 7.66 (d, J=7.9 Hz, 1H), 7.32-7.24 (dd, J=6.4, 10.3 Hz, 2H), 5.81 (d, J=7.8 Hz, 1H), 5.06-4.97 (m, 2H), 4.47 (d, J=17.0 Hz, 1H), 4.39-4.30 (m, 1H), 4.26-4.17 (m, 1H), 1.29 (d, J=6.8 Hz, 3H)

Example 281

(6S)-6-methyl-3-(5-oxo-3-pyrimidin-2-yl-imidazolidin-1-yl)-N-(3,4,5-trifluorophenyl)-6,7-dihydro-4H-pyrazolo[1,5-a]pyrazine-5-carboxamide

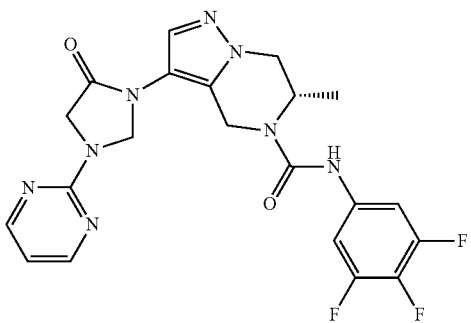 [SMILES: C[C@H]1Cn2ncc(N3CN(c4ncccn4)CC3=O)c2CN1C(=O)Nc1cc(F)c(F)c(F)c1]

The title compound was prepared according to the following scheme:

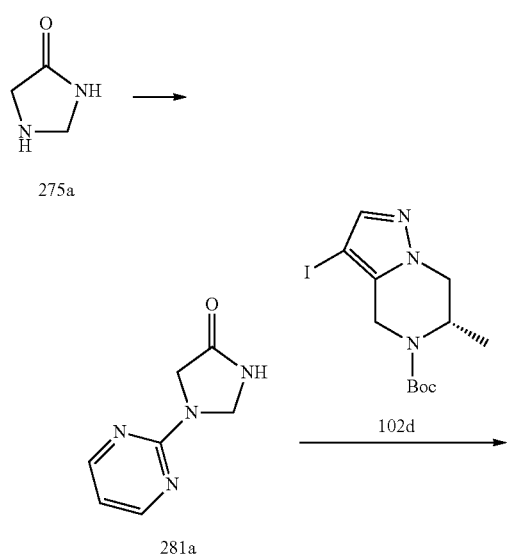

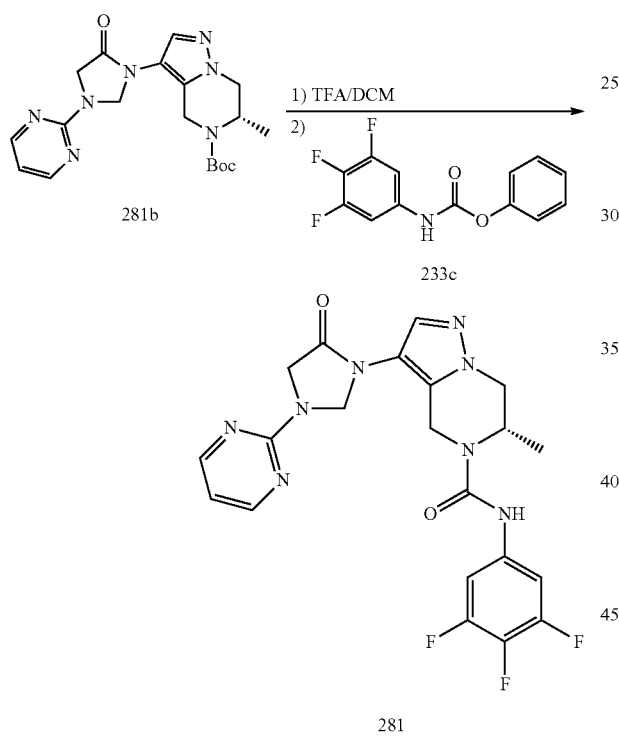

Preparation of 1-(pyrimidin-2-yl)imidazolidin-4-one (compound 281a)

A mixture of imidazolidin-4-one hydrochloride (500 mg, 4.08 mmol), 2-bromopyrimidine (973 mg, 6.12 mmol) and potassium carbonate (1.69 g, 12.2 mmol) in dioxane (15 mL) were heated at 80° C. for 2 hours. The reaction mixture was filtered and the filtrate was concentrated. The crude product was purified by flash chromatography (silica gel, 10% to 20% MeOH in DCM) to give compound 281a as a white solid (50 mg). LCMS (M+H⁺): 165.

Preparation of (6S)-6-methyl-3-(5-oxo-3-pyrimidin-2-yl-imidazolidin-1-yl)-N-(3,4,5-trifluorophenyl)-6,7-dihydro-4H-pyrazolo[1,5-a]pyrazine-5-carboxamide (Example 281)

The title compound was prepared in analogy to Example 262 by using 1-(pyrimidin-2-yl)imidazolidin-4-one (compound 281a) instead of (S)-3-hydroxypyrrolidin-2-one. Example 281 was obtained as a white solid (30 mg). LCMS (M+H⁺): 499. ¹H NMR (400 MHz, MeOD) δ ppm 8.47 (d, J=4.9 Hz, 2H), 7.77 (s, 1H), 7.32-7.27 (m, 2H), 6.83 (t, J=4.9 Hz, 1H), 5.44-5.31 (m, 2H), 5.12 (d, J=16.9 Hz, 1H), 5.03-4.96 (m, 1H), 4.58 (d, J=16.9 Hz, 1H), 4.38-4.29 (m, 3H), 4.25-4.15 (m, 1H), 1.30 (d, J=6.8 Hz, 3H)

Example 282

(6S)-6-methyl-3-[4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide

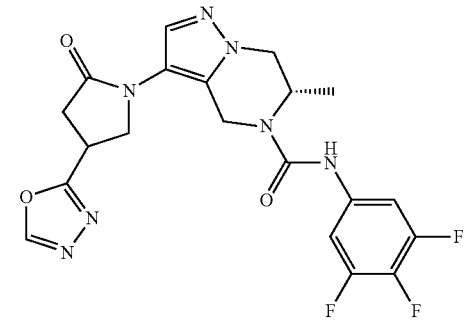 [SMILES: C[C@H]1Cn2ncc(N3CC(c4nnco4)CC3=O)c2CN1C(=O)Nc1cc(F)c(F)c(F)c1]

The title compound was prepared according to the following scheme:

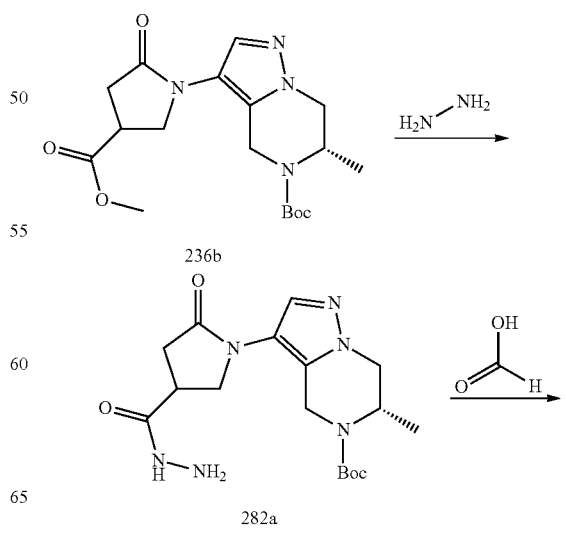

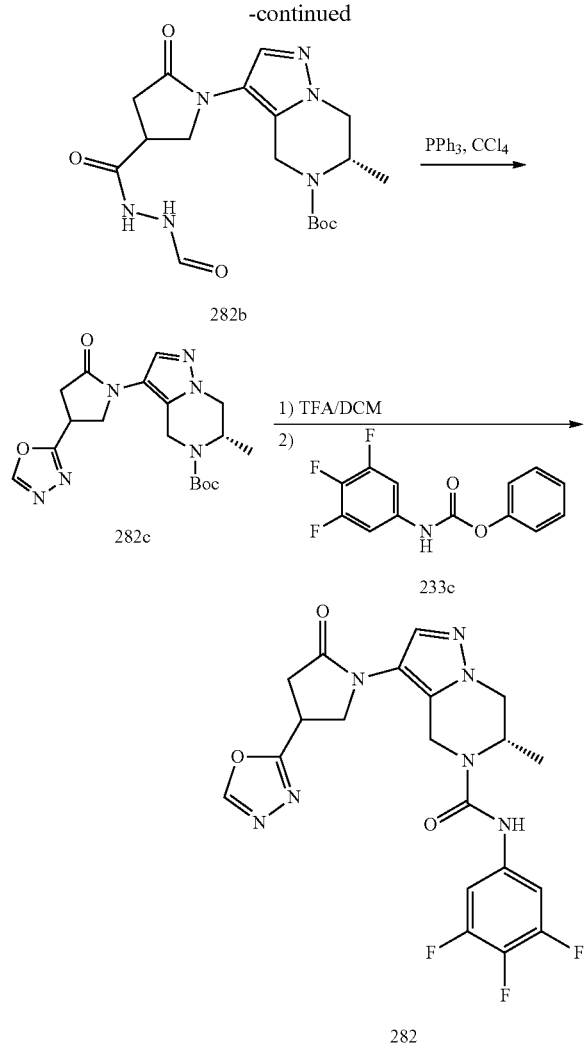

Step 1: Preparation of (6S)-tert-butyl 3-(4-(hydrazinecarbonyl)-2-oxopyrrolidin-1-yl)-6-methyl-6,7-dihydropyrazolo[1,5-a]pyrazine-5(4H)-carboxylate (compound 282a)

A mixture of (6S)-tert-butyl 3-(4-(methoxycarbonyl)-2-oxopyrrolidin-1-yl)-6-methyl-6,7-dihydropyrazolo[1,5-a]pyrazine-5(4H)-carboxylate (1.0 g, 2.64 mmol) and hydrazine hydrate (1.32 g, 26.4 mmol) in EtOH (20 mL) was stirred at 85° C. for 15 hours. The reaction mixture was concentrated in vacuo to give crude compound 282a as a white solid (0.9 g). LCMS (M+H$^+$): 379.

Step 2: Preparation of (6S)-tert-butyl 3-(4-(2-formylhydrazinecarbonyl)-2-oxopyrrolidin-1-yl)-6-methyl-6,7-dihydropyrazolo[1,5-a]pyrazine-5(4H)-carboxylate (compound 282b)

A mixture of (6S)-tert-butyl 3-(4-(hydrazinecarbonyl)-2-oxopyrrolidin-1-yl)-6-methyl-6,7-dihydropyrazolo[1,5-a]pyrazine-5(4H)-carboxylate (compound 282a, 500 mg, 1.32 mmol) and HCOOH (2 mL) in DCM (10 mL) was stirred at 50° C. for 2 hours. The reaction mixture was then concentrated in vacuo to give crude compound 282b as a white solid (0.55 g). LCMS (M+H$^+$): 407.

Step 3: Preparation of (6S)-tert-butyl 3-(4-(1,3,4-oxadiazol-2-yl)-2-oxopyrrolidin-1-yl)-6-methyl-6,7-dihydropyrazolo[1,5-a]pyrazine-5(4H)-carboxylate (compound 282c)

A mixture of (6S)-tert-butyl 3-(4-(2-formylhydrazinecarbonyl)-2-oxopyrrolidin-1-yl)-6-methyl-6,7-dihydropyrazolo[1,5-a]pyrazine-5(4H)-carboxylate (compound 282b, 500 mg, 1.23 mmol), triphenylphosphine (1.94 g, 7.38 mmol), triethylamine (622 mg, 6.15 mmol) and CCl$_4$ (1.89 g, 12.3 mmol) in acetonitrile (12 mL) was stirred at room temperature for 1 hour. The reaction mixture was diluted with EtOAc (50 mL), and washed with saturated aqueous NaHCO$_3$ solution (20 mL) and brine (20 mL). The organic layer was dried over Na$_2$SO$_4$ and concentrated in vacuo. The crude product was purified by flash chromatography (silica gel, 10% MeOH in EtOAc) to give compound 282c as a colorless oil (0.3 g). LCMS (M+H$^+$): 389.

Step 4: Preparation of (6S)-6-methyl-3-[4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide (Example 282)

A solution of (6S)-tert-butyl 3-(4-(1,3,4-oxadiazol-2-yl)-2-oxopyrrolidin-1-yl)-6-methyl-6,7-dihydropyrazolo[1,5-a]pyrazine-5(4H)-carboxylate (compound 282c, 300 mg, 0.77 mmol) in 2,2,2-trifluoroacetic acid (5 mL) and DCM (10 mL) was stirred at room temperature for 30 mins. The reaction mixture was concentrated and the residue was dissolved in DMF (5 mL), then to which were added N-ethyl-N-isopropylpropan-2-amine (499 mg, 3.86 mmol), and phenyl (3,4,5-trifluorophenyl)carbamate (248 mg, 0.92 mmol). The reaction mixture was stirred at 70° C. for 0.5 hours. The reaction mixture was purified by prep-HPLC to give Example 282 as a white solid (90 mg). LCMS (M+H$^+$): 462. $^1$H NMR (400 MHz, MeOD) δ ppm 8.99 (s, 0.5H), 8.98 (s, 0.5H) 7.68 (s, 0.5H), 7.67 (s, 0.5H), 7.32-7.27 (m, 2H), 5.05 (dd, J=12.2, 16.9 Hz, 1H), 4.99-4.92 (m, 1H), 4.51 (dd, J=8.0, 16.8 Hz, 1H), 4.40-4.26 (m, 2H), 4.25-4.10 (m, 3H), 3.18-3.07 (m, 1H), 3.04-2.92 (m, 1H), 1.29-1.26 (m, 3H).

Example 283

(6S)-6-methyl-3-[4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide

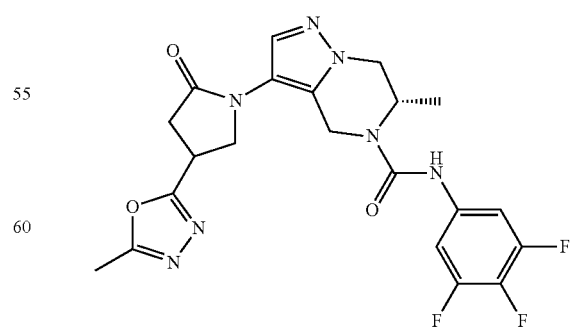

The title compound was prepared according to the following scheme:

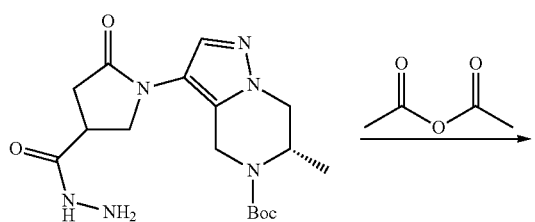

282a

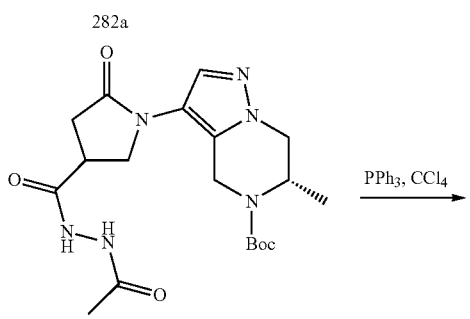

283a

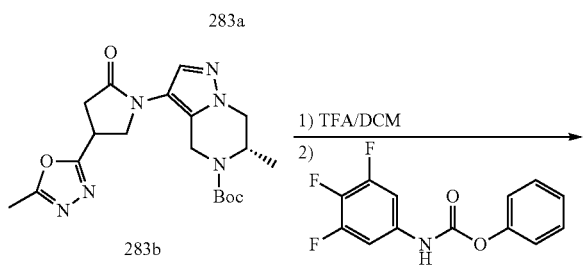

283b

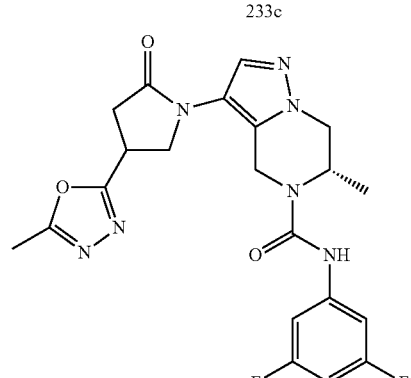

283

Preparation of tert-butyl (6S)-3-[4-(acetamidocarbamoyl)-2-oxo-pyrrolidin-1-yl]-6-methyl-6,7-dihydro-4H-pyrazolo[1,5-a]pyrazine-5-carboxylate (compound 283a)

A mixture of acetic anhydride (162 mg, 1.59 mmol) and (6S)-tert-butyl 3-(4-(hydrazinecarbonyl)-2-oxopyrrolidin-1-yl)-6-methyl-6,7-dihydropyrazolo[1,5-a]pyrazine-5(4H)-carboxylate (compound 282a, 300 mg, 793 μmol) in DCM (10 mL) was stirred at room temperature for 2 hours. The reaction mixture was concentrated in vacuo to give compound 283a as a white solid (350 mg). LCMS (M+H$^+$): 421

Preparation of (6S)-6-methyl-3-[4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide (Example 283)

The title compound was prepared in analogy to Example 282 by using tert-butyl (6S)-3-[4-(acetamidocarbamoyl)-2-oxo-pyrrolidin-1-yl]-6-methyl-6,7-dihydro-4H-pyrazolo[1,5-a]pyrazine-5-carboxylate (compound 283a) instead of (6S)-tert-butyl 3-(4-(2-formylhydrazinecarbonyl)-2-oxopyrrolidin-1-yl)-6-methyl-6,7-dihydropyrazolo[1,5-a]pyrazine-5(4H)-carboxylate (compound 282b). Example 283 was obtained as a white solid (30 mg). LCMS (M+H$^+$): 476. $^1$H NMR (400 MHz, MeOD) δ ppm 7.66 (s, 1H), 7.32-7.27 (m, 2H), 5.10-4.93 (m, 2H), 4.51 (dd, J=7.3, 17.1 Hz, 1H), 4.35-4.25 (m, 2H), 4.20-4.09 (m, 3H), 3.16-3.02 (m, 1H), 3.00-2.90 (m, 1H), 2.57 (s, 1.5H), 2.56 (s, 1.5H), 1.29-1.26 (m, 3H).

Example 284

(6S)-6-methyl-3-[4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide

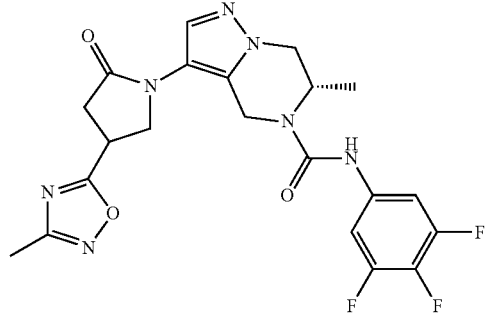 [SMILES: Cc1noc(C2CC(=O)N(c3cnn4c3CN(C(=O)Nc3cc(F)c(F)c(F)c3)[C@@H](C)C4)C2)n1]

The title compound was prepared according to the following scheme:

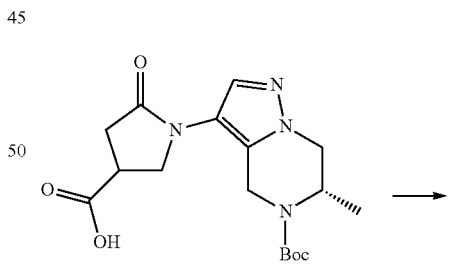

229a

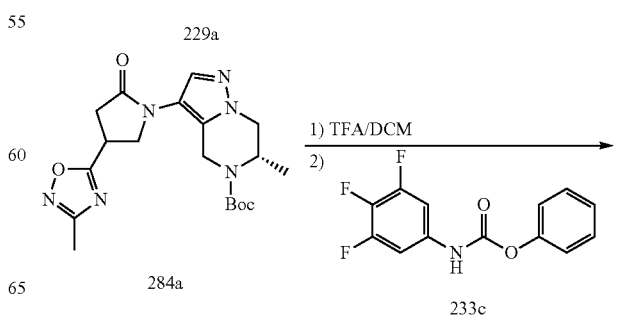

284a

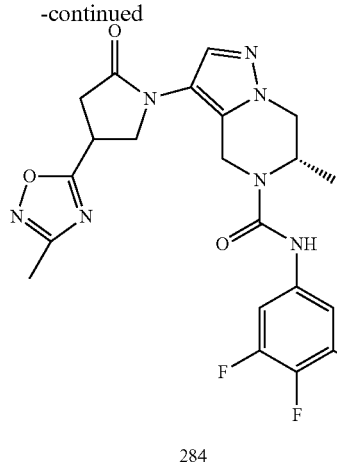

284

Step 1: Preparation of tert-butyl (6S)-6-methyl-3-[4-(3-methyl-1,2,4-oxadiazol-5-yl)-2-oxo-pyrrolidin-1-yl]-6,7-dihydro-4H-pyrazolo[1,5-a]pyrazine-5-carboxylate (compound 284a)

A mixture of compound N'-hydroxyacetimidamide (915 mg, 12.3 mmol), 1-((S)-5-(tert-butoxycarbonyl)-6-methyl-4,5,6,7-tetrahydropyrazolo[1,5-a]pyrazin-3-yl)-5-oxopyrrolidine-3-carboxylic acid (compound 229a, 3 g, 8.23 mmol), EDCI (2.37 g, 12.3 mmol), DIPEA (10.6 g, 82.3 mmol) and HOBt (334 mg, 2.47 mmol) in DCE (20 mL) was stirred at 80° C. for 16 hours. The reaction mixture was washed with water, the organic phase was dried and concentrated. The residue was purified by silica gel column to give compound 284a as a light brown oil. LCMS (M+H+): 403.

Step 2: Preparation of (6S)-6-methyl-3-[4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide (Example 284)

Removal of Boc protection in acidic conditions and condensation with phenyl (3,4,5-trifluorophenyl)carbamate were carried out in analogy to Example 282 to give Example 284 as white solid (15 mg). LCMS (M+H+): 476. ¹H NMR (400 MHz, MeOD) δ ppm 7.66 (s, 1H), 7.32-7.27 (m, 2H), 5.05 (dd, J=9.4, 16.9 Hz, 1H), 4.98-4.92 (m, 1H), 4.51 (dd, J=4.0, 17.1 Hz, 1H), 4.37-4.25 (m, 2H), 4.23-4.05 (m, 3H), 3.17-3.05 (m, 1H), 3.00-2.87 (m, 1H), 2.40 (s, 1.5H), 2.39 (s, 1.5H), 1.29-1.26 (m, 3H).

Example 285

(6S)-6-methyl-3-[4-(5-methyl-1,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide

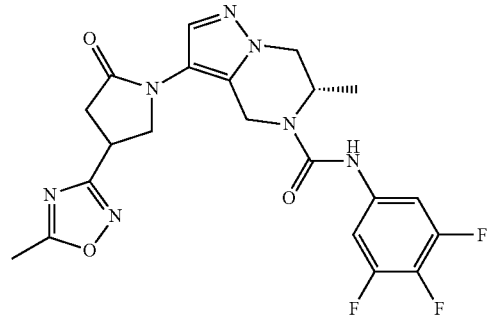 [SMILES: Cc1nc(C2CC(=O)N(c3cnn4c3CN(C(=O)Nc3cc(F)c(F)c(F)c3)[C@@H](C)C4)C2)no1]

285

The title compound was prepared according to the following scheme:

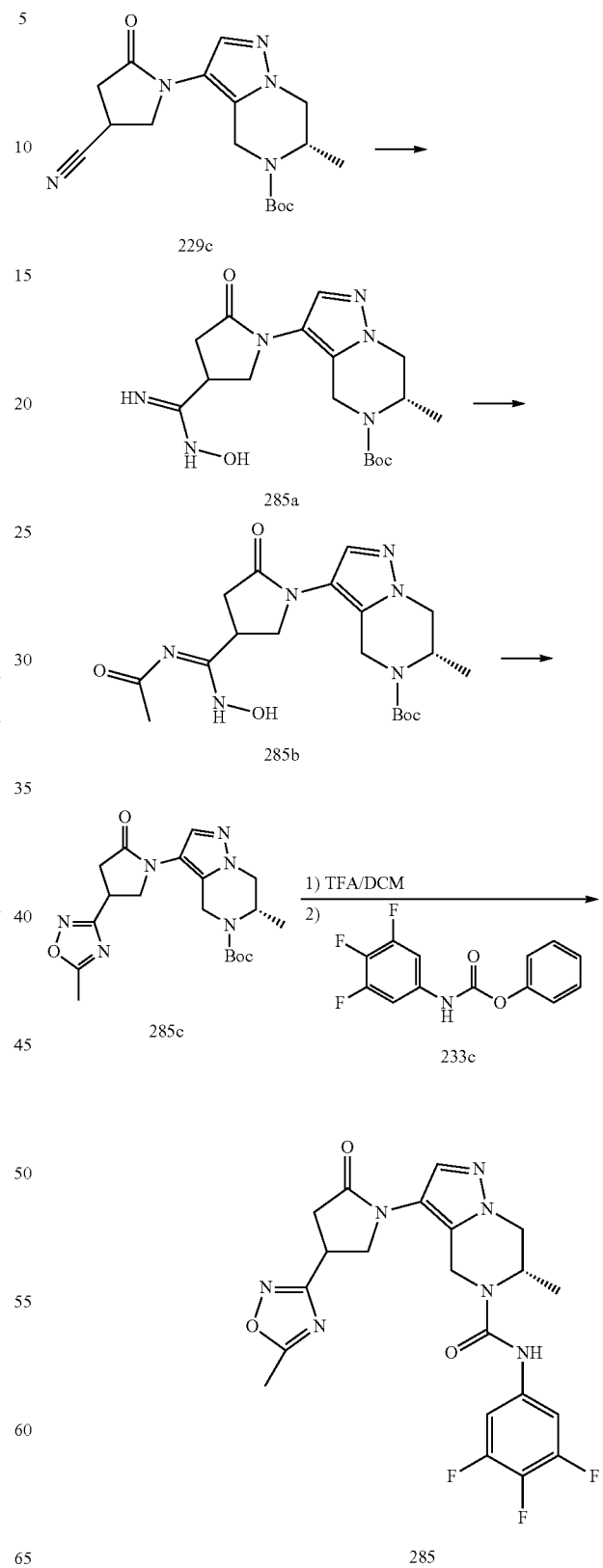

Step 1: Preparation of (6S)-tert-butyl 3-(4-(N-hydroxycarbamimidoyl)-2-oxopyrrolidin-1-yl)-6-methyl-6,7-dihydropyrazolo[1,5-a]pyrazine-5(4H)-carboxylate (compound 285a)

A mixture of (6S)-tert-butyl 3-(4-cyano-2-oxopyrrolidin-1-yl)-6-methyl-6,7-dihydropyrazolo[1,5-a]pyrazine-5(4H)-carboxylate (compound 229c, 300 mg, 869 μmol), hydroxylamine hydrochloride (60.4 mg, 869 μmol) and DIPEA (112 mg, 152 μL, 869 μmol) in EtOH was stirred at 80° C. for 2 hours. The reaction mixture was concentrated in vacuo to give crude compound 285a as a white solid (330 mg). LCMS (M+H⁺): 379.

Step 2: Preparation of (6S)-tert-butyl 3-(4-N'-acetyl-N-hydroxycarbamimidoyl)-2-oxopyrrolidin-1-yl)-6-methyl-6,7-dihydropyrazolo[1,5-a]pyrazine-5(4H)-carboxylate (compound 285b)

A mixture of acetic anhydride (108 mg, 1.06 mmol) and (6S)-tert-butyl 3-(4-(N-hydroxycarbamimidoyl)-2-oxopyrrolidin-1-yl)-6-methyl-6,7-dihydropyrazolo[1,5-a]pyrazine-5(4H)-carboxylate (compound 285a, 200 mg, 529 μmol) in DCM (10 mL) was stirred at room temperature for 1 hour. The reaction mixture was concentrated in vacuo to give compound 285b as a colorless oil (200 mg). LCMS (M+H⁺): 421.

Step 3: Preparation of (6S)-tert-butyl 6-methyl-3-(4-(5-methyl-1,2,4-oxadiazol-3-yl)-2-oxopyrrolidin-1-yl)-6,7-dihydropyrazolo[1,5-a]pyrazine-5(4H)-carboxylate (compound 285c)

A mixture of (6S)-tert-butyl 3-(4-N'-acetyl-N-hydroxycarbamimidoyl)-2-oxopyrrolidin-1-yl)-6-methyl-6,7-dihydropyrazolo[1,5-a]pyrazine-5(4H)-carboxylate (compound 285b, 200 mg, 476 μmol) and pyridine (5 mL) was stirred at 110° C. for 25 hours. The reaction mixture was concentrated in vacuo to give crude compound 285c as a brown oil (200 mg). LCMS (M+H⁺): 403.

Step 4: Preparation of (6S)-6-methyl-3-[4-(5-methyl-1,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide (Example 285)

A solution of (6S)-tert-butyl 6-methyl-3-(4-(5-methyl-1,2,4-oxadiazol-3-yl)-2-oxopyrrolidin-1-yl)-6,7-dihydropyrazolo[1,5-a]pyrazine-5(4H)-carboxylate (compound 285c, 200 mg, 497 μmol) in 2,2,2-trifluoroacetic acid (3 mL) and DCM (6 mL) was stirred at room temperature for 30 mins. The reaction mixture was concentrated, and the resulting residue was dissolved in DMF (3 mL), to which then was added DIPEA (321 mg, 2.48 mmol), and phenyl (3,4,5-trifluorophenyl)carbamate (159 mg, 596 μmol). The reaction mixture was stirred at 70° C. for 0.5 hours, cooled down to room temperature, and then purified by prep-HPLC to give Example 285 as white solid (120 mg). LCMS (M+H⁺): 476. ¹H NMR (400 MHz, MeOD) δ ppm 7.66 (s, 0.5H), 7.65 (s, 0.5H), 7.34-7.24 (m, 2H), 5.06 (dd, J=3.8, 17.1 Hz, 1H), 4.96 (d, J=6.3 Hz, 1H), 4.51 (d, J=17.1 Hz, 1H), 4.36-4.21 (m, 2H), 4.20-4.13 (m, 1H), 4.08-3.98 (m, 2H), 3.04 (dd, J=8.8, 16.6 Hz, 1H), 2.93-2.82 (m, 1H), 2.62 (d, J=2.8 Hz, 3H), 1.29-1.26 (m, 3H).

Example 286

(6S)-6-methyl-3-[2-oxo-4-[5-(trifluoromethyl)-1,3,4-oxadiazol-2-yl]pyrrolidin-1-yl]-N-(3,4,5-trifluorophenyl)-6,7-dihydro-4H-pyrazolo[1,5-a]pyrazine-5-carboxamide

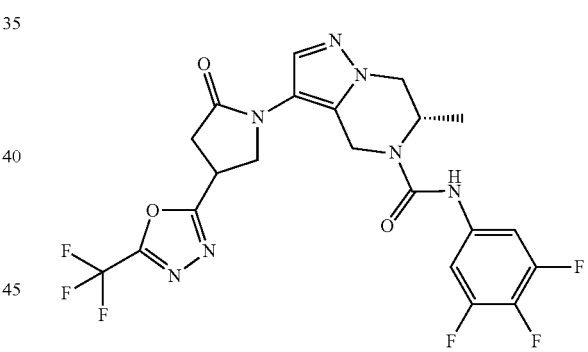

The title compound was prepared according to the following scheme:

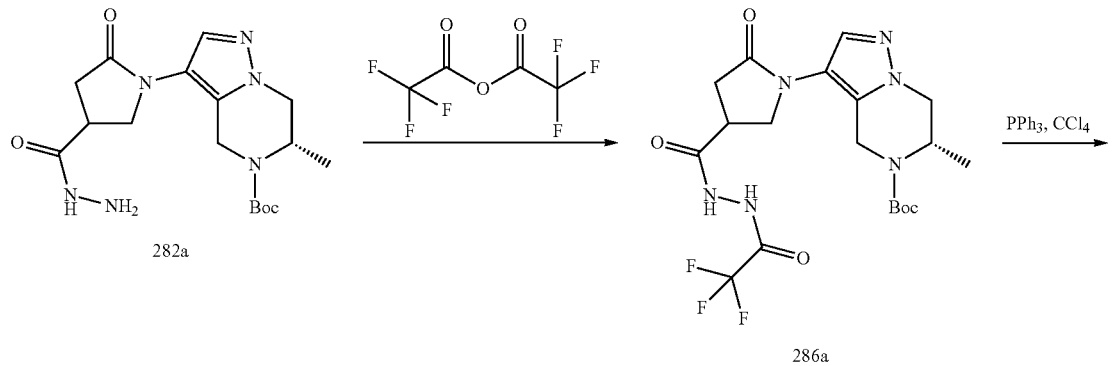

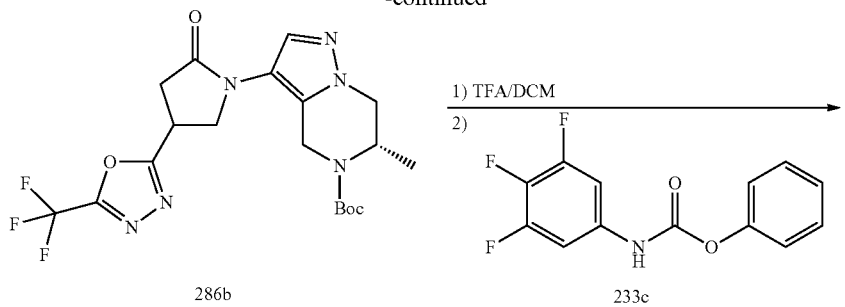

Preparation of tert-butyl (6S)-6-methyl-3-[2-oxo-4-[[(2,2,2-trifluoroacetyl)amino]carbamoyl]pyrrolidin-1-yl]-6,7-dihydro-4H-pyrazolo[1,5-a]pyrazine-5-carboxylate (compound 286a)

A mixture of 2,2,2-trifluoroacetic anhydride (167 mg, 793 µmol) and (6S)-tert-butyl 3-(4-(hydrazinecarbonyl)-2-oxopyrrolidin-1-yl)-6-methyl-6,7-dihydropyrazolo[1,5-a]pyrazine-5(4H)-carboxylate (compound 282a, 150 mg, 396 µmol) in DCM (10 mL) was stirred at room temperature for 2 hours. The reaction mixture was concentrated in vacuo to give crude compound 286a as a white solid (200 mg). LCMS (M+H$^+$): 475

Preparation of (6S)-6-methyl-3-[2-oxo-4-[5-(trifluoromethyl)-1,3,4-oxadiazol-2-yl]pyrrolidin-1-yl]-N-(3,4,5-trifluorophenyl)-6,7-dihydro-4H-pyrazolo[1,5-a]pyrazine-5-carboxamide (Example 286)

The title compound was prepared in analogy to Example 282 by using tert-butyl (6S)-6-methyl-3-[2-oxo-4-[[(2,2,2-trifluoroacetyl)amino]carbamoyl]pyrrolidin-1-yl]-6,7-dihydro-4H-pyrazolo[1,5-a]pyrazine-5-carboxylate (compound 286a) instead of (6S)-tert-butyl 3-(4-(2-formylhydrazinecarbonyl)-2-oxopyrrolidin-1-yl)-6-methyl-6,7-dihydropyrazolo[1,5-a]pyrazine-5(4H)-carboxylate (compound 282b). Example 286 was obtained as a white solid (3 mg). LCMS (M+H$^+$): 530. $^1$H NMR (400 MHz, MeOD) δ ppm 7.69 (s, 0.5H), 7.65 (s, 0.5H), 7.32-7.27 (m, 2H), 5.12-5.00 (m, 1H), 4.99-4.92 (m, 1H), 4.56-4.46 (m, 1H), 4.37-4.22 (m, 4H), 4.20-4.13 (m, 1H), 3.19-3.10 (m, 1H), 3.09-2.99 (m, 1H), 1.28 (d, J=6.8 Hz, 3H).

Example 287

(6S)-6-methyl-3-[2-oxo-4-[5-(trifluoromethyl)-1,2,4-oxadiazol-3-yl]pyrrolidin-1-yl]-N-(3,4,5-trifluorophenyl)-6,7-dihydro-4H-pyrazolo[1,5-a]pyrazine-5-carboxamide

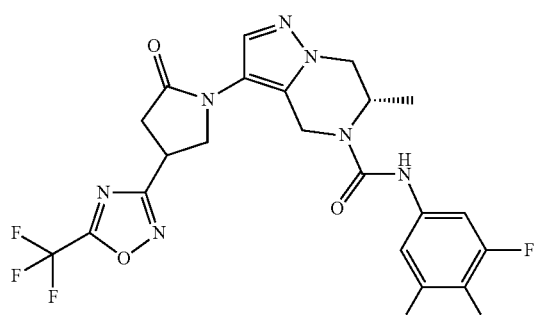

The title compound was prepared according to the following scheme:

331

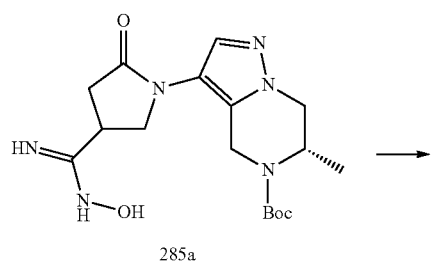
285a

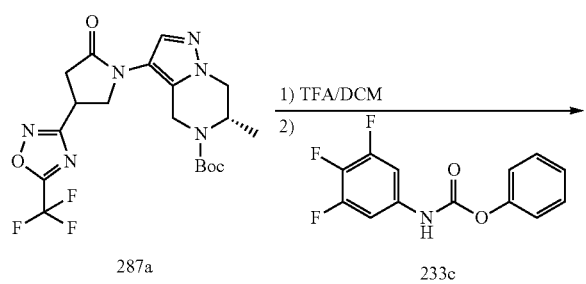
287a  233c

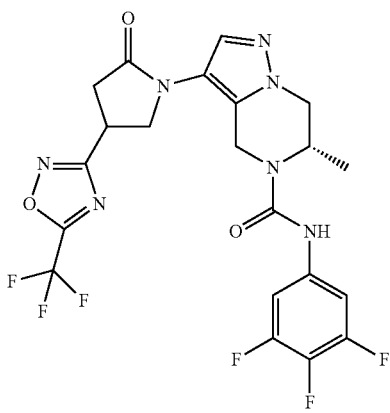
287

Preparation of (6S)-6-methyl-3-[2-oxo-4-[5-(trifluoromethyl)-1,2,4-oxadiazol-3-yl]pyrrolidin-1-yl]-N-(3,4,5-trifluorophenyl)-6,7-dihydro-4H-pyrazolo[1,5-a]pyrazine-5-carboxamide (Example 287)

The title compound was prepared in analogy to Example 285 by using 2,2,2-trifluoroacetic anhydride instead of acetic anhydride. Example 287 was obtained as a white solid (100 mg). LCMS (M+H$^+$): 530. $^1$H NMR (400 MHz, MeOD) δ ppm 7.69 (s, 0.5H), 7.65 (s, 0.5H), 7.33-7.24 (m, 2H), 5.06 (dd, J=12.4, 16.9 Hz, 1H), 5.00-4.94 (m, 1H), 4.52 (dd, J=4.5, 17.1 Hz, 1H), 4.39-4.27 (m, 2H), 4.25-4.05 (m, 3H), 3.18-3.06 (m, 1H), 3.00-2.90 (m, 1H), 1.29-1.26 (m, 3H).

332

Example 288

(6S)-N-[2-(difluoromethyl)-4-pyridyl]-3-(5-fluoropyrimidin-2-yl)-6-methyl-6,7-dihydro-4H-pyrazolo[1,5-a]pyrazine-5-carboxamide

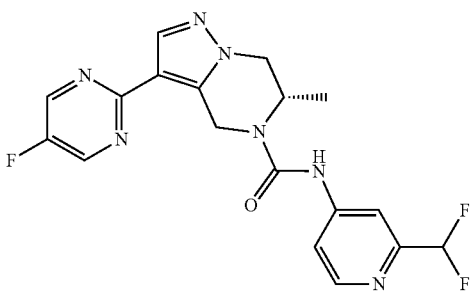 [SMILES: C[C@H]1Cn2ncc(-c3ncc(F)cn3)c2CN1C(=O)Nc1ccnc(C(F)F)c1]

The title compound was prepared according to the following scheme:

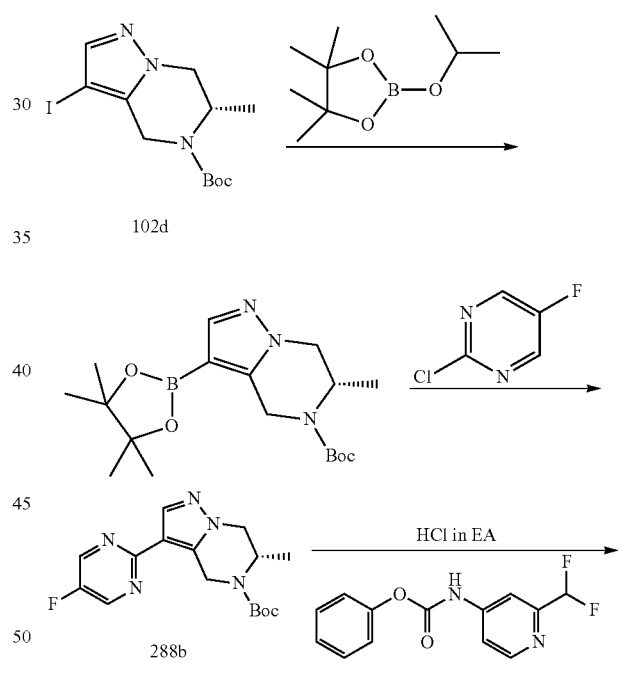
102d 288b  218c

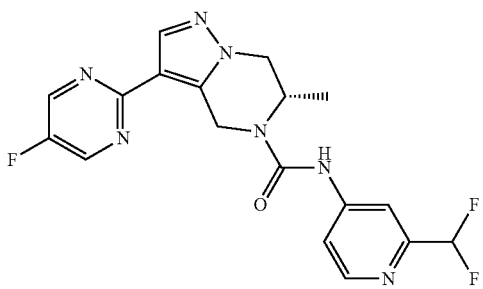
288

Preparation of tert-butyl (6S)-3-(5-fluoropyrimidin-2-yl)-6-methyl-6,7-dihydro-4H-pyrazolo[1,5-a]pyrazine-5-carboxylate (compound 288b)

The compound 288b was prepared in analogy to compound 67c by using 2-chloro-5-fluoropyrimidine instead of 2-chloro-4-(trifluoromethyl)pyridine. Compound 288b was obtained as a white solid (150 mg). LCMS (M+H$^+$): 334. $^1$H NMR (400 MHz, MeOD) δ ppm 8.72 (d, J=0.6 Hz, 2H), 8.18 (s, 1H), 5.40 (d, J=18.9 Hz, 1H), 4.89 (d, J=5.5 Hz, 1H), 4.65 (d, J=18.7 Hz, 1H), 4.34-4.25 (m, 1H), 4.22-4.12 (m, 1H), 1.55 (s, 9H), 1.23 (d, J=7.0 Hz, 3H).

Preparation of (6S)-N-[2-(difluoromethyl)-4-pyridyl]-3-(5-fluoropyrimidin-2-yl)-6-methyl-6,7-dihydro-4H-pyrazolo[1,5-a]pyrazine-5-carboxamide (Example 288)

The title compound was prepared in analogy to Example 223 by using tert-butyl (6S)-3-(5-fluoropyrimidin-2-yl)-6-methyl-6,7-dihydro-4H-pyrazolo[1,5-a]pyrazine-5-carboxylate (compound 288b) instead of tert-butyl (6S)-6-methyl-3-(2-oxopyrrolidin-1-yl)-6,7-dihydro-4H-pyrazolo[1,5-a]pyrazine-5-carboxylate (compound 223b). Example 288 was obtained as a white solid (6 mg). LCMS (M+H$^+$): 390. $^1$H NMR (400 MHz, CDCl$_3$) δ ppm 8.63 (s, 2H), 8.55 (d, J=6.3 Hz, 1H), 8.26 (s, 1H), 7.68 (d, J=2.5 Hz, 2H), 6.94 (s, 1H), 6.64 (t, J=17.1 Hz, 1H), 5.30 (d, J=17.1 Hz, 1H), 5.22-5.10 (m, 1H), 4.95 (d, J=17.1 Hz, 1H), 4.47-4.35 (m, 1H), 4.33-4.23 (m, 1H), 1.33 (d, J=7.0 Hz, 3H).

Example 289

(6S)-6-methyl-3-[5-(1-methylimidazol-2-yl)-2-oxo-oxazolidin-3-yl]-N-(3,4,5-trifluorophenyl)-6,7-dihydro-4H-pyrazolo[1,5-a]pyrazine-5-carboxamide

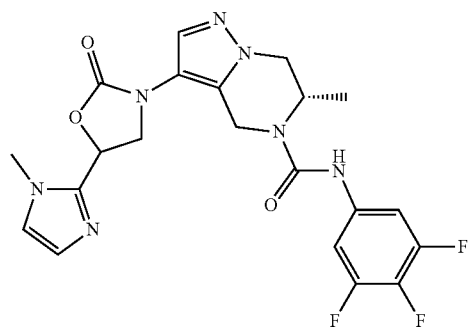 [SMILES: C[C@H]1Cn2ncc(N3CC(c4nccn4C)OC3=O)c2CN1C(=O)Nc1cc(F)c(F)c(F)c1]

The title compound was prepared according to the following scheme:

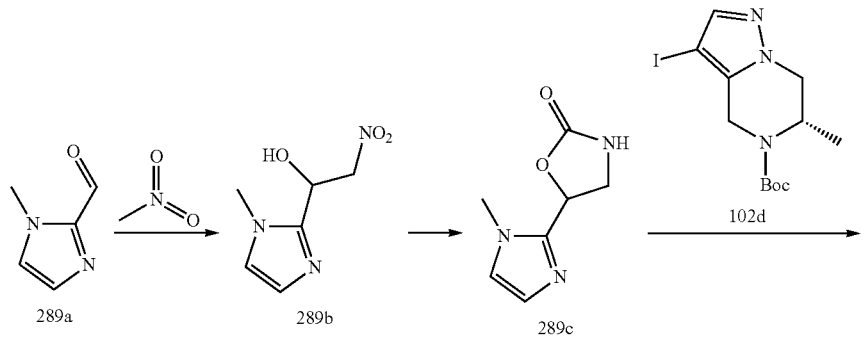

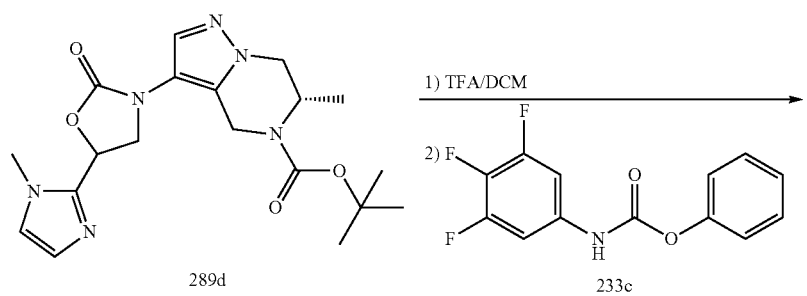

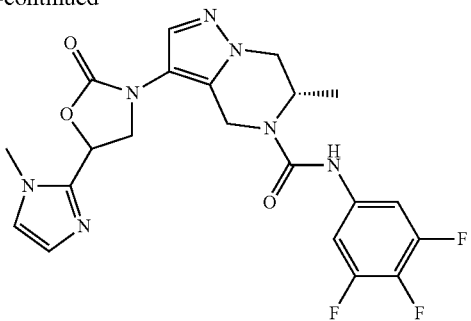

289

Preparation of 1-(1-methyl-1H-imidazol-2-yl)-2-nitroethanol (compound 289b)

A mixture of 1-methyl-1H-imidazole-2-carbaldehyde (1.1 g, 10 mmol), barium hydroxide (171 mg, 1 mmol) and nitromethane (6.1 g, 100 mmol) in water (20 mL) was stirred for 2 hours at room temperature. The reaction mixture was extracted with EtOAc (50 mL) three times. The organic layers were combined, dried over $Na_2SO_4$ and concentrated in vacuo to give crude compound 289b (1.5 g) as a yellow solid.

Preparation of 5-(1-methylimidazol-2-yl)oxazolidin-2-one (compound 289c)

A mixture of 1-(1-methyl-1H-imidazol-2-yl)-2-nitroethanol (compound 289b, 1.5 g, 8.76 mmol), hydrochloric acid (1.75 mL, 1M) and Pd/C (187 mg, 1.75 mmol) in ethanol (20 mL) was stirred at 50° C. for 16 hours under hydrogen balloon. The reaction mixture was filtered through celite and the filtrate was concentrated. The residue was dissolved in DCM (20 mL), to which was added triethylamine (887 mg, 8.76 mmol), and triphosgene (1.04 g, 3.51 mmol) slowly at room temperature. After stirred at room temperature for 30 mins, the reaction mixture was concentrated in vacuo. The resulting residue was purified by flash chromatography (silica gel, 10% MeOH in EtOAc) to give compound 289c as yellow solid (200 mg). LCMS (M+H+): 168.

Preparation of (6S)-6-methyl-3-[5-(1-methylimidazol-2-yl)-2-oxo-oxazolidin-3-yl]-N-(3,4,5-trifluorophenyl)-6,7-dihydro-4H-pyrazolo[1,5-a]pyrazine-5-carboxamide (Example 289)

The title compound was prepared in analogy to Example 262 by using 5-(1-methylimidazol-2-yl)oxazolidin-2-one (compound 289c) instead of (S)-3-hydroxypyrrolidin-2-one. Example 289 was obtained as a white solid (83 mg). LCMS (M+H+): 476. $^1$H NMR (400 MHz, MeOD) δ ppm 7.75 (d, J=4.0 Hz, 1H), 7.34-7.30 (m, 2H), 7.25 (s, 1H), 7.07 (s, 1H), 6.05-6.00 (m, 1H), 5.13 (dd, J=9.9, 16.8 Hz, 1H), 5.06-4.95 (m, 1H), 4.71-4.53 (m, 2H), 4.43-4.28 (m, 2H), 4.22-4.13 (m, 1H), 3.86 (s, 3H), 1.29-1.26 (m, 3H).

Example 290

(6S)-6-methyl-3-(2-oxo-4-thiazol-5-yl-pyrrolidin-1-yl)-N-(3,4,5-trifluorophenyl)-6,7-dihydro-4H-pyrazolo[1,5-a]pyrazine-5-carboxamide

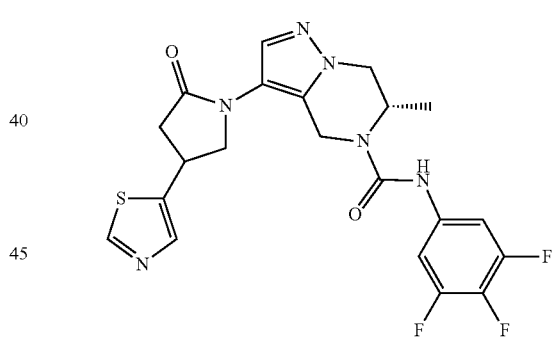

The title compound was prepared according to the following scheme:

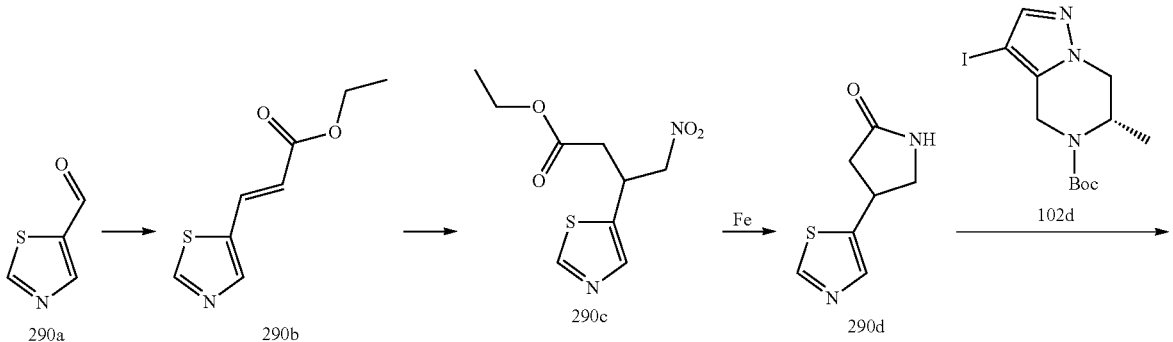

-continued

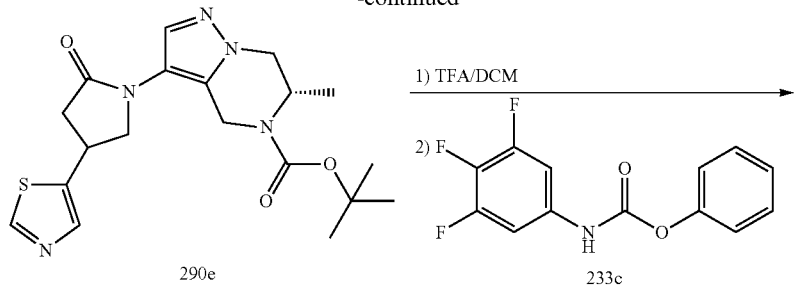

290e

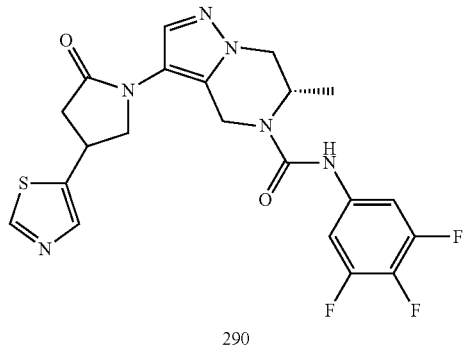

233c

1) TFA/DCM
2) →

290

Preparation of ethyl 3-(thiazol-5-yl)acrylate (compound 290b)

A mixture of thiazole-5-carbaldehyde (1.13 g, 10 mmol) and ethyl 2-(triphenylphosphoranylidene)acetate (3.48 g, 10 mmol) in THF (30 mL) was stirred at room temperature for 30 minutes. The reaction mixture was concentrated in vacuo. The crude product was purified by flash chromatography (silica gel, 20% to 30% EtOAc in hexanes) to give compound 290b as a colorless oil (1.8 g). LCMS (M+H$^+$): 184.

Preparation of ethyl 4-nitro-3-(thiazol-5-yl)butanoate (compound 290c)

A mixture of ethyl 3-(thiazol-5-yl)acrylate (compound 290b, 0.91 g, 4.97 mmol), DBU (1.51 g, 9.93 mmol) and nitromethane (3.03 g, 49.7 mmol) in EtOH (20 mL) was stirred at 80° C. for 15 hours. The reaction mixture was concentrated in vacuo. The crude product was purified by flash chromatography (silica gel, 10% to 30% EtOAc in hexanes) to give compound 290c as a light yellow oil (600 mg). LCMS (M+H$^+$): 245.

Preparation of 4-thiazol-5-ylpyrrolidin-2-one (compound 290d)

A mixture of ethyl 4-nitro-3-(thiazol-5-yl)butanoate (366 mg, 1.5 mmol), Fe (418 mg, 7.49 mmol) and ammonium chloride (401 mg, 7.49 mmol) in EtOH (10 mL)/water (2 mL) was stirred at 80° C. for 1 hour. The reaction mixture was filtered through celite and the filtrate was concentrated in vacuo. The crude product was purified by flash chromatography (silica gel, 10% MeOH in DCM) to give compound 290d as light yellow oil (150 mg). LCMS (M+H$^+$): 169.

Preparation of (6S)-6-methyl-3-(2-oxo-4-thiazol-5-yl-pyrrolidin-1-yl)-N-(3,4,5-trifluorophenyl)-6,7-dihydro-4H-pyrazolo[1,5-a]pyrazine-5-carboxamide (Example 290)

The title compound was prepared in analogy to Example 262 by using 4-thiazol-5-ylpyrrolidin-2-one (compound 290d) instead of (S)-3-hydroxypyrrolidin-2-one. Example 290 was obtained as a white solid (30 mg). LCMS (M+H$^+$): 477. $^1$H NMR (400 MHz, MeOD) δ ppm 8.97 (d, J=3.0 Hz, 1H), 7.88 (s, 1H), 7.66 (s, 1H), 7.34-7.25 (m, 2H), 5.08 (dd, J=4.4, 16.9 Hz, 1H), 4.98-4.92 (m, 1H), 4.53 (dd, J=5.6, 16.9 Hz, 1H), 4.36-4.23 (m, 3H), 4.17 (d, J=12.5 Hz, 1H), 3.97-3.88 (m, 1H), 3.09 (dd, J=8.0, 17.1 Hz, 1H), 2.75 (dd, J=7.2, 17.2 Hz, 1H), 1.30-1.26 (m, 3H).

Example 291

(6S)-6-methyl-3-(2-oxo-4-thiazol-2-yl-pyrrolidin-1-yl)-N-(3,4,5-trifluorophenyl)-6,7-dihydro-4H-pyrazolo[1,5-a]pyrazine-5-carboxamide

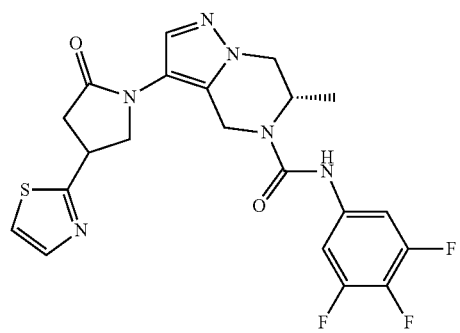 [SMILES: C[C@H]1Cn2ncc(N3CC(c4nccs4)CC3=O)c2CN1C(=O)Nc1cc(F)c(F)c(F)c1]

The title compound was prepared according to the following scheme:

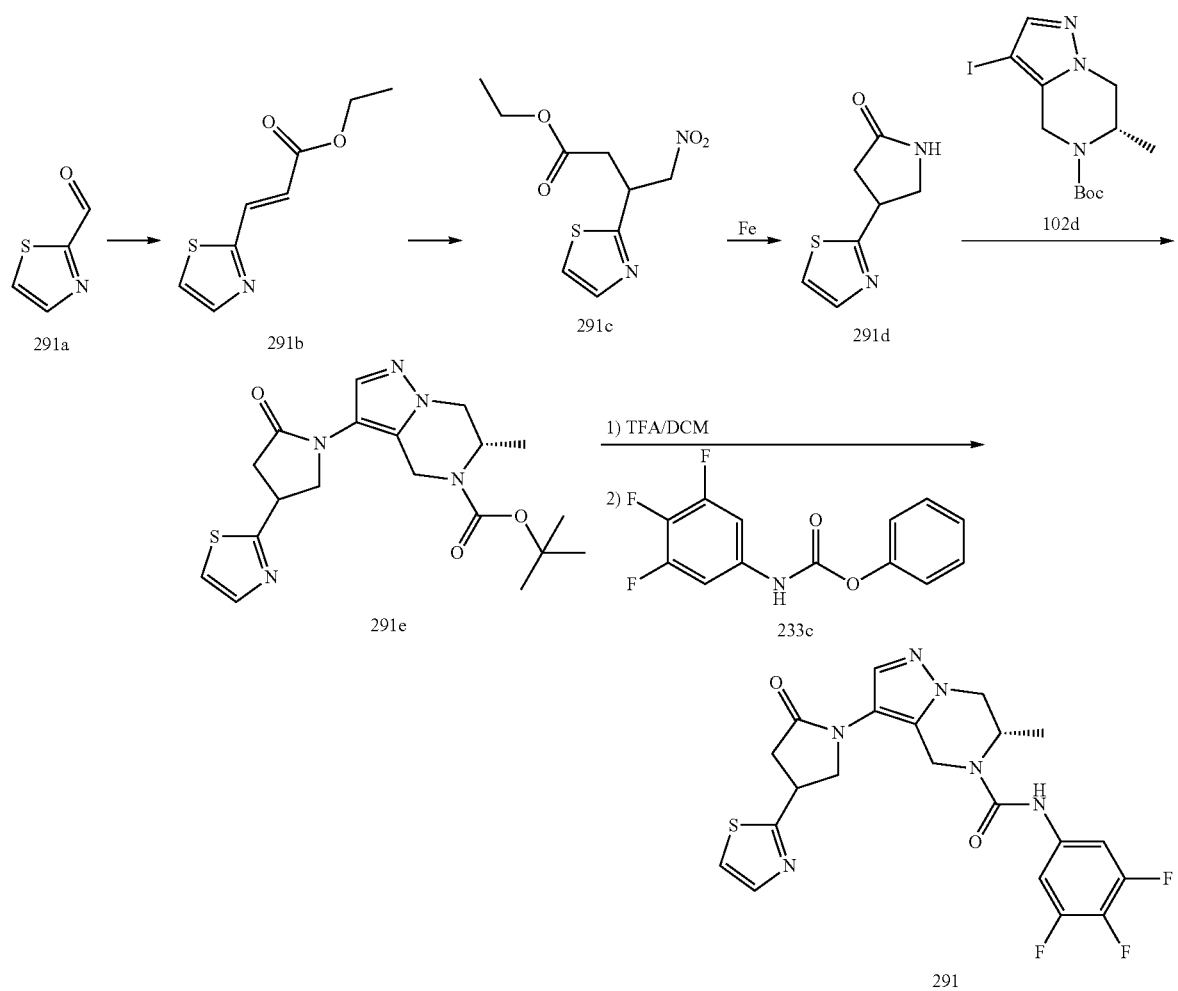

Preparation of 4-thiazol-2-ylpyrrolidin-2-one (compound 291d)

Compound 291d was prepared in analogy to compound 290d by using thiazole-2-carbaldehyde instead of thiazole-5-carbaldehyde. Compound 291d was obtained as a light yellow oil (150 mg). LCMS (M+H$^+$): 169.

Preparation of (6S)-6-methyl-3-(2-oxo-4-thiazol-2-yl-pyrrolidin-1-yl)-N-(3,4,5-trifluorophenyl)-6,7-dihydro-4H-pyrazolo[1,5-a]pyrazine-5-carboxamide (Example 291)

The title compound was prepared in analogy to Example 262 by using 4-thiazol-2-ylpyrrolidin-2-one (compound 291d) instead of (S)-3-hydroxypyrrolidin-2-one. Example 291 was obtained as a white solid (7 mg). LCMS (M+H$^+$): 477. $^1$H NMR (400 MHz, MeOD) δ ppm 7.81 (d, J=3.0 Hz, 0.5H), 7.79 (d, J=3.0 Hz, 0.5H), 7.66 (s, 0.5H), 7.65 (s, 0.5H), 7.58 (d, J=3.6 Hz, 0.5H), 7.56 (d, J=3.6 Hz, 0.5H), 7.36-7.23 (m, 2H), 5.07 (dd, J=2.5, 16.8 Hz, 1H), 5.01-4.94 (m, 1H), 4.53 (dd, J=2.1, 16.9 Hz, 1H), 4.37-4.25 (m, 3H), 4.20-4.13 (m, 1H), 4.12-4.03 (m, 1H), 3.12 (dd, J=8.8, 17.1 Hz, 1H), 2.97-2.87 (m, 1H), 1.29-1.26 (m, 3H).

Example 292

(6S)-6-methyl-3-(2-oxo-1,3-oxazinan-3-yl)-N-(3,4,5-trifluorophenyl)-6,7-dihydro-4H-pyrazolo[1,5-a]pyrazine-5-carboxamide

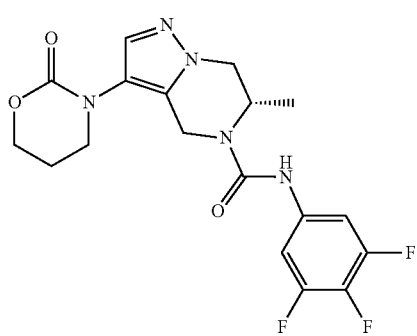 [SMILES: C[C@H]1Cn2ncc(N3CCCOC3=O)c2CN1C(=O)Nc1cc(F)c(F)c(F)c1]

Preparation of (6S)-6-methyl-3-(2-oxo-1,3-oxazinan-3-yl)-N-(3,4,5-trifluorophenyl)-6,7-dihydro-4H-pyrazolo[1,5-a]pyrazine-5-carboxamide (Example 292)

The title compound was prepared in analogy to Example 223 by using 1,3-oxazinan-2-one instead of pyrrolidin-2-one and phenyl N-(3,4,5-trifluoro-phenyl)carbamate (compound 233c) instead of phenyl N-[2-(difluoromethyl)-4-pyridyl]carbamate (compound 218c). Example 292 was obtained as a white solid (25 mg). LCMS (M+H$^+$): 410. $^1$H NMR (400 MHz, MeOD) δ ppm 7.64 (s, 1H), 7.33-7.27 (m, 2H), 5.02-4.92 (m, 2H), 4.51-4.39 (m, 3H), 4.35-4.24 (m, 1H), 4.16 (dd, J=1.0, 12.8 Hz, 1H), 3.84-3.66 (m, 2H), 2.23 (q, J=5.8 Hz, 2H), 1.26 (d, J=7.0 Hz, 3H).

Example 293

(6S)-6-methyl-3-(2-oxohexahydropyrimidin-1-yl)-N-(3,4,5-trifluorophenyl)-6,7-dihydro-4H-pyrazolo[1,5-a]pyrazine-5-carboxamide

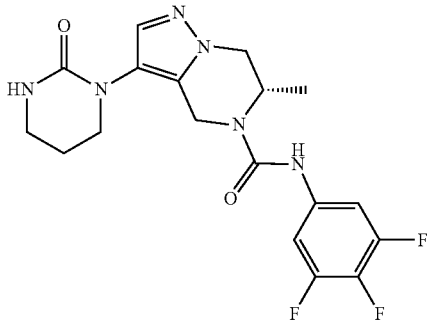 [SMILES: C[C@H]1Cn2ncc(N3CCCNC3=O)c2CN1C(=O)Nc1cc(F)c(F)c(F)c1]

Preparation of (6S)-6-methyl-3-(2-oxohexahydropyrimidin-1-yl)-N-(3,4,5-trifluorophenyl)-6,7-dihydro-4H-pyrazolo[1,5-a]pyrazine-5-carboxamide (Example 293)

The title compound was prepared in analogy to Example 223 by using hexahydropyrimidin-2-one instead of pyrrolidin-2-one and phenyl N-(3,4,5-trifluoro-phenyl)carbamate (compound 233c) instead of phenyl N-[2-(difluoromethyl)-4-pyridyl]carbamate (compound 218c). Example 293 was obtained as a white solid (7 mg). LCMS (M+H$^+$): 409. $^1$H NMR (400 MHz, MeOD) δ ppm 7.55 (s, 1H), 7.34-7.28 (m, 2H), 5.01-4.91 (m, 2H), 4.44 (d, J=16.6 Hz, 1H), 4.32-4.23 (m, 1H), 4.18-4.09 (m, 1H), 3.68 (t, J=5.8 Hz, 2H), 3.40 (t, J=5.8 Hz, 2H), 2.10 (q, J=5.8 Hz, 2H), 1.26 (d, J=7.0 Hz, 3H).

Example 294

(6S)-3-(5,5-dimethyl-2-oxo-1,3-oxazinan-3-yl)-6-methyl-N-(3,4,5-trifluorophenyl)-6,7-dihydro-4H-pyrazolo[1,5-a]pyrazine-5-carboxamide

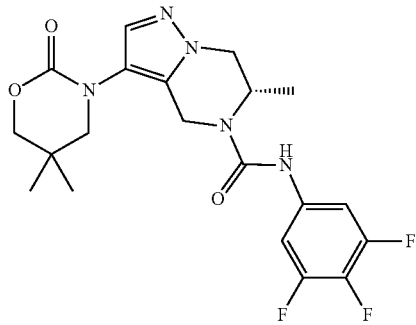 [SMILES: C[C@H]1Cn2ncc(N3CC(C)(C)COC3=O)c2CN1C(=O)Nc1cc(F)c(F)c(F)c1]

Preparation of (6S)-3-(5,5-dimethyl-2-oxo-1,3-oxazinan-3-yl)-6-methyl-N-(3,4,5-trifluorophenyl)-6,7-dihydro-4H-pyrazolo[1,5-a]pyrazine-5-carboxamide (Example 294)

The title compound was prepared in analogy to Example 223 by using 5,5-dimethyl-1,3-oxazinan-2-one instead of pyrrolidin-2-one and phenyl N-(3,4,5-trifluoro-phenyl)carbamate (compound 233c) instead of phenyl N-[2-(difluoromethyl)-4-pyridyl]carbamate (compound 218c). Example 294 was obtained as a white solid (16 mg). LCMS (M+H$^+$): 438. $^1$H NMR (400 MHz, MeOD) δ ppm 7.61 (s, 1H), 7.32-7.24 (m, 2H), 5.00-4.93 (m, 2H), 4.42 (d, J=16.8 Hz, 1H), 4.30 (dd, J=4.4, 12.4 Hz, 1H), 4.21-4.10 (m, 3H), 3.54-3.44 (m, 2H), 1.26 (d, J=7.0 Hz, 3H), 1.21 (s, 3H), 1.20 (s, 3H).

Example 295

(6S)-N-(3-chloro-4-fluoro-phenyl)-3-[4-(methoxymethyl)-2-oxo-pyrrolidin-1-yl]-6-methyl-6,7-dihydro-4H-pyrazolo[1,5-a]pyrazine-5-carboxamide

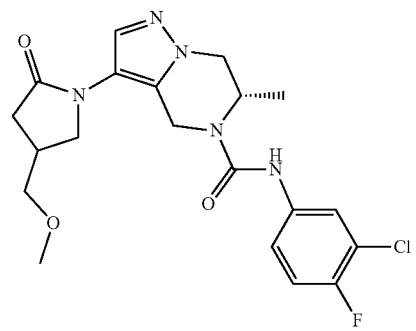 [SMILES: COCC1CC(=O)N(c2cnn3c2CN(C(=O)Nc2ccc(F)c(Cl)c2)[C@@H](C)C3)C1]

The title compound was prepared according to the following scheme:

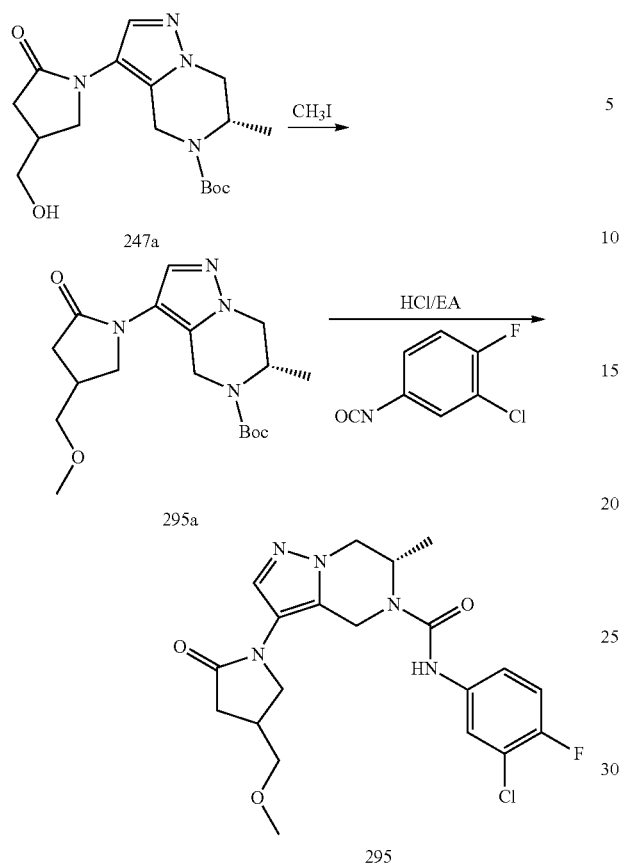

Step 1: Preparation of tert-butyl (6S)-3-[4-(methoxymethyl)-2-oxo-pyrrolidin-1-yl]-6-methyl-6,7-dihydro-4H-pyrazolo[1,5-a]pyrazine-5-carboxylate (compound 295a)

To a solution of tert-butyl (6S)-3-[4-(hydroxymethyl)-2-oxo-pyrrolidin-1-yl]-6-methyl-6,7-dihydro-4H-pyrazolo[1,5-a]pyrazine-5-carboxylate (compound 247a, 50 mg, 0.143 mmol) in THF (5 mL) was added NaH (8.3 mg, 0.215 mmol, 60%) and then CH$_3$I (40.6 mg, 0.286 mmol) at 0° C. The reaction mixture was stirred at room temperature for 48 hours. Then the reaction was quenched with H$_2$O and extracted with EtOAc (20 mL). The organic phase was dried over Na$_2$SO$_4$ and then concentrated to give crude compound 295a, which was used in next step without further purification. LCMS (M+H$^+$): 365.

Step 2: Preparation of (6S)-N-(3-chloro-4-fluoro-phenyl)-3-[4-(methoxymethyl)-2-oxo-pyrrolidin-1-yl]-6-methyl-6,7-dihydro-4H-pyrazolo[1,5-a]pyrazine-5-carboxamide (Example 295)

The title compound was prepared in analogy to Example 246 by using tert-butyl (6S)-3-[4-(methoxymethyl)-2-oxo-pyrrolidin-1-yl]-6-methyl-6,7-dihydro-4H-pyrazolo[1,5-a]pyrazine-5-carboxylate (compound 295a) instead of tert-butyl (6S)-3-(3,6-dioxo-4,7,8,8a-tetrahydro-1H-pyrrolo[1,2-a]pyrazin-2-yl)-6-methyl-6,7-dihydro-4H-pyrazolo[1,5-a]pyrazine-5-carboxylate (compound 246f). Example 295 was obtained as a white solid (8 mg). LCMS (M+H$^+$): 436. $^1$H NMR: (400 MHz, DMSO-d$_6$) δ ppm 8.95 (d, J=2.3 Hz, 1H), 7.73 (dd, J=2.4, 6.9 Hz, 1H), 7.60 (d, J=2.3 Hz, 1H), 7.42 (d, J=8.8 Hz, 1H), 7.37-7.28 (m, 1H), 4.97 (dd, J=2.4, 17.2 Hz, 1H), 4.91-4.81 (m, 1H), 4.36 (dd, J=5.5, 17.1 Hz, 1H), 4.23-4.16 (m, 1H), 4.14-4.07 (m, 1H), 3.91-3.75 (m, 1H), 3.56-3.44 (m, 1H), 3.40 (dd, J=4.0, 6.5 Hz, 2H), 3.29 (d, J=2.3 Hz, 3H), 2.81-2.65 (m, 2H), 2.20 (dd, J=6.7, 16.9 Hz, 1H), 1.14 (d, J=6.5 Hz, 3H).

Example 296

(6S)-N-(3-chloro-4-fluoro-phenyl)-6-methyl-3-(3-oxo-8-oxa-2-azaspiro[4.5]decan-2-yl)-6,7-dihydro-4H-pyrazolo[1,5-a]pyrazine-5-carboxamide

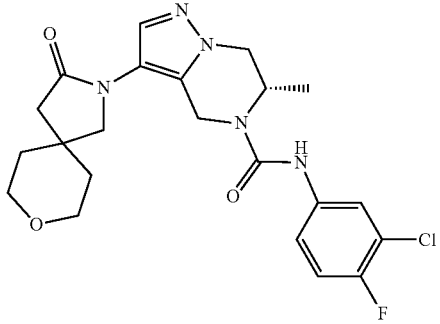 [SMILES: C[C@H]1Cn2ncc(N3CC4(CCOCC4)CC3=O)c2CN1C(=O)Nc1ccc(F)c(Cl)c1]

Preparation of (6S)-N-(3-chloro-4-fluoro-phenyl)-6-methyl-3-(3-oxo-8-oxa-2-azaspiro[4.5]decan-2-yl)-6,7-dihydro-4H-pyrazolo[1,5-a]pyrazine-5-carboxamide (Example 296)

The title compound was prepared in analogy to Example 246 by using 8-oxa-2-azaspiro[4.5]decan-3-one instead of 1,2,4,7,8,8a-hexahydropyrrolo[1,2-a]pyrazine-3,6-dione (compound 246e). Example 296 was obtained as a white solid (24.3 mg). LCMS: (M+H$^+$): 462. $^1$H NMR (400 MHz, METHANOL-d$_4$) δ ppm 7.62 (s, 1H), 7.59 (dd, J=2.6, 6.7 Hz, 1H), 7.32 (ddd, J=2.8, 4.1, 9.0 Hz, 1H), 7.19-7.12 (m, 1H), 5.05-4.91 (m, 2H), 4.48 (d, J=17.1 Hz, 1H), 4.28 (dd, J=4.5, 12.7 Hz, 1H), 4.19-4.09 (m, 1H), 3.79-3.67 (m, 6H), 2.54 (s, 2H), 1.83-1.70 (m, 4H), 1.26 (d, J=6.8 Hz, 3H).

Example 297

(6S)-N-(3-chloro-4-fluoro-phenyl)-6-methyl-3-(3-methyl-2-oxo-pyrrolidin-1-yl)-6,7-dihydro-4H-pyrazolo[1,5-a]pyrazine-5-carboxamide

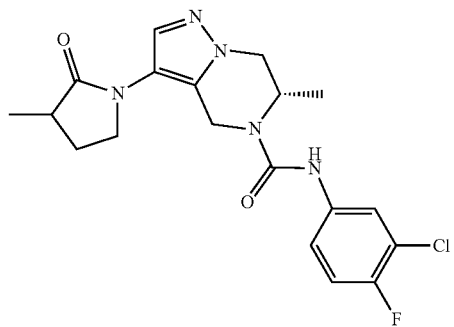 [SMILES: CC1CCN(c2cnn3c2CN(C(=O)Nc2ccc(F)c(Cl)c2)[C@@H](C)C3)C1=O]

Preparation of (6S)-N-(3-chloro-4-fluoro-phenyl)-6-methyl-3-(3-methyl-2-oxo-pyrrolidin-1-yl)-6,7-dihydro-4H-pyrazolo[1,5-a]pyrazine-5-carboxamide (Example 297)

The title compound was prepared in analogy to Example 246 by using 3-methylpyrrolidin-2-one instead of 1,2,4,7,8,8a-hexahydropyrrolo[1,2-a]pyrazine-3,6-dione (compound 246e). Example 297 was obtained as a white solid (28.7 mg). LCMS (M+H$^+$): 406. $^1$H NMR (400 MHz, DMSO-d$_6$) δ ppm 8.95 (d, J=4.8 Hz, 1H), 7.74 (dd, J=1.8, 6.5 Hz, 1H), 7.62 (d, J=2.3 Hz, 1H), 7.46-7.39 (m, 1H), 7.35-7.28 (m, 1H), 4.99 (dd, J=9.5, 17.1 Hz, 1H), 4.90-4.81 (m, 1H), 4.44-4.34 (m, 2H), 4.25-4.16 (m, 1H), 4.15-4.07 (m, 1H), 3.77-3.68 (m, 1H), 3.68-3.60 (m, 1H), 2.38-2.28 (m, 1H), 1.79-1.67 (m, 1H), 1.23-1.08 (m, 6H).

Example 298

(6S)-N-(3-chloro-4-fluoro-phenyl)-3-[4-(hydroxymethyl)-2-oxo-pyrrolidin-1-yl]-6-methyl-6,7-dihydro-4H-pyrazolo[1,5-a]pyrazine-5-carboxamide

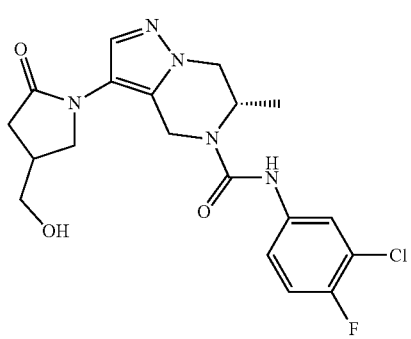 [SMILES: C[C@H]1Cn2ncc(N3CC(CO)CC3=O)c2CN1C(=O)Nc1ccc(F)c(Cl)c1]

The title compound was prepared according to the following scheme:

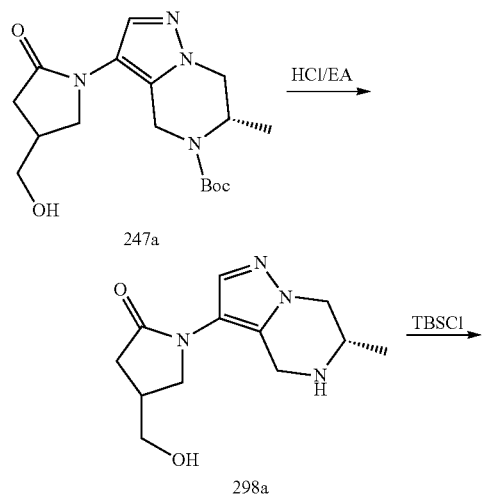

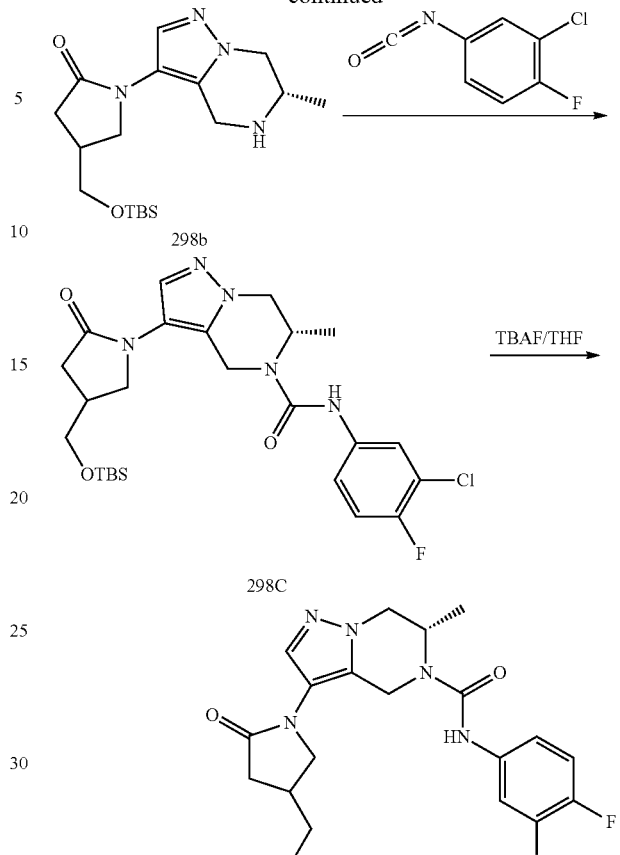

Step 1: Preparation of 4-(hydroxymethyl)-1-[(6S)-6-methyl-4,5,6,7-tetrahydropyrazolo[1,5-a]pyrazin-3-yl]pyrrolidin-2-one (compound 298a)

A solution of tert-butyl (6S)-3-[4-(hydroxymethyl)-2-oxo-pyrrolidin-1-yl]-6-methyl-6,7-dihydro-4H-pyrazolo[1,5-a]pyrazine-5-carboxylate (compound 247a, 400.0 mg, 1.14 mmol) in HCl/EtOAc (5.0 mL, 1M) was stirred at 25° C. for 1 hour. Then the reaction mixture was concentrated in vacuo to provide crude compound 298a (500 mg), which was used directly in the next step without further purification.

Step 2: Preparation of 4-[[tert-butyl(dimethyl)silyl]oxymethyl]-1-[(6S)-6-methyl-4,5,6,7-tetrahydropyrazolo[1,5-a]pyrazin-3-yl]pyrrolidin-2-one (compound 298b)

To a solution of 4-(hydroxymethyl)-1-[(6S)-6-methyl-4,5,6,7-tetrahydropyrazolo[1,5-a]pyrazin-3-yl]pyrrolidin-2-one (compound 298a, 100.0 mg, 0.35 mmol) in DCM (15 mL) was added imidazole (142.97 mg 2.1 mmol) and TBSCl (79.53 mg, 0.53 mmol) under N$_2$ then the reaction mixture was stirred at room temperature for 12 hours. The reaction mixture was partitioned between H$_2$O (30 mL) and EtOAc (50 mL). The organic phase was separated and concentrated. The obtained residue was purified by silica gel column chromatography (DCM: MeOH=50:1 to 10:1) to give compound 298b (100.0 mg). LCMS (M+H$^+$): 365.

Step 3: Preparation of (6S)-3-[4-[[tert-butyl(dimethyl)silyl]oxymethyl]-2-oxo-pyrrolidin-1-yl]-N-(3-chloro-4-fluoro-phenyl)-6-methyl-6,7-dihydro-4H-pyrazolo[1,5-a]pyrazine-5-carboxamide (compound 298c)

To a solution of 4-[[tert-butyl(dimethyl)silyl]oxymethyl]-1-[(6S)-6-methyl-4,5,6,7-tetrahydropyrazolo[1,5-a]pyrazin-3-yl]pyrrolidin-2-one (compound 298b, 100.0 mg, 0.28 mmol) in DCM (5.0 mL) was added DIPEA (108.36 mg 0.84 mmol) and 2-chloro-1-fluoro-4-isocyanato-benzene (58.33 mg 0.34 mmol) at 0° C., then the reaction was stirred at room temperature for 12 hours. The reaction mixture was partitioned between H$_2$O (20 mL) and DCM (20 mL). The organic phase was separated and concentrated in vacuo to give crude compound 298c (110 mg). LCMS (M+H$^+$): 536.

Step 4: Preparation of (6S)-N-(3-chloro-4-fluoro-phenyl)-3-[4-(hydroxymethyl)-2-oxo-pyrrolidin-1-yl]-6-methyl-6,7-dihydro-4H-pyrazolo[1,5-a]pyrazine-5-carboxamide (Example 298)

To a solution of (6S)-3-[4-[[tert-butyl(dimethyl)silyl]oxymethyl]-2-oxo-pyrrolidin-1-yl]-N-(3-chloro-4-fluoro-phenyl)-6-methyl-6,7-dihydro-4H-pyrazolo[1,5-a]pyrazine-5-carboxamide (compound 298c, 110.0 mg, 0.21 mmol) in THF (5.0 mL) was added a solution of TBAF in THF (0.32 mL, 0.32 mmol). The reaction mixture was stirred at room temperature for 12 hours, then diluted with EtOAc, and washed with brine. The organic layer was concentrated, and the residue was purified by silica gel column chromatography (DCM: MeOH=100:1 to 60:1) to provide Example 298 (25 mg). LCMS (M+H$^+$): 422. $^1$H NMR (400 MHz, MeOH) δ ppm 7.69-7.57 (m, 2H), 7.34 (td, J=3.5, 8.5 Hz, 1H), 7.21-7.14 (m, 1H), 5.03 (dd, J=2.3, 16.8 Hz, 1H), 5.00-4.94 (m, 1H), 4.51 (d, J=16.8 Hz, 1H), 4.30 (dd, J=4.4, 12.7 Hz, 1H), 4.19-4.13 (m, 1H), 3.96 (td, J=8.9, 13.1 Hz, 1H), 3.74-3.61 (m, 3H), 2.79-2.63 (m, 2H), 2.45-2.37 (m, 1H), 1.32-1.23 (m, 3H).

Example 299

(6S)-3-[4-(methoxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide

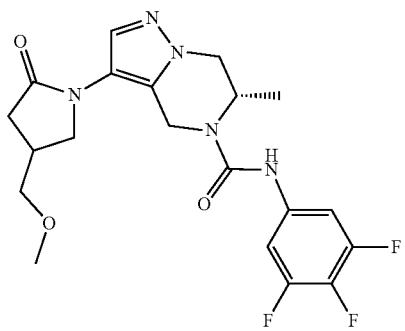 [SMILES: COCC1CC(=O)N(c2cnn3c2CN(C(=O)Nc2cc(F)c(F)c(F)c2)[C@@H](C)C3)C1]

Preparation of (6S)-3-[4-(methoxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide (Example 297)

The title compound was prepared in analogy to the preparation of Example 11 by 3,4,5-trifluoroaniline instead of 3-(trifluoromethyl)aniline and tert-butyl (6S)-3-[4-(methoxymethyl)-2-oxo-pyrrolidin-1-yl]-6-methyl-6,7-dihydro-4H-pyrazolo[1,5-a]pyrazine-5-carboxylate (compound 295a) instead of tert-butyl 3-(4-fluorophenyl)-6,7-dihydro-4H-pyrazolo[1,5-a]pyrazine-5-carboxylate (compound 11a). Example 299 was obtained as white solid (10.5 mg). LCMS: (M+H$^+$): 438. $^1$H NMR (400 MHz, MeOD) δ ppm 7.63 (s, 1H), 7.34-7.21 (m, 2H), 5.03 (d, J=16.9 Hz, 1H), 4.99-4.94 (m, 1H), 4.49 (dd, J=1.8, 16.9 Hz, 1H), 4.35-4.25 (m, 1H), 4.16 (dd, J=1.1, 12.7 Hz, 1H), 3.96 (ddd, J=8.2, 9.7, 15.6 Hz, 1H), 3.71-3.61 (m, 1H), 3.54-3.46 (m, 2H), 3.41 (d, J=1.1 Hz, 3H), 2.90-2.78 (m, 1H), 2.74-2.64 (m, 1H), 2.40 (dd, J=6.3, 17.2 Hz, 1H), 1.27 (d, J=6.9 Hz, 3H).

Example 300

(6S)-3-[4-(methoxymethyl)-2-oxo-pyrrolidin-1-yl]-6-methyl-N-[2-(trifluoromethyl)-4-pyridyl]-6,7-dihydro-4H-pyrazolo[1,5-a]pyrazine-5-carboxamide

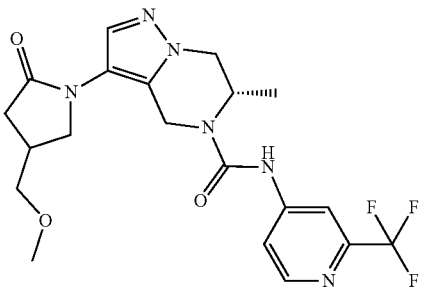 [SMILES: COCC1CC(=O)N(c2cnn3c2CN(C(=O)Nc2ccnc(C(F)(F)F)c2)[C@@H](C)C3)C1]

To a mixture of 2-(trifluoromethyl)pyridin-4-amine (29.7 mg, 0.18 mmol) and pyridine (66.4 mg, 0.83 mmol) in THF (5.0 mL) was added phenyl chloroformate (28.6 mg, 0.18 mmol) under N$_2$ at 0° C. The reaction mixture was stirred at room temperature for 2 hours, then concentrated. To the resulting residue was added DMF (2.5 mL), tert-butyl (6S)-3-[4-(methoxymethyl)-2-oxo-pyrrolidin-1-yl]-6-methyl-6,7-dihydro-4H-pyrazolo[1,5-a]pyrazine-5-carboxylate (compound 295a, 50.0 mg, 0.166 mmol) and DPIEA (0.2 mL), and the reaction mixture was stirred at 100° C. for 2 hours. Then the reaction mixture was purified by Prep-HPLC to give Example 300 as a white solid (27.6 mg). LCMS: (M+H$^+$): 453. $^1$H NMR (400 MHz, MeOH) δ ppm 8.49 (d, J=5.6 Hz, 1H), 8.02 (s, 1H), 7.76 (d, J=5.6 Hz, 1H), 7.63 (s, 1H), 5.10 (d, J=16.9 Hz, 1H), 5.05-4.96 (m, 1H), 4.54 (dd, J=2.3, 17.0 Hz, 1H), 4.33 (dd, J=2.4, 12.8 Hz, 1H), 4.17 (d, J=12.7 Hz, 1H), 3.96 (ddd, J=8.2, 9.7, 14.8 Hz, 1H), 3.66 (ddd, J=5.5, 9.8, 13.3 Hz, 1H), 3.56-3.47 (m, 2H), 3.41 (d, J=1.3 Hz, 3H), 2.91-2.79 (m, 1H), 2.75-2.65 (m, 1H), 2.41 (dd, J=6.1, 17.2 Hz, 1H), 1.30 (d, J=6.8 Hz, 3H).

Example 301

(6S)-N-(3-chloro-4-fluoro-phenyl)-6-methyl-3-(4-oxo-3,3a,6,6a-tetrahydro-1H-furo[3,4-c]pyrrol-5-yl)-6,7-dihydro-4H-pyrazolo[1,5-a]pyrazine-5-carboxamide

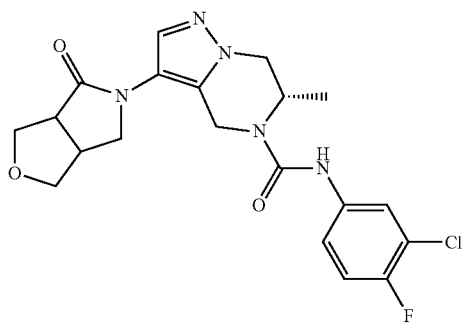 [SMILES: C[C@H]1Cn2ncc(N3CC4COCC4C3=O)c2CN1C(=O)Nc1ccc(F)c(Cl)c1]

The title compound was prepared according to the following scheme:

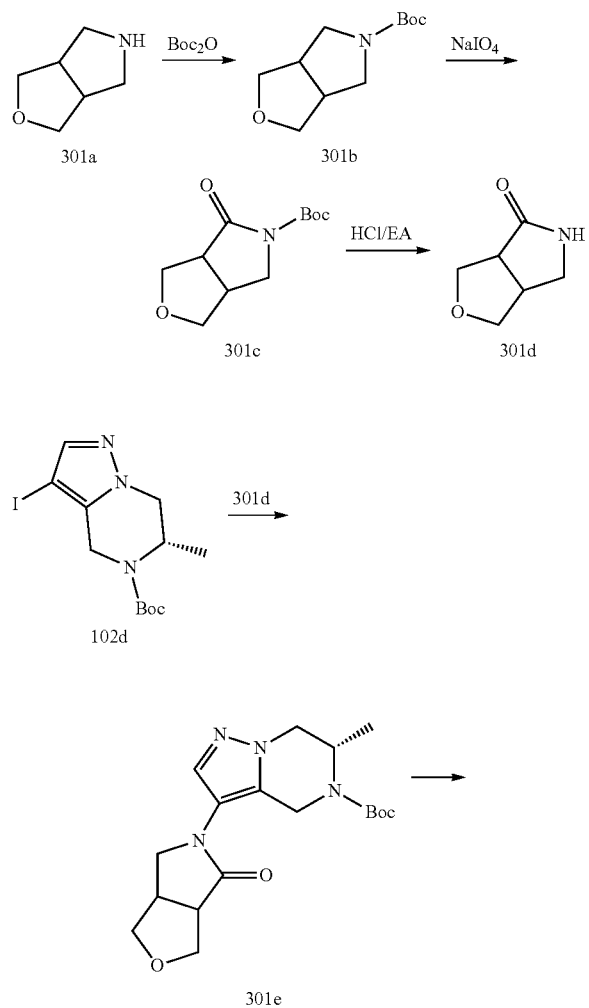

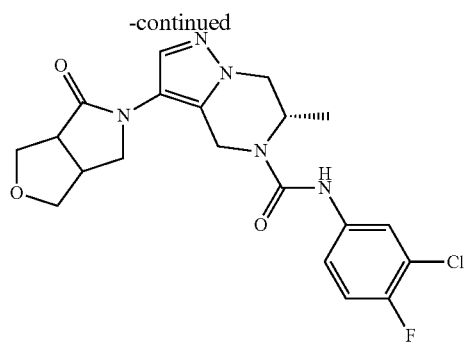

Preparation of tert-butyl 1,3,3a,4,6,6a-hexahydro-furo[3,4-c]pyrrole-5-carboxylate (compound 301b)

To a solution of 3,3a,4,5,6,6a-hexahydro-1H-furo[3,4-c]pyrrole 301a (298.1 mg, 2.0 mmol) and Et₃N (607.2 mg, 6.0 mmol) in DCM (10.0 mL) was added Boc₂O (481.0 mg, 2.2 mmol) at 0° C. The reaction mixture was stirred at room temperature for 2 hours, and then washed with water (10 mL). The organic phase was concentrated to afford compound 301b as colorless oil (400 mg). LCMS (M+H$^+$): 338

Preparation of tert-butyl 4-oxo-3,3a,6,6a-tetrahydro-1H-furo[3,4-c]pyrrole-5-carboxylate (compound 301c)

To a solution of tert-butyl 1,3,3a,4,6,6a-hexahydrofuro[3,4-c]pyrrole-5-carboxylate (compound 301b, 400.0 mg, 1.88 mmol) in EtOAc (6.0 mL) was added NaIO₄ (1.9 g, 8.8 mmol) in H₂O (20 mL) and RuO₂ (75.6 mg, 0.564 mmol). The reaction mixture was stirred at room temperature for 24 hours. The organic phase was separated and the aqueous phase was extracted with ethyl acetate (20 mL). The organic phase was treated with isopropyl alcohol (2.0 mL), and then washed with brine and concentrated to afford compound 301c as colorless oil (400 mg). LCMS (M+H$^+$): 228

Preparation of 1,3,3a,5,6,6a-hexahydrofuro[3,4-c]pyrrol-4-one (compound 301d)

A mixture of tert-butyl 4-oxo-3,3a,6,6a-tetrahydro-1H-furo[3,4-c]pyrrole-5-carboxylate (compound 301c, 400.0 mg, 1.76 mmol) in HCl/EtOAc (5.0 mL) was stirred at room temperature for 1 hour. The reaction mixture was concentrated to afford compound 301d as a colorless oil (218 mg). LCMS (M+H$^+$): 128

Preparation of (6S)-N-(3-chloro-4-fluoro-phenyl)-6-methyl-3-(4-oxo-3,3a,6,6a-tetrahydro-1H-furo[3,4-c]pyrrol-5-yl)-6,7-dihydro-4H-pyrazolo[1,5-a]pyrazine-5-carboxamide (Example 301)

The title compound was prepared in analogy to Example 246 by using 1,3,3a,5,6,6a-hexahydrofuro[3,4-c]pyrrol-4-one (compound 301d) instead of 1,2,4,7,8,8a-hexahydropyrrolo[1,2-a]pyrazine-3,6-dione (compound 246e). Example 301 was obtained as white solid (16 mg). LCMS (M+H$^+$): 434. $^1$H NMR (300 MHz, MeOD) δ ppm 7.80 (s, 1H), 7.62-7.58 (m, 1H), 7.34-7.31 (m, 1H), 7.18-7.12 (m, 1H), 5.07-4.92 (m, 2H), 4.75-4.71 (m, 1H), 4.53-4.49 (m, 1H), 4.32-4.16 (m, 4H), 3.92-3.80 (m, 3H), 3.67-3.61 (m, 1H), 3.20-3.16 (m, 1H), 1.27 (d, J=7.0 Hz, 3H).

Example 302

(6S)-N-(3-chloro-4-fluoro-phenyl)-3-(4-ethyl-2-oxo-pyrrolidin-1-yl)-6-methyl-6,7-dihydro-4H-pyrazolo[1,5-a]pyrazine-5-carboxamide

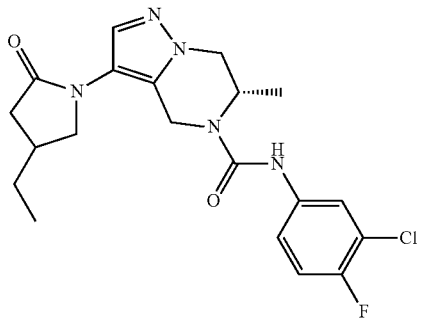 [SMILES: CCC1CC(=O)N(c2cnn3c2CN(C(=O)Nc2ccc(F)c(Cl)c2)[C@@H](C)C3)C1]

Preparation of (6S)-N-(3-chloro-4-fluoro-phenyl)-3-(4-ethyl-2-oxo-pyrrolidin-1-yl)-6-methyl-6,7-dihydro-4H-pyrazolo[1,5-a]pyrazine-5-carboxamide (Example 302)

The title compound was prepared in analogy to Example 246 by using 4-ethylpyrrolidin-2-one instead of 1,2,4,7,8,8a-hexahydropyrrolo[1,2-a]pyrazine-3,6-dione (compound 246e). Example 302 was obtained as white solid (27 mg). LCMS (M+H$^+$): 420.0. $^1$H NMR (400 MHz, MeOD) δ ppm 7.66-7.56 (m, 2H), 7.36-7.30 (m, 1H), 7.16 (t, 1H), 5.06-4.98 (m, 1H), 4.98-4.92 (m, 1H), 4.50 (m, 1H), 4.34-4.24 (m, 1H), 4.20-4.11 (m, 1H), 3.93 (dd, J=8.0, 9.6, 14.4 Hz, 1H), 3.53 (dd, 9.6, 13.2 Hz, 1H), 2.68 (dd, J=8.7, 16.8 Hz, 1H), 2.56-2.44 (m, 1H), 2.33-2.22 (m, 1H), 1.67-1.55 (m, 2H), 1.28-1.24 (m, 3H), 1.01 (t, J=7.4 Hz, 3H).

Example 303

(6S)-N-(3-chloro-4-fluoro-phenyl)-6-methyl-3-(8-oxo-2-oxa-7-azaspiro[4.4]nonan-7-yl)-6,7-dihydro-4H-pyrazolo[1,5-a]pyrazine-5-carboxamide

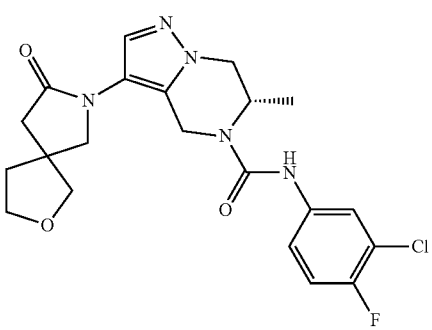 [SMILES: C[C@H]1Cn2ncc(N3CC4(CCOC4)CC3=O)c2CN1C(=O)Nc1ccc(F)c(Cl)c1]

Preparation of Example 303

The title compound was prepared in analogy to Example 246 by using 4-2-oxa-7-azaspiro[4.4]nonane instead of 1,2,4,7,8,8a-hexahydropyrrolo[1,2-a]pyrazine-3,6-dione (compound 246e). Example 303 was obtained as brown solid (8 mg). LCMS: (M+H$^+$): 448. $^1$H NMR (400 MHz, MeOD) δ ppm 7.65 (s, 1H), 7.62 (dd, J=2.5, 6.5 Hz, 1H), 7.37-7.31 (m, 1H), 7.18 (t, J=9.0 Hz, 1H), 5.04 (dd, J=4.3, 17.1 Hz, 1H), 4.52 (dd, J=3.5, 16.8 Hz, 1H), 4.30 (dd, J=4.4, 12.7 Hz, 1H), 4.16 (d, J=12.8 Hz, 1H), 3.97 (t, J=7.2 Hz, 2H), 3.84 (dd, J=3.1, 7.4 Hz, 2H), 3.73 (d, J=8.3 Hz, 1H), 3.37 (s, 2H), 2.67 (s, 2H), 2.20-2.09 (m, 2H), 1.32-1.25 (m, 3H).

Example 304

(6S)-N-(3-chloro-4-fluoro-phenyl)-6-methyl-3-(4-methylsulfonyl-2-oxo-pyrrolidin-1-yl)-6,7-dihydro-4H-pyrazolo[1,5-a]pyrazine-5-carboxamide

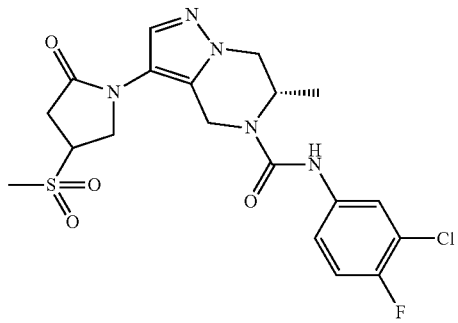 [SMILES: C[C@H]1Cn2ncc(N3CC(S(C)(=O)=O)CC3=O)c2CN1C(=O)Nc1ccc(F)c(Cl)c1]

The title compound was prepared according to the following scheme:

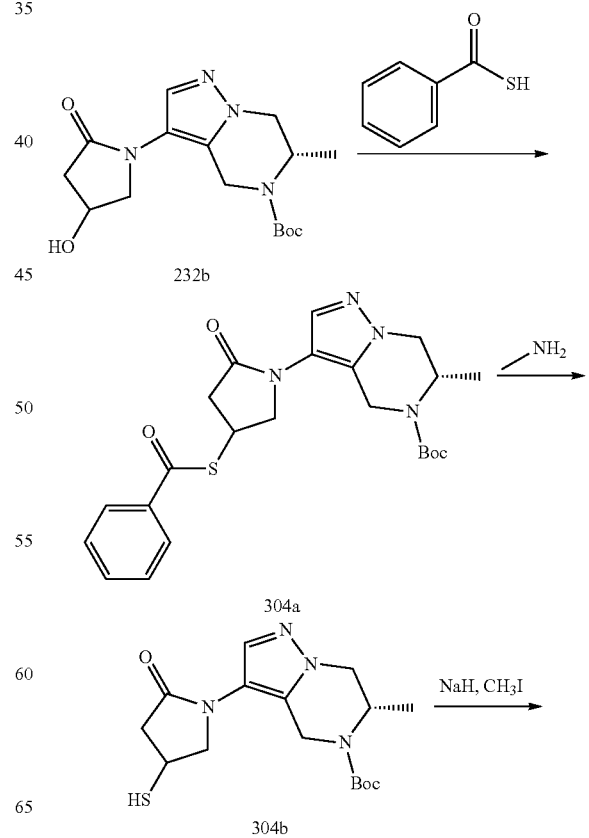

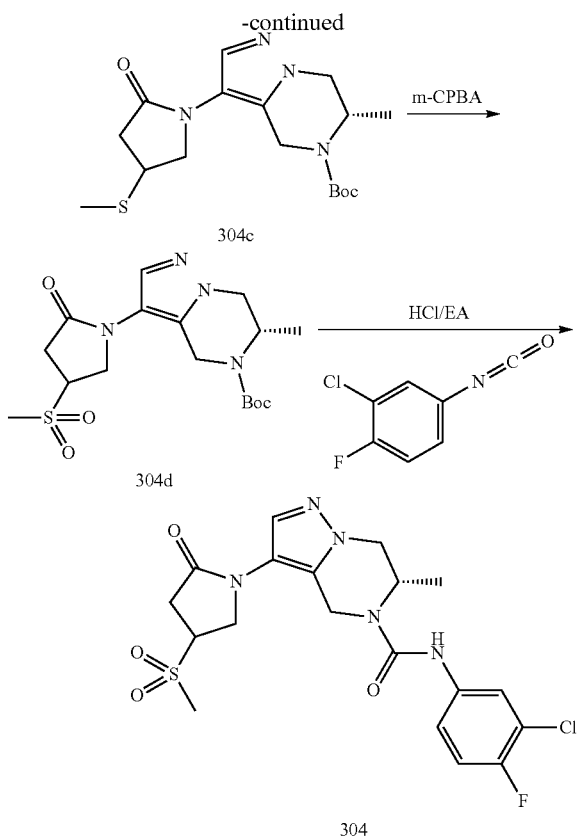

Step 1: Preparation of tert-butyl (6S)-3-(4-benzoyl-sulfanyl-2-oxo-pyrrolidin-1-yl)-6-methyl-6,7-di-hydro-4H-pyrazolo[1,5-a]pyrazine-5-carboxylate (compound 304a)

To a solution of PPh₃ (290.8 mg, 1.11 mmol) in THF (10.0 mL) was added DEAD (193.1 mg, 1.11 mmol) at 0° C. under N₂ and the reaction mixture was stirred at 0° C. for 10 mins, then tert-butyl (6S)-3-(4-hydroxy-2-oxo-pyrrolidin-1-yl)-6-methyl-6,7-dihydro-4H-pyrazolo[1,5-a]pyrazine-5-car-boxylate (compound 232b, 250.0 mg, 0.74 mmol) and benzenecarbothioic S-acid (204.2 mg, 1.48 mmol) were added. The reaction mixture was stirred for 24 hours at room temperature, and then was purified by prep-HPLC to afford compound 304a as white solid (200 mg). LCMS (M+H⁺): 457

Step 2: Preparation of tert-butyl (6S)-6-methyl-3-(2-oxo-4-sulfanyl-pyrrolidin-1-yl)-6,7-dihydro-4H-pyrazolo[1,5-a]pyrazine-5-carboxylate (compound 304b)

To a solution of tert-butyl (6S)-3-(4-benzoylsulfanyl-2-oxo-pyrrolidin-1-yl)-6-methyl-6,7-dihydro-4H-pyrazolo[1,5-a]pyrazine-5-carboxylate (compound 304a, 100.0 mg, 0.22 mmol) in MeOH (2.0 mL) was added methylamine (4.40 mL, 1M in THF) at room temperature under N₂ and the reaction mixture was stirred at same temperature for 1 hour. The reaction mixture was concentrated to give crude compound 304b as a white solid (100 mg). LCMS: (M+H⁺): 353.

Step 3: Preparation of tert-butyl (6S)-6-methyl-3-(4-methylsulfanyl-2-oxo-pyrrolidin-1-yl)-6,7-di-hydro-4H-pyrazolo[1,5-a]pyrazine-5-carboxylate (compound 304c)

To a solution of tert-butyl (6S)-6-methyl-3-(2-oxo-4-sul-fanyl-pyrrolidin-1-yl)-6,7-dihydro-4H-pyrazolo[1,5-a]pyra-zine-5-carboxylate (compound 304b, 100.0 mg, 0.28 mmol) in DMF (2.0 mL) was added NaH (56.0 mg, 1.4 mmol) at 0° C. under N₂ and then CH₃I (397.6 mg, 2.8 mmol). The reaction mixture was then allowed to stir at room temperature for 1 hour. The reaction mixture was filtered and the filtrate was purified by prep-HPLC to afford compound 304c as a white solid (30 mg). LCMS (M+H⁺): 367.

Step 4: Preparation of tert-butyl (6S)-6-methyl-3-(4-methylsulfonyl-2-oxo-pyrrolidin-1-yl)-6,7-di-hydro-4H-pyrazolo[1,5-a]pyrazine-5-carboxylate (compound 304d)

To a solution of tert-butyl (6S)-6-methyl-3-(4-methylsul-fanyl-2-oxo-pyrrolidin-1-yl)-6,7-dihydro-4H-pyrazolo[1,5-a]pyrazine-5-carboxylate (compound 304c, 30.0 mg, 0.081 mmol) in DCM (2.0 mL) was added m-CPBA (17.4 mg, 0.081 mmol) at room temperature. The reaction mixture was stirred at room temperature for 1 hour, and then washed with aqueous sodium sulfite solution. The organic phase was dried over Na₂SO₄, and concentrated to afford crude compound 304d as a white solid (24 mg). LCMS (M+H⁺): 399.

Preparation of (6S)-N-(3-chloro-4-fluoro-phenyl)-6-methyl-3-(4-methylsulfonyl-2-oxo-pyrrolidin-1-yl)-6,7-dihydro-4H-pyrazolo[1,5-a]pyrazine-5-carbox-amide (Example 304)

The title compound was prepared in analogy to Example 246 by using tert-butyl (6S)-6-methyl-3-(4-methyl sulfonyl-2-oxo-pyrrolidin-1-yl)-6,7-dihydro-4H-pyrazolo[1,5-a]pyrazine-5-carboxylate (compound 304d) instead of tert-butyl (6S)-3-(3,6-dioxo-4,7,8,8a-tetrahydro-1H-pyrrolo[1,2-a]pyrazin-2-yl)-6-methyl-6,7-dihydro-4H-pyrazolo[1,5-a]pyrazine-5-carboxylate (compound 246f). Example 304 was obtained as white solid (3 mg). LCMS (M+H⁺): 470. ¹H NMR (300 MHz, MeOD) δ ppm 7.66 (s, 1H), 7.64-7.59 (m, 1H), 7.38-7.29 (m, 1H), 7.16 (s, 1H), 5.09-4.98 (m, 2H), 4.56-4.42 (m, 1H), 4.34-4.11 (m, 5H), 3.09 (d, J=1.1 Hz, 5H), 1.29-1.24 (m, 3H)

Example 305

(6S)-N-(3-chloro-4-fluoro-phenyl)-3-(4-hydroxy-2-oxo-1-piperidyl)-6-methyl-6,7-dihydro-4H-pyrazolo[1,5-a]pyrazine-5-carboxamide

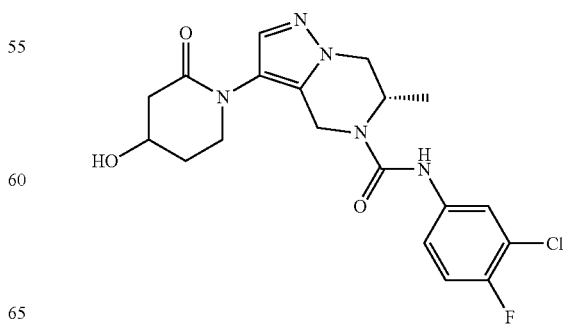

The title compound was prepared according to the following scheme:

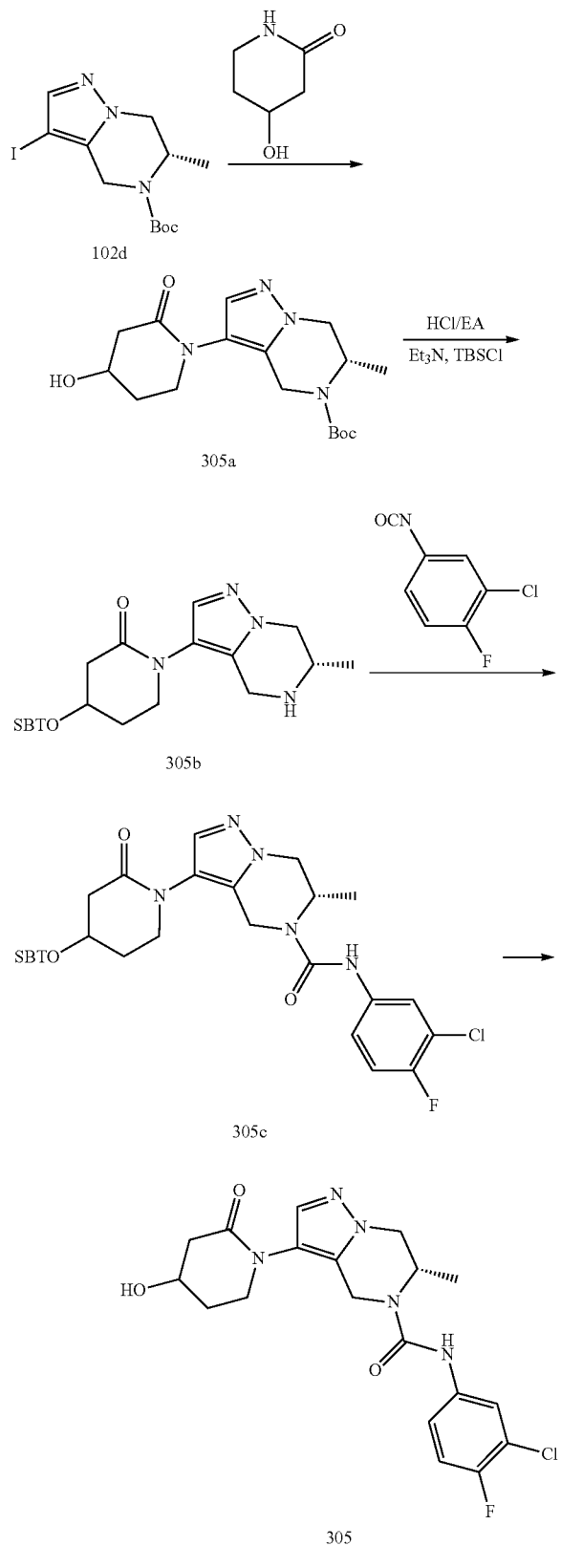

Preparation of tert-butyl (6S)-3-(4-hydroxy-2-oxo-1-piperidyl)-6-methyl-6,7-dihydro-4H-pyrazolo[1,5-a]pyrazine-5-carboxylate (compound 305a)

Compound 305a was prepared in analogy to compound 246f by using 4-hydroxypiperidin-2-one instead of 1,2,4,7,8,8a-hexahydropyrrolo[1,2-a]pyrazine-3,6-dione (compound 246e). Compound 305a was obtained as a white solid (270 mg). LCMS (M+H$^+$): 351.

Preparation of (6S)-N-(3-chloro-4-fluoro-phenyl)-3-(4-hydroxy-2-oxo-1-piperidyl)-6-methyl-6,7-dihydro-4H-pyrazolo[1,5-a]pyrazine-5-carboxamide (Example 305)

The title compound was prepared in analogy to Example 298 by using tert-butyl (6S)-3-(4-hydroxy-2-oxo-1-piperidyl)-6-methyl-6,7-dihydro-4H-pyrazolo[1,5-a]pyrazine-5-carboxylate (compound 305a) instead of 4-(hydroxymethyl)-1-[(6S)-6-methyl-4,5,6,7-tetrahydropyrazolo[1,5-a]pyrazin-3-yl]pyrrolidin-2-one (compound 298a). Example 305 was obtained as a white solid (8.7 mg). LCMS (M+H$^+$): 422. $^1$H NMR (400 MHz, MeOD) δ ppm 7.88 (d, J=4.52 Hz, 1H), 7.64 (dd, J=6.52, 1.76 Hz, 1H), 7.32-7.39 (m, 1H), 7.17 (t, J=9.03 Hz, 1H), 4.98-5.00 (m, 2H), 4.20-4.46 (m, 4H), 3.82-4.00 (m, 1H), 3.61-3.77 (m, 1H), 2.83 (dt, J=17.69, 4.83 Hz, 1H), 2.53 (dt, J=17.57, 4.27 Hz, 1H), 1.97-2.25 (m, 2H), 1.29 (d, J=6.78 Hz, 3H).

Example 306

(6S)-6-methyl-3-[4-(methylsulfonylmethyl)-2-oxo-pyrrolidin-1-yl]-N-(3,4,5-trifluorophenyl)-6,7-dihydro-4H-pyrazolo[1,5-a]pyrazine-5-carboxamide

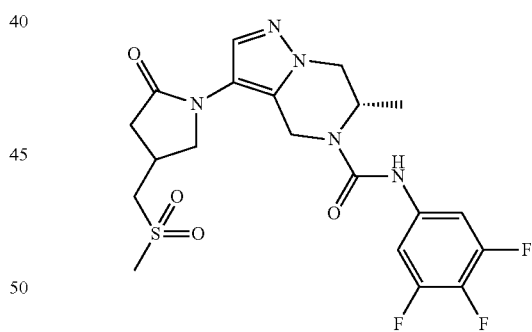

The title compound was prepared according to the following scheme:

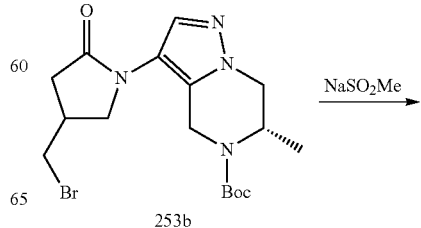

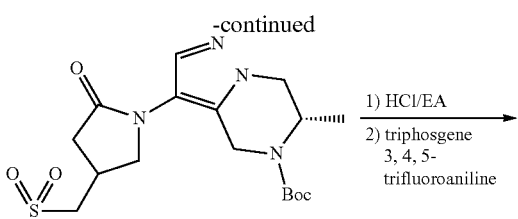

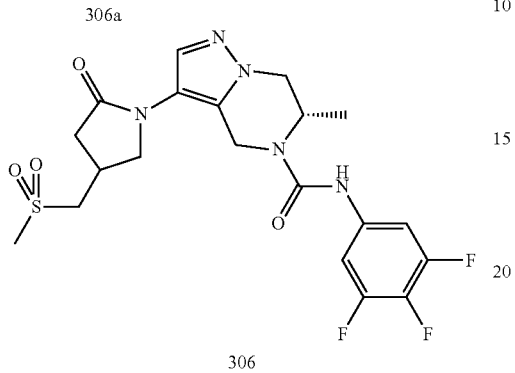

Step 1: Preparation of tert-butyl (6S)-6-methyl-3-[4-(methylsulfonylmethyl)-2-oxo-pyrrolidin-1-yl]-6,7-dihydro-4H-pyrazolo[1,5-a]pyrazine-5-carboxylate (compound 306a)

To a solution of tert-butyl (6S)-3-[4-(bromomethyl)-2-oxo-pyrrolidin-1-yl]-6-methyl-6,7-dihydro-4H-pyrazolo[1,5-a]pyrazine-5-carboxylate (compound 253b, 50.0 mg, 0.12 mmol) in DMF (5.0 mL) was added CH$_3$SO$_2$Na (18.54 mg, 0.18 mmol), then the reaction was stirred at 110° C. for 12 hours. The reaction was concentrated and the crude product was purified by Prep-HPLC to give compound 306a (30.0 mg) as white solid. LCMS (M+H$^+$): 413.

Step 2: Preparation of (6S)-6-methyl-3-[4-(methylsulfonylmethyl)-2-oxo-pyrrolidin-1-yl]-N-(3,4,5-trifluorophenyl)-6,7-dihydro-4H-pyrazolo[1,5-a]pyrazine-5-carboxamide (Example 306)

The title compound was prepared in analogy to the preparation of Example 11 by 3,4,5-trifluoroaniline instead of 3-(trifluoromethyl)aniline and tert-butyl (6S)-6-methyl-3-[4-(methylsulfonylmethyl)-2-oxo-pyrrolidin-1-yl]-6,7-dihydro-4H-pyrazolo[1,5-a]pyrazine-5-carboxylate (compound 306a) instead of tert-butyl 3-(4-fluorophenyl)-6,7-dihydro-4H-pyrazolo[1,5-a]pyrazine-5-carboxylate (compound 11a). Example 306 was obtained as a white solid (7 mg). LCMS (M+H$^+$): 486. $^1$H NMR (400 MHz, DMSO-d$_6$) δ ppm 9.15 (br. s., 1H), 8.47 (s, 1H), 7.58 (d, J=5.5 Hz, 1H), 7.43 (dd, J=6.5, 10.8 Hz, 1H), 4.97 (dd, J=11.3, 17.1 Hz, 1H), 4.85 (br. s., 1H), 4.41-4.31 (m, 1H), 4.25-4.08 (m, 2H), 3.99-3.84 (m, 1H), 3.71-3.58 (m, 1H), 3.47-3.43 (m, 1H), 3.21-3.13 (m, 2H), 3.10-2.88 (m, 3H), 2.65 (dd, J=8.7, 16.7 Hz, 1H), 2.45-2.33 (m, 1H), 1.22-0.99 (m, 3H).

Example 307

(6S)-6-methyl-3-[4-[[methyl(methylsulfonyl)amino]methyl]-2-oxo-pyrrolidin-1-yl]-N-(3,4,5-trifluorophenyl)-6,7-dihydro-4H-pyrazolo[1,5-a]pyrazine-5-carboxamide

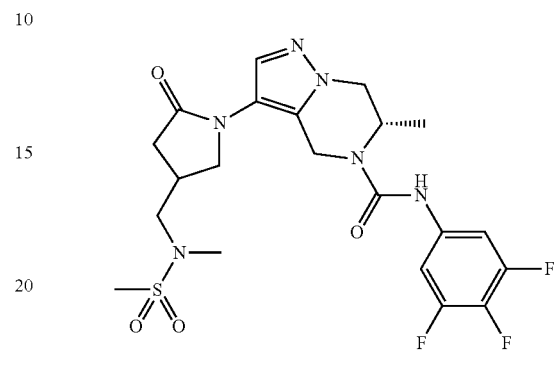

The title compound was prepared according to the following scheme:

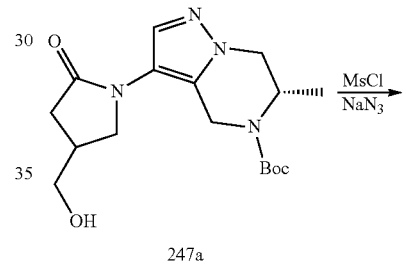

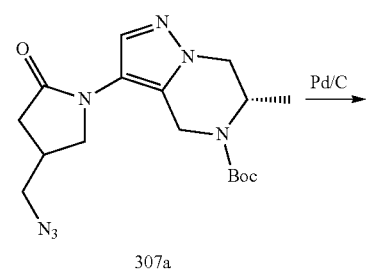

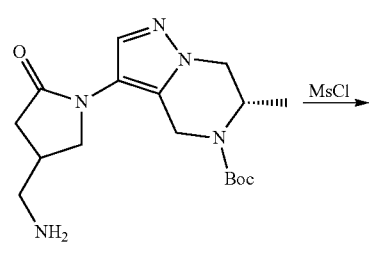

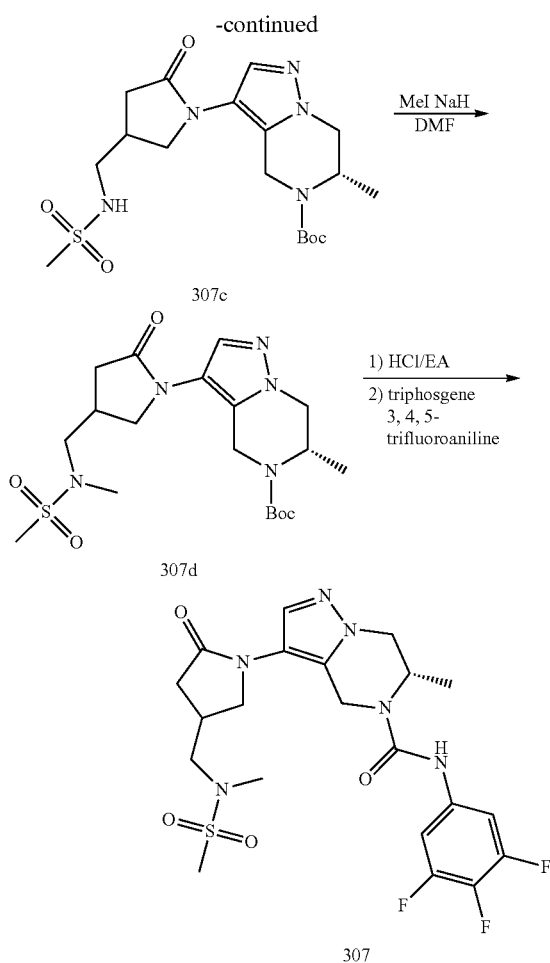

Step 1: Preparation of tert-butyl (6S)-3-[4-(azidomethyl)-2-oxo-pyrrolidin-1-yl]-6-methyl-6,7-dihydro-4H-pyrazolo[1,5-a]pyrazine-5-carboxylate (compound 307a)

To a solution of tert-butyl (6S)-3-[4-(hydroxymethyl)-2-oxo-pyrrolidin-1-yl]-6-methyl-6,7-dihydro-4H-pyrazolo[1,5-a]pyrazine-5-carboxylate (compound 247a, 300.0 mg, 0.86 mmol) in DCM (10 mL) was added TEA (260.58 mg, 2.58 mmol) and MsCl (117.37 mg 1.03 mmol). After stirred at room temperature for 6 hours, the reaction mixture was concentrated. The obtained residue was dissolved in DMF (5.0 mL), to which was added NaN₃ (46.15 mg 0.71 mmol). Then the reaction mixture was stirred at 120° C. for 12 hours and concentrated, then the crude product was purified by Prep-HPLC to give compound 307a as a white solid (150 mg). LCMS (M+H⁺): 376.

Step 2: Preparation of tert-butyl (6S)-3-[4-(aminomethyl)-2-oxo-pyrrolidin-1-yl]-6-methyl-6,7-dihydro-4H-pyrazolo[1,5-a]pyrazine-5-carboxylate (compound 307b)

To a solution of tert-butyl (6S)-3-[4-(azidomethyl)-2-oxo-pyrrolidin-1-yl]-6-methyl-6,7-dihydro-4H-pyrazolo[1,5-a] pyrazine-5-carboxylate (compound 307a, 150.0 mg, 0.4 mmol) in MeOH/THF (15 mL, v/v=1:1) was added 10% Pd/C (20 mg). The reaction mixture was stirred under H₂ of 30 psi. at room temperature for 2 hours. Then the reaction mixture was filtered and the filtrate was concentrated to give the crude product (60.0 mg), which was used directly in the next step without further purification. LCMS (M+H⁺): 350.

Step 3: Preparation of tert-butyl (6S)-3-[4-(methanesulfonamidomethyl)-2-oxo-pyrrolidin-1-yl]-6-methyl-6,7-dihydro-4H-pyrazolo[1,5-a]pyrazine-5-carboxylate (compound 307c)

A mixture of tert-butyl (6S)-3-[4-(aminomethyl)-2-oxo-pyrrolidin-1-yl]-6-methyl-6,7-dihydro-4H-pyrazolo[1,5-a] pyrazine-5-carboxylate (compound 307b, 20.0 mg, 0.05 mmol), TEA (10.1 mg, 0.1 mmol) and MsCl (9.1 mg, 0.08 mmol) in DCM (5 mL) was stirred at room temperature for 12 hours. The reaction mixture was concentrated to give the crude product (35.0 mg), which was used directly in the next step without further purification. LCMS (M+H⁺): 428.

Step 4: Preparation of tert-butyl (6S)-6-methyl-3-[4-[[methyl(methylsulfonyl)amino]methyl]-2-oxo-pyrrolidin-1-yl]-6,7-dihydro-4H-pyrazolo[1,5-a] pyrazine-5-carboxylate (compound 307d)

To a solution of tert-butyl (6S)-3-[4-(methanesulfonamidomethyl)-2-oxo-pyrrolidin-1-yl]-6-methyl-6,7-dihydro-4H-pyrazolo[1,5-a]pyrazine-5-carboxylate (compound 307c, 30.0 mg, 0.07 mmol) in DMF (5.0 mL) was added NaH (5.04 mg 0.21 mmol) slowly, and then MeI (15.61 mg, 0.11 mmol). After stirred at room temperature for 12 hours, the reaction mixture was poured into H₂O (30 mL) and EtOAc (30 mL). The organic phase was separated and concentrated in vacuo to provide the crude product (31 mg).

Step 5: Preparation of (6S)-6-methyl-3-[4-[[methyl(methylsulfonyl)amino]methyl]-2-oxo-pyrrolidin-1-yl]-N-(3,4,5-trifluorophenyl)-6,7-dihydro-4H-pyrazolo[1,5-a]pyrazine-5-carboxamide (Example 307)

The title compound was prepared in analogy to the preparation of Example 11 by using tert-butyl (6S)-6-methyl-3-[4-[[methyl(methylsulfonyl)amino]methyl]-2-oxo-pyrrolidin-1-yl]-6,7-dihydro-4H-pyrazolo[1,5-a]pyrazine-5-carboxylate (compound 307d) instead of tert-butyl 3-(4-fluorophenyl)-6,7-dihydro-4H-pyrazolo[1,5-a]pyrazine-5-carboxylate (compound 11a). Example 307 was obtained as a white solid (15 mg). LCMS (M+H⁺): 515. ¹H NMR (400 MHz, DMSO-d₆) δppm 9.14 (br. s., 1H), 7.60 (s, 0.5H), 7.58 (s, 0.5H), 7.51-7.32 (m, 2H), 4.97 (d, J=17.3 Hz, 1H), 4.84 (d, J=5.0 Hz, 1H), 4.36 (dd, J=4.0, 17.1 Hz, 1H), 4.24-4.17 (m, 1H), 4.15-4.09 (m, 1H), 3.92-3.78 (m, 1H), 3.57-3.48 (m, 1H), 3.25-3.15 (m, 1H), 3.07 (dd, J=6.8, 13.3 Hz, 1H), 2.98-2.87 (m, 3H), 2.80 (s, 3H), 2.59 (ddd, J=3.5, 8.8, 16.8 Hz, 1H), 2.25-2.15 (m, 1H), 2.10-2.01 (m, 1H), 1.20-1.00 (m, 3H).

Example 308

(6S)-6-methyl-3-(2-oxopyrrolidin-3-yl)-N-(3,4,5-trifluorophenyl)-6,7-dihydro-4H-pyrazolo[1,5-a]pyrazine-5-carboxamide

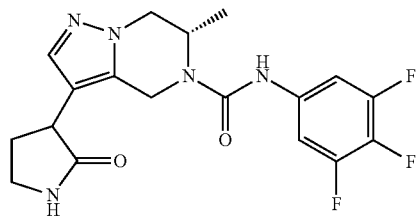 [SMILES: C[C@H]1Cn2ncc(C3CCNC3=O)c2CN1C(=O)Nc1cc(F)c(F)c(F)c1]

The title compound was prepared according to the following scheme:

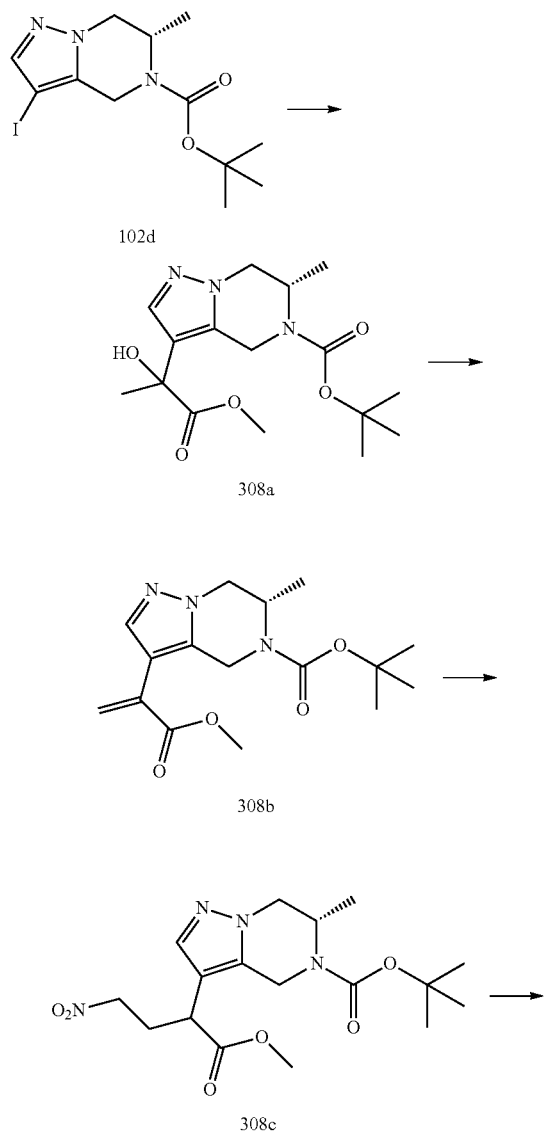

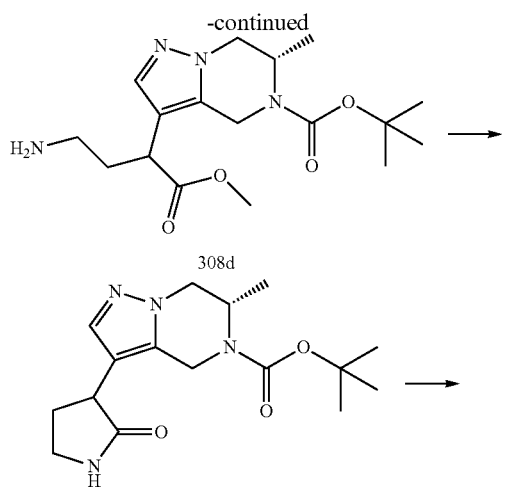

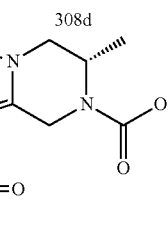

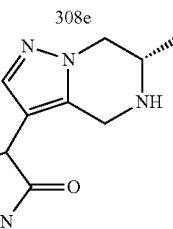

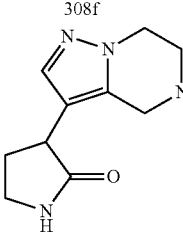

Step 1: Preparation of tert-butyl (6S)-3-(1-hydroxy-2-methoxy-1-methyl-2-oxo-ethyl)-6-methyl-6,7-dihydro-4H-pyrazolo[1,5-a]pyrazine-5-carboxylate (compound 308a)

To a solution of tert-butyl (6S)-3-iodo-6-methyl-6,7-dihydro-4H-pyrazolo[1,5-a]pyrazine-5-carboxylate (compound 102d, 500 mg, 1.38 mmol) in THF (10 mL) was added isopropylmagnesium chloride (1.4 mL, 2.76 mmol, 2.0 M in THF) at −10° C. under N$_2$ atmosphere. The reaction mixture was stirred at 0° C. for 1 hour, then methyl 2-oxo-propanoate (281 mg, 2.76 mmol) was added. The resulting mixture was stirred at room temperature for 2 hours, and then quenched with water (10 mL). The resulting mixture was subjected to prep-HPLC to give compound 308a as a yellow oil (260 mg).

Step 2: Preparation of tert-butyl (6S)-3-(1-methoxy-carbonylvinyl)-6-methyl-6,7-dihydro-4H-pyrazolo[1,5-a]pyrazine-5-carboxylate (compound 308b)

To a solution of tert-butyl (6S)-3-(1-hydroxy-2-methoxy-1-methyl-2-oxo-ethyl)-6-methyl-6,7-dihydro-4H-pyrazolo[1,5-a]pyrazine-5-carboxylate (compound 308a, 260 mg, 0.77 mmol) and Et$_3$N (1.55 g, 15.32 mmol) in DCM (8 mL)

was added methanesulfonyl chloride (1.66 g, 18.9 mmol) under nitrogen atmosphere. The reaction mixture was stirred at room temperature for 12 hours, and then quenched with water (8 mL). The resulting mixture was purified by prep-HPLC to give compound 308b as a yellow oil (210 mg).

Step 3: Preparation of tert-butyl (6S)-3-(1-methoxycarbonyl-3-nitro-propyl)-6-methyl-6,7-dihydro-4H-pyrazolo[1,5-a]pyrazine-5-carboxylate (compound 308c)

To a solution of tert-butyl (6S)-3-(1-methoxycarbonylvinyl)-6-methyl-6,7-dihydro-4H-pyrazolo[1,5-a]pyrazine-5-carboxylate (compound 308b, 150 mg, 0.47 mmol) in THF (2 mL) was added nitromethane (4 mL) and DBU (7 mg, 0.047 mmol). The reaction mixture was stirred at room temperature for 4 hours, and then purified by prep-HPLC to give compound 308c as a yellow oil (140 mg).

Step 4: Preparation of tert-butyl (6S)-3-(3-amino-1-methoxycarbonyl-propyl)-6-methyl-6,7-dihydro-4H-pyrazolo[1,5-a]pyrazine-5-carboxylate (compound 308d)

To a mixture of tert-butyl (6S)-3-(1-methoxycarbonyl-3-nitro-propyl)-6-methyl-6,7-dihydro-4H-pyrazolo[1,5-a]pyrazine-5-carboxylate (compound 308c, 140 mg, 0.35 mmol) and $NH_4Cl$ (56 mg, 1.06 mmol) in $EtOH/H_2O$ (10 mL/3 mL) was added Fe (79 mg, 1.41 mmol). The reaction mixture was heated at 80° C. with stirring for 4 hrs. After being cooled to room temperature, the reaction mixture was concentrated in vacuo to give crude compound 308d, which was used in the next step without further purification.

Step 5: Preparation of tert-butyl (6S)-6-methyl-3-(2-oxopyrrolidin-3-yl)-6,7-dihydro-4H-pyrazolo[1,5-a]pyrazine-5-carboxylate (compound 308e)

A suspension of crude tert-butyl (6S)-3-(3-amino-1-methoxycarbonyl-propyl)-6-methyl-6,7-dihydro-4H-pyrazolo[1,5-a]pyrazine-5-carboxylate (compound 308d,124 mg, 0.35 mmol) in toluene (10 mL) was stirred at 100-110° C. for 12 hours. The resulting mixture was concentrated in vacuo and the residue was purified by prep-HPLC to give compound 308e as a yellow oil (14 mg).

Step 6: Preparation of 3-[(6S)-6-methyl-4,5,6,7-tetrahydropyrazolo[1,5-a]pyrazin-3-yl]pyrrolidin-2-one (compound 308f)

A mixture of tert-butyl (6S)-6-methyl-3-(2-oxopyrrolidin-3-yl)-6,7-dihydro-4H-pyrazolo[1,5-a]pyrazine-5-carboxylate (compound 308e, 7 mg, 0.022 mmol) in a solution of HCl in EtOAc (3 mL) was stirred at room temperature for 2 hours. The reaction mixture was concentrated in vacuo to give compound 308f as a yellow oil (5 mg), which was used in the next step without further purification.

Step 7: Preparation of (6S)-6-methyl-3-(2-oxopyrrolidin-3-yl)-N-(3,4,5-trifluorophenyl)-6,7-dihydro-4H-pyrazolo[1,5-a]pyrazine-5-carboxamide (Example 308)

To a mixture of 3-[(6S)-6-methyl-4,5,6,7-tetrahydropyrazolo[1,5-a]pyrazin-3-yl]pyrrolidin-2-one (compound 308f, 5 mg, 0.021 mmol) and phenyl N-(3,4,5-trifluorophenyl) carbamate (6 mg, 0.021 mmol) in DMF (2 mL) was added $Et_3N$ (6 mg, 0.063 mmol). The reaction mixture was stirred at room temperature for 12 hours, and then concentrated in vacuo. The residue was purified by prep-HPLC to give Example 308 as a white solid (5 mg). LCMS (M+H$^+$): 394. $^1$H NMR (400 MHz, MeOD) δ ppm 8.53 (br. s., 1H), 7.50 (s, 1H), 7.22-7.39 (m, 2H), 5.01-5.23 (m, 2H), 4.50 (d, 1H), 4.23-4.36 (m, 1H), 4.11-4.20 (m, 1H), 3.63-3.73 (m, 1H), 3.41-3.56 (m, 2H), 2.55-2.65 (m, 1H), 2.27 (dt, 1H), 1.17-1.34 (m, 3H).

Example 309

(6S)-6-methyl-3-(2-oxo-4-phenyl-pyrrolidin-1-yl)-N-(3,4,5-trifluorophenyl)-6,7-dihydro-4H-pyrazolo[1,5-a]pyrazine-5-carboxamide

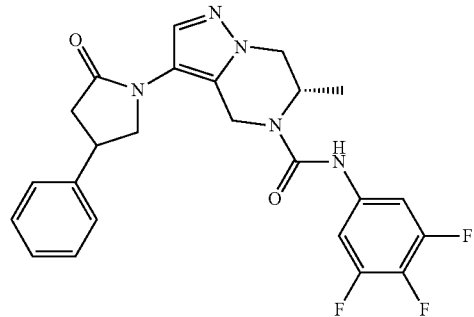 [SMILES: C[C@H]1Cn2ncc(N3CC(c4ccccc4)CC3=O)c2CN1C(=O)Nc1cc(F)c(F)c(F)c1]

Preparation of (6S)-6-methyl-3-(2-oxo-4-phenyl-pyrrolidin-1-yl)-N-(3,4,5-trifluorophenyl)-6,7-dihydro-4H-pyrazolo[1,5-a]pyrazine-5-carboxamide (Example 309)

The title compound was prepared in analogy to Example 223 by using 4-phenylpyrrolidin-2-one instead of pyrrolidin-2-one and phenyl N-(3,4,5-trifluoro-phenyl)carbamate (compound 233c) instead of phenyl N-[2-(difluoromethyl)-4-pyridyl]carbamate (compound 218c). Example 309 (6 mg) was obtained as a white solid. LCMS (M+H$^+$): 470. $^1$H NMR (400 MHz, MeOD) δ ppm 7.65 (d, J=1.1 Hz, 1H), 7.40-7.35 (m, 5H), 7.29-7.25 (m, 2H), 5.12-4.91 (m, 1H), 4.60 (s, 1H), 4.56-4.49 (m, 1H), 4.32-4.26 (m, 1H), 4.21-4.14 (m, 2H), 3.93-3.84 (m, 2H), 2.99-2.93 (m, 1H), 2.78-2.71 (m, 1H), 1.29-1.25 (m, 3H).

Example 310

(6S)-3-[4-(1-hydroxy-1-methyl-ethyl)-2-oxo-pyrrolidin-1-yl]-6-methyl-N-(3,4,5-trifluorophenyl)-6,7-dihydro-4H-pyrazolo[1,5-a]pyrazine-5-carboxamide

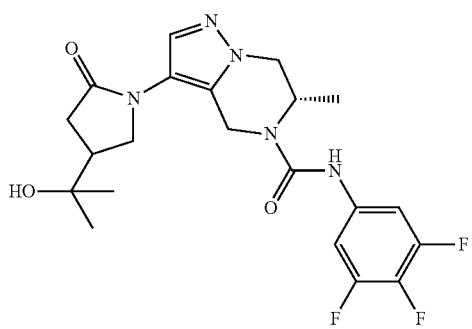 [SMILES: C[C@H]1Cn2ncc(N3CC(C(C)(C)O)CC3=O)c2CN1C(=O)Nc1cc(F)c(F)c(F)c1]

The title compound was prepared according to the following scheme:

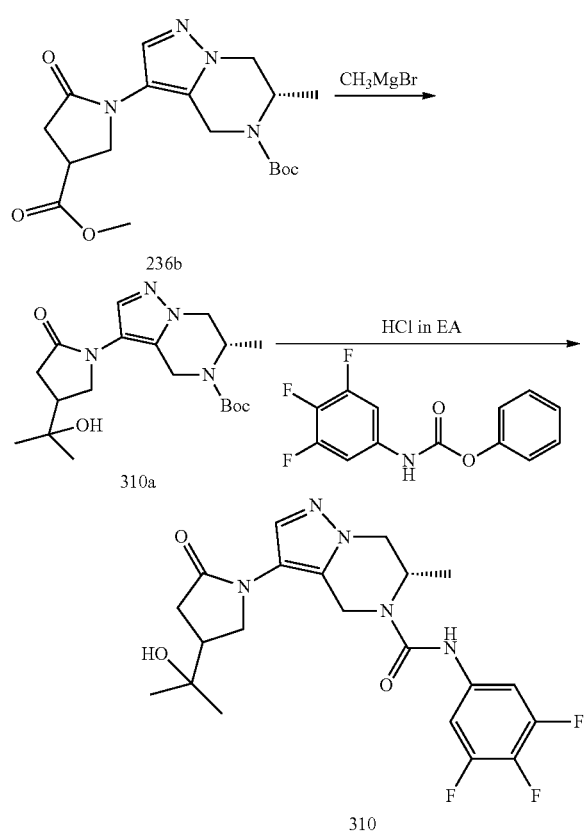

Step 1: Preparation of tert-butyl (6S)-3-[4-(1-hydroxy-1-methyl-ethyl)-2-oxo-pyrrolidin-1-yl]-6-methyl-6,7-dihydro-4H-pyrazolo[1,5-a]pyrazine-5-carboxylate (compound 310a)

To a solution of (6S)-tert-butyl 3-(4-(methoxycarbonyl)-2-oxopyrrolidin-1-yl)-6-methyl-6,7-dihydropyrazolo[1,5-a]pyrazine-5(4H)-carboxylate (compound 236b, 150.0 mg, 0.4 mmol) in THF (20.0 mL) was added a solution of $CH_3MgBr$ (1.4 mL, 4.0 mmol) in THF at 0° C. The reaction mixture was stirred at room temperature for 5 hours, and then concentrated. The crude product was purified by prep-TLC (PE: EtOAc=1:1) to give compound 310a as a colorless oil (100 mg).

Step 2: Preparation of (6S)-3-[4-(1-hydroxy-1-methyl-ethyl)-2-oxo-pyrrolidin-1-yl]-6-methyl-N-(3,4,5-trifluorophenyl)-6,7-dihydro-4H-pyrazolo[1,5-a]pyrazine-5-carboxamide (Example 310)

The title compound was prepared in analogy to Example 223 by using tert-butyl (6S)-3-[4-(1-hydroxy-1-methyl-ethyl)-2-oxo-pyrrolidin-1-yl]-6-methyl-6,7-dihydro-4H-pyrazolo[1,5-a]pyrazine-5-carboxylate (compound 310a) instead of tert-butyl (6S)-6-methyl-3-(2-oxopyrrolidin-1-yl)-6,7-dihydro-4H-pyrazolo[1,5-a]pyrazine-5-carboxylate (compound 223b) and phenyl N-(3,4,5-trifluoro-phenyl)carbamate (compound 233c) instead of phenyl N-[2-(difluoromethyl)-4-pyridyl]carbamate (compound 218c). Example 310 was obtained as a yellow solid (8.3 mg). LCMS (M+H⁺): 452. $^1$H NMR (400 MHz, MeOD) δ ppm 7.64 (s, 1H), 7.33-7.26 (m, 2H), 5.05-5.00 (m, 1H), 4.98-4.95 (m, 1H), 4.49 (dd, J=16.94, 9.66 Hz, 1H), 4.33-4.26 (m, 1H), 4.16 (d, J=12.80 Hz, 1H), 3.89-3.79 (m, 2H), 2.73-2.65 (m, 1H), 2.63-2.49 (m, 2H), 1.28-1.26 (m, 9 H).

Example 311

(6S)-3-(4-acetamido-2-oxo-pyrrolidin-1-yl)-N-(3-chloro-4-fluoro-phenyl)-6-methyl-6,7-dihydro-4H-pyrazolo[1,5-a]pyrazine-5-carboxamide

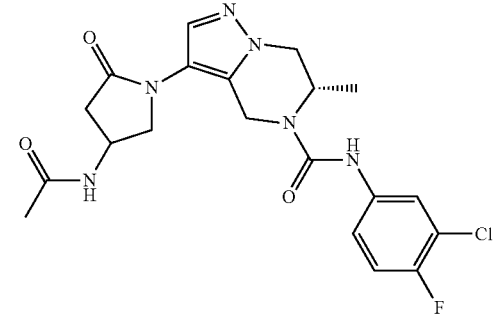 [SMILES: CC(=O)NC1CC(=O)N(c2cnn3c2CN(C(=O)Nc2ccc(F)c(Cl)c2)[C@@H](C)C3)C1]

The title compound was prepared according to the following scheme:

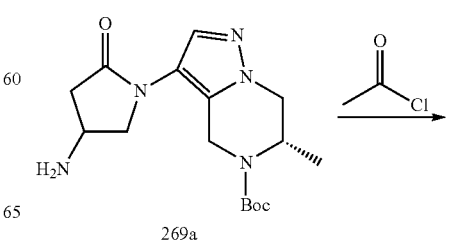

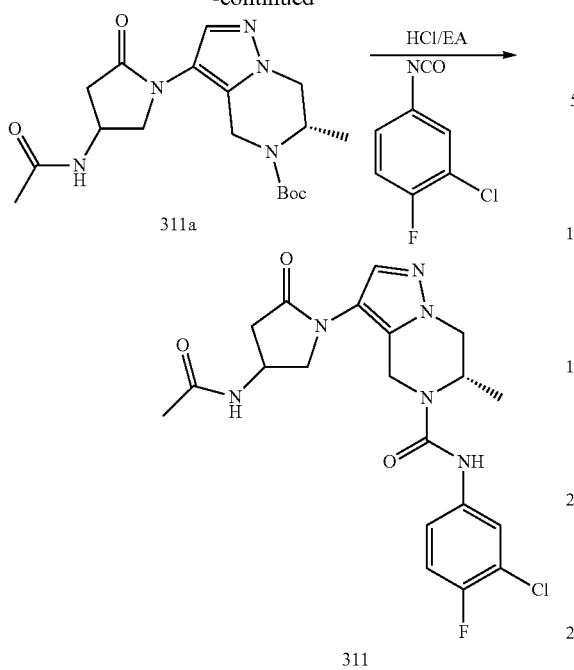

311a

311

Step 1: Preparation of tert-butyl (6S)-3-(4-acetamido-2-oxo-pyrrolidin-1-yl)-6-methyl-6,7-dihydro-4H-pyrazolo[1,5-a]pyrazine-5-carboxylate (compound 311a)

To a solution of (6S)-tert-butyl 3-(4-amino-2-oxopyrrolidin-1-yl)-6-methyl-6,7-dihydropyrazolo[1,5-a]pyrazine-5(4H)-carboxylate (compound 269a, 100.0 mg, 0.30 mmol) in DCM (5.0 mL) was added Et$_3$N (60.2 mg, 0.596 mmol) and acetyl chloride (28.1 mg, 0.36 mmol) at 0° C., then the reaction mixture was stirred at room temperature for 1 hour. The reaction mixture was concentrated to give crude compound 311a as a yellow solid (100 mg). LCMS: (M+H$^+$): 378.

Step 2: Preparation of (6S)-3-(4-acetamido-2-oxo-pyrrolidin-1-yl)-N-(3-chloro-4-fluoro-phenyl)-6-methyl-6,7-dihydro-4H-pyrazolo[1,5-a]pyrazine-5-carboxamide (Example 311)

The title compound was prepared in analogy to Example 246 by using tert-butyl (6S)-3-(4-acetamido-2-oxo-pyrrolidin-1-yl)-6-methyl-6,7-dihydro-4H-pyrazolo[1,5-a]pyrazine-5-carboxylate (compound 311a) instead of tert-butyl (6S)-3-(3,6-dioxo-4,7,8,8a-tetrahydro-1H-pyrrolo[1,2-a]pyrazin-2-yl)-6-methyl-6,7-dihydro-4H-pyrazolo[1,5-a]pyrazine-5-carboxylate (compound 246f). Example 311 was obtained as a white solid. LCMS: (M+H$^+$): 449. $^1$H NMR (400 MHz, MeOD) δ 7.65-7.60 (m, 2H), 7.40-7.31 (m, 1H), 7.18 (t, J=9.0 Hz, 1H), 5.05 (d, J=17.1 Hz, 1H), 4.97 (d, J=6.0 Hz, 1H), 4.63-4.55 (m, 1H), 4.51 (dd, J=3.6, 16.9 Hz, 1H), 4.31 (dd, J=4.4, 12.7 Hz, 1H), 4.21-4.12 (m, 2H), 3.67 (dt, J=3.9, 9.6 Hz, 1H), 2.95 (dd, J=8.5, 17.3 Hz, 1H), 2.50 (dd, J=4.4, 17.4 Hz, 1H), 2.00 (d, J=2.0 Hz, 3H), 1.29-1.27 (m, 3H).

Example 312

(6S)-N-(3-chloro-4-fluoro-phenyl)-3-[4-(methanesulfonamido)-2-oxo-pyrrolidin-1-yl]-6-methyl-6,7-dihydro-4H-pyrazolo[1,5-a]pyrazine-5-carboxamide

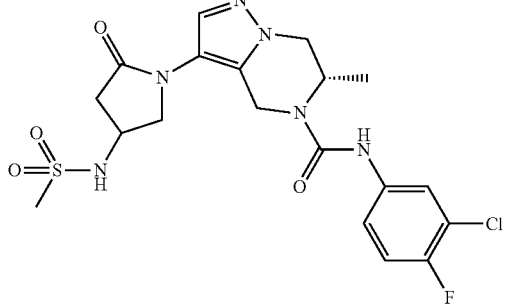

The title compound was prepared according to the following scheme:

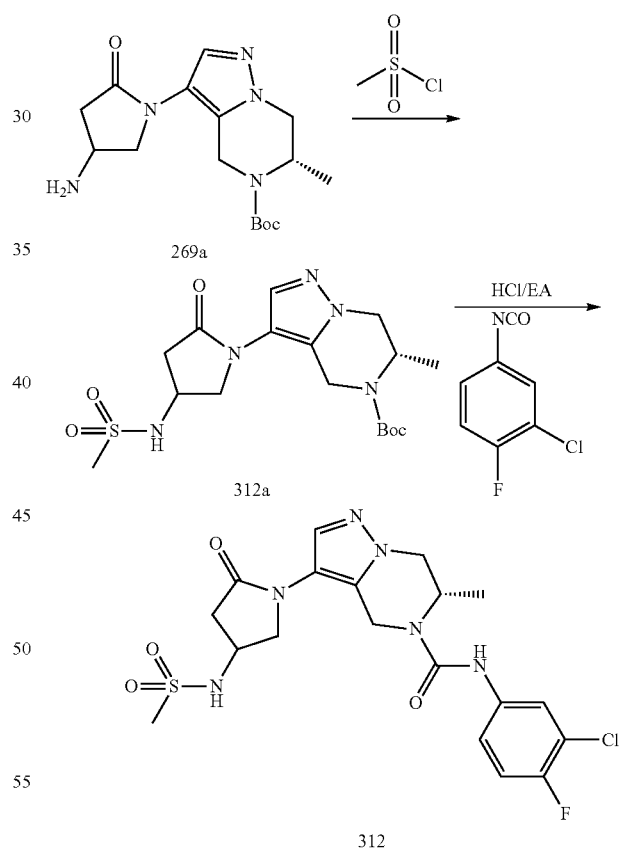

Step 1: Preparation of tert-butyl (6S)-3-[4-(methanesulfonamido)-2-oxo-pyrrolidin-1-yl]-6-methyl-6,7-dihydro-4H-pyrazolo[1,5-a]pyrazine-5-carboxylate (compound 312a)

To a solution of (6S)-tert-butyl 3-(4-amino-2-oxopyrrolidin-1-yl)-6-methyl-6,7-dihydropyrazolo[1,5-a]pyrazine-5

(4H)-carboxylate (compound 269a, 100.0 mg, 0.30 mmol) in DCM (5 mL) was added Et₃N (60.2 mg, 0.60 mmol) and methanesulfonyl chloride (41.1 mg, 0.36 mmol) at 0° C., then the reaction mixture was stirred at room temperature for 1 hour. The reaction mixture was concentrated to give crude compound 312a as a yellow solid (100 mg). LCMS: (M+H⁺): 414.

Step 2: Preparation of (6S)-N-(3-chloro-4-fluoro-phenyl)-3-[4-(methanesulfonamido)-2-oxo-pyrrolidin-1-yl]-6-methyl-6,7-dihydro-4H-pyrazolo[1,5-a]pyrazine-5-carboxamide (Example 312)

The title compound was prepared in analogy to Example 246 by using tert-butyl (6S)-3-[4-(methanesulfonamido)-2-oxo-pyrrolidin-1-yl]-6-methyl-6,7-dihydro-4H-pyrazolo[1,5-a]pyrazine-5-carboxylate (compound 312a) instead of tert-butyl (6S)-3-(3,6-dioxo-4,7,8,8a-tetrahydro-1H-pyrrolo[1,2-a]pyrazin-2-yl)-6-methyl-6,7-dihydro-4H-pyrazolo[1,5-a]pyrazine-5-carboxylate (compound 246f). Example 312 was obtained as a white solid (9 mg). LCMS: (M+H⁺): 485. ¹H NMR (400 MHz, MeOD) δ 7.68-7.58 (m, 2H), 7.34 (td, J=3.4, 8.8 Hz, 1H), 7.18 (t, J=9.0 Hz, 1H), 5.05 (dd, J=3.9, 16.9 Hz, 1H), 4.95 (br. s., 1H), 4.50 (d, J=17.1 Hz, 1H), 4.39-4.28 (m, 2H), 4.20-4.11 (m, 2H), 3.78 (ddd, J=4.8, 7.7, 10.2 Hz, 1H), 3.04 (s, 3H), 2.98 (dd, J=8.0, 17.3 Hz, 1H), 2.56 (dd, J=5.4, 17.2 Hz, 1H), 1.30-1.26 (m, 3H).

Example 313

(6S)-N-(3-chloro-4-fluoro-phenyl)-6-methyl-3-[4-[methyl(methylsulfonyl)amino]-2-oxo-pyrrolidin-1-yl]-6,7-dihydro-4H-pyrazolo[1,5-a]pyrazine-5-carboxamide

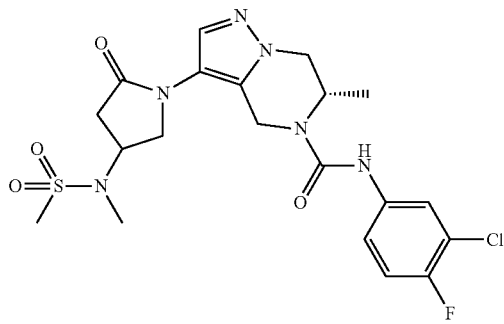 [SMILES: C[C@H]1Cn2ncc(N3CC(N(C)S(C)(=O)=O)CC3=O)c2CN1C(=O)Nc1ccc(F)c(Cl)c1]

The title compound was prepared according to the following scheme:

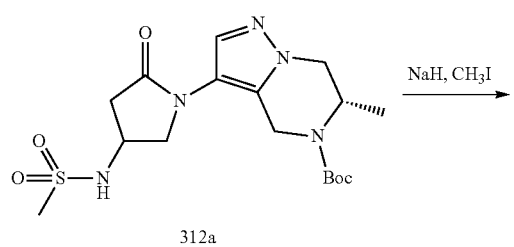

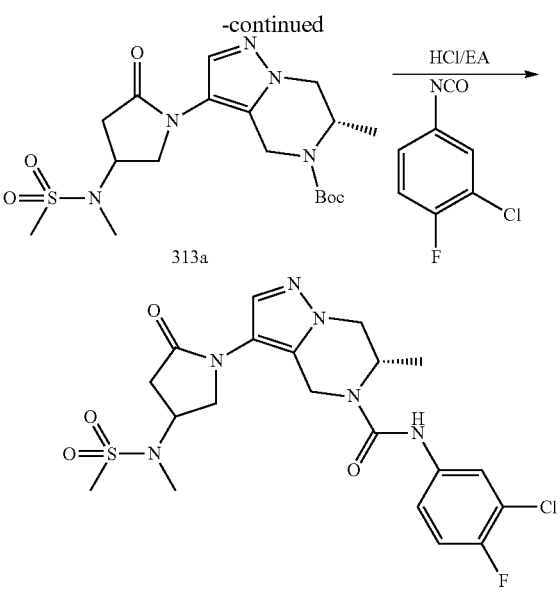

Step 1: Preparation of tert-butyl (6S)-6-methyl-3-[4-[methyl(methylsulfonyl)amino]-2-oxo-pyrrolidin-1-yl]-6,7-dihydro-4H-pyrazolo[1,5-a]pyrazine-5-carboxylate (compound 313a)

To a solution of tert-butyl (6S)-3-[4-(methanesulfonamido)-2-oxo-pyrrolidin-1-yl]-6-methyl-6,7-dihydro-4H-pyrazolo[1,5-a]pyrazine-5-carboxylate (compound 312a, 60.0 mg, 0.15 mmol) in DCM (5 mL) was added NaH (11.6 mg, 0.29 mmol) and MeI (13.7 mg, 0.17 mmol) at 0° C., then the reaction mixture was stirred at room temperature for 2 hours. The reaction mixture was poured into ice-water, extracted with DCM. The organic layer was washed with brine, dried over Na₂SO₄ and concentrated to give crude compound 313a as a yellow oil (40 mg). LCMS: (M+H⁺): 428.

Step 2: Preparation of (6S)-N-(3-chloro-4-fluoro-phenyl)-6-methyl-3-[4-[methyl(methylsulfonyl)amino]-2-oxo-pyrrolidin-1-yl]-6,7-dihydro-4H-pyrazolo[1,5-a]pyrazine-5-carboxamide (Example 313)

The title compound was prepared in analogy to Example 246 by using tert-butyl (6S)-6-methyl-3-[4-[methyl(methylsulfonyl)amino]-2-oxo-pyrrolidin-1-yl]-6,7-dihydro-4H-pyrazolo[1,5-a]pyrazine-5-carboxylate (compound 313a) instead of tert-butyl (6S)-3-(3,6-dioxo-4,7,8,8a-tetrahydro-1H-pyrrolo[1,2-a]pyrazin-2-yl)-6-methyl-6,7-dihydro-4H-pyrazolo[1,5-a]pyrazine-5-carboxylate (compound 246f). Example 313 was obtained as a white solid (13 mg). LCMS: (M+H⁺): 499. ¹H NMR (400 MHz, MeOD) δ ppm 7.69 (d, J=3.3 Hz, 1H), 7.62 (dd, J=2.5, 6.5 Hz, 1H), 7.37-7.30 (m, 1H), 7.18 (t, J=8.9 Hz, 1H), 5.05 (dd, J=2.5, 16.8 Hz, 1H), 4.96 (d, J=5.5 Hz, 2H), 4.51 (dd, J=4.4, 16.9 Hz, 1H), 4.35-4.27 (m, 1H), 4.21-4.07 (m, 2H), 3.96-3.85 (m, 1H), 2.97 (s, 3H), 2.94 (s, 3H), 2.91-2.86 (m, 1H), 2.81-2.66 (m, 1H), 1.31-1.25 (m, 3H).

Example 314

(6S)-3-[4-(2,5-dioxopyrrolidin-1-yl)-2-oxo-pyrrolidin-1-yl]-6-methyl-N-(3,4,5-trifluorophenyl)-6,7-dihydro-4H-pyrazolo[1,5-a]pyrazine-5-carboxamide

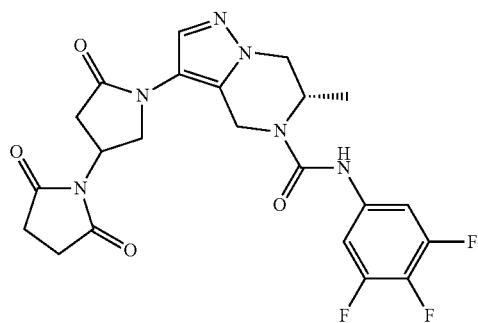 [SMILES: C[C@H]1Cn2ncc(N3CC(N4C(=O)CCC4=O)CC3=O)c2CN1C(=O)Nc1cc(F)c(F)c(F)c1]

The title compound was prepared according to the following scheme:

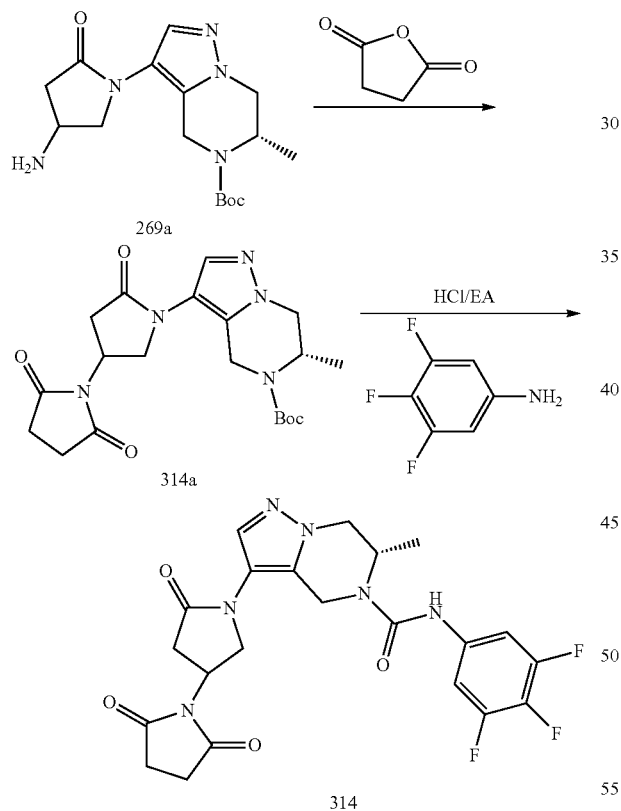

Step 1: Preparation of tert-butyl (6S)-3-[4-(2,5-dioxopyrrolidin-1-yl)-2-oxo-pyrrolidin-1-yl]-6-methyl-6,7-dihydro-4H-pyrazolo[1,5-a]pyrazine-5-carboxylate (compound 314a)

To a solution of (6S)-tert-butyl 3-(4-amino-2-oxopyrrolidin-1-yl)-6-methyl-6,7-dihydropyrazolo[1,5-a]pyrazine-5 (4H)-carboxylate (compound 269a, 100 mg, 0.29 mmol) in DMF (5 mL) was added tetrahydrofuran-2,5-dione (44.0 mg 0.44 mmol) and DMAP (18.3 mg, 0.15 mmol), then the reaction mixture was stirred at 110° C. for 12 hours. The reaction mixture was concentrated in vacuo to provide the crude product, which was purified by Prep-HPLC to give compound 314a as a white solid (50 mg). LCMS: (M+H$^+$): 418.

Step 2: Preparation of (6S)-3-[4-(2,5-dioxopyrrolidin-1-yl)-2-oxo-pyrrolidin-1-yl]-6-methyl-N-(3,4,5-trifluorophenyl)-6,7-dihydro-4H-pyrazolo[1,5-a]pyrazine-5-carboxamide (Example 314)

The title compound was prepared in analogy to the preparation of Example 11 by using tert-butyl (6S)-3-[4-(2,5-dioxopyrrolidin-1-yl)-2-oxo-pyrrolidin-1-yl]-6-methyl-6,7-dihydro-4H-pyrazolo[1,5-a]pyrazine-5-carboxylate (compound 314a) instead of tert-butyl 3-(4-fluorophenyl)-6,7-dihydro-4H-pyrazolo[1,5-a]pyrazine-5-carboxylate (compound 11a). Example 314 was obtained as white solid (15 mg). LCMS (M+H$^+$):491. $^1$H NMR (400 MHz, DMSO-d$_6$) δ ppm 9.20-9.14 (m, 1H), 7.57 (d, J=4.0 Hz, 1H), 7.43 (dd, J=6.5, 10.8 Hz, 2H), 5.10-4.98 (m, 1H), 4.95-4.77 (m, 2H), 4.42-4.31 (m, 1H), 4.27-4.18 (m, 1H), 4.16-4.00 (m, 2H), 3.83-3.68 (m, 1H), 3.66-3.47 (m, 1H), 2.87-2.74 (m, 1H), 2.65-2.59 (m, 3H), 2.42-2.31 (m, 1H), 1.19-1.15 (m, 3H).

Example 315

(6S)-6-methyl-3-[2-oxo-4-(2-oxopyrrolidin-1-yl)pyrrolidin-1-yl]-N-(3,4,5-trifluorophenyl)-6,7-dihydro-4H-pyrazolo[1,5-a]pyrazine-5-carboxamide

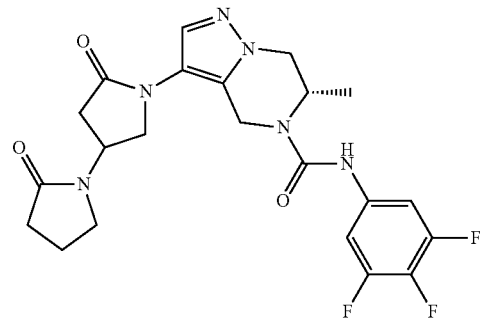 [SMILES: C[C@H]1Cn2ncc(N3CC(N4CCCC4=O)CC3=O)c2CN1C(=O)Nc1cc(F)c(F)c(F)c1]

The title compound was prepared according to the following scheme:

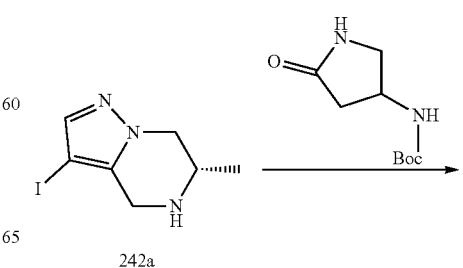

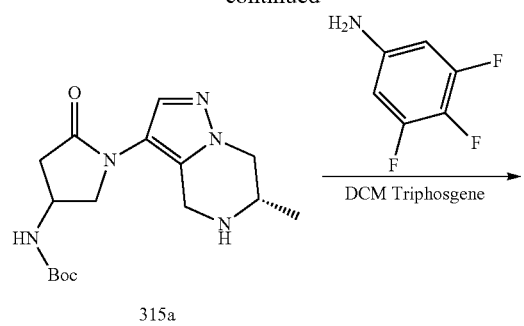

315a

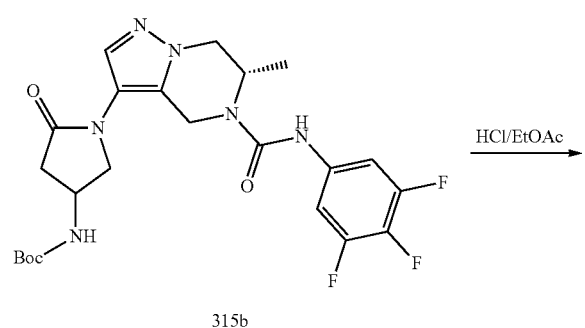

315b

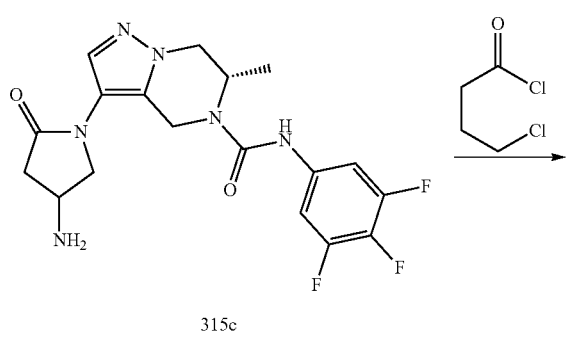

315c

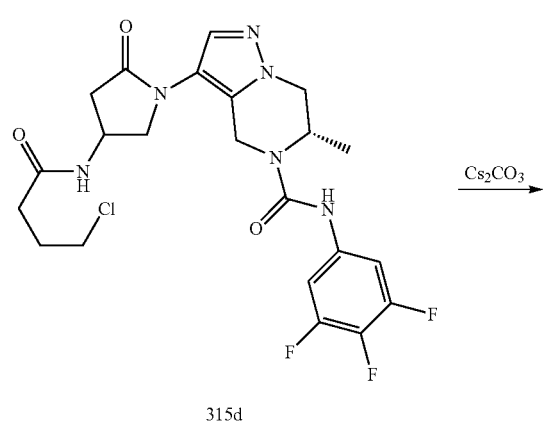

315d

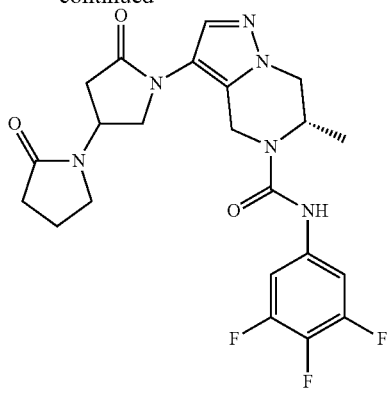

315

Step 1: Preparation of tert-butyl N-[1-[(6S)-6-methyl-4,5,6,7-tetrahydropyrazolo[1,5-a]pyrazin-3-yl]-5-oxo-pyrrolidin-3-yl]carbamate (compound 315a)

To a solution of tert-butyl N-(5-oxopyrrolidin-3-yl)carbamate (0.88 g, 4.4 mmol) in dioxane (15 mL) was added (6S)-3-iodo-6-methyl-4,5,6,7-tetrahydropyrazolo[1,5-a]pyrazine(compound 242a, 1.05 g, 4.0 mmol), (1R,2R)-N1,N2-dimethylcyclohexane-1,2-diamine (57.0 mg, 0.4 mmol), $K_3PO_4$ (1.7 g, 8.0 mmol) and CuI (76.0 mg, 0.4 mmol) under $N_2$, and the reaction mixture was stirred at 120° C. for 12 hours. The reaction mixture was filtered and concentrated in vacuo, and the residue was purified by silica gel column chromatography (DCM/MeOH=50/1 to 10/1) to give compound 315a as white solid (800 mg). LCMS (M+H$^+$): 336.

Step 2: Preparation of tert-butyl N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]carbamate (compound 315b)

To a mixture of 3,4,5-trifluoroaniline (88.82 mg 0.6 mmol) and DIPEA (154.8 mg 1.2 mmol) in DCM (10 mL) was added triphosgene (53.42 mg 0.18 mmol) between 0° C. and 5° C. The reaction mixture was stirred at room temperature for 1 hour, and then tert-butyl N-[1-[(6S)-6-methyl-4,5,6,7-tetrahydropyrazolo[1,5-a]pyrazin-3-yl]-5-oxo-pyrrolidin-3-yl]carbamate (compound 315a, 100.0 mg 0.3 mmol) was added. The resulting mixture was stirred at 30° C. for 12 hours, and then concentrated to afford a residue, which was purified by prep-HPLC to give compound 315b as white solid (95 mg). LCMS (M+H$^+$): 509.

Step 3: Preparation of (6S)-3-(4-amino-2-oxo-pyrrolidin-1-yl)-6-methyl-N-(3,4,5-trifluorophenyl)-6,7-dihydro-4H-pyrazolo[1,5-a]pyrazine-5-carboxamide (compound 315c)

A solution of tert-butyl N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]carbamate (compound 315b, 95 mg, 0.19 mmol) in HCl/EtOAc (10 mL) was stirred at room temperature for 1 hour. The reaction mixture was concentrated in vacuo to give crude compound 315c (80 mg) which was used directly without further purification. LCMS (M+H+): 409.

Step 4: Preparation of (6S)-3-[4-(4-chlorobutanoylamino)-2-oxo-pyrrolidin-1-yl]-6-methyl-N-(3,4,5-trifluorophenyl)-6,7-dihydro-4H-pyrazolo[1,5-a]pyrazine-5-carboxamide (compound 315d)

To a mixture of (6S)-3-(4-amino-2-oxo-pyrrolidin-1-yl)-6-methyl-N-(3,4,5-trifluorophenyl)-6,7-dihydro-4H-pyrazolo[1,5-a]pyrazine-5-carboxamide (compound 315c, 100 mg, 0.24 mmol) and Et$_3$N (74.2 mg, 0.74 mmol) in DCM (3 mL) at 0° C. was added 4-chlorobutanoyl chloride (41.4 mg, 0.3 mmol). The reaction mixture was stirred at room temperature for 12 hours and concentrated to afford the crude product which was purified by prep-HPLC to give compound 315d as a white solid (55 mg). LCMS (M+H+): 514.

Step 5: Preparation of (6S)-6-methyl-3-[2-oxo-4-(2-oxopyrrolidin-1-yl)pyrrolidin-1-yl]-N-(3,4,5-trifluorophenyl)-6,7-dihydro-4H-pyrazolo[1,5-a]pyrazine-5-carboxamide (Example 315)

A mixture of (6S)-3-[4-(4-chlorobutanoylamino)-2-oxo-pyrrolidin-1-yl]-6-methyl-N-(3,4,5-trifluorophenyl)-6,7-dihydro-4H-pyrazolo[1,5-a]pyrazine-5-carboxamide (compound 315d, 45.0 mg, 0.09 mmol) and Cs$_2$CO$_3$ (162.9 mg, 0.5 mmol) in DMF (2 mL) was stirred at 80° C. for 12 hours. The reaction mixture was filtered, and the solvents were removed in vacuo. The crude product was purified by prep-HPLC to give Example 315 as yellow solid (15 mg). LCMS (M+H+): 477. $^1$H NMR (400 MHz, MeOD) δ ppm 7.67 (s, 0.5H), 7.66 (s, 0.5H), 7.33-7.24 (m, 2 H), 5.12-4.97 (m, 3 H), 4.52 (dd, J=17.07, 9.29 Hz, 1 H), 4.30 (dd, J=12.80, 4.27 Hz, 1 H), 4.21-4.09 (m, 2 H), 3.83 (m, J=13.36, 10.23, 3.76 Hz, 1 H), 3.56 (t, J=7.03 Hz, 2 H), 2.92 (dd, J=17.57, 9.03 Hz, 1 H), 2.67 (dd, J=17.94, 4.14 Hz, 1 H), 2.44 (td, J=8.09, 2.38 Hz, 2 H), 2.17-2.08 (m, 2 H), 1.30-1.24 (m, 3H).

Example 316

N-methyl-N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]oxazole-5-carboxamide The title compound was prepared according to the following scheme:

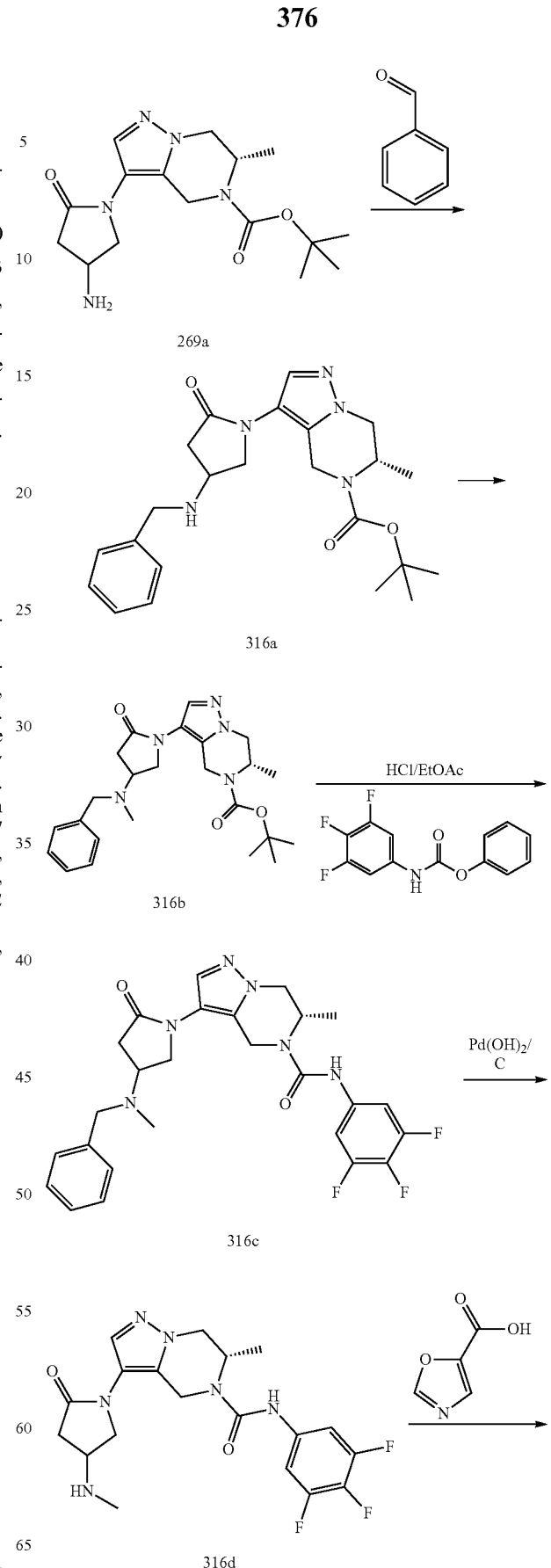

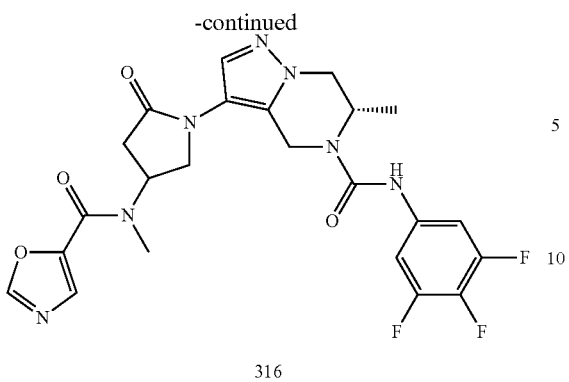

316

Step 1: Preparation of tert-butyl (6S)-3-[4-(benzylamino)-2-oxo-pyrrolidin-1-yl]-6 methyl-6,7-dihydro-4H-pyrazolo[1,5-a]pyrazine-5-carboxylate (compound 316a)

A mixture of tert-butyl (6S)-3-(4-amino-2-oxo-pyrrolidin-1-yl)-6-methyl-6,7-dihydro-4H-pyrazolo[1,5-a]pyrazine-5-carboxylate (compound 269a, 1.7 g 5.07 mmol) and benzaldehyde (0.65 g, 6.08 mmol) in MeOH (10.0 mL) was stirred at room temperature for 1 hour. Then NaBH$_4$ (0.2 g, 5.07 mmol) was added to previous reaction mixture. The resulting reaction mixture was stirred for 12 hours and concentrated in vacuo to afford a crude product, which was purified by column chromatography (DCM: MeOH=10:1) to give compound 316a as a white solid (2.1 g). LCMS (M+H$^+$): 336

Step 2: Preparation of tert-butyl (6S)-3-[4-[benzyl(methyl)amino]-2-oxo-pyrrolidin-1-yl]-6-methyl-6,7-dihydro-4H-pyrazolo[1,5-a]pyrazine-5-carboxylate (compound 316b)

A mixture of tert-butyl (6S)-3-[4-(benzylamino)-2-oxo-pyrrolidin-1-yl]-6 methyl-6,7-dihydro-4H-pyrazolo[1,5-a]pyrazine-5-carboxylate (compound 316a, 2.1 g, 4.9 mmol) and paraformaldehyde (177.0 mg, 5.88 mmol) in CH$_3$CN (20 mL) was stirred at room temperature for 1 hour. Then NaBH(OAc)$_3$ (1.04 g, 4.9 mmol) was added to previous reaction mixture. The resulting reaction mixture was stirred for another 12 hours, then H$_2$O (5.0 mL) and EtOAc (50.0 mL) were added, and the organic phase was separated and concentrated to give crude compound 316b (2.2 g) which was used directly without further purification. LCMS (M+H$^+$): 440.

Step 3: Preparation of (6S)-3-[4-[benzyl(methyl)amino]-2-oxo-pyrrolidin-1-yl]-6-methyl-N-(3,4,5-trifluorophenyl)-6,7-dihydro-4H-pyrazolo[1,5-a]pyrazine-5-carboxamide (compound 316c)

Compound 316c was prepared in analogy to Example 223 by using tert-butyl (6S)-3-[4-[benzyl(methyl)amino]-2-oxo-pyrrolidin-1-yl]-6-methyl-6,7-dihydro-4H-pyrazolo[1,5-a]pyrazine-5-carboxylate (compound 316b) instead of tert-butyl (6S)-6-methyl-3-(2-oxopyrrolidin-1-yl)-6,7-dihydro-4H-pyrazolo[1,5-a]pyrazine-5-carboxylate (compound 223b), and phenyl N-(3,4,5-trifluorophenyl)carbamate (compound 233c) instead of phenyl N-[2-(difluoromethyl)-4-pyridyl]carbamate (compound 218c). Compound 316c was obtained as a light yellow oil (1.8 g). LCMS (M+H$^+$): 513.

Step 4: Preparation of (6S)-6-methyl-3-[4-(methylamino)-2-oxo-pyrrolidin-1-yl]-N-(3,4,5-trifluorophenyl)-6,7-dihydro-4H-pyrazolo[1,5-a]pyrazine-5-carboxamide (compound 316d)

To a solution of (6S)-3-[4-[benzyl(methyl)amino]-2-oxo-pyrrolidin-1-yl]-6-methyl-N-(3,4,5-trifluorophenyl)-6,7-dihydro-4H-pyrazolo[1,5-a]pyrazine-5-carboxamide (compound 316c, 302.2 mg, 0.59 mmol) in MeOH (5 mL) was added Pd(OH)$_2$/C (41.97 mg, 0.3 mmol). The resulting mixture was stirred at room temperature under H$_2$ at 50 psi for 1 hour. The reaction mixture was filtered and concentrated in vacuo to provide crude compound 316d (160 mg) which was used directly without further purification. LCMS (M+H$^+$): 423.

Step 5: Preparation of N-methyl-N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]oxazole-5-carboxamide (Example 316)

A mixture of oxazole-5-carboxylic acid (11.3 mg, 0.10 mmol), DIPEA (56.8 mg, 0.44 mmol), EDCI (38.5 mg, 0.33 mmol) and HOBT (26.4 mg, 0.33 mmol) in DMF (1.0 mL) was stirred for 30 mins before the addition of (6S)-6-methyl-3-[4-(methylamino)-2-oxo-pyrrolidin-1-yl]-N-(3,4,5-trifluorophenyl)-6,7-dihydro-4H-pyrazolo[1,5-a]pyrazine-5-carboxamide (compound 316d, 50.0 mg, 0.11 mmol) in DMF (5 mL). The reaction mixture was stirred at 30° C. for 12 hours. The reaction mixture was filtered and concentrated to afford the residue which was purified by prep-HPLC to give Example 316 as a white solid (10 mg). LCMS (M+H$^+$): 518. $^1$H NMR (400 MHz, DMSO-d6) δ ppm 9.20 (s, 0.5H), 9.18 (s, 0.5H), 8.59 (s, 1H), 7.78 (br. s., 1H), 7.71-7.61 (m, 1H), 7.49-7.41 (m, 2H), 5.26 (br. s., 1H), 5.10-4.98 (m, 1H), 4.87 (br. s., 1H), 4.40 (d, J=17.07 Hz, 1H), 4.26-4.18 (m, 1H), 4.17-4.00 (m, 2H), 3.93-3.76 (m, 1H), 3.16 (br. s., 2H), 2.94-2.65 (m, 3H), 1.19-1.13 (m, 3H).

Example 317

N-methyl-N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]oxazole-4-carboxamide

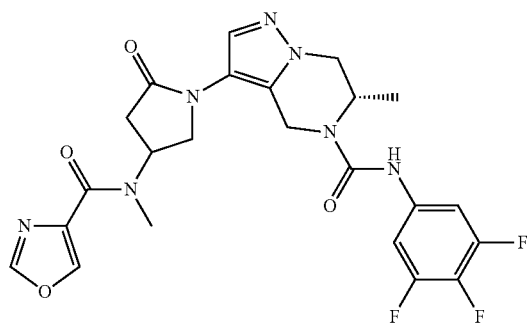 [SMILES: C[C@H]1Cn2ncc(N3CC(N(C)C(=O)c4cocn4)CC3=O)c2CN1C(=O)Nc1cc(F)c(F)c(F)c1]

Preparation of Example 317

The title compound was prepared in analogy to Example 316 by using oxazole-4-carboxylic acid instead of oxazole-5-carboxylic acid. Example 317 was obtained as a white solid (9.4 mg). LCMS (M+H$^+$): 518.1. $^1$H NMR (400 MHz, DMSO-d6) δ ppm 9.27 (s, 0.5H), 9.25 (s, 0.5H) 8.62 (s, 1H), 8.54 (br. s., 1H), 7.66 (d, J=5.27 Hz, 1H), 7.50-7.43 (m, 2H), 5.49-5.26 (m, 1H), 5.06 (dd, J=17.32, 7.78 Hz, 1H), 4.89 (br. s., 1H), 4.39 (d, J=17.32 Hz, 1H), 4.26-4.17 (m, 1H), 4.16-3.98 (m, 2H), 3.84 (br. s., 1H), 3.22 (br. s., 2H), 2.97-2.65 (m, 3H), 1.19-1.13 (m, 3H).

Example 318

N-methyl-N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]oxazole-2-carboxamide

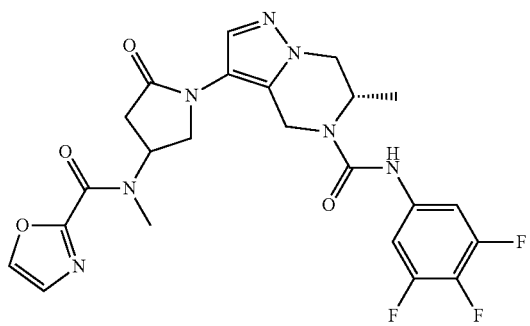 [SMILES: C[C@H]1Cn2ncc(N3CC(N(C)C(=O)c4ncco4)CC3=O)c2CN1C(=O)Nc1cc(F)c(F)c(F)c1]

Preparation of Example 318

The title compound was prepared in analogy to Example 316 by using oxazole-2-carboxylic acid instead of oxazole-5-carboxylic acid. Example 318 was obtained as a white solid (6.2 mg). LCMS (M+H$^+$): 518. $^1$H NMR (400 MHz, MeOH) δ ppm 8.14-8.06 (m, 1H), 7.73-7.65 (m, 1H), 7.41 (s, 1H), 7.33-7.27 (m, 2H), 5.10-5.05 (m, 1H), 4.97 (br. s., 1H), 4.64-4.49 (m, 2H), 4.36-4.22 (m, 2H), 4.20-4.13 (m, 1H), 4.07-3.89 (m, 1H), 3.51 (s, 2H), 3.17 (s, 1H), 3.08-2.96 (m, 1H), 2.89-2.78 (m, 1H), 1.30-1.26 (m, 3H).

Example 319

(6S)-6-methyl-3-[2-oxo-4-(2-oxooxazolidin-3-yl)pyrrolidin-1-yl]-N-(3,4,5-trifluorophenyl)-6,7-dihydro-4H-pyrazolo[1,5-a]pyrazine-5-carboxamide

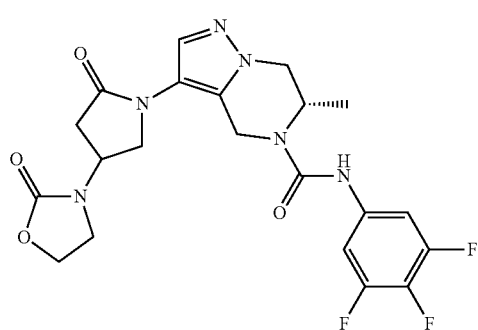 [SMILES: C[C@H]1Cn2ncc(N3CC(N4CCOC4=O)CC3=O)c2CN1C(=O)Nc1cc(F)c(F)c(F)c1]

The title compound was prepared according to the following scheme:

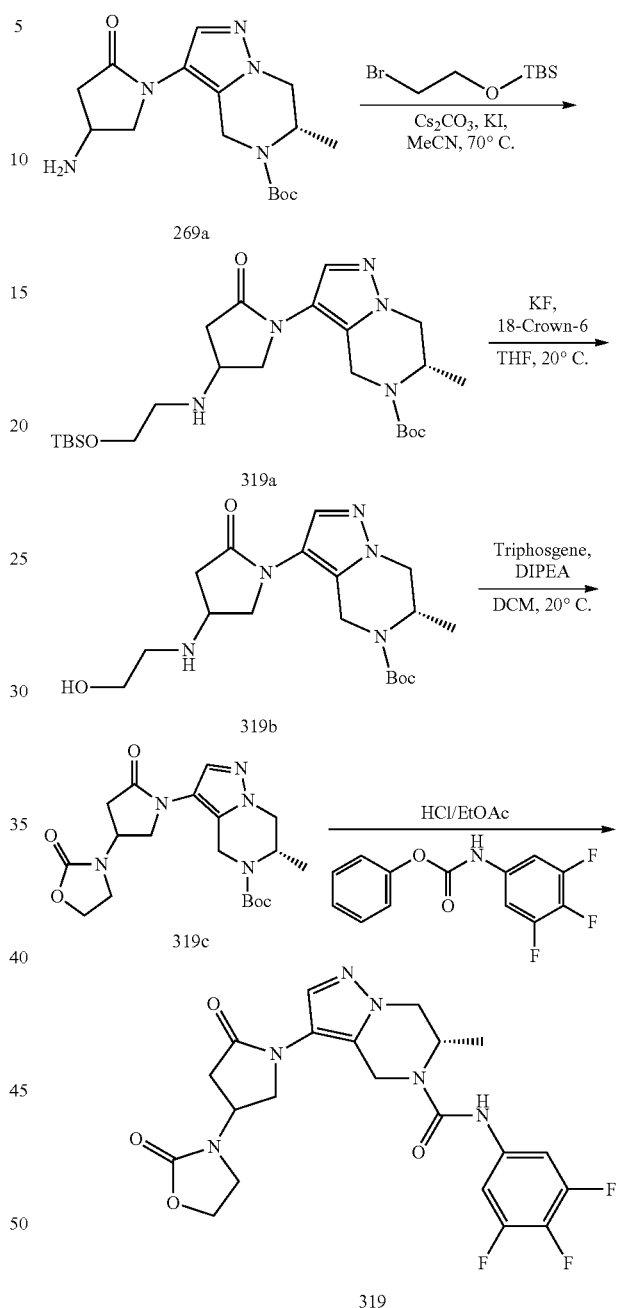

Step 1: Preparation of (6S)-tert-butyl 3-(4-(2-(tert-butyldimethylsilyloxy)ethylamino)-2-oxopyrrolidin-1-yl)-6-methyl-6,7-dihydropyrazolo[1,5-a]pyrazine-5(4H)-carboxylate (compound 319a)

A mixture of tert-butyl (6S)-3-(4-amino-2-oxo-pyrrolidin-1-yl)-6-methyl-6,7-dihydro-4H-pyrazolo[1,5-a]pyrazine-5-carboxylate (compound 269a, 400.0 mg, 1.19 mmol), (2-bromoethoxy)(tert-butyl)dimethylsilane (313.8 mg, 1.31 mmol), Cs$_2$CO$_3$ (777.1 mg, 2.39 mmol) and KI (39.6 mg, 0.34 mmol) in MeCN (5.0 mL) was stirred at 70° C. for 12

381 hours. The reaction mixture was concentrated and the residue was purified by prep-TLC to give compound 319a as a yellow oil (100 mg).

Step 2: Preparation of (6S)-tert-butyl 3-(4-(2-hydroxyethylamino)-2-oxopyrrolidin-1-yl)-6-methyl-6,7-dihydropyrazolo[1,5-a]pyrazine-5(4H)-carboxylate (compound 319b)

To a solution of (6S)-tert-butyl 3-(4-(2-(tert-butyldimethylsilyloxy)ethylamino)-2-oxopyrrolidin-1-yl)-6-methyl-6,7-dihydropyrazolo[1,5-a]pyrazine-5(4H)-carboxylate (compound 319a, 100.0 mg, 0.20 mmol) in THF (5 mL) was added KF (81.9 mg, 1.41 mmol) and 18-Crown-6 (372.7 mg, 1.41 mmol), and the reaction mixture was stirred at room temperature for 16 hours. The reaction mixture was concentrated and the residue was purified by prep-TLC (DCM:MeOH=10:1, Rf=0.25) to give compound 319b as a yellow oil (32 mg).

Step 3: Preparation of (6S)-tert-butyl 6-methyl-3-(2-oxo-4-(2-oxooxazolidin-3-yl)pyrrolidin-1-yl)-6,7-dihydropyrazolo[1,5-a]pyrazine-5(4H)-carboxylate (compound 319c)

To a solution of (6S)-tert-butyl 3-(4-(2-hydroxyethylamino)-2-oxopyrrolidin-1-yl)-6-methyl-6,7-dihydropyrazolo[1,5-a]pyrazine-5(4H)-carboxylate (compound 319b, 22.0 mg, 0.06 mmol) in DCM (2 mL) was added DIPEA (22.5 mg, 0.17 mmol) and triphosgene (9.0 mg, 0.03 mmol), and the reaction mixture was stirred at room temperature for 15 hours. The reaction mixture was concentrated and the residue was purified by prep-TLC (DCM:MeOH=10:1) to afford compound 319c as yellow oil (11 mg).

Step 4: (6S)-6-methyl-3-[2-oxo-4-(2-oxooxazolidin-3-yl)pyrrolidin-1-yl]-N-(3,4,5-trifluorophenyl)-6,7-dihydro-4H-pyrazolo[1,5-a]pyrazine-5-carboxamide (Example 319)

The title compound was prepared in analogy to Example 223 by using (6S)-tert-butyl 6-methyl-3-(2-oxo-4-(2-oxooxazolidin-3-yl)pyrrolidin-1-yl)-6,7-dihydropyrazolo[1,5-a]pyrazine-5(4H)-carboxylate (compound 319c) instead of tert-butyl (6S)-6-methyl-3-(2-oxopyrrolidin-1-yl)-6,7-dihydro-4H-pyrazolo[1,5-a]pyrazine-5-carboxylate (compound 223b) and phenyl N-(3,4,5-trifluoro-phenyl)carbamate (compound 233c) instead of phenyl N-[2-(difluoromethyl)-4-pyridyl]carbamate (compound 218c). Example 319 was obtained as a white solid (5.9 mg). LCMS: (M+H⁺): 479. $^1$H NMR (400 MHz, MeOD) δ ppm 7.69-7.63 (m, 1H), 7.34-7.22 (m, 2H), 5.11-5.01 (m, 1H), 5.00-4.90 (m, 1H), 4.74-4.64 (m, 1H), 4.56-4.46 (m, 1H), 4.46-4.38 (m, 2H), 4.34-4.26 (m, 1H), 4.18 (s, 2H), 3.97-3.85 (m, 1H), 3.75 (d, J=8.8 Hz, 2H), 3.03-2.86 (m, 1H), 2.78-2.69 (m, 1H), 1.32-1.24 (m, 3H).

Example 320

(6S)-6-methyl-3-[2-oxo-4-(3-oxomorpholin-4-yl)pyrrolidin-1-yl]-N-(3,4,5-trifluorophenyl)-6,7-dihydro-4H-pyrazolo[1,5-a]pyrazine-5-carboxamide

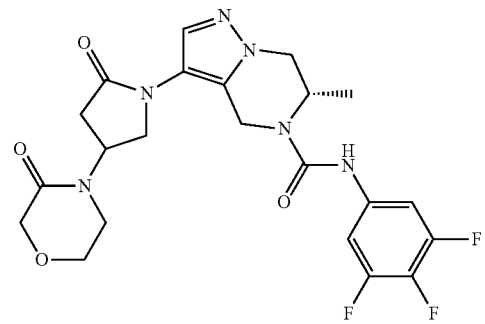 [SMILES: C[C@H]1Cn2ncc(N3CC(N4CCOCC4=O)CC3=O)c2CN1C(=O)Nc1cc(F)c(F)c(F)c1]

The title compound was prepared according to the following scheme:

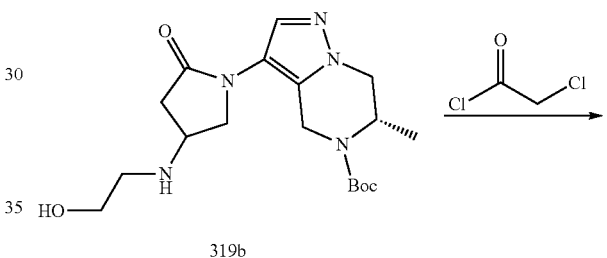

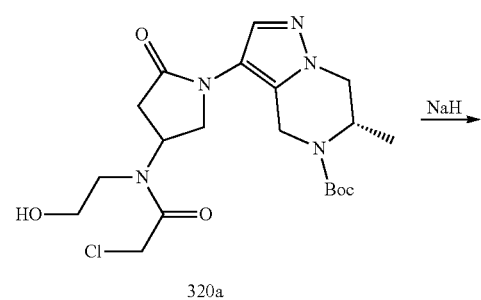

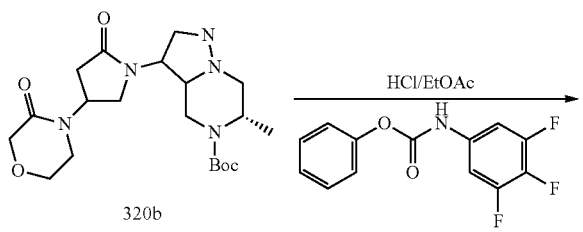

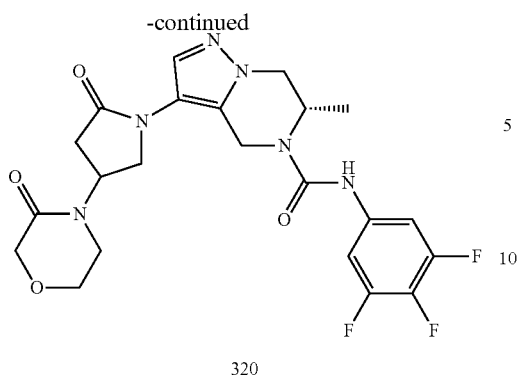

320

Step 1: Preparation of (6S)-tert-butyl 3-(4-(2-chloro-N-(2-hydroxyethyl)acetamido)-2-oxopyrrolidin-1-yl)-6-methyl-6,7-dihydropyrazolo[1,5-a]pyrazine-5(4H)-carboxylate (compound 320a)

To a mixture of (6S)-tert-butyl 3-(4-(2-hydroxyethylamino)-2-oxopyrrolidin-1-yl)-6-methyl-6,7-dihydropyrazolo[1,5-a]pyrazine-5(4H)-carboxylate (compound 319b, 100.0 mg, 0.26 mmol) and Et$_3$N (29.3 mg 0.29 mmol) in DCM (5.0 mL) was added 2-chloroacetyl chloride (29.1 mg, 0.26 mmol) dropwise. The reaction mixture was stirred at room temperature for 12 hours, and then concentrated. The residue was purified by Prep-HPLC to give compound 320a as a yellow oil (50 mg). LCMS: (M+H$^+$): 456.

Step 2: Preparation of (6S)-tert-butyl 6-methyl-3-(2-oxo-4-(3-oxomorpholino)pyrrolidin-1-yl)-6,7-dihydropyrazolo[1,5-a]pyrazine-5(4H)-carboxylate (compound 320b)

To a solution of (6S)-tert-butyl 3-(4-(2-chloro-N-(2-hydroxyethyl)acetamido)-2-oxopyrrolidin-1-yl)-6-methyl-6,7-dihydropyrazolo[1,5-a]pyrazine-5(4H)-carboxylate (compound 320a, 50.0 mg, 0.11 mmol) in THF (5.0 mL) was added NaH (8.8 mg, 0.22 mmol) at 0° C. The reaction mixture was stirred at room temperature for 1 hour, quenched with H$_2$O (20 mL) and extracted with EtOAc (20 mL) twice. The combined organic layer was concentrated to provide crude compound 320b as a colorless oil (20 mg). LCMS: (M+H$^+$): 420.

Step 3: Preparation of (6S)-6-methyl-3-[2-oxo-4-(3-oxomorpholin-4-yl)pyrrolidin-1-yl]-N-(3,4,5-trifluorophenyl)-6,7-dihydro-4H-pyrazolo[1,5-a]pyrazine-5-carboxamide (Example 320)

The title compound was prepared in analogy to Example 223 by using (6S)-tert-butyl 6-methyl-3-(2-oxo-4-(3-oxomorpholino)pyrrolidin-1-yl)-6,7-dihydropyrazolo[1,5-a]pyrazine-5(4H)-carboxylate (compound 320b) instead of tert-butyl (6S)-6-methyl-3-(2-oxopyrrolidin-1-yl)-6,7-dihydro-4H-pyrazolo[1,5-a]pyrazine-5-carboxylate (compound 223b) and phenyl N-(3,4,5-trifluoro-phenyl)carbamate (compound 233c) instead of phenyl N-[2-(difluoromethyl)-4-pyridyl]carbamate (compound 218c). Example 320 was obtained as white solid (10.5 mg). LCMS: (M+H$^+$): 493. $^1$H NMR (400 MHz, DMSO-d$_6$) δ ppm 8.45 (br. s., 1H), 7.66 (s, 0.5H), 7.64 (s, 0.5H), 7.36-7.50 (m, 2H), 5.23 (br. s., 1H), 4.99 (dd, J=17.1, 3.5 Hz, 1H), 4.86 (br. s., 1H), 4.38 (dd, J=17.2, 3.6 Hz, 1H), 3.94-4.25 (m, 5H), 3.68-3.91 (m, 3H), 2.77 (dd, J=17.4, 9.4 Hz, 1H), 2.60 (d, J=4.0 Hz, 1H), 2.53-2.57 (m, 2H), 1.15 (d, J=6.8 Hz, 3H).

Example 321

(6S)-N-(3-chloro-4-fluoro-phenyl)-6-methyl-3-(5-methyl-2-oxo-oxazolidin-3-yl)-6,7-dihydro-4H-pyrazolo[1,5-a]pyrazine-5-carboxamide

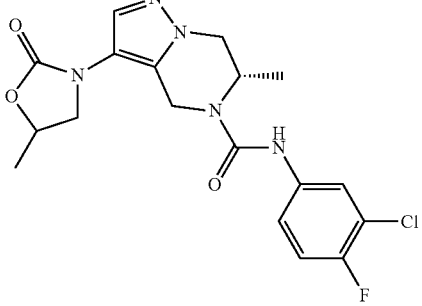

Preparation of Example 321

The title compound was prepared in analogy to Example 246 by using 5-methyloxazolidin-2-one instead of 1,2,4,7,8,8a-hexahydropyrrolo[1,2-a]pyrazine-3,6-dione (compound 246e). Example 321 was obtained as a white solid (47.6 mg). LCMS (M+H$^+$):408. $^1$H NMR (400 MHz, DMSO-d$_6$) δppm 8.95 (s, 1H), 7.74 (dd, J=2.5, 6.8 Hz, 1H), 7.61 (s, 1H), 7.48-7.39 (m, 1H), 7.37-7.28 (m, 1H), 5.02 (dd, J=4.9, 16.9 Hz, 1H), 4.93-4.85 (m, 1H), 4.85-4.77 (m, 1H), 4.39 (dd, J=4.5, 17.1 Hz, 1H), 4.25-4.17 (m, 1H), 4.15-4.08 (m, 1H), 4.08-4.00 (m, 1H), 3.65-3.52 (m, 1H), 1.47-1.39 (m, 3H), 1.18-1.08 (m, 3H).

Example 322

(6S)-N-(3-chloro-4-fluoro-phenyl)-6-methyl-3-(3-oxo-5,6,8,8a-tetrahydro-1H-imidazo[5,1-c][1,4]oxazin-2-yl)-6,7-dihydro-4H-pyrazolo[1,5-a]pyrazine-5-carboxamide

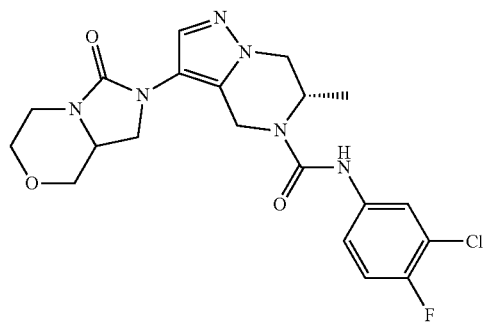 [SMILES: C[C@H]1Cn2ncc(N3CC4COCCN4C3=O)c2CN1C(=O)Nc1ccc(F)c(Cl)c1]

The title compound was prepared according to the following scheme:

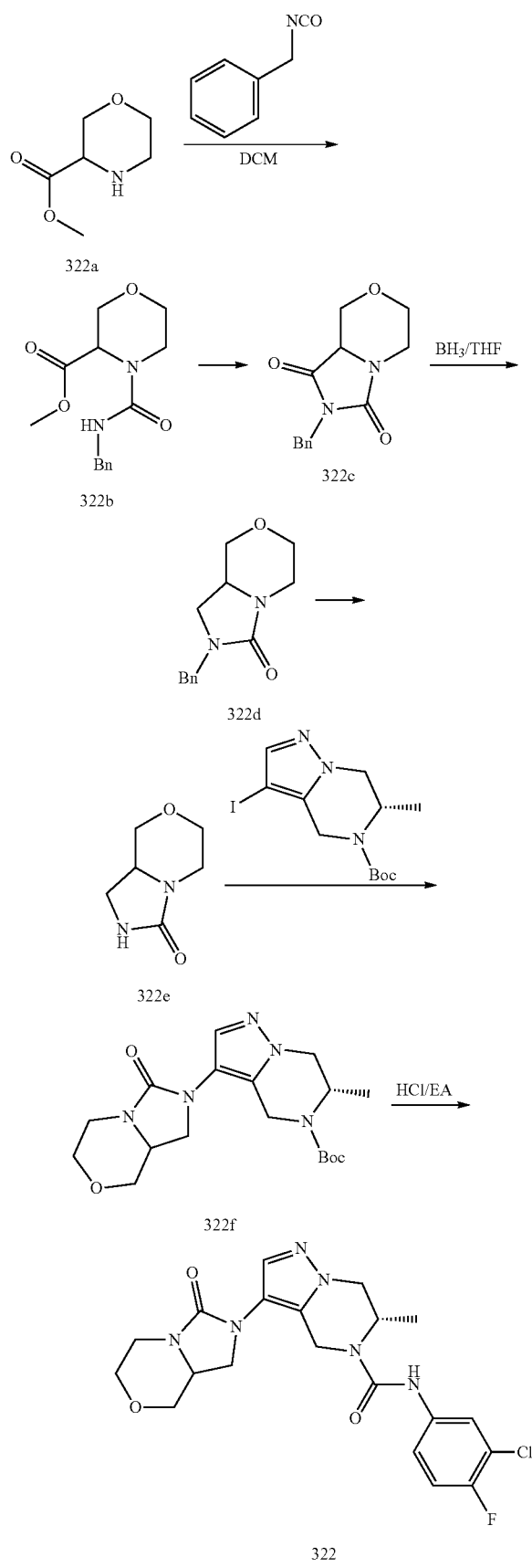

Step 1: Preparation of methyl 4-(benzylcarbamoyl)morpholine-3-carboxylate (compound 322b)

To a solution of methyl morpholine-3-carboxylate (compound 322a, 300.0 mg, 2.06 mmol) in DCM (3 mL) was added (isocyanatomethyl)benzene (275.2 mg, 2.06 mmol). The reaction mixture was stirred at room temperature for 2 hours, then washed with brine, dried over $Na_2SO_4$, and concentrated to give crude compound 322b (500 mg) as a colourless oil, which was used in next step directly. LCMS: $(M+H^+)$: 279.

Step 2: Preparation of 2-benzyl-tetrahydro-2H-imidazo[5,1-c][1,4]oxazine-1,3-dione (compound 322c)

A solution of methyl 4-(benzylcarbamoyl)morpholine-3-carboxylate (compound 322b, 500 mg, 1.80 mmol) in EtOH (6 mL) was stirred at 90° C. for 12 hours, and then concentrated. The residue was purified by silica gel column chromatography (PE/EtOAc=5/1) to give compound 322c as colorless oil (450 mg). LCMS: $(M+H^+)$: 247

Step 3: Preparation of 2-benzyl-hexahydroimidazo[5,1-c][1,4]oxazin-3-one (compound 322d)

To a solution of 2-benzyl-tetrahydro-2H-imidazo[5,1-c][1,4]oxazine-1,3-dione (compound 322c, 350.0 mg, 1.42 mmol) in THF (2 mL) was added $BH_3$/THF (14.2 mL, 14.2 mmol) at 0° C. and the reaction mixture was stirred at 80° C. for 12 hours, then MeOH was added and the reaction mixture was concentrated to afford the residue which was purified by silica gel column chromatography (PE/EtOAc=3/1) to give compound 322d as colorless oil (300 mg). LCMS: $(M+H^+)$: 233.

Step 4: Preparation of hexahydroimidazo[5,1-c][1,4]oxazin-3-one (compound 322e)

To a solution of 2-benzyl-hexahydroimidazo[5,1-c][1,4]oxazin-3-one (compound 322d, 300.0 mg, 1.29 mmol) in THF (3.0 mL) at −78° C. was added liquid ammonia (10 mL), then EtOH (1 mL) and Na (150.0 mg). The resulting dark blue mixture was stirred for 30 mins at −78° C. and quenched with solid $NH_4Cl$. After warmed to room temperature, the reaction mixture was taken up in EtOAc (10 mL) and washed with water (5 mL). The organic layer was dried over $Na_2SO_4$, filtered and concentrated. The residue was purified by Prep-HPLC to give compound 322e as a white solid. $^1H$ NMR(400 MHz, MeOD) δ ppm 3.91-3.78 (m, 3H), 3.63 (dd, J=2.8, 13.6 Hz, 1H), 3.51 (t, J=8.9 Hz, 1H), 3.44-3.37 (m, 1H), 3.13-3.03 (m, 1H), 3.00 (dd, J=4.5, 9.5 Hz, 1H).

Preparation of (6S)-N-(3-chloro-4-fluoro-phenyl)-6-methyl-3-(3-oxo-5,6,8,8a-tetrahydro-1H-imidazo[5,1-c][1,4]oxazin-2-yl)-6,7-dihydro-4H-pyrazolo[1,5-a]pyrazine-5-carboxamide (Example 322)

The title compound was prepared in analogy to Example 246 by using hexahydroimidazo[5,1-c][1,4]oxazin-3-one (compound 322e) instead of 1,2,4,7,8,8a-hexahydropyrrolo[1,2-a]pyrazine-3,6-dione (compound 246e). Example 322 was obtained as white solid (4.7 mg). LCMS: $(M+H^+)$: 449. $^1H$ NMR (400 MHz, DMSO-$d_6$) δ ppm 8.95 (d, J=3.6 Hz, 1H), 7.74 (dd, J=2.6, 6.8 Hz, 1H), 7.54 (d, J=2.1 Hz, 1H), 7.47-7.40 (m, 1H), 7.36-7.28 (m, 1H), 5.00 (dd, J=13.2, 16.8 Hz, 1H), 4.86 (d, J=5.0 Hz, 1H), 4.40 (dd, J=9.9, 16.9 Hz, 1H), 4.23-4.14 (m, 1H), 4.13-4.06 (m, 1H), 3.93-3.71 (m, 4H), 3.61-3.55 (m, 1H), 3.31 (br. s., 3H), 3.08-3.00 (m, 1H), 1.17-1.10 (m, 3H).

Example 323

(6S)-6-methyl-3-(3-oxo-5,6,8,8a-tetrahydro-1H-imidazo[5,1-c][1,4]oxazin-2-yl)-N-(3,4,5-trifluoro-phenyl)-6,7-dihydro-4H-pyrazolo[1,5-a]pyrazine-5-carboxamide

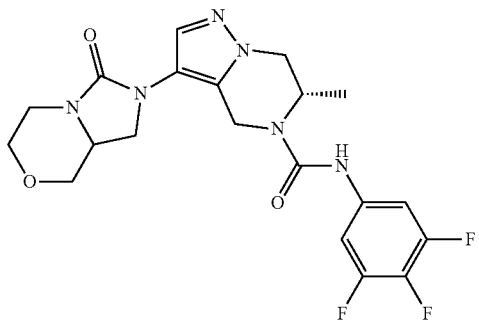 [SMILES: C[C@H]1Cn2ncc(N3CC4COCCN4C3=O)c2CN1C(=O)Nc1cc(F)c(F)c(F)c1]

Preparation of Example 323

The title compound was prepared in analogy to Example 223 by using hexahydroimidazo[5,1-c][1,4]oxazin-3-one (compound 322e) instead of pyrrolidin-2-one and phenyl (3,4,5-trifluorophenyl)carbamate (compound 233c) instead of phenyl N-[2-(difluoromethyl)-4-pyridyl]carbamate (compound 218c). Example 323 was obtained as a white solid (22.5 mg). LCMS: 451. $^1$H NMR (400 MHz, DMSO-d$_6$) δ ppm 9.10 (d, J=5.8 Hz, 1H), 7.54 (d, J=2.0 Hz, 1H), 7.43 (ddd, J=2.3, 6.6, 10.6 Hz, 2H), 5.06-4.93 (m, 1H), 4.91-4.76 (m, 1H), 4.41 (dd, J=12.6, 16.9 Hz, 1H), 4.25-4.15 (m, 1H), 4.14-4.06 (m, 1H), 3.94-3.70 (m, 4H), 3.57 (dd, J=2.6, 13.4 Hz, 1H), 3.33-3.25 (m, 3H), 3.04 (dt, J=3.8, 12.6 Hz, 1H), 1.17-1.10 (m, 3H).

Example 324

(6S)-N-(2-chloro-4-pyridyl)-3-(5,5-dimethyl-2-oxo-oxazolidin-3-yl)-6-methyl-6,7-dihydro-4H-pyrazolo[1,5-a]pyrazine-5-carboxamide

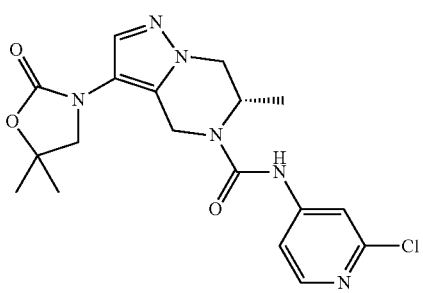 [SMILES: C[C@H]1Cn2ncc(N3CC(C)(C)OC3=O)c2CN1C(=O)Nc1ccnc(Cl)c1]

Preparation of Example 324

The title compound was prepared in analogy to Example 223 by using 5,5-dimethyloxazolidin-2-one instead of pyrrolidin-2-one and phenyl N-(2-chloro-4-pyridyl)carbamate instead of phenyl N-[2-(difluoromethyl)-4-pyridyl]carbamate (compound 218c). Example 324 was obtained as a white solid (5.6 mg). LCMS (M+H$^+$): 405. $^1$H NMR(400 MHz, MeOD) δ ppm 8.45 (d, J=6.02 Hz, 1H), 8.19 (s, 1H), 7.95 (d, J=5.52 Hz, 1H), 7.70 (s, 1H), 5.26 (d, J=16.81 Hz, 1H), 5.07 (br. s., 1H), 4.65 (d, J=16.31 Hz, 1H), 4.36 (d, J=9.79 Hz, 1H), 4.20 (d, J=12.55 Hz, 1H), 3.86 (br. s., 2H), 1.58 (s, 6H), 1.32 (d, J=6.53 Hz, 3H)

Example 325

(6S)-3-(5,5-dimethyl-2-oxo-oxazolidin-3-yl)-6-methyl-N-[2-(trifluoromethyl)-4-pyridyl]-6,7-dihydro-4H-pyrazolo[1,5-a]pyrazine-5-carboxamide

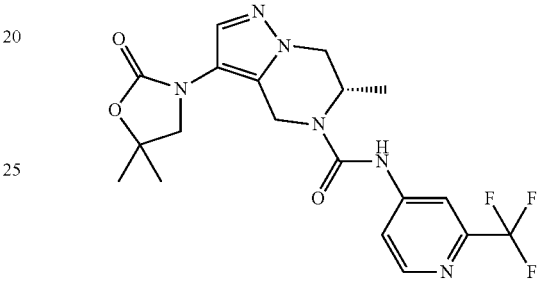

Preparation of Example 325

The title compound was prepared in analogy to Example 223 by using 5,5-dimethyloxazolidin-2-one instead of pyrrolidin-2-one and phenyl N-(2-trifluoromethyl-4-pyridyl)carbamate instead of phenyl N-[2-(difluoromethyl)-4-pyridyl]carbamate (compound 218c). Example 325 was obtained as a white solid (15 mg). LCMS (M+H$^+$): 439. $^1$H NMR (400 MHz, MeOD)δppm 8.71 (d, J=6.53 Hz, 1H), 8.55 (d, J=5.27 Hz, 1H), 8.25-8.33 (m, 1H), 7.84-7.93 (m, 1H), 5.39 (dd, J=17.19, 8.41 Hz, 1H), 5.22 (br. s., 1H), 4.71 (d, J=17.07 Hz, 1H), 4.39-4.49 (m, 1H), 4.26 (d, J=12.80 Hz, 1H), 3.86-3.95 (m, 2H), 1.59 (s, 6H), 1.35 (d, J=6.78 Hz, 3H).

Example 326

(6S)-N-(3-chloro-4-fluoro-phenyl)-6-methyl-3-(4-methyl-2-oxo-imidazolidin-1-yl)-6,7-dihydro-4H-pyrazolo[1,5-a]pyrazine-5-carboxamide

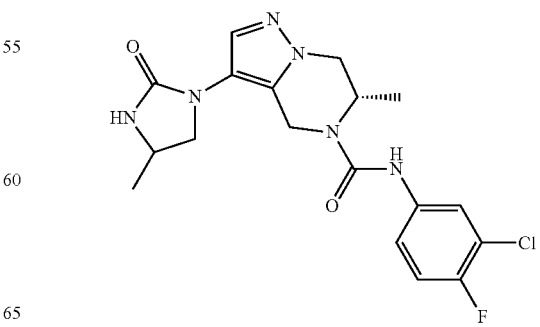

Preparation of Example 326

The title compound was prepared in analogy to Example 246 by using 4-methylimidazolidin-2-one instead of 1,2,4,7,8,8a-hexahydropyrrolo[1,2-a]pyrazine-3,6-dione (compound 246e). Example 326 was obtained as a white solid (15 mg). LCMS: (M+H⁺): 407. ¹H NMR (400 MHz, MeOD) δ ppm 7.63 (dd, J=2.5, 6.5 Hz, 1H), 7.57 (s, 1H), 7.35 (td, J=4.2, 7.2 Hz, 1H), 7.18 (t, J=8.9 Hz, 1H), 5.06 (dd, J=3.9, 16.7 Hz, 1H), 4.97 (d, J=5.5 Hz, 1H), 4.54 (dd, J=3.9, 16.7 Hz, 1H), 4.29 (d, J=12.8 Hz, 1H), 4.14 (d, J=12.8 Hz, 1H), 4.02-3.92 (m, 2H), 3.46 (br. s., 1H), 1.34 (d, J=5.5 Hz, 3H), 1.29-1.22 (m, 3H).

Example 327

(6S)-6-methyl-3-[(4R)-2-oxo-4-phenyl-oxazolidin-3-yl]-N-(3,4,5-trifluorophenyl)-6,7-dihydro-4H-pyrazolo[1,5-a]pyrazine-5-carboxamide

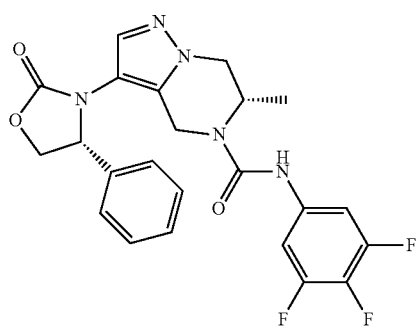 [SMILES: C[C@H]1Cn2ncc(N3C(=O)OC[C@H]3c3ccccc3)c2CN1C(=O)Nc1cc(F)c(F)c(F)c1]

The title compound was prepared according to the following scheme:

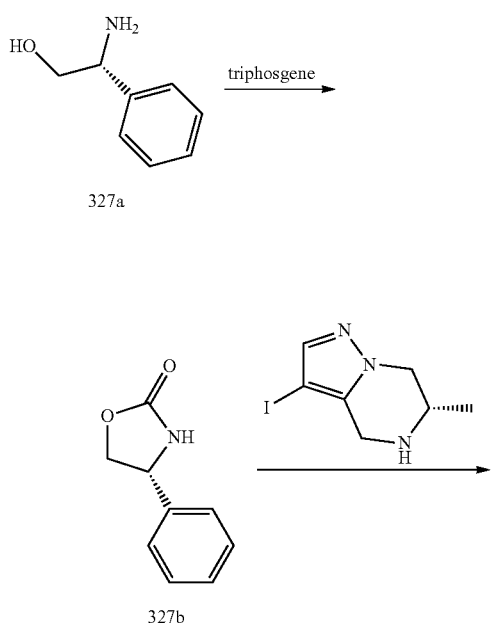

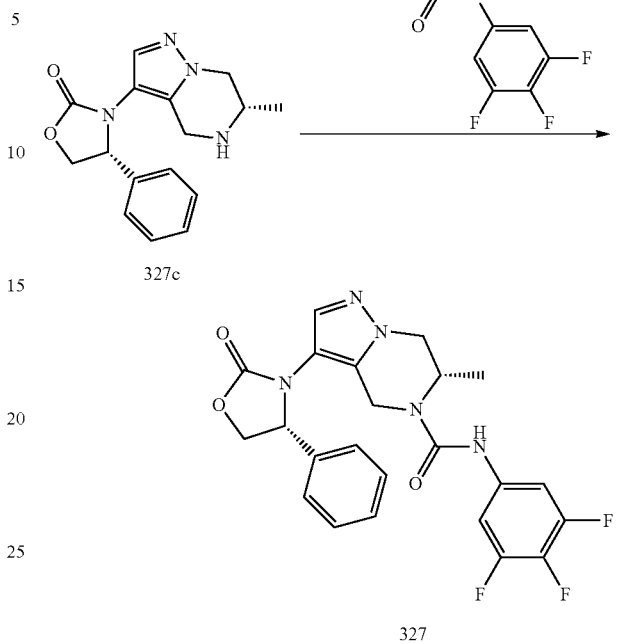

Step 1: Preparation of (4R)-4-phenyloxazolidin-2-one (compound 327b)

To a solution of (2R)-2-amino-2-phenyl-ethanol (274.4 mg, 2.0 mmol) in DCM (3 mL) was added Et₃N (607.1 mg, 6.0 mmol) and triphosgene (77.8 mg, 0.6 mmol) at 0° C. The reaction mixture was stirred at room temperature for 12 hours, then concentrated in vacuo to give crude product, which was purified by prep-HPLC to give compound 327b as a white solid (130 mg). LCMS(M+H⁺): 164.

Step 2: Preparation of (4R)-3-[(6S)-6-methyl-4,5,6,7-tetrahydropyrazolo[1,5-a]pyrazin-3-yl]-4-phenyl-oxazolidin-2-one (compound 327c)

To a solution of (4R)-4-phenyloxazolidin-2-one (compound 327b, 67.7 mg, 0.42) in dioxane (15 mL) was added (6S)-3-iodo-6-methyl-4,5,6,7-tetrahydropyrazolo[1,5-a]pyrazine(compound 242a, 100.0 mg, 0.38 mmol), (1R,2R)-N1,N2-dimethylcyclohexane-1,2-diamine (21.3 mg, 0.15 mmol), K₃PO₄ (161.9 mg, 0.76 mmol) and CuI (28.5 mg, 0.15 mmol) under N₂, and the reaction mixture was stirred at 120° C. for 12 hours, then filtered and concentrated in vacuo, and the residue was purified by prep-HPLC to give compound 327c as colorless oil (20 mg). LCMS (M+H⁺): 299.

Step 3: Preparation of (6S)-6-methyl-3-[(4R)-2-oxo-4-phenyl-oxazolidin-3-yl]-N-(3,4,5-trifluorophenyl)-6,7-dihydro-4H-pyrazolo[1,5-a]pyrazine-5-carboxamide (Example 327)

To a solution of (4R)-3-[(6S)-6-methyl-4,5,6,7-tetrahydropyrazolo[1,5-a]pyrazin-3-yl]-4-phenyl-oxazolidin-2-one (compound 327c, 20.0 mg, 0.067 mg) and DIPEA (17.3 mg, 0.134 mmol) in DMF (2 mL) was added phenyl (3,4,5- trifluorophenyl)carbamate (compound 233c, 19.7 mg, 0.074 mmol) at room temperature and the reaction mixture was stirred at room temperature for 2 hours. The reaction mixture was then purified by prep-HPLC to afford Example 327 as white solid (7.5 mg). LCMS (M+H$^+$): 472. $^1$H NMR (400 MHz, MeOD) δ ppm 7.45-7.25 (m, 8H), 5.44-5.29 (m, 1H), 4.94-4.92 (m, 2H), 4.84-4.74 (m, 1H), 4.56-4.48 (m, 1H), 4.45-4.36 (m, 1H), 4.24-4.15 (m, 1H), 4.09-4.00 (m, 1H), 1.19 (d, J=6.9 Hz, 3H)

Example 328

(6S)-6-methyl-3-[(4S)-2-oxo-4-phenyl-oxazolidin-3-yl]-N-(3,4,5-trifluorophenyl)-6,7-dihydro-4H-pyrazolo[1,5-a]pyrazine-5-carboxamide

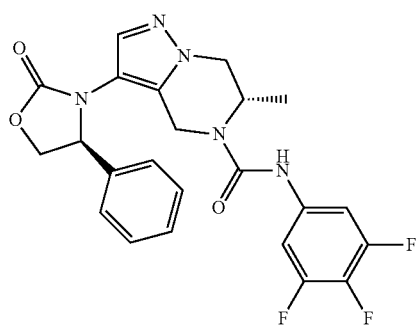 [SMILES: C[C@H]1Cn2ncc(N3C(=O)OC[C@@H]3c3ccccc3)c2CN1C(=O)Nc1cc(F)c(F)c(F)c1]

Preparation of Example 328

The title compound was prepared in analogy to Example 327 by using (2S)-2-amino-2-phenyl-ethanol instead of (2R)-2-amino-2-phenyl-ethanol (compound 327a). Example 328 was obtained as a white solid (12 mg). LCMS (M+H$^+$): 472. $^1$H NMR (400 MHz, MeOD) δ ppm 7.50-7.22 (m, 8H), 5.31 (dd, J=6.7, 8.8 Hz, 1H), 5.04-4.90 (m, 3H), 4.55-4.44 (m, 1H), 4.21 (dd, J=4.2, 12.9 Hz, 1H), 4.12-3.97 (m, 2H), 0.94 (d, J=6.9 Hz, 3H).

Example 329

(6S)-6-methyl-3-(2-oxo-4-phenyl-imidazolidin-1-yl)-N-(3,4,5-trifluorophenyl)-6,7-dihydro-4H-pyrazolo[1,5-a]pyrazine-5-carboxamide

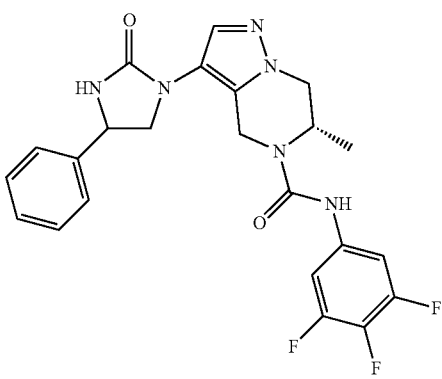 [SMILES: C[C@H]1Cn2ncc(N3CC(c4ccccc4)NC3=O)c2CN1C(=O)Nc1cc(F)c(F)c(F)c1]

The title compound was prepared according to the following scheme:

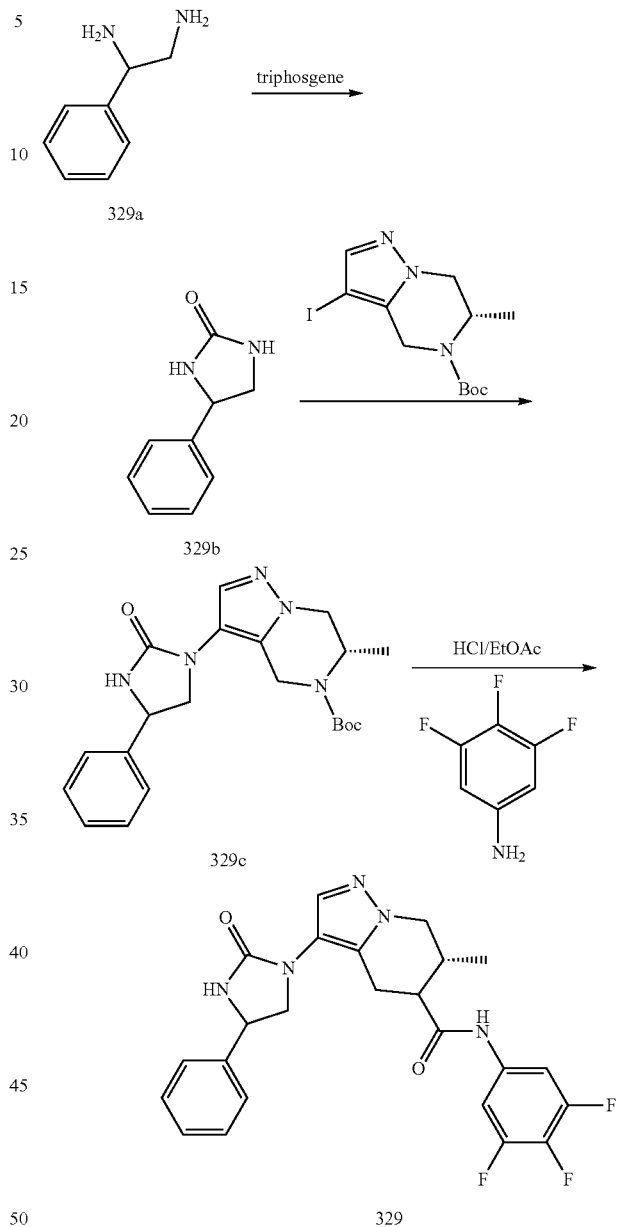

Step 1: Preparation of 4-phenylimidazolidin-2-one (compound 329b)

To a solution of 1-phenylethane-1,2-diamine (compound 329a, 300.0 mg 1.44 mmol) in THF (5 mL) was added DIPEA (557.3 mg, 4.32 mmol) and triphosgene (213.66 mg 0.72 mmol) while keeping inner temperature below 0° C. The reaction mixture was stirred at 30° C. for 12 hours, and then concentrated. The residue was purified by prep-HPLC to give compound 329b as a white solid (30 mg). LCMS: (M+H$^+$): 163

Step 2: Preparation of (6S)-tert-butyl 6-methyl-3-(2-oxo-4-phenylimidazolidin-1-yl)-6,7-dihydropyrazolo[1,5-a]pyrazine-5(4H)-carboxylate (compound 329c)

To a solution of 4-phenylimidazolidin-2-one (compound 329b, 47.2 mg, 0.13 mmol) in dioxane (5 mL) was added (1R,2R)-N1,N2-dimethylcyclohexane-1,2-diamine (2.84 mg, 0.02 mmol), (6S)-tert-butyl 3-iodo-6-methyl-6,7-dihydropyrazolo[1,5-a]pyrazine-5(4H)-carboxylate (compound 102d, 30.0 mg, 0.19 mmol), K$_3$PO$_4$ (54.93 mg, 0.26 mmol) and CuI (3.8 mg, 0.02 mmol) under N$_2$ at room temperature, and the reaction mixture was stirred at 110° C. for 12 hours. Then the reaction mixture was concentrated and the crude product was purified by prep-TLC to provide compound 329c as a green oil (70 mg) which was used directly without further purification. LCMS: (M+H$^+$): 398.

Step 3: Preparation of (6S)-6-methyl-3-(2-oxo-4-phenyl-imidazolidin-1-yl)-N-(3,4,5-trifluorophenyl)-6,7-dihydro-4H-pyrazolo[1,5-a]pyrazine-5-carboxamide (Example 329)

A solution of (6S)-tert-butyl 6-methyl-3-(2-oxo-4-phenylimidazolidin-1-yl)-6,7-dihydropyrazolo[1,5-a]pyrazine-5(4H)-carboxylate (compound 329c, 70.0 mg, 0.18 mmol) in HCl/EtOAc (5.0 mL) was stirred at room temperature for 12 hours, and then concentrated to give a crude product (60 mg) which was used directly without further purification.

To a mixture of 3,4,5-trifluoroaniline (52.9 mg 0.36 mmol) and DIPEA (92.9 mg, 0.72 mmol) in DCM (10.0 mL) was added triphosgene (32.65 mg 0.11 mmol) at 0° C. After 1 hour to the reaction mixture was added above obtained crude product (60.0 mg 0.18 mmol), and the resulting mixture was stirred at room temperature for 12 hours. Then the reaction mixture was concentrated and the residue was purified by prep-HPLC to give Example 329 as a white solid (12.3 mg). LCMS: (M+H$^+$): 471. $^1$H NMR (400 MHz, CDCl$_3$) δ ppm 8.19 (s, 1H), 7.54-7.36 (m, 7H), 7.34-7.30 (m, 2H), 5.22-5.18 (m, 1H), 5.01 (d, J=4.8 Hz, 1H), 4.44-4.39 (m, 1H), 4.31-4.26 (m, 1H), 4.13 (t, J=8.9 Hz, 1H), 4.03-3.98 (m, 1H), 3.84 (t, J=8.7 Hz, 1H), 3.69 (dd, J=6.1, 8.9 Hz, 1H), 1.43-1.39 (m, 3H)

Example 330

(6S)-3-(4,4-dimethyl-2-oxo-imidazolidin-1-yl)-6-methyl-N-(3,4,5-trifluorophenyl)-6,7-dihydro-4H-pyrazolo[1,5-a]pyrazine-5-carboxamide

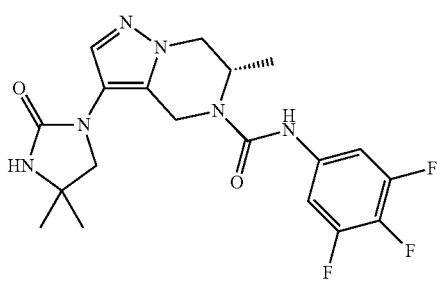 [SMILES: C[C@H]1Cn2ncc(N3CC(C)(C)NC3=O)c2CN1C(=O)Nc1cc(F)c(F)c(F)c1]

Preparation of (6S)-3-(4,4-dimethyl-2-oxo-imidazolidin-1-yl)-6-methyl-N-(3,4,5-trifluorophenyl)-6,7-dihydro-4H-pyrazolo[1,5-a]pyrazine-5-carboxamide (Example 330)

The title compound was prepared in analogy to Example 329 by using 2-methylpropane-1,2-diamine instead of 1-phenylethane-1,2-diamine (compound 329a). Example 330 was obtained as a white solid (5 mg). LCMS: (M+H$^+$): 423. $^1$H NMR (400 MHz, DMSO-d$_6$) δ ppm 9.17 (s, 1H), 8.46 (br. s., 1H), 7.50 (s, 1H), 7.43 (dd, J=6.4, 10.9 Hz, 2H), 5.00 (d, J=17.1 Hz, 1H), 4.85 (d, J=4.8 Hz, 1H), 4.42 (d, J=17.1 Hz, 1H), 4.20-4.14 (m, 1H), 4.12-4.05 (m, 1H), 3.52 (s, 1H), 3.48 (br. s., 1H), 2.10-2.04 (m, 3H), 1.28 (s, 3H), 1.14 (d, J=6.8 Hz, 3H).

Example 331

(6S)-6-methyl-3-(5-oxo-4-oxa-6-azaspiro[2.4]heptan-6-yl)-N-(3,4,5-trifluorophenyl)-6,7-dihydro-4H-pyrazolo[1,5-a]pyrazine-5-carboxamide

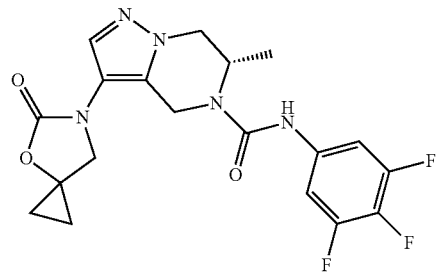 [SMILES: C[C@H]1Cn2ncc(N3CC4(CC4)OC3=O)c2CN1C(=O)Nc1cc(F)c(F)c(F)c1]

Preparation of (6S)-6-methyl-3-(5-oxo-4-oxa-6-azaspiro[2.4]heptan-6-yl)-N-(3,4,5-trifluorophenyl)-6,7-dihydro-4H-pyrazolo[1,5-a]pyrazine-5-carboxamide (Example 331)

The title compound was prepared in analogy to Example 329 by using 1-(aminomethyl)cyclopropanol instead of 1-phenylethane-1,2-diamine (compound 329a). Example 331 (24 mg) was obtained as white solid. LCMS: (M+H$^+$): 422. $^1$H NMR (400 MHz, MeOD) δ ppm 7.66 (s, 1H), 7.28 (dd, J=6.3, 10.2 Hz, 2H), 5.08 (d, J=16.9 Hz, 1H), 5.02-4.93 (m, 1H), 4.54 (d, J=16.9 Hz, 1H), 4.32-4.25 (m, 1H), 4.17-4.08 (m, 3H), 1.26-1.21 (m, 5H), 0.94-0.86 (m, 2H).

Example 332

(6S)-6-methyl-3-(6-oxo-5-oxa-7-azaspiro[3.4]octan-7-yl)-N-(3,4,5-trifluorophenyl)-6,7-dihydro-4H-pyrazolo[1,5-a]pyrazine-5-carboxamide

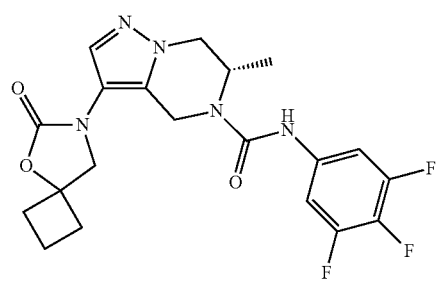 [SMILES: C[C@H]1Cn2ncc(N3CC4(CCC4)OC3=O)c2CN1C(=O)Nc1cc(F)c(F)c(F)c1]

Preparation of (6S)-6-methyl-3-(6-oxo-5-oxa-7-azaspiro[3.4]octan-7-yl)-N-(3,4,5-trifluorophenyl)-6,7-dihydro-4H-pyrazolo[1,5-a]pyrazine-5-carboxamide (Example 332)

The title compound was prepared in analogy to Example 329 by using 1-(aminomethyl)cyclobutanol instead of 1-phenylethane-1,2-diamine (compound 329a). Example 332 (15.0 mg) was obtained as white solid. LCMS: (M+H⁺): 437. ¹H NMR (400 MHz, MeOD) δ ppm 7.64 (s, 1H), 7.33-7.23 (m, 2H), 5.06 (d, J=16.8 Hz, 1H), 5.01-4.94 (m, 1H), 4.53 (d, J=16.8 Hz, 1H), 4.29 (dd, J=4.3, 12.8 Hz, 1H), 4.19-4.06 (m, 3H), 2.64-2.52 (m, 2H), 2.39 (m, J=3.8, 8.4, 12.4 Hz, 2H), 2.00-1.88 (m, 1H), 1.83-1.68 (m, 1H), 1.26 (d, J=7.0 Hz, 3H).

Example 333 methyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate

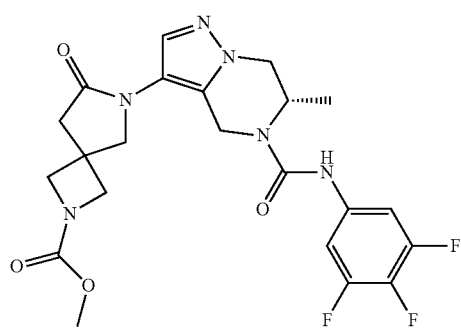 [SMILES: COC(=O)N1CC2(CC(=O)N(c3cnn4c3CN(C(=O)Nc3cc(F)c(F)c(F)c3)[C@@H](C)C4)C2)C1]

The title compound was prepared according to the following scheme:

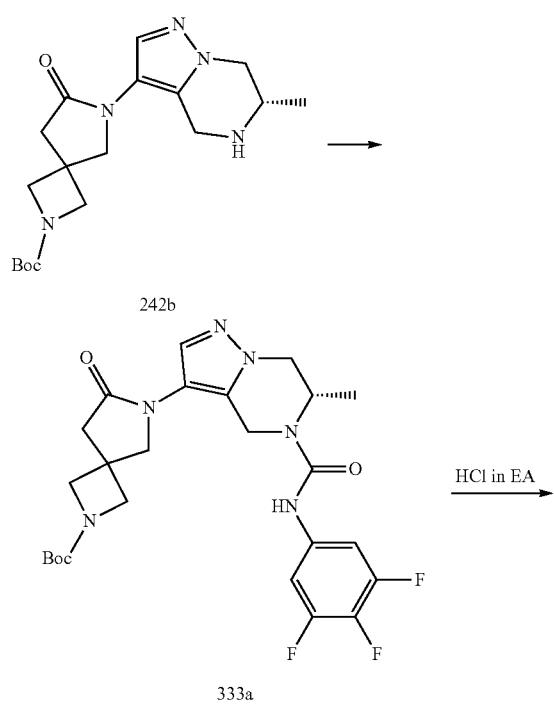

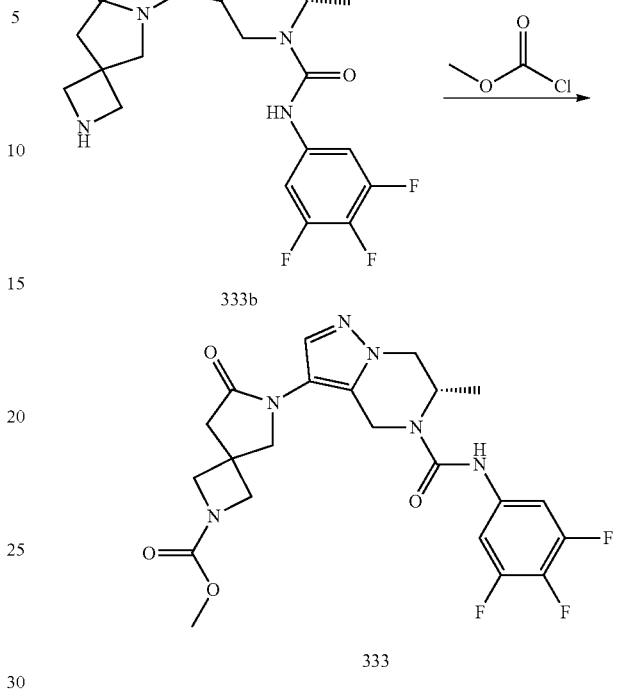

Step 1: Preparation of tert-butyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate (compound 333a)

A mixture of 3,4,5-trifluoroaniline (244.0 mg, 1.66 mmol), DIPEA (428 mg, 3.32 mmol) and triphosgene (148 mg 0.5 mmol) in DCM (10 mL) was stirred at 0° C. for 1 hour, to which was added tert-butyl 6-[(6S)-6-methyl-4,5,6,7-tetrahydropyrazolo[1,5-a]pyrazin-3-yl]-7-oxo-2,6-diazaspiro[3.4]octane-2-carboxylate (compound 242b, 300.0 mg 0.83 mmol). The resulting mixture was stirred at room temperature for 12 hours, and was concentrated. The residue was purified by prep-HPLC to give compound 333a (60.0 mg) as a white solid. LCMS (M+H⁺): 535

Step 2: Preparation of (6S)-6-methyl-3-(7-oxo-2,6-diazaspiro[3.4]octan-6-yl)-N-(3,4,5-trifluorophenyl)-6,7-dihydro-4H-pyrazolo[1,5-a]pyrazine-5-carboxamide (compound 333b)

A solution of tert-butyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate (compound 333a, 60 mg, 0.11 mmol) in HCl/EtOAc (10 mL) was stirred at room temperature for 1 hour, and then was concentrated to provide crude compound 333b (60 mg).

Step 3: Preparation of methyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate (Example 333)

To a solution of (6S)-6-methyl-3-(7-oxo-2,6-diazaspiro[3.4]octan-6-yl)-N-(3,4,5-trifluorophenyl)-6,7-dihydro-4H- pyrazolo[1,5-a]pyrazine-5-carboxamide (compound 333b, 20 mg) in DCM (5 mL) was added Et₃N (10 mg) and methyl carbonochloridate (6 mg). The reaction mixture was stirred at 25° C. for 1 hour, and then concentrated in vacuo. The obtained residue was purified by prep-HPLC to give Example 333 (16 mg) as a white solid. LCMS (M+1): 493. ¹H NMR (400 MHz, DMSO-d₆) δ ppm 9.12 (s, 1H), 7.60 (s, 1H), 7.45-7.39 (m, 2H), 4.96 (d, J=17.1 Hz, 1H), 4.88-4.79 (m, 1H), 4.38 (d, J=17.3 Hz, 1H), 4.24-4.16 (m, 1H), 4.15-4.08 (m, 1H), 4.02-3.93 (m, 5H), 3.57 (s, 3H), 2.77 (s, 2H), 2.08 (s, 1H), 1.14 (d, J=6.8 Hz, 3H).

Example 334 ethyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate

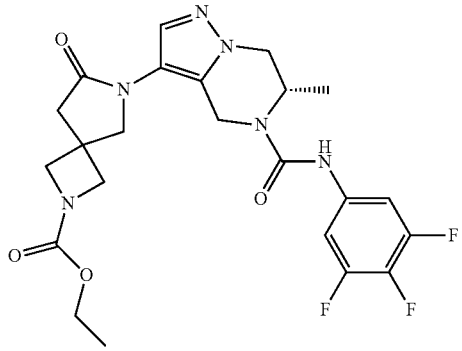 [SMILES: CCOC(=O)N1CC2(CC(=O)N(c3cnn4c3CN(C(=O)Nc3cc(F)c(F)c(F)c3)[C@@H](C)C4)C2)C1]

Preparation of Example 334

The title compound was prepared in analogy to Example 333 by using ethyl carbonochloridate instead of methyl carbonochloridate. Example 334 (16 mg) was obtained as a white solid. LCMS: (M+H⁺): 507. ¹H NMR (400 MHz, DMSO-d₆) δ ppm 9.12 (s, 1H), 7.61 (s, 1H), 7.45-7.39 (m, 2H), 4.96 (d, J=17.1 Hz, 1H), 4.90-4.80 (m, 1H), 4.38 (d, J=17.1 Hz, 1H), 4.23-4.16 (m, 1H), 4.15-4.08 (m, 1H), 4.04-3.90 (m, 7H), 2.76 (s, 2H), 2.08 (s, 1H), 1.24-1.08 (m, 6H).

Example 335

(6S)-6-methyl-3-(5-methyl-2-oxo-pyrrolidin-3-yl)-N-(3,4,5-trifluorophenyl)-6,7-dihydro-4H-pyrazolo[1,5-a]pyrazine-5-carboxamide

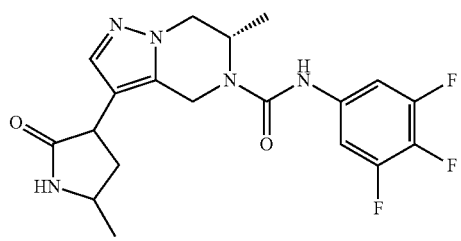 [SMILES: CC1CC(c2cnn3c2CN(C(=O)Nc2cc(F)c(F)c(F)c2)[C@@H](C)C3)C(=O)N1]

Preparation of Example 335

The title compound was prepared in analogy to Example 308 by using nitroethane instead of nitromethane. Example 335 (5 mg) was obtained as a white solid. LCMS (M+H⁺): 408. ¹H NMR (400 MHz, MeOD) δ ppm 7.45-7.55 (m, 1H), 7.20-7.37 (m, 2H), 4.96-5.19 (m, 2H), 4.43-4.58 (m, 1H), 4.25-4.32 (m, 1H), 4.09-4.19 (m, 1H), 3.72-3.97 (m, 2H), 1.77-2.70 (m, 2H), 1.13-1.36 (m, 6H).

Example 336

(6S)-6-methyl-3-[2-(oxazole-2-carbonyl)-7-oxo-2,6-diazaspiro[3.4]octan-6-yl]-N-(3,4,5-trifluorophenyl)-6,7-dihydro-4H-pyrazolo[1,5-a]pyrazine-5-carboxamide

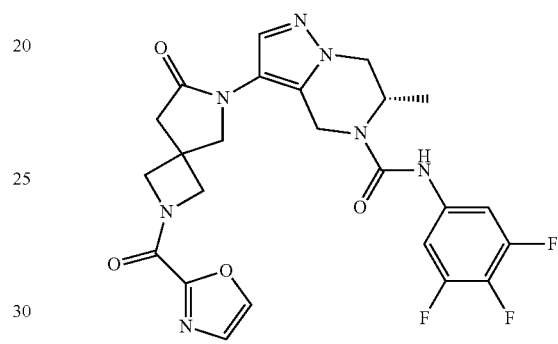

Preparation of Example 336

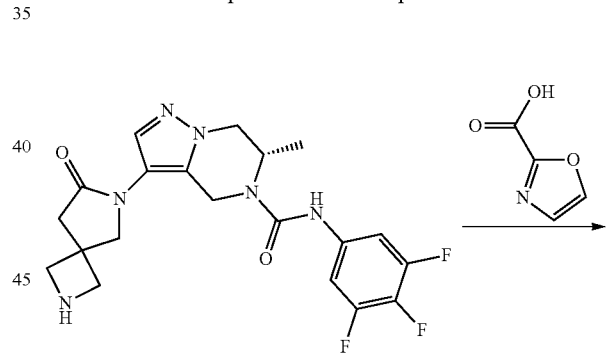

333b

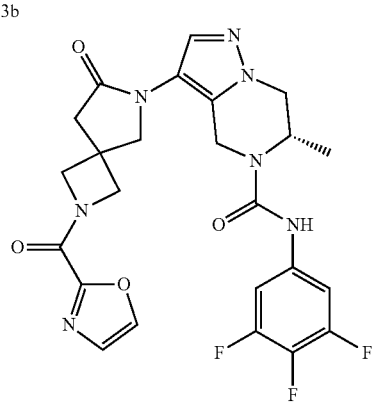

336

A mixture of (6S)-6-methyl-3-(7-oxo-2,6-diazaspiro[3.4]octan-6-yl)-N-(3,4,5-trifluorophenyl)-6,7-dihydro-4H-pyrazolo[1,5-a]pyrazine-5-carboxamide (compound 333b, 120.0 mg, 0.28 mmol), oxazole-2-carboxylic acid (35.1 mg, 0.31 mmol), DIPEA (144.5 mg, 1.14 mmol), EDCI (98.0 mg, 0.84 mmol) and HOBt (113.5 mg, 0.84 mmol) in DMF (5 mL) was stirred at 30° C. for 12 hours, and then concentrated in vacuo. The crude product was purified by prep-HPLC to give Example 336 (6.7 mg) as a white solid. LCMS (M+H⁺): 530. ¹H NMR (400 MHz, MeOD) δ ppm 8.10 (s, 1H), 7.66 (s, 1H), 7.40 (s, 1H), 7.33-7.26 (m, 2H), 5.03 (s, 1H), 4.99-4.94 (m, 1H), 4.83-4.75 (m, 2H), 4.52 (d, J=17.1 Hz, 1H), 4.35-4.27 (m, 3H), 4.19-4.10 (m, 3H), 2.97 (s, 2H), 1.28 (d, J=6.8 Hz, 3H).

Example 337

(6S)-6-methyl-3-(7-oxo-2-pyrimidin-2-yl-2,6-diazaspiro[3.4]octan-6-yl)-N-(3,4,5-trifluorophenyl)-6,7-dihydro-4H-pyrazolo[1,5-a]pyrazine-5-carboxamide

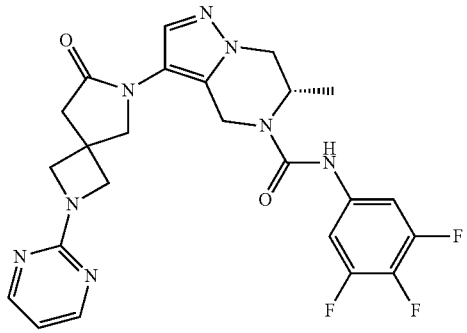 [SMILES: C[C@H]1Cn2ncc(N3CC4(CC3=O)CN(c3ncccn3)C4)c2CN1C(=O)Nc1cc(F)c(F)c(F)c1]

Preparation of Example 337

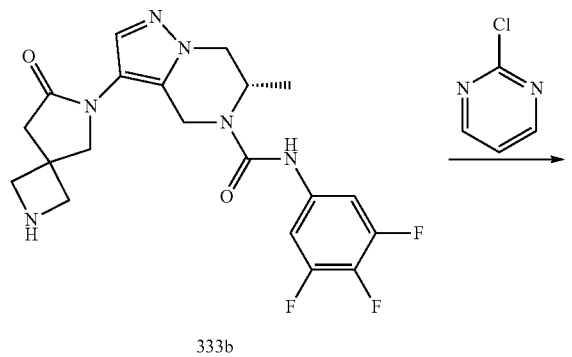

333b

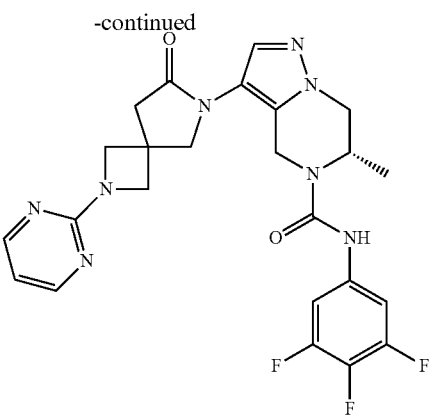

337

A mixture of (6S)-6-methyl-3-(7-oxo-2,6-diazaspiro[3.4]octan-6-yl)-N-(3,4,5-trifluorophenyl)-6,7-dihydro-4H-pyrazolo[1,5-a]pyrazine-5-carboxamide (compound 333b, 120.0 mg, 0.28 mmol), 2-chloropyrimidine (42.0 mg, 0.36 mmol), Cs₂CO₃ (81.6 mg, 0.6 mmol), Pd(dba)₂ (55.2 mg, 0.06 mmol), Xantphos (CAS:161265-03-8, 34.8 mg, 0.06 mmol) in dioxane (5 mL) was stirred at 90° C. in microwave and under N₂ for 2 hours. The reaction mixture was concentrated and the residue was purified by prep-HPLC to give Example 337 as a yellow solid (5.6 mg). LCMS (M+H⁺): 513. ¹H NMR (400 MHz, MeOD) δ ppm 8.37 (d, J=5.0 Hz, 2H), 7.67 (s, 1H), 7.33-7.25 (m, 2H), 6.74 (t, J=4.9 Hz, 1H), 5.05 (d, J=16.8 Hz, 1H), 4.98 (d, J=5.3 Hz, 1H), 4.62 (s, 2H), 4.54 (d, J=16.8 Hz, 1H), 4.33-4.23 (m, 3H), 4.21-4.13 (m, 3H), 2.95 (s, 2H), 1.28 (d, J=7.0 Hz, 3H).

Example 338

(6S)-6-methyl-3-(2-oxoindolin-1-yl)-N-(3,4,5-trifluorophenyl)-6,7-dihydro-4H-pyrazolo[1,5-a]pyrazine-5-carboxamide

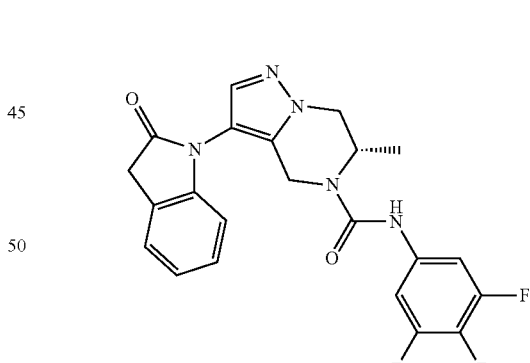

Preparation of Example 338

The title compound was prepared in analogy to Example 223 by using indolin-2-one instead of pyrrolidin-2-one and phenyl N-[3,4,5-trifluoro-phenyl]carbamate (compound 233c) instead of phenyl N-[2-(difluoromethyl)-4-pyridyl]carbamate (compound 218c). Example 338 was obtained as a grey solid (38 mg). LCMS (M+H⁺): 442. ¹H NMR (400 MHz, MeOD) δ ppm 7.73 (s, 1H), 7.36 (d, J=7.4 Hz, 1H), 7.28-7.21 (m, 3H), 7.13-7.08 (m, 1H), 6.82 (d, J=7.9 Hz, 1H), 5.04-4.98 (m, 1H), 4.96-4.91 (m, 1H), 4.44-4.33 (m, 2H), 4.26-4.20 (m, 1H), 3.74 (s, 2H), 1.29 (d, J=6.9 Hz, 3H).

Example 339

(6S)-6-methyl-3-(1-oxoisoindolin-2-yl)-N-(3,4,5-trifluorophenyl)-6,7-dihydro-4H-pyrazolo[1,5-a]pyrazine-5-carboxamide

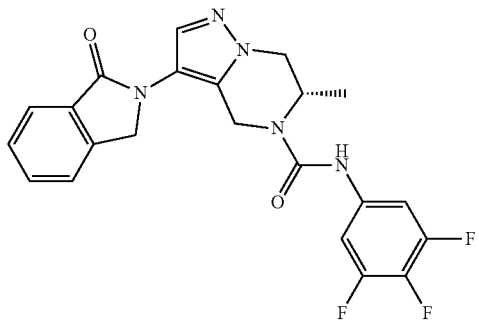 [SMILES: C[C@H]1Cn2ncc(N3Cc4ccccc4C3=O)c2CN1C(=O)Nc1cc(F)c(F)c(F)c1]

Preparation of Example 339

The title compound was prepared in analogy to Example 223 by using isoindolin-1-one instead of pyrrolidin-2-one and phenyl N-[3,4,5-trifluoro-phenyl]carbamate (compound 233c) instead of phenyl N-[2-(difluoromethyl)-4-pyridyl]carbamate (compound 218c). Example 339 was obtained as a grey solid (200 mg). LCMS (M+H$^+$): 442. $^1$H NMR (400 MHz, MeOD) δ ppm 7.82 (d, J=7.7 Hz, 1H), 7.77 (s, 1H), 7.63 (s, 2H), 7.54 (s, 1H), 7.29-7.21 (m, 2H), 5.12 (d, J=16.8 Hz, 1H), 4.99 (br. s., 1H), 4.89 (d, J=10.3 Hz, 2H), 4.61 (d, J=16.9 Hz, 1H), 4.33-4.26 (m, 1H), 4.21-4.15 (m, 1H), 1.28 (d, J=6.9 Hz, 3H).

Example 340

(6S)-6-methyl-3-(5-oxo-7H-pyrrolo[3,4-b]pyridin-6-yl)-N-(3,4,5-trifluorophenyl)-6,7-dihydro-4H-pyrazolo[1,5-a]pyrazine-5-carboxamide

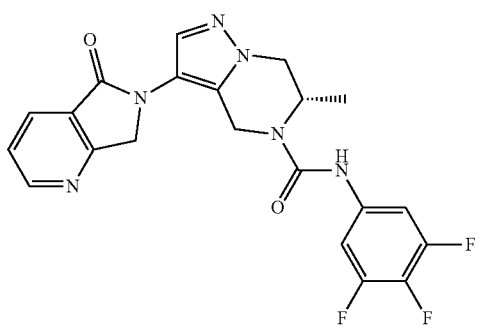 [SMILES: C[C@H]1Cn2ncc(N3Cc4ncccc4C3=O)c2CN1C(=O)Nc1cc(F)c(F)c(F)c1]

Preparation of Example 340

The title compound was prepared in analogy to Example 223 by using 6,7-dihydropyrrolo[3,4-b]pyridin-5-one instead of pyrrolidin-2-one and phenyl N-[3,4,5-trifluoro-phenyl]carbamate (compound 233c) instead of phenyl N-[2-(difluoromethyl)-4-pyridyl]carbamate (compound 218c). Example 340 was obtained as a grey solid (90 mg). LCMS (M+H$^+$): 443. $^1$H NMR (400 MHz, MeOD) δ ppm 8.80 (dd, J=1.4, 5.0 Hz, 1H), 8.24 (dd, J=1.4, 7.7 Hz, 1H), 7.82 (s, 1H), 7.61 (dd, J=5.0, 7.8 Hz, 1H), 7.29-7.22 (m, 2H) 5.14 (d, J=16.9 Hz, 1H), 4.98 (d, J=8.8 Hz, 3H), 4.61 (d, J=16.9 Hz, 1H), 4.35-4.29 (m, 1H), 4.23-4.17 (m, 1H), 1.30 (d, J=6.9 Hz, 3H).

Example 341

(6S)-3-(5-fluoropyrimidin-2-yl)-6-methyl-N-(3,4,5-trifluorophenyl)-6,7-dihydro-4H-pyrazolo[1,5-a]pyrazine-5-carboxamide

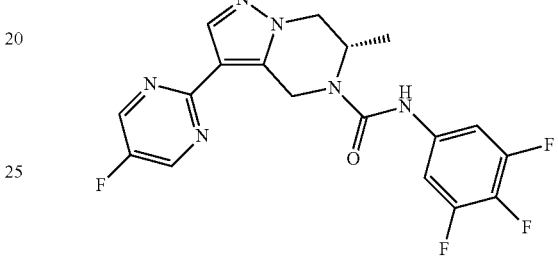

Preparation of Example 341

The title compound was prepared in analogy to Example 223 by using tert-butyl (6S)-3-(5-fluoropyrimidin-2-yl)-6-methyl-6,7-dihydro-4H-pyrazolo[1,5-a]pyrazine-5-carboxylate (compound 288b) instead of tert-butyl (6S)-6-methyl-3-(2-oxopyrrolidin-1-yl)-6,7-dihydro-4H-pyrazolo[1,5-a]pyrazine-5-carboxylate (compound 223b) and phenyl N-(3,4,5-trifluoro-phenyl)carbamate (compound 233c) instead of phenyl N-[2-(difluoromethyl)-4-pyridyl]carbamate (compound 218c). Example 341 was obtained as a white solid (16.8 mg). LCMS: (M+H$^+$): 407. $^1$H NMR (400 MHz, MeOD) δ ppm 8.72 (d, J=0.6 Hz, 2H), 8.18 (s, 1H), 7.32-7.23 (m, 2H), 5.50 (d, J=18.4 Hz, 1H), 5.00-4.93 (m, 1H), 4.80 (d, J=18.3 Hz, 1H), 4.37 (dd, J=4.3, 12.9 Hz, 1H), 4.25-4.19 (m, 1H), 1.27 (d, J=6.9 Hz, 3H).

Example 342

(6S)-3-[4-(hydroxymethyl)pyrazol-1-yl]-6-methyl-N-(3,4,5-trifluorophenyl)-6,7-dihydro-4H-pyrazolo[1,5-a]pyrazine-5-carboxamide

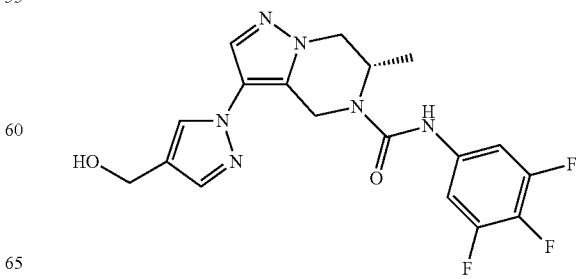

The title compound was prepared according to the following scheme:

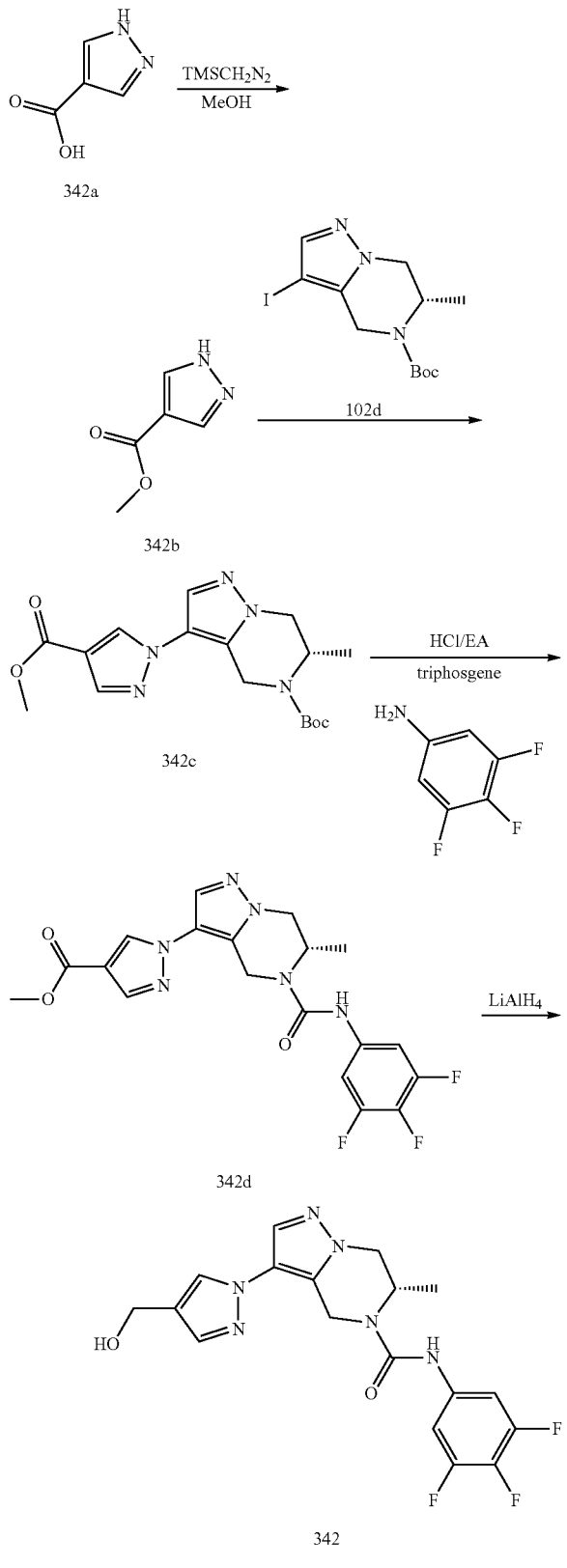

Step 1: Preparation of methyl 1H-pyrazole-4-carboxylate (compound 342b)

To a solution of 1H-pyrazole-4-carboxylic acid (450.0 mg, 4.01 mmol) in MeOH (15.0 mL) was added TMSCH$_2$N$_2$ (20.1 mL, 40.1 mmol), and the reaction mixture was stirred at room temperature for 2 hours. The reaction mixture was concentrated to give crude compound 342b as a white solid (500 mg). LCMS (M+H$^+$): 127. $^1$H NMR (400 MHz, DMSO-d$_6$) δ ppm 8.16-8.08 (m, 2H), 3.74 (s, 3H).

Step 2: Preparation of methyl tert-butyl (6S)-3-(4-methoxycarbonylpyrazol-1-yl)-6-methyl-6,7-dihydro-4H-pyrazolo[1,5-a]pyrazine-5-carboxylate (compound 342c)

To a solution of tert-butyl (6S)-3-iodo-6-methyl-6,7-dihydro-4H-pyrazolo[1,5-a]pyrazine-5-carboxylate (compound 102d, 363.0 mg, 1.0 mmol) in CH$_3$CN (5 mL) was added methyl 1H-pyrazole-4-carboxylate (compound 342b, 189.2 mg, 1.5 mmol), (1R,2R)-N1,N2-dimethylcyclohexane-1,2-diamine (14.2 mg, 0.1 mmol), Cs$_2$CO$_3$ (651.6 mg, 2.0 mmol) and Cu$_2$O (18.9 mg, 0.1 mmol) under N$_2$ at room temperature, and the reaction mixture was stirred at 80° C. for 12 hours. The solvent was removed in vacuo, and the residue was purified by silica gel column chromatography(PE/EtOAc: 10/1 to 1/1) to give compound 342c as a colorless oil (50.0 mg). LCMS: (M+H$^+$): 362.

Step 3: Preparation of methyl 1-[(6S)-6-methyl-5-[(3,4,5-trifluorophenyl)carbamoyl]-6,7-dihydro-4H-pyrazolo[1,5-a]pyrazin-3-yl]pyrazole-4-carboxylate (compound 342d)

Compound 342d was prepared in analogy to the preparation of Example 11 by using 3,4,5-trifluoroaniline instead of 3-(trifluoromethyl)aniline, and methyl tert-butyl (6S)-3-(4-methoxycarbonylpyrazol-1-yl)-6-methyl-6,7-dihydro-4H-pyrazolo[1,5-a]pyrazine-5-carboxylate (compound 342c) instead of tert-butyl 3-(4-fluorophenyl)-6,7-dihydro-4H-pyrazolo[1,5-a]pyrazine-5-carboxylate (compound 11a). Compound 342d was obtained as white solid (20 mg). LCMS (M+H$^+$): 435.

Step 4: Preparation of (6S)-3-[4-(hydroxymethyl)pyrazol-1-yl]-6-methyl-N-(3,4,5-trifluorophenyl)-6,7-dihydro-4H-pyrazolo[1,5-a]pyrazine-5-carboxamide (Example 342)

To a solution of methyl 1-[(6S)-6-methyl-5-[(3,4,5-trifluorophenyl)carbamoyl]-6,7-dihydro-4H-pyrazolo[1,5-a]pyrazin-3-yl]pyrazole-4-carboxylate (compound 342d) (20.0 mg, 0.046 mmol) in THF (5.0 mL) was added LiAlH$_4$ (3.5 mg, 0.092 mmol) at 0° C. The resulting reaction mixture was stirred at 0° C. for 1 hour. After a few drops of water was added, the solvent was removed in vacuo, and the residue was purified by prep-HPLC to give Example 342 as white solid (7.7 mg). LCMS: (M+H$^+$): 407. $^1$H NMR (400 MHz, MeOD) δ ppm 7.94 (s, 1H), 7.82 (s, 1H), 7.69 (s, 1H), 7.31-7.23 (m, 2H) 5.23 (d, J=16.7 Hz, 1H), 4.99 (br. s., 1H), 4.66 (d, J=17.2 Hz, 1H), 4.59 (s, 2H), 4.38-4.29 (m, 1H), 4.24-4.16 (m, 1H), 1.28 (d, J=6.7 Hz, 3H).

Example 343

(6S)-3-[4-(methoxymethyl)pyrazol-1-yl]-6-methyl-N-(3,4,5-trifluorophenyl)-6,7-dihydro-4H-pyrazolo[1,5-a]pyrazine-5-carboxamide

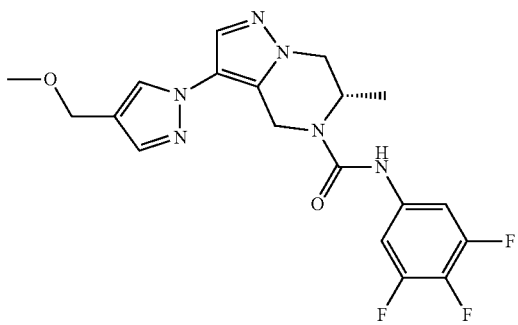 [SMILES: COCc1cnn(-c2cnn3c2CN(C(=O)Nc2cc(F)c(F)c(F)c2)[C@@H](C)C3)c1]

The title compound was prepared according to the following scheme:

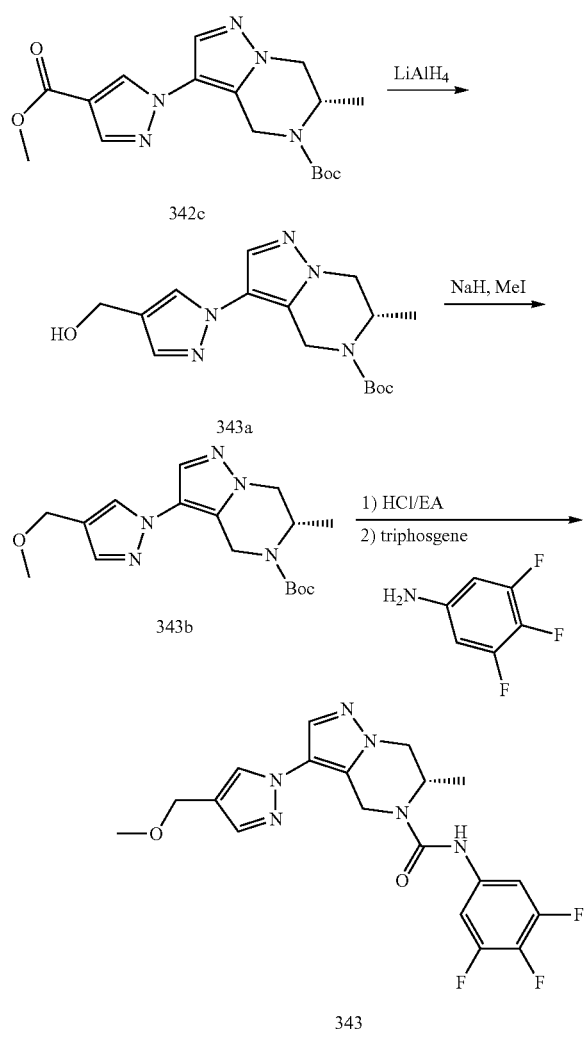

Step 1: Preparation of tert-butyl (6S)-3-[4-(hydroxymethyl)pyrazol-1-yl]-6-methyl-6,7-dihydro-4H-pyrazolo[1,5-a]pyrazine-5-carboxylate (compound 343a)

To a solution of methyl tert-butyl (6S)-3-(4-methoxycarbonylpyrazol-1-yl)-6-methyl-6,7-dihydro-4H-pyrazolo[1,5-a]pyrazine-5-carboxylate (compound 342c, 50.0 mg, 0.14 mmol) in THF (5 mL) was added LiAlH$_4$ (5.3 mg, 0.14 mmol) and the reaction mixture was stirred at 5° C. for 1 hour. The reaction mixture was poured into ice-water (5 mL) and extracted with EtOAc (20 mL), the organic layer was concentrated in vacuo to provide the crude product compound 343a as a yellow oil (30.0 mg). LCMS: (M+H$^+$): 334.2

Step 2: Preparation of tert-butyl (6S)-3-[4-(methoxymethyl)pyrazol-1-yl]-6-methyl-6,7-dihydro-4H-pyrazolo[1,5-a]pyrazine-5-carboxylate (compound 343b)

To a solution of tert-butyl (6S)-3-[4-(hydroxymethyl)pyrazol-1-yl]-6-methyl-6,7-dihydro-4H-pyrazolo[1,5-a]pyrazine-5-carboxylate (compound 343a, 30.0 mg, 0.089 mmol) in THF (5 mL) was added NaH (4.32 mg, 0.11 mmol) and CH$_3$I (15.3 mg, 0.11 mmol) at 0° C. The reaction mixture was stirred at 30° C. for 1 hour, quenched with aqueous NH$_4$Cl solution and extracted with EtOAc (20 mL). The organic layer was concentrated to give crude compound 342b as a colorless oil (30 mg), which was used in next step directly without further purification. LCMS: (M+H$^+$): 348.

Step 3: Preparation of (6S)-3-[4-(methoxymethyl)pyrazol-1-yl]-6-methyl-N-(3,4,5-trifluorophenyl)-6,7-dihydro-4H-pyrazolo[1,5-a]pyrazine-5-carboxamide (Example 343)

The title compound was prepared in analogy to the preparation of Example 11 by 3,4,5-trifluoroaniline instead of 3-(trifluoromethyl)aniline, and tert-butyl (6S)-3-[4-(methoxymethyl)pyrazol-1-yl]-6-methyl-6,7-dihydro-4H-pyrazolo[1,5-a]pyrazine-5-carboxylate (compound 343b) instead of tert-butyl 3-(4-fluorophenyl)-6,7-dihydro-4H-pyrazolo[1,5-a]pyrazine-5-carboxylate (compound 11a). Example 343 was obtained as a white solid (5.3 mg). LCMS: (M+H$^+$): 421. $^1$H NMR (400 MHz, MeOD) δ ppm 8.01 (s, 1H), 7.85 (s, 1H), 7.72 (s, 1H), 7.34-7.26 (m, 2H) 5.26 (d, J=17.1 Hz, 1H), 5.05-4.98 (m, 1H), 4.69 (d, J=17.1 Hz, 1H), 4.46 (s, 2H), 4.39-4.32 (m, 1H), 4.25-4.20 (m, 1H), 3.40 (s, 3H), 1.30 (d, J=6.9 Hz, 3H).

Example 344

(6S)-6-methyl-3-(2-oxo-5-phenyl-oxazolidin-3-yl)-N-(3,4,5-trifluorophenyl)-6,7-dihydro-4H-pyrazolo[1,5-a]pyrazine-5-carboxamide

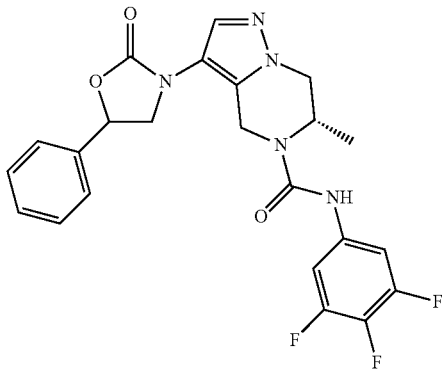 [SMILES: C[C@H]1Cn2ncc(N3CC(c4ccccc4)OC3=O)c2CN1C(=O)Nc1cc(F)c(F)c(F)c1]

The title compound was prepared according to the following scheme:

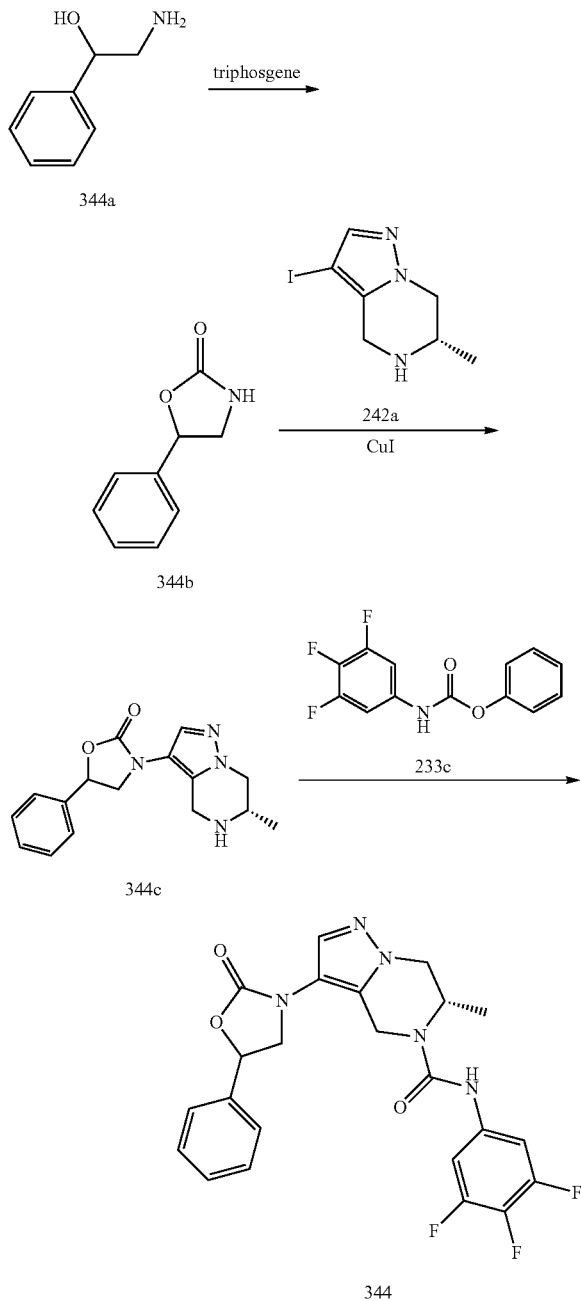

Step 1: Preparation of 5-phenyloxazolidin-2-one (compound 344b)

To a solution of 2-amino-1-phenyl-ethanol (compound 344a, 1.1 g, 8.0 mmol) and TEA (2.4 g, 24.0 mmol) in DCM (10.0 mL) was added triphosgene (0.71 g, 2.4 mmol) at 0° C. The reaction mixture was stirred at room temperature for 12 hours, and then concentrated in vacuo. The resulting residue was purified by prep-HPLC to give compound 344b as a white solid (290 mg). LCMS (M+H$^+$): 164.

Step 2: Preparation of 3-[(6S)-6-methyl-4,5,6,7-tetrahydropyrazolo[1,5-a]pyrazin-3-yl]-5-phenyl-oxazolidin-2-one (compound 344c)

To a solution of 5-phenyloxazolidin-2-one (compound 344b, 75.1 mg, 0.46 mmol) in dioxane (3 mL) was added (6S)-3-iodo-6-methyl-4,5,6,7-tetrahydropyrazolo[1,5-a]pyrazine (compound 242a, 100.0 mg, 0.38 mmol), (1R,2R)-N1,N2-dimethylcyclohexane-1,2-diamine (5.6 mg, 0.04 mmol) K$_3$PO$_4$ (160.6 mg, 0.76 mmol), and CuI (7.6 mg, 0.04 mmol). The reaction mixture was flushed with nitrogen and stirred at 120° C. for 15 hours. The reaction mixture was then filtered and the filtrate was concentrated in vacuo. The resulting residue was purified by silica gel column (DCM:MeOH=30:1-10:1) to give compound 344c as a yellow oil (80.0 mg). LCMS (M+H$^+$): 299.

Step 3: Preparation of (6S)-6-methyl-3-(2-oxo-5-phenyl-oxazolidin-3-yl)-N-(3,4,5-trifluorophenyl)-6,7-dihydro-4H-pyrazolo[1,5-a]pyrazine-5-carboxamide (Example 344)

To a solution of 3-[(6S)-6-methyl-4,5,6,7-tetrahydropyrazolo[1,5-a]pyrazin-3-yl]-5-phenyl-oxazolidin-2-one (compound 344c, 62.8 mg 0.3 mmol) in DCM (2.0 mL) was added DIPEA (104.5 mg, 0.8 mmol), and a solution of phenyl N-(3,4,5-trifluorophenyl)carbamate (compound 233c, 80.0 mg 0.27 mmol) in DCM (1.0 mL). The reaction mixture was stirred at 20° C. for 3 hrs, and concentrated in vacuo. The residue was purified by prep-HPLC to give Example 344 (16 mg). LCMS (M+H$^+$): 472. $^1$H NMR (400 MHz, CD$_3$OD) δ ppm 7.69 (d, J=1.76 Hz, 1 H), 7.56-7.40 (m, 5 H), 7.29 (ddd, J=10.29, 6.40, 3.64 Hz, 2 H), 5.80 (t, J=8.16 Hz, 1 H), 5.12 (dd, J=16.94, 4.64 Hz, 1 H), 5.02-4.94 (m, 1H), 4.58 (d, J=17.32 Hz, 1 H), 4.42 (dt, J=13.80, 8.78 Hz, 1 H), 4.35-4.27 (m, 1 H), 4.21-4.14 (m, 1 H), 3.99 (dt, J=11.86, 8.38 Hz, 1 H), 1.32-1.26 (m, 3 H).

Example 345

(6S)-6-methyl-3-[2-oxo-5-(2-pyridyl)oxazolidin-3-yl]-N-(3,4,5-trifluorophenyl)-6,7-dihydro-4H-pyrazolo[1,5-a]pyrazine-5-carboxamide

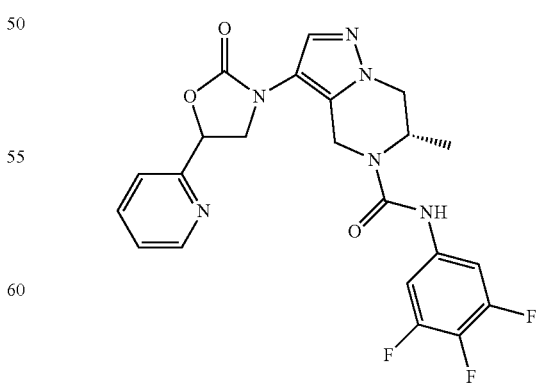

The title compound was prepared according to the following scheme:

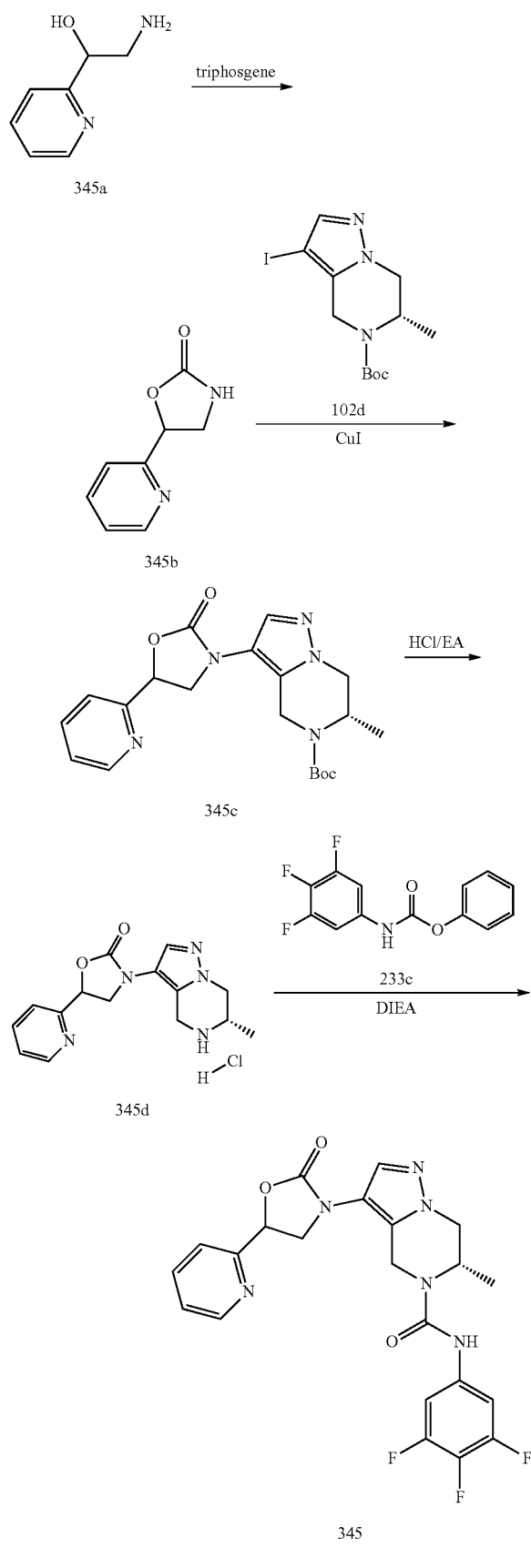

Step 1: Preparation of 5-(2-pyridyl)oxazolidin-2-one (compound 345b)

To a solution of 2-amino-1-(2-pyridyl)ethanol (compound 345a, 200.0 mg, 1.45 mmol) in DCM (2 mL) was added DIPEA (560.9 mg, 4.34 mmol), and triphosgene (214.8 mg, 0.72 mmol). The reaction mixture was stirred at room temperature for 5 hours, and then concentrated in vacuo and purified by prep-TLC (DCM:MeOH=10:1) to afford compound 345b as a yellow oil (107.0 mg). LCMS (M+H$^+$): 165.

Step 2: Preparation of tert-butyl (6S)-6-methyl-3-[2-oxo-5-(2-pyridyl)oxazolidin-3-yl]-6,7-dihydro-4H-pyrazolo[1,5-a]pyrazine-5-carboxylate (compound 345c)

To a mixture of 5-(2-pyridyl)oxazolidin-2-one (compound 345b, 80.0 mg, 0.49 mmol), CuI (18.6 mg, 0.10 mmol), K$_3$PO$_4$ (206.9 mg, 0.97 mmol) and (1R,2R)-N1,N2-dimethylcyclohexane-1,2-diamine (14.2 mg, 0.10 mmol) in dioxane (2 mL) was added tert-butyl (6S)-3-iodo-6-methyl-6,7-dihydro-4H-pyrazolo[1,5-a]pyrazine-5-carboxylate (compound 102d, 177.0 mg, 0.49 mmol). The reaction mixture was stirred at 100° C. for 15 hours, and then filtered and concentrated in vacuo. The resulting residue was purified by prep-TLC (DCM:MeOH=10:1, Rf=0.25) to afford compound 345c (50.0 mg) as yellow oil. LCMS (M+H$^+$): 400.

Step 3: Preparation of 3-[(6S)-6-methyl-4,5,6,7-tetrahydropyrazolo[1,5-a]pyrazin-3-yl]-5-(2-pyridyl)oxazolidin-2-one; hydrochloride (compound 345d)

Tert-butyl (6S)-6-methyl-3-[2-oxo-5-(2-pyridyl)oxazolidin-3-yl]-6,7-dihydro-4H-pyrazolo[1,5-a]pyrazine-5-carboxylate (compound 345c, 50.0 mg, 0.13 mmol) was dissolved in HCl/EtOAc (2.0 mL) and the reaction mixture was stirred at room temperature for 0.5 hour, and then concentrated to afford compound 345d as a yellow oil (40.0 mg). LCMS (M+H$^+$): 300.

Step 4: Preparation of (6S)-6-methyl-3-[2-oxo-5-(2-pyridyl)oxazolidin-3-yl]-N-(3,4,5-trifluorophenyl)-6,7-dihydro-4H-pyrazolo[1,5-a]pyrazine-5-carboxamide (Example 345)

To a mixture of 3-[(6S)-6-methyl-4,5,6,7-tetrahydropyrazolo[1,5-a]pyrazin-3-yl]-5-(2-pyridyl)oxazolidin-2-one (compound 345d, 40.0 mg, 0.13 mmol), and DIPEA (51.8 mg, 0.40 mmol) in DMF (1 mL) was added phenyl N-(3,4,5-trifluorophenyl)carbamate (compound 233c, 42.9 mg, 0.16 mmol). The reaction mixture was stirred at room temperature for 5 hours, then was purified by prep-HPLC to afford Example 345 as a white solid (6.6 mg). LCMS (M+H$^+$): 473. $^1$H NMR (400 MHz, chloroform-d) δ ppm 8.78-8.69 (m, 1H), 8.10-8.01 (m, 1H), 7.80-7.73 (m, 1H), 7.72-7.61 (m, 1H), 7.58-7.52 (m, 2H), 7.27-7.15 (m, 2H), 6.01-5.86 (m, 1H), 5.19-5.07 (m, 2H), 4.62-4.41 (m, 2H), 4.35-4.16 (m, 2H), 4.16-4.12 (m, 1H), 1.35-1.29 (m, 3H).

Example 346

(6S)-6-methyl-3-[2-oxo-5-(4-pyridyl)oxazolidin-3-yl]-N-(3,4,5-trifluorophenyl)-6,7-dihydro-4H-pyrazolo[1,5-a]pyrazine-5-carboxamide

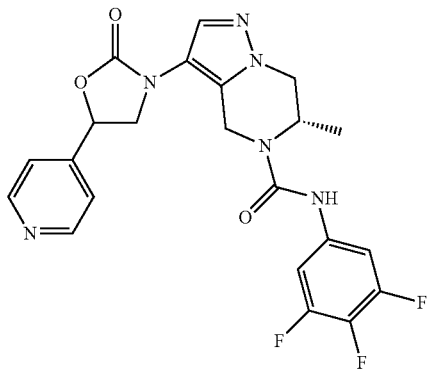 [SMILES: C[C@H]1Cn2ncc(N3CC(c4ccncc4)OC3=O)c2CN1C(=O)Nc1cc(F)c(F)c(F)c1]

Preparation of (6S)-6-methyl-3-[2-oxo-5-(4-pyridyl)oxazolidin-3-yl]-N-(3,4,5-trifluorophenyl)-6,7-dihydro-4H-pyrazolo[1,5-a]pyrazine-5-carboxamide (Example 346)

The title compound was prepared in analogy to Example 345 by using 2-amino-1-(4-pyridyl)ethanol instead of 2-amino-1-(2-pyridyl)ethanol. Example 346 was obtained as a light yellow solid (60.0 mg). LCMS: (M+H$^+$): 473. $^1$H NMR (400 MHz, MeOD) δ ppm 8.66 (d, J=5.8 Hz, 2H), 7.67 (d, J=3.8 Hz, 1H), 7.58 (d, J=5.5 Hz, 2H), 7.34-7.23 (m, 2H), 5.88 (t, J=8.0 Hz, 1H), 5.10 (dd, J=9.7, 16.9 Hz, 1H), 4.96 (dd, J=3.4, 6.7 Hz, 1H), 4.60-4.45 (m, 2H), 4.35-4.25 (m, 1H), 4.22-4.12 (m, 1H), 3.96 (td, J=8.2, 12.7 Hz, 1H), 1.32-1.21 (m, 3H).

Example 347

(6S)-6-methyl-3-[2-oxo-5-(3-pyridyl)oxazolidin-3-yl]-N-(3,4,5-trifluorophenyl)-6,7-dihydro-4H-pyrazolo[1,5-a]pyrazine-5-carboxamide

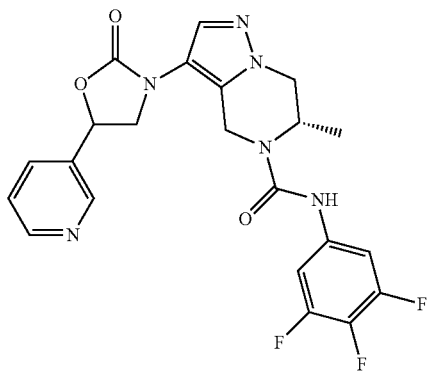 [SMILES: C[C@H]1Cn2ncc(N3CC(c4cccnc4)OC3=O)c2CN1C(=O)Nc1cc(F)c(F)c(F)c1]

Preparation of (6S)-6-methyl-3-[2-oxo-5-(3-pyridyl)oxazolidin-3-yl]-N-(3,4,5-trifluorophenyl)-6,7-dihydro-4H-pyrazolo[1,5-a]pyrazine-5-carboxamide (Example 347)

The title compound was prepared in analogy to Example 345 by using 2-amino-1-(3-pyridyl)ethanol instead of 2-amino-1-(2-pyridyl)ethanol. Example 347 was obtained as a light yellow solid (5 mg). LCMS: (M+H$^+$): 473. $^1$H NMR (400 MHz, DMSO-d$_6$) ppm 9.14 (s, 1H), 8.75 (br. s., 1H), 8.65 (d, J=4.0 Hz, 1H), 8.02 (d, J=8.3 Hz, 1H), 7.67 (d, J=2.8 Hz, 1H), 7.51-7.57 (m, 1H), 7.43 (dd, J=10.5, 6.3 Hz, 2H), 5.86 (t, J=8.0 Hz, 1H), 5.06 (dd, J=16.9, 4.6 Hz, 1H), 4.88 (br. s., 1H), 4.33-4.48 (m, 2H), 4.18-4.26 (m, 1H), 4.10-4.17 (m, 1H), 3.97-4.07 (m, 1H), 1.19-1.12 (m, 3H)

Example 348

(6S)-6-methyl-3-(5-oxazol-4-yl-2-oxo-oxazolidin-3-yl)-N-(3,4,5-trifluorophenyl)-6,7-dihydro-4H-pyrazolo[1,5-a]pyrazine-5-carboxamide

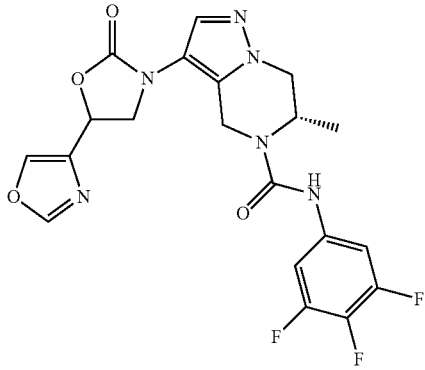 [SMILES: C[C@H]1Cn2ncc(N3CC(c4cocn4)OC3=O)c2CN1C(=O)Nc1cc(F)c(F)c(F)c1]

Preparation of (6S)-6-methyl-3-(5-oxazol-4-yl-2-oxo-oxazolidin-3-yl)-N-(3,4,5-trifluorophenyl)-6,7-dihydro-4H-pyrazolo[1,5-a]pyrazine-5-carboxamide (Example 348)

The title compound was prepared in analogy to Example 289 by using oxazole-4-carbaldehyde instead of 1-methyl-1H-imidazole-2-carbaldehyde. Example 348 was obtained as a white solid (11 mg). LCMS (M+H$^+$): 463. $^1$H NMR (400 MHz, MeOD) δ ppm 8.34 (s, 1H), 8.20 (s, 1H), 7.70 (s, 1H), 7.36-7.25 (m, 2H), 5.85 (t, J=7.8 Hz, 1H), 5.15 (dd, J=10.9, 16.9 Hz, 1H), 5.04-4.96 (m, 1H), 4.59 (dd, J=4.6, 16.9 Hz, 1H), 4.40-4.29 (m, 2H), 4.23-4.14 (m, 2H), 1.31-1.25 (m, 3H).

Example 349

(6S)-6-methyl-3-[4-(2-methyloxazol-5-yl)-2-oxo-pyrrolidin-1-yl]-N-(3,4,5-trifluorophenyl)-6,7-di-hydro-4H-pyrazolo[1,5-a]pyrazine-5-carboxamide

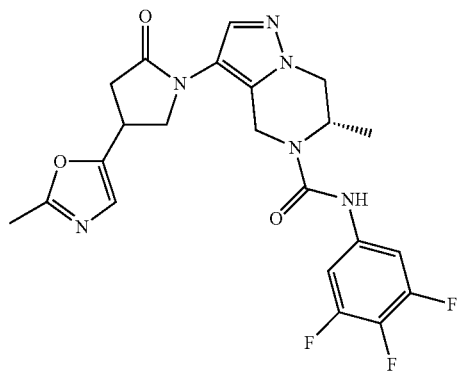 [SMILES: Cc1ncc(C2CC(=O)N(c3cnn4c3CN(C(=O)Nc3cc(F)c(F)c(F)c3)[C@@H](C)C4)C2)o1]

The title compound was prepared according to the following scheme:

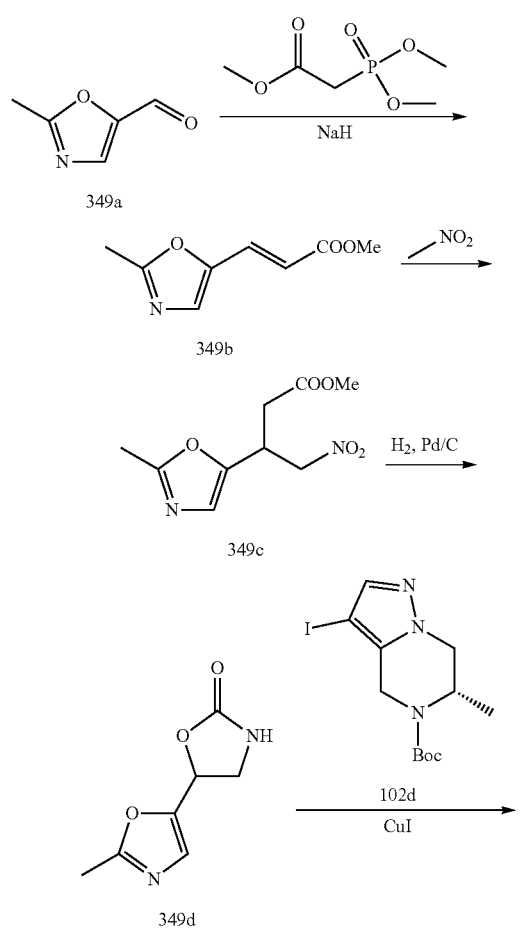

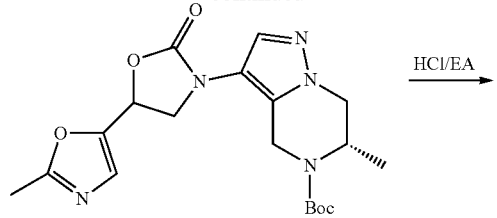

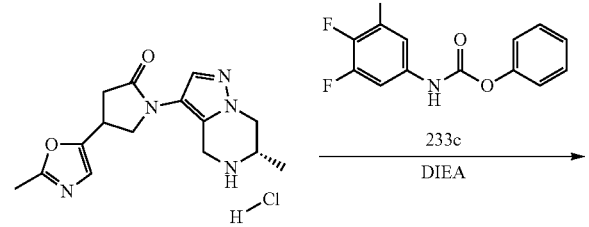

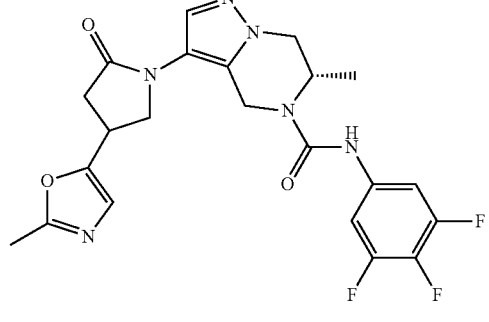

Preparation of methyl (E)-3-(2-methyloxazol-5-yl)prop-2-enoate (compound 349b)

To a solution of 2-methyloxazole-5-carbaldehyde (compound 349a, 1.4 g, 12.6 mmol) and methyl 2-dimethoxyphosphorylacetate (4.7 g, 13.7 mmol) in THF (30.0 mL) was added NaH (1.0 g, 25.2 mmol) at 0° C., and the reaction mixture was stirred at room temperature for 12 hours, and then quenched with ice-water (20 mL) and extracted with ethyl acetate. The organic layer was washed with brine and dried over $Na_2SO_4$, and evaporated to give crude compound 349b (2.0 g) which was used in the next step without further purification. LCMS (M+H$^+$): 168.

Preparation of methyl 3-(2-methyloxazol-5-yl)-4-nitro-butanoate (compound 349c)

To a solution of (E)-3-(2-methyloxazol-5-yl)prop-2-enoate (compound 349b, 2.0 g, 12.0 mmol) in nitromethane (20 mL) was added DBU (2.0 g, 13.2 mmol) at 0° C., and the reaction mixture was stirred at room temperature for 12 hours, then concentrated and purified by silica gel column to give compound 349c as a yellow oil (1.9 g). LCMS (M+H$^+$): 229.

Preparation of 4-(2-methyloxazol-5-yl)pyrrolidin-2-one (compound 349d)

A reaction mixture of methyl 3-(2-methyloxazol-5-yl)-4-nitro-butanoate (compound 349c, 1.9 g, 8.3 mmol) and Pd/C (200 mg) in methanol (20 mL) was stirred at 50° C. for 12 hours under H₂ at 1 atm, then concentrated and purified by prep-HPLC to give compound 349d as a white solid (260 mg). LCMS (M+H⁺): 167.

Preparation of (6S)-6-methyl-3-[4-(2-methyloxazol-5-yl)-2-oxo-pyrrolidin-1-yl]-N-(3,4,5-trifluorophenyl)-6,7-dihydro-4H-pyrazolo[1,5-a]pyrazine-5-carboxamide (Example 349)

The title compound was prepared in analogy to Example 345 by using 4-(2-methyloxazol-5-yl)pyrrolidin-2-one (compound 349d) instead of 5-(2-pyridyl)oxazolidin-2-one (compound 345b). Example 349 was obtained as a white solid (20 mg). LCMS (M+H⁺): 475. ¹H NMR (400 MHz, MeOD) δ ppm 7.66 (s, 1 H), 7.28 (dd, J=10.29, 6.53 Hz, 2 H), 6.95 (s, 1 H), 5.09-5.00 (m, 1 H), 4.99-4.93 (m, 1 H), 4.50 (dd, J=16.94, 1.63 Hz, 1 H), 4.30 (dd, J=12.67, 3.64 Hz, 1 H), 4.23-4.12 (m, 2 H), 4.03-3.89 (m, 2 H), 2.97 (dd, J=17.07, 8.78 Hz, 1 H), 2.77 (dd, J=17.19, 7.40 Hz, 1 H), 2.46 (d, J=1.25 Hz, 3 H), 1.31-1.29 (m, 3 H).

Example 350

(6S)-6-methyl-3-[4-(2-methyloxazol-4-yl)-2-oxo-pyrrolidin-1-yl]-N-(3,4,5-trifluorophenyl)-6,7-dihydro-4H-pyrazolo[1,5-a]pyrazine-5-carboxamide

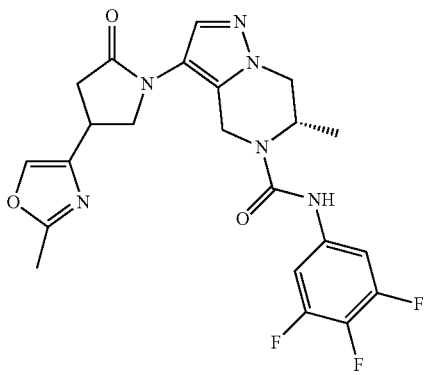 [SMILES: Cc1nc(C2CC(=O)N(c3cnn4c3CN(C(=O)Nc3cc(F)c(F)c(F)c3)[C@@H](C)C4)C2)co1]

Preparation of (6S)-6-methyl-3-[4-(2-methyloxazol-4-yl)-2-oxo-pyrrolidin-1-yl]-N-(3,4,5-trifluorophenyl)-6,7-dihydro-4H-pyrazolo[1,5-a]pyrazine-5-carboxamide (Example 350)

The title compound was prepared in analogy to Example 349 by using 2-methyloxazole-4-carbaldehyde instead of 2-methyloxazole-5-carbaldehyde. Example 350 was obtained as a white solid (25 mg). LCMS (M+H⁺): 475. ¹H NMR (400 MHz, MeOD) δ ppm 7.75 (d, J=1.25 Hz, 1 H), 7.65 (s, 1 H), 7.29 (dd, J=10.92, 6.40 Hz, 2 H), 5.06 (dd, J=17.07, 5.27 Hz, 1 H), 5.00-4.93 (m, 1 H), 4.52 (dd, J=16.94, 5.90 Hz, 1 H), 4.30 (dd, J=12.80, 4.52 Hz, 1 H), 4.20-4.08 (m, 2 H), 3.93-3.75 (m, 2 H), 2.96-2.87 (m, 1 H), 2.73 (dd, J=17.07, 7.53 Hz, 1 H), 2.47 (s, 1.5 H), 2.46 (s, 1.5 H), 1.31-1.29 (m, 3 H).

Example 351

(6S)-6-methyl-3-[2-oxo-4-(3-pyridyl)pyrrolidin-1-yl]-N-(3,4,5-trifluorophenyl)-6,7-dihydro-4H-pyrazolo[1,5-a]pyrazine-5-carboxamide

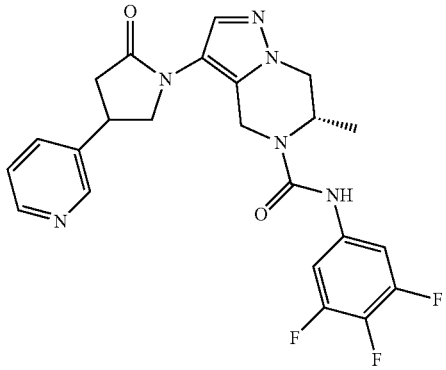 [SMILES: C[C@H]1Cn2ncc(N3CC(c4cccnc4)CC3=O)c2CN1C(=O)Nc1cc(F)c(F)c(F)c1]

Preparation of (6S)-6-methyl-3-[2-oxo-4-(3-pyridyl)pyrrolidin-1-yl]-N-(3,4,5-trifluorophenyl)-6,7-dihydro-4H-pyrazolo[1,5-a]pyrazine-5-carboxamide (Example 351)

The title compound was prepared in analogy to Example 349 by using pyridine-3-carbaldehyde instead of 2-methyloxazole-5-carbaldehyde. Example 351 was obtained as a white solid (15 mg). LCMS (M+H⁺): 471. ¹H NMR (400 MHz, MeOD) δ ppm 8.70-8.42 (m, 2H), 7.94 (d, J=7.9 Hz, 1H), 7.66 (d, J=1.0 Hz, 1H), 7.54-7.44 (m, 1H), 7.27 (dd, J=6.4, 10.3 Hz, 2H), 5.08 (dd, J=11.2, 16.9 Hz, 1H), 4.98-4.93 (m, 1H), 4.53 (dd, J=13.1, 16.9 Hz, 1H), 4.30-4.13 (m, 3H), 3.98-3.90 (m, 2H), 3.04-2.96 (m, 1H), 2.82-2.74 (m, 1H), 1.29-1.23 (m, 3H).

Example 352

(6S)-6-methyl-3-(4-oxazol-4-yl-2-oxo-pyrrolidin-1-yl)-N-(3,4,5-trifluorophenyl)-6,7-dihydro-4H-pyrazolo[1,5-a]pyrazine-5-carboxamide

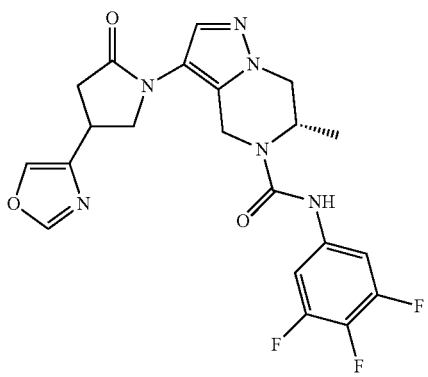 [SMILES: C[C@H]1Cn2ncc(N3CC(c4cocn4)CC3=O)c2CN1C(=O)Nc1cc(F)c(F)c(F)c1]

Preparation of (6S)-6-methyl-3-(4-oxazol-4-yl-2-oxo-pyrrolidin-1-yl)-N-(3,4,5-trifluorophenyl)-6,7-dihydro-4H-pyrazolo[1,5-a]pyrazine-5-carboxamide (Example 352)

The title compound was prepared in analogy to Example 349 by using oxazole-4-carbaldehyde instead of 2-methyloxazole-5-carbaldehyde. Example 352 was obtained as a white solid (11 mg). LCMS (M+H⁺): 461. ¹H NMR (400 MHz, MeOD) δ ppm 8.23 (s, 1 H), 7.92 (s, 1 H), 7.65 (d, J=1.25 Hz, 1 H), 7.34-7.24 (m, 2 H), 5.07 (dd, J=16.94, 4.89 Hz, 1 H), 5.00-4.95 (m, 1 H), 4.52 (dd, J=17.07, 4.27 Hz, 1 H), 4.30 (dd, J=12.67, 4.39 Hz, 1 H), 4.22-4.11 (m, 2 H), 3.98-3.82 (m, 2 H), 2.94 (dd, J=17.07, 8.78 Hz, 1 H), 2.83-2.70 (m, 1 H), 1.28 (d, J=7.03 Hz, 3 H).

Example 353

(6S)-6-methyl-3-[2-oxo-4-(2-pyridyl)pyrrolidin-1-yl]-N-(3,4,5-trifluorophenyl)-6,7-dihydro-4H-pyrazolo[1,5-a]pyrazine-5-carboxamide

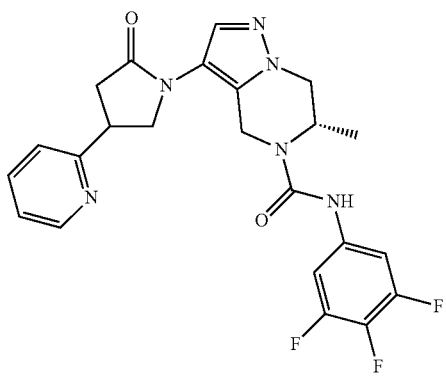 [SMILES: C[C@H]1Cn2ncc(N3CC(c4ccccn4)CC3=O)c2CN1C(=O)Nc1cc(F)c(F)c(F)c1]

Preparation of (6S)-6-methyl-3-[2-oxo-4-(2-pyridyl)pyrrolidin-1-yl]-N-(3,4,5-trifluorophenyl)-6,7-dihydro-4H-pyrazolo[1,5-a]pyrazine-5-carboxamide (Example 353)

The title compound was prepared in analogy to Example 349 by using pyridine-2-carbaldehyde instead of 2-methyloxazole-5-carbaldehyde. Example 353 was obtained as a white solid (56 mg). LCMS (M+H⁺): 471. ¹H NMR (400 MHz, MeOD) δ ppm 8.57 (d, J=4.8 Hz, 1H), 7.80 (tt, J=1.9, 7.7 Hz, 1H), 7.64 (d, J=1.3 Hz, 1H), 7.46-7.40 (m, 1H), 7.34-7.23 (m, 3H), 5.07 (dd, J=11.1, 16.9 Hz, 1H), 4.99-4.91 (m, 1H), 4.53 (dd, J=9.0, 16.9 Hz, 1H), 4.31-4.12 (m, 3H), 4.06-3.97 (m, 2H), 3.01-2.85 (m, 2H), 1.29-1.23 (m, 3H).

Example 354

(6S)-6-methyl-3-[2-oxo-4-(4-pyridyl)pyrrolidin-1-yl]-N-(3,4,5-trifluorophenyl)-6,7-dihydro-4H-pyrazolo[1,5-a]pyrazine-5-carboxamide

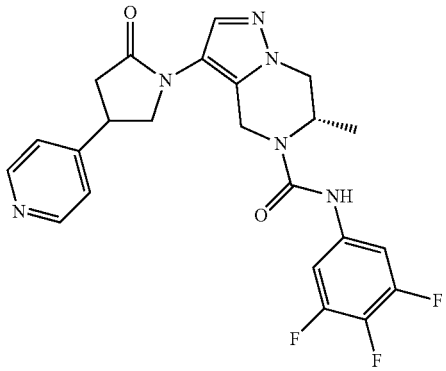 [SMILES: C[C@H]1Cn2ncc(N3CC(c4ccncc4)CC3=O)c2CN1C(=O)Nc1cc(F)c(F)c(F)c1]

Preparation of (6S)-6-methyl-3-[2-oxo-4-(4-pyridyl)pyrrolidin-1-yl]-N-(3,4,5-trifluorophenyl)-6,7-dihydro-4H-pyrazolo[1,5-a]pyrazine-5-carboxamide (Example 354)

The title compound was prepared in analogy to Example 349 by using pyridine-4-carbaldehyde instead of 2-methyloxazole-5-carbaldehyde. Example 354 was obtained as a white solid (17 mg). LCMS (M+H+): 471. ¹H NMR (400 MHz, MeOD) δ ppm 9.20 (d, J=6.0 Hz, 1H), 8.57 (br. s., 2H), 7.63 (d, J=3.6 Hz, 1H), 7.52-7.33 (m, 4H), 5.12-4.94 (m, 1H), 4.92-4.76 (m, 1H), 4.52-4.32 (m, 1H), 4.25-4.05 (m, 3H), 3.88-3.75 (m, 2H), 2.85 (dd, J=8.5, 16.9 Hz, 1H), 2.69-2.61 (m, 1H), 1.18-1.12 (m, 3H).

Example 355

(6S)-N-(3-chloro-4-fluoro-phenyl)-6-methyl-3-(2-oxopyrrolidin-1-yl)-6,7-dihydro-4H-pyrazolo[1,5-a]pyrazine-5-carboxamide

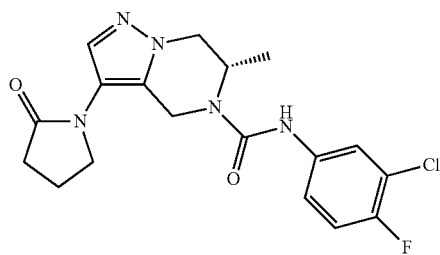 [SMILES: C[C@H]1Cn2ncc(N3CCCC3=O)c2CN1C(=O)Nc1ccc(F)c(Cl)c1]

Preparation of (6S)-N-(3-chloro-4-fluoro-phenyl)-6-methyl-3-(2-oxopyrrolidin-1-yl)-6,7-dihydro-4H-pyrazolo[1,5-a]pyrazine-5-carboxamide (Example 355)

The title compound was prepared in analogy to Example 223 by using phenyl N-(3-chloro-4-fluoro-phenyl)carbamate (compound 12i) instead of phenyl N-[2-(difluoromethyl)-4-pyridyl] (compound 218c). Example 355 was obtained as a solid (100 mg). LCMS (M+H$^+$): 392. $^1$H NMR (400 MHz, chloroform-d) δ ppm 7.65 (dd, J=2.6, 6.7 Hz, 2H), 7.43 (s, 1H), 7.35-7.29 (m, 1H), 7.10-7.02 (m, 1H), 5.18-5.05 (m, 2H), 4.43-4.35 (m, 1H), 4.34-4.26 (m, 1H), 4.07-4.01 (m, 1H), 3.99-3.90 (m, 1H), 3.82-3.73 (m, 1H), 2.66-2.57 (m, 2H), 2.34-2.21 (m, 2H), 1.38 (d, J=7.0 Hz, 3H).

Example 356

(6S)-6-methyl-3-(2-oxopyrrolidin-1-yl)-N-(3,4,5-trifluorophenyl)-6,7-dihydro-4H-pyrazolo[1,5-a]pyrazine-5-carboxamide

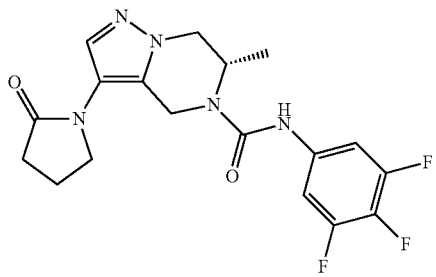 [SMILES: C[C@H]1Cn2ncc(N3CCCC3=O)c2CN1C(=O)Nc1cc(F)c(F)c(F)c1]

Preparation of (6S)-6-methyl-3-(2-oxopyrrolidin-1-yl)-N-(3,4,5-trifluorophenyl)-6,7-dihydro-4H-pyrazolo[1,5-a]pyrazine-5-carboxamide (Example 356)

The title compound was prepared in analogy to Example 223 by using phenyl N-(3,4,5-trifluorophenyl)carbamate (compound 233c) instead of phenyl N-[2-(difluoromethyl)-4-pyridyl] (compound 218c). Example 356 was obtained as a solid (933 mg). LCMS (M+H$^+$): 394. $^1$H NMR (400 MHz, CD$_3$OD) δ ppm 7.63 (s, 1H), 7.34-7.24 (m, 2H), 5.08-5.00 (m, 1H), 5.00-4.93 (m, 1H), 4.55-4.47 (m, 1H), 4.34-4.25 (m, 1H), 4.21-4.11 (m, 1H), 3.94-3.81 (m, 2H), 2.62-2.52 (m, 2H), 2.31-2.19 (m, 2H), 1.27 (d, J=7.0 Hz, 3H).

Example 358

(6S)-6-methyl-3-(5-methyl-2-oxo-1-piperidyl)-N-(3,4,5-trifluorophenyl)-6,7-dihydro-4H-pyrazolo[1,5-a]pyrazine-5-carboxamide

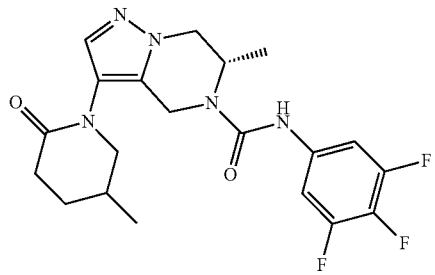 [SMILES: CC1CCC(=O)N(c2cnn3c2CN(C(=O)Nc2cc(F)c(F)c(F)c2)[C@@H](C)C3)C1]

Preparation of (6S)-6-methyl-3-(5-methyl-2-oxo-1-piperidyl)-N-(3,4,5-trifluorophenyl)-6,7-dihydro-4H-pyrazolo[1,5-a]pyrazine-5-carboxamide (Example 358)

The title compound was prepared in analogy to Example 223 by using 5-methylpiperidin-2-one instead of pyrrolidin-2-one, and phenyl N-(3,4,5-trifluorophenyl)carbamate (compound 233c) instead of phenyl N-[2-(difluoromethyl)-4-pyridyl] (compound 218c). Example 358 was obtained as a solid (24 mg). LCMS (M+H$^+$): 422. $^1$H NMR (400 MHz, chloroform-d) δ ppm 8.22 (s, 0.5H), 7.98 (s, 0.5H), 7.48 (s, 0.5H), 7.47 (s, 0.5H), 7.36-7.29 (m, 1H), 7.28-7.22 (m, 1H), 5.07 (m, 1H), 4.89 (d, J=17.1 Hz, 0.5H), 4.78 (d, J=16.8 Hz, 0.5H), 4.32-4.15 (m, 2H), 4.06-3.96 (m, 1H), 3.83-3.74 (m, 0.5H), 3.62-3.48 (m, 1H), 3.31 (dd, J=10.0, 12.0 Hz, 0.5H), 2.75-2.54 (m, 2H), 2.28-2.09 (m, 1H), 2.06-1.96 (m, 1H), 1.65-1.56 (m, 1H), 1.45-1.36 (m, 3H), 1.16-1.10 (m, 3H).

Example 359

(6S)-3-(4-cyano-2-oxo-pyrrolidin-1-yl)-N-[2-(difluoromethyl)-4-pyridyl]-6-methyl-6,7-dihydro-4H-pyrazolo[1,5-a]pyrazine-5-carboxamide

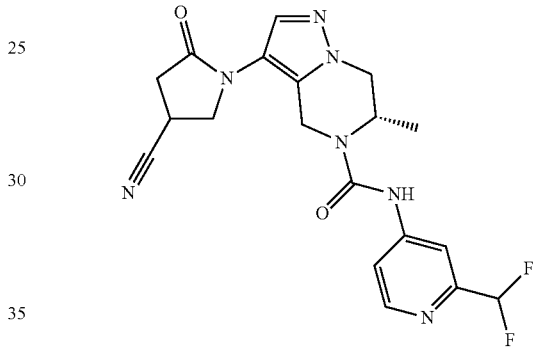

The title compound was prepared according to the following scheme:

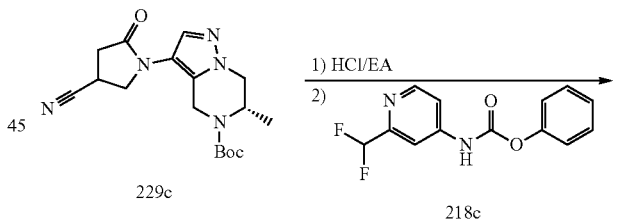

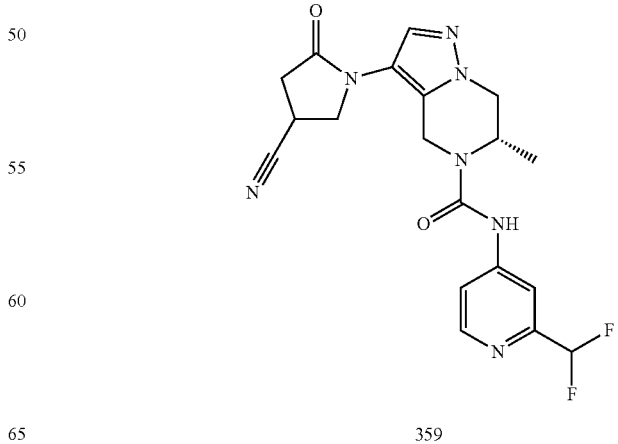

359

421

Preparation of (6S)-3-(4-cyano-2-oxo-pyrrolidin-1-yl)-N-[2-(difluoromethyl)-4-pyridyl]-6-methyl-6,7-dihydro-4H-pyrazolo[1,5-a]pyrazine-5-carboxamide (Example 240)

The title compound was prepared in analogy to Example 229 by using phenyl N-[2-(difluoromethyl)-4-pyridyl]carbamate (compound 218c) instead of phenyl N-(3-chloro-4-fluoro-phenyl)carbamate (compound 12i). Example 359 was obtained as a solid (14 mg). LCMS (M+H$^+$): 416. $^1$H NMR (400 MHz, chloroform-d) δ ppm 8.49 (d, J=4.8 Hz, 1H), 7.99 (s, 0.5H), 7.91 (s, 0.5H), 7.80-7.75 (m, 1H), 7.66-7.60 (m, 1H), 7.46 (s, 0.5H), 7.43 (s, 0.5H), 6.76-6.44 (m, 1H), 5.17-5.03 (m, 2H), 4.46-4.39 (m, 1H), 4.39-4.31 (m, 1H), 4.29-4.02 (m, 3H), 3.68-3.53 (m, 1H), 3.12-2.94 (m, 2H), 1.43 (d, J=6.8 Hz, 1.5H), 1.40 (d, J=7.0 Hz, 1.5H).

Example 360

(6S)-3-[4-cyano-4-(hydroxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide

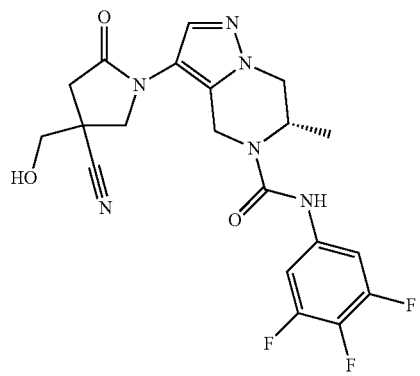 [SMILES: C[C@H]1Cn2ncc(N3CC(C#N)(CO)CC3=O)c2CN1C(=O)Nc1cc(F)c(F)c(F)c1]

The title compound was prepared according to the following scheme:

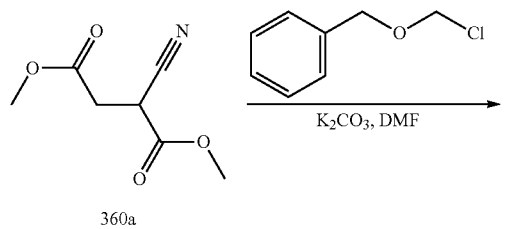

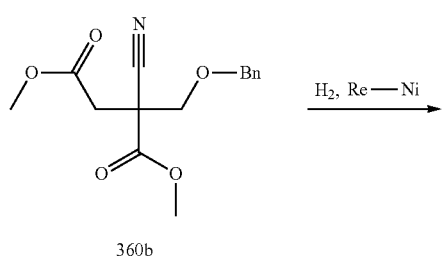

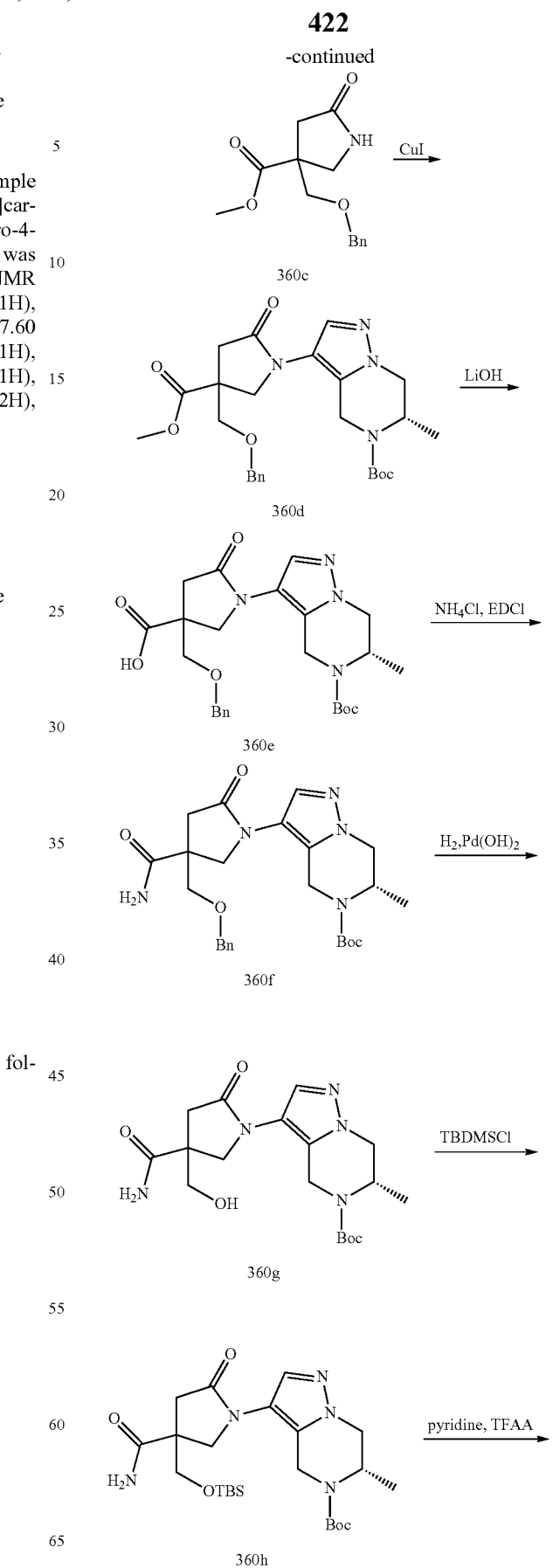

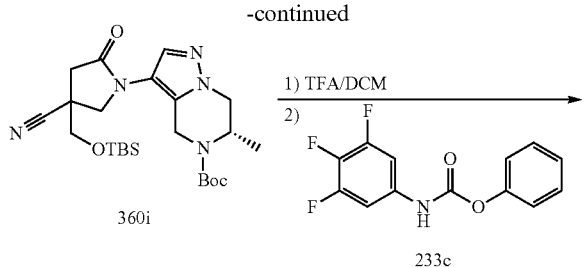

dimethyl 2-((benzyloxy)methyl)-2-cyanosuccinate (compound 360b, 470 mg, 1.61 mmol) in MeOH (1 mL). The reaction mixture was flushed with hydrogen and stirred at 40° C. overnight. The reaction mixture was filtered and concentrated to give crude compound 360c (370 mg). LCMS (M+H$^+$): 264.

Step 3: Preparation of (6S)-tert-butyl 3-(4-((benzyloxy)methyl)-4-(methoxycarbonyl)-2-oxopyrrolidin-1-yl)-6-methyl-6,7-dihydropyrazolo[1,5-a]pyrazine-5(4H)-carboxylate (compound 360d)

The reaction mixture of methyl 3-((benzyloxy)methyl)-5-oxopyrrolidine-3-carboxylate (compound 360c, 370 mg, 1.41 mmol), (6S)-3-iodo-6-methyl-6,7-dihydro-4H-pyrazolo[1,5-a]pyrazine-5-carboxylate (compound 102d, 459 mg, 1.26 mmol), K$_3$PO$_4$ (597 mg, 2.81 mmol), CuI (53.5 mg, 281 μmol) and (1R,2R)-N1,N2-dimethylcyclohexane-1,2-diamine (40 mg, 281 μmol) in DMSO (15 mL) was flushed with nitrogen and sealed. The reaction mixture was stirred at 105° C. in microwave for 2 hours. After cooled down, the reaction mixture was diluted with EtOAc, and washed with water. The aqueous phase was extracted with EtOAc three times. The combined organic layer was dried over Na$_2$SO$_4$, and concentrated in vacuo. The residue was purified by silica gel column to give compound 360d (561 mg). LCMS (M+H$^+$): 499.

Step 4: Preparation of 3-((benzyloxy)methyl)-14(S)-5-(tert-butoxycarbonyl)-6-methyl-4,5,6,7-tetrahydropyrazolo[1,5-a]pyrazin-3-yl)-5-oxopyrrolidine-3-carboxylic acid (compound 360e)

To a solution of compound (6S)-tert-butyl 3-(4-((benzyloxy)methyl)-4-(methoxycarbonyl)-2-oxopyrrolidin-1-yl)-6-methyl-6,7-dihydropyrazolo[1,5-a]pyrazine-5(4H)-carboxylate (compound 360d, 561 mg, 1.13 mmol) in THF (2.5 mL) was added a solution of lithium hydroxide monohydrate (236 mg, 5.63 mmol) in water (2.5 mL). The reaction mixture was stirred at room temperature for 1 hour, then acidified with 1N HCl aqueous solution to pH 5.0, and extracted with DCM twice. The combined organic phase was dried over Na$_2$SO$_4$, filtrated and concentrated to give crude product 360e (518 mg) which was used directly for next step without further purification. LCMS (M+H$^+$): 485.

Step 5: Preparation of (6S)-tert-butyl 3-(4-((benzyloxy)methyl)-4-carbamoyl-2-oxopyrrolidin-1-yl)-6-methyl-6,7-dihydropyrazolo[1,5-a]pyrazine-5(4H)-carboxylate (compound 360f)

To a solution of compound 3-((benzyloxy)methyl)-14(S)-5-(tert-butoxycarbonyl)-6-methyl-4,5,6,7-tetrahydropyrazolo[1,5-a]pyrazin-3-yl)-5-oxopyrrolidine-3-carboxylic acid (compound 360e, 570 mg, 1.18 mmol) in DCM (10 mL) was added ammonia hydrochloride (189 mg, 3.53 mmol), EDCI (293 mg, 1.53 mmol), DIPEA (1.55 g, 2.05 mL, 12 mmol) and hydroxybenzotriazole (47.7 mg, 353 μmol). The reaction mixture was sealed and stirred at 50° C. for 4 hours. The reaction mixture was washed with water, and the aqueous phase was extracted with DCM twice. The combined organic phase was dried over Na$_2$SO$_4$, filtered and concentrated to give crude compound 360f (569 mg) which was used directly for next step without further purification. LCMS (M+H$^+$): 484.

Step 1: Preparation of dimethyl 2-((benzyloxy)methyl)-2-cyanosuccinate (compound 360b)

To a solution of dimethyl 2-cyanosuccinate (compound 360a, 342 mg, 2 mmol) in DMF (3 mL) was added ((chloromethoxy)methyl)benzene (470 mg, 417 μL, 3 mmol) and K$_2$CO$_3$ (553 mg, 4 mmol). The reaction mixture was stirred at 40° C. for 2 hours. The reaction mixture was diluted with PE/EtOAc (v/v=2/1), and washed with water. The aqueous phase was extracted with PE/EtOAc (v/v=2/1) twice. The combined organic phase was concentrated, and the residue was purified by silica gel column to give compound 360b (470 mg). LCMS (M+H$^+$): 292.

Step 2: Preparation of methyl 3-((benzyloxy)methyl)-5-oxopyrrolidine-3-carboxylate (compound 360c)

To a suspension of Raney nickel (138 mg, 1.61 mmol) (pre-washed by methanol) in MeOH (10 mL) was added

Step 6: Preparation of tert-butyl (6S)-3-[4-carbamoyl-4-(hydroxymethyl)-2-oxo-pyrrolidin-1-yl]-6-methyl-6,7-dihydro-4H-pyrazolo[1,5-a]pyrazine-5-carboxylate (compound 360g)

To a solution of compound (6S)-tert-butyl 3-(4-((benzyloxy)methyl)-4-carbamoyl-2-oxopyrrolidin-1-yl)-6-methyl-6,7-dihydropyrazolo[1,5-a]pyrazine-5(4H)-carboxylate (compound 360f, 569 mg, 1.18 mmol) in EtOH (5 mL) was added palladium hydroxide on carbon (165 mg, 1.18 mmol). The reaction mixture was stirred at 50° C. for 3 hours under $H_2$ at 1 atm. The reaction mixture was filtrated and concentrated to give crude product 360 g (463 mg) which was used directly for next step without further purification. LCMS (M+H$^+$): 394.

Step 7: Preparation of (6S)-tert-butyl 3-(4-(((tert-butyldimethylsilyl)oxy)methyl)-4-carbamoyl-2-oxopyrrolidin-1-yl)-6-methyl-6,7-dihydropyrazolo[1,5-a]pyrazine-5(4H)-carboxylate (compound 360h)

To a solution of compound (6S)-tert-butyl 3-(4-carbamoyl-4-(hydroxymethyl)-2-oxopyrrolidin-1-yl)-6-methyl-6,7-dihydropyrazolo[1,5-a]pyrazine-5(4H)-carboxylate (compound 360g, 463 mg, 1.18 mmol) in DMF (3 mL) were added imidazole (160 mg, 2.35 mmol), and tert-butyldimethylchlorosilane (355 mg, 2.35 mmol). After stirred at 35° C. for 3 hours, the reaction mixture was quenched with ice-water, extracted with EtOAc twice. The combined organic phase was dried over Na$_2$SO$_4$ and concentrated to give crude compound 360h (597 mg) which was used directly for next step without further purification. LCMS (M+H$^+$): 508.

Step 8: Preparation of (6S)-tert-butyl 3-(4-(((tert-butyldimethylsilyl)oxy)methyl)-4-cyano-2-oxopyrrolidin-1-yl)-6-methyl-6,7-dihydropyrazolo[1,5-a]pyrazine-5(4H)-carboxylate (compound 360i)

To a solution of compound (6S)-tert-butyl 3-(4-(((tert-butyldimethylsilypoxy)methyl)-4-carbamoyl-2-oxopyrrolidin-1-yl)-6-methyl-6,7-dihydropyrazolo[1,5-a]pyrazine-5(4H)-carboxylate (compound 360h, 597 mg, 1.18 mmol) in dry THF (5 mL) was added pyridine (489 mg, 0.5 mL, 6.18 mmol). The reaction mixture was flushed with N$_2$ and cooled to 0° C., to which was added dropwise a solution of trifluoroacetic anhydride (752 mg, 0.5 mL, 3.58 mmol) in dry THF (0.5 mL). The resulting reaction mixture was stirred at 0° C. for 3 hours, quenched with ice-water, and extracted with EtOAc twice. The organic phase was dried over Na$_2$SO$_4$, and concentrated. The residue was purified by silica gel column to give compound 360i (350 mg). LCMS (M+H$^+$): 490.

Step 9: Preparation of (6S)-3-(4-(((tert-butyldimethylsilyl)oxy)methyl)-4-cyano-2-oxopyrrolidin-1-yl)-6-methyl-N-(3,4,5-trifluorophenyl)-6,7-dihydropyrazolo[1,5-a]pyrazine-5(4H)-carboxamide (compound 360j)

The reaction mixture of compound (6S)-tert-butyl 3-(4-(((tert-butyldimethylsilyl)oxy)methyl)-4-cyano-2-oxopyrrolidin-1-yl)-6-methyl-6,7-dihydropyrazolo[1,5-a]pyrazine-5(4H)-carboxylate (compound 360i, 350 mg, 715 μmol) and trifluoroacetic acid (2.96 g, 2 mL, 26 mmol) in DCM (1 mL) was stirred at room temperature for 30 minutes. The reaction mixture was concentrated, then toluene was added for azeotropic distillation. The residue was dissolved in DMF (2 mL), to which were added DIPEA (754 mg, 1 mL, 5.83 mmol) and phenyl (3,4,5-trifluorophenyl)carbamate (compound 233c, 191 mg, 715 μmol). The reaction mixture was stirred for 3 hours at 40° C., then quenched with ice-water, and extracted with EtOAc twice. The combined organic phase was dried over Na$_2$SO$_4$ and concentrated. The residue was purified by silica gel column to give compound 360j (330 mg). LCMS (M+H$^+$): 563.

Step 10: Preparation of (6S)-3-[4-cyano-4-(hydroxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide (Example 360)

To a solution of compound (6S)-3-(4-(((tert-butyldimethylsilyl)oxy)methyl)-4-cyano-2-oxopyrrolidin-1-yl)-6-methyl-N-(3,4,5-trifluorophenyl)-6,7-dihydropyrazolo[1,5-a]pyrazine-5(4H)-carboxamide (compound 360j, 330 mg, 587 μmol) in THF (2 mL) was added tetrabutylammonium fluoride (1.81 g, 2 mL, 2 mmol). The reaction mixture was stirred at room temperature for 2 hours, and then washed with brine. The aqueous phase was extracted with EtOAc twice. The combined organic phase was dried over Na$_2$SO$_4$ and concentrated. The residue was purified by silica gel column to give Example 360 (150 mg). LCMS (M+H$^+$): 449. $^1$H NMR (400 MHz, CD$_3$OD) δ ppm 7.66 (s, 0.5H), 7.65 (s, 0.5H), 7.35-7.19 (m, 2H), 5.06 (d, J=5.0 Hz, 0.5H), 5.01 (d, J=4.8 Hz, 0.5H), 4.99-4.92 (m, 1H), 4.50 (d, J=17.1 Hz, 1H), 4.36-4.26 (m, 1H), 4.24-4.08 (m, 3H), 4.04-3.96 (m, 1H), 3.88-3.80 (m, 2H), 3.07-2.99 (m, 1H), 2.91-2.81 (m, 1H), 1.30-1.26 (m, 3H).

Example 361

(6S)-3-(4-cyano-4-methyl-2-oxo-pyrrolidin-1-yl)-N-[3-(difluoromethyl)-4,5-difluoro-phenyl]-6-methyl-6,7-dihydro-4H-pyrazolo[1,5-a]pyrazine-5-carboxamide

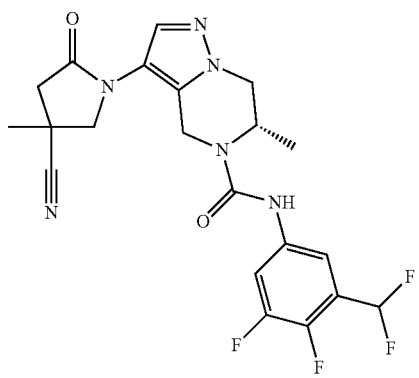 [SMILES: C[C@H]1Cn2ncc(N3CC(C)(C#N)CC3=O)c2CN1C(=O)Nc1cc(F)c(F)c(C(F)F)c1]

The title compound was prepared according to the following scheme:

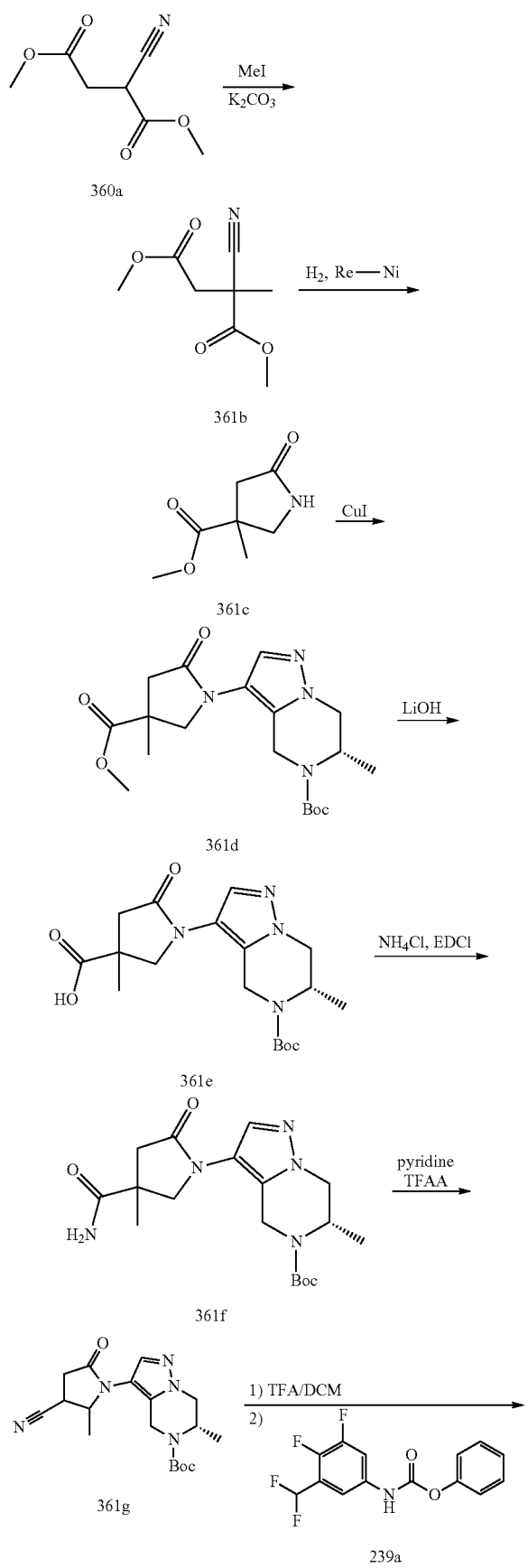

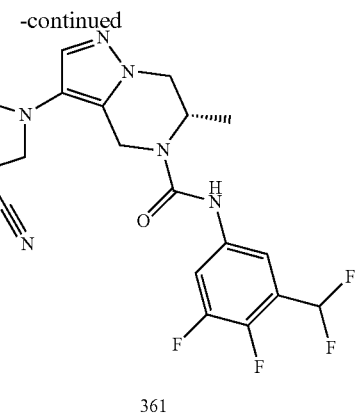

361

Preparation of methyl 3-methyl-5-oxo-pyrrolidine-3-carboxylate (compound 361c)

Methyl 3-methyl-5-oxo-pyrrolidine-3-carboxylate (compound 361c) was prepared in analogy to methyl 3-((benzyloxy)methyl)-5-oxopyrrolidine-3-carboxylate (compound 360c) by using methyl iodide instead of ((chloromethoxy)methyl)benzene.

Preparation of (6S)-3-(4-cyano-4-methyl-2-oxo-pyrrolidin-1-yl)-N-[3-(difluoromethyl)-4,5-difluoro-phenyl]-6-methyl-6,7-dihydro-4H-pyrazolo[1,5-a]pyrazine-5-carboxamide (Example 361)

The title compound was prepared in analogy to Example 229 by using methyl 3-methyl-5-oxo-pyrrolidine-3-carboxylate (compound 361c) instead of methyl 5-oxopyrrolidine-3-carboxylate, and phenyl N-[3-(difluoromethyl)-4,5-difluoro-phenyl]carbamate (compound 239a) instead of phenyl N-(3-chloro-4-fluoro-phenyl)carbamate. Example 361 was obtained as a solid (64 mg). LCMS (M+H$^+$):465. $^1$H NMR (400 MHz, CD$_3$OD) δ ppm 7.75-7.62 (m, 2H), 7.45 (br. s., 1H), 7.19-6.84 (m, 1H), 5.08 (d, J=6.8 Hz, 0.5H), 5.04 (d, J=7.0 Hz, 0.5H) 5.01-4.93 (m, 1H), 4.57-4.47 (m, 1H), 4.36-4.15 (m, 3H), 3.92-3.85 (m, 1H), 3.09 (d, J=17.1 Hz, 1H), 2.75 (d, J=17.1 Hz, 1H), 1.69 (s, 3H), 1.28 (d, J=7.0 Hz, 3H).

Example 362

(6S)-3-[4-(hydroxymethyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide

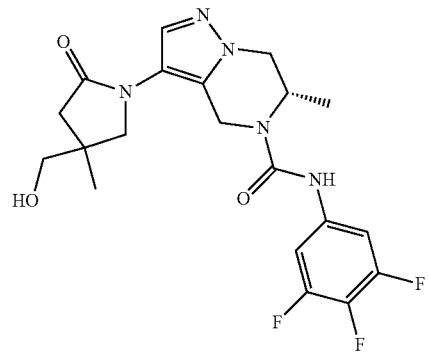 [SMILES: C[C@H]1Cn2ncc(N3CC(C)(CO)CC3=O)c2CN1C(=O)Nc1cc(F)c(F)c(F)c1]

The title compound was prepared according to the following scheme:

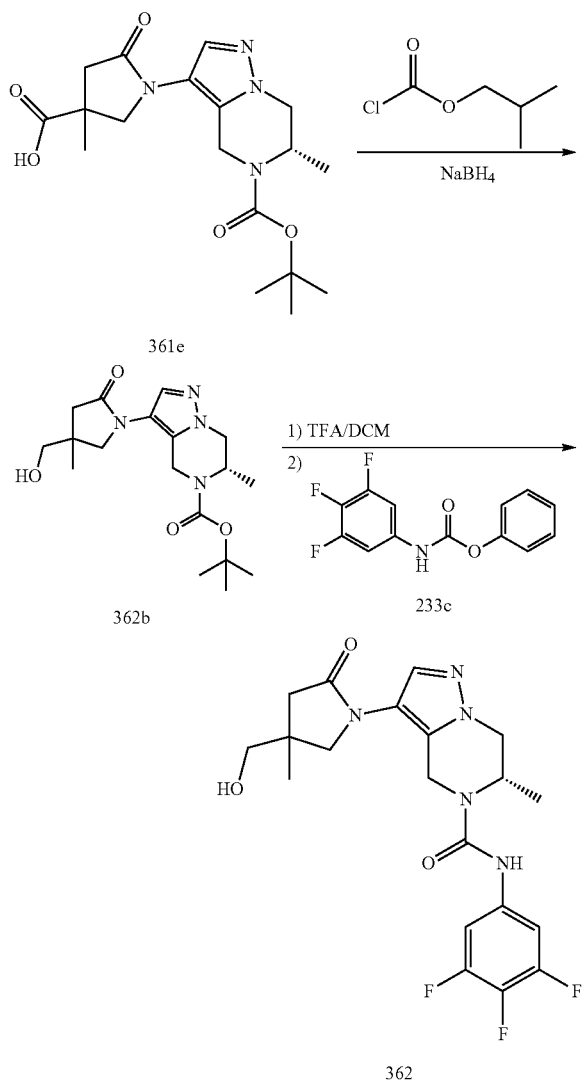

Step 1: Preparation of (6S)-tert-butyl 3-(4-(hydroxymethyl)-4-methyl-2-oxopyrrolidin-1-yl)-6-methyl-6,7-dihydropyrazolo[1,5-a]pyrazine-5(4H)-carboxylate (compound 362b)

To a mixture of compound 1-((S)-5-(tert-butoxycarbonyl)-6-methyl-4,5,6,7-tetrahydropyrazolo[1,5-a]pyrazin-3-yl)-3-methyl-5-oxopyrrolidine-3-carboxylic acid (compound 361e, 189 mg, 0.5 mmol) and 4-methylmorpholine (75.9 mg, 82.5 µL, 750 µmol) in dry THF (3 mL) at −10° C. was added dropwise isobutyl chloroformate (81.9 mg, 78.2 µL, 600 µmol). After stirred at the same temperature for 2 hours, the reaction mixture was added dropwise to a mixture of sodium borohydride (37.8 mg, 1 mmol) and ice (3 g). The reaction mixture was extracted with DCM twice, the organic phase was combined and concentrated. The residue was purified by silica gel column to give compound 362b (100 mg). LCMS (M+H$^+$): 365.

Step 2: Preparation of (6S)-3-[4-(hydroxymethyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide (Example 362)

A solution of compound (6S)-tert-butyl 3-(4-(hydroxymethyl)-4-methyl-2-oxopyrrolidin-1-yl)-6-methyl-6,7-dihydropyrazolo[1,5-a]pyrazine-5(4H)-carboxylate (compound 362b, 100 mg, 274 µmol) in trifluoroacetic acid (2 mL) and DCM (1 mL) was stirred at room temperature for 1 hour. The reaction mixture was concentrated. The residue was dissolved in DMF (2 mL), to which was added DIPEA (371 mg, 0.5 mL, 2.87 mmol), and phenyl (3,4,5-trifluorophenyl)carbamate (compound 233c, 95.3 mg, 357 µmol). The reaction mixture was stirred at 50° C. for 2 hours, then was purified by prep-HPLC to give Example 362 (46 mg). LCMS (M+H$^+$): 438. $^1$H NMR (400 MHz, CD$_3$OD) δ ppm 7.63 (s, 1H), 7.34-7.23 (m, 2H), 5.05 (d, J=4.5 Hz, 0.5H), 5.01 (d, J=4.6 Hz, 0.5H), 4.99-4.92 (m, 1H), 4.54-4.46 (m, 1H), 4.35-4.27 (m, 1H), 4.19-4.12 (m, 1H), 3.83-3.75 (m, 1H), 3.58-3.48 (m, 3H), 2.63-2.55 (m, 1H), 2.36-2.29 (m, 1H), 1.30-1.23 (m, 6H).

Example 363

(6S)-6-methyl-3-[4-[methyl(pyrimidin-2-yl)amino]-2-oxo-pyrrolidin-1-yl]-N-(3,4,5-trifluorophenyl)-6,7-dihydro-4H-pyrazolo[1,5-a]pyrazine-5-carboxamide

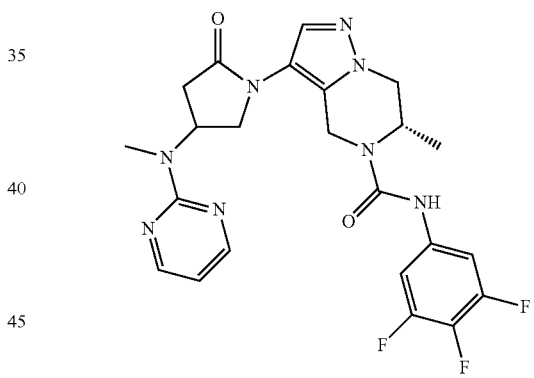

The title compound was prepared according to the following scheme:

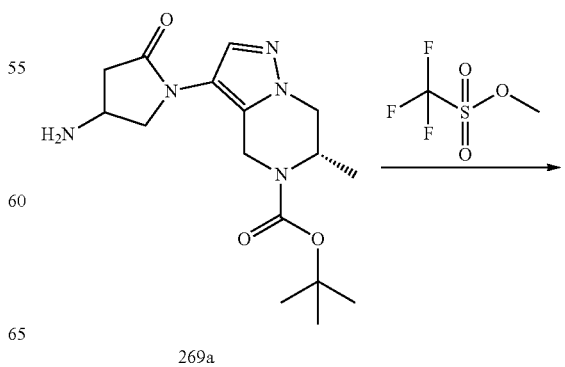

-continued

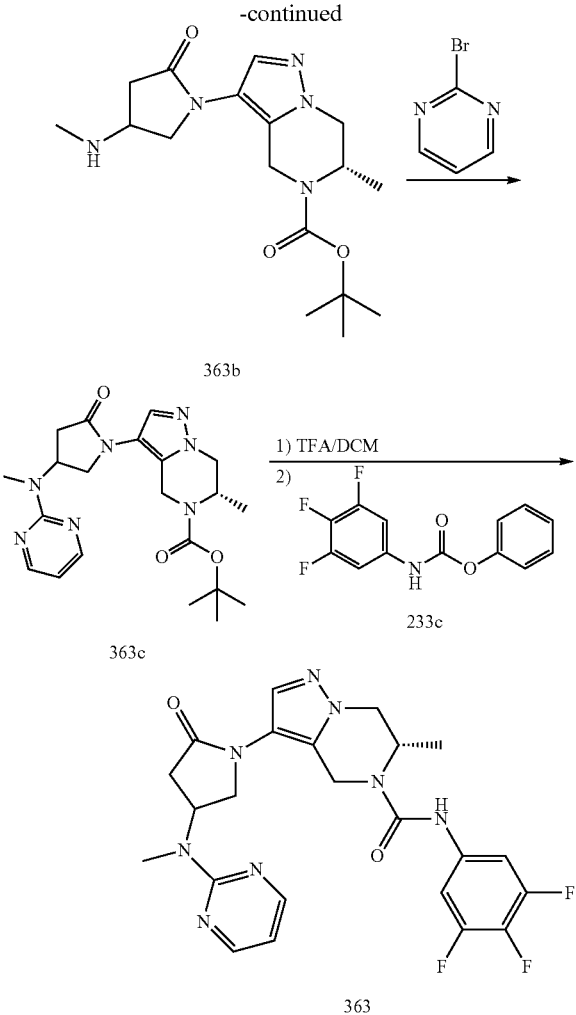

and 2-bromopyrimidine (17.5 mg, 110 µmol). The reaction mixture was stirred at 60° C. for 3 hours. The reaction mixture was then cooled down, poured into ice-water and extracted with EtOAc twice. The organic layers were combined and concentrated to give crude compound 363c (28 mg). LCMS (M+H$^+$): 428.

Step 3: Preparation of (6S)-6-methyl-3-[4-[methyl (pyrimidin-2-yl)amino]-2-oxo-pyrrolidin-1-yl]-N-(3, 4,5-trifluorophenyl)-6,7-dihydro-4H-pyrazolo[1,5-a] pyrazine-5-carboxamide (Example 363)

A solution of (6S)-tert-butyl 6-methyl-3-(4-(methyl(pyrimidin-2-yl)amino)-2-oxopyrrolidin-1-yl)-6,7-dihydropyrazolo[1,5-a]pyrazine-5(4H)-carboxylate (compound 363c, 70 mg, 164 µmol) in trifluoroacetic acid (2 mL) and DCM (1 mL) was stirred at room temperature for 1 hour. The reaction mixture was concentrated. The residue was dissolved in DCE (2 mL), to which was added DIPEA (371 mg, 0.5 mL, 2.87 mmol), and phenyl (3,4,5-trifluorophenyl) carbamate (compound 233c, 56.9 mg, 213 µmol). The reaction mixture was stirred at 50° C. for 2 hours. The reaction mixture was cooled down, washed with ice-water, extracted with DCM twice. The organic layers were combined and concentrated. The residue was purified by prep-HPLC separation to give Example 363 (28 mg). LCMS (M+H$^+$): 501. $^1$H NMR (400 MHz, CD$_3$OD) δ ppm 8.41-8.37 (m, 2H), 7.67 (s, 1H), 7.39-7.23 (m, 2H), 6.69-6.64 (m, 1H), 5.65-5.47 (m, 1H), 5.12-5.04 (m, 1H), 5.01-4.93 (m, 1H), 4.54 (d, J=17.0 Hz, 1H), 4.35-4.27 (m, 1H), 4.25-4.12 (m, 2H), 3.96-3.87 (m, 1H), 3.22 (s, 3H), 2.97-2.88 (m, 1H), 2.82-2.72 (m, 1H), 1.33-1.26 (m, 3H).

Example 364

(6S)-N-(3-chloro-4-fluoro-phenyl)-6-methyl-3-(3-oxomorpholin-4-yl)-6,7-dihydro-4H-pyrazolo[1,5-a] pyrazine-5-carboxamide

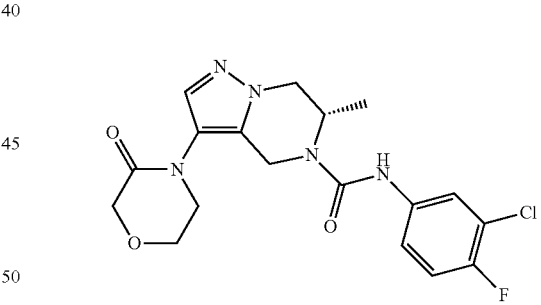

Preparation of (6S)-N-(3-chloro-4-fluoro-phenyl)-6-methyl-3-(3-oxomorpholin-4-yl)-6,7-dihydro-4H-pyrazolo[1,5-a]pyrazine-5-carboxamide (Example 364)

Step 1: Preparation of (6S)-tert-butyl 6-methyl-3-(4-(methylamino)-2-oxopyrrolidin-1-yl)-6,7-dihydropyrazolo[1,5-a]pyrazine-5(4H)-carboxylate (compound 363b)

To a solution of compound (6S)-tert-butyl 3-(4-amino-2-oxopyrrolidin-1-yl)-6-methyl-6,7-dihydropyrazolo[1,5-a]pyrazine-5(4H)-carboxylate (compound 269a, 33.5 mg, 0.1 mmol) in 1,1,1,3,3,3-hexafluoro-2-propanol (810 mg, 0.5 mL) was added methyl trifluoromethanesulfonate (24.6 mg, 17 µL, 150 µmol) in 1,1,1,3,3,3-hexafluoro-2-propanol (324 mg, 0.2 mL). The resulting mixture was stirred at room temperature for 5 hours, and then concentrated. The residue was purified by silica gel column to give compound 363b (17.5 mg). LCMS (M+H$^+$): 350.

Step 2: Preparation of (6S)-tert-butyl 6-methyl-3-(4-(methyl(pyrimidin-2-yl)amino)-2-oxopyrrolidin-1-yl)-6,7-dihydropyrazolo[1,5-a]pyrazine-5(4H)-carboxylate (compound 363c)

To a solution of compound (6S)-tert-butyl 6-methyl-3-(4-(methylamino)-2-oxopyrrolidin-1-yl)-6,7-dihydropyrazolo[1,5-a]pyrazine-5(4H)-carboxylate (compound 363b, 34.9 mg, 0.1 mmol) in DMF (1 mL) was added DIPEA (377 mg, 0.5 mL, 2.92 mmol), potassium iodide (24.9 mg, 150 µmol), The title compound was prepared in analogy to the preparation of Example 223 by using morpholin-3-one instead of pyrrolidin-2-one, and phenyl N-(3-chloro-4-fluoro-phenyl)carbamate (compound 12i) instead of phenyl N-[2-(difluoromethyl)-4-pyridyl]carbamate (compound 218c). Example 364 was obtained as a solid (35 mg). LCMS (M+H$^+$): 408. $^1$H NMR (400 MHz, chloroform-d) δ ppm 7.62 (dd, J=2.8, 6.5 Hz, 1H), 7.52 (s, 1H), 7.49-7.41 (m, 1H), 7.28-7.25 (m, 1H), 7.06 (t, J=8.8 Hz, 1H), 5.15-5.03 (m, 1H), 4.89 (d, J=16.6 Hz, 1H), 4.38 (s, 2H), 4.36-4.26 (m, 2H), 4.15-4.00 (m, 3H), 3.97-3.90 (m, 1H), 3.74 (ddd, J=4.0, 5.8, 12.0 Hz, 1H), 1.36 (d, J=7.0 Hz, 3H).

Example 365

(6S)-6-methyl-3-(2-oxooxazolidin-3-yl)-N-(3,4,5-trifluorophenyl)-6,7-dihydro-4H-pyrazolo[1,5-a]pyrazine-5-carboxamide

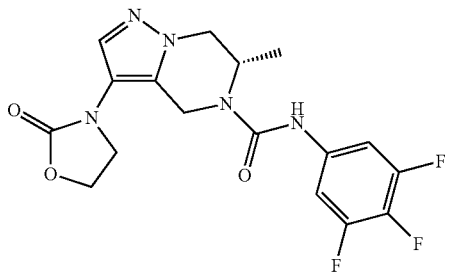 [SMILES: C[C@H]1Cn2ncc(N3CCOC3=O)c2CN1C(=O)Nc1cc(F)c(F)c(F)c1]

Preparation of (6S)-6-methyl-3-(2-oxooxazolidin-3-yl)-N-(3,4,5-trifluorophenyl)-6,7-dihydro-4H-pyrazolo[1,5-a]pyrazine-5-carboxamide (Example 365)

The title compound was prepared in analogy to the preparation of Example 223 by using oxazolidin-2-one instead of pyrrolidin-2-one, and phenyl N-(3,4,5-trifluoropheny)carbamate (compound 233c) instead of phenyl N-[2-(difluoromethyl)-4-pyridyl]carbamate (compound 218c). Example 365 was obtained as a solid (30 mg). LCMS (M+H$^+$): 396. $^1$H NMR (400 MHz, chloroform-d) δ ppm 7.46 (s, 1H), 7.29 (s, 1H), 7.18 (dd, J=6.3, 9.8 Hz, 2H), 5.15-5.01 (m, 2H), 4.67-4.54 (m, 2H), 4.46 (d, J=16.8 Hz, 1H), 4.27 (dd, J=5.3, 12.8 Hz, 1H), 4.19-3.97 (m, 3H), 1.33 (d, J=7.0 Hz, 3H).

Example 366

(6S)-N-[2-(difluoromethyl)-4-pyridyl]-6-methyl-3-(3-oxomorpholin-4-yl)-6,7-dihydro-4H-pyrazolo[1,5-a]pyrazine-5-carboxamide

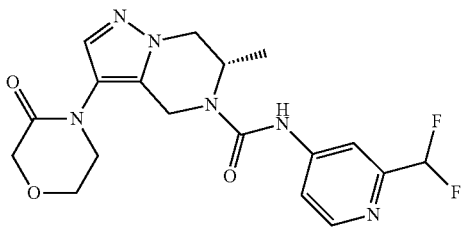 [SMILES: C[C@H]1Cn2ncc(N3CCOCC3=O)c2CN1C(=O)Nc1ccnc(C(F)F)c1]

Preparation of (6S)-N-[2-(difluoromethyl)-4-pyridyl]-6-methyl-3-(3-oxomorpholin-4-yl)-6,7-dihydro-4H-pyrazolo[1,5-a]pyrazine-5-carboxamide (Example 366)

The title compound was prepared in analogy to Example 223 by using morpholin-3-one instead of pyrrolidin-2-one. Example 366 was obtained as a solid (14 mg). LCMS (M+H$^+$): 407. $^1$H NMR (400 MHz, chloroform-d) δ ppm 8.48 (d, J=5.5 Hz, 1H), 8.23 (s, 1H), 7.79 (d, J=1.8 Hz, 1H), 7.67-7.60 (m, 1H), 7.53 (s, 1H), 6.75-6.45 (m, 1H), 5.17-5.04 (m, 1H), 4.96 (d, J=17.1 Hz, 1H), 4.41 (s, 2H), 4.37-4.31 (m, 2H), 4.15-4.03 (m, 3H), 4.02-3.95 (m, 1H), 3.74 (ddd, J=3.6, 5.6, 11.8 Hz, 1H), 1.43 (d, J=7.0 Hz, 3H).

Example 367

(6S)-N-(2-chloro-4-pyridyl)-6-methyl-3-(3-oxomorpholin-4-yl)-6,7-dihydro-4H-pyrazolo[1,5-a]pyrazine-5-carboxamide

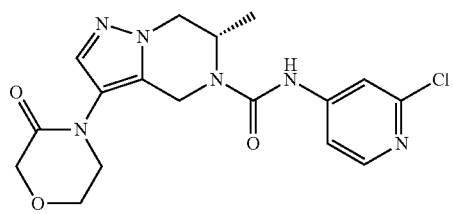 [SMILES: C[C@H]1Cn2ncc(N3CCOCC3=O)c2CN1C(=O)Nc1ccnc(Cl)c1]

Preparation of (6S)-N-(2-chloro-4-pyridyl)-6-methyl-3-(3-oxomorpholin-4-yl)-6,7-dihydro-4H-pyrazolo[1,5-a]pyrazine-5-carboxamide (Example 367)

The title compound was prepared in analogy to the preparation of Example 223 by using morpholin-3-one instead of pyrrolidin-2-one, and N-(2-chloro-4-pyridyl)carbamate instead of phenyl N-[2-(difluoromethyl)-4-pyridyl]carbamate (compound 218c). Example 367 was obtained as a solid (41 mg). LCMS (M+H$^+$): 391. $^1$H NMR (400 MHz, chloroform-d) δ ppm 8.31-8.13 (m, 2H), 7.61 (d, J=1.8 Hz, 1H), 7.52 (s, 1H), 7.38 (dd, J=1.9, 5.6 Hz, 1H), 5.14-5.03 (m, 1H), 4.94 (d, J=17.1 Hz, 1H), 4.40 (s, 2H), 4.36-4.26 (m, 2H), 4.15-3.93 (m, 4H), 3.73 (ddd, 5.7, 12.0 Hz, 1H), 1.43 (d, J=7.0 Hz, 3H).

Example 368

(6S)-6-methyl-3-(2-oxoimidazolidin-1-yl)-N-(3,4,5-trifluorophenyl)-6,7-dihydro-4H-pyrazolo[1,5-a]pyrazine-5-carboxamide

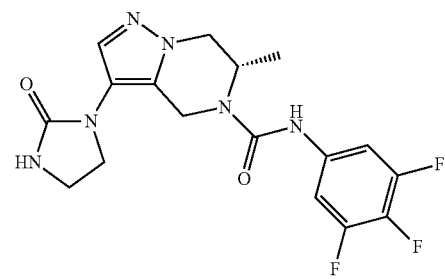 [SMILES: C[C@H]1Cn2ncc(N3CCNC3=O)c2CN1C(=O)Nc1cc(F)c(F)c(F)c1]

Preparation of (6S)-6-methyl-3-(2-oxoimidazolidin-1-yl)-N-(3,4,5-trifluorophenyl)-6,7-dihydro-4H-pyrazolo[1,5-a]pyrazine-5-carboxamide (Example 368)

The title compound was prepared in analogy to the preparation of Example 223 by using imidazolidin-2-one instead of pyrrolidin-2-one, and phenyl N-(3,4,5-trifluorophenyl)carbamate (compound 223c) instead of phenyl N-[2-(difluoromethyl)-4-pyridyl]carbamate (compound 218c). Example 368 was obtained as a solid (20 mg). LCMS (M+H$^+$): 395. $^1$H NMR (400 MHz, chloroform-d) δ ppm 8.16 (s, 1H), 7.39 (s, 1H), 7.28-7.22 (m, 2H), 5.15 (d, J=17.1 Hz, 1H), 5.10-5.01 (m, 1H), 4.69-4.63 (m, 1H), 4.34 (d, J=16.8 Hz, 1H), 4.31-4.24 (m, 1H), 4.09-4.01 (m, 1H), 4.01-3.95 (m, 1H), 3.89-3.80 (m, 1H), 3.71-3.64 (m, 2H), 1.42 (d, J=7.0 Hz, 3H).

Example 371

(6S)-N-(3-chloro-4-fluoro-phenyl)-3-(2,2-dimethyl-5-oxo-morpholin-4-yl)-6-methyl-6,7-dihydro-4H-pyrazolo[1,5-a]pyrazine-5-carboxamide

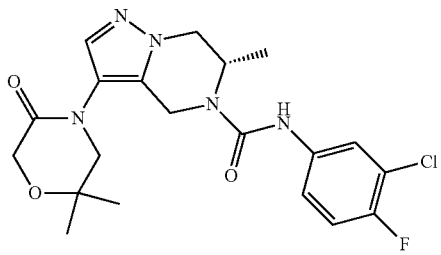 [SMILES: C[C@H]1Cn2ncc(N3CC(C)(C)OCC3=O)c2CN1C(=O)Nc1ccc(F)c(Cl)c1]

Preparation of (6S)-N-(3-chloro-4-fluoro-phenyl)-3-(2,2-dimethyl-5-oxo-morpholin-4-yl)-6-methyl-6,7-dihydro-4H-pyrazolo[1,5-a]pyrazine-5-carboxamide (Example 371)

The title compound was prepared in analogy to Example 223 by using 6,6-dimethylmorpholin-3-one instead of pyrrolidin-2-one, phenyl N-(3-chloro-4-fluoro-phenyl)carbamate (compound 12i) instead of phenyl N-[2-(difluoromethyl)-4-pyridyl]carbamate (compound 218c). Example 371 was obtained as a solid (4 mg). LCMS (M+H$^+$): 436. $^1$H NMR (400 MHz, CD$_3$OD) δ ppm 7.63 (s, 2H), 7.37-7.31 (m, 1H), 7.18 (s, 1H), 5.03-4.92 (m, 2H), 4.46-4.38 (m, 1H), 4.31 (s, 3H), 4.20-4.14 (m, 1H), 3.72-3.63 (m, 2H), 1.43 (d, J=3.0 Hz, 6H), 1.28 (d, J=7.0 Hz, 3H).

Example 372

(6S)-6-methyl-3-[(3S)-3-methyl-5-oxo-morpholin-4-yl]-N-(3,4,5-trifluorophenyl)-6,7-dihydro-4H-pyrazolo[1,5-a]pyrazine-5-carboxamide

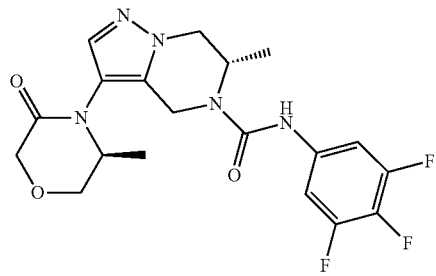 [SMILES: C[C@H]1Cn2ncc(N3C(=O)COC[C@@H]3C)c2CN1C(=O)Nc1cc(F)c(F)c(F)c1]

Preparation of (6S)-6-methyl-3-[(3S)-3-methyl-5-oxo-morpholin-4-yl]-N-(3,4,5-trifluorophenyl)-6,7-dihydro-4H-pyrazolo[1,5-a]pyrazine-5-carboxamide (Example 372)

The title compound was prepared in analogy to Example 223 by using (5S)-5-methylmorpholin-3-one instead of pyrrolidin-2-one, and phenyl N-(3,4,5-trifluorophenyl)carbamate (compound 233c) instead of phenyl N-[2-(difluoromethyl)-4-pyridyl]carbamate (compound 218c). Example 372 was obtained as a solid (14 mg). LCMS (M+H$^+$): 424. $^1$H NMR (400 MHz, chloroform-d) δ ppm 7.91 (s, 1H), 7.49 (s, 1H), 7.25 (dd, J=6.3, 9.8 Hz, 2H), 5.12 (quin, J=6.6 Hz, 1H), 4.84 (d, J=16.8 Hz, 1H), 4.38 (d, J=4.5 Hz, 2H), 4.32-4.25 (m, 1H), 4.18 (d, J=17.1 Hz, 2H), 4.05 (s, 2H), 3.86-3.79 (m, 1H), 1.40 (d, J=7.0 Hz, 3H), 1.25 (d, J=6.5 Hz, 3H).

Example 373

(6S)-N-[3-(difluoromethyl)-4,5-difluoro-phenyl]-6-methyl-3-(2-oxoimidazolidin-1-yl)-6,7-dihydro-4H-pyrazolo[1,5-a]pyrazine-5-carboxamide

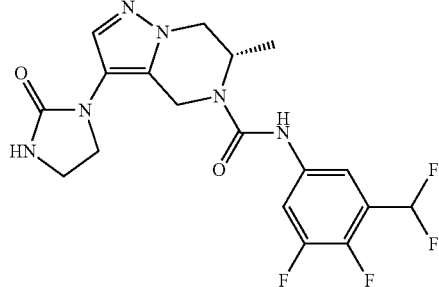 [SMILES: C[C@H]1Cn2ncc(N3CCNC3=O)c2CN1C(=O)Nc1cc(F)c(F)c(C(F)F)c1]

Preparation of (6S)-N-[3-(difluoromethyl)-4,5-difluoro-phenyl]-6-methyl-3-(2-oxoimidazolidin-1-yl)-6,7-dihydro-4H-pyrazolo[1,5-a]pyrazine-5-carboxamide (Example 373)

The title compound was prepared in analogy to the preparation of Example 223 by using imidazolidin-2-one instead of pyrrolidin-2-one, and phenyl N-[3-(difluoromethyl)-4,5-difluoro-phenyl]carbamate (compound 239a) instead of phenyl N-[2-(difluoromethyl)-4-pyridyl]carbamate (compound 218c). Example 373 was obtained as a solid (4 mg). LCMS (M+H$^+$): 427. $^1$H NMR (400 MHz, chloroform-d) δ ppm 8.16-8.07 (m, 1H), 7.78-7.68 (m, 1H), 7.45-7.37 (m, 2H), 6.84 (s, 1H), 5.16 (d, J=16.8 Hz, 1H), 5.10-5.00 (m, 1H), 4.81-4.72 (m, 1H), 4.45-4.34 (m, 1H), 4.33-4.24 (m, 1H), 4.08-3.97 (m, 2H), 3.90-3.79 (m, 1H), 3.70-3.62 (m, 2H), 1.40 (d, J=7.0 Hz, 3H).

Example 374

(6S)-3-(3-acetyl-5-oxo-imidazolidin-1-yl)-6-methyl-N-(3,4,5-trifluorophenyl)-6,7-dihydro-4H-pyrazolo[1,5-a]pyrazine-5-carboxamide

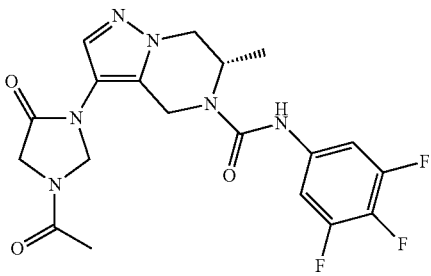 [SMILES: CC(=O)N1CC(=O)N(c2cnn3c2CN(C(=O)Nc2cc(F)c(F)c(F)c2)[C@@H](C)C3)C1]

Preparation of (6S)-3-(3-acetyl-5-oxo-imidazolidin-1-yl)-6-methyl-N-(3,4,5-trifluorophenyl)-6,7-dihydro-4H-pyrazolo[1,5-a]pyrazine-5-carboxamide (Example 374)

The title compound was prepared in analogy to Example 248 by using acetyl chloride instead of methylsulfonyl methanesulfonate. Example 374 was obtained as a white solid (41 mg). LCMS (M+H$^+$): 427. $^1$H NMR (400 MHz, chloroform-d) δ ppm 7.73 (s, 1H), 7.57-7.47 (m, 1H), 7.27-7.16 (m, 2H), 5.39-5.28 (m, 1H), 5.26-5.15 (m, 1H), 5.12-4.99 (m, 2H), 4.42 (d, J=16.8 Hz, 1H), 4.35-4.21 (m, 3H), 4.08 (dd, J=1.6, 12.9 Hz, 1H), 2.24-2.12 (m, 3H), 1.40-1.30 (m, 3H).

Example 375

(6S)-N-[2-(difluoromethyl)-4-pyridyl]-3-(2,2-dimethyl-5-oxo-morpholin-4-yl)-6-methyl-6,7-dihydro-4H-pyrazolo[1,5-a]pyrazine-5-carboxamide

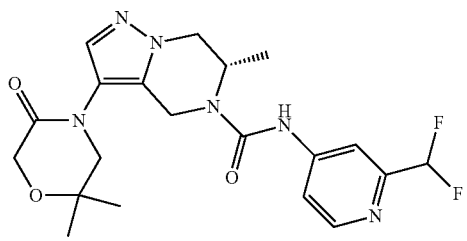 [SMILES: C[C@H]1Cn2ncc(N3CC(C)(C)OCC3=O)c2CN1C(=O)Nc1ccnc(C(F)F)c1]

Preparation of (6S)-N-[2-(difluoromethyl)-4-pyridyl]-3-(2,2-dimethyl-5-oxo-morpholin-4-yl)-6-methyl-6,7-dihydro-4H-pyrazolo[1,5-a]pyrazine-5-carboxamide (Example 375)

The title compound was prepared in analogy to Example 223 by using 6,6-dimethylmorpholin-3-one instead of pyrrolidin-2-one. Example 375 was obtained as a solid (34 mg). LCMS (M+H$^+$): 435. $^1$H NMR (400 MHz, chloroform-d) δ ppm 8.46 (d, J=5.8 Hz, 1H), 8.36 (s, 1H), 8.12 (br. s., 1H), 7.79 (d, J=2.0 Hz, 1H), 7.65 (dd, J=1.9, 5.6 Hz, 1H), 7.51-7.43 (m, 1H), 6.78-6.44 (m, 1H), 5.15-5.03 (m, 1H), 4.97 (d, J=16.8 Hz, 1H), 4.44-4.26 (m, 4H), 4.06 (dd, J=1.5, 13.1 Hz, 1H), 3.73 (d, J=12.0 Hz, 1H), 3.55 (d, J=12.3 Hz, 1H), 1.44 (d, J=8.5 Hz, 6H), 1.37 (d, J=7.0 Hz, 3H).

Example 376

(6S)-3-[(4R)-4-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide

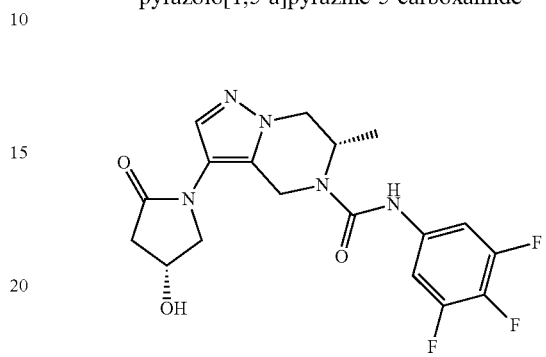

The title compound was prepared according to the following scheme:

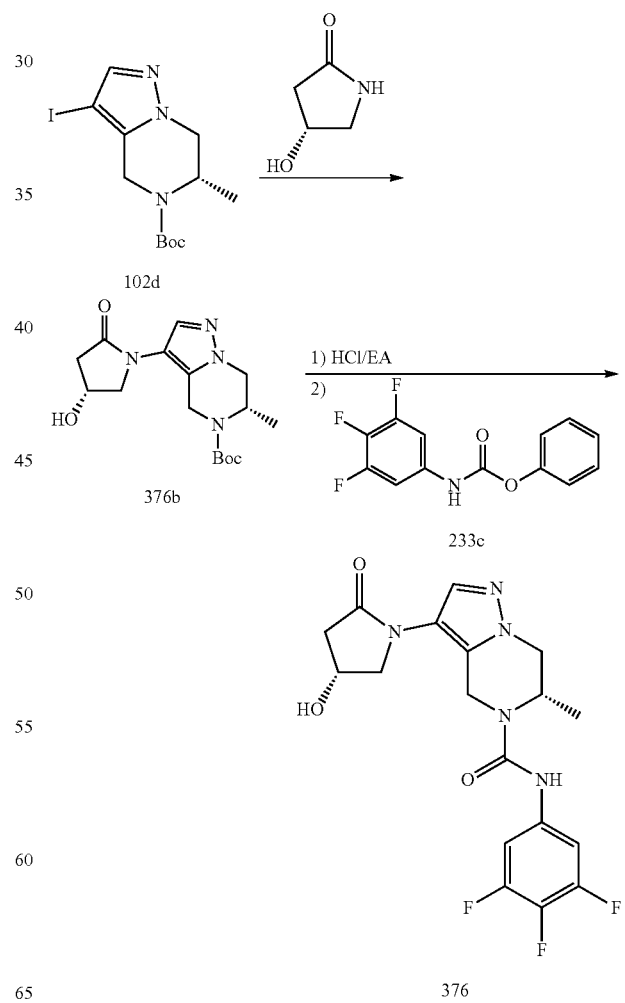

439

Preparation of (6S)-3-[(4R)-4-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide (Example 376)

The title compound was prepared in analogy to Example 223 by using (4R)-4-hydroxypyrrolidin-2-one instead of pyrrolidin-2-one, and phenyl N-(3,4,5-trifluorophenyl)carbamate (compound 233c) instead of phenyl N-[2-(difluoromethyl)-4-pyridyl]carbamate (compound 218c). Example 376 was obtained as a solid (26 mg). LCMS (M+H⁺): 410. ¹H NMR (400 MHz, chloroform-d) δ ppm 8.02-7.92 (m, 1H), 7.44 (s, 1H), 7.27-7.16 (m, 2H), 5.14-5.05 (m, 1H), 5.01 (d, J=16.8 Hz, 1H), 4.72 (t, J=6.0 Hz, 1H), 4.45 (d, J=16.8 Hz, 1H), 4.31 (dd, J=5.4, 12.9 Hz, 1H), 4.10-4.01 (m, 2H), 3.80 (dd, J=2.1, 10.9 Hz, 1H), 2.91 (dd, J=6.5, 17.6 Hz, 1H), 2.57 (dd, J=2.5, 17.6 Hz, 1H), 1.37 (d, J=7.0 Hz, 3H).

Example 377

(6S)-3-[(4S)-4-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide

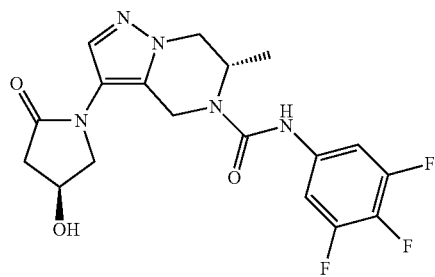 [SMILES: C[C@H]1Cn2ncc(N3C[C@@H](O)CC3=O)c2CN1C(=O)Nc1cc(F)c(F)c(F)c1]

The title compound was prepared according to the following scheme:

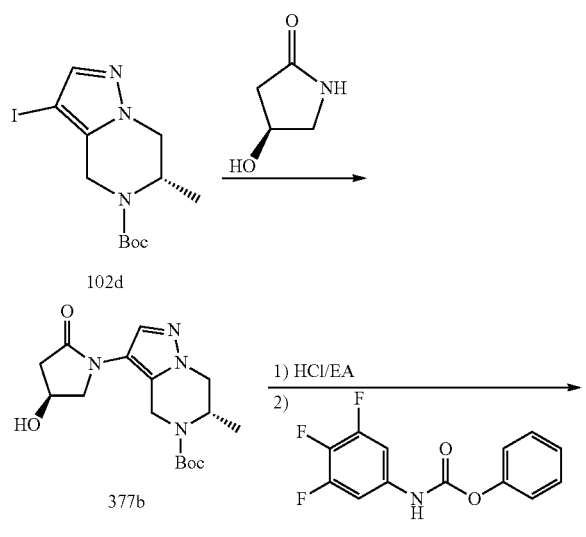

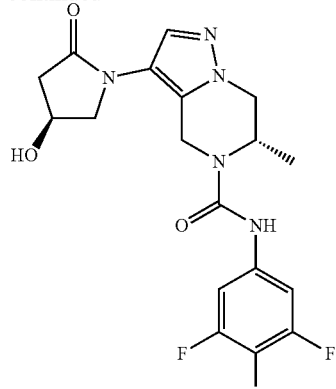

377

Preparation of (6S)-3-[(4S)-4-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide (Example 377)

The title compound was prepared in analogy to Example 223 by using (4S)-4-hydroxypyrrolidin-2-one instead of pyrrolidin-2-one, and phenyl N-(3,4,5-trifluorophenyl)carbamate (compound 233c) instead of phenyl N-[2-(difluoromethyl)-4-pyridyl]carbamate (compound 218c). Example 377 was obtained as a solid (15 mg). LCMS (M+H⁺): 410. ¹H NMR (400 MHz, chloroform-d) δ ppm 8.07 (s, 1H), 7.41 (s, 1H), 7.23 (dd, J=6.3, 9.8 Hz, 2H), 5.19 (d, J=16.8 Hz, 1H), 5.08 (t, J=7.2 Hz, 1H), 4.75 (t, J=5.4 Hz, 1H), 4.38-4.18 (m, 3H), 4.02 (dd, J=2.0, 13.1 Hz, 1H), 3.68 (d, J=10.8 Hz, 1H), 2.95 (dd, J=6.1, 17.7 Hz, 1H), 2.62 (d, J=18.1 Hz, 1H), 2.38 (br. s., 1H), 1.38 (d, J=7.0 Hz, 3H).

Example 378

(6S)-3-[(4S)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide

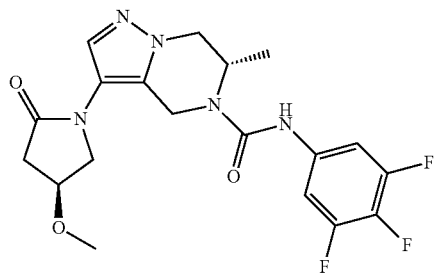 [SMILES: CO[C@H]1CC(=O)N(c2cnn3c2CN(C(=O)Nc2cc(F)c(F)c(F)c2)[C@@H](C)C3)C1]

The title compound was prepared according to the following scheme:

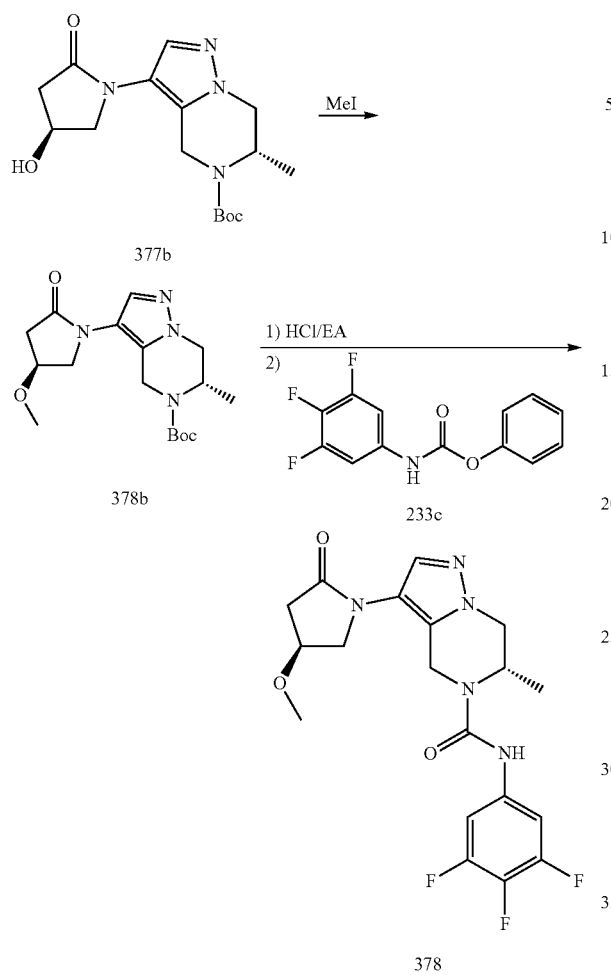

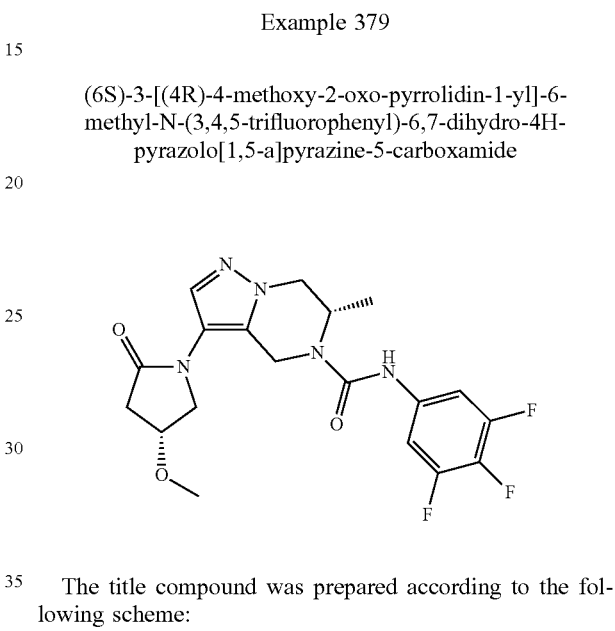

DMF (2 mL), to which was added DIPEA (226 mg, 0.3 mL, 1.75 mmol), phenyl (3,4,5-trifluorophenyl)carbamate (compound 233c, 29.3 mg, 110 μmol). The reaction mixture was stirred at 40° C. for 2 hours, and then purified by prep-HPLC to give Example 378 (20 mg). LCMS (M+H$^+$): 424. $^1$H NMR (400 MHz, chloroform-d) δ ppm 8.06 (s, 1H), 7.40 (s, 1H), 7.30 (s, 1H), 7.27 (d, J=6.3 Hz, 1H), 5.12 (s, 1H), 5.10-5.02 (m, 1H), 4.31 (d, J=16.6 Hz, 2H), 4.25-4.19 (m, 1H), 4.17-4.11 (m, 1H), 4.03-3.96 (m, 1H), 3.79-3.71 (m, 1H), 3.42 (s, 3H), 2.92-2.81 (m, 1H), 2.74-2.65 (m, 1H), 1.40 (d, J=7.0 Hz, 3H).

Example 379

(6S)-3-[(4R)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide The title compound was prepared according to the following scheme:

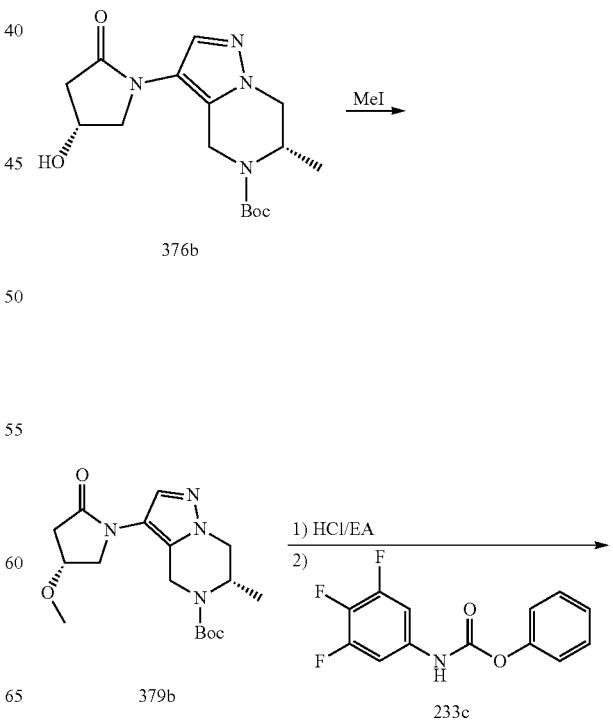

Step 1: Preparation of (S)-tert-butyl 34(S)-4-methoxy-2-oxopyrrolidin-1-yl)-6-methyl-6,7-dihydropyrazolo[1,5-a]pyrazine-5(4H)-carboxylate (compound 378b)

To a solution of compound (S)-tert-butyl 3-((S)-4-hydroxy-2-oxopyrrolidin-1-yl)-6-methyl-6,7-dihydropyrazolo[1,5-a]pyrazine-5(4H)-carboxylate (compound 377b, 336 mg, 1 mmol) in acetonitrile (5 mL) was added Ag$_2$O (695 mg, 3 mmol), triethylamine (101 mg, 139 μL, 1 mmol) and iodomethane (4.26 g, 30 mmol). The reaction mixture was flushed with nitrogen and stirred at 80° C. in microwave for 25 minutes. The reaction mixture was filtrated and concentrated. The residue was purified by silica gel column to give compound 378b (175 mg). LCMS (M+H$^+$): 351.

Step 2: Preparation of (6S)-3-[(4S)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide (Example 378)

mixture solution of compound (S)-tert-butyl 3-((S)-4-methoxy-2-oxopyrrolidin-1-yl)-6-methyl-6,7-dihydropyrazolo[1,5-a]pyrazine-5(4H)-carboxylate (compound 378b, 32 mg, 91.3 μmol) in HCl/EtOAc (ca. 1 mol/L, 5 mL, 5 mmol) was stirred at room temperature overnight. The reaction mixture was concentrated. The residue was dissolved in

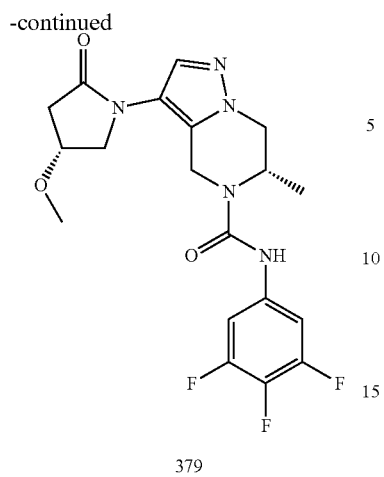

379

Preparation of (6S)-3-[(4R)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide (Example 379)

The title compound was prepared in analogy to Example 378 by using (R)-tert-butyl 3-((R)-4-hydroxy-2-oxopyrrolidin-1-yl)-6-methyl-6,7-dihydropyrazolo[1,5-a]pyrazine-5(4H)-carboxylate (compound 376b) instead of (S)-tert-butyl 3-((S)-4-hydroxy-2-oxopyrrolidin-1-yl)-6-methyl-6,7-dihydropyrazolo[1,5-a]pyrazine-5(4H)-carboxylate (compound 377b). Example 379 was obtained as a solid (39 mg). LCMS (M+H$^+$): 424. $^1$H NMR (400 MHz, chloroform-d) δ ppm 7.88 (s, 1H), 7.44 (s, 1H), 7.28-7.21 (m, 2H), 5.13-4.98 (m, 2H), 4.40 (d, J=16.6 Hz, 1H), 4.33-4.26 (m, 1H), 4.25-4.19 (m, 1H), 4.06-3.97 (m, 2H), 3.90-3.84 (m, 1H), 3.43 (s, 3H), 2.90-2.81 (m, 1H), 2.73-2.64 (m, 1H), 1.39 (d, J=6.8 Hz, 3H).

Example 380

(6S)-N-[2-(difluoromethyl)-4-pyridyl]-3-[(4S)-4-methoxy-2-oxo-pyrrolidin-1-yl]-6-methyl-6,7-dihydro-4H-pyrazolo[1,5-a]pyrazine-5-carboxamide

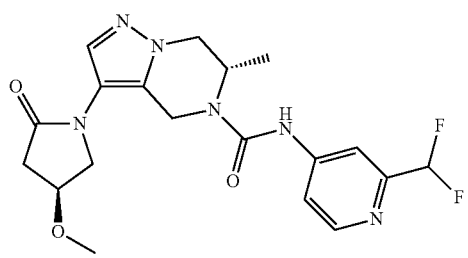 [SMILES: CO[C@H]1CC(=O)N(c2cnn3c2CN(C(=O)Nc2ccnc(C(F)F)c2)[C@@H](C)C3)C1]

The title compound was prepared according to the following scheme:

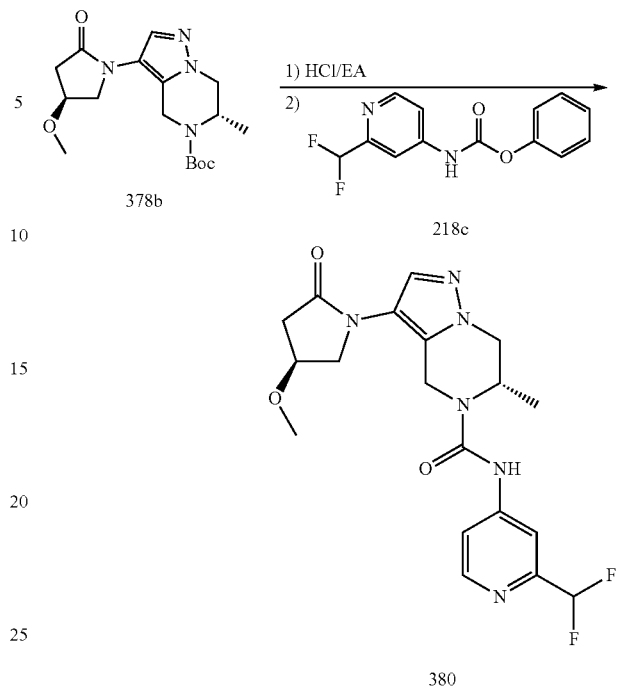

Preparation of (6S)-N-[2-(difluoromethyl)-4-pyridyl]-3-[(4S)-4-methoxy-2-oxo-pyrrolidin-1-yl]-6-methyl-6,7-dihydro-4H-pyrazolo[1,5-a]pyrazine-5-carboxamide (Example 380)

The title compound was prepared in analogy to the preparation of Example 378 by using phenyl N-[2-(difluoromethyl)-4-pyridyl]carbamate (compound 218c) instead of phenyl (3,4,5-trifluorophenyl)carbamate (compound 233c). Example 380 was obtained as a solid (19 mg). LCMS (M+H$^+$): 421. $^1$H NMR (400 MHz, chloroform-d) δ ppm 8.47 (d, J=4.3 Hz, 2H), 7.83 (s, 1H), 7.66 (d, J=5.0 Hz, 1H), 7.40 (s, 1H), 6.59 (s, 1H), 5.24 (d, J=17.1 Hz, 1H), 5.08 (br. s., 1H), 4.40-4.28 (m, 2H), 4.25-4.18 (m, 1H), 4.17-4.11 (m, 1H), 4.02 (dd, J=2.0, 13.1 Hz, 1H), 3.76 (d, J=10.8 Hz, 1H), 3.42 (s, 3H), 2.86 (dd, J=6.3, 17.8 Hz, 1H), 2.79-2.63 (m, 1H), 1.41 (d, J=7.0 Hz, 3H).

Example 381

(6S)-6-methyl-3-[(4S)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide

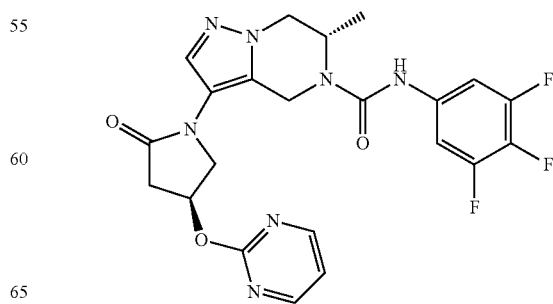

445

The title compound was prepared according to the following scheme:

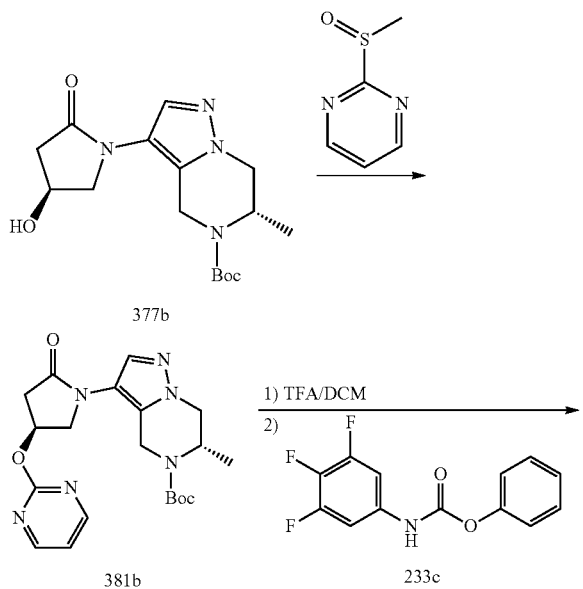

Step 1: Preparation of (S)-tert-butyl 6-methyl-3-((S)-2-oxo-4-(pyrimidin-2-yloxy)pyrrolidin-1-yl)-6,7-dihydropyrazolo[1,5-a]pyrazine-5(4H)-carboxylate (compound 381b)

The reaction mixture of compound (S)-tert-butyl 3-((S)-4-hydroxy-2-oxopyrrolidin-1-yl)-6-methyl-6,7-dihydropyrazolo[1,5-a]pyrazine-5(4H)-carboxylate (compound 377b, 67.3 mg, 0.2 mmol) and 2-(methylsulfinyl)pyrimidine (114 mg, 800 μmol) in dry acetonitrile (2 mL) was refluxed for 10 minutes, then to which was added K₂CO₃ (55.3 mg, 400 μmol). The reaction mixture was stirred at 85° C. for 5 hours. The reaction mixture was diluted with EtOAc, and centrifuged. The organic phase was separated and concentrated. The residue was purified by silica gel column to give compound 381b (50 mg). LCMS (M+H⁺): 415.

446

Step 2: Preparation of (6S)-6-methyl-3-[(4S)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide (Example 381)

A solution of compound (S)-tert-butyl 6-methyl-3-((S)-2-oxo-4-(pyrimidin-2-yloxy)pyrrolidin-1-yl)-6,7-dihydropyrazolo[1,5-a]pyrazine-5(4H)-carboxylate (compound 381b, 100 mg, 241 μmol) in trifluoroacetic acid (2 mL) and DCM (1 mL) was stirred at room temperature for 1 hour. The reaction mixture was concentrated. The residue was dissolved in DCE (2 mL), to which was added DIPEA (371 mg, 0.5 mL, 2.87 mmol), and phenyl (3,4,5-trifluorophenyl) carbamate (compound 233c, 83.8 mg, 314 μmol). The reaction mixture was stirred at 50° C. for 2 hours, and then concentrated. the residue was purified first by silica gel column and then prep-HPLC to give Example 381 (50 mg). LCMS (M+H⁺): 488. $^1$H NMR (400 MHz, chloroform-d) δ ppm 8.63 (d, J=4.8 Hz, 2H), 7.65 (s, 1H), 7.38-7.23 (m, 2H), 7.18 (s, 1H), 5.78 (dt, J=1.7, 5.3 Hz, 1H), 5.09 (d, J=16.9 Hz, 1H), 5.03-4.93 (m, 1H), 4.55-4.46 (m, 1H), 4.42-4.35 (m, 1H), 4.34-4.26 (m, 1H), 4.18 (s, 1H), 3.99 (d, J=1.2 Hz, 1H), 3.24-3.12 (m, 1H), 2.82-2.69 (m, 1H), 1.26 (d, J=6.8 Hz, 3H).

Example 382

(6S)-3-[(4S)-4-(5-fluoropyrimidin-2-yl)oxy-2-oxo-pyrrolidin-1-yl]-6-methyl-N-(3,4,5-trifluorophenyl)-6,7-dihydro-4H-pyrazolo[1,5-a]pyrazine-5-carboxamide

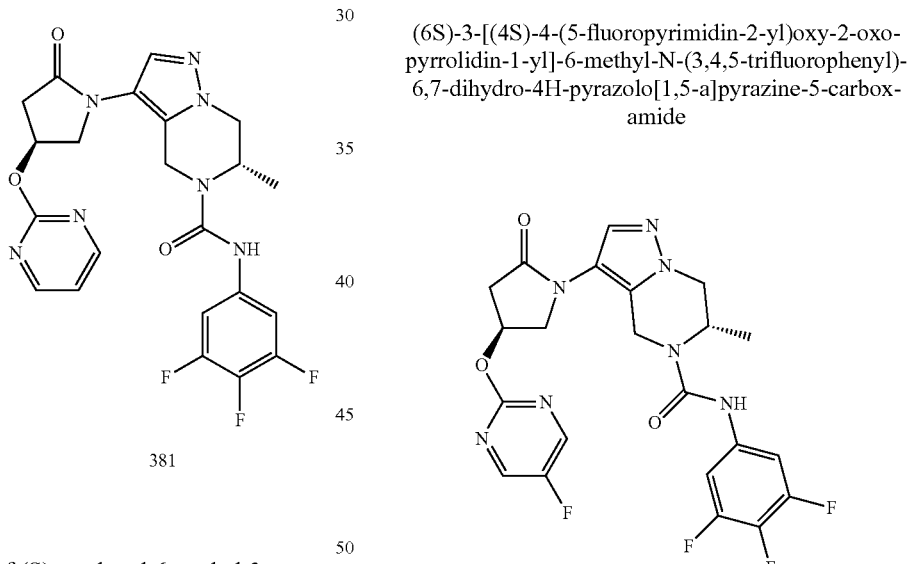

The title compound was prepared according to the following scheme:

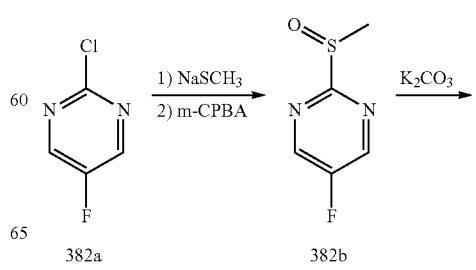

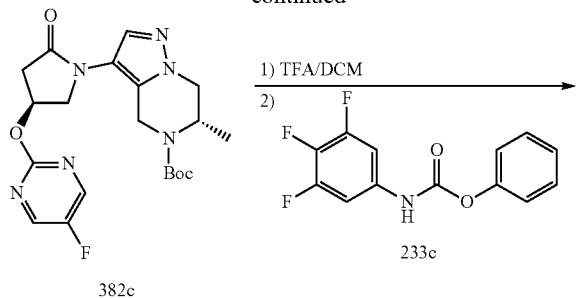

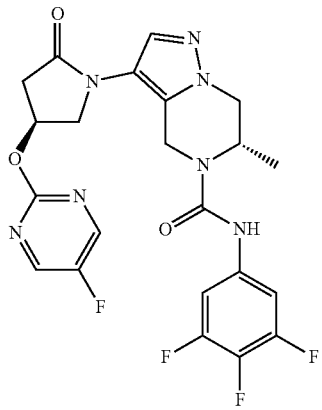

382

Step 1: Preparation of 5-fluoro-2-(methylsulfinyl)pyrimidine (compound 382b)

To a solution of 2-chloro-5-fluoropyrimidine (compound 382a, 398 mg, 3 mmol) in DMF (6 mL) at 5° C. was added dropwise sodium thiomethoxide (1.26 g, 1.15 mL, 2.7 mmol) (ca. 15% in water). The reaction mixture was stirred at 5° C. for 1 hour, then diluted with mixed solvent of PE/EtOAc (v/v=5/1), and washed with water. The organic phase was separated and concentrated to give crude intermediate 5-fluoro-2-methylsulfanyl-pyrimidine. The intermediate was dissolved in DCM (6 mL), then to which was added 3-chloroperoxybenzoic acid (m-CPBA) (518 mg, 3 mmol). The reaction mixture was stirred at room temperature for 2 hours, and then purified by silica gel column to give compound 382b (160 mg). LCMS (M+H$^+$): 161.

Step 2: Preparation of (S)-tert-butyl 34(S)-4-((5-fluoropyrimidin-2-yl)oxy)-2-oxopyrrolidin-1-yl)-6-methyl-6,7-dihydropyrazolo[1,5-a]pyrazine-5(4H)-carboxylate (compound 382c)

Compound 382c was prepared in analogy to compound 381b by using 5-fluoro-2-(methylsulfinyl)pyrimidine (compound 382b) instead of 2-(methylsulfinyl)pyrimidine. Compound 382c was obtained as a solid (108 mg). LCMS (M+H$^+$): 433.

Step 3: Preparation of (6S)-3-[(4S)-4-(5-fluoropyrimidin-2-yl)oxy-2-oxo-pyrrolidin-1-yl]-6-methyl-N-(3,4,5-trifluorophenyl)-6,7-dihydro-4H-pyrazolo[1,5-a]pyrazine-5-carboxamide

Example 382

The title compound was prepared in analogy to the preparation of Example 381 by using (S)-tert-butyl 3-((S)-4-((5-fluoropyrimidin-2-yl)oxy)-2-oxopyrrolidin-1-yl)-6-methyl-6,7-dihydropyrazolo[1,5-a]pyrazine-5(4H)-carboxylate (compound 382c) instead of (S)-tert-butyl 6-methyl-3-((S)-2-oxo-4-(pyrimidin-2-yloxy)pyrrolidin-1-yl)-6,7-dihydropyrazolo[1,5-a]pyrazine-5(4H)-carboxylate (compound 381b) to give Example 382 (77 mg). LCMS (M+H$^+$): 506. $^1$H NMR (400 MHz, CD$_3$OD) δ ppm 8.58 (s, 2H), 7.65 (s, 1H), 7.37-7.18 (m, 2H), 5.75-5.68 (m, 1H), 5.09 (d, J=16.9 Hz, 1H), 5.01-4.93 (m, 1H), 4.50 (d, J=16.9 Hz, 1H), 4.42-4.34 (m, 1H), 4.33-4.27 (m, 1H), 4.22-4.11 (m, 1H), 4.02-3.94 (m, 1H), 3.17 (dd, J=6.8, 18.1 Hz, 1H), 2.74 (dd, J=1.8, 18.0 Hz, 1H), 1.26 (d, J=6.8 Hz, 3H).

Example 384

(6S)-3-[4-[2-hydroxyethyl(methyl)carbamoyl]-2-oxo-pyrrolidin-1-yl]-6-methyl-N-(3,4,5-trifluorophenyl)-6,7-dihydro-4H-pyrazolo[1,5-a]pyrazine-5-carboxamide

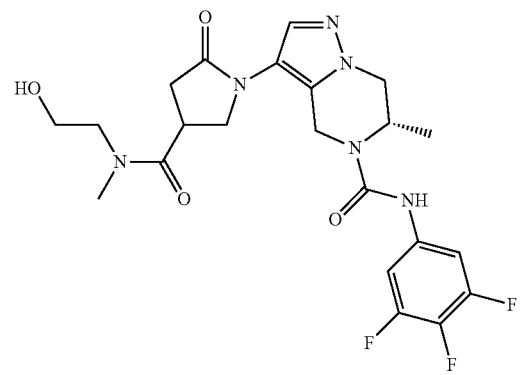 [SMILES: C[C@H]1Cn2ncc(N3CC(C(=O)N(C)CCO)CC3=O)c2CN1C(=O)Nc1cc(F)c(F)c(F)c1]

The title compound was prepared according to the following scheme:

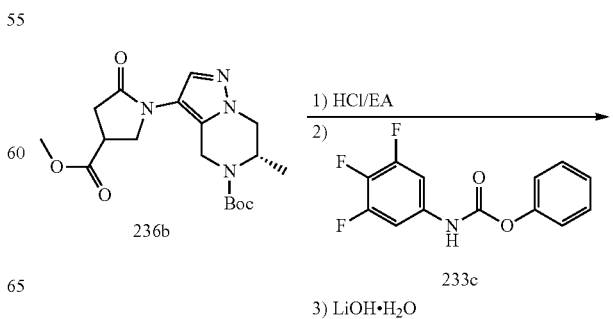

449
-continued

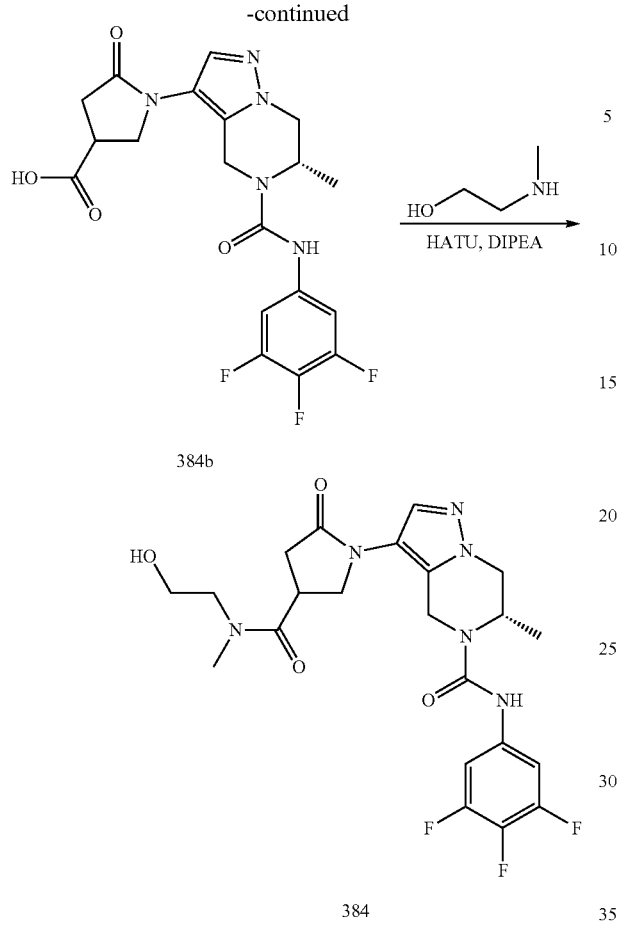

384b

384

Preparation of 1-((S)-6-methyl-54(3,4,5-trifluoro-phenyl)carbamoyl)-4,5,6,7-tetrahydropyrazolo[1,5-a]pyrazin-3-yl)-5-oxopyrrolidine-3-carboxylic acid (compound 384b)

The compound 384b was prepared in analogy to the preparation of compound 236d by using phenyl N-(3,4,5-trifluorophenyl)carbamate (compound 233c) instead of phenyl N-(3-chloro-4-fluoro-phenyl)carbamate (compound 12i). LCMS (M+H$^+$): 438.

Preparation of (6S)-3-[4-[2-hydroxyethyl(methyl)carbamoyl]-2-oxo-pyrrolidin-1-yl]-6-methyl-N-(3,4,5-trifluorophenyl)-6,7-dihydro-4H-pyrazolo[1,5-a]pyrazine-5-carboxamide (Example 384)

To a solution of 1-((S)-6-methyl-5-(3,4,5-trifluorophenyl)carbamoyl)-4,5,6,7-tetrahydropyrazolo[1,5-a]pyrazin-3-yl)-5-oxopyrrolidine-3-carboxylic acid (compound 384b, 122 mg, 0.28 mmol) in DMF (2 mL) was added 2-(methylamino)ethanol (42.1 mg, 44.8 µL, 560 µmol), DIPEA (151 mg, 0.2 mL, 1.17 mmol) and HATU (128 mg, 336 µmol) sequentially. The reaction mixture was stirred at room temperature overnight, and then purified by prep-HPLC to give Example 384 (13 mg). LCMS (M+H$^+$): 495. $^1$H NMR (400 MHz, CD$_3$OD) δ ppm 7.64 (d, J=4.3 Hz, 1H), 7.36-7.24 (m, 2H), 5.04 (d, J=16.8 Hz, 2H), 4.56-4.48 (m, 1H), 4.33-4.26 (m, 1H), 4.18 (s, 1H), 4.13-3.83 (m, 3H), 3.74 (d, J=5.5 Hz, 2H), 3.67-3.50 (m, 2H), 3.23-3.01 (m, 3H), 2.80 (s, 2H), 1.26 (d, J=7.0 Hz, 3H).

450

Example 385

(6S)-3-[4-[(2-hydroxy-1,1-dimethyl-ethyl)carbamoyl]-2-oxo-pyrrolidin-1-yl]-6-methyl-N-(3,4,5-trifluorophenyl)-6,7-dihydro-4H-pyrazolo[1,5-a]pyrazine-5-carboxamide

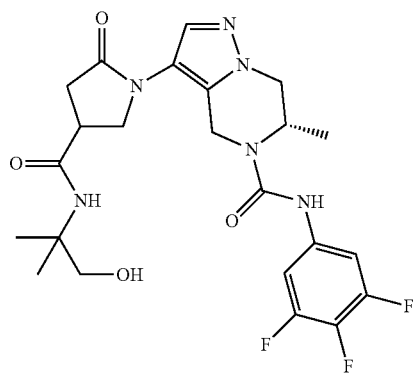 [SMILES: C[C@H]1Cn2ncc(N3CC(C(=O)NC(C)(C)CO)CC3=O)c2CN1C(=O)Nc1cc(F)c(F)c(F)c1]

Preparation of (6S)-3-[4-[(2-hydroxy-1,1-dimethyl-ethyl)carbamoyl]-2-oxo-pyrrolidin-1-yl]-6-methyl-N-(3,4,5-trifluorophenyl)-6,7-dihydro-4H-pyrazolo[1,5-a]pyrazine-5-carboxamide (Example 385)

The title compound was prepared in analogy to Example 384 by using 2-amino-2-methylpropan-1-ol instead of 2-(methylamino)ethanol. Example 385 was obtained as a white solid (16 mg). LCMS (M+H+): 509. $^1$H NMR (400 MHz, MeOD) δ ppm 7.64 (s, 1H), 7.30 (dd, J=6.3, 10.3 Hz, 2H), 5.04 (d, J=16.8 Hz, 1H), 5.00-4.93 (m, 1H), 4.52 (d, J=16.8 Hz, 1H), 4.33-4.25 (m, 1H), 4.18 (s, 1H), 3.99 (d, J=8.8 Hz, 1H), 3.92 (d, J=5.5 Hz, 1H), 3.65 (d, J=6.0 Hz, 2H), 3.42-3.35 (m, 1H), 2.84-2.69 (m, 2H), 1.33-1.24 (m, 9H).

Example 386

(6S)-6-methyl-3-[4-(morpholine-4-carbonyl)-2-oxo-pyrrolidin-1-yl]-N-(3,4,5-trifluorophenyl)-6,7-dihydro-4H-pyrazolo[1,5-a]pyrazine-5-carboxamide

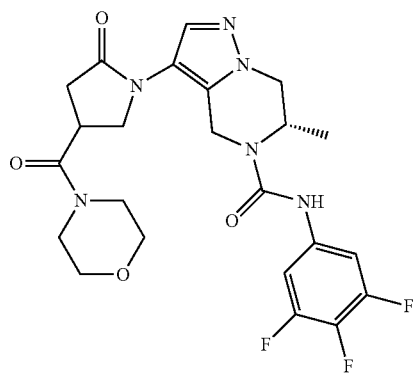 [SMILES: C[C@H]1Cn2ncc(N3CC(C(=O)N4CCOCC4)CC3=O)c2CN1C(=O)Nc1cc(F)c(F)c(F)c1]

Preparation of (6S)-6-methyl-3-[4-(morpholine-4-carbonyl)-2-oxo-pyrrolidin-1-yl]-N-(3,4,5-trifluorophenyl)-6,7-dihydro-4H-pyrazolo[1,5-a]pyrazine-5-carboxamide (Example 386)

The title compound was prepared in analogy to Example 384 by using morpholine instead of 2-(methylamino)ethanol. Example 386 was obtained as a white solid (20 mg). LCMS (M+H+): 507. $^1$H NMR (400 MHz, MeOD) δ ppm 7.65 (s, 1H), 7.35-7.23 (m, 2H), 5.04 (d, J=17.1 Hz, 2H), 4.50 (d, J=16.8 Hz, 1H), 4.35-4.26 (m, 1H), 4.19-3.92 (m, 3H), 3.89-3.79 (m, 1H), 3.75-3.60 (m, 8H), 2.93-2.75 (m, 2H), 1.30-1.23 (m, 3H).

Example 387

(6S)-3-[4-[(3S)-3-hydroxypyrrolidine-1-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide

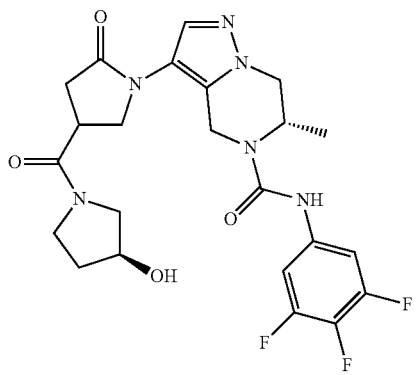 [SMILES: C[C@H]1Cn2ncc(N3CC(C(=O)N4CC[C@H](O)C4)CC3=O)c2CN1C(=O)Nc1cc(F)c(F)c(F)c1]

Preparation of (6S)-3-[4-[(3S)-3-hydroxypyrrolidine-1-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide (Example 387)

The title compound was prepared in analogy to Example 384 by using (S)-pyrrolidin-3-ol instead of 2-(methylamino)ethanol. Example 387 was obtained as a white solid (35 mg). LCMS (M+H+): 507. $^1$H NMR (400 MHz, MeOD) δ ppm 7.66 (s, 0.5H), 7.65 (s, 0.5H), 7.36-7.25 (m, 2H), 5.10-4.94 (m, 2H), 4.58-4.42 (m, 2H), 4.33-4.26 (m, 1H), 4.19-4.06 (m, 2H), 4.01-3.88 (m, 1H), 3.78-3.48 (m, 5H), 2.94-2.74 (m, 2H), 2.20-1.93 (m, 2H), 1.30-1.24 (m, 3H).

Example 388

(6S)-3-[4-[(3R)-3-hydroxypyrrolidine-1-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide

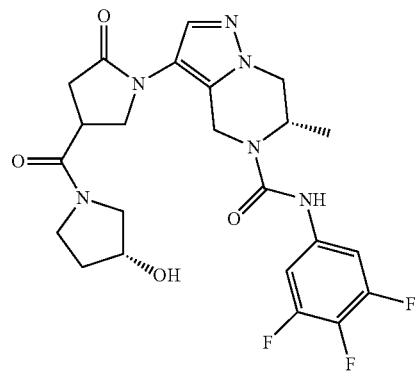 [SMILES: C[C@H]1Cn2ncc(N3CC(C(=O)N4CC[C@@H](O)C4)CC3=O)c2CN1C(=O)Nc1cc(F)c(F)c(F)c1]

Preparation of (6S)-3-[4-[(3R)-3-hydroxypyrrolidine-1-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide (Example 388)

The title compound was prepared in analogy to Example 384 by using (R)-pyrrolidin-3-ol instead of 2-(methylamino)ethanol. Example 388 was obtained as a white solid (15 mg). LCMS (M+H+): 507. $^1$H NMR (400 MHz, MeOD) δ ppm 7.66 (s, 0.5H), 7.65 (s, 0.5H), 7.35-7.26 (m, 2H), 5.08-4.96 (m, 2H), 4.56-4.43 (m, 2H), 4.34-4.26 (m, 1H), 4.19-4.03 (m, 2H), 4.00-3.90 (m, 1H), 3.79-3.47 (m, 5H), 2.94-2.74 (m, 2H), 2.20-1.94 (m, 2H), 1.30-1.24 (m, 3H).

Example 389

(6S)-3-[4-(3-hydroxyazetidine-1-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide

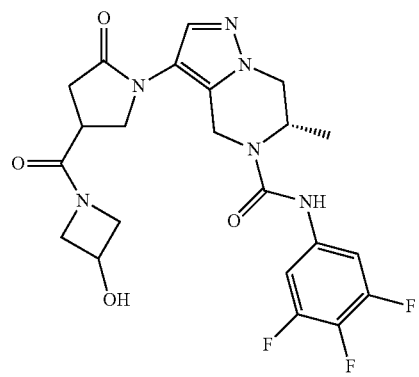 [SMILES: C[C@H]1Cn2ncc(N3CC(C(=O)N4CC(O)C4)CC3=O)c2CN1C(=O)Nc1cc(F)c(F)c(F)c1]

Preparation of (6S)-3-[4-(3-hydroxyazetidine-1-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide (Example 389)

The title compound was prepared in analogy to Example 384 by using azetidin-3-ol instead of 2-(methylamino)ethanol. Example 389 was obtained as a white solid (16 mg). LCMS (M+H+): 493. $^1$H NMR (400 MHz, MeOD) δ ppm 7.64 (s, 0.5H), 7.64 (s, 0.5H) 7.34-7.25 (m, 2H), 5.07-4.94 (m, 2H), 4.67-4.59 (m, 1H), 4.55-4.47 (m, 2H), 4.33-4.22 (m, 2H), 4.19-4.13 (m, 1H), 4.11-3.98 (m, 2H), 3.94-3.78 (m, 2H), 3.54-3.44 (m, 1H), 2.87-2.68 (m, 2H), 1.30-1.24 (m, 3H).

Example 390

(6S)-3-[4-(dimethylcarbamoyl)-2-oxo-pyrrolidin-1-yl]-6-methyl-N-(3,4,5-trifluorophenyl)-6,7-dihydro-4H-pyrazolo[1,5-a]pyrazine-5-carboxamide

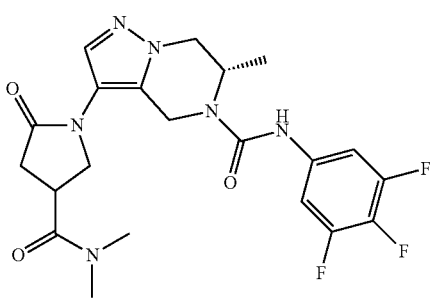 [SMILES: C[C@H]1Cn2ncc(N3CC(C(=O)N(C)C)CC3=O)c2CN1C(=O)Nc1cc(F)c(F)c(F)c1]

Preparation of (6S)-3-[4-(dimethylcarbamoyl)-2-oxo-pyrrolidin-1-yl]-6-methyl-N-(3,4,5-trifluorophenyl)-6,7-dihydro-4H-pyrazolo[1,5-a]pyrazine-5-carboxamide (Example 390)

The title compound was prepared in analogy to Example 384 by using dimethylamine instead of 2-(methylamino)ethanol. Example 390 was obtained as a white solid (30 mg). LCMS (M+H+): 465. $^1$H NMR (400 MHz, MeOD) δ ppm 7.64 (s, 1H), 7.35-7.25 (m, 2H), 5.08-4.94 (m, 2H), 4.56-4.47 (m, 1H), 4.33-4.25 (m, 1H), 4.19-4.03 (m, 2H), 3.99-3.81 (m, 2H), 3.16 (s, 3H), 3.01 (s, 3H), 2.92-2.82 (m, 1H), 2.80-2.72 (m, 1H), 1.30-1.24 (m, 3H).

Example 391

(6S)-6-methyl-3-[2-oxo-4-(pyrrolidine-1-carbonyl)pyrrolidin-1-yl]-N-(3,4,5-trifluorophenyl)-6,7-dihydro-4H-pyrazolo[1,5-a]pyrazine-5-carboxamide

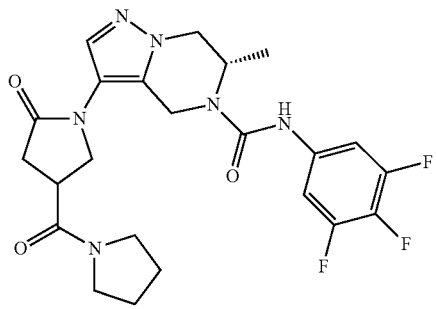 [SMILES: C[C@H]1Cn2ncc(N3CC(C(=O)N4CCCC4)CC3=O)c2CN1C(=O)Nc1cc(F)c(F)c(F)c1]

Preparation of (6S)-6-methyl-3-[2-oxo-4-(pyrrolidine-1-carbonyl)pyrrolidin-1-yl]-N-(3,4,5-trifluorophenyl)-6,7-dihydro-4H-pyrazolo[1,5-a]pyrazine-5-carboxamide (Example 391)

The title compound was prepared in analogy to Example 384 by using pyrrolidine instead of 2-(methylamino)ethanol. Example 391 was obtained as a white solid (28 mg). LCMS (M+H+): 491. $^1$H NMR (400 MHz, MeOD) δ ppm 7.64 (s, 1H), 7.35-7.25 (m, 2H), 5.07-4.93 (m, 2H), 4.55-4.48 (m, 1H), 4.33-4.25 (m, 1H), 4.19-4.04 (m, 2H), 3.99-3.89 (m, 1H), 3.76-3.66 (m, 1H), 3.65-3.56 (m, 2H), 3.51-3.45 (m, 2H), 2.92-2.82 (m, 1H), 2.80-2.73 (m, 1H), 2.08-1.99 (m, 2H), 1.97-1.88 (m, 2H), 1.30-1.24 (m, 3H)

Example 392

(6S)-6-methyl-3-[4-(oxazol-2-ylcarbamoyl)-2-oxo-pyrrolidin-1-yl]-N-(3,4,5-trifluorophenyl)-6,7-dihydro-4H-pyrazolo[1,5-a]pyrazine-5-carboxamide

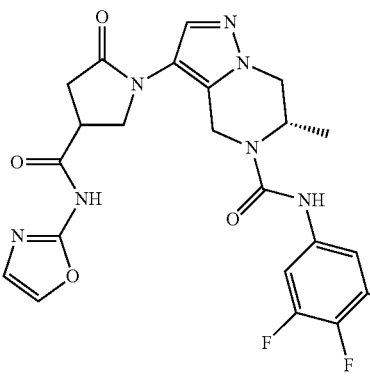

Preparation of (6S)-6-methyl-3-[4-(oxazol-2-ylcarbamoyl)-2-oxo-pyrrolidin-1-yl]-N-(3,4,5-trifluorophenyl)-6,7-dihydro-4H-pyrazolo[1,5-a]pyrazine-5-carboxamide (Example 392)

The title compound was prepared in analogy to Example 384 by using oxazol-2-amine instead of 2-(methylamino)

ethanol. Example 392 was obtained as a white solid (5 mg). LCMS (M+H+): 504. ¹H NMR (400 MHz, MeOD) δ ppm 7.70-7.60 (m, 2H), 7.35-7.25 (m, 2H), 7.10 (s, 1H), 5.08-4.94 (m, 2H), 4.55-4.46 (m, 1H), 4.28 (d, J=4.5 Hz, 1H), 4.20-3.99 (m, 3H), 3.62 (br. s., 1H), 3.54-3.45 (m, 1H), 2.99-2.81 (m, 2H), 1.33-1.21 (m, 3H).

Example 393

(6S)-3-[4-(2,2-dimethylmorpholine-4-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide

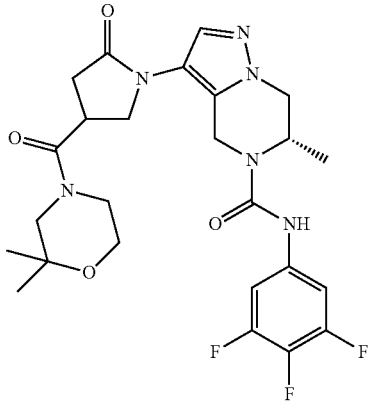 [SMILES: C[C@H]1Cn2ncc(N3CC(C(=O)N4CCOC(C)(C)C4)CC3=O)c2CN1C(=O)Nc1cc(F)c(F)c(F)c1]

Preparation of (6S)-3-[4-(2,2-dimethylmorpholine-4-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide (Example 393)

The title compound was prepared in analogy to Example 384 by using 2,2-dimethylmorpholine instead of 2-(methylamino)ethanol. Example 393 was obtained as a white solid (23 mg). LCMS (M+H+): 535. ¹H NMR (400 MHz, MeOD) δ ppm 7.64 (s, 1H), 7.34-7.25 (m, 2H), 5.07-4.95 (m, 2H), 4.54-4.47 (m, 1H), 4.33-4.27 (m, 1H), 4.16 (d, J=12.5 Hz, 1H), 4.12-4.05 (m, 1H), 4.02-3.93 (m, 1H), 3.91-3.74 (m, 3H), 3.65-3.57 (m, 2H), 3.52-3.44 (m, 2H), 2.81 (d, J=6.5 Hz, 2H), 1.30-1.19 (m, 9H).

Example 394

(6S)-6-methyl-3-[4-[(2R)-2-methylmorpholine-4-carbonyl]-2-oxo-pyrrolidin-1-yl]-N-(3,4,5-trifluorophenyl)-6,7-dihydro-4H-pyrazolo[1,5-a]pyrazine-5-carboxamide

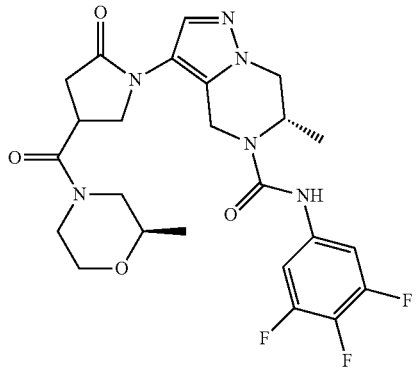 [SMILES: C[C@@H]1CN(C(=O)C2CC(=O)N(c3cnn4c3CN(C(=O)Nc3cc(F)c(F)c(F)c3)[C@@H](C)C4)C2)CCO1]

Preparation of (6S)-6-methyl-3-[4-[(2R)-2-methylmorpholine-4-carbonyl]-2-oxo-pyrrolidin-1-yl]-N-(3,4,5-trifluorophenyl)-6,7-dihydro-4H-pyrazolo[1,5-a]pyrazine-5-carboxamide (Example 394)

The title compound was prepared in analogy to Example 384 by using (R)-2-methylmorpholine instead of 2-(methylamino)ethanol. Example 394 was obtained as a white solid (21 mg). LCMS (M+H+): 521. ¹H NMR (400 MHz, MeOD) δ ppm 7.66-7.62 (m, 1H), 7.34-7.25 (m, 2H), 5.09-4.94 (m, 2H), 4.56-4.46 (m, 1H), 4.42-4.35 (m, 1H), 4.34-4.27 (m, 1H), 4.17 (s, 1H), 4.12-3.83 (m, 5H), 3.54 (br. s., 2H), 3.05-2.44 (m, 4H), 1.30-1.17 (m, 6H).

Example 395

(6S)-6-methyl-3-[4-[(2S)-2-methylmorpholine-4-carbonyl]-2-oxo-pyrrolidin-1-yl]-N-(3,4,5-trifluorophenyl)-6,7-dihydro-4H-pyrazolo[1,5-a]pyrazine-5-carboxamide

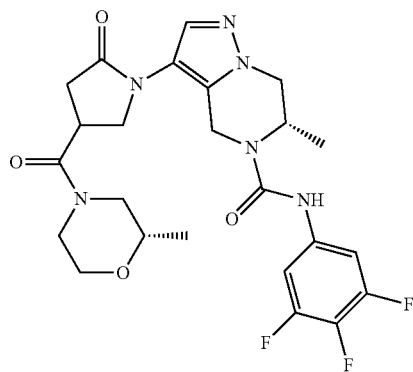 [SMILES: C[C@H]1CN(C(=O)C2CC(=O)N(c3cnn4c3CN(C(=O)Nc3cc(F)c(F)c(F)c3)[C@@H](C)C4)C2)CCO1]

Preparation of (6S)-6-methyl-3-[4-[(2S)-2-methylmorpholine-4-carbonyl]-2-oxo-pyrrolidin-1-yl]-N-(3,4,5-trifluorophenyl)-6,7-dihydro-4H-pyrazolo[1,5-a]pyrazine-5-carboxamide (Example 395)

The title compound was prepared in analogy to Example 384 by using (S)-2-methylmorpholine instead of 2-(methylamino)ethanol. Example 395 was obtained as a white solid (14 mg). LCMS (M+H+): 521. ¹H NMR (400 MHz, MeOD) δ ppm 7.66-7.62 (m, 1H), 7.34-7.25 (m, 2H), 5.07-4.93 (m, 2H), 4.55-4.46 (m, 1H), 4.41-4.26 (m, 2H), 4.18-3.83 (m, 6H), 3.64-3.48 (m, 2H), 3.02-2.49 (m, 4H), 1.31-1.18 (m, 6H).

Example 396

(6S)-3-[4-[trans-2,6-dimethylmorpholine-4-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide

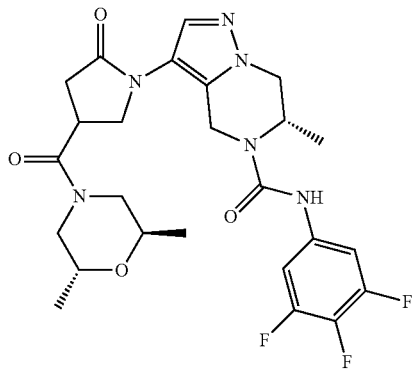 [SMILES: C[C@@H]1CN(C(=O)C2CC(=O)N(c3cnn4c3CN(C(=O)Nc3cc(F)c(F)c(F)c3)[C@@H](C)C4)C2)C[C@@H](C)O1]

Preparation of (6S)-3-[4-[trans-2,6-dimethylmorpholine-4-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide (Example 396)

The title compound was prepared in analogy to Example 384 by using trans-2,6-dimethylmorpholine instead of 2-(methylamino)ethanol. Example 396 was obtained as a white solid (20 mg). LCMS (M+H+): 535. $^1$H NMR (400 MHz, MeOD) δ ppm 7.64 (m, 1H), 7.35-7.23 (m, 2H), 5.08-4.93 (m, 2H), 4.55-4.45 (m, 1H), 4.44-4.36 (m, 1H), 4.33-4.25 (m, 1H), 4.19-3.83 (m, 5H), 3.69-3.51 (m, 2H), 2.94-2.72 (m, 3H), 2.43 (dd, J=10.8, 13.1 Hz, 1H), 1.31-1.17 (m, 9H).

Example 397

(6S)-3-[4-[cis-2,6-dimethylmorpholine-4-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide

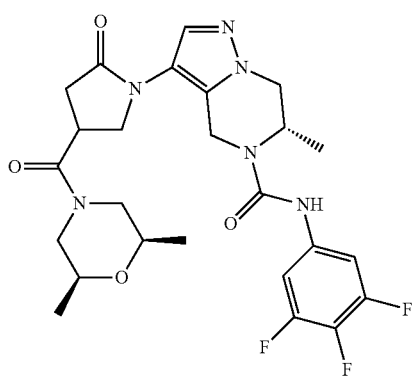 [SMILES: C[C@@H]1CN(C(=O)C2CC(=O)N(c3cnn4c3CN(C(=O)Nc3cc(F)c(F)c(F)c3)[C@@H](C)C4)C2)C[C@H](C)O1]

Preparation of (6S)-3-[4-[cis-2,6-dimethylmorpholine-4-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide

Example 397

The title compound was prepared in analogy to Example 384 by using cis-2,6-dimethylmorpholine instead of 2-(methylamino)ethanol. Example 397 was obtained as a white solid (24 mg). LCMS (M+H+): 535. $^1$H NMR (400 MHz, MeOD) δ ppm 7.66-7.62 (m, 1H), 7.34-7.25 (m, 2H), 5.08-4.92 (m, 2H), 4.54-4.46 (m, 1H), 4.34-4.25 (m, 1H), 4.19-4.13 (m, 1H), 4.12-3.82 (m, 5H), 3.76-3.38 (m, 3H), 2.96-2.35 (m, 3H), 1.31-1.17 (m, 9H).

Example 398

(6S)-3-[4-(3,3-difluoropyrrolidine-1-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide

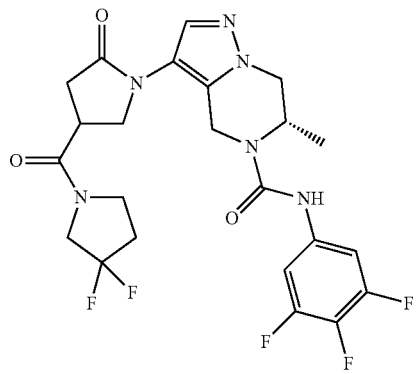 [SMILES: C[C@H]1Cn2ncc(N3CC(C(=O)N4CCC(F)(F)C4)CC3=O)c2CN1C(=O)Nc1cc(F)c(F)c(F)c1]

Preparation of (6S)-3-[4-(3,3-difluoropyrrolidine-1-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide (Example 398)

The title compound was prepared in analogy to Example 384 by using 3,3-difluoropyrrolidine hydrochloride instead of 2-(methylamino)ethanol. Example 398 was obtained as a white solid (3 mg). LCMS (M+H+): 527. $^1$H NMR (400 MHz, MeOD) δ ppm 7.64 (s, 1H), 7.34-7.25 (m, 2H), 5.08-4.94 (m, 2H), 4.56-4.46 (m, 1H), 4.35-4.25 (m, 1H), 4.18-3.63 (m, 8H), 2.93-2.84 (m, 1H), 2.81-2.72 (m, 1H), 2.60-2.39 (m, 2H), 1.30-1.24 (m, 3H).

Example 399

(6S)-6-methyl-3-[4-[methyl(oxazol-2-yl)carbamoyl]-2-oxo-pyrrolidin-1-yl]-N-(3,4,5-trifluorophenyl)-6,7-dihydro-4H-pyrazolo[1,5-a]pyrazine-5-carboxamide

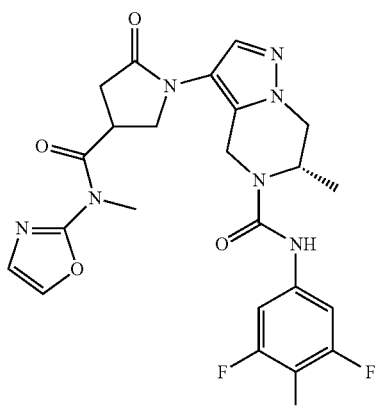

Preparation of (6S)-6-methyl-3-[4-[methyboxazol-2-yl)carbamoyl]-2-oxo-pyrrolidin-1-yl]-N-(3,4,5-trifluorophenyl)-6,7-dihydro-4H-pyrazolo[1,5-a]pyrazine-5-carboxamide (Example 399)

The title compound was prepared in analogy to Example 384 by using N-methyl-2-Oxazolamine instead of 2-(methylamino)ethanol. Example 399 was obtained as a white solid (13 mg). LCMS (M+H+): 518. $^1$H NMR (400 MHz, MeOD) δ ppm 7.87 (s, 1H), 7.63 (s, 1H), 7.34-7.25 (m, 2H), 7.20 (s, 1H), 5.07-4.93 (m, 2H), 4.54-4.46 (m, 1H), 4.33-4.26 (m, 1H), 4.18-3.98 (m, 4H), 3.41 (d, J=1.8 Hz, 3H), 2.88-2.77 (m, 2H), 1.31-1.25 (m, 3H).

Example 400

(6S)-3-[4-(3,3-difluoropyrrolidine-1-carbonyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide

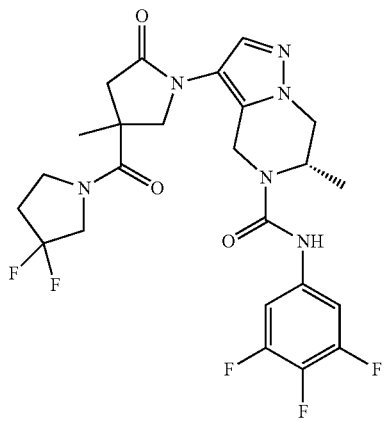 [SMILES: C[C@H]1Cn2ncc(N3CC(C)(C(=O)N4CCC(F)(F)C4)CC3=O)c2CN1C(=O)Nc1cc(F)c(F)c(F)c1]

The title compound was prepared according to the following scheme:

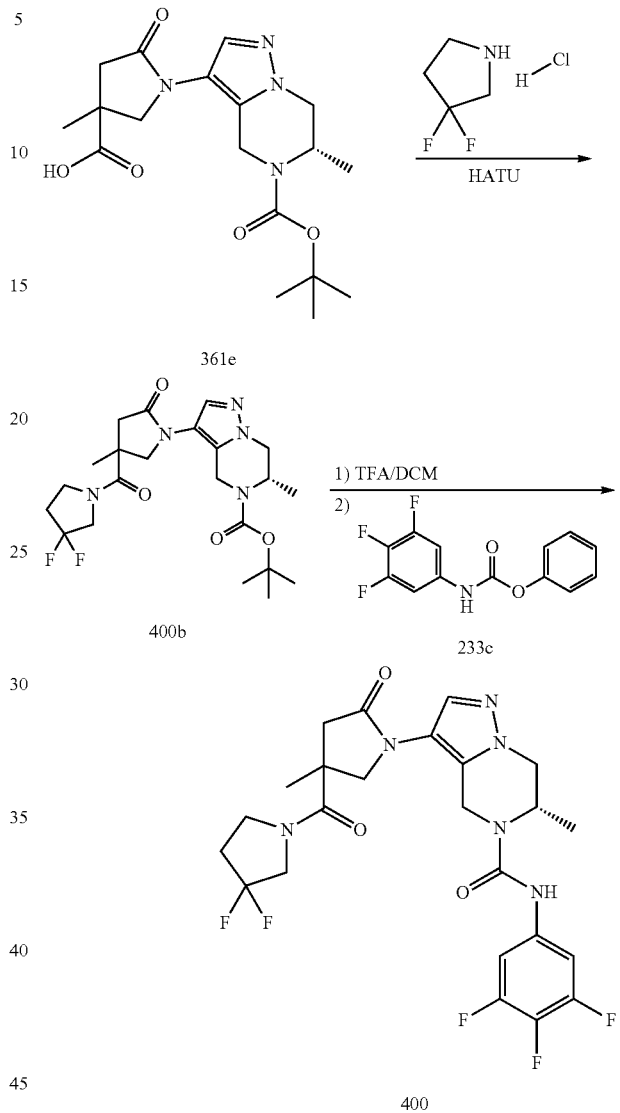

Step 1: Preparation of (6S)-tert-butyl 3-(4-(3,3-difluoropyrrolidine-1-carbonyl)-4-methyl-2-oxopyrrolidin-1-yl)-6-methyl-6,7-dihydropyrazolo[1,5-a]pyrazine-5(4H)-carboxylate (compound 400b)

To a solution of 1-((S)-5-(tert-butoxycarbonyl)-6-methyl-4,5,6,7-tetrahydropyrazolo[1,5-a]pyrazin-3-yl)-3-methyl-5-oxopyrrolidine-3-carboxylic acid (compound 361e, 120 mg, 317 μmol) in DCM (5 mL) was added 3,3-difluoropyrrolidine hydrochloride (68.3 mg, 476 μmol), DIPEA (377 mg, 0.5 mL, 2.92 mmol) and HATU (145 mg, 381 μmol). The reaction mixture was stirred at 40° C. overnight and then was concentrated and purified by silica gel column to give compound 400b (120 mg). LCMS (M+H$^+$): 468.

Step 2: Preparation of (6S)-3-[4-(3,3-difluoropyrrolidine-1-carbonyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide (Example 400)

A mixture of (6S)-tert-butyl 3-(4-(3,3-difluoropyrrolidine-1-carbonyl)-4-methyl-2-oxopyrrolidin-1-yl)-6-methyl-6,7-dihydropyrazolo[1,5-a]pyrazine-5(4H)-carboxylate (compound 400b, 120 mg, 257 µmol), trifluoroacetic acid (2.98 g, 2 mL, 26.1 mmol) and DCM (1 mL) was stirred at room temperature for 1 hour. The reaction mixture was concentrated. The residue was dissolved in DMF (2 mL), to which was added DIPEA (302 mg, 0.4 mL, 2.33 mmol), and phenyl (3,4,5-trifluorophenyl)carbamate (compound 233c, 89.2 mg, 334 µmol). The reaction mixture was stirred at 50° C. for 2 hours. Then the reaction mixture was concentrated and purified by prep-HPLC to give Example 400 (56 mg). LCMS (M+H+): 541. $^1$H NMR (400 MHz, CD$_3$OD) δ ppm 7.66 (m, 1H), 7.33-7.24 (m, 2H), 5.09-4.92 (m, 2H), 4.61-4.44 (m, 1H), 4.41-4.25 (m, 2H), 4.19-4.13 (m, 1H), 4.10-3.72 (m, 4H), 3.72-3.63 (m, 1H), 3.19 (br. s., 1H), 2.63-2.34 (m, 3H), 1.58 (br. s., 3H), 1.31-1.24 (m, 3H).

Example 401

(6S)-3-[4-(4,4-difluoropiperidine-1-carbonyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide

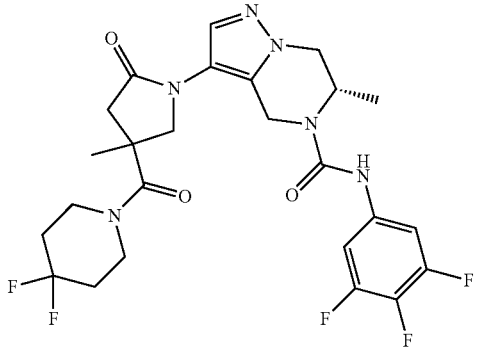 [SMILES: C[C@H]1Cn2ncc(N3CC(C)(C(=O)N4CCC(F)(F)CC4)CC3=O)c2CN1C(=O)Nc1cc(F)c(F)c(F)c1]

Preparation of (6S)-3-[4-(4,4-difluoropiperidine-1-carbonyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide (Example 401)

The title compound was prepared in analogy to Example 400 by using 4,4-difluoropiperidine hydrochloride instead of 3,3-difluoropyrrolidine hydrochloride. Example 401 was obtained as a white solid (65 mg). LCMS (M+H+): 555. $^1$H NMR (400 MHz, MeOD) δ ppm 7.66 (s, 1H), 7.33-7.23 (m, 2H), 5.08-4.92 (m, 2H), 4.56-4.37 (m, 2H), 4.34-4.26 (m, 1H), 4.19-4.13 (m, 1H), 3.82-3.68 (m, 5H), 3.23 (dd, J=3.4, 16.9 Hz, 1H), 2.66 (dd, J=1.8, 17.1 Hz, 1H), 2.16-1.96 (m, 4H), 1.60 (s, 3H), 1.31-1.24 (m, 3H).

Example 402

(6S)-6-methyl-3-[4-methyl-4-(morpholine-4-carbonyl)-2-oxo-pyrrolidin-1-yl]-N-(3,4,5-trifluorophenyl)-6,7-dihydro-4H-pyrazolo[1,5-a]pyrazine-5-carboxamide

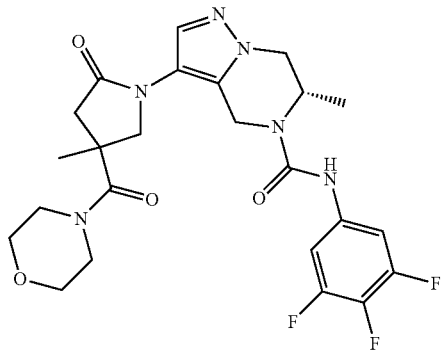 [SMILES: C[C@H]1Cn2ncc(N3CC(C)(C(=O)N4CCOCC4)CC3=O)c2CN1C(=O)Nc1cc(F)c(F)c(F)c1]

Preparation of (6S)-6-methyl-3-[4-methyl-4-(morpholine-4-carbonyl)-2-oxo-pyrrolidin-1-yl]-N-(3,4,5-trifluorophenyl)-6,7-dihydro-4H-pyrazolo[1,5-a]pyrazine-5-carboxamide (Example 402)

The title compound was prepared in analogy to Example 400 by using morpholine instead of 3,3-difluoropyrrolidine hydrochloride. Example 402 was obtained as a white solid (54 mg). LCMS (M+H+): 521. $^1$H NMR (400 MHz, MeOD) δ ppm 7.66 (s, 1H), 7.32-7.24 (m, 2H), 5.03 (dd, J=13.6, 16.8 Hz, 2H), 4.57-4.36 (m, 2H), 4.33-4.26 (m, 1H), 4.21-4.12 (m, 1H), 3.77-3.58 (m, 9H), 3.26-3.17 (m, 1H), 2.66 (d, J=1.5 Hz, 1H), 1.59 (s, 3H), 1.32-1.24 (m, 3H).

Example 403

(6S)-6-methyl-3-[4-methyl-4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide

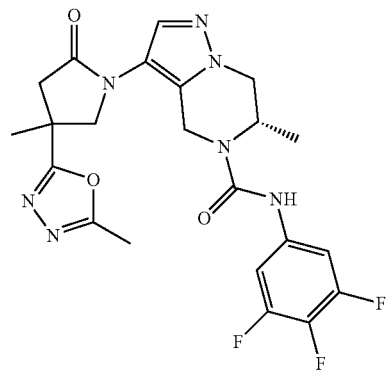 [SMILES: Cc1nnc(C2(C)CC(=O)N(c3cnn4c3CN(C(=O)Nc3cc(F)c(F)c(F)c3)[C@@H](C)C4)C2)o1]

Preparation of (6S)-6-methyl-3-[4-methyl-4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide (Example 403)

The title compound was prepared in analogy to Example 283 by using (6S)-tert-butyl 3-(4-(methoxycarbonyl)-4-methyl-2-oxopyrrolidin-1-yl)-6-methyl-6,7-dihydropyrazolo[1,5-a]pyrazine-5(4H)-carboxylate (compound 361d) instead of (6S)-tert-butyl 3-(4-(methoxycarbonyl)-2-oxopyrrolidin-1-yl)-6-methyl-6,7-dihydropyrazolo[1,5-a]pyrazine-5(4H)-carboxylate (compound 236b). Example 403 was obtained as a white solid (64 mg). LCMS (M+H+): 490. ¹H NMR (400 MHz, MeOD) δ ppm 7.65 (s, 1H), 7.29 (ddd, J=3.1, 6.6, 10.1 Hz, 2H), 5.09-4.92 (m, 2H), 4.49 (dd, J=11.8, 17.1 Hz, 1H), 4.34-4.22 (m, 2H), 4.19-4.13 (m, 1H), 3.97 (dd, J=10.0, 14.3 Hz, 1H), 3.17 (d, J=17.1 Hz, 1H), 2.81 (d, J=17.1 Hz, 1H), 2.57 (d, J=2.8 Hz, 3H), 1.73 (s, 3H), 1.32-1.23 (m, 3H).

Example 404

(6S)-6-methyl-3-[4-methyl-4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide

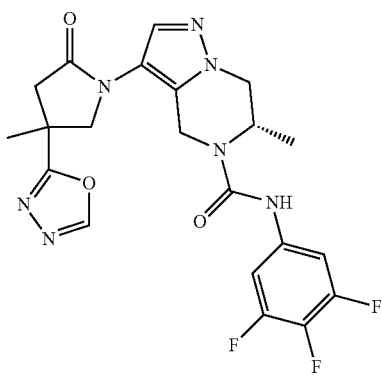 [SMILES: C[C@H]1Cn2ncc(N3CC(C)(c4nnco4)CC3=O)c2CN1C(=O)Nc1cc(F)c(F)c(F)c1]

Preparation of (6S)-6-methyl-3-[4-methyl-4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide (Example 404)

The title compound was prepared in analogy to Example 282 by using (6S)-tert-butyl 3-(4-(methoxycarbonyl)-4-methyl-2-oxopyrrolidin-1-yl)-6-methyl-6,7-dihydropyrazolo[1,5-a]pyrazine-5(4H)-carboxylate (compound 361d) instead of (6S)-tert-butyl 3-(4-(methoxycarbonyl)-2-oxopyrrolidin-1-yl)-6-methyl-6,7-dihydropyrazolo[1,5-a]pyrazine-5(4H)-carboxylate (compound 236b). Example 404 was obtained as a white solid (12 mg). LCMS (M+H+): 476. 1H NMR (400 MHz, MeOD) δ ppm 9.00 (s, 0.5H), 8.99 (s, 0.5H), 7.66 (s, 0.5H), 7.65 (s, 0.5H), 7.33-7.24 (m, 2H), 5.10-4.95 (m, 2H), 4.55-4.45 (m, 1H), 4.36-4.27 (m, 2H), 4.20-4.14 (m, 1H), 4.04-3.96 (m, 1H), 3.20 (d, J=17.1 Hz, 1H), 2.84 (d, J=16.8 Hz, 1H), 1.77 (s, 3H), 1.32-1.23 (m, 3H).

Example 405

(6S)-6-methyl-3-[4-methyl-4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide

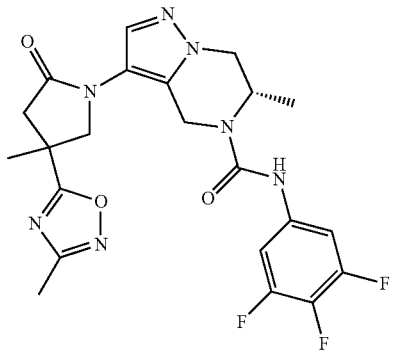 [SMILES: Cc1noc(C2(C)CC(=O)N(c3cnn4c3CN(C(=O)Nc3cc(F)c(F)c(F)c3)[C@@H](C)C4)C2)n1]

Preparation of (6S)-6-methyl-3-[4-methyl-4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide (Example 405)

The title compound was prepared in analogy to Example 284 by using 1-((S)-5-(tert-butoxycarbonyl)-6-methyl-4,5,6,7-tetrahydropyrazolo[1,5-a]pyrazin-3-yl)-3-methyl-5-oxopyrrolidine-3-carboxylic acid (compound 361e) instead of 1-((S)-5-(tert-butoxycarbonyl)-6-methyl-4,5,6,7-tetrahydropyrazolo[1,5-a]pyrazin-3-yl)-5-oxopyrrolidine-3-carboxylic acid (compound 229a). Example 405 was obtained as a white solid (35 mg). LCMS (M+H+): 490. ¹H NMR (400 MHz, MeOD) δ ppm 7.64 (s, 1H), 7.33-7.23 (m, 2H), 5.09-4.93 (m, 2H), 4.54-4.45 (m, 1H), 4.35-4.21 (m, 2H), 4.20-4.13 (m, 1H), 3.98 (dd, J=10.1, 14.9 Hz, 1H), 3.17 (dd, J=3.4, 16.9 Hz, 1H), 2.83 (d, J=17.0 Hz, 1H), 2.39 (d, J=3.5 Hz, 3H), 1.75 (s, 3H), 1.32-1.23 (m, 3H).

Example 406

(6S)-6-methyl-3-[4-methyl-4-(5-methyl-1,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide

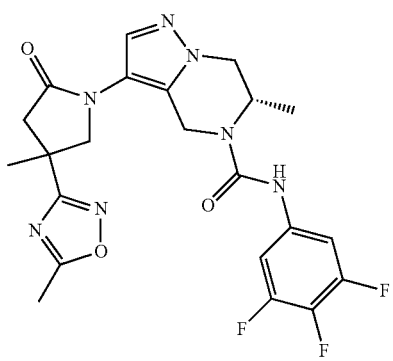 [SMILES: Cc1nc(C2(C)CC(=O)N(c3cnn4c3CN(C(=O)Nc3cc(F)c(F)c(F)c3)[C@@H](C)C4)C2)no1]

Preparation of (6S)-6-methyl-3-[4-methyl-4-(5-methyl-1,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide (Example 406)

The title compound was prepared in analogy to Example 285 by using (6S)-tert-butyl 3-(4-cyano-4-methyl-2-oxopyrrolidin-1-yl)-6-methyl-6,7-dihydropyrazolo[1,5-a]pyrazine-5(4H)-carboxylate (compound 361g) instead of (6S)-tert-butyl 3-(4-cyano-2-oxopyrrolidin-1-yl)-6-methyl-6,7-dihydropyrazolo[1,5-a]pyrazine-5(4H)-carboxylate (compound 229c). Example 406 was obtained as a white solid (50 mg). LCMS (M+H+): 490. $^1$H NMR (400 MHz, MeOD) δ ppm 7.51 (s, 0.5H), 7.50 (s, 0.5H) 7.21-7.11 (m, 2H), 4.97-4.81 (m, 2H), 4.36 (dd, J=5.6, 17.0 Hz, 1H), 4.23-4.13 (m, 1H), 4.12-4.00 (m, 2H), 3.80 (dd, J=9.9, 14.8 Hz, 1H), 2.98 (dd, J=4.0, 16.9 Hz, 1H), 2.62 (d, J=16.9 Hz, 1H), 2.49 (d, J=3.7 Hz, 3H), 1.56 (s, 3H), 1.20-1.11 (m, 3H).

Example 407

(6S)-6-methyl-3-[(2S)-2-oxazol-5-yl-5-oxo-morpholin-4-yl]-N-(3,4,5-trifluorophenyl)-6,7-dihydro-4H-pyrazolo[1,5-a]pyrazine-5-carboxamide

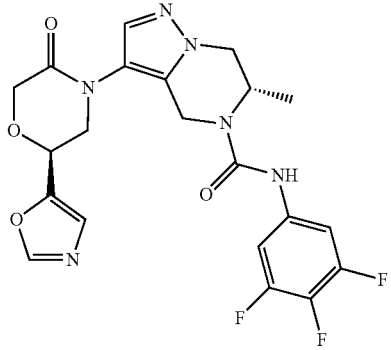 [SMILES: C[C@H]1Cn2ncc(N3C[C@@H](c4cnco4)OCC3=O)c2CN1C(=O)Nc1cc(F)c(F)c(F)c1]

Preparation of (6S)-6-methyl-3-[(2S)-2-oxazol-5-yl-5-oxo-morpholin-4-yl]-N-(3,4,5-trifluorophenyl)-6,7-dihydro-4H-pyrazolo[1,5-a]pyrazine-5-carboxamide (Example 407)

The title compound was prepared in analogy to Example 247 by using (S)-6-(hydroxymethyl)morpholin-3-one instead of 4-(hydroxymethyl)pyrrolidin-2-one. Example 407 was obtained as a white solid (4 mg). LCMS (M+H+): 477. $^1$H NMR (400 MHz, MeOD) δ ppm 8.28 (s, 1H), 7.70 (s, 1H), 7.33-7.24 (m, 3H), 5.34 (dd, J=3.4, 9.7 Hz, 1H), 5.03-4.92 (m, 2H), 4.56-4.40 (m, 3H), 4.35-4.14 (m, 3H), 3.95 (dd, J=3.4, 12.2 Hz, 1H), 1.29 (d, J=6.8 Hz, 3H).

Example 408

(6S)-6-methyl-3-[5-(3-methyl-1,2,4-oxadiazol-5-yl)-2-oxo-oxazolidin-3-yl]-N-(3,4,5-trifluorophenyl)-6,7-dihydro-4H-pyrazolo[1,5-a]pyrazine-5-carboxamide

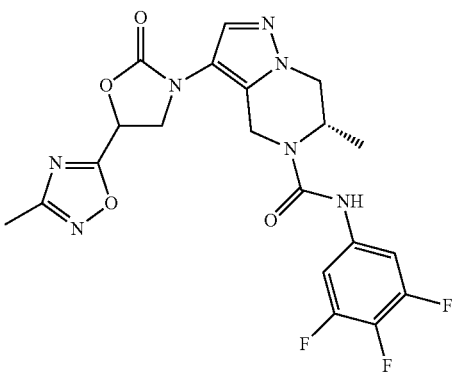 [SMILES: Cc1noc(C2CN(c3cnn4c3CN(C(=O)Nc3cc(F)c(F)c(F)c3)[C@@H](C)C4)C(=O)O2)n1]

The title compound was prepared according to the following scheme:

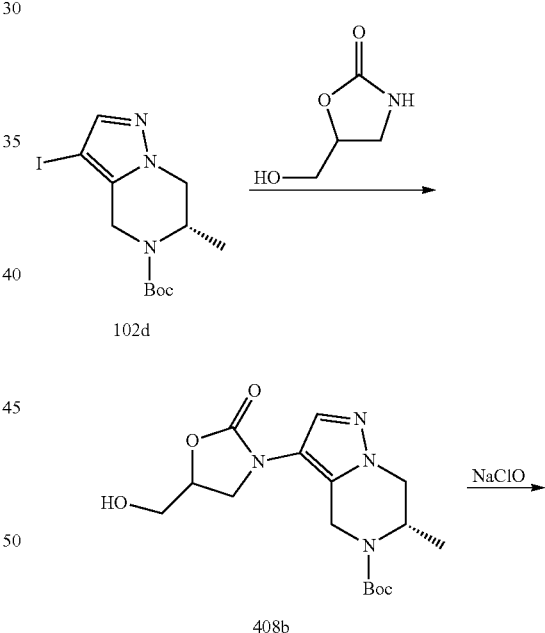

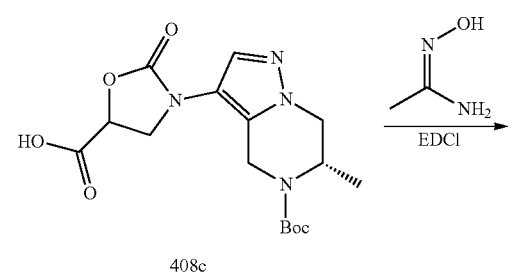

467

-continued

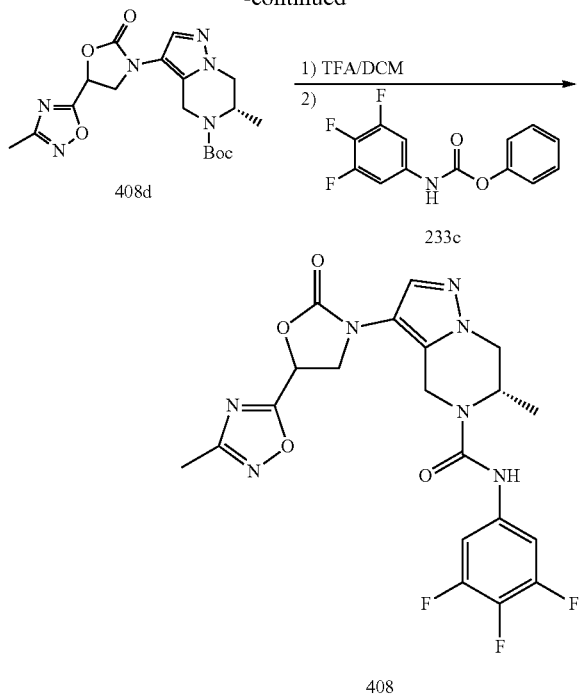

Step 1: Preparation of (6S)-tert-butyl 3-(5-(hydroxymethyl)-2-oxooxazolidin-3-yl)-6-methyl-6,7-dihydropyrazolo[1,5-a]pyrazine-5(4H)-carboxylate (compound 408b)

A mixture of 5-(hydroxymethyl)oxazolidin-2-one (266 mg, 2.27 mmol), (6S)-tert-butyl 3-iodo-6-methyl-6,7-dihydro-4H-pyrazolo[1,5-a]pyrazine-5-carboxylate (compound 102d, 550 mg, 1.51 mmol), $K_3PO_4$ (643 mg, 3.03 mmol), CuI (57.7 mg, 303 μmol) and (1R,2R)-N1,N2-dimethylcyclohexane-1,2-diamine (43.1 mg, 303 μmol) in DMSO (15 mL) was stirred at 105° C. in microwave for 2 hours. After cooled down to room temperature, the reaction mixture was diluted with EtOAc, and washed with water. The aqueous phase was extracted with EtOAc three times. The combined organic layer was dried over $Na_2SO_4$ and concentrated under vacuum. The residue was purified by silica gel column to give compound 408b (300 mg). LCMS (M+H⁺): 353.

Step 2: Preparation of 3-((S)-5-(tert-butoxycarbonyl)-6-methyl-4,5,6,7-tetrahydropyrazolo[1,5-a]pyrazin-3-yl)-2-oxooxazolidine-5-carboxylic acid (compound 408c)

To a solution of (6S)-tert-butyl 3-(5-(hydroxymethyl)-2-oxooxazolidin-3-yl)-6-methyl-6,7-dihydropyrazolo[1,5-a]pyrazine-5(4H)-carboxylate (compound 408b, 740 mg, 2.1 mmol) in MeCN (2.1 mL) and water (21 mL) was added TEMPO (32.8 mg, 210 μmol) and Br (25 mg, 210 μmol). The reaction mixture was stirred for 10 minutes, to which was added dropwise NaCl (>14.5% Cl) (3.86 mL, 18.9 mmol) aqueous solution and then 2N sodium hydroxide aqueous solution till pH=8-10. The reaction mixture was stirred at room temperature for 2 hours, and quenched by ethanol. The solvent was removed, and the residue was acidified to pH=4-5, and extracted with DCM/i-PrOH=5/1

468 twice. The organic layers were combined and concentrated to give crude compound 408c (500 mg). LCMS (M+H⁺): 367.

Step 3: Preparation of (6S)-tert-butyl 6-methyl-3-(5-(3-methyl-1,2,4-oxadiazol-5-yl)-2-oxooxazolidin-3-yl)-6,7-dihydropyrazolo[1,5-a]pyrazine-5(4H)-carboxylate (compound 408d)

To a solution of N'-hydroxyacetimidamide (91 mg, 1.23 mmol) in DCM (8 mL) was added 3-((S)-5-(tert-butoxycarbonyl)-6-methyl-4,5,6,7-tetrahydropyrazolo[1,5-a]pyrazin-3-yl)-2-oxooxazolidine-5-carboxylic acid (compound 408c, 150 mg, 409 μmol), N1-((ethylimino)methylene)-N3,N3-dimethylpropane-1,3-diamine hydrochloride (102 mg, 532 μmol), DIPEA (3.02 g, 4 mL, 23.3 mmol) and 1H-benzo[d][1,2,3]triazol-1-ol (16.6 mg, 123 μmol). The reaction mixture was sealed and stirred at 80° C. overnight. The reaction mixture was cooled down and concentrated. The residue was purified by silica gel column to give compound 408d (66 mg). LCMS (M+H⁺): 405.

Step 4: Preparation of (6S)-6-methyl-3-[5-(3-methyl-1,2,4-oxadiazol-5-yl)-2-oxo-oxazolidin-3-yl]-N-(3,4,5-trifluorophenyl)-6,7-dihydro-4H-pyrazolo[1,5-a]pyrazine-5-carboxamide (Example 408)

A mixture of (6S)-tert-butyl 6-methyl-3-(5-(3-methyl-1,2,4-oxadiazol-5-yl)-2-oxooxazolidin-3-yl)-6,7-dihydropyrazolo[1,5-a]pyrazine-5(4H)-carboxylate (compound 408d, 170 mg, 420 μmol), trifluoroacetic acid (2.98 g, 2 mL, 26.1 mmol) and DCM (1 mL) was stirred at room temperature for 1 hour. The reaction mixture was concentrated. The residue was dissolved in DMF (2 mL), to which was added DIPEA (754 mg, 1 mL, 5.83 mmol), and phenyl (3,4,5-trifluorophenyl)carbamate (compound 233c, 146 mg, 546 μmol). The reaction mixture was stirred at 50° C. for 2 hours, and then was purified by HPLC to give Example 408 (27 mg). LCMS (M+H+): 478. ¹H NMR (400 MHz, MeOD) δ ppm 7.70 (s, 1H), 7.32-7.24 (m, 2H), 6.03 (ddd, J=1.0, 5.1, 9.2 Hz, 1H), 5.11 (dd, J=11.2, 16.9 Hz, 1H), 5.02-4.92 (m, 1H), 4.61-4.45 (m, 2H), 4.40-4.28 (m, 2H), 4.22-4.14 (m, 1H), 2.45 (d, J=2.3 Hz, 3H), 1.31-1.24 (m, 3H).

Example 409

(6S)-3-[5-(6-chloro-3-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide

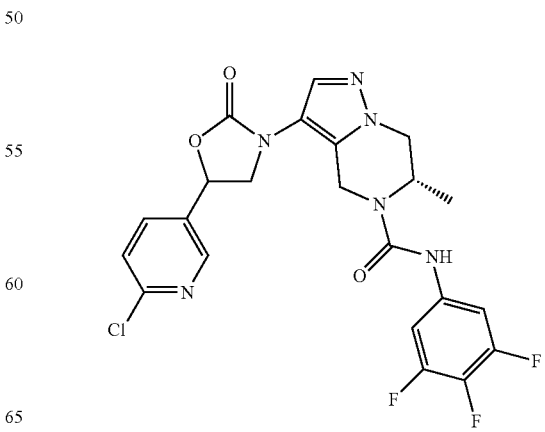

Preparation of (6S)-3-[5-(6-chloro-3-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide (Example 409)

The title compound was prepared in analogy to Example 289 by using 6-chloropyridine-3-carbaldehyde instead of 1-methyl-1H-imidazole-2-carbaldehyde. Example 409 was obtained as a white solid (66 mg). LCMS (M+H+): 507. $^1$H NMR (400 MHz, MeOD) δ ppm 8.54 (d, J=2.5 Hz, 1H), 8.06-8.11 (m, 1H), 7.69 (s, 0.5H), 7.69 (s, 0.5H), 7.60 (d, J=8.5 Hz, 1H), 7.34-7.24 (m, 2H), 5.89 (t, J=8.3 Hz, 1H), 5.12 (dd, J=1.8, 16.8 Hz, 1H), 5.02-4.94 (m, 1H), 4.58 (d, J=16.8 Hz, 1H), 4.45 (td, J=9.0, 14.9 Hz, 1H), 4.35-4.27 (m, 1H), 4.21-4.14 (m, 1H), 4.03 (ddd, J=7.8, 9.0, 13.8 Hz, 1H), 1.30-1.25 (m, 3H).

Example 410

(6S)-3-[5-(5-fluoro-2-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide

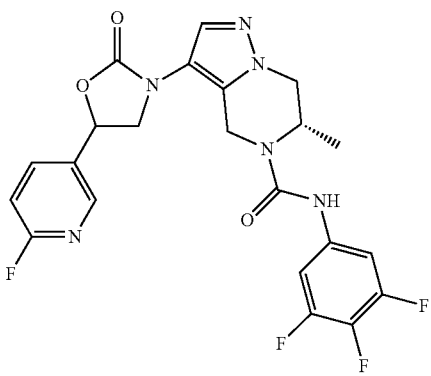 [SMILES: C[C@H]1Cn2ncc(N3CC(c4ccc(F)nc4)OC3=O)c2CN1C(=O)Nc1cc(F)c(F)c(F)c1]

Preparation of (6S)-3-[5-(5-fluoro-2-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide (Example 410)

The title compound was prepared in analogy to Example 289 by using 5-fluoropyridine-2-carbaldehyde instead of 1-methyl-1H-imidazole-2-carbaldehyde. Example 410 was obtained as a white solid (65 mg). LCMS (M+H+): 491. $^1$H NMR (400 MHz, MeOD) δ ppm 8.59 (d, J=2.7 Hz, 1H), 7.77-7.65 (m, 3H), 7.33-7.24 (m, 2H), 5.85 (dd, J=6.5, 8.9 Hz, 1H), 5.18-5.09 (m, 1H), 5.01-4.93 (m, 1H), 4.56 (d, J=17.0 Hz, 1H), 4.44 (td, J=8.8, 14.1 Hz, 1H), 4.31 (dd, J=4.4, 12.7 Hz, 1H), 4.27-4.14 (m, 2H), 1.30-1.24 (m, 3H).

Example 411

(6S)-3-[5-(6-fluoro-2-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide

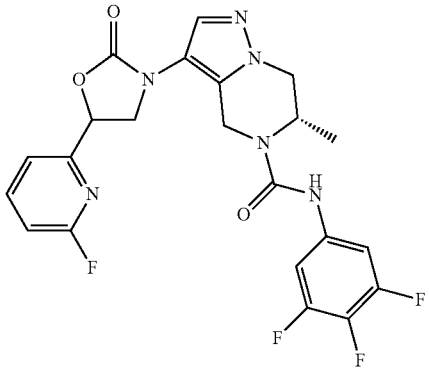 [SMILES: C[C@H]1Cn2ncc(N3CC(c4cccc(F)n4)OC3=O)c2CN1C(=O)Nc1cc(F)c(F)c(F)c1]

Preparation of (6S)-3-[5-(6-fluoro-2-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide (Example 411)

The title compound was prepared in analogy to Example 289 by using 6-fluoropyridine-2-carbaldehyde instead of 1-methyl-1H-imidazole-2-carbaldehyde. Example 411 was obtained as a white solid (84 mg). LCMS (M+H+): 491. $^1$H NMR (400 MHz, MeOD) δ ppm 8.06 (q, J=7.9 Hz, 1H), 7.68 (s, 0.5H), 7.67 (s, 0.5H), 7.53 (dd, J=2.1, 7.3 Hz, 1H), 7.33-7.23 (m, 2H), 7.12 (dd, J=2.2, 8.3 Hz, 1H), 5.87-5.74 (m, 1H), 5.16-5.06 (m, 1H), 5.03-4.92 (m, 1H), 4.62-4.53 (m, 1H), 4.49-4.39 (m, 1H), 4.30 (dd, J=4.4, 12.7 Hz, 1H), 4.21-4.08 (m, 2H), 1.31-1.23 (m, 3H).

Example 412

(6S)-6-methyl-3-[4-(1-methylpyrazol-4-yl)-2-oxo-pyrrolidin-1-yl]-N-(3,4,5-trifluorophenyl)-6,7-dihydro-4H-pyrazolo[1,5-a]pyrazine-5-carboxamide

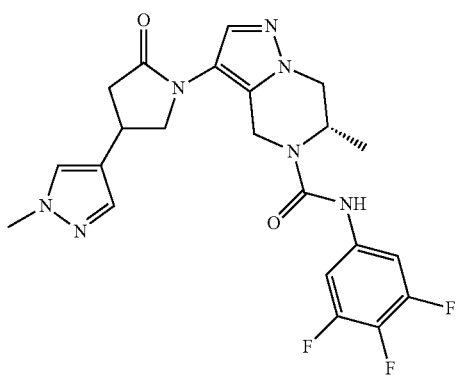 [SMILES: C[C@H]1Cn2ncc(N3CC(c4cnn(C)c4)CC3=O)c2CN1C(=O)Nc1cc(F)c(F)c(F)c1]

Preparation of (6S)-6-methyl-3-[4-(1-methylpyrazol-4-yl)-2-oxo-pyrrolidin-1-yl]-N-(3,4,5-trifluorophenyl)-6,7-dihydro-4H-pyrazolo[1,5-a]pyrazine-5-carboxamide (Example 412)

The title compound was prepared in analogy to Example 290 by using 1-methylpyrazole-4-carbaldehyde instead of thiazole-5-carbaldehyde. Example 412 was obtained as a white solid (36 mg). LCMS (M+H+): 474. $^1$H NMR (400 MHz, MeOD) δ ppm 7.67-7.60 (m, 2H), 7.51 (s, 1H), 7.33-7.25 (m, 2H), 5.09-5.01 (m, 1H), 4.98-4.91 (m, 1H), 4.56-4.46 (m, 1H), 4.36-4.26 (m, 1H), 4.20-4.09 (m, 2H), 3.89 (s, 1.5H), 3.88 (s, 1.5H), 3.87-3.74 (m, 2H), 2.96-2.88 (m, 1H), 2.69-2.60 (m, 1H), 1.32-1.24 (m, 3H).

Example 413

(6S)-6-methyl-3-(2-oxo-4-pyrimidin-5-yl-pyrrolidin-1-yl)-N-(3,4,5-trifluorophenyl)-6,7-dihydro-4H-pyrazolo[1,5-a]pyrazine-5-carboxamide Preparation of (6S)-6-methyl-3-(2-oxo-4-pyrimidin-5-yl-pyrrolidin-1-yl)-N-(3,4,5-trifluorophenyl)-6,7-dihydro-4H-pyrazolo[1,5-a]pyrazine-5-carboxamide (Example 413)

The title compound was prepared in analogy to Example 290 by using pyrimidine-5-carbaldehyde instead of thiazole-5-carbaldehyde. Example 413 (125 mg) was obtained as a white solid. LCMS (M+H$^+$): 472. $^1$H NMR (400 MHz, METHANOL-d$_4$) δ ppm 9.12 (s, 1H), 8.90 (s, 2H), 7.68 (s, 1H), 7.31-7.27 (m, 2H), 5.13-5.05 (m, 1H), 4.96 (br, 1H), 4.59-4.51 (m, 1H), 4.36-4.13 (m, 3H), 4.07-3.87 (m, 2H), 3.07-3.00 (m, 1H), 2.92-2.78 (m, 1H), 1.31-1.27 (m, 3H)

Example 414

(6S)-3-[4-[(5-fluoropyrimidin-2-yl)amino]-2-oxo-pyrrolidin-1-yl]-6-methyl-N-(3,4,5-trifluorophenyl)-6,7-dihydro-4H-pyrazolo[1,5-a]pyrazine-5-carboxamide Preparation of (6S)-3-[4-[(5-fluoropyrimidin-2-yl)amino]-2-oxo-pyrrolidin-1-yl]-6-methyl-N-(3,4,5-trifluorophenyl)-6,7-dihydro-4H-pyrazolo[1,5-a]pyrazine-5-carboxamide (Example 414)

The title compound was prepared in analogy to Example 269 by using 2-bromo-5-fluoropyrimidine instead of 2-chloro-pyrimidine. Example 414 was obtained as a solid (20 mg). LCMS (M+H$^+$): 505. $^1$H NMR (400 MHz, METHANOL-d$_4$) δ ppm 8.30 (s, 2H), 7.63 (s, 0.5H), 7.62 (s, 0.5H), 7.30-7.26 (m, 2H), 5.08-5.03 (m, 1H), 4.98-4.91 (m, 1H), 4.75-4.64 (m, 1H), 4.57-4.44 (m, 1H), 4.35-4.19 (m, 2H), 4.15 (d, J=12.7 Hz, 1H), 3.76 (dt, J=4.2, 9.9 Hz, 1H), 3.01 (dd, J=8.3, 17.4 Hz, 1H), 2.61 (dd, J=4.9, 17.4 Hz, 1H), 1.29-1.26 (m, 3H)

Example 415

(6S)-6-methyl-3-[(4R)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide

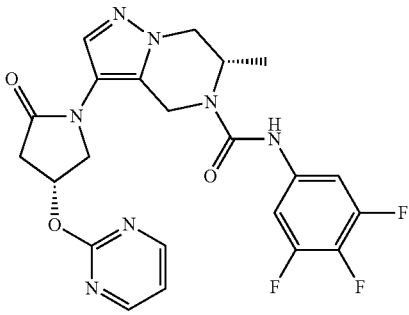 [SMILES: C[C@H]1Cn2ncc(N3C[C@H](Oc4ncccn4)CC3=O)c2CN1C(=O)Nc1cc(F)c(F)c(F)c1]

Preparation of Example 415

The title compound was prepared in analogy to Example 381 by using (R)-tert-butyl 3-((R)-4-hydroxy-2-oxopyrrolidin-1-yl)-6-methyl-6,7-dihydropyrazolo[1,5-a]pyrazine-5

(4H)-carboxylate (compound 376b) instead of (S)-tert-butyl 3-((S)-4-hydroxy-2-oxopyrrolidin-1-yl)-6-methyl-6,7-dihydropyrazolo[1,5-a]pyrazine-5(4H)-carboxylate (compound 377b). Example 415 was obtained as a white solid (36 mg). LCMS (M+H+): 488. ¹H NMR (400 MHz, CD3OD) δ ppm 8.63 (d, J=4.9 Hz, 2H), 7.65 (s, 1H), 7.35-7.25 (m, 2H), 7.18 (t, J=4.8 Hz, 1H), 5.82-5.75 (m, 1H), 5.07-4.94 (m, 2H), 4.58 (d, J=16.9 Hz, 1H), 4.43 (dd, J=5.5, 11.5 Hz, 1H), 4.29 (dd, J=4.5, 12.8 Hz, 1H), 4.20-4.13 (m, 1H), 3.94 (dd, 11.5 Hz, 1H), 3.18 (dd, J=6.8, 18.1 Hz, 1H), 2.75 (dd, J=1.7, 18.1 Hz, 1H), 1.29 (d, J=7.0 Hz, 3H).

Example 416

(6S)-3-[(3R,4R)-3,4-dihydroxy-2-oxo-pyrrolidin-1-yl]-6-methyl-N-(3,4,5-trifluorophenyl)-6,7-dihydro-4H-pyrazolo[1,5-a]pyrazine-5-carboxamide

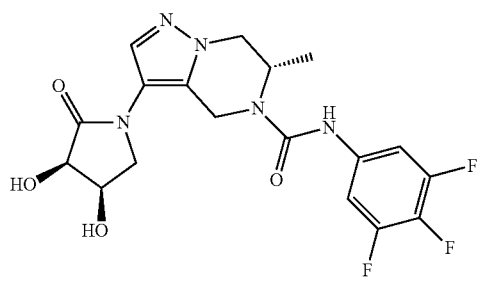 [SMILES: C[C@H]1Cn2ncc(N3C[C@@H](O)[C@@H](O)C3=O)c2CN1C(=O)Nc1cc(F)c(F)c(F)c1]

The title compound was prepared according to the following scheme:

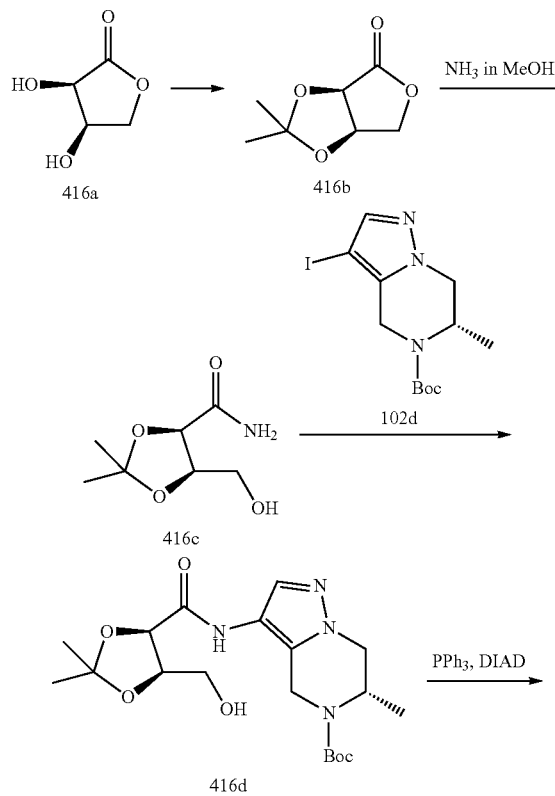

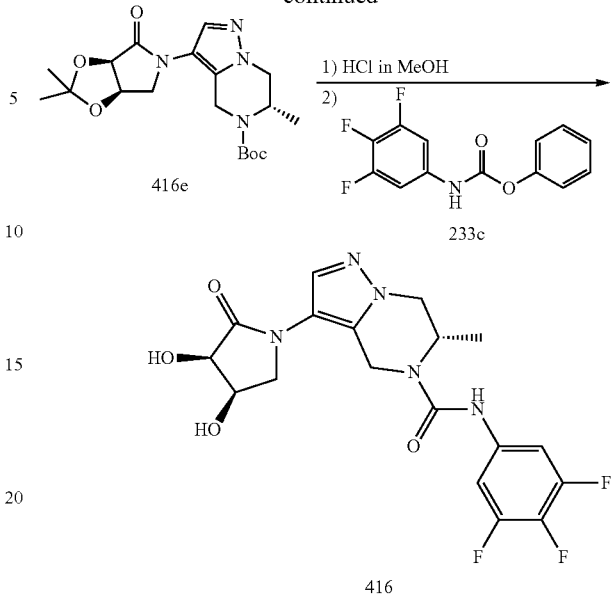

Step 1: Preparation of (3aR,6aR)-2,2-dimethyl-6,6a-dihydro-3aH-furo[3,4-d][1,3]dioxol-4-one (compound 416b)

A mixture of (3R,4R)-3,4-dihydroxydihydrofuran-2(3H)-one (2.36 g, 20 mmol), 2,2-dimethoxypropane (compound 416a, 6.24 g, 60 mmol) and 4-methylbenzenesulfonic acid hydrate (380 mg, 2 mmol) in acetone (50 mL) was stirred at room temperature for 6 hours. The reaction mixture was then concentrated in vacuo, and the residue was purified by flash chromatography (silica gel, 40 g, 0% to 30% EtOAc in hexanes) to give compound 416b as a light yellow solid (2.4 g).

Step 2: Preparation of (4R,5R)-5-(hydroxymethyl)-2,2-dimethyl-1,3-dioxolane-4-carboxamide (compound 416c)

A mixture of (3aR,6aR)-2,2-dimethyl-6,6a-dihydro-3aH-furo[3,4-d][1,3]dioxol-4-one (compound 416b, 2.4 g, 15.2 mmol) and ammonia in methanol (7M, 21.7 mL, 152 mmol) was stirred at room temperature for 30 mins. The reaction mixture was concentrated in vacuo to give crude compound 416c as a white solid (2.66 g). LCMS (M+H+): 176.

Step 3: Preparation of (S)-tert-butyl 34(4R,5R)-5-(hydroxymethyl)-2,2-dimethyl-1,3-dioxolane-4-carboxamido)-6-methyl-6,7-dihydropyrazolo[1,5-a]pyrazine-5(4H)-carboxylate (compound 416d)

A mixture of (4R,5R)-5-(hydroxymethyl)-2,2-dimethyl-1,3-dioxolane-4-carboxamide (compound 416c, 724 mg, 4.13 mmol), (S)-tert-butyl 3-iodo-6-methyl-6,7-dihydropyrazolo[1,5-a]pyrazine-5(4H)-carboxylate (compound 102d, 1 g, 2.75 mmol), potassium phosphate (1.17 g, 5.51 mmol), copper(I) iodide (210 mg, 1.1 mmol) and (1R,2R)-N1,N2-dimethylcyclohexane-1,2-diamine (157 mg, 1.1 mmol) in DMSO (15 mL) was flushed with N₂ and sealed. The reaction mixture was heated in microwave at 120° C. for 2 hours, then diluted with water, extracted with DCM/i-PrOH (v/v=5/1). The combined organic layer was dried over Na₂SO₄ and then concentrated. The crude material was purified by flash chromatography (silica gel, 12 g, 10% to 30% MeOH in DCM) to give compound 416d as light yellow oil (500 mg). LCMS (M+H⁺): 411

Step 4: Preparation of (S)-tert-butyl 34(3aR,6aR)-2, 2-dimethyl-4-oxodihydro-3aH-[1,3]dioxolo[4,5-c] pyrrol-5(4H)-yl)-6-methyl-6,7-dihydropyrazolo[1,5-a]pyrazine-5(4H)-carboxylate (compound 416e)

To a mixture of (S)-tert-butyl 3-((4R,5R)-5-(hydroxymethyl)-2,2-dimethyl-1,3-dioxolane-4-carboxamido)-6-methyl-6,7-dihydropyrazolo[1,5-a]pyrazine-5(4H)-carboxylate (compound 416d, 500 mg, 1.22 mmol) and triphenylphosphine (383 mg, 1.46 mmol) in dry THF (10 mL) was added diisopropyl diazene-1,2-dicarboxylate (369 mg, 1.83 mmol) slowly at room temperature. The reaction mixture was stirred for 30 mins, and then concentrated in vacuo. The residue was purified by flash chromatography (silica gel, 12 g, 10% to 60% EtOAc in hexanes, where EtOAc contains 10% Methanol) to give compound 416e as a light yellow oil (400 mg). LCMS (M+H⁺): 393.

Step 5: Preparation of (6S)-3-[(3R,4R)-3,4-dihydroxy-2-oxo-pyrrolidin-1-yl]-6-methyl-N-(3,4,5-trifluorophenyl)-6,7-dihydro-4H-pyrazolo[1,5-a]pyrazine-5-carboxamide (Example 416)

A mixture of (S)-tert-butyl 3-((3aR,6aR)-2,2-dimethyl-4-oxodihydro-3aH-[1,3]dioxolo[4,5-c]pyrrol-5(4H)-yl)-6-methyl-6,7-dihydropyrazolo[1,5-a]pyrazine-5(4H)-carboxylate (compound 416e, 50 mg, 127 μmol) in HCl/MeOH (5 mL) was stirred at room temperature for 12 hours, and then concentrated. The resulting residue was dissolved in DMF (5 mL), to which was added N-ethyl-N-isopropylpropan-2-amine (82.3 mg, 637 μmol) and phenyl (3,4,5-trifluorophenyl)carbamate (40.9 mg, 153 μmol). The reaction mixture was stirred at 70° C. for 0.5 hours and then purified by prep-HPLC to give Example 416 as a white solid (20 mg). LCMS (M+H⁺): 426. ¹H NMR (400 MHz, METHANOL-d₄) δ ppm 7.62 (s, 1H), 7.33-7.28 (m, 2H), 5.11 (d, J=16.9 Hz, 1H), 5.02-4.94 (m, 1H), 4.55-4.38 (m, 3H), 4.35-4.26 (m, 1H), 4.17 (dd, J=1.2, 12.8 Hz, 1H), 4.03 (dd, J=3.7, 10.9 Hz, 1H), 3.59 (d, J=10.9 Hz, 1H), 1.25 (d, J=6.8 Hz, 3H)

Example 417

(6S)-3-(3-hydroxy-4,4-dimethyl-2-oxo-pyrrolidin-1-yl)-6-methyl-N-(3,4,5-trifluorophenyl)-6,7-dihydro-4H-pyrazolo[1,5-a]pyrazine-5-carboxamide

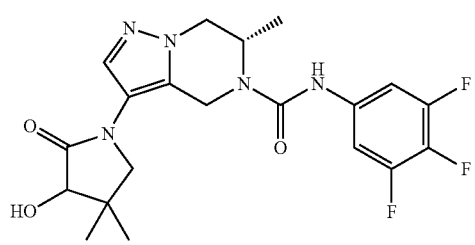 [SMILES: C[C@H]1Cn2ncc(N3CC(C)(C)C(O)C3=O)c2CN1C(=O)Nc1cc(F)c(F)c(F)c1]

The title compound was prepared according to the following scheme:

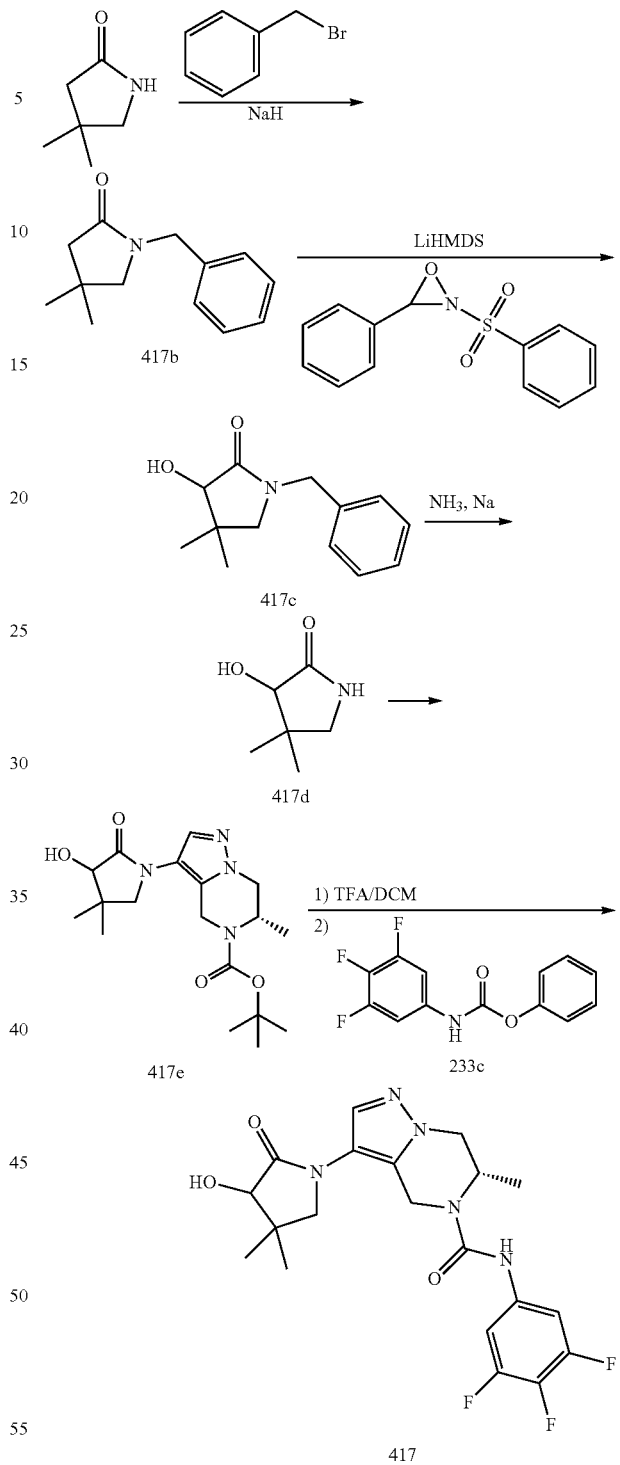

Step 1: Preparation of 1-benzyl-4,4-dimethyl-pyrrolidin-2-one (compound 417b)

To a solution of 4,4-dimethylpyrrolidin-2-one (1.5 g, 13.4 mmol) in DMF (20.0 mL) was added NaH (0.8 g, 20.0 mmol, 60% wt) at 0° C. The reaction mixture was stirred at 0° C. for 1 hour, then to which was added bromomethylbenzene (2.3 g, 13.4 mmol). The resulting mixture was stirred at room temperature for another 16 hours, and then concentrated. The residue was purified by silica gel chromatography (PE/EtOAc=3/1) to give compound 417b as a colorless oil (2.3 g). LCMS (M+H$^+$): 204.

Step 2: Preparation of 1-benzyl-3-hydroxy-4,4-dimethyl-pyrrolidin-2-one (compound 417c)

To a solution of 1-benzyl-4,4-dimethyl-pyrrolidin-2-one (compound 417b, 2.7 g, 13.2 mmol) in THF (50.0 mL) was added a solution of LiHMDS in THF (26.6 mL, 26.6 mmol) at −78° C., and the reaction mixture was stirred at −78° C. for 1 hour, to which was then added a solution of 2-(benzenesulfonyl)-3-phenyl-oxaziridine (4.1 g, 15.8 mmol) in THF (10 mL), then the resulting mixture was allowed to warm slowly to room temperature, and stirred for additional 16 hours. The reaction mixture was concentrated and purified by prep-HPLC to give compound 417c (1.3 g) as white solid. LCMS (M+H$^+$): 220.

Step 3: Preparation of 3-hydroxy-4,4-dimethylpyrrolidin-2-one (compound 417d)

To a solution of 1-benzyl-3-hydroxy-4,4-dimethyl-pyrrolidin-2-one (compound 417c, 1.0 g, 4.6 mmol) in THF (10.0 mL) at −78° C. was bubbled ammonia (~3 mL), followed by addition of Na (1.05 g, 45.6 mmol). The reaction mixture was stirred at −78° C. for 10 mins, and then quenched with saturated aqueous solution of NH$_4$Cl (5.0 mL) and concentrated. The residue was taken up in PE/EA=1/1, and the solid was filtered off. The filtrate was concentrated to give crude compound 417d (0.5 g) as a white solid. LCMS (M+H$^+$): 130.

Step 4: Preparation of (6S)-tert-butyl 3-(3-hydroxy-4,4-dimethyl-2-oxopyrrolidin-1-yl)-6-methyl-6,7-dihydropyrazolo[1,5-a]pyrazine-5(4H)-carboxylate (compound 417e)

The reaction mixture of 3-hydroxy-4,4-dimethylpyrrolidin-2-one (53.3 mg, 413 μmol), tert-butyl (6S)-3-iodo-6-methyl-6,7-dihydro-4H-pyrazolo[1,5-a]pyrazine-5-carboxylate (compound 102d, 150 mg, 413 μmol), K$_3$PO$_4$ (175 mg, 826 μmol), CuI(15.7 mg, 82.6 μmol) and (1R,2R)-N1,N2-dimethylcyclohexane-1,2-diamine (11.7 mg, 82.6 μmol) in DMSO (7.0 mL) was flushed with nitrogen and sealed. The reaction mixture was stirred at 105° C. in microwave for 2 hours. After cooled down, the reaction mixture was diluted with ethyl acetate (30 mL), and washed with water. The aqueous phase was extracted with ethyl acetate three times. The combined organic layer was dried over Na$_2$SO$_4$ and concentrated in vacuum. The residue was purified by silica gel column to give compound 417e (100 mg). LCMS (M+H$^+$): 365.

Step 5: Preparation of (6S)-3-(3-hydroxy-4,4-dimethyl-2-oxo-pyrrolidin-1-yl)-6-methyl-N-(3,4,5-trifluorophenyl)-6,7-dihydro-4H-pyrazolo[1,5-a]pyrazine-5-carboxamide (Example 417)

The reaction mixture of (6S)-tert-butyl 3-(3-hydroxy-4,4-dimethyl-2-oxopyrrolidin-1-yl)-6-methyl-6,7-dihydropyrazolo[1,5-a]pyrazine-5(4H)-carboxylate (compound 417e, 100 mg, 274, TFA (2 mL) in DCM (1 mL) was stirred at room temperature for 1 hour. The reaction mixture was concentrated. The residue was dissolved in DCE (2.0 m:), to which was then added DIPEA (742 mg, 1 mL, 5.74 mmol), and phenyl (3,4,5-trifluorophenyl)carbamate (95.3 mg, 357 μmol). The reaction mixture was stirred at 50° C. for 2 hours. The reaction was concentrated and purified by prep-HPLC to give Example 417 (60 mg). LCMS (M+H$^+$): 501. $^1$H NMR (400 MHz, CD$_3$OD) δ ppm 7.62 (s, 1H), 7.34-7.24 (m, 2H), 5.15-4.94 (m, 2H), 4.62-4.44 (m, 1H), 4.30 (dd, J=4.4, 12.7 Hz, 1H), 4.16 (d, J=13.8 Hz, 1H), 4.13 (d, J=5.0 Hz, 1H), 3.64-3.59 (m, 1H), 3.45-3.38 (m, 1H), 1.31-1.23 (m, 6H), 1.14 (s, 3H).

Example 418

(6S)-6-methyl-3-(2-oxo-3H-pyrrolo[3,2-c]pyridin-1-yl)-N-(3,4,5-trifluorophenyl)-6,7-dihydro-4H-pyrazolo[1,5-a]pyrazine-5-carboxamide

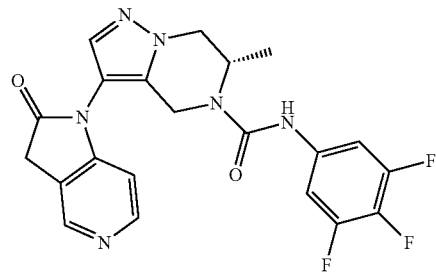 [SMILES: C[C@H]1Cn2ncc(N3C(=O)Cc4cnccc43)c2CN1C(=O)Nc1cc(F)c(F)c(F)c1]

The title compound was prepared according to the following scheme:

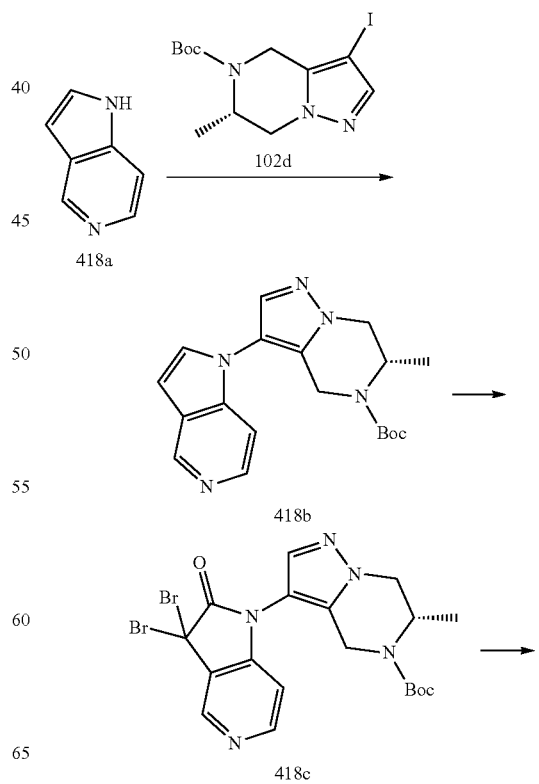

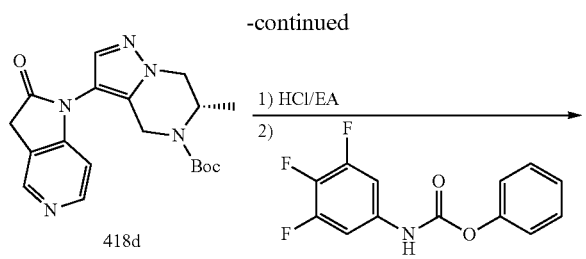

Step 1: Preparation of tert-butyl (6S)-6-methyl-3-pyrrolo[3,2-c]pyridin-1-yl-6,7-dihydro-4H-pyrazolo[1,5-a]pyrazine-5-carboxylate (compound 418b)

A mixture of 1H-pyrrolo[3,2-c]pyridine (compound 418a, 500 mg, 4.3 mmol), (S)-tert-butyl 3-iodo-6-methyl-6,7-dihydropyrazolo[1,5-a]pyrazine-5(4H)-carboxylate (compound 102d, 1.72 g, 4.7 mmol), potassium phosphate (2.75 g, 13 mmol), copper(I) iodide (95 mg, 0.5 mmol) and (1R,2R)-N1,N2-dimethylcyclohexane-1,2-diamine (71 mg, 0.5 mmol) in dioxane (30 mL) was flushed with nitrogen. The reaction mixture was stirred at 120° C. for 12 hours and then concentrated. The residue was purified by prep-HPLC to give compound 418b (600 mg) as a yellow oil. LCMS (M+H+): 354.

Step 2: Preparation of tert-butyl (6S)-3-(3,3-dibromo-2-oxo-pyrrolo[3,2-c]pyridin-1-yl)-6-methyl-6,7-dihydro-4H-pyrazolo[1,5-a]pyrazine-5-carboxylate (compound 418c)

To a solution of tert-butyl (6S)-6-methyl-3-pyrrolo[3,2-c]pyridin-1-yl-6,7-dihydro-4H-pyrazolo[1,5-a]pyrazine-5-carboxylate (compound 418b, 0.3 g, 0.85 mmol) in t-BuOH (4.0 mL) and H$_2$O (5.0 mL) was added a solution of Br$_2$ (0.5 g, 3.4 mmol) in t-BuOH (1.0 mL) dropwise at room temperature, then the reaction mixture was stirred at same temperature for 1 hour. The reaction mixture was basified to PH 6.5-7 with sodium bicarbonate solution, and extracted with EtOAc (20 mL). The organic phase was dried over Na$_2$SO$_4$ and concentrated to give compound 418c as a yellow oil (0.4 g, crude).

Step 3: Preparation of tert-butyl (6S)-6-methyl-3-(2-oxo-3H-pyrrolo[3,2-c]pyridin-1-yl)-6,7-dihydro-4H-pyrazolo[1,5-a]pyrazine-5-carboxylate (compound 418d)

To a solution of tert-butyl (6S)-3-(3,3-dibromo-2-oxo-pyrrolo[3,2-c]pyridin-1-yl)-6-methyl-6,7-dihydro-4H-pyrazolo[1,5-a]pyrazine-5-carboxylate (compound 418c, 400.0 mg, 0.76 mmol) in EtOH (10.0 mL) was added Pd/C (40.0 mg), and the reaction mixture was stirred at room temperature for 12 hours under H$_2$ (50 psi) and then concentrated, the residue was purified by prep-HPLC to give compound 418d (30.0 mg) as a brown oil. LCMS (M+H+): 370

Step 4: Preparation of (6S)-6-methyl-3-(2-oxo-3H-pyrrolo[3,2-c]pyridin-1-yl)-N-(3,4,5-trifluorophenyl)-6,7-dihydro-4H-pyrazolo[1,5-a]pyrazine-5-carboxamide (Example 418)

The title compound was prepared in analogy to Example 223 by using tert-butyl (6S)-6-methyl-3-(2-oxo-3H-pyrrolo[3,2-c]pyridin-1-yl)-6,7-dihydro-4H-pyrazolo[1,5-a]pyrazine-5-carboxylate (compound 418d) instead of tert-butyl (6S)-6-methyl-3-(2-oxopyrrolidin-1-yl)-6,7-dihydro-4H-pyrazolo[1,5-a]pyrazine-5-carboxylate (compound 223b) and phenyl N-(3,4,5-trifluoro-phenyl)carbamate (compound 233c) instead of phenyl N-[2-(difluoromethyl)-4-pyridyl]carbamate (compound 218c). Example 413 was obtained as a white solid (6.0 mg). LCMS (M+H+): 443. $^1$H NMR (400 MHz, DMSO-d6) δ ppm 9.05 (s, 1H), 8.45-8.37 (m, 2H), 7.74 (s, 1H), 7.42-7.37 (m, 2H), 6.82 (d, J=5.3 Hz, 1H), 4.97-4.86 (m, 2H), 4.41-4.15 (m, 3H), 3.83 (s, 2H), 1.18 (d, J=6.8 Hz, 3H).

Example 419

(6S)-6-methyl-3-(6-oxo-4,7-dihydropyrazolo[1,5-a]pyrazin-5-yl)-N-(3,4,5-trifluorophenyl)-6,7-dihydro-4H-pyrazolo[1,5-a]pyrazine-5-carboxamide

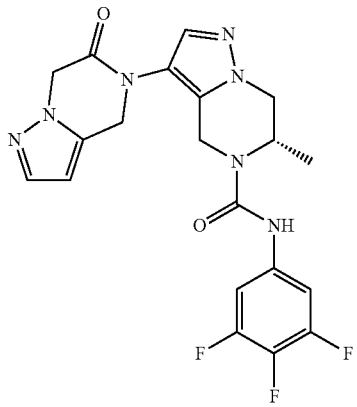 [SMILES: C[C@H]1Cn2ncc(N3Cc4ccnn4CC3=O)c2CN1C(=O)Nc1cc(F)c(F)c(F)c1]

The title compound was prepared according to the following scheme:

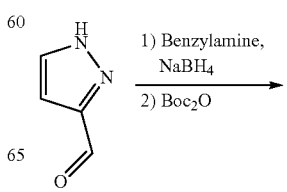

481

-continued

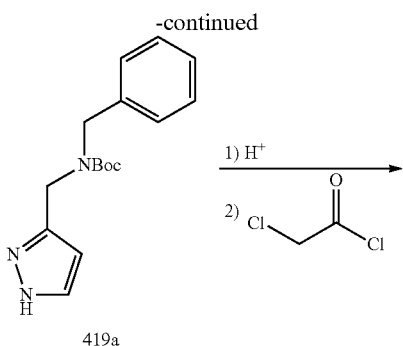

482

-continued

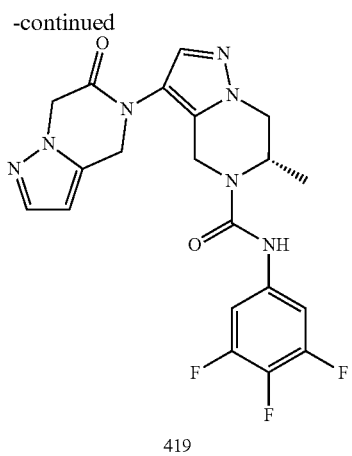

Preparation of tert-butyl N-benzyl-N-(1H-pyrazol-3-ylmethyl)carbamate (compound 419a)

To the solution of 1H-pyrazole-3-carbaldehyde (5.00 g, 52.03 mmol) in MeOH (50 mL) was added benzylamine (5.58 g, 52.03 mmol) at room temperature. After stirred at same temperature for 1 hour, the reaction mixture was cooled to 0° C., and to which was added NaBH$_4$(1.97 g, 52.03 mmol) slowly. Ten minutes later, H$_2$O (10 mL) was added to the reaction mixture slowly at 0° C., followed by (Boc)$_2$O (11.36 g, 52.03 mmol). The resulting mixture was stirred at room temperature for 3 hours, and then most of the solvent was removed under vacuum. The residue was taken up in brine (100 mL), and extracted with EtOAc (100 mL) three times. The combined organic layer was dried over Na$_2$SO$_4$ and concentrated to give a crude product, which was purified by silica gel column chromatography (eluent: PE/EtOAc=7:1 to 3:1) to give compound 419a as a colorless oil (10.5 g). LCMS (M+H$^+$): 288.2

Preparation of N-benzyl-2-chloro-N-(1H-pyrazol-5-ylmethyl)acetamide (compound 419b)

To a solution of tert-butyl N-benzyl-N-(1H-pyrazol-3-ylmethyl)carbamate (compound 419a, 5.0 g, 17.4 mmol) in EtOAc(20 mL) was added EtOAc/HCl (1M, 50 mL) at 0° C. The reaction mixture was stirred at room temperature for 2 hours, and then filtered. The filter cake was washed with EtOAc (30 mL), dried, and collected to give 1-phenyl-N-(1H-pyrazol-3-ylmethyl)methanamine in HCl salt form (3.90 g, crude) as a white solid. To a suspension of 1-phenyl-N-(1H-pyrazol-3-ylmethyl)methanamine hydrochloride (3.90 g, 17.4 mmol) in DCM (50 mL) at 0° C. was added TEA (5.28 g, 52.2 mmol) and 2-chloroacetyl chloride (2.95 g, 26.1 mmol). The reaction mixture was stirred at room temperature for 2 hours and then poured into H$_2$O (100 mL). The aqueous phase was extracted with EtOAc (100 mL) three times, and the combined organic layer was washed with brine (100 mL), and concentrated. The obtained residue was purified by silica gel column chromatography (PE/EtOAc=1/2-1/4) to give compound 419b as a colorless oil (3.50 g). LCMS (M+1): 264.1

Preparation of 5-benzyl-4,7-dihydropyrazolo[1,5-a]pyrazin-6-one (compound 419c)

To a suspension of NaH (0.92 g, 22.75 mmol) in THF (50 mL) at 70° C. under nitrogen was added dropwise a solution

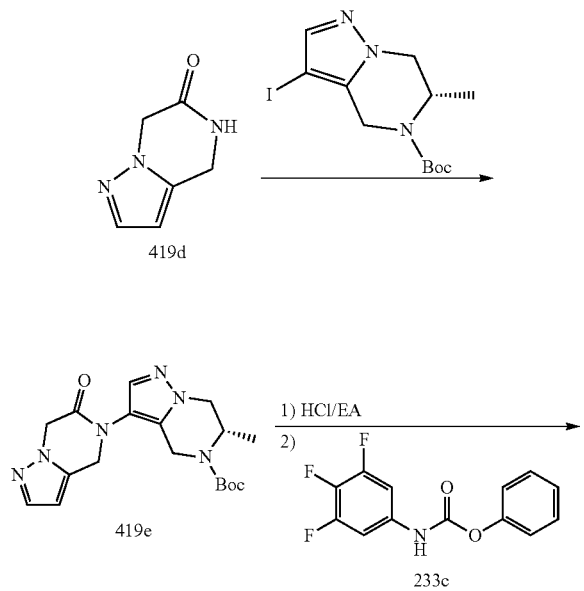

of N-benzyl-2-chloro-N-(1H-pyrazol-5-ylmethyl)acetamide (3.0 g, 11.37 mmol) in THF (50 mL). After completion of addition, the reaction mixture was stirred at 70° C. for 1 hour, and then cooled to room temperature. The reaction mixture was poured into saturated NH₄Cl aqueous solution (50 mL) and extracted with EtOAc (50 mL) three times. The combined organic layer was dried over Na₂SO₄ and concentrated. The obtained residue was purified by silica gel column chromatography (PE/EtOAc=1/2-1/3) to give compound 419c as a white solid (700 mg). LCMS (M+1): 228.1

Preparation of (6S)-6-methyl-3-(6-oxo-4,7-dihydropyrazolo[1,5-a]pyrazin-5-yl)-N-(3,4,5-trifluorophenyl)-6,7-dihydro-4H-pyrazolo[1,5-a]pyrazine-5-carboxamide (example 419)

The title compound was prepared in analogy to Example 417 by using 5-benzyl-4,7-dihydropyrazolo[1,5-a]pyrazin-6-one (compound 419c) instead of 1-benzyl-3-hydroxy-4,4-dimethyl-pyrrolidin-2-one (compound 417c). Example 417 was obtained as a white solid (6.4 mg). LCMS (M+1): 446.2; ¹H NMR (300 MHz, DMSO-d⁶) ppm 9.01 (s, 1H), 7.68 (s, 1H), 7.56 (s, 1H), 7.50-7.25 (m, 2H), 6.24 (s, 1H), 5.15-4.80 (m, 6H), 4.39-4.03 (m, 3H), 1.14 (d, J=6.2 Hz, 3H)

Example 420

(6S)-3-(3-cyano-2-methyl-5-oxo-pyrrolidin-1-yl)-6-methyl-N-(3,4,5-trifluorophenyl)-6,7-dihydro-4H-pyrazolo[1,5-a]pyrazine-5-carboxamide

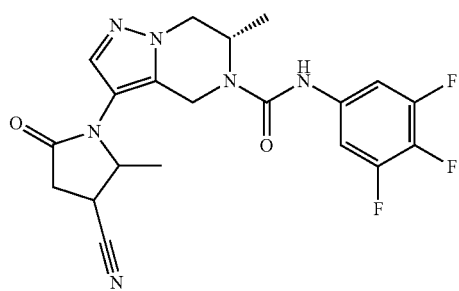 [SMILES: CC1C(C#N)CC(=O)N1c1cnn2c1CN(C(=O)Nc1cc(F)c(F)c(F)c1)[C@@H](C)C2]

The title compound was prepared according to the following scheme:

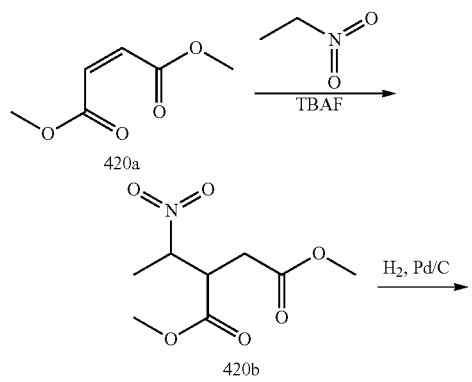

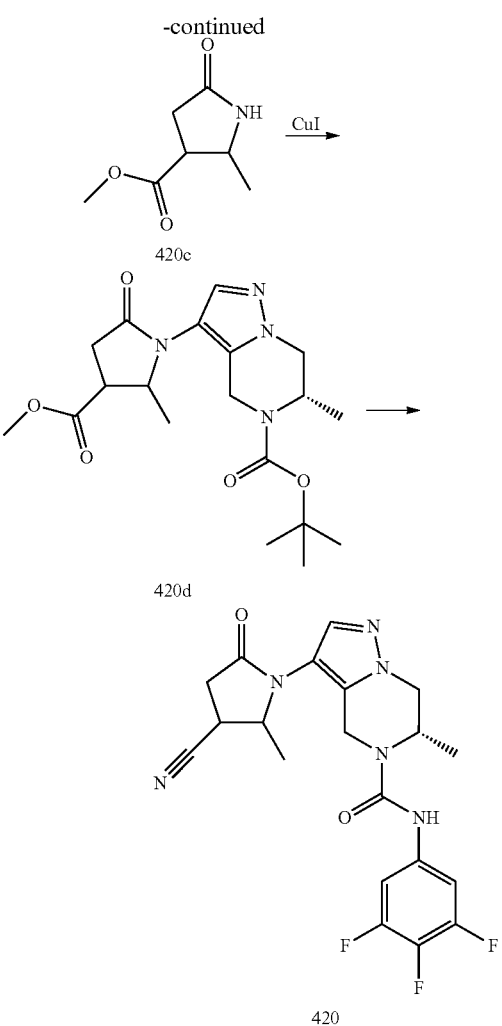

Preparation of dimethyl 2-(1-nitroethyl)butanedioate (compound 420b)

To a mixture of dimethyl (Z)-but-2-enedioate (compound 420a, 10.0 g, 69.4 mmol) and nitroethane (60 mL) in THF (500 mL) was added a solution of tetrabutylammonium fluoride (7.0 mmol) in THF (7 mL). The reaction mixture was stirred at room temperature for 2 hours, and then quenched with saturated NH₄Cl aqueous solution. The aqueous phase was extracted with DCM three times. The combined organic layer was dried over Na₂SO₄, filtrated and concentrated. The residue was purified by silica gel column to give compound 420b as a yellow oil (10 g). LCMS (M+H⁺): 220.

Preparation of methyl 2-methyl-5-oxo-pyrrolidine-3-carboxylate (compound 420c)

To a solution of dimethyl 2-(1-nitroethyl)butanedioate (compound 420b, 8.0 g, 36.4 mmol) in EtOH (100 mL) was added Pd/C (400 mg). The reaction mixture was stirred under 1 atm of H₂ at 50° C. for 24 hours, and then concentrated. The residue was purified by prep-HPLC to give compound 420c as a light-red oil (3.6 g). LCMS (M+H⁺): 158.

Preparation of tert-butyl (6S)-3-(3-methoxycarbo-
nyl-2-methyl-5-oxo-pyrrolidin-1-yl)-6-methyl-6,7-
dihydro-4H-pyrazolo[1,5-a]pyrazine-5-carboxylate
(compound 420d)

To a solution of tert-butyl (6S)-3-iodo-6-methyl-6,7-dihydro-4H-pyrazolo[1,5-a]pyrazine-5-carboxylate (compound 102d,3.8 g, 10.5 mmol) in dioxane (50 mL) was added methyl 2-methyl-5-oxo-pyrrolidine-3-carboxylate (compound 420c, 1.5 g, 9.5 mmol), (1R,2R)-N1,N2-dimethylcyclohexane-1,2-diamine (142.2 mg, 1.0 mmol), $K_3PO_4$ (6.1 g, 28.5 mmol), and CuI (190.5 mg, 1.0 mmol) under nitrogen at 25° C. The reaction mixture was stirred at 120° C. for 16 hours. After cooled down to room temperature, the reaction mixture was filtered, and concentrated. The resulting residue was purified by silica gel column and prep-HPLC (TFA) sequentially to give compound 420d (2.0 g) as white solid. LCMS (M+1): 393. Compound 420d was then subjected to chiral SFC separation to give four isomers.

Compound 420d-1 (93.4 mg). $^1$H NMR (400 MHz, DMSO-d$^6$) δ ppm 7.47 (s, 1H), 4.78 (d, J=17.2 Hz, 1H), 4.65 (br. s., 1H), 4.22-4.00 (m, 4H), 3.69 (s, 3H), 3.09-3.00 (m, 1H), 2.73 (dd, J=16.8, 9.2 Hz, 1H), 2.60 (dd, J=16.8, 7.2 Hz, 1H), 1.43 (s, 9H), 1.20 (d, J=6.3 Hz, 3H), 1.01 (d, J=6.8 Hz, 3H).

Compound 420d-2 (230.3 mg). $^1$H NMR (400 MHz, DMSO-d$^6$) δ ppm 7.50 (s, 1H), 4.66 (brs., 1H), 4.57 (d, J=17.4 Hz, 1H), 4.35-4.25 (m, 1H), 4.18 (d, J=17.2 Hz, 1H), 4.17-4.10 (m, 1H), 4.03 (d, J=12.8 Hz, 1H), 3.68 (s, 3H), 3.60 (q, J=8.1 Hz, 1H), 2.70 (dd, J=16.8, 8.0 Hz, 1H), 2.55-2.45 (m, 1H), 1.43 (s, 9H), 1.09 (d, J=6.9 Hz, 3H), 0.97 (d, J=6.5 Hz, 3H).

Compound 420d-3 (245.5 mg). $^1$H NMR (400 MHz, DMSO-d$_6$) δ ppm 7.52 (s, 1H), 4.80 (d, J=17.4 Hz, 1H), 4.64 (brs., 1H), 4.38-4.24 (m, 1H), 4.23-4.11 (m, 1H), 4.08-3.95 (m, 2H), 3.68 (s, 3H), 3.61 (q, J=8.4 Hz, 1H), 2.71 (dd, J=16.8, 8.4 Hz, 1H), 2.56-2.52 (m, 1H), 1.44 (s, 9H), 1.00 (d, J=6.8 Hz, 3H), 0.95 (d, J=6.5 Hz, 3H).

Compound 420d-4 (97.9 mg). $^1$H NMR (400 MHz, DMSO-d$_6$) δ ppm 7.48 (s, 1H), 4.66 (brs., 1H), 4.59 (d, J=17.3 Hz, 1H), 4.23-3.99 (m, 4H), 3.69 (s, 3H), 3.13-3.01 (m, 1H), 2.76 (dd, J=17.2, 9.2 Hz, 1H), 2.60 (dd, J=17.0, 7.2 Hz, 1H), 1.43 (s, 9H), 1.20 (d, J=6.3 Hz, 3H), 1.08 (d, J=6.9 Hz, 3H).

Preparation of (6S)-3-(3-cyano-2-methyl-5-oxo-
pyrrolidin-1-yl)-6-methyl-N-(3,4,5-trifluorophenyl)-
6,7-dihydro-4H-pyrazolo[1,5-a]pyrazine-5-carbox-
amide (Example 420)

The title compound was prepared in analogy to Example 240 by using tert-butyl (6S)-3-(3-methoxycarbonyl-2-methyl-5-oxo-pyrrolidin-1-yl)-6-methyl-6,7-dihydro-4H-pyrazolo[1,5-a]pyrazine-5-carboxylate (compound 420d) instead of (6S)-tert-butyl 3-(4-(methoxycarbonyl)-2-oxopyrrolidin-1-yl)-6-methyl-6,7-dihydropyrazolo[1,5-a]pyrazine-5(4H)-carboxylate (compound 236b).

Example 420-1 was obtained as a white solid (17 mg). LCMS (M+H+): 433. $^1$H NMR (400 MHz, CD$_3$OD) δ ppm 7.46 (s, 1H), 7.21-7.12 (m, 2H), 4.88 (d, J=16.9 Hz, 1H), 4.85-4.80 (m, 1H), 4.25-4.17 (m, 3H), 4.06 (d, J=12.7 Hz, 1H), 3.27-3.23 (m, 1H), 2.88 (dd, J=17.0, 9.0 Hz, 1H), 2.78(dd, J=17.0, 8.8 Hz, 1H), 1.25 (d, J=6.4 Hz, 3H), 1.10 (d, J=6.7 Hz, 3H).

Example 420-2 was obtained as a white solid (59 mg). LCMS (M+H+): 433. $^1$H NMR (400 MHz, CD$_3$OD) δ ppm 7.59 (s, 1H), 7.32-7.23 (m, 2H), 5.01-4.93 (m, 1H), 4.91-4.89 (m, 1H), 4.48 (d, J=16.9 Hz, 1H), 4.43-4.29 (m, 2H), 4.17 (d, J=12.4 Hz, 1H), 3.92 (td, J=9.0, 7.2 Hz, 1H), 2.99 (dd, J=17.0, 9.0 Hz, 1H), 2.90 (dd, J=17.0, 7.0 Hz, 1H), 1.41 (d, J=6.5 Hz, 3H), 1.29 (d, J=7.0 Hz, 3H).

Example 420-3 was obtained as a white solid (40 mg). LCMS (M+H+): 433. $^1$H NMR (400 MHz, CD$_3$OD) δ ppm 7.58 (s, 1H), 7.35-7.24 (m, 2H), 5.05-4.94 (m, 2H), 4.40-4.29 (m, 3H), 4.18 (d, J=12.8 Hz, 1H), 3.91 (td, J=8.9, 7.0 Hz, 1H), 3.00 (dd, J=17.0, 9.0 Hz, 1H), 2.90 (dd, J=17.0, 6.7 Hz, 1H), 1.42 (d, J=6.6 Hz, 3H), 1.23 (d, J=6.8 Hz, 3H).

Example 420-4 was obtained as a white solid (54 mg). LCMS (M+H+): 433. $^1$H NMR (400 MHz, CD$_3$OD) δ ppm 7.59 (s, 1H), 7.31-7.23 (m, 2H), 5.00-4.92 (m, 1H), 4.92-4.84 (m, 1H), 4.46 (d, J=17.0 Hz, 1H), 4.40-4.28 (m, 2H), 4.17 (d, J=12.8 Hz, 1H), 3.37-3.34 (m, 1H), 3.00 (dd, J=17.0, 9.1 Hz, 1H), 2.89 (dd, J=17.0, 8.7 Hz, 1H), 1.36 (d, J=6.4 Hz, 3H), 1.30 (d, J=6.8 Hz, 3H).

Example 421

(6S)-6-methyl-3-(7-oxo-6-azaspiro[3.4]octan-6-yl)-
N-(3,4,5-trifluorophenyl)-6,7-dihydro-4H-pyrazolo
[1,5-a]pyrazine-5-carboxamide

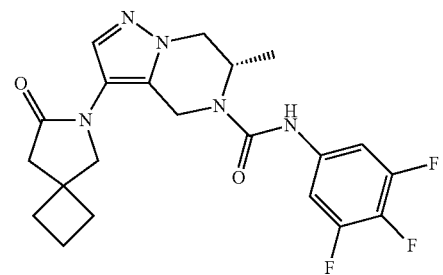 [SMILES: C[C@H]1Cn2ncc(N3CC4(CCC4)CC3=O)c2CN1C(=O)Nc1cc(F)c(F)c(F)c1]

The title compound was prepared according to the following scheme:

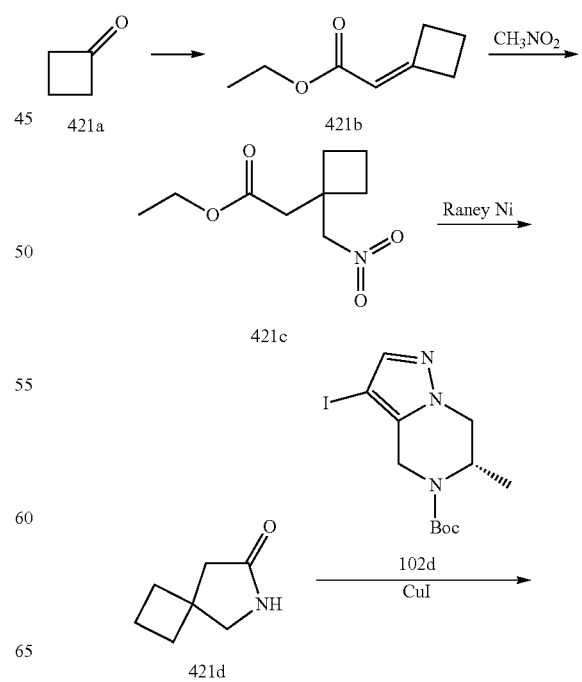

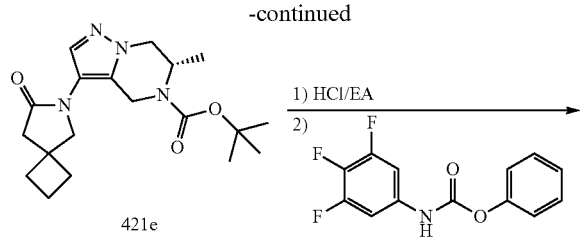

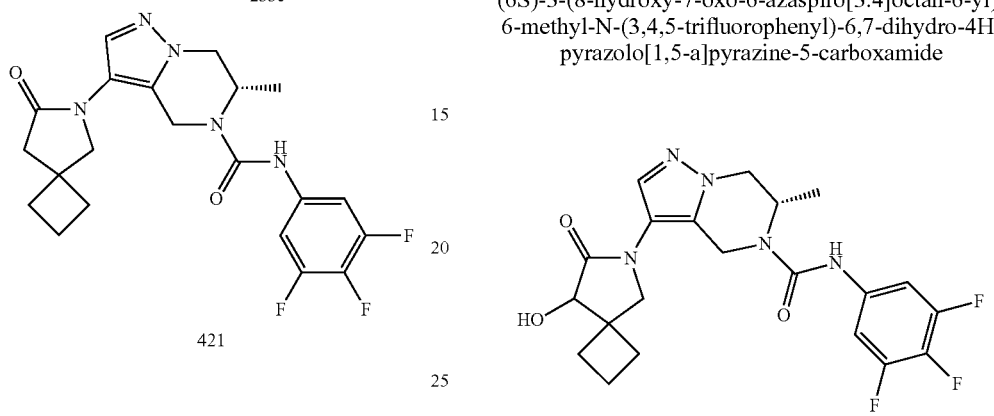

Preparation of 6-azaspiro[3.4]octan-7-one (compound 421d)

Step 1: To a solution of methyl 2-(dimethoxyphosphoryl)acetate (36.4 g, 199.7 mmol) in THF was added NaH (7.4 g, 185.4 mmol) with ice bath cooling. The resulting mixture was stirred at the same temperature for 1 hour, and then a solution of cyclobutanone (compound 421a, 10.0 g, 142.7 mmol) in THF (100 mL) was added. The mixture was then warmed to room temperature and stirred for 11 hours and quenched with saturated aqueous ammonium chloride (100 mL). The mixture was extracted with hexane (500 mL). The organic layer was washed with brine (200 mL) twice, dried over anhydrous $Na_2SO_4$ and concentrated under reduced pressure to give compound 421b as a pale yellow oil (18.9 g).

Step 2: To a solution of methyl 2-cyclobutylideneacetate (compound 421b, 18.0 g, 142.7 mmol) in nitromethane (180 mL) was added DBU (21.7 g, 14.7 mmol). The mixture was stirred at 25° C. for 4 hours, and then concentrated under reduced pressure, and the residue was purified by column chromatography to give compound 421c as a pale yellow oil (21.1 g).

Step 3: To a solution of methyl 2-[1-(nitromethyl)cyclobutyl]acetate (compound 421c, 10.0 g, 53.4 mmol) in MeOH (100 mL) was added Raney Ni (1.0 g). The mixture was stirred at 50° C. under 50 psi of hydrogen for 4 hours and then filtered. The filtrated was concentrated under reduced pressure to give compound 421d as a white solid (5.9 g). LCMS (M+H$^+$): 126.

Preparation of (6S)-6-methyl-3-(7-oxo-6-azaspiro[3.4]octan-6-yl)-N-(3,4,5-trifluorophenyl)-6,7-dihydro-4H-pyrazolo[1,5-a]pyrazine-5-carboxamide (Example 421)

The title compound was prepared in analogy to Example 223 by using 6-azaspiro[3.4]octan-7-one (compound 421d) instead of pyrrolidin-2-one and phenyl N-(3,4,5-trifluorophenyl)carbamate (compound 233c) instead of phenyl N-[2-(difluoromethyl)-4-pyridyl]carbamate (compound 218c).

Example 421 was obtained as a white solid (8 mg). LCMS (M+H$^+$): 434. $^1$H NMR (400 MHz, CDCl$_3$) δ ppm 7.98 (br. s., 1H), 7.30 (s, 1H), 7.17 (d, 2H), 5.12-4.91 (m, 2H), 4.34-4.13 (m, 2H), 3.92 (d, 1H), 3.82 (d, 1H), 3.67 (d, 1H), 2.62 (s, 2H), 2.23-2.01 (m, 4H), 2.00-1.83 (m, 2H), 1.30 (d, 3H).

Example 422

(6S)-3-(8-hydroxy-7-oxo-6-azaspiro[3.4]octan-6-yl)-6-methyl-N-(3,4,5-trifluorophenyl)-6,7-dihydro-4H-pyrazolo[1,5-a]pyrazine-5-carboxamide The title compound was prepared according to the following scheme:

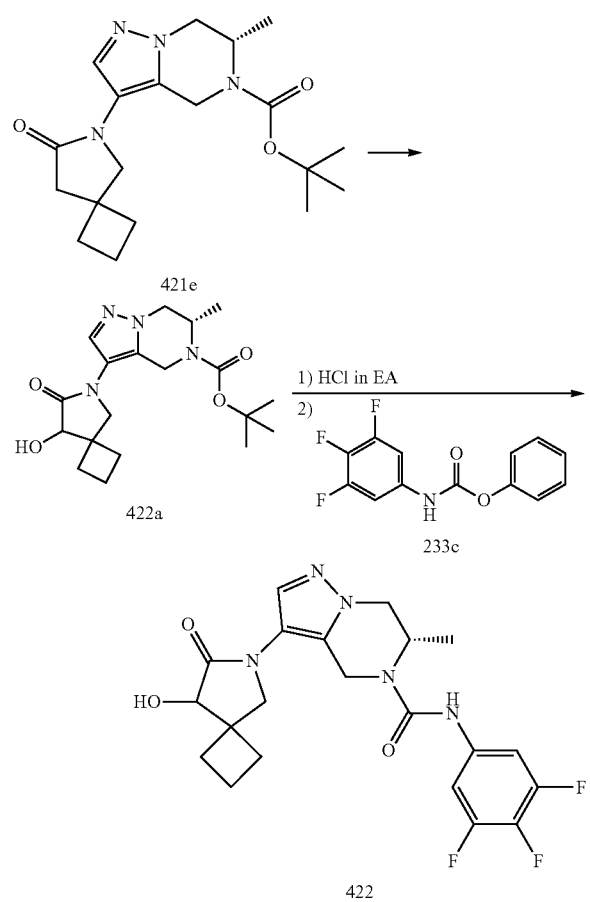

Preparation of tert-butyl (6S)-3-(8-hydroxy-7-oxo-6-azaspiro[3.4]octan-6-yl)-6-methyl-6,7-dihydro-4H-pyrazolo[1,5-a]pyrazine-5-carboxylate (compound 422a)

To a solution of tert-butyl (6S)-6-methyl-3-(7-oxo-6-azaspiro[3.4]octan-6-yl)-6,7-dihydro-4H-pyrazolo[1,5-a]pyrazine-5-carboxylate (compound 421e, 190 mg, 0.53 mmol) in THF (5 mL) was added LiHMDS (1.1 mL, 1.1 mmol) at −78° C. The mixture was stirred at −78° C. for 30 minutes, then 3-phenyl-2-(phenylsulfonyl)-1,2-oxaziridine (165 mg, 0.63 mmol) was added. The resulting mixture was allowed to warm to room temperature and stirred for 1.5 hours, and then quenched with H$_2$O (5 mL). The mixture was concentrated under reduced pressure, and the residue was purified by prep-HPLC to give compound 422a as a yellow oil (90 mg). LCMS (M+H$^+$): 377.

Preparation of (6S)-3-(8-hydroxy-7-oxo-6-azaspiro[3.4]octan-6-yl)-6-methyl-N-(3,4,5-trifluorophenyl)-6,7-dihydro-4H-pyrazolo[1,5-a]pyrazine-5-carboxamide (Example 422)

A mixture of tert-butyl (6S)-3-(8-hydroxy-7-oxo-6-azaspiro[3.4]octan-6-yl)-6-methyl-6,7-dihydro-4H-pyrazolo[1,5-a]pyrazine-5-carboxylate (compound 422a, 90 mg, 0.24 mmol) in a solution of HCl in EtOAc (10 mL, 4 M) was stirred at 20° C. for 2 hours. Then the mixture was concentrated. To the residue was added triethylamine (73 mg, 0.72 mmol) and phenyl N-(3,4,5-trifluorophenyl)carbamate (compound 233c, 64 mg, 0.24 mmol) in DMF (4 mL). The mixture was stirred at 20° C. for 4 hours, and then concentrated under reduced pressure. The residue was purified by prep-HPLC to give Example 422 as a white solid (10 mg). LCMS (M+H$^+$): 450. $^1$H NMR (400 MHz, DMSO-d$_6$) δ ppm 7.56 (d, 1H), 7.48-7.32 (m, 2H), 5.07-4.97 (m, 1H), 4.94-4.83 (m, 1H), 4.47-4.34 (m, 1H), 4.27-4.17 (m, 1H), 4.13-3.95 (m, 2H), 3.82-3.72 (m, 1H), 3.70-3.60 (m, 1H), 2.22-1.68 (m, 6H), 1.24-1.10 (m, 3H).

Example 424

(6S)-3-(7-hydroxy-6-oxo-5-azaspiro[2.4]heptan-5-yl)-6-methyl-N-(3,4,5-trifluorophenyl)-6,7-dihydro-4H-pyrazolo[1,5-a]pyrazine-5-carboxamide

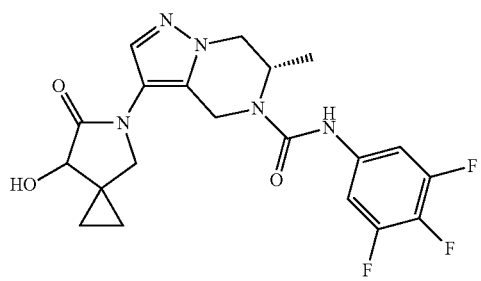 [SMILES: C[C@H]1Cn2ncc(N3CC4(CC4)C(O)C3=O)c2CN1C(=O)Nc1cc(F)c(F)c(F)c1]

Preparation of (6S)-3-(7-hydroxy-6-oxo-5-azaspiro[2.4]heptan-5-yl)-6-methyl-N-(3,4,5-trifluorophenyl)-6,7-dihydro-4H-pyrazolo[1,5-a]pyrazine-5-carboxamide (Example 424)

The title compound was prepared in analogy to Example 422 by using tert-butyl (6S)-6-methyl-3-(6-oxo-5-azaspiro[2.4]heptan-5-yl)-6,7-dihydro-4H-pyrazolo[1,5-a]pyrazine-5-carboxylate (compound 252e) instead of tert-butyl (6S)-6-methyl-3-(7-oxo-6-azaspiro[3.4]octan-6-yl)-6,7-dihydro-4H-pyrazolo[1,5-a]pyrazine-5-carboxylate (compound 421e). Example 424 was obtained as a white solid (124 mg). LCMS (M+H$^+$): 436. $^1$H NMR (400 MHz, CDCl$_3$) δ ppm 7.87-7.41 (m, 2H), 7.26-7.16 (m, 2H), 5.26-4.98 (m, 2H), 4.55-4.25 (m, 3H), 4.12-3.46 (m, 3H), 3.37 (br. s., 1H), 1.34 (dd, 3H), 1.30-1.22 (m, 1H), 0.95-0.81 (m, 2H), 0.66-0.54 (m, 1H).

Example 425

(6S)-6-methyl-3-(6-methyl-2-oxo-1,3-oxazinan-3-yl)-N-(3,4,5-trifluorophenyl)-6,7-dihydro-4H-pyrazolo[1,5-a]pyrazine-5-carboxamide

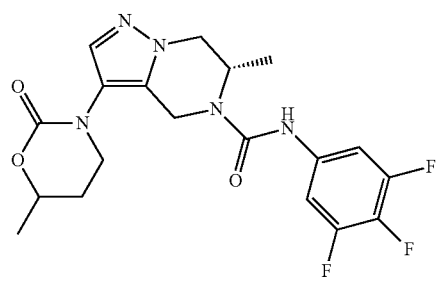 [SMILES: CC1CCN(c2cnn3c2CN(C(=O)Nc2cc(F)c(F)c(F)c2)[C@@H](C)C3)C(=O)O1]

The title compound was prepared according to the following scheme:

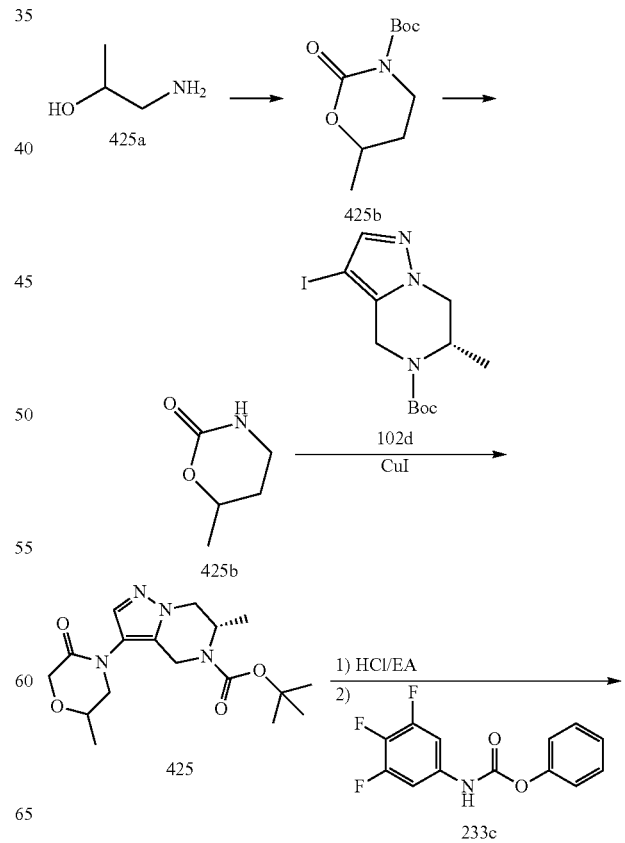

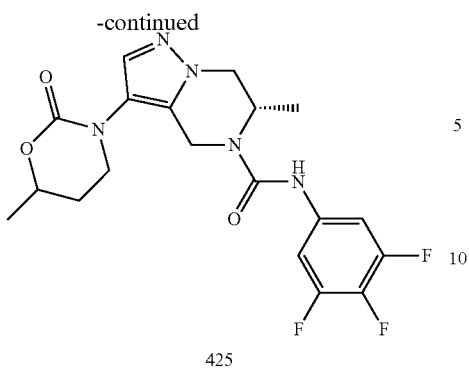

Preparation of 6-methyl-1,3-oxazinan-2-one (compound 425c)

Step 1: A solution of Boc₂O (1.5 g, 6.73 mmol), triethylamine (682 mg, 6.73 mmol) and DMAP (55 mg, 0.45 mmol) in CH$_3$CN (5 mL) was stirred at 20° C. for 1 hour. To the above solution was added a solution of 4-aminobutan-2-ol (compound 425a, 200 mg, 2.25 mmol) in CH$_3$CN (5 mL). The resulting mixture was stirred at 20° C. for 12 hours and then concentrated under reduced pressure. The residue was purified by prep-HPLC to give compound 425b as a colorless oil (320 mg).

Step 2: To a solution of tert-butyl 6-methyl-2-oxo-1,3-oxazinane-3-carboxylate (compound 425b, 200 mg, 0.93 mmol) in DCM (3 mL) was added TFA (0.3 mL). The mixture was stirred at 20° C. for 16 hours and then partitioned between DCM (50 mL) and saturated aqueous NaHCO$_3$ solution (20 mL). The organic layer was washed with brine (20 mL), dried over anhydrous Na$_2$SO$_4$ and concentrated to give compound 425c as a yellow solid (60 mg). LCMS (M+H⁺): 116.

Preparation of (6S)-6-methyl-3-(6-methyl-2-oxo-1,3-oxazinan-3-yl)-N-(3,4,5-trifluorophenyl)-6,7-dihydro-4H-pyrazolo[1,5-a]pyrazine-5-carboxamide (Example 425)

The title compound was prepared in analogy to Example 223 by using 6-methyl-1,3-oxazinan-2-one (compound 425c) instead of pyrrolidin-2-one and phenyl N-(3,4,5-trifluorophenyl)carbamate (compound 233c) instead of phenyl N-[2-(difluoromethyl)-4-pyridyl]carbamate (compound 218c). Example 425 was obtained as a white solid (46 mg). LCMS (M+H⁺): 424. ¹H NMR (400 MHz, CDCl$_3$) δ ppm 7.74-7.52 (m, 1H), 7.41 (d, 1H), 7.18-7.07 (m, 2H), 5.07-4.94 (m, 1H), 7.92-4.73 (m, 1H), 4.61-4.47 (m, 1H), 4.31-4.12 (m, 2H), 3.95 (dd, 1H), 3.89-3.70 (m, 1H), 3.66-3.46 (m, 1H), 2.18-2.05 (m, 1H), 2.04-1.89 (m, 1H), 1.43 (d, 3H), 1.26 (t, 3H).

Example 426

(6S)-6-methyl-3-(4-methyl-2-oxo-1,3-oxazinan-3-yl)-N-(3,4,5-trifluorophenyl)-6,7-dihydro-4H-pyrazolo[1,5-a]pyrazine-5-carboxamide

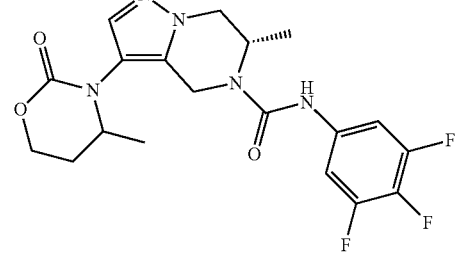

The title compound was prepared according to the following scheme:

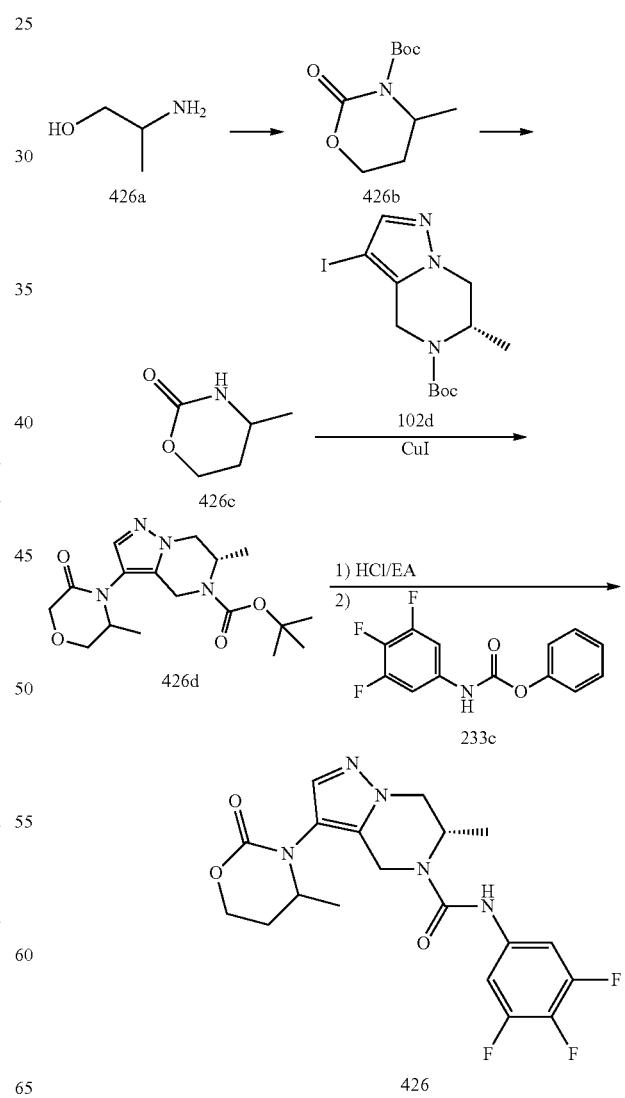

Preparation of 4-methyl-1,3-oxazinan-2-one (compound 426c)

The compound 426c was prepared in analogy to compound 425c by using 3-aminobutan-1-ol (compound 426a) instead of 4-aminobutan-2-ol (compound 425a). Compound 426c was obtained as a colorless oil (1.8 g). LCMS (M+H$^+$): 116.

Preparation of (6S)-6-methyl-3-(4-methyl-2-oxo-1,3-oxazinan-3-yl)-N-(3,4,5-trifluorophenyl)-6,7-dihydro-4H-pyrazolo[1,5-a]pyrazine-5-carboxamide (Example 426)

The title compound was prepared in analogy to Example 223 by using 4-methyl-1,3-oxazinan-2-one (compound 426c) instead of pyrrolidin-2-one and phenyl N-(3,4,5-trifluorophenyl)carbamate (compound 233c) instead of phenyl N-[2-(difluoromethyl)-4-pyridyl]carbamate (compound 218c). Example 426 was obtained as a white solid (26 mg).
LCMS (M+H$^+$): 424. $^1$H NMR (400 MHz, CDCl$_3$) δ ppm 7.59-7.22 (m, 2H), 7.16-7.01 (m, 2H), 5.07-4.58 (m, 2H), 4.47-3.84 (m, 6H), 2.38-2.28 (m, 1H), 1.95-1.84 (m, 1H), 1.34-1.01 (m, 6H).

Example 427

(6S)-3-[(3S,4R)-3,4-dihydroxy-2-oxo-pyrrolidin-1-yl]-6-methyl-N-(3,4,5-trifluorophenyl)-6,7-dihydro-4H-pyrazolo[1,5-a]pyrazine-5-carboxamide

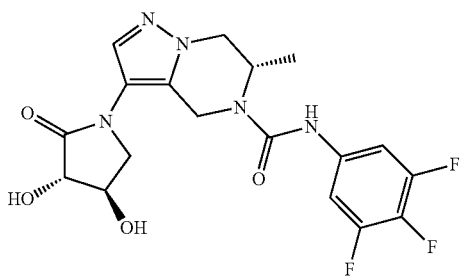 [SMILES: C[C@H]1Cn2ncc(N3C[C@@H](O)[C@H](O)C3=O)c2CN1C(=O)Nc1cc(F)c(F)c(F)c1]

The title compound was prepared according to the following scheme:

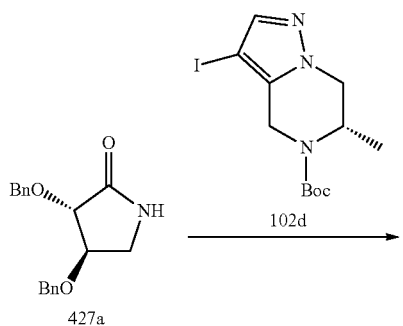

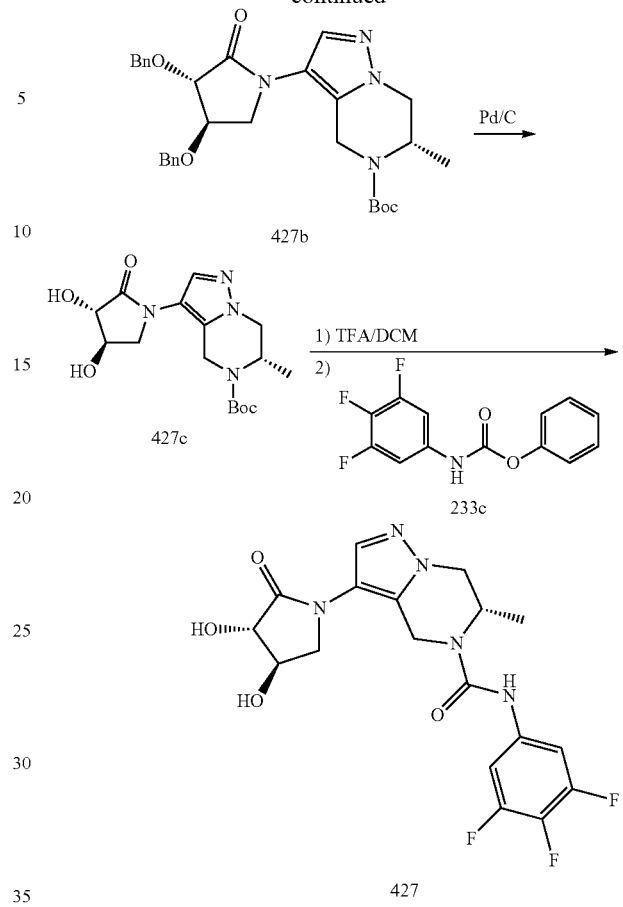

Preparation of tert-butyl (6S)-3-[(3S,4R)-3,4-dihydroxy-2-oxo-pyrrolidin-1-yl]-6-methyl-6,7-dihydro-4H-pyrazolo[1,5-a]pyrazine-5-carboxylate (compound 427c)

Step 1: To a mixture of tert-butyl (6S)-3-iodo-6-methyl-6,7-dihydro-4H-pyrazolo[1,5-a]pyrazine-5-carboxylate (compound 102d, 1 g, 2.75 mmol), (3S,4R)-3,4-bis(benzyloxy)pyrrolidin-2-one (819 mg, 2.75 mmol, synthesis refers to: J. Org. Chem. 2014, 79, 10487-10503, starting from dimethyl (2S,3S)-2,3-dihydroxybutanedioate), (1R,2R)-N1,N2-dimethylcyclohexane-1,2-diamine (157 mg, 1.1 mmol, 0.4 eq.) and K$_3$PO$_4$ (877 mg, 4.13 mmol) in DMSO (15 mL) was added CuI (210 mg, 1.1 mmol) under N$_2$. The resulting mixture was stirred under microwave for 2 hours at 115° C. The reaction mixture was diluted by water, extracted with EtOAc (50 mL) two times. The combined organic layer was dried over Na$_2$SO$_4$, and concentrated. The crude material was purified by flash chromatography (silica gel, 10% to 60% EtOAc in hexanes) to give compound 427b as a colorless oil (1.2 g). LCMS (M+H$^+$): 533.

Step 2: A suspension of (S)-tert-butyl 3-((3S,4R)-3,4-bis(benzyloxy)-2-oxopyrrolidin-1-yl)-6-methyl-6,7-dihydropyrazolo[1,5-a]pyrazine-5(4H)-carboxylate (1.2 g, 2.25 mmol) and palladium on carbon (240 mg) in MeOH (50 mL) was heated to 60° C. and stirred for 12 hours under 1 atm of hydrogen. The reaction mixture was filtered and the filtrate was concentrated to give compound 427c as a white solid (700 mg). LCMS (M+H$^+$): 353.

495

Preparation of (6S)-3-[(3S,4R)-3,4-dihydroxy-2-oxo-pyrrolidin-1-yl]-6-methyl-N-(3,4,5-trifluorophenyl)-6,7-dihydro-4H-pyrazolo[1,5-a]pyrazine-5-carboxamide (Example 427)

A mixture of (S)-tert-butyl 3-((3S,4R)-3,4-dihydroxy-2-oxopyrrolidin-1-yl)-6-methyl-6,7-dihydropyrazolo[1,5-a]pyrazine-5(4H)-carboxylate (compound 427c, 30 mg, 85.1 µmol) in TFA (1 mL) and DCM (1 mL) was stirred at rt for 30 mins, and then concentrated. The residue was dissolved in DMF (1 mL), to it was added N-ethyl-N-isopropylpropan-2-amine (55 mg, 426 µmol) and phenyl (3,4,5-trifluorophenyl)carbamate (compound 233c, 27.3 mg, 102 µmol). The reaction mixture was stirred at 70° C. for 0.5 hours. Then the reaction mixture purified by prep-HPLC to give Example 427 as a white solid (10 mg). LCMS (M+H$^+$): 426. $^1$H NMR (400 MHz, METHANOL-d$_4$) δ ppm 7.64 (s, 1H) 7.31-7.27 (m, 2H) 4.93-5.06 (m, 2H) 4.57 (d, J=16.99 Hz, 1H) 4.21-4.37 (m, 3H) 4.12-4.19 (m, 1H) 3.92 (dd, J=9.54, 7.34 Hz, 1H) 3.59 (dd, J=9.66, 6.72 Hz, 1H) 1.28 (d, J=6.85 Hz, 3H).

496

Example 428

(6S)-3-[(3S,4R)-3-hydroxy-2-oxo-4-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide

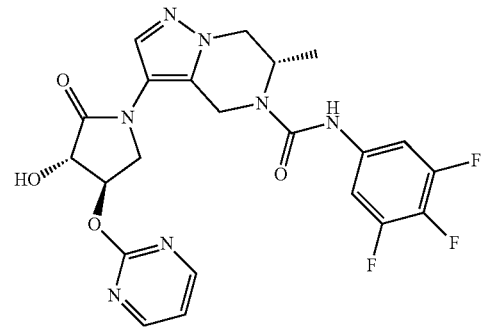 [SMILES: C[C@H]1Cn2ncc(N3C[C@@H](Oc4ncccn4)[C@H](O)C3=O)c2CN1C(=O)Nc1cc(F)c(F)c(F)c1]

The title compound was prepared according to the following scheme:

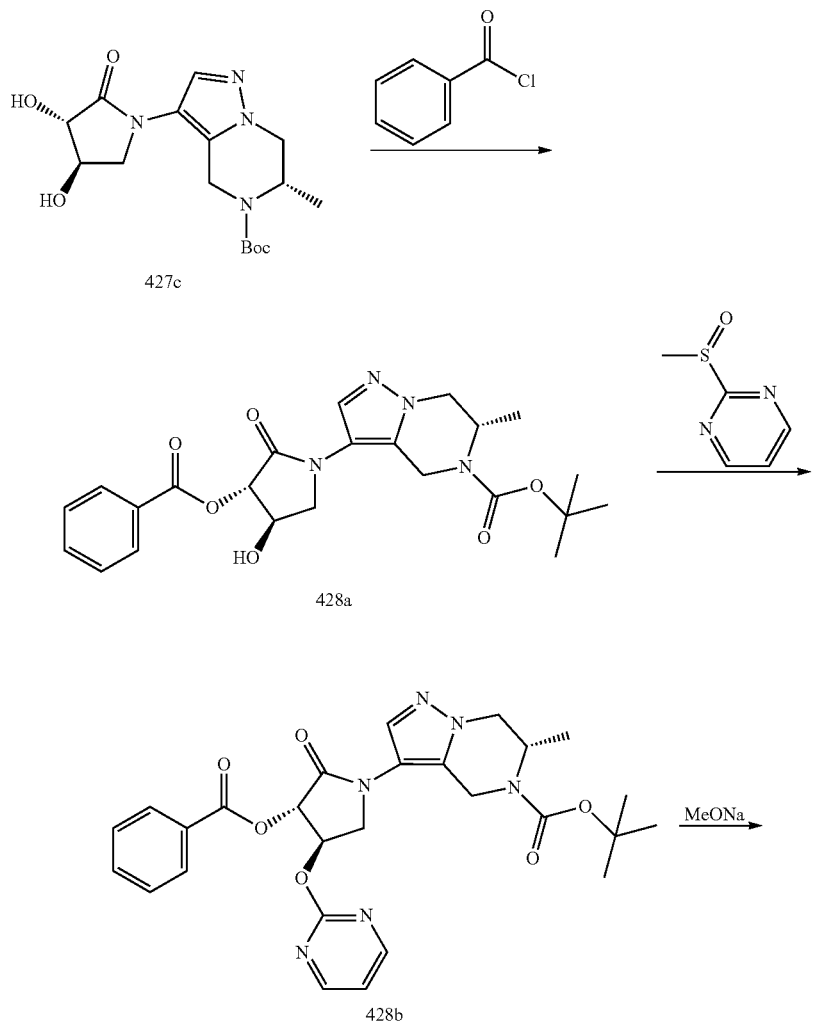

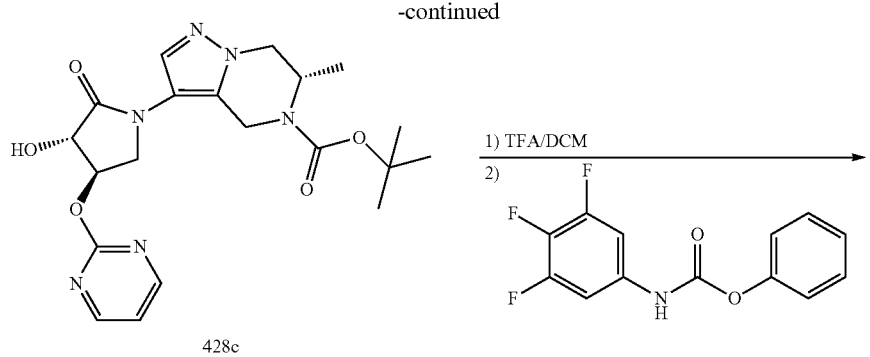

428c

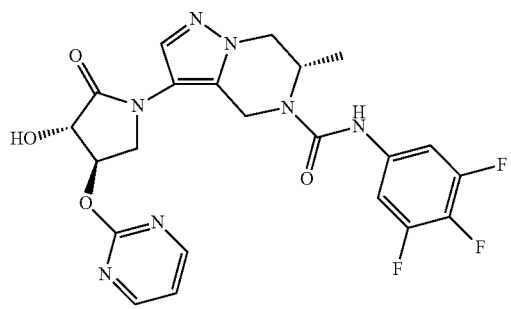

428

Preparation of tert-butyl (6S)-3-[(3S,4R)-3-hydroxy-2-oxo-4-pyrimidin-2-yloxy-pyrrolidin-1-yl]-6-methyl-6,7-dihydro-4H-pyrazolo[1,5-a]pyrazine-5-carboxylate (compound 428c)

Step 1: To a mixture of (S)-tert-butyl 3-((3S,4R)-3,4-dihydroxy-2-oxopyrrolidin-1-yl)-6-methyl-6,7-dihydropyrazolo[1,5-a]pyrazine-5(4H)-carboxylate (compound 427c, 400 mg, 1.14 mmol) and pyridine (269 mg, 3.41 mmol) in DCM (10 mL) was added benzoyl chloride (319 mg, 2.27 mmol) slowly. The reaction mixture was stirred at room temperature for 10 minutes and then concentrated. The crude material was purified by flash chromatography (silica gel, 12 g, 20% to 100% EtOAc in hexanes) to give compound 428a as a white solid (350 mg). LCMS (M+H+): 457.

Step 2: To a 20 mL vial was added (S)-tert-butyl 3-((3S,4R)-3-(benzoyloxy)-4-hydroxy-2-oxopyrrolidin-1-yl)-6-methyl-6,7-dihydropyrazolo[1,5-a]pyrazine-5(4H)-carboxylate (compound 428a, 300 mg, 0.66 mmol), 2-(methylsulfinyl)pyrimidine (140 mg, 1.0 mmol), sodium carbonate (139 mg, 1.3 mmol) and dioxane (10 mL). The vial was sealed and heated at 90° C. for 2 hours. The crude reaction mixture was concentrated in vacuo. The crude material was purified by flash chromatography (silica gel, 12 g, 20% to 80% EtOAc in hexanes) to give compound 428b as a white solid (250 mg). LCMS (M+H+): 535.

Step 3: A mixture of (S)-tert-butyl 3-((3S,4R)-3-(benzoyloxy)-2-oxo-4-(pyrimidin-2-yloxy)pyrrolidin-1-yl)-6-methyl-6,7-dihydropyrazolo[1,5-a]pyrazine-5(4H)-carboxylate (compound 428b, 250 mg) and sodium methanolate (126 mg) in MeOH (20 mL) was stirred at room temperature for 3 hours, and then concentrated in vacuo. The crude material was purified by flash chromatography (silica gel, 12 g, 10% to 70% EtOAc in hexanes, EtOAc contain 10% MeOH) to give compound 428c as a colorless oil (150 mg). LCMS (M+H+): 431.

Preparation of (6S)-3-[(3S,4R)-3-hydroxy-2-oxo-4-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide (Example 428)

The title compound was prepared in analogy to Example 427 by using tert-butyl (6S)-3-[(3S,4R)-3-hydroxy-2-oxo-4-pyrimidin-2-yloxy-pyrrolidin-1-yl]-6-methyl-6,7-dihydro-4H-pyrazolo[1,5-a]pyrazine-5-carboxylate (compound 428c) instead of (S)-tert-butyl 3-((3S,4R)-3,4-dihydroxy-2-oxopyrrolidin-1-yl)-6-methyl-6,7-dihydropyrazolo[1,5-a]pyrazine-5(4H)-carboxylate (compound 427c). Example 428 was obtained as a white solid (65 mg). LCMS (M+H+): 504. $^1$H NMR (400 MHz, METHANOL-4) δ ppm 8.64 (d, J=4.8 Hz, 2H), 7.67 (s, 1H), 7.35-7.24 (m, 2H), 7.20 (t, J=4.9 Hz, 1H), 5.53 (td, J=6.1, 7.3 Hz, 1H), 5.07 (d, J=17.0 Hz, 1H), 5.02-4.94 (m, 1H), 4.70 (d, J=6.2 Hz, 1H), 4.60 (d, J=16.9 Hz, 1H), 4.38 (dd, J=7.5, 10.3 Hz, 1H), 4.30 (dd, J=4.4, 12.7 Hz, 1H), 4.22-4.12 (m, 1H), 3.83 (dd, J=5.9, 10.2 Hz, 1H), 1.28 (d, J=6.8 Hz, 3H)

Example 435

(6S)-6-methyl-3-[5-methyl-5-(morpholine-4-carbonyl)-2-oxo-1,3-oxazinan-3-yl]-N-(3,4,5-trifluorophenyl)-6,7-dihydro-4H-pyrazolo[1,5-a]pyrazine-5-carboxamide

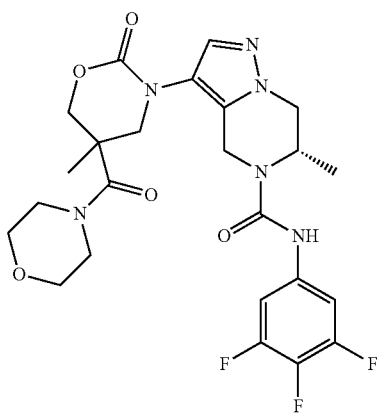 [SMILES: C[C@H]1Cn2ncc(N3CC(C)(C(=O)N4CCOCC4)COC3=O)c2CN1C(=O)Nc1cc(F)c(F)c(F)c1]

The title compound was prepared according to the following scheme:

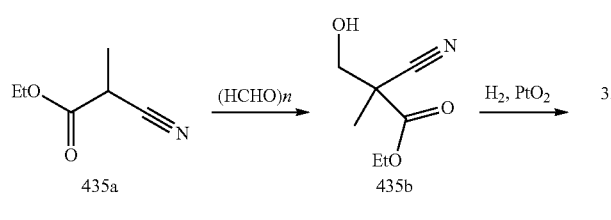

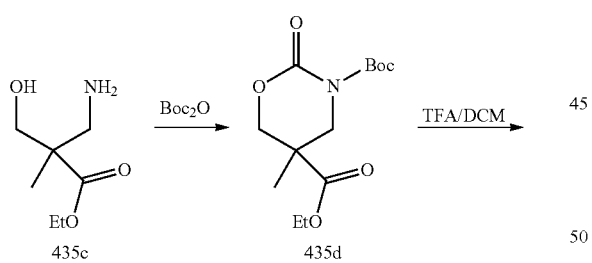

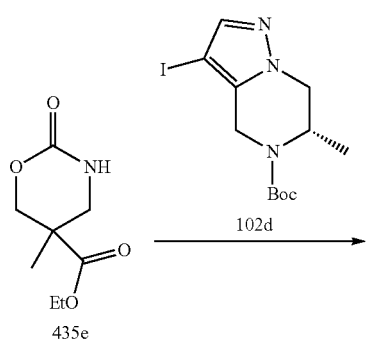

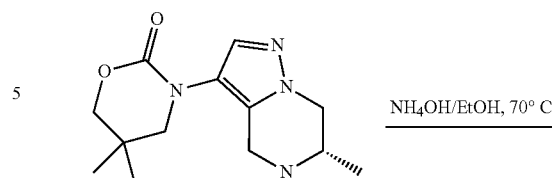

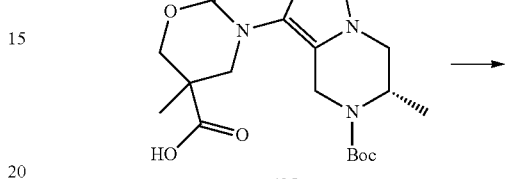

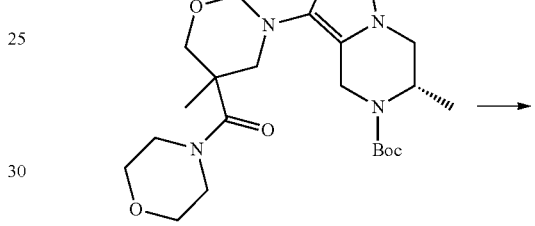

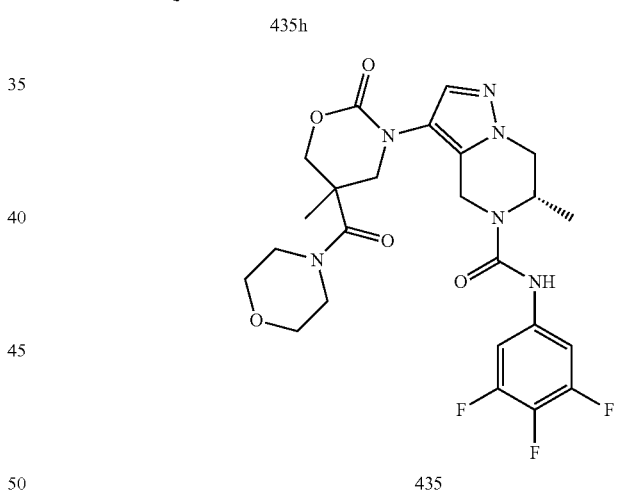

Step 1: Preparation of ethyl 2-cyano-3-hydroxy-2-methyl-propanoate (compound 435b)

To a solution of ethyl 2-cyanopropanoate (compound 435a, 40.0 g, 314.6 mmol) in ethanol (400.0 mL) was added $K_2CO_3$ (124.4 g, 943.8 mmol) and formaldehyde (14.2 g, 471.9 mmol). The reaction mixture was stirred at 25° C. for 12 h. The reaction mixture was filtered and the filtrate was concentrated. The residue was dissolved in EA, and washed with brine. The organic phase was separated and concentrated. The residue was purified by silica gel column to give compound 435b as colorless oil (16 g). LCMS (M+H⁺): 158.

Step 2: Preparation of ethyl 2-(aminomethyl)-3-hydroxy-2-methyl-propanoate (compound 435c)

To a solution of ethyl 2-cyano-3-hydroxy-2-methyl-propanoate (compound 435b, 16.0 g, 101.8 mmol) in ethanol (200.0 mL) was added platinum oxide (2.3 g, 10.2 mmol) and HCl solution (4 M in dioxane, 50.9 mL, 203.6 mmol). The reaction mixture was stirred at 25° C. for 12 hours under $H_2$ (50 psi) atmosphere. The reaction mixture was filtered and the filtrate was concentrated to give compound 435c as colorless oil (19.4 g). LCMS (M+H$^+$): 162.

Step 3: Preparation of O3-tert-butyl O5-ethyl 5-methyl-2-oxo-1,3-oxazinane-3,5-dicarboxylate (compound 435d)

To a solution of ethyl 2-(aminomethyl)-3-hydroxy-2-methyl-propanoate (compound 435c, 19.0 g, 96.1 mmol) in acetonitrile (200.0 mL) was added $K_2CO_3$ (26.6 g, 192.2 mmol). After stirring at 25° C. for 30 minutes, the mixture was added into a stirring mixture of Boc2O (62.9 g, 288.4 mmol), Et3N (29.2 g, 288.4 mmol) and DMAP (2.4 g, 19.2 mmol) in acetonitrile (200 mL). The resulting reaction mixture was stirred for 12 h at 25° C., and then filtered. The filtrate was concentrated, and the obtained residue was partitioned between $H_2O$ (500 mL) and EtOAc (500 mL). The EtOAc phase was washed with brine (300 mL), concentrated and the residue was purified by column chromatography (PE/EtOAc=3/1) to give compound 435d as a colorless oil (11 g). LCMS (M+H$^+$): 288.

Step 4: Preparation of ethyl 5-methyl-2-oxo-1,3-oxazinane-5-carboxylate (compound 435e)

To a solution of compound O3-tert-butyl O5-ethyl 5-methyl-2-oxo-1,3-oxazinane-3,5-dicarboxylate (compound 435d, 11.0 g, 38.3 mmol) in DCM (70 mL) was added TFA (14 mL). after being stirred at 25° C. for 2 hours, the reaction mixture was basified to pH 10 by adding sodium hydroxide solution (2.0 M, aqueous). The mixture was then partitioned between $H_2O$ (400 mL) and DCM (400 mL). The DCM phase was washed with brine (200 mL), and then concentrated to give crude compound 435e (4.2 g). LCMS (M+H$^+$): 188.

Step 5: Preparation of ethyl 3-((S)-5-(tert-butoxycarbonyl)-6-methyl-4,5,6,7-tetrahydropyrazolo[1,5-a]pyrazin-3-yl)-5-methyl-2-oxo-1,3-oxazinane-5-carboxylate (compound 435f)

A mixture of ethyl 5-methyl-2-oxo-1,3-oxazinane-5-carboxylate (compound 435e, 515 mg, 2.75 mmol), (S)-tert-butyl 3-iodo-6-methyl-6,7-dihydropyrazolo[1,5-a]pyrazine-5(4H)-carboxylate (compound 102d, 1.0 g, 2.75 mmol), $K_3PO_4$ (1.17 g, 5.51 mmol), CuI (105 mg, 0.55 mmol) and (1R,2R)-N1,N2-dimethylcyclohexane-1,2-diamine (78.3 mg, 0.55 mmol) in DMSO (16 mL) was flushed with $N_2$ and sealed. The reaction mixture was heated to 105° C. in microwave for 2 hours. The reaction mixture was cooled down, diluted with DCM, and then washed with ice-water. The aqueous phase was extracted with DCM/i-PrOH (v/v=5/1) twice. The combined organic layer was dried over $Na_2SO_4$ and concentrated in vacuo. The residue was purified by silica gel column to give compound 435f (0.63 g). LCMS (M+H$^+$): 423.

Step 6: Preparation of 34(S)-5-(tert-butoxycarbonyl)-6-methyl-4,5,6,7-tetrahydropyrazolo[1,5-a]pyrazin-3-yl)-5-methyl-2-oxo-1,3-oxazinane-5-carboxylic acid (compound 435g)

To a solution of ethyl 3-((S)-5-(tert-butoxycarbonyl)-6-methyl-4,5,6,7-tetrahydropyrazolo[1,5-a]pyrazin-3-yl)-5-methyl-2-oxo-1,3-oxazinane-5-carboxylate (compound 435f, 0.6 g, 1.42 mmol) in ethanol (8.0 mL) was added 25%-28% ammonia aqueous solution (8 mL). The reaction mixture was sealed and heated to 70° C. overnight. The reaction mixture was concentrated and 2-methyltetrahydrofuran was added to azeotropically remove residue water to give compound 435g (0.5 g). LCMS (M+H$^+$): 395.

Step 7: Preparation of (6S)-tert-butyl 6-methyl-3-(5-methyl-5-(morpholine-4-carbonyl)-2-oxo-1,3-oxazinan-3-yl)-6,7-dihydropyrazolo[1,5-a]pyrazine-5(4H)-carboxylate (compound 435h)

To a solution of 3-((S)-5-(tert-butoxycarbonyl)-6-methyl-4,5,6,7-tetrahydropyrazolo[1,5-a]pyrazin-3-yl)-5-methyl-2-oxo-1,3-oxazinane-5-carboxylic acid (compound 435g, 78.9 mg, 0.2 mmol) in DCE (3.0 mL) was added morpholine (26.1 mg, 26 µL, 300 µmol), DIPEA (151 mg, 0.2 mL, 1.17 mmol) and HATU (114 mg, 300 µmol). The reaction mixture was stirred at 50° C. for 2 hours. The reaction mixture was cooled down, washed with ice-water, and aqueous phase was extracted with DCM twice. The organic phase was combined, dried over $Na_2SO_4$, filtrated and concentrated. The residue was purified by silica gel column to give compound 435h (70 mg). LCMS (M+H$^+$): 464.

Step 8: Preparation of (6S)-6-methyl-3-[5-methyl-5-(morpholine-4-carbonyl)-2-oxo-1,3-oxazinan-3-yl]-N-(3,4,5-trifluorophenyl)-6,7-dihydro-4H-pyrazolo[1,5-a]pyrazine-5-carboxamide (Example 435)

A mixture of (6S)-tert-butyl 6-methyl-3-(5-methyl-5-(morpholine-4-carbonyl)-2-oxo-1,3-oxazinan-3-yl)-6,7-dihydropyrazolo[1,5-a]pyrazine-5(4H)-carboxylate (compound 435h, 69.5 mg, 0.15 mmol), TFA (2.0 mL) and DCM (1.0 mL) was stirred at room temperature for 1 hour. The reaction mixture was concentrated. The residue was dissolved in DCE (3.0 mL), to it was then added DIPEA (0.5 mL) and phenyl (3,4,5-trifluorophenyl)carbamate (compound 233c, 60 mg, 225 µmol). The reaction mixture was stirred at 55° C. for 2 hours, and then concentrated. The residue was first purified by silica gel column, and then by pre-HPLC to give Example 435 (25 mg). LCMS (M+H$^+$): 537. $^1$H NMR (400 MHz, CD$_3$OD) δ ppm 7.67 (s, 0.5H), 7.66 (s, 0.5H), 7.34-7.23 (m, 2H), 5.06-4.97 (m, 2H), 4.78-4.71 (m, 1H), 4.51-4.38 (m, 2H), 4.34-4.26 (m, 1H), 4.19-4.12 (m, 1H), 4.11-4.02 (m, 1H), 3.74-3.65 (m, 9H), 1.45 (s, 1.5H), 1.44 (s, 1.5H), 1.30-1.24 (m, 3H)

Example 436

(6S)-3-[(2R,3R,4S)-4-hydroxy-2-methyl-5-oxo-3-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide

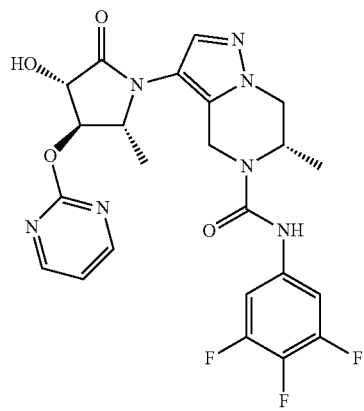 [SMILES: C[C@@H]1[C@@H](Oc2ncccn2)[C@H](O)C(=O)N1c1cnn2c1CN(C(=O)Nc1cc(F)c(F)c(F)c1)[C@@H](C)C2]

The title compound was prepared according to the following scheme:

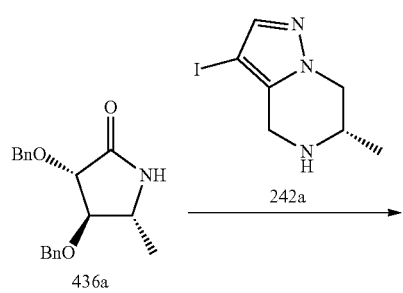

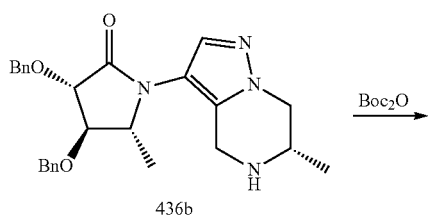

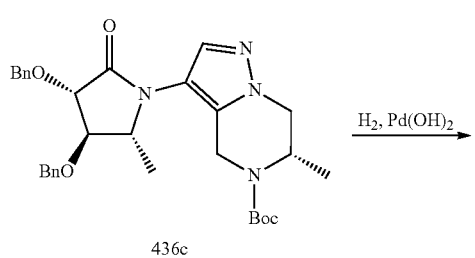

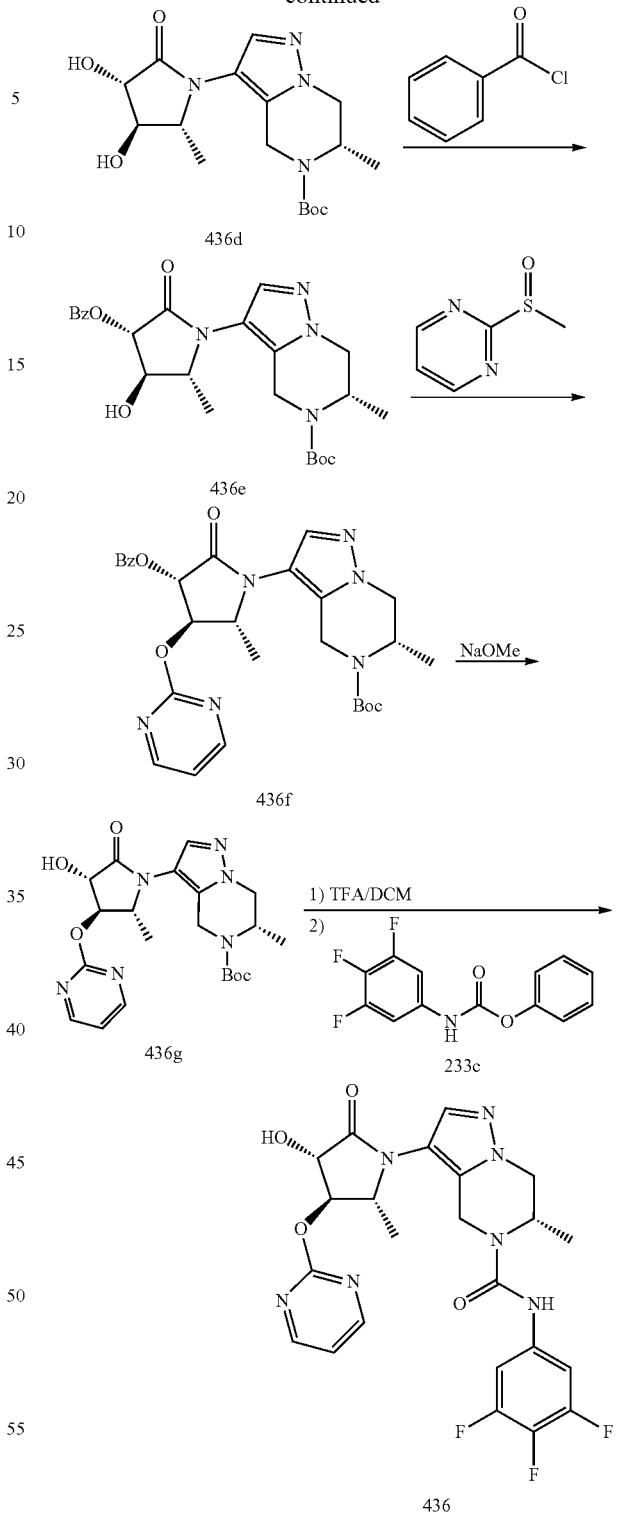

Preparation of (3S,4R,5R)-3,4-bis(benzyloxy)-5-methyl-1-(4(S)-6-methyl-4,5,6,7-tetrahydropyrazolo[1,5-a]pyrazin-3-yl)pyrrolidin-2-one (compound 436b)

A mixture of (3S,4R,5R)-3,4-bis(benzyloxy)-5-methyl-pyrrolidin-2-one (compound 436a, 250 mg, 0.80 mmol, synthesis refers to: Hidemi Yoda et al., *Tetrahedron Letters*, 1996, 37, 5531-5534), (S)-3-iodo-6-methyl-4,5,6,7-tetrahydropyrazolo[1,5-a]pyrazine (compound 242a, 253 mg, 0.96 mmol), $K_3PO_4$ (341 mg, 1.61 mmol), CuI (30.6 mg, 0.16 mmol) and (1R,2R)-N1,N2-dimethylcyclohexane-1,2-diamine (22.8 mg, 0.16 mmol) in DMSO (12 mL) was flushed with $N_2$ and sealed. The reaction mixture was heated at 110° C. in microwave for 2 hours. After cooled down, the reaction mixture was quenched with ice-water, and extracted with EA twice. The combined organic phase was concentrated and the residue was purified by silica gel column to give compound 436b (251 mg). LCMS (M+H$^+$): 447.

Preparation of (S)-tert-butyl 3-((2R,3R,4S)-3,4-bis(benzyloxy)-2-methyl-5-oxopyrrolidin-1-yl)-6-methyl-6,7-dihydropyrazolo[1,5-a]pyrazine-5(4H)-carboxylate (compound 436c)

To a solution of (3S,4R,5R)-3,4-bis(benzyloxy)-5-methyl-14(S)-6-methyl-4,5,6,7-tetrahydropyrazolo[1,5-a]pyrazin-3-yl)pyrrolidin-2-one (compound 436b, 330 mg, 0.74 mmol) in THF (9.0 mL) and water (3.0 mL) was added sequentially di-tert-butyl dicarbonate (194 mg, 204 µL, 0.89 mmol) and $Na_2CO_3$ (78.3 mg, 0.74 mmol). The reaction mixture was stirred at room temperature overnight, then extracted with EA twice. The combined organic phase was concentrated, and the residue was purified by silica gel column to give compound 436c (300 mg). LCMS (M+H$^+$): 547.

Preparation of (S)-tert-butyl 3-((2R,3R,4S)-3,4-dihydroxy-2-methyl-5-oxopyrrolidin-1-yl)-6-methyl-6,7-dihydropyrazolo[1,5-a]pyrazine-5(4H)-carboxylate (compound 436d)

To a solution of (S)-tert-butyl 3-((2R,3R,4S)-3,4-bis(benzyloxy)-2-methyl-5-oxopyrrolidin-1-yl)-6-methyl-6,7-dihydropyrazolo[1,5-a]pyrazine-5(4H)-carboxylate (compound 436c, 300 mg, 0.55 mmol) in EtOH (8.0 mL) was added Pd(OH)$_2$ on carbon. The reaction mixture was stirred at 42° C. for 3 hours under 1 atm of $H_2$. The reaction mixture was filtrated and concentrated to give crude compound 436d (200 mg). LCMS (M+H$^+$): 367.

Preparation of (6S)-3-[(2R,3R,4S)-4-hydroxy-2-methyl-5-oxo-3-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide (Example 436)

The title compound was prepared in analogy to Example 428 by using (S)-tert-butyl 3-((2R,3R,4S)-3,4-dihydroxy-2-methyl-5-oxopyrrolidin-1-yl)-6-methyl-6,7-dihydropyrazolo[1,5-a]pyrazine-5(4H)-carboxylate (compound 436d) instead of (S)-tert-butyl 3-((3S,4R)-3,4-dihydroxy-2-oxopyrrolidin-1-yl)-6-methyl-6,7-dihydropyrazolo[1,5-a]pyrazine-5(4H)-carboxylate (compound 427c). Example 436 was obtained as a white solid (23 mg). LCMS (M+H$^+$): 518. $^1$H NMR (400 MHz, CD$_3$OD) δ ppm 8.66 (d, J=4.9 Hz, 2H), 7.62 (s, 1H), 7.34-7.25 (m, 2H), 7.21 (t, J=4.8 Hz, 1H), 5.44 (t, J=4.8 Hz, 1H), 5.04-4.96 (m, 1H), 4.93 (d, J=17.0 Hz, 1H), 4.60-4.54 (m, 2H), 4.32 (dd, J=4.6, 12.8 Hz, 1H), 4.22-4.14 (m, 2H), 1.42 (d, J=6.5 Hz, 3H), 1.31 (d, J=7.0 Hz, 3H).

Example 437

(6S)-6-methyl-3-(2-oxo-4-pyrimidin-2-yl-pyrrolidin-1-yl)-N-(3,4,5-trifluorophenyl)-6,7-dihydro-4H-pyrazolo[1,5-a]pyrazine-5-carboxamide

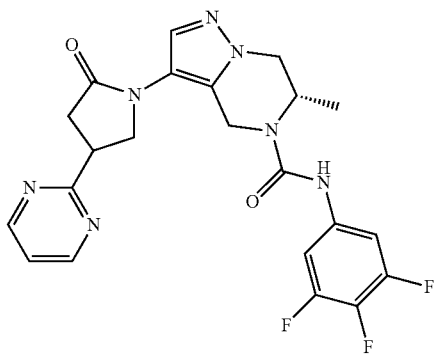 [SMILES: C[C@H]1Cn2ncc(N3CC(c4ncccn4)CC3=O)c2CN1C(=O)Nc1cc(F)c(F)c(F)c1]

Preparation of (6S)-6-methyl-3-(2-oxo-4-pyrimidin-2-yl-pyrrolidin-1-yl)-N-(3,4,5-trifluorophenyl)-6,7-dihydro-4H-pyrazolo[1,5-a]pyrazine-5-carboxamide (Example 437)

The title compound was prepared in analogy to Example 290 by using pyrimidine-2-carbaldehyde instead of thiazole-5-carbaldehyde. Example 437 was obtained as a white solid (26 mg). LCMS (M+H$^+$): 472. $^1$H NMR (400 MHz, CD$_3$OD) δ ppm 8.82 (d, J=5.0 Hz, 2H), 7.66 (s, 0.5H), 7.65 (s, 0.5H), 7.43-7.38 (m, 1H), 7.34-7.24 (m, 2H), 5.08 (d, J=16.9 Hz, 1H), 5.00-4.92 (m, 1H), 4.56-4.48 (m, 1H), 4.36-4.26 (m, 2H), 4.21-4.06 (m, 3H), 3.11-2.98 (m, 2H), 1.32-1.24 (m, 3H).

Example 438

(6S)-3-(3-hydroxy-2-oxo-4-phenyl-pyrrolidin-1-yl)-6-methyl-N-(3,4,5-trifluorophenyl)-6,7-dihydro-4H-pyrazolo[1,5-a]pyrazine-5-carboxamide

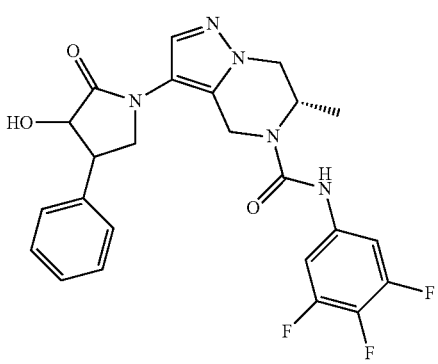 [SMILES: C[C@H]1Cn2ncc(N3CC(c4ccccc4)C(O)C3=O)c2CN1C(=O)Nc1cc(F)c(F)c(F)c1]

The title compound was prepared according to the following scheme:

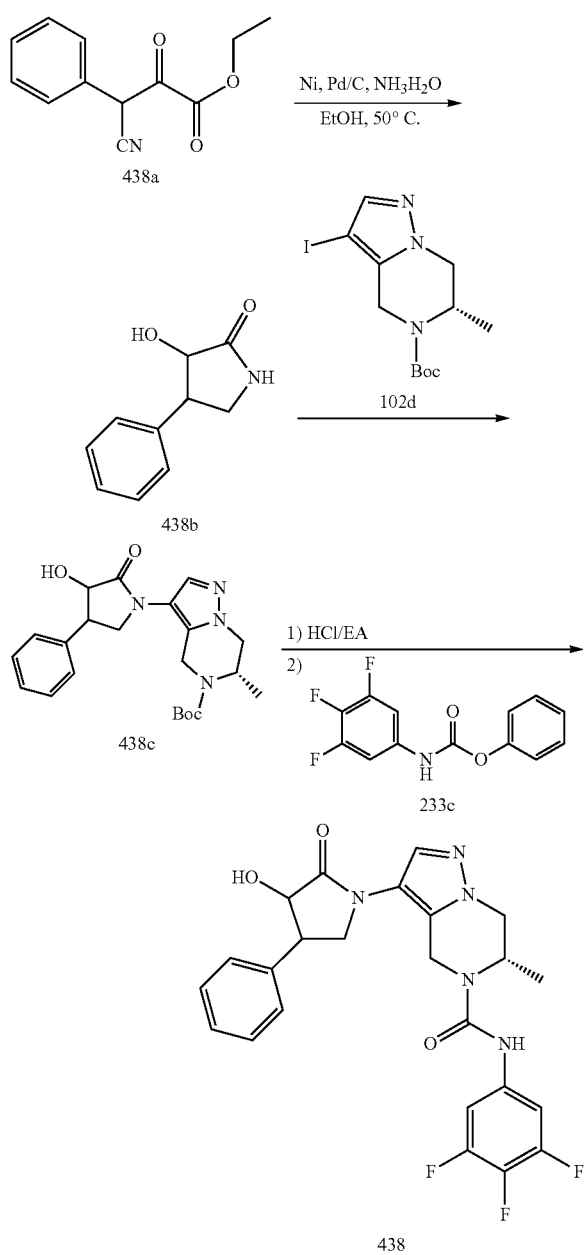

1H), 5.58 (d, J=6.0 Hz, 1H), 4.15 (dd, J=10, 6.4 Hz, 1H), 3.54-3.44 (m, 1H), 3.27-3.20 (m, 1H), 3.20-3.10 (m, 1H).

Preparation of (6S)-3-(3-hydroxy-2-oxo-4-phenyl-pyrrolidin-1-yl)-6-methyl-N-(3,4,5-trifluorophenyl)-6,7-dihydro-4H-pyrazolo[1,5-a]pyrazine-5-carboxamide (Example 438)

The title compound was prepared in analogy to Example 223 by using 3-hydroxy-4-phenyl-pyrrolidin-2-one (compound 438b-1 or 438b-2) instead of pyrrolidin-2-one and phenyl N-(3,4,5-trifluorophenyl)carbamate (compound 233c) instead of phenyl N-[2-(difluoromethyl)-4-pyridyl]carbamate (compound 218c). Example 438A and Example 438B were synthesized from cis-enantiomer 438b-1 and separated by chiral SFC; Example 438C and Example 438D were synthesized from trans-enantiomer 438b-2 and separated by chiral SFC.

Example 438A (25 mg), white solid. LCMS (M+H$^+$): 486. $^1$H NMR (400 MHz, MeOD) δ ppm 7.71 (s, 1H), 7.43-7.19 (m, 7H), 5.09 (d, J=16.9 Hz, 1H), 5.01-4.93 (m, 1H), 4.67-4.54 (m, 2H), 4.32 (dd, J=4.3, 12.7 Hz, 1H), 4.23-4.14 (m, 2H), 4.02 (dd, J=5.3, 9.9 Hz, 1H), 3.91-3.82 (m, 1H), 1.29 (d, J=6.9 Hz, 3H).

Example 438B (32 mg), white solid, LCMS (M+H$^+$): 486. $^1$H NMR (400 MHz, MeOD) δ ppm 7.60 (s, 1H), 7.30-7.11 (m, 7H), 5.04 (d, J=16.9 Hz, 1H), 4.92-4.84 (m, 1H), 4.53 (d, J=7.2 Hz, 1H), 4.44 (d, J=17.1 Hz, 1H), 4.17 (d, J=4.4 Hz, 1H), 4.11-4.02 (m, 2H), 3.92 (dd, J=5.1, 10.0 Hz, 1H), 3.74 (dt, J=5.1, 7.0 Hz, 1H), 1.17 (d, J=6.9 Hz, 3H).

Example 438C (15 mg), white solid. LCMS (M+H$^+$): 486. $^1$H NMR (400 MHz, MeOD) δ ppm 7.70 (s, 1H), 7.53-7.46 (m, 2H), 7.41 (t, J=7.5 Hz, 2H), 7.35-7.26 (m, 3H), 5.17 (d, J=16.8 Hz, 1H), 5.02-4.96 (m, 1H), 4.62 (d, J=10.2 Hz, 1H), 4.54 (d, J=16.9 Hz, 1H), 4.32 (dd, J=4.3, 12.9 Hz, 1H), 4.21-4.13 (m, 1H), 4.09-4.00 (m, 1H), 3.90 (t, J=9.7 Hz, 1H), 3.64-3.53 (m, 1H), 1.26 (d, J=6.9 Hz, 3H).

Example 438D (21 mg), white solid, LCMS (M+H$^+$): 486. $^1$H NMR (400 MHz, MeOD) δ ppm 7.58 (s, 1H), 7.37 (d, J=7.3 Hz, 2H), 7.29 (t, J=7.5 Hz, 2H), 7.23-7.13 (m, 3H), 4.96 (d, J=16.9 Hz, 1H), 4.90-4.82 (m, 1H), 4.57-4.44 (m, 2H), 4.22-4.13 (m, 1H), 4.10-4.01 (m, 1H), 3.94-3.86 (m, 1H), 3.83-3.76 (m, 1H), 3.51-3.41 (m, 1H), 1.18 (d, J=6.8 Hz, 3H).

Example 439

(6S)-3-[(5S)-5-methoxy-2-oxo-1,3-oxazinan-3-yl]-6-methyl-N-(3,4,5trifluorophenyl)-6,7-dihydro-4H-pyrazolo[1,5-a]pyrazine-5-carboxamide

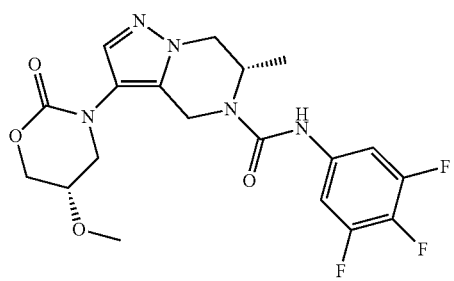 [SMILES: CO[C@@H]1COC(=O)N(c2cnn3c2CN(C(=O)Nc2cc(F)c(F)c(F)c2)[C@@H](C)C3)C1]

The title compound was prepared according to the following scheme:

Preparation of 3-hydroxy-4-phenyl-pyrrolidin-2-one (compound 438b)

To a mixture of ethyl 3-cyano-2-oxo-3-phenyl-propanoate (compound 438a, 1.5 g, 6.9 mmol) and NH$_3$·H$_2$O (0.2 mL) in EtOH (50 mL) was added Raney Ni (2.0 g) and Pd/C (1.0 g). The resulting mixture was stirred at 50° C. for 24 hours under H$_2$ (50 psi). The reaction mixture was filtered and the filtrate was concentrated. The residue was purified by prep-HPLC to afford cis-enantiomer 438b-1 (100 mg) and trans-enantiomer 438b-2 (50 mg) as white solids. LCMS (M+H$^+$): 178. Cis-enantiomer 438b-1: $^1$H NMR (400 MHz, DMSO-d$^6$) δ ppm 7.87 (s, 1H), 7.40-7.15 (m, 5H), 5.43 (d, J=6.0 Hz, 1H), 4.11 (t, J=6.0 Hz, 1H), 3.60-3.40 (m, 2H), 3.38-3.30 (m, 1H); trans-enantiomer 438b-2: $^1$H NMR (400 MHz, DMSO-d$^6$) δ ppm 7.85 (s, 1H), 7.45-7.30 (m, 4H), 7.29-7.20 (m,

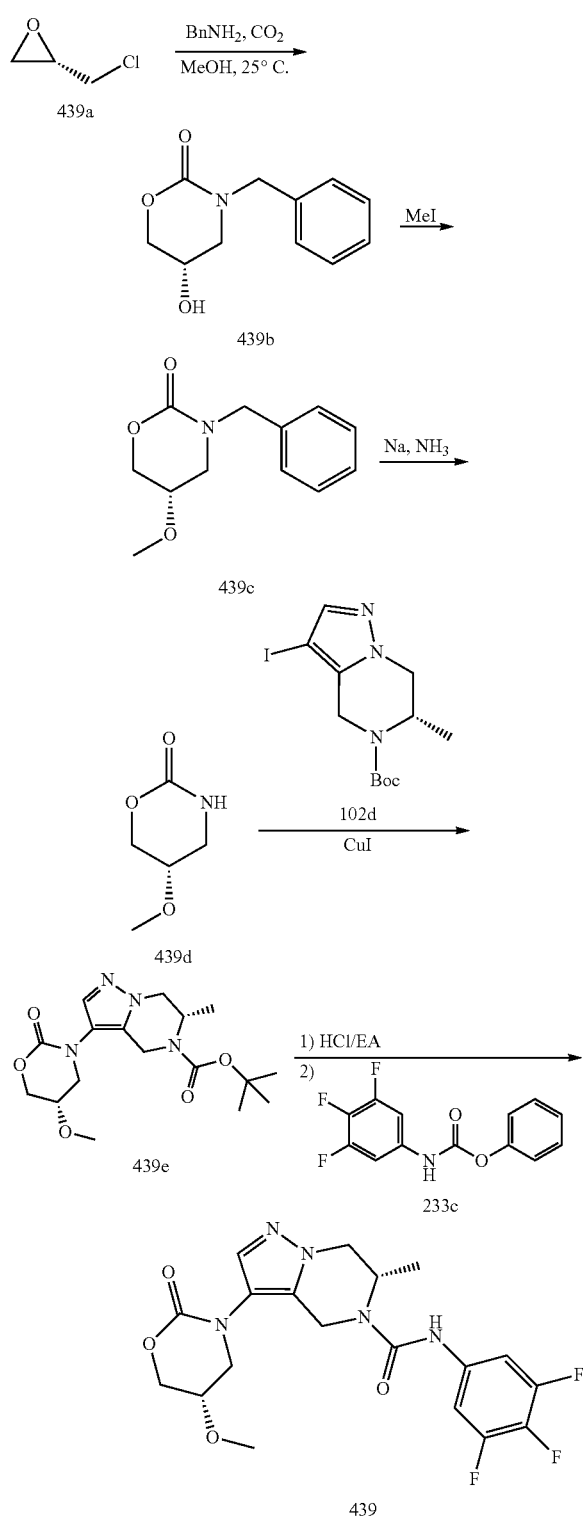

Preparation of (5S)-5-methoxy-1,3-oxazinan-2-one (compound 439d)

Step 1: A mixture of (2S)-2-(chloromethyl)oxirane (compound 439a, 60.0 g, 648.5 mmol), BnNH$_2$ (209.0 g, 1945.5 mmol) and MeOH (1.5 L) in 2 L of autoclave was stirred 48 hours under 1 Mpa of CO$_2$. The reaction was concentrated, and the residue was dissolved in water (200 mL) and acidified by 5N HCl to pH 3~4. The solution was extracted with DCM (300 mL×10). The organic layer was concentrated, and the residue was purified by column chromatography (from PE: EtOAc=2:1 to DCM: MeOH=10:1) to give a crude product (15.0 g). The crude product was further purified by prep-HPLC (NH$_3$.H$_2$O as additive) to give compound 439b as a white solid (5.0 g). LCMS (M+H$^+$): 208. $^1$H NMR: (400 MHz, CDCl$_3$) δ ppm 7.36-7.28 (m, 5H), 4.67 (d, J=15.1 Hz, 1H), 4.48 (d, J=15.1 Hz, 1H), 4.31-4.24 (m, 2H), 4.16 (br. s., 1H), 3.44 (dd, J=3.6, 12.2 Hz, 1H), 3.22 (d, J=11.5 Hz, 2H).

Step 2: To a solution of (5S)-3-benzyl-5-hydroxy-1,3-oxazinan-2-one (compound 439b, 450.0 mg, 2.17 mmol) in MeCN (10.0 mL) was added Ag$_2$O (2.5 g, 10.85 mmol) and MeI (3.0 g, 21.7 mmol). The mixture was stirred at 40° C. for 5 hours. The reaction was filtered and the filtrate was concentrated. The residue was purified by prep-TLC (EtOAc) to give compound 439c as a white solid (950 mg). LCMS (M+H$^+$): 222. $^1$H NMR: (400 MHz, MeOD) δ ppm 7.39-7.30 (m, 5H), 4.68 (d, J=15.3 Hz, 1H), 4.47-4.28 (m, 3H), 3.73 (br. s., 1H), 3.49 (dd, J=3.3, 12.8 Hz, 1H), 3.37-3.32 (m, 1H), 3.30 (s, 3H).

Step 3: NH$_3$ (gas) was bubbled through a solution of (5S)-3-benzyl-5-methoxy-1,3-oxazinan-2-one (compound 439c, 400.0 mg, 1.81 mmol) in THF (10.0 mL) at −78° C. for 5 minutes, and then Na (125.0 mg, 5.43 mmol) was added. The mixture was stirred at −78° C. for 15 minutes, and then poured into 10 mL aqueous NH$_4$Cl solution (3.0 g). The resulting mixture was concentrated and the residue was triturated with THF (20 mL). The suspension was filtered and the filtrate was concentrated to give compound 439d as a colorless oil (100 mg, crude). LCMS (M+H$^+$): 132. $^1$H NMR: (400 MHz, MeOD) δ ppm 4.29 (td, J=2.6, 11.9 Hz, 1H), 4.20 (d, J=11.8 Hz, 1H), 3.63 (br. s., 1H), 3.41-3.23 (m, 5H).

Preparation of (6S)-3-[(5S)-5-methoxy-2-oxo-1,3-oxazinan-3-yl]-6-methyl-N-(3,4,5trifluorophenyl)-6,7-dihydro-4H-pyrazolo[1,5-a]pyrazine-5-carboxamide (Example 439)

The title compound was prepared in analogy to Example 223 by using (5S)-5-methoxy-1,3-oxazinan-2-one (compound 439d) instead of pyrrolidin-2-one and phenyl N-(3,4,5-trifluorophenyl)carbamate (compound 233c) instead of phenyl N-[2-(difluoromethyl)-4-pyridyl]carbamate (compound 218c). Example 439 was obtained as a white solid (8 mg). LCMS (M+H$^+$): 440. $^1$H NMR (400 MHz, MeOD) δ ppm 7.62 (s, 1H), 7.39-7.23 (m, 2H), 4.99-4.96 (m, 2H), 4.62-4.39 (m, 3H), 4.30 (dd, J=4.1, 12.7 Hz, 1H), 4.16 (d, J=12.8 Hz, 1H), 4.03 (dd, 12.7 Hz, 1H), 3.90 (br. s., 1H), 3.68 (d, J=12.8 Hz, 1H), 3.50 (s, 3H), 1.27 (d, J=6.8 Hz, 3H).

Example 440

(6S)-3-[(5R)-5-methoxy-2-oxo-1,3-oxazinan-3-yl]-6-methyl-N-(3,4,5-trifluorophenyl)-6,7-dihydro-4H-pyrazolo[1,5-a]pyrazine-5-carboxamide

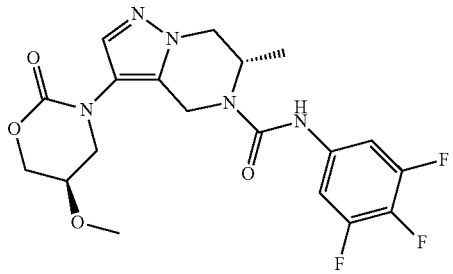 [SMILES: CO[C@H]1COC(=O)N(c2cnn3c2CN(C(=O)Nc2cc(F)c(F)c(F)c2)[C@@H](C)C3)C1]

The title compound was prepared in analogy to Example 439 by using (2R)-2-(chloromethyl)oxirane instead of (2S)-2-(chloromethyl)oxirane. Example 440 was obtained as a white solid (29 mg). LCMS (M+H$^+$): 440. $^1$H NMR (400 MHz, MeOD) δ ppm 7.60 (s, 1H), 7.31-7.23 (m, 2H), 5.05-4.90 (m, 2H), 4.60-4.43 (m, 2H), 4.37 (d, J=16.8 Hz, 1H), 4.27 (d, J=12.8 Hz, 1H), 4.14 (d, J=12.8 Hz, 1H), 3.98 (d, J=12.4 Hz, 1H), 3.88 (s., 1H), 3.69 (d, J=12.4 Hz, 1H), 3.49 (s, 3H), 1.23 (d, J=6.8 Hz, 3H).

Example 441

HBV Inhibition Assays

Cell Line and Culture Conditions:

HepG2.2.15 is a stably-transfected cell line containing the HBV genome. It is derived from the hepatoblastoma cell line Hep G2 (American Type Culture Collection, ATCC® HB-8065™) by the published procedures described in reference: MA Selles et al. Proc. Natl. Acad. Sci. USA 1987, 84, 1005-1009. The cell line was maintained in Dulbecco's modified Eagle's medium (DMEM)-F12 medium supplemented with 10% fetal bovine serum, 100 U/mL penicillin, 100 μg/mL streptomycin, and 0.5 mg/mL of G418.

Anti-HBV Activity In Vitro:

HepG2.2.15 cells were seeded into 96-well plates (3×10$^4$ cells in 100 μL media per well) and incubated overnight at 37° C. The test compounds were serially half-log diluted in DMSO, then diluted 100 times in culture media. 100 μL diluted compounds were added into the plates to reach 0.5% final concentration of DMSO in every well. Five days after compound treatment, culture supernatant was collected for further analysis.

For quantitative PCR detection of extracellular HBV DNA, culture supernatant was processed by Proteinase K digestion. After heat inactivation of the enzyme, the samples were subjected to HBV DNA quantification by qPCR. The effective compound concentration at which HBV replication is inhibited by 50% (EC$_{50}$) was determined.

The Examples of the present invention were tested in the above assays as described herein and found to have EC$_{50}$ of about 0.009 μM to about 3 μM in HepG2.2.15 assay. Particular compounds of the present invention were found to have EC50 below 0.1 μM as shown in Table 1 below.

TABLE 1

Activity of compounds of this invention in HepG2.2.15 assay

| Example No | EC$_{50}$ (μM) |
|---|---|
| 21 | 0.076 |
| 24 | 0.033 |
| 30 | 0.072 |
| 33 | 0.085 |
| 34 | 0.052 |
| 50 | 0.036 |
| 51 | 0.068 |
| 53 | 0.034 |
| 61 | 0.029 |
| 67 | 0.029 |
| 68 | 0.075 |
| 73 | 0.045 |
| 76 | 0.095 |
| 78 | 0.029 |
| 79 | 0.028 |
| 81 | 0.032 |
| 85 | 0.011 |
| 86 | 0.066 |
| 92 | 0.013 |
| 94 | 0.033 |
| 96 | 0.072 |
| 99 | 0.024 |
| 100 | 0.061 |
| 102 | 0.014 |
| 122 | 0.093 |
| 127 | 0.086 |
| 134 | 0.085 |
| 135 | 0.023 |
| 136 | 0.056 |
| 138 | 0.037 |
| 139 | 0.046 |
| 142 | 0.056 |
| 150 | 0.058 |
| 155 | 0.040 |
| 156 | 0.025 |
| 157 | 0.083 |
| 158 | 0.044 |
| 167 | 0.015 |
| 170 | 0.046 |
| 171 | 0.045 |
| 174 | 0.066 |
| 176 | 0.052 |
| 178 | 0.013 |
| 183 | 0.068 |
| 198 | 0.030 |
| 199 | 0.030 |
| 200 | 0.038 |
| 201 | 0.013 |
| 202 | 0.051 |
| 203 | 0.097 |
| 204 | 0.036 |
| 212 | 0.033 |
| 215 | 0.100 |
| 218 | 0.014 |
| 229 | 0.047 |
| 230 | 0.052 |
| 231 | 0.025 |
| 232 | 0.049 |
| 233 | 0.076 |
| 235 | 0.039 |
| 237 | 0.074 |
| 238 | 0.021 |
| 239 | 0.038 |
| 240 | 0.016 |
| 240-1 | 0.055 |
| 240-2 | 0.009 |
| 241 | 0.075 |
| 243 | 0.031 |
| 245 | 0.053 |
| 247 | 0.014 |
| 248 | 0.093 |
| 249 | 0.099 |
| 250 | 0.021 |
| 251 | 0.045 |

TABLE 1-continued
Activity of compounds of this invention in HepG2.2.15 assay
| Example No | EC$_{50}$ (μM) |
|---|---|
| 252 | 0.015 |
| 253 | 0.044 |
| 254 | 0.039 |
| 255 | 0.028 |
| 256 | 0.068 |
| 257 | 0.015 |
| 259 | 0.023 |
| 261 | 0.040 |
| 262 | 0.065 |
| 267 | 0.039 |
| 268 | 0.096 |
| 269 | 0.012 |
| 270 | 0.017 |
| 271 | 0.038 |
| 272 | 0.104 |
| 273 | 0.039 |
| 274 | 0.040 |
| 275 | 0.064 |
| 276 | 0.006 |
| 278 | 0.027 |
| 281 | 0.052 |
| 282 | 0.057 |
| 283 | 0.047 |
| 284 | 0.010 |
| 285 | 0.007 |
| 286 | 0.026 |
| 290 | 0.011 |
| 291 | 0.007 |
| 292 | 0.048 |
| 294 | 0.013 |
| 295 | 0.033 |
| 296 | 0.030 |
| 297 | 0.068 |
| 298 | 0.104 |
| 299 | 0.080 |
| 302 | 0.020 |
| 303 | 0.081 |
| 309 | 0.005 |
| 318 | 0.045 |
| 321 | 0.047 |
| 326 | 0.046 |
| 329 | 0.004 |
| 331 | 0.012 |
| 332 | 0.011 |
| 333 | 0.046 |
| 334 | 0.022 |
| 336 | 0.066 |
| 337 | 0.015 |
| 338 | 0.014 |
| 341 | 0.040 |
| 342 | 0.041 |
| 344 | 0.007 |
| 345 | 0.017 |
| 346 | 0.012 |
| 348 | 0.094 |
| 349 | 0.015 |
| 350 | 0.015 |
| 351 | 0.012 |
| 352 | 0.014 |
| 353 | 0.005 |
| 354 | 0.013 |
| 355 | 0.036 |
| 356 | 0.050 |
| 358 | 0.043 |
| 360 | 0.043 |
| 361 | 0.011 |
| 362 | 0.032 |
| 363 | 0.009 |
| 364 | 0.028 |
| 368 | 0.047 |
| 369 | 0.034 |
| 370 | 0.028 |
| 371 | 0.020 |
| 372 | 0.050 |
| 373 | 0.022 |
| 376 | 0.088 |
| 377 | 0.081 |
| 378 | 0.028 |
| 379 | 0.038 |
| 381 | 0.005 |
| 382 | 0.016 |
| 386 | 0.088 |
| 390 | 0.103 |
| 391 | 0.074 |
| 392 | 0.088 |
| 393 | 0.070 |
| 394 | 0.065 |
| 395 | 0.088 |
| 396 | 0.058 |
| 397 | 0.060 |
| 398 | 0.080 |
| 399 | 0.019 |
| 400 | 0.094 |
| 401 | 0.088 |
| 403 | 0.031 |
| 404 | 0.042 |
| 405 | 0.010 |
| 406 | 0.006 |
| 407 | 0.024 |
| 408 | 0.022 |
| 409 | 0.016 |
| 410 | 0.037 |
| 411 | 0.018 |
| 412 | 0.021 |
| 413 | 0.076 |
| 414 | 0.017 |
| 415 | 0.025 |
| 419 | 0.071 |
| 420-1 | 0.027 |
| 420-2 | 0.030 |
| 420-3 | 0.003 |
| 421 | 0.014 |
| 422 | 0.065 |
| 424 | 0.044 |
| 425 | 0.087 |
| 426 | 0.029 |
| 428 | 0.006 |
| 436 | 0.016 |
| 437 | 0.006 |
| 438-1 | 0.010 |
| 438-2 | 0.108 |
| 438-3 | 0.044 |
| 438-4 | 0.010 |
The invention claimed is:
1. A compound of formula (I),
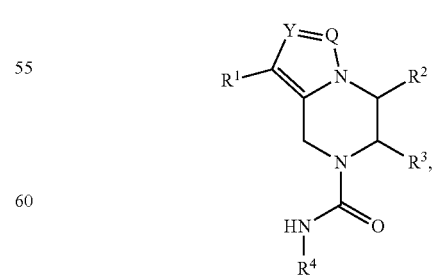
wherein
R$^1$ is heterocyclyl, said heterocyclyl being unsubstituted or substituted with one, two or three substituents independently selected from (C$_{1-6}$alkyl)$_2$aminocarbonyl, (C$_{1-6}$alkyl)$_2$morpholinylcarbonyl, C$_{1-6}$alkoxy, C$_{1-6}$alkoxyC$_{1-6}$alkyl, C$_{1-6}$alkoxycarbonyl, C$_{1-6}$alkyl, C$_{1-6}$alkyl(C$_{1-6}$alkylsulfonyl)amino, C$_{1-6}$alkylaminocarbonyl, C$_{1-6}$alkylcarbonyl, C$_{1-6}$alkylcarbonylamino, C$_{1-6}$alkylimidazolyl, C$_{1-6}$alkylmorpholinylcarbonyl, C$_{1-6}$alkyloxadiazolyl, C$_{1-6}$alkyloxazolyl, C$_{1-6}$alkylpyrazolyl, C$_{1-6}$alkylsulfonyl, C$_{1-6}$alkylsulfonylamino, C$_{1-6}$alkylsulfonylC$_{1-6}$alkyl, carbamoyl, cyano, dioxopyrrolidinyl, haloC$_{1-6}$alkyl, haloC$_{1-6}$alkyloxadiazolyl, halogen, halopiperidinylcarbonyl, halopyridinyl, halopyrimidinylamino, halopyrimidinyloxy, halopyrrolidinylcarbonyl, hydroxy, hydroxyazetidinylcarbonyl, hydroxyC$_{1-6}$alkyl, hydroxyC$_{1-6}$alkyl(C$_{1-6}$alkyl)aminocarbonyl, hydroxyC$_{1-6}$alkylaminocarbonyl, hydroxypyrrolidinylcarbonyl, morpholinylcarbonyl, oxadiazolyl, oxazolyl, oxazolylaminocarbonyl, oxazolyl(C$_{1-6}$alkyl)aminocarbonyl, oxazolylcarbonyl, oxazolylcarbonyl(C$_{1-6}$alkyl)amino, oxomorpholinyl, oxooxazolidinyl, oxopyrrolidinyl, phenyl, phenylcarbonyl, pyrazolylC$_{1-6}$alkyl, pyridinyl, pyrimidinyl, pyrimidinylamino, pyrimidinyl(C$_{1-6}$alkyl)amino, pyrimidinyloxy, pyrimidinyloxyC$_{1-6}$alkyl, pyrrolidinylcarbonyl and thiazolyl;

heteroaryl, said heteroaryl being unsubstituted or substituted with one, two or three substituents independently selected from halogen, cyano, C$_{1-6}$alkyl, haloC$_{1-6}$alkyl, hydroxy C$_{1-6}$alkyl and C$_{1-6}$alkoxyC$_{1-6}$alkyl;

phenyl, said phenyl being unsubstituted or substituted with one, two or three substituents independently selected from halogen, cyano, hydroxy, C$_{1-6}$alkyl, C$_{1-6}$alkoxy, C$_{3-7}$cycloalkyl, haloC$_{1-6}$alkoxy and haloC$_{1-6}$alkyl; or C$_{3-7}$cycloalkyl;

R$^2$ and R$^3$ are independently selected from hydrogen and C$_{1-6}$alkyl;

R$^4$ is heteroaryl, said heteroaryl being unsubstituted or substituted with one, two or three substituents independently selected from halogen, cyano, C$_{1-6}$alkyl, haloC$_{1-6}$ alkyl, C$_{1-6}$alkoxy, C$_{3-7}$cycloalkyl and (C$_{1-6}$alkyl)$_2$amino;

aryl, said aryl being unsubstituted or substituted with one, two or three substituents independently selected from halogen, cyano, C$_{3-7}$cycloalkyl, C$_{1-6}$alkyl, C$_{2-6}$alkynyl, C$_{1-6}$alkoxy, haloC$_{1-6}$alkyl and haloC$_{1-6}$alkoxy;

phenylC$_{1-6}$alkyl, said phenylC$_{1-6}$alkyl being unsubstituted or substituted with one, two or three halogens; or C$_{3-7}$cycloalkyl; and Y and Q are independently selected from CH and N;

or a pharmaceutically acceptable salt, enantiomer or diastereomer thereof.

2. A compound of formula (I) according to claim 1, wherein

R$^1$ is azabicyclo[3.1.0]hexanyl;

dioxopiperazinyl;

dioxopyrimidinyl;

dioxotetrahydropyrrolo[1,2-a]pyrazinyl;

morpholinyl, said morpholinyl being unsubstituted or substituted with one, two or three C$_{1-6}$alkyl;

oxaazabicyclo[3.2.1]octanyl;

oxoazabicyclo[3.1.0]hexanyl;

oxoazaspiro[2.4]heptanyl, said oxoazaspiro[2.4]heptanyl being unsubstituted or substituted with hydroxy;

oxoazaspiro[4.4]nonanyl;

oxoazaspiro[3.4]octanyl, said oxoazaspiro[3.4]octanyl being unsubstituted or substituted with hydroxy;

oxodiazaspiro[3.4]octanyl, said oxodiazaspiro[3.4]octanyl being unsubstituted or substituted with one, two or three substituents independently selected from C$_{1-6}$alkylcarbonyl, C$_{1-6}$alkoxycarbonyl, oxazolylcarbonyl and pyrimidinyl;

oxodihydropyrazolo[1,5-a]pyrazinyl;

oxohexahydropyrimidinyl;

oxoimidazolidinyl, said oxoimidazolidinyl being unsubstituted or substituted with one, two or three substituents independently selected from C$_{1-6}$alkyl, C$_{1-6}$alkylcarbonyl, C$_{1-6}$alkylsulfonyl, phenyl, phenylcarbonyl and pyrimidinyl;

oxoindolinyl;

oxoisoindolinyl;

oxomorpholinyl, said oxomorpholinyl being unsubstituted or substituted with one, two or three substituents independently selected from C$_{1-6}$alkyl and oxazolyl;

oxooxaazaspiro[2.4]heptanyl;

oxooxaazaspiro[3.4]octanyl;

oxooxaazaspiro[4.4]nonanyl;

oxooxaazaspiro[4.5]decanyl;

oxooxazinanyl, said oxooxazinanyl being unsubstituted or substituted with one, two or three substituents independently selected from C$_{1-6}$alkyl, C$_{1-6}$alkoxy and morpholinylcarbonyl;

oxooxazolidinyl, said oxooxazolidinyl being unsubstituted or substituted with one, two or three substituents independently selected from C$_{1-6}$alkyl, phenyl, pyridinyl, halopyridinyl, oxazolyl, C$_{1-6}$alkylimidazolyl and C$_{1-6}$alkyloxadiazolyl;

oxopiperidyl, said oxopiperidyl being unsubstituted or substituted with one, two or three substituents independently selected from C$_{1-6}$alkyl and hydroxy;

oxopyrrolidinyl, said oxopyrrolidinyl being unsubstituted or substituted with one, two or three substituents independently selected from (C$_{1-6}$alkyl)$_2$aminocarbonyl, (C$_{1-6}$alkyl)$_2$morpholinylcarbonyl, C$_{1-6}$alkoxy, C$_{1-6}$alkoxyC$_{1-6}$alkyl, C$_{1-6}$alkyl, C$_{1-6}$alkyl(C$_{1-6}$alkylsulfonyl)amino, C$_{1-6}$alkylaminocarbonyl, C$_{1-6}$alkylcarbonylamino, C$_{1-6}$alkylmorpholinylcarbonyl, C$_{1-6}$alkyloxadiazolyl, C$_{1-6}$alkyloxazolyl, C$_{1-6}$alkylpyrazolyl, C$_{1-6}$alkylsulfonyl, C$_{1-6}$alkylsulfonylamino, C$_{1-6}$alkylsulfonylC$_{1-6}$alkyl, cyano, dioxopyrrolidinyl, haloC$_{1-6}$alkyl, haloC$_{1-6}$alkyloxadiazolyl, halopiperidinylcarbonyl, halopyrimidinylamino, halopyrimidinyloxy, halopyrrolidinylcarbonyl, hydroxy, hydroxyazetidinylcarbonyl, hydroxyC$_{1-6}$alkyl, hydroxyC$_{1-6}$alkyl(C$_{1-6}$alkyl)aminocarbonyl, hydroxyC$_{1-6}$alkylaminocarbonyl, hydroxypyrrolidinylcarbonyl, morpholinylcarbonyl, oxadiazolyl, oxazolyl, oxazolylaminocarbonyl, oxazolyl(C$_{1-6}$alkyl)aminocarbonyl, oxazolylcarbonyl (C$_{1-6}$alkyl)amino, oxomorpholinyl, oxooxazolidinyl, oxopyrrolidinyl, phenyl, pyrazolylC$_{1-6}$alkyl, pyridinyl, pyrimidinyl, pyrimidinylamino, pyrimidinylC$_{1-6}$alkylamino, pyrimidinyloxy, pyrimidinyloxyC$_{1-6}$alkyl, pyrrolidinylcarbonyl and thiazolyl;

oxopyrrolo[3,2-c]pyridinyl;

oxopyrrolo[3,4-b]pyridinyl;

oxotetrahydrofuro[3,4-c]pyrrolyl;

oxotetrahydroimidazo[5,1-c][1,4]oxazinyl;

piperidinyl, said piperidinyl being unsubstituted or substituted with one, two or three substituents independently selected from halogen, hydroxy and C$_{1-6}$alkylcarbonyl;

pyrazolyl, said pyrazolyl being unsubstituted or substituted with one, two or three substituents independently selected from halogen, cyano, $C_{1-6}$alkyl, hydroxy$C_{1-6}$alkyl and $C_{1-6}$alkoxy$C_{1-6}$alkyl;

pyridinyl, said pyridinyl being unsubstituted or substituted with one, two or three substituents independently selected from halogen, cyano, $C_{1-6}$alkyl and halo$C_{1-6}$alkyl;

pyrimidinyl, said pyrimidinyl being unsubstituted or substituted with one, two or three substituents independently selected from halogen and $C_{1-6}$alkyl;

pyrrolidinyl, said pyrrolidinyl being unsubstituted or substituted with one, two or three substituents independently selected from halogen, cyano, hydroxy, $C_{1-6}$alkyl, halo$C_{1-6}$alkyl, $C_{1-6}$alkoxy and $C_{1-6}$alkoxy$C_{1-6}$alkyl;

tetrahydrofuranyl;

thiazolyl, said thiazolyl being unsubstituted or substituted with one, two or three substituents independently selected from halogen and halo$C_{1-6}$alkyl;

phenyl, said phenyl being unsubstituted or substituted with one, two or three substituents independently selected from halogen, cyano, hydroxy, $C_{3-7}$cycloalkyl, $C_{1-6}$alkyl, $C_{1-6}$alkoxy, halo$C_{1-6}$alkyl and halo$C_{1-6}$alkoxy; or $C_{3-7}$cycloalkyl;

$R^2$ and $R^3$ are independently selected from hydrogen and $C_{1-6}$alkyl;

$R^4$ is benzofuranyl;
benzothiophenyl;
benzoxazolyl;
indolyl;
$C_{1-6}$alkylbenzothiazolyl;

pyridinyl, said pyridinyl being unsubstituted or substituted with one, two or three substituents independently selected from halogen, cyano, $C_{1-6}$alkyl, $C_{3-7}$cycloalkyl, $C_{1-6}$alkoxy, halo$C_{1-6}$alkyl and $(C_{1-6}$alkyl$)_2$amino;

bicyclo[4.2.0]octa-1(6),2,4-trienyl;
indanyl;

phenyl, said phenyl being unsubstituted or substituted with one, two or three substituents independently selected from halogen, cyano, $C_{3-7}$cycloalkyl, $C_{1-6}$alkyl, $C_{2-6}$alkynyl, $C_{1-6}$alkoxy, halo$C_{1-6}$alkyl and halo$C_{1-6}$alkoxy;

phenyl$C_{1-6}$alkyl, said phenyl$C_{1-6}$alkyl being unsubstituted or substituted with one, two or three halogens; or $C_{3-7}$cycloalkyl; and Y and Q are independently selected from CH and N;

or a pharmaceutically acceptable salt, enantiomer or diastereomer thereof.

3. A compound of formula (I) according to claim 1, wherein $R^1$ is pyrazolyl substituted by halogen, cyano, $C_{1-6}$alkyl, hydroxy$C_{1-6}$alkyl or $C_{1-6}$alkoxy$C_{1-6}$alkyl;

pyridinyl, said pyridinyl being unsubstituted or substituted with one or two substituents independently selected from halogen, cyano, $C_{1-6}$alkyl and halo$C_{1-6}$alkyl;

pyrimidinyl substituted with one or two substituents independently selected from halogen and $C_{1-6}$alkyl;

thiazolyl, said thiazolyl being unsubstituted or substituted by halogen or halo$C_{1-6}$alkyl; or phenyl, said phenyl being unsubstituted or substituted with one or two substituents independently selected from halogen, cyano, hydroxy, $C_{3-7}$cycloalkyl, $C_{1-6}$alkyl, $C_{1-6}$alkoxy, halo$C_{1-6}$alkyl and halo$C_{1-6}$alkoxy;

$R^2$ and $R^3$ are independently selected from hydrogen and $C_{1-6}$alkyl with the proviso that $R^2$ and $R^3$ are not $C_{1-6}$alkyl simultaneously;

$R^4$ is benzothiophenyl;
benzoxazolyl;
indolyl;
benzothiazolyl substituted by $C_{1-6}$alkyl;

pyridinyl, said pyridinyl being unsubstituted or substituted with one or two substituents independently selected from halogen, cyano, $C_{1-6}$alkyl, $C_{3-7}$cycloalkyl, $C_{1-6}$alkoxy, halo$C_{1-6}$alkyl and $(C_{1-6}$alkyl$)_2$amino;

bicyclo[4.2.0]octa-1(6),2,4-trienyl;

phenyl, said phenyl being unsubstituted or substituted with one, two or three substituents independently selected from halogen, cyano, $C_{3-7}$cycloalkyl, $C_{1-6}$alkyl, $C_{2-6}$alkynyl, $C_{1-6}$alkoxy, halo$C_{1-6}$alkyl and halo$C_{1-6}$alkoxy;

phenyl$C_{1-6}$alkyl, said phenyl$C_{1-6}$alkyl being unsubstituted or substituted with one or two halogens; or $C_{3-7}$cycloalkyl; and Y and Q are independently selected from CH and N;

or a pharmaceutically acceptable salt, enantiomer or diastereomer thereof.

4. A compound of formula (I) according to claim 3, wherein $R^1$ is fluorophenyl, phenyl, chlorophenyl, trifluoromethylphenyl, cyanophenyl, methoxyphenyl, methylphenyl, difluorophenyl, fluorochlorophenyl, difluoromethylphenyl, methylfluorophenyl, cyclopropylphenyl, hydroxyphenyl, trifluoromethoxyphenyl, bromophenyl, methylpyrazolyl, cyanopyrazolyl, fluoropyrazolyl, hydroxymethylpyrazolyl, methoxymethylpyrazolyl, trifluoromethylpyridinyl, cyanopyridinyl, methylfluoropyridinyl, pyridinyl, chloropyridinyl, fluoropyridinyl, fluorochloropyridinyl, fluoropyrimidinyl, methylfluoropyrimidinyl, thiazolyl, trifluoromethylthiazolyl or chlorothiazolyl;

$R^2$ and $R^3$ are independently selected from hydrogen and methyl with the proviso that $R^2$ and $R^3$ are not methyl simultaneously;

$R^4$ is phenyl, trifluoromethylphenyl, fluorochlorophenyl, fluorophenyl, chlorophenyl, cyanophenyl, pyridinyl, methylfluoropyridinyl, fluorotrifluoromethylphenyl, trifluorophenyl, fluorochlorobenzyl, dichlorobenzyl, methylchloropyridinyl, methylbenzothiazolyl, benzothiophenyl, trifluoromethylpyridinyl, difluorophenyl, fluorocyanophenyl, indolyl, methylfluorophenyl, chloropyridinyl, cyanopyridinyl, chloromethoxypyridinyl, methyltrifluoromethylphenyl, chlorotrifluoromethylphenyl, chlorocyanophenyl, ethylphenyl, ethynylphenyl, isopropylphenyl, methoxyphenyl, ethynylfluorophenyl, dimethylpyridinyl, fluorobromophenyl, difluoromethoxyphenyl, fluorotrifluoromethoxyphenyl, difluoromethylphenyl, methylphenyl, difluorocyanophenyl, fluorochloropyridinyl, cyclopropylphenyl, methyldifluorophenyl, difluorochlorophenyl, cyclopropyldifluorophenyl, difluoroethylphenyl, cyclopropylfluorophenyl, methoxydifluorophenyl, benzyl, fluoropyridinyl, benzoxazolyl, methylpyridinyl, difluoropyridinyl, cyclopentyl, cyclohexyl, bicyclo[4.2.0]octa-1(6),2,4-trienyl, bromopyridinyl, cyclopropylpyridinyl, dimethylaminopyridinyl or difluoromethylpyridinyl; and Y and Q are independently selected from CH and N;

or a pharmaceutically acceptable salt, enantiomer or diastereomer thereof.

5. A compound of formula (I) according to claim 3, wherein $R^1$ is phenyl, said phenyl being unsubstituted or substituted with one, two or three substituents independently selected from halogen, cyano, hydroxy, $C_{3-7}$cycloalkyl, $C_{1-6}$alkyl, $C_{1-6}$alkoxy, halo$C_{1-6}$alkyl and halo$C_{1-6}$alkoxy; or a pharmaceutically acceptable salt, enantiomer or diastereomer thereof.

6. A compound of formula (I) according to claim 5, wherein $R^1$ is phenyl, bromophenyl, chlorophenyl, cyanophenyl, cyclopropylphenyl, difluorophenyl, difluoromethylphenyl, fluorophenyl, fluorochlorophenyl, fluoromethylphenyl, hydroxyphenyl, methoxyphenyl, methylphenyl, trifluoromethoxyphenyl or trifluoromethylphenyl; or a pharmaceutically acceptable salt, enantiomer or diastereomer thereof.

7. A compound of formula (I) according to claim 3, wherein $R^4$ is phenyl, said phenyl being unsubstituted or substituted with one, two or three substituents independently selected from halogen, cyano, $C_{3-7}$cycloalkyl, $C_{1-6}$alkyl, $C_{2-6}$alkynyl, $C_{1-6}$alkoxy, halo$C_{1-6}$alkyl and halo$C_{1-6}$alkoxy; or a pharmaceutically acceptable salt, enantiomer or diastereomer thereof.

8. A compound of formula (I) according to claim 7, wherein $R^4$ is phenyl, chlorophenyl, chlorocyanophenyl, chlorotrifluoromethylphenyl, cyanophenyl, cyclopropylphenyl, difluorophenyl, difluoroethylphenyl, difluoromethoxyphenyl, difluoromethylphenyl, ethylphenyl, ethynylphenyl, fluorophenyl, fluorobromophenyl, fluorochlorophenyl, fluorocyanophenyl, fluorocyclopropylphenyl, fluoroethynylphenyl, difluorochlorophenyl, difluorocyanophenyl, difluorocyclopropylphenyl, methoxydifluorophenyl, methyldifluorophenyl, methylfluorophenyl, fluorotrifluoromethoxyphenyl, fluorotrifluoromethylphenyl, isopropylphenyl, methoxyphenyl, methylphenyl, methyltrifluoromethylphenyl, trifluorophenyl or trifluoromethylphenyl; or a pharmaceutically acceptable salt, enantiomer or diastereomer thereof.

9. A compound of formula (I) according to claim 3, wherein
$R^1$ is pyrazolyl substituted by halogen or hydroxy$C_{1-6}$alkyl;
pyridinyl substituted by halogen;
pyrimidinyl substituted by halogen; or
phenyl substituted once or twice by halogen;
$R^2$ is H;
$R^3$ is H or $C_{1-6}$alkyl;
$R^4$ is pyridinyl substituted by halo$C_{1-6}$alkyl; or
phenyl substituted with one, two or three substituents independently selected from halogen and cyano; and
Y and Q are independently selected from CH and N, with proviso that Y and Q are not CH simultaneously;
or a pharmaceutically acceptable salt, enantiomer or diastereomer thereof.

10. A compound of formula (I) according to claim 9, wherein
$R^1$ is fluoropyrazolyl, hydroxymethylpyrazolyl, fluoropyridinyl, fluoropyrimidinyl, fluorophenyl or difluorophenyl;
$R^2$ is H;
$R^3$ is H or methyl;
$R^4$ is difluoromethylpyridinyl, fluorochlorophenyl, fluorocyanophenyl or trifluorophenyl; and
Y and Q are independently selected from CH and N, with proviso that Y and Q are not CH simultaneously;
or a pharmaceutically acceptable salt, enantiomer or diastereomer thereof.

11. A compound according to claim 9, selected from
N-(3-cyano-4-fluoro-phenyl)-3-(2,4-difluorophenyl)-6-methyl-6,7-dihydro-4H-pyrazolo[1,5-a]pyrazine-5-carboxamide;
N-(3-chloro-4-fluoro-phenyl)-3-(2,4-difluorophenyl)-6-methyl-6,7-dihydro-4H-pyrazolo[1,5-a]pyrazine-5-carboxamide;
N-(3-chloro-4-fluoro-phenyl)-3-(5-fluoro-2-pyridyl)-6-methyl-6,7-dihydro-4H-pyrazolo[1,5-a]pyrazine-5-carboxamide;
3-(5-fluoro-2-pyridyl)-6-methyl-N-(3,4,5-trifluorophenyl)-6,7-dihydro-4H-pyrazolo[1,5-a]pyrazine-5-carboxamide;
(6S)-N-(3-chloro-4-fluoro-phenyl)-3-(4-fluorophenyl)-6-methyl-6,7-dihydro-4H-pyrazolo[1,5-a]pyrazine-5-carboxamide;
N-(3-chloro-4-fluoro-phenyl)-1-(2,4-difluorophenyl)-6,8-dihydro-5H-imidazo[1,5-a]pyrazine-7-carboxamide;
1-(2,4-difluorophenyl)-N-(3,4,5-trifluorophenyl)-6,8-dihydro-5H-imidazo[1,5-a]pyrazine-7-carboxamide;
N-(3-chloro-4-fluoro-phenyl)-3-(2,4-difluorophenyl)-6,7-dihydro-4H-triazolo[1,5-a]pyrazine-5-carboxamide;
N-(3-chloro-4-fluoro-phenyl)-3-(4-fluoropyrazol-1-yl)-6-methyl-6,7-dihydro-4H-pyrazolo[1,5-a]pyrazine-5-carboxamide;
N-[2-(difluoromethyl)-4-pyridyl]-3-(2,4-difluorophenyl)-6-methyl-6,7-dihydro-4H-pyrazolo[1,5-a]pyrazine-5-carboxamide;
(6S)-3-(5-fluoropyrimidin-2-yl)-6-methyl-N-(3,4,5-trifluorophenyl)-6,7-dihydro-4H-pyrazolo[1,5-a]pyrazine-5-carboxamide; and
(6S)-3-[4-(hydroxymethyl)pyrazol-1-yl]-6-methyl-N-(3,4,5-trifluorophenyl)-6,7-dihydro-4H-pyrazolo[1,5-a]pyrazine-5-carboxamide;
or a pharmaceutically acceptable salt, enantiomer or diastereomer thereof.

12. A compound of formula (I) according to claim 1, wherein
$R^1$ is azabicyclo[3.1.0]hexanyl;
morpholinyl, said morpholinyl being unsubstituted or substituted twice by $C_{1-6}$alkyl;
oxaazabicyclo[3.2.1]octanyl;
piperidinyl, said piperidinyl being unsubstituted or substituted with one or two substituents independently selected from halogen, hydroxy and $C_{1-6}$alkylcarbonyl;
pyrrolidinyl, said pyrrolidinyl being unsubstituted or substituted with one or two substituents independently selected from halogen, cyano, hydroxy, $C_{1-6}$alkyl, halo$C_{1-6}$alkyl, $C_{1-6}$alkoxy and $C_{1-6}$alkoxy$C_{1-6}$alkyl;
tetrahydrofuranyl; or
$C_{3-7}$cycloalkyl;
$R^2$ is H;
$R^3$ is H or $C_{1-6}$alkyl;
$R^4$ is benzofuranyl;
pyridinyl, said pyridinyl being substituted with one or two substituents independently selected from halogen and halo$C_{1-6}$alkyl;
indanyl;
phenyl, said phenyl being unsubstituted or substituted with one, two or three substituents independently selected from halogen, cyano and $C_{1-6}$alkyl; or
phenyl$C_{1-6}$alkyl; and
Y is CH when Q is N; or Y is N when Q is CH;
or a pharmaceutically acceptable salt, enantiomer or diastereomer thereof.

13. A compound of formula (I) according to claim 12, wherein

R¹ is azabicyclo[3.1.0]hexanyl, cyclohexyl, cyclopentyl, morpholinyl, dimethylmorpholinyl, oxaazabicyclo[3.2.1]octanyl, piperidinyl, difluoropiperidinyl, hydroxypiperidinyl, acetylpiperidinyl, pyrrolidinyl, methylpyrrolidinyl, methoxymethylpyrrolidinyl, methoxypyrrolidinyl, trifluoromethylpyrrolidinyl, cyanopyrrolidinyl, methylhydroxypyrrolidinyl, difluoropyrrolidinyl or tetrahydrofuranyl;

R² is H;

R³ is H or methyl;

R⁴ is benzofuranyl, indanyl, benzyl, phenyl, fluorochlorophenyl, fluorocyanophenyl, trifluorophenyl, methyldifluorophenyl, chloropyridinyl, fluorochloropyridinyl or trifluoromethylpyridinyl; and Y is CH when Q is N; or Y is N when Q is CH;

or a pharmaceutically acceptable salt, enantiomer or diastereomer thereof.

14. A compound of formula (I) according to claim 1, wherein

R¹ is dioxopiperazinyl;
dioxopyrimidinyl;
dioxotetrahydropyrrolo[1,2-a]pyrazinyl;
oxoazabicyclo[3.1.0]hexanyl;
oxoazaspiro[2.4]heptanyl, said oxoazaspiro[2.4]heptanyl being unsubstituted or substituted with hydroxy;
oxoazaspiro[4.4]nonanyl;
oxoazaspiro[3.4]octanyl, said oxoazaspiro[3.4]octanyl being unsubstituted or substituted with hydroxy;
oxodiazaspiro[3.4]octanyl, said oxodiazaspiro[3.4]octanyl being substituted by C₁₋₆alkylcarbonyl, C₁₋₆alkoxycarbonyl, oxazolylcarbonyl or pyrimidinyl;
oxodihydropyrazolo[1,5-a]pyrazinyl;
oxohexahydropyrimidinyl;
oxoimidazolidinyl, said oxoimidazolidinyl being unsubstituted or substituted with one or two substituents independently selected from C₁₋₆alkyl, C₁₋₆alkylcarbonyl, C₁₋₆alkylsulfonyl, phenyl, phenylcarbonyl and pyrimidinyl;
oxoindolinyl;
oxomorpholinyl, said oxomorpholinyl being unsubstituted or substituted with one or two substituents independently selected from C₁₋₆alkyl and oxazolyl;
oxooxaazaspiro[2.4]heptanyl;
oxooxaazaspiro[3.4]octanyl;
oxooxaazaspiro[4.4]nonanyl;
oxooxaazaspiro[4.5]decanyl;
oxooxazinanyl, said oxooxazinanyl being unsubstituted or substituted with one or two substituents independently selected from C₁₋₆alkyl, C₁₋₆alkoxy and morpholinylcarbonyl;
oxooxazolidinyl, said oxooxazolidinyl being unsubstituted or substituted with one or two substituents independently selected from C₁₋₆alkyl, phenyl, pyridinyl, halopyridinyl, oxazolyl, C₁₋₆alkylimidazolyl and C₁₋₆alkyloxadiazolyl;
oxopiperidyl substituted by C₁₋₆alkyl or hydroxy;
oxopyrrolidinyl, said oxopyrrolidinyl being unsubstituted or substituted with one, two or three substituents independently selected from (C₁₋₆alkyl)₂aminocarbonyl, (C₁₋₆alkyl)₂morpholinylcarbonyl, C₁₋₆alkoxy, C₁₋₆alkoxyC₁₋₆alkyl, C₁₋₆alkyl, C₁₋₆alkyl(C₁₋₆alkylsulfonyl)amino, C₁₋₆alkylaminocarbonyl, C₁₋₆alkylcarbonylamino, C₁₋₆alkylmorpholinylcarbonyl, C₁₋₆alkyloxadiazolyl, C₁₋₆alkyloxazolyl, C₁₋₆alkylpyrazolyl, C₁₋₆alkylsulfonyl, C₁₋₆alkylsulfonylamino, C₁₋₆alkylsulfonylC₁₋₆alkyl, cyano, dioxopyrrolidinyl, haloC₁₋₆alkyl, haloC₁₋₆alkyloxadiazolyl, halopiperidinylcarbonyl, halopyrimidinylamino, halopyrimidinyloxy, halopyrrolidinylcarbonyl, hydroxy, hydroxyazetidinylcarbonyl, hydroxyC₁₋₆alkyl, hydroxyC₁₋₆alkyl, hydroxyC₁₋₆alkyl(C₁₋₆alkyl)aminocarbonyl, hydroxyC₁₋₆alkylaminocarbonyl, hydroxypyrrolidinylcarbonyl, morpholinylcarbonyl, oxadiazolyl, oxazolyl, oxazolylaminocarbonyl, oxazolyl(C₁₋₆alkyl)aminocarbonyl, oxazolylcarbonyl(C₁₋₆alkyl)amino, oxomorpholinyl, oxooxazolidinyl, oxopyrrolidinyl, phenyl, pyrazolylC₁₋₆alkyl, pyridinyl, pyrimidinyl, pyrimidinylamino, pyrimidinyl(C₁₋₆alkyl)amino, pyrimidinyloxy, pyrimidinyloxyC₁₋₆alkyl, pyrrolidinylcarbonyl and thiazolyl;
oxopyrrolo[3,2-c]pyridinyl;
oxopyrrolo[3,4-b]pyridinyl;
oxotetrahydrofuro[3,4-c]pyrrolyl; or
oxotetrahydroimidazo[5,1-c][1,4]oxazinyl;

R² and R³ are independently selected from hydrogen and C₁₋₆alkyl with the proviso that R² is not C₁₋₆alkyl when R³ is H;

R⁴ is pyridinyl substituted with one or two substituents independently selected from halogen and haloC₁₋₆alkyl; or phenyl substituted with one, two or three substituents independently selected from halogen and haloC₁₋₆alkyl;

Y is CH; and

Q is N;

or a pharmaceutically acceptable salt, enantiomer or diastereomer thereof.

15. A compound of formula (I) according to claim 14, wherein

R¹ is dioxopiperazinyl, dioxopyrimidinyl, dioxotetrahydropyrrolo[1,2-a]pyrazinyl, oxoazabicyclo[3.1.0]hexanyl, oxoazaspiro[2.4]heptanyl, hydroxy oxoazaspiro[2.4]heptanyl, oxoazaspiro[4.4]nonanyl, oxoazaspiro[3.4]octanyl, hydroxyoxoazaspiro[3.4]octanyl, acetyloxodiazaspiro[3.4]octanyl, methoxycarbonyloxodiazaspiro[3.4]octanyl, ethoxycarbonyloxodiazaspiro[3.4]octanyl, oxazolylcarbonyloxodiazaspiro[3.4]octanyl, pyrimidinyloxodiazaspiro[3.4]octanyl, oxodihydropyrazolo[1,5-a]pyrazinyl, oxohexahydropyrimidinyl, oxoimidazolidinyl, acetyloxoimidazolidinyl, benzoyloxoimidazolidinyl, dimethyloxoimidazolidinyl, methyloxoimidazolidinyl, methylsulfonyloxoimidazolidinyl, phenyloxoimidazolidinyl, pyrimidinyloxoimidazolidinyl, oxoindolinyl, oxomorpholinyl, methyloxomorpholinyl, dimethyloxomorpholinyl, oxazolyloxomorpholinyl, oxooxaazaspiro[4.5]decanyl, oxooxaazaspiro[4.4]nonanyl, oxooxaazaspiro[2.4]heptanyl, oxooxaazaspiro[3.4]octanyl, oxooxazinanyl, methyloxooxazinanyl, dimethyloxooxazinanyl, methoxyoxooxazinanyl, morpholinylcarbonyl(methyl)oxooxazinanyl, oxooxazolidinyl, dimethyloxooxazolidinyl, chloropyridinyloxooxazolidinyl, fluoropyridinyloxooxazolidinyl, methyloxooxazolidinyl, methylimidazolyloxooxazolidinyl, methyloxadiazolyloxooxazolidinyl, oxazolyloxooxazolidinyl, phenyloxooxazolidinyl, pyridinyloxooxazolidinyl, hydroxyoxopiperidyl, methyloxopiperidyl, oxopyrrolidinyl, acetylaminooxopyrrolidinyl, cyanooxopyrrolidinyl, difluoropiperidinylcarbonyl(methyl)oxopyrrolidinyl, difluoropyrrolidinylcarbonyloxopyrrolidinyl, difluoropyrrolidinylcarbonyl(methyl)oxopyrrolidinyl, dihydroxyoxopyrrolidinyl, dimethyloxopyrrolidinyl, dimethylaminocarbonyloxopyrrolidinyl, dimethylmorpholinylcarbonyloxopyrrolidinyl, dioxopyrrolidinyloxopyrrolidinyl, ethyloxopyrrolidinyl, fluoropyrimidinylaminooxopyrrolidinyl, fluoropyrimidinyloxyoxopyrrolidinyl, hydroxyoxopyrrolidinyl, hydroxyazetidinylcarbonyloxopyrrolidinyl, hydroxyethyl(methyl)aminocarbonyloxopyrrolidinyl, hydroxy(dimethyl)oxopyrrolidinyl, hydroxydimethylethylaminooxopyrrolidinyl, hydroxymethyloxopyrrolidinyl, hydroxy(methyl)cyanooxopyrrolidinyl, hydroxymethyl(cyano)oxopyrrolidinyl, hydroxymethylethyloxopyrrolidinyl, hydroxypyrrolidinylcarbonyloxopyrrolidinyl, methoxyoxopyrrolidinyl, methoxymethyloxopyrrolidinyl, methyloxopyrrolidinyl, methyl(methylsulfonyl)aminooxopyrrolidinyl, methylaminocarbonyloxopyrrolidinyl, methylcyanooxopyrrolidinyl, methyl(hydroxymethyl)oxopyrrolidinyl, methylmorpholinylcarbonyloxopyrrolidinyl, methyloxadiazolyloxopyrrolidinyl, methyloxadiazolyl(methyl)oxopyrrolidinyl, methyloxazolyloxopyrrolidinyl, methylpyrazolyloxopyrrolidinyl, methylsulfonyloxopyrrolidinyl, methylsulfonylaminooxopyrrolidinyl, methylsulfonylmethyloxopyrrolidinyl, morpholinylcarbonyloxopyrrolidinyl, morpholinylcarbonyl(methyl)oxopyrrolidinyl, oxadiazolyloxopyrrolidinyl, oxadiazolyl(methyl)oxopyrrolidinyl, oxazolyloxopyrrolidinyl, oxazolylaminocarbonyloxopyrrolidinyl, oxazolylcarbonyl(methyl)aminooxopyrrolidinyl, oxazolyl(methyl)aminocarbonyloxopyrrolidinyl, oxomorpholinyloxopyrrolidinyl, oxooxazolidinyloxopyrrolidinyl, oxopyrrolidinyloxopyrrolidinyl, phenyloxopyrrolidinyl, phenyl(hydroxy)oxopyrrolidinyl, pyrazolylmethyloxopyrrolidinyl, pyridinyloxopyrrolidinyl, pyrimidinyloxopyrrolidinyl, pyrimidinylaminooxopyrrolidinyl, pyrimidinyl(methyl)aminooxopyrrolidinyl, pyrimidinyloxyoxopyrrolidinyl, pyrimidinyloxy(hydroxy)oxopyrrolidinyl, pyrimidinyloxy(hydroxy)(methyl)oxopyrrolidinyl, pyrimidinyloxymethyloxopyrrolidinyl, pyrrolidinylcarbonyloxopyrrolidinyl, thiazolyloxopyrrolidinyl, trifluoromethyloxopyrrolidinyl, trifluoromethyloxadiazolyloxopyrrolidinyl, oxotetrahydrofuro[3,4-c]pyrrolyl, oxotetrahydroimidazo[5,1-c][1,4]oxazinyl, oxopyrrolo[3,4-b]pyridinyl or oxopyrrolo[3,2-c]pyridinyl;

$R^2$ and $R^3$ are independently selected from hydrogen and methyl with the proviso that $R^2$ is not methyl when $R^3$ is H;

$R^4$ is chloropyridinyl, difluoromethylpyridinyl, fluorochloropyridinyl, fluorodifluoromethylpyridinyl, trifluoromethylpyridinyl, difluorochlorophenyl, difluorodifluoromethylphenyl, fluorochlorophenyl, fluorotrifluoromethylphenyl or trifluorophenyl;

Y is CH; and

Q is N;

or a pharmaceutically acceptable salt, enantiomer or diastereomer thereof.

16. A compound of formula (I) according to claim 14, wherein $R^1$ is
oxoazabicyclo[3.1.0]hexanyl;
oxodiazaspiro[3.4]octanyl substituted by $C_{1-6}$alkoxycarbonyl or pyrimidinyl;
oxoimidazolidinyl;
oxoindolinyl;
oxomorpholinyl, said oxomorpholinyl being unsubstituted or substituted once or twice by $C_{1-6}$alkyl;
oxooxaazaspiro[2.4]heptanyl;
oxooxaazaspiro[4.5]decanyl;
oxooxazinanyl, said oxooxazinanyl being unsubstituted or substituted once or twice by $C_{1-6}$alkyl;
oxooxazolidinyl, said oxooxazolidinyl being unsubstituted or substituted twice by $C_{1-6}$alkyl; or
oxopyrrolidinyl said oxopyrrolidinyl being unsubstituted or substituted with one or two substituents independently selected from $(C_{1-6}alkyl)_2$aminocarbonyl, $C_{1-6}$alkyl, $C_{1-6}$alkoxy, $C_{1-6}$alkyloxadiazolyl, cyano, halopyrimidinyloxy, halo$C_{1-6}$alkyl, hydroxy, hydroxy$C_{1-6}$alkyl, morpholinylcarbonyl, oxadiazolyl, pyrimidinylamino, pyrimidinyloxy and pyrrolidinylcarbonyl;

or a pharmaceutically acceptable salt, enantiomer or diastereomer thereof.

17. A compound of formula (I) according to claim 14, wherein $R^1$ is oxoazabicyclo[3.1.0]hexanyl, methoxycarbonyloxodiazaspiro[3.4]octanyl, ethoxycarbonyloxodiazaspiro[3.4]octanyl, pyrimidinyloxodiazaspiro[3.4]octanyl, oxoimidazolidinyl, oxoindolinyl, oxomorpholinyl, dimethyloxomorpholinyl, oxooxaazaspiro[4.5]decanyl, oxooxaazaspiro[2.4]heptanyl, oxooxazinanyl, methyloxooxazinanyl, dimethyloxooxazinanyl, oxooxazolidinyl, dimethyloxooxazolidinyl, oxopyrrolidinyl, cyanooxopyrrolidinyl, hydroxyoxopyrrolidinyl, methoxyoxopyrrolidinyl, trifluoromethyloxopyrrolidinyl, pyrimidinylaminooxopyrrolidinyl, oxadiazolyloxopyrrolidinyl, methyloxadiazolyloxopyrrolidinyl, hydroxymethylcyanooxopyrrolidinyl, methylcyanooxopyrrolidinyl, methyl(hydroxymethyl)oxopyrrolidinyl, morpholinylcarbonyloxopyrrolidinyl, pyrimidinyloxyoxopyrrolidinyl, pyrimidinyloxy(hydroxy)oxopyrrolidinyl, fluoropyrimidinyloxyoxopyrrolidinyl, dimethylaminocarbonyloxopyrrolidinyl or pyrrolidinylcarbonyloxopyrrolidinyl; or a pharmaceutically acceptable salt, enantiomer or diastereomer thereof.

18. A compound of formula (I) according to claim 14, wherein $R^4$ is pyridinyl substituted by halo$C_{1-6}$alkyl; or phenyl substituted with two or three substituents independently selected from halogen and halo$C_{1-6}$alkyl; or a pharmaceutically acceptable salt, enantiomer or diastereomer thereof.

19. A compound of formula (I) according to claim 14, wherein $R^4$ is difluoromethylpyridinyl, fluorochlorophenyl, difluorodifluoromethylphenyl or trifluorophenyl; or a pharmaceutically acceptable salt, enantiomer or diastereomer thereof.

20. A compound of formula (I) according to claim 14, wherein
$R^1$ is oxoazabicyclo[3.1.0]hexanyl;
oxodiazaspiro[3.4]octanyl substituted with $C_{1-6}$alkoxycarbonyl or pyrimidinyl;
oxoimidazolidinyl;
oxoindolinyl;
oxomorpholinyl, said oxomorpholinyl being unsubstituted or substituted once or twice by $C_{1-6}$alkyl;
oxooxaazaspiro[2.4]heptanyl;
oxooxaazaspiro[4.5]decanyl;
oxooxazinanyl, said oxooxazinanyl being unsubstituted or substituted once or twice by $C_{1-6}$alkyl;
oxooxazolidinyl, said oxooxazolidinyl being unsubstituted or substituted once or twice by $C_{1-6}$alkyl; or
oxopyrrolidinyl said oxopyrrolidinyl being unsubstituted or substituted with one or two substituents independently selected from $(C_{1-6}alkyl)_2$aminocarbonyl, $C_{1-6}$alkyl, $C_{1-6}$alkoxy, $C_{1-6}$alkyloxadiazolyl, cyano, halopyrimidinyloxy, halo$C_{1-6}$alkyl, hydroxy, hydroxyC$_{1-6}$alkyl, morpholinylcarbonyl, oxadiazolyl, pyrimidinylamino, pyrimidinyloxy and pyrrolidinylcarbonyl;

R$^2$ is H;

R$^3$ is H or C$_{1-6}$alkyl;

R$^4$ is pyridinyl substituted by haloC$_{1-6}$alkyl; or phenyl substituted with two or three substituents independently selected from halogen and haloC$_{1-6}$alkyl;

Y is CH; and

Q is N;

or a pharmaceutically acceptable salt, enantiomer or diastereomer thereof.

21. A compound of formula (I) according to claim 14, wherein

R$^1$ is oxoazabicyclo[3.1.0]hexanyl, methoxycarbonyloxodiazaspiro[3.4]octanyl, ethoxycarbonyloxodiazaspiro[3.4]octanyl, pyrimidinyloxodiazaspiro[3.4]octanyl, oxoimidazolidinyl, oxoindolinyl, oxomorpholinyl, dimethyloxomorpholinyl, oxooxaazaspiro[4.5]decanyl, oxooxaazaspiro[2.4]heptanyl, oxooxazinanyl, methyloxooxazinanyl, dimethyloxooxazinanyl, oxooxazolidinyl, dimethyloxooxazolidinyl, oxopyrrolidinyl, cyanooxopyrrolidinyl, hydroxyoxopyrrolidinyl, methoxyoxopyrrolidinyl, trifluoromethyloxopyrrolidinyl, pyrimidinylaminooxopyrrolidinyl, oxadiazolyloxopyrrolidinyl, methyloxadiazolyloxopyrrolidinyl, hydroxymethylcyanooxopyrrolidinyl, methylcyanooxopyrrolidinyl, methyl(hydroxymethyl)oxopyrrolidinyl, morpholinylcarbonyloxopyrrolidinyl, pyrimidinyloxyoxopyrrolidinyl, pyrimidinyloxy(hydroxy)oxopyrrolidinyl, fluoropyrimidinyloxyoxopyrrolidinyl, dimethylaminocarbonyloxopyrrolidinyl or pyrrolidinylcarbonyloxopyrrolidinyl;

R$^2$ is H;

R$^3$ is H or methyl;

R$^4$ is difluoromethylpyridinyl, fluorochlorophenyl, difluorodifluoromethylphenyl or trifluorophenyl;

Y is CH; and

Q is N;

or a pharmaceutically acceptable salt, enantiomer or diastereomer thereof.

22. A compound according to claim 20, selected from

N-(3-chloro-4-fluoro-phenyl)-3-(2-oxopyrrolidin-1-yl)-6,7-dihydro-4H-pyrazolo[1,5-a]pyrazine-5-carboxamide;

6-methyl-3-(2-oxopyrrolidin-1-yl)-N-(3,4,5-trifluorophenyl)-6,7-dihydro-4H-pyrazolo[1,5-a]pyrazine-5-carboxamide;

N-(3-chloro-4-fluoro-phenyl)-6-methyl-3-(2-oxopyrrolidin-1-yl)-6,7-dihydro-4H-pyrazolo[1,5-a]pyrazine-5-carboxamide;

(6S)-N-[2-(difluoromethyl)-4-pyridyl]-6-methyl-3-(2-oxopyrrolidin-1-yl)-6,7-dihydro-4H-pyrazolo[1,5-a]pyrazine-5-carboxamide;

(6S)-N-(3-chloro-4-fluoro-phenyl)-3-(4-cyano-2-oxo-pyrrolidin-1-yl)-6-methyl-6,7-dihydro-4H-pyrazolo[1,5-a]pyrazine-5-carboxamide;

(6S)-N-(3-chloro-4-fluoro-phenyl)-3-(4-hydroxy-2-oxo-pyrrolidin-1-yl)-6-methyl-6,7-dihydro-4H-pyrazolo[1,5-a]pyrazine-5-carboxamide;

(6S)-6-methyl-3-(3-oxomorpholin-4-yl)-N-(3,4,5-trifluorophenyl)-6,7-dihydro-4H-pyrazolo[1,5-a]pyrazine-5-carboxamide;

N-(3-chloro-4-fluoro-phenyl)-6-methyl-3-(2-oxooxazolidin-3-yl)-6,7-dihydro-4H-pyrazolo[1,5-a]pyrazine-5-carboxamide;

(6S)-N-(3-chloro-4-fluoro-phenyl)-3-(4-methoxy-2-oxo-pyrrolidin-1-yl)-6-methyl-6,7-dihydro-4H-pyrazolo[1,5-a]pyrazine-5-carboxamide;

(6S)-N-[3-(difluoromethyl)-4,5-difluoro-phenyl]-6-methyl-3-(2-oxopyrrolidin-1-yl)-6,7-dihydro-4H-pyrazolo[1,5-a]pyrazine-5-carboxamide;

(6S)-3-(4-cyano-2-oxo-pyrrolidin-1-yl)-6-methyl-N-(3,4,5-trifluorophenyl)-6,7-dihydro-4H-pyrazolo[1,5-a]pyrazine-5-carboxamide;

(6S)-3-[(4R)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4S)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-[2-(difluoromethyl)-4-pyridyl]-6-methyl-3-[2-oxo-4-(trifluoromethyl)pyrrolidin-1-yl]-6,7-dihydro-4H-pyrazolo[1,5-a]pyrazine-5-carboxamide;

(6S)-3-(5,5-dimethyl-2-oxo-oxazolidin-3-yl)-6-methyl-N-(3,4,5-trifluorophenyl)-6,7-dihydro-4H-pyrazolo[1,5-a]pyrazine-5-carboxamide;

(6S)-6-methyl-3-(2-oxo-3-azabicyclo[3.1.0]hexan-3-yl)-N-(3,4,5-trifluorophenyl)-6,7-dihydro-4H-pyrazolo[1,5-a]pyrazine-5-carboxamide;

(6S)-6-methyl-3-[2-oxo-4-(pyrimidin-2-ylamino)pyrrolidin-1-yl]-N-(3,4,5-trifluorophenyl)-6,7-dihydro-4H-pyrazolo[1,5-a]pyrazine-5-carboxamide;

(6S)-N-[3-(difluoromethyl)-4,5-difluoro-phenyl]-6-methyl-3-(3-oxomorpholin-4-yl)-6,7-dihydro-4H-pyrazolo[1,5-a]pyrazine-5-carboxamide;

(6S)-N-[2-(difluoromethyl)-4-pyridyl]-3-(5,5-dimethyl-2-oxo-oxazolidin-3-yl)-6-methyl-6,7-dihydro-4H-pyrazolo[1,5-a]pyrazine-5-carboxamide;

(6S)-N-[3-(difluoromethyl)-4,5-difluoro-phenyl]-3-(5,5-dimethyl-2-oxo-oxazolidin-3-yl)-6-methyl-6,7-dihydro-4H-pyrazolo[1,5-a]pyrazine-5-carboxamide;

(6S)-6-methyl-3-(5-methyl-2-oxo-1,3-oxazinan-3-yl)-N-(3,4,5-trifluorophenyl)-6,7-dihydro-4H-pyrazolo[1,5-a]pyrazine-5-carboxamide;

(6S)-6-methyl-3-[4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(5-methyl-1,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-(2-oxo-1,3-oxazinan-3-yl)-N-(3,4,5-trifluorophenyl)-6,7-dihydro-4H-pyrazolo[1,5-a]pyrazine-5-carboxamide;

(6S)-3-(5,5-dimethyl-2-oxo-1,3-oxazinan-3-yl)-6-methyl-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(3-oxo-8-oxa-2-azaspiro[4.5]decan-2-yl)-6,7-dihydro-4H-pyrazolo[1,5-a]pyrazine-5-carboxamide;

(6S)-6-methyl-3-(5-oxo-4-oxa-6-azaspiro[2.4]heptan-6-yl)-N-(3,4,5-trifluorophenyl)-6,7-dihydro-4H-pyrazolo[1,5-a]pyrazine-5-carboxamide;

methyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate;

ethyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate;

(6S)-6-methyl-3-(7-oxo-2-pyrimidin-2-yl-2,6-diazaspiro[3.4]octan-6-yl)-N-(3,4,5-trifluorophenyl)-6,7-dihydro-4H-pyrazolo[1,5-a]pyrazine-5-carboxamide;

(6S)-6-methyl-3-(2-oxoindolin-1-yl)-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(2-oxopyrrolidin-1-yl)-6,7-dihydro-4H-pyrazolo[1,5-a]pyrazine-5-carboxamide;

(6S)-6-methyl-3-(2-oxopyrrolidin-1-yl)-N-(3,4,5-trifluorophenyl)-6,7-dihydro-4H-pyrazolo[1,5-a]pyrazine-5-carboxamide;

(6S)-3-[4-cyano-4-(hydroxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-(4-cyano-4-methyl-2-oxo-pyrrolidin-1-yl)-N-[3-(difluoromethyl)-4,5-difluoro-phenyl]-6-methyl-6,7-dihydro-4H-pyrazolo[1,5-a]pyrazine-5-carboxamide;

(6S)-3-[4-(hydroxymethyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(3-oxomorpholin-4-yl)-6,7-dihydro-4H-pyrazolo[1,5-a]pyrazine-5-carboxamide;

(6S)-N-(3-chloro-4-fluoro-phenyl)-3-(2,2-dimethyl-5-oxo-morpholin-4-yl)-6-methyl-6,7-dihydro-4H-pyrazolo[1,5-a]pyrazine-5-carboxamide;

(6S)-N-[3-(difluoromethyl)-4,5-difluoro-phenyl]-6-methyl-3-(2-oxoimidazolidin-1-yl)-6,7-dihydro-4H-pyrazolo[1,5-a]pyrazine-5-carboxamide;

(6S)-3-[(4S)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4R)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[(4S)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;

(6S)-3-[(4S)-4-(5-fluoropyrimidin-2-yl)oxy-2-oxo -pyrrolidin-1-yl]-6-methyl-N-(3,4,5-trifluorophenyl)-6,7-dihydro-4H-pyrazolo[1,5-a]pyrazine-5-carboxamide;

(6S)-3-[4-(dimethylcarbamoyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[2-oxo-4-(pyrrolidine-1-carbonyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[(4R)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;

(6S)-3-(3-cyano-2-methyl-5-oxo-pyrrolidin-1-yl)-6-methyl-N-(3,4,5-trifluorophenyl)-6,7-dihydro-4H-pyrazolo[1,5-a]pyrazine-5-carboxamide;

(6S)-3-(5-hydroxy-2-oxo-1,3-oxazinan-3-yl)-6-methyl-N-(3,4,5-trifluorophenyl)-6,7-dihydro-4H-pyrazolo[1,5-a]pyrazine-5-carboxamide; and (6S)-3-[(3S,4R)-3-hydroxy-2-oxo-4-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide;

or a pharmaceutically acceptable salt, enantiomer or diastereomer thereof.

23. A compound of formula (I) according to claim 1, wherein $R^1$ is oxopyrrolidinyl, said oxopyrrolidinyl being unsubstituted or substituted with one or two substituents independently selected from $(C_{1-6}alkyl)_2$aminocarbonyl, $(C_{1-6}alkyl)_2$morpholinylcarbonyl, $C_{1-6}$alkoxy, $C_{1-6}$alkoxy$C_{1-6}$alkyl, $C_{1-6}$alkyl, $C_{1-6}$alkyl($C_{1-6}$alkylsulfonyl)amino, $C_{1-6}$alkylaminocarbonyl, $C_{1-6}$alkylcarbonylamino, $C_{1-6}$alkylmorpholinylcarbonyl, $C_{1-6}$alkyloxadiazolyl, $C_{1-6}$alkyloxazolyl, $C_{1-6}$alkylpyrazolyl, $C_{1-6}$alkylsulfonyl, $C_{1-6}$alkylsulfonylamino, $C_{1-6}$alkylsulfonyl$C_{1-6}$alkyl, cyano, dioxopyrrolidinyl, halo$C_{1-6}$alkyl, halo$C_{1-6}$alkyloxadiazolyl, halopiperidinylcarbonyl, halopyrimidinylamino, halopyrimidinyloxy, halopyrrolidinylcarbonyl, hydroxy, hydroxyazetidinylcarbonyl, hydroxy$C_{1-6}$alkyl, hydroxy$C_{1-6}$alkyl($C_{1-6}$alkyl)aminocarbonyl, hydroxy$C_{1-6}$alkylaminocarbonyl, hydroxypyrrolidinylcarbonyl, morpholinylcarbonyl, oxadiazolyl, oxazolyl, oxazolylaminocarbonyl, oxazolyl($C_{1-6}$alkyl)aminocarbonyl, oxazolylcarbonyl($C_{1-6}$alkyl)amino, oxomorpholinyl, oxooxazolidinyl, oxopyrrolidinyl, phenyl, pyrazolyl$C_{1-6}$alkyl, pyridinyl, pyrimidinyl, pyrimidinylamino, pyrimidinyl($C_{1-6}$alkyl)amino, pyrimidinyloxy, pyrimidinyloxy$C_{1-6}$alkyl, pyrrolidinylcarbonyl and thiazolyl;

$R^2$ and $R^3$ are independently selected from hydrogen and $C_{1-6}$alkyl with the proviso that $R^2$ is not $C_{1-6}$alkyl when $R^3$ is H;

$R^4$ is pyridinyl substituted with one or two substituents independently selected from halogen and halo$C_{1-6}$alkyl; or phenyl substituted with one, two or three substituents independently selected from halogen and halo$C_{1-6}$alkyl;

Y is CH; and

Q is N;

or a pharmaceutically acceptable salt, enantiomer or diastereomer thereof.

24. A compound of formula (I) according to claim 23, wherein $R^1$ is oxopyrrolidinyl, acetylaminooxopyrrolidinyl, cyanooxopyrrolidinyl, difluoropiperidinylcarbonyl(methyl)oxopyrrolidinyl, difluoropyrrolidinylcarbonyloxopyrrolidinyl, difluoropyrrolidinylcarbonyl(methyl) oxopyrrolidinyl, dihydroxyoxopyrrolidinyl, dimethylaminocarbonyloxopyrrolidinyl, dimethylmorpholinylcarbonyloxopyrrolidinyl, dioxopyrrolidinyloxopyrrolidinyl, ethyloxopyrrolidinyl, fluoropyrimidinylaminooxopyrrolidinyl, fluoropyrimidinyloxyoxopyrrolidinyl, hydroxyoxopyrrolidinyl, hydroxyazetidinylcarbonyloxopyrrolidinyl, hydroxyethyl(methyl)aminocarbonyloxopyrrolidinyl, hydroxydimethylethylaminooxopyrrolidinyl, hydroxymethyloxopyrrolidinyl, hydroxymethyl(cyano)oxopyrrolidinyl, (1-hydroxy-1-methyl-ethyl)oxopyrrolidinyl, hydroxypyrrolidinylcarbonyloxopyrrolidinyl, methoxyoxopyrrolidinyl, methoxymethyloxopyrrolidinyl, methyloxopyrrolidinyl, methyl(methylsulfonyl)aminooxopyrrolidinyl, methylaminocarbonyloxopyrrolidinyl, methylcyanooxopyrrolidinyl, methyl(hydroxymethyl)oxopyrrolidinyl, methylmorpholinylcarbonyloxopyrrolidinyl, methyloxadiazolyloxopyrrolidinyl, methyloxadiazolyl(methyl)oxopyrrolidinyl, methyloxazolyloxopyrrolidinyl, methylpyrazolyloxopyrrolidinyl, methylsulfonyloxopyrrolidinyl, methylsulfonylaminooxopyrrolidinyl, methylsulfonylmethyloxopyrrolidinyl, morpholinylcarbonyloxopyrrolidinyl, morpholinylcarbonyl(methyl)oxopyrrolidinyl, oxadiazolyloxopyrrolidinyl, oxadiazolyl(methyl)oxopyrrolidinyl, oxazolyloxopyrrolidinyl, oxazolylaminocarbonyloxopyrrolidinyl, oxazolylcarbonyl(methyl)aminooxopyrrolidinyl, oxazolyl(methyl)aminocarbonyloxopyrrolidinyl, oxomorpholinyloxopyrrolidinyl, oxooxazolidinyloxopyrrolidinyl, oxopyrrolidinyloxopyrrolidinyl, phenyloxopyrrolidinyl, phenyl(hydroxy)oxopyrrolidinyl, pyrazolylmethyloxopyrrolidinyl, pyridinyloxopyrrolidinyl, pyrimidinyloxopyrrolidinyl, pyrimidinylaminooxopyrrolidinyl, pyrimidinyl(methyl)aminooxopyrrolidinyl, pyrimidinyloxyoxopyrrolidinyl, pyrimidinyloxy(hydroxy)oxopyrrolidinyl, pyrimidinyloxy(hydroxy)(methyl)oxopyrrolidinyl, pyrimidinyloxymethyloxopyrrolidinyl, pyrrolidinylcarbonyloxopyrrolidinyl, thiazolyloxopyrrolidinyl, trifluoromethyloxopyrrolidinyl or trifluoromethyloxadiazolyloxopyrrolidinyl;

$R^2$ and $R^3$ are independently selected from hydrogen and methyl with the proviso that $R^2$ is not methyl when $R^3$ is H;

$R^4$ is chloropyridinyl, difluoromethylpyridinyl, fluorochloropyridinyl, trifluoromethylpyridinyl, difluorochlorophenyl, difluorodifluoromethylphenyl, fluorochlorophenyl, fluorotrifluoromethylphenyl or trifluorophenyl;

Y is CH; and

Q is N;

or a pharmaceutically acceptable salt, enantiomer or diastereomer thereof.

25. A compound of formula (I) according to claim 23, wherein $R^1$ is oxopyrrolidinyl, said oxopyrrolidinyl being unsubstituted or substituted with one or two substituents independently selected from $(C_{1-6}alkyl)_2aminocarbonyl$, $C_{1-6}alkoxy$, $C_{1-6}alkyl$, $C_{1-6}alkyloxadiazolyl$, cyano, $haloC_{1-6}alkyl$, halopyrimidinyloxy, hydroxy, hydroxy$C_{1-6}$alkyl, morpholinylcarbonyl, oxadiazolyl, pyrimidinylamino, pyrimidinyloxy and pyrrolidinylcarbonyl; or a pharmaceutically acceptable salt, enantiomer or diastereomer thereof.

26. A compound of formula (I) according to claim 25, wherein $R^1$ is oxopyrrolidinyl, cyanooxopyrrolidinyl, hydroxyoxopyrrolidinyl, methoxyoxopyrrolidinyl, trifluoromethyloxopyrrolidinyl, pyrimidinylaminooxopyrrolidinyl, oxadiazolyloxopyrrolidinyl, methyloxadiazolyloxopyrrolidinyl, hydroxymethylcyanooxopyrrolidinyl, methylcyanooxopyrrolidinyl, methyl(hydroxymethyl)oxopyrrolidinyl, pyrimidinyloxyoxopyrrolidinyl, pyrimidinyloxy(hydroxy)oxopyrrolidinyl, fluoropyrimidinyloxyoxopyrrolidinyl, morpholinylcarbonyloxopyrrolidinyl, dimethylaminocarbonyloxopyrrolidinyl or pyrrolidinylcarbonyloxopyrrolidinyl; or a pharmaceutically acceptable salt, enantiomer or diastereomer thereof.

27. A compound of formula (I) according to claim 23, wherein $R^2$ is H; and $R^3$ is H or $C_{1-6}$alkyl; or a pharmaceutically acceptable salt, enantiomer or diastereomer thereof.

28. A compound of formula (I) according to claim 27, wherein $R^2$ is H; and $R^3$ is H or methyl; or a pharmaceutically acceptable salt, enantiomer or diastereomer thereof.

29. A compound of formula (I) according to claim 23, wherein $R^4$ is pyridinyl substituted by halo$C_{1-6}$alkyl; or phenyl substituted with one, two or three substituents independently selected from halogen and halo$C_{1-6}$alkyl; or a pharmaceutically acceptable salt, enantiomer or diastereomer thereof.

30. A compound of formula (I) according to claim 29, wherein $R^4$ is difluoromethylpyridinyl, fluorochlorophenyl, difluorodifluoromethylphenyl or trifluorophenyl; or a pharmaceutically acceptable salt, enantiomer or diastereomer thereof.

31. A compound of formula (I) according to claim 23, wherein $R^1$ is oxopyrrolidinyl, said oxopyrrolidinyl being unsubstituted or substituted with one or two substituents independently selected from $(C_{1-6}alkyl)_2aminocarbonyl$, $C_{1-6}alkoxy$, $C_{1-6}alkyl$, $C_{1-6}alkyloxadiazolyl$, cyano, halo$C_{1-6}$alkyl, halopyrimidinyloxy, hydroxy, hydroxy$C_{1-6}$alkyl, morpholinylcarbonyl, oxadiazolyl, pyrimidinylamino, pyrimidinyloxy and pyrrolidinylcarbonyl;

$R^2$ is H;

$R^3$ is H or $C_{1-6}$alkyl;

$R^4$ is pyridinyl substituted by halo$C_{1-6}$alkyl; or phenyl substituted with one, two or three substituents independently selected from halogen and halo$C_{1-6}$alkyl;

Y is CH; and

Q is N;

or a pharmaceutically acceptable salt, enantiomer or diastereomer thereof.

32. A compound of formula (I) according to claim 31, wherein $R^1$ is oxopyrrolidinyl, cyanooxopyrrolidinyl, hydroxyoxopyrrolidinyl, methoxyoxopyrrolidinyl, trifluoromethyloxopyrrolidinyl, pyrimidinylaminooxopyrrolidinyl, oxadiazolyloxopyrrolidinyl, methyloxadiazolyloxopyrrolidinyl, hydroxymethylcyanooxopyrrolidinyl, methylcyanooxopyrrolidinyl, methyl(hydroxymethyl)oxopyrrolidinyl, pyrimidinyloxyoxopyrrolidinyl, pyrimidinyloxy(hydroxy)oxopyrrolidinyl, fluoropyrimidinyloxyoxopyrrolidinyl, morpholinylcarbonyloxopyrrolidinyl, dimethylaminocarbonyloxopyrrolidinyl or pyrrolidinylcarbonyloxopyrrolidinyl;

$R^2$ is H;

$R^3$ is H or $C_{1-6}$alkyl;

$R^4$ is difluoromethylpyridinyl, fluorochlorophenyl, difluorodifluoromethylphenyl or trifluorophenyl;

Y is CH; and

Q is N;

or a pharmaceutically acceptable salt, enantiomer or diastereomer thereof.

33. A compound according to claim 23, selected from

N-(3-chloro-4-fluoro-phenyl)-3-(2-oxopyrrolidin-1-yl)-6,7-dihydro-4H-pyrazolo[1,5-a]pyrazine-5-carboxamide;

6-methyl-3-(2-oxopyrrolidin-1-yl)-N-(3,4,5-trifluorophenyl)-6,7-dihydro-4H-pyrazolo[1,5-a]pyrazine-5-carboxamide;

N-(3-chloro-4-fluoro-phenyl)-6-methyl-3-(2-oxopyrrolidin-1-yl)-6,7-dihydro-4H-pyrazolo[1,5-a]pyrazine-5-carboxamide;

(6S)-N-(3-chloro-4-fluoro-phenyl)-3-(4-cyano-2-oxopyrrolidin-1-yl)-6-methyl-6,7-dihydro-4H-pyrazolo[1,5-a]pyrazine-5-carboxamide;

(6S)-N-(3-chloro-4-fluoro-phenyl)-3-(4-hydroxy-2-oxopyrrolidin-1-yl)-6-methyl-6,7-dihydro-4H-pyrazolo[1,5-a]pyrazine-5-carboxamide;

(6S)-N-(3-chloro-4-fluoro-phenyl)-3-(4-methoxy-2-oxopyrrolidin-1-yl)-6-methyl-6,7-dihydro-4H-pyrazolo[1,5-a]pyrazine-5-carboxamide;

(6S)-N-[3-(difluoromethyl)-4,5-difluoro-phenyl]-6-methyl-3-(2-oxopyrrolidin-1-yl)-6,7-dihydro-4H-pyrazolo[1,5-a]pyrazine-5-carboxamide;

(6S)-3-(4-cyano-2-oxo-pyrrolidin-1-yl)-6-methyl-N-(3,4,5-trifluorophenyl)-6,7-dihydro-4H-pyrazolo[1,5-a]pyrazine-5-carboxamide;

(6S)-3-[(4R)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4S)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-[2-(difluoromethyl)-4-pyridyl]-6-methyl-3-[2-oxo-4-(trifluoromethyl)pyrrolidin-1-yl]-6,7-dihydro-4H-pyrazolo[1,5-a]pyrazine-5-carboxamide;

(6S)-6-methyl-3-[2-oxo-4-(pyrimidin-2-ylamino)pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(5-methyl-1,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(2-oxopyrrolidin-1-yl)-6,7-dihydro-4H-pyrazolo[1,5-a]pyrazine-5-carboxamide;

(6S)-6-methyl-3-(2-oxopyrrolidin-1-yl)-N-(3,4,5-trifluorophenyl)-6,7-dihydro-4H-pyrazolo[1,5-a]pyrazine-5-carboxamide;

(6S)-3-[4-cyano-4-(hydroxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-(4-cyano-4-methyl-2-oxo-pyrrolidin-1-yl)-N-[3-(difluoromethyl)-4,5-difluoro-phenyl]-6-methyl-6,7-dihydro-4H-pyrazolo[1,5-a]pyrazine-5-carboxamide;

(6S)-3-[4-(hydroxymethyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4S)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4R)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[(4S)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;

(6S)-3-[(4S)-4-(5-fluoropyrimidin-2-yl)oxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[4-(morpholine-4-carbonyl)-2-oxo-pyrrolidin-1-yl]-N-(3,4,5-trifluorophenyl)-6,7-dihydro-4H-pyrazolo[1,5-a]pyrazine-5-carboxamide;

(6S)-3-[4-(dimethylcarbamoyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[2-oxo-4-(pyrrolidine-1-carbonyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[(4R)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;

(6S)-3-(3-cyano-2-methyl-5-oxo-pyrrolidin-1-yl)-6-methyl-N-(3,4,5-trifluorophenyl)-6,7-dihydro-4H-pyrazolo[1,5-a]pyrazine-5-carboxamide; and (6S)-3-[(3S,4R)-3-hydroxy-2-oxo-4-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide;

or a pharmaceutically acceptable salt, enantiomer or diastereomer thereof.

34. A compound according to claim 1, selected from
3-(4-fluorophenyl)-N-phenyl-6,7-dihydro-4H-pyrazolo[1,5-a]pyrazine-5-carboxamide;
N,3-diphenyl-6,7-dihydro-4H-pyrazolo[1,5-a]pyrazine-5-carboxamide;
3-(3-fluorophenyl)-N-phenyl-6,7-dihydro-4H-pyrazolo[1,5-a]pyrazine-5-carboxamide;
3-(3-chlorophenyl)-N-phenyl-6,7-dihydro-4H-pyrazolo[1,5-a]pyrazine-5-carboxamide;
N-phenyl-3-[3-(trifluoromethyl)phenyl]-6,7-dihydro-4H-pyrazolo[1,5-a]pyrazine-5-carboxamide;
3-(2-fluorophenyl)-N-phenyl-6,7-dihydro-4H-pyrazolo[1,5-a]pyrazine-5-carboxamide;
3-(2-chlorophenyl)-N-phenyl-6,7-dihydro-4H-pyrazolo[1,5-a]pyrazine-5-carboxamide;
N-phenyl-3-[2-(trifluoromethyl)phenyl]-6,7-dihydro-4H-pyrazolo[1,5-a]pyrazine-5-carboxamide;
1-(4-fluorophenyl)-N-phenyl-6,8-dihydro-5H-imidazo[1,5-a]pyrazine-7-carboxamide;
3-(4-fluorophenyl)-N-phenyl-6,7-dihydro-4H-triazolo[1,5-a]pyrazine-5-carboxamide;
3-(4-fluorophenyl)-N-[3-(trifluoromethyl)phenyl]-6,7-dihydro-4H-pyrazolo[1,5-a]pyrazine-5-carboxamide;
N-(3-chloro-4-fluoro-phenyl)-8-(4-fluorophenyl)-3,4-dihydro-1H-pyrrolo[1,2-a]pyrazine-2-carboxamide;
N-(2-fluorophenyl)-3-(4-fluorophenyl)-6,7-dihydro-4H-pyrazolo[1,5-a]pyrazine-5-carboxamide;
N,3-bis(4-fluorophenyl)-6,7-dihydro-4H-pyrazolo[1,5-a]pyrazine-5-carboxamide;
N-(3-chlorophenyl)-3-(4-fluorophenyl)-6,7-dihydro-4H-pyrazolo[1,5-a]pyrazine-5-carboxamide;
N-(3-cyanophenyl)-3-(4-fluorophenyl)-6,7-dihydro-4H-pyrazolo[1,5-a]pyrazine-5-carboxamide;
N-(4-chlorophenyl)-3-(4-fluorophenyl)-6,7-dihydro-4H-pyrazolo[1,5-a]pyrazine-5-carboxamide;
3-(2-cyanophenyl)-N-phenyl-6,7-dihydro-4H-pyrazolo[1,5-a]pyrazine-5-carboxamide;
N-(3-fluorophenyl)-3-(4-fluorophenyl)-6,7-dihydro-4H-pyrazolo[1,5-a]pyrazine-5-carboxamide;
N-(4-chloro-3-fluoro-phenyl)-3-(4-fluorophenyl)-6,7-dihydro-4H-pyrazolo[1,5-a]pyrazine-5-carboxamide;
N-(3-chloro-4-fluoro-phenyl)-3-(4-fluorophenyl)-6,7-dihydro-4H-pyrazolo[1,5-a]pyrazine-5-carboxamide;
3-(4-fluorophenyl)-N-(4-pyridyl)-6,7-dihydro-4H-pyrazolo[1,5-a]pyrazine-5-carboxamide;
N-(4-cyanophenyl)-3-(4-fluorophenyl)-6,7-dihydro-4H-pyrazolo[1,5-a]pyrazine-5-carboxamide;
N-(3-chloro-4-fluoro-phenyl)-3-(2-fluorophenyl)-6,7-dihydro-4H-pyrazolo[1,5-a]pyrazine-5-carboxamide;
3-(3-methoxyphenyl)-N-phenyl-6,7-dihydro-4H-pyrazolo[1,5-a]pyrazine-5-carboxamide;
3-cyclopentyl-N-phenyl-6,7-dihydro-4H-pyrazolo[1,5-a]pyrazine-5-carboxamide;
3-(2-methoxyphenyl)-N-phenyl-6,7-dihydro-4H-pyrazolo[1,5-a]pyrazine-5-carboxamide;

N-phenyl-3-[4-(trifluoromethyl)-2-pyridyl]-6,7-dihydro-4H-pyrazolo[1,5-a]pyrazine-5-carboxamide;
3-(4-cyano-2-pyridyl)-N-phenyl-6,7-dihydro-4H-pyrazolo[1,5-a]pyrazine-5-carboxamide;
N-(3-chlorophenyl)-3-(2-fluorophenyl)-6,7-dihydro-4H-pyrazolo[1,5-a]pyrazine-5-carboxamide;
N-(3-chlorophenyl)-3-(o-tolyl)-6,7-dihydro-4H-pyrazolo[1,5-a]pyrazine-5-carboxamide;
N-(5-fluoro-6-methyl-2-pyridyl)-3-(4-fluorophenyl)-6,7-dihydro-4H-pyrazolo[1,5-a]pyrazine-5-carboxamide;
3-(2-fluorophenyl)-N-(4-fluorophenyl)-6,7-dihydro-4H-pyrazolo[1,5-a]pyrazine-5-carboxamide;
3-(2-fluorophenyl)-N-[4-fluoro-3-(trifluoromethyl)phenyl]-6,7-dihydro-4H-pyrazolo[1,5-a]pyrazine-5-carboxamide;
N-(3-chlorophenyl)-3-(2,4-difluorophenyl)-6,7-dihydro-4H-pyrazolo[1,5-a]pyrazine-5-carboxamide;
N-(3-chlorophenyl)-3-(2,3-difluorophenyl)-6,7-dihydro-4H-pyrazolo[1,5-a]pyrazine-5-carboxamide;
3-(3-cyano-2-pyridyl)-N-phenyl-6,7-dihydro-4H-pyrazolo[1,5-a]pyrazine-5-carboxamide;
3-(3-chloro-2-fluoro-phenyl)-N-(3-chlorophenyl)-6,7-dihydro-4H-pyrazolo[1,5-a]pyrazine-5-carboxamide;
3-(5-chloro-2-fluoro-phenyl)-N-(3-chlorophenyl)-6,7-dihydro-4H-pyrazolo[1,5-a]pyrazine-5-carboxamide;
N-(3-chlorophenyl)-3-(2,5-difluorophenyl)-6,7-dihydro-4H-pyrazolo[1,5-a]pyrazine-5-carboxamide;
3-[3-(difluoromethyl)phenyl]-N-phenyl-6,7-dihydro-4H-pyrazolo[1,5-a]pyrazine-5-carboxamide;
3-(5-fluoro-6-methyl-2-pyridyl)-N-phenyl-6,7-dihydro-4H-pyrazolo[1,5-a]pyrazine-5-carboxamide;
3-(5-fluoro-4-methyl-2-pyridyl)-N-phenyl-6,7-dihydro-4H-pyrazolo[1,5-a]pyrazine-5-carboxamide;
N-phenyl-3-(2-pyridyl)-6,7-dihydro-4H-pyrazolo[1,5-a]pyrazine-5-carboxamide;
N-phenyl-3-thiazol-2-yl-6,7-dihydro-4H-pyrazolo[1,5-a]pyrazine-5-carboxamide;
N-phenyl-3-[4(trifluoromethyl)thiazol-2-yl]-6,7-dihydro-4H-pyrazolo[1,5-a]pyrazine-5-carboxamide;
3-(5-chlorothiazol-2-yl)-N-phenyl-6,7-dihydro-4H-pyrazolo[1,5-a]pyrazine-5-carboxamide;
3-(3,4-difluorophenyl)-N-phenyl-6,7-dihydro-4H-pyrazolo[1,5-a]pyrazine-5-carboxamide;
3-(6-chloro-2-pyridyl)-N-phenyl-6,7-dihydro-4H-pyrazolo[1,5-a]pyrazine-5-carboxamide;
N-(3-chloro-4-fluoro-phenyl)-3-(2,4-difluorophenyl)-6,7-dihydro-4H-pyrazolo[1,5-a]pyrazine-5-carboxamide;
3-(2,4-difluorophenyl)-N-(3,4,5-trifluorophenyl)-6,7-dihydro-4H-pyrazolo[1,5-a]pyrazine-5-carboxamide;
3-(4-fluoro-3-methyl-phenyl)-N-phenyl-6,7-dihydro-4H-pyrazolo[1,5-a]pyrazine-5-carboxamide;
3-(4-fluorophenyl)-6-methyl-N-(3,4,5-trifluorophenyl)-6,7-dihydro-4H-pyrazolo[1,5-a]pyrazine-5-carboxamide;
N-[(3-chloro-4-fluoro-phenyl)methyl]-3-(4-fluorophenyl)-6,7-dihydro-4H-pyrazolo[1,5-a]pyrazine-5-carboxamide;
N-[(3,5-dichlorophenyl)methyl]-3-(4-fluorophenyl)-6,7-dihydro-4H-pyrazolo[1,5-a]pyrazine-5-carboxamide;
N-(4-chloro-5-methyl-2-pyridyl)-3-(4-fluorophenyl)-6,7-dihydro-4H-pyrazolo[1,5-a]pyrazine-5-carboxamide;
3-(4-chloro-2-pyridyl)-N-phenyl-6,7-dihydro-4H-pyrazolo[1,5-a]pyrazine-5-carboxamide;
N-[(2-chloro-3-fluoro-phenyl)methyl]-3-(4-fluorophenyl)-6,7-dihydro-4H-pyrazolo[1,5-a]pyrazine-5-carboxamide;
N-[(2,6-dichlorophenyl)methyl]-3-(4-fluorophenyl)-6,7-dihydro-4H-pyrazolo[1,5-a]pyrazine-5-carboxamide;
3-(2,4-difluorophenyl)-N-(5-fluoro-6-methyl-2-pyridyl)-6,7-dihydro-4H-pyrazolo[1,5-a]pyrazine-5-carboxamide;
N-(3-chloro-4-fluoro-phenyl)-3-(4-fluorophenyl)-6-methyl-6,7-dihydro-4H-pyrazolo[1,5-a]pyrazine-5-carboxamide;
3-(4-fluorophenyl)-N-(2-methyl-1,3-benzothiazol-5-yl)-6,7-dihydro-4H-pyrazolo[1,5-a]pyrazine-5-carboxamide;
N-(benzothiophen-3-yl)-3-(4-fluorophenyl)-6,7-dihydro-4H-pyrazolo[1,5-a]pyrazine-5-carboxamide;
3-(2,4-difluorophenyl)-N-[2-(trifluoromethyl)-4-pyridyl]-6,7-dihydro-4H-pyrazolo[1,5-a]pyrazine-5-carboxamide;
3-(3-cyclopropylphenyl)-N-phenyl-6,7-dihydro-4H-pyrazolo[1,5-a]pyrazine-5-carboxamide;
3-(2-hydroxyphenyl)-N-phenyl-6,7-dihydro-4H-pyrazolo[1,5-a]pyrazine-5-carboxamide;
N-(3-chloro-4-fluoro-phenyl)-3-[4-(trifluoromethyl)-2-pyridyl]-6,7-dihydro-4H-pyrazolo[1,5-a]pyrazine-5-carboxamide;
N-(3-chloro-4-fluoro-phenyl)-3-(5-fluoro-4-methyl-2-pyridyl)-6,7-dihydro-4H-pyrazolo[1,5-a]pyrazine-5-carboxamide;
N-(3-chloro-4-fluoro-phenyl)-3-(5-fluoro-2-pyridyl)-6,7-dihydro-4H-pyrazolo[1,5-a]pyrazine-5-carboxamide;
N-(2-chloro-4-pyridyl)-3-(2,4-difluorophenyl)-6,7-dihydro-4H-pyrazolo[1,5-a]pyrazine-5-carboxamide;
3-[4-(trifluoromethyl)-2-pyridyl]-N-(3,4,5-trifluorophenyl)-6,7-dihydro-4H-pyrazolo[1,5-a]pyrazine-5-carboxamide;
N,3-bis(3-chloro-4-fluoro-phenyl)-6,7-dihydro-4H-pyrazolo[1,5-a]pyrazine-5-carboxamide;
N-(3-chloro-4-fluoro-phenyl)-3-cyclohexyl-6,7-dihydro-4H-pyrazolo[1,5-a]pyrazine-5-carboxamide;
N-(3-cyano-4-fluoro-phenyl)-3-(5-fluoro-4-methyl-2-pyridyl)-6,7-dihydro-4H-pyrazolo[1,5-a]pyrazine-5-carboxamide;
3-(5-fluoro-2-pyridyl)-N-(3,4,5-trifluorophenyl)-6,7-dihydro-4H-pyrazolo[1,5-a]pyrazine-5-carboxamide;
N-(3-cyano-4-fluoro-phenyl)-3-(5-fluoro-2-pyridyl)-6,7-dihydro-4H-pyrazolo[1,5-a]pyrazine-5-carboxamide;
3-(4-fluorophenyl)-N-(1H-indol-6-yl)-6,7-dihydro-4H-pyrazolo[1,5-a]pyrazine-5-carboxamide;
N-(3-chloro-4-fluoro-phenyl)-3-cyclopentyl-6,7-dihydro-4H-pyrazolo[1,5-a]pyrazine-5-carboxamide;
N-(3-cyano-4-fluoro-phenyl)-3-cyclopentyl-6,7-dihydro-4H-pyrazolo[1,5-a]pyrazine-5-carboxamide;
3-(4-fluorophenyl)-N-[4-fluoro-3-(trifluoromethyl)phenyl]-6,7-dihydro-4H-pyrazolo[1,5-a]pyrazine-5-carboxamide;
N-(4-fluoro-3-methyl-phenyl)-3-(4-fluorophenyl)-6,7-dihydro-4H-pyrazolo[1,5-a]pyrazine-5-carboxamide;
3-cyclopentyl-N-indan-5-yl-6,7-dihydro-4H-pyrazolo[1,5-a]pyrazine-5-carboxamide;
3-cyclopentyl-N-indan-1-yl-6,7-dihydro-4H-pyrazolo[1,5-a]pyrazine-5-carboxamide;
N-benzyl-3-cyclopentyl-6,7-dihydro-4H-pyrazolo[1,5-a]pyrazine-5-carboxamide;
N-(3-cyano-4-fluoro-phenyl)-3-(2,4-difluorophenyl)-6-methyl-6,7-dihydro-4H-pyrazolo[1,5-a]pyrazine-5-carboxamide;
N-(3-cyano-4-fluoro-phenyl)-3-(4-fluorophenyl)-6-methyl-6,7-dihydro-4H-pyrazolo[1,5-a]pyrazine-5-carboxamide;

N-(3-chloro-4-fluoro-phenyl)-3-pyrrolidin-1-yl-6,7-dihydro-4H-pyrazolo[1,5-a]pyrazine-5-carboxamide;
3-(2,4-difluorophenyl)-6-methyl-N-[2-(trifluoromethyl)-4-pyridyl]-6,7-dihydro-4H-pyrazolo[1,5-a]pyrazine-5-carboxamide;
N-(3-chloro-4-fluoro-phenyl)-3-(1-piperidyl)-6,7-dihydro-4H-pyrazolo[1,5-a]pyrazine-5-carboxamide;
N-(3-chloro-4-fluoro-phenyl)-3-(4,4-difluoro-1-piperidyl)-6,7-dihydro-4H-pyrazolo[1,5-a]pyrazine-5-carboxamide;
N-(3-chloro-4-fluoro-phenyl)-3-thiazol-2-yl-6,7-dihydro-4H-pyrazolo[1,5-a]pyrazine-5-carboxamide;
N-(3-chloro-4-fluoro-phenyl)-3-(2,4-difluorophenyl)-6-methyl-6,7-dihydro-4H-pyrazolo[1,5-a]pyrazine-5-carboxamide;
N-(2-chloro-4-pyridyl)-3-(2,4-difluorophenyl)-6-methyl-6,7-dihydro-4H-pyrazolo[1,5-a]pyrazine-5-carboxamide;
N-(3-chloro-4-fluoro-phenyl)-3-(5-fluoro-2-pyridyl)-6-methyl-6,7-dihydro-4H-pyrazolo[1,5-a]pyrazine-5-carboxamide;
N-(3-chloro-4-fluoro-phenyl)-3-(3,3-difluoro-1-piperidyl)-6,7-dihydro-4H-pyrazolo[1,5-a]pyrazine-5-carboxamide;
N-(2-chloro-4-pyridyl)-3-cyclopentyl-6-methyl-6,7-dihydro-4H-pyrazolo[1,5-a]pyrazine-5-carboxamide;
N-(2-cyano-4-pyridyl)-3-(4-fluorophenyl)-6,7-dihydro-4H-pyrazolo[1,5-a]pyrazine-5-carboxamide;
N-(2-chloro-6-methoxy-4-pyridyl)-3-(4-fluorophenyl)-6,7-dihydro-4H-pyrazolo[1,5-a]pyrazine-5-carboxamide;
3-(5-fluoro-2-pyridyl)-6-methyl-N-(3,4,5-trifluorophenyl)-6,7-dihydro-4H-pyrazolo[1,5-a]pyrazine-5-carboxamide;
N-(3-cyano-4-fluoro-phenyl)-3-(5-fluoro-2-pyridyl)-6-methyl-6,7-dihydro-4H-pyrazolo[1,5-a]pyrazine-5-carboxamide;
(6R)-N-(3-chloro-4-fluoro-phenyl)-3-(4-fluorophenyl)-6-methyl-6,7-dihydro-4H-pyrazolo[1,5-a]pyrazine-5-carboxamide;
(6S)-N-(3-chloro-4-fluoro-phenyl)-3-(4-fluorophenyl)-6-methyl-6,7-dihydro-4H-pyrazolo[1,5-a]pyrazine-5-carboxamide;
N-(2-chloro-4-pyridyl)-3-cyclopentyl-6,7-dihydro-4H-pyrazolo[1,5-a]pyrazine-5-carboxamide;
N-(benzofuran-6-yl)-3-cyclopentyl-6-methyl-6,7-dihydro-4H-pyrazolo[1,5-a]pyrazine-5-carboxamide;
N-(3-cyano-4-fluoro-phenyl)-3-(4-fluorophenyl)-6,7-dihydro-4H-pyrazolo[1,5-a]pyrazine-5-carboxamide;
N-(3-cyano-5-fluoro-phenyl)-3-(4-fluorophenyl)-6,7-dihydro-4H-pyrazolo[1,5-a]pyrazine-5-carboxamide;
3-(4-fluorophenyl)-N-[4-methyl-3-(trifluoromethyl)phenyl]-6,7-dihydro-4H-pyrazolo[1,5-a]pyrazine-5-carboxamide;
N-[3-chloro-5-(trifluoromethyl)phenyl]-3-(4-fluorophenyl)-6,7-dihydro-4H-pyrazolo[1,5-a]pyrazine-5-carboxamide;
N-(3,4-difluorophenyl)-3-(4-fluorophenyl)-6,7-dihydro-4H-pyrazolo[1,5-a]pyrazine-5-carboxamide;
N-(3-chloro-4-cyano-phenyl)-3-(4-fluorophenyl)-6,7-dihydro-4H-pyrazolo[1,5-a]pyrazine-5-carboxamide;
3-(4-fluorophenyl)-N-(3,4,5-trifluorophenyl)-6,7-dihydro-4H-pyrazolo[1,5-a]pyrazine-5-carboxamide;
N-(3,5-difluorophenyl)-3-(4-fluorophenyl)-6,7-dihydro-4H-pyrazolo[1,5-a]pyrazine-5-carboxamide;
N-[4-chloro-3-(trifluoromethyl)phenyl]-3-(4-fluorophenyl)-6,7-dihydro-4H-pyrazolo[1,5-a]pyrazine-5-carboxamide;
N-(3-ethylphenyl)-3-(4-fluorophenyl)-6,7-dihydro-4H-pyrazolo[1,5-a]pyrazine-5-carboxamide;
N-(3-ethynylphenyl)-3-(4-fluorophenyl)-6,7-dihydro-4H-pyrazolo[1,5-a]pyrazine-5-carboxamide;
3-(4-fluorophenyl)-N-(3-isopropylphenyl)-6,7-dihydro-4H-pyrazolo[1,5-a]pyrazine-5-carboxamide;
3-(4-fluorophenyl)-N-(3-methoxyphenyl)-6,7-dihydro-4H-pyrazolo[1,5-a]pyrazine-5-carboxamide;
N-phenyl-3-[2-(trifluoromethoxy)phenyl]-6,7-dihydro-4H-pyrazolo[1,5-a]pyrazine-5-carboxamide;
3-(3-chloro-4-fluoro-phenyl)-N-phenyl-6,7-dihydro-4H-pyrazolo[1,5-a]pyrazine-5-carboxamide;
3-(m-tolyl)-N-phenyl-6,7-dihydro-4H-pyrazolo[1,5-a]pyrazine-5-carboxamide;
3-(3-bromophenyl)-N-phenyl-6,7-dihydro-4H-pyrazolo[1,5-a]pyrazine-5-carboxamide;
N-(3-ethynyl-4-fluoro-phenyl)-3-(4-fluorophenyl)-6,7-dihydro-4H-pyrazolo[1,5-a]pyrazine-5-carboxamide;
N-(3-chloro-5-fluoro-phenyl)-3-(4-fluorophenyl)-6,7-dihydro-4H-pyrazolo[1,5-a]pyrazine-5-carboxamide;
N-(2-chloro-4-pyridyl)-3-(4-fluorophenyl)-6,7-dihydro-4H-pyrazolo[1,5-a]pyrazine-5-carboxamide;
N-(2,6-dimethyl-4-pyridyl)-3-(4-fluorophenyl)-6,7-dihydro-4H-pyrazolo[1,5-a]pyrazine-5-carboxamide;
3-(4-fluorophenyl)-N-[2-(trifluoromethyl)-4-pyridyl]-6,7-dihydro-4H-pyrazolo[1,5-a]pyrazine-5-carboxamide;
N-(3-chloro-4-fluoro-phenyl)-1-(4-fluorophenyl)-6,8-dihydro-5H-imidazo[1,5-a]pyrazine-7-carboxamide;
N-(3-bromo-4-fluoro-phenyl)-3-(4-fluorophenyl)-6,7-dihydro-4H-pyrazolo[1,5-a]pyrazine-5-carboxamide;
N-[3-(difluoromethoxy)phenyl]-3-(4-fluorophenyl)-6,7-dihydro-4H-pyrazolo[1,5-a]pyrazine-5-carboxamide;
3-(4-fluorophenyl)-N-[4-fluoro-3-(trifluoromethoxy)phenyl]-6,7-dihydro-4H-pyrazolo[1,5-a]pyrazine-5-carboxamide;
N-[3-(difluoromethyl)phenyl]-3-(4-fluorophenyl)-6,7-dihydro-4H-pyrazolo[1,5-a]pyrazine-5-carboxamide;
3-(4-fluorophenyl)-N-(m-tolyl)-6,7-dihydro-4H-pyrazolo[1,5-a]pyrazine-5-carboxamide;
N-phenyl-3-[3-(trifluoromethoxy)phenyl]-6,7-dihydro-4H-pyrazolo[1,5-a]pyrazine-5-carboxamide;
1-(2,4-difluorophenyl)-N-(3-ethynyl-4-fluoro-phenyl)-6,8-dihydro-5H-imidazo[1,5-a]pyrazine-7-carboxamide;
N-(3-chloro-4-fluoro-phenyl)-1-(2,4-difluorophenyl)-6,8-dihydro-5H-imidazo[1,5-a]pyrazine-7-carboxamide;
N-(3-cyano-4-fluoro-phenyl)-1-(2,4-difluorophenyl)-6,8-dihydro-5H-imidazo[1,5-a]pyrazine-7-carboxamide;
N-(3-cyano-4,5-difluoro-phenyl)-1-(2,4-difluorophenyl)-6,8-dihydro-5H-imidazo[1,5-a]pyrazine-7-carboxamide;
1-(2,4-difluorophenyl)-N-(3,4,5-trifluorophenyl)-6,8-dihydro-5H-imidazo[1,5-a]pyrazine-7-carboxamide;
3-(2,4-difluorophenyl)-N-(3-ethynyl-4-fluoro-phenyl)-6,7-dihydro-4H-pyrazolo[1,5-a]pyrazine-5-carboxamide;
N-(6-chloro-5-fluoro-2-pyridyl)-3-(4-fluorophenyl)-6,7-dihydro-4H-pyrazolo[1,5-a]pyrazine-5-carboxamide;
N-(3-cyclopropylphenyl)-3-(4-fluorophenyl)-6,7-dihydro-4H-pyrazolo[1,5-a]pyrazine-5-carboxamide;
N-(3-cyano-4-fluoro-phenyl)-3-(2,4-difluorophenyl)-6,7-dihydro-4H-pyrazolo[1,5-a]pyrazine-5-carboxamide;

N-(6-chloro-5-fluoro-2-pyridyl)-3-(2,4-difluorophenyl)-6,7-dihydro-4H-pyrazolo[1,5-a]pyrazine-5-carboxamide;
N-(3,4-difluoro-5-methyl-phenyl)-3-(4-fluorophenyl)-6,7-dihydro-4H-pyrazolo[1,5-a]pyrazine-5-carboxamide;
N-(3-chloro-4,5-difluoro-phenyl)-3-(4-fluorophenyl)-6,7-dihydro-4H-pyrazolo[1,5-a]pyrazine-5-carboxamide;
N-(3-cyclopropyl-4,5-difluoro-phenyl)-3-(4-fluorophenyl)-6,7-dihydro-4H-pyrazolo[1,5-a]pyrazine-5-carboxamide;
N-[3-(1,1-difluoroethyl)phenyl]-3-(4-fluorophenyl)-6,7-dihydro-4H-pyrazolo[1,5-a]pyrazine-5-carboxamide;
N-(3-chloro-4-fluoro-phenyl)-3-(4-chloro-5-fluoro-2-pyridyl)-6,7-dihydro-4H-pyrazolo[1,5-a]pyrazine-5-carboxamide;
N-(3-chloro-4-fluoro-phenyl)-3-(2-chloro-5-fluoro-4-pyridyl)-6,7-dihydro-4H-pyrazolo[1,5-a]pyrazine-5-carboxamide;
N-(3-cyclopropyl-4-fluoro-phenyl)-3-(2,4-difluorophenyl)-6,7-dihydro-4H-pyrazolo[1,5-a]pyrazine-5-carboxamide;
N-(2-chloro-4-pyridyl)-1-(2,4-difluorophenyl)-6,8-dihydro-5H-imidazo[1,5-a]pyrazine-7-carboxamide;
1-(2,4-difluorophenyl)-N-[2-(trifluoromethyl)-4-pyridyl]-6,8-dihydro-5H-imidazo[1,5-a]pyrazine-7-carboxamide;
N-(3-chloro-4-fluoro-phenyl)-3-(4-fluorophenyl)-6,7-dihydro-4H-triazolo[1,5-a]pyrazine-5-carboxamide;
N-(6-chloro-5-fluoro-2-pyridyl)-1-(2,4-difluorophenyl)-6,8-dihydro-5H-imidazo[1,5-a]pyrazine-7-carboxamide;
N-(3-chloro-4-fluoro-phenyl)-3-(2,4-difluorophenyl)-6,7-dihydro-4H-triazolo[1,5-a]pyrazine-5-carboxamide;
N-(3,4-difluoro-5-methyl-phenyl)-3-(5-fluoro-2-pyridyl)-6-methyl-6,7-dihydro-4H-pyrazolo[1,5-a]pyrazine-5-carboxamide;
N-(3-cyclopropyl-4-fluoro-phenyl)-3-(5-fluoro-2-pyridyl)-6-methyl-6,7-dihydro-4H-pyrazolo[1,5-a]pyrazine-5-carboxamide;
N-(3-chloro-4,5-difluoro-phenyl)-3-(5-fluoro-2-pyridyl)-6-methyl-6,7-dihydro-4H-pyrazolo[1,5-a]pyrazine-5-carboxamide;
N-(3,4-difluoro-5-methoxy-phenyl)-3-(5-fluoro-2-pyridyl)-6-methyl-6,7-dihydro-4H-pyrazolo[1,5-a]pyrazine-5-carboxamide;
N-(3-cyclopropyl-4,5-difluoro-phenyl)-3-(5-fluoro-2-pyridyl)-6-methyl-6,7-dihydro-4H-pyrazolo[1,5-a]pyrazine-5-carboxamide;
N-(6-chloro-5-fluoro-2-pyridyl)-3-(2,4-difluorophenyl)-6-methyl-6,7-dihydro-4H-pyrazolo[1,5-a]pyrazine-5-carboxamide;
N-(3-chloro-4-fluoro-phenyl)-1-cyclopentyl-6,8-dihydro-5H-imidazo[1,5-a]pyrazine-7-carboxamide;
1-cyclopentyl-N-(3,4,5-trifluorophenyl)-6,8-dihydro-5H-imidazo[1,5-a]pyrazine-7-carboxamide;
1-cyclopentyl-N-(3,4-difluoro-5-methyl-phenyl)-6,8-dihydro-5H-imidazo[1,5-a]pyrazine-7-carboxamide;
N-(3-cyclopropyl-4,5-difluoro-phenyl)-1-(2,4-difluorophenyl)-6,8-dihydro-5H-imidazo[1,5-a]pyrazine-7-carboxamide;
N-(3,4-difluoro-5-methoxy-phenyl)-1-(2,4-difluorophenyl)-6,8-dihydro-5H-imidazo[1,5-a]pyrazine-7-carboxamide;
N-(3,4-difluoro-5-methyl-phenyl)-1-(2,4-difluorophenyl)-6,8-dihydro-5H-imidazo[1,5-a]pyrazine-7-carboxamide;
N-(3-chloro-4-fluoro-phenyl)-3-(2-methylpyrrolidin-1-yl)-6,7-dihydro-4H-pyrazolo[1,5-a]pyrazine-5-carboxamide;
N-(3-chloro-4-fluoro-phenyl)-3-morpholino-6,7-dihydro-4H-pyrazolo[1,5-a]pyrazine-5-carboxamide;
N-(3-chloro-4-fluoro-phenyl)-3-(2-oxopyrrolidin-1-yl)-6,7-dihydro-4H-pyrazolo[1,5-a]pyrazine-5-carboxamide;
N-(3-chloro-4-fluoro-phenyl)-3-(4-methylpyrazol-1-yl)-6,7-dihydro-4H-pyrazolo[1,5-a]pyrazine-5-carboxamide;
N-benzyl-3-(4-fluorophenyl)-6-methyl-6,7-dihydro-4H-pyrazolo[1,5-a]pyrazine-5-carboxamide;
3-(4-fluorophenyl)-N-(2-fluoro-4-pyridyl)-6-methyl-6,7-dihydro-4H-pyrazolo[1,5-a]pyrazine-5-carboxamide;
3-(2,4-difluorophenyl)-N-(2-fluoro-4-pyridyl)-6-methyl-6,7-dihydro-4H-pyrazolo[1,5-a]pyrazine-5-carboxamide;
N-(1,3-benzoxazol-6-yl)-3-(4-fluorophenyl)-6,7-dihydro-4H-pyrazolo[1,5-a]pyrazine-5-carboxamide;
3-(4-fluorophenyl)-N-(2-methyl-4-pyridyl)-6,7-dihydro-4H-pyrazolo[1,5-a]pyrazine-5-carboxamide;
N-(2,6-difluoro-4-pyridyl)-3-(4-fluorophenyl)-6,7-dihydro-4H-pyrazolo[1,5-a]pyrazine-5-carboxamide;
3-(2,4-difluorophenyl)-6-methyl-N-(3,4,5-trifluorophenyl)-6,7-dihydro-4H-pyrazolo[1,5-a]pyrazine-5-carboxamide;
3-(2,4-difluorophenyl)-N-(5-fluoro-4-methyl-2-pyridyl)-6-methyl-6,7-dihydro-4H-pyrazolo[1,5-a]pyrazine-5-carboxamide;
N-cyclopentyl-3-(2,4-difluorophenyl)-6-methyl-6,7-dihydro-4H-pyrazolo[1,5-a]pyrazine-5-carboxamide;
N-cyclohexyl-3-(2,4-difluorophenyl)-6-methyl-6,7-dihydro-4H-pyrazolo[1,5-a]pyrazine-5-carboxamide;
N-(3-chloro-4-fluoro-phenyl)-3-tetrahydrofuran-3-yl-6,7-dihydro-4H-pyrazolo[1,5-a]pyrazine-5-carboxamide;
6-methyl-3-(2-oxopyrrolidin-1-yl)-N-(3,4,5-trifluorophenyl)-6,7-dihydro-4H-pyrazolo[1,5-a]pyrazine-5-carboxamide;
N-(4-bicyclo[4.2.0]octa-1(6),2,4-trienyl)-3-(4-fluorophenyl)-6,7-dihydro-4H-pyrazolo[1,5-a]pyrazine-5-carboxamide;
N-(3-chloro-4-fluoro-phenyl)-3-(5-fluoropyrimidin-2-yl)-6,7-dihydro-4H-pyrazolo[1,5-a]pyrazine-5-carboxamide;
N-(3-chloro-4-fluoro-phenyl)-3-(5-fluoro-4-methyl-pyrimidin-2-yl)-6,7-dihydro-4H-pyrazolo[1,5-a]pyrazine-5-carboxamide;
3-(2,4-difluorophenyl)-6-methyl-N-(2-methyl-4-pyridyl)-6,7-dihydro-4H-pyrazolo[1,5-a]pyrazine-5-carboxamide;
N-(2-chloro-4-pyridyl)-3-(5-fluoro-2-pyridyl)-6-methyl-6,7-dihydro-4H-pyrazolo[1,5-a]pyrazine-5-carboxamide;
N-(3-chloro-4-fluoro-phenyl)-3-(4-methylpyrazol-1-yl)-6,7-dihydro-4H-pyrazolo[1,5-a]pyrazine-5-carboxamide;
N-(2-chloro-4-pyridyl)-6-methyl-3[4-(trifluoromethyl)-2-pyridyl]-6,7-dihydro-4H-pyrazolo[1,5-a]pyrazine-5-carboxamide;
N-(2-chloro-4-pyridyl)-6-methyl-3-(2-oxopyrrolidin-1-yl)-6,7-dihydro-4H-pyrazolo[1,5-a]pyrazine-5-carboxamide;

N-(2-bromo-4-pyridyl)-3-(4-fluorophenyl)-6,7-dihydro-4H-pyrazolo[1,5-a]pyrazine-5-carboxamide;

N-(3-chloro-2-methyl-4-pyridyl)-3-(2,4-difluorophenyl)-6-methyl-6,7-dihydro-4H-pyrazolo[1,5-a]pyrazine-5-carboxamide;

3-(2,4-difluorophenyl)-N-(5-fluoro-2-methyl-4-pyridyl)-6-methyl-6,7-dihydro-4H-pyrazolo[1,5-a]pyrazine-5-carboxamide;

N-(5-chloro-2-methyl-4-pyridyl)-3-(2,4-difluorophenyl)-6-methyl-6,7-dihydro-4H-pyrazolo[1,5-a]pyrazine-5-carboxamide;

N-[(2-chloro-3-fluoro-phenyl)methyl]-3-(2,4-difluorophenyl)-6-methyl-6,7-dihydro-4H-pyrazolo[1,5-a]pyrazine-5-carboxamide;

3-(2,4-difluorophenyl)-N-(5-fluoro-6-methyl-2-pyridyl)-6-methyl-6,7-dihydro-4H-pyrazolo[1,5-a]pyrazine-5-carboxamide;

(6S)-3-(5-fluoro-2-pyridyl)-6-methyl-N-(3,4,5-trifluorophenyl)-6,7-dihydro-4H-pyrazolo[1,5-a]pyrazine-5-carboxamide;

N-(3-chloro-4-fluoro-phenyl)-6-methyl-3-(4-methylpyrazol-1-yl)-6,7-dihydro-4H-pyrazolo[1,5-a]pyrazine-5-carboxamide;

N-(3-chloro-4-fluoro-phenyl)-3-(4-cyanopyrazol-1-yl)-6-methyl-6,7-dihydro-4H-pyrazolo[1,5-a]pyrazine-5-carboxamide;

N-(3-chloro-4-fluoro-phenyl)-3-(4-fluoropyrazol-1-yl)-6-methyl-6,7-dihydro-4H-pyrazolo[1,5-a]pyrazine-5-carboxamide;

N-(3-chloro-4-fluoro-phenyl)-6-methyl-3-(2-oxopyrrolidin-1-yl)-6,7-dihydro-4H-pyrazolo[1,5-a]pyrazine-5-carboxamide;

N-[4-fluoro-3-(trifluoromethyl)phenyl]-6-methyl-3-(2-oxopyrrolidin-1-yl)-6,7-dihydro-4H-pyrazolo[1,5-a]pyrazine-5-carboxamide;

3-cyclopentyl-6-methyl-N-(3,4,5-trifluorophenyl)-6,7-dihydro-4H-pyrazolo[1,5-a]pyrazine-5-carboxamide;

3-cyclopentyl-6-methyl-N-[2-(trifluoromethyl)-4-pyridyl]-6,7-dihydro-4H-pyrazolo[1,5-a]pyrazine-5-carboxamide;

N-(6-chloro-5-fluoro-2-pyridyl)-3-cyclopentyl-6-methyl-6,7-dihydro-4H-pyrazolo[1,5-a]pyrazine-5-carboxamide;

N-(2-cyclopropyl-4-pyridyl)-3-(2,4-difluorophenyl)-6,7-dihydro-4H-pyrazolo[1,5-a]pyrazine-5-carboxamide;

3-(2,4-difluorophenyl)-N-[2-(dimethylamino)-4-pyridyl]-6,7-dihydro-4H-pyrazolo[1,5-a]pyrazine-5-carboxamide;

N-(3-chloro-4-fluoro-phenyl)-3-[2-(methoxymethyl)pyrrolidin-1-yl]-6,7-dihydro-4H-pyrazolo[1,5-a]pyrazine-5-carboxamide;

N-(3-chloro-4-fluoro-phenyl)-3-[3-(methoxymethyl)pyrrolidin-1-yl]-6,7-dihydro-4H-pyrazolo[1,5-a]pyrazine-5-carboxamide;

N-(3-chloro-4-fluoro-phenyl)-3-(3-methoxypyrrolidin-1-yl)-6,7-dihydro-4H-pyrazolo[1,5-a]pyrazine-5-carboxamide;

N-(3-chloro-4-fluoro-phenyl)-3-(4,4-dimethyl-2-oxopyrrolidin-1-yl)-6-methyl-6,7-dihydro-4H-pyrazolo[1,5-a]pyrazine-5-carboxamide;

N-(3-chloro-4-fluoro-phenyl)-3-[3-(trifluoromethyl)pyrrolidin-1-yl]-6,7-dihydro-4H-pyrazolo[1,5-a]pyrazine-5-carboxamide;

N-(3-chloro-4-fluoro-phenyl)-3-(3-cyanopyrrolidin-1-yl)-6,7-dihydro-4H-pyrazolo[1,5-a]pyrazine-5-carboxamide;

3-(3-azabicyclo[3.1.0]hexan-3-yl)-N-(3-chloro-4-fluoro-phenyl)-6,7-dihydro-4H-pyrazolo[1,5-a]pyrazine-5-carboxamide;

N-(3-chloro-4-fluoro-phenyl)-3-(3-hydroxy-3-methyl-pyrrolidin-1-yl)-6,7-dihydro-4H-pyrazolo[1,5-a]pyrazine-5-carboxamide;

N-(3-chloro-4-fluoro-phenyl)-3-(2,2-dimethylmorpholin-4-yl)-6,7-dihydro-4H-pyrazolo[1,5-a]pyrazine-5-carboxamide;

N-[2-(difluoromethyl)-4-pyridyl]-3-(2,4-difluorophenyl)-6-methyl-6,7-dihydro-4H-pyrazolo[1,5-a]pyrazine-5-carboxamide;

N-(3-chloro-4-fluoro-phenyl)-3-(8-oxa-3-azabicyclo[3.2.1]octan-3-yl)-6,7-dihydro-4H-pyrazolo[1,5-a]pyrazine-5-carboxamide;

N-(3-chloro-4-fluoro-phenyl)-3-(3-oxomorpholin-4-yl)-6,7-dihydro-4H-pyrazolo[1,5-a]pyrazine-5-carboxamide;

N-(3-chloro-4-fluoro-phenyl)-3-(3-methyl-5-oxo-morpholin-4-yl)-6,7-dihydro-4H-pyrazolo[1,5-a]pyrazine-5-carboxamide;

(6S)-N-[2-(difluoromethyl)-4-pyridyl]-6-methyl-3-(2-oxopyrrolidin-1-yl)-6,7-dihydro-4H-pyrazolo[1,5-a]pyrazine-5-carboxamide;

(6S)-N-(3-chloro-4-fluoro-phenyl)-3-(3,3-difluoropyrrolidin-1-yl)-6-methyl-6,7-dihydro-4H-pyrazolo[1,5-a]pyrazine-5-carboxamide;

(6S)-N-(3-chloro-4-fluoro-phenyl)-3-[trans-2,6-dimethylmorpholin-4-yl]-6-methyl-6,7-dihydro-4H-pyrazolo[1,5-a]pyrazine-5-carboxamide;

(6S)-N-(3-chloro-4-fluoro-phenyl)-3-[cis-2,6-dimethylmorpholin-4-yl]-6-methyl-6,7-dihydro-4H-pyrazolo[1,5-a]pyrazine-5-carboxamide;

(6S)-N-(3-chloro-4-fluoro-phenyl)-3-(4-hydroxy-1-piperidyl)-6-methyl-6,7-dihydro-4H-pyrazolo[1,5-a]pyrazine-5-carboxamide;

(6S)-N-(3-chloro-4-fluoro-phenyl)-6-methyl-3-(3-methyl-2-oxo-imidazolidin-1-yl)-6,7-dihydro-4H-pyrazolo[1,5-a]pyrazine-5-carboxamide;

(6S)-N-(3-chloro-4-fluoro-phenyl)-3-(4-cyano-2-oxo-pyrrolidin-1-yl)-6-methyl-6,7-dihydro-4H-pyrazolo[1,5-a]pyrazine-5-carboxamide;

N-(3-chloro-4-fluoro-phenyl)-3-(4-fluorophenyl)-7-methyl-6,7-dihydro-4H-pyrazolo[1,5-a]pyrazine-5-carboxamide;

(6S)-N-(3-chloro-4,5-difluoro-phenyl)-6-methyl-3-(2-oxopyrrolidin-1-yl)-6,7-dihydro-4H-pyrazolo[1,5-a]pyrazine-5-carboxamide;

(6S)-N-(3-chloro-4-fluoro-phenyl)-3-(4-hydroxy-2-oxo-pyrrolidin-1-yl)-6-methyl-6,7-dihydro-4H-pyrazolo[1,5-a]pyrazine-5-carboxamide;

(6S)-6-methyl-3-(3-oxomorpholin-4-yl)-N-(3,4,5-trifluorophenyl)-6,7-dihydro-4H-pyrazolo[1,5-a]pyrazine-5-carboxamide;

3-(1-acetyl-4-piperidyl)-N-(3-chloro-4-fluoro-phenyl)-6-methyl-6,7-dihydro-4H-pyrazolo[1,5-a]pyrazine-5-carboxamide;

(6S)-N-(3-chloro-4,5-difluoro-phenyl)-6-methyl-3-(3-oxomorpholin-4-yl)-6,7-dihydro-4H-pyrazolo[1,5-a]pyrazine-5-carboxamide;

(6S)-N-(3-chloro-4-fluoro-phenyl)-6-methyl-3-[4-(methylcarbamoyl)-2-oxo-pyrrolidin-1-yl]-6,7-dihydro-4H-pyrazolo[1,5-a]pyrazine-5-carboxamide;

N-(3-chloro-4-fluoro-phenyl)-6-methyl-3-(2-oxooxazolidin-3-yl)-6,7-dihydro-4H-pyrazolo[1,5-a]pyrazine-5-carboxamide;

(6S)-N-(3-chloro-4-fluoro-phenyl)-3-(4-methoxy-2-oxo-pyrrolidin-1-yl)-6-methyl-6,7-dihydro-4H-pyrazolo[1,5-a]pyrazine-5-carboxamide;

(6S)-N-[3-(difluoromethyl)-4,5-difluoro-phenyl]-6-methyl-3-(2-oxopyrrolidin-1-yl)-6,7-dihydro-4H-pyrazolo[1,5-a]pyrazine-5-carboxamide;

(6S)-3-(4-cyano-2-oxo-pyrrolidin-1-yl)-6-methyl-N-(3,4,5-trifluorophenyl)-6,7-dihydro-4H-pyrazolo[1,5-a]pyrazine-5-carboxamide;

(6S)-3-[(4R)-4-cyano-2-oxo-pyrrolidin-1-yl]-6-methyl-N-(3,4,5-trifluorophenyl)-6,7-dihydro-4H -pyrazolo[1,5-a]pyrazine-5-carboxamide;

(6S)-3-[(4S)-4-cyano-2-oxo-pyrrolidin-1-yl]-6-methyl-N-(3,4,5-trifluorophenyl)-6,7-dihydro-4H -pyrazolo[1,5-a]pyrazine-5-carboxamide;

(6S)-N-[2-(difluoromethyl)-4-pyridyl]-6-methyl-3-[2-oxo-4-(trifluoromethyl)pyrrolidin-1-yl]-6,7-dihydro-4H-pyrazolo[1,5-a]pyrazine-5-carboxamide;

(6S)-3-(2-acetyl-7-oxo-2,6-diazaspiro[3.4]octan-6-yl)-N-(3-chloro-4-fluoro-phenyl)-6-methyl-6,7-dihydro-4H-pyrazolo[1,5-a]pyrazine-5-carboxamide;

(6S)-6-methyl-3-(2-methyl-5-oxo-morpholin-4-yl)-N-(3,4,5-trifluorophenyl)-6,7-dihydro-4H-pyrazolo[1,5-a]pyrazine-5-carboxamide;

N-(3-chloro-4-fluoro-phenyl)-3-(2,5-dioxopiperazin-1-yl)-6-methyl-6,7-dihydro-4H-pyrazolo[1,5-a]pyrazine-5-carboxamide;

(6S)-N-(3-chloro-4-fluoro-phenyl)-3-(4,4-dimethyl-2-oxo-imidazolidin-1-yl)-6-methyl-6,7-dihydro-4H-pyrazolo[1,5-a]pyrazine-5-carboxamide;

(6S)-N-(3-chloro-4-fluoro-phenyl)-3-(3,6-dioxo-4,7,8,8a-tetrahydro-1H-pyrrolo[1,2-a]pyrazin-2-yl)-6-methyl-6,7-dihydro-4H-pyrazolo[1,5-a]pyrazine-5-carboxamide;

(6S)-6-methyl-3-(4-oxazol-5-yl-2-oxo-pyrrolidin-1-yl)-N-(3,4,5-trifluorophenyl)-6,7-dihydro-4H-pyrazolo[1,5-a]pyrazine-5-carboxamide;

(6S)-6-methyl-3-(3-methylsulfonyl-5-oxo-imidazolidin-1-yl)-N-(3,4,5-trifluorophenyl)-6,7-dihydro-4H-pyrazolo[1,5-a]pyrazine-5-carboxamide;

(6S)-3-(5,5-dimethyl-2-oxo-oxazolidin-3-yl)-6-methyl-N-(3,4,5-trifluorophenyl)-6,7-dihydro-4H-pyrazolo[1,5-a]pyrazine-5-carboxamide;

(6S,7S)-6,7-dimethyl-3-(2-oxopyrrolidin-1-yl)-N-(3,4,5-trifluorophenyl)-6,7-dihydro-4H-pyrazolo[1,5-a]pyrazine-5-carboxamide;

(6S)-6-methyl-3-(6-oxo-5-azaspiro[2.4]heptan-5-yl)-N-(3,4,5-trifluorophenyl)-6,7-dihydro-4H-pyrazolo[1,5-a]pyrazine-5-carboxamide;

(6S)-6-methyl-3-(2-oxo-3-azabicyclo[3.1.0]hexan-3-yl)-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(4-methyl-2-oxo-pyrrolidin-1-yl)-6,7-dihydro-4H-pyrazolo[1,5-a]pyrazine-5-carboxamide;

(6S)-N-(3-chloro-4-fluoro-phenyl)-6-methyl-3-[2-oxo-4-(trifluoromethyl)pyrrolidin-1-yl]-6,7-dihydro-4H-pyrazolo[1,5-a]pyrazine-5-carboxamide;

(6S)-N-(3-chloro-4-fluoro-phenyl)-3-(3-hydroxy-2-oxo-pyrrolidin-1-yl)-6-methyl-6,7-dihydro-4H-pyrazolo[1,5-a]pyrazine-5-carboxamide;

(6S)-N-(3-chloro-4-fluoro-phenyl)-3-(4,4-dimethyl-2-oxo-pyrrolidin-1-yl)-6-methyl-6,7-dihydro-4H-pyrazolo[1,5-a]pyrazine-5-carboxamide;

(6S)-N-[2-(difluoromethyl)-4-pyridyl]-3-(4,4-dimethyl-2-oxo-pyrrolidin-1-yl)-6-methyl-6,7-dihydro-4H-pyrazolo[1,5-a]pyrazine-5-carboxamide;

(6S)-6-methyl-3-[2-oxo-4-(trifluoromethyl)pyrrolidin-1-yl]-N-(3,4,5-trifluorophenyl)-6,7-dihydro-4H-pyrazolo[1,5-a]pyrazine-5-carboxamide;

(6S)-N-(2-chloro-4-pyridyl)-6-methyl-3-[2-oxo-4-(trifluoromethyl)pyrrolidin-1-yl]-6,7-dihydro-4H-pyrazolo[1,5-a]pyrazine-5-carboxamide;

(6S,7R)-6,7-dimethyl-3-(2-oxopyrrolidin-1-yl)-N-(3,4,5-trifluorophenyl)-6,7-dihydro-4H-pyrazolo[1,5-a]pyrazine-5-carboxamide;

(6S)-3-[(3S)-3-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-(6-chloro-5-fluoro-2-pyridyl)-3-(4,4-dimethyl-2-oxo-pyrrolidin-1-yl)-6-methyl-6,7-dihydro-4H-pyrazolo[1,5-a]pyrazine-5-carboxamide;

(6S)-3-[(3R)-3-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-[6-(difluoromethyl)-5-fluoro-2-pyridyl]-6-methyl-3-(3-oxo-2-azaspiro[4.4]nonan-2-yl)-6,7-dihydro-4H-pyrazolo[1,5-a]pyrazine-5-carboxamide;

(6S)-N-[2-(difluoromethyl)-4-pyridyl]-6-methyl-3-(3-oxo-2-azaspiro[4.4]nonan-2-yl)-6,7-dihydro-4H-pyrazolo[1,5-a]pyrazine-5-carboxamide;

(6S)-6-methyl-3-[2-oxo-4-(pyrimidin-2-yloxymethyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[2-oxo-4-(pyrazol-1-ylmethyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[2-oxo-4-(pyrimidin-2-ylamino)pyrrolidin-1-yl]-N-(3,4,5-trifluorophenyl)-6,7-dihydro-4H-pyrazolo[1,5-a]pyrazine-5-carboxamide;

(6S)-3-[4-[(5-fluoropyrimidin-4-yl)amino]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-[3-(difluoromethyl)-4,5-difluoro-phenyl]-6-methyl-3-(3-oxomorpholin-4-yl)-6,7-dihydro-4H-pyrazolo[1,5-a]pyrazine-5-carboxamide;

(6S)-N-[2-(difluoromethyl)-4-pyridyl]-3-(5,5-dimethyl-2-oxo-oxazolidin-3-yl)-6-methyl-6,7-dihydro-4H-pyrazolo[1,5-a]pyrazine-5-carboxamide;

(6S,7S)-6,7-dimethyl-3-(2-oxoimidazolidin-1-yl)-N-(3,4,5-trifluorophenyl)-6,7-dihydro-4H-pyrazolo[1,5-a]pyrazine-5-carboxamide;

(6S,7S)-6,7-dimethyl-3-(3-oxomorpholin-4-yl)-N-(3,4,5-trifluorophenyl)-6,7-dihydro-4H-pyrazolo[1,5-a]pyrazine-5-carboxamide;

(6S)-3-(3-benzoyl-5-oxo-imidazolidin-1-yl)-6-methyl-N-(3,4,5-trifluorophenyl)-6,7-dihydro-4H-pyrazolo[1,5-a]pyrazine-5-carboxamide;

(6S)-N-[3-(difluoromethyl)-4,5-difluoro-phenyl]-3-(5,5-dimethyl-2-oxo-oxazolidin-3-yl)-6-methyl-6,7-dihydro-4H-pyrazolo[1,5-a]pyrazine-5-carboxamide;

(6S)-N-[6-(difluoromethyl)-5-fluoro-2-pyridyl]-3-(5,5-dimethyl-2-oxo-oxazolidin-3-yl)-6-methyl-6,7-dihydro-4H-pyrazolo[1,5-a]pyrazine-5-carboxamide;

(6S)-6-methyl-3-(5-methyl-2-oxo-1,3-oxazinan-3-yl)-N-(3,4,5-trifluorophenyl)-6,7-dihydro-4H-pyrazolo[1,5-a]pyrazine-5-carboxamide;

(6S)-3-(2,4-dioxo-1H-pyrimidin-3-yl)-6-methyl-N-(3,4,5-trifluorophenyl)-6,7-dihydro-4H-pyrazolo[1,5-a]pyrazine-5-carboxamide;

(6S)-3-(2,4-dioxopyrimidin-1-yl)-6-methyl-N-(3,4,5-trifluorophenyl)-6,7-dihydro-4H-pyrazolo[1,5-a]pyrazine-5-carboxamide;

(6S)-6-methyl-3-(5-oxo-3-pyrimidin-2-yl-imidazolidin-1-yl)-N-(3,4,5-trifluorophenyl)-6,7-dihydro-4H-pyrazolo[1,5-a]pyrazine-5-carboxamide;
(6S)-6-methyl-3-[4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;
(6S)-6-methyl-3-[4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;
(6S)-6-methyl-3-[4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide;
(6S)-6-methyl-3-[4-(5-methyl-1,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide;
(6S)-6-methyl-3-[2-oxo-4-[5-(trifluoromethyl)-1,3,4-oxadiazol-2-yl]pyrrolidin-1-yl]-N-(3,4,5-trifluorophenyl)-6,7-dihydro-4H-pyrazolo[1,5-a]pyrazine-5-carboxamide;
(6S)-6-methyl-3-[2-oxo-4-[5-(trifluoromethyl)-1,2,4-oxadiazol-3-yl]pyrrolidin-1-yl]-N-(3,4,5-trifluorophenyl)-6,7-dihydro-4H-pyrazolo[1,5-a]pyrazine-5-carboxamide;
(6S)-N-[2-(difluoromethyl)-4-pyridyl]-3-(5-fluoropyrimidin-2-yl)-6-methyl-6,7-dihydro-4H-pyrazolo[1,5-a]pyrazine-5-carboxamide;
(6S)-6-methyl-3-[5-(1-methylimidazol-2-yl)-2-oxo-oxazolidin-3-yl]-N-(3,4,5-trifluorophenyl)-6,7-dihydro-4H-pyrazolo[1,5-a]pyrazine-5-carboxamide;
(6S)-6-methyl-3-(2-oxo-4-thiazol-5-yl-pyrrolidin-1-yl)-N-(3,4,5-trifluorophenyl)-6,7-dihydro-4H-pyrazolo[1,5-a]pyrazine-5-carboxamide;
(6S)-6-methyl-3-(2-oxo-4-thiazol-2-yl-pyrrolidin-1-yl)-N-(3,4,5-trifluorophenyl)-6,7-dihydro-4H-pyrazolo[1,5-a]pyrazine-5-carboxamide;
(6S)-6-methyl-3-(2-oxo-1,3-oxazinan-3-yl)-N-(3,4,5-trifluorophenyl)-6,7-dihydro-4H-pyrazolo[1,5-a]pyrazine-5-carboxamide;
(6S)-6-methyl-3-(2-oxohexahydropyrimidin-1-yl)-N-(3,4,5-trifluorophenyl)-6,7-dihydro-4H-pyrazolo[1,5-a]pyrazine-5-carboxamide;
(6S)-3-(5,5-dimethyl-2-oxo-1,3-oxazinan-3-yl)-6-methyl-N-(3,4,5-trifluorophenyl)-6,7-dihydro-4H-pyrazolo[1,5-a]pyrazine-5-carboxamide;
(6S)-N-(3-chloro-4-fluoro-phenyl)-3-[4-(methoxymethyl)-2-oxo-pyrrolidin-1-yl]-6-methyl-6,7-dihydro-4H-pyrazolo[1,5-a]pyrazine-5-carboxamide;
(6S)-N-(3-chloro-4-fluoro-phenyl)-6-methyl-3-(3-oxo-8-oxa-2-azaspiro[4.5]decan-2-yl)-6,7-dihydro-4H-pyrazolo[1,5-a]pyrazine-5-carboxamide;
(6S)-N-(3-chloro-4-fluoro-phenyl)-3-(3-methyl-2-oxo-pyrrolidin-1-yl)-6,7-dihydro-4H-pyrazolo[1,5-a]pyrazine-5-carboxamide;
(6S)-N-(3-chloro-4-fluoro-phenyl)-3-[4-(hydroxymethyl)-2-oxo-pyrrolidin-1-yl]-6-methyl-6,7-dihydro-4H-pyrazolo[1,5-a]pyrazine-5-carboxamide;
(6S)-3-[4-(methoxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-3-[4-(methoxymethyl)-2-oxo-pyrrolidin-1-yl]-6-methyl-N-[2-(trifluoromethyl)-4-pyridyl]-6,7-dihydro-4H-pyrazolo[1,5-a]pyrazine-5-carboxamide;
(6S)-N-(3-chloro-4-fluoro-phenyl)-6-methyl-3-(4-oxo-3,3a,6,6a-tetrahydro-1H-furo[3,4-c]pyrrol-5-yl)-6,7-dihydro-4H-pyrazolo[1,5-a]pyrazine-5-carboxamide;
(6S)-N-(3-chloro-4-fluoro-phenyl)-3-(4-ethyl-2-oxo-pyrrolidin-1-yl)-6-methyl-6,7-dihydro-4H-pyrazolo[1,5-a]pyrazine-5-carboxamide;
(6S)-N-(3-chloro-4-fluoro-phenyl)-6-methyl-3-(8-oxo-2-oxa-7-azaspiro[4.4]nonan-7-yl)-6,7-dihydro-4H-pyrazolo[1,5-a]pyrazine-5-carboxamide;
(6S)-N-(3-chloro-4-fluoro-phenyl)-6-methyl-3-(4-methylsulfonyl-2-oxo-pyrrolidin-1-yl)-6,7-dihydro-4H-pyrazolo[1,5-a]pyrazine-5-carboxamide;
(6S)-N-(3-chloro-4-fluoro-phenyl)-3-(4-hydroxy-2-oxo-1-piperidyl)-6-methyl-6,7-dihydro-4H-pyrazolo[1,5-a]pyrazine-5-carboxamide;
(6S)-6-methyl-3-[4-(methylsulfonylmethyl)-2-oxo-pyrrolidin-1-yl]-N-(3,4,5-trifluorophenyl)-6,7-dihydro-4H-pyrazolo[1,5-a]pyrazine-5-carboxamide;
(6S)-6-methyl-3-[4-[[methyl(methylsulfonyl)amino]methyl]-2-oxo-pyrrolidin-1-yl]-N-(3,4,5-trifluorophenyl)-6,7-dihydro-4H-pyrazolo[1,5-a]pyrazine-5-carboxamide;
(6S)-6-methyl-3-(2-oxopyrrolidin-3-yl)-N-(3,4,5-trifluorophenyl)-6,7-dihydro-4H-pyrazolo[1,5-a]pyrazine-5-carboxamide;
(6S)-6-methyl-3-(2-oxo-4-phenyl-pyrrolidin-1-yl)-N-(3,4,5-trifluorophenyl)-6,7-dihydro-4H-pyrazolo[1,5-a]pyrazine-5-carboxamide;
(6S)-3-[4-(1-hydroxy-1-methyl-ethyl)-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-3-(4-acetamido-2-oxo-pyrrolidin-1-yl)-N-(3-chloro-4-fluoro-phenyl)-6-methyl-6,7-dihydro-4H-pyrazolo[1,5-a]pyrazine-5-carboxamide;
(6S)-N-(3-chloro-4-fluoro-phenyl)-3-[4-(methanesulfonamido)-2-oxo-pyrrolidin-1-yl]-6-methyl-6,7-dihydro-4H-pyrazolo[1,5-a]pyrazine-5-carboxamide;
(6S)-N-(3-chloro-4-fluoro-phenyl)-6-methyl-3-[4-[methyl(methylsulfonyl)amino]-2-oxo-pyrrolidin-1-yl]-6,7-dihydro-4H-pyrazolo[1,5-a]pyrazine-5-carboxamide;
(6S)-3-[4-(2,5-dioxopyrrolidin-1-yl)-2-oxo-pyrrolidin-1-yl]-6-methyl-N-(3,4,5-trifluorophenyl)-6,7-dihydro-4H-pyrazolo[1,5-a]pyrazine-5-carboxamide;
(6S)-6-methyl-3-[2-oxo-4-(2-oxopyrrolidin-1-yl)pyrrolidin-1-yl]-N-(3,4,5-trifluorophenyl)-6,7-dihydro-4H-pyrazolo[1,5-a]pyrazine-5-carboxamide;
N-methyl-N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]oxazole-5-carboxamide;
N-methyl-N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]oxazole-4-carboxamide;
N-methyl-N-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]oxazole-2-carboxamide;
(6S)-6-methyl-3-[2-oxo-4-(2-oxooxazolidin-3-yl)pyrrolidin-1-yl]-N-(3,4,5-trifluorophenyl)-6,7-dihydro-4H-pyrazolo[1,5-a]pyrazine-5-carboxamide;
(6S)-6-methyl-3-[2-oxo-4-(3-oxomorpholin-4-yl)pyrrolidin-1-yl]-N-(3,4,5-trifluorophenyl)-6,7-dihydro-4H-pyrazolo[1,5-a]pyrazine-5-carboxamide;
(6S)-N-(3-chloro-4-fluoro-phenyl)-6-methyl-3-(5-methyl-2-oxo-oxazolidin-3-yl)-6,7-dihydro-4H-pyrazolo[1,5-a]pyrazine-5-carboxamide;
(6S)-N-(3-chloro-4-fluoro-phenyl)-6-methyl-3-(3-oxo-5,6,8,8a-tetrahydro-1H-imidazo[5,1-c][1,4]oxazin-2-yl)-6,7-dihydro-4H-pyrazolo[1,5-a]pyrazine-5-carboxamide;

(6S)-6-methyl-3-(3-oxo-5,6,8,8a-tetrahydro-1H-imidazo[5,1-c][1,4]oxazin-2-yl)-N-(3,4,5-trifluorophenyl)-6,7-dihydro-4H-pyrazolo[1,5-a]pyrazine-5-carboxamide;

(6S)-N-(2-chloro-4-pyridyl)-3-(5,5-dimethyl-2-oxo-oxazolidin-3-yl)-6-methyl-6,7-dihydro-4H-pyrazolo[1,5-a]pyrazine-5-carboxamide;

(6S)-3-(5,5-dimethyl-2-oxo-oxazolidin-3-yl)-6-methyl-N-[2-(trifluoromethyl)-4-pyridyl]-6,7-dihydro-4H-pyrazolo[1,5-a]pyrazine-5-carboxamide;

(6S)-N-(3-chloro-4-fluoro-phenyl)-6-methyl-3-(4-methyl-2-oxo-imidazolidin-1-yl)-6,7-dihydro-4H-pyrazolo[1,5-a]pyrazine-5-carboxamide;

(6S)-6-methyl-3-[(4R)-2-oxo-4-phenyl-oxazolidin-3-yl]-N-(3,4,5-trifluorophenyl)-6,7-dihydro-4H-pyrazolo[1,5-a]pyrazine-5-carboxamide;

(6S)-6-methyl-3-[(4S)-2-oxo-4-phenyl-oxazolidin-3-yl]-N-(3,4,5-trifluorophenyl)-6,7-dihydro-4H-pyrazolo[1,5-a]pyrazine-5-carboxamide;

(6S)-6-methyl-3-(2-oxo-4-phenyl-imidazolidin-1-yl)-N-(3,4,5-trifluorophenyl)-6,7-dihydro-4H-pyrazolo[1,5-a]pyrazine-5-carboxamide;

(6S)-3-(4,4-dimethyl-2-oxo-imidazolidin-1-yl)-6-methyl-N-(3,4,5-trifluorophenyl)-6,7-dihydro-4H-pyrazolo[1,5-a]pyrazine-5-carboxamide;

(6S)-6-methyl-3-(5-oxo-4-oxa-6-azaspiro[2.4]heptan-6-yl)-N-(3,4,5-trifluorophenyl)-6,7-dihydro-4H-pyrazolo[1,5-a]pyrazine-5-carboxamide;

(6S)-6-methyl-3-(6-oxo-5-oxa-7-azaspiro[3.4]octan-7-yl)-N-(3,4,5-trifluorophenyl)-6,7-dihydro-4H-pyrazolo[1,5-a]pyrazine-5-carboxamide;

methyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate;

ethyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3.4]octane-2-carboxylate;

(6S)-6-methyl-3-(5-methyl-2-oxo-pyrrolidin-3-yl)-N-(3,4,5-trifluorophenyl)-6,7-dihydro-4H-pyrazolo[1,5-a]pyrazine-5-carboxamide;

(6S)-6-methyl-3-[2-(oxazole-2-carbonyl)-7-oxo-2,6-diazaspiro[3.4]octan-6-yl]-N-(3,4,5-trifluorophenyl)-6,7-dihydro-4H-pyrazolo[1,5-a]pyrazine-5-carboxamide;

(6S)-6-methyl-3-(7-oxo-2-pyrimidin-2-yl-2,6-diazaspiro[3.4]octan-6-yl)-N-(3,4,5-trifluorophenyl)-6,7-dihydro-4H-pyrazolo[1,5-a]pyrazine-5-carboxamide;

(6S)-6-methyl-3-(2-oxoindolin-1-yl)-N-(3,4,5-trifluorophenyl)-6,7-dihydro-4H-pyrazolo[1,5-a]pyrazine-5-carboxamide;

(6S)-6-methyl-3-(1-oxoisoindolin-2-yl)-N-(3,4,5-trifluorophenyl)-6,7-dihydro-4H-pyrazolo[1,5-a]pyrazine-5-carboxamide;

(6S)-6-methyl-3-(5-oxo-7H-pyrrolo[3,4-b]pyridin-6-yl)-N-(3,4,5-trifluorophenyl)-6,7-dihydro-4H-pyrazolo[1,5-a]pyrazine-5-carboxamide;

(6S)-3-(5-fluoropyrimidin-2-yl)-6-methyl-N-(3,4,5-trifluorophenyl)-6,7-dihydro-4H-pyrazolo[1,5-a]pyrazine-5-carboxamide;

(6S)-3-[4-(hydroxymethyl)pyrazol-1-yl]-6-methyl-N-(3,4,5-trifluorophenyl)-6,7-dihydro-4H-pyrazolo[1,5-a]pyrazine-5-carboxamide;

(6S)-3-[4-(methoxymethyl)pyrazol-1-yl]-6-methyl-N-(3,4,5-trifluorophenyl)-6,7-dihydro-4H-pyrazolo[1,5-a]pyrazine-5-carboxamide;

(6S)-6-methyl-3-(2-oxo-5-phenyl-oxazolidin-3-yl)-N-(3,4,5-trifluorophenyl)-6,7-dihydro-4H-pyrazolo[1,5-a]pyrazine-5-carboxamide;

(6S)-6-methyl-3-[2-oxo-5-(2-pyridyl)oxazolidin-3-yl]-N-(3,4,5-trifluorophenyl)-6,7-dihydro-4H-pyrazolo[1,5-a]pyrazine-5-carboxamide;

(6S)-6-methyl-3-[2-oxo-5-(4-pyridyl)oxazolidin-3-yl]-N-(3,4,5-trifluorophenyl)-6,7-dihydro-4H-pyrazolo[1,5-a]pyrazine-5-carboxamide;

(6S)-6-methyl-3-[2-oxo-5-(3-pyridyl)oxazolidin-3-yl]-N-(3,4,5-trifluorophenyl)-6,7-dihydro-4H-pyrazolo[1,5-a]pyrazine-5-carboxamide;

(6S)-6-methyl-3-(5-oxazol-4-yl-2-oxo-oxazolidin-3-yl)-N-(3,4,5-trifluorophenyl)-6,7-dihydro-4H-pyrazolo[1,5-a]pyrazine-5-carboxamide;

(6S)-6-methyl-3-[4-(2-methyloxazol-5-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(2-methyloxazol-4-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[2-oxo-4-(3-pyridyl)pyrrolidin-1-yl]-N-(3,4,5-trifluorophenyl)-6,7-dihydro-4H-pyrazolo[1,5-a]pyrazine-5-carboxamide;

(6S)-6-methyl-3-(4-oxazol-4-yl-2-oxo-pyrrolidin-1-yl)-N-(3,4,5-trifluorophenyl)-6,7-dihydro-4H-pyrazolo[1,5-a]pyrazine-5-carboxamide;

(6S)-6-methyl-3-[2-oxo-4-(2-pyridyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[2-oxo-4-(4-pyridyl)pyrrolidin-1-yl]-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(2-oxopyrrolidin-1-yl)-6,7-dihydro-4H-pyrazolo[1,5-a]pyrazine-5-carboxamide;

(6S)-6-methyl-3-(2-oxopyrrolidin-1-yl)-N-(3,4,5-trifluorophenyl)-6,7-dihydro-4H-pyrazolo[1,5-a]pyrazine-5-carboxamide;

(6S)-6-methyl-3-(5-methyl-2-oxo-1-piperidyl)-N-(3,4,5-trifluorophenyl)-6,7-dihydro-4H-pyrazolo[1,5-a]pyrazine-5-carboxamide;

(6S)-3-(4-cyano-2-oxo-pyrrolidin-1-yl)-N-[2-(difluoromethyl)-4-pyridyl]-6-methyl-6,7-dihydro-4H-pyrazolo[1,5-a]pyrazine-5-carboxamide;

(6S)-3-[4-cyano-4-(hydroxymethyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-(4-cyano-4-methyl-2-oxo-pyrrolidin-1-yl)-N-[3-(difluoromethyl)-4,5-difluoro-phenyl]-6-methyl-6,7-dihydro-4H-pyrazolo[1,5-a]pyrazine-5-carboxamide;

(6S)-3-[4-(hydroxymethyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[4-[methyl(pyrimidin-2-yl)amino]-2-oxo-pyrrolidin-1-yl]-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-(3-oxomorpholin-4-yl)-6,7-dihydro-4H-pyrazolo[1,5-a]pyrazine-5-carboxamide;

(6S)-6-methyl-3-(2-oxooxazolidin-3-yl)-N-(3,4,5-trifluorophenyl)-6,7-dihydro-4H-pyrazolo[1,5-a]pyrazine-5-carboxamide;

(6S)-N-[2-(difluoromethyl)-4-pyridyl]-6-methyl-3-(3-oxomorpholin-4-yl)-6,7-dihydro-4H-pyrazolo[1,5-a]pyrazine-5-carboxamide;

(6S)-N-(2-chloro-4-pyridyl)-6-methyl-3-(3-oxomorpholin-4-yl)-6,7-dihydro-4H-pyrazolo[1,5-a]pyrazine-5-carboxamide;

(6S)-6-methyl-3-(2-oxoimidazolidin-1-yl)-N-(3,4,5-trifluorophenyl)-6,7-dihydro-4H-pyrazolo[1,5-a]pyrazine-5-carboxamide;

(6S)-N-(3-chloro-4-fluoro-phenyl)-3-(2,2-dimethyl-5-oxo-morpholin-4-yl)-6-methyl-6,7-dihydro-4H-pyrazolo[1,5-a]pyrazine-5-carboxamide;

(6S)-6-methyl-3-[(3S)-3-methyl-5-oxo-morpholin-4-yl]-N-(3,4,5-trifluorophenyl)-6,7-dihydro-4H-pyrazolo[1,5-a]pyrazine-5-carboxamide;

(6S)-N-[3-(difluoromethyl)-4,5-difluoro-phenyl]-6-methyl-3-(2-oxoimidazolidin-1-yl)-6,7-dihydro-4H-pyrazolo[1,5-a]pyrazine-5-carboxamide;

(6S)-3-(3-acetyl-5-oxo-imidazolidin-1-yl)-6-methyl-N-(3,4,5-trifluorophenyl)-6,7-dihydro-4H-pyrazolo[1,5-a]pyrazine-5-carboxamide;

(6S)-N-[2-(difluoromethyl)-4-pyridyl]-3-(2,2-dimethyl-5-oxo-morpholin-4-yl)-6-methyl-6,7-dihydro-4H-pyrazolo[1,5-a]pyrazine-5-carboxamide;

(6S)-3-[(4R)-4-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4S)-4-hydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4S)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(4R)-4-methoxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-N-[2-(difluoromethyl)-4-pyridyl]-3-[(4S)-4-methoxy-2-oxo-pyrrolidin-1-yl]-6-methyl-6,7-dihydro-4H-pyrazolo[1,5-a]pyrazine-5-carboxamide;

(6S)-6-methyl-3-[(4S)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;

(6S)-3-[(4S)-4-(5-fluoropyrimidin-2-yl)oxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-[2-hydroxyethyl(methyl)carbamoyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-[(2-hydroxy-1,1-dimethyl-ethyl)carbamoyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[4-(morpholine-4-carbonyl)-2-oxo-pyrrolidin-1-yl]-N-(3,4,5-trifluorophenyl)-6,7-dihydro-4H-pyrazolo[1,5-a]pyrazine-5-carboxamide;

(6S)-3-[4-[(3S)-3-hydroxypyrrolidine-1-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-[(3R)-3-hydroxypyrrolidine-1-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-(3-hydroxyazetidine-1-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-(dimethylcarbamoyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[2-oxo-4-(pyrrolidine-1-carbonyl)pyrrolidin-1-yl]-N-(3,4,5-trifluorophenyl)-6,7-dihydro-4H-pyrazolo[1,5-a]pyrazine-5-carboxamide;

(6S)-6-methyl-3-[4-(oxazol-2-ylcarbamoyl)-2-oxo-pyrrolidin-1-yl]-N-(3,4,5-trifluorophenyl)-6,7-dihydro-4H-pyrazolo[1,5-a]pyrazine-5-carboxamide;

(6S)-3-[4-(2,2-dimethylmorpholine-4-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[4-[(2R)-2-methylmorpholine-4-carbonyl]-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-[(2S)-2-methylmorpholine-4-carbonyl]-2-oxo-pyrrolidin-1-yl]-N-(3,4,5-trifluorophenyl)-6,7-dihydro-4H-pyrazolo[1,5-a]pyrazine-5-carboxamide;

(6S)-3-[4-[trans-2,6-dimethylmorpholine-4-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-[cis-2,6-dimethylmorpholine-4-carbonyl]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-(3,3-difluoropyrrolidine-1-carbonyl)-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[4-[methyl(oxazol-2-yl)carbamoyl]-2-oxo-pyrrolidin-1-yl]-N-(3,4,5-trifluorophenyl)-6,7-dihydro-4H-pyrazolo[1,5-a]pyrazine-5-carboxamide;

(6S)-3-[4-(3,3-difluoropyrrolidine-1-carbonyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[4-(4,4-difluoropiperidine-1-carbonyl)-4-methyl-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[4-methyl-4-(morpholine-4-carbonyl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-methyl-4-(5-methyl-1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-methyl-4-(1,3,4-oxadiazol-2-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-methyl-4-(3-methyl-1,2,4-oxadiazol-5-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[4-methyl-4-(5-methyl-1,2,4-oxadiazol-3-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-[(2S)-2-oxazol-5-yl-5-oxo-morpholin-4-yl]-N-(3,4,5-trifluorophenyl)-6,7-dihydro-4H-pyrazolo[1,5-a]pyrazine-5-carboxamide;

(6S)-6-methyl-3-[5-(3-methyl-1,2,4-oxadiazol-5-yl)-2-oxo-oxazolidin-3-yl]-N-(3,4,5-trifluorophenyl)-6,7-dihydro-4H-pyrazolo[1,5-a]pyrazine-5-carboxamide;

(6S)-3-[5-(6-chloro-3-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide;

(6S)-3-[5-(5-fluoro-2-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide;

(6S)-3-[5-(6-fluoro-2-pyridyl)-2-oxo-oxazolidin-3-yl]-6-methyl-N-(3,4,5-trifluorophenyl)-6,7-dihydro-4H-pyrazolo[1,5-a]pyrazine-5-carboxamide;

(6S)-6-methyl-3-[4-(1-methylpyrazol-4-yl)-2-oxo-pyrrolidin-1-yl]-N-(3,4,5-trifluorophenyl)-6,7-dihydro-4H-pyrazolo[1,5-a]pyrazine-5-carboxamide;

(6S)-6-methyl-3-(2-oxo-4-pyrimidin-5-yl-pyrrolidin-1-yl)-N-(3,4,5-trifluorophenyl)-6,7-dihydro-4H-pyrazolo[1,5-a]pyrazine-5-carboxamide;

(6S)-3-[4-[(5-fluoropyrimidin-2-yl)amino]-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[(4R)-2-oxo-4-pyrimidin-2-yloxy-pyrrolidin-1-yl]-N-(3,4,5-trifluorophenyl)-6,7-dihydro-4H-pyrazolo[1,5-a]pyrazine-5-carboxamide;

(6S)-3-[(3R,4R)-3,4-dihydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-(3-hydroxy-4,4-dimethyl-2-oxo-pyrrolidin-1-yl)-6-methyl-N-(3,4,5-trifluorophenyl)-6,7-dihydro-4H-pyrazolo[1,5-a]pyrazine-5-carboxamide;

(6S)-6-methyl-3-(2-oxo-3H-pyrrolo[3,2-c]pyridin-1-yl)-N-(3,4,5-trifluorophenyl)-6,7-dihydro-4H-pyrazolo[1,5-a]pyrazine-5-carboxamide;

(6S)-6-methyl-3-(6-oxo-4,7-dihydropyrazolo[1,5-a]pyrazin-5-yl)-N-(3,4,5-trifluorophenyl)-6,7-dihydro-4H-pyrazolo[1,5-a]pyrazine-5-carboxamide;

(6S)-3-(3-cyano-2-methyl-5-oxo-pyrrolidin-1-yl)-6-methyl-N-(3,4,5-trifluorophenyl)-6,7-dihydro-4H-pyrazolo[1,5-a]pyrazine-5-carboxamide;

(6S)-3-(5-hydroxy-2-oxo-1,3-oxazinan-3-yl)-6-methyl-N-(3,4,5-trifluorophenyl)-6,7-dihydro-4H-pyrazolo[1,5-a]pyrazine-5-carboxamide;

(6S)-6-methyl-3-(7-oxo-6-azaspiro[3.4]octan-6-yl)-N-(3,4,5-trifluorophenyl)-6,7-dihydro-4H-pyrazolo[1,5-a]pyrazine-5-carboxamide;

(6S)-3-(8-hydroxy-7-oxo-6-azaspiro[3.4]octan-6-yl)-6-methyl-N-(3,4,5-trifluorophenyl)-6,7-dihydro-4H-pyrazolo[1,5-a]pyrazine-5-carboxamide;

(6S)-3-(7-hydroxy-6-oxo-5-azaspiro[2.4]heptan-5-yl)-6-methyl-N-(3,4,5-trifluorophenyl)-6,7-dihydro-4H-pyrazolo[1,5-a]pyrazine-5-carboxamide;

(6S)-6-methyl-3-(6-methyl-2-oxo-1,3-oxazinan-3-yl)-N-(3,4,5-trifluorophenyl)-6,7-dihydro-4H-pyrazolo[1,5-a]pyrazine-5-carboxamide;

(6S)-6-methyl-3-(4-methyl-2-oxo-1,3-oxazinan-3-yl)-N-(3,4,5-trifluorophenyl)-6,7-dihydro-4H-pyrazolo[1,5-a]pyrazine-5-carboxamide;

(6S)-3-[4(3S,4R)-3,4-dihydroxy-2-oxo-pyrrolidin-1-yl]-6-methyl-N-(3,4,5-trifluorophenyl)-6,7-dihydro-4H-pyrazolo[1,5-a]pyrazine-5-carboxamide;

(6S)-3-[(3S,4R)-3-hydroxy-2-oxo-4-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-[5-methyl-5-(morpholine-4-carbonyl)-2-oxo-1,3-oxazinan-3-yl]-N-(3,4,5-trifluorophenyl)-6,7-dihydro-4H-pyrazolo[1,5-a]pyrazine-5-carboxamide;

(6S)-3-[(2R,3R,4S)-4-hydroxy-2-methyl-5-oxo-3-pyrimidin-2-yloxy-pyrrolidin-1-yl]-6-methyl-N-(3,4,5-trifluorophenyl)-6,7-dihydro-4H-pyrazolo[1,5-a]pyrazine-5-carboxamide;

(6S)-6-methyl-3-(2-oxo-4-pyrimidin-2-yl-pyrrolidin-1-yl)-N-(3,4,5-trifluorophenyl)-6,7-dihydro-4H-pyrazolo[1,5-a]pyrazine-5-carboxamide;

(6S)-3-(3-hydroxy-2-oxo-4-phenyl-pyrrolidin-1-yl)-6-methyl-N-(3,4,5-trifluorophenyl)-6,7-dihydro-4H-pyrazolo[1,5-a]pyrazine-5-carboxamide;

(6S)-3-[(5S)-5-methoxy-2-oxo-1,3-oxazinan-3-yl]-6-methyl-N-(3,4,5trifluorophenyl)-6,7-dihydro-4H-pyrazolo[1,5-a]pyrazine-5-carboxamide; and (6S)-3-[(5R)-5-methoxy-2-oxo-1,3-oxazinan-3-yl]-6-methyl-N-(3,4,5trifluorophenyl)-6,7-dihydro-4H-pyrazolo[1,5-a]pyrazine-5-carboxamide;

or a pharmaceutically acceptable salt, enantiomer or diastereomer thereof.

35. A pharmaceutical composition comprising a compound in accordance with claim 1, or a pharmaceutically acceptable salt, enantiomer or diastereomer thereof, and a therapeutically inert carrier.

36. A method for the treatment or prophylaxis of hepatitis B virus infection, which method comprises administering a therapeutically effective amount of a compound of claim 1, or a pharmaceutically acceptable salt, enantiomer or diastereomer thereof, to a patient in need thereof.

37. A compound which is (6S)-N-(3-chloro-4-fluoro-phenyl)-6-methyl-3-[4-(methylcarbamoyl)-2-oxo-pyrrolidin-1-yl]-6,7-dihydro-4H-pyrazolo[1,5-a]pyrazine-5-carboxamide, or a pharmaceutically acceptable salt thereof.

38. A compound which is (6S)-3-(4-cyano-2-oxo-pyrrolidin-l-yl)-6-methyl-N-(3,4,5-trifluorophenyl)-6,7-dihydro-4H-pyrazolo[1,5-a]pyrazine-5-carboxamide, or a pharmaceutically acceptable salt thereof.

39. A compound which is (6S)-3-[(4R)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide, or a pharmaceutically acceptable salt thereof.

40. A compound which is (6S)-3-[(4S)-4-cyano-2-oxo-pyrrolidin-1-yl]-6-methyl-N-(3,4,5-trifluorophenyl)-6,7-dihydro-4H-pyrazolo[1,5-a]pyrazine-5-carboxamide, or a pharmaceutically acceptable salt thereof.

41. A compound which is (6S)-3-(5,5-dimethyl-2-oxo-oxazolidin-3-yl) -6-methyl-N-(3,4,5-trifluorophenyl)-6,7-dihydro-4H-pyrazolo[1,5-a]pyrazine-5-carboxamide, or a pharmaceutically acceptable salt thereof.

42. A compound which is (6S)-N-[2-(difluoromethyl)-4-pyridyl]-3-(5,5-dimethyl-2-oxo-oxazolidin-3-yl) -6-methyl-6,7-dihydro-4H-pyrazolo[1,5-a]pyrazine-5-carboxamide, or a pharmaceutically acceptable salt thereof.

43. A compound which is (6S)-6-methyl-3-[4-(1,3,4-oxadiazol-2-yl) -2-oxo-pyrrolidin-1-yl]-N-(3,4,5-trifluorophenyl)-6,7-dihydro -4H-pyrazolo[1,5-a]pyrazine-5-carboxamide, or a pharmaceutically acceptable salt thereof.

44. A compound which is (6S)-6-methyl-3-(2-oxo-1,3-oxazinan-3-yl) -N-(3,4,5-trifluorophenyl)-6,7-dihydro-4H-pyrazolo[1,5-a]pyrazine-5-carboxamide, or a pharmaceutically acceptable salt thereof.

45. A compound which is methyl 6-[(6S)-6-methyl-5-[(3,4,5-trifluorophenyl)carbamoyl]-6,7-dihydro-4H-pyrazolo[1,5-a]pyrazin-3-yl]-7-oxo-2,6-diazaspiro[3,4]octane -2-carboxylate, or a pharmaceutically acceptable salt thereof.

46. A compound which is (6S)-3-[4-(hydroxymethyl) pyrazol-1-yl]-6-methyl-N-(3,4,5-trifluorophenyl) -6,7-dihydro-4H-pyrazolo[1,5-a]pyrazine-5-carboxamide, or a pharmaceutically acceptable salt thereof.

47. A compound which is (6S)-6-methyl-3-(2-oxopyrrolidin-1-yl) -N-(3,4,5-trifluorophenyl)-6,7-dihydro-4H-pyrazolo[1,5-a]pyrazine-5-carboxamide, or a pharmaceutically acceptable salt thereof.

48. A compound which is (6S)-6-methyl-3-(2-oxooxazolidin-3-yl) -N-(3,4,5-trifluorophenyl)-6,7-dihydro-4H-pyrazolo[1,5-a]pyrazine-5-carboxamide, or a pharmaceutically acceptable salt thereof.

49. A compound which is (6S)-6-methyl-3-(2-oxoimidazolidin-1-yl) -N-(3,4,5-trifluorophenyl)-6,7-dihydro-4H-pyrazolo[1,5-a]pyrazine-5-carboxamide, or a pharmaceutically acceptable salt thereof.

50. A compound which is (6S)-3-[(3S,4R) -3-hydroxy-2-oxo-4-pyrimidin-2-yloxy-pyrrolidin-1-yl]-6-methyl-N-(3,4,5-trifluorophenyl) -6,7-dihydro-4H-pyrazolo[1,5-a]pyrazine-5-carboxamide, or a pharmaceutically acceptable salt thereof.

* * * * *